(12) United States Patent
Anand et al.

(10) Patent No.: US 8,648,066 B2
(45) Date of Patent: Feb. 11, 2014

(54) BENZOXAZEPINES AS INHIBITORS OF PI3K/MTOR AND METHODS OF THEIR USE AND MANUFACTURE

(75) Inventors: Neel Kumar Anand, Burlingame, CA (US); Charles M. Blazey, San Francisco, CA (US); Owen Joseph Bowles, Pacifica, CA (US); Chris Allen Buhr, Redwood City, CA (US); Joerg Bussenius, Foster City, CA (US); Jeffry Kimo Curtis, San Anselmo, CA (US); Steven Charles DeFina, Burlingame, CA (US); Larisa Dubenko, San Francisco, CA (US); Jason R. Harris, San Bruno, CA (US); Eileen E. Jackson-Ugueto, Palo Alto, CA (US); Anagha Joshi, Fremont, CA (US); Angie Inyoung Kim, San Mateo, CA (US); Amy Lew Tsuhako, Milpitas, CA (US); Sunghoon Ma, Foster City, CA (US); Jean-Claire Limun Manalo, Daly City, CA (US); Stephanie Ng, Palo Alto, CA (US); Csaba J. Peto, Alameda, CA (US); Kenneth D. Rice, San Rafael, CA (US); Tsze H. Tsang, El Cerrito, CA (US); Cristiana A. Zaharia, Redwood City, CA (US)

(73) Assignee: Exelixis, Inc., South San Francisco, CA (US)

( * ) Notice: Subject to any disclaimer, the term of this patent is extended or adjusted under 35 U.S.C. 154(b) by 260 days.

(21) Appl. No.: 12/784,254

(22) Filed: May 20, 2010

(65) Prior Publication Data

US 2010/0298290 A1    Nov. 25, 2010

Related U.S. Application Data

(60) Provisional application No. 61/216,980, filed on May 22, 2009.

(51) Int. Cl.
*A61P 35/00* (2006.01)
*A61K 31/553* (2006.01)
*C07D 267/14* (2006.01)

(52) U.S. Cl.
USPC ..................... 514/211.09; 540/552

(58) Field of Classification Search
USPC ..................... 514/211.09; 540/552
See application file for complete search history.

(56) References Cited

U.S. PATENT DOCUMENTS 5,221,681 A    6/1993 Kabbe et al.
2004/0044048 A1    3/2004 Sikorski et al.

2006/0148800 A1    7/2006 Stadtmueller et al.
2008/0221093 A1    9/2008 Gege et al.
2012/0258953 A1    10/2012 Aay et al.

FOREIGN PATENT DOCUMENTS

| CN | 101497612 | 8/2009 |
|---|---|---|
| EP | 0496238 | 7/1992 |
| EP | 0540334 | 1/1996 |
| EP | 2123644 | 11/2009 |
| WO | 97/24122 | 7/1997 |
| WO | 97/24124 | 7/1997 |
| WO | 00/46215 | 8/2000 |
| WO | 01/16263 | 3/2001 |
| WO | 01/16274 | 3/2001 |
| WO | 01/16275 | 3/2001 |
| WO | 01/16276 | 3/2001 |
| WO | 02/096873 | 12/2002 |
| WO | 03/059898 | 7/2003 |
| WO | 03/075858 | 9/2003 |
| WO | 2004/078733 | 9/2004 |
| WO | 2006/125119 | 11/2006 |
| WO | 2008/108445 | 9/2008 |
| WO | 2008/109599 | 9/2008 |
| WO | 2008/144483 | 11/2008 |
| WO | 2009/026444 | 2/2009 |
| WO | 2009/042092 | 4/2009 |
| WO | 2009/076631 | 6/2009 |

OTHER PUBLICATIONS

International Search Report for PCT/US2010/035565, mailed Aug. 27, 2010.
U.S. Appl. No. 13/322,160, filed Nov. 23, 2011 Gembeh, Shirley V., Pending.
U.S. Appl. No. 13/989,330, filed May 23, 2011, To Be Determined, Pending.
U.S. Appl. No. 13/988,903, filed May 23, 2011, To Be Determined, Pending.
U.S. Appl. No. 13/988,948, filed May 23, 2011, To Be Determined, Pending.

(Continued)

*Primary Examiner* — Brenda Coleman
(74) *Attorney, Agent, or Firm* — Honigman Miller Schwartz and Cohn LLP; Heidi M. Berven; Jonathan P. O'Brien

(57) ABSTRACT

The invention is directed to Compounds of Formula I:

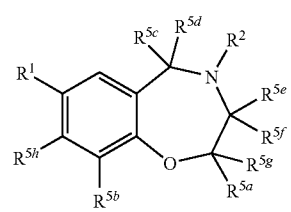

and pharmaceutically acceptable salts or solvates thereof, as well as methods of making and using the compounds.

34 Claims, No Drawings

(56) References Cited

OTHER PUBLICATIONS

U.S. Appl. No. 13/989,156, filed May 23, 2011, To Be Determined, Pending.
U.S. Appl. No. 13/989,366, filed May 23, 2011, To Be Determined, Pending.
U.S. Appl. No. 13/885,307, filed May 14, 2013, To Be Determined, Pending.
U.S. Appl. No. 13/885,323, filed May 14, 2013, To Be Determined, Pending.

BENZOXAZEPINES AS INHIBITORS OF PI3K/MTOR AND METHODS OF THEIR USE AND MANUFACTURE

CROSS-REFERENCE TO RELATED APPLICATIONS

This application claims the benefit of priority of U.S. provisional application 61/216,980, filed May 22, 2009, which is hereby incorporated by reference in its entirety.

BACKGROUND OF THE INVENTION

1. Field of the Invention

This invention relates to the field of protein kinases and inhibitors thereof. In particular, the invention relates to inhibitors of mammalian target of rapamycin (mTOR) signaling pathways, and methods of their use and preparation.

2. Background of the Invention

Phosphatidylinositol 3-kinase (PI3Kα), a dual specificity protein kinase, is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer (Campbell et al., *Cancer Res* 2004, 64, 7678-7681; Levine et al., *Clin Cancer Res* 2005, 11, 2875-2878; Wang et al., *Hum Mutat* 2005, 25, 322; Lee et al., *Gynecol Oncol* 2005, 97, 26-34), cervical cancer, breast cancer (Bachman, et al. *Cancer Biol Ther* 2004, 3, 772-775; Levine, et al., supra; Li et al., *Breast Cancer Res Treat* 2006, 96, 91-95; Saal et al., *Cancer Res* 2005, 65, 2554-2559; Samuels and Velculescu, *Cell Cycle* 2004, 3, 1221-1224), colorectal cancer (Samuels, et al. *Science* 2004, 304, 554; Velho et al. *Eur J Cancer* 2005, 41, 1649-1654), endometrial cancer (Oda et al. *Cancer Res.* 2005, 65, 10669-10673), gastric carcinomas (Byun et al., *Int J Cancer* 2003, 104, 318-327; Li et al., supra; Velho et al., supra; Lee et al., *Oncogene* 2005, 24, 1477-1480), hepatocellular carcinoma (Lee et al., id.), small and non-small cell lung cancer (Tang et al., *Lung Cancer* 2006, 51, 181-191; Massion et al., *Am J Respir Crit. Care Med* 2004, 170, 1088-1094), thyroid carcinoma (Wu et al., *J Clin Endocrinol Metab* 2005, 90, 4688-4693), acute myelogenous leukemia (AML) (Sujobert et al., *Blood* 1997, 106, 1063-1066), chronic myelogenous leukemia (CML) (Hickey and Cotter *J Biol Chem* 2006, 281, 2441-2450), and glioblastomas (Hartmann et al. *Acta Neuropathol (Berl)* 2005, 109, 639-642; Samuels et al., supra).

The mammalian target, mTOR is a protein kinase that integrates both extracellular and intracellular signals of cellular growth, proliferation, and survival. Extracellular mitogenic growth factor signaling from cell surface receptors and intracellular pathways that convey hypoxic stress, energy and nutrient status all converge at mTOR. mTOR exists in two distinct complexes: mTOR complex 1 (mTORC1) and mTOR complex 2 (mTORC2). mTORC1 is a key mediator of transcription and cell growth (via its substrates p70S6 kinase and 4E-BP1) and promotes cell survival via the serum and glucocorticoid-activated kinase SGK, whereas mTORC2 promotes activation of the pro-survival kinase AKT. Given its central role in cellular growth, proliferation and survival, it is perhaps not surprising that mTOR signaling is frequently dysregulated in cancer and other diseases (Bjornsti and Houghton *Rev Cancer* 2004, 4(5), 335-48; Houghton and Huang *Microbiol Immunol* 2004, 279, 339-59; Inoki, Corradetti et al. *Nat Genet* 2005, 37(1), 19-24).

mTOR is a member of the PIKK (PI3K-related Kinase) family of atypical kinases which includes ATM, ATR, and DNAPK, and its catalytic domain is homologous to that of PI3K. Dyregulation of PI3K signaling is a common function of tumor cells. In general, mTOR inhibition may be considered as a strategy in many of the tumor types in which PI3K signaling is implicated such as those discussed below.

Inhibitors of mTOR may be useful in treating a number of cancers, including the following: breast cancer (Nagata, Lan et al., *Cancer Cell* 2004, 6(2), 117-27; Pandolfi *N Engl J Med* 2004, 351(22), 2337-8; Nahta, Yu et al. *Nat Clin Pract Oncol* 2006, 3(5), 269-280); antle cell lymphoma (MCL) (Dal Col, Zancai et al. *Blood* 2008, 111(10), 5142-51); renal cell carcinoma (Thomas, Tran et al. *Nat Med* 2006, 12(1), 122-7; Atkins, Hidalgo et al. *J Clin Oncol* 2004, 22(5), 909-18; Motzer, Hudes et al. *J Clin Oncol* 2007, 25(25), 3958-64); acute myelogenous leukemia (AML) (Sujobert, Bardet et al. *Blood* 2005, 106(3), 1063-6; Billottet, Grandage et al. *Oncogene* 2006, 25(50), 6648-6659; Tamburini, Elie et al. *Blood* 2007, 110(3), 1025-8); chronic myelogenous leukemia (CML) (Skorski, Bellacosa et al. *Embo J* 1997, 16(20), 6151-61; Bai, Ouyang et al. *Blood* 2000, 96(13), 4319-27; Hickey and Cotter *Biol Chem* 2006, 281(5), 2441-50); diffuse large B cell lymphoma (DLBCL) (Uddin, Hussain et al. *Blood* 2006, 108(13), 4178-86); several subtypes of sarcoma (Hernando, Charytonowicz et al. *Nat Med* 2007, 13(6), 748-53; Wan and Helman *Oncologist* 2007, 12(8), 1007-18); rhabdomyosarcoma (Cao, Yu et al. *Cancer Res* 2008, 68(19), 8039-8048; Wan, Shen et al. *Neoplasia* 2006, 8(5), 394-401); ovarian cancer (Shayesteh, Lu et al. *Nat Genet,* 1999, 21(1), 99-102; (Lee, Choi et al. *Gynecol Oncol* 2005, 97(1) 26-34); endometrial tumors (Obata, Morland et al. *Cancer Res* 1998, 58(10), 2095-7; Lu, Wu et al. *Clin Cancer Res* 2008, 14(9), 2543-50); non small cell lung carcinoma (NSCLC) (Tang, He et al. *Lung Cancer* 2006, 51(2), 181-91; Marsit, Zheng et al. *Hum Pathol* 2005, 36(7), 768-76); small cell, squamous, large cell and adenocarcinoma (Massion, Taflan et al. *Am J Respir Crit. Care Med* 2004, 170(10), 1088-94); lung tumors in general (Kokubo, Gemma et al. *Br J Cancer* 2005, 92(9), 1711-9; Pao, Wang et al. *Pub Library of Science Med* 2005, 2(1), e17); colorectal tumors (Velho, Oliveira et al. *Eur J Cancer* 2005, 41(11), 1649-54; Foukas, Claret et al. *Nature,* 2006, 441 (7091), 366-370), particularly those that display microsatellite instability (Goel, Arnold et al. *Cancer Res* 2004, 64(9), 3014-21; Nassif, Lobo et al. *Oncogene* 2004, 23(2), 617-28), KRAS-mutated colorectal tumors (Bos *Cancer Res* 1989. 49(17), 4682-9; Fearon *Ann NY Acad Sci* 1995, 768, 101-10); gastric carcinomas (Byun, Cho et al. *Int J Cancer* 2003, 104(3), 318-27); hepatocellular tumors (Lee, Soung et al. *Oncogene* 2005, 24(8), 1477-80); liver tumors (Hu, Huang et al. *Cancer* 2003, 97(8), 1929-40; Wan, Jiang et al. *Cancer Res Clin Oncol* 2003, 129(2), 100-6); primary melanomas and associated increased tumor thickness (Guldberg, thor Straten et al. *Cancer Res* 1997, 57(17), 3660-3; Tsao, Zhang et al. *Cancer Res* 2000, 60(7), 1800-4; Whiteman, Zhou et al. *Int J Cancer* 2002, 99(1), 63-7; Goel, Lazar et al. *J Invest Dermatol* 126(1), 2006, 154-60); pancreatic tumors (Asano, Yao et al. *Oncogene* 2004, 23(53), 8571-80); prostate carcinoma (Cairns, Okami et al. *Cancer Res* 1997, 57(22), 4997-5000; Gray, Stewart et al. *Br J Cancer* 1998, 78(10), 1296-300; Wang, Parsons et al. *Clin Cancer Res* 1998, 4(3), 811-5; Whang, Wu et al. *Proc Natl Acad Sci USA* 1998, 95(9), 5246-50; Majumder and Sellers *Oncogene* 2005, 24(50) 7465-74; Wang, Garcia et al. *Proc Natl Acad Sci USA* 2006, 103(5), 1480-5; (Lu, Ren et al. *Int J Oncol* 2006, 28(1), 245-51; Mulholland, Dedhar et al. *Oncogene* 25(3), 2006, 329-37; Xin, Teitell et al. *Proc Natl Acad Sci USA* 12006, 03(20), 7789-94; Mikhailova, Wang et al. *Adv Exp Med Biol* 2008, 617, 397-405; Wang, Mikhailova et al. *Oncogene* 2008, 27(56), 7106-7117); thyroid carcinoma, particularly in the anaplastic subtype (Garcia-Rostan, Costa et al. *Cancer Res* 2005, 65(22), 10199-207); follicular thyroid carcinoma (Wu, Mambo et al. *J Clin Endocrinol Metab* 2005, 90(8), 4688-93); anaplastic large cell lymphoma (ALCL); hamaratomas, angiomyelolipomas, TSC-associated and sporadic lymphangioleiomyomatosis: Cowden's disease (multiple hamaratoma syndrome) (Bissler, McCormack et al. *N Engl J Med* 2008, 358(2), 140-151); sclerosing hemangioma (Randa M. S. Amin *Pathology International* 2008, 58(1), 38-44); Peutz-Jeghers syndrome (PJS); head and neck cancer (Gupta, McKenna et al. *Clin Cancer Res* 2002, 8(3), 885-892); neurofibromatosis (Ferner *Eur J Hum Genet* 2006, 15(2), 131-138; Sabatini *Nat Rev Cancer* 2006, 6(9), 729-734; Johannessen, Johnson et al. *Current Biology* 2008, 18(1), 56-62); macular degeneration; macular edema; myeloid leukemia; systemic lupus; and autoimmune lymphoproliferative syndrome (ALPS).

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

We recognized the important role of PI3K and mTOR in biological processes and disease states and, therefore, realized that inhibitors of these protein kinases would be desirable. Accordingly, the invention provides compounds that inhibit, regulate, and/or modulate PI3K and/or mTOR and are useful in the treatment of hyperproliferative diseases, such as cancer, in mammals. This invention also provides methods of making the compound, methods of using such compounds in the treatment of hyperproliferative diseases in mammals, especially humans, and to pharmaceutical compositions containing such compounds.

A first aspect of the invention provides a Compound of Formula I:

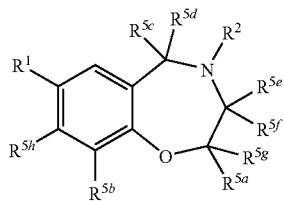

I or a single stereoisomer or mixture of stereoisomers thereof and additionally optionally as a pharmaceutically acceptable salt thereof, where $R^1$ is phenyl optionally substituted with one, two, or three $R^6$ groups; or $R^1$ is heteroaryl optionally substituted with one, two, or three $R^7$;

$R^2$ is heteroaryl substituted with $R^3$, $R^{3a}$, $R^{3b}$, $R^{3c}$, and $R^{3d}$;

$R^3$, $R^{3a}$, $R^{3b}$, $R^{3c}$, and $R^{3d}$ are independently hydrogen, cyano, alkyl, alkenyl, halo, haloalkyl, hydroxyalkyl, alkoxyalkyl, cyanoalkyl, —$SR^{12}$, —$S(O)_2R^{20}$, —C(O)$OR^4$, halocarbonyl, —$NR^{11}R^{11a}$, —$OR^{11a}$, optionally substituted phenyl, optionally substituted phenylalkyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, or alkyl substituted with one or two $R^{16}$; or two of $R^3$, $R^{3a}$, $R^{3b}$, $R^{3c}$, and $R^{3d}$, when attached to the same carbon, form an optionally substituted cycloalkyl or an optionally substituted heterocycloalkyl; and the other of $R^3$, $R^{3a}$, $R^{3b}$, $R^{3c}$, and $R^{3d}$ are independently hydrogen, cyano, alkyl, alkenyl, halo, haloalkyl, hydroxyalkyl, alkoxyalkyl, cyanoalkyl, —$SR^{12}$, —$S(O)_2R^{20}$, —C(O)$OR^4$, halocarbonyl, —$NR^{11}R^{11a}$, —$OR^{11a}$, optionally substituted phenyl, optionally substituted phenylalkyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, or alkyl substituted with one or two $R^{16}$;

$R^4$ is alkyl, alkenyl, alkynyl, hydroxyalkyl, alkoxyalkyl, haloalkyl, benzyl, or optionally substituted heterocycloalkylalkyl;

$R^{5a}$ and $R^{5c}$ are independently hydrogen or alkyl;

$R^{5h}$ is hydrogen or halo;

$R^{5b}$ is hydrogen, amino, or halo;

$R^{5d}$, $R^{5e}$, $R^{5f}$, and $R^{5g}$ are hydrogen;

each $R^6$, when $R^6$ is present, is independently nitro; cyano; halo; alkyl; alkenyl; alkynyl; haloalkyl; —$OR^{8a}$; —$NR^8R^{8a}$; —$C(O)NR^8R^{8a}$; —$S(O)_2R^8$; —$NR^8C(O)OR^9$; —$NR^8C(O)R^9$; —$NR^8S(O)_2R^{8a}$; —$NR^8C(O)NR^{8a}R^9$; carboxy; —$C(O)OR^9$; halocarbonyl; alkylcarbonyl; alkyl substituted with one or two —$C(O)NR^8R^{8a}$; heteroaryl optionally substituted with 1, 2, or 3 $R^{14}$; or optionally substituted heterocycloalkyl;

each $R^7$, when $R^7$ is present, is independently oxo; nitro; cyano; alkyl; alkenyl; alkynyl; halo; haloalkyl; hydroxyalkyl; alkoxyalkyl; —$OR^{8a}$; —$SR^{13}$; —$S(O)R^{13}$; —$S(O)_2R^{13a}$; —$NR^8R^{8a}$; —$C(O)NR^8R^{8a}$; —$NR^8C(O)OR^9$; —$NR^8C(O)R^9$; —$NR^8S(O)_2R^{8a}$; —$NR^8C(O)NR^{8a}R^9$; —$C(O)OR^9$; halocarbonyl; alkylcarbonyl; —$S(O)_2NR^8R^9$; alkylsulfonylalkyl; alkyl substituted with one or two —$NR^8R^{8a}$; alkyl substituted with one or two —$NR^8C(O)OR^{8a}$; alkyl substituted with one or two —$NR^8C(O)OR^9$; alkyl substituted with one or two —$S(O)_2R^{13a}$; optionally substituted cycloalkyl; optionally substituted cycloalkylalkyl; optionally substituted heterocycloalkyl; optionally substituted heterocycloalkylalkyl; optionally substituted phenyl; optionally substituted phenylalkyl; optionally substituted heteroaryl; or optionally substituted heteroarylalkyl;

each $R^8$, $R^{11}$, $R^{15}$, $R^{17}$, and $R^{18}$ are independently hydrogen, alkyl, alkenyl, alkynyl, hydroxyalkyl, alkoxyalkyl, or haloalkyl;

each $R^{8a}$, $R^{11a}$, and $R^{15a}$ are independently hydrogen, alkyl, alkenyl, alkynyl, haloalkyl, hydroxyalkyl, cyanoalkyl, aminoalkyl, alkylaminoalkyl, dialkylaminoalkyl, alkoxyalkyl, carboxyalkyl, optionally substituted cycloalkyl, optionally substituted cycloalkylalkyl, optionally substituted heterocycloalkyl, optionally substituted heterocycloalkylalkyl, optionally substituted phenyl, optionally substituted phenylalkyl, optionally substituted heteroaryl, or optionally substituted heteroarylalkyl;

$R^9$ is hydrogen; alkyl; alkenyl; alkynyl; hydroxyalkyl; alkoxyalkyl; aminoalkyl; alkylaminoalkyl; dialkylaminoalkyl; haloalkyl; hydroxyalkyl substituted with one, two, or three groups which are independently halo, amino, alkylamino, or dialkylamino; alkyl substituted with one or two aminocarbonyl; optionally substituted phenyl; optionally substituted phenylalkyl; optionally substituted cycloalkyl; optionally substituted cycloalkylalkyl; optionally substituted heteroaryl; optionally substituted heteroarylalkyl; optionally substituted heterocycloalkyl; or optionally substituted heterocycloalkylalkyl;

$R^{12}$ is alkyl or optionally substituted phenylalkyl;

$R^{13}$ is alkyl, hydroxyalkyl, or haloalkyl; and $R^{13a}$ is hydroxy, alkyl, haloalkyl, hydroxyalkyl, or heterocycloalkyl optionally substituted with one or two groups which are independently halo, amino, alkylamino, dialkylamino, hydroxy, alkyl, or hydroxyalkyl;

each $R^{14}$, when $R^{14}$ is present, is independently amino, alkylamino, dialkylamino, acylamino, halo, hydroxy, alkyl, haloalkyl, hydroxyalkyl, aminoalkyl, alkylaminoalkyl, dialkylaminoalkyl, alkoxycarbonyl, aminocarbonyl, alkylaminocarbonyl, dialkylaminocarbonyl, or optionally substituted phenyl;

each $R^{16}$ is independently $-NR^{11}R^{11a}$, $-NR^{15}S(O)R^{15a}$, $-OC(O)R^{17}$, or $-OR^{18}$; and $R^{20}$ is alkyl, haloalkyl, hydroxyalkyl, amino, alkylamino, dialkylamino, or heterocycloalkyl.

In a second aspect, the invention is directed to a pharmaceutical composition which comprises 1) a Compound of Formula I or a single stereoisomer or mixture of stereoisomers thereof, optionally as a pharmaceutically acceptable salt or solvate thereof and 2) a pharmaceutically acceptable carrier, excipient, or diluent.

In a third aspect of the invention is a method of inhibiting the in vivo activity of PI3K and/or mTOR, the method comprising administering to a patient an effective PI3K-inhibiting and/or mTOR-inhibiting amount of a Compound of Formula I a Compound of Formula I or a single stereoisomer or mixture of stereoisomers thereof, optionally as a pharmaceutically acceptable salt or solvate thereof or pharmaceutical composition thereof.

In a fourth aspect, the Invention provides a method for treating a disease, disorder, or syndrome which method comprises administering to a patient a therapeutically effective amount of a Compound of Formula I or a single stereoisomer or mixture of stereoisomers thereof, optionally as a pharmaceutically acceptable salt or solvate thereof, or a pharmaceutical composition comprising a therapeutically effective amount of a Compound of Formula I or a single stereoisomer or mixture of stereoisomers thereof, optionally as a pharmaceutically acceptable salt or solvate thereof, and a pharmaceutically acceptable carrier, excipient, or diluent.

In a fifth aspect, the Invention provides a method for making a Compound of Formula I(a) which method comprises (a) reacting the following, or a salt thereof:

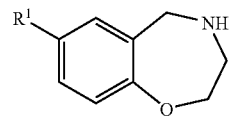

where $R^1$ is as defined in the Summary of the Invention for a Compound of Formula I; with an intermediate of Formula $R^2X$ where X is halo, and $R^2$ is as defined in the Summary of the Invention for a Compound of Formula I to yield a Compound of the Invention of Formula I(a)

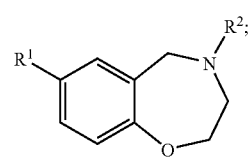

I(a)

and optionally separating individual isomers; and optionally modifying any of the $R^1$ and $R^2$ groups; and optionally forming a pharmaceutically acceptable salt thereof; or (b) reacting the following, or a salt thereof:

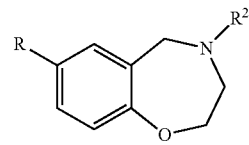

where R is halo or $-B(OR')_2$ (where both R' are hydrogen or the two R' together form a boronic ester), and $R^2$ is as defined in the Summary of the Invention for a Compound of Formula I; with an intermediate of Formula $R^1Y$ where Y is halo when R is $-B(OR')_2$ and Y is $-B(OR')_2$ when R is halo, and $R^2$ is as defined in the Summary of the Invention for a Compound of Formula I to yield a Compound of the Invention of Formula I(a); and optionally separating individual isomers; and optionally modifying any of the $R^1$ and $R^2$ groups; and optionally forming a pharmaceutically acceptable salt, hydrate, solvate or combination thereof.

DETAILED DESCRIPTION OF THE INVENTION

Abbreviations and Definitions

The following abbreviations and terms have the indicated meanings throughout:

| Abbreviation | Meaning |
| --- | --- |
| br | broad |
| ° C. | degrees Celsius |
| d | doublet |
| dd | doublet of doublet |
| dt | doublet of triplet |
| DCM | dichloromethane |
| DIEA or DIPEA | N,N-di-isopropyl-N-ethylamine |
| DMA | N,N-dimethylacetamide |
| DME | 1,2-dimethoxyethane |
| DMF | N,N-dimethylformamide |
| DMSO | dimethyl sulfoxide |

| Abbreviation | Meaning |
| --- | --- |
| dppf | 1,1'-bis(diphenylphosphano)ferrocene |
| EI | Electron Impact ionization |
| g | gram(s) |
| GC/MS | gas chromatography/mass spectrometry |
| h or hr | hour(s) |
| HPLC | high pressure liquid chromatography |
| L | liter(s) |
| LC/MS | liquid chromatography/mass spectrometry |
| M | molar or molarity |
| m | Multiplet |
| MeOH | methanol |
| mg | milligram(s) |
| MHz | megahertz (frequency) |
| min | minute(s) |
| mL | milliliter(s) |
| μL | microliter(s) |
| μM | micromolar |
| μmol | micromole(s) |
| mM | Millimolar |
| mmol | millimole(s) |
| mol | mole(s) |
| MS | mass spectral analysis |
| N | normal or normality |
| nM | nanomolar |
| NMP | N-methyl-2-pyrrolidone |
| NMR | nuclear magnetic resonance spectroscopy |
| q | Quartet |
| rt | Room temperature |
| s | Singlet |
| t or tr | Triplet |
| THF | tetrahydrofuran |

The symbol "—" means a single bond, "=" means a double bond, "≡" means a triple bond, "⸺" means a single or double bond. The symbol "∿" refers to a group on a double-bond as occupying either position on the terminus of a double bond to which the symbol is attached; that is, the geometry, E- or Z-, of the double bond is ambiguous. When a group is depicted removed from its parent Formula, the "∿" symbol will be used at the end of the bond which was theoretically cleaved in order to separate the group from its parent structural Formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual Formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

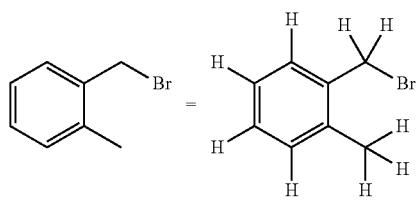

If a group "R" is depicted as "floating" on a ring system, as for example in the Formula:

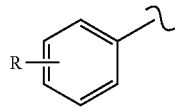

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the Formula e:

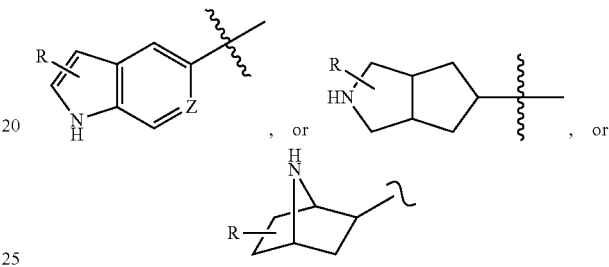

then, unless otherwise defined, a substituent "R" may reside on any atom of the fused ring system, assuming replacement of a depicted hydrogen (for example the —NH— in the Formula above), implied hydrogen (for example as in the Formula above, where the hydrogens are not shown but understood to be present), or expressly defined hydrogen (for example where in the Formula above, "Z" equals =CH—) from one of the ring atoms, so long as a stable structure is formed. In the example depicted, the "R" group may reside on either the 5-membered or the 6-membered ring of the fused ring system.

When a group "R" is depicted as existing on a ring system containing saturated carbons, as for example in the Formula:

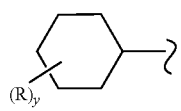

where, in this example, "y" can be more than one, assuming each replaces a currently depicted, implied, or expressly defined hydrogen on the ring; then, unless otherwise defined, where the resulting structure is stable, two "R's" may reside on the same carbon. In another example, two R's on the same carbon, including that carbon, may form a ring, thus creating a spirocyclic ring structure with the depicted ring as for example in the Formula:

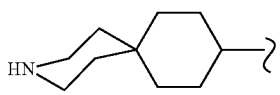

"Acyl" means a —C(O)R radical where R is alkyl, alkenyl, cycloalkyl, cycloalkylalkyl, aryl, aralkyl, heteroaryl, heteroaralkyl, heterocycloalkyl, or heterocycloalkylalkyl, as defined herein, e.g., acetyl, trifluoromethylcarbonyl, or 2-methoxyethylcarbonyl, and the like.

"Acylamino" means a —NRR' radical where R is hydrogen, hydroxy, alkyl, or alkoxy and R' is acyl, as defined herein.

"Acyloxy" means an —OR radical where R is acyl, as defined herein, e.g. cyanomethylcarbonyloxy, and the like.

"Administration" and variants thereof (e.g., "administering" a compound) in reference to a Compound of the invention means introducing the Compound or a prodrug of the Compound into the system of the animal in need of treatment. When a Compound of the invention or prodrug thereof is provided in combination with one or more other active agents (e.g., surgery, radiation, and chemotherapy, etc.), "administration" and its variants are each understood to include concurrent and sequential introduction of the Compound or prodrug thereof and other agents.

"Alkenyl" means a means a linear monovalent hydrocarbon radical of two to six carbon atoms or a branched monovalent hydrocarbon radical of three to six carbon atoms which radical contains at least one double bond, e.g., ethenyl, propenyl, 1-but-3-enyl, and 1-pent-3-enyl, and the like.

"Alkoxy" means an —OR group where R is alkyl group as defined herein. Examples include methoxy, ethoxy, propoxy, isopropoxy, and the like.

"Alkoxyalkyl" means an alkyl group, as defined herein, substituted with at least one, specifically one, two, or three, alkoxy groups as defined herein. Representative examples include methoxymethyl and the like.

"Alkoxycarbonyl" means a —C(O)R group where R is alkoxy, as defined herein.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), or pentyl (including all isomeric forms), and the like.

"Alkylamino" means an —NHR group where R is alkyl, as defined herein.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a —C(O)R group where R is alkyl, as defined herein.

"Alkylsulfonyl" means an —S(O)$_2$R group where R is alkyl, as defined herein.

"Alkylsulfonylalkyl" means an alkyl group, as defined herein, substituted with one or two —S(O)$_2$R group where R is alkyl, as defined herein.

"Alkynyl" means a linear monovalent hydrocarbon radical of two to six carbon atoms or a branched monovalent hydrocarbon radical of three to 6 carbon atoms which radical contains at least one triple bond, e.g., ethynyl, propynyl, butynyl, pentyn-2-yl and the like.

"Amino" means —NH$_2$.

"Aminoalkyl" means an alkyl group substituted with at least one, specifically one, two or three, amino groups.

"Aminoalkyloxy" means an —OR group where R is aminoalkyl, as defined herein.

"Aminocarbonyl" means a —C(O)NH$_2$ group.

"Alkylaminocarbonyl" means a —C(O)NHR group where R is alkyl as defined herein.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylalkyl" means an alkyl radical, as defined herein, substituted with one or two aryl groups, as defined herein, e.g., benzyl and phenethyl, and the like.

"Cyanoalkyl" means an alkyl group, as defined herein, substituted with one or two cyano groups.

"Cycloalkyl" means a monocyclic or fused bicyclic, saturated or partially unsaturated (but not aromatic), monovalent hydrocarbon radical of three to ten carbon ring atoms. Fused bicyclic hydrocarbon radical includes spiro and bridged ring systems. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, or cyclohex-3-enyl, and the like.

"Cycloalkylalkyl" means an alkyl group substituted with at least one, specifically one or two, cycloalkyl group(s) as defined herein.

"Dialkylamino" means an —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminoalkyloxy" means an —OR group where R is dialkylaminoalkyl, as defined herein. Representative examples include 2-(N,N-diethylamino)-ethyloxy, and the like.

"Dialkylaminocarbonyl" means a —C(O)NRR' group where R and R' are alkyl as defined herein.

"Fused ring system" means a polycyclic ring system that contains bridged or fused rings; that is, where two rings have more than one shared atom in their ring structures. In this application, fused ring systems are not necessarily all aromatic ring systems. Typically, but not necessarily, fused ring systems share a vicinal set of atoms, for example naphthalene or 1,2,3,4-tetrahydro-naphthalene. Fused ring systems of the invention may themselves have spiro rings attached thereto via a single ring atom of the fused ring system. In some examples, as appreciated by one of ordinary skill in the art, two adjacent groups on an aromatic system may be fused together to form a ring structure. The fused ring structure may contain heteroatoms and may be optionally substituted with one or more groups.

"Halogen" or "halo" refers to fluorine, chlorine, bromine and iodine.

"Haloalkoxy" means an —OR' group where R' is haloalkyl as defined herein, e.g., trifluoromethoxy or 2,2,2-trifluoroethoxy, and the like.

"Haloalkyl" mean an alkyl group substituted with one or more halogens, specifically 1, 2, 3, 4, 5, or 6 halo atoms, e.g., trifluoromethyl, 2-chloroethyl, and 2,2-difluoroethyl, and the like.

"Halocarbonyl" means a —C(O)X group where X is halo.

"Heteroaryl" means a monocyclic or fused bicyclic or tricyclic monovalent radical of 5 to 14 ring atoms containing one or more, specifically one, two, three, or four ring heteroatoms where each heteroatom is independently —O—, —S(O)$_n$— (n is 0, 1, or 2), —N=, —NH—, or N-oxide, with the remaining ring atoms being carbon, wherein the ring comprising a monocyclic radical is aromatic and wherein at least one of the fused rings comprising the bicyclic radical is aromatic. One or two ring carbon atoms of any nonaromatic rings comprising a bicyclic radical may be replaced by a —C(O)—, —C(S)—, or —C(=NH)— group. Fused bicyclic radical includes bridged ring systems. Unless stated otherwise, the valency may be located on any atom of any ring of the heteroaryl group, valency rules permitting. When the point of valency is located on the nitrogen, $R^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, 5,6,7,8-tetrahydroquinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, 5,6,7,8-tetrahydroquinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, 2,3-dihydrobenzofuranyl, benzo[d][1,3]dioxolyl, 2,3-dihydrobenzo[b][1,4]dioxinyl, thiazolyl, isothiazolyl, thiadiazolyl, benzothiazolyl, benzothienyl, 6,7-dihydro-5H-cyclopenta[b]pyridinyl, 6,7-dihydro-5H-cyclopenta[c]pyridinyl, 6,7-dihydro-5H-cyclopenta[d]pyrimidinyl, 5,6,7,8-tetrahydro-5,8-ethanoquinazolin-4-yl, and 6,7,8,9-tetrahydropyrimido[4,5-b]indolizin-4-yl, and the N-oxide thereof and a protected derivative thereof.

"Heteroarylalkyl" means an alkyl group, as defined herein, substituted with at least one, specifically one or two heteroaryl group(s), as defined herein.

"Heterocycloalkyl" means a saturated or partially unsaturated (but not aromatic) monovalent monocyclic group of 3 to 8 ring atoms or a saturated or partially unsaturated (but not aromatic) monovalent fused or spirocyclic bicyclic group of 5 to 12 ring atoms in which one or more, specifically one, two, three, or four ring heteroatoms where each heteroatom is independently O, $S(O)_n$ (n is 0, 1, or 2), —NH—, or —N=, the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. When the point of valency is located on a nitrogen atom, $R^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydrocyclopenta[c]pyrrolyl, octahydroindolyl, octahydroisoindolyl, decahydroisoquinolyl, 2,6-diazaspiro[3.3]heptan-2-yl, tetrahydrofuryl, and tetrahydropyranyl, and the derivatives thereof and N-oxide or a protected derivative thereof.

"Heterocycloalkylalkyl" means an alkyl radical, as defined herein, substituted with one or two heterocycloalkyl groups, as defined herein, e.g., morpholinylmethyl, N-pyrrolidinylethyl, and 3-(N-azetidinyl)propyl, and the like.

"Hydroxyalkyl" means an alkyl group, as defined herein, substituted with at least one, particularly, 1, 2, 3, or 4, hydroxy groups.

"Phenylalkyl" means an alkyl group, as defined herein, substituted with one or two phenyl groups.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise. A list of exemplary optional substitutions is presented below in the definition of "substituted."

"Optionally substituted aryl" means an aryl group, as defined herein, optionally substituted with one, two, three, or four substituents where the substituents are independently acyl, acylamino, acyloxy, alkyl, haloalkyl, hydroxyalkyl, alkoxyalkyl, aminoalkyl, alkylaminoalkyl, dialkylaminoalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy; or aryl is pentafluorophenyl. Within the optional substituents on "aryl", the alkyl and alkenyl, either alone or as part of another group (including, for example, the alkyl in alkoxycarbonyl), are independently optionally substituted with one, two, three, four, or five halo (e.g. alkoxycarbonyl includes trifluoromethyloxycarbonyl).

"Optionally substituted arylalkyl" means an alkyl group, as defined herein, substituted with optionally substituted aryl, as defined herein.

"Optionally substituted cycloalkyl" means a cycloalkyl group, as defined herein, substituted with one, two, or three groups where the groups are independently acyl, acyloxy, acylamino, alkyl, haloalkyl, hydroxyalkyl, alkoxyalkyl, aminoalkyl, alkylaminoalkyl, dialkylaminoalkyl, alkenyl, alkoxy, alkenyloxy, alkoxycarbonyl, alkenyloxycarbonyl, alkylthio, alkylsulfinyl, alkylsulfonyl, aminosulfonyl, alkylaminosulfonyl, dialkylaminosulfonyl, alkylsulfonylamino, halo, hydroxy, amino, alkylamino, dialkylamino, aminocarbonyl, alkylaminocarbonyl, dialkylaminocarbonyl, nitro, alkoxyalkyloxy, aminoalkoxy, alkylaminoalkoxy, dialkylaminoalkoxy, carboxy, or cyano. Within the above optional substitutents on "cycloalkyl", the alkyl and alkenyl, either alone or as part of another substituent on the cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl group substituted with at least one, specifically one or two, optionally substituted cycloalkyl groups, as defined herein.

"Optionally substituted heteroaryl" means a heteroaryl group optionally substituted with one, two, three, or four substituents where the substituents are independently acyl, acylamino, acyloxy, alkyl, haloalkyl, hydroxyalkyl, alkoxyalkyl, aminoalkyl, alkylaminoalkyl, dialkylaminoalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, alkylaminoalkoxy, or dialkylaminoalkoxy. Within the optional substituents on "heteroaryl", the alkyl and alkenyl, either alone or as part of another group (including, for example, the alkyl in alkoxycarbonyl), are independently optionally substituted with one, two, three, four, or five halo (e.g. alkoxycarbonyl includes trifluoromethyloxycarbonyl).

"Optionally substituted heteroarylalkyl" means an alkyl group, as defined herein, substituted with at least one, specifically one or two, optionally substituted heteroaryl group(s), as defined herein.

"Optionally substituted heterocycloalkyl" means a heterocycloalkyl group, as defined herein, optionally substituted with one, two, three, or four substituents where the substituents are independently acyl, acylamino, acyloxy, alkyl, haloalkyl, hydroxyalkyl, alkoxyalkyl, aminoalkyl, alkylaminoalkyl, dialkylaminoalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or phenylalkyl. Within the optional substituents on "heterocycloalkyl", the alkyl and alkenyl, either alone or as part of another group (including, for example, the alkyl in alkoxycarbonyl), are independently optionally substituted with one, two, three, four, or five halo (e.g. alkoxycarbonyl includes trifluoromethyloxycarbonyl).

"Optionally substituted heterocycloalkylalkyl" means an alkyl group, as defined herein, substituted with at least one, specifically one or two, optionally substituted heterocycloalkyl group(s) as defined herein.

"Optionally substituted phenyl" means a phenyl group optionally substituted with one, two, or three substituents where the substituents are independently acyl, acylamino, acyloxy, alkyl, haloalkyl, hydroxyalkyl, alkoxyalkyl, aminoalkyl, alkylaminoalkyl, dialkylaminoalkyl, alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, or aminoalkoxy. "Optionally substituted phenyl" in addition includes pentafluorophenyl. Within the optional substituents on "phenyl", the alkyl and alkenyl, either alone or as part of another group (including, for example, the alkyl in alkoxycarbonyl), are independently optionally substituted with one, two, three, four, or five halo (e.g. alkoxycarbonyl includes trifluoromethyloxycarbonyl).

"Optionally substituted phenylalkyl" means an alkyl group, as defined herein, substituted with one or two optionally substituted phenyl groups, as defined herein.

"Oxo" means an oxygen which is attached via a double bond.

"Yield" for each of the reactions described herein is expressed as a percentage of the theoretical yield.

"Metabolite" refers to the break-down or end product of a Compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a Compound of the invention or its salt may be the biologically active form of the Compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a Compound of the present invention is known to one of skill in the art in light of the present disclosure.

"Patient" for the purposes of the present invention includes humans and other animals, particularly mammals, and other organisms. Thus the methods are applicable to both human therapy and veterinary applications. In a specific embodiment the patient is a mammal, and in a more specific embodiment the patient is human.

A "pharmaceutically acceptable salt" of a Compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent Compound is replaced by a metal ion, such as sodium, potassium, lithium, ammonium, calcium, magnesium, iron, zinc, copper, manganese, aluminum salts and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine. "Platin(s)," and "platin-containing agent(s)" include, for example, cisplatin, carboplatin, and oxaliplatin.

"Prodrug" refers to compounds that are transformed (typically rapidly) in vivo to yield the parent Compound of the above Formula e, for example, by hydrolysis in blood. Common examples include, but are not limited to, ester and amide forms of a Compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a Compound of the invention, that when administered to a patient, ameliorates a symptom of the disease. The amount of a Compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Preventing" or "prevention" of a disease, disorder, or syndrome includes inhibiting the disease from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

"Treating" or "treatment" of a disease, disorder, or syndrome, as used herein, includes (i) inhibiting the disease, disorder, or syndrome, i.e., arresting its development; and (ii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Embodiments of the Invention

The following paragraphs present a number of embodiments of compounds of the invention. In each instance the embodiment includes both the recited compounds, as well as a single stereoisomer or mixture of stereoisomers thereof, as well as a pharmaceutically acceptable salt thereof.

Embodiments (A1)

In one embodiment, the Compound of Formula I is that where $R^{5a}$ is hydrogen or alkyl and $R^{5c}$, $R^{5d}$, $R^{5e}$, $R^{5f}$, and $R^{5g}$ are hydrogen; and all other groups are independently as defined in the Summary of the Invention for a Compound of Formula I. In another embodiment, the Compound of Formula I is that where $R^{5a}$ is alkyl and $R^{5c}$, $R^{5d}$, $R^{5e}$, $R^{5f}$, and $R^{5g}$ are hydrogen; and all other groups are independently as defined in the Summary of the Invention for a Compound of Formula I.

Embodiments (A2)

In another embodiment, the Compound of Formula I is that where $R^{5b}$ is hydrogen, amino, or halo and $R^{5a}$, $R^{5c}$, $R^{5d}$, $R^{5e}$, $R^{5f}$, $R^{5g}$, and $R^{5h}$ are hydrogen; and all other groups are independently as defined in the Summary of the Invention for a Compound of Formula I. In another embodiment, the Compound of Formula I is that where $R^{5b}$ is halo and $R^{5a}$, $R^{5c}$, $R^{5d}$, $R^{5e}$, $R^{5f}$, $R^{5g}$, and $R^{5h}$ are hydrogen; and all other groups are independently as defined in the Summary of the Invention for a Compound of Formula I. In another embodiment, the Compound of Formula I is that where $R^{5b}$ is fluoro and $R^{5a}$, $R^{5c}$, $R^{5d}$, $R^{5e}$, $R^{5f}$, $R^{5g}$, and $R^{5h}$ are hydrogen; and all other groups are independently as defined in the Summary of the Invention for a Compound of Formula I. In another embodiment, the Compound of Formula I is that where $R^{5b}$ is amino; $R^{5a}$, $R^{5c}$, $R^{5d}$, $R^{5e}$, $R^{5f}$, $R^{5g}$, and $R^{5h}$ are hydrogen; and all other groups are independently as defined in the Summary of the Invention for a Compound of Formula I.

Embodiments (A3)

In another embodiment, the Compound of Formula I is that where $R^{5c}$ is hydrogen or alkyl and $R^{5a}$, $R^{5d}$, $R^{5e}$, $R^{5f}$, and $R^{5g}$ are hydrogen; and all other groups are independently as defined in the Summary of the Invention for a Compound of Formula I. In another embodiment, the Compound of Formula I is that where $R^{5c}$ is alkyl and $R^{5a}$, $R^{5d}$, $R^{5e}$, $R^{5f}$, and $R^{5g}$ are hydrogen; and all other groups are independently as defined in the Summary of the Invention for a Compound of Formula I.

Embodiments (A4)

In another embodiment, the Compound of Formula I is that where $R^{5h}$ is hydrogen or halo and $R^{5a}$, $R^{5c}$, $R^{5d}$, $R^{5e}$, $R^{5f}$, $R^{5g}$, and $R^{5b}$ are hydrogen; and all other groups are independently as defined in the Summary of the Invention for a Compound of Formula I. In another embodiment, the Compound of Formula I is that where $R^{5h}$ is halo and $R^{5a}$, $R^{5c}$, $R^{5d}$, $R^{5e}$, $R^{5f}$, $R^{5g}$, and $R^{5b}$ are hydrogen; and all other groups are independently as defined in the Summary of the Invention for a Compound of Formula I. In another embodiment, the Compound of Formula I is that where $R^{5h}$ is fluoro and $R^{5a}$, $R^{5c}$, $R^{5d}$, $R^{5e}$, $R^{5f}$, $R^{5g}$, and $R^{5b}$ are hydrogen; and all other groups are independently as defined in the Summary of the Invention for a Compound of Formula I.

Another embodiment of the Invention is directed to a Compound of Formula I(a)

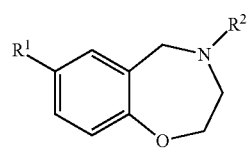

I(a)

where $R^1$ and $R^2$ are independently as defined in the Summary of the Invention for a Compound of Formula I.

Embodiment (1)

In another embodiment, the Compound of Formula I(a) is that where
$R^1$ is phenyl optionally substituted with one, two, or three $R^6$ groups; or
$R^1$ is heteroaryl optionally substituted with one, two, or three $R^7$;
$R^2$ is heteroaryl substituted with $R^3$, $R^{3a}$, $R^{3b}$, $R^{3c}$, and $R^{3d}$;

$R^3$, $R^{3a}$, $R^{3b}$, $R^{3c}$, and $R^{3d}$ are independently hydrogen; cyano; alkyl; alkenyl; halo; haloalkyl; hydroxyalkyl; alkoxyalkyl; cyanoalkyl; $SR^{12}$; —S(O)$_2$R$^{20}$; carboxy; alkoxycarbonyl; halocarbonyl; —NR$^{11}$R$^{11a}$; —OR$^{11a}$; phenyl optionally substituted with one or two groups which are independently alkyl or halo; phenylalkyl optionally substituted with one or two R$^{19}$; cycloalkyl; cycloalkylalkyl; heterocycloalkyl optionally substituted with one or two groups which are independently alkyl, alkoxycarbonyl, or benzyloxycarbonyl; heterocycloalkylalkyl optionally substituted with one or two groups which are independently alkyl, alkoxycarbonyl, or benzyloxycarbonyl; heteroaryl; heteroarylalkyl; or alkyl substituted with one or two R$^{16}$; or two of R$^3$, R$^{3a}$, R$^{3b}$, R$^{3c}$, and R$^{3d}$, when attached to the same carbon, form a cycloalkyl or a heterocycloalkyl; and the other of R$^3$, R$^{3a}$, R$^{3b}$, R$^{3c}$, and R$^{3d}$ are hydrogen;

each R$^6$, when R$^6$ is present, is independently nitro; cyano; halo; alkyl; halo; haloalkyl; —OR$^{8a}$; —NR$^8$R$^{8a}$; —C(O)NR$^8$R$^{8a}$; —S(O)$_2$R$^8$; —NR$^8$C(O)R$^9$; —NR$^8$S(O)$_2$R$^{8a}$; —NHC(O)NHR$^9$; carboxy, —C(O)OR$^9$; or heteroaryl optionally substituted with 1, 2, or 3 R$^{14}$;

each R$^7$, when R$^7$ is present, is independently oxo; nitro; cyano; alkyl; alkenyl; halo; haloalkyl; hydroxyalkyl; alkoxyalkyl; —OR$^{8a}$; —SR$^{13}$; —S(O)R$^{13}$; —S(O)$_2$R$^{13a}$; —NR$^8$R$^{8a}$; —C(O)NR$^8$R$^{8a}$; —NR$^8$C(O)OR$^9$; —NR$^8$C(O)R$^9$; —NR$^8$S(O)$_2$R$^{8a}$; —NR$^8$C(O)NR$^{8a}$R$^9$; —C(O)OR$^9$; halocarbonyl; —S(O)$_2$NR$^8$R$^9$; alkylsulfonylalkyl; alkyl substituted with one or two —NR$^8$R$^{8a}$; alkyl substituted with one or two —NR$^8$C(O)R$^{8a}$; alkyl substituted with one or two —NR$^8$C(O)OR$^9$; alkyl substituted with one or two —S(O)$_2$R$^{13a}$; cycloalkyl; cycloalkylalkyl; heterocycloalkyl optionally substituted with one or two groups which are independently alkyl or amino; phenyl; phenylalkyl; heterocycloalkylalkyl; heteroaryl; or heteroarylalkyl;

R$^8$, R$^{11}$, R$^{15}$, R$^{17}$, and R$^{18}$ are independently hydrogen, alkyl, alkenyl, alkynyl, hydroxyalkyl, alkoxyalkyl, or haloalkyl;

R$^{8a}$; R$^{11a}$; and R$^{15a}$ are independently hydrogen; alkyl; alkenyl; alkynyl; haloalkyl; hydroxyalkyl; cyanoalkyl; aminoalkyl; alkylaminoalkyl; dialkylaminoalkyl; alkoxyalkyl; carboxyalkyl; cycloalkyl; cycloalkylalkyl; heterocycloalkyl optionally substituted with one or two groups which are independently alkyl, alkoxycarbonyl, or benzyloxy; heterocycloalkylalkyl optionally substituted with one or two groups which are independently alkyl, alkoxycarbonyl, or benzyloxy; phenyl optionally substituted with one or two groups which are independently halo, alkyl, or alkoxy; phenylalkyl; heteroaryl; or heteroarylalkyl;

R$^9$ is hydrogen; alkyl; alkenyl; alkynyl; hydroxyalkyl; alkoxyalkyl; aminoalkyl; alkylaminoalkyl; dialkylaminoalkyl; haloalkyl; hydroxyalkyl substituted with one, two, or three groups which are independently halo, amino, alkylamino, or dialkylamino; alkyl substituted with one or two aminocarbonyl; phenyl; phenylalkyl; cycloalkyl; cycloalkylalkyl optionally substituted with one or two groups which are independently amino or alkyl; heterocycloalkyl optionally substituted with one or two groups which are independently alkyl, alkoxycarbonyl, or benzyloxy; or heterocycloalkylalkyl optionally substituted with one or two groups which are independently alkyl, alkoxycarbonyl, or benzyloxy;

R$^{12}$ is alkyl or phenylalkyl;

R$^{13}$ is alkyl, hydroxyalkyl, or haloalkyl; and

R$^{13a}$ is hydroxy, alkyl, haloalkyl, hydroxyalkyl, or heterocycloalkyl optionally substituted with one or two groups which are independently halo, amino, alkylamino, dialkylamino, hydroxy, alkyl, or hydroxyalkyl;

each R$^{14}$, when R$^{14}$ is present, is independently amino, alkylamino, dialkylamino, acylamino, halo, hydroxy, alkyl, haloalkyl, hydroxyalkyl, aminoalkyl, alkylaminoalkyl, dialkylaminoalkyl, alkoxycarbonyl, aminocarbonyl, alkylaminocarbonyl, dialkylaminocarbonyl, or phenyl;

each R$^{16}$ is independently —NR$^{11}$R$^{11a}$, —NR$^{15}$S(O)R$^{15a}$, —OC(O)R$^{17}$, or —OR$^{18}$;

each R$^{19}$ is independently halo, alkyl, haloalkyl, amino, alkylamino, dialkylamino, or alkoxy; and R$^{20}$ is amino, alkylamino, dialkylamino, or heterocycloalkyl.

Embodiment (B)

In another embodiment, the Compound of Formula I(a) is that where R$^1$ is heteroaryl optionally substituted with one, two, or three R$^7$ groups; where each R$^7$ independently of each other (when R$^7$ is present) and all other groups are independently as defined in the Summary of the Invention for a Compound of Formula I or as defined in any of Embodiments (A1), (A2), (A3), (A4), and (1). In another embodiment, the Compound is according to Formula I(a) where R$^1$ is 3,4-dihydro-2H-pyrido[3,2-b][1,4]oxazinyl, pyrido[2,3-b]pyrazinyl, imidazo[1,2-c]pyrimidinyl, imidazo[1,2-c]pyridinyl, triazolo[1,5-a]pyridinyl, indolyl, 2,3-dihydrobenzofuranyl, benzo[b]thienyl, quinolinyl, benzimidazolyl, indazolyl, 1H-pyrrolo[2,3-b]pyridinyl, pyridinyl, pyrimidinyl, pyridazinyl, thienyl, thiazolyl, benzothiazolyl, imidazopyridinyl, pyrazolopyridinyl, pyrrolopyridinyl, or thiazolopyridinyl, where R$^1$ is optionally substituted with one, two, or three R$^7$; where each R$^7$ independently of each other (when R$^7$ is present) and all other groups are independently as defined in the Summary of the Invention for a Compound of Formula I or as defined in any of Embodiments (A1), (A2), (A3), (A4), and (1).

Embodiments (H1)

In another embodiment, the Compound is according to Formula I(a) where R$^1$ is a 9-membered heteroaryl optionally substituted with one, two, or three R$^7$; where each R$^7$ independently of each other (when R$^7$ is present) and all other groups are independently as defined in the Summary of the Invention for a Compound of Formula I or as defined in any of Embodiments (A1), (A2), (A3), (A4), and (1). In another embodiment, the Compound is according to Formula I(a) where R$^1$ is benzimidazolyl, imidazo[4,5-b]pyridinyl, imidazo[4,5-c]pyridinyl, 3H-imidazo[4,5-c]pyridinyl, indazolyl, 1H-pyrazolo[3,4-b]pyridinyl, indolyl, 1H-pyrrolo[2,3-b]pyridinyl, 1H-pyrrolo[3,2-b]pyridinyl, benzo[d]thiazolyl, thiazolo[4,5-b]pyridinyl, thiazolo[4,5-c]pyridinyl, thiazolo[5,4-c]pyridinyl, or thiazolo[5,4-b]pyridinyl, and R$^1$ is optionally substituted with one, two, or three R$^7$; where each R$^7$ independently of each other (when R$^7$ is present) and all other groups are independently as defined in the Summary of the Invention for a Compound of Formula I or as defined in any of Embodiments (A1), (A2), (A3), (A4), and (1).

Embodiments (B1)

In another embodiment, the Compound is according to Formula I(a) where R$^1$ is 3H-imidazo[4,5-b]pyridinyl, 1H-imidazo[4,5-b]pyridinyl, 3H-imidazo[4,5-c]pyridinyl, or 1H-imidazo[4,5-c]pyridinyl, where R$^1$ is optionally substituted with one, two, or three R$^7$ groups; where each R$^7$ independently of each other (when R$^7$ is present) and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 3H-imidazo[4,5-b]pyridin-5-yl, 1H-imidazo[4,5-b]pyridin-5-yl, 3H-imidazo[4,5-b]pyridin-6-yl, 1H-imidazo[4,5-b]pyridin-6-yl, 3H-imidazo[4,5-c]pyridin-6-yl, 1H-imidazo[4,5-c]pyridin-6-yl, 3H-imidazo[4,5-c]pyridin-5-yl, or 1H-imidazo[4,5-c]pyridin-5-yl, where $R^1$ is optionally substituted with one, two, or three $R^7$ groups; where each $R^7$ independently of each other (when $R^7$ is present) and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 3H-imidazo[4,5-b]pyridin-5-yl, 1H-imidazo[4,5-b]pyridin-5-yl, 3H-imidazo[4,5-b]pyridin-6-yl, 1H-imidazo[4,5-b]pyridin-6-yl, 3H-imidazo[4,5-c]pyridin-6-yl, 1H-imidazo[4,5-c]pyridin-6-yl, 3H-imidazo[4,5-c]pyridin-5-yl, or 1H-imidazo[4,5-c]pyridin-5-yl, where $R^1$ is optionally substituted with one or two $R^7$; each $R^7$, when $R^7$ is present, is independently halo, alkyl, cycloalkyl, haloalkyl, hydroxyalkyl, alkoxyalkyl, alkyl substituted with one or two —$NR^8R^{8a}$, alkyl substituted with one or two —$NR^8C(O)OR^9$, —$NR^8R^{8a}$, or —$NR^8C(O)OR^9$; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 3H-imidazo[4,5-b]pyridin-5-yl, 1H-imidazo[4,5-b]pyridin-5-yl, 3H-imidazo[4,5-b]pyridin-6-yl, 1H-imidazo[4,5-b]pyridin-6-yl, 3H-imidazo[4,5-c]pyridin-6-yl, 1H-imidazo[4,5-c]pyridin-6-yl, 3H-imidazo[4,5-c]pyridin-5-yl, or 1H-imidazo[4,5-c]pyridin-5-yl, where $R^1$ is optionally substituted with one or two $R^7$; each $R^7$, when $R^7$ is present, is independently halo, alkyl, cycloalkyl, haloalkyl, hydroxyalkyl, alkoxyalkyl, alkyl substituted with one or two —$NR^8R^{8a}$, alkyl substituted with one or two —$NR^8C(O)OR^9$, —$NR^8R^{8a}$, or —$NR^8C(O)OR^9$; $R^8$ and $R^{8a}$ are independently hydrogen or alkyl; $R^9$ is alkyl, benzyl, or haloalkyl; and all other groups are independently as defined in the Summary of the Invention for a Compound of Formula I or as defined in any of Embodiments (A1), (A2), (A3), (A4), and (1).

Embodiments (B2)

In another embodiment, the Compound is according to Formula I(b1) or I(b2)

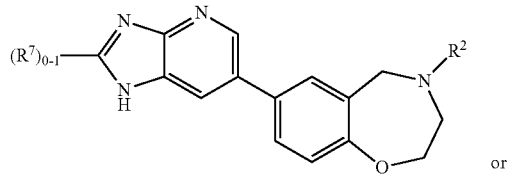

I(b1)

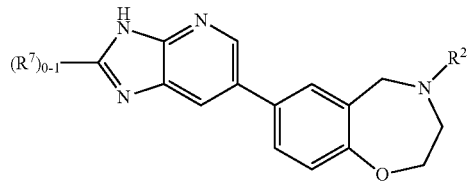

I(b2)

where $R^7$, when $R^7$ is present, is halo, alkyl, cycloalkyl, haloalkyl, hydroxyalkyl, alkoxyalkyl, alkyl substituted with one or two —$NR^8R^{8a}$, alkyl substituted with one or two —$NR^8C(O)OR^9$, —$NR^8R^{8a}$, or —$NR^8C(O)OR^9$; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(b1) or I(b2), where $R^7$, when $R^7$ is present, is alkyl, cycloalkyl, haloalkyl, hydroxyalkyl, alkyl substituted with one or two —$NR^8C(O)OR^9$, —$NR^8R^{8a}$, or —$NR^8C(O)OR^9$; $R^8$ is hydrogen or alkyl; $R^{8a}$ is hydrogen, alkyl, or haloalkyl; $R^9$ is alkyl or benzyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(b1) or I(b2), where $R^7$, when $R^7$ is present, is methyl, ethyl, n-propyl, isopropyl, cyclopropyl, cyclobutyl, monofluoromethyl, difluoromethyl, trifluoromethyl, 1-hydroxyethyl, 2-hydroxyethyl, amino, methylamino, ethylamino, methoxycarbonylamino, benzyloxycarbonylamino, aminomethyl, methylaminomethyl, or dimethylaminomethyl; and $R^2$ and all other groups are independently as defined in the Summary of the Invention for a Compound of Formula I or as defined in any of Embodiments (A1), (A2), (A3), (A4), and (1).

Embodiments (B3)

In another embodiment, the Compound of Formula I is according to Formula I(a) where $R^1$ is benzo[d]thiazolyl, thiazolo[5,4-b]pyridinyl, thiazolo[5,4-c]pyridinyl, thiazolo[4,5-b]pyridinyl, or thiazolo[4,5-c]pyridinyl, where $R^1$ is optionally substituted with one, two, or three $R^7$ groups; where all other groups and each $R^7$, when $R^7$ is present, are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is benzo[d]thiazol-5-yl, benzo[d]thiazol-6-yl, thiazolo[5,4-b]pyridin-5-yl, thiazolo[5,4-b]pyridin-6-yl, thiazolo[5,4-c]pyridin-6-yl, thiazolo[4,5-b]pyridin-5-yl, thiazolo[4,5-b]pyridin-6-yl, or thiazolo[4,5-c]pyridin-6-yl, where $R^1$ is optionally substituted with one, two, or three $R^7$ groups; where all other groups and each $R^7$, when $R^7$ is present, are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is thiazolo[5,4-b]pyridin-6-yl or thiazolo[4,5-b]pyridin-6-yl optionally substituted with one $R^7$ where $R^7$ is alkyl, —$NR^8R^{8a}$, or —$NR^8C(O)OR^9$; and other groups are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is thiazolo[5,4-b]pyridin-6-yl or thiazolo[4,5-b]pyridin-6-yl optionally substituted with one $R^7$ where $R^7$ is —$NR^8R^{8a}$; and other groups are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is thiazolo[5,4-b]pyridin-6-yl or thiazolo[4,5-b]pyridin-6-yl optionally substituted with one $R^7$ where $R^7$ is alkyl, —$NR^8R^{8a}$, or —$NR^8C(O)OR^9$; each $R^8$, $R^{8a}$, and $R^9$, independently of each other, are hydrogen or alkyl; and other groups are independently as defined in the Summary of the Invention for a Compound of Formula I or as defined in any of Embodiments (A1), (A2), (A3), (A4), and (1).

Embodiments (B4)

In another embodiment, the Compound is according to Formula I(c1) or I(c2)

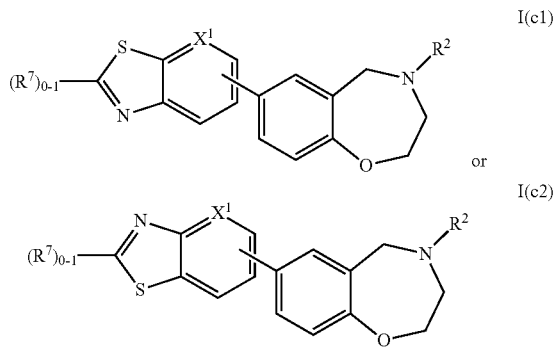

where $X^1$ is N or CH; $R^7$ (when present), $R^2$, and all other groups are independently as defined in the Summary of the Invention for a Compound of Formula I or as defined in any of Embodiments (A1), (A2), (A3), (A4), and (1). In another embodiment, the Compound is according to Formula I(c1) or I(c2) where $X^1$ is N or CH; $R^7$, when $R^7$ is present, is alkyl, —$NR^8R^{8a}$, or —$NR^8C(O)R^9$; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(c1) or I(c2) where $X^1$ is N or CH; $R^7$, when $R^7$ is present, is alkyl, —$NR^8R^{8a}$, or —$NR^8C(O)R^9$; each $R^8$ and $R^{8a}$ are independently hydrogen or alkyl and $R^9$ is alkyl; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is N or CH; $R^7$, when $R^7$ is present, is $C_{1-3}$-alkyl, amino, or $C_{1-3}$-alkylcarbonylamino; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(c1) or I(c2) where $X^1$ is N or CH; $R^7$, when $R^7$ is present, is —$NR^8R^{8a}$ where $R^8$ and $R^{8a}$ are independently hydrogen or alkyl; and $R^2$ and all other groups are independently as defined in the Summary of the Invention for a Compound of Formula I or as defined in any of Embodiments (A1), (A2), (A3), (A4), and (1). In another embodiment, the N or CH; $R^7$, when $R^7$ is present, is —$NR^8R^{8a}$ where $R^8$ and $R^{8a}$ are independently hydrogen or $C_{1-3}$-alkyl; and $R^2$ and all other groups are independently as defined in the Summary of the Invention for a Compound of Formula I or as defined in any of Embodiments (A1), (A2), (A3), (A4), and (1).

Embodiments (B4a)

In another embodiment, the Compound of Formula I is according to Formula I(c1) or I(c2) where $X^1$ is N; $R^7$ (when present), $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c) where $X^1$ is N; $R^7$, when $R^7$ is present, is alkyl, —$NR^8R^{8a}$, or —$NR^8C(O)R^9$; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is N; $R^7$, when $R^7$ is present, is alkyl, —$NR^8R^{8a}$, or —$NR^8C(O)R^9$; each $R^8$ and $R^{8a}$ are independently hydrogen or alkyl and $R^9$ is alkyl; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is N; $R^7$, when $R^7$ is present, is $C_{1-3}$-alkyl, amino, or $C_{1-3}$-alkylcarbonylamino; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is N; $R^7$, when $R^7$ is present, is —$NR^8R^{8a}$; each $R^8$ and $R^{8a}$ are independently hydrogen or alkyl; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is N; $R^7$, when $R^7$ is present, is —$NR^8R^{8a}$; each $R^8$ and $R^{8a}$ are independently hydrogen or $C_{1-3}$-alkyl; and $R^2$ and all other groups are independently as defined in the Summary of the Invention for a Compound of Formula I or as defined in any of Embodiments (A1), (A2), (A3), (A4), and (1).

Embodiments (B4b)

In another embodiment, the Compound of Formula I is according to Formula I(c1) or I(c2) where $X^1$ is C; $R^7$ (when present), $R^2$, and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is C; $R^7$, when $R^7$ is present, is alkyl, —$NR^8R^{8a}$, or —$NR^8C(O)R^9$; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is C; $R^7$, when $R^7$ is present, is alkyl, —$NR^8R^{8a}$, or —$NR^8C(O)R^9$; each $R^8$ and $R^{8a}$ are independently hydrogen or alkyl and $R^9$ is alkyl; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is C; $R^7$, when $R^7$ is present, is $C_{1-3}$-alkyl, amino, or $C_{1-3}$-alkylcarbonylamino; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is C; $R^7$, when $R^7$ is present, is —$NR^8R^{8a}$; each $R^8$ and $R^{8a}$ are independently hydrogen or alkyl; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(c1) or I(c2) where $X^1$ is C; $R^7$, when $R^7$ is present, is —$NR^8R^{8a}$; each $R^8$ and $R^{8a}$ are independently hydrogen or $C_{1-3}$-alkyl; and $R^2$ and all other groups are independently as defined in the Summary of the Invention for a Compound of Formula I or as defined in any of Embodiments (A1), (A2), (A3), (A4), and (1).

Embodiments (B5)

In another embodiment, the Compound of Formula I is according to Formula I(a) where $R^1$ is benzimidazolyl optionally substituted with one, two, or three $R^7$ groups; where all other groups and each $R^7$ independently of each other (when $R^7$ is present) are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is benzimidazolyl optionally substituted with one or two $R^7$ groups; and all other groups and each $R^7$ (when $R^7$ is present) are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is benzimidazolyl optionally substituted with one $R^7$; and all other groups are independently as defined in the Summary of the Invention for a Compound of Formula I or as defined in any of Embodiments (A1), (A2), (A3), (A4), and (1).

Embodiments (B6)

In another embodiment, the Compound of Formula I is according to Formula I(d1) or I(d2)

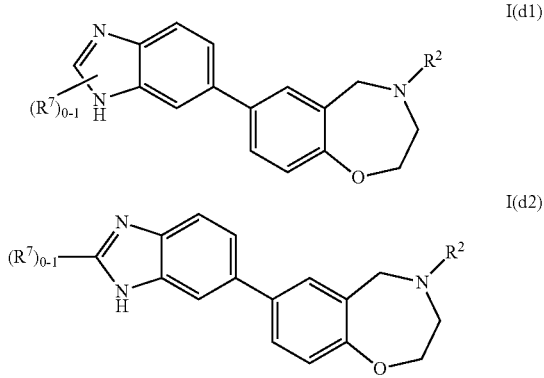

where $R^7$, when $R^7$ is present, is alkyl, haloalkyl, alkoxyalkyl, —$SR^{13}$, —$NR^8R^{8a}$, —$NR^8C(O)R^9$, —$NR^8C(O)OR^9$, —$NR^8C(O)NR^{8a}R^9$, cycloalkyl, heterocycloalkyl, or heteroaryl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$, when $R^7$ is present, is alkyl, alkoxyalkyl, —$SR^{13}$, —$NR^8R^{8a}$, —$NR^8C(O)R^9$, —$NR^8C(O)OR^9$, cycloalkyl, heterocycloalkyl, or heteroaryl; $R^8$ and $R^{8a}$ are independently hydrogen or alkyl; $R^9$ is alkyl, alkoxyalkyl, or optionally substituted heterocycloalkylalkyl; $R^{13}$ is alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$, when $R^7$ is present, is alkyl, alkoxyalkyl, —$SR^{13}$, —$NR^8R^{8a}$, —$NR^8C(O)R^9$, —$NR^8C(O)OR^9$, cycloalkyl, heterocycloalkyl, or heteroaryl; $R^8$ and $R^{8a}$ are independently hydrogen or alkyl; $R^9$ is alkyl; $R^{13}$ is alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$, when $R^7$ is present, is $C_{1-3}$-alkyl, alkoxyalkyl, —$SR^{13}$, —$NR^8R^{8a}$, —$NR^8C(O)R^9$, —$NR^8C(O)OR^9$, cycloalkyl, heterocycloalkyl, or heteroaryl; $R^8$ and $R^{8a}$ are independently hydrogen or $C_{1-3}$-alkyl; $R^9$ is $C_{1-3}$-alkyl; $R^{13}$ is $C_{1-3}$-alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$, when $R^7$ is present, is methyl, ethyl, n-propyl, isopropyl, methoxymethyl, amino, methylamino, ethylamino, isopropylamino, dimethylamino, 3-piperidinylpropylcarbonylamino, methoxycarbonylamino, 2-(methoxy)-ethyloxycarbonylamino, cyclopropyl, cyclobutyl, cyclopentyl, cyclohexyl, azetidinyl, piperidinyl, or pyridinyl; and $R^2$ and all other groups are independently as defined in the Summary of the Invention for a Compound of Formula I or as defined in any of Embodiments (A1), (A2), (A3), (A4), and (1).

Embodiment (B7)

In another embodiment, the Compound is according to Formula I(d1) or I(d2) where $R^7$ is present and is alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is $C_{1-3}$-alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is —$NR^8R^{8a}$; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is —$NR^8R^{8a}$; $R^8$ and $R^{8a}$ are independently hydrogen or alkyl; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is —$NR^8R^{8a}$; $R^8$ and $R^{8a}$ are independently hydrogen or $C_{1-3}$-alkyl; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is —$NR^8C(O)OR^9$; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is —$NR^8C(O)OR^9$; $R^8$ and $R^9$ are independently hydrogen or alkyl; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is —$NR^8C(O)OR^9$; $R^8$ and $R^9$ are independently hydrogen or $C_{1-3}$-alkyl; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is —$SR^{13}$; and all other groups are independently as defined in the Summary of the Invention for a Compound of Formula I or as defined in any of Embodiments (A1), (A2), (A3), (A4), and (1).

In another embodiment, the Compound is according to Formula I(d1) or I(d2) where $R^7$ is present and is haloalkyl; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is cycloalkyl; and all other groups are independently as defined in the Summary of the Invention for a Compound of Formula I or as defined in any of Embodiments (A1), (A2), (A3), (A4), and (1). In another embodiment, the Compound is according to Formula I(d1) or I(d2) where $R^7$ is present and is cyclopropyl; and all other groups are independently as defined in the Summary of the Invention for a Compound of Formula I or as defined in any of Embodiments (A1), (A2), (A3), (A4), and (1).

Embodiment (B8)

In another embodiment, the Compound is according to Formula I(f)

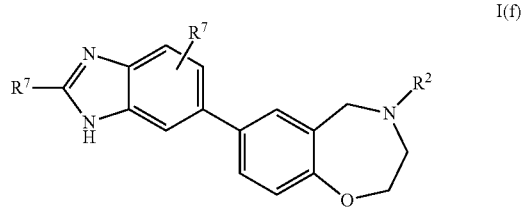

I(f)

where the $R^7$ at the 2-position is —$NR^8R^{8a}$ or —$NR^8C(O)OR^9$ and the other $R^7$ is halo; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(f) where the $R^7$ at the 2-position is —$NR^8R^{8a}$ or —$NR^8C(O)OR^9$ and the other $R^7$ is halo; $R^8$, $R^{8a}$, and $R^9$ are independently hydrogen or alkyl; and $R^2$ and all other groups are independently as defined in the Summary of the Invention for a Compound of Formula I or as defined in any of Embodiments (A1), (A2), (A3), (A4), and (1). In another embodiment, the Compound of Formula I is according to Formula I(f) where the $R^7$ at the 2-position is —$NR^8R^{8a}$ or —$NR^8C(O)OR^9$ and the other $R^7$ is halo; $R^8$, $R^{8a}$, and $R^9$ are independently hydrogen or $C_{1-3}$-alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(f) where the $R^7$ at the 2-position is methoxycarbonylamino or amino and the other the $R^7$ is fluoro; and $R^2$ and all other groups are independently as defined in the Summary of the Invention for a Compound of Formula I or as defined in any of Embodiments (A1), (A2), (A3), (A4), and (1).

Embodiment (B9)

In another embodiment, the Compound is according to Formula I(a) where $R^1$ is a 5-membered heteroaryl, where $R^1$ is optionally substituted with one or two $R^7$; each $R^7$ (when present), and all other groups are independently as defined in the Summary of the Invention for a Compound of Formula I or as defined in any of Embodiments (A1), (A2), (A3), (A4), and (1).

Embodiments (B10)

In another embodiment, the Compound is according to Formula I(a) where $R^1$ is thiazol-2-yl, thiazol-4-yl, or thiazol-5-yl, where $R^1$ is optionally substituted with one or two $R^7$; each $R^7$ (when present), and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is thiazol-2-yl, thiazol-4-yl, or thiazol-5-yl, where $R^1$ is optionally substituted with one $R^7$; $R^7$, all other groups are independently as defined in the Summary of the Invention for a Compound of Formula I or as defined in any of Embodiments (A1), (A2), (A3), (A4), and (1).

Embodiments (B11)

In another embodiment, the Compound is according to Formula I(a) where $R^1$ is thiazol-2-yl, thiazol-4-yl, or thiazol-5-yl, where $R^1$ is optionally substituted with one or two $R^7$; where each $R^7$ (when present), where each $R^7$ is independently alkyl, —$NR^8C(O)OR^9$, —$C(O)NR^8R^{8a}$, or —$NR^8R^{8a}$; each $R^8$ and $R^{8a}$ are independently hydrogen or alkyl and $R^9$ is alkyl (in another embodiment each alkyl in $R^8$, $R^{8a}$, and $R^9$ are $C_{1-3}$-alkyl); and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is thiazol-2-yl, thiazol-4-yl, or thiazol-5-yl, where $R^1$ is optionally substituted with one or two $R^7$; where each $R^7$ (when present), where each $R^7$ is independently alkyl, —$NR^8C(O)OR^9$, —$C(O)NR^8R^{8a}$, or —$NR^8R^{8a}$; each $R^8$ and $R^{8a}$ are independently hydrogen or $C_{1-3}$-alkyl and $R^9$ is $C_{1-3}$-alkyl; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is thiazol-2-yl, thiazol-4-yl, or thiazol-5-yl, where $R^1$ is optionally substituted with one or two $R^7$; each $R^7$, when $R^7$ is present, is independently methyl, or amino; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is thiazol-2-yl, thiazol-4-yl, or thiazol-5-yl, where $R^1$ is substituted with two $R^7$; where one $R^7$, is alkyl and the other $R^7$—$NR^8R^{8a}$; and all other groups are independently as defined in the Summary of the Invention for a Compound of Formula I or as defined in any of Embodiments (A1), (A2), (A3), (A4), and (1).

Embodiments (B12)

In another embodiment, the Compound is according to Formula I(a) where $R^1$ is thien-2-yl, thien-3-yl, thien-4-yl, or thien-5-yl, where $R^1$ is optionally substituted with one or two $R^7$ groups; where each $R^7$ (when present), and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is thien-2-yl, thien-3-yl, thien-4-yl, or thien-5-yl; and all other groups are independently as defined in the Summary of the Invention for a Compound of Formula I or as defined in any of Embodiments (A1), (A2), (A3), (A4), and (1).

Embodiments (B13)

In another embodiment, the Compound is according to Formula I(a) where $R^1$ is pyrazol-1-yl, pyrazol-3-yl, pyrazol-4-yl, or pyrazol-5-yl, where $R^1$ is optionally substituted with one or two $R^7$ groups; where each $R^7$ (when present), and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is pyrazol-1-yl, pyrazol-3-yl, pyrazol-4-yl, or pyrazol-5-yl; and all other groups are independently as defined in the Summary of the Invention for a Compound of Formula I or as defined in any of Embodiments (A1), (A2), (A3), (A4), and (1).

Embodiment (B14)

In another embodiment, the Compound is according to Formula I(a) where $R^1$ is a 6-membered heteroaryl, where $R^1$ is optionally substituted with one or two $R^7$ groups; where each $R^7$ (when present), and all other groups are independently as defined in the Summary of the Invention for a Compound of Formula I or as defined in any of Embodiments (A1), (A2), (A3), (A4), and (1).

Embodiments (B15)

In another embodiment, the Compound is according to Formula I(a) where $R^1$ is pyrimidin-2-yl, pyrimidin-4-yl, pyrimidin-5-yl, pyrimidin-6-yl, where $R^1$ is optionally substituted with one or two $R^7$ groups; where each $R^7$ (when present), and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is pyrimidin-2-yl, pyrimidin-4-yl, pyrimidin-5-yl, pyrimidin-6-yl, where $R^1$ is optionally substituted with one $R^7$ where $R^7$ is —$NR^8R^{8a}$; $R^8$ and $R^{8a}$ are independently hydrogen or alkyl; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is pyrimidin-2-yl, pyrimidin-4-yl, pyrimidin-5-yl, pyrimidin-6-yl, where $R^1$ is optionally substituted with one $R^7$ where $R^7$ is —$NR^8R^{8a}$; $R^8$ and $R^{8a}$ are independently hydrogen or $C_{1-3}$-alkyl; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is $R^1$ is 2-amino-pyrimidin-5-yl; and all other groups are independently as defined in the Summary of the Invention for a Compound of Formula I or as defined in any of Embodiments (A1), (A2), (A3), (A4), and (1).

Embodiments (B16)

In another embodiment, the Compound is according to Formula I(a) where $R^1$ is pyridin-2-yl, pyridin-3-yl, pyridin-4-yl, pyridin-5-yl, or pyridin-6-yl, where $R^1$ is optionally substituted with one or two $R^7$ groups; where each $R^7$ (when present), and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is pyridinyl where $R^1$ is optionally substituted with one or two $R^7$ where each $R^7$ is independently halo, cyano, alkylsulfonylalkyl, —$OR^{8a}$, —$C(O)NR^8R^{8a}$, $S(O)_2OH$, —$S(O)R^{13}$, —$S(O)_2R^{13a}$, —$S(O)_2NR^8R^9$, —$NR^8R^{8a}$, —$NR^8C(O)OR^9$, —$NR^8C(O)R^9$, —$NR^8S(O)_2R^{8a}$, or heterocycloalkyl optionally substituted with one amino; and all other groups are independently as defined in the Summary of the Invention for a Compound of Formula I or as defined in any of Embodiments (A1), (A2), (A3), (A4), and (1).

Embodiments (B16a)

In another embodiment, the Compound is according to Formula I(a) where $R^1$ is pyridinyl where $R^1$ is optionally substituted with one or two $R^7$ where each $R^7$ is independently halo, cyano, alkylsulfonylalkyl, —$OR^{8a}$, —$C(O)NR^8R^{8a}$, $S(O)_2OH$, —$S(O)R^{13}$, —$S(O)_2R^{13a}$, —$S(O)_2NR^8R^9$, —$NR^8R^{8a}$, —$NR^8C(O)OR^9$, —$NR^8C(O)R^9$, —$NR^8S(O)_2R^{8a}$, heterocycloalkyl optionally substituted with one amino; where each $R^8$ is independently hydrogen, haloalkyl, or alkyl;
each $R^{8a}$ is independently hydrogen, alkyl, benzyl, or phenyl which phenyl is optionally substituted with one or two groups which are independently halo or alkyl;
each $R^9$ is independently hydrogen; alkyl; hydroxyalkyl; alkoxyalkyl; aminoalkyl; alkylaminoalkyl; dialkylaminoalkyl; haloalkyl; hydroxyalkyl substituted with one, two, or three halo, heterocycloalkylalkyl optionally substituted with one alkyl; heterocycloalkyl optionally substituted with one alkyl; cycloalkylalkyl optionally substituted with one amino; cycloalkyl;
$R^{13}$ is alkyl or hydroxyalkyl;
$R^{13a}$ is alkyl; hydroxyalkyl; heterocycloalkyl optionally substituted with one or two groups which are independently halo, amino, alkylamino, dialkylamino, hydroxy, alkyl, or hydroxyalkyl;

and all other groups are independently as defined in the Summary of the Invention for a Compound of Formula I or as defined in any of Embodiments (A1), (A2), (A3), (A4), and (1).

Embodiments (B16b)

In another embodiment, the Compound of Formula I is according to Formula I(e)

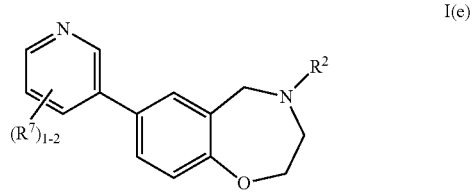

I(e)

where each $R^7$ and $R^2$ are independently as defined in the Summary of the Invention for a Compound of Formula I or as defined in any of Embodiments (A1), (A2), (A3), (A4), and (1). In another embodiment, the Compound of Formula I is according to Formula I(e) where each $R^7$ is independently as defined in embodiment B16a and $R^2$ is as defined in the Summary of the Invention for a Compound of Formula I or as defined in any of Embodiments (A1), (A2), (A3), (A4), and (1).

Embodiments (B16c)

In another embodiment, the Compound of Formula I is according to Formula I(e1)

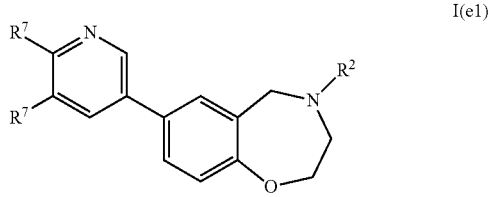

I(e1)

where each $R^7$ and $R^2$ are independently as defined in the Summary of the Invention for a Compound of Formula I or as defined in any of Embodiments (A1), (A2), (A3), (A4), and (1). In another embodiment, the Compound of Formula I is according to Formula I(e) where each $R^7$ is independently as defined in embodiment B16a and $R^2$ is as defined in the Summary of the Invention for a Compound of Formula I or as defined in any of Embodiments (A1), (A2), (A3), (A4), and (1). In another embodiment, the Compound of Formula I is according to Formula I(e1) where the $R^7$ in the 2-position is hydrogen, halo, cyano, alkoxy, alkyl, or —$NR^8R^{8a}$ and the $R^7$ in the 3-position is —$NR^8S(O)_2R^{8a}$; and $R^2$ and all other groups are as defined in the Summary of the Invention for a Compound of Formula I or as defined in any of Embodiments (A1), (A2), (A3), (A4), and (1). In another embodiment, the Compound of Formula I is according to Formula I(e1) where the $R^7$ in the 2-position is hydroxy or —$NR^8R^{8a}$ and the $R^7$ in the 3-position is —$S(O)R^{13}$, —$S(O)_2R^{13a}$, —$S(O)_2NR^8R^9$; and $R^2$ and all other groups are as defined in the Summary of the Invention for a Compound of Formula I or as defined in any of Embodiments (A1), (A2), (A3), (A4), and (1). In another embodiment, the Compound of Formula I is according to Formula I(e1) where the $R^7$ in the 2-position is hydroxy or —$NR^8R^{8a}$ and the $R^7$ in the 3-position is —$S(O)R^{13}$, —$S(O)_2R^{13a}$, —$S(O)_2NR^8R^9$; $R^{13}$ is hydroxyalkyl; $R^{13a}$ is alkyl or heterocycloalkyl optionally substituted with one group which is amino, alkyl, hydroxyalkyl, or hydroxy; each $R^8$ and $R^{8a}$ are independently hydrogen or alkyl; $R^9$ is hydrogen, haloalkyl, alkoxyalkyl, hydroxyalkyl, aminoalkyl, alkylaminoalkyl, dialkylaminoalkyl, cycloalkyl, heterocycloalkyl, heterocycloalkylalkyl, alkyl substituted with one aminocarbonyl, or hydroxyalkyl which is substituted with one amino or 3 halo; and $R^2$ and all other groups are as defined in the Summary of the Invention for a Compound of Formula I or as defined in any of Embodiments (A1), (A2), (A3), (A4), and (1).

Embodiments (B17)

In another embodiment, the Compound of Formula I is according to Formula I(a) where $R^1$ is pyridazin-3-yl, pyridazin-4-yl, pyridazin-5-yl, or pyridazin-6-yl, where $R^1$ is optionally substituted with one or two $R^7$ groups; where each $R^7$ (when present), and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is pyridazin-3-yl, pyridazin-4-yl, pyridazin-5-yl, or pyridazin-6-yl, where $R^1$ is optionally substituted with one or two $R^7$ groups where each $R^7$ is independently —$NR^8R^{8a}$; $R^8$ and $R^{8a}$ are independently hydrogen or alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 3-aminopyridazin-6-yl; and all other groups are independently as defined in the Summary of the Invention for a Compound of Formula I or as defined in any of Embodiments (A1), (A2), (A3), (A4), and (1).

Embodiments (B18)

In another embodiment, the Compound is according to Formula I(a) where $R^1$ is pyrazin-2-yl, pyrazin-3-yl, pyrazin-5-yl, or pyrazin-6-yl, where $R^1$ is optionally substituted with one or two $R^7$ groups; where each $R^7$ (when present), and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is pyrazin-2-yl, pyrazin-3-yl, pyrazin-5-yl, or pyrazin-6-yl, where $R^1$ is optionally substituted with one $R^7$ where $R^7$ is —$NR^8R^{8a}$; $R^8$ and $R^{8a}$ are independently hydrogen or alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 5-amino-pyrazin-2-yl; and $R^2$ and all other groups are independently as defined in the Summary of the Invention for a Compound of Formula I or as defined in any of Embodiments (A1), (A2), (A3), (A4), and (1).

Embodiments (B19)

In another embodiment, the Compound is according to Formula I(a) where $R^1$ is 1H-pyrrolo[2,3-b]pyridinyl, optionally substituted with one or two $R^7$ groups; where each $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 1H-pyrrolo[2,3-b]pyridin-5-yl, optionally substituted with one or two $R^7$ groups; where each $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 1H-pyrrolo[2,3-b]pyridin-5-yl, optionally substituted with one $R^7$; where the $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 1H-pyrrolo[2,3-b]pyridin-5-yl, optionally substituted with one $R^7$; $R^7$, when $R^7$ is present, is methyl or ethyl; and all other groups are independently as defined in the Summary of the Invention for a Compound of Formula I or as defined in any of Embodiments (A1), (A2), (A3), (A4), and (1).

Embodiments (B20)

In another embodiment, the Compound is according to Formula I(a) where $R^1$ is indazolyl, optionally substituted with one or two $R^7$ groups; where $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is indazol-5-yl or indazol-6-yl, where $R^1$ is optionally substituted with one or two $R^7$ groups; where $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is indazol-5-yl or indazol-6-yl, where $R^1$ is optionally substituted with one $R^7$; $R^7$, when present, is alkyl or amino; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is indazol-5-yl, indazol-6-yl, or N-methyl-indazol-5-yl; and all other groups are independently as defined in the Summary of the Invention for a Compound of Formula I or as defined in any of Embodiments (A1), (A2), (A3), (A4), and (1).

Embodiment (B21)

In another embodiment, the Compound is according to Formula I(a) where $R^1$ is benzimidazolyl substituted with two $R^7$ groups where each $R^7$ is alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is benzimidazolyl substituted with two $R^7$ groups where each $R^7$ is $C_{1-3}$-alkyl; and $R^2$ and all other groups are independently as defined in the Summary of the Invention for a Compound of Formula I or as defined in any of Embodiments (A1), (A2), (A3), (A4), and (1).

Embodiments (B22)

In another embodiment, the Compound is according to Formula I(a) where $R^1$ is quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, quinazolin-2-yl, quinazolin-3-yl, quinazolin-5-yl, quinazolin-6-yl, quinazolin-7-yl, or quinazolin-8-yl, where $R^1$ is optionally substituted with one or two $R^7$ groups; where each $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is quinolin-2-yl, quinolin-3-yl, quinolin-4-yl, quinolin-5-yl, quinolin-6-yl, quinolin-7-yl, quinolin-8-yl, quinazolin-2-yl, quinazolin-3-yl, quinazolin-5-yl, quinazolin-6-yl, quinazolin-7-yl, or quinazolin-8-yl; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is quinolin-3-yl or quinazolin-6-yl; and $R^2$ and all other groups are independently as defined in the Summary of the Invention for a Compound of Formula I or as defined in any of Embodiments (A1), (A2), (A3), (A4), and (1).

Embodiments (B24)

In another embodiment, the Compound is according to Formula I(a) where $R^1$ is 2,3-dihydrobenzofuran-4-yl, 2,3-dihydrobenzofuran-5-yl, 2,3-dihydrobenzofuran-6-yl, or 2,3-dihydrobenzofuran-7-yl, where $R^1$ is optionally substituted with one or two $R^7$ groups; where each $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 2,3-dihydrobenzofuran-4-yl, 2,3-dihydrobenzofuran-5-yl, 2,3-dihydrobenzofuran-6-yl, or 2,3-dihydrobenzofuran-7-yl; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is 2,3-dihydrobenzofuran-5-yl; and $R^2$ and all other groups are independently as defined in the Summary of the Invention for a Compound of Formula I or as defined in any of Embodiments (A1), (A2), (A3), (A4), and (1).

Embodiments (B25)

In another embodiment, the Compound is according to Formula I(a) where $R^1$ is indol-1-yl, indol-2-yl, indol-3-yl, indol-4-yl, indol-5-yl, indol-6-yl, or indol-7-yl, where $R^1$ is optionally substituted with one or two $R^7$ groups; where each $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is indol-1-yl, indol-2-yl, indol-3-yl, indol-4-yl, indol-5-yl, indol-6-yl, or indol-7-yl where $R^1$ is optionally substituted with one $R^7$ where $R^7$ is alkyl; and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is indol-5-yl optionally substituted with one $R^7$ where $R^7$ is alkyl; and all other groups are independently as defined in the Summary of the Invention for a Compound of Formula I or as defined in any of Embodiments (A1), (A2), (A3), (A4), and (1).

Embodiments (B26)

In another embodiment, the Compound is according to Formula I(a) where $R^1$ is [1,2,4]triazolo[1,5-a]pyridin-2-yl, [1,2,4]triazolo[1,5-a]pyridin-5-yl, [1,2,4]triazolo[1,5-a]pyridin-6-yl, [1,2,4]triazolo[1,5-a]pyridin-7-yl, or [1,2,4]triazolo[1,5-a]pyridin-8-yl, where $R^1$ is optionally substituted with one or two $R^7$ groups; where each $R^7$, when $R^7$ is present, and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is [1,2,4]triazolo[1,5-a]pyridin-2-yl, [1,2,4]triazolo[1,5-a]pyridin-5-yl, [1,2,4]triazolo[1,5-a]pyridin-6-yl, [1,2,4]triazolo[1,5-a]pyridin-7-yl, or [1,2,4]triazolo[1,5-a]pyridin-8-yl, where $R^1$ is optionally substituted with one $R^7$ where $R^7$ is —$NR^8R^{8a}$; $R^8$ and $R^8$ are independently hydrogen or alkyl; and $R^2$ and all other groups are independently as defined in the Summary of the Invention for a Compound of Formula I or as defined in any of Embodiments (A1), (A2), (A3), (A4), and (1). In another embodiment, the Compound is according to Formula I(a) where $R^1$ is [1,2,4]triazolo[1,5-a]pyridin-6-yl, or [1,2,4]triazolo[1,5-a]pyridin-7-yl, optionally substituted with one $R^7$ where $R^7$ is amino; and all other groups are independently as defined in the Summary of the Invention for a Compound of Formula I or as defined in any of Embodiments (A1), (A2), (A3), (A4), and (1).

Embodiments (B27)

In another embodiment, the Compound is according to Formula I(g)

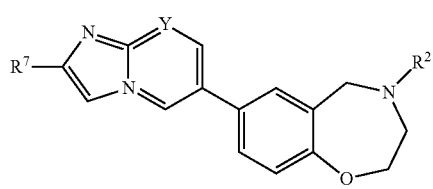

I(g)

where Y is N or CH; and $R^2$ and $R^7$ are independently as defined in the Summary of the Invention for a Compound of Formula I or as defined in any of Embodiments (A1), (A2), (A3), (A4), and (1). In another embodiment the Compound of Formula I(g) is that where $R^7$, when present, is —$NR^8R^{8a}$ or —$NR^8C(O)R^9$; and $R^2$ and all other groups are independently as defined in the Summary of the Invention for a Compound of Formula I or as defined in any of Embodiments (A1), (A2), (A3), (A4), and (1). In another embodiment the Compound of Formula I(g) is that where $R^7$, when present, is —$NR^8R^{8a}$ or —$NR^8C(O)R^9$; $R^8$ and $R^{8a}$ are independently hydrogen or alkyl; $R^9$ is alkyl or haloalkyl; and $R^2$ and all other groups are independently as defined in the Summary of the Invention for a Compound of Formula I or as defined in any of Embodiments (A1), (A2), (A3), (A4), and (1). In another embodiment the Compound of Formula I(g) is that where $R^7$, when present, is —$NR^8R^{8a}$ or —$NR^8C(O)R^9$; $R^8$ and $R^{8a}$ are independently hydrogen or $C_{1-3}$-alkyl; $R^9$ is $C_{1-3}$-alkyl or halo-$C_{1-3}$-alkyl; and $R^2$ and all other groups are independently as defined in the Summary of the Invention for a Compound of Formula I or as defined in any of Embodiments (A1), (A2), (A3), (A4), and (1). In another embodiment the Compound of Formula I(g) is that where $R^7$, when present, is amino or trifluoromethylcarbonylamino; and $R^2$ and all other groups are independently as defined in the Summary of the Invention for a Compound of Formula I or as defined in any of Embodiments (A1), (A2), (A3), (A4), and (1).

Embodiments (B28)

In another embodiment, the Compound of Formula I is according to Formula I(a) where $R^1$ is pyrido[2,3-b]pyrazinyl optionally substituted with one or two $R^7$ groups; where $R^7$ and all other groups are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is unsubstituted pyrido[2,3-b]pyrazinyl where all other groups are independently as defined in the Summary of the Invention for a Compound of Formula I or as defined in any of Embodiments (A1), (A2), (A3), (A4), and (1).

Embodiments (B29)

In another embodiment, the Compound of Formula I is according to Formula I(a) where $R^1$ is 3,4-dihydro-2H-pyrido[3,2-b][1,4]oxazinyl optionally substituted with one or two $R^7$ groups; where $R^7$ and all other groups are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is unsubstituted 3,4-dihydro-2H-pyrido[3,2-b][1,4]oxazinyl where all other groups are independently as defined in the Summary of the Invention for a Compound of Formula I or as defined in any of Embodiments (A1), (A2), (A3), (A4), and (1).

Embodiments (C)

In another embodiment, the Compound of Formula I is according to Formula I(a) where $R^1$ is phenyl optionally substituted with one, two, or three $R^6$ groups; where each $R^6$, when $R^6$ is present, and all other groups are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is phenyl optionally substituted with one or two $R^6$ groups; where each $R^6$, when $R^6$ is present, and all other groups are independently as defined in the Summary of the Invention for a Compound of Formula I or as defined in any of Embodiments (A1), (A2), (A3), (A4), and (1).

Embodiments (C1)

In another embodiment, the Compound of Formula I is according to Formula I(a) where $R^1$ is phenyl optionally substituted with one, two, or three $R^6$ groups; where each $R^6$ is independently nitro, halo, alkoxy, —$OR^{8a}$, —$S(O)_2R^8$, —$NR^8R^{8a}$, —$NR^8S(O)_2R^{8a}$, —$NR^8C(O)R^9$, —$C(O)NR^8R^{8a}$, —$NR^8C(O)NR^{8a}R^9$, carboxy, alkoxycarbonyl, or heteroaryl optionally substituted with one or two $R^{14}$; and all other groups are independently as defined in the Summary of the Invention for a Compound of Formula I or as defined in any of Embodiments (A1), (A2), (A3), (A4), and (1). In another embodiment, the Compound of Formula I is according to Formula I(a) where $R^1$ is phenyl optionally substituted with one, two, or three R⁶ groups; where each R⁶ is independently —S(O)₂R⁸, —C(O)NR⁸R⁸ᵃ or heteroaryl optionally substituted with one or two R¹⁴; and all other groups are independently as defined in the Summary of the Invention for a Compound of Formula I or as defined in any of Embodiments (A1), (A2), (A3), (A4), and (1).

Embodiment (C2)

In another embodiment, the Compound is according to Formula I(a) where R¹ is phenyl optionally substituted with one, two, or three R⁶ groups; where each R⁶ is independently nitro, halo, alkoxy, —OR⁸ᵃ, —S(O)₂R⁸, —NR⁸R⁸ᵃ, —NR⁸S(O)₂R⁸ᵃ, —NR⁸C(O)R⁹, —C(O)NR⁸R⁸ᵃ, —NR⁸C(O)NR⁸ᵃR⁹, carboxy, alkoxycarbonyl, or heteroaryl optionally substituted with one or two R¹⁴; each R⁸ is independently hydrogen or alkyl; each R⁸ᵃ is independently hydrogen, alkyl, haloalkyl, optionally substituted cycloalkyl, or optionally substituted heterocycloalkyl; R⁹ is alkyl; R¹⁴, when present, is hydroxyalkyl; and all other groups are independently as defined in the Summary of the Invention for a Compound of Formula I or as defined in any of Embodiments (A1), (A2), (A3), (A4), and (1). In another embodiment, the Compound is according to Formula I(a) where R¹ is phenyl optionally substituted with one, two, or three R⁶ groups; where each R⁶ is independently nitro, halo, alkoxy, —OR⁸ᵃ, —S(O)₂R⁸, —NR⁸R⁸ᵃ, —NR⁸S(O)₂R⁸ᵃ, —NR⁸C(O)R⁹, —C(O)NR⁸R⁸ᵃ, —NR⁸C(O)NR⁸ᵃR⁹, carboxy, alkoxycarbonyl, or heteroaryl optionally substituted with one or two R¹⁴; each R⁸ is independently hydrogen or $C_{1-3}$-alkyl; each R⁸ᵃ is independently hydrogen, alkyl, haloalkyl, optionally substituted cycloalkyl, or optionally substituted heterocycloalkyl; R⁹ is $C_{1-3}$-alkyl; R¹⁴, when present, is hydroxyalkyl; and all other groups are independently as defined in the Summary of the Invention for a Compound of Formula I or as defined in any of Embodiments (A1), (A2), (A3), (A4), and (1).

Embodiment (C3)

In another embodiment, the Compound is according to Formula I(a) where R¹ is phenyl optionally substituted with one or two R⁶ groups where each R⁶ is independently nitro, chloro, methoxy, methylsulfonyl, amino, methylaminocarbonylamino, methylamino, carboxy, methylcarbonylamino, aminocarbonyl, methylaminocarbonyl, ethylaminocarbonyl, n-propylaminocarbonyl, isopropylaminocarbonyl, 2-monofluoroethylaminocarbonyl, 2,2-difluoroethylaminocarbonyl, 2,2,2-trifluoroethylaminocarbonyl, 1,1,1-trifluoroprop-2-ylaminocarbonyl, cyclopropylaminocarbonyl, pyrrolidinylaminocarbonyl, methoxycarbonyl, imidazolyl, imidazolyl substituted with hydroxymethyl, or pyrazolyl; and R² and all other groups are independently as defined in the Summary of the Invention for a Compound of Formula I or as defined in any of Embodiments (A1), (A2), (A3), (A4), and (1).

In a Compound as described by any one of Formula I, I(a), I(b1), I(b2), I(c1), I(c2), I(d1), I(d2), I(e1), I(e2), I(f), and I(g), or by any of the above embodiments (1), (A1), (A2), (A3), (A4), (B), (H1), (H2), (B1), (B2), (B3), (B4), (B4a), (B4b), (B5), (B6), (B8), (B9), (B10), (B11), (B12), (B13), (B14), (B15), (B16), (B16a), (B16b), (B16c), (B17), (B18), (B19), (B20), (B21), (B22), (B23), (B24), (B25), (B26), (B27), (C), (C1), (C2), and (C3), R² can be described according to any of the following embodiments.

Embodiments (D)

In another embodiment, R² is a 6-membered heteroaryl substituted with R³, R³ᵃ, R³ᵇ, and R³ᶜ; R³, R³ᵃ, R³ᵇ, and R³ᶜ and all other groups are independently as defined in the Summary of the Invention for a Compound of Formula I or as defined in embodiment (1).

Embodiments (D1)

In another embodiment, R² is pyrimidinyl substituted with R³, R³ᵃ, and R³ᵇ; where R³, R³ᵃ, R³ᵇ, and all other groups are independently as defined in the Summary of the Invention for a Compound of Formula I or as defined in embodiment (1).

Embodiments (D2)

In another embodiment, R² is according to Formula (a)

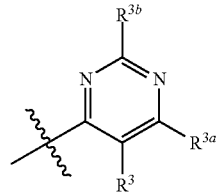

(a)

where R³, R³ᵃ, and R³ᵇ are independently hydrogen; alkyl; halo; hydroxyalkyl; cyanoalkyl; —NR¹¹R¹¹ᵃ; —S(O)₂R²⁰; optionally substituted cycloalkylalkyl; optionally substituted heterocycloalkyl; optionally substituted phenylalkyl; alkyl substituted with one or two R¹⁶; or —OR¹¹ᵃ; and all other groups are independently as defined in the Summary of the Invention for a Compound of Formula I or as defined in embodiment (1). In another embodiment, R² is according to Formula (a) where R³, R³ᵃ, and R³ᵇ are independently hydrogen; alkyl; halo; hydroxyalkyl; cyanoalkyl; —NR¹¹R¹¹ᵃ; —S(O)₂R²⁰; cycloalkylalkyl; heterocycloalkyl optionally substituted with one or two alkyl; phenylalkyl optionally substituted with one or two R¹⁹; alkyl substituted with one or two R¹⁶; or —OR¹¹ᵃ; and all other groups are independently as defined in the Summary of the Invention for a Compound of Formula I or as defined in embodiment (1). In another embodiment, R² is according to Formula (a) where R³, R³ᵃ, and R³ᵇ are independently hydrogen; alkyl; halo; hydroxyalkyl; cyanoalkyl; —NR¹¹R¹¹ᵃ; —S(O)₂R²⁰; cycloalkylalkyl; heterocycloalkyl optionally substituted with one or two alkyl; phenylalkyl optionally substituted with one or two R¹⁹; alkyl substituted with one or two R¹⁶; or —OR¹¹ᵃ; each R¹⁹ is independently halo, alkyl, haloalkyl, alkoxy, amino, alkylamino, or dialkylamino; each R¹⁶ is independently —NR¹¹R¹¹ᵃ or —OC(O)R¹⁷; R¹⁷ is alkyl; each R¹¹ is independently hydrogen, alkyl (in another embodiment each alkyl is $C_{1-3}$-alkyl), or cycloalkyl; each R¹¹ᵃ is independently hydrogen; alkyl (in another embodiment each alkyl is $C_{1-3}$-alkyl); aminoalkyl; alkylaminoalkyl; dialkylaminoalkyl; phenyl; phenyl substituted with one alkoxy; phenylalkyl; heterocycloalkyl; heterocycloalkyl substituted with one or two alkyl; heterocycloalkylalkyl; heterocycloalkylalkyl substituted with one or two alkyl; R²⁰ is amino, alkylamino, dialkylamino, or heterocycloalkyl; and all other groups are independently as defined in the Summary of the Invention for a Compound of Formula I or as defined in embodiment (1). In another embodiment, R² is according to Formula (a) where R³, R³ᵃ, and R³ᵇ are independently hydrogen; alkyl (in another embodiment alkyl is $C_{1-3}$-alkyl); phenylalkyl optionally substituted with one or two groups which are independently halo, haloalkyl, alkoxy, amino, alkylamino, or dialkylamino; —NR$^{11}$R$^{11a}$; heterocycloalkyl; cycloalkylalkyl; alkyl substituted with one or two R$^{16}$; or hydroxyalkyl; where each R$^{11}$ is independently hydrogen or alkyl (in another embodiment each alkyl is C$_{1-3}$-alkyl); each R$^{11a}$ is independently alkyl (in another embodiment each alkyl is C$_{1-3}$-alkyl), phenyl optionally substituted with alkoxy, or is heterocycloalkyl optionally substituted with one or two alkyl; each R$^{16}$ is independently amino, alkylamino, dialkylamino, or cyclopropylamino; and all other groups are independently as defined in the Summary of the Invention for a Compound of Formula I or as defined in embodiment (1).

Embodiments (D3)

In another embodiment, R$^2$ is according to Formula (a) where R$^3$ is hydrogen, halo, alkyl, cycloalkylalkyl, or phenylalkyl optionally substituted with one or two R$^{19}$; R$^{3a}$ is hydrogen, alkyl, halo, optionally substituted heterocycloalkyl, or —NR$^{11}$R$^{11a}$; and R$^{3b}$ is hydrogen, alkyl, hydroxyalkyl, cyanoalkyl, or alkyl substituted with one or two R$^{16}$; and all other groups are independently as defined in the Summary of the Invention for a Compound of Formula I or as defined in embodiment (1).

Embodiments (D3a)

In another embodiment, R$^2$ is according to Formula (a) where R$^3$ is phenylalkyl optionally substituted with one or two R$^{19}$; R$^{3a}$ is alkyl; and R$^{3b}$ is hydrogen, alkyl, hydroxyalkyl, or alkyl substituted with one R$^{16}$; and all other groups are independently as defined in the Summary of the Invention for a Compound of Formula I or as defined in embodiment (1). In another embodiment, R$^2$ is according to Formula (a) where R$^3$ is phenylalkyl optionally substituted with one or two R$^{19}$; each R$^{19}$ is independently halo, alkyl, haloalkyl, alkoxy, amino, alkylamino, or dialkylamino; R$^{3a}$ is alkyl (in another embodiment alkyl is C$_{1-3}$-alkyl); and R$^{3b}$ is hydrogen, alkyl, hydroxyalkyl, or alkyl substituted with one R$^{16}$; R$^{16}$ is amino, alkylamino, dialkylamino, cyclopropylamino, or —OC(O)CH$_3$; and all other groups are independently as defined in the Summary of the Invention for a Compound of Formula I or as defined in embodiment (1).

Embodiments (D3b)

In another embodiment, R$^2$ is according to Formula (a) where R$^3$ is phenylalkyl optionally substituted with one or two R$^{19}$; R$^{3a}$ and R$^{3b}$ are alkyl; and all other groups are independently as defined in the Summary of the Invention for a Compound of Formula I or as defined in embodiment (1). In another embodiment, R$^2$ is according to Formula (a) where R$^3$ is phenylalkyl optionally substituted with one or two R$^{19}$; each R$^{19}$ are independently halo, alkyl, haloalkyl, amino, alkylamino, dialkylamino, or alkoxy; R$^{3a}$ and R$^{3b}$ are alkyl (in another embodiment each alkyl is C$_{1-2}$-alkyl); and all other groups are independently as defined in the Summary of the Invention for a Compound of Formula I or as defined in embodiment (1). In another embodiment, R$^2$ is according to Formula (a) where R$^3$ is phenylalkyl optionally substituted with one or two halo; R$^{3a}$ and R$^{3b}$ are alkyl (in another embodiment each alkyl is C$_{1-2}$-alkyl); and all other groups are independently as defined in the Summary of the Invention for a Compound of Formula I or as defined in embodiment (1). In another embodiment, R$^2$ is according to Formula (a) where R$^3$ is phenylalkyl optionally substituted with one or two R$^{19}$; each R$^{19}$ are independently halo, alkyl, haloalkyl, amino, alkylamino, dialkylamino, or alkoxy; R$^{3a}$ and R$^{3b}$ are methyl; and all other groups are independently as defined in the Summary of the Invention for a Compound of Formula I or as defined in embodiment (1).

Embodiments (D3c)

In another embodiment, R$^2$ is according to Formula (a) where R$^3$ and R$^{3a}$ are alkyl (in another embodiment each alkyl is C$_{1-2}$-alkyl); R$^{3b}$ is hydrogen, alkyl, or alkyl substituted with one R$^{16}$; and all other groups are independently as defined in the Summary of the Invention for a Compound of Formula I or as defined in embodiment (1). In another embodiment, R$^2$ is according to Formula (a) where R$^3$ and R$^{3a}$ are alkyl (in another embodiment alkyl is C$_{1-2}$-alkyl); R$^{3b}$ is hydrogen; and all other groups are independently as defined in the Summary of the Invention for a Compound of Formula I or as defined in embodiment (1). In another embodiment, R$^2$ is according to Formula (a) where R$^3$, R$^{3a}$, and R$^{3b}$ are alkyl (in another embodiment each alkyl is C$_{1-2}$-alkyl); and all other groups are independently as defined in the Summary of the Invention for a Compound of Formula I or as defined in embodiment (1). In another embodiment, R$^2$ is according to Formula (a) where R$^3$ and R$^{3a}$ are alkyl (in another embodiment each alkyl is C$_{1-2}$-alkyl); and R$^{3b}$ is alkyl substituted with one R$^{16}$; and all other groups are independently as defined in the Summary of the Invention for a Compound of Formula I or as defined in embodiment (1). In another embodiment, R$^2$ is according to Formula (a) where R$^3$ and R$^{3a}$ are alkyl (in another embodiment each alkyl is C$_{1-2}$-alkyl); and R$^{3b}$ is alkyl substituted with one R$^{16}$; R$^{16}$ is amino, alkylamino, dialkylamino, or cycloalkylamino; and all other groups are independently as defined in the Summary of the Invention for a Compound of Formula I or as defined in embodiment (1).

Embodiments (D3d)

In another embodiment, R$^2$ is according to Formula (a) where R$^3$ is alkyl; R$^{3a}$ and R$^{3b}$ are hydrogen; and all other groups are independently as defined in the Summary of the Invention for a Compound of Formula I or as defined in embodiment (1). In another embodiment, R$^2$ is according to Formula (a) where R$^3$ is C$_{1-2}$-alkyl; R$^{3a}$ and R$^{3b}$ are hydrogen; and all other groups are independently as defined in the Summary of the Invention for a Compound of Formula I or as defined in embodiment (1).

Embodiments (D3e)

In another embodiment, R$^2$ is according to Formula (a) where R$^3$ is phenylalkyl optionally substituted with one or two R$^{19}$; R$^{3a}$ is alkyl; and R$^{3b}$ is hydrogen; and all other groups are independently as defined in the Summary of the Invention for a Compound of Formula I or as defined in embodiment (1). In another embodiment, R$^2$ is according to Formula (a) where R$^3$ is phenylalkyl optionally substituted with one or two R$^{19}$; each R$^{19}$ is independently halo, alkyl, haloalkyl, amino, alkylamino, dialkylamino, or alkoxy; R$^{3a}$ is alkyl; and R$^{3b}$ is hydrogen; and all other groups are independently as defined in the Summary of the Invention for a Compound of Formula I or as defined in embodiment (1).

Embodiments (D3f)

In another embodiment, R$^2$ is according to Formula (a) where R$^3$ is phenylalkyl optionally substituted with one or two R$^{19}$; R$^{3a}$ is alkyl; and R$^{3b}$ is alkyl substituted with one $R^{16}$; and all other groups are independently as defined in the Summary of the Invention for a Compound of Formula I or as defined in embodiment (1). In another embodiment, $R^2$ is according to Formula (a) where $R^3$ is phenylalkyl optionally substituted with one or two $R^{19}$; each $R^{19}$ is independently halo, alkyl, haloalkyl, amino, alkylamino, dialkylamino, or alkoxy; $R^{3a}$ is alkyl (in another embodiment alkyl is $C_{1-2}$-alkyl); and $R^{3b}$ is alkyl substituted with one $R^{16}$; $R^{16}$ is amino, alkylamino, dialkylamino, or cycloalkylamino; and all other groups are independently as defined in the Summary of the Invention for a Compound of Formula I or as defined in embodiment (1).

Embodiments (D3g)

In another embodiment, $R^2$ is according to Formula (a) where $R^3$ is alkyl or phenylalkyl optionally substituted with one or two $R^{19}$; $R^{3a}$ is alkyl; and $R^{3b}$ is hydrogen, alkyl, or alkyl substituted with $R^{16}$; and all other groups are independently as defined in the Summary of the Invention for a Compound of Formula I or as defined in embodiment (1). In another embodiment, $R^2$ is according to Formula (a) where $R^3$ is alkyl (in another embodiment alkyl is $C_{1-2}$-alkyl) or phenylalkyl optionally substituted with one or two $R^{19}$; $R^{3a}$ is alkyl (in another embodiment alkyl is $C_{1-2}$-alkyl); and $R^{3b}$ is hydrogen, alkyl (in another embodiment alkyl is $C_{1-2}$-alkyl), or alkyl substituted with $R^{16}$; $R^{16}$ is amino, alkylamino, dialkylamino, or cycloalkylamino; each $R^{19}$ is independently halo, alkyl, haloalkyl, amino, alkylamino, dialkylamino, or alkoxy; and all other groups are independently as defined in the Summary of the Invention for a Compound of Formula I or as defined in embodiment (1).

Embodiments (D3h)

In another embodiment, $R^2$ is according to Formula (a) where $R^3$ is optionally substituted phenyloxy; $R^{3a}$ is alkyl; and $R^{3b}$ is hydrogen; and all other groups are independently as defined in the Summary of the Invention for a Compound of Formula I or as defined in embodiment (1). In another embodiment, $R^2$ is according to Formula (a) where $R^3$ is phenyloxy optionally substituted with one or two groups which groups are independently halo, alkyl, haloalkyl, amino, alkylamino, dialkylamino, or alkoxy; $R^{3a}$ is alkyl (in another embodiment alkyl is $C_{1-2}$-alkyl); and $R^{3b}$ is hydrogen; and all other groups are independently as defined in the Summary of the Invention for a Compound of Formula I or as defined in embodiment (1). In another embodiment, $R^2$ is according to Formula (a) where $R^3$ is phenyloxy; $R^{3a}$ is alkyl (in another embodiment alkyl is $C_{1-2}$-alkyl); and $R^{3b}$ is hydrogen; and all other groups are independently as defined in the Summary of the Invention for a Compound of Formula I or as defined in embodiment (1).

Embodiments (D3i)

In another embodiment, $R^2$ is according to Formula (a) where $R^3$ is optionally substituted cycloalkylalkyl; $R^{3a}$ is alkyl; and $R^{3b}$ is hydrogen or alkyl; and all other groups are independently as defined in the Summary of the Invention for a Compound of Formula I or as defined in embodiment (1). In another embodiment, $R^2$ is according to Formula (a) where $R^3$ is cycloalkylalkyl; $R^{3a}$ is alkyl (in another embodiment alkyl is $C_{1-2}$-alkyl); and $R^{3b}$ is hydrogen or alkyl (in another embodiment alkyl is $C_{1-2}$-alkyl); and all other groups are independently as defined in the Summary of the Invention for a Compound of Formula I or as defined in embodiment (1).

Embodiments (D3j)

In another embodiment, $R^2$ is according to Formula (a) where $R^3$ is alkyl; $R^{3a}$ is phenylalkyl optionally substituted with one or two $R^{19}$; and $R^{3b}$ is hydrogen; and all other groups are independently as defined in the Summary of the Invention for a Compound of Formula I or as defined in embodiment (1). In another embodiment, $R^2$ is according to Formula (a) where $R^3$ is alkyl (in another embodiment alkyl is $C_{1-2}$-alkyl); $R^{3a}$ is phenylalkyl optionally substituted with one or two $R^{19}$; each $R^{19}$ is independently halo, alkyl, haloalkyl, amino, alkylamino, dialkylamino, or alkoxy; and $R^{3b}$ is hydrogen; and all other groups are independently as defined in the Summary of the Invention for a Compound of Formula I or as defined in embodiment (1). In another embodiment, $R^2$ is according to Formula (a) where $R^3$ is alkyl (in another embodiment alkyl is $C_{1-2}$-alkyl); $R^{3a}$ is phenylalkyl; and $R^{3b}$ is hydrogen; and all other groups are independently as defined in the Summary of the Invention for a Compound of Formula I or as defined in embodiment (1).

Embodiments (D3k)

In another embodiment, $R^2$ is according to Formula (a) where $R^3$ is alkyl; $R^{3a}$ is $-NR^{11}R^{11a}$; and $R^{3b}$ is hydrogen or alkyl; and all other groups are independently as defined in the Summary of the Invention for a Compound of Formula I or as defined in embodiment (1). In another embodiment, $R^2$ is according to Formula (a) where $R^3$ is alkyl (in another embodiment alkyl is $C_{1-2}$-alkyl); $R^{3a}$ is $-NR^{11}R^{11a}$; $R^{3b}$ is hydrogen or alkyl (in another embodiment alkyl is $C_{1-2}$-alkyl); $R^{11}$ is hydrogen or alkyl (in another embodiment alkyl is $C_{1-2}$-alkyl); $R^{11a}$ is alkyl, aminoalkyl, alkylaminoalkyl, dialkylaminoalkyl, optionally substituted heterocycloalkyl, optionally substituted heterocycloalkylalkyl, optionally substituted phenyl, or optionally substituted phenylalkyl; and all other groups are independently as defined in the Summary of the Invention for a Compound of Formula I or as defined in embodiment (1). In another embodiment, $R^2$ is according to Formula (a) where $R^3$ is alkyl (in another embodiment alkyl is $C_{1-2}$-alkyl); $R^{3a}$ is $-NR^{11}R^{11a}$; $R^{3b}$ is hydrogen or alkyl (in another embodiment alkyl is $C_{1-2}$-alkyl); $R^{11}$ is hydrogen or alkyl (in another embodiment alkyl is $C_{1-2}$-alkyl); $R^{11a}$ is alkyl, aminoalkyl, alkylaminoalkyl, dialkylaminoalkyl, heterocycloalkyl, heterocycloalkylalkyl (optionally substituted with one or two alkyl), phenylalkyl, phenyl (optionally substituted with one or two groups which are independently halo, alkyl, haloalkyl, amino, alkylamino, dialkylamino, or alkoxy); and all other groups are independently as defined in the Summary of the Invention for a Compound of Formula I or as defined in embodiment (1).

Embodiments (D4)

In another embodiment, $R^2$ is according to Formula (a) where $R^{3a}$ is alkyl (in another embodiment alkyl is $C_{1-2}$-alkyl), or $-NR^{11}R^{11a}$; $R^3$ and $R^{3b}$ are hydrogen; and all other groups are independently as defined in the Summary of the Invention for a Compound of Formula I or as defined in embodiment (1).

Embodiments (D4a)

In another embodiment, $R^2$ is according to Formula (a) where $R^{3a}$ is alkyl (in another embodiment alkyl is $C_{1-2}$- alkyl), and $R^3$ and $R^{3b}$ are hydrogen; and all other groups are independently as defined in the Summary of the Invention for a Compound of Formula I or as defined in embodiment (1).

Embodiments (D4b)

In another embodiment, $R^2$ is according to Formula (a) where $R^{3a}$ is —$NR^{11}R^{11a}$; $R^3$ and $R^{3b}$ are hydrogen; and all other groups are independently as defined in the Summary of the Invention for a Compound of Formula I or as defined in embodiment (1). In another embodiment, $R^2$ is according to Formula (a) where $R^{3a}$ is —$NR^{11}R^{11a}$; $R^3$ and $R^{3b}$ are hydrogen; $R^{11}$ is hydrogen or alkyl; $R^{11a}$ is optionally substituted phenyl; and all other groups are independently as defined in the Summary of the Invention for a Compound of Formula I or as defined in embodiment (1). In another embodiment, $R^2$ is according to Formula (a) where $R^{3a}$ is —$NR^{11}R^{11a}$; $R^3$ and $R^{3b}$ are hydrogen; $R^{11}$ is hydrogen or alkyl (in another embodiment alkyl is $C_{1-2}$-alkyl); $R^{11a}$ is phenyl optionally substituted with one or two groups which groups are independently halo, alkyl, haloalkyl, amino, alkylamino, dialkylamino, or alkoxy; and all other groups are independently as defined in the Summary of the Invention for a Compound of Formula I or as defined in embodiment (1).

Embodiments (D5)

In another embodiment, $R^2$ is according to Formula (a) where $R^3$ and $R^{3a}$ are hydrogen; $R^{3b}$ is —$NR^{11}R^{11a}$; and all other groups are independently as defined in the Summary of the Invention for a Compound of Formula I or as defined in embodiment (1). In another embodiment, $R^2$ is according to Formula (a) where $R^3$ and $R^{3a}$ are hydrogen; $R^{3b}$ is —$NR^{11}R^{11a}$; $R^{11}$ is hydrogen or alkyl (in another embodiment alkyl is $C_{1-2}$-alkyl); $R^{11a}$ is optionally substituted phenyl; and all other groups are independently as defined in the Summary of the Invention for a Compound of Formula I or as defined in embodiment (1). In another embodiment, $R^2$ is according to Formula (a) where $R^3$ and $R^{3a}$ are hydrogen; $R^{3b}$ is —$NR^{11}R^{11a}$; and all other groups are independently as defined in the Summary of the Invention for a Compound of Formula I or as defined in embodiment (1). In another embodiment, $R^2$ is according to Formula (a) where $R^3$ and $R^{3a}$ are hydrogen; $R^{3b}$ is —$NR^{11}R^{11a}$; $R^{11}$ is hydrogen or alkyl (in another embodiment alkyl is $C_{1-2}$-alkyl); $R^{11a}$ is hydrogen, alkyl (in another embodiment alkyl is $C_{1-2}$-alkyl), or optionally substituted phenyl; and all other groups are independently as defined in the Summary of the Invention for a Compound of Formula I or as defined in embodiment (1). In another embodiment, $R^2$ is according to Formula (a) where $R^3$ and $R^{3a}$ are hydrogen; $R^{3b}$ is —$NR^{11}R^{11a}$; $R^{11}$ is hydrogen or alkyl (in another embodiment alkyl is $C_{1-2}$-alkyl); $R^{11a}$ is hydrogen, alkyl (in another embodiment alkyl is $C_{1-2}$-alkyl), or phenyl optionally substituted with one or two groups which groups are independently halo, alkyl, haloalkyl, amino, alkylamino, dialkylamino, or alkoxy; and all other groups are independently as defined in the Summary of the Invention for a Compound of Formula I or as defined in embodiment (1). In another embodiment, $R^2$ is according to Formula (a) where $R^3$ and $R^{3a}$ are hydrogen; $R^{3b}$ is —$NR^{11}R^{11a}$; $R^{11}$ is hydrogen or alkyl (in another embodiment alkyl is $C_{1-2}$-alkyl); $R^{11a}$ is hydrogen, alkyl (in another embodiment alkyl is $C_{1-2}$-alkyl), or phenyl; and all other groups are independently as defined in the Summary of the Invention for a Compound of Formula I or as defined in embodiment (1).

Embodiments (D6)

In another embodiment, $R^2$ is according to Formula (a) where $R^3$ is hydrogen; $R^{3a}$ is alkyl (in another embodiment alkyl is $C_{1-2}$-alkyl) or —$NR^{11}R^{11a}$; $R^{3b}$ is hydrogen or alkyl (in another embodiment alkyl is $C_{1-2}$-alkyl); and all other groups are independently as defined in the Summary of the Invention for a Compound of Formula I or as defined in embodiment (1).

Embodiments (D6a)

In another embodiment, $R^2$ is according to Formula (a) where $R^3$ is hydrogen; $R^{3a}$ is alkyl (in another embodiment alkyl is $C_{1-2}$-alkyl); $R^{3b}$ is hydrogen; and all other groups are independently as defined in the Summary of the Invention for a Compound of Formula I or as defined in embodiment (1).

Embodiments (D6b)

In another embodiment, $R^2$ is according to Formula (a) where $R^{3a}$—$NR^{11}R^{11a}$; $R^3$ and $R^{3b}$ are hydrogen; and all other groups are independently as defined in the Summary of the Invention for a Compound of Formula I or as defined in embodiment (1). In another embodiment, $R^2$ is according to Formula (a) where $R^{3a}$ is —$NR^{11}R^{11a}$; $R^3$ and $R^{3b}$ are hydrogen; $R^{11}$ is hydrogen or alkyl (in another embodiment alkyl is $C_{1-2}$-alkyl); $R^{11a}$ is hydrogen, alkyl (in another embodiment alkyl is $C_{1-2}$-alkyl), or optionally substituted phenyl; and all other groups are independently as defined in the Summary of the Invention for a Compound of Formula I or as defined in embodiment (1). In another embodiment, $R^2$ is according to Formula (a) where $R^{3a}$ is —$NR^{11}R^{11a}$; $R^3$ and $R^{3b}$ are hydrogen; $R^{11}$ is hydrogen or alkyl (in another embodiment alkyl is $C_{1-2}$-alkyl); $R^{11a}$ is hydrogen, alkyl (in another embodiment alkyl is $C_{1-2}$-alkyl), or phenyl optionally substituted with one or two groups which groups are independently halo, alkyl, haloalkyl, amino, alkylamino, dialkylamino, or alkoxy; and all other groups are independently as defined in the Summary of the Invention for a Compound of Formula I or as defined in embodiment (1). In another embodiment, $R^2$ is according to Formula (a) where $R^{3a}$ is —$NR^{11}R^{11a}$; and $R^3$ and $R^{3b}$ are hydrogen; $R^{11}$ is hydrogen or alkyl (in another embodiment alkyl is $C_{1-2}$-alkyl); $R^{11a}$ is hydrogen, alkyl (in another embodiment each alkyl is $C_{1-2}$-alkyl), or phenyl optionally substituted with one alkoxy; and all other groups are independently as defined in the Summary of the Invention for a Compound of Formula I or as defined in embodiment (1).

Embodiments (D6c)

In another embodiment, $R^2$ is according to Formula (a) where $R^3$, $R^{3a}$, and $R^{3b}$ are hydrogen; and all other groups are independently as defined in the Summary of the Invention for a Compound of Formula I or as defined in embodiment (1).

Embodiments (D6d)

In another embodiment, $R^2$ is pyrimidin-2-yl, pyrimidin-4-yl, 5-(phenylmethyl)-6-methyl-pyrimidin-4-yl, 6-(phenylmethyl)-5-methyl-pyrimidin-4-yl, 5-(1-phenylethyl)-6-methyl-pyrimidin-4-yl, 2,6-dimethyl-5-(phenylmethyl)-pyrimidin-4-yl, 5-(phenylmethyl)-6-ethyl-pyrimidin-4-yl, 2-methyl-pyrimidin-4-yl, 5-methyl-pyrimidin-4-yl, 6-methyl-pyrimidin-4-yl, 5,6-dimethyl-pyrimidin-4-yl, 6-isopropyl-pyrimidin-4-yl, 5-methyl-6-ethyl-pyrimidin-4-yl, 5-isopropyl-6-methyl-pyrimidin-4-yl, 5-isoamyl-6-methyl-pyrimidin-4-yl, 5-ethyl-6-isopropyl-pyrimidin-4-yl, 5-methyl-6-isopropyl-pyrimidin-4-yl, 5-(phenylmethyl)-6-chloro-pyrimidin-4-yl, 5-(phenylmethyl)-pyrimidin-4-yl, 5-phenyloxy-6-methyl-pyrimidin-4-yl, 5-(cyclopropylmethyl)-6-methyl-pyrimidin-4-yl, 2-amino-pyrimidin-4-yl, 5-(2-chloro-phenylmethyl)-6-methyl-pyrimidin-4-yl, 5-(3-chloro-phenylmethyl)-6-methyl-pyrimidin-4-yl, 5-(4-chloro-phenylmethyl)-6-methyl-pyrimidin-4-yl, 5-(2-fluoro-phenylmethyl)-6-methyl-pyrimidin-4-yl, 5-(3-fluoro-phenylmethyl)-6-methyl-pyrimidin-4-yl, 5-(4-fluoro-phenylmethyl)-6-methyl-pyrimidin-4-yl, 5-(3,4-difluoro-phenylmethyl)-6-methyl-pyrimidin-4-yl, 5-(3,5-difluoro-phenylmethyl)-6-methyl-pyrimidin-4-yl, 5-(3-chloro-5-fluoro-phenylmethyl)-6-methyl-pyrimidin-4-yl, 5-(1-(3-fluorophenyl)-ethyl)-6-methyl-pyrimidin-4-yl, 2,6-dimethyl-5-(4-fluoro-phenylmethyl)-pyrimidin-4-yl, 5-(2-methyl-phenylmethyl)-6-methyl-pyrimidin-4-yl, 5-(3-methyl-phenylmethyl)-6-methyl-pyrimidin-4-yl, 5-(4-methyl-phenylmethyl)-6-methyl-pyrimidin-4-yl, 5-(4-chloro-3-(dimethylamino)-phenylmethyl)-6-methyl-pyrimidin-4-yl, 5-(2-methoxy-phenylmethyl)-6-methyl-pyrimidin-4-yl, 5-(3-methoxy-phenylmethyl)-6-methyl-pyrimidin-4-yl, 5-(4-methoxy-phenylmethyl)-6-methyl-pyrimidin-4-yl, 2-(phenylamino)-pyrimidin-4-yl, 6-(phenylamino)-pyrimidin-4-yl, 6-(4-methoxy-phenylamino)-pyrimidin-4-yl, 5-methyl-6-(phenylamino)-pyrimidin-4-yl, 5-(2-trifluoromethyl-phenylmethyl)-6-methyl-pyrimidin-4-yl, 5-(3-trifluoromethyl-phenylmethyl)-6-methyl-pyrimidin-4-yl, 5-(4-trifluoromethyl-phenylmethyl)-6-methyl-pyrimidin-4-yl, or 5-phenylmethyl-6-trifluoromethyl-pyrimidin-4-yl; and all other groups are independently as defined in the Summary of the Invention for a Compound of Formula I or as defined in embodiment (1).

Embodiments (D7)

In another embodiment, $R^2$ is pyridinyl substituted with $R^3$, $R^{3a}$, $R^{3b}$, and $R^{3c}$; where $R^3$, $R^{3a}$, $R^{3b}$, and $R^{3c}$ and all other groups are independently as defined in the Summary of the Invention for a Compound of Formula I or as defined in embodiment (1).

Embodiments (D7a)

In another embodiment, $R^2$ is pyridinyl substituted with $R^3$, $R^{3a}$, $R^{3b}$, and $R^{3c}$ where $R^3$, $R^{3a}$, $R^{3b}$, and $R^{3c}$ are independently hydrogen, alkyl, or phenylalkyl optionally substituted with one or two $R^{19}$; and all other groups are independently as defined in the Summary of the Invention for a Compound of Formula I or as defined in embodiment (1). In another embodiment, $R^2$ is pyridinyl substituted with $R^3$, $R^{3a}$, $R^{3b}$, and $R^{3c}$; where $R^3$, $R^{3a}$, $R^{3b}$, and $R^{3c}$ are independently hydrogen, alkyl, phenylalkyl, or phenylalkyl substituted with one or two halo; and all other groups are independently as defined in the Summary of the Invention for a Compound of Formula I or as defined in embodiment (1).

Embodiments (D7b)

In another embodiment, $R^2$ is pyridinyl substituted with $R^3$, $R^{3a}$, $R^{3b}$, and $R^{3c}$; where $R^3$ is alkyl (in another embodiment alkyl is $C_{1-2}$-alkyl); $R^3$, $R^{3a}$, $R^{3b}$, and $R^{3c}$ are hydrogen; and all other groups are independently as defined in the Summary of the Invention for a Compound of Formula I or as defined in embodiment (1).

Embodiments (D7c)

In another embodiment, $R^2$ is pyridin-2-yl, pyridin-3-yl, pyridin-4-yl, 2-amino-pyridin-4-yl, 3-methyl-pyridin-2-yl, 2-methyl-3-(phenylmethyl)-pyridin-4-yl, 3-(2-fluoro-phenylmethyl)-2-methyl-pyridin-4-yl, 3-(3-fluoro-phenylmethyl)-2-methyl-pyridin-4-yl, or 3-(4-fluoro-phenylmethyl)-2-methyl-pyridin-4-yl; and all other groups are independently as defined in the Summary of the Invention for a Compound of Formula I or as defined in embodiment (1).

Embodiments (D7d)

In another embodiment, $R^2$ is according to Formula (b)

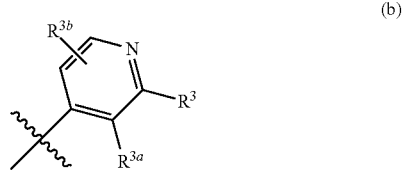

(b)

where $R^3$, $R^{3a}$, and $R^{3b}$ are independently as defined in the Summary of the Invention for a Compound of Formula I or as defined in embodiment (1).

Embodiments (E)

In another embodiment, $R^2$ is a 10-membered heteroaryl substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently as defined in the Summary of the Invention for a Compound of Formula I or as defined in embodiment (1). In another embodiment, $R^2$ is a 10-membered heteroaryl and the 10-membered heteroaryl is quinazolin-2-yl, quinazolin-4-yl, quinazolin-5-yl, quinazolin-6-yl, quinazolin-7-yl, quinazolin-8-yl, pyrido[3,2-d]pyrimidin-4-yl, pyrido[4,3-d]pyrimidin-4-yl, pyrido[3,4-d]pyrimidin-4-yl, pyrido[2,3-d]pyrimidin-4-yl, 6,7-dihydro-5H-cyclopenta[d]pyrimidin-4-yl, 5,6,7,8-tetrahydroquinazolin-4-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, thieno[2,3-d]pyrimidin-4-yl, 7H-pyrrolo[2,3-d]pyrimidin-4-yl, 1H-pyrrolo[2,3-b]pyridin-4-yl, 1H-pyrrolo[3,2-c]pyridin-4-yl, thieno[2,3-b]pyridin-4-yl, thieno[3,2-c]pyridin-4-yl, 5,7-dihydrothieno[3,4-d]pyrimidin-4-yl, 5,6,7,8-tetrahydropyrido[3,4-d]pyrimidin-4-yl, 5,6,7,8-tetrahydropyrido[4,3-d]pyrimidin-4-yl, 5,6,7,8-tetrahydropyrido[2,3-d]pyrimidin-4-yl, 5,6,7,8-tetrahydropyrido[3,2-d]pyrimidin-4-yl, 6,7-dihydro-5H-pyrrolo[3,4-d]pyrimidin-4-yl, 6,7-dihydro-5H-pyrrolo[3,2-d]pyrimidin-4-yl, 6,7-dihydro-5H-pyrrolo[2,3-d]pyrimidin-4-yl, or 5,6-dihydroquinazolinyl where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently as defined in the Summary of the Invention for a Compound of Formula I or as defined in embodiment (1).

Embodiments (E1)

In another embodiment, $R^2$ is quinazolin-2-yl, quinazolin-4-yl, quinazolin-5-yl, quinazolin-6-yl, quinazolin-7-yl, or quinazolin-8-yl, where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently as defined in the Summary of the Invention for a Compound of Formula I or as defined in embodiment (1).

Embodiments (E2)

In another embodiment, $R^2$ is quinazolin-4-yl substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ are independently hydrogen, halo, alkyl, haloalkyl, alkoxycarbonyl, optionally substituted phenyl, —S(O)$_2$R$^{20}$, —NR$^{11}$R$^{11a}$, or —OR$^{11a}$; and all other groups are independently as defined in the Summary of the Invention for a Compound of Formula I or as defined in embodiment (1).

Embodiments (E2a)

In another embodiment, $R^2$ is quinazolin-4-yl substituted with $R^3$, $R^{3a}$, $R^{3b}$, $R^{3c}$, and $R^{3d}$; $R^{3c}$ and $R^{3d}$ are hydrogen and $R^3$, $R^{3a}$, and $R^{3b}$ are independently cyano, alkyl, alkenyl, halo, haloalkyl, hydroxyalkyl, alkoxyalkyl, —SR$^{12}$; —S(O)$^2$R$^{20}$, —C(O)OR$^4$, halocarbonyl, —NR$^{11}$R$^{11a}$, —OR$^{11a}$, optionally substituted phenyl, optionally substituted phenylalkyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, or alkyl substituted with one or two $R^{16}$; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3c}$ and $R^{3d}$ are hydrogen and $R^3$, $R^{3a}$, and $R^{3b}$ are independently alkyl, halo, or —OR$^{11a}$; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3c}$ and $R^{3d}$ are hydrogen and $R^3$, $R^{3a}$, and $R^{3b}$ are independently alkyl, halo, or —OR$^{11a}$; $R^{11a}$ is hydrogen, alkyl, or alkoxyalkyl; and all other groups are independently as defined in the Summary of the Invention for a Compound of Formula I or as defined in embodiment (1).

Embodiments (E2b)

In another embodiment, $R^2$ is quinazolin-4-yl substituted with $R^3$, $R^{3a}$, $R^{3b}$, $R^{3c}$, and $R^{3d}$; $R^{3b}$, $R^{3c}$, and $R^{3d}$ are hydrogen, and $R^3$ and $R^{3a}$ are independently cyano, alkyl, alkenyl, halo, haloalkyl, hydroxyalkyl, alkoxyalkyl, —SR$^{12}$; —S(O)$_2$R$^{20}$, —C(O)OR$^4$, halocarbonyl, —NR$^{11}$R$^{11a}$, —OR$^{11a}$, optionally substituted phenyl, optionally substituted phenylalkyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, or alkyl substituted with one or two $R^{16}$; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3b}$, $R^{3c}$, and $R^{3d}$ are hydrogen, and $R^3$ and $R^{3a}$ are independently alkyl, halo, —S(O)$_2$R$^{20}$; —OR$^{11a}$, or alkyl substituted with one $R^{16}$; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3b}$, $R^{3c}$, and $R^{3d}$ are hydrogen, and $R^3$ and $R^{3a}$ are independently alkyl, halo, —S(O)$_2$R$^{20}$; —OR$^{11a}$, or alkyl substituted with one $R^{16}$; $R^{11a}$ is hydrogen, alkyl, aminoalkyl, alkylaminoalkyl, dialkylaminoalkyl, phenyl, cycloalkylalkyl, phenylalkyl, or heteroaryl; $R^{16}$ is amino, alkylamino, dialkylamino, or cycloalkylamino; $R^{20}$ is alkyl; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3b}$, $R^{3c}$, and $R^{3d}$ are hydrogen, and $R^3$ is —OR$^{11a}$ and $R^{3a}$ is hydrogen, alkyl (in another embodiment alkyl is $C_{1-2}$-alkyl), or alkyl substituted with one $R^{16}$; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3b}$, $R^{3c}$, and $R^{3d}$ are hydrogen, and $R^3$ is —OR$^{11a}$ and $R^{3a}$ is hydrogen, alkyl, or alkyl substituted with one $R^{16}$; $R^{11a}$ is hydrogen or alkyl; $R^{16}$ is amino, alkylamino, dialkylamino, or cycloalkylamino; and all other groups are independently as defined in the Summary of the Invention for a Compound of Formula I or as defined in embodiment (1).

Embodiments (E2c)

In another embodiment, $R^2$ is quinazolin-4-yl substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen and $R^3$ is cyano, alkyl, alkenyl, halo, haloalkyl, hydroxyalkyl, alkoxyalkyl, —SR$^{12}$, —S(O)$_2$R$^{20}$, —C(O)OR$^4$, halocarbonyl, —NR$^{11}$R$^{11a}$, —OR$^{11a}$, optionally substituted phenyl, optionally substituted phenylalkyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, or alkyl substituted with one or two $R^{16}$; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen and $R^3$ is alkyl, halo, haloalkyl, alkylsulfonyl, optionally substituted phenyl, carboxy, alkoxycarbonyl, —NR$^{11}$R$^{11a}$, alkyl substituted with one $R^{16}$, or —OR$^{11a}$; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen and $R^3$ is alkyl, halo, haloalkyl, alkylsulfonyl, phenyl, carboxy, alkoxycarbonyl, —NR$^{11}$R$^{11a}$, alkyl substituted with one $R^{16}$, or —OR$^{11a}$; $R^{11}$ is hydrogen or alkyl; $R^{11a}$ is hydrogen, alkyl, alkoxyalkyl, cyanoalkyl, or optionally substituted phenylalkyl; $R^{16}$ is amino, alkylamino, dialkylamino, or cycloalkylamino; and all other groups are independently as defined in the Summary of the Invention for a Compound of Formula I or as defined in embodiment (1). In another embodiment, $R^2$ is quinazolin-4-yl substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen and $R^3$ is methyl, ethyl, n-propyl, isopropyl, n-butyl, sec-butyl, isoamyl, bromo, chloro, fluoro, iodo, trifluoromethyl, methylsulfonyl, phenyl, methoxycarbonyl, ethoxycarbonyl, amino, methylamino, ethylamino, n-propylamino, isopropylamino, dimethylamino, diethylamino, N-methyl-N-ethylamino, hydroxy, methoxy, ethyloxy, n-propoxy, isopropoxy, n-butyloxy, sec-butyloxy, isoamyloxy, 2-aminoethyloxy, 2-(methylamino)-ethyloxy, 2-(dimethylamino)-ethyloxy, 3-amino-propyloxy, 3-(methylamino)-propyloxy, 3-(dimethylamino)-propyloxy, 2-methoxy-ethyloxy, cyanomethyloxy, and benzyloxy; and all other groups are independently as defined in the Summary of the Invention for a Compound of Formula I or as defined in embodiment (1).

Embodiments (E2d)

In another embodiment, $R^2$ is quinazolin-4-yl, pyrido[3,2-d]pyrimidin-4-yl, pyrido[4,3-d]pyrimidin-4-yl, pyrido[3,4-d]pyrimidin-4-yl, pyrido[2,3-d]pyrimidin-4-yl, 2-methyl-quinazolin-4-yl, 6-methyl-quinazolin-4-yl, 7-methyl-quinazolin-4-yl, 8-methyl-quinazolin-4-yl, 2-ethyl-quinazolin-4-yl, 2-phenyl-quinazolin-4-yl, 7-(quinolin-2-ylmethyloxy)-8-methoxy-quinazolin-4-yl, 7-(2-dimethylamino-ethyloxy)-8-methoxy-quinazolin-4-yl, 6-(3-dimethylamino-propyloxy)-8-methoxy-quinazolin-4-yl, 7-(cyclopropylmethyloxy)-8-methoxy-quinazolin-4-yl, 6-(cyanomethyloxy)-quinazolin-4-yl, 6-methoxy-quinazolin-4-yl, 7-methoxy-quinazolin-4-yl, 8-methoxy-quinazolin-4-yl, 6-ethoxy-quinazolin-4-yl, 6-(n-propoxy)-quinazolin-4-yl, 6,7-dimethoxy-quinazolin-4-yl, 7,8-dimethoxy-quinazolin-4-yl, 7-isoamyloxy-8-methoxy-quinazolin-4-yl, 5-bromo-quinazolin-4-yl, 6-bromo-quinazolin-4-yl, 7-bromo-quinazolin-4-yl, 8-bromo-quinazolin-4-yl, 5-chloro-quinazolin-4-yl, 6-chloro-quinazolin-4-yl, 7-chloro-quinazolin-4-yl, 8-chloro-quinazolin-4-yl, 5-fluoro-quinazolin-4-yl, 6-fluoro-quinazolin-4-yl, 7-fluoro-quinazolin-4-yl, 8-fluoro-quinazolin-4-yl, 5-iodo-quinazolin-4-yl, 6-iodo-quinazolin-4-yl, 7-iodo-quinazolin-4-yl, 8-iodo-quinazolin-4-yl, 6-bromo-7-chloro-quinazolin-4-yl, 6-iodo-7-chloro-quinazolin-4-yl, 6,8-dichloro-quinazolin-4-yl, 6,7-difluoro-quinazolin-4-yl, 6,8-dibromo-quinazolin-4-yl, 2-methyl-7-methoxy-quinazolin-4-yl, 2-ethyl-7-methoxy-quinazolin-4-yl, 2-methyl-6,7-dimethoxy-quinazolin-4-yl, 6-iodo-7-methoxy-quinazolin-4-yl, 6-chloro-7-methoxy-quinazolin-4-yl, 2-chloro-6-methoxy-quinazolin-4-yl, 6-bromo-7-methoxy-quinazolin-4-yl, 7-bromo-8-methoxy-quinazolin-4-yl, 7-bromo-6-methoxy-quinazolin-4-yl, 6-chloro-7,8-dimethoxy-quinazolin-4-yl, 6,7,8-trimethoxy-quinazolin-4-yl, 6-(2-methoxy-ethyloxy)-quinazolin-4-yl, 6-(benzyoxy)-quinazolin-4-yl, 6-hydroxy-quinazolin-4-yl, 7-(benzyoxy)-8-methoxy-quinazolin-4-yl, 7-hydroxy-8-methoxy-quinazolin-4-yl, 7-(benzyoxy)-6-methoxy-quinazolin-4-yl, 7-hydroxy-6-methoxy-quinazolin-4-yl, 6-iodo-8-methyl-quinazolin-4-yl, 6-methyl-8-bromo-quinazolin-4-yl, 2-ethoxycarbonyl-quinazolin-4-yl, 2-methylamino-quinazolin-4-yl, 2-ethylamino-quinazolin-4-yl, 2-(diethylamino)-quinazolin-4-yl, 2-(trifluoromethyl)-quinazolin-4-yl, 7-(trifluoromethyl)-quinazolin-4-yl, 8-(trifluoromethyl)-quinazolin-4-yl, 6-methylsulfonyl-quinazolin-4-yl, 7-methylsulfonyl-quinazolin-4-yl, quinazolin-4-yl, quinazolin-4-yl, or quinazolin-4-yl; and all other groups are independently as defined in the Summary of the Invention for a Compound of Formula I or as defined in embodiment (1).

Embodiments (E2e)

In another embodiment, $R^2$ is pyrido[3,2-d]pyrimidin-4-yl; and all other groups are independently as defined in the Summary of the Invention for a Compound of Formula I or as defined in embodiment (1).

Embodiments (E3)

In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, 7',8'-dihydro-5'H-spiro[cyclopropane-1,6'-quinazoline]-4'-yl, or 6',8'-dihydro-5'H-spiro[cyclopropane-1,7'-quinazoline]-4'-yl where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, 7',8'-dihydro-5'H-spiro[cyclopropane-1,6'-quinazoline]-4'-yl, or 6',8'-dihydro-5'H-spiro[cyclopropane-1,7'-quinazoline]-4'-yl where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ are hydrogen; and all other groups are independently as defined in the Summary of the Invention for a Compound of Formula I or as defined in embodiment (1).

Embodiments (E3a)

In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ are independently hydrogen, alkyl, alkenyl, halo, haloalkyl, hydroxyalkyl, cyanoalkyl, —$SR^{12}$, optionally substituted phenyl, —$OR^{11a}$, alkyl substituted with one $R^{16}$, optionally substituted heterocycloalkyl, optionally substituted heterocycloalkylalkyl, or optionally substituted heteroaryl; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ are independently hydrogen, alkyl, alkenyl, halo, haloalkyl, hydroxyalkyl, cyanoalkyl, —$SR^{12}$, phenyl, —$OR^{11a}$, alkyl substituted with one $R^{16}$, heterocycloalkyl (optionally substituted with alkoxycarbonyl, phenylalkyloxycarbonyl, or alkyl), heterocycloalkylalkyl (optionally substituted with one or two halo), or heteroaryl; $R^{12}$ is alkyl or phenylalkyl; $R^{16}$ is $NR^{11}R^{11a}$, —$NR^{15}S(O)R^{15a}$, —$OR^{18}$, or —$OC(O)R^{17}$; $R^{11}$ is hydrogen or alkyl; each $R^{11a}$ is independently hydrogen, alkyl, haloalkyl, alkoxyalkyl, carboxyalkyl, cycloalkyl, or cycloalkylalkyl; and all other groups are independently as defined in the Summary of the Invention for a Compound of Formula I or as defined in embodiment (1).

Embodiments (E3b)

In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3a}$, $R^{3b}$, $R^{3c}$, and $R^{3d}$ are hydrogen, and $R^3$ and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3a}$, $R^{3b}$, $R^{3c}$, and $R^{3d}$ are hydrogen, and $R^3$ is alkyl, alkenyl, hydroxyalkyl, alkoxyalkyl, haloalkyl, optionally substituted phenyl, alkyl substituted with one $R^{16}$, or —$SR^{12}$; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3a}$, $R^{3b}$, $R^{3c}$, and $R^{3d}$ are hydrogen, and $R^3$ is alkyl, alkenyl, hydroxyalkyl, alkoxyalkyl, haloalkyl, phenyl, alkyl substituted with one $R^{16}$, or —$SR^{12}$; $R^{12}$ is alkyl or optionally substituted phenylalkyl; and all other groups are independently as defined in the Summary of the Invention for a Compound of Formula I or as defined in embodiment (1).

Embodiments (E3c)

In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3b}$, $R^{3c}$, $R^{3d}$ are hydrogen, and $R^3$ and $R^{3a}$ are independently alkyl, halo, optionally substituted phenyl, —$SR^{12}$, or alkyl substituted with one $R^{16}$; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3b}$, $R^{3c}$, $R^{3d}$ are hydrogen, and $R^3$ and $R^{3a}$ are independently alkyl, halo, phenyl, alkyl substituted with one $R^{16}$, or —$SR^{12}$; $R^{12}$ is alkyl or phenyl; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3b}$, $R^{3c}$, $R^{3d}$ are hydrogen, $R^3$ is alkyl (in another embodiment alkyl is $C_{1-2}$-alkyl), and $R^{3a}$ is alkyl (in another embodiment alkyl is $C_{1-2}$-alkyl), halo, phenyl, alkyl substituted with one $R^{16}$, —$SR^{12}$; or $R^{12}$ is alkyl or phenyl; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3b}$, $R^{3c}$, $R^{3d}$ are hydrogen, $R^3$ and $R^{3a}$ are alkyl, (in another embodiment each alkyl is $C_{1-2}$-alkyl); and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3b}$, $R^{3c}$, $R^{3d}$ are hydrogen, $R^3$ and $R^{3a}$ are halo; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3b}$, $R^{3c}$, $R^{3d}$ are hydrogen, $R^3$ is alkyl (in another embodiment alkyl is $C_{1-2}$-alkyl), and $R^{3a}$ is hydrogen, alkyl, or alkyl substituted with $R^{16}$; and all other groups are independently as defined in the Summary of the Invention for a Compound of Formula I or as defined in embodiment (1).

Embodiments (E3d)

In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3c}$, $R^{3d}$ are hydrogen, and $R^3$, $R^{3a}$, and $R^{3b}$ are independently alkyl, alkenyl, halo, hydroxyalkyl, cyanoalkyl, alkyl substituted with $R^{16}$, heterocycloalkyl, or heterocycloalkylalkyl (optionally substituted with one or two halo); and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3c}$, $R^{3d}$ are hydrogen, and $R^3$, $R^{3a}$, and $R^{3b}$ are independently alkyl, alkenyl, halo, hydroxyalkyl, cyanoalkyl, alkyl substituted with $R^{16}$, heterocycloalkyl, or heterocycloalkylalkyl (optionally substituted with one or two halo); $R^{16}$ is $NR^{11}R^{11a}$ where $R^{11}$ is hydrogen or alkyl and $R^{11a}$ is alkyl, haloalkyl, alkoxyalkyl, cycloalkyl, cycloalkylalkyl, or carboxyalkyl; or $R^{16}$ is —$NR^{15}S(O)R^{15a}$ where $R^{15}$ and $R^{15a}$ are independently hydrogen or alkyl; or $R^{16}$ is —$OC(O)R^{17}$ where $R^{17}$ is alkyl; $R^{16}$ is —$OR^{18}$ where $R^{18}$ is alkyl or alkoxyalkyl; and all other groups are independently as defined in the Summary of the Invention for a Compound of Formula I or as defined in embodiment (1).

Embodiments (E3e)

In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3c}$, $R^{3d}$ are hydrogen, and $R^3$, $R^{3a}$, and $R^{3b}$ are alkyl (in another embodiment each alkyl is $C_{1-2}$-alkyl); and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3c}$, $R^{3d}$ are hydrogen, $R^3$ and $R^{3a}$ are alkyl (in another embodiment each alkyl is $C_{1-2}$-alkyl), and $R^{3b}$ is alkyl substituted with $R^{16}$; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3c}$, $R^{3d}$ are hydrogen, $R^3$ and $R^{3a}$ are alkyl (in another embodiment each alkyl is $C_{1-2}$-alkyl), and $R^{3b}$ is heterocycloalkylalkyl; and all other groups are independently as defined in the Summary of the Invention for a Compound of Formula I or as defined in embodiment (1). In another embodiment, $R^2$ is 5,6,7,8-tetrahydroquinazolin-4-yl, 6,7-dihydro-5H-cyclopenta[d]pyrimidin-4-yl, 6,7,8,9-tetrahydro-5H-cyclohepta[d]pyrimidin-4-yl, 5,6-dihydroquinazolin-4-yl, or 7',8'-dihydro-5'H-spiro[cyclopropane-1,6'-quinazoline]-4'-yl, where $R^2$ is substituted with $R^3$, $R^{3a}$, $R^{3b}$, $R^{3c}$, and $R^{3d}$; where $R^{3c}$, $R^{3d}$ are hydrogen, $R^3$ and $R^{3a}$ are alkyl (in another embodiment each alkyl is $C_{1-2}$-alkyl), and $R^{3b}$ is heterocycloalkyl; and all other groups are independently as defined in the Summary of the Invention for a Compound of Formula I or as defined in embodiment (1).

Embodiments (E3f)

In another embodiment, $R^2$ is 6,7-dihydro-5H-cyclopenta[d]pyrimidin-4-yl, 6-methyl-6,7-dihydro-5H-cyclopenta[d]pyrimidin-4-yl, 6,6-dimethyl-6,7-dihydro-5H-cyclopenta[d]pyrimidin-4-yl, 6-methyl-2-(methylthio)-6,7-dihydro-5H-cyclopenta[d]pyrimidin-4-yl, 2-(ethylthio)-6,7-dihydro-5H-cyclopenta[d]pyrimidin-4-yl, 2-(phenylmethylthio)-6,7-dihydro-5H-cyclopenta[d]pyrimidin-4-yl, 5-phenyl-6,7-dihydro-5H-cyclopenta[d]pyrimidin-4-yl, 6-phenyl-6,7-dihydro-5H-cyclopenta[d]pyrimidin-4-yl, 5,6,7,8-tetrahydroquinazolin-4-yl, 6-methyl-5,6,7,8-tetrahydroquinazolin-4-yl, 6-ethyl-5,6,7,8-tetrahydroquinazolin-4-yl, 7-methyl-5,6,7,8-tetrahydroquinazolin-4-yl, 7-methyl-7-phenyl-5,6,7,8-tetrahydroquinazolin-4-yl, 6,6-dimethyl-5,6,7,8-tetrahydroquinazolin-4-yl, or 7,7-dimethyl-5,6,7,8-tetrahydroquinazolin-4-yl; and all other groups are independently as defined in the Summary of the Invention for a Compound of Formula I or as defined in embodiment (1).

Embodiments (E4)

In another embodiment, $R^2$ is according to Formula (c)

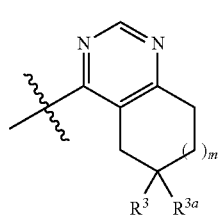

(c)

where m is 0 or 1 and $R^3$, $R^{3a}$ and all other groups are independently as defined in the Summary of the Invention for a Compound of Formula I or as defined in embodiment (1). In another embodiment, $R^2$ is according to Formula (c) where m is 0 or 1 and $R^3$ and $R^{3a}$, together with the carbon to which they are attached, form an optionally substituted cycloalkyl or an optionally substituted heterocycloalkyl; and all other groups are independently as defined in the Summary of the Invention for a Compound of Formula I or as defined in embodiment (1). In another embodiment, $R^2$ is according to Formula (c) where m is 0 or 1 and $R^3$ and $R^{3a}$ are alkyl (in another embodiment each alkyl is $C_{1-2}$-alkyl); and all other groups are independently as defined in the Summary of the Invention for a Compound of Formula I or as defined in embodiment (1). In another embodiment, $R^2$ is according to Formula (c) where m is 0 or 1 and $R^3$ and $R^{3a}$ are halo; and all other groups are independently as defined in the Summary of the Invention for a Compound of Formula I or as defined in embodiment (1).

Embodiments (E4a)

In another embodiment, $R^2$ is according to formula (c), m is 1, $R^3$ and $R^{3a}$ are as defined in any of the embodiments (E4d); and all other groups are as defined in the Summary of the Invention for a Compound of Formula I or as defined in embodiment (1).

Embodiments (E4b)

In another embodiment, $R^2$ is 6,6-dimethyl-5,6,7,8-tetrahydroquinazolin-4-yl, 6,6-dichloro-5,6,7,8-tetrahydroquinazolin-4-yl, 6,6-difluoro-5,6,7,8-tetrahydroquinazolin-4-yl, 7,7-dimethyl-5,6,7,8-tetrahydroquinazolin-4-yl, 7,7-dichloro-5,6,7,8-tetrahydroquinazolin-4-yl, 7',8'-dihydro-5'H-spiro[cyclopropane-1,6'-quinazoline]-4'-yl, or 6',8'-dihydro-5'H-spiro[cyclopropane-1,7'-quinazoline]-4'-yl, where $R^2$ is substituted with $R^{3b}$ where $R^{3b}$ is hydrogen, alkyl, or haloalkyl; and all other groups are independently as defined in the Summary of the Invention for a Compound of Formula I or as defined in embodiment (1).

Embodiments (E4d)

In another embodiment, $R^2$ is according to Formula (d)

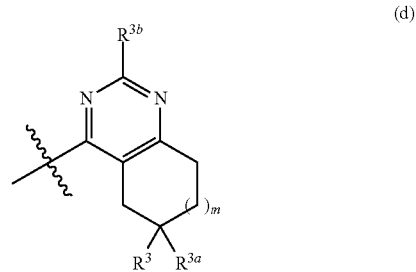

(d)

where m is 0 or 1; $R^3$, $R^{3a}$, $R^{3b}$, and all other groups are independently as defined in the Summary of the Invention for a Compound of Formula I or as defined in embodiment (1). In another embodiment, $R^2$ is according to Formula (d) where m is 0 or 1; $R^3$ and $R^{3a}$ are alkyl (in another embodiment each alkyl is $C_{1-2}$-alkyl); and all other groups are independently as defined in the Summary of the Invention for a Compound of Formula I or as defined in embodiment (1). In another embodiment, $R^2$ is according to Formula (d) where m is 0 or 1; $R^3$ and $R^{3a}$ are halo; and all other groups are independently as defined in the Summary of the Invention for a Compound of Formula I or as defined in embodiment (1). In another embodiment, $R^2$ is according to Formula (d) where m is 1; $R^3$ and $R^{3a}$ are alkyl (in another embodiment each alkyl is $C_{1-2}$-alkyl); and all other groups are independently as defined in the Summary of the Invention for a Compound of Formula I or as defined in embodiment (1). In another embodiment, $R^2$ is according to Formula (d) where m is 1; $R^3$ and $R^{3a}$ are halo;

and all other groups are independently as defined in the Summary of the Invention for a Compound of Formula I or as defined in embodiment (1). In another embodiment, R² is according to Formula (d) where m is 1; R³ and R³ᵃ are alkyl (in another embodiment each alkyl is C₁₋₂-alkyl); R³ᵇ is hydrogen, alkyl, alkenyl, hydroxyalkyl, cyanoalkyl, heterocycloalkyl (optionally substituted with alkoxycarbonyl, benzyloxycarbonyl, or alkyl), heterocycloalkylalkyl (optionally substituted with one or two halo), or alkyl substituted with one R¹⁶; and all other groups are independently as defined in the Summary of the Invention for a Compound of Formula I or as defined in embodiment (1). In another embodiment, R² is according to Formula (d) where m is 1; R³ and R³ᵃ are alkyl (in another embodiment each alkyl is C₁₋₂-alkyl); R³ᵇ is hydrogen, alkyl, alkenyl, hydroxyalkyl, cyanoalkyl, heterocycloalkyl (optionally substituted with alkoxycarbonyl, benzyloxycarbonyl, or alkyl), heterocycloalkylalkyl (optionally substituted with one or two halo), or alkyl substituted with one R¹⁶; R¹⁶ is —NR¹¹R¹¹ᵃ, —NR¹⁵S(O)₂R¹⁵ᵃ, —OC(O)R¹⁷, or —OR¹⁸; and all other groups are independently as defined in the Summary of the Invention for a Compound of Formula I or as defined in embodiment (1). In another embodiment, R² is according to Formula (d) where m is 1; R³ and R³ᵃ are alkyl (in another embodiment each alkyl is C₁₋₂-alkyl); R³ᵇ is hydrogen, alkyl (in another embodiment alkyl is C₁₋₂-alkyl), cyanoalkyl, or alkyl substituted with one R¹⁶; and all other groups are independently as defined in the Summary of the Invention for a Compound of Formula I or as defined in embodiment (1).

In another embodiment, the Compound is according to Formula I(a), R² is according to embodiments (E4d) and R¹ is according to embodiments (Z)-(Z5).

Embodiments (E5a)

In another embodiment, R² is according to Formula (e)

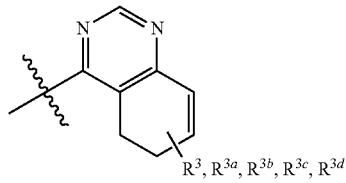

where R³, R³ᵃ, R³ᵇ, R³ᶜ, and R³ᵈ are positioned on any substitutable carbon of ring (e); and all other groups are independently as defined in the Summary of the Invention for a Compound of Formula I or as defined in embodiment (1). In another embodiment, R² is according to Formula (e) where one of R³, R³ᵃ, R³ᵇ, R³ᶜ, and R³ᵈ is hydrogen, alkyl (in another embodiment each alkyl is C₁₋₂-alkyl), or alkyl substituted with one R¹⁶ and the other of R³, R³ᵃ, R³ᵇ, R³ᶜ, and R³ᵈ and all other groups are independently as defined in the Summary of the Invention for a Compound of Formula or as defined in embodiment (1). In another embodiment, R² is according to Formula (e) where one of R³, R³ᵃ, R³ᵇ, R³ᶜ, and R³ᵈ is hydrogen, alkyl (in another embodiment alkyl is C₁₋₂-alkyl), or alkyl substituted with one R¹⁶ and the other of R³, R³ᵃ, R³ᵇ, R³ᶜ, and R³ᵈ are independently hydrogen or alkyl (in another embodiment each alkyl is C₁₋₂-alkyl); and all other groups are as defined in the Summary of the Invention for a Compound of Formula or as defined in embodiment (1). In another embodiment, R² is according to Formula (e) where one of R³, R³ᵃ, R³ᵇ, R³ᶜ, and R³ᵈ is hydrogen, alkyl (in another embodiment each alkyl is C₁₋₂-alkyl), or alkyl substituted with one R¹⁶ and the other of R³, R³ᵃ, R³ᵇ, R³ᶜ, and R³ᵈ are alkyl, (in another embodiment each alkyl is C₁₋₂-alkyl); and all other groups are as defined in the Summary of the Invention for a Compound of Formula or as defined in embodiment (1). In another embodiment, R² is according to Formula (e) where one of R³, R³ᵃ, R³ᵇ, R³ᶜ, and R³ᵈ is hydrogen, alkyl (in another embodiment alkyl is C₁₋₂-alkyl), or alkyl substituted with one R¹⁶, a second of R³, R³ᵃ, R³ᵇ, R³ᶜ, and R³ᵈ is hydrogen, and the other of R³, R³ᵃ, R³ᵇ, R³ᶜ, and R³ᵈ are alkyl (in another embodiment each alkyl is C₁₋₂-alkyl); and all other groups are as defined in the Summary of the Invention for a Compound of Formula or as defined in embodiment (1).

In another embodiment, the Compound is according to Formula I(a), R² is according to embodiments (E5a) and R¹ is according to embodiments (Z)-(Z5).

Embodiments (E5b)

In another embodiment, R² is according to Formula (f)

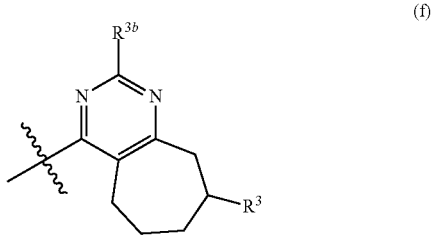

where R³ᵇ is hydrogen, alkyl (in another embodiment alkyl is C₁₋₃-alkyl), cyanoalkyl, or alkyl substituted with one R¹⁶; and R³ is hydrogen, alkyl (in another embodiment alkyl is C₁₋₃-alkyl), or alkenyl; and all other groups are as defined in the Summary of the Invention for a Compound of Formula or as defined in embodiment (1).

In another embodiment, the Compound is according to Formula I(a), R² is according to embodiments (E5b) and R¹ is according to embodiments (Z)-(Z5).

Embodiments (E5c)

In another embodiment, R² is according to Formula (g)

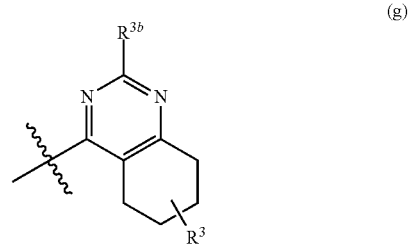

where R³ᵇ is hydrogen, alkyl (in another embodiment alkyl is C₁₋₃-alkyl), cyanoalkyl, or alkyl substituted with one R¹⁶; and R³ is alkyl (in another embodiment alkyl is C₁₋₃-alkyl), hydroxyalkyl, alkoxyalkyl, or haloalkyl, and is located at the 6- or 7-position of the ring; and all other groups are as defined in the Summary of the Invention for a Compound of Formula or as defined in embodiment (1).

In another embodiment, the Compound is according to Formula I(a), $R^2$ is according to embodiments (E5c) and $R^1$ is according to embodiments (Z)-(Z5).

Embodiments (E5d)

In another embodiment, $R^2$ is according to Formula (h)

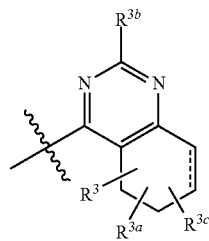

(h)

where $R^3$, $R^{3a}$, $R^{3b}$, and $R^{3c}$ and all other groups are as defined in the Summary of the Invention for a Compound of Formula or as defined in embodiment (1). In another embodiment, $R^2$ is according to Formula (h) where $R^{3b}$ is hydrogen, alkyl, cyanoalkyl, or alkyl substituted with one $R^{16}$; and all other groups are as defined in the Summary of the Invention for a Compound of Formula or as defined in embodiment (1). In another embodiment, $R^2$ is according to Formula (h) where $R^{3b}$ is hydrogen, cyanoalkyl, alkyl (in another embodiment alkyl is $C_{1-3}$-alkyl), or alkyl substituted with one $R^{16}$; $R^3$, $R^{3a}$, and $R^{3c}$ are independently hydrogen, alkyl (in another embodiment alkyl is $C_{1-3}$-alkyl), alkenyl, halo, haloalkyl, hydroxyalkyl, —$SR^{12}$, optionally substituted phenyl, —$OR^{11a}$, alkyl substituted with one $R^{16}$, optionally substituted heterocycloalkyl, optionally substituted heterocycloalkylalkyl, or optionally substituted heteroaryl; and all other groups are as defined in the Summary of the Invention for a Compound of Formula or as defined in embodiment (1).

In another embodiment, the Compound is according to Formula I(a), $R^2$ is according to embodiments (E5d) and $R^1$ is according to embodiments (Z)-(Z5).

Embodiments (E6)

In another embodiment, $R^2$ is quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, or isoquinolin-8-yl, where $R^2$ is substituted with $R^3$, $R^{3a}$, $R^{3b}$, and $R^{3c}$; where $R^3$, $R^{3a}$, $R^{3b}$, and $R^{3c}$ and all other groups are independently as defined in the Summary of the Invention for a Compound of Formula I or as defined in embodiment (1). In another embodiment, $R^2$ is quinolin-4-yl or isoquinolin-1-yl, where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently as defined in the Summary of the Invention for a Compound of Formula I or as defined in embodiment (1).

Embodiments (E6a)

In another embodiment, $R^2$ is quinolin-4-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, or isoquinolin-8-yl, where $R^2$ is substituted with $R^3$, $R^{3a}$, $R^{3b}$, $R^{3c}$, and $R^{3d}$; $R^{3b}$, $R^{3c}$, and $R^{3d}$ are hydrogen; $R^3$ and $R^{3a}$ are independently hydrogen, cyano, alkyl, halo, haloalkyl, —$OR^{11a}$, phenyl, phenylalkyl optionally substituted with one or two $R^{19}$, or alkyl substituted with one or two $R^{16}$; and all other groups are independently as defined in the Summary of the Invention for a Compound of Formula I or as defined in embodiment (1). In another embodiment, $R^2$ is quinolin-4-yl or isoquinolin-1-yl, where $R^2$ is substituted with $R^3$, $R^{3a}$, $R^{3b}$, $R^{3c}$, and $R^{3d}$; $R^{3b}$, $R^{3c}$, and $R^{3d}$ are hydrogen; $R^3$ and $R^{3a}$ are independently $R^3$ and $R^{3a}$ are independently hydrogen, cyano, alkyl (in another embodiment alkyl is $C_{1-3}$-alkyl), halo, haloalkyl, —$OR^{11a}$, phenyl, phenylalkyl optionally substituted with one or two $R^{19}$, or alkyl substituted with one or two $R^{16}$; and all other groups are independently as defined in the Summary of the Invention for a Compound of Formula I or as defined in embodiment (1).

Embodiments (E6b)

In another embodiment, $R^2$ is 6,7-dimethoxy-quinolin-4-yl, 7-cyano-quinolin-4-yl, 5-fluoro-quinolin-4-yl, 6-fluoro-quinolin-4-yl, 7-fluoro-quinolin-4-yl, 8-fluoro-quinolin-4-yl, 2-phenyl-quinolin-4-yl, 2-methyl-quinolin-4-yl, 2-methyl-7-methoxy-quinolin-4-yl, 2-trifluoromethyl-quinolin-4-yl, or isoquinolin-1-yl; and all other groups are independently as defined in the Summary of the Invention for a Compound of Formula I or as defined in embodiment (1).

Embodiments (E7)

In another embodiment, $R^2$ is 5H-pyrrolo[3,2-d]pyrimidin-4-yl, thieno[2,3-d]pyrimidin-4-yl, 7H-pyrrolo[2,3-d]pyrimidin-4-yl, 1H-pyrrolo[2,3-b]pyridin-4-yl, 1H-pyrrolo[3,2-c]pyridin-4-yl, thieno[2,3-b]pyridin-4-yl, or thieno[3,2-c]pyridin-4-yl, where $R^2$ is substituted with $R^3$, $R^{3a}$, $R^{3b}$, $R^{3c}$, and $R^{3d}$; $R^3$, $R^{3a}$, $R^{3b}$, $R^{3c}$, and $R^{3d}$ and all other groups are independently as defined in the Summary of the Invention for a Compound of Formula I or as defined in embodiment (1). In another embodiment, $R^2$ is thieno[2,3-d]pyrimidin-4-yl or 7H-pyrrolo[2,3-d]pyrimidin-4-yl, where $R^2$ is substituted with $R^3$, $R^{3a}$, $R^{3b}$, $R^{3c}$, and $R^{3d}$; $R^3$, $R^{3a}$, $R^{3b}$, $R^{3c}$, and $R^{3d}$ and all other groups are independently as defined in the Summary of the Invention for a Compound of Formula I or as defined in embodiment (1). In another embodiment, $R^2$ is thieno[2,3-d]pyrimidin-4-yl or 7H-pyrrolo[2,3-d]pyrimidin-4-yl, where $R^2$ is substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen; $R^3$ is hydrogen or alkyl (in another embodiment alkyl is $C_{1-3}$-alkyl); and all other groups are independently as defined in the Summary of the Invention for a Compound of Formula I or as defined in embodiment (1). In another embodiment, $R^2$ is thieno[2,3-d]pyrimidin-4-yl, 5-methyl-thieno[2,3-d]pyrimidin-4-yl, or 7H-pyrrolo[2,3-d]pyrimidin-4-yl; and all other groups are independently as defined in the Summary of the Invention for a Compound of Formula I or as defined in embodiment (1).

Embodiments (E8)

In another embodiment, $R^2$ is 5,7-dihydrothieno[3,4-d]pyrimidin-4-yl, 5,6,7,8-tetrahydropyrido[3,4-d]pyrimidin-4-yl, 5,6,7,8-tetrahydropyrido[4,3-d]pyrimidin-4-yl, 5,6,7,8-tetrahydropyrido[2,3-d]pyrimidin-4-yl, 5,6,7,8-tetrahydropyrido[3,2-d]pyrimidin-4-yl, 6,7-dihydro-5H-pyrrolo[3,4-d]pyrimidin-4-yl, 6,7-dihydro-5H-pyrrolo[3,2-d]pyrimidin-4-yl, or 6,7-dihydro-5H-pyrrolo[2,3-d]pyrimidin-4-yl, where $R^2$ is substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently

57 as defined in the Summary of the Invention for a Compound of Formula I or as defined in embodiment (1).

Embodiments (E8a)

In another embodiment, $R^2$ is 5,7-dihydrothieno[3,4-d]pyrimidin-4-yl, 5,6,7,8-tetrahydropyrido[3,4-d]pyrimidin-4-yl, 5,6,7,8-tetrahydropyrido[4,3-d]pyrimidin-4-yl, or 6,7-dihydro-5H-pyrrolo[3,4-d]pyrimidin-4-yl, where $R^2$ is substituted with $R^3$, $R^{3a}$, $R^{3b}$, $R^{3c}$, and $R^{3d}$; $R^3$, $R^{3a}$, $R^{3b}$, $R^{3c}$, and $R^{3d}$ and all other groups are independently as defined in the Summary of the Invention for a Compound of Formula I or as defined in embodiment (1).

Embodiments (E8b)

In another embodiment, $R^2$ is 5,7-dihydrothieno[3,4-d]pyrimidin-4-yl, 5,6,7,8-tetrahydropyrido[3,4-d]pyrimidin-4-yl, 5,6,7,8-tetrahydropyrido[4,3-d]pyrimidin-4-yl, or 6,7-dihydro-5H-pyrrolo[3,4-d]pyrimidin-4-yl, where $R^2$ is substituted with $R^3$, $R^{3a}$, $R^{3b}$, $R^{3c}$, and $R^{3d}$; $R^3$, $R^{3a}$, $R^{3b}$, $R^{3c}$, and $R^{3d}$ and all other groups are independently as defined in the Summary of the Invention for a Compound of Formula I or as defined in embodiment (1). In another embodiment, $R^2$ is 5,7-dihydrothieno[3,4-d]pyrimidin-4-yl, 5,6,7,8-tetrahydropyrido[3,4-d]pyrimidin-4-yl, 5,6,7,8-tetrahydropyrido[4,3-d]pyrimidin-4-yl, or 6,7-dihydro-5H-pyrrolo[3,4-d]pyrimidin-4-yl, where $R^2$ is substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen; $R^3$ is hydrogen, alkyl (in another embodiment alkyl is $C_{1-3}$-alkyl), haloalkyl, optionally substituted phenyl, optionally substituted phenylalkyl, optionally substituted cycloalkyl, or optionally substituted cycloalkylalkyl; and all other groups are independently as defined in the Summary of the Invention for a Compound of Formula I or as defined in embodiment (1).

Embodiments (E8c)

In another embodiment, $R^2$ is 5,7-dihydrothieno[3,4-d]pyrimidin-4-yl, 5,6,7,8-tetrahydropyrido[3,4-d]pyrimidin-4-yl, 7-ethyl-5,6,7,8-tetrahydropyrido[3,4-d]pyrimidin-4-yl, 7-benzyl-5,6,7,8-tetrahydropyrido[3,4-d]pyrimidin-4-yl, 5,6,7,8-tetrahydropyrido[4,3-d]pyrimidin-4-yl, 6-cyclopropyl-5,6,7,8-tetrahydropyrido[4,3-d]pyrimidin-4-yl, 6,7-dihydro-5H-pyrrolo[3,4-d]pyrimidin-4-yl, 6-p-tolyl-6,7-dihydro-5H-pyrrolo[3,4-d]pyrimidin-4-yl, or 6-cyclopropyl-6,7-dihydro-5H-pyrrolo[3,4-d]pyrimidin-4-yl; and all other groups are independently as defined in the Summary of the Invention for a Compound of Formula I or as defined in embodiment (1).

Embodiments (E9)

In another embodiment, $R^2$ is 7H-pyrrolo[2,3-d]pyrimidin-4-yl substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen; $R^3$ and all other groups are independently as defined in the Summary of the Invention for a Compound of Formula I or as defined in embodiment (1). In another embodiment, $R^2$ is 7H-pyrrolo[2,3-d]pyrimidin-4-yl substituted with $R^3$, $R^{3a}$, $R^{3b}$, $R^{3c}$, and $R^{3d}$; $R^3$, $R^{3a}$, $R^{3b}$, $R^{3c}$, and $R^{3d}$ are hydrogen; and all other groups are independently as defined in the Summary of the Invention for a Compound of Formula I or as defined in embodiment (1).

Embodiments (E10)

In another embodiment, $R^2$ is 1H-pyrazolo[3,4-d]pyrimidin-4-yl substituted with $R^3$, $R^{3a}$, $R^{3b}$, $R^{3c}$, and $R^{3d}$; $R^{3a}$, $R^{3b}$,

58

$R^{3c}$, and $R^{3d}$ are hydrogen; $R^3$ and all other groups are independently as defined in the Summary of the Invention for a Compound of Formula I or as defined in embodiment (1). In another embodiment, $R^2$ is 1H-pyrazolo[3,4-d]pyrimidin-4-yl substituted with $R^3$, $R^{3a}$, $R^{3b}$, $R^{3c}$, and $R^{3d}$; $R^3$, $R^{3a}$, $R^{3b}$, $R^{3c}$, and $R^{3d}$ are hydrogen; and all other groups are independently as defined in the Summary of the Invention for a Compound of Formula I or as defined in embodiment (1).

Embodiments (E11)

In another embodiment, $R^2$ is 6,7,8,9-tetrahydropyrimido[4,5-b]indolizin-4-yl substituted with $R^3$, $R^{3a}$, $R^{3b}$, $R^{3c}$, and $R^{3d}$; where $R^3$, $R^{3a}$, $R^{3b}$, $R^{3c}$, and $R^{3d}$ and all other groups are independently as defined in the Summary of the Invention for a Compound of Formula I or as defined in embodiment (1). In another embodiment, $R^2$ is 6,7,8,9-tetrahydropyrimido[4,5-b]indolizin-4-yl substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen; $R^3$ is hydrogen or cyano; and all other groups are independently as defined in the Summary of the Invention for a Compound of Formula I or as defined in embodiment (1). In another embodiment, $R^2$ is 6,7,8,9-tetrahydropyrimido[4,5-b]indolizin-4-yl or 10-cyano-6,7,8,9-tetrahydropyrimido[4,5-b]indolizin-4-yl; and all other groups are independently as defined in the Summary of the Invention for a Compound of Formula I or as defined in embodiment (1).

In another embodiment, the Compound is according to any of embodiments (B) and (H1) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B) and (H1) and $R^2$ is according to any one of embodiments (D2), (D3a)-(D3c), (D3g), (D3i), (E2), (E2b), (E3c), (E4a), (E4d), and (E5a)-(E5d).

In another embodiment, the Compound is according to any of embodiments (B1)-(B2) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B1) and $R^2$ is according to any one of embodiments (D2), (D3a)-(D3c), (D3g), (D3i), (E2), (E2b), (E3c), (E4a), (E4d), and (E5a)-(E5d).

In another embodiment, the Compound is according to any of embodiments (B3), (B4), (B4a), and (B4b) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B4a) and $R^2$ is according to any one of embodiments (D2), (D3a)-(D3c), (D3g), (D3i), (E2), (E2b), (E3c), (E4a), (E4d), and (E5a)-(E5d).

In another embodiment, the Compound is according to any of embodiments (B5), (B6), (B7), and (B8) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B7) and $R^2$ is according to any one of embodiments (D2), (D3a)-(D3c), (D3g), (D3i), (E2), (E2b), (E3c), (E4a), (E4d), and (E5a)-(E5d).

In another embodiment, the Compound is according to any of embodiments (B9)-(B13) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B9)-(B13) and $R^2$ is according to any one of embodiments (D2), (D3a)-(D3c), (D3g), (D3i), (E2), (E2b), (E3c), (E4a), (E4d), and (E5a)-(E5d).

In another embodiment, the Compound is according to any of embodiments (B16), (B16a)-(B16c), (B17), and (B18) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B16a)-(B16c) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B16a)-(B16c) and $R^2$ is according to any one of embodiments (D2), (D3a)-(D3c), (D3g), (D3i), (E2), (E2b), (E3c), (E4a), (E4d), and (E5a)-(E5d).

In another embodiment, the Compound is according to any of embodiments (B19)-(B29) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (B19)-(B29) and $R^2$ is according to any one of embodiments (D2), (D3a)-(D3c), (D3g), (D3i), (E2), (E2b), (E3c), (E4a), (E4d), and (E5a)-(E5d).

In another embodiment, the Compound is according to any of embodiments (C)-(C3) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (C2) and $R^2$ is according to any one of embodiments (D)-(D2), (D3)-(D3k), (D4)-(D4b), (D5), (D6-D6d), (D7)-(D7d), (E)-(E2), (E2a)-(E2e), (E3)-(E3f), (E4)-(E4d), (E5a)-(E5d), (E6)-(E6b), (E7), (E8)-(E8c), and (E9)-(E11). In another embodiment, the Compound is according to any of embodiments (C2) and $R^2$ is according to any one of embodiments (D2), (D3a)-(D3c), (D3g), (D3i), (E2), (E2b), (E3c), (E4a), (E4d), and (E5a)-(E5d).

Embodiments Z

In another embodiment, the Compound is that where $R^1$ is benzimidazol-6-yl optionally substituted with one or two $R^7$; and $R^7$ is as defined in the Summary of the Invention for a Compound of Formula I or as defined in embodiment (1). In another embodiment, the Compound is that where $R^1$ is benzimidazol-6-yl optionally substituted with one or two $R^7$; each $R^7$, when present, is alkyl, haloalkyl, $—NR^8R^{8a}$, $—NR^8C(O)OR^9$, or cycloalkyl; and $R^8$, $R^{8a}$, and $R^9$ are independently as defined in the Summary of the Invention for a Compound of Formula I or as defined in embodiment (1). In another embodiment, the Compound is that where $R^1$ is benzimidazol-6-yl optionally substituted with one or two $R^7$; each $R^7$, when present, is independently alkyl (in another embodiment alkyl is $C_{1-3}$-alkyl), haloalkyl, $—NR^8R^{8a}$, $—NR^8C(O)OR^9$, or cycloalkyl; $R^8$ is hydrogen; $R^{8a}$ is hydrogen, alkyl (in another embodiment alkyl is $C_{1-3}$-alkyl), or haloalkyl; $R^9$ is hydrogen or alkyl (in another embodiment alkyl is $C_{1-3}$-alkyl).

Embodiments Z1

In another embodiment, the Compound is that where $R^1$ is thiazolo[5,4-b]pyridin-6-yl or thiazolo[4,5-b]pyridin-6-yl optionally substituted with one or two $R^7$; and $R^7$ is as defined in the Summary of the Invention for a Compound of Formula I or as defined in embodiment (1). In another embodiment, the Compound is that where $R^1$ is thiazolo[5,4-b]pyridin-6-yl or thiazolo[4,5-b]pyridin-6-yl optionally substituted with one or two $R^7$; each $R^7$, when present, is independently alkyl, haloalkyl, $—NR^8R^{8a}$, $—NR^8C(O)OR^9$, or cycloalkyl; and $R^8$, $R^{8a}$, and $R^9$ are independently as defined in the Summary of the Invention for a Compound of Formula I or as defined in embodiment (1). In another embodiment, the Compound is that where $R^1$ is thiazolo[5,4-b]pyridin-6-yl or thiazolo[4,5-b]pyridin-6-yl optionally substituted with one or two $R^7$; each $R^7$, when present, is independently alkyl (in another embodiment alkyl is $C_{1-3}$-alkyl), haloalkyl, $—NR^8R^{8a}$, $—NR^8C(O)OR^9$, or cycloalkyl; $R^8$ is hydrogen; $R^{8a}$ is hydrogen, alkyl (in another embodiment alkyl is $C_{1-3}$-alkyl), or haloalkyl; $R^9$ is hydrogen or alkyl (in another embodiment alkyl is $C_{1-3}$-alkyl).

Embodiments Z2

In another embodiment, the Compound is that where $R^1$ is 1H-imidazo[4,5-b]pyridin-5-yl, 1H-imidazo[4,5-b]pyridin-6-yl, 3H-imidazo[4,5-b]pyridin-5-yl, or 3H-imidazo[4,5-b]pyridin-6-yl where $R^1$ is optionally substituted with $R^7$; and $R^7$ is as defined in the Summary of the Invention for a Compound of Formula I or as defined in embodiment (1). In another embodiment, the Compound is that where $R^1$ is 1H-imidazo[4,5-b]pyridin-5-yl, 1H-imidazo[4,5-b]pyridin-6-yl, 3H-imidazo[4,5-b]pyridin-5-yl, or 3H-imidazo[4,5-b]pyridin-6-yl where $R^1$ is optionally substituted with one or two $R^7$; each $R^7$, when present, is independently alkyl (in another embodiment alkyl is $C_{1-3}$-alkyl), haloalkyl, $—NR^8R^{8a}$, $—NR^8C(O)OR^9$, or cycloalkyl; and $R^8$, $R^{8a}$, and $R^9$ are independently as defined in the Summary of the Invention for a Compound of Formula I or as defined in embodiment (1). In another embodiment, the Compound is that where $R^1$ is 1H-imidazo[4,5-b]pyridin-5-yl, 1H-imidazo[4,5-b]pyridin-6-yl, 3H-imidazo[4,5-b]pyridin-5-yl, or 3H-imidazo[4,5-b]pyridin-6-yl where $R^1$ is optionally substituted with $R^7$; each $R^7$, when present, is independently alkyl (in another embodiment alkyl is $C_{1-3}$-alkyl), haloalkyl, $—NR^8R^{8a}$, $—NR^8C(O)OR^9$, or cycloalkyl; $R^8$ is hydrogen; $R^{8a}$ is hydrogen, alkyl (in another embodiment alkyl is $C_{1-3}$-alkyl), or haloalkyl; $R^9$ is hydrogen or alkyl (in another embodiment alkyl is $C_{1-3}$-alkyl).

Embodiments Z3

In another embodiment, the Compound is that where $R^1$ is 1H-imidazo[4,5-c]pyridin-6-yl or 3H-imidazo[4,5-c]pyridin-6-yl optionally substituted with one or two $R^7$; and $R^7$ is as defined in the Summary of the Invention for a Compound of Formula I or as defined in embodiment (1). In another embodiment, the Compound is that where $R^1$ is 1H-imidazo[4,5-c]pyridin-6-yl or 3H-imidazo[4,5-c]pyridin-6-yl optionally substituted with one or two $R^7$; each $R^7$, when present, is independently alkyl (in another embodiment alkyl is $C_{1-3}$-alkyl), haloalkyl, $—NR^8R^{8a}$, $—NR^8C(O)OR^9$, or cycloalkyl;

and R[8], R[8a], and R[9] are independently as defined in the Summary of the Invention for a Compound of Formula I or as defined in embodiment (1). In another embodiment, the Compound is that where R[1] is 1H-imidazo[4,5-c]pyridin-6-yl or 3H-imidazo[4,5-c]pyridin-6-yl optionally substituted with one or two R[7]; each R[7], when present, is independently alkyl (in another embodiment alkyl is $C_{1-3}$-alkyl), haloalkyl, —NR[8]R[8a], —NR[8]C(O)OR[9], or cycloalkyl; R[8] is hydrogen; R[8a] is hydrogen, alkyl (in another embodiment alkyl is $C_{1-3}$-alkyl), or haloalkyl; R[9] is hydrogen or alkyl (in another embodiment alkyl is $C_{1-3}$-alkyl).

Embodiments Z4

In another embodiment, the Compound is that where R[1] is benzo[d]thiazol-5-yl or benzo[d]thiazol-6-yl optionally substituted with one or two R[7]; and R[7] is as defined in the Summary of the Invention for a Compound of Formula I or as defined in embodiment (1). In another embodiment, the Compound is that where R[1] is benzo[d]thiazol-5-yl or benzo[d]thiazol-6-yl optionally substituted with one or two R[7]; each R[7], when present, is independently alkyl (in another embodiment alkyl is $C_{1-3}$-alkyl), haloalkyl, —NR[8]R[8a], —NR[8]C(O)OR[9], or cycloalkyl; and R[8], R[8a], and R[9] are independently as defined in the Summary of the Invention for a Compound of Formula I or as defined in embodiment (1). In another embodiment, the Compound is that where R[1] is benzo[d]thiazol-5-yl or benzo[d]thiazol-6-yl optionally substituted with one or two R[7]; each R[7], when present, is independently alkyl (in another embodiment alkyl is $C_{1-3}$-alkyl), haloalkyl, —NR[8]R[8a], —NR[8]C(O)OR[9], or cycloalkyl; R[8] is hydrogen; R[8a] is hydrogen, alkyl (in another embodiment alkyl is $C_{1-3}$-alkyl), or haloalkyl; R[9] is hydrogen or alkyl (in another embodiment alkyl is $C_{1-3}$-alkyl).

Embodiments Z5

In another embodiment, the Compound is that where R[1] is pyridin-3-yl optionally substituted with one or two R[7]; and R[7] is as defined in the Summary of the Invention for a Compound of Formula I or as defined in embodiment (1). In another embodiment, the Compound is that where R[1] is pyridin-3-yl optionally substituted with one or two R[7]; each R[7], when present, is independently hydrogen, halo, cyano, hydroxy, alkoxy, alkyl, —NR[8]R[8a], —NR[8]S(O)$_2$R[8a], —S(O)R[13], —S(O)$_2$R[13a], or —S(O)$_2$NR[8]R[9]; and all other groups are independently as defined in the Summary of the Invention for a Compound of Formula I or as defined in embodiment (1). In another embodiment, the Compound is that where R[1] is pyridin-3-yl optionally substituted with two R[7]; one R[7] is hydrogen, halo, cyano, alkoxy, alkyl (in another embodiment alkyl is $C_{1-3}$-alkyl), or —NR[8]R[8a] and the other R[7] is —NR[8]S(O)$_2$R[8a]; or one R[7] is hydroxy or —NR[8]R[8a] and the other R[7] is —S(O)R[13], —S(O)$_2$R[13a], —S(O)$_2$NR[8]R[9]; and all other groups are independently as defined in the Summary of the Invention for a Compound of Formula I or as defined in embodiment (1). In another embodiment, the Compound is that where R[1] is pyridin-3-yl optionally substituted with two R[7]; one R[7] is hydrogen, halo, cyano, alkoxy, alkyl (in another embodiment alkyl is $C_{1-3}$-alkyl), or —NR[8]R[8a] and the other R[7] is —NR[8]S(O)$_2$R[8a]; or one R[7] is hydroxy or —NR[8]R[8a] and the other R[7] is —S(O)R[13], —S(O)$_2$R[13a], —S(O)$_2$NR[8]R[9]; R[13] is hydroxyalkyl; R[13a] is alkyl or heterocycloalkyl optionally substituted with one group which is amino, alkyl, hydroxyalkyl, or hydroxy; each R[8] and R[8a] are independently hydrogen or alkyl; R[9] is hydrogen, haloalkyl, alkoxyalkyl, hydroxyalkyl, aminoalkyl, alkylaminoalkyl, dialkyl-aminoalkyl, cycloalkyl, heterocycloalkyl, heterocycloalkylalkyl, alkyl substituted with one aminocarbonyl, or hydroxyalkyl which is substituted with one amino or 3 halo; and all other groups are independently as defined in the Summary of the Invention for a Compound of Formula I or as defined in embodiment (1).

Embodiments (X)

In another embodiment, the Compound is that where R[6] is —S(O)$_2$R[8], —C(O)NR[8]R[8a] or heteroaryl optionally substituted with 1, 2, or 3 R[14]; and R[8], R[8a], and R[14] are independently as defined in the Summary of the Invention for a Compound of Formula I or as defined in embodiment (1). In another embodiment, the Compound is that where R[6] is located in the para position of the phenyl ring to which it is attached; R[6] is —C(O)NR[8]R[8a] or heteroaryl optionally substituted with 1, 2, or 3 R[14]; and R[8], R[8a], and R[14] are independently as defined in the Summary of the Invention for a Compound of Formula I or as defined in embodiment (1). In another embodiment, the Compound is that where R[6] is located in the para position of the phenyl ring to which it is attached; R[6] is —C(O)NR[8]R[8a] or heteroaryl optionally substituted with 1, 2, or 3 R[14]; R[8] is hydrogen; R[8a] is hydrogen, alkyl (in another embodiment alkyl is $C_{1-3}$-alkyl), haloalkyl, or optionally substituted heterocycloalkyl; R[14] is alkyl (in another embodiment alkyl is $C_{1-3}$-alkyl) or alkoxycarbonyl. In another embodiment, the Compound is that where R[6] is located in the para position of the phenyl ring to which it is attached; R[6] is —C(O)NR[8]R[8a], imidazolyl, or pyrazolyl where the imidazolyl and pyrazolyl are optionally substituted with 1, 2, or 3 R[14]; R[8] is hydrogen; R[8a] is hydrogen, alkyl (in another embodiment alkyl is $C_{1-3}$-alkyl), haloalkyl, or optionally substituted pyrrolidinyl; R[14] is alkyl (in another embodiment alkyl is $C_{1-3}$-alkyl) or alkoxycarbonyl. In another embodiment, the Compound is that where R[6] is located in the meta position of the phenyl ring to which it is attached; R[6] is —S(O)$_2$R[8]; and R[8] is as defined in the Summary of the Invention for a Compound of Formula I or as defined in embodiment (1). In another embodiment, the Compound is that where R[6] is located in the meta position of the phenyl ring to which it is attached; R[6] is —S(O)$_2$R[8]; R[8] is alkyl.

Embodiments (J)

In another embodiment, the Compound is according to Formula I(h)

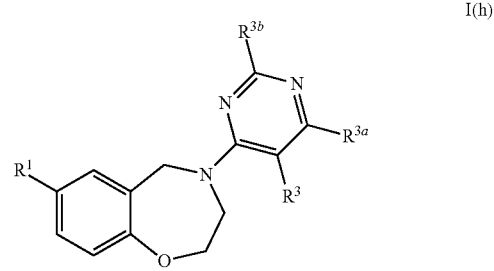

I(h)

where R[1], R[3], R[3a], and R[3b] are independently as defined in the Summary of the Invention for a Compound of Formula I or as defined in embodiment (1). In another embodiment, the Compound of Formula I(h) is that where R[3], R[3a], and R[3b] are as described in any of embodiments (D3a)-(D3c), (D3g), and (D3i); and all other groups are as defined in the Summary of the Invention for a Compound of Formula I or as defined in embodiment (1).

In another embodiment of embodiments (J), the Compound of Formula I(h) is that where $R^1$ is according to any of embodiments (Z)-(Z5); and all other groups are as defined in the Summary of the Invention for a Compound of Formula I or as defined in embodiment (1).

In another embodiment of embodiments (K), the Compound of Formula I is according to Formula I(j)

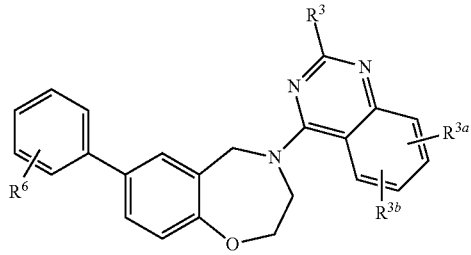

where $R^3$, $R^{3a}$, $R^{3b}$, and $R^6$ are independently as defined in the Summary of the Invention for a Compound of Formula I or as defined in embodiment (1). In another embodiment, the Compound is of Formula I(j) where $R^3$, $R^{3a}$, and $R^{3b}$ are as defined in embodiments (E2b); and all other groups are as defined in the Summary of the Invention for a Compound of Formula I or as defined in embodiment (1). In another embodiment, the Compound is of Formula I(j) where $R^3$ is hydrogen, alkyl (in another embodiment alkyl is $C_{1-3}$-alkyl), halo, —$OR^{11a}$, or alkyl substituted with one $R^{16}$; $R^3$ is hydrogen; $R^{3a}$ is hydrogen or alkoxy; and $R^6$ is as defined in the Summary of the Invention for a Compound of Formula I or as defined in embodiment (1).

In another embodiment of embodiments (K), the Compound of Formula I(j) is that where $R^6$ is according to embodiments (X); and all other groups are as defined in the Summary of the Invention for a Compound of Formula I or as defined in embodiment (1).

In another embodiment of embodiments (L), the Compound of Formula I is according to Formula I(k)

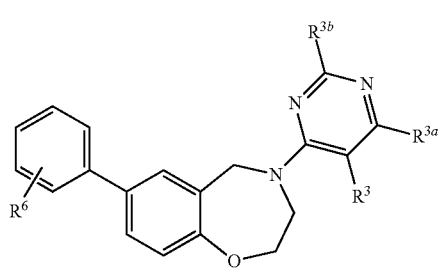

where $R^3$, $R^{3a}$, $R^{3b}$, and $R^6$ are independently as defined in the Summary of the Invention for a Compound of Formula I or as defined in embodiment (1). In another embodiment, the Compound of Formula I(h) is that where $R^3$, $R^{3a}$, and $R^{3b}$ are as described in any of embodiments (D3a)-(D3c), (D3g), and (D3i); and all other groups are as defined in the Summary of the Invention for a Compound of Formula I or as defined in embodiment (1).

In another embodiment of embodiments (L), the Compound of Formula I(k) is that where $R^6$ is according to embodiments (X); and all other groups are as defined in the Summary of the Invention for a Compound of Formula I or as defined in embodiment (1).

In another embodiment of embodiments (M), the Compound of Formula I is according to Formula I(m)

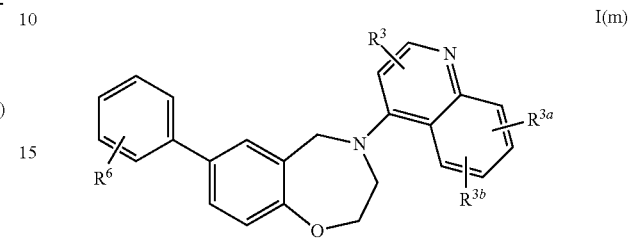

where $R^3$, $R^{3a}$, $R^{3b}$, and $R^6$ are independently as defined in the Summary of the Invention for a Compound of Formula I or as defined in embodiment (1). In another embodiment, the Compound is of Formula I(m) where $R^3$ is hydrogen, alkyl (in another embodiment alkyl is $C_{1-3}$-alkyl), or alkyl substituted with one $R^{16}$, —$OR^{11a}$; $R^{3a}$ is hydrogen or —$OR^{11a}$; and $R^{3b}$ is hydrogen or alkyl; and $R^6$ is as defined in the Summary of the Invention for a Compound of Formula I or as defined in embodiment (1). In another embodiment, the Compound is of Formula I(m) where $R^3$, $R^{3a}$, and $R^{3b}$ are as defined in embodiments (E6a); and $R^6$ is as defined in the Summary of the Invention for a Compound of Formula I or as defined in embodiment (1).

In another embodiment of embodiments (M), the Compound of Formula I(m) is that where $R^6$ is according to embodiments (X); and all other groups are as defined in the Summary of the Invention for a Compound of Formula I or as defined in embodiment (1).

In another embodiment of embodiments (N), the Compound is of Formula I(n)

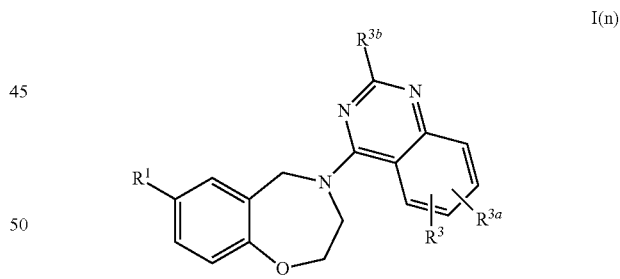

where $R^1$ is as defined in the Summary of the Invention for a Compound of Formula I or as defined in embodiment (1); and one of $R^3$, $R^{3a}$, and $R^{3b}$ and all other groups are independently as defined in the Summary of the Invention for a Compound of Formula I or as defined in embodiment (1). In another embodiment of embodiments (N), the Compound is of Formula I(n) where $R^3$, $R^{3a}$, $R^{3b}$, and $R^1$ are independently as defined in the Summary of the Invention for a Compound of Formula I or as defined in embodiment (1). In another embodiment, the Compound is of Formula I(n) where $R^3$, $R^{3a}$, and $R^{3b}$ is as defined in embodiments (E2b); and all other groups are as defined in the Summary of the Invention for a Compound of Formula I or as defined in embodiment (1). In another embodiment, the Compound is of Formula I(n) where $R^3$ is hydrogen, alkyl (in another embodiment alkyl is $C_{1-3}$-alkyl), halo, $—OR^{11a}$, or alkyl substituted with one $R^{16}$; $R^3$ is hydrogen; $R^{3a}$ is hydrogen or alkoxy; and $R^1$ is as defined in the Summary of the Invention for a Compound of Formula I or as defined in embodiment (1). In another embodiment, the Compound is of Formula I(n) where $R^1$ is as defined in the Summary of the Invention for a Compound of Formula I or as defined in embodiment (1); and two of $R^3$, $R^{3a}$, and $R^{3b}$ are hydrogen and the others are independently as defined in the Summary of the Invention for a Compound of Formula I or as defined in embodiment (1). In another embodiment, the Compound is of Formula I(n) where $R^1$ is as defined in the Summary of the Invention for a Compound of Formula I or as defined in embodiment (1); and three of $R^3$, $R^{3a}$, and $R^{3b}$ are hydrogen and the others are independently as defined in the Summary of the Invention for a Compound of Formula I or as defined in embodiment (1).

In another embodiment of embodiments (N), the Compound of Formula I(n) is that where $R^1$ is according to any of embodiments (Z)-(Z5); and all other groups are as defined in the Summary of the Invention for a Compound of Formula I or as defined in embodiment (1).

Embodiments (P)

In another embodiment, the Compound is of Formula I(p)

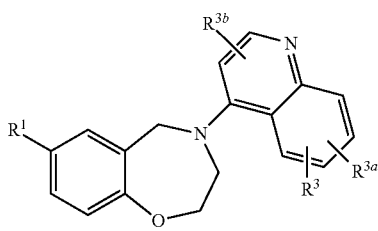

I(p)

where $R^1$ is as defined in the Summary of the Invention for a Compound of Formula I; and one of $R^3$, $R^{3a}$, and $R^{3b}$ is hydrogen and the others are independently as defined in the Summary of the Invention for a Compound of Formula I. In another embodiment, the Compound is of Formula I(p) where $R^1$ is as defined in the Summary of the Invention for a Compound of Formula I; and one of $R^3$, $R^{3a}$, and $R^{3b}$ are hydrogen and the others are independently as defined in the Summary of the Invention for a Compound of Formula I. In another embodiment, the Compound is of Formula I(p) where $R^1$ is as defined in the Summary of the Invention for a Compound of Formula I; and two of $R^3$, $R^{3a}$, and $R^{3b}$ are hydrogen and the others are independently as defined in the Summary of the Invention for a Compound of Formula I. In another embodiment, the Compound is of Formula I(p) where $R^3$ is hydrogen, alkyl (in another embodiment alkyl is $C_{1-3}$-alkyl), or alkyl substituted with one $R^{16}$, $—OR^{11a}$; $R^{3a}$ is hydrogen or $—OR^{11a}$; and $R^{3b}$ is hydrogen or alkyl; and $R^6$ is as defined in the Summary of the Invention for a Compound of Formula I or as defined in embodiment (1). In another embodiment, the Compound is of Formula I(p) where $R^3$, $R^{3a}$, and $R^{3b}$ are as defined in embodiments (E6a); and $R^6$ is as defined in the Summary of the Invention for a Compound of Formula I or as defined in embodiment (1).

In another embodiment of embodiments (P), the Compound of Formula I(p) is that where $R^1$ is according to any of embodiments (Z)-(Z5); and all other groups are as defined in the Summary of the Invention for a Compound of Formula I or as defined in embodiment (1).

Embodiments Q

In another embodiment, the Compound is of Formula I(q)

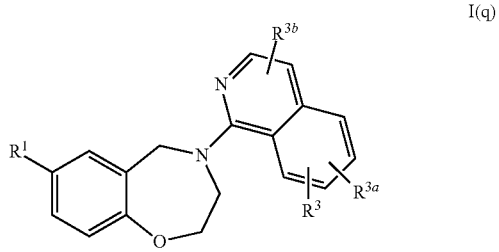

I(q)

where $R^1$ is as defined in the Summary of the Invention for a Compound of Formula I; and one of $R^3$, $R^{3a}$, and $R^{3b}$ is hydrogen and the others are independently as defined in the Summary of the Invention for a Compound of Formula I. In another embodiment, the Compound is of Formula I(q) where $R^1$ is as defined in the Summary of the Invention for a Compound of Formula I; and two of $R^3$, $R^{3a}$, and $R^{3b}$ are hydrogen and the others are independently as defined in the Summary of the Invention for a Compound of Formula I. In another embodiment, the Compound is of Formula I(q) where $R^1$ is as defined in the Summary of the Invention for a Compound of Formula I; and three of $R^3$, $R^{3a}$, and $R^{3b}$ are hydrogen and the others are independently as defined in the Summary of the Invention for a Compound of Formula I.

In another embodiment of embodiments (Q), the Compound of Formula I(q) is that where $R^1$ is according to any of embodiments (Z)-(Z5); and all other groups are as defined in the Summary of the Invention for a Compound of Formula I or as defined in embodiment (1).

Embodiment (F)

In another embodiment, the Compound is of Formula I(r)

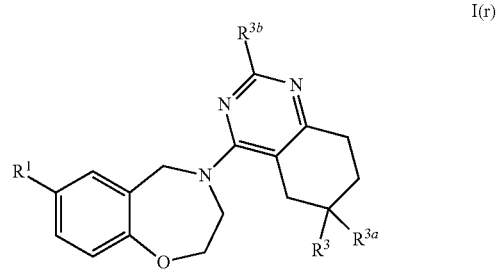

I(r)

where $R^1$, $R^3$, $R^{3a}$, and $R^{3b}$ are independently as defined in the Summary of the Invention for a Compound of Formula I. In another embodiment, the Compound of Formula I(r) is where $R^3$ and $R^{3a}$ are alkyl (in another embodiment alkyl is $C_{1-3}$-alkyl) and $R^{3b}$ is hydrogen, alkyl (in another embodiment alkyl is $C_{1-3}$-alkyl), haloalkyl, or alkyl substituted with one $R^{16}$; and all other groups are as defined in the Summary of the Invention for a Compound of Formula I or as defined in embodiment (1). In another embodiment, the Compound of Formula I(r) is where $R^3$ and $R^{3a}$ are halo and $R^{3b}$ is hydrogen, alkyl (in another embodiment alkyl is $C_{1-3}$-alkyl), haloalkyl, or alkyl substituted with one $R^{16}$; and all other groups are as defined in the Summary of the Invention for a Compound of Formula I or as defined in embodiment (1). In another embodiment, the Compound of Formula I(r) is where $R^3$ and $R^{3a}$ together with the carbon to which they are attached form an optionally substituted cycloalkyl and $R^{3b}$ is hydrogen, alkyl (in another embodiment alkyl is $C_{1-3}$-alkyl), haloalkyl, or alkyl substituted with one $R^{16}$; and all other groups are as defined in the Summary of the Invention for a Compound of Formula I or as defined in embodiment (1).

In another embodiment of embodiments (F), the Compound of Formula I(r) is that where $R^1$ is according to any of embodiments (Z)-(Z5); and all other groups are as defined in the Summary of the Invention for a Compound of Formula I or as defined in embodiment (1).

Embodiments (S)

In another embodiment, the Compound is of Formula I(s)

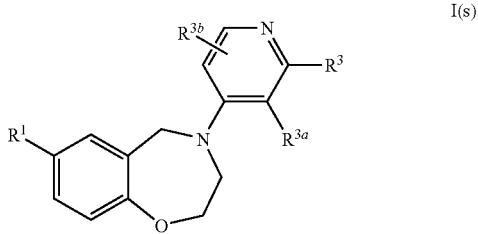

I(s)

where $R^3$ is cyano, alkyl (in another embodiment alkyl is $C_{1-3}$-alkyl), halo, haloalkyl, —$SR^{12}$, alkylsulfonyl, optionally substituted phenyl, optionally substituted phenylalkyl, optionally substituted cycloalkyl, optionally substituted cycloalkylalkyl, carboxy, —C(O)OR$^4$, —NR$^{11}$R$^{11a}$, or —OR$^{11a}$; and $R^1$, $R^{3a}$, $R^{3b}$, $R^4$, $R^{11}$, and $R^{11a}$ are independently as defined in the Summary of the Invention for a Compound of Formula I.

In another embodiment of embodiments (5), the Compound of Formula I(s) is that where $R^1$ is according to any of embodiments (Z)-(Z5); and all other groups are as defined in the Summary of the Invention for a Compound of Formula I or as defined in embodiment (1).

Embodiments (T)

In another embodiment, the Compound is of Formula I(t)

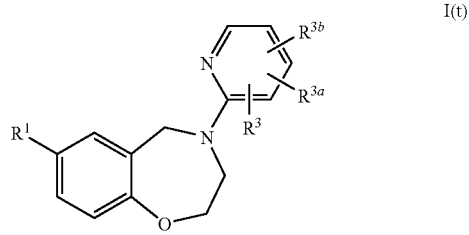

I(t)

where $R^1$, $R^3$, $R^{3a}$, and $R^{3b}$ are independently as defined in the Summary of the Invention for a Compound of Formula I.

In another embodiment of embodiments (T), the Compound of Formula I(t) is that where $R^1$ is according to any of embodiments (Z)-(Z5); and all other groups are as defined in the Summary of the Invention for a Compound of Formula I or as defined in embodiment (1).

Embodiment (U)

In another embodiment, the Compound is according to Formula I(a) where $R^1$ is heteroaryl optionally substituted with one or two $R^7$; each $R^7$, when present, is independently halo, alkyl, cycloalkyl, haloalkyl, hydroxyalkyl, alkoxyalkyl, —NR$^8$R$^{8a}$, or —NR$^8$C(O)OR$^9$; and all other groups are independently as defined in the Summary of the Invention for a Compound of Formula I. In another embodiment, the Compound is according to Formula I(a) where $R^1$ is heteroaryl optionally substituted with one or two $R^7$; each $R^7$, when present, is independently alkyl (in another embodiment alkyl is $C_{1-3}$-alkyl), cycloalkyl, haloalkyl, —NR$^8$R$^{8a}$, or —NR$^8$C(O)OR$^9$; and all other groups are independently as defined in the Summary of the Invention for a Compound of Formula I. In another embodiment, the Compound is according to Formula I(a) where $R^1$ is heteroaryl optionally substituted with one or two $R^7$; each $R^7$, when present, is independently alkyl (in another embodiment alkyl is $C_{1-3}$-alkyl), cycloalkyl, haloalkyl, —NR$^8$R$^{8a}$, or —NR$^8$C(O)OR$^9$; $R^8$ is hydrogen; $R^{8a}$ is hydrogen, alkyl (in another embodiment alkyl is $C_{1-3}$-alkyl), or haloalkyl; and $R^9$ is hydrogen or alkyl (in another embodiment alkyl is $C_{1-3}$-alkyl); and all other groups are independently as defined in the Summary of the Invention for a Compound of Formula I.

In another embodiment, the Compound is according to Formula I(a) where $R^2$ is 5,6,7,8-tetrahydroquinolin-4-yl or 5,6,7,8-tetrahydroisoquinolin-1-yl, where $R^2$ is substituted with $R^3$, $R^{3a}$, $R^{3b}$, $R^{3c}$, and $R^{3d}$; and $R^1$, $R^3$, $R^{3a}$, $R^{3b}$, $R^{3c}$, and $R^{3d}$ are independently as defined in the Summary of the Invention for a Compound of Formula I. In another embodiment, the Compound is according to Formula I(a) where $R^2$ is 5,6,7,8-tetrahydroquinolin-4-yl or 5,6,7,8-tetrahydroisoquinolin-1-yl, where $R^2$ is substituted with $R^3$, $R^{3a}$, $R^{3b}$, $R^{3c}$, and $R^{3d}$; $R^{3d}$ is hydrogen; and $R^1$, $R^3$, $R^{3a}$, $R^{3b}$, and $R^{3c}$ are independently as defined in the Summary of the Invention for a Compound of Formula I. In another embodiment, the Compound is according to Formula I(a) where $R^2$ is 5,6,7,8-tetrahydroquinolin-4-yl or 5,6,7,8-tetrahydroisoquinolin-1-yl, where $R^2$ is substituted with $R^3$, $R^{3a}$, $R^{3b}$, $R^{3c}$, and $R^{3d}$; $R^{3b}$, $R^{3c}$, and $R^{3d}$ are hydrogen; and $R^1$, $R^3$, and $R^{3a}$ are independently as defined in the Summary of the Invention for a Compound of Formula I. In another embodiment, the Compound is according to Formula I(a) where $R^2$ is 5,6,7,8-tetrahydroquinolin-4-yl or 5,6,7,8-tetrahydroisoquinolin-1-yl, where $R^2$ is substituted with $R^3$, $R^{3a}$, $R^{3b}$, $R^{3c}$, and $R^{3d}$; $R^{3a}$, $R^{3b}$, $R^{3c}$, and $R^{3d}$ are hydrogen; and $R^1$, and $R^3$ are independently as defined in the Summary of the Invention for a Compound of Formula I. In another embodiment, the Compound is according to Formula I(a) where $R^2$ is 5,6,7,8-tetrahydroquinolin-4-yl or 5,6,7,8-tetrahydroisoquinolin-1-yl, where $R^2$ is substituted with $R^3$, $R^{3a}$, $R^{3b}$, $R^{3c}$, and $R^{3d}$; $R^3$, $R^{3a}$, $R^{3b}$, $R^{3c}$, and $R^{3d}$ are hydrogen; and $R^1$ is as defined in the Summary of the Invention for a Compound of Formula I.

Another embodiment provides a pharmaceutical composition which comprises 1) a compound, as a single stereoisomer or mixture of stereoisomers thereof, according to any one of Formula I, (I(a), I(b1), I(b2), I(c1), I(c2), I(d1), I(d2), I(e), I(e1), I(f), I(g), I(h), I(j), I(k), I(m), I(n), I(p), I(q), I(r), I(s), and I(t) or according to any one of the above embodiments, optionally as a pharmaceutically acceptable salt thereof, and 2) a pharmaceutically acceptable carrier, excipient, and/or diluent thereof.

Another embodiment is a method of treating disease, disorder, or syndrome where the disease is associated with uncontrolled, abnormal, and/or unwanted cellular activities effected directly or indirectly by PI3K and/or mTOR which method comprises administering to a human in need thereof a therapeutically effective amount of a Compound of any of Formula I, (I(a), I(b1), I(b2), I(c1), I(c2), I(d1), I(d2), I(e), I(e1), I(f), I(g), I(h), I(j), I(k), I(m), I(n), I(p), I(q), I(r), I(s), and I(t), a Compound of any one of the above embodiments, or a Compound from Table 1, optionally as a pharmaceutically acceptable salt or pharmaceutical composition thereof. In another embodiment the disease is cancer. In another embodiment, the disease is cancer and the Compound is of Formula I(a) or a Compound from Table 1.

Embodiment (G)

Another embodiment is directed to a method of treating a disease, disorder, or syndrome which method comprises administering to a patient a therapeutically effective amount of a Compound of any of Formula I, (I(a), I(b1), I(b2), I(c1), I(c2), I(d1), I(d2), I(e), I(e1), I(f), I(g), I(h), I(j), I(k), I(m), I(n), I(p), I(q), I(r), I(s), and I(t), a Compound of any one of the above embodiments, or a Compound from Table 1, optionally as a pharmaceutically acceptable salt thereof, or a pharmaceutical composition comprising a therapeutically effective amount of a Compound of Formula I, (I(a), I(b1), I(b2), I(c1), I(c2), I(d1), I(d2), I(e), I(e1), I(f), I(g), I(h), I(j), I(k), I(m), I(n), I(p), I(q), I(r), I(s), and I(t), a Compound of any one of the above embodiments, or a Compound from Table 1, and a pharmaceutically acceptable carrier, excipient, or diluent. In another embodiment the disease is cancer.

In another embodiment of any of the embodiments of Embodiment (G), the cancer is breast cancer, mantle cell lymphoma, renal cell carcinoma, acute myelogenous leukemia, chronic myelogenous leukemia, NPM/ALK-transformed anaplastic large cell lymphoma, diffuse large B cell lymphoma, rhabdomyosarcoma, ovarian cancer, endometrial cancer, cervical cancer, non small cell lung carcinoma, small cell lung carcinoma, adenocarcinoma, colon cancer, rectal cancer, gastric carcinoma, hepatocellular carcinoma, melanoma, pancreatic cancer, prostate carcinoma, thyroid carcinoma, anaplastic large cell lymphoma, hemangioma, glioblastoma, or head and neck cancer.

All Compounds in Table 1 were tested in the assays described in Biological Examples 1 and 3.

Embodiments (V)

In one embodiment the Compound of the Invention has an PI3K-alpha-inhibitory activity of about 2.0 µM or less and is inactive for mTOR (when tested at a concentration of 3.0 µM or greater) or is selective for PI3K-alpha over mTOR by about 5-fold or greater, about 7-fold or greater, or about 10-fold or greater. In another embodiment the Compound of the Invention has an PI3K-alpha-inhibitory activity of about 1.0 µM or less and is inactive for mTOR (when tested at a concentration of 2.0 µM or greater) or is selective for PI3K-alpha over mTOR by about 5-fold or greater, about 7-fold or greater, or about 10-fold or greater. In another embodiment the Compound of the Invention has an PI3K-alpha-inhibitory activity of about 0.5 µM or less and is inactive for mTOR (when tested at a concentration of 2.0 µM or greater) or is selective for PI3K-alpha over mTOR by about 5-fold or greater, about 7-fold or greater, or about 10-fold or greater. In another embodiment the Compound of the Invention has an PI3K-alpha-inhibitory activity of about 0.3 µM or less and is inactive for mTOR (when tested at a concentration of 2.0 µM or greater) or is selective for PI3K-alpha over mTOR by about 5-fold or greater, about 7-fold or greater, or about 10-fold or greater. In another embodiment the Compound of the Invention has an PI3K-alpha-inhibitory activity of about 0.2 µM or less and is selective for PI3K-alpha over mTOR by about 5-fold or greater, about 7-fold or greater, or about 10-fold or greater. In another embodiment the Compound of the Invention has an PI3K-alpha-inhibitory activity of about 0.1 µM or less and is selective for PI3K-alpha over mTOR by about 5-fold or greater, about 7-fold or greater, or about 10-fold or greater. In another embodiment the Compound of the Invention has an PI3K-alpha-inhibitory activity of about 0.05 µM or less and is selective for PI3K-alpha over mTOR by about 5-fold or greater, about 7-fold or greater, or about 10-fold or greater. In another embodiment the Compound of the Invention has an PI3K-alpha-inhibitory activity of about 0.025 µM or less and is selective for PI3K-alpha over mTOR by about 5-fold or greater, about 7-fold or greater, or about 10-fold or greater. In another embodiment the Compound of the Invention has an PI3K-alpha-inhibitory activity of about 0.01 µM or less and is selective for PI3K-alpha over mTOR by about 5-fold or greater, about 7-fold or greater, or about 10-fold or greater.

Embodiments (W)

In one embodiment the Compound of the Invention has an PI3K-alpha-inhibitory activity of about 2.0 µM or less and an mTOR-inhibitory activity of about 2.0 µM or less and the selectivity for one of the targets over the other does not exceed 3-fold. In another embodiment the Compound of the Invention has an PI3K-alpha-inhibitory activity of about 1.0 µM or less and an mTOR-inhibitory activity of about 1.0 µM or less and the selectivity for one of the targets over the other does not exceed 3-fold. In another embodiment the Compound of the Invention has an PI3K-alpha-inhibitory activity of about 0.5 µM or less and an mTOR-inhibitory activity of about 0.5 µM or less and the selectivity for one of the targets over the other does not exceed 3-fold. In another embodiment the Compound of the Invention has an PI3K-alpha-inhibitory activity of about 0.3 µM or less and an mTOR-inhibitory activity of about 0.3 µM or less and the selectivity for one of the targets over the other does not exceed 3-fold. In another embodiment the Compound of the Invention has an PI3K-alpha-inhibitory activity of about 0.15 µM or less and an mTOR-inhibitory activity of about 0.15 µM or less and the selectivity for one of the targets over the other does not exceed 2-fold. In another embodiment the Compound of the Invention has an PI3K-alpha-inhibitory activity of about 0.1 µM or less and an mTOR-inhibitory activity of about 0.1 µM or less. In another embodiment the Compound of the Invention has an PI3K-alpha-inhibitory activity of about 0.05 µM or less and an mTOR-inhibitory activity of about 0.05 µM or less. In another embodiment the Compound of the Invention has an PI3K-alpha-inhibitory activity of about 0.02 µM or less and an mTOR-inhibitory activity of about 0.02 µM or less. In another embodiment the Compound of the Invention has an PI3K-alpha-inhibitory activity of about 0.01 µM or less and an mTOR-inhibitory activity of about 0.01 µM or less.

In another embodiment, Compounds of the invention are also useful as inhibitors of PI3Kα and/or mTOR in vivo for studying the in vivo role of PI3Kα and/or mTOR in biological processes, including the diseases described herein. Accordingly, the invention also comprises a method of inhibiting PI3Kα and/or mTOR in vivo comprising administering a compound or composition of the invention to a mammal.

Representative Compounds

Representative compounds of Formula I are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Specifically, names in Table 1 were generated using ACD/Labs naming software 8.00 release, product version 8.08 or later.

| Cmpd No. | Structure | Name |
|---|---|---|
| 1 | 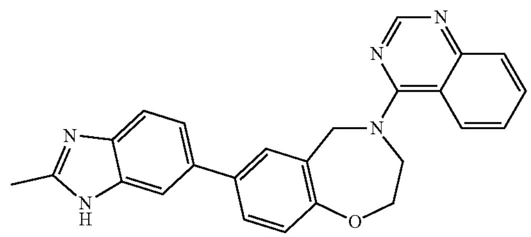 [SMILES: Cc1nc2ccc(-c3ccc4c(c3)CN(c3ncnc5ccccc35)CCO4)cc2[nH]1] | 7-(2-methyl-1H-benzimidazol-6-yl)-4-quinazolin-4-yl-2,3,4,5-tetrahydro-1,4-benzoxazepine |
| 2 | 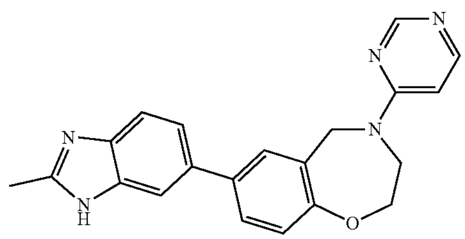 [SMILES: Cc1nc2ccc(-c3ccc4c(c3)CN(c3ccncn3)CCO4)cc2[nH]1] | 7-(2-methyl-1H-benzimidazol-6-yl)-4-pyrimidin-4-yl-2,3,4,5-tetrahydro-1,4-benzoxazepine |
| 3 | 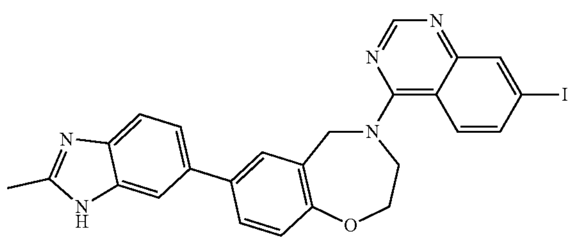 [SMILES: Cc1nc2ccc(-c3ccc4c(c3)CN(c3ncnc5cc(I)ccc35)CCO4)cc2[nH]1] | 4-(7-iodoquinazolin-4-yl)-7-(2-methyl-1H-benzimidazol-6-yl)-2,3,4,5-tetrahydro-1,4-benzoxazepine |
| 4 | 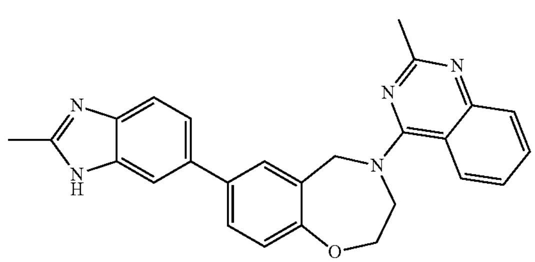 [SMILES: Cc1nc(N2CCOc3ccc(-c4ccc5nc(C)[nH]c5c4)cc3C2)c2ccccc2n1] | 7-(2-methyl-1H-benzimidazol-6-yl)-4-(2-methylquinazolin-4-yl)-2,3,4,5-tetrahydro-1,4-benzoxazepine |
| 5 | 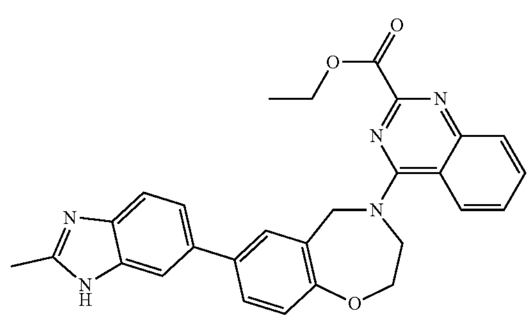 [SMILES: CCOC(=O)c1nc(N2CCOc3ccc(-c4ccc5nc(C)[nH]c5c4)cc3C2)c2ccccc2n1] | ethyl 4-[7-(2-methyl-1H-benzimidazol-6-yl)-2,3-dihydro-1,4-benzoxazepin-4(5H)-yl]quinazoline-2-carboxylate |

-continued

| Cmpd No. | Structure | Name |
|---|---|---|
| 6 | 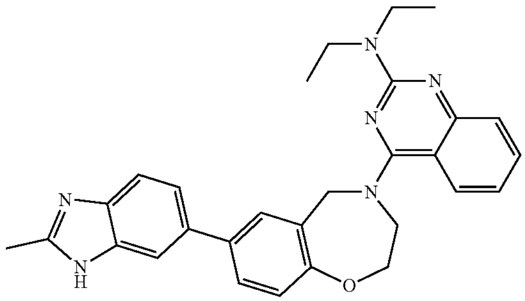 [SMILES: CCN(CC)c1nc(N2CCOc3ccc(-c4ccc5nc(C)[nH]c5c4)cc3C2)c2ccccc2n1] | N,N-diethyl-4-[7-(2-methyl-1H-benzimidazol-6-yl)-2,3-dihydro-1,4-benzoxazepin-4(5H)-yl]quinazolin-2-amine |
| 7 | 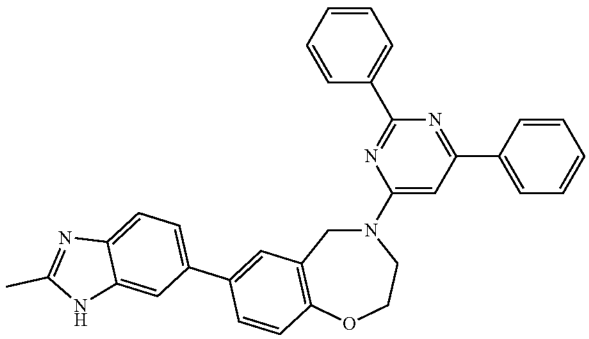 [SMILES: Cc1nc2ccc(-c3ccc4c(c3)CN(c3cc(-c5ccccc5)nc(-c5ccccc5)n3)CCO4)cc2[nH]1] | 4-(2,6-diphenylpyrimidin-4-yl)-7-(2-methyl-1H-benzimidazol-6-yl)-2,3,4,5-tetrahydro-1,4-benzoxazepine |
| 8 | 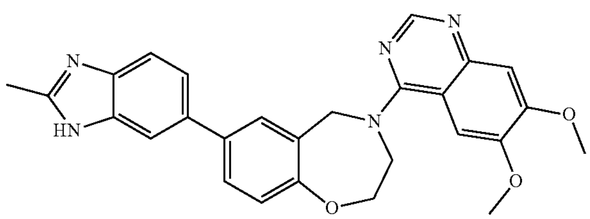 | 4-[6,7-bis(methyloxy)quinazolin-4-yl]-7-(2-methyl-1H-benzimidazol-6-yl)-2,3,4,5-tetrahydr-1,4-benzoxazepine |
| 9 | 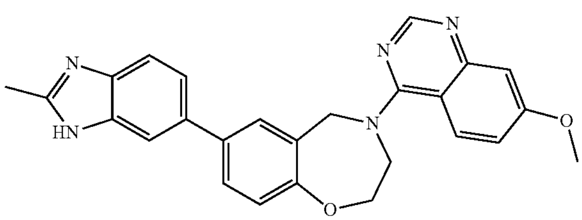 | 7-(2-methyl-1H-benzimidazol-6-yl)-4-[7-(methyloxy)quinazolin-4-yl]-2,3,4,5-tetrahydro-1,4-benzoxazepine |
| 10 | 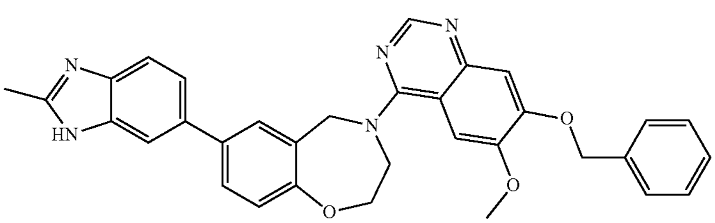 [SMILES: COc1cc2c(N3CCOc4ccc(-c5ccc6nc(C)[nH]c6c5)cc4C3)ncnc2cc1OCc1ccccc1] | 7-(2-methyl-1H-benzimidazol-6-yl)-4-{6-(methyloxy)-7-[(phenylmethyl)oxy]quinazolin-4-yl}-2,3,4,5-tetrahydro-1,4-benzoxazepine |
| 11 | 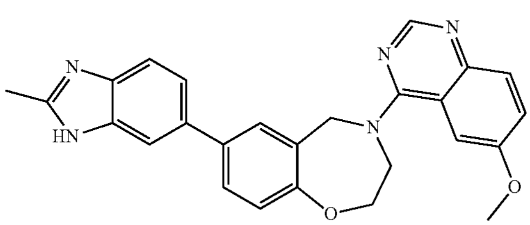 [SMILES: COc1ccc2ncnc(N3CCOc4ccc(-c5ccc6nc(C)[nH]c6c5)cc4C3)c2c1] | 7-(2-methyl-1H-benzimidazol-6-yl)-4-[6-(methyloxy)quinazolin-4-yl]-2,3,4,5-tetrahydro-1,4-benzoxazepine |

-continued

| Cmpd No. | Structure | Name |
|---|---|---|
| 12 | 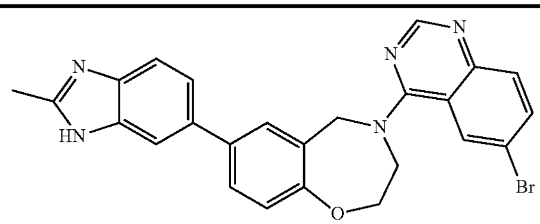 | 4-(6-bromoquinazolin-4-yl)-7-(2-methyl-1H-benzimidazol-6-yl)-2,3,4,5-tetrahydro-1,4-benzoxazepine |
| 13 | 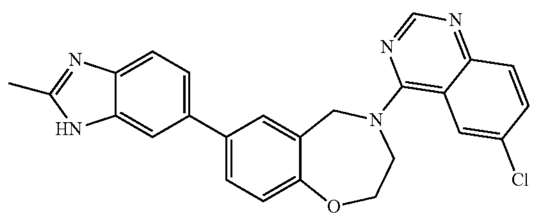 [SMILES: Cc1nc2ccc(-c3ccc4c(c3)CN(c3ncnc5ccc(Cl)cc35)CCO4)cc2[nH]1] | 4-(6-chloroquinazolin-4-yl)-7-(2-methyl-1H-benzimidazol-6-yl)-2,3,4,5-tetrahydro-1,4-benzoxazepine |
| 14 | 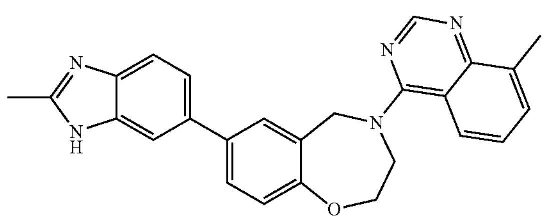 | 7-(2-methyl-1H-benzimidazol-6-yl)-4-(8-methylquinazolin-4-yl)-2,3,4,5-tetrahydro-1,4-benzoxazepine |
| 15 | 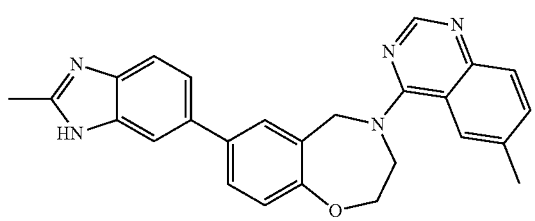 [SMILES: Cc1ccc2ncnc(N3CCOc4ccc(-c5ccc6nc(C)[nH]c6c5)cc4C3)c2c1] | 7-(2-methyl-1H-benzimidazol-6-yl)-4-(6-methylquinazolin-4-yl)-2,3,4,5-tetrahydro-1,4-benzoxazepine |
| 16 | 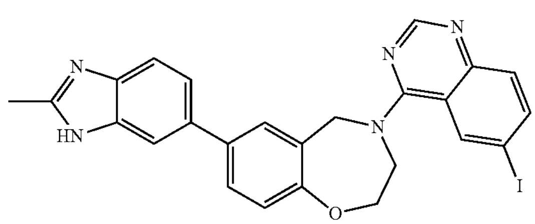 [SMILES: Cc1nc2ccc(-c3ccc4c(c3)CN(c3ncnc5ccc(I)cc35)CCO4)cc2[nH]1] | 4-(6-iodoquinazolin-4-yl)-7-(2-methyl-1H-benzimidazol-6-yl)-2,3,4,5-tetrahydro-1,4-benzoxazepine |
| 17 | 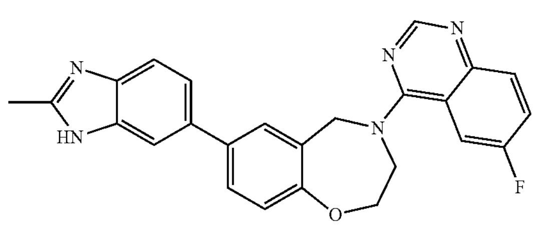 | 4-(6-fluoroquinazolin-4-yl)-7-(2-methyl-1H-benzimidazol-6-yl)-2,3,4,5-tetrahydro-1,4-benzoxazepine |
| 18 | 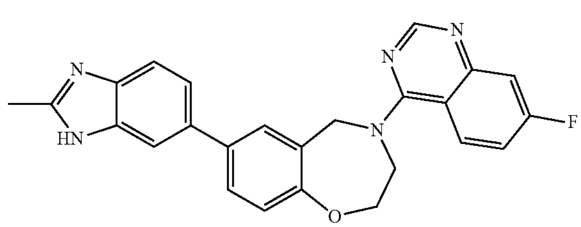 [SMILES: Cc1nc2ccc(-c3ccc4c(c3)CN(c3ncnc5cc(F)ccc35)CCO4)cc2[nH]1] | 4-(7-fluoroquinazolin-4-yl)-7-(2-methyl-1H-benzimidazol-6-yl)-2,3,4,5-tetrahydro-1,4-benzoxazepine |

-continued

| Cmpd No. | Structure | Name |
|---|---|---|
| 19 | 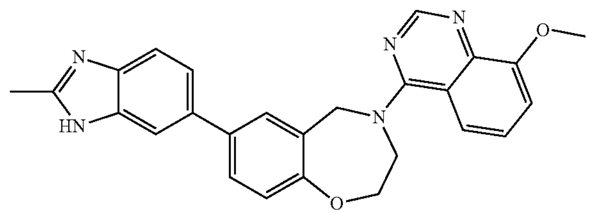 | 7-(2-methyl-1H-benzimidazol-6-yl)-4-[8-(methyloxy)quinazolin-4-yl]-2,3,4,5-tetrahydro-1,4-benzoxazepine |
| 20 | 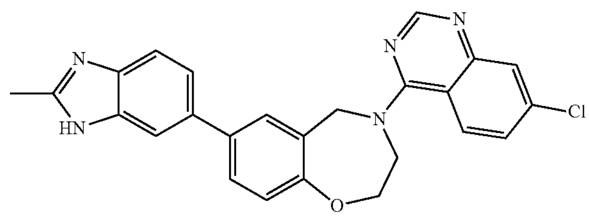 [SMILES: Cc1nc2ccc(-c3ccc4c(c3)CN(c3ncnc5cc(Cl)ccc35)CCO4)cc2[nH]1] | 4-(7-chloroquinazolin-4-yl)-7-(2-methyl-1H-benzimidazol-6-yl)-2,3,4,5-tetrahydro-1,4-benzoxazepine |
| 21 | 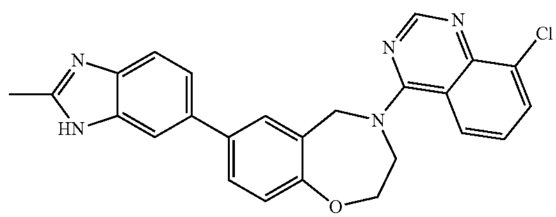 [SMILES: Cc1nc2ccc(-c3ccc4c(c3)CN(c3ncnc5c(Cl)cccc35)CCO4)cc2[nH]1] | 4-(8-chloroquinazolin-4-yl)-7-(2-methyl-1H-benzimidazol-6-yl)-2,3,4,5-tetrahydro-1,4-benzoxazepine |
| 22 | 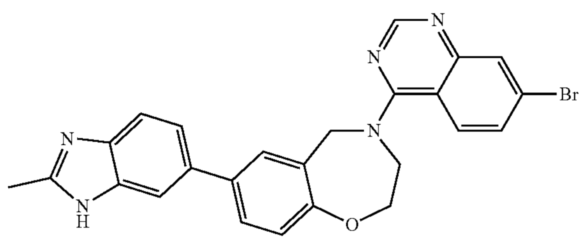 [SMILES: Cc1nc2ccc(-c3ccc4c(c3)CN(c3ncnc5cc(Br)ccc35)CCO4)cc2[nH]1] | 4-(7-bromoquinazolin-4-yl)-7-(2-methyl-1H-benzimidazol-6-yl)-2,3,4,5-tetrahydro-1,4-benzoxazepine |
| 23 | 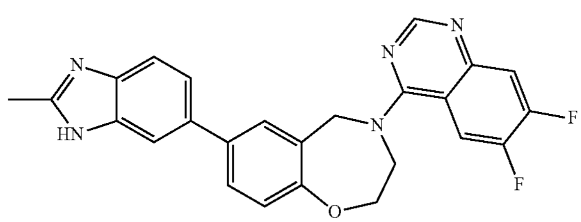 [SMILES: Cc1nc2ccc(-c3ccc4c(c3)CN(c3ncnc5cc(F)c(F)cc35)CCO4)cc2[nH]1] | 4-(6,7-difluoroquinazolin-4-yl)-7-(2-methyl-1H-benzimidazol-6-yl)-2,3,4,5-tetrahydro-1,4-benzoxazepine |
| 24 | 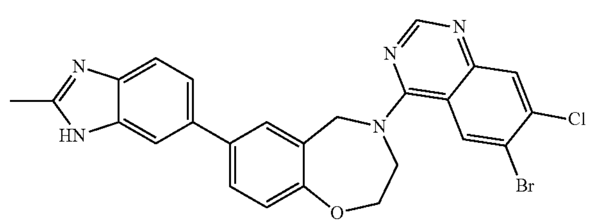 [SMILES: Cc1nc2ccc(-c3ccc4c(c3)CN(c3ncnc5cc(Cl)c(Br)cc35)CCO4)cc2[nH]1] | 4-(6-bromo-7-chloroquinazolin-4-yl)-7-(2-methyl-1H-benzimidazol-6-yl)-2,3,4,5-tetrahydro-1,4-benzoxazepine |
| 25 | 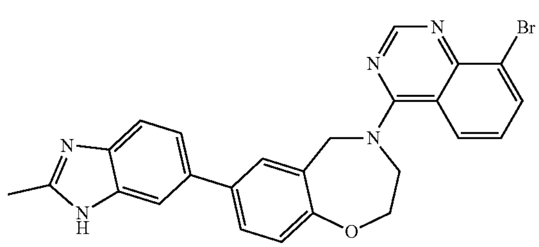 [SMILES: Cc1nc2ccc(-c3ccc4c(c3)CN(c3ncnc5c(Br)cccc35)CCO4)cc2[nH]1] | 4-(8-bromoquinazolin-4-yl)-7-(2-methyl-1H-benzimidazol-6-yl)-2,3,4,5-tetrahydro-1,4-benzoxazepine |

-continued

| Cmpd No. | Structure | Name |
|---|---|---|
| 26 | 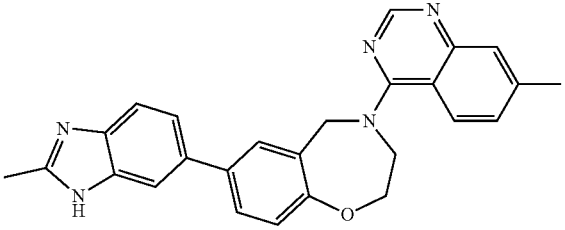 | 7-(2-methyl-1H-benzimidazol-6-yl)-4-(7-methylquinazolin-4-yl)-2,3,4,5-tetrahydro-1,4-benzoxazepine |
| 27 | 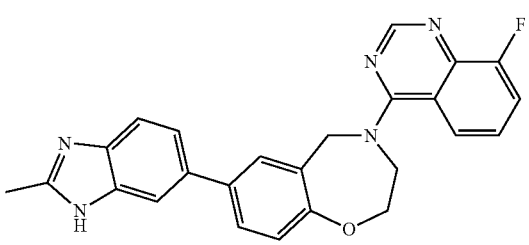 [SMILES: Cc1nc2ccc(-c3ccc4c(c3)CN(c3ncnc5c(F)cccc35)CCO4)cc2[nH]1] | 4-(8-fluoroquinazolin-4-yl)-7-(2-methyl-1H-benzimidazol-6-yl)-2,3,4,5-tetrahydro-1,4-benzoxazepine |
| 28 | 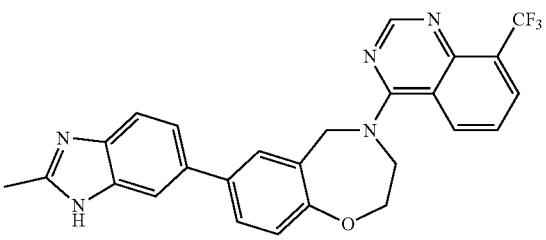 [SMILES: Cc1nc2ccc(-c3ccc4c(c3)CN(c3ncnc5c(C(F)(F)F)cccc35)CCO4)cc2[nH]1] | 7-(2-methyl-1H-benzimidazol-6-yl)-4-[8-(trifluoromethyl)quinazolin-4-yl]-2,3,4,5-tetrahydro-1,4-benzoxazepine |
| 29 | 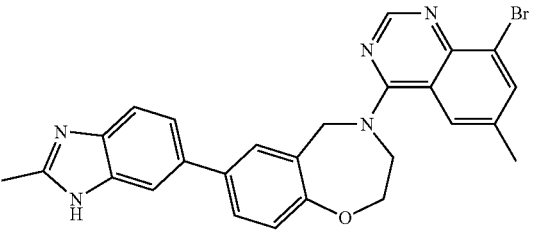 | 4-(8-bromo-6-methylquinazolin-4-yl)-7-(2-methyl-1H-benzimidazol-6-yl)-2,3,4,5-tetrahydro-1,4-benzoxazepine |
| 30 | 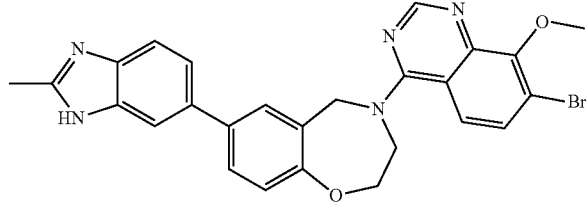 | 4-[7-bromo-8-(methyloxy)quinazolin-4-yl]-7-(2-methyl-1H-benzimidazol-6-yl)-2,3,4,5-tetrahydro-1,4-benzoxazepine |
| 31 | 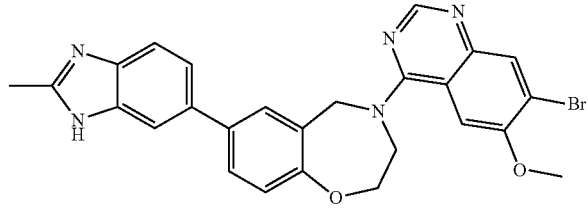 [SMILES: COc1cc2c(N3CCOc4ccc(-c5ccc6nc(C)[nH]c6c5)cc4C3)ncnc2cc1Br] | 4-[7-bromo-6-(methyloxy)quinazolin-4-yl]-7-(2-methyl-1H-benzimidazol-6-yl)-2,3,4,5-tetrahydro-1,4-benzoxazepine |

-continued

| Cmpd No. | Structure | Name |
|---|---|---|
| 32 | 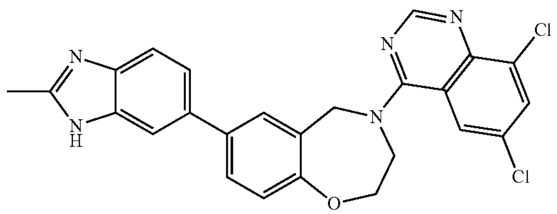 [SMILES: Cc1nc2ccc(-c3ccc4c(c3)CN(c3ncnc5c(Cl)cc(Cl)cc35)CCO4)cc2[nH]1] | 4-(6,8-dichloroquinazolin-4-yl)-7-(2-methyl-1H-benzimidazol-6-yl)-2,3,4,5-tetrahydro-1,4-benzoxazepine |
| 33 | 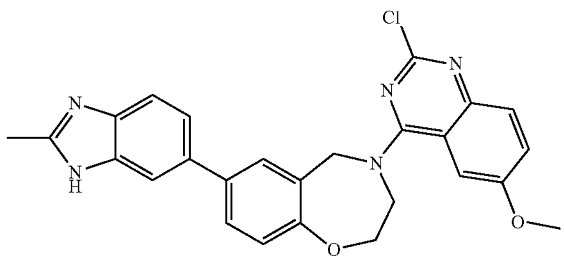 | 4-[2-chloro-6-(methyloxy)quinazolin-4-yl]-7-(2-methyl-1H-benzimidazol-6-yl)-2,3,4,5-tetrahydro-1,4-benzoxazepine |
| 34 | 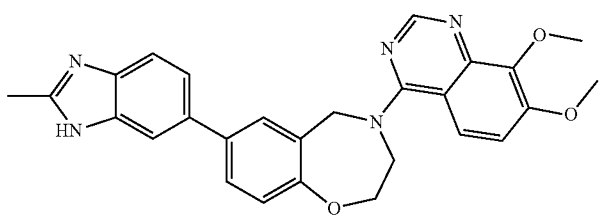 | 4-[7,8-bis(methyloxy)quinazolin-4-yl]-7-(2-methyl-1H-benzimidazol-6-yl)-2,3,4,5-tetrahydro-1,4-benzoxazepine |
| 35 | 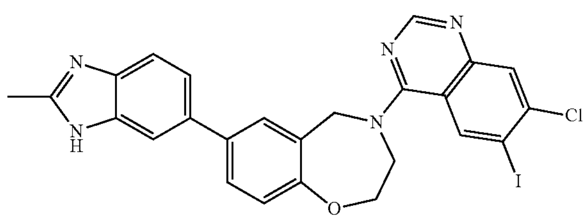 [SMILES: Cc1nc2ccc(-c3ccc4c(c3)CN(c3ncnc5cc(Cl)c(I)cc35)CCO4)cc2[nH]1] | 4-(7-chloro-6-iodoquinazolin-4-yl)-7-(2-methyl-1H-benzimidazol-6-yl)-2,3,4,5-tetrahydro-1,4-benzoxazepine |
| 36 | 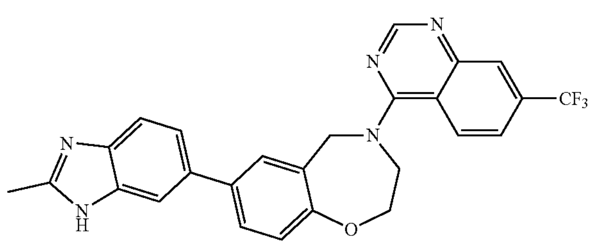 [SMILES: Cc1nc2ccc(-c3ccc4c(c3)CN(c3ncnc5cc(C(F)(F)F)ccc35)CCO4)cc2[nH]1] | 7-(2-methyl-1H-benzimidazol-6-yl)-4-[7-(trifluoromethyl)quinazolin-4-yl]-2,3,4,5-tetrahydro-1,4-benzoxazepine |
| 37 | 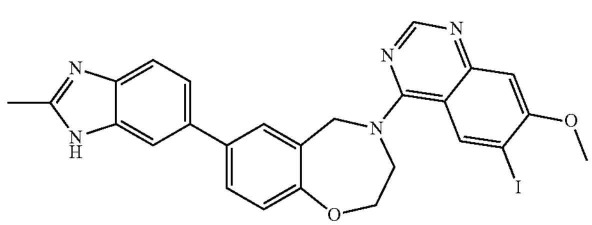 | 4-[6-iodo-7-(methyloxy)quinazolin-4-yl]-7-(2-methyl-1H-benzimidazol-6-yl)-2,3,4,5-tetrahydro-1,4-benzoxazepine |

-continued

| Cmpd No. | Structure | Name |
|---|---|---|
| 38 | 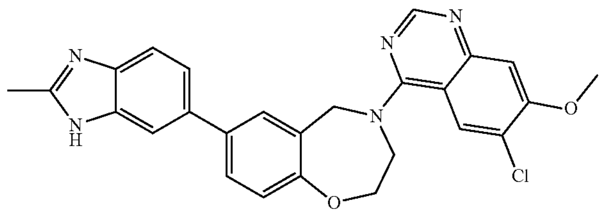 | 4-[6-chloro-7-(methyloxy)quinazolin-4-yl]-7-(2-methyl-1H-benzimidazol-6-yl)-2,3,4,5-tetrahydro-1,4-benzoxazepine |
| 39 | 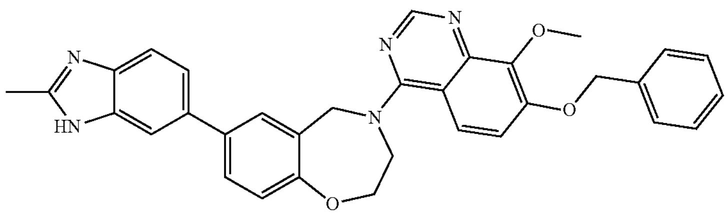 [SMILES: COc1c(OCc2ccccc2)ccc2c(N3CCOc4ccc(-c5ccc6nc(C)[nH]c6c5)cc4C3)ncnc12] | 7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine |
| 40 | 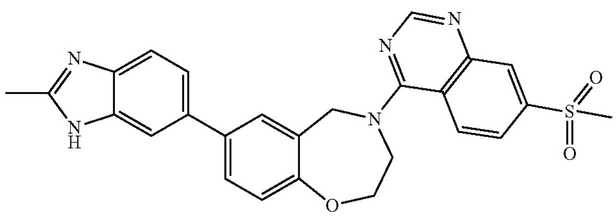 | 7-(2-methyl-1H-benzimidazol-6-yl)-4-[7-(methylsulfonyl)quinazolin-4-yl]-2,3,4,5-tetrahydro-1,4-benzoxazepine |
| 41 | 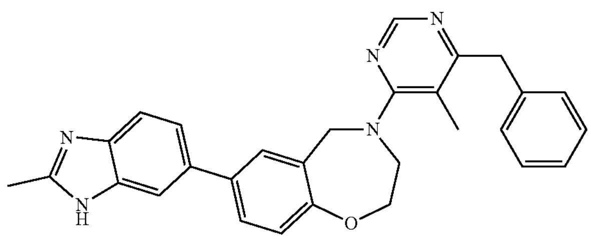 [SMILES: Cc1nc2ccc(-c3ccc4c(c3)CN(c3ncnc(Cc5ccccc5)c3C)CCO4)cc2[nH]1] | 7-(2-methyl-1H-benzimidazol-6-yl)-4-[5-methyl-6-(phenylmethyl)pyrimidin-4-yl]-2,3,4,5-tetrahydro-1,4-benzoxazepine |
| 42 | 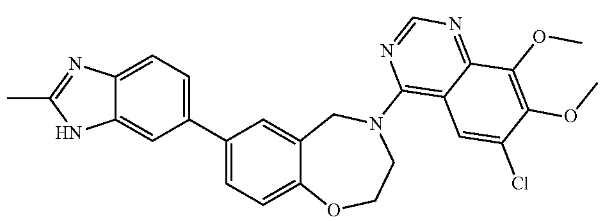 | 4-[6-chloro-7,8-bis(methyloxy)quinazolin-4-yl]-7-(2-methyl-1H-benzimidazol-6-yl)-2,3,4,5-tetrahydro-1,4-benzoxazepine |
| 43 | 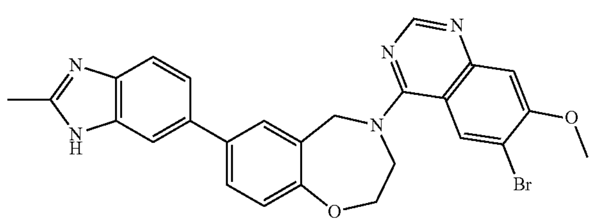 | 4-[6-bromo-7-(methyloxy)quinazlolin-4-yl]-7-(2-methyl-1H-benzimidazol-6-yl)-2,3,4,5-tetrahydro-1,4-benzoxazepine |
| 44 | 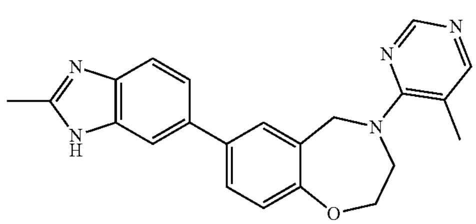 [SMILES: Cc1nc2ccc(-c3ccc4c(c3)CN(c3ncncc3C)CCO4)cc2[nH]1] | 7-(2-methyl-1H-benzimidazol-6-yl)-4-(5-methylpyrimidin-4-yl)-2,3,4,5-tetrahydro-1,4-benzoxazepine |

| Cmpd No. | Structure | Name |
| --- | --- | --- |
| 45 | 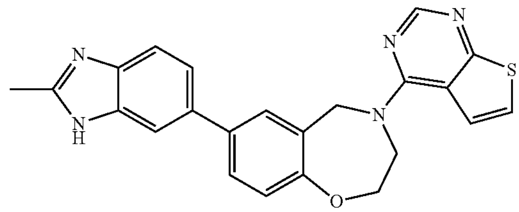 [SMILES: Cc1nc2ccc(-c3ccc4c(c3)CN(c3ncnc5sccc35)CCO4)cc2[nH]1] | 7-(2-methyl-1H-benzimidazol-6-yl)-4-thieno[2,3-d]pyrimidin-4-yl-2,3,4,5-tetrahydro-1,4-benzoxazepine |
| 46 | 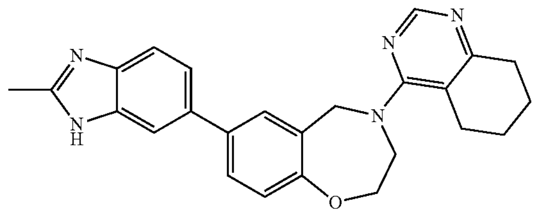 [SMILES: Cc1nc2ccc(-c3ccc4c(c3)CN(c3ncnc5c3CCCC5)CCO4)cc2[nH]1] | 7-(2-methyl-1H-benzimidazol-6-yl)-4-(5,6,7,8-tetrahydroquinazolin-4-yl)-2,3,4,5-tetrahydro-1,4-benzoxazepine |
| 47 | 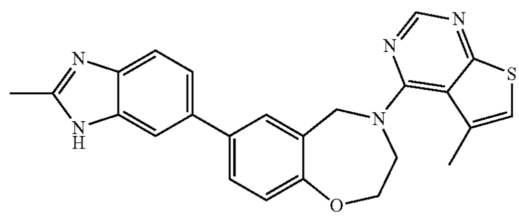 [SMILES: Cc1nc2ccc(-c3ccc4c(c3)CN(c3ncnc5scc(C)c35)CCO4)cc2[nH]1] | 7-(2-methyl-1H-benzimidazol-6-yl)-4-(5-methylthieno[2,3-d]pyrimidin-4-yl)-2,3,4,5-tetrahydro-1,4-benzoxazepine |
| 48 | 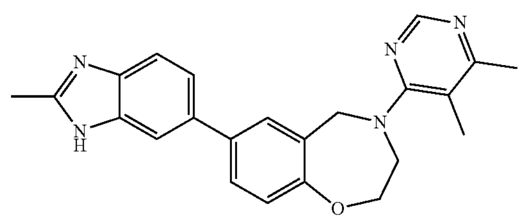 | 4-(5,6-dimethylpyrimidin-4-yl)-7-(2-methyl-1H-benimidazol-6-yl)-2,3,4,5-tetrahydro-1,4-benzoxazepine |
| 49 | 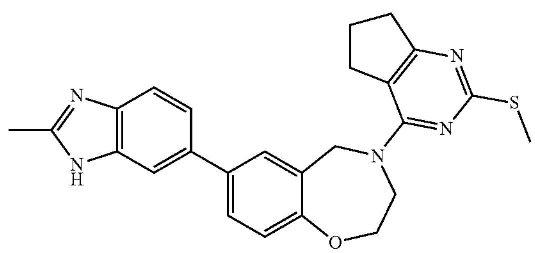 | 7-(2-methyl-1H-benzimidazol-6-yl)-4-[2-(methylthio)-6,7-dihydro-5H-cyclopenta[d]pyrimidin-4-yl]-2,3,4,5-tetrahydro-1,4-benzoxazepine |
| 50 | 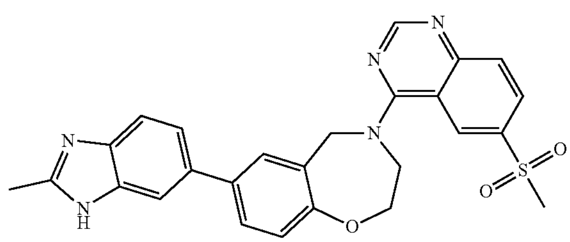 [SMILES: Cc1nc2ccc(-c3ccc4c(c3)CN(c3ncnc5ccc(S(C)(=O)=O)cc35)CCO4)cc2[nH]1] | 7-(2-methyl-1H-benzimidazol-6-yl)-4-[6-(methylsulfonyl)quinazolin-4-yl]-2,3,4,5-tetrahydro-1,4-benzoxazepine |
| 51 | 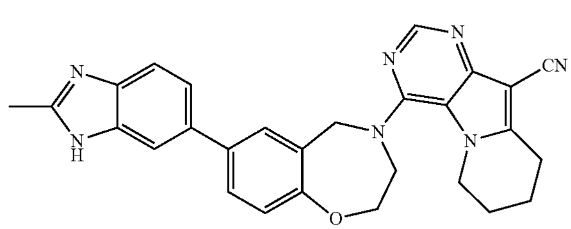 [SMILES: Cc1nc2ccc(-c3ccc4c(c3)CN(c3ncnc5c(C#N)c6n(c35)CCCC6)CCO4)cc2[nH]1] | 4-[7-(2-methyl-1H-benzimidazol-6-yl)-2,3-dihydro-1,4-benzoxazepin-4(5H)-yl]-6,7,8,9-tetrahydropyrimido[4,5-b]indolizine-10-carbonitrile |

-continued

| Cmpd No. | Structure | Name |
|---|---|---|
| 52 | 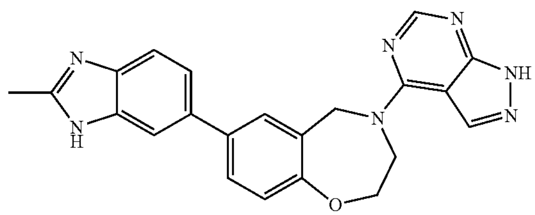 [SMILES: Cc1nc2ccc(-c3ccc4c(c3)CN(c3ncnc5[nH]ncc35)CCO4)cc2[nH]1] | 7-(2-methyl-1H-benzimidazol-6-yl)-4-(1H-pyrazolo[3,4-d]pyrimidin-4-yl)-2,3,4,5-tetrahydro-1,4-benzoxazepine |
| 53 | 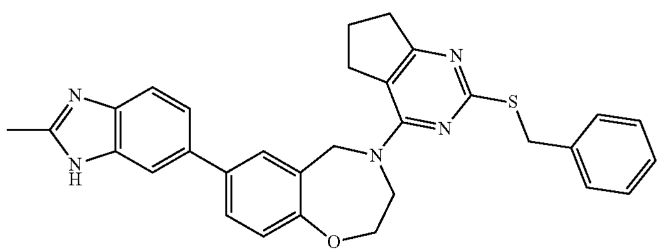 [SMILES: Cc1nc2ccc(-c3ccc4c(c3)CN(c3nc(SCc5ccccc5)nc5c3CCC5)CCO4)cc2[nH]1] | 7-(2-methyl-1H-benzimidazol-6-yl)-4-{2-[(phenylmethyl)thio]-6,7-dihydro-5H-cyclopenta[d]pyrimidin-4-yl}-2,3,4,5-tetrahydro-1,4-benzoxazepine |
| 54 | 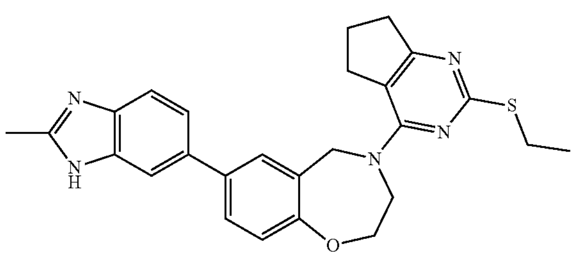 [SMILES: CCSc1nc2c(c(N3CCOc4ccc(-c5ccc6nc(C)[nH]c6c5)cc4C3)n1)CCC2] | 4-[2-(ethylthio)-6,7-dihydro-5H-cyclopenta[d]pyrimidin-4-yl]-7-(2-methyl-1H-benzimidazol-6-yl)-2,3,4,5-tetrahydro-1,4-benzoxazepine |
| 55 | 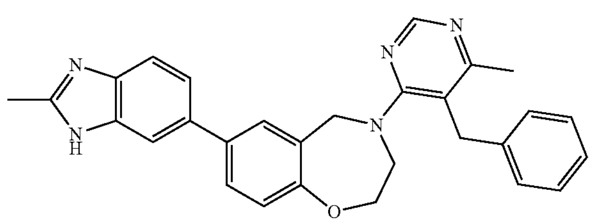 [SMILES: Cc1nc2ccc(-c3ccc4c(c3)CN(c3ncnc(C)c3Cc3ccccc3)CCO4)cc2[nH]1] | 7-(2-methyl-1H-benzimidazol-6-yl)-4-[6-methyl-5-(phenylmethyl)pyrimidin-4-yl]-2,3,4,5-tetrahydro-1,4-benzoxazepine |
| 56 | 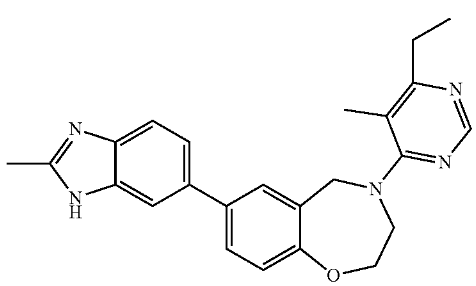 [SMILES: CCc1ncnc(N2CCOc3ccc(-c4ccc5nc(C)[nH]c5c4)cc3C2)c1C] | 4-(6-ethyl-5-methylpyrimidin-4-yl)-7-(2-methyl-1H-benzimidazol-6-yl)-2,3,4,5-tetrahydro-1,4-benzoxazepine |
| 57 | 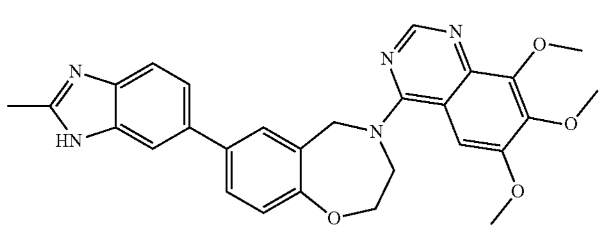 | 7-(2-methyl-1H-benzimidazol-6-yl)-4-[6,7,8-tris(methyloxy)quinazolin-4-tris(methyloxy)quinazolin-4-yl]-2,3,4,5-tetrahydro-1,4-benzoxazepine |

-continued

| Cmpd No. | Structure | Name |
| --- | --- | --- |
| 58 | 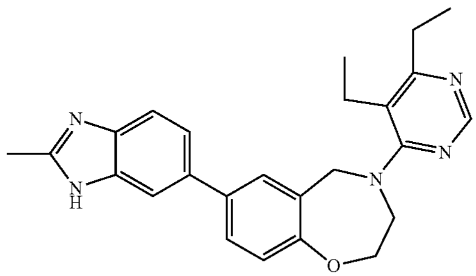 [SMILES: CCc1ncnc(N2CCOc3ccc(-c4ccc5nc(C)[nH]c5c4)cc3C2)c1CC] | 4-(5,6-diethylpyrimidin-4-yl)-7-(2-methyl-1H-benzimidazol-6-yl)-2,3,4,5-tetrahydro-1,4-benzoxazepine |
| 59 | 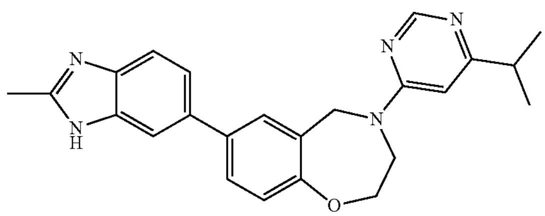 [SMILES: Cc1nc2ccc(-c3ccc4c(c3)CN(c3cc(C(C)C)ncn3)CCO4)cc2[nH]1] | 7-(2-methyl-1H-benzimidazol-6-yl)-4-[6-(1-methylethyl)pyrimidin-4-yl]-2,3,4,5-tetrahydro-1,4-benzoxazepine |
| 60 | 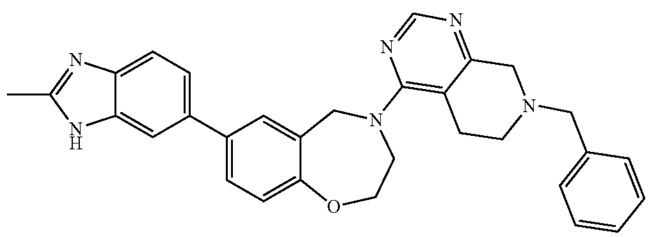 [SMILES: Cc1nc2ccc(-c3ccc4c(c3)CN(c3ncnc5c3CCN(Cc3ccccc3)C5)CCO4)cc2[nH]1] | 7-(2-methyl-1H-benzimidazol-6-yl)-4-[7-(phenylmethyl)-5,6,7,8-tetrahydropyrido[3,4-d]pyrimidin-4-yl]-2,3,4,5-tetrahydro-1,4-benzoxazepine |
| 61 | 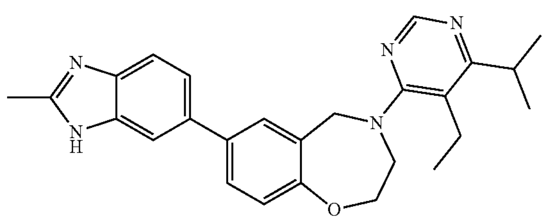 [SMILES: CCc1c(C(C)C)ncnc1N1CCOc2ccc(-c3ccc4nc(C)[nH]c4c3)cc2C1] | 4-[5-ethyl-6-(1-methylethyl)pyrimidin-4-yl]-7-(2-methyl-1H-benzimidazol-6-yl)-2,3,4,5-tetrahydro-1,4-benzoxazepine |
| 62 | 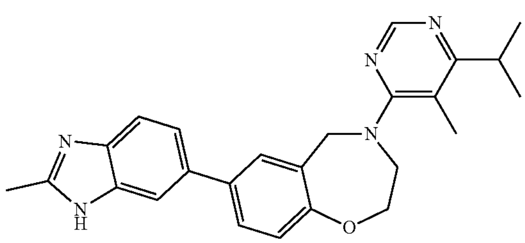 [SMILES: Cc1nc2ccc(-c3ccc4c(c3)CN(c3ncnc(C(C)C)c3C)CCO4)cc2[nH]1] | 7-(2-methyl-1H-benzimidazol-6-yl)-4-[5-methyl-6-(1-methylethyl)pyrimidin-4-yl]-2,3,4,5-tetrahydro-1,4-benzoxazepine |
| 63 | 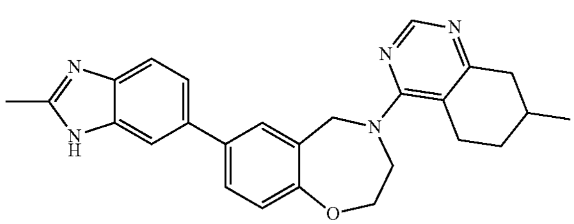 | 7-(2-methyl-1H-benzimidazol-6-yl)-4-(7-methyl-5,6,7,8-tetrahydroquinazolin-4-yl)-2,3,4,5-tetrahydro-1,4-benzoxazepine |

-continued

| Cmpd No. | Structure | Name |
|---|---|---|
| 64 | 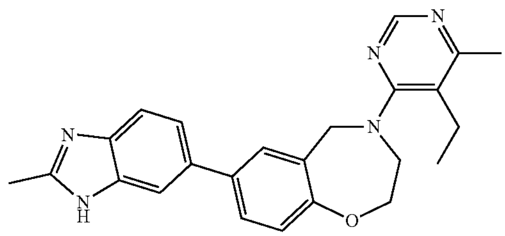 | 4-(5-ethyl-6-methylpyrimidin-4-yl)-7-(2-methyl-1H-benzimidazol-6-yl)-2,3,4,5-tetrahydro-1,4-benzoxazepine |
| 65 | 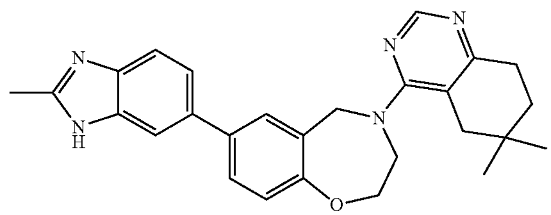 | 4-(6,6-dimethyl-5,6,7,8-tetrahydroquinazolin-4-yl)-7-(2-methyl-1H-benzimidazol-6-yl)-2,3,4,5-tetrahydro-1,4-benzoxazepine |
| 66 | 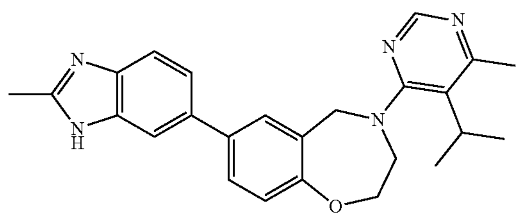 | 7-(2-methyl-1H-benzimidazol-6-yl)-4-[6-methyl-5-(1-methylethyl)pyrimidin-4-yl]-2,3,4,5-tetrahydro-1,4-benzoxazepine |
| 67 | 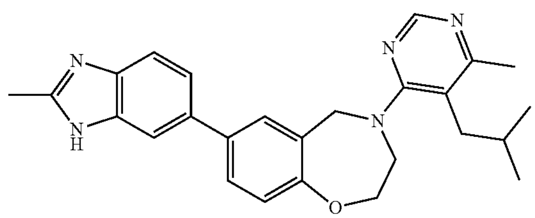 [SMILES: Cc1nc2ccc(-c3ccc4c(c3)CN(c3ncnc(C)c3CC(C)C)CCO4)cc2[nH]1] | 7-(2-methyl-1H-benzimidazol-6-yl)-4-[6-methyl-5-(2-methylpropyl)pyrimidin-4-yl]-2,3,4,5-tetrahydro-1,4-benzoxazepine |
| 68 | 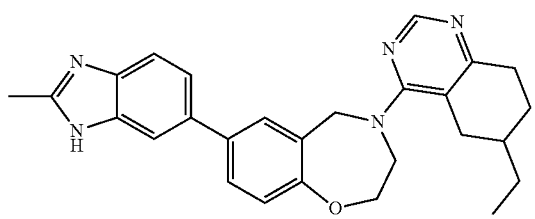 [SMILES: CCC1CCc2ncnc(N3CCOc4ccc(-c5ccc6nc(C)[nH]c6c5)cc4C3)c2C1] | 4-(6-ethyl-5,6,7,8-tetrahydroquinazolin-4-yl)-7-(2-methyl-1H-benzimidazol-6-yl)-2,3,4,5-tetrahydro-1,4-benzoxazepine |
| 69 | 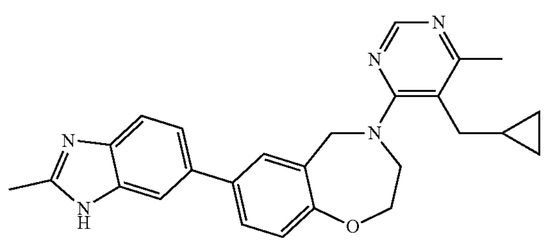 [SMILES: Cc1nc2ccc(-c3ccc4c(c3)CN(c3ncnc(C)c3CC3CC3)CCO4)cc2[nH]1] | 4-[5-(cyclopropylmethyl)-6-methylpyrimidin-4-yl]-7-(2-methyl-1H-benzimidazol-6-yl)-2,3,4,5-tetrahydro-1,4-benzoxazepine |
| 70 | 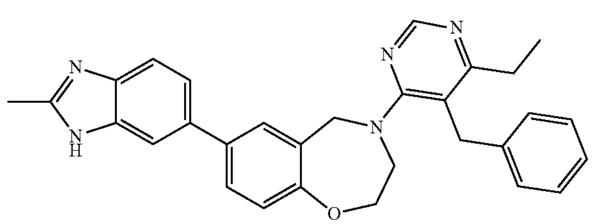 [SMILES: CCc1ncnc(N2CCOc3ccc(-c4ccc5nc(C)[nH]c5c4)cc3C2)c1Cc1ccccc1] | 4-[6-ethyl-5-(phenylmethyl)pyrimidin-4-yl]-7-(2-methyl-1H-benzimidazol-6-yl)-2,3,4,5-tetrahydro-1,4-benzoxazepine |

-continued

| Cmpd No. | Structure | Name |
|---|---|---|
| 71 | 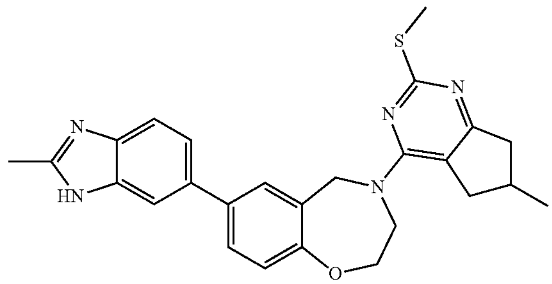 | 7-(2-methyl-1H-benzimidazol-6-yl)-4-[6-methyl-2-(methylthio)-6,7-dihydro-5H-cyclopenta[d]pyrimidin-4-yl]-2,3,4,5-tetrahydro-1,4-benzoxazepine |
| 72 | 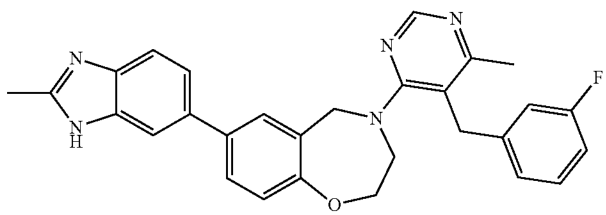 [SMILES: Cc1nc2ccc(-c3ccc4c(c3)CN(c3ncnc(C)c3Cc3cccc(F)c3)CCO4)cc2[nH]1] | 4-{5-[(3-fluorophenyl)methyl]-6-methylpyrimidin-4-yl}-7-(2-methyl-1H-benzimidazol-6-yl)-2,3,4,5-tetrahydro-1,4-benzoxazepine |
| 73 | 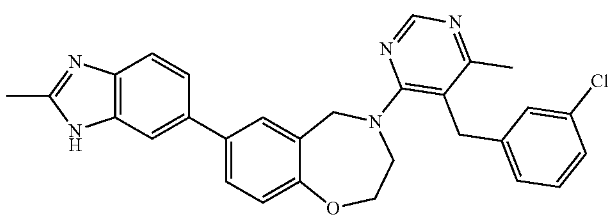 [SMILES: Cc1nc2ccc(-c3ccc4c(c3)CN(c3ncnc(C)c3Cc3cccc(Cl)c3)CCO4)cc2[nH]1] | 4-{5-[(3-chlorophenyl)methyl]-6-methylpyrimidin-4-yl}-7-(2-methyl-1H-benzimidazol-6-yl)-2,3,4,5-tetrahydro-1,4-benzoxazepine |
| 74 | 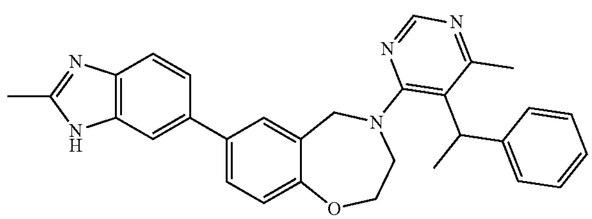 [SMILES: Cc1nc2ccc(-c3ccc4c(c3)CN(c3ncnc(C)c3C(C)c3ccccc3)CCO4)cc2[nH]1] | 7-(2-methyl-1H-benzimidazol-6-yl)-4-[6-methyl-5-(1-phenylethyl)pyrimidin-4-yl)]-2,3,4,5-tetrahydro-1,4-benzoxazepine |
| 75 | 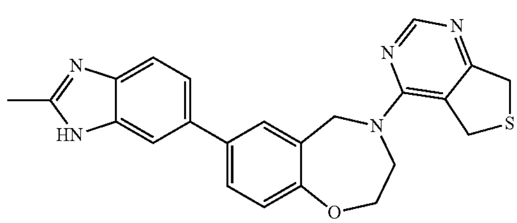 [SMILES: Cc1nc2ccc(-c3ccc4c(c3)CN(c3ncnc5c3CSC5)CCO4)cc2[nH]1] | 4-(5,7-dihydrothieno[3,4-d]pyrimidin-4-yl)-7-(2-methyl-1H-benzimidazol-6-yl)-2,3,4,5-tetrahydro-1,4-benzoxazepine |
| 76 | 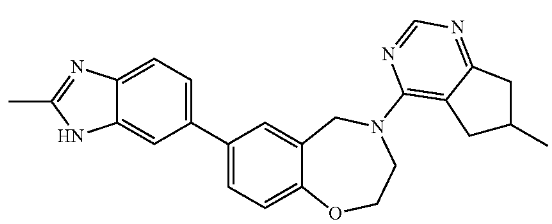 | 7-(2-methyl-1H-benzimidazol-6-yl)-4-(6-methyl-6,7-dihydro-5H-cyclopenta[d]pyrimidin-4-yl)-2,3,4,5-tetrahydro-1,4-benzoxazepine |

-continued

| Cmpd No. | Structure | Name |
|---|---|---|
| 77 | 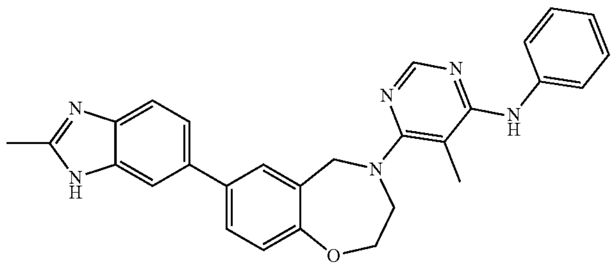 [SMILES: Cc1nc2ccc(-c3ccc4c(c3)CN(c3ncnc(Nc5ccccc5)c3C)CCO4)cc2[nH]1] | 5-methyl-6-[7-(2-methyl-1H-benzimidazol-6-yl)-2,3-dihydro-1,4-benzoxazepine-4(5H)-yl]-N-phenylpyrimidin-4-amine |
| 78 | 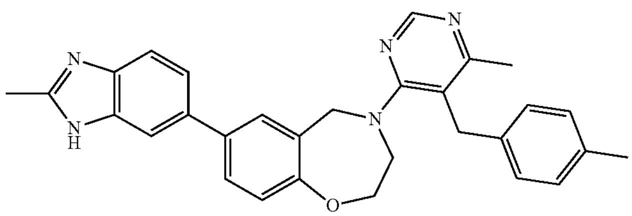 | 7-(2-methyl-1H-benzimidazol-6-yl)-4-{6-methyl-5-[(4-methylphenyl)methyl]pyrimidin-4-yl}-2,3,4,5-tetrahydro-1,4-benzoxazepine |
| 79 | 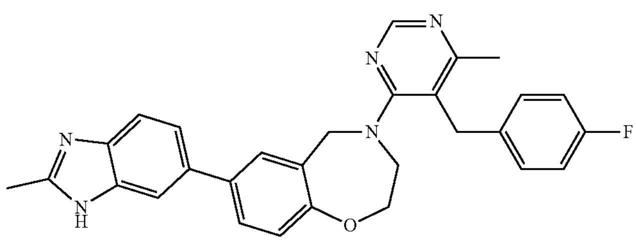 [SMILES: Cc1nc2ccc(-c3ccc4c(c3)CN(c3ncnc(C)c3Cc3ccc(F)cc3)CCO4)cc2[nH]1] | 4-{5-[(4-fluorophenyl)methyl]-6-methylpyrimidin-4-yl}-7-(2-methyl-1H-benzimidazol-6-yl)-2,3,4,5-tetrahydro-1,4-benzoxazepine |
| 80 | 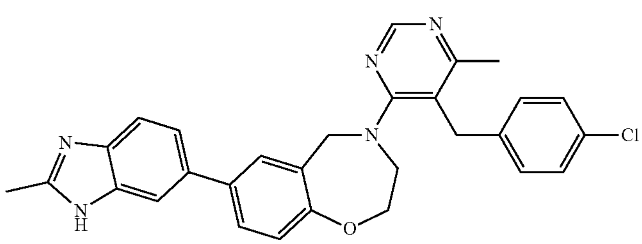 [SMILES: Cc1nc2ccc(-c3ccc4c(c3)CN(c3ncnc(C)c3Cc3ccc(Cl)cc3)CCO4)cc2[nH]1] | 4-{5-[(4-chlorophenyl)methyl]-6-methylpyrimidin-4-yl}-7-(2-methyl-1H-benzimidazol-6-yl)-2,3,4,5-tetrahydro-1,4-benzoxazepine |
| 81 | 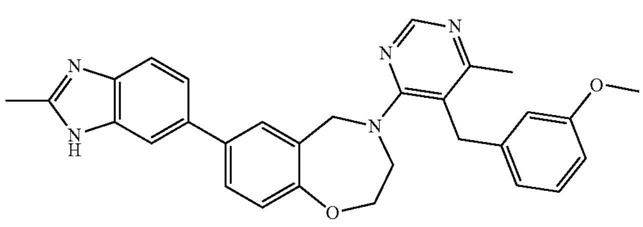 | 7-(2-methyl-1H-benzimidazol-6-yl)-4-(6-methyl-5-{[3-(methyloxy)phenyl]methyl}pyrimidin-4-yl)-2,3,4,5-tetrahydro-1,4-benzoxazepine |
| 82 | 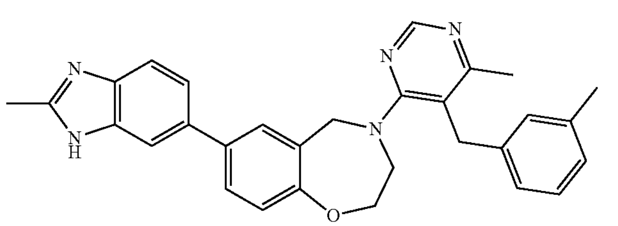 | 7-(2-methyl-1H-benzimidazol-6-yl)-4-{6-methyl-5-[(3-methylphenyl)methyl]pyrimidin-4-yl}-2,3,4,5-tetrahydro-1,4-benzoxazepine |

-continued

| Cmpd No. | Structure | Name |
|---|---|---|
| 83 | 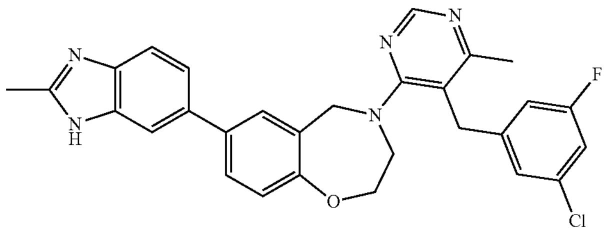 [SMILES: Cc1nc2ccc(-c3ccc4c(c3)CN(c3ncnc(C)c3Cc3cc(F)cc(Cl)c3)CCO4)cc2[nH]1] | 4-{5-[(3-chloro-5-fluorophenyl)methyl]-6-methylpyrimidin-4-yl}-7-(2-methyl-1H-benzimidazol-6-yl)-2,3,4,5-tetrahydro-1,4-benzoxazepine |
| 84 | 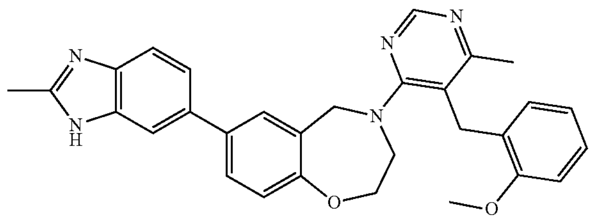 [SMILES: COc1ccccc1Cc1c(C)ncnc1N1CCOc2ccc(-c3ccc4nc(C)[nH]c4c3)cc2C1] | 7-(2-methyl-1H-benzimidazol-6-yl)-4-(6-methyl-5-{[2-(methyloxy)phenyl]methyl}pyrimidin-4-yl)-2,3,4,5-tetrahydro-1,4-benzoxazepine |
| 85 | 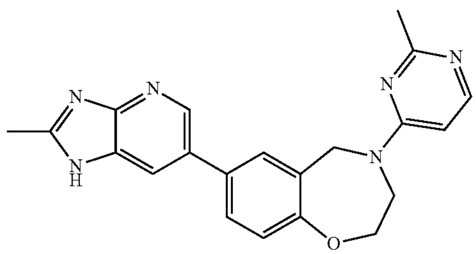 [SMILES: Cc1nccc(N2CCOc3ccc(-c4cnc5nc(C)[nH]c5c4)cc3C2)n1] | 7-(2-methyl-1H-imidazo[4,5-b]pyridin-6-yl)-4-(2-methylpyrimidin-4-yl)-2,3,4,5-tetrahydro-1,4-benzoxazepine |
| 86 | 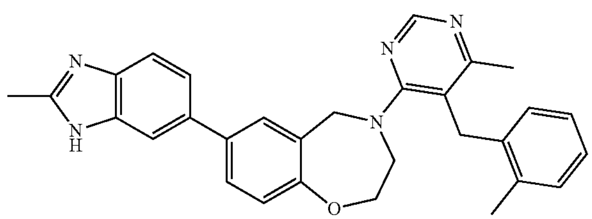 | 7-(2-methyl-1H-benzimidazol-6-yl)-4-{6-methyl-5-[(2-methylphenyl)methyl]pyrimidin-4-yl}-2,3,4,5-tetrahydro-1,4-benzoxazepine |
| 87 | 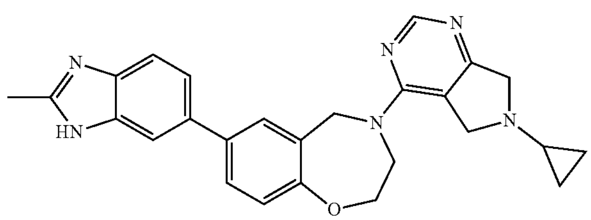 [SMILES: Cc1nc2ccc(-c3ccc4c(c3)CN(c3ncnc5c3CN(C3CC3)C5)CCO4)cc2[nH]1] | 4-(6-cyclopropyl-6,7-dihydro-5H-pyrrolo[3,4-d]pyrimidin-4-yl)-7-(2-methyl-1H-benzimidazol-6-yl)-2,3,4,5-tetrahydro-1,4-benzoxazepine |
| 88 | 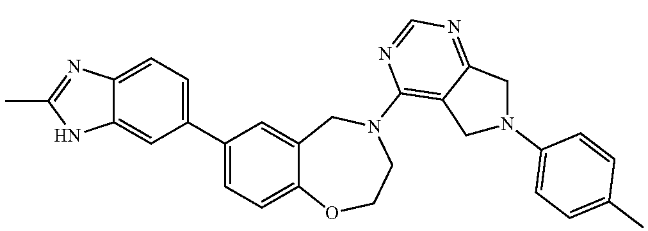 | 7-(2-methyl-1H-benzimidazol-6-yl)-4-[6-(4-methylphenyl)-6,7-dihydro-5H-pyrrolo[3,4-d]pyrimidin-4-yl]-2,3,4,5-tetrahydro-1,4-benzoxazepine |

| Cmpd No. | Structure | Name |
|---|---|---|
| 89 | 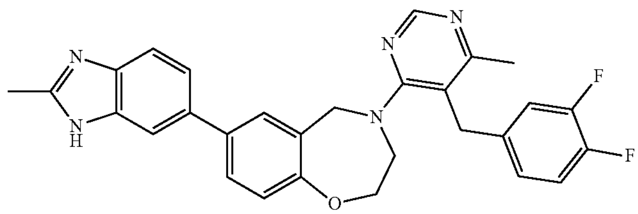 [SMILES: Cc1nc2ccc(-c3ccc4c(c3)CN(c3ncnc(C)c3Cc3ccc(F)c(F)c3)CCO4)cc2[nH]1] | 4-{5-[(3,4-difluorophenyl)methyl]-6-methylpyrimidin-4-yl}-7-(2-methyl-1H-benzimidazol-6-yl)-2,3,4,5-tetrahydro-1,4-benzoxazepine |
| 90 | 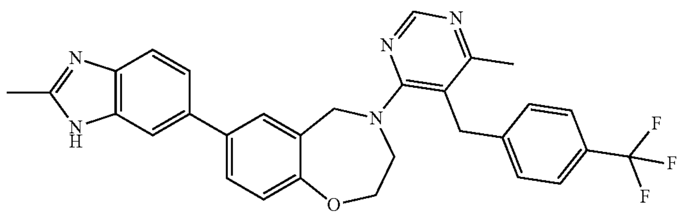 [SMILES: Cc1nc2ccc(-c3ccc4c(c3)CN(c3ncnc(C)c3Cc3ccc(C(F)(F)F)cc3)CCO4)cc2[nH]1] | 7-(2-methyl-1H-benzimidazol-6-yl)-4-(6-methyl-5-{[4-(trifluoromethyl)phenyl]methyl}pyrimidin-4-yl)-2,3,4,5-tetrahydro-1,4-benzoxazepine |
| 91 | 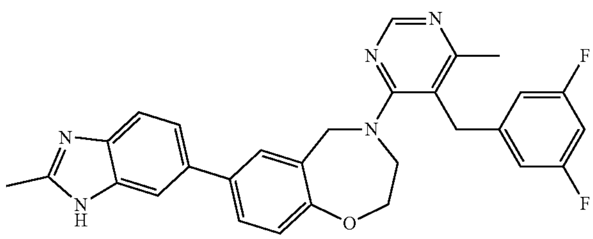 [SMILES: Cc1nc2ccc(-c3ccc4c(c3)CN(c3ncnc(C)c3Cc3cc(F)cc(F)c3)CCO4)cc2[nH]1] | 4-{5-[(3,5-difluorophenyl)methyl]-6-methylpyrimidin-4-yl}-7-(2-methyl-1H-benzimidazol-6-yl)-2,3,4,5-tetrahydro-1,4-benzoxazepine |
| 92 | 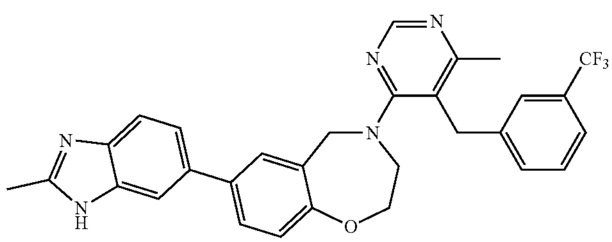 [SMILES: Cc1nc2ccc(-c3ccc4c(c3)CN(c3ncnc(C)c3Cc3cccc(C(F)(F)F)c3)CCO4)cc2[nH]1] | 7-(2-methyl-1H-benzimidazol-6-yl)-4-(6-methyl-5-{[3-(trifluoromethyl)phenyl]methyl}pyrimidin-4-yl)-2,3,4,5-tetrahydro-1,4-benzoxazepine |
| 93 | 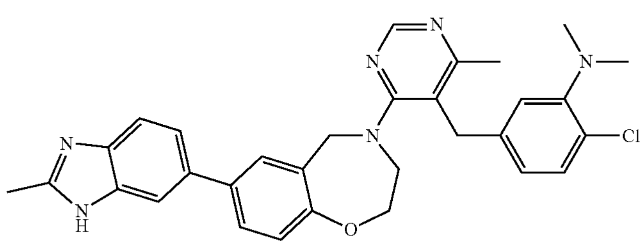 [SMILES: Cc1nc2ccc(-c3ccc4c(c3)CN(c3ncnc(C)c3Cc3ccc(Cl)c(N(C)C)c3)CCO4)cc2[nH]1] | 2-chloro-N,N-dimethyl-5-({4-methyl-6-[7-(2-methyl-1H-benzimidazol-6-yl)-2,3-dihydro-1,4-benzoxazepin-4(5H)-yl]pyrimidin-5-yl}methyl)aniline |
| 94 | 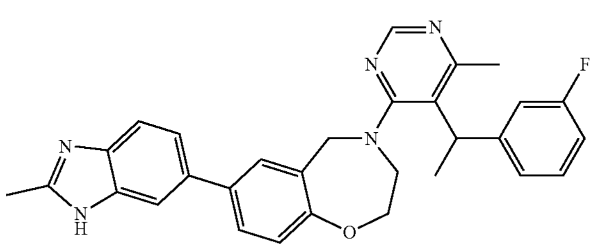 [SMILES: Cc1nc2ccc(-c3ccc4c(c3)CN(c3ncnc(C)c3C(C)c3cccc(F)c3)CCO4)cc2[nH]1] | 4-{5-[1-(3-fluorophenyl)ethyl]-6-methylpyrimidin-4-yl}-7-(2-methyl-1H-benzimidazol-6-yl)-2,3,4,5-tetrahydro-1,4-benzoxazepine |

-continued

| Cmpd No. | Structure | Name |
|---|---|---|
| 95 | 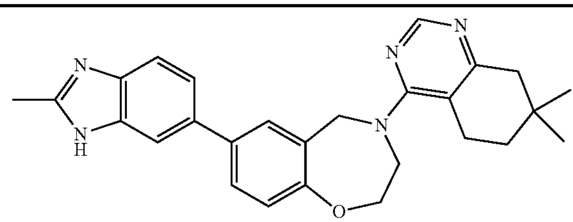 | 4-(7,7-dimethyl-5,6,7,8-tetrahydroquinazolin-4-yl)-7-(2-methyl-1H-benzimidazol-6-yl)-2,3,4,5-tetrahydro-1,4-benzoxazepine |
| 96 | 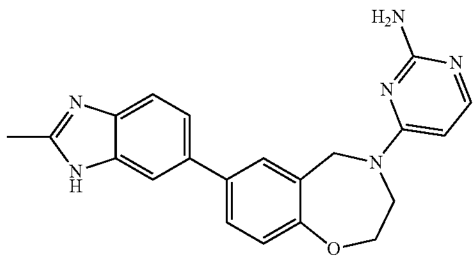 [SMILES: Cc1nc2ccc(-c3ccc4c(c3)CN(c3ccnc(N)n3)CCO4)cc2[nH]1] | 4-[7-(2-methyl-1H-benzimidazol-6-yl)-2,3-dihydro-1,4-benzoxazepin-4(5H)-yl]pyrimidin-2-amine |
| 97 | 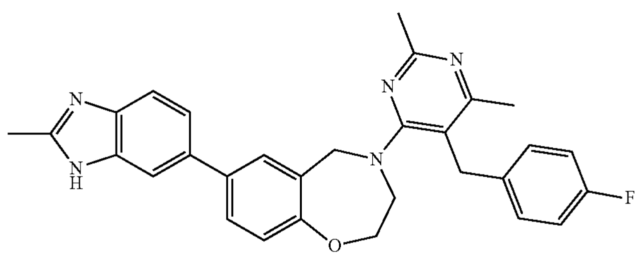 [SMILES: Cc1nc(C)c(Cc2ccc(F)cc2)c(N2CCOc3ccc(-c4ccc5nc(C)[nH]c5c4)cc3C2)n1] | 4-{5-[(4-fluorrophenyl)methyl]-2,6-dimethylpyrimidin-4-yl}-7-(2-methyl-1H-benzimidazol-6-yl)-2,3,4,5-tetrahydro-1,4-benzoxazepine |
| 98 | 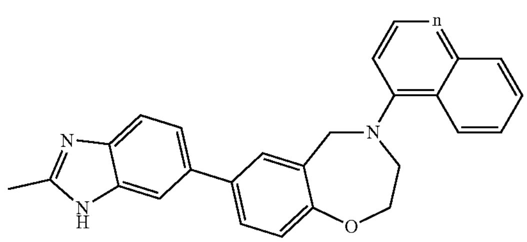 | 7-(2-methyl-1H-benzimidazol-6-yl)-4-quinolin-4-yl-2,3,4,5-tetrahydro-1,4-benzoxazepine |
| 99 | 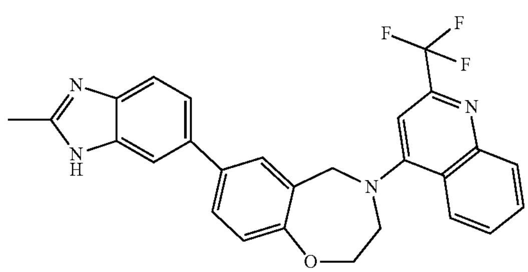 [SMILES: Cc1nc2ccc(-c3ccc4c(c3)CN(c3cc(C(F)(F)F)nc5ccccc35)CCO4)cc2[nH]1] | 7-(2-methyl-1H-benzimidazol-6-yl)-4-[2-(trifluoromethyl)quinolin-4-yl]-2,3,4,5-tetrahydro-1,4-benzoxazepine |
| 100 | 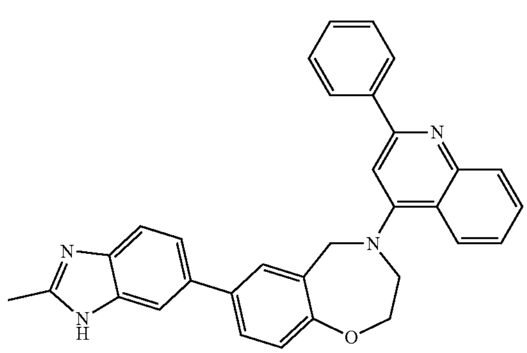 [SMILES: Cc1nc2ccc(-c3ccc4c(c3)CN(c3cc(-c5ccccc5)nc5ccccc35)CCO4)cc2[nH]1] | 7-(2-methyl-1H-benzimidazol-6-yl)-4-(2-phenylquinolin-4-yl)-2,3,4,5-tetrahydro-1,4-benzoxazepine |

-continued

| Cmpd No. | Structure | Name |
|---|---|---|
| 101 | 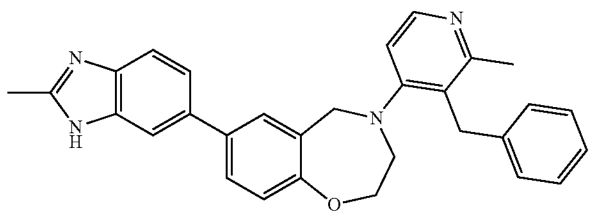 [SMILES: Cc1nc2ccc(-c3ccc4c(c3)CN(c3ccnc(C)c3Cc3ccccc3)CCO4)cc2[nH]1] | 7-(2-methyl-1H-benzimidazol-6-yl)-4-[2-methyl-3-(phenylmethyl)pyridin-4-yl]-2,3,4,5-tetrahydro-1,4-benzoxazepine |
| 102 | 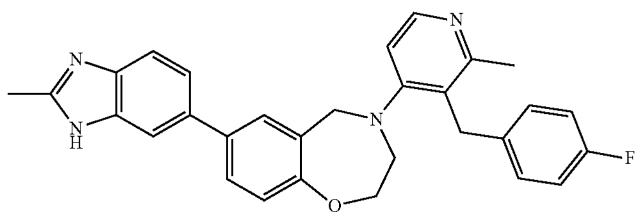 [SMILES: Cc1nc2ccc(-c3ccc4c(c3)CN(c3ccnc(C)c3Cc3ccc(F)cc3)CCO4)cc2[nH]1] | 4-{3-[(4-fluorophenyl)methyl]-2-methylpyridin-4-yl}-7-(2-methyl-1H-benzimidazol-6-yl)-2,3,4,5-tetrahydro-1,4-benzoxazepine |
| 103 | 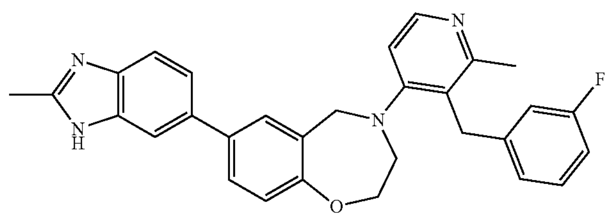 [SMILES: Cc1nc2ccc(-c3ccc4c(c3)CN(c3ccnc(C)c3Cc3cccc(F)c3)CCO4)cc2[nH]1] | 4-{3-[(3-fluorophenyl)methyl]-2-methylpyridin-4-yl}-7-(2-methyl-1H-benzimidazol-6-yl)-2,3,4,5-tetrahydro-1,4-benzoxazepine |
| 104 | 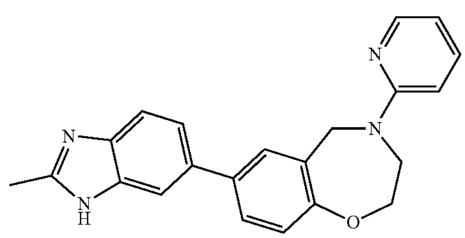 [SMILES: Cc1nc2ccc(-c3ccc4c(c3)CN(c3ccccn3)CCO4)cc2[nH]1] | 7-(2-methyl-1H-benzimidazol-6-yl)-4-pyridin-2-yl-2,3,4,5-tetrahydro-1,4-benzoxazepine |
| 105 | 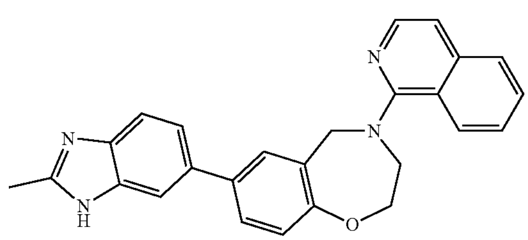 [SMILES: Cc1nc2ccc(-c3ccc4c(c3)CN(c3nccc5ccccc35)CCO4)cc2[nH]1] | 4-isoquinolin-1-yl-7-(2-methyl-1H-benzimidazol-6-yl)-2,3,4,5-tetrahydro-1,4-benzoxazepine |
| 106 | 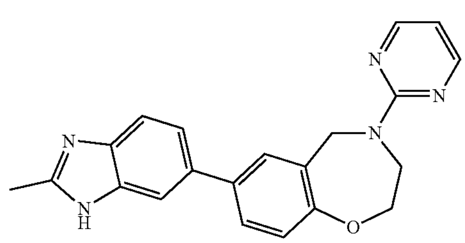 [SMILES: Cc1nc2ccc(-c3ccc4c(c3)CN(c3ncccn3)CCO4)cc2[nH]1] | 7-(2-methyl-1H-benzimidazol-6-yl)-4-pyrimidin-2-yl-2,3,4,5-tetrahydro-1,4-benzoxazepine |

-continued

| Cmpd No. | Structure | Name |
|---|---|---|
| 107 | 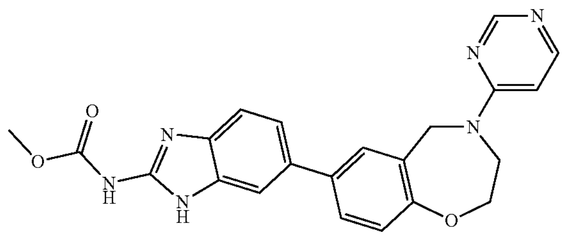 [SMILES: COC(=O)Nc1nc2ccc(-c3ccc4c(c3)CN(c3ccncn3)CCO4)cc2[nH]1] | methyl -6[(4-pyrimidin-4-yl-2,3,4,5-tetrahydro-1,4-benzoxazepin-7-yl)-1H-benzimidazol-2-yl]carbamate |
| 108 | 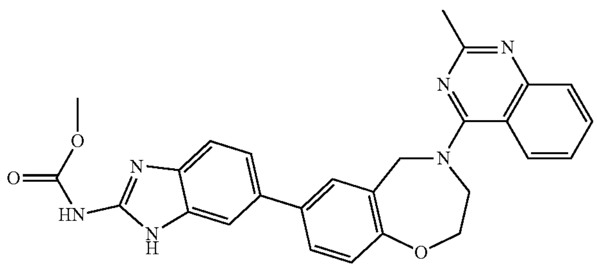 [SMILES: COC(=O)Nc1nc2ccc(-c3ccc4c(c3)CN(c3nc(C)nc5ccccc35)CCO4)cc2[nH]1] | methyl {6-[4-(2-methylquinazolin-4-yl)-2,3,4,5-tetrahydro-1,4-benzoxazepin-7-yl]-1H-benzimidazol-2-yl}carbamate |
| 109 | 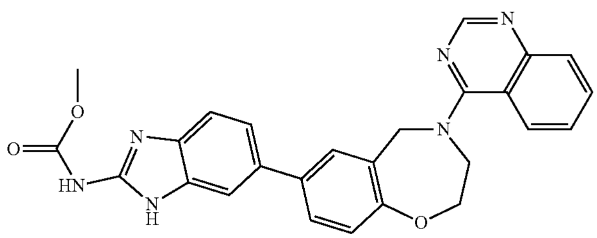 [SMILES: COC(=O)Nc1nc2ccc(-c3ccc4c(c3)CN(c3ncnc5ccccc35)CCO4)cc2[nH]1] | methyl [6-(4-quinazolin-4-yl-2,3,4,5-tetrahydro-1,4-benzoxazepin-7-yl)-1H-benzimidazol-2-yl]carbamate |
| 110 | 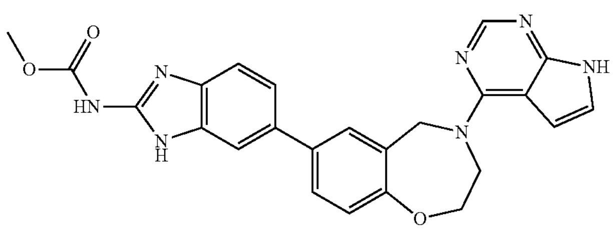 [SMILES: COC(=O)Nc1nc2ccc(-c3ccc4c(c3)CN(c3ncnc5[nH]ccc35)CCO4)cc2[nH]1] | methyl {6-[4-(7H-pyrrolo[2,3-d]pyrimidin-4-yl)-2,3,4,5-tetrahydro-1,4-benzoxazepin-7-yl]-1H-benzimidazol-2-yl}carbamate |
| 111 | 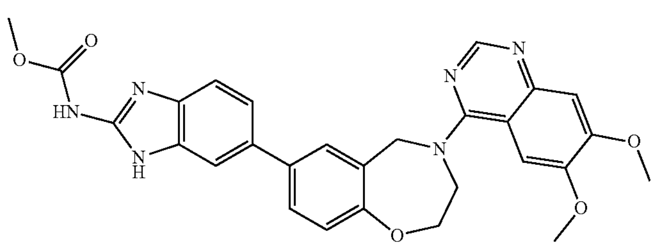 | methyl (6-{4-[6,7-bis(methyloxy)quinazolin-4-yl]-2,3,4,5-tetrahydro-1,4-benzoxazepin-7-yl}-1H-benzimidazol-2-yl)carbamate |
| 112 | 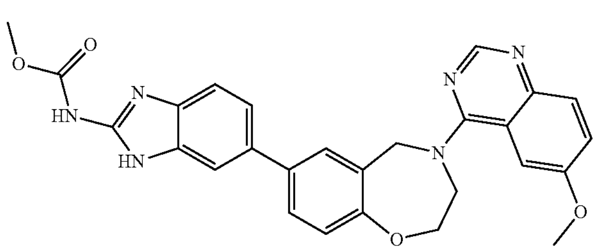 [SMILES: COC(=O)Nc1nc2ccc(-c3ccc4c(c3)CN(c3ncnc5ccc(OC)cc35)CCO4)cc2[nH]1] | methyl (6-{4-[6-(methyloxy)quinazolin-4-yl]-2,3,4,5-tetrahydro-1,4-benzoxazepin-7-yl}-1H-benzimidazol-2-yl)carbamate |

-continued

| Cmpd No. | Structure | Name |
|---|---|---|
| 113 | 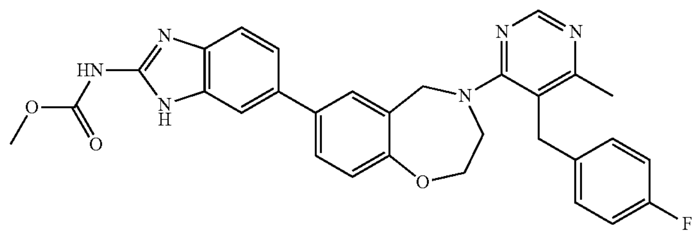 [SMILES: COC(=O)Nc1nc2ccc(-c3ccc4c(c3)CN(c3ncnc(C)c3Cc3ccc(F)cc3)CCO4)cc2[nH]1] | methyl [6-(4-{5-[(4-fluorophenyl)methyl]-6-methylpyrimidin-4-yl}-2,3,4,5-tetrahydro-1,4-benzoxazepin-7-yl)-1H-benzimidazol-2-yl]carbamate |
| 114 | 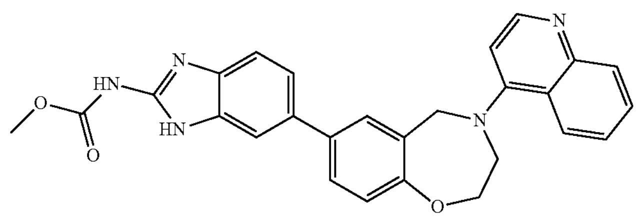 [SMILES: COC(=O)Nc1nc2ccc(-c3ccc4c(c3)CN(c3ccnc5ccccc35)CCO4)cc2[nH]1] | methyl [6-(4-quinolin-4-yl-2,3,4,5-tetrahydro-1,4-benzoxazepin-7-yl)-1H-benzimidazol-2-yl]carbamate |
| 115 | 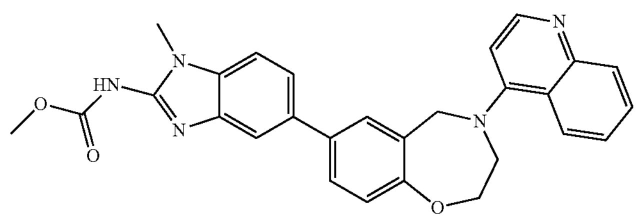 [SMILES: COC(=O)Nc1nc2cc(-c3ccc4c(c3)CN(c3ccnc5ccccc35)CCO4)ccc2n1C] | methyl [1-methyl-5-(4-quinolin-4-yl-2,3,4,5-tetrahydro-1,4-benzoxazepin-7-yl)-1H-benzimidazol-2-yl]carbamate |
| 116 | 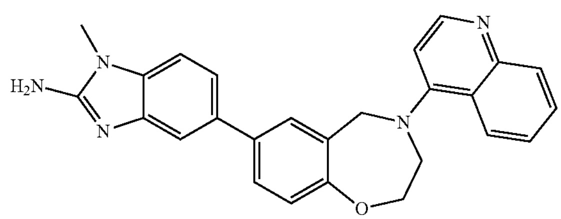 [SMILES: Cn1c(N)nc2cc(-c3ccc4c(c3)CN(c3ccnc5ccccc35)CCO4)ccc21] | 1-methyl-5-(4-quinolin-4-yl-2,3,4,5-tetrahydro-1,4-benzoxazepin-7-yl)-1H-benzimidazol-2-amine |
| 117 | 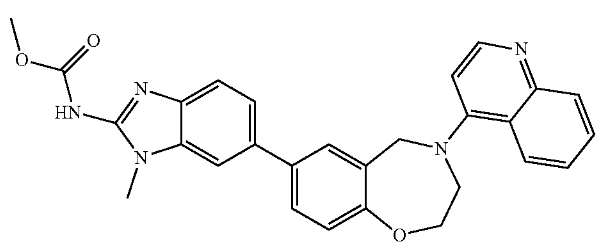 [SMILES: COC(=O)Nc1nc2ccc(-c3ccc4c(c3)CN(c3ccnc5ccccc35)CCO4)cc2n1C] | methyl [1-methyl-6-(4-quinolin-4-yl-2,3,4,5-tetrahydro-1,4-benzoxazepin-7-yl)-1H-benzimidazol-2-yl]carbamate |
| 118 | 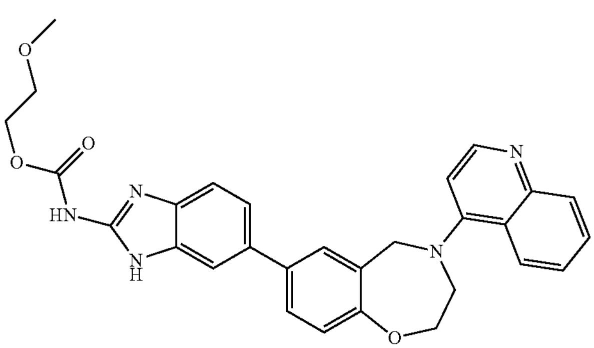 [SMILES: COCCOC(=O)Nc1nc2ccc(-c3ccc4c(c3)CN(c3ccnc5ccccc35)CCO4)cc2[nH]1] | 2-(methyloxy)ethyl [6-(4-quinolin-4-yl-2,3,4,5-tetrahydro-1,4-benzoxazepin-7-yl)-1H-benzimidazol-2-yl]carbamate |

-continued

| Cmpd No. | Structure | Name |
| --- | --- | --- |
| 119 | 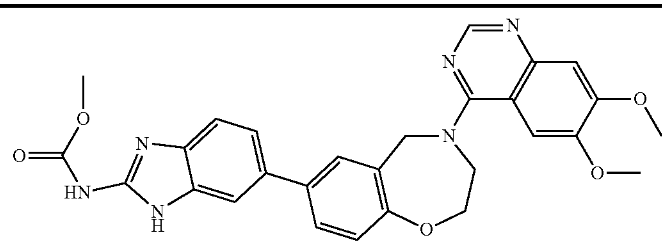 | methyl (6-{4-[6,7-bis(methyloxy)quinolin-4-yl]-2,3,4,5-tetrahydro-1,4-benzoxazepin-7-yl}-1H-benzimidazol-2-yl)carbamate |
| 120 | 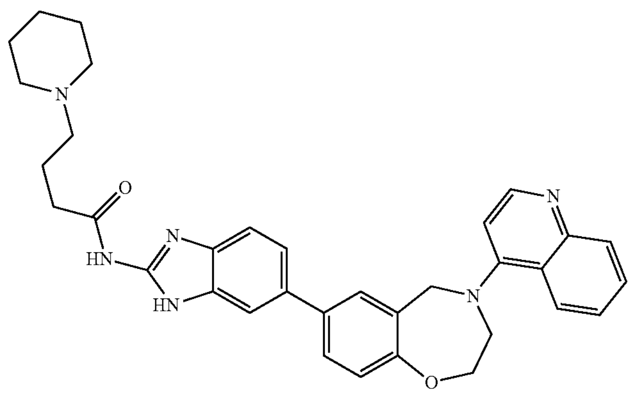 [SMILES: O=C(CCCN1CCCCC1)Nc1nc2ccc(-c3ccc4c(c3)CN(c3ccnc5ccccc35)CCO4)cc2[nH]1] | 4-piperidin-1-yl-N-[6-(4-quinolin-4-yl-2,3,4,5-tetrahydro-1,4-benzoxazepin-7-yl)-1H-benzimidazol-2-yl]butanamide |
| 121 | 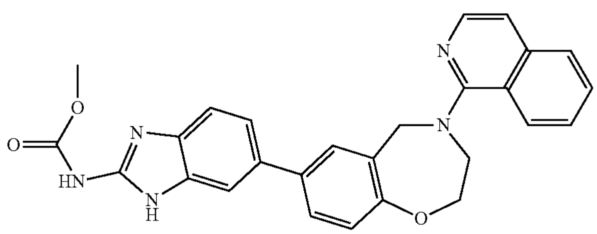 [SMILES: COC(=O)Nc1nc2ccc(-c3ccc4c(c3)CN(c3nccc5ccccc35)CCO4)cc2[nH]1] | methyl [6-(4-isoquinolin-1-yl-2,3,4,5-tetrahydro-1,4-benzoxazepin-7-yl)-1H-benzimidazol-2-yl]carbamate |
| 122 | 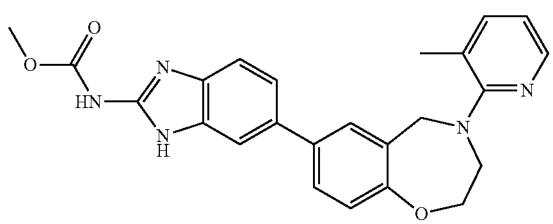 [SMILES: COC(=O)Nc1nc2ccc(-c3ccc4c(c3)CN(c3ncccc3C)CCO4)cc2[nH]1] | methyl {6-[4-(3-methylpyridin-2-yl)-2,3,4,5-tetrahydro-1,4-benzoxazepin-7-yl]-1H-benzimidazol-2-yl}carbamate |
| 123 | 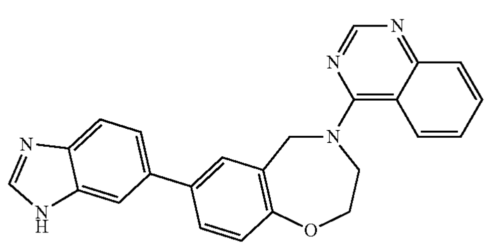 [SMILES: c1ccc2c(N3CCOc4ccc(-c5ccc6nc[nH]c6c5)cc4C3)ncnc2c1] | 7-(1H-benzimidazol-6-yl)-4-quinazolin-4-yl-2,3,4,5-tetrahydro-1,4-benzoxazepine |
| 124 | 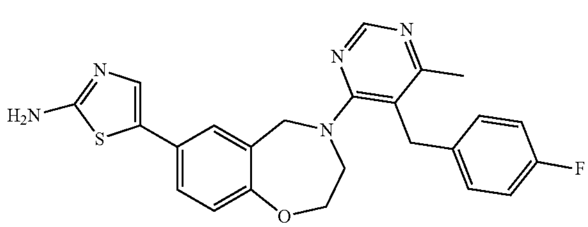 [SMILES: Cc1ncnc(N2CCOc3ccc(-c4cnc(N)s4)cc3C2)c1Cc1ccc(F)cc1] | 5-(4-{5-[(4-fluorophenyl)methyl]-6-methylpyrimidin-4-yl}-2,3,4,5-tetrahydro-1,4-benzoxazepin-7-yl)-1,3-thiazol-2-amine |

-continued

| Cmpd No. | Structure | Name |
|---|---|---|
| 125 | 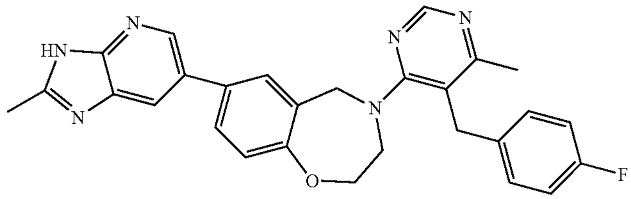 [SMILES: Cc1nc2cc(-c3ccc4c(c3)CN(c3ncnc(C)c3Cc3ccc(F)cc3)CCO4)cnc2[nH]1] | 4-{5-[(4-fluorophenyl)methyl]-6-methylpyrimidin-4-yl}-7-(2-methyl-3H-imidazo[4,5-b]pyridin-6-yl)-2,3,4,5-tetrahydro-1,4-benzodiazepine |
| 126 | 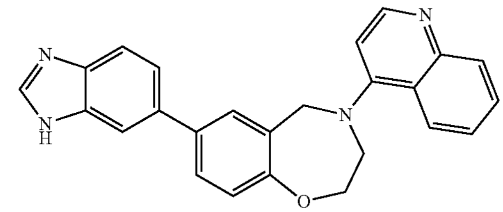 [SMILES: c1ccc2c(N3CCOc4ccc(-c5ccc6nc[nH]c6c5)cc4C3)ccnc2c1] | 7-(1H-benzimidazol-6-yl)-4-quinolin-4-yl-2,3,4,5-tetrahydro-1,4-benzoxazepine |
| 127 | 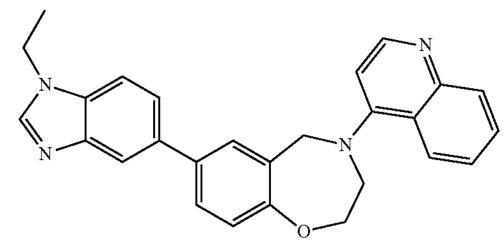 [SMILES: CCn1cnc2cc(-c3ccc4c(c3)CN(c3ccnc5ccccc35)CCO4)ccc21] | 7-(1-ethyl-1H-benzimidazol-5-yl)-4-quinolin-4-yl-2,3,4,5-tetrahydro-1,4-benzoxazepine |
| 128 | 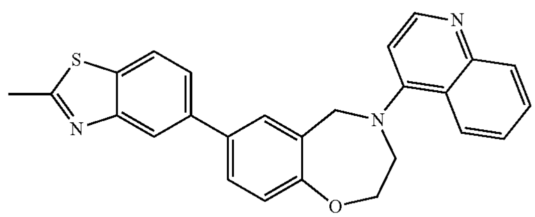 [SMILES: Cc1nc2cc(-c3ccc4c(c3)CN(c3ccnc5ccccc35)CCO4)ccc2s1] | 7-(2-methyl-1,3-benzothiazol-5-yl)-4-quinolin-4-yl-2,3,4,5-tetrahydro-1,4-benzoxazepine |
| 129 | 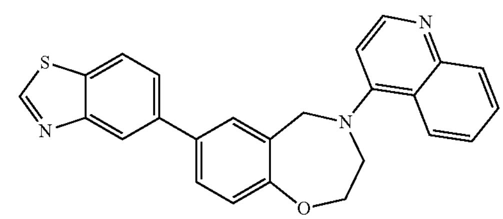 [SMILES: c1ccc2c(N3CCOc4ccc(-c5ccc6scnc6c5)cc4C3)ccnc2c1] | 7-(1,3-benzothiazol-5-yl)-4-quinolin-4-yl-2,3,4,5-tetrahydro-1,4-benzoxazepine |
| 130 | 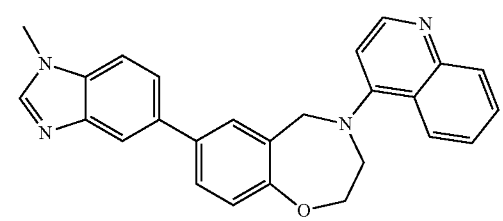 [SMILES: Cn1cnc2cc(-c3ccc4c(c3)CN(c3ccnc5ccccc35)CCO4)ccc21] | 7-(1-methyl-1H-benzimidazol-5-yl)-4-quinolin-4-yl-2,3,4,5-tetrahydro-1,4-benzodiazepine |
| 131 | 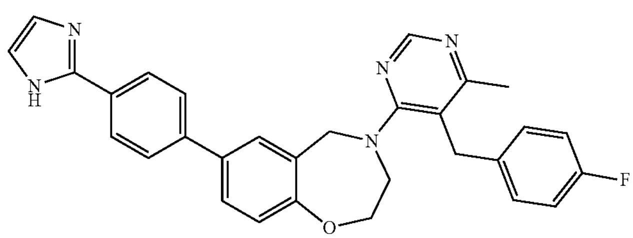 [SMILES: Cc1ncnc(N2CCOc3ccc(-c4ccc(-c5ncc[nH]5)cc4)cc3C2)c1Cc1ccc(F)cc1] | 4-{5-[(4-fluorophenyl)methyl]-6-methylpyrimidin-4-yl}-7-[4-(1H-imidazol-2-yl)phenyl]-2,3,4,5-tetrahydro-1,4-benzoxazepine |

| Cmpd No. | Structure | Name |
| --- | --- | --- |
| 132 | 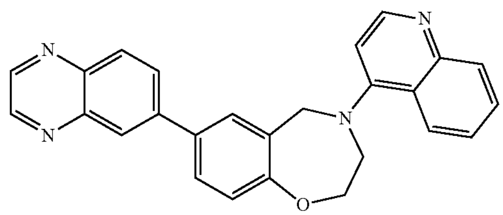 [SMILES: c1ccc2c(N3CCOc4ccc(-c5ccc6nccnc6c5)cc4C3)ccnc2c1] | 4-quinolin-4-yl-7-quinoxalin-6-yl-2,3,4,5-tetrahydro-1,4-benzoxazepine |
| 133 | 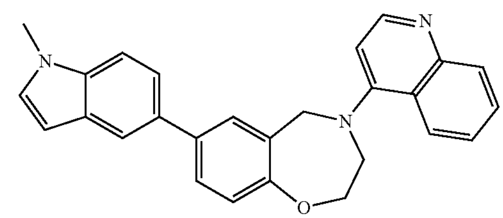 [SMILES: Cn1ccc2cc(-c3ccc4c(c3)CN(c3ccnc5ccccc35)CCO4)ccc21] | 7-(1-methyl-1H-indol-5-yl)-4-quinolin-4-yl-2,3,4,5-tetrahydro-1,4-benzodiazepine |
| 134 | 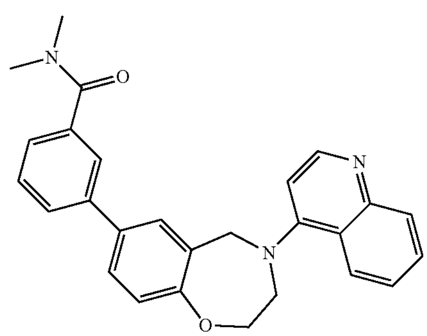 [SMILES: CN(C)C(=O)c1cccc(-c2ccc3c(c2)CN(c2ccnc4ccccc24)CCO3)c1] | N,N-dimethyl-3-(4-quinolin-4-yl-2,3,4,5-tetrahydro-1,4-benzoxazepin-7-yl)benzamide |
| 135 | 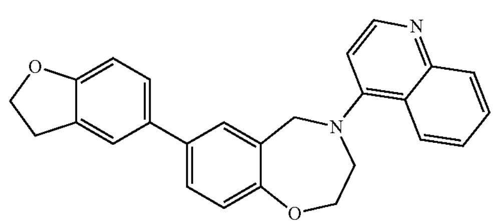 [SMILES: c1ccc2c(N3CCOc4ccc(-c5ccc6c(c5)CCO6)cc4C3)ccnc2c1] | 7-(2,3-dihydro-1-benzofuran-5-yl)-4-quinolin-4-yl-2,3,4,5-tetrahydro-1,4-benzoxazepine |
| 136 | 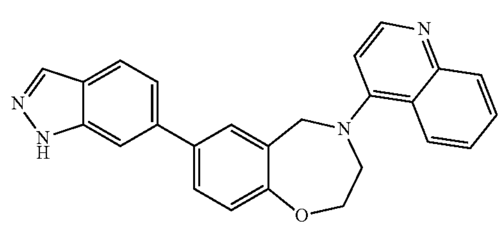 [SMILES: c1ccc2c(N3CCOc4ccc(-c5ccc6cn[nH]c6c5)cc4C3)ccnc2c1] | 7-(1H-indazol-6-yl)-4-quinolin-4-yl-2,3,4,5-tetrahydro-1,4-benzoxazepine |
| 137 | 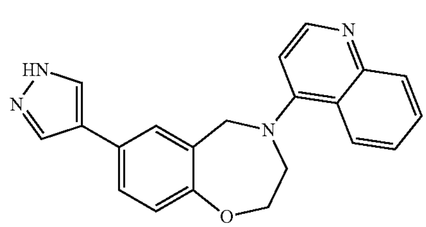 [SMILES: c1ccc2c(N3CCOc4ccc(-c5cn[nH]c5)cc4C3)ccnc2c1] | 7-(1H-pyrazol-4-yl)-4-quinolin-4-yl-2,3,4,5-tetrahydro-1,4-benzoxazepine |

-continued

| Cmpd No. | Structure | Name |
|---|---|---|
| 138 | 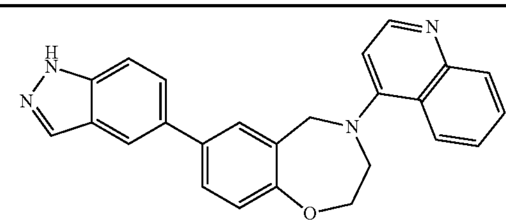 | 7-(1H-indazol-5-yl)-4-quinolin-4-yl-2,3,4,5-tetrahydro-1,4-benzoxazepine |
| 139 | 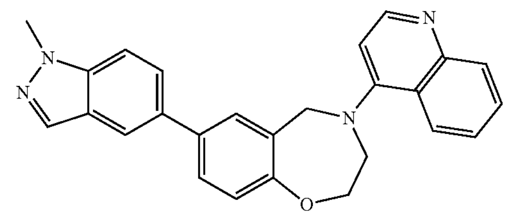 [SMILES: Cn1ncc2cc(-c3ccc4c(c3)CN(c3ccnc5ccccc35)CCO4)ccc21] | 7-(1-methyl-1H-indazol-5-yl)-4-quinolin-4-yl-2,3,4,5-tetrahydro-1,4-benzoxazepine |
| 140 | 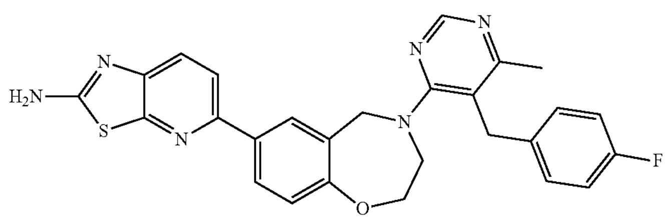 [SMILES: Cc1ncnc(N2CCOc3ccc(-c4ccc5nc(N)sc5n4)cc3C2)c1Cc1ccc(F)cc1] | 5-(4-{5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine |
| 141 | 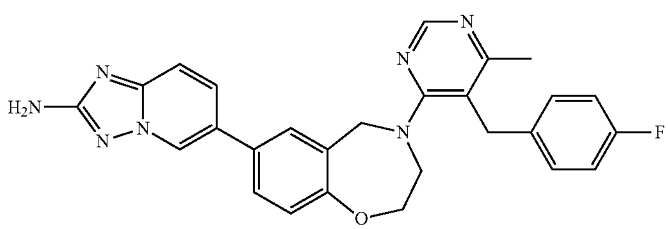 [SMILES: Cc1ncnc(N2CCOc3ccc(-c4ccc5nc(N)nn5c4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)[1,2,4]triazolo[1,5-a]pyridin-2-amine |
| 142 | 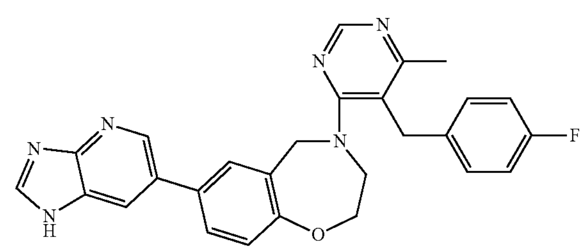 [SMILES: Cc1ncnc(N2CCOc3ccc(-c4cnc5nc[nH]c5c4)cc3C2)c1Cc1ccc(F)cc1] | 4-{5-[(4-fluorophenyl)methyl]-6-methylpyrimidin-4-yl}-7-(1H-imidazo[4,5-b]pyridin-6-yl)-2,3,4,5-tetrahydro-1,4-benzoxazepine |
| 143 | 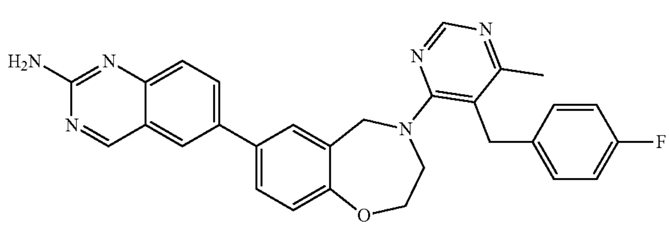 [SMILES: Cc1ncnc(N2CCOc3ccc(-c4ccc5nc(N)ncc5c4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)quinazolin-2-amine |
| 144 | 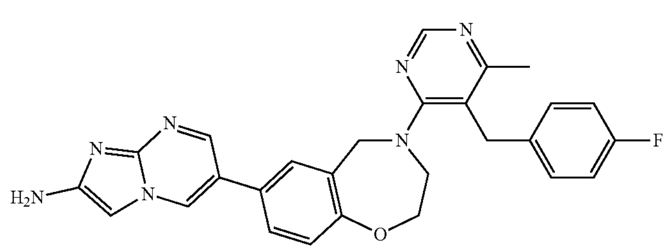 [SMILES: Cc1ncnc(N2CCOc3ccc(-c4cnc5nc(N)cn5c4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)imidazo[1,2-a]pyrimidin-2-amine |

-continued

| Cmpd No. | Structure | Name |
|---|---|---|
| 145 | 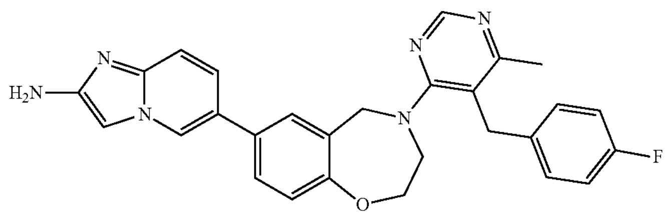 [SMILES: Cc1ncnc(N2CCOc3ccc(-c4ccc5nc(N)cn5c4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)imidazo[1,2-a]pyridin-2-amine |
| 146 | 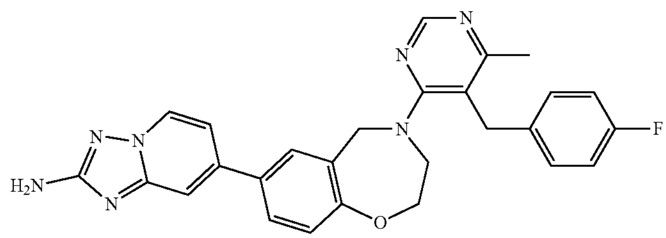 [SMILES: Cc1ncnc(N2CCOc3ccc(-c4ccn5nc(N)nc5c4)cc3C2)c1Cc1ccc(F)cc1] | 7-(4-{5-[(4-fluorophenyl)methyl]-6-methylpyrimidin-4-yl}-2,3,4,5-tetrahydro-1,4-benzoxazepin-7-yl)[1,2,4]triazolo[1,5-a]pyridin-2-amine |
| 147 | 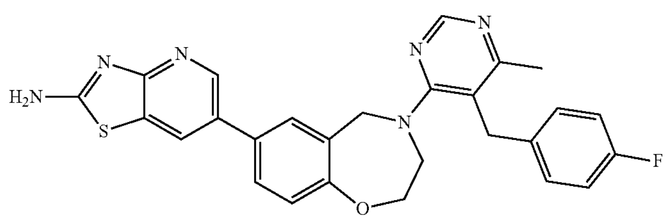 [SMILES: Cc1ncnc(N2CCOc3ccc(-c4cnc5nc(N)sc5c4)cc3C2)c1Cc1ccc(F)cc1] | 5-(4-{5-[(4-fluorophenyl)methyl]-6-methylpyrimidin-4-yl}-2,3,4,5-tetrahydro-1,4-benzoxazepin-7-yl)[1,3]thiazolo[4,5-b]pyridin-2-amine |
| 148 | 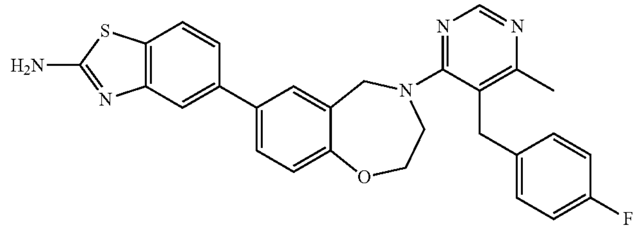 [SMILES: Cc1ncnc(N2CCOc3ccc(-c4ccc5sc(N)nc5c4)cc3C2)c1Cc1ccc(F)cc1] | 5-(4-{5-[(4-fluorophenyl)methyl]-6-methylpyrimidin-4-yl}-2,3,4,5-tetrahydro-1,4-benzoxazepin-7-yl)-1,3-benzothiazol-2-amine |
| 149 | 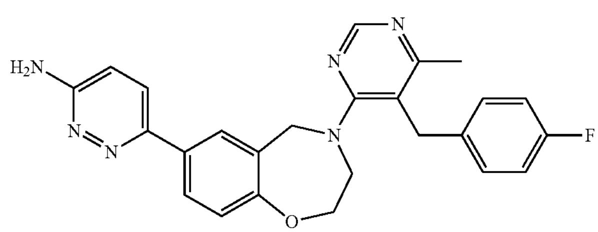 [SMILES: Cc1ncnc(N2CCOc3ccc(-c4ccc(N)nn4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)pyridazin-3-amine |
| 150 | 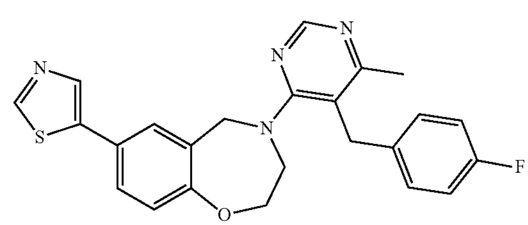 [SMILES: Cc1ncnc(N2CCOc3ccc(-c4cncs4)cc3C2)c1Cc1ccc(F)cc1] | 4-{5-[(4-fluorrophenyl)methyl]-6-methylpyrimidin-4-yl}-7-(1,3-thiazol-5-yl)-2,3,4,5-tetrahydro-1,4-benzoxazepine |

| Cmpd No. | Structure | Name |
|---|---|---|
| 151 | 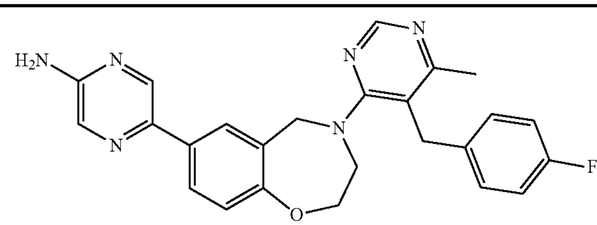 | 5-(4-{5-[(4-fluorophenyl)methyl]-6-methylpyrimidin-4-yl}-2,3,4,5-tetrahydro-1,4-benzoxazepin-7-yl)pyrazin-2-amine |
| 152 | 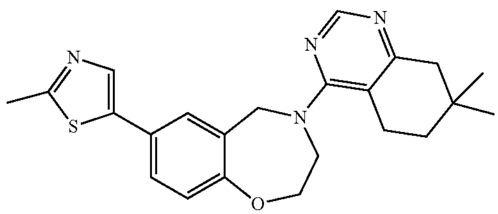 | 4-(7,7-dimethyl-5,6,7,8-tetrahydroquinoazlin-4-yl)-7-(2-methyl-1,3-thiazol-5-yl)-2,3,4,5-tetrahydro-1,4-benzoxazepine |
| 153 | 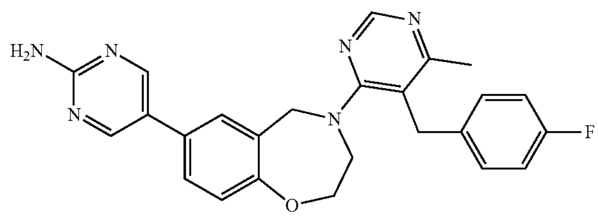 [SMILES: Cc1ncnc(N2CCOc3ccc(-c4cnc(N)nc4)cc3C2)c1Cc1ccc(F)cc1] | 5-(4-{5-[(4-fluorophenyl)methyl]-6-methylpyrimidin-4-yl}-2,3,4,5-tetrahydro-1,4-benzoxazepin-7-yl)pyrimidin-2-amine |
| 154 | 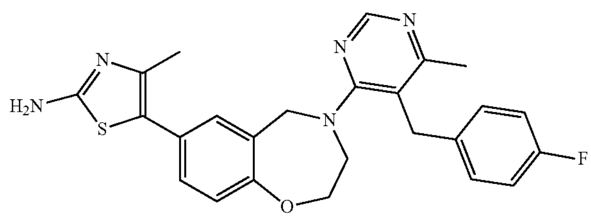 [SMILES: Cc1nc(N)sc1-c1ccc2c(c1)CN(c1ncnc(C)c1Cc1ccc(F)cc1)CCO2] | 5-(4-{5-[(4-fluorophenyl)methyl]-6-methylpyrimidin-4-yl}-2,3,4,5-tetrahydro-1,4-benzoxazepin-7-yl)-4-methyl-1,3-thiazol-2-amine |
| 155 | 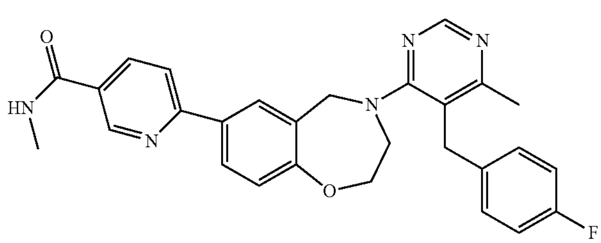 [SMILES: CNC(=O)c1ccc(-c2ccc3c(c2)CN(c2ncnc(C)c2Cc2ccc(F)cc2)CCO3)nc1] | 6-(4-{5-[(4-fluorophenyl)methyl]-6-methylpyrimidin-4-yl}-2,3,4,5-tetrahydro-1,4-benzoxazepin-7-yl)-N-methylpyridine-3-carboxamide |
| 156 | 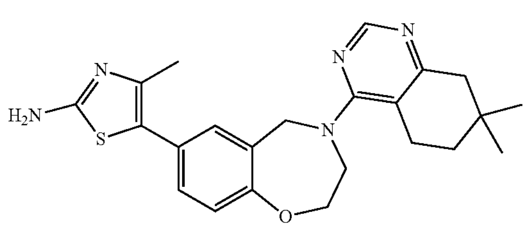 [SMILES: Cc1nc(N)sc1-c1ccc2c(c1)CN(c1ncnc3c1CCC(C)(C)C3)CCO2] | 5-[4-(7,7-dimethyl-5,6,7,8-tetrahydroquinazolin-4-yl)-2,3,4,5-tetrahydro-1,4-benzoxazepin-7-yl]-4-methyl-1,3-thiazol-2-amine |
| 157 | 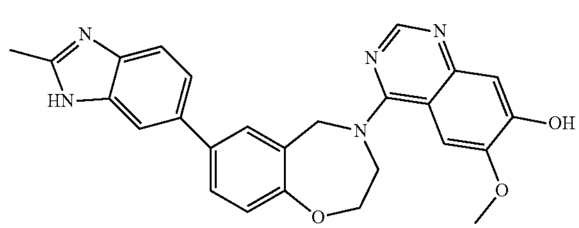 [SMILES: COc1cc2c(N3CCOc4ccc(-c5ccc6nc(C)[nH]c6c5)cc4C3)ncnc2cc1O] | 4-[7-(2-methyl-1H-benzimidazol-6-yl)-2,3-dihydro-1,4-benzoxazepin-4(5H)-yl]-6-(methyloxy)quinazolin-7-ol |

-continued

| Cmpd No. | Structure | Name |
|---|---|---|
| 158 | 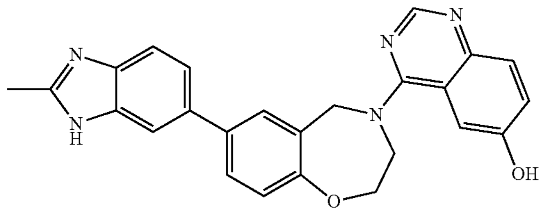 [SMILES: Cc1nc2ccc(-c3ccc4c(c3)CN(c3ncnc5ccc(O)cc35)CCO4)cc2[nH]1] | 4-[7-(2-methyl-1H-benzimidazol-6-yl)-2,3-dihydro-1,4-benzoxazepin-4(5H)-yl]quinazolin-6-ol |
| 159 | 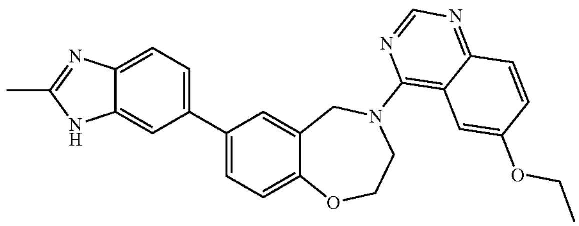 [SMILES: CCOc1ccc2ncnc(N3CCOc4ccc(-c5ccc6nc(C)[nH]c6c5)cc4C3)c2c1] | 4-[6-(ethyloxy)quinazolin-4-yl]-7-(2-methyl-1H-benzimidazol-6-yl)-2,3,4,5-tetrahydro-1,4-benzoxazepine |
| 160 | 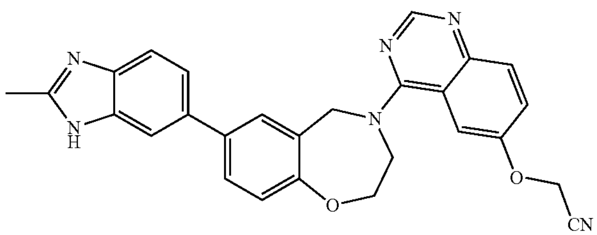 [SMILES: Cc1nc2ccc(-c3ccc4c(c3)CN(c3ncnc5ccc(OCC#N)cc35)CCO4)cc2[nH]1] | ({4-[7-(2-methyl-1H-benzimidazol-6-yl)-2,3-dihydro-1,4-benzoxazepin-4(5H)-yl]quinazolin-6-yl}oxy)acetonitrile |
| 161 | 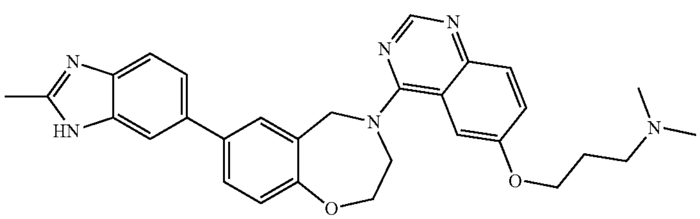 | N,N-dimethyl-3-({4-[7-(2-methyl-1H-benzimidazol-6-yl)-2,3-dihydro-1,4-benzoxazepin-4(5H)-yl]quinazolin-6-yl}oxy)propan-1-amine |
| 162 | 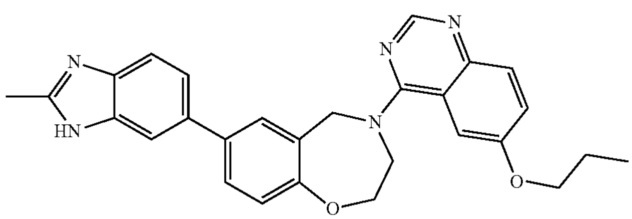 [SMILES: CCCOc1ccc2ncnc(N3CCOc4ccc(-c5ccc6nc(C)[nH]c6c5)cc4C3)c2c1] | 7-(2-methyl-1H-benzimidazol-6-yl)-4-[6-(propyloxy)quinazolin-4-yl]-2,3,4,5-tetrahydro-1,4-benzoxazepine |
| 163 | 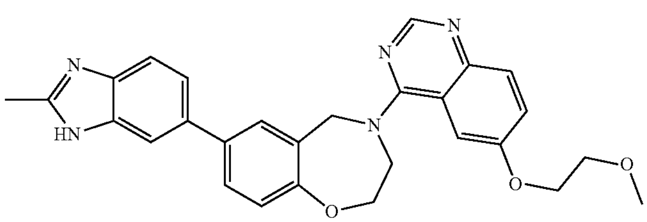 | 7-(2-methyl-1H-benzimidazol-6-yl)-4-(6-{[2-(methyloxy)ethyl]oxy}quinazolin-4-yl)-2,3,4,5-tetrahydro-1,4-benzoxazepine |
| 164 | 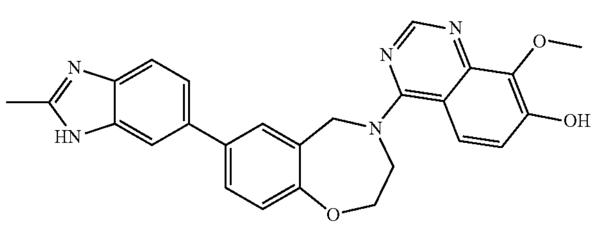 | 4-[7-(2-methyl-1H-benzimidazol-6-yl)-2,3-dihydro-1,4-benzoxazepin-4(5H)-yl]-8-(methyloxy)quinazolin-7-ol |

-continued

| Cmpd No. | Structure | Name |
|---|---|---|
| 165 | 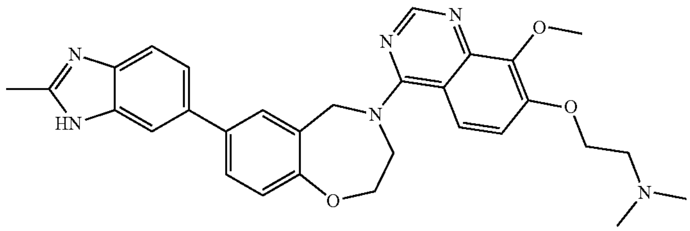 | N,N-dimethyl-2-({4-[7-(2-methyl-1H-benzimidazol-6-yl)-2,3-dihydro-1,4-benzoxazepin-4(5H)-yl]-8-(methyloxy)quinazolin-7-yl}oxy)ethanamine |
| 166 | 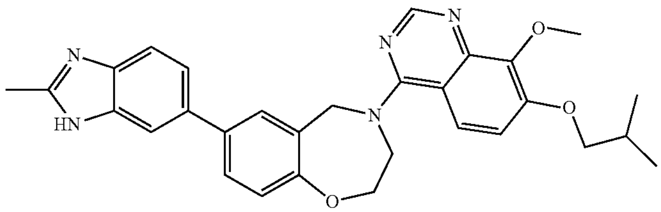 [SMILES: COc1c(OCC(C)C)ccc2c(N3CCOc4ccc(-c5ccc6nc(C)[nH]c6c5)cc4C3)ncnc12] | 7-(2-methyl-1H-benzimidazol-6-yl)-4-{8-(methyloxy)-7-[(2-methylpropyl)oxy]quinazolin-4-yl}-2,3,4,5-tetrahydro-1,4-benzoxazepine |
| 167 | 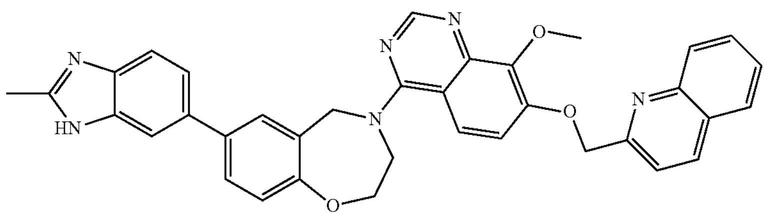 [SMILES: COc1c(OCc2ccc3ccccc3n2)ccc2c(N3CCOc4ccc(-c5ccc6nc(C)[nH]c6c5)cc4C3)ncnc12] | 7-(2-methyl-1H-benzimidazol-6-yl)-4-{8-(methyloxy)-7-[(quinolin-2-ylmethyl)oxy]quinazolin-4-yl}-2,3,4,5-tetrahydro-1,4-benzoxazepine |
| 168 | 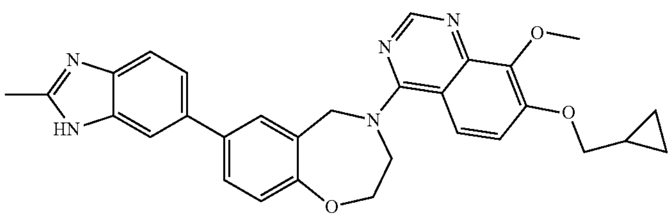 [SMILES: COc1c(OCC2CC2)ccc2c(N3CCOc4ccc(-c5ccc6nc(C)[nH]c6c5)cc4C3)ncnc12] | 4-{7-[(cyclopropylmethyl)oxy]-8-(methyloxy)quinazolin-4-yl}-7-(2-methyl-1H-benzimidazol-6-yl)-2,3,4,5-tetrahydro-1,4-benzoxazepine |
| 169 | 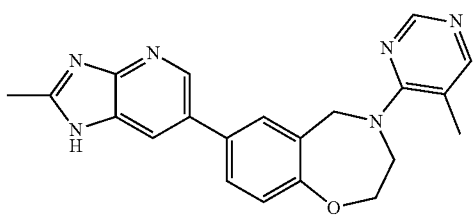 [SMILES: Cc1nc2ncc(-c3ccc4c(c3)CN(c3ncncc3C)CCO4)cc2[nH]1] | 7-(2-methyl-1H-imidazo[4,5-b]pyridin-6-yl)-4-(5-methylpyrimidin-4-yl)-2,3,4,5-tetrahydro-1,4-benzoxazepine |
| 170 | 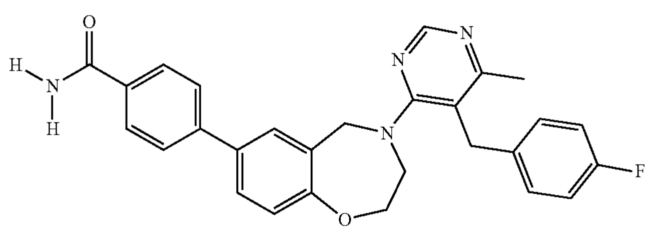 [SMILES: Cc1ncnc(N2CCOc3ccc(-c4ccc(C(N)=O)cc4)cc3C2)c1Cc1ccc(F)cc1] | 4-(4-{5-[(4-fluorophenyl)methyl]-6-methylpyrimidin-4-yl}-2,3,4,5-tetrahydro-1,4-benzoxazepin-7-yl)benzamide |
| 171 | 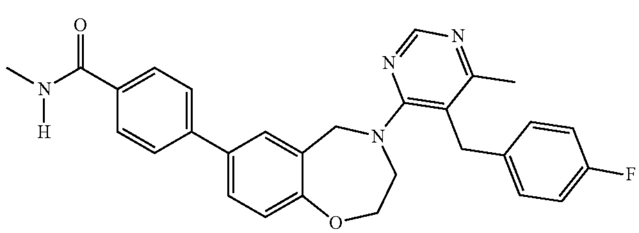 [SMILES: CNC(=O)c1ccc(-c2ccc3c(c2)CN(c2ncnc(C)c2Cc2ccc(F)cc2)CCO3)cc1] | 4-(4-{5-[(4-fluorophenyl)methyl]-6-methylpyrimidin-4-yl}-2,3,4,5-tetrahydro-1,4-benzoxazepin-7-yl)-N-methylbenzamide |

-continued

| Cmpd No. | Structure | Name |
|---|---|---|
| 172 | 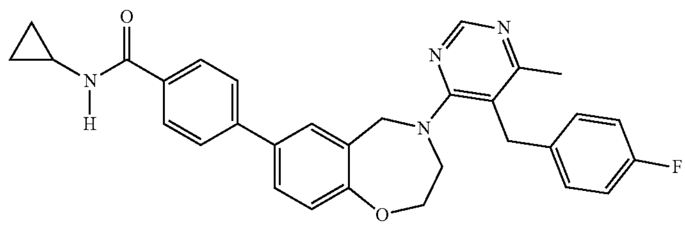 [SMILES: Cc1ncnc(N2CCOc3ccc(-c4ccc(C(=O)NC5CC5)cc4)cc3C2)c1Cc1ccc(F)cc1] | N-cyclopropyl-4-(4-{5-[(4-fluorophenyl)methyl]-6-methylpyrimidin-4-yl}-2,3,4,5-tetrahydro-1,4-benzoxazepin-7-yl)benzamide |
| 173 | 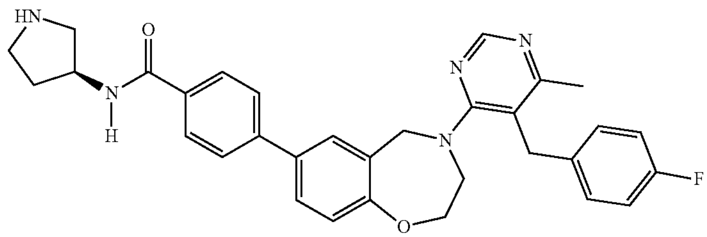 [SMILES: Cc1ncnc(N2CCOc3ccc(-c4ccc(C(=O)N[C@H]5CCNC5)cc4)cc3C2)c1Cc1ccc(F)cc1] | 4-(4-{5-[(4-fluorophenyl)methyl]-6-methylpyrimidin-4-yl}-2,3,4,5-tetrahydro-1,4-benzoxazepin-7-yl)-N-[(3S)-pyrrolidin-3-yl]benzamide |
| 174 | 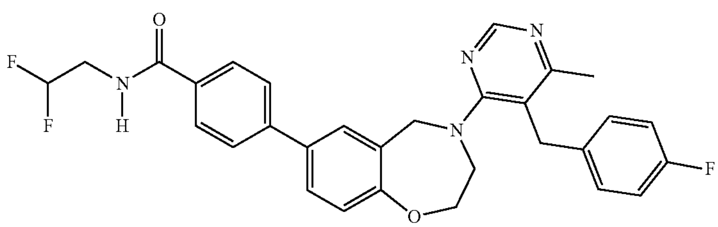 [SMILES: Cc1ncnc(N2CCOc3ccc(-c4ccc(C(=O)NCC(F)F)cc4)cc3C2)c1Cc1ccc(F)cc1] | N-(2,2-difluoroethyl)-4-(4-{5-[(4-fluorophenyl)methyl]-6-methylpyrimidin-4-yl}-2,3,4,5-tetrahydro-1,4-benzoxazepin-7-yl)benzamide |
| 175 | 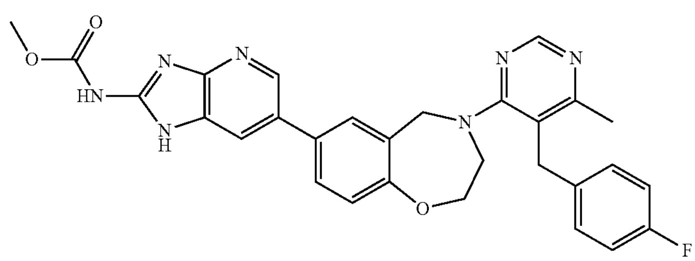 [SMILES: COC(=O)Nc1nc2ncc(-c3ccc4c(c3)CN(c3ncnc(C)c3Cc3ccc(F)cc3)CCO4)cc2[nH]1] | methyl [6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-yl]carbamate |
| 176 | 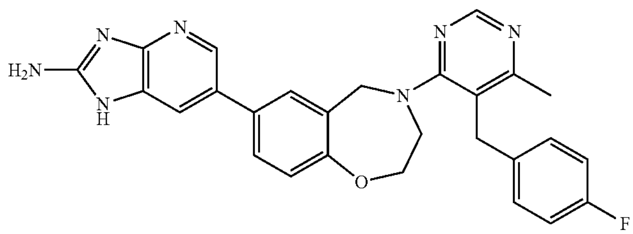 [SMILES: Cc1ncnc(N2CCOc3ccc(-c4cnc5nc(N)[nH]c5c4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine |
| 177 | 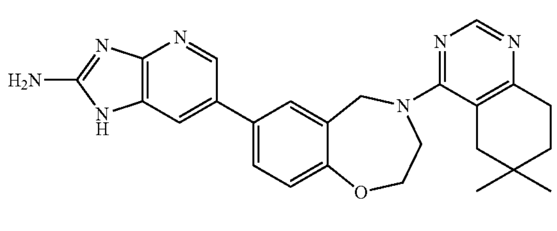 [SMILES: CC1(C)CCc2ncnc(N3CCOc4ccc(-c5cnc6nc(N)[nH]c6c5)cc4C3)c2C1] | 6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-amine |

| Cmpd No. | Structure | Name |
|---|---|---|
| 178 | 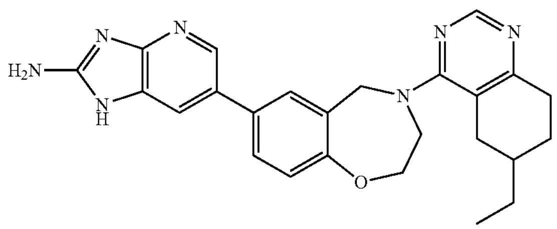 [SMILES: CCC1CCc2ncnc(N3CCOc4ccc(-c5cnc6nc(N)[nH]c6c5)cc4C3)c2C1] | 6-[4-(6-ethyl-5,6,7,8-tetrahydroquinazolin-4-yl)-2,3,4,5-tetrahydro-1,4-benzoxazepin-7-yl]-1H-imidazo[4,5-b]pyridin-2-amine |
| 179 | 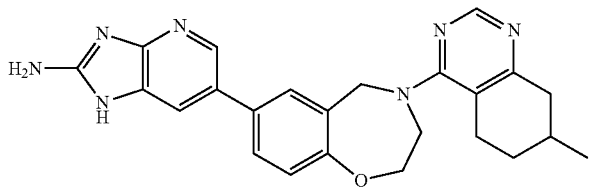 [SMILES: CC1CCc2c(ncnc2N2CCOc3ccc(-c4cnc5nc(N)[nH]c5c4)cc3C2)C1] | 6-[4-(7-methyl-5,6,7,8-tetrahydroquinazolin-4-yl)-2,3,4,5-tetrahydro-1,4-benzoxazepin-7-yl]-1H-imidazo[4,5-b]pyridin-2-amine |
| 180 | 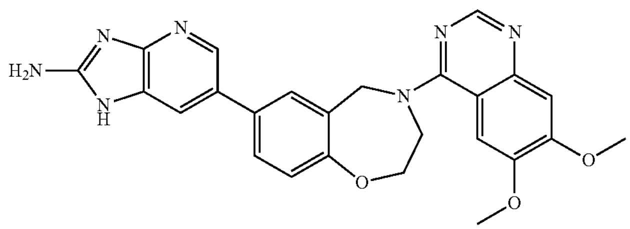 [SMILES: COc1cc2ncnc(N3CCOc4ccc(-c5cnc6nc(N)[nH]c6c5)cc4C3)c2cc1OC] | 6-{4-[6,7-bis(methyloxy)quinazolin-4-yl]-2,3,4,5-tetrahydro-1,4-benzoxazepin-7-yl}-1H-imidazo[4,5-b]pyridin-2-amine |
| 181 | 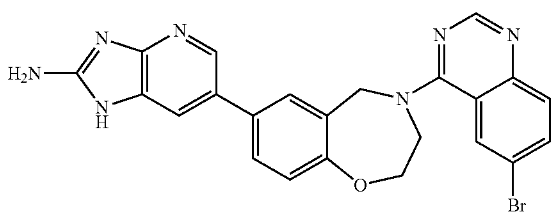 [SMILES: Nc1nc2ncc(-c3ccc4c(c3)CN(c3ncnc5ccc(Br)cc35)CCO4)cc2[nH]1] | 6-[4-(6-brromoquinazolin-4-yl)-2,3,4,5-tetrahydro-1,4-benzoxazepin-7-yl]-1H-imidazo[4,5-b]pyridin-2-amine |
| 182 | 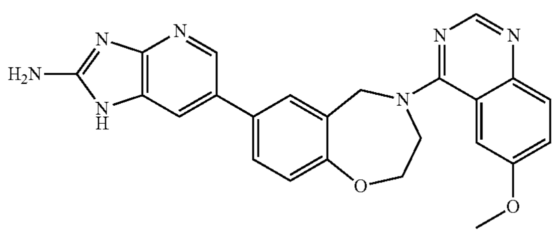 [SMILES: COc1ccc2ncnc(N3CCOc4ccc(-c5cnc6nc(N)[nH]c6c5)cc4C3)c2c1] | 6-{4-[6-(methyloxy)quinazolin-4-yl]-2,3,4,5-tetrahydro-1,4-benzoxazepin-7-yl}-1H-imidazo[4,5-b]pyridin-2-amine |
| 183 | 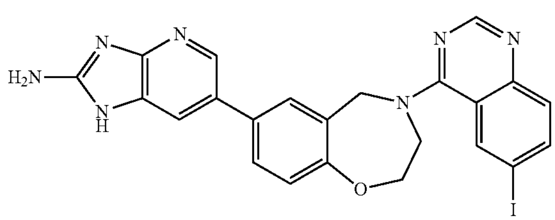 [SMILES: Nc1nc2ncc(-c3ccc4c(c3)CN(c3ncnc5ccc(I)cc35)CCO4)cc2[nH]1] | 6-[4-(6-iodoquinazolin-4-yl)-2,3,4,5-tetrahydro-1,4-benzoxazepin-7-yl]-1H-imidazo[4,5-b]pyridin-2-amine |
| 184 | 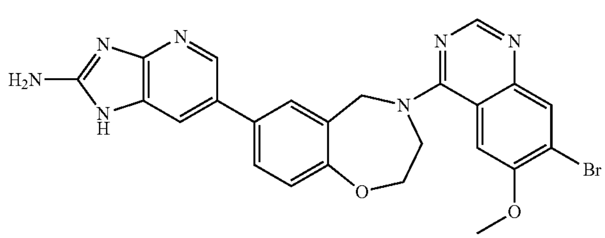 [SMILES: COc1cc2c(N3CCOc4ccc(-c5cnc6nc(N)[nH]c6c5)cc4C3)ncnc2cc1Br] | 6-{4-[7-bromo-6-(methyloxy)quinazolin-4-yl]-2,3,4,5-tetrahydro-1,4-benzoxazepin-7-yl}-1H-imidazo[4,5-b]pyridin-2-amine |

| Cmpd No. | Structure | Name |
|---|---|---|
| 185 | 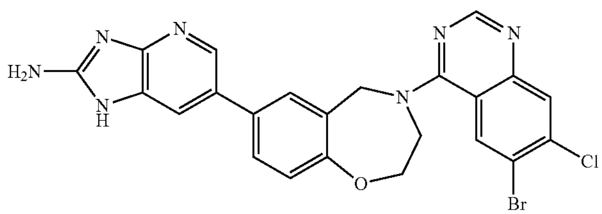 [SMILES: Nc1nc2ncc(-c3ccc4c(c3)CN(c3ncnc5cc(Cl)c(Br)cc35)CCO4)cc2[nH]1] | 6-[4-(6-bromo-7-chloroquinazolin-4-yl)-2,3,4,5-tetrahydro-1,4-benzoxazepin-7-yl]-1H-imidazo[4,5-b]pyridin-2-amine |
| 186 | 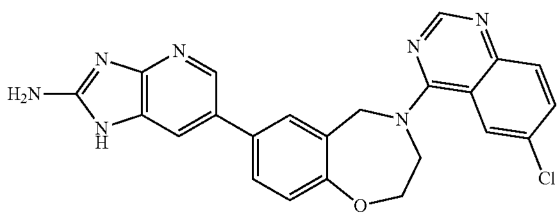 [SMILES: Nc1nc2ncc(-c3ccc4c(c3)CN(c3ncnc5ccc(Cl)cc35)CCO4)cc2[nH]1] | 6-[4-(6-chloroquinazolin-4-yl)-2,3,4,5-tetrahydro-1,4-benzoxazepin-7-yl]-1H-imidazo[4,5-b]pyridin-2-amine |
| 187 | 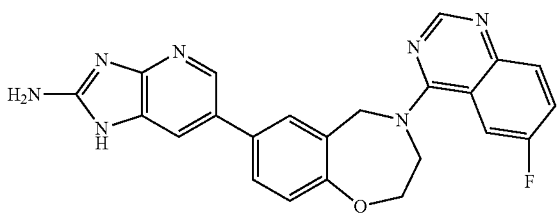 [SMILES: Nc1nc2ncc(-c3ccc4c(c3)CN(c3ncnc5ccc(F)cc35)CCO4)cc2[nH]1] | 6-[4-(6-fluoroquinazolin-4-yl)-2,3,4,5-tetrahydro-1,4-benzoxazepin-7-yl]-1H-imidazo[4,5-b]pyridin-2-amine |
| 188 | 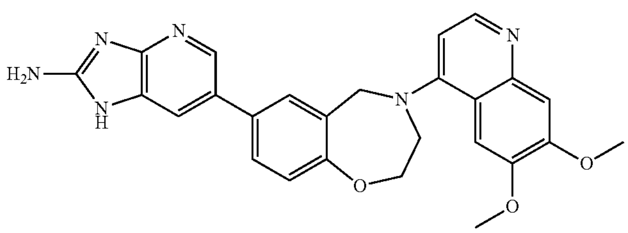 [SMILES: COc1cc2nccc(N3CCOc4ccc(-c5cnc6nc(N)[nH]c6c5)cc4C3)c2cc1OC] | 6-{4-[6,7-bis(methyloxy)quinolin-4-yl]-2,3,4,5-tetrahydro-1,4-benzoxazepin-7-yl}-1H-imidazo[4,5-b]pyridin-2-amine |
| 189 | 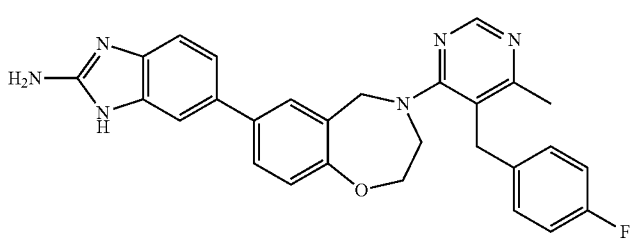 [SMILES: Cc1ncnc(N2CCOc3ccc(-c4ccc5nc(N)[nH]c5c4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)-1H-benzimidazol-2-amine |
| 190 | 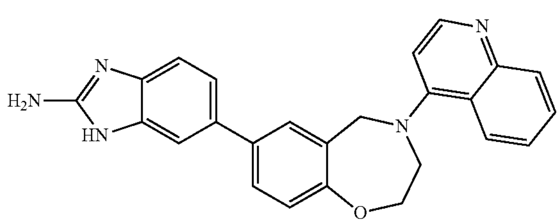 [SMILES: Nc1nc2ccc(-c3ccc4c(c3)CN(c3ccnc5ccccc35)CCO4)cc2[nH]1] | 6-(4-quinolin-4-yl-2,3,4,5-tetrahydro-1,4-benzoxazepin-7-yl)-1H-benzimidazol-2-amine |

| Cmpd No. | Structure | Name |
|---|---|---|
| 191 | 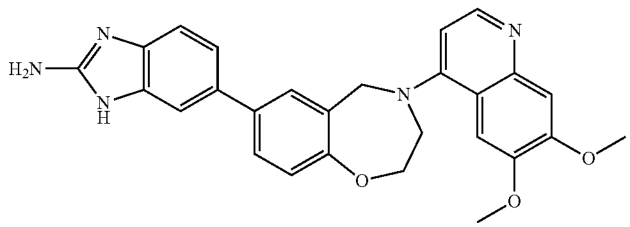 [SMILES: COc1cc2nccc(N3CCOc4ccc(-c5ccc6nc(N)[nH]c6c5)cc4C3)c2cc1OC] | 6-{4-[6,7-bis(methyloxy)quinolin-4-yl]-2,3,4,5-tetrahydro-1,4-benzoxazepin-7-yl}-1H-benzimidazol-2-amine |
| 192 | 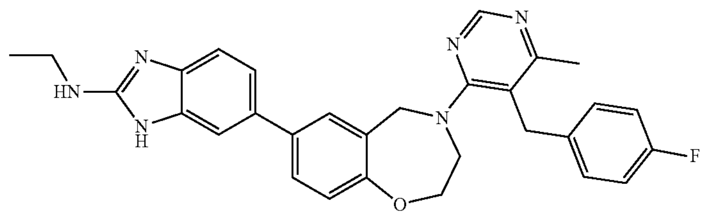 [SMILES: CCNc1nc2ccc(-c3ccc4c(c3)CN(c3ncnc(C)c3Cc3ccc(F)cc3)CCO4)cc2[nH]1] | N-ethyl-6-(4-{5-[(4-fluorophenyl)methyl]-6-methylpyrimidin-4-yl}-2,3,4,5-tetrahydro-1,4-benzoxazepin-7-yl)-1H-benzimidazol-2-amine |
| 193 | 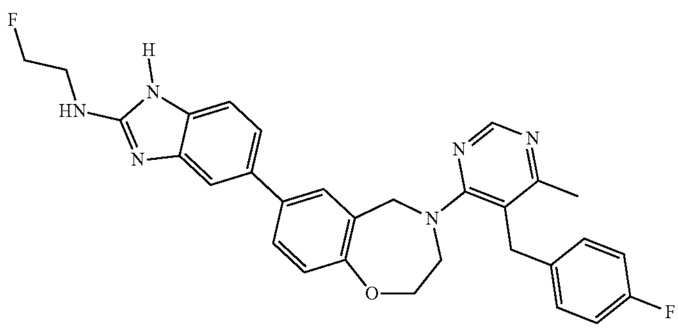 [SMILES: Cc1ncnc(N2CCOc3ccc(-c4ccc5[nH]c(NCCF)nc5c4)cc3C2)c1Cc1ccc(F)cc1] | N-(2-fluoroethyl)-5-(4-{5-[(4-fluorophenyl)methyl]-6-methylpyrimidin-4-yl}-2,3,4,5-tetrahydro-1,4-benzoxazepin-7-yl)-1H-benzimidazol-2-amine |
| 194 | 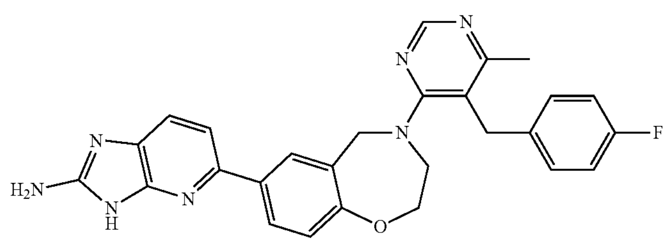 [SMILES: Cc1ncnc(N2CCOc3ccc(-c4ccc5nc(N)[nH]c5n4)cc3C2)c1Cc1ccc(F)cc1] | 5-(4-{5-[(4-fluorophenyl)methyl]-6-methylpyrimidin-4-yl}-2,3,4,5-tetrahydro-1,4-benzoxazepin-7-yl)-3H-imidazo[4,5-b]pyridin-2-amine |
| 195 | 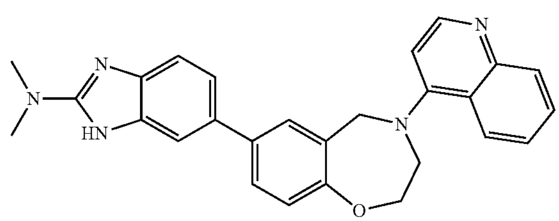 [SMILES: CN(C)c1nc2ccc(-c3ccc4c(c3)CN(c3ccnc5ccccc35)CCO4)cc2[nH]1] | N,N-dimethyl-6-(4-quinolin-4-yl-2,3,4,5-tetrahydro-1,4-benzoxazepin-7-yl)-1H-benzimidazol-2-amine |
| 196 | 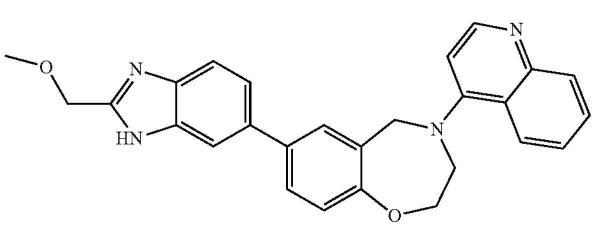 [SMILES: COCc1nc2ccc(-c3ccc4c(c3)CN(c3ccnc5ccccc35)CCO4)cc2[nH]1] | 7-{2-[(methyloxy)methyl]-1H-benzimidazol-6-yl}-4-quinolin-4-yl-2,3,4,5-tetrahydro-1,4-benzoxazepine |

-continued

| Cmpd No. | Structure | Name |
|---|---|---|
| 197 | 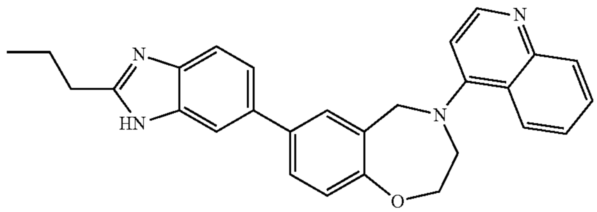 [SMILES: CCCc1nc2ccc(-c3ccc4c(c3)CN(c3ccnc5ccccc35)CCO4)cc2[nH]1] | 7-(2-propyl-1H-benzimidazol-6-yl)-4-quinolin-4-yl-2,3,4,5-tetrahydro-1,4-benzoxazepine |
| 198 | 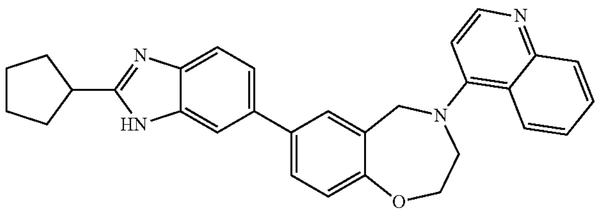 [SMILES: c1ccc2c(N3CCOc4ccc(-c5ccc6nc(C7CCCC7)[nH]c6c5)cc4C3)ccnc2c1] | 7-(2-cyclopentyl-1H-benzimidazol-6-yl)-4-quinolin-4-yl-2,3,4,5-tetrahydro-1,4-benzoxazepine |
| 199 | 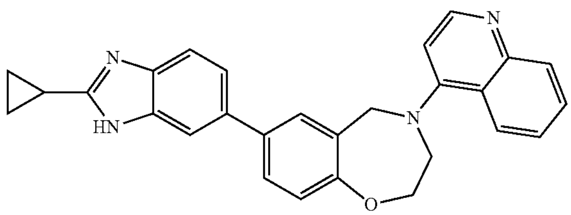 [SMILES: c1ccc2c(N3CCOc4ccc(-c5ccc6nc(C7CC7)[nH]c6c5)cc4C3)ccnc2c1] | 7-(2-cyclopropyl-1H-benzimidazol-6-yl)-4-quinolin-4-yl-2,3,4,5-tetrahydro-1,4-benzoxazepine |
| 200 | 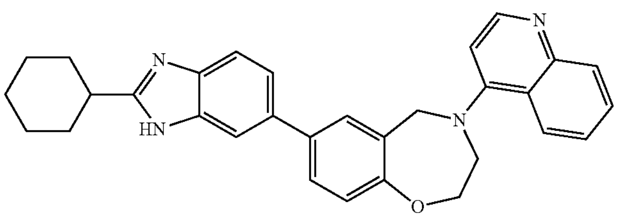 [SMILES: c1ccc2c(N3CCOc4ccc(-c5ccc6nc(C7CCCCC7)[nH]c6c5)cc4C3)ccnc2c1] | 7-(2-cyclohexyl-1H-benzimidazol-6-yl)-4-quinolin-4-yl-2,3,4,5-tetrahydro-1,4-benzoxazepine |
| 201 | 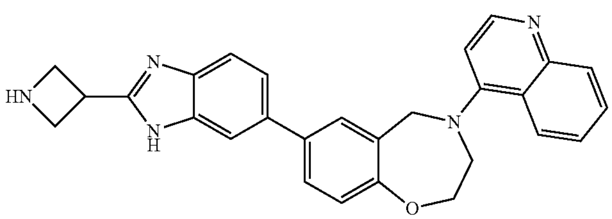 [SMILES: c1ccc2c(N3CCOc4ccc(-c5ccc6nc(C7CNC7)[nH]c6c5)cc4C3)ccnc2c1] | 7-(2-azetidin-3-yl-1H-benzimidazol-6-yl)-4-quinolin-4-yl-2,3,4,5-tetrahydro-1H-benzoxazepine |
| 202 | 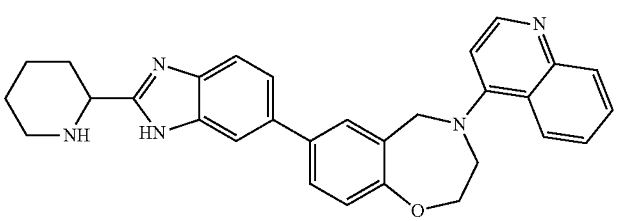 [SMILES: c1ccc2c(N3CCOc4ccc(-c5ccc6nc(C7CCCCN7)[nH]c6c5)cc4C3)ccnc2c1] | 7-(2-piperidin-2-yl-1H-benzimidazol-6-yl)-4-quinolin-4-yl-2,3,4,5-tetrahydro-1,4-benzoxazepine |
| 203 | 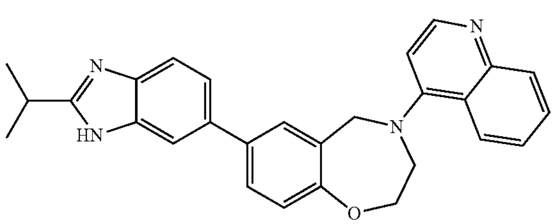 [SMILES: CC(C)c1nc2ccc(-c3ccc4c(c3)CN(c3ccnc5ccccc35)CCO4)cc2[nH]1] | 7-[2-(1-methylethyl)-1H-benzimidazol-6-yl]-4-quinolin-4-yl-2,3,4,5-tetrahydro-1,4-benzoxazepine |

| Cmpd No. | Structure | Name |
| --- | --- | --- |
| 204 | 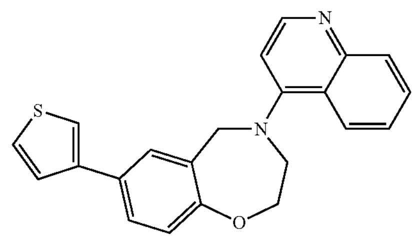 [SMILES: c1ccc2c(N3CCOc4ccc(-c5ccsc5)cc4C3)ccnc2c1] | 4-quinolin-4-yl-7-(3-thienyl)-2,3,4,5-tetrahydro-1,4-benzoxazepine |
| 205 | 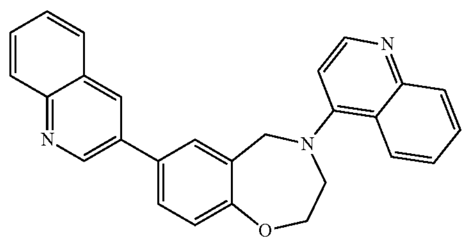 [SMILES: c1ccc2ncc(-c3ccc4c(c3)CN(c3ccnc5ccccc35)CCO4)cc2c1] | 7-quinolin-3-yl-4-quinolin-4-yl-2,3,4,5-tetrahydro-1,4-benzoxazepine |
| 206 | 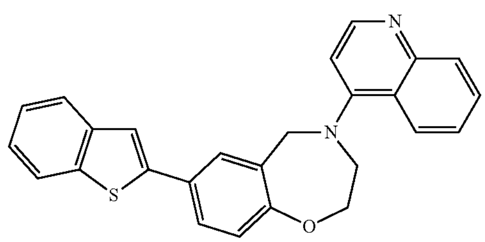 [SMILES: c1ccc2sc(-c3ccc4c(c3)CN(c3ccnc5ccccc35)CCO4)cc2c1] | 7-(1-benzothien-2-yl)-4-quinolin-4-yl-2,3,4,5-tetrahydro-1,4-benzoxazepine |
| 207 | 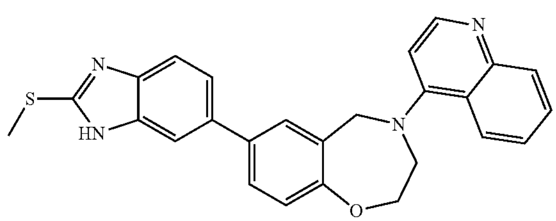 [SMILES: CSc1nc2ccc(-c3ccc4c(c3)CN(c3ccnc5ccccc35)CCO4)cc2[nH]1] | 7-[2-(methylthio)-1H-benzimidazol-6-yl]-4-quinolin-4-yl-2,3,4,5-tetrahydro-1,4-benzoxazepine |
| 208 | 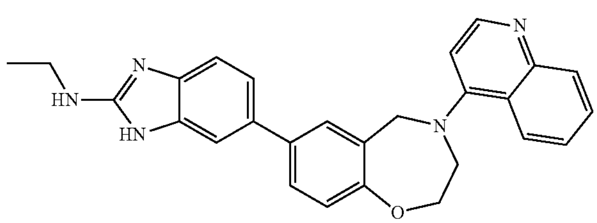 [SMILES: CCNc1nc2ccc(-c3ccc4c(c3)CN(c3ccnc5ccccc35)CCO4)cc2[nH]1] | N-ethyl-6-(4-quinolin-4-yl-2,3,4,5-tetrahydro-1,4-benzoxazepin-7-yl)-1H-benzimidazol-2-amine |
| 209 | 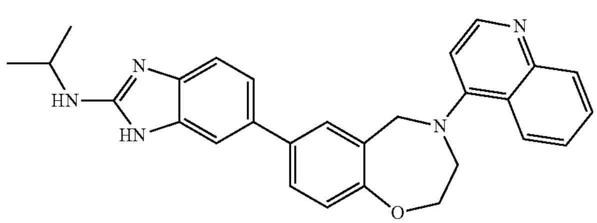 [SMILES: CC(C)Nc1nc2ccc(-c3ccc4c(c3)CN(c3ccnc5ccccc35)CCO4)cc2[nH]1] | N-(1-methylethyl)-6-(4-quinolin-4-yl-2,3,4,5-tetrahydro-1,4-benzoxazepin-7-yl)-1H-benzimidazol-2-amine |

| Cmpd No. | Structure | Name |
|---|---|---|
| 210 | 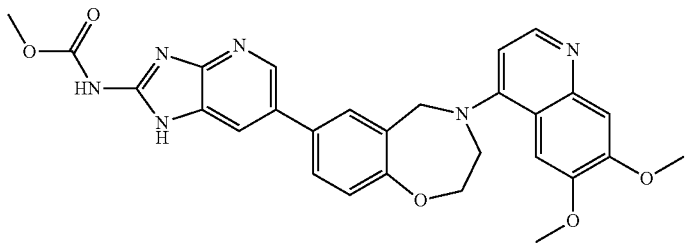 | methyl (6-{4-[6,7-bis(methyloxy)quinolin-4-yl]-2,3,4,5-tetrahydro-1,4-benzoxazepin-7-yl}-1H-imidazo[4,5-b]pyridin-2-yl)carbamate |
| 211 | 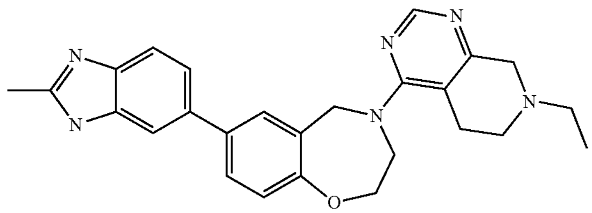 [SMILES: CCN1CCc2c(ncnc2N2CCOc3ccc(-c4ccc5nc(C)[nH]c5c4)cc3C2)C1] | 4-(7-ethyl-5,6,7,8-tetrahydropyrido[3,4-d]pyrimidin-4-yl)-7-(2-methyl-1H-benzimidazol-6-yl)-2,3,4,5-tetrahydro-1,4-benzoxazepine |
| 212 | 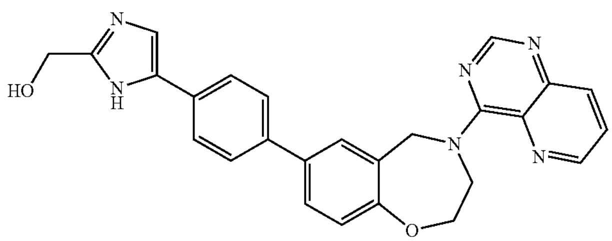 [SMILES: OCc1ncc(-c2ccc(-c3ccc4c(c3)CN(c3ncnc5cccnc35)CCO4)cc2)[nH]1] | {5-[4-(4-pyrido[3,2-d]pyrimidin-4-yl-2,3,4,5-tetrahydro-1,4-benzoxazepin-7-yl)phenyl]-1H-imidazol-2-yl}methanol |
| 213 | 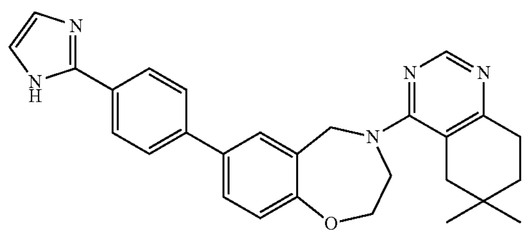 [SMILES: CC1(C)CCc2ncnc(N3CCOc4ccc(-c5ccc(-c6ncc[nH]6)cc5)cc4C3)c2C1] | 4-(6,6-dimethyl-5,6,7,8-tetrahydroquinazolin-4-yl)-7-[4-(1H-imidazol-2-yl)phenyl]-2,3,4,5-tetrahydro-1,4-benzoxazepine |
| 214 | 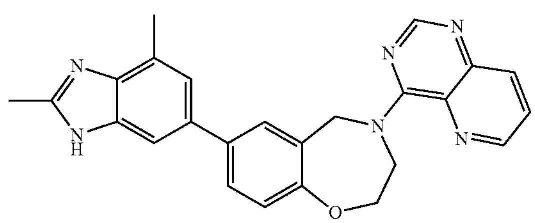 [SMILES: Cc1nc2c(C)cc(-c3ccc4c(c3)CN(c3ncnc5cccnc35)CCO4)cc2[nH]1] | 7-(2,4-dimethyl-1H-benzimidazol-6-yl)-4-pyrido[3,2-d]pyrimidin-4-yl-2,3,4,5-tetrahydro-1,4-benzoxazepine |
| 215 | 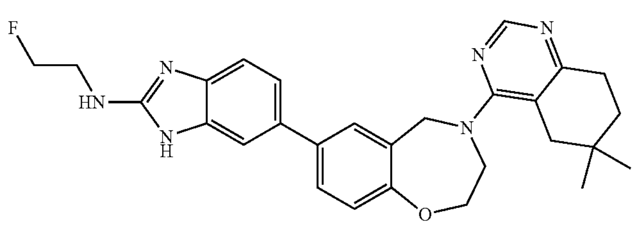 [SMILES: CC1(C)CCc2ncnc(N3CCOc4ccc(-c5ccc6nc(NCCF)[nH]c6c5)cc4C3)c2C1] | 6-[4-(6,6-dimethyl-5,6,7,8-tetrahydroquinazolin-4-yl)-2,3,4,5-tetrahydro-1,4-benzoxazepin-7-yl]-N-(2-fluoroethyl)-1H-benzimidazol-2-amine |

-continued

| Cmpd No. | Structure | Name |
|---|---|---|
| 216 | 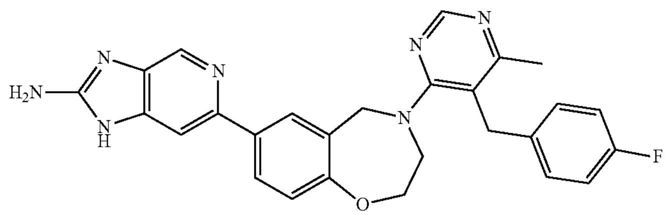 [SMILES: Cc1ncnc(N2CCOc3ccc(-c4cc5[nH]c(N)nc5cn4)cc3C2)c1Cc1ccc(F)cc1] | 6-(4-{5-[(4-fluorophenyl)merthyl]-6-methylpyrimidin-4-yl}-2,3,4,5-tetrahydro-1,4-benzoxazepin-7-yl)-1H-imidazo[4,5-c]pyridin-2-amine |
| 217 | 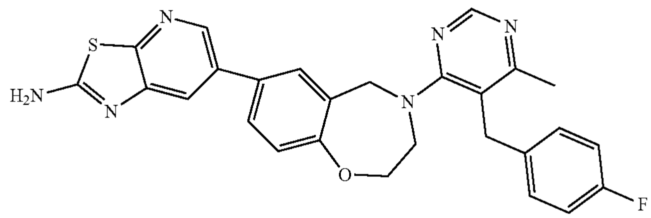 [SMILES: Cc1ncnc(N2CCOc3ccc(-c4cnc5sc(N)nc5c4)cc3C2)c1Cc1ccc(F)cc1] | 6-(4-{5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine |
| 218 | 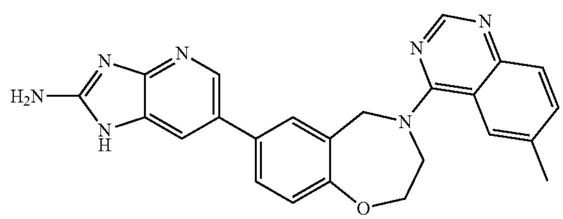 [SMILES: Cc1ccc2ncnc(N3CCOc4ccc(-c5cnc6nc(N)[nH]c6c5)cc4C3)c2c1] | 6-[4-(6-methylquinazolin-4-yl)-2,3,4,5-tetrahydro-1,4-benzoxazpin-7-yl]-1H-imidazo[4,5-b]pyridin-2-amine |
| 219 | 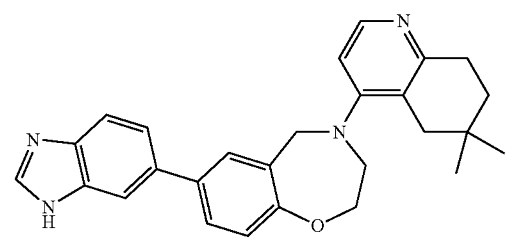 [SMILES: CC1(C)CCc2nccc(N3CCOc4ccc(-c5ccc6nc[nH]c6c5)cc4C3)c2C1] | 7-(1H-benzimidazol-6-yl)-4-(6,6-dimethyl-5,6,7,8-tetrahydroquinazolin-4-yl)-2,3,4,5-tetrahydro-1,4-benzoxazepine |
| 220 | 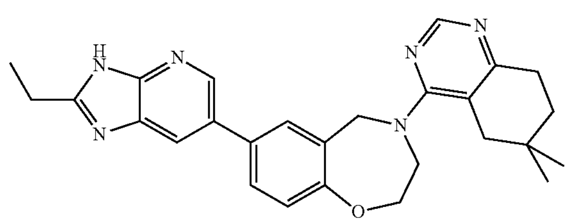 [SMILES: CCc1nc2cc(-c3ccc4c(c3)CN(c3ncnc5c3CC(C)(C)CC5)CCO4)cnc2[nH]1] | 4-(6,6-dimethyl-5,6,7,8-tetrahydroquinazolin-4-yl)-7-(2-ethyl-3H-imidazo[4,5-b]pyridin-6-yl)-2,3,4,5-tetrahydro-1,4-benzoxazepine |
| 221 | 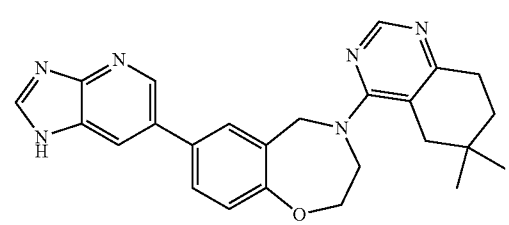 [SMILES: CC1(C)CCc2ncnc(N3CCOc4ccc(-c5cnc6nc[nH]c6c5)cc4C3)c2C1] | 4-(6,6-dimethyl-5,6,7,8-tetrahydroquinazolin-4-yl)-7-(1H-imidazo[4,5-b]pyridin-6-yl)-2,3,4,5-tetrahydro-1,4-benzoxazepine |
| 222 | 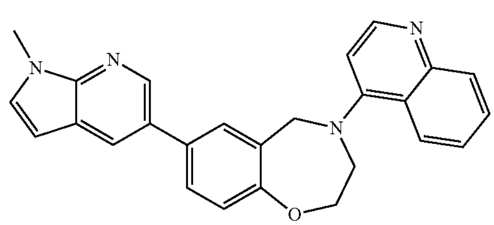 [SMILES: Cn1ccc2cc(-c3ccc4c(c3)CN(c3ccnc5ccccc35)CCO4)cnc21] | 7-(1-methyl-1H-pyrrolo[2,3-b]pyridin-5-yl)-4-quinolin-4-yl-2,3,4,5-tetrahydro-1,4-benzoxazepine |

-continued

| Cmpd No. | Structure | Name |
|---|---|---|
| 223 | 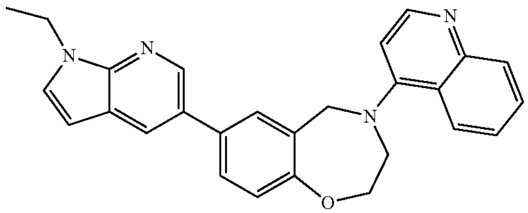 [SMILES: CCn1ccc2cc(-c3ccc4c(c3)CN(c3ccnc5ccccc35)CCO4)cnc21] | 7-(1-ethyl-1H-pyrrolo[2,3-b]pyridin-5-yl)-4-quinolin-4-yl-2,3,4,5-tetrahydro-1,4-benzoxazepine |
| 224 | 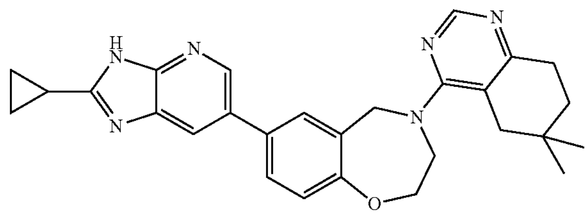 [SMILES: CC1(C)CCc2ncnc(N3CCOc4ccc(-c5cnc6[nH]c(C7CC7)nc6c5)cc4C3)c2C1] | 7-(2-cyclopropyl-3H-imidazo[4,5-b]pyridin-6-yl)-4-(6,6-dimethyl-5,6,7,8-tetrahydroquinazolin-4-yl)-2,3,4,5-tetrahydro-1,4-benzoxazepine |
| 225 | 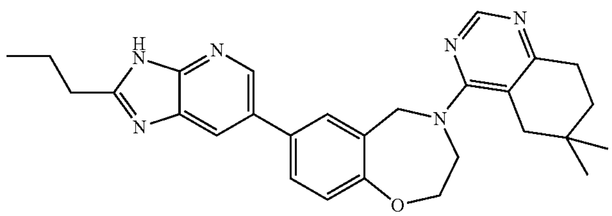 [SMILES: CCCc1nc2cc(-c3ccc4c(c3)CN(c3ncnc5c3CC(C)(C)CC5)CCO4)cnc2[nH]1] | 4-(6,6-dimethyl-5,6,7,8-tetrahydroquinazolin-4-yl)-7-(2-propyl-3H-imidazo[4,5-b]pyridin-6-yl)-2,3,4,5-tetrahydro-1,4-benzoxazepine |
| 226 | 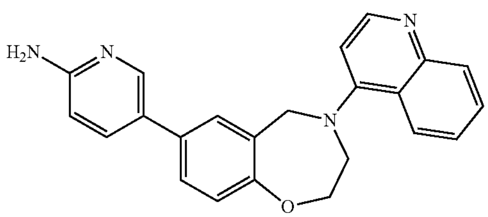 [SMILES: Nc1ccc(-c2ccc3c(c2)CN(c2ccnc4ccccc24)CCO3)cn1] | 5-(4-quinolin-4-yl-2,3,4,5-tetrahydro-1,4-benzoxazepin-7-yl)pyridin-2-amine |
| 227 | 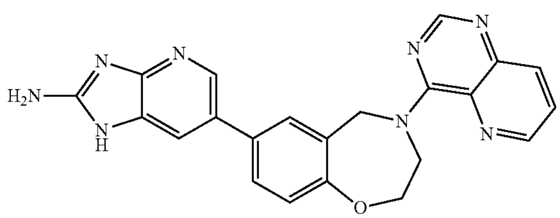 [SMILES: Nc1nc2ncc(-c3ccc4c(c3)CN(c3ncnc5cccnc35)CCO4)cc2[nH]1] | 6-(4-pyrido[3,2-d]pyrimidin-4-yl-2,3,4,5-tetrahydro-1,4-benzoxazepin-7-yl)-1H-imidazo[4,5-b]pyridin-2-amine |
| 228 | 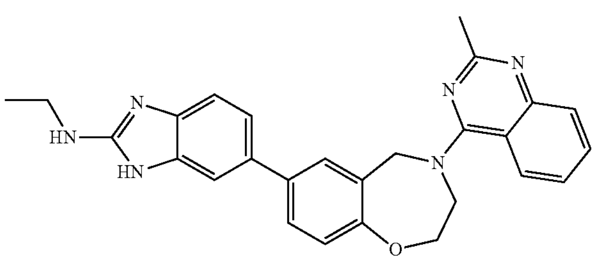 [SMILES: CCNc1nc2ccc(-c3ccc4c(c3)CN(c3nc(C)nc5ccccc35)CCO4)cc2[nH]1] | N-ethyl-6-[4-(2-methylquinazolin-4-yl)-2,3,4,5-tetrahydro-1,4-benzoxazepin-7-yl]-1H-benzimidazol-2-amine |
| 229 | 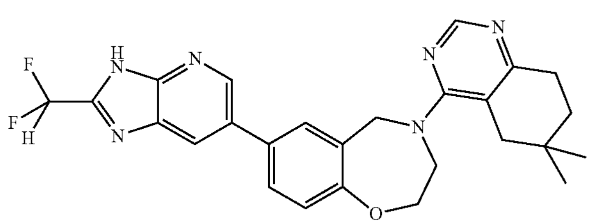 [SMILES: CC1(C)CCc2ncnc(N3CCOc4ccc(-c5cnc6[nH]c(C(F)F)nc6c5)cc4C3)c2C1] | 7-[2-(difluoromethyl)-3H-imidazo[4,5-b]pyridin-6-yl]-4-(6,6-dimethyl-5,6,7,8-tetrahydroquinazolin-4-yl)-2,3,4,5-tetrahydro-1,4-benzoxazepine |

-continued

| Cmpd No. | Structure | Name |
|---|---|---|
| 230 | 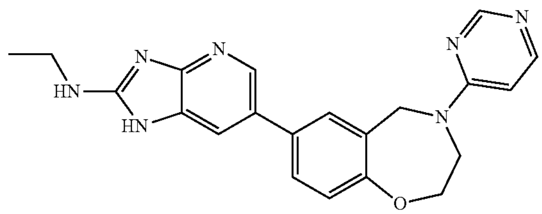 [SMILES: CCNc1nc2ncc(-c3ccc4c(c3)CN(c3ccncn3)CCO4)cc2[nH]1] | N-ethyl-6-(4-pyrimidin-4-yl-2,3,4,5-tetrahydro-1,4-benzoxazepin-7-yl)-1H-imidazo[4,5-b]pyridin-2-amine |
| 231 | 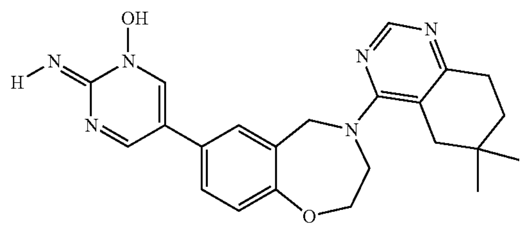 [SMILES: [H]/N=c1\ncc(-c2ccc3c(c2)CN(c2ncnc4c2CC(C)(C)CC4)CCO3)cn1O] | (2E)-5-[4-(6,6-dimethyl-5,6,7,8-tetrahydroquinazolin-4-yl)-2,3,4,5-tetrahydro-1,4-benzoxazepin-7-yl]-2-iminopyrimidin-1(2H)-ol |
| 232 | 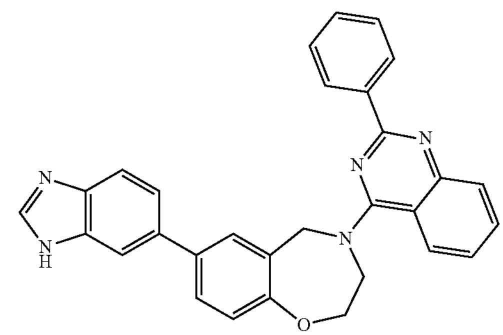 [SMILES: c1ccc(-c2nc(N3CCOc4ccc(-c5ccc6nc[nH]c6c5)cc4C3)c3ccccc3n2)cc1] | 7-(1H-benzimidazol-6-yl)-4-(2-phenylquinazolin-4-yl)-2,3,4,5-tetrahydro-1,4-benzoxazepine |
| 233 | 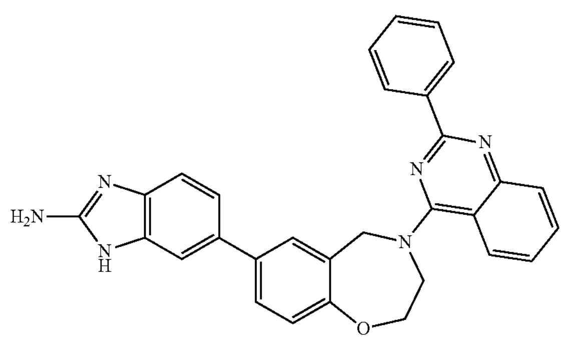 [SMILES: Nc1nc2ccc(-c3ccc4c(c3)CN(c3nc(-c5ccccc5)nc5ccccc35)CCO4)cc2[nH]1] | 6-[4-(2-phenylquinazolin-4-yl)-2,3,4,5-tetrahydro-1,4-benzoxazepin-7-yl]-1H-benzimidazol-2-amine |
| 234 | 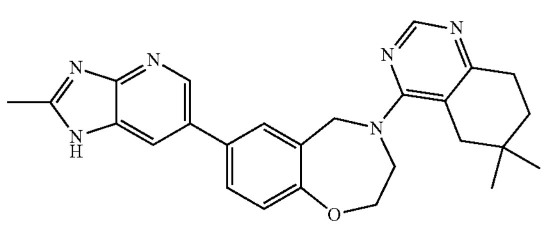 | 4-(6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine |
| 235 | 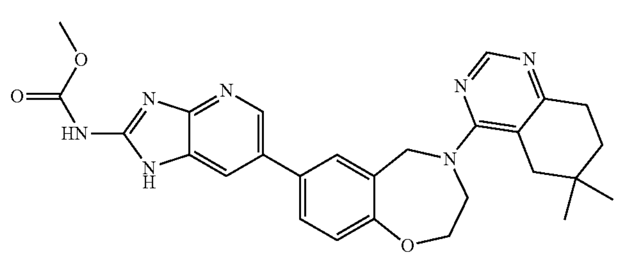 [SMILES: COC(=O)Nc1nc2ncc(-c3ccc4c(c3)CN(c3ncnc5c3CC(C)(C)CC5)CCO4)cc2[nH]1] | methyl {6-[4-(6,6-dimethyl-5,6,7,8-tetrahydroquinazolin-4-yl)-2,3,4,5-tetrahydro-1,4-benzoxazepin-7-yl]-1H-benzimidazol-2-yl}carbamate |

| Cmpd No. | Structure | Name |
| --- | --- | --- |
| 236 | 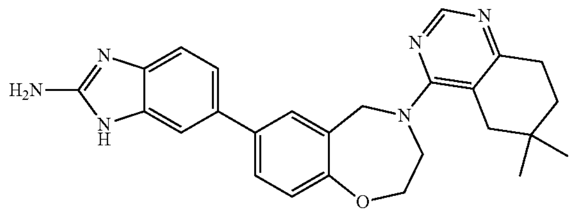 [SMILES: CC1(C)CCc2ncnc(N3CCOc4ccc(-c5ccc6nc(N)[nH]c6c5)cc4C3)c2C1] | 6-[4-(6,6-dimethyl-5,6,7,8-tetrahydroquinazolin-4-yl)-2,3,4,5-tetrahydro-1,4-benzoxazepin-7-yl]-1H-benzimidazol-2-amine |
| 237 | 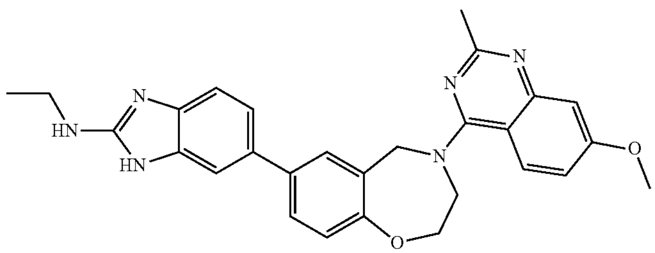 [SMILES: CCNc1nc2ccc(-c3ccc4c(c3)CN(c3nc(C)nc5cc(OC)ccc35)CCO4)cc2[nH]1] | N-ethyl-6-{4-[2-methyl-7-(methyloxy)quinazolin-4-yl]-2,3,4,5-tetrahydro-1,4-benzoxazepin-7-yl}-1H-benzimidazol-2-amine |
| 238 | 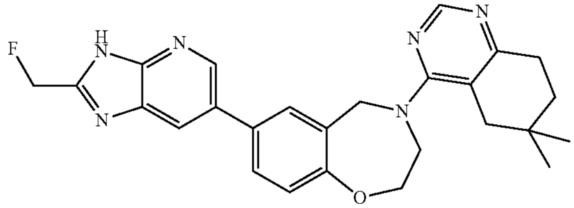 [SMILES: CC1(C)CCc2ncnc(N3CCOc4ccc(-c5cnc6[nH]c(CF)nc6c5)cc4C3)c2C1] | 4-(6,6-dimethyl-5,6,7,8-tetrahydroquinazolin-4-yl)-7-[2-(fluoromethyl)-3H-imidazo[4,5-b]pyridin-6-yl]-2,3,4,5-tetrahydro-1,4-benzoxazepine |
| 239 | 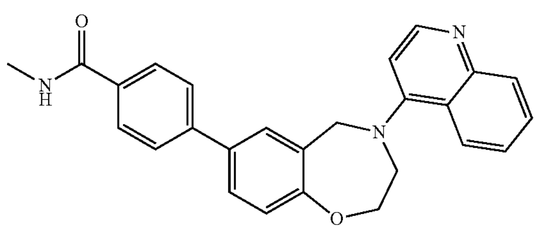 [SMILES: CNC(=O)c1ccc(-c2ccc3c(c2)CN(c2ccnc4ccccc24)CCO3)cc1] | N-methyl-4-(4-quinolin-4-yl-2,3,4,5-tetrahydro-1,4-benzoxazepin-7-yl)benzamide |
| 240 | 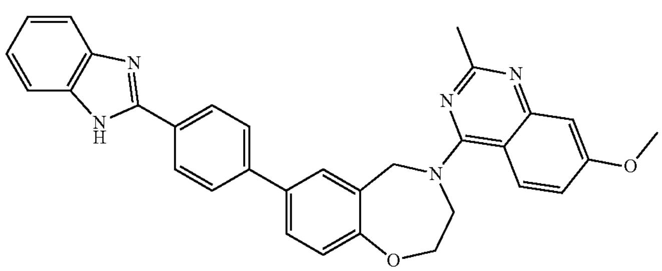 [SMILES: COc1ccc2c(N3CCOc4ccc(-c5ccc(-c6nc7ccccc7[nH]6)cc5)cc4C3)nc(C)nc2c1] | 7-[4-(1H-benzimidazol-2-yl)phenyl]-4-[2-methyl-7-(methyloxy)quinoazlin-4-yl]-2,3,4,5-tetrahydro-1,4-benzoxazepine |
| 241 | 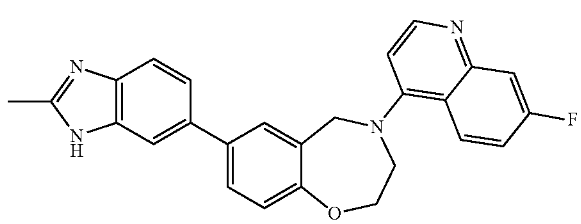 [SMILES: Cc1nc2ccc(-c3ccc4c(c3)CN(c3ccnc5cc(F)ccc35)CCO4)cc2[nH]1] | 4-(7-fluoroquinolin-4-yl)-7-(2-methyl-1H-benzimidazol-6-yl)-2,3,4,5-tetrahydro-1,4-benzoxazepine |

-continued

| Cmpd No. | Structure | Name |
|---|---|---|
| 242 | 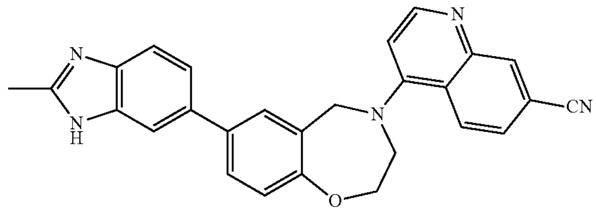 [SMILES: Cc1nc2ccc(-c3ccc4c(c3)CN(c3ccnc5cc(C#N)ccc35)CCO4)cc2[nH]1] | 4-[7-(2-methyl-1H-benzimidazol-6-yl)-2,3-dihydro-1,4-benzoxazepin-4(5H)-yl]quinolin-7-carbonitrile |
| 243 | 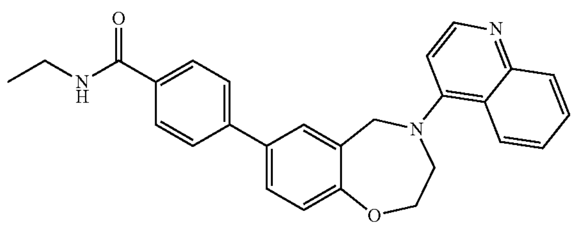 [SMILES: CCNC(=O)c1ccc(-c2ccc3c(c2)CN(c2ccnc4ccccc24)CCO3)cc1] | N-ethyl-4-(4-quinolin-4-yl-2,3,4,5-tetrahydro-1,4-benzoxazepin-7-yl)benzamide |
| 244 | 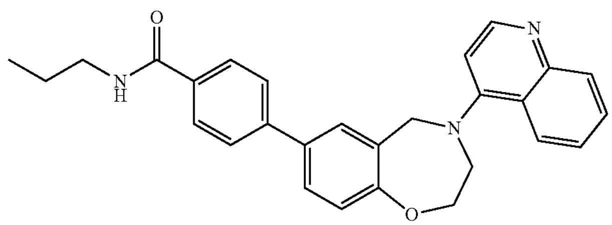 [SMILES: CCCNC(=O)c1ccc(-c2ccc3c(c2)CN(c2ccnc4ccccc24)CCO3)cc1] | N-propyl-4-(4-quinolin-4-yl-2,3,4,5-tetrahydro-1,4-benzoxazepin-7-yl)benzamide |
| 245 | 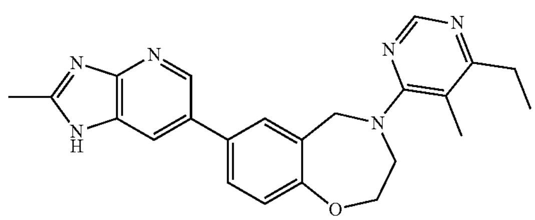 [SMILES: CCc1ncnc(N2CCOc3ccc(-c4cnc5nc(C)[nH]c5c4)cc3C2)c1C] | 4-(6-ethyl-5-methylpyrimidin-4-yl)-7-(2-methyl-1H-imidazo[4,5-b]pyridin-6-yl)-2,3,4,5-tetrahydro-1,4-benzoxazepine |
| 246 | 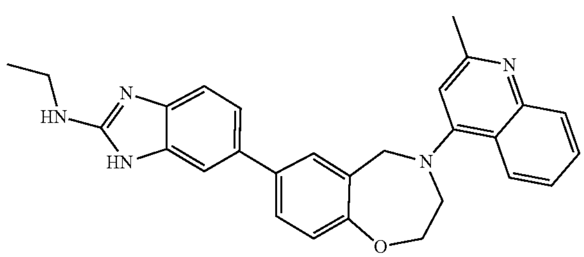 [SMILES: CCNc1nc2ccc(-c3ccc4c(c3)CN(c3cc(C)nc5ccccc35)CCO4)cc2[nH]1] | N-ethyl-6-[4-(2-methylquinolin-4-yl)-2,3,4,5-tetrahydro-1,4-benzoxazepin-7-yl]-1H-benzimidazol-2-amine |
| 247 | 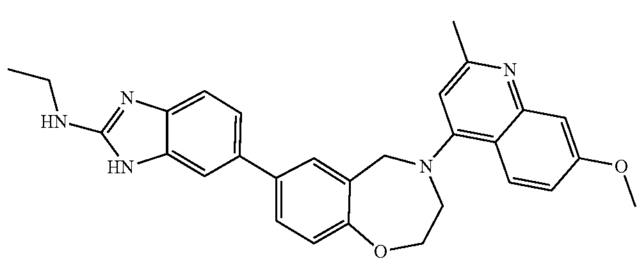 [SMILES: CCNc1nc2ccc(-c3ccc4c(c3)CN(c3cc(C)nc5cc(OC)ccc35)CCO4)cc2[nH]1] | N-ethyl-6-{4-[2-methyl-7-(methyloxy)quinolin-4-yl]-2,3,4,5-tetrahydro-1,4-benzoxazepin-7-yl}-1H-benzimidazol-2-amine |

| Cmpd No. | Structure | Name |
|---|---|---|
| 248 | 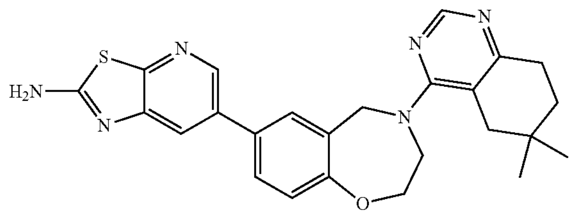 [SMILES: CC1(C)CCc2ncnc(N3CCOc4ccc(-c5cnc6sc(N)nc6c5)cc4C3)c2C1] | 6-[4-(6,6-dimethyl-5,6,7,8-tetrahydroquinazolin-4-yl)-2,3,4,5-tetrahydro-1,4-benzoxazepin-7-yl][1,3]thiazolo[5,4-b]pyridin-2-amine |
| 249 | 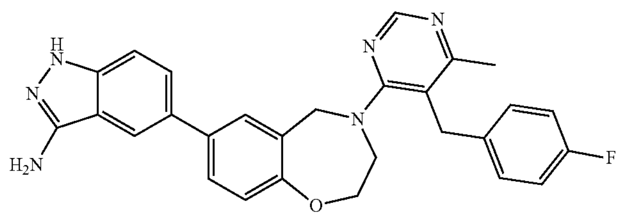 [SMILES: Cc1ncnc(N2CCOc3ccc(-c4ccc5[nH]nc(N)c5c4)cc3C2)c1Cc1ccc(F)cc1] | 5-(4-{5-[(4-fluorophenyl)methyl]-6-methylpyrimidin-4-yl}-2,3,4,5-tetrahydro-1,4-benzoxazepin-7-yl)-1H-indazol-3-amine |
| 250 | 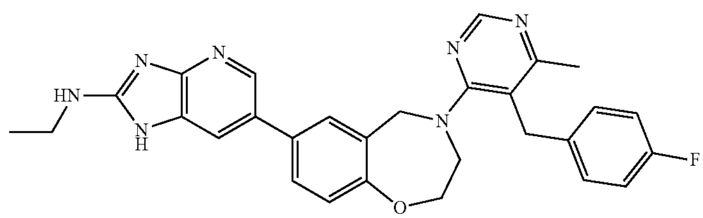 [SMILES: CCNc1nc2ncc(-c3ccc4c(c3)CN(c3ncnc(C)c3Cc3ccc(F)cc3)CCO4)cc2[nH]1] | N-ethyl-6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine |
| 251 | 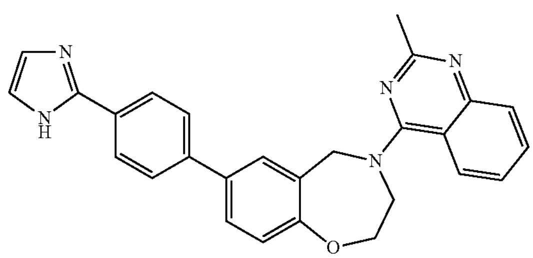 [SMILES: Cc1nc(N2CCOc3ccc(-c4ccc(-c5ncc[nH]5)cc4)cc3C2)c2ccccc2n1] | 7-[4-(1H-imidazol-2-yl)phenyl]-4-(2-methylquinazolin-4-yl)-2,3,4,5-tetrahydro-1,4-benzoxazepine |
| 252 | 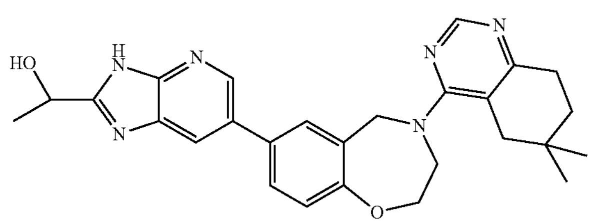 [SMILES: CC(O)c1nc2cc(-c3ccc4c(c3)CN(c3ncnc5c3CC(C)(C)CC5)CCO4)cnc2[nH]1] | 1-{6-[4-(6,6-dimethyl-5,6,7,8-tetrahydroquinazolin-4-yl)-2,3,4,5-tetrahydro-1,4-benzoxazepin-7-yl]-3H-imidazo[4,5-b]pyridin-2-yl}ethanol |
| 253 | 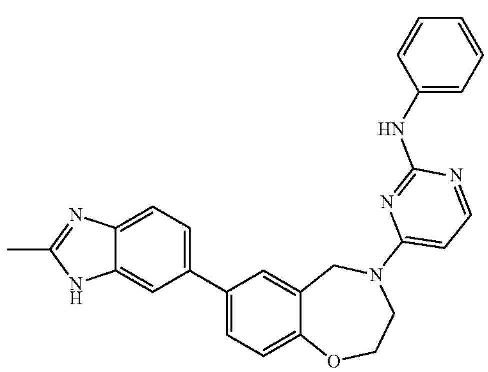 [SMILES: Cc1nc2ccc(-c3ccc4c(c3)CN(c3ccnc(Nc5ccccc5)n3)CCO4)cc2[nH]1] | 4-[7-(2-methyl-1H-benzimidazol-6-yl)-2,3-dihydro-1,4-benzoxazepin-4(5H)-yl]-N-phenylpyrimidin-2-amine |

| Cmpd No. | Structure | Name |
|---|---|---|
| 254 | 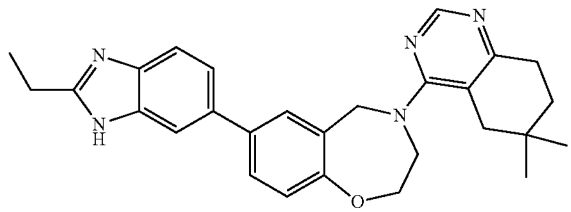 [SMILES: CCc1nc2ccc(-c3ccc4c(c3)CN(c3ncnc5c3CC(C)(C)CC5)CCO4)cc2[nH]1] | 4-(6,6-dimethyl-5,6,7,8-tetrahydroquinazolin-4-yl)-7-(2-ethyl-1H-benzimidazol-6-yl)-2,3,4,5-tetrahydro-1,4-benzoxazepine |
| 255 | 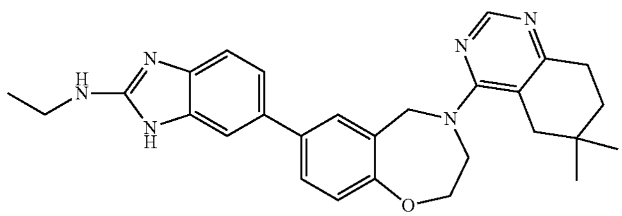 [SMILES: CCNc1nc2ccc(-c3ccc4c(c3)CN(c3ncnc5c3CC(C)(C)CC5)CCO4)cc2[nH]1] | 6-[4-(6,6-dimethyl-5,6,7,8-tetrahydroquinazolin-4-yl)-2,3,4,5-tetrahydro-1,4-benzoxazepin-7-yl]-N-ethyl-1H-benzimidazol-2-amine |
| 256 | 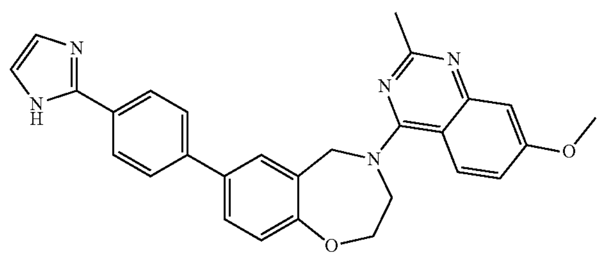 [SMILES: COc1ccc2c(N3CCOc4ccc(-c5ccc(-c6ncc[nH]6)cc5)cc4C3)nc(C)nc2c1] | 7-[4-(1H-imidazol-2-yl)phenyl]-4-[2-methyl-7-(methyloxy)quinazolin-4-yl]-2,3,4,5-tetrahydro-1,4-benzoxazepine |
| 257 | 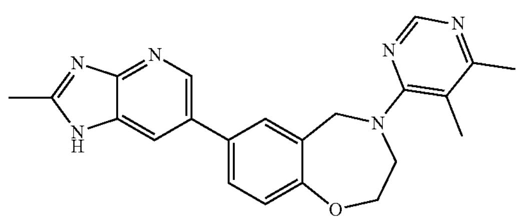 | 4-(5,6-dimethylpyrimidin-4-yl)-7-(2-methyl-1H-imidazo[4,5-b]pyridin-6-yl)-2,3,4,5-tetrahydro-1,4-benzoxazepine |
| 258 | 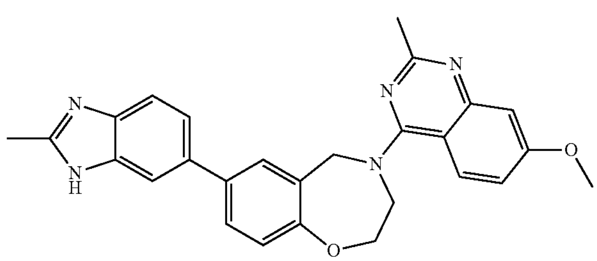 | 7-(2-methyl-1H-benzimidazol-6-yl)-4-[2-methyl-7-(methyloxy)quinoazolin-4-yl]-2,3,4,5-tetrahydro-1,4-benzoxazepine |
| 259 | 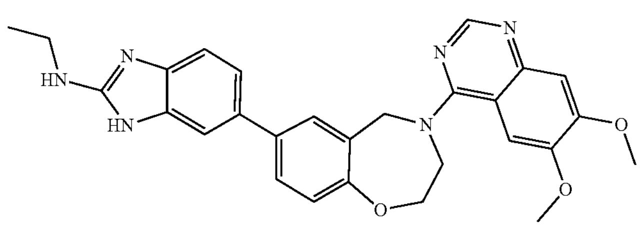 [SMILES: CCNc1nc2ccc(-c3ccc4c(c3)CN(c3ncnc5cc(OC)c(OC)cc35)CCO4)cc2[nH]1] | 6-{4-[6,7-bis(methyloxy)quinazolin-4-yl]-2,3,4,5-tetrahydro-1,4-benzoxazepin-7-yl}-N-ethyl-1H-benzimidazol-2-amine |

-continued

| Cmpd No. | Structure | Name |
|---|---|---|
| 260 | 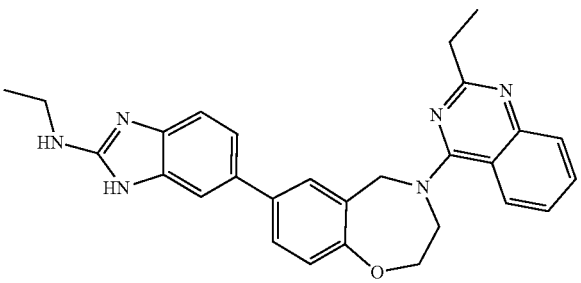 [SMILES: CCNc1nc2ccc(-c3ccc4c(c3)CN(c3nc(CC)nc5ccccc35)CCO4)cc2[nH]1] | N-ethyl-6-[4-(2-ethylquinazolin-4-yl)-2,3,4,5-tetrahydro-1,4-benzoxazepin-7-yl]-1H-benzimidazol-2-amine |
| 261 | 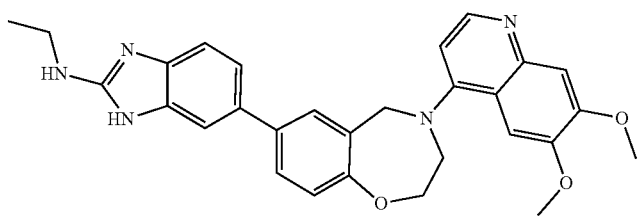 [SMILES: CCNc1nc2ccc(-c3ccc4c(c3)CN(c3ccnc5cc(OC)c(OC)cc35)CCO4)cc2[nH]1] | 6-{4-[6,7-bis(methyloxy)quinolin-4-yl]-2,3,4,5-tetrahydro-1,4-benzoxazepin-7-yl}-N-ethyl-1H-benzimidazol-2-amine |
| 262 | 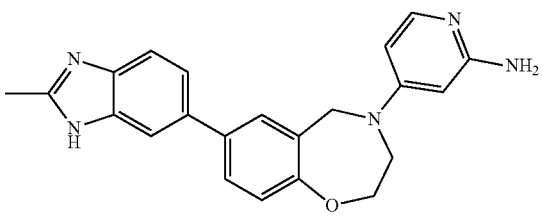 [SMILES: Cc1nc2ccc(-c3ccc4c(c3)CN(c3ccnc(N)c3)CCO4)cc2[nH]1] | 4-[7-(2-methyl-1H-benzimidazol-6-yl)-2,3-dihydro-1,4-benzoxazepin-4(5H)-yl]pyridin-2-amine |
| 263 | 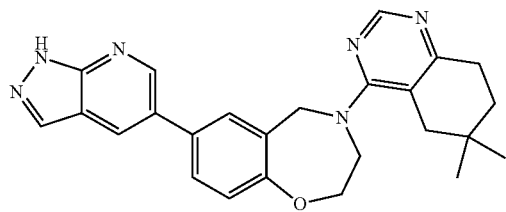 [SMILES: CC1(C)CCc2ncnc(N3CCOc4ccc(-c5cnc6[nH]ncc6c5)cc4C3)c2C1] | 4-(6,6-dimethyl-5,6,7,8-tetrahydroquinazolin-4-yl)-7-(1H-pyrazolo[3,4-b]pyridin-5-yl)-2,3,4,5-tetrahydro-1,4-benzoxazepine |
| 264 | 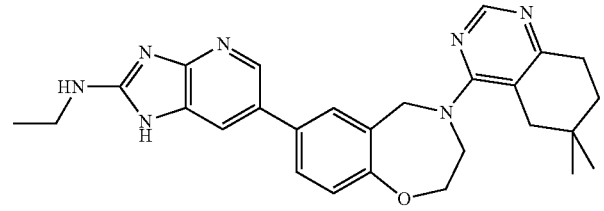 [SMILES: CCNc1nc2ncc(-c3ccc4c(c3)CN(c3ncnc5c3CC(C)(C)CC5)CCO4)cc2[nH]1] | 6-[4-(6,6-dimethyl-5,6,7,8-tetrahydroquinbazolin-4-yl)-2,3,4,5-tetrahydro-1,4-benzoxazepin-7-yl]-N-ethyl-1H-imidazo[4,5-b]pyridin-2-amine |
| 265 | 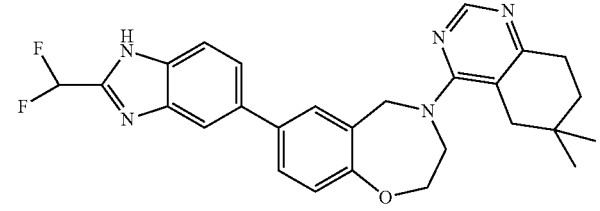 [SMILES: CC1(C)CCc2ncnc(N3CCOc4ccc(-c5ccc6[nH]c(C(F)F)nc6c5)cc4C3)c2C1] | 7-[2-(difluoromethyl)-1H-benzimidazol-5-yl]-4-(6,6-dimethyl-5,6,7,8-tetrahydroquinazolin-4-yl)-2,3,4,5-tetrahydro-1,4-benzoazepine |

-continued

| Cmpd No. | Structure | Name |
|---|---|---|
| 266 | 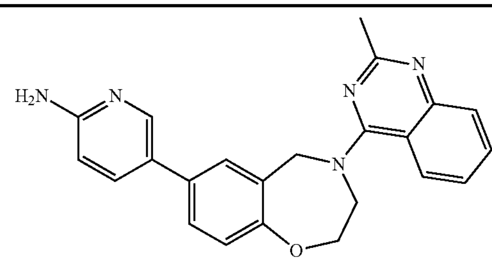 | 5-[4-(2-methylquinazolin-4-yl)-2,3,4,5-tetrahydro-1,4-benzoxazepin-7-yl]pyridin-2-amine |
| 267 | 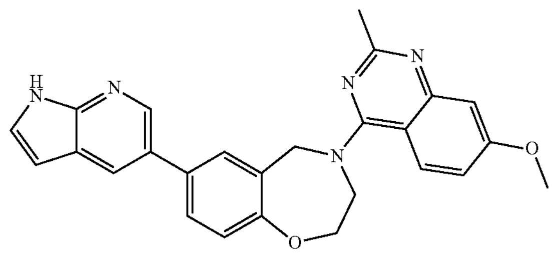 [SMILES: COc1ccc2c(N3CCOc4ccc(-c5cnc6[nH]ccc6c5)cc4C3)nc(C)nc2c1] | 4-[2-methyl-7-(methyloxy)quinazolin-4-yl]-7-(1H-pyrrolo[2,3-b]pyridin-5-yl)-2,3,4,5-tetrahydro-1,4-benzoxazepine |
| 268 | 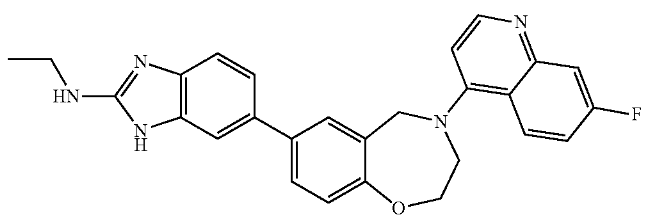 [SMILES: CCNc1nc2ccc(-c3ccc4c(c3)CN(c3ccnc5cc(F)ccc35)CCO4)cc2[nH]1] | N-ethyl-6-[4-(7-fluoroquinolin-4-yl)-2,3,4,5-tetrahydro-1,4-benzoxazepin-7-yl]-1H-benzimidazol-2-amine |
| 269 | 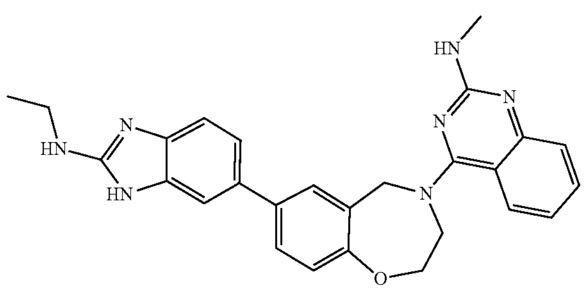 [SMILES: CCNc1nc2ccc(-c3ccc4c(c3)CN(c3nc(NC)nc5ccccc35)CCO4)cc2[nH]1] | 4-{7-[2-(ethylamino)-1H-benzimidazol-6-yl]-2,3-dihydro-1,4-benzoxazepin-4(5H)-yl}-N-methylquinazolin-2-amine |
| 270 | 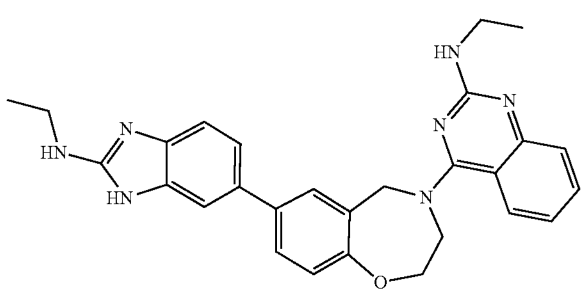 [SMILES: CCNc1nc(N2CCOc3ccc(-c4ccc5nc(NCC)[nH]c5c4)cc3C2)c2ccccc2n1] | N-ethyl-4-{7-[2-(ethylamino)-1H-benzimidazol-6-yl]-2,3-dihydro-1,4-benzoxazepin-4(5H)-yl}quinazolin-2-amine |
| 271 | 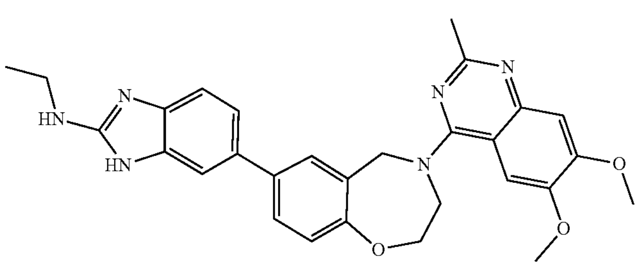 [SMILES: CCNc1nc2ccc(-c3ccc4c(c3)CN(c3nc(C)nc5cc(OC)c(OC)cc35)CCO4)cc2[nH]1] | N-ethyl-6-{4-[2-methyl-6,7-bis(methyloxy)quinazolin-4-yl]-2,3,4,5-tetrahydro-1,4-benzoxazepin-7-yl}-1H-benzimidazol-2-amine |

-continued

| Cmpd No. | Structure | Name |
|---|---|---|
| 272 | 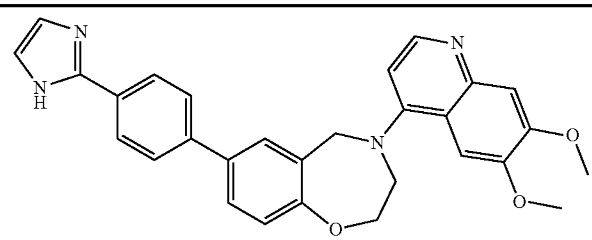 | 4-[6,7-bis(methyloxy)quinolin-4-yl]-7-[4-(1H-imidazol-2-yl)phenyl]-2,3,4,5-tetrahydro-1,4-benzoxazepine |
| 273 | 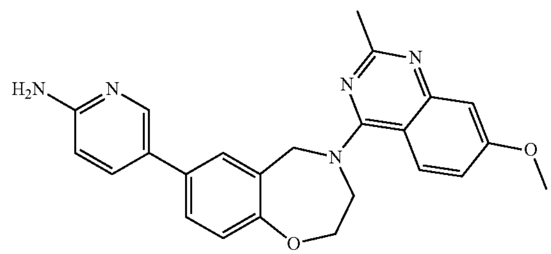 [SMILES: COc1ccc2c(N3CCOc4ccc(-c5ccc(N)nc5)cc4C3)nc(C)nc2c1] | 5-{4-[2-methyl-7-(methyloxy)quinazolin-4-yl]-2,3,4,5-tetrahydro-1,4-benzoxazepin-7-yl}pyridin-2-amine |
| 274 | 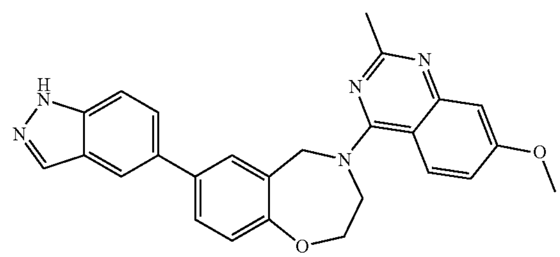 [SMILES: COc1ccc2c(N3CCOc4ccc(-c5ccc6[nH]ncc6c5)cc4C3)nc(C)nc2c1] | 7-(1H-indazol-5-yl)-4-[2-methyl-7-(methyloxy)quinazolin-4-yl]-2,3,4,5-tetrahydro-1,4-benzoxazepine |
| 275 | 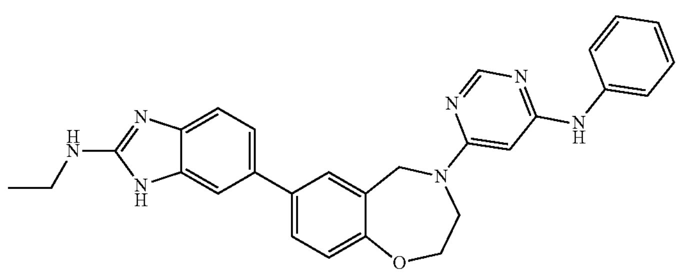 [SMILES: CCNc1nc2ccc(-c3ccc4c(c3)CN(c3cc(Nc5ccccc5)ncn3)CCO4)cc2[nH]1] | N-ethyl-6-{4-[6-(phenylamino)pyrimidin-4-yl]-2,3,4,5-tetrahydro-1,4-benzoxazepin-7-yl}-1H-benzimidazol-2-amine |
| 276 | 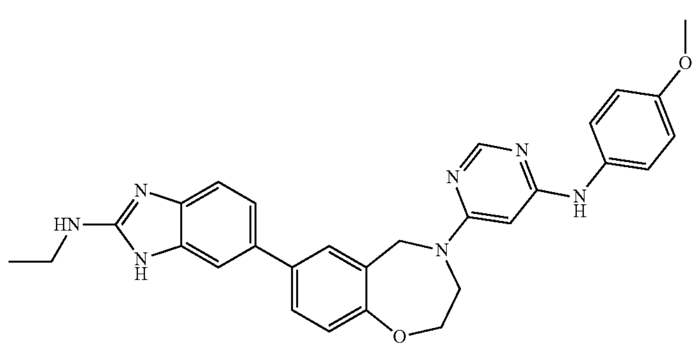 [SMILES: CCNc1nc2ccc(-c3ccc4c(c3)CN(c3cc(Nc5ccc(OC)cc5)ncn3)CCO4)cc2[nH]1] | N-ethyl-6-[4-(6-{[4-(methyloxy)phenyl]amino}pyrimidin-4-yl)-2,3,4,5-tetrahydro-1H-benzoxazepin-7-yl]-1H-benzimidazol-2-amine |
| 277 | 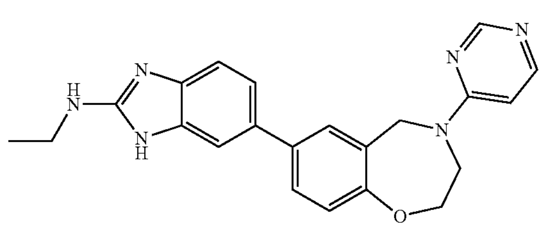 [SMILES: CCNc1nc2ccc(-c3ccc4c(c3)CN(c3ccncn3)CCO4)cc2[nH]1] | N-ethyl-6-(4-pyrimidin-4-yl-2,3,4,5-tetrahydro-1,4-benzoxazepin-7-yl)-1H-benzimidazol-2-amine |

-continued

| Cmpd No. | Structure | Name |
|---|---|---|
| 278 | 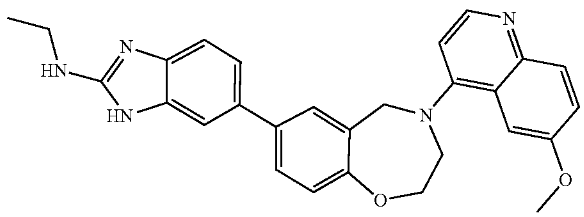 [SMILES: CCNc1nc2ccc(-c3ccc4c(c3)CN(c3ccnc5ccc(OC)cc35)CCO4)cc2[nH]1] | N-ethyl-6-{4-[6-(methyloxy)quinolin-4-yl]-2,3,4,5-tetrahydro-1,4-benzoxazepin-7-yl}-1H-benzimidazol-2-amine |
| 279 | 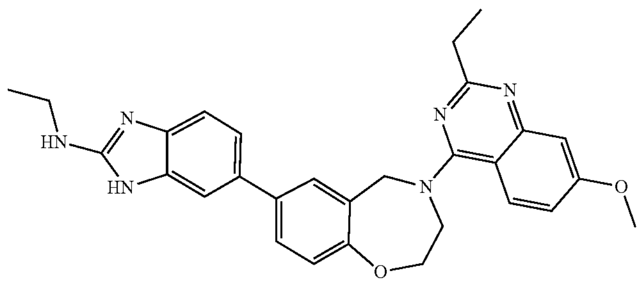 [SMILES: CCNc1nc2ccc(-c3ccc4c(c3)CN(c3nc(CC)nc5cc(OC)ccc35)CCO4)cc2[nH]1] | N-ethyl-6-{4-[2-ethyl-7-(methyloxy)quinazolin-4-yl]-2,3,4,5-tetrahydro-1,4-benzoxazepin-7-yl}-1H-benzimidazol-2-amine |
| 280 | 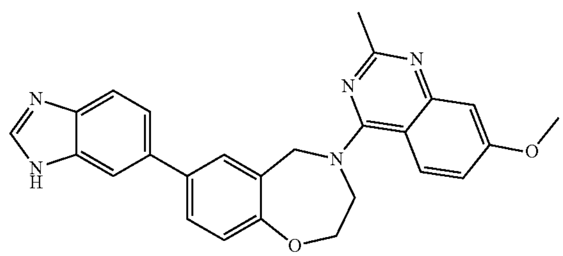 [SMILES: COc1ccc2c(N3CCOc4ccc(-c5ccc6nc[nH]c6c5)cc4C3)nc(C)nc2c1] | 7-(1H-benzimidazol-6-yl)-4-[2-methyl-7-(methyloxy)quinoazolin-4-yl]-2,3,4,5-tetrahydro-1,4-benzoxazepine |
| 281 | 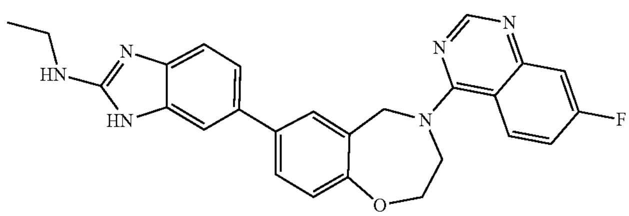 [SMILES: CCNc1nc2ccc(-c3ccc4c(c3)CN(c3ncnc5cc(F)ccc35)CCO4)cc2[nH]1] | N-ethyl-6-[4-(7-fluoroquinazolin-4-yl)-2,3,4,5-tetrahydro-1,4-benzoxazepin-7-yl]-1H-benzimidazol-2-amine |
| 282 | 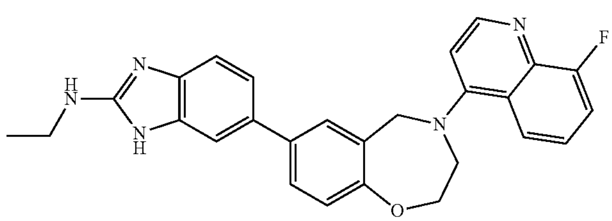 [SMILES: CCNc1nc2ccc(-c3ccc4c(c3)CN(c3ccnc5c(F)cccc35)CCO4)cc2[nH]1] | N-ethyl-6-[4-(8-fluoroquinolin-4-yl)-2,3,4,5-tetrahydro-1,4-benzoxazepin-7-yl]-1H-benzimidazol-2-amine |
| 283 | 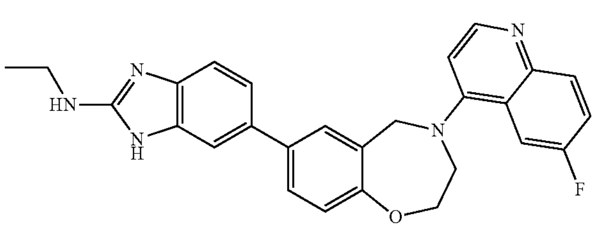 [SMILES: CCNc1nc2ccc(-c3ccc4c(c3)CN(c3ccnc5ccc(F)cc35)CCO4)cc2[nH]1] | N-ethyl-6-[4-(6-fluoroquinolin-4-yl)-2,3,4,5-tetrahydro-1,4-benzoxazepin-7-yl]-1H-benzimidazol-2-amine |

-continued

| Cmpd No. | Structure | Name |
|---|---|---|
| 284 | 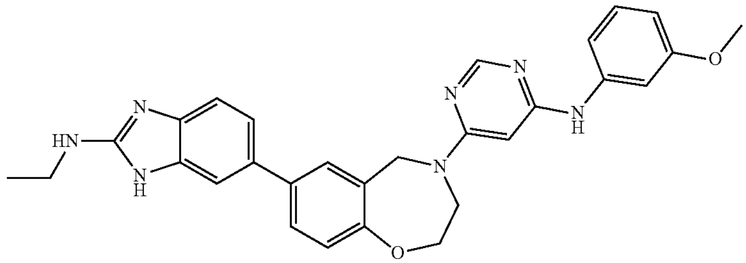 [SMILES: CCNc1nc2ccc(-c3ccc4c(c3)CN(c3cc(Nc5cccc(OC)c5)ncn3)CCO4)cc2[nH]1] | N-ethyl-6-[4-(6-{[3-(methyloxy)phenyl]amino}pyrimidin-4-yl)-2,3,4,5-tetrahydro-1,4-benzoxazepin-7-yl]-1H-benzimidazol-2-amine |
| 285 | 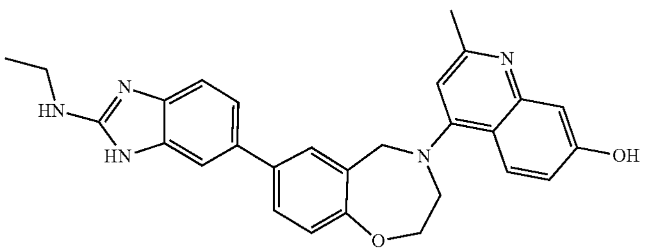 [SMILES: CCNc1nc2ccc(-c3ccc4c(c3)CN(c3cc(C)nc5cc(O)ccc35)CCO4)cc2[nH]1] | 4-{7-[2-(ethylamino)-1H-benzimidazol-6-yl]-2,3-dihydro-1,4-benzoxazepin-4(5H)-yl}-2-methylquinazolin-2-ol |
| 286 | 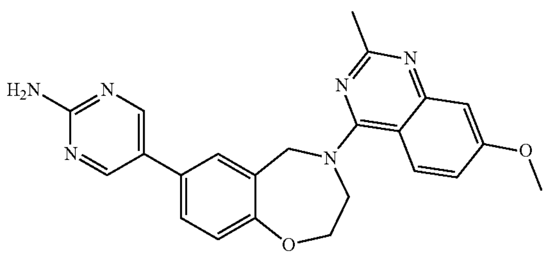 [SMILES: COc1ccc2c(N3CCOc4ccc(-c5cnc(N)nc5)cc4C3)nc(C)nc2c1] | 5-{4-[2-methyl-7-(methyloxy)quinazolin-4-yl]-2,3,4,5-tetrahydro-1,4-benzoxazepin-7-yl}pyrimidin-2-amine |
| 287 | 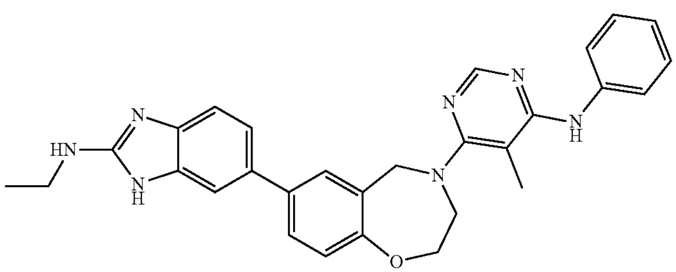 [SMILES: CCNc1nc2ccc(-c3ccc4c(c3)CN(c3ncnc(Nc5ccccc5)c3C)CCO4)cc2[nH]1] | N-ethyl-6-{4-[5-methyl-6-(phenylamino)pyrimidin-4-yl]-2,3,4,5-tetrahydro-1,4-benzoxazepin-7-yl}-1H-benzimidazol-2-amine |
| 288 | 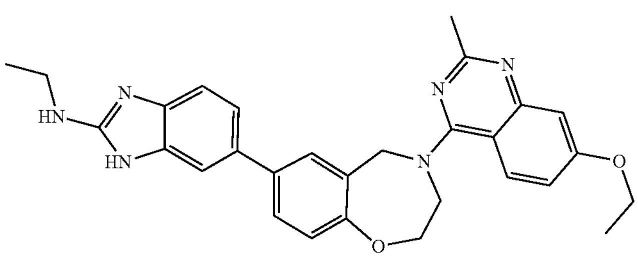 [SMILES: CCNc1nc2ccc(-c3ccc4c(c3)CN(c3nc(C)nc5cc(OCC)ccc35)CCO4)cc2[nH]1] | N-ethyl-6-{4-[7-(ethyloxy)-2-methylquinazolin-4-yl]-2,3,4,5-tetrahydro-1,4-benzoxazepin-7-yl}-1H-benzimidazol-2-amine |
| 289 | 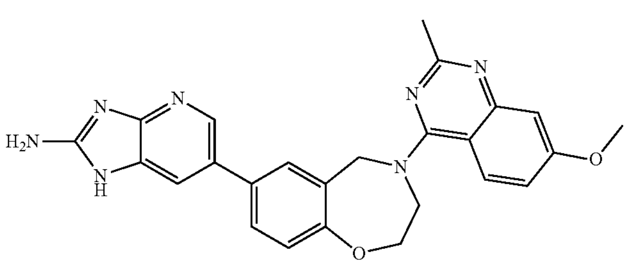 [SMILES: COc1ccc2c(N3CCOc4ccc(-c5cnc6nc(N)[nH]c6c5)cc4C3)nc(C)nc2c1] | 6-{4-[2-methyl-7-(methyloxy)quinazolin-4-yl]-2,3,4,5-tetrahydro-1,4-benzoxazepin-7-yl}-1H-imidazo[4,5-b]pyridin-2-amine |

-continued

| Cmpd No. | Structure | Name |
|---|---|---|
| 290 | 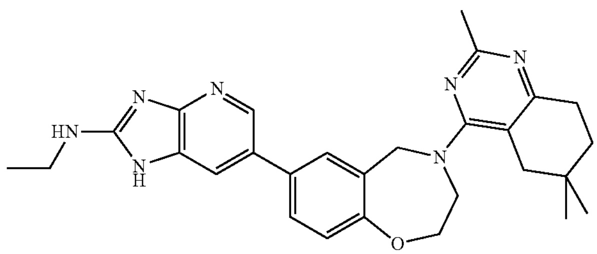 [SMILES: CCNc1nc2ncc(-c3ccc4c(c3)CN(c3nc(C)nc5c3CC(C)(C)CC5)CCO4)cc2[nH]1] | N-ethyl-6-[4-(2,6,6-trimethyl-5,6,7,8-tetrahydroquinazolin-4-yl)-2,3,4,5-tetrahydro-1,4-benzoxazepin-7-yl]-1H-imidazo[4,5-b]pyridin-2-amine |
| 291 | 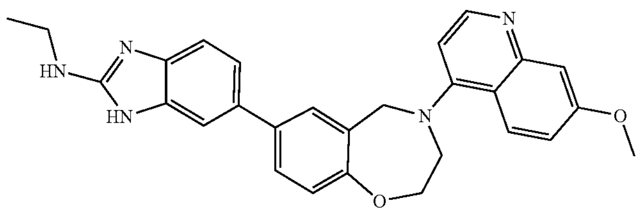 [SMILES: CCNc1nc2ccc(-c3ccc4c(c3)CN(c3ccnc5cc(OC)ccc35)CCO4)cc2[nH]1] | N-ethyl-6-{4-[7-(methyloxy)quinolin-4-yl]-2,3,4,5-tetrahydro-1,4-benzoxazepin-7-yl}-1H-benzimidazol-2-amine |
| 292 | 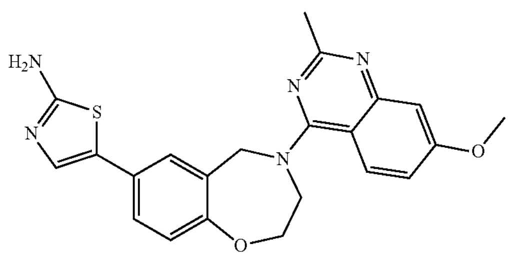 [SMILES: COc1ccc2c(N3CCOc4ccc(-c5cnc(N)s5)cc4C3)nc(C)nc2c1] | 5-{4-[2-methyl-7-(methyloxy)quinazolin-4-yl]-2,3,4,5-tetrahydro-1,4-benzoxazepin-7-yl}-1,3-thiazol-2-amine |
| 293 | 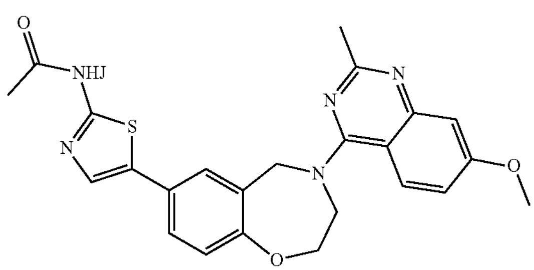 | N-(5-{4-[2-methyl-7-(methyloxy)quinazolin-4-yl]-2,3,4,5-tetrahydro-1,4-benzoxazepin-7-yl}-1,3-thiazol-2-yl)acetamide |
| 294 | 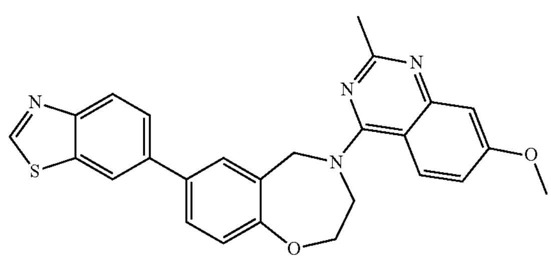 [SMILES: COc1ccc2c(N3CCOc4ccc(-c5ccc6ncsc6c5)cc4C3)nc(C)nc2c1] | 7-(1,3-benzothiazol-6-yl)-4-[2-methyl-7-(methyloxy)quinazolin-4-yl]-2,3,4,5-tetrahydro-1,4-benzoxazepine |
| 295 | 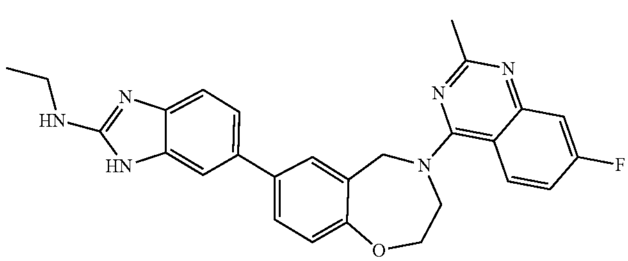 [SMILES: CCNc1nc2ccc(-c3ccc4c(c3)CN(c3nc(C)nc5cc(F)ccc35)CCO4)cc2[nH]1] | N-ethyl-6-[4-(7-fluoro-2-methylquinazolin-4-yl)-2,3,4,5-tetrahydro-1,4-benzoxazepin-7-yl]-1H-benzimidazol-2-amine |

| Cmpd No. | Structure | Name |
|---|---|---|
| 296 | 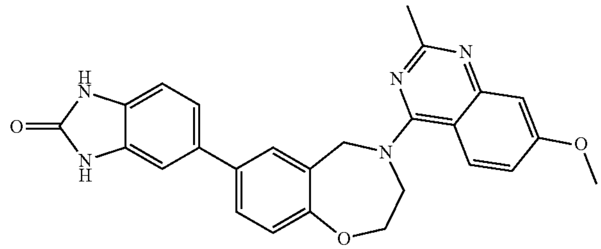 [SMILES: COc1ccc2c(N3CCOc4ccc(-c5ccc6[nH]c(=O)[nH]c6c5)cc4C3)nc(C)nc2c1] | 5-{4-[2-methyl-7-(methyloxy)quinazolin-4-yl]-2,3,4,5-tetrahydro-1,4-benzoxazepin-7-yl}-1,3-dihydro-2H-benzimidazol-2-one |
| 297 | 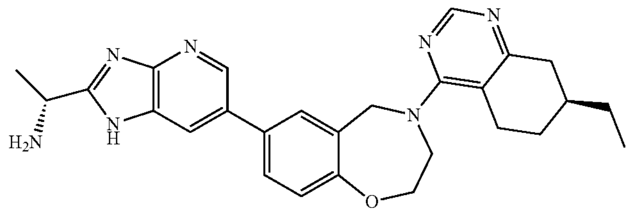 [SMILES: CC[C@H]1CCc2c(ncnc2N2CCOc3ccc(-c4cnc5nc([C@@H](C)N)[nH]c5c4)cc3C2)C1] | (1R)-1-(6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)ethanamine |
| 298 | 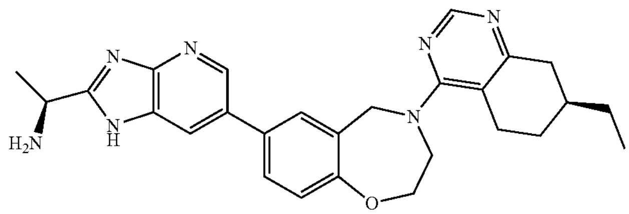 [SMILES: CC[C@H]1CCc2c(ncnc2N2CCOc3ccc(-c4cnc5nc([C@H](C)N)[nH]c5c4)cc3C2)C1] | (1S)-1-(6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)ethanamine |
| 299 | 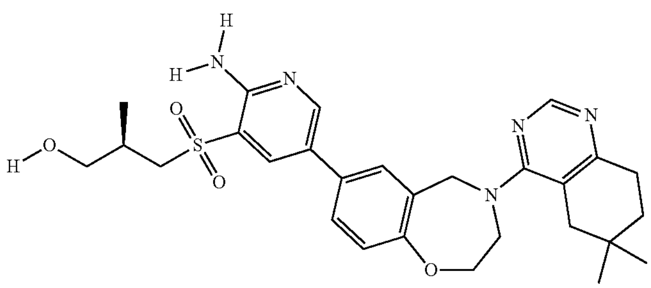 [SMILES: C[C@H](CO)CS(=O)(=O)c1cc(-c2ccc3c(c2)CN(c2ncnc4c2CC(C)(C)CC4)CCO3)cnc1N] | (2R)-3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylpropan-1-ol |
| 300 | 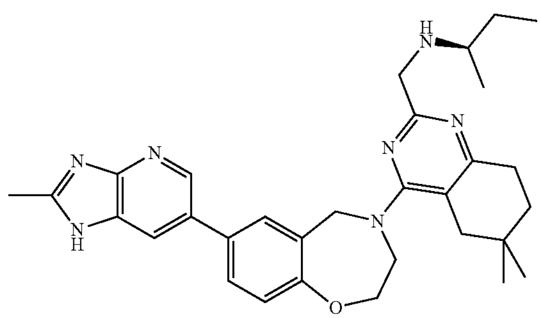 [SMILES: CC[C@@H](C)NCc1nc2c(c(N3CCOc4ccc(-c5cnc6nc(C)[nH]c6c5)cc4C3)n1)CC(C)(C)CC2] | (2R)-N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)butan-2-amine |
| 301 | 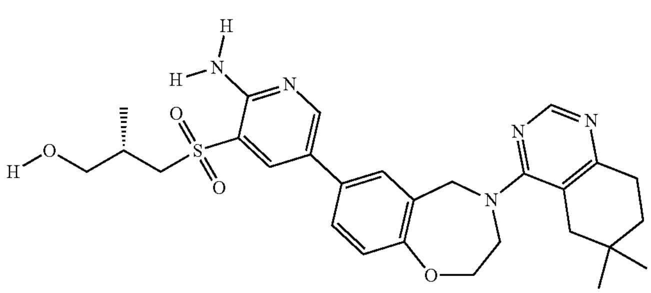 [SMILES: C[C@@H](CO)CS(=O)(=O)c1cc(-c2ccc3c(c2)CN(c2ncnc4c2CC(C)(C)CC4)CCO3)cnc1N] | (2S)-3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylpropan-1-ol |

-continued

| Cmpd No. | Structure | Name |
| --- | --- | --- |
| 302 | 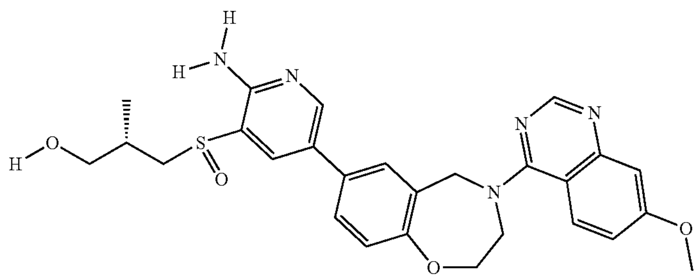 [SMILES: COc1ccc2c(N3CCOc4ccc(-c5cnc(N)c(S(=O)C[C@@H](C)CO)c5)cc4C3)ncnc2c1] | (2S)-3-[(2-amino-5-{4-[7-(methyloxy)quinazolin-4-yl]-2,3,4,5-tetrahydro-1,4-benzoxazolin-7-yl}pyridin-3-yl)sulfinyl]-2-methylpropan-1-ol |
| 303 | 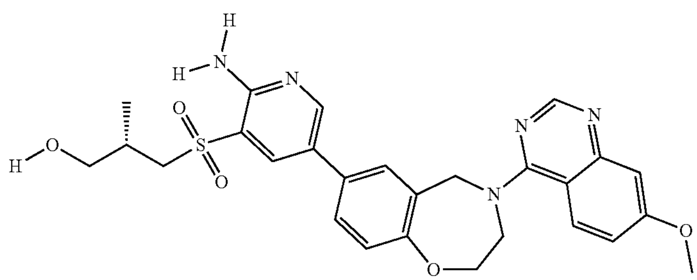 [SMILES: COc1ccc2c(N3CCOc4ccc(-c5cnc(N)c(S(=O)(=O)C[C@@H](C)CO)c5)cc4C3)ncnc2c1] | (2S)-3-[(2-amino-5-{4-[7-(methyloxy)quinazolin-4-yl]-2,3,4,5-tetrahydro-1,4-benzoxazepin-7-yl}pyridin-3-yl)sulfonyl]-2-methylpropan-1-ol |
| 304 | 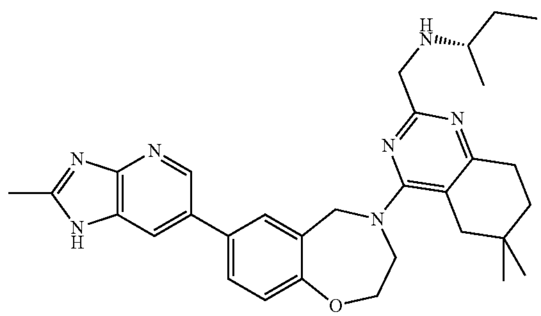 [SMILES: CC[C@H](C)NCc1nc2c(c(N3CCOc4ccc(-c5cnc6nc(C)[nH]c6c5)cc4C3)n1)CC(C)(C)CC2] | (2S)-N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)butan-2-amine |
| 305 | 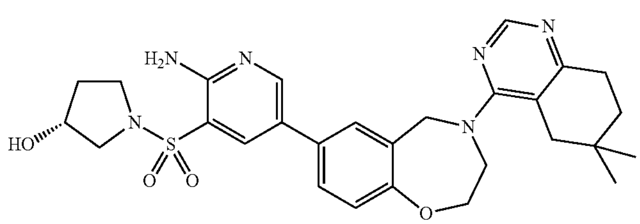 [SMILES: CC1(C)CCc2ncnc(N3CCOc4ccc(-c5cnc(N)c(S(=O)(=O)N6CC[C@@H](O)C6)c5)cc4C3)c2C1] | (3R)-1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-ol |
| 306 | 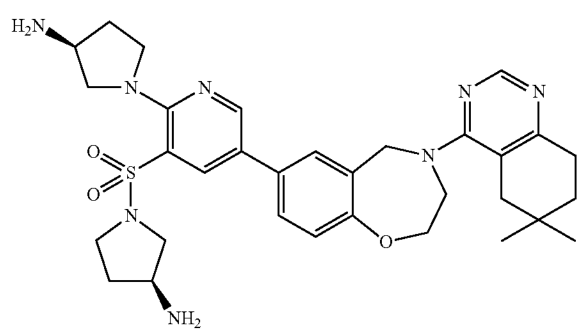 [SMILES: CC1(C)CCc2ncnc(N3CCOc4ccc(-c5cnc(N6CC[C@H](N)C6)c(S(=O)(=O)N6CC[C@H](N)C6)c5)cc4C3)c2C1] | (3S)-1-({2-[(3S)-3-aminopyrrolidin-1-yl]-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-amine |

| Cmpd No. | Structure | Name |
|---|---|---|
| 307 | 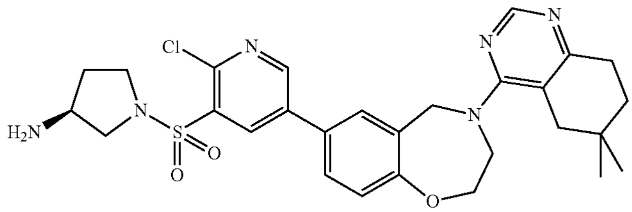 [SMILES: CC1(C)CCc2ncnc(N3CCOc4ccc(-c5cnc(Cl)c(S(=O)(=O)N6CC[C@H](N)C6)c5)cc4C3)c2C1] | (3S)-1-({2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-amine |
| 308 | 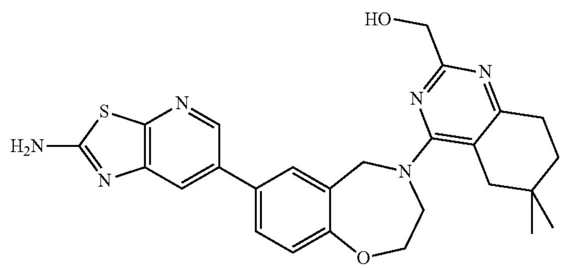 [SMILES: CC1(C)CCc2nc(CO)nc(N3CCOc4ccc(-c5cnc6sc(N)nc6c5)cc4C3)c2C1] | {4-[7-(2-amino[1,3]thiazolo[5,4-b]pyridin-6-yl)-2,3-dihydro-1,4-benzoxazepin-4(5H)-yl]-6,6-dimethyl-5,6,7,8-tetrahydroquinazolin-2-yl}methanol |
| 309 | 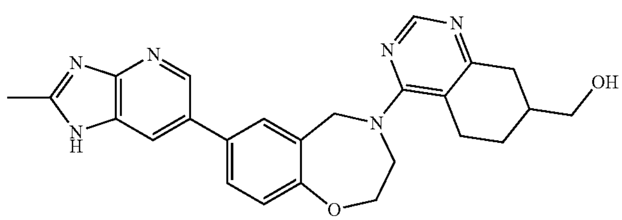 [SMILES: Cc1nc2ncc(-c3ccc4c(c3)CN(c3ncnc5c3CCC(CO)C5)CCO4)cc2[nH]1] | {4-[7-(2-methyl-1H-imidazo[4,5-b]pyridin-6-yl)-2,3-dihydro-1,4-benzoxazepin-4(5H)-yl]-5,6,7,8-tetrahydroquinazolin-7-yl}methanol |
| 310 | 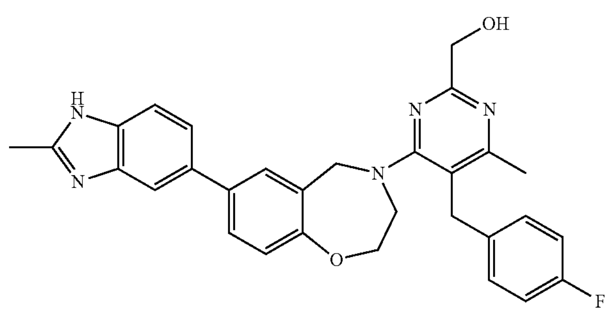 [SMILES: Cc1nc2cc(-c3ccc4c(c3)CN(c3nc(CO)nc(C)c3Cc3ccc(F)cc3)CCO4)ccc2[nH]1] | {5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}methanol |
| 311 | 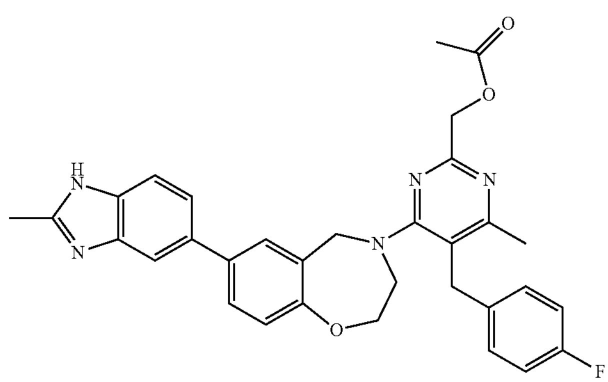 [SMILES: CC(=O)OCc1nc(C)c(Cc2ccc(F)cc2)c(N2CCOc3ccc(-c4ccc5[nH]c(C)nc5c4)cc3C2)n1] | {5-[4(fluorophenyl)methyl]-4-methyl-6-[7-(2-methyl-1H-benzimidazol-5-yl)-2,3-dihydro-1,4-benzoxazepin-4(5H)-yl]pyrimidin-2-yl}methyl acetate |

| Cmpd No. | Structure | Name |
| --- | --- | --- |
| 312 | 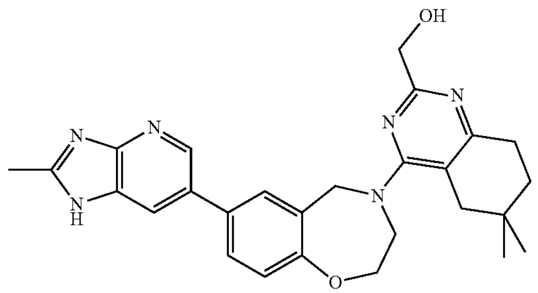 [SMILES: Cc1nc2ncc(-c3ccc4c(c3)CN(c3nc(CO)nc5c3CC(C)(C)CC5)CCO4)cc2[nH]1] | {6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methanol |
| 313 | 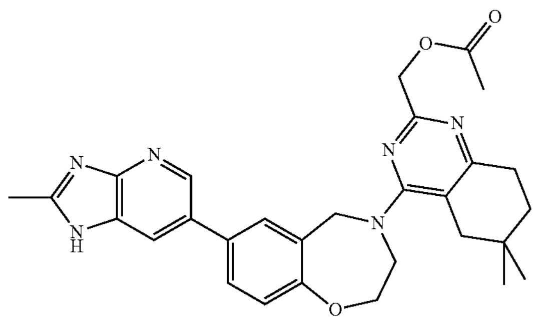 [SMILES: CC(=O)OCc1nc2c(c(N3CCOc4ccc(-c5cnc6nc(C)[nH]c6c5)cc4C3)n1)CC(C)(C)CC2] | {6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl acetate |
| 314 | 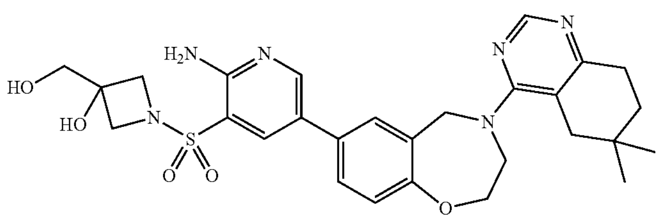 [SMILES: CC1(C)CCc2ncnc(N3CCOc4ccc(-c5cnc(N)c(S(=O)(=O)N6CC(O)(CO)C6)c5)cc4C3)c2C1] | 1-({2-amino-5-[4-(6,6-dimethyl-5,6,7,8-tetrahydroquinazolin-4-yl)-2,3,4,5-tetrahydro-1,4-benbzoxazepin-7-yl]pyridin-3-yl}sulfonyl)-3-(hydroxymethyl)azetidin-3-ol |
| 315 | 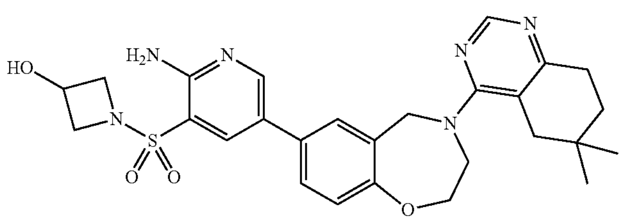 [SMILES: CC1(C)CCc2ncnc(N3CCOc4ccc(-c5cnc(N)c(S(=O)(=O)N6CC(O)C6)c5)cc4C3)c2C1] | 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)azetidin-3-ol |
| 316 | 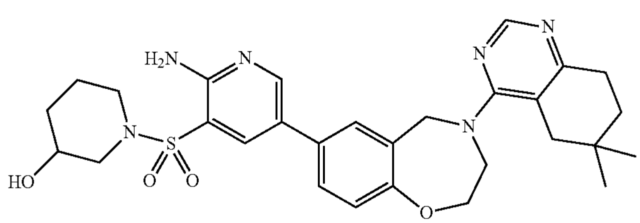 [SMILES: CC1(C)CCc2ncnc(N3CCOc4ccc(-c5cnc(N)c(S(=O)(=O)N6CCCC(O)C6)c5)cc4C3)c2C1] | 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl{sulfonyl)piperidin-3-ol |
| 317 | 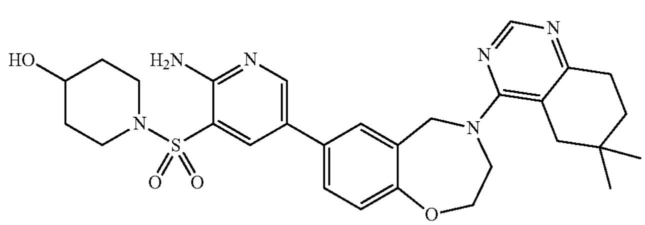 [SMILES: CC1(C)CCc2ncnc(N3CCOc4ccc(-c5cnc(N)c(S(=O)(=O)N6CCC(O)CC6)c5)cc4C3)c2C1] | 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)piperidin-4-ol |

| Cmpd No. | Structure | Name |
|---|---|---|
| 318 | 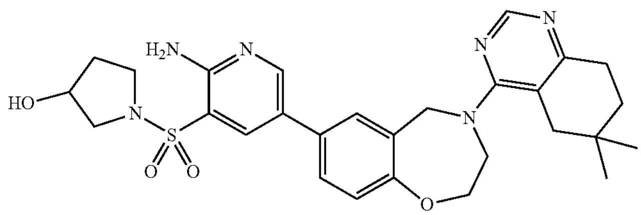 [SMILES: CC1(C)CCc2ncnc(N3CCOc4ccc(-c5cnc(N)c(S(=O)(=O)N6CCC(O)C6)c5)cc4C3)c2C1] | 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-ol |
| 319 | 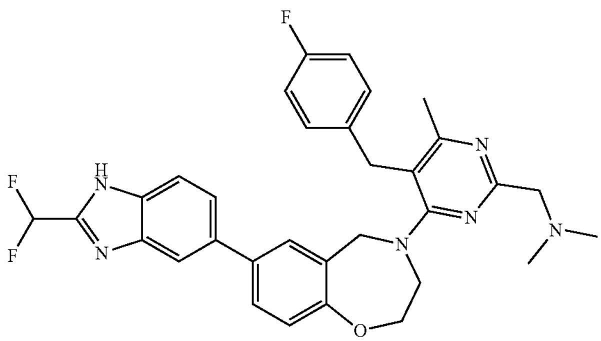 [SMILES: Cc1nc(CN(C)C)nc(N2CCOc3ccc(-c4ccc5[nH]c(C(F)F)nc5c4)cc3C2)c1Cc1ccc(F)cc1] | 1-(4-{7-[2-(difluoromethyl)-1H-benzimidazol-5-yl]-2,3-dihydro-1,4-benzoxazepin-4(5H)-yl}-5-[(4-fluorophenyl)methyl]-6-methylpyrimidin-2-yl)-N,N-dimethylmethanamine |
| 320 | 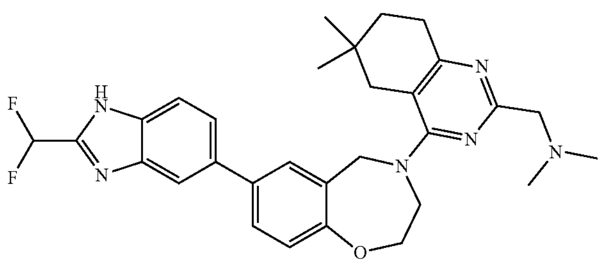 [SMILES: CN(C)Cc1nc2c(c(N3CCOc4ccc(-c5ccc6[nH]c(C(F)F)nc6c5)cc4C3)n1)CC(C)(C)CC2] | 1-(4[{7-[2-(difluoromethyl)-1H-benzimidazol-5-yl]-2,3-dihydro-1,4-benzoxazepin-4(5H)-yl}-6,6-dimethyl-5,6,7,8-tetrahydroquinazolin-2-yl)-N,N-dimethylmethanamine |
| 321 | 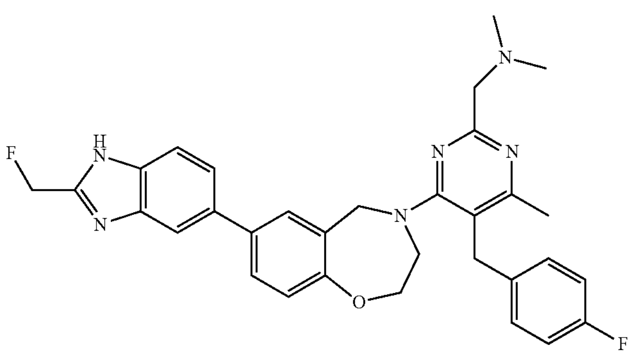 [SMILES: Cc1nc(CN(C)C)nc(N2CCOc3ccc(-c4ccc5[nH]c(CF)nc5c4)cc3C2)c1Cc1ccc(F)cc1] | 1-(4[{7-[2-(fluoromethyl)-1H-benzimidazol-5-yl]-2,3-dihydro-1,4-benzoxazepin-4(5H)-yl}-5-[(4-fluorophenyl)methyl]-6-methylpyrimidin-2-yl)-N,N-dimethylmethanamine |
| 322 | 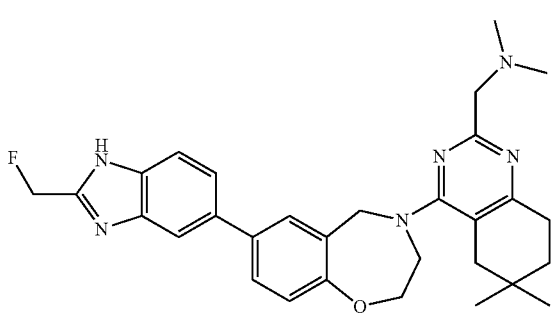 [SMILES: CN(C)Cc1nc2c(c(N3CCOc4ccc(-c5ccc6[nH]c(CF)nc6c5)cc4C3)n1)CC(C)(C)CC2] | 1-(4[{7-[2-(fluoromethyl)-1H-benzimidazol-5-yl]-2,3-dihydro-1,4-benzoxazepin-4(5H)-yl}-6,6-dimethyl-5,6,7,8-tetrahydroquinazolin-2-yl)-N,N-dimethylmethanamine |

-continued

| Cmpd No. | Structure | Name |
|---|---|---|
| 323 | 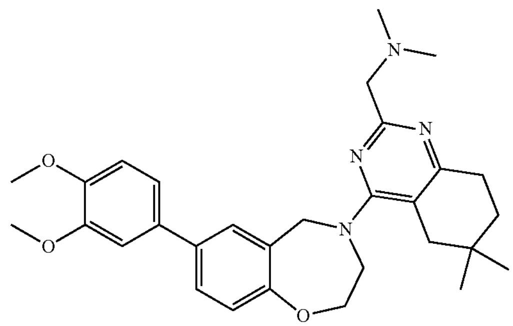 | 1-(4-{7-[3,4-bis(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine |
| 324 | 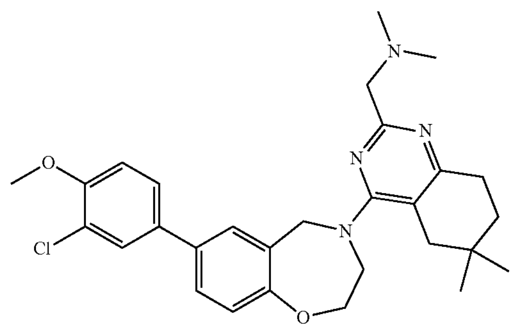 | 1-(4-{7-[3-chloro-4-(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine |
| 325 | 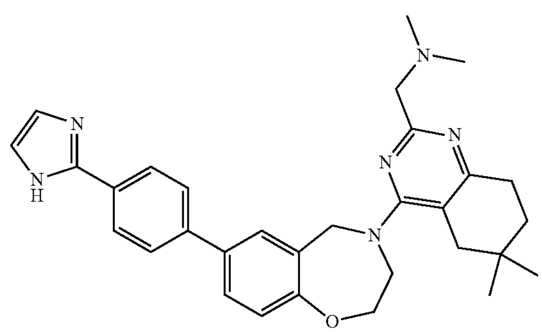 [SMILES: CN(C)Cc1nc2c(c(N3CCOc4ccc(-c5ccc(-c6ncc[nH]6)cc5)cc4C3)n1)CC(C)(C)CC2] | 1-(4[{7-[4-(1H-imidazol-2-yl)phenyl]-2,3-dihydro-1,4-benzoxazepin-4(5H)-yl}-6,6-dimethyl-5,6,7,8-tetrahydroquinazolin-2-yl)-N,N-dimethylmethanamine |
| 326 | 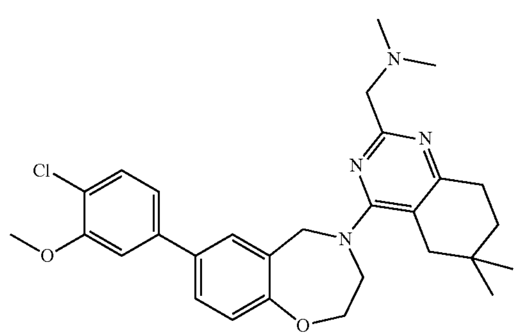 | 1-(4[{7-[4-chloro-3-(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine |

| Cmpd No. | Structure | Name |
|---|---|---|
| 327 | 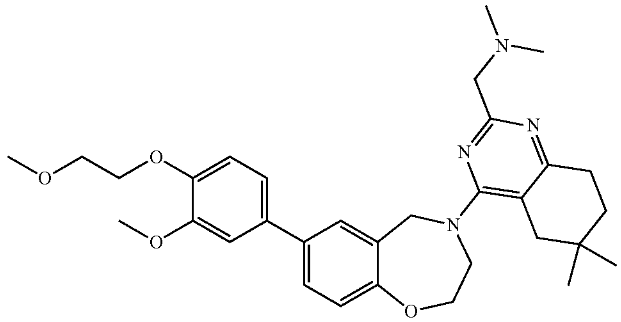 | 1-(6,6-dimethyl-4-{7-[3-(methyloxy)-4-{[2-(methyloxy)ethyl]oxy}phenyl]-2,3-dihydro-1,4-benzoxazepin-4(5H)-yl}-5,6,7,8-tetrahydroquinazolin-2-yl)-N,N-dimethylmethanamine |
| 328 | 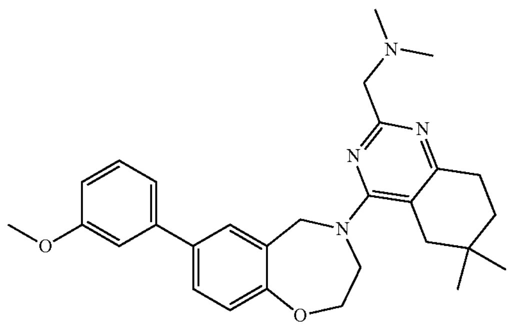 | 1-(6,6-dimethyl-4-{7-[3-(methyloxy)phenyl]-2,3-dihydro-1,4-benzoxazepin-4(5H)-yl]-5,6,7,8-tetrahydroquinazolin-2-yl)-N,N-dimethylmethanamine |
| 329 | 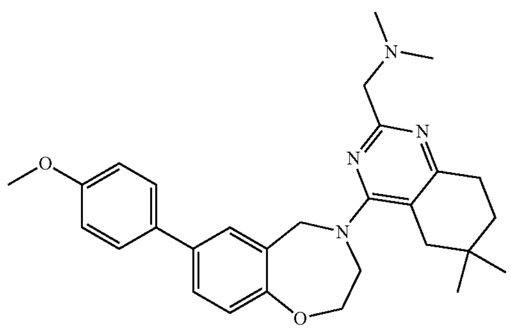 | 1-(6,6-dimethyl-4-{7-[4-(methyloxy)phenyl]-2,3-dihydro-1,4-benzoxazepin-4(5H)-yl}-5,6,7,8-tetrahydroquinazolin-2-yl)-N,N-dimethylmethanamine |
| 330 | 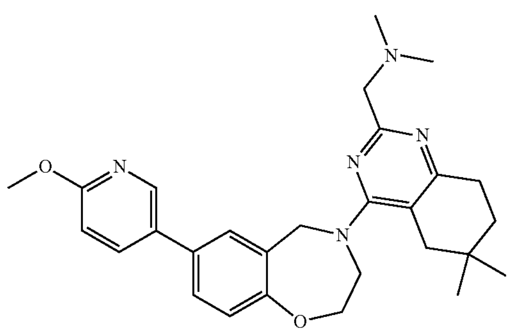 | 1-(6,6-dimethyl-4-{7-[6-(methyloxy)pyridin-3-yl]-2,3-dihydro-1,4-benzoxazepin-4(5H)-yl}-5,6,7,8-tetrahydroquinazolin-2-yl)-N,N-dimethylmethanamine |
| 331 | 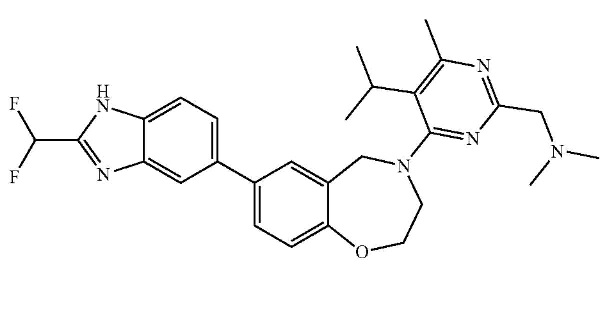 [SMILES: Cc1nc(CN(C)C)nc(N2CCOc3ccc(-c4ccc5[nH]c(C(F)F)nc5c4)cc3C2)c1C(C)C] | 1-[4-{7-[2-(difluoromethyl)-1H-benzimidazol-5-yl]-2,3-dihydro-1,4-benzoxazepin-4(5H)-yl}-6-methyl-5-(1-methylethyl)pyrimidin-2-yl]-N,N-dimethylmethanamine |

| Cmpd No. | Structure | Name |
|---|---|---|
| 332 | 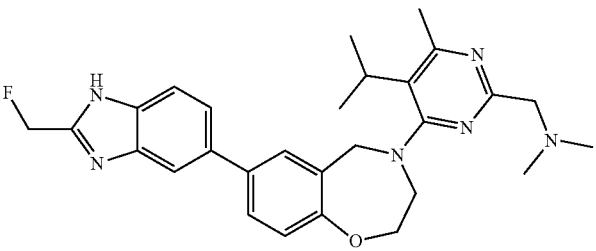 [SMILES: Cc1nc(CN(C)C)nc(N2CCOc3ccc(-c4ccc5[nH]c(CF)nc5c4)cc3C2)c1C(C)C] | 1-[4-{7-[2-(fluoromethyl)-1H-benzimidazol-5-yl]-2,3-dihydro-1,4-benzoxazepin-4(5H)-yl}-6-methyl-5-(1-methylethyl)pyrimidin-2-yl]-N,N-dimethylmethanamine |
| 333 | 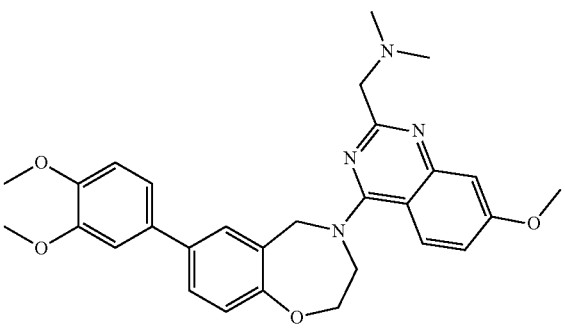 | 1-[4-{7-[3,4-bis(methyloxy)phenyl]-2,3-dihydro-1,4-benzoxazepin-4(5H)-yl}-7-(methyloxy)quinazolin-2-yl]-N,N-dimethylmethanamine |
| 334 | 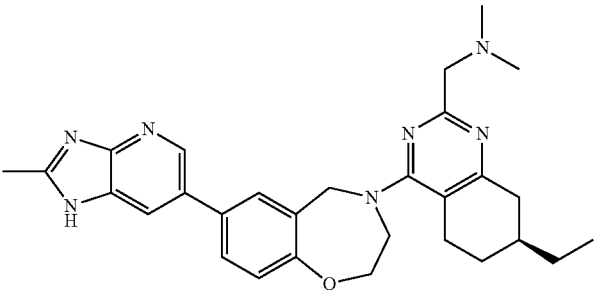 [SMILES: CC[C@H]1CCc2c(nc(CN(C)C)nc2N2CCOc3ccc(-c4cnc5nc(C)[nH]c5c4)cc3C2)C1] | 1-{(7S)-7-ethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N,N-dimethylmethanamine |
| 335 | 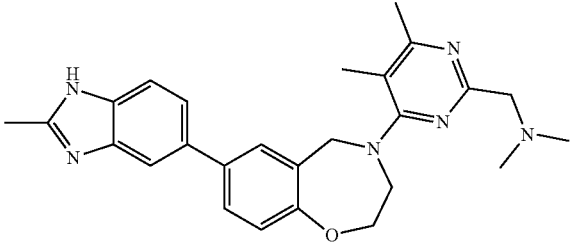 | 1-{4,5-dimethyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine |
| 336 | 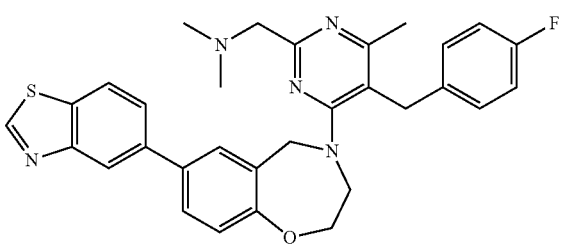 [SMILES: Cc1nc(CN(C)C)nc(N2CCOc3ccc(-c4ccc5scnc5c4)cc3C2)c1Cc1ccc(F)cc1] | 1-{4-[7-(1,3-benzothiazol-5-yl)-2,3-dihydro-1,4-benzoxazepin-4(5H)-yl]-5-[(4-fluorophenyl)methyl]-6-methylpyrimidin-2-yl}-N,N-dimethylmethanamine |

| Cmpd No. | Structure | Name |
|---|---|---|
| 337 | 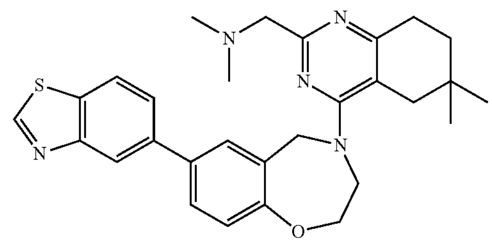 [SMILES: CN(C)Cc1nc2c(c(N3CCOc4ccc(-c5ccc6scnc6c5)cc4C3)n1)CC(C)(C)CC2] | 1-{4-[7-(1,3-benzothiazol-5-yl)-2,3-dihydro-1,4-benzoxazepin-4(5H)-yl]-6,6-dimethyl-5,6,7,8-tetrahydroquinazolin-2-yl}-N,N-dimethylmethanamine |
| 338 | 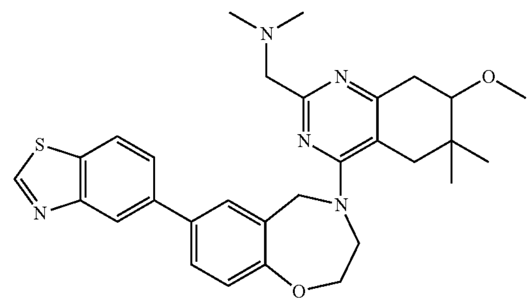 [SMILES: COC1Cc2nc(CN(C)C)nc(N3CCOc4ccc(-c5ccc6scnc6c5)cc4C3)c2CC1(C)C] | 1-{4-[7-(1,3-benzothiazol-5-yl)-2,3-dihydro-1,4-benzoxazepin-4(5H)-yl]-6,6-dimethyl-7-(methyloxy)-5,6,7,8-tetrahydroquinazolin-2-yl}-N,N-dimethylmethanamine |
| 339 | 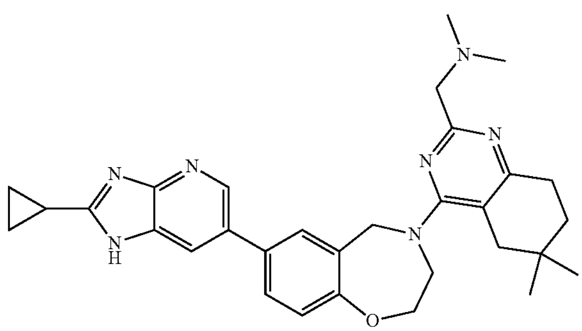 [SMILES: CN(C)Cc1nc2c(c(N3CCOc4ccc(-c5cnc6nc(C7CC7)[nH]c6c5)cc4C3)n1)CC(C)(C)CC2] | 1-{4-[7-(2-cyclopropyl-1H-imidazo[4,5-b]pyridin-6-yl)-2,3-dihydro-1,4-benzoxazepin-4(5H)-yl]-6,6-dimethyl-5,6,7,8-tetrahydroquinazolin-2-yl}-N,N-dimethylmethanamine |
| 340 | 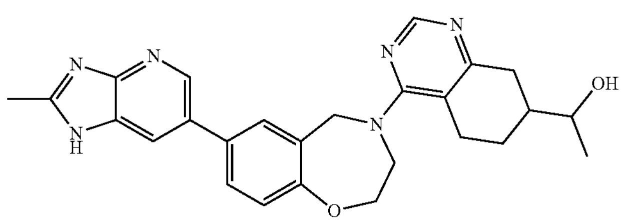 [SMILES: Cc1nc2ncc(-c3ccc4c(c3)CN(c3ncnc5c3CCC(C(C)O)C5)CCO4)cc2[nH]1] | 1-{4-[7-(2-methyl-1H-imidazo[4,5-b]pyridin-6-yl)-2,3-dihydro-1,4-benzoxazepin-4(5H)-yl]-5,6,7,8-tetrahydroquinazolin-7-yl}ethanol |
| 341 | 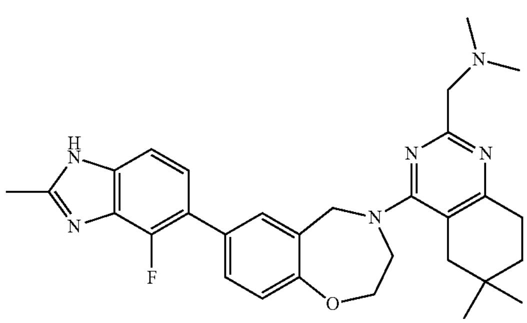 | 1-{4-[7-(4-fluoro-2-methyl-1H-benzimidazol-5-yl)-2,3-dihydro-1,4-benzoxazepin-4(5H)-yl]-6,6-dimethyl-5,6,7,8-tetrahydroquinazolin-2-yl}-N,N-dimethylmethanamine |

-continued

| Cmpd No. | Structure | Name |
|---|---|---|
| 342 | 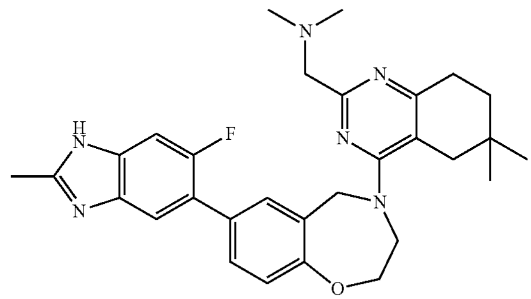 | 1-{4-[7-(6-fluoro-2-methyl-1H-benzimidazol-5-yl)-2,3-dihydro-1,4-benzoxazepin-4(5H)-yl]-6,6-dimethyl-5,6,7,8-tetrahydroquinazolin-2-yl}-N,N-dimethylmethanamine |
| 343 | 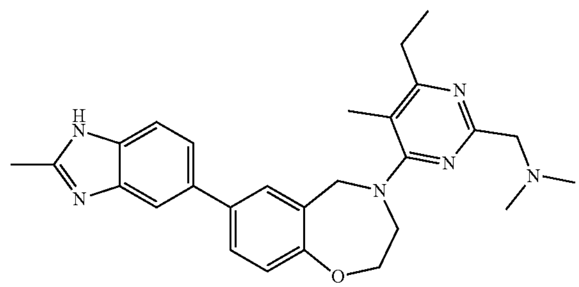 | 1-{4-ethyl-5-methyl-6-[7-(2-methyl-1H-benzimidazol-5-yl)-2,3-dihydro-1,4-benzoxazepin-4(5H)-yl]pyrimidin-2-yl}-N,N-dimethylmethanamine |
| 344 | 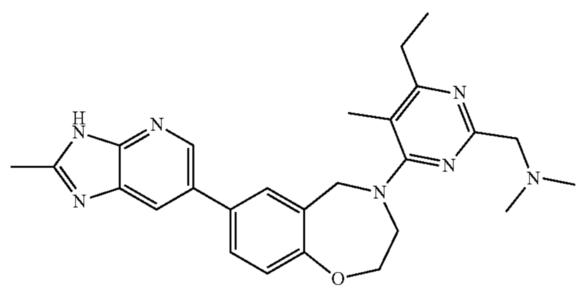 | 1-{4-ethyl-5-methyl-6-[7-(2-methyl-3H-imidazo[4,5-b]pyridin-6-yl)-2,3-dihydro-1,4-benzoazepin-4(5H)-yl]pyrimnidin-2-yl}-N,N-dimethylmethanamine |
| 345 | 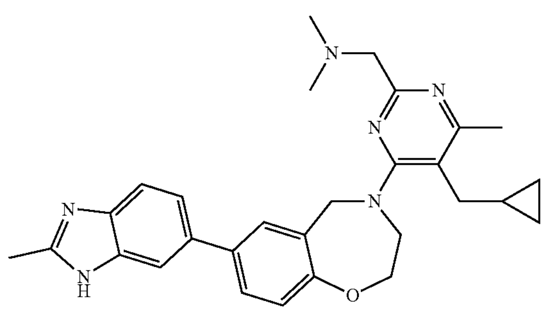 [SMILES: Cc1nc2ccc(-c3ccc4c(c3)CN(c3nc(CN(C)C)nc(C)c3CC3CC3)CCO4)cc2[nH]1] | 1-{5-(cyclopropylmethyl)-4-methyl-6-[7-(2-methyl-1H-benzimidazo-6-yl)-2,3-dihydro-1,4-benzoxazepin-4(5H)-yl]pyrimidin-2-yl}-N,N-dimethylmethanamine |
| 346 | 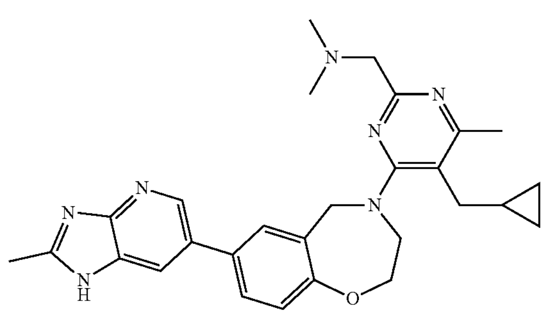 [SMILES: Cc1nc2ncc(-c3ccc4c(c3)CN(c3nc(CN(C)C)nc(C)c3CC3CC3)CCO4)cc2[nH]1] | 1-{5-(cyclopropylmethyl)-4-methyl-6-[7-(2-methyl-1H-imidazo[4,5-b]pyridin-6-yl)-2,3-dihydro-1,4-benzoxazepin-4(5H)-yl]pyrimidin-2-yl}-N,N-dimethylmethanamine |

| Cmpd No. | Structure | Name |
|---|---|---|
| 347 | 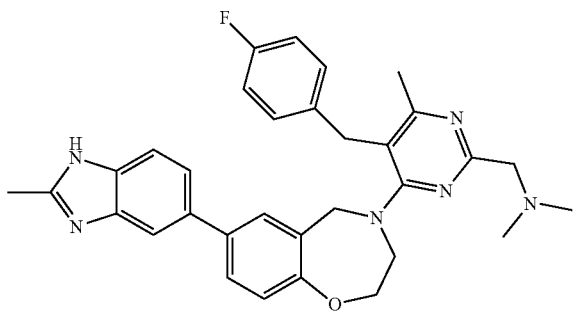 | 1-{5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine |
| 348 | 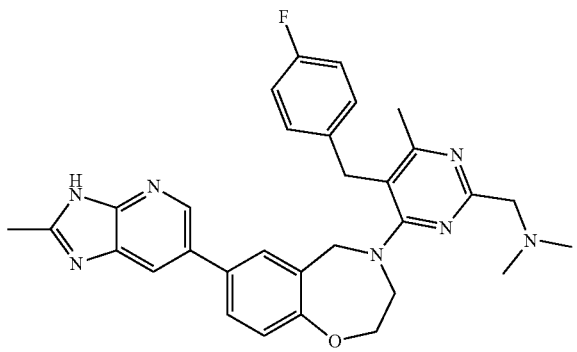 | 1-{5-[(4-fluorophenyl)methyl]-4-methyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine |
| 349 | 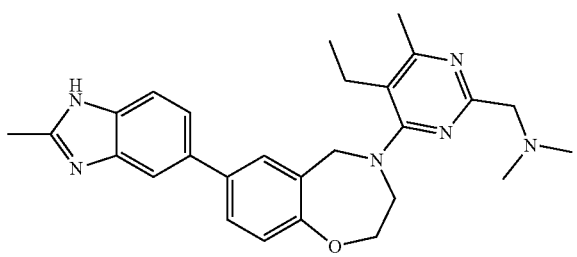 | 1-{5-ethyl-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine |
| 350 | 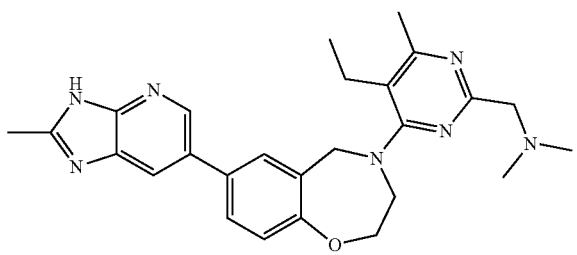 | 1-{5-ethyl-4-methyl-6-[7-(2-methyl-3H-imidazo[4,5-b]pyridin-6-yl)-2,3-dihydro-1,4-benzoxazepin-4(5H)-yl]pyrimidin}-N,N-dimethylmethanamine |
| 351 | 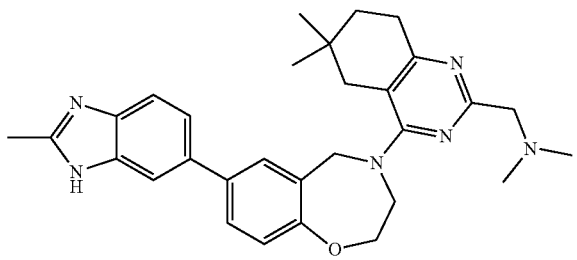 | 1-{6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}-N,N-dimethylmethanamine |

| Cmpd No. | Structure | Name |
|---|---|---|
| 352 | 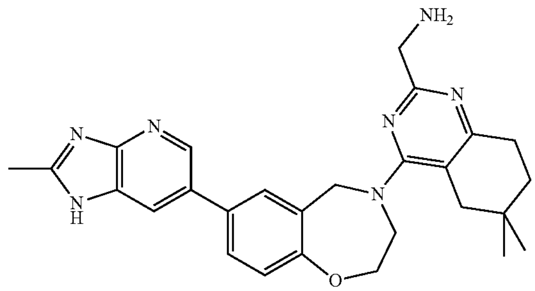 [SMILES: Cc1nc2ncc(-c3ccc4c(c3)CN(c3nc(CN)nc5c3CC(C)(C)CC5)CCO4)cc2[nH]1] | 1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methanamine |
| 353 | 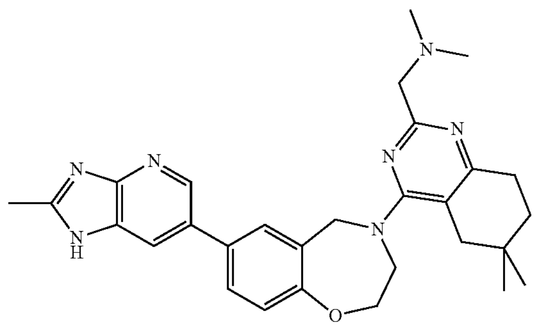 [SMILES: Cc1nc2ncc(-c3ccc4c(c3)CN(c3nc(CN(C)C)nc5c3CC(C)(C)CC5)CCO4)cc2[nH]1] | 1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N,N-dimethylmethanamine |
| 354 | 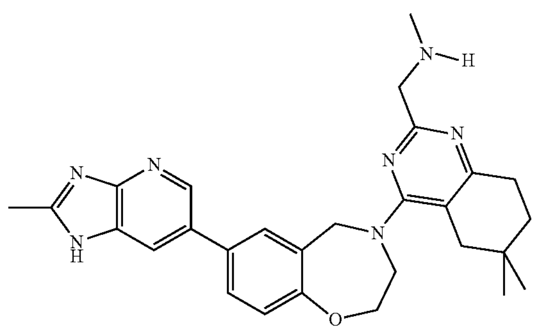 [SMILES: CNCc1nc2c(c(N3CCOc4ccc(-c5cnc6nc(C)[nH]c6c5)cc4C3)n1)CC(C)(C)CC2] | 1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N-methylmethanamine |
| 355 | 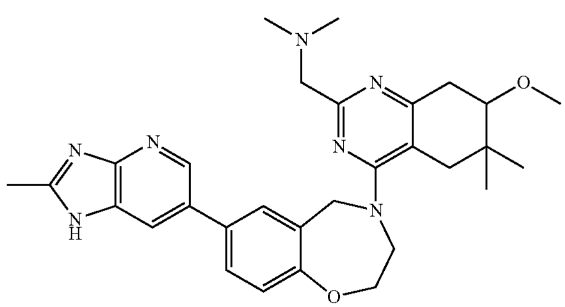 | 1-{6,6-dimethyl-4-[7-(2-methyl-1H-imidazo[4,5-b]pyridin-6-yl)-2,3-dihydro-1,4-benzoxazepin-4(5H)-yl]-7-(methyloxy)-5,6,7,8-tetrahydroquinazolin-2-yl}-N,N-dimethylmethanamine |
| 356 | 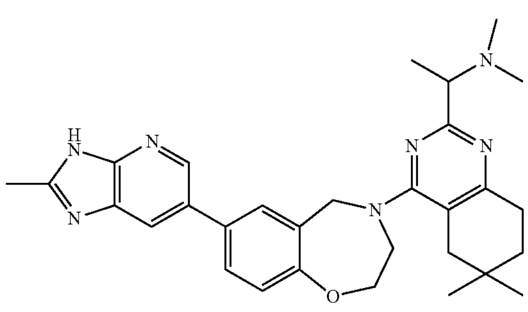 | 1-{6,6-dimethyl-4-[7-(2-methyl-3H-imidazo[4,5-b]pyridin-6-yl)-2,3-dihydro-1,4-benzoxazepin-4(5H)-yl]-5,6,7,8-tetrahydroquinazolin-2-yl}-N,N-dimethylethanamine |

-continued

| Cmpd No. | Structure | Name |
|---|---|---|
| 357 | 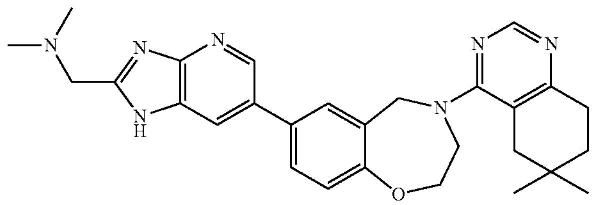 | 1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}-N,N-dimethylmethanamine |
| 358 | 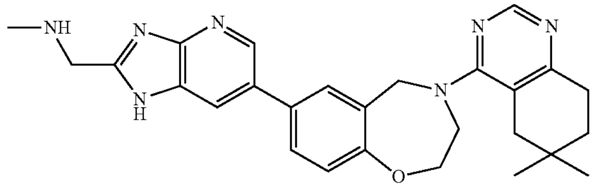 | 1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}-N-methylmethanamine |
| 359 | 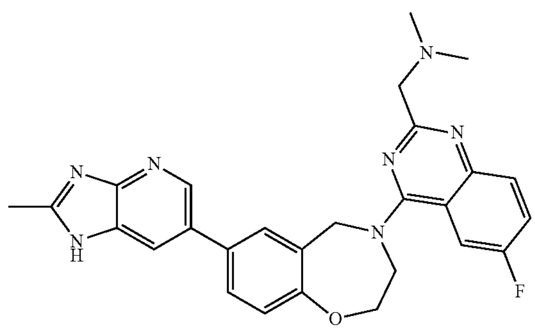 [SMILES: Cc1nc2ncc(-c3ccc4c(c3)CN(c3nc(CN(C)C)nc5ccc(F)cc35)CCO4)cc2[nH]1] | 1-{6-fluoro-4-[7-(2-methyl-1H-imidazo[4,5-b]pyridin-6-yl)-2,3-dihydro-1,4-benzoxazepin-4(5H)-yl]quinazolin-2-yl}-N,N-dimethylmethanamine |
| 360 | 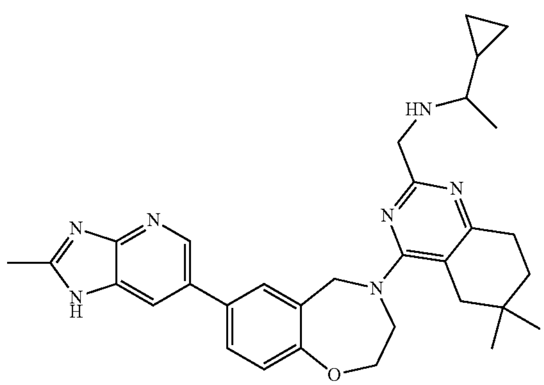 | 1-cyclopropyl-N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)ethanamine |
| 361 | 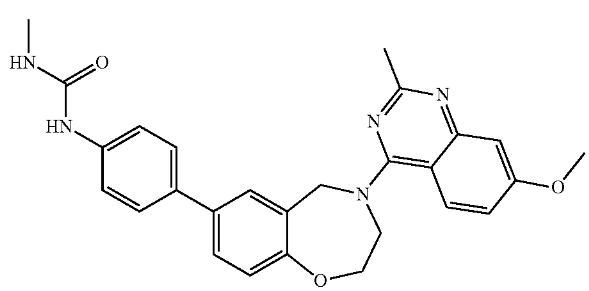 [SMILES: CNC(=O)Nc1ccc(-c2ccc3c(c2)CN(c2nc(C)nc4cc(OC)ccc24)CCO3)cc1] | 1-methyl-3-(4-{4-[2-methyl-7-(methyloxy)quinazolin-4-yl]-2,3,4,5-tetrahydro-1,4-benzoxazepin-7-yl}phenyl)urea |

-continued

| Cmpd No. | Structure | Name |
|---|---|---|
| 362 | 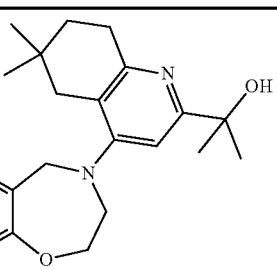 | 2-{6,6-dimethyl-4-[7-(2-methyl-1H-benzimidazol-6-yl)-2,3-benzimidazol-6-yl)-2,3-dihydro-1,4-benzoxazepin-4(5H)-yl]-5,6,7,8-tetrahydroquinazolin-2-yl}propan-2-ol |
| 363 | 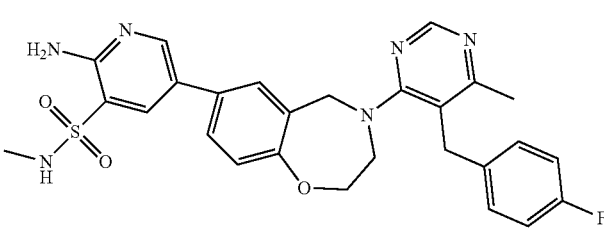 [SMILES: CNS(=O)(=O)c1cc(-c2ccc3c(c2)CN(c2ncnc(C)c2Cc2ccc(F)cc2)CCO3)cnc1N] | 2-amino-5-(4-{5-[(4-fluorophenyl)methyl]-6-methylpyrimidin-4-yl}-2,3,4,5-tetrahydro-1,4-benzoxazepin-7-yl)-N-methylpyridine-3-sulfonamide |
| 364 | 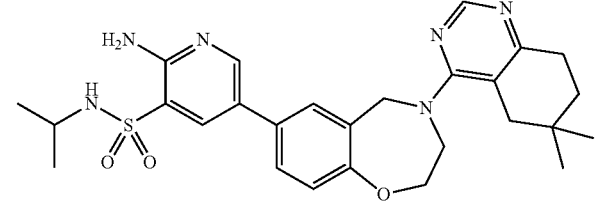 [SMILES: CC(C)NS(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-(1-methylethyl)pyridin-3-sulfonamide |
| 365 | 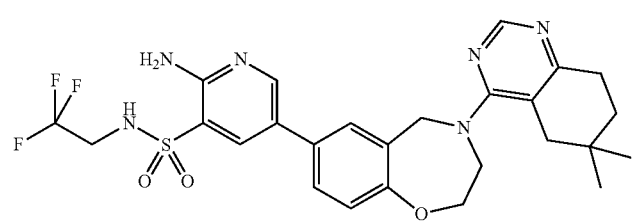 [SMILES: CC1(C)CCc2ncnc(N3CCOc4ccc(-c5cnc(N)c(S(=O)(=O)NCC(F)(F)F)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(2,2,2-trifluoroethyl)pyridine-3-sulfonamide |
| 366 | 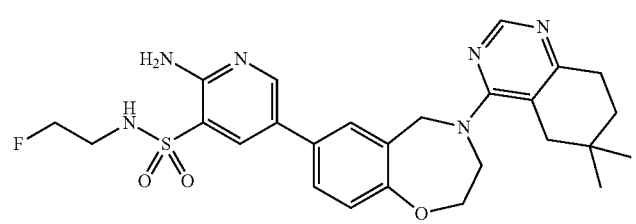 [SMILES: CC1(C)CCc2ncnc(N3CCOc4ccc(-c5cnc(N)c(S(=O)(=O)NCCF)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(2-fluoroethyl)pyridine-3-sulfonamide |
| 367 | 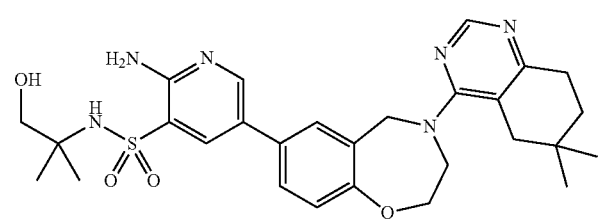 [SMILES: CC1(C)CCc2ncnc(N3CCOc4ccc(-c5cnc(N)c(S(=O)(=O)NC(C)(C)CO)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-1,1-dimethylethyl)pyridine-3-sulfonamide |
| 368 | 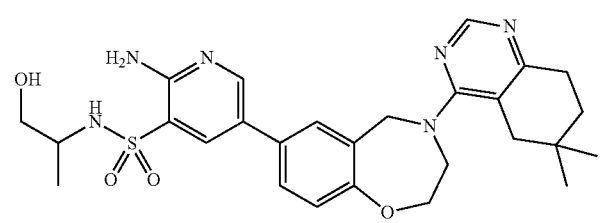 [SMILES: CC(CO)NS(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-1-methylethyl)pyridine-3-sulfonamide |

| Cmpd No. | Structure | Name |
|---|---|---|
| 369 | 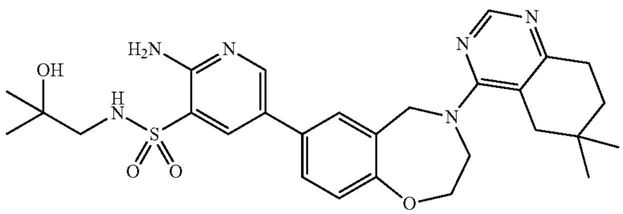 [SMILES: CC(C)(O)CNS(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-2-methylpropyl)pyridine-3-sulfonamide |
| 370 | 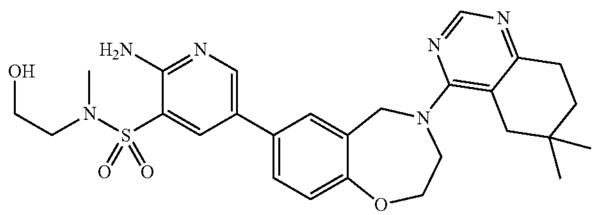 [SMILES: CN(CCO)S(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxyethyl)-N-methylpyridine-3-sulfonamide |
| 371 | 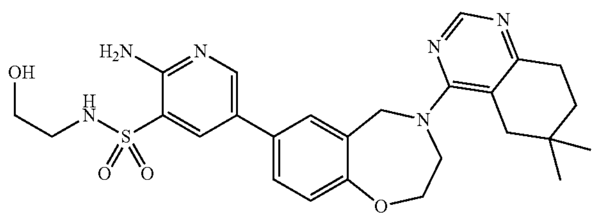 [SMILES: CC1(C)CCc2ncnc(N3CCOc4ccc(-c5cnc(N)c(S(=O)(=O)NCCO)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxyethyl)pyridine-3-sulfonamide |
| 372 | 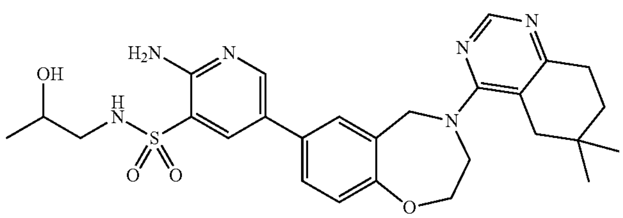 [SMILES: CC(O)CNS(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxypropyl)pyridine-2-sulfonamide |
| 373 | 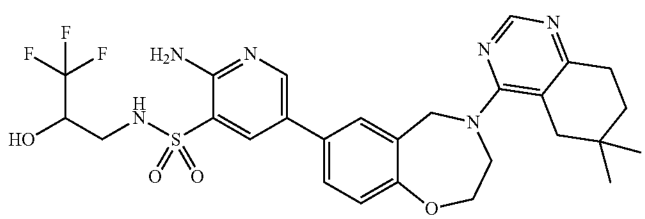 [SMILES: CC1(C)CCc2ncnc(N3CCOc4ccc(-c5cnc(N)c(S(=O)(=O)NCC(O)C(F)(F)F)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(3,3,3-trifluoro-2-hydroxypropyl)pyridine-3-sulfonamide |
| 374 | 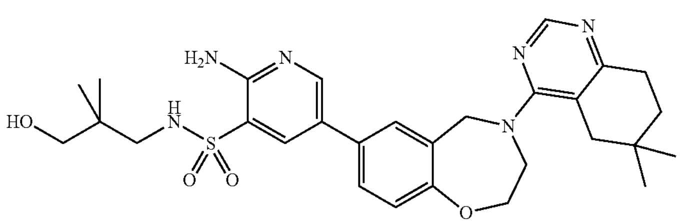 [SMILES: CC(C)(CO)CNS(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-(3-hydroxy-2,2-dimethylpropyl)pyridine-3-sulfonamide |
| 375 | 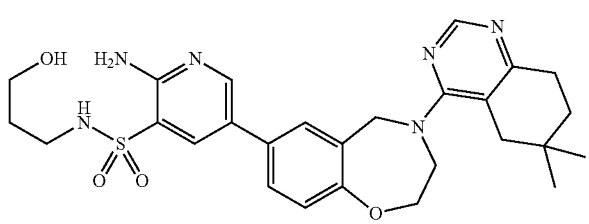 [SMILES: CC1(C)CCc2ncnc(N3CCOc4ccc(-c5cnc(N)c(S(=O)(=O)NCCCO)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(3-hydroxypropyl)pyridine-3-sulfonamide |

-continued

| Cmpd No. | Structure | Name |
|---|---|---|
| 376 | 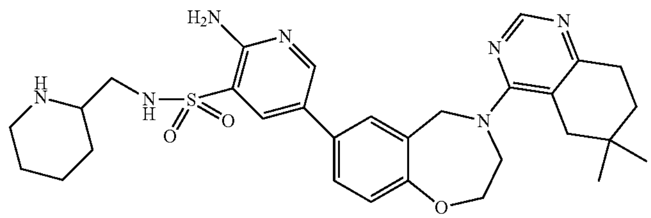 [SMILES: CC1(C)CCc2ncnc(N3CCOc4ccc(-c5cnc(N)c(S(=O)(=O)NCC6CCCCN6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(piperidin-2-ylmethyl)pyridine-3-sulfonamide |
| 377 | 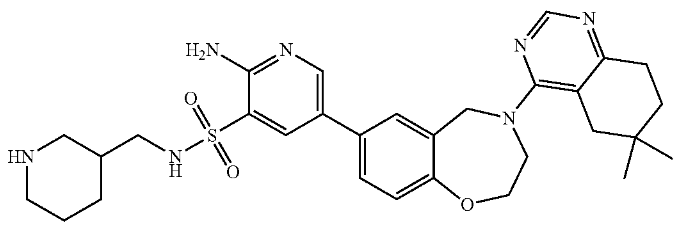 [SMILES: CC1(C)CCc2ncnc(N3CCOc4ccc(-c5cnc(N)c(S(=O)(=O)NCC6CCCNC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(piperidin-3-ylmethyl)pyridine-3-sulfonamide |
| 378 | 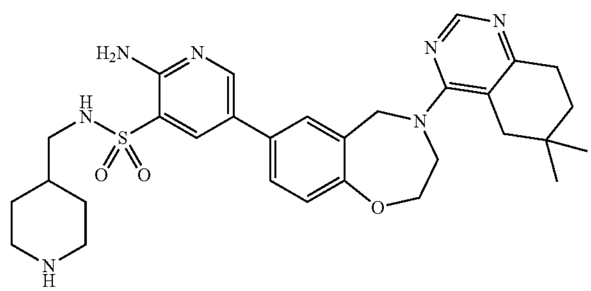 [SMILES: CC1(C)CCc2ncnc(N3CCOc4ccc(-c5cnc(N)c(S(=O)(=O)NCC6CCNCC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-(piperidin-4-ylmethyl)pyridine-3-sulfonamide |
| 379 | 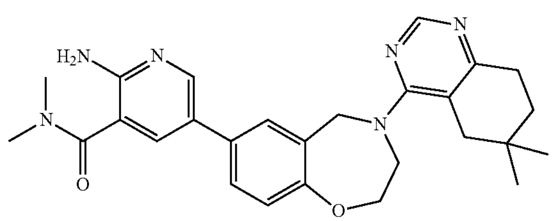 | 2-amino-5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-carboxamide |
| 380 | 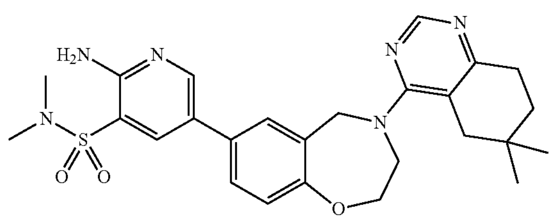 | 2-amino-5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-sulfonamide |
| 381 | 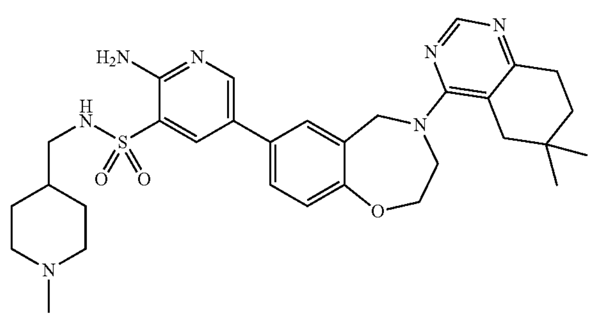 [SMILES: CN1CCC(CNS(=O)(=O)c2cc(-c3ccc4c(c3)CN(c3ncnc5c3CC(C)(C)CC5)CCO4)cnc2N)CC1] | 2-amino-5-[4-(6,6-dimethyl-5,6,7,8-tetrahydroquinazolin-4-yl)-2,3,4,5-tetrahydro-1,4-benzoxazepin-7-yl]-N-[(1-methylpiperidin-4-yl)methyl]pyridine-3-sulfonamide |

-continued

| Cmpd No. | Structure | Name |
|---|---|---|
| 382 | 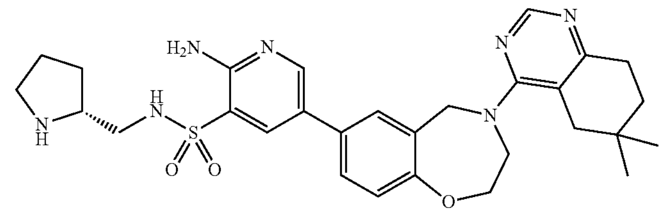 [SMILES: CC1(C)CCc2ncnc(N3CCOc4ccc(-c5cnc(N)c(S(=O)(=O)NC[C@H]6CCCN6)c5)cc4C3)c2C1] | 2-amino-5-[4-(6,6-dimethyl-5,6,7,8-tetrahydrquinazolin-4-yl)-2,3,4,5-tetrahydro-1,4-benzoxazepin-7-yl]-N-[(2R)-pyrrolidin-2-ylmethyl]pyridine-3-sulfonamide |
| 383 | 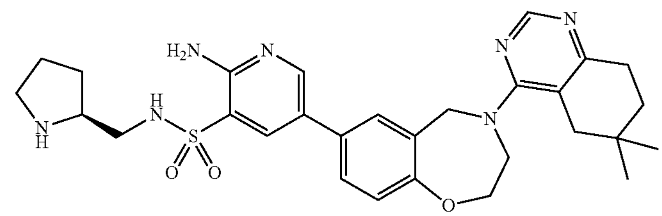 [SMILES: CC1(C)CCc2ncnc(N3CCOc4ccc(-c5cnc(N)c(S(=O)(=O)NC[C@@H]6CCCN6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(2S)-pyrrolidin-2-ylmethyl]pyridine-3-sulfonamide |
| 384 | 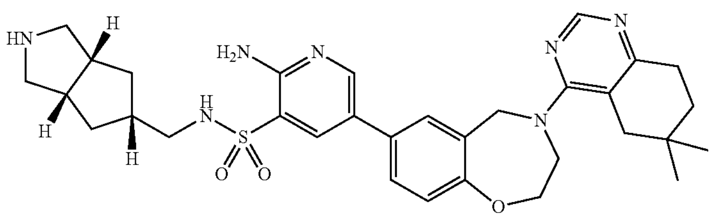 [SMILES: CC1(C)CCc2ncnc(N3CCOc4ccc(-c5cnc(N)c(S(=O)(=O)NC[C@H]6C[C@H]7CNC[C@H]7C6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3aR,5r,6aS)-octahydrocyclopenta[c]pyrrol-5-ylmethyl]pyridine-3-sulfonamide |
| 385 | 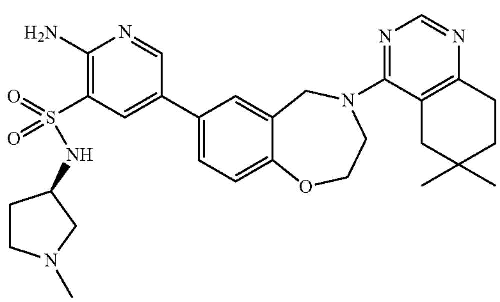 [SMILES: CN1CC[C@@H](NS(=O)(=O)c2cc(-c3ccc4c(c3)CN(c3ncnc5c3CC(C)(C)CC5)CCO4)cnc2N)C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3R)-1-methylpyrrolidin-3-yl]pyridine-3-sulfonamide |
| 386 | 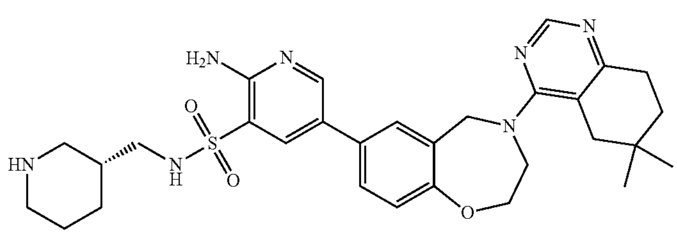 [SMILES: CC1(C)CCc2ncnc(N3CCOc4ccc(-c5cnc(N)c(S(=O)(=O)NC[C@@H]6CCCNC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3R)-piperidin-3-ylmethyl]pyridine-3-sulfonamide |
| 387 | 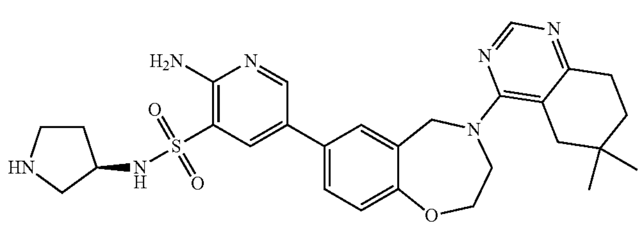 [SMILES: CC1(C)CCc2ncnc(N3CCOc4ccc(-c5cnc(N)c(S(=O)(=O)N[C@@H]6CCNC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3R)-pyrrolidin-3-yl]pyridine-3-sulfonamide |

| Cmpd No. | Structure | Name |
|---|---|---|
| 388 | 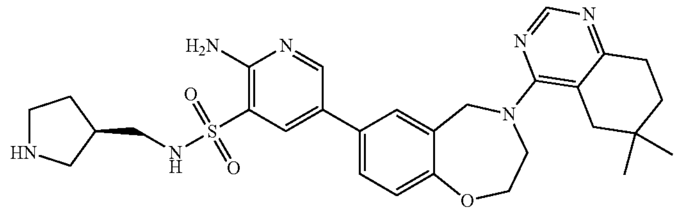 [SMILES: CC1(C)CCc2ncnc(N3CCOc4ccc(-c5cnc(N)c(S(=O)(=O)NC[C@@H]6CCNC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3R)-pyrrolidin-3-ylmethyl]pyridine-3-sulfonamide |
| 389 | 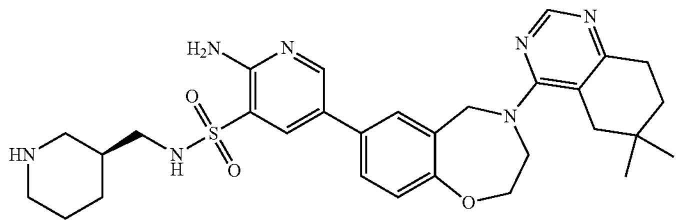 [SMILES: CC1(C)CCc2ncnc(N3CCOc4ccc(-c5cnc(N)c(S(=O)(=O)NC[C@H]6CCCNC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3S)-piperidin-3-ylmethyl]pyridine-3-sulfonamide |
| 390 | 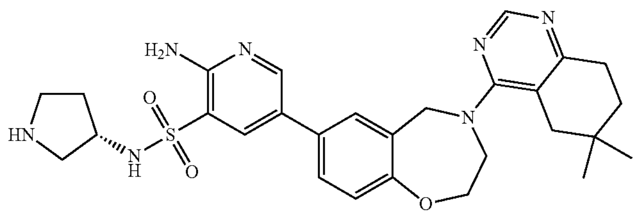 [SMILES: CC1(C)CCc2ncnc(N3CCOc4ccc(-c5cnc(N)c(S(=O)(=O)N[C@H]6CCNC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3S)-pyrrolidin-2-yl]pyridine-3-sulfonamide |
| 391 | 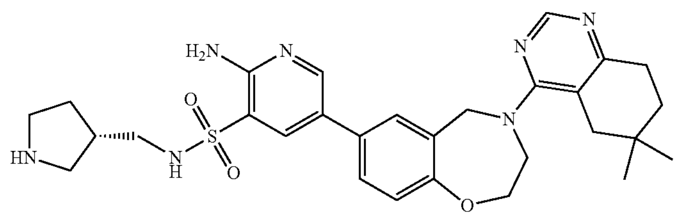 [SMILES: CC1(C)CCc2ncnc(N3CCOc4ccc(-c5cnc(N)c(S(=O)(=O)NC[C@H]6CCNC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-[(3S)-pyrrolidin-3-ylmethyl]pyridine-3-sulfonamide |
| 392 | 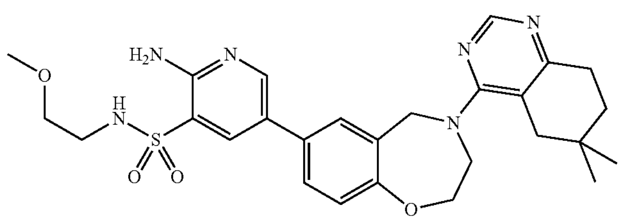 | 2-amino-5-[4-(6,6-dimethyl-5,6,7,8-tetrahydroquinazolin-4-yl)-2,3,4,5-tetrahydro-1,4-benzoxazepin-7-yl]-N-[2-(methyloxy)ethyl]pyridine-3-sulfonamide |
| 393 | 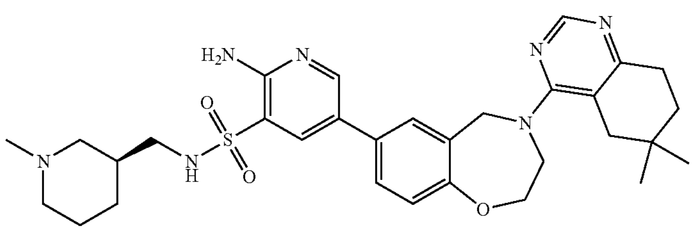 | 2-amino-5-[4-(6,6-dimethyl-5,6,7,8-tetrahydroquinazolin-4-yl)-2,3,4,5-tetrahydro-1,4-benzoxazepin-7-yl]-N-{[(3S)-1-methylpiperidin-3-yl]methyl}pyridine-3-sulfonamide |
| 394 | 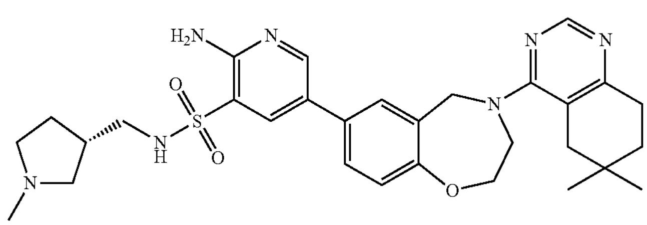 | 2-amino-5-[4-(6,6-dimethyl-5,6,7,8-tetrahydroquinazolin-4-yl)-2,3,4,5-tetrahydro-1,4-benzoxazepin-7-yl]-N-{[(3S)-1-methylpyrrolidin-3-yl]methyl}pyridine-3-sulfonamide |

| Cmpd No. | Structure | Name |
|---|---|---|
| 395 | 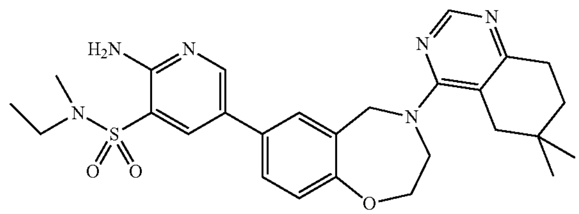 [SMILES: CCN(C)S(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-ethyl-N-methylpyridine-3-sulfonamide |
| 396 | 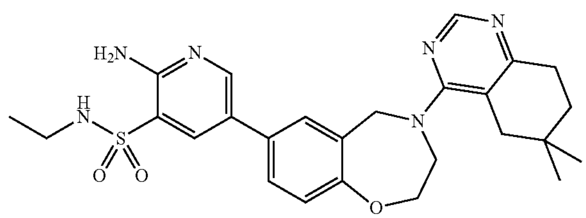 [SMILES: CCNS(=O)(=O)c1cc(-c2ccc3c(c2)CN(c2ncnc4c2CC(C)(C)CC4)CCO3)cnc1N] | 2-amino-5-[4-(6,6-dimethyl-5,6,7,8-tetrahydroquinazolin-4-yl)-2,3,4,5-tetrahydro-1,4-benzoxazepin-7-yl]-N-ethylpyridine-3-sulfonamide |
| 397 | 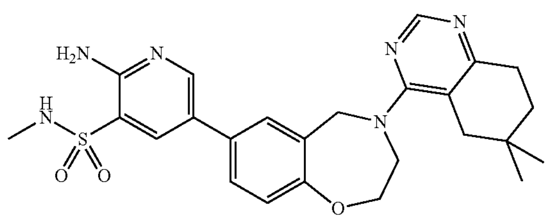 | 2-amino-5-[4-(6,6-dimethyl-5,6,7,8-tetrahydroquinazolin-4-yl)-2,3,4,5-tetrahydro-1,4-benzoxazepin-7-yl]-N-methylpyridine-3-sulfonamide |
| 398 | 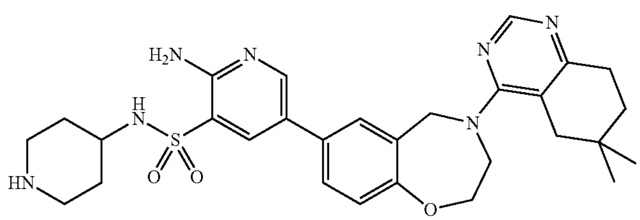 [SMILES: CC1(C)CCc2ncnc(N3CCOc4ccc(-c5cnc(N)c(S(=O)(=O)NC6CCNCC6)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]-N-piperidin-4-yl]pyridine-3-sulfonamide |
| 399 | 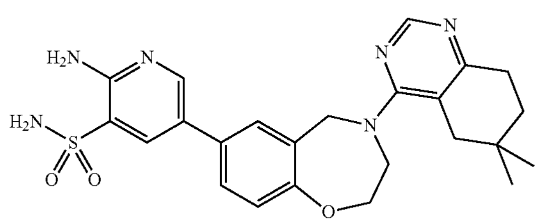 [SMILES: CC1(C)CCc2ncnc(N3CCOc4ccc(-c5cnc(N)c(S(N)(=O)=O)c5)cc4C3)c2C1] | 2-amino-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 400 | 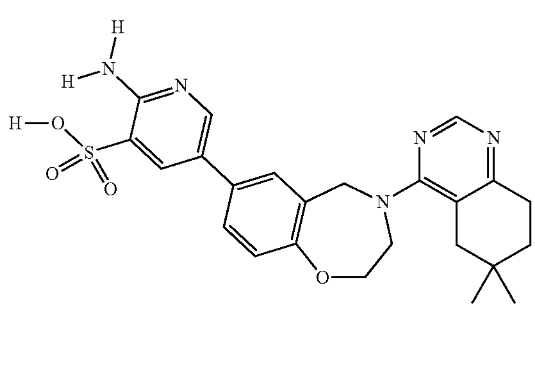 [SMILES: CC1(C)CCc2ncnc(N3CCOc4ccc(-c5cnc(N)c(S(=O)(=O)O)c5)cc4C3)c2C1] | 2-amino-5-[4-(6,6-dimethyl-5,6,7,8-tetrahydrquinazolin-4-yl)-2,3,4,5-tetrahydro-1,4-benzoxazepin-7-yl]pyridine-3-sulfonic acid |

| Cmpd No. | Structure | Name |
|---|---|---|
| 401 | 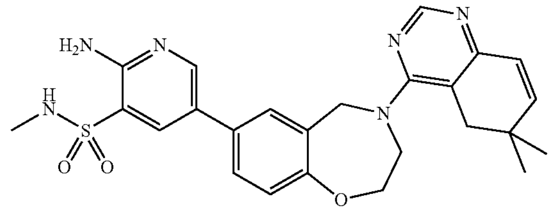 | 2-amino-5-[4-(6,6-dimethyl-5,6-dihydroquinazolin-4-yl)-2,3,4,5-tetrahydro-1,4-benzoxazepin-7-yl]-N-methylpyridine-3-sulfonamide |
| 402 | 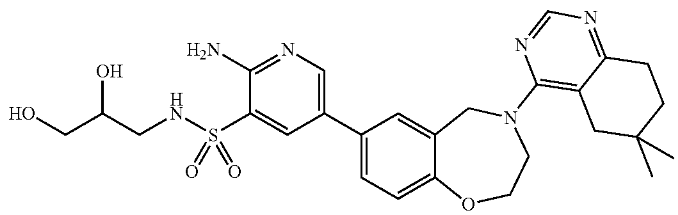 [SMILES: CC1(C)CCc2ncnc(N3CCOc4ccc(-c5cnc(N)c(S(=O)(=O)NCC(O)CO)c5)cc4C3)c2C1] | 2-amino-N-(2,3-dihydroxypropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 403 | 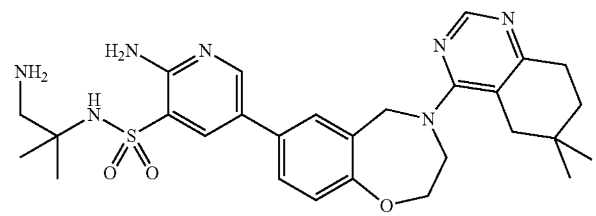 [SMILES: CC1(C)CCc2ncnc(N3CCOc4ccc(-c5cnc(N)c(S(=O)(=O)NC(C)(C)CN)c5)cc4C3)c2C1] | 2-amino-N-(2-amino-1,1-dimethylethyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 405 | 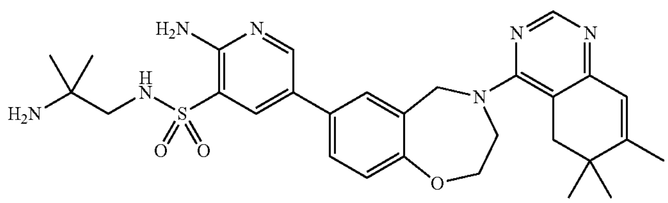 [SMILES: CC1=Cc2ncnc(N3CCOc4ccc(-c5cnc(N)c(S(=O)(=O)NCC(C)(C)N)c5)cc4C3)c2CC1(C)C] | 2-amino-N-(2-amino-2-methylpropyl)-5-[4-(6,6,7-trimethyl-5,6-dihydroquinazolin-4-yl)-2,3,4,5-tetrahydro-1,4-benzoxazepin-7-yl]pyridine-3-sulfonamide |
| 406 | 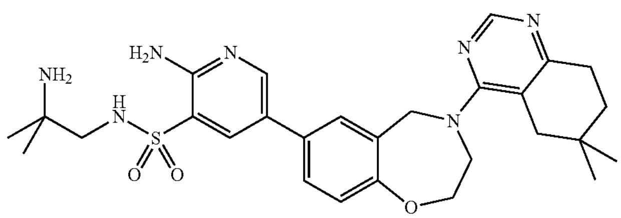 [SMILES: CC(C)(N)CNS(=O)(=O)c1cc(-c2ccc3c(c2)CN(c2ncnc4c2CC(C)(C)CC4)CCO3)cnc1N] | 2-amino-N-(2-amino-2-methylpropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 407 | 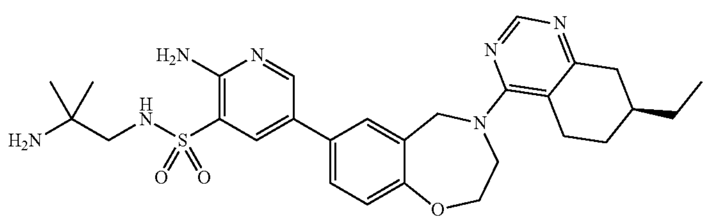 [SMILES: CC[C@H]1CCc2c(ncnc2N2CCOc3ccc(-c4cnc(N)c(S(=O)(=O)NCC(C)(C)N)c4)cc3C2)C1] | 2-amino-N-(2-amino-2-methylpropyl)-5-{4-[(7S)-7-ethyl-5,6,7,8-tetrahydroquinazolin-4-yl]-2,3,4,5-tetrahydro-1,4-benzoxazepin-7-yl}pyridine-3-sulfonamide |
| 408 | 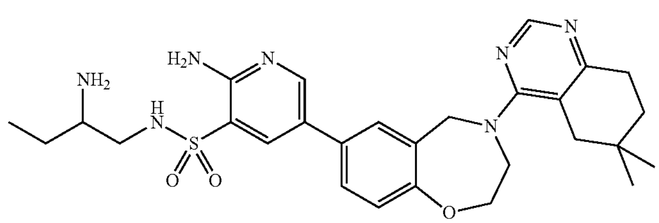 [SMILES: CCC(N)CNS(=O)(=O)c1cc(-c2ccc3c(c2)CN(c2ncnc4c2CC(C)(C)CC4)CCO3)cnc1N] | 2-amino-N-(2-aminobutyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |

-continued

| Cmpd No. | Structure | Name |
|---|---|---|
| 409 | 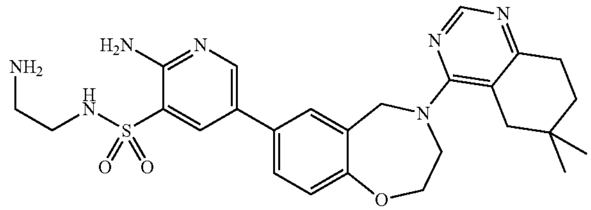 [SMILES: CC1(C)CCc2ncnc(N3CCOc4ccc(-c5cnc(N)c(S(=O)(=O)NCCN)c5)cc4C3)c2C1] | 2-amino-N-(2-aminoethyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 410 | 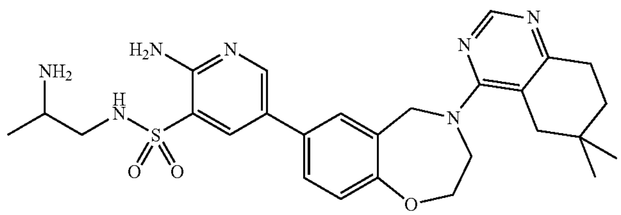 [SMILES: CC(N)CNS(=O)(=O)c1cc(-c2ccc3c(c2)CN(c2ncnc4c2CC(C)(C)CC4)CCO3)cnc1N] | 2-amino-N-(2-aminopropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 411 | 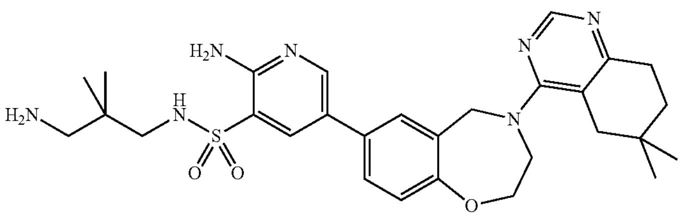 [SMILES: CC(C)(CN)CNS(=O)(=O)c1cc(-c2ccc3c(c2)CN(c2ncnc4c2CC(C)(C)CC4)CCO3)cnc1N] | 2-amino-N-(3-amino-2,2-dimethylpropyl)-5-[4-(6,6-dimethyl-5,6,7,8-tetrahydroquinazol-4-yl)-2,3,4,5-tetrahydro-1,4-benzoxazepin-7-yl]pyridine-3-sulfonamide |
| 412 | 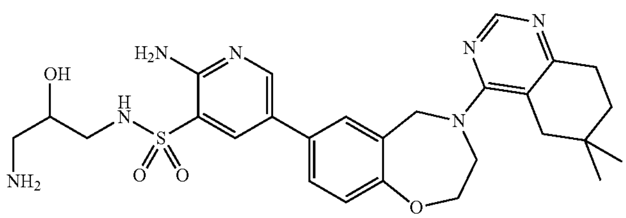 [SMILES: CC1(C)CCc2ncnc(N3CCOc4ccc(-c5cnc(N)c(S(=O)(=O)NCC(O)CN)c5)cc4C3)c2C1] | 2-amino-N-(3-amino-2-hydroxypropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 413 | 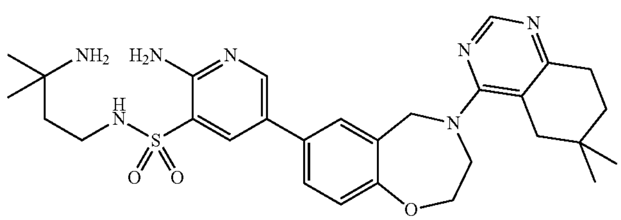 [SMILES: CC(C)(N)CCNS(=O)(=O)c1cc(-c2ccc3c(c2)CN(c2ncnc4c2CC(C)(C)CC4)CCO3)cnc1N] | 2-amino-N-(3-amino-3-methylbutyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 414 | 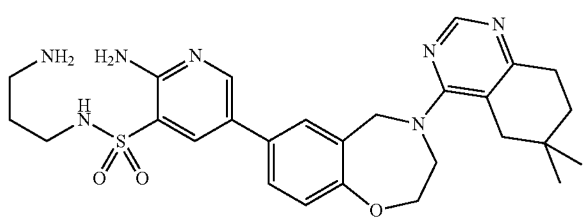 [SMILES: CC1(C)CCc2ncnc(N3CCOc4ccc(-c5cnc(N)c(S(=O)(=O)NCCCN)c5)cc4C3)c2C1] | 2-amino-N-(3-aminopropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 415 | 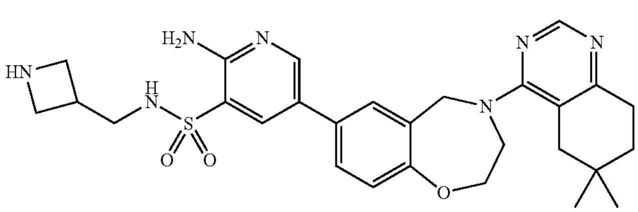 [SMILES: CC1(C)CCc2ncnc(N3CCOc4ccc(-c5cnc(N)c(S(=O)(=O)NCC6CNC6)c5)cc4C3)c2C1] | 2-amino-N-(azetidin-3-ylmethyl)-5-[4-(6,6-dimethyl-5,6,7,8-tetrahydroquinazolin-4-yl)-2,3,4,5-tetrahydreo-1,4-benzoxazepin-7-yl]pyridine-3-sulfonamide |

| Cmpd No. | Structure | Name |
|---|---|---|
| 416 | 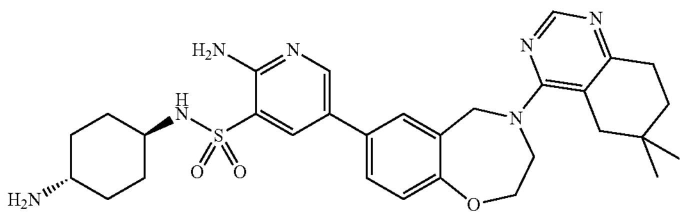 [SMILES: CC1(C)CCc2ncnc(N3CCOc4ccc(-c5cnc(N)c(S(=O)(=O)N[C@H]6CC[C@H](N)CC6)c5)cc4C3)c2C1] | 2-amino-N-(trans-4-aminocyclohexyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 417 | 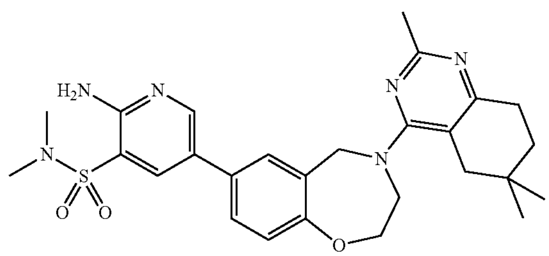 | 2-amino-N,N-dimethyl-5-[4-(2,6,6-trimethyl-5,6,7,8-tetrahydroquinazolin-4-yl)-2,3,4,5-tetrahydro-1,4-benzoxazepin-7-yl]pyridine-3-sulfonamide |
| 418 | 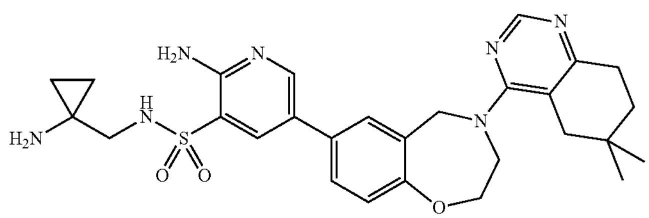 [SMILES: CC1(C)CCc2ncnc(N3CCOc4ccc(-c5cnc(N)c(S(=O)(=O)NCC6(N)CC6)c5)cc4C3)c2C1] | 2-amino-N-[(1-aminocyclopropyl)methyl]-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 419 | 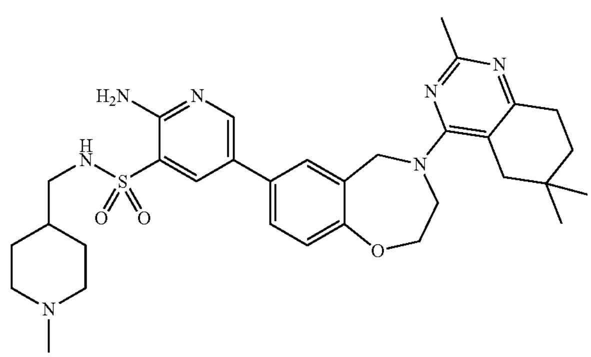 [SMILES: Cc1nc2c(c(N3CCOc4ccc(-c5cnc(N)c(S(=O)(=O)NCC6CCN(C)CC6)c5)cc4C3)n1)CC(C)(C)CC2] | 2-amino-N-[(1-methylpiperidin-4-yl)methyl]-5-[4-(2,6,6-trimethyl-5,6,7,8-tetrahydroquinazolin-4-yl)-2,3,4,5-tetrahydro-1,4-benzoxazepin-7-yl]pyridine-3-sulfonamide |
| 420 | 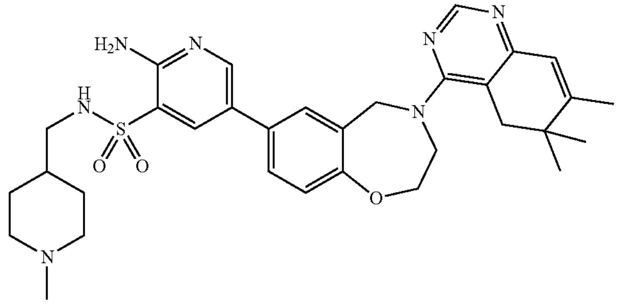 [SMILES: CC1=Cc2ncnc(N3CCOc4ccc(-c5cnc(N)c(S(=O)(=O)NCC6CCN(C)CC6)c5)cc4C3)c2CC1(C)C] | 2-amino-N-[(1-methylpiperidin-4-yl)methyl]-5-[4-(6,6,7-trimethyl-5,6-dihydroquinazolin-4-yl)-2,3,4,5-tetrahydro-1,4-benzoaxepin-7-yl]pyridine-3-sulfonamide |

| Cmpd No. | Structure | Name |
|---|---|---|
| 421 | 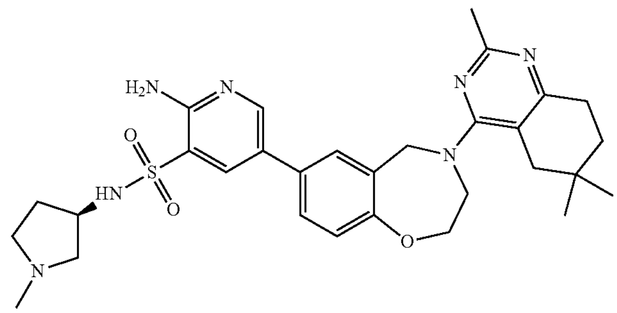 [SMILES: Cc1nc2c(c(N3CCOc4ccc(-c5cnc(N)c(S(=O)(=O)N[C@@H]6CCN(C)C6)c5)cc4C3)n1)CC(C)(C)CC2] | 2-amino-N-[(3R)-1-methylpyrrolidin-3-yl]-5-[4-(2,6,6-trimethyl-5,6,7,8-tetrahydroquinazolin-4-yl)-2,3,4,5-tetrahydro-1,4-benzoxazepin-7-yl]pyridine-3-sulfonamide |
| 422 | 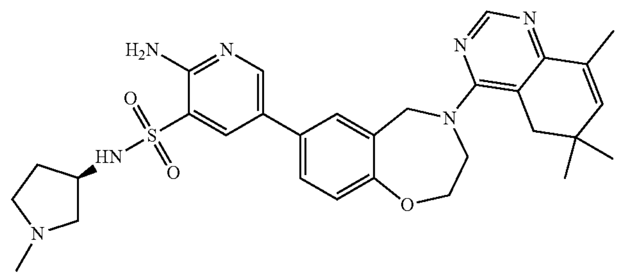 [SMILES: CC1=CC(C)(C)Cc2c1ncnc2N1CCOc2ccc(-c3cnc(N)c(S(=O)(=O)N[C@@H]4CCN(C)C4)c3)cc2C1] | 2-amino-N-[(3R)-1-methylpyrrolidin-3-yl]-5-[4-(6,6,8-trimethyl-5,6-dihydroquinazolin-4-yl)-2,3,4,5-tetrahydro-1,4-benzoxazepin-7-yl]pyridine-3-sulfonamide |
| 423 | 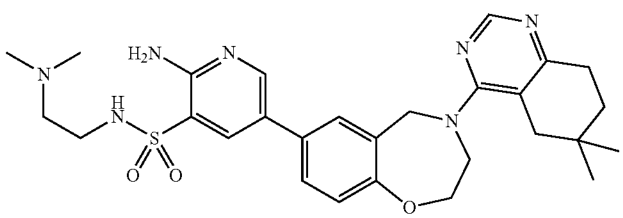 | 2-amino-N-[2-(dimethylamino)ethyl]-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 424 | 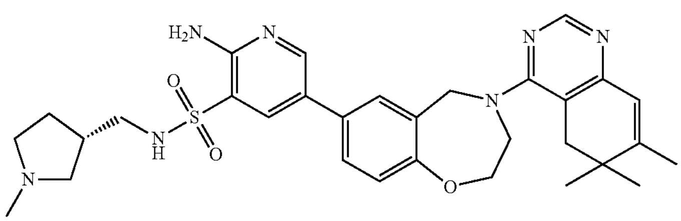 | 2-amino-N-{[(3S)-1-methylpyrrolidin-3-yl]methyl}-5-[4-(6,6,7-trimethyl-5,6-dihydroquinazolin-4-yl)-2,3,4,5-tetrahydro-1,4-benzoxazepin-7-yl]pyridine-3-sulfonamide |
| 425 | 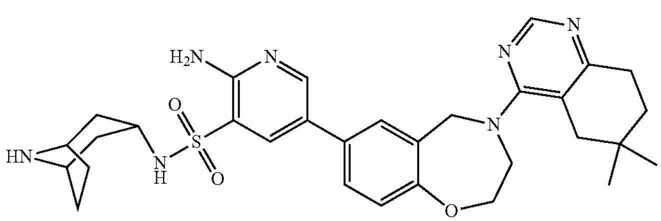 [SMILES: CC1(C)CCc2ncnc(N3CCOc4ccc(-c5cnc(N)c(S(=O)(=O)NC6CC7CCC(C6)N7)c5)cc4C3)c2C1] | 2-amino-N-8-azabicyclo[3.2.1]oct-3-yl-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 426 | 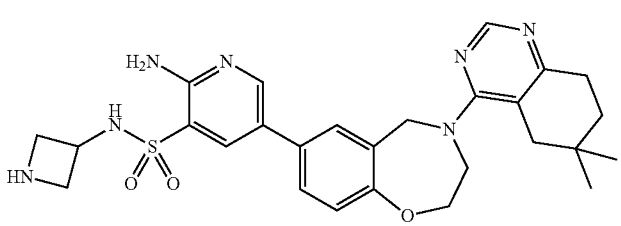 [SMILES: CC1(C)CCc2ncnc(N3CCOc4ccc(-c5cnc(N)c(S(=O)(=O)NC6CNC6)c5)cc4C3)c2C1] | 2-amino-N-azetidin-3-yl-5-[4-(6,6-dimethyl-5,6,7,8-tetrahydroquinazolin-4-yl)-2,3,4,5-tetrahydro-1,4-benzoxazepin-7-yl]pyridine-3-sulfonamide |

-continued

| Cmpd No. | Structure | Name |
|---|---|---|
| 427 | 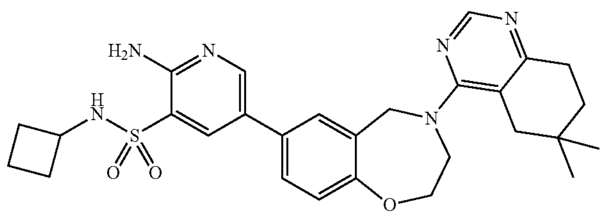 [SMILES: CC1(C)CCc2ncnc(N3CCOc4ccc(-c5cnc(N)c(S(=O)(=O)NC6CCC6)c5)cc4C3)c2C1] | 2-amino-N-cyclobutyl-5-[4-(6,6-dimethyl-5,6,7,8-tetrahydroquinazolin-4-yl)-2,3,4,5-tetrahydro-1,4-benzoxazepin-7-yl]pyridine-3-sulfonamide |
| 428 | 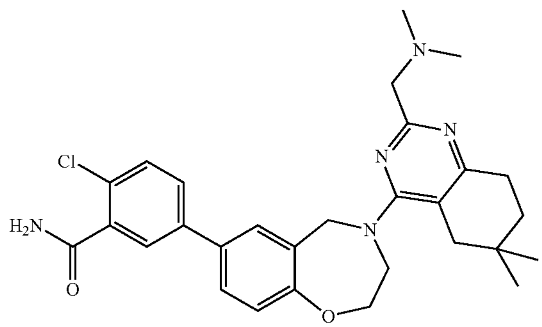 [SMILES: CN(C)Cc1nc2c(c(N3CCOc4ccc(-c5ccc(Cl)c(C(N)=O)c5)cc4C3)n1)CC(C)(C)CC2] | 2-chloro-5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)benzamide |
| 429 | 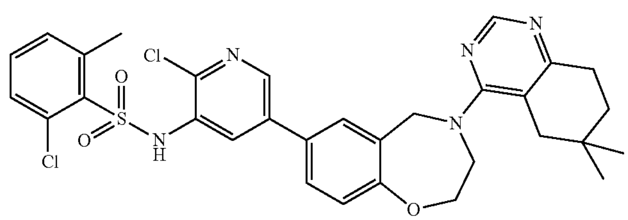 [SMILES: Cc1cccc(Cl)c1S(=O)(=O)Nc1cc(-c2ccc3c(c2)CN(c2ncnc4c2CC(C)(C)CC4)CCO3)cnc1Cl] | 2-chloro-N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}-6-methylbenzenesulfonamide |
| 430 | 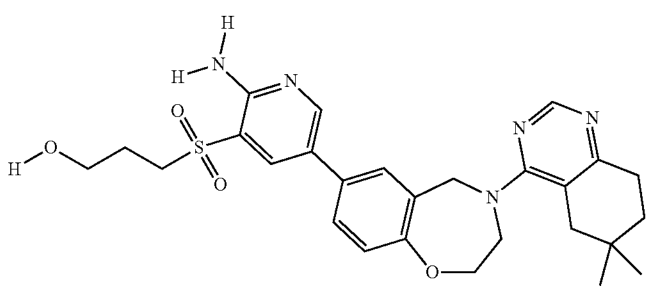 [SMILES: CC1(C)CCc2ncnc(N3CCOc4ccc(-c5cnc(N)c(S(=O)(=O)CCCO)c5)cc4C3)c2C1] | 3-({2-amino-5-[4-(6,6-dimethyl-5,6,7,8-tetrahydroquinazolin-4-yl)-2,3,4,5-tetrahydro-1,4-benzoazepin-7-yl]pyridin-3-yl}sulfonyl)propan-1-ol |
| 431 | 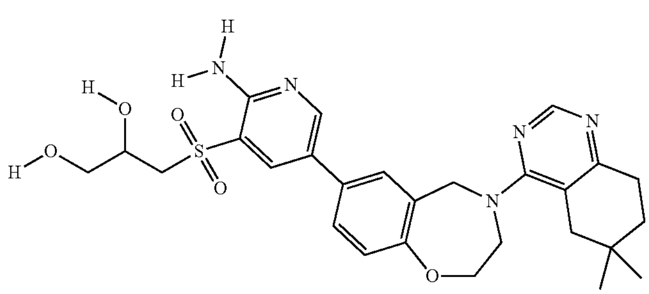 [SMILES: CC1(C)CCc2ncnc(N3CCOc4ccc(-c5cnc(N)c(S(=O)(=O)CC(O)CO)c5)cc4C3)c2C1] | 3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)propane-1,2-diol |
| 432 | 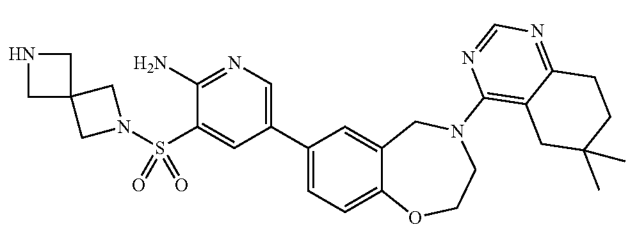 [SMILES: CC1(C)CCc2ncnc(N3CCOc4ccc(-c5cnc(N)c(S(=O)(=O)N6CC7(CNC7)C6)c5)cc4C3)c2C1] | 3-(2,6-diazaspiro[3.3]hept-2-ylsulfonyl)-5-[4-(6,6-dimethyl-5,6,7,8-tetrahydroquinazolin-4-yl)-2,3,4,5-tetrahydro-1,4-benzoxazepin-7-yl]pyridin-2-amine |

| Cmpd No. | Structure | Name |
|---|---|---|
| 433 | 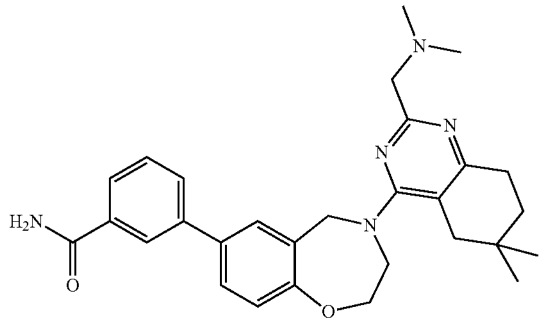 [SMILES: CN(C)Cc1nc2c(c(N3CCOc4ccc(-c5cccc(C(N)=O)c5)cc4C3)n1)CC(C)(C)CC2] | 3-(4-{2-[(dimethylamino)methyl]-6,6-dimethyl-5,6,7,8-tetrahydroquinazolin-4-yl}-2,3,4,5-tetrahydro-1,4-benzoxazepin-7-yl)benzamide |
| 434 | 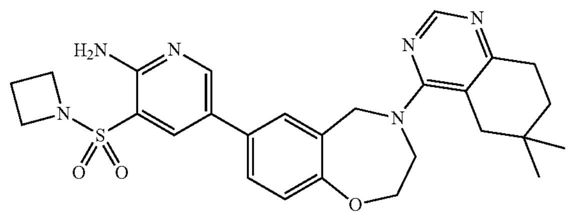 [SMILES: CC1(C)CCc2ncnc(N3CCOc4ccc(-c5cnc(N)c(S(=O)(=O)N6CCC6)c5)cc4C3)c2C1] | 3-(azetidin-1-ylsulfonyl)-5-[4-(6,6-dimethyl-5,6,7,8-tetrahydroquinazolin-4-yl)-2,3,4,5-tetrahydro-1,4-benzoxazepin-7-yl]pyridine-2-amine |
| 435 | 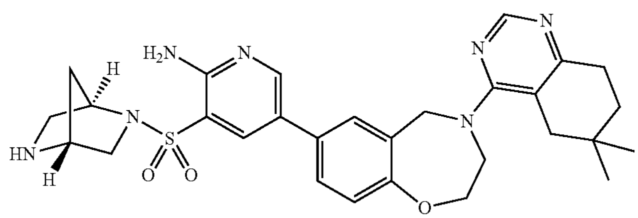 [SMILES: CC1(C)CCc2ncnc(N3CCOc4ccc(-c5cnc(N)c(S(=O)(=O)N6C[C@H]7C[C@@H]6CN7)c5)cc4C3)c2C1] | 2-[(1R,4R)-2,5-diazabicyclo[2.2.1]hept-2-ylsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |
| 436 | 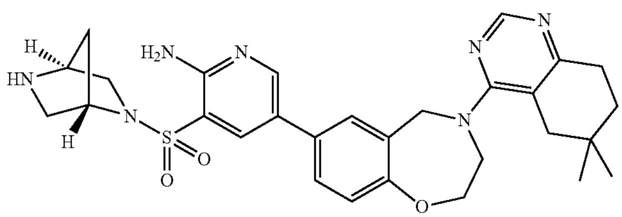 [SMILES: CC1(C)CCc2ncnc(N3CCOc4ccc(-c5cnc(N)c(S(=O)(=O)N6C[C@@H]7C[C@H]6CN7)c5)cc4C3)c2C1] | 3-[(1S,4S)-2,5-diazabicyclo[2.2.1]hept-2-ylsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |
| 437 | 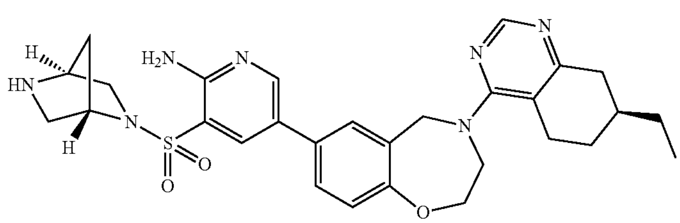 [SMILES: CC[C@H]1CCc2c(ncnc2N2CCOc3ccc(-c4cnc(N)c(S(=O)(=O)N5C[C@@H]6C[C@H]5CN6)c4)cc3C2)C1] | 3-[(1S,4S)-2,5-diazabicyclo[2.2.1]hept-2-ylsulfonyl]-5-{4-[(7S)-7-ethyl-5,6,7,8-tetrahydroquinazolin-4-yl]-2,3,4,5-tetrahydro-1,4-benzoxazepin-7-yl}pyridin-2-amine |
| 438 | 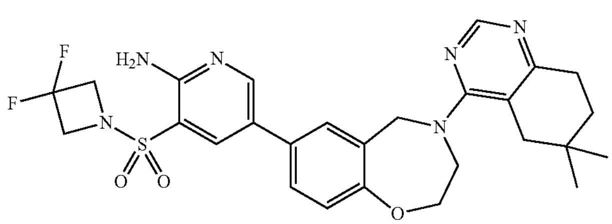 [SMILES: CC1(C)CCc2ncnc(N3CCOc4ccc(-c5cnc(N)c(S(=O)(=O)N6CC(F)(F)C6)c5)cc4C3)c2C1] | 3-[(3,3-difluoroazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |

-continued

| Cmpd No. | Structure | Name |
|---|---|---|
| 439 | 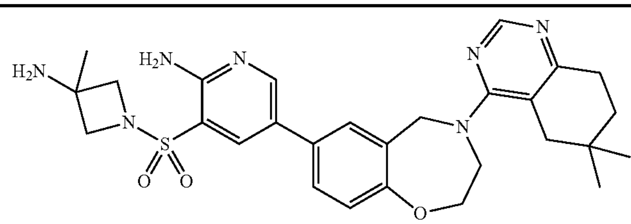 | 3-[(3-amino-3-methylazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |
| 440 | 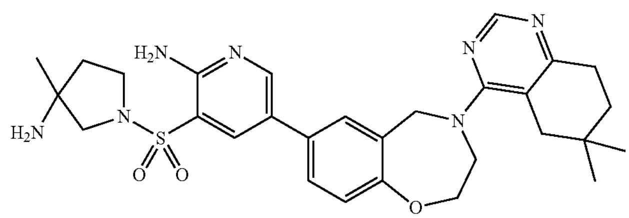 | 3-[(3-amino-3-methylpyrrolidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |
| 441 | 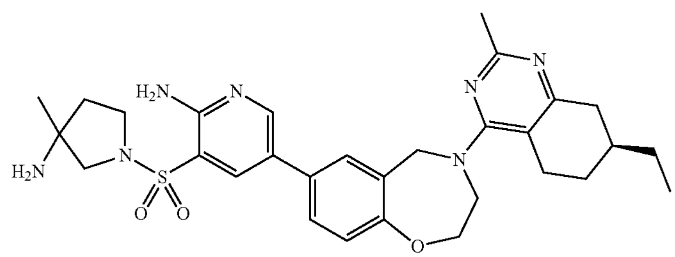 [SMILES: CC[C@H]1CCc2c(nc(C)nc2N2CCOc3ccc(-c4cnc(N)c(S(=O)(=O)N5CCC(C)(N)C5)c4)cc3C2)C1] | 3-[(3-amino-3-methylpyrrolidin-1-yl)sulfonyl]-5-{4-[(7S)-7-ethyl-2-methyl-5,6,7,8-tetrahydroquinazolin-4-yl]-2,3,4,5-tetrahydro-1,4-benzoxazepin-7-yl}pyridin-2-amine |
| 442 | 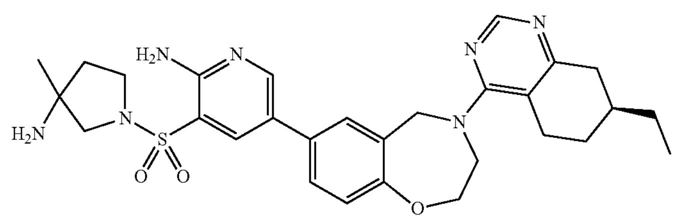 [SMILES: CC[C@H]1CCc2c(ncnc2N2CCOc3ccc(-c4cnc(N)c(S(=O)(=O)N5CCC(C)(N)C5)c4)cc3C2)C1] | 3-[(3-amino-3-methylpyrrolidin-1-yl)sulfonyl]-5-{4-[(7S)-7-ethyl-5,6,7,8-tetrahydroquinazolin-4-yl]-2,3,4,5-tetrahydro-1,4-benzoxazepin-7-yl}pyridin-2-amine |
| 443 | 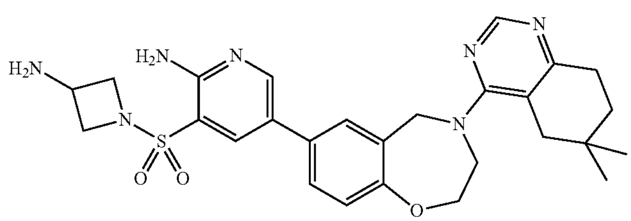 [SMILES: CC1(C)CCc2ncnc(N3CCOc4ccc(-c5cnc(N)c(S(=O)(=O)N6CC(N)C6)c5)cc4C3)c2C1] | 3-[(3-aminoazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |
| 444 | 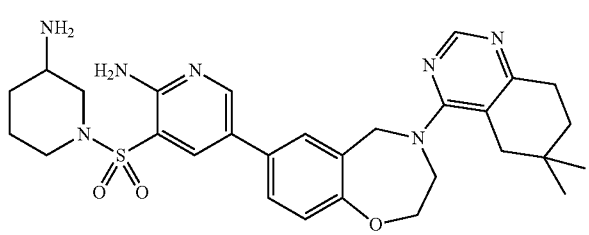 [SMILES: CC1(C)CCc2ncnc(N3CCOc4ccc(-c5cnc(N)c(S(=O)(=O)N6CCCC(N)C6)c5)cc4C3)c2C1] | 3-[(3-aminopiperidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |
| 445 | 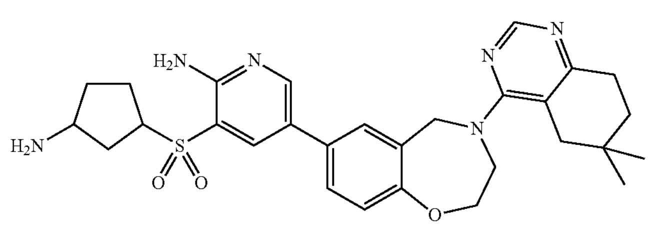 [SMILES: CC1(C)CCc2ncnc(N3CCOc4ccc(-c5cnc(N)c(S(=O)(=O)C6CCC(N)C6)c5)cc4C3)c2C1] | 3-[(3-aminopyrrolidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |

| Cmpd No. | Structure | Name |
|---|---|---|
| 446 | 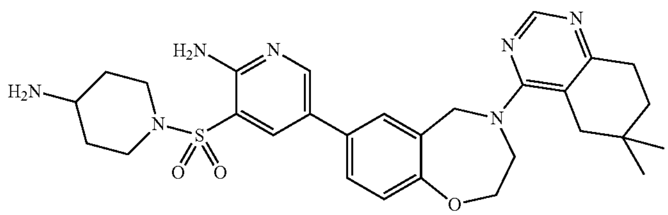 [SMILES: CC1(C)CCc2ncnc(N3CCOc4ccc(-c5cnc(N)c(S(=O)(=O)N6CCC(N)CC6)c5)cc4C3)c2C1] | 3-[(4-aminopiperidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine |
| 447 | 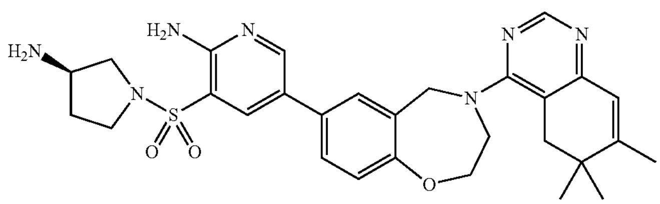 [SMILES: CC1=Cc2ncnc(N3CCOc4ccc(-c5cnc(N)c(S(=O)(=O)N6CC[C@@H](N)C6)c5)cc4C3)c2CC1(C)C] | 3-{[(3R)-3-aminopyrrolidin-1-yl]sulfonyl}-5-[4-(6,6,7-trimethyl-5,6-dihydroquinazolin-4-yl)-2,3,4,5-tetrahydro-1,4-benzoxazepin-7-yl]pyridin-2-amine |
| 448 | 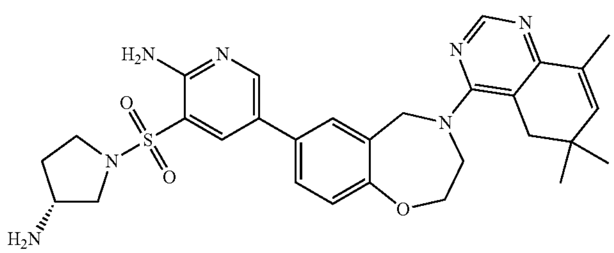 [SMILES: CC1=CC(C)(C)Cc2c1ncnc2N1CCOc2ccc(-c3cnc(N)c(S(=O)(=O)N4CC[C@@H](N)C4)c3)cc2C1] | 3-{[(3R)-3-aminopyrrolidin-1-yl]sulfonyl}-5-[4-(6,6,8-trimethyl-5,6-dihydroquinazolin-4-yl)-2,3,4,5-tetrahydro-1,4-benzoxazepin-7-yl]pyridin-2-amine |
| 449 | 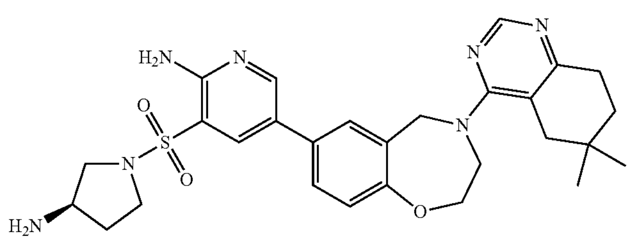 [SMILES: CC1(C)CCc2ncnc(N3CCOc4ccc(-c5cnc(N)c(S(=O)(=O)N6CC[C@@H](N)C6)c5)cc4C3)c2C1] | 3-{[(3R)-3-aminpyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine |
| 450 | 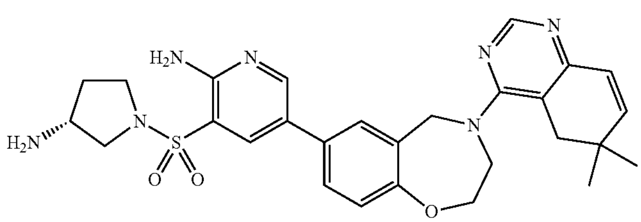 [SMILES: CC1(C)C=Cc2ncnc(N3CCOc4ccc(-c5cnc(N)c(S(=O)(=O)N6CC[C@@H](N)C6)c5)cc4C3)c2C1] | 3-{[(3R)-3-aminopyrrolidin-1-yl]sulfonyl}-5-[4-(6,6-dimethyl-5,6-dihydroquinazolin-4-yl)-2,3,4,5-tetrahydro-1,4-benzoxazepin-7-yl]pyridin-2-amine |
| 451 | 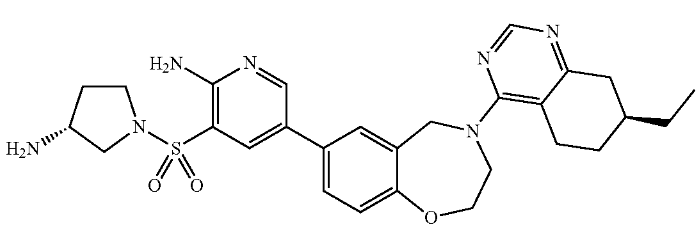 [SMILES: CC[C@H]1CCc2c(ncnc2N2CCOc3ccc(-c4cnc(N)c(S(=O)(=O)N5CC[C@@H](N)C5)c4)cc3C2)C1] | 3-{[(3R)-3-aminopyrrolidin-1-yl]sulfonyl}-5-{4-[(7S)-7-ethyl-5,6,7,8-tetrahydroquinazolin-4-yl]-2,3,4,5-tetrahydro-1,4-benzoxazepin-7-yl}pyridin-2-amine |

-continued

| Cmpd No. | Structure | Name |
|---|---|---|
| 452 | 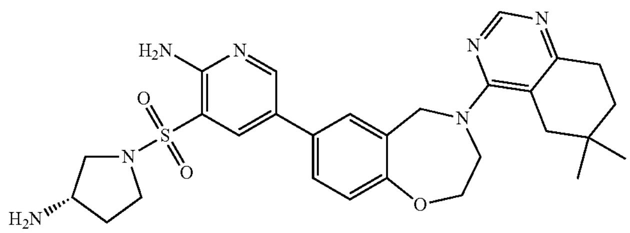 [SMILES: CC1(C)CCc2ncnc(N3CCOc4ccc(-c5cnc(N)c(S(=O)(=O)N6CC[C@H](N)C6)c5)cc4C3)c2C1] | 3-{[(3S)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine |
| 453 | 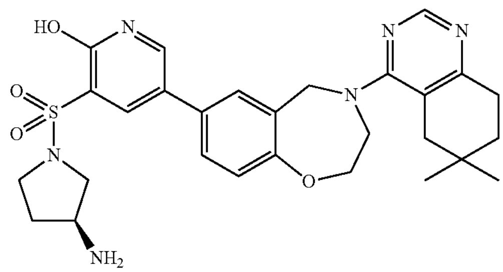 [SMILES: CC1(C)CCc2ncnc(N3CCOc4ccc(-c5cnc(O)c(S(=O)(=O)N6CC[C@H](N)C6)c5)cc4C3)c2C1] | 3-{[(3S)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-ol |
| 454 | 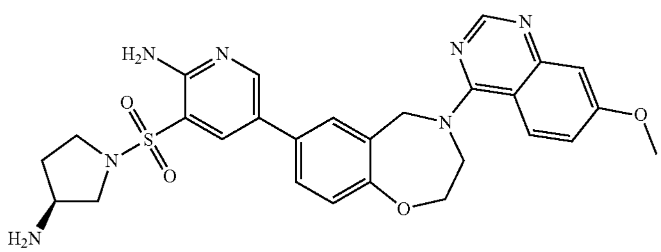 [SMILES: COc1ccc2c(N3CCOc4ccc(-c5cnc(N)c(S(=O)(=O)N6CC[C@H](N)C6)c5)cc4C3)ncnc2c1] | 3-{[(3S)-3-aminopyrrolidin-1-yl]sulfonyl}-5-{4-[7-(methyloxy)quinazolin-4-yl]-2,3,4,5-tetrahydro-1,4-benzoxazepin-7-yl}pyridin-2-amine |
| 455 | 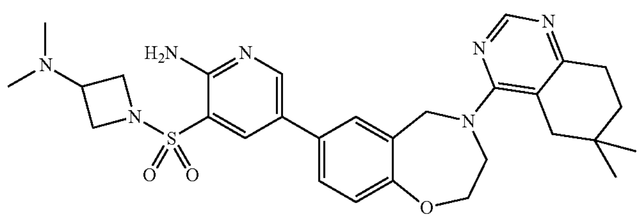 | 3-{[3-(dimethylamino)azetidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine |
| 456 | 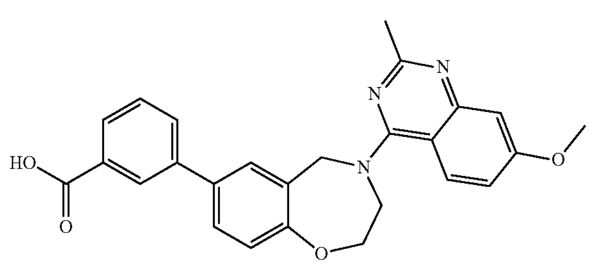 [SMILES: COc1ccc2c(N3CCOc4ccc(-c5cccc(C(=O)O)c5)cc4C3)nc(C)nc2c1] | 3-{4-[2-methyl-7-(methyloxy)quinazolin-4-yl]-2,3,4,5-tetrahydro-1,4-benzoxazepin-7-yl}benzoic acid |
| 457 | 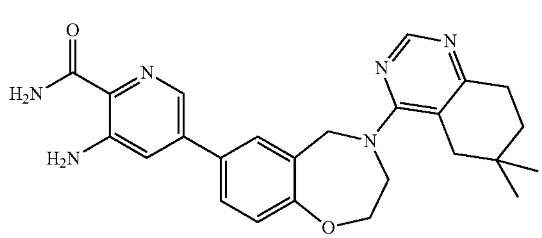 [SMILES: CC1(C)CCc2ncnc(N3CCOc4ccc(-c5cnc(C(N)=O)c(N)c5)cc4C3)c2C1] | 3-amino-5-[4-(6,6-dimethyl-5,6,7,8-tetrahydroquinazolin-4-yl)-2,3,4,5-tetrahydro-1,4-benzoxazepin-7-yl]pyridine-2-carboxamide |

-continued

| Cmpd No. | Structure | Name |
|---|---|---|
| 458 | 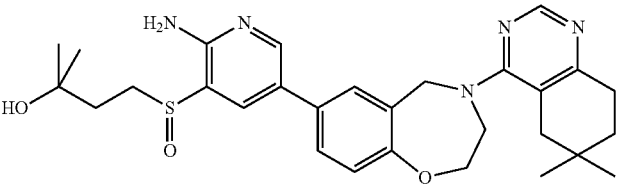 [SMILES: CC(C)(O)CCS(=O)c1cc(-c2ccc3c(c2)CN(c2ncnc4c2CC(C)(C)CC4)CCO3)cnc1N] | 4-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfinyl)-2-methylbutan-2-ol |
| 459 | 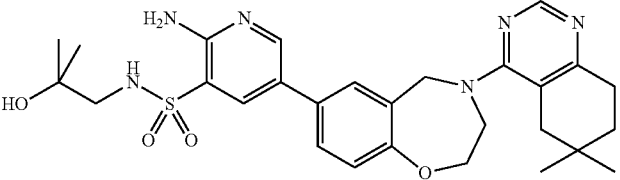 [SMILES: CC(C)(O)CNS(=O)(=O)c1cc(-c2ccc3c(c2)CN(c2ncnc4c2CC(C)(C)CC4)CCO3)cnc1N] | 4-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylbutan-2-ol |
| 460 | 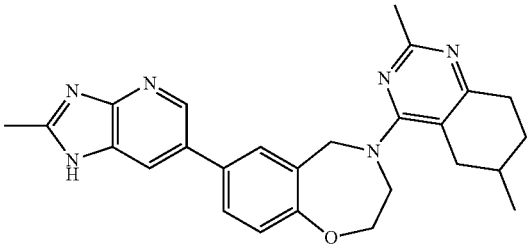 [SMILES: Cc1nc2c(c(N3CCOc4ccc(-c5cnc6nc(C)[nH]c6c5)cc4C3)n1)CC(C)CC2] | 4-(2,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine |
| 461 | 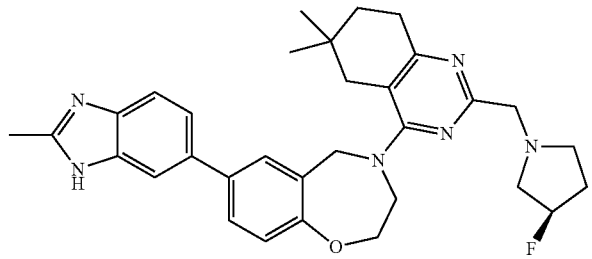 [SMILES: Cc1nc2ccc(-c3ccc4c(c3)CN(c3nc(CN5CC[C@@H](F)C5)nc5c3CC(C)(C)CC5)CCO4)cc2[nH]1] | 4-(2-{[(3R)-3-fluoropyridin-1-yl]methyl}-6,6-dimethyl-5,6,7,8-tetrahydroquinazolin-4-yl)-7-(2-methyl-1H-benzimidazol-6-yl)-2,3,4,5-tetrahydro-1,4-benzoxazepin |
| 462 | 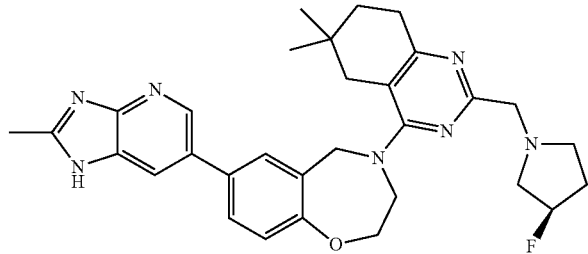 [SMILES: Cc1nc2ncc(-c3ccc4c(c3)CN(c3nc(CN5CC[C@@H](F)C5)nc5c3CC(C)(C)CC5)CCO4)cc2[nH]1] | 4-(2-{[(3R)-3-fluoropyridin-1-yl]methyl}-6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine |
| 463 | 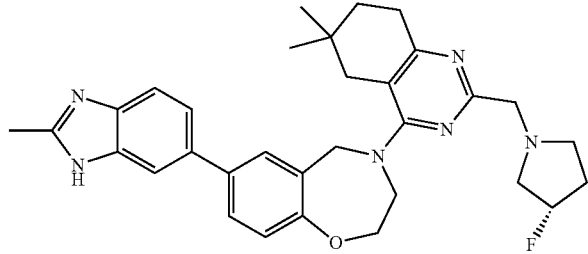 [SMILES: Cc1nc2ccc(-c3ccc4c(c3)CN(c3nc(CN5CC[C@H](F)C5)nc5c3CC(C)(C)CC5)CCO4)cc2[nH]1] | 4-(2-{[(3S)-3-fluoropyrrolidin-1-yl]methyl}-6,6-dimethyl-5,6,7,8-tetrahydroquinazolin-4-yl)-7-(2-methyl-1H-benzimidazol-6-yl)-2,3,4,5-tetrahydro-1,4-benzoxazepine |

-continued

| Cmpd No. | Structure | Name |
|---|---|---|
| 464 | 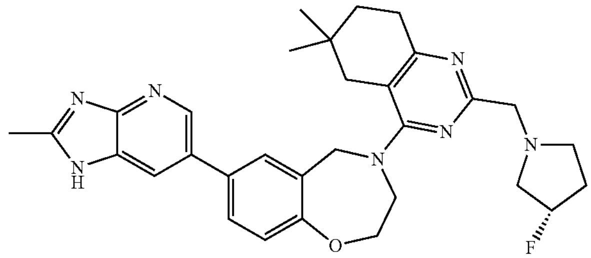 [SMILES: Cc1nc2ncc(-c3ccc4c(c3)CN(c3nc(CN5CC[C@H](F)C5)nc5c3CC(C)(C)CC5)CCO4)cc2[nH]1] | 4-(2-{[(3S)-3-fluoropyrrolidin-1-yl]methyl}-6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine |
| 465 | 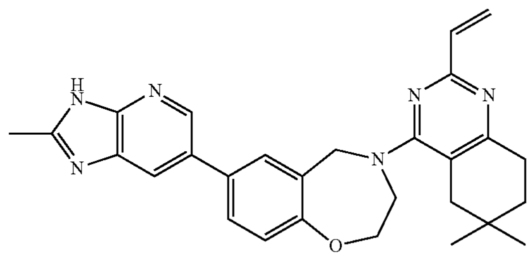 | 4-(2-ethenyl-6,6-dimethyl-5,6,7,8-tetrahydroquinazolin-4-yl)-7-(2-methyl-3H-imidazo[4,5-b]pyridin-6-yl)-2,3,4,5-tetrahydro-1,4-benzoxazepine |
| 466 | 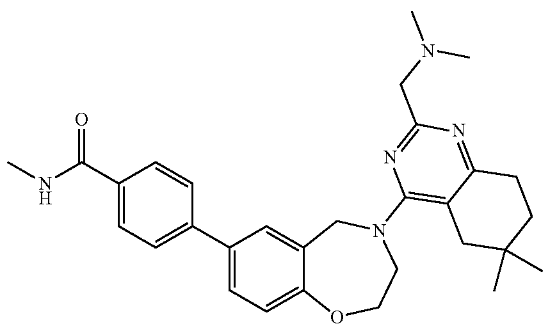 | 4-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-N-methylbenzamide |
| 468 | 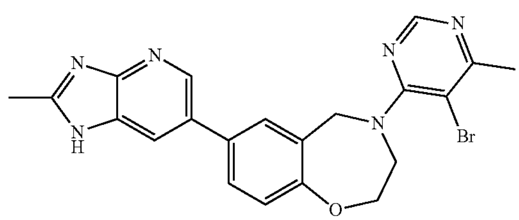 | 4-(5-bromo-6-methylpyrimidin-4-yl)-7-(2-methyl-1H-imidazao[4,5-b]pyridin-6-yl)-2,3,4,5-tetrahydro-1,4-benzoxazepine |
| 469 | 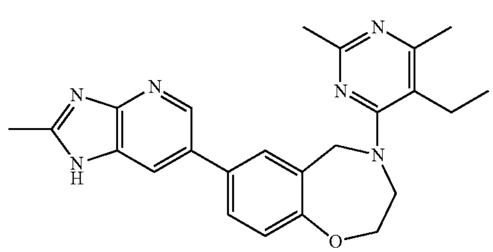 [SMILES: CCc1c(C)nc(C)nc1N1CCOc2ccc(-c3cnc4nc(C)[nH]c4c3)cc2C1] | 4-(5-ethyl-2,6-dimethylpyrimidin-4-yl)-7-(2-methyl-1H-imidazo[4,5-b]pyridin-6-yl)-2,3,4,5-tetrahydro-1,4-benzoxazepine |
| 470 | 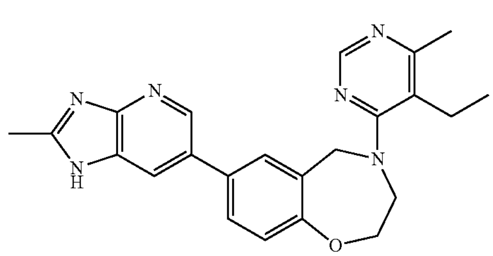 [SMILES: CCc1c(C)ncnc1N1CCOc2ccc(-c3cnc4nc(C)[nH]c4c3)cc2C1] | 4-(5-ethyl-6-methylpyrimidin-4-yl)-7-(2-methyl-1H-imidazo[4,5-b]pyridin-6-yl)-2,3,4,5-tetrahydro-1,4-benzoxazepine |

-continued

| Cmpd No. | Structure | Name |
|---|---|---|
| 471 | 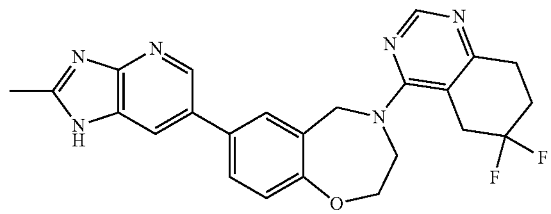 [SMILES: Cc1nc2ncc(-c3ccc4c(c3)CN(c3ncnc5c3CC(F)(F)CC5)CCO4)cc2[nH]1] | 4-(6,6-difluoro-5,6,7,8-tetrahydcroquinazolin-4-yl)-7-(2-methyl-1H-imidazo[4,5-b]pyridin-6-yl)-2,3,4,5-tetrahydro-1,4-benzoxazepine |
| 472 | 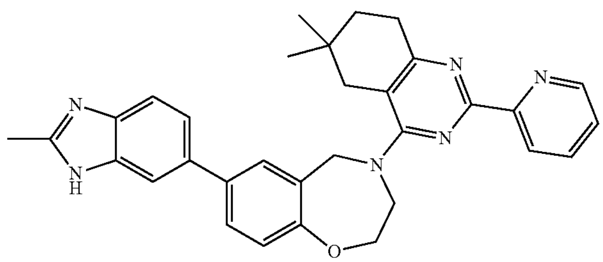 [SMILES: Cc1nc2ccc(-c3ccc4c(c3)CN(c3nc(-c5ccccn5)nc5c3CC(C)(C)CC5)CCO4)cc2[nH]1] | 4-(6,6-dimethyl-2-pyridin-2-yl-5,6,7,8-tetrahydroquinazolin-4-yl)-7-(2-methyl-1H-benzimidazol-6-yl)-2,3,4,5-tetrahydro-1,4-benzoxazepine |
| 473 | 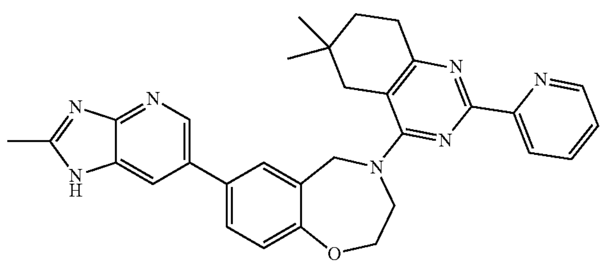 [SMILES: Cc1nc2ncc(-c3ccc4c(c3)CN(c3nc(-c5ccccn5)nc5c3CC(C)(C)CC5)CCO4)cc2[nH]1] | 4-(6,6-dimethyl-2-pyridin-2-yl-5,6,7,8-tetrahydroquinazolin-4-yl)-7-(2-methyl-1H-imidazo[4,5-b]pyridin-6-yl)-2,3,4,5-tetrahydro-1,4-benzoxazepine |
| 474 | 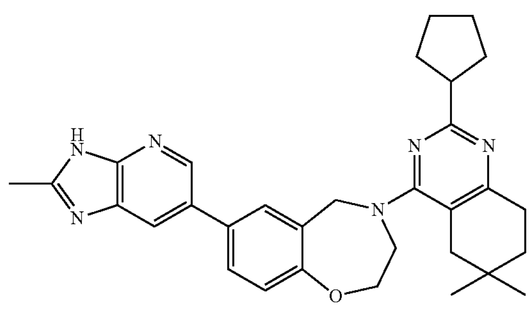 | 4-(6,6-dimethyl-2-pyrrolidin-2-yl-5,6,7,8-tetrahydroquinazolin-4-yl)-7-(2-methyl-3H-imidazo[4,5-b]pyridin-6-yl)-2,3,4,5-tetrahydro-1,4-benzoxazepine |
| 475 | 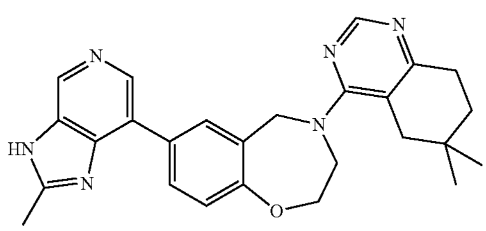 | 4-(6,6-dimethyl-5,6,7,8-tetrahydroquinazolin-4-yl)-7-(2-methyl-3H-imidazo[4,5-c]pyridin-7-yl)-2,3,4,5-tetrahydro-1,4-benzoxazepine |
| 476 | 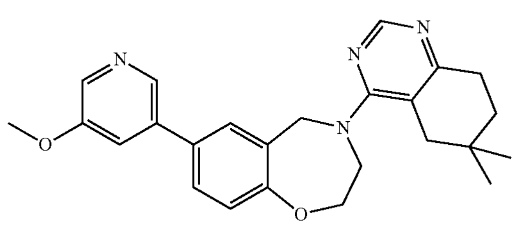 | 4-(6,6-dimethyl-5,6,7,8-tetrahydroquinazolin-4-yl)-7-[5-(methyloxy)pyridin-3-yl]-2,3,4,5-tetrahydro-1,4-benzoxazepine |

| Cmpd No. | Structure | Name |
|---|---|---|
| 477 | 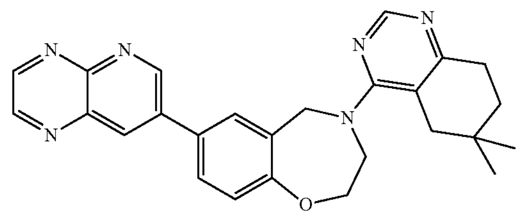 [SMILES: CC1(C)CCc2ncnc(N3CCOc4ccc(-c5cnc6nccnc6c5)cc4C3)c2C1] | 4-(6,6-dimethyl-5,6,7,8-tetrahydroquinazolin-4-yl)-7-pyrido[2,3-b]pyrazin-7-yl-2,3,4,5-tetrahydro-1,4-benzoxazepine |
| 478 | 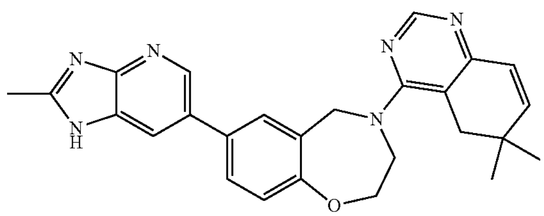 | 4-(6,6-dimethyl-5,6-dihydroquinazolin-4-yl)-7-(2-methyl-1H-imidazo[4,5-b]pyridin-6-yl)-2,3,4,5-tetrahydro-1,4-benzoxazepine |
| 479 | 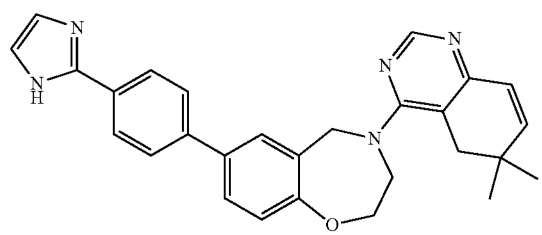 [SMILES: CC1(C)C=Cc2ncnc(N3CCOc4ccc(-c5ccc(-c6ncc[nH]6)cc5)cc4C3)c2C1] | 4-(6,6-dimethyl-5,6-dihydroquinazolin-4-yl)-7-[4-(1H-imidazo-2-yl)phenyl]-2,3,4,5-tetrahydro-1,4-benzoxazepine |
| 480 | 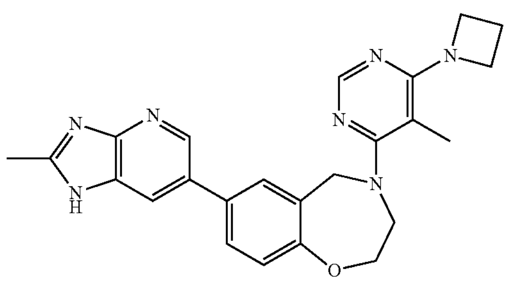 [SMILES: Cc1nc2ncc(-c3ccc4c(c3)CN(c3ncnc(N5CCC5)c3C)CCO4)cc2[nH]1] | 4-(6-azetidin-1-yl-5-methylpyrimidin-4-yl)-7-(2-methyl-1H-imidazo[4,5-b]pyridin-6-yl)-2,3,4,5-tetrahydro-1,4-benzoxazepine |
| 481 | 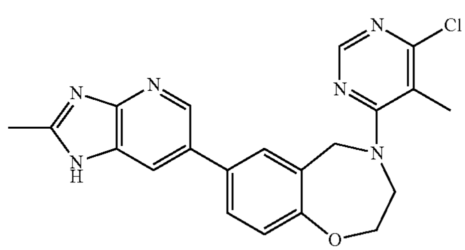 | 4-(6-chloro-5-methylpyrimidin-4-yl)-7-(2-methyl-1H-imidazo[4,5-b]pyridin-6-yl)-2,3,4,5-tetrahydro-1,4-benzoxazepine |
| 482 | 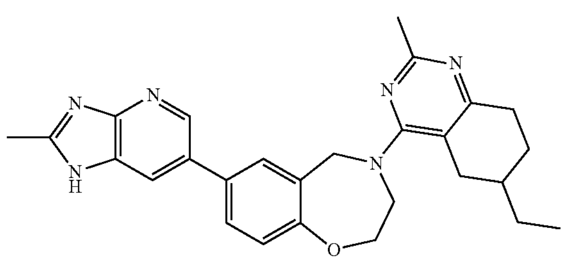 [SMILES: CCC1CCc2nc(C)nc(N3CCOc4ccc(-c5cnc6nc(C)[nH]c6c5)cc4C3)c2C1] | 4-(6-ethyl-2-methyl-5,6,7,8-tetrahydroquinazolin-4-yl)-7-(2-methyl-1H-imidazo[4,5-b]pyridin-6-yl)-2,3,4,5-tetrahydro-1,4-benzoxazepine |

| Cmpd No. | Structure | Name |
|---|---|---|
| 483 | 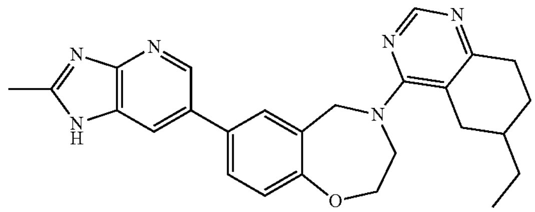 [SMILES: CCC1CCc2ncnc(N3CCOc4ccc(-c5cnc6nc(C)[nH]c6c5)cc4C3)c2C1] | 4-(6-ethyl-5,6,7,8-tetrahydroquinazolin-4-yl)-7-(2-methyl-1H-imidaz[4,5-b]pyridin-6-yl)-2,3,4,5-tetrahydro-1,4-benzoxazepine |
| 484 | 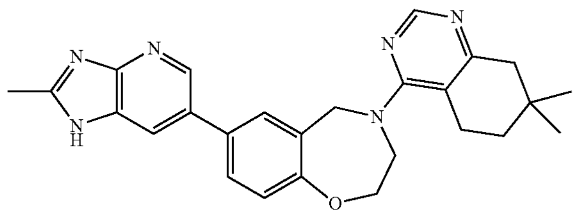 | 4-(7,7-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine |
| 485 | 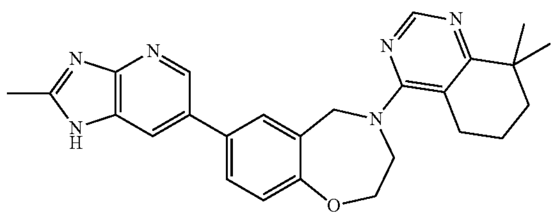 | 4-(8,8-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine |
| 486 | 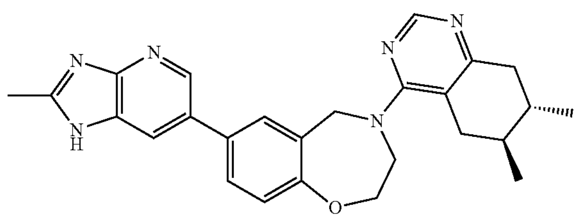 | 4-[(6S,7S)-6,7-dimethyl-5,6,7,8-tetrahydroquinazolin-4-yl]-7-(2-methyl-1H-imidazo[4,5-b]pyridin-6-yl)-2,3,4,5-tetrahydro-1,4-benzoxazepine |
| 487 | 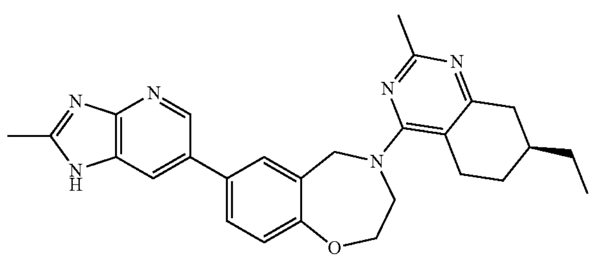 [SMILES: CC[C@H]1CCc2c(nc(C)nc2N2CCOc3ccc(-c4cnc5nc(C)[nH]c5c4)cc3C2)C1] | 4-[(7S)-7-ethyl-2-methyl-5,6,7,8-tetrahydroquinazolin-4-yl]-7-(2-methyl-1H-imidazo[4,5-b]pyridin-6-yl)-2,3,4,5-tetrahydro-1,4-benzoxazepine |
| 488 | 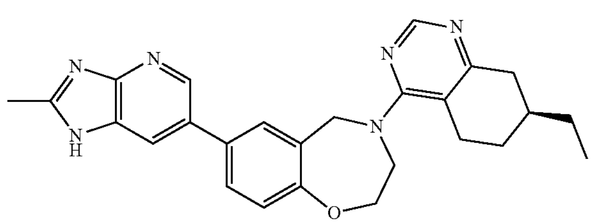 [SMILES: CC[C@H]1CCc2c(ncnc2N2CCOc3ccc(-c4cnc5nc(C)[nH]c5c4)cc3C2)C1] | 4-[(7S)-7-ethyl-5,6,7,8-tetrahydroquinazolin-4-yl]-7-(2-methyl-1H-imidazo[4,5-b]pyridin-6-yl)-2,3,4,5-tetrahydro-1,4-benzoxazepine |
| 489 | 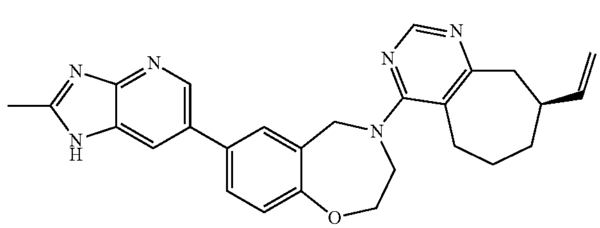 [SMILES: C=C[C@H]1CCCc2c(ncnc2N2CCOc3ccc(-c4cnc5nc(C)[nH]c5c4)cc3C2)C1] | 4-[(8S)-8-ethenyl-6,7,8,9-tetrahydro-5H-cyclohept[d]pyrimidin-4-yl]-7-(2-methyl-1H-imidazo[4,5-b]pyridin-6-yl)-2,3,4,5-tetrahydro-1,4-benzoxazepine |

| Cmpd No. | Structure | Name |
|---|---|---|
| 490 | 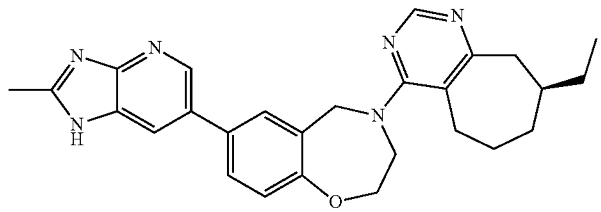 [SMILES: CC[C@H]1CCCc2c(ncnc2N2CCOc3ccc(-c4cnc5nc(C)[nH]c5c4)cc3C2)C1] | 4-[(8S)-3-ethyl-6,7,8,9-tetrahydro-5H-cyclohepta[d]pyrimidin-4-yl]-7-(2-methyl-1H-imidazo[4,5-b]pyridin-6-yl)-2,3,4,5-tetrahydro-1,4-benzoxazepine |
| 491 | 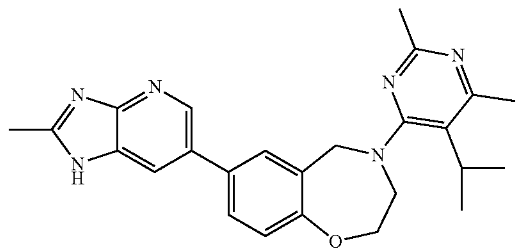 | 4-[2,6-dimethyl-5-(1-methylethyl)pyrimidin-4-yl]-7-(2-methyl-1H-imidazo[4,5-b]pyridin-6-yl)-2,3,4,5-tetrahydro-1,4-benzoxazepine |
| 492 | 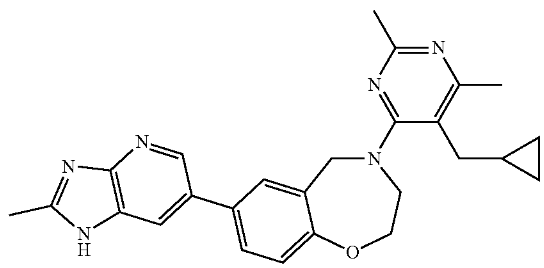 [SMILES: Cc1nc(C)c(CC2CC2)c(N2CCOc3ccc(-c4cnc5nc(C)[nH]c5c4)cc3C2)n1] | 4-[5-(cyclopropylmethyl)-2,6-dimethylpyrimidin-4-yl]-7-(2-methyl-1H-imidazo[4,5-b]pyridin-6-yl)-2,3,4,5-tetrahydro-1,4-benzoxazepine |
| 493 | 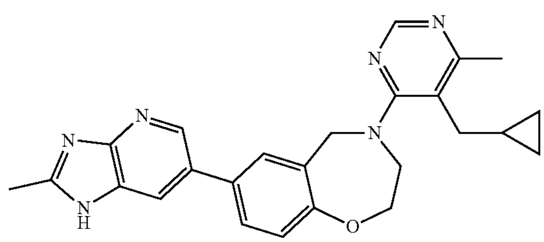 [SMILES: Cc1nc2ncc(-c3ccc4c(c3)CN(c3ncnc(C)c3CC3CC3)CCO4)cc2[nH]1] | 4-[5-(cyclopropylmethyl)-6-methylpyrimidin-4-yl]-7-(2-methyl-1H-imidazo[4,5-b]pyridin-6-yl)-2,3,4,5-tetrahydro-1,4-benzoxazepine |
| 494 | 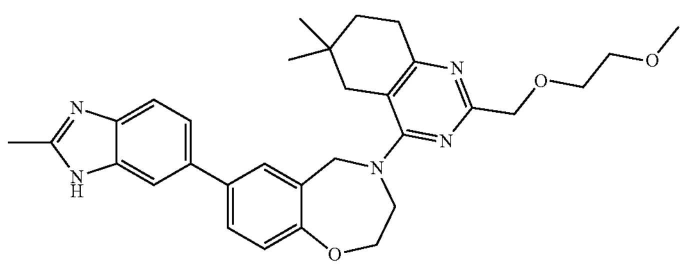 | 4-[6,6-dimethyl-2-({[2-(methyloxy)ethyl]oxy}methyl)-5,6,7,8-tetrahydroquinazolin-4-yl]-7-(2-methyl-1H-benzimidazol-6-yl)-2,3,4,5-tetrahydro-1,4-benzoxazepine |
| 495 | 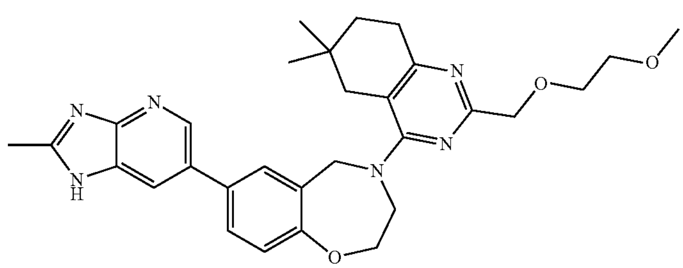 | 4-[6,6-dimethyl-2-({[2-(methyloxy)ethyl]oxy}methyl)-5,6,7,8-tetrahydroquinazolin-4-yl]-7-(2-methyl-1H-imidazo[4,5-b]pyridin-6-yl)-2,3,4,5-tetrahydro-1,4-benzoxazepine |

-continued

| Cmpd No. | Structure | Name |
|---|---|---|
| 496 | 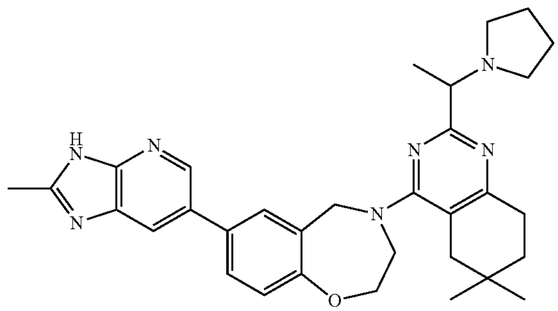 [SMILES: Cc1nc2cc(-c3ccc4c(c3)CN(c3nc(C(C)N5CCCC5)nc5c3CC(C)(C)CC5)CCO4)cnc2[nH]1] | 4-[6,6-dimethyl-2-(1-pyrrolidin-1-ylethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine |
| 497 | 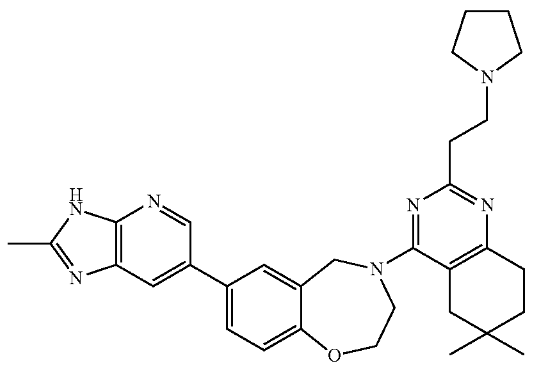 | 4-[6,6-dimethyl-2-(2-pyrrolidin-1-ylethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine |
| 498 | 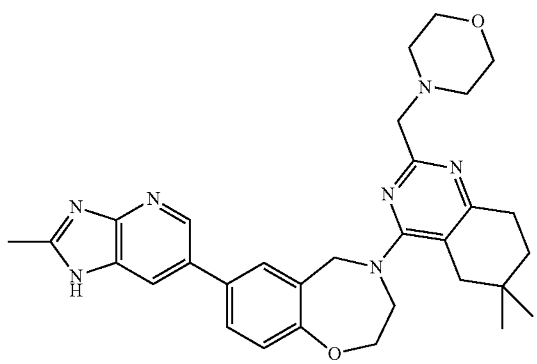 | 4-[6,6-dimethyl-2-(morpholin-4-ylmethyl)-5,6,7,8-tetrahydroquinazolin-4-yl]-7-(2-methyl-1H-imidazo[4,5-b]pyridin-6-yl)-2,3,4,5-tetrahydro-1,4-benzoxazepine |
| 499 | 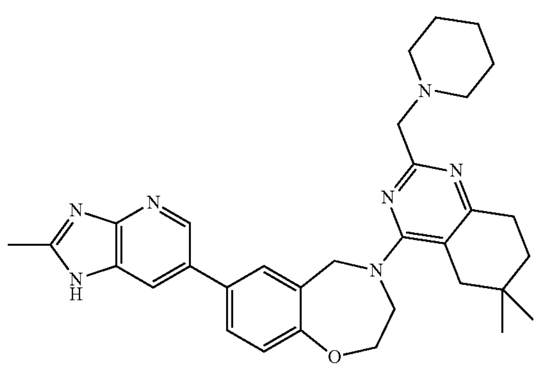 | 4-[6,6-dimethyl-2-(piperidin-1-ylmethyl)-5,6,7,8-tetrahydroquinazolin-4-yl]-7-(2-methyl-1H-imidazo[4,5-b]pyridin-6-yl)-2,3,4,5-tetrahydro-1,4-benzoxazepine |

-continued

| Cmpd No. | Structure | Name |
|---|---|---|
| 500 | 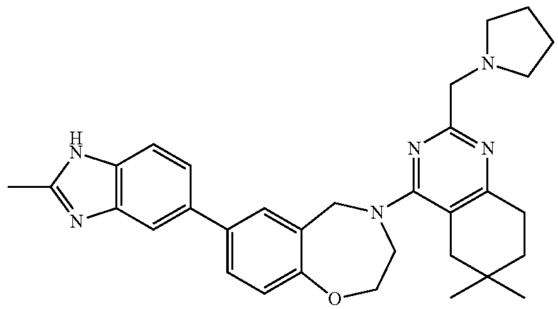 [SMILES: Cc1nc2cc(-c3ccc4c(c3)CN(c3nc(CN5CCCC5)nc5c3CC(C)(C)CC5)CCO4)ccc2[nH]1] | 4-[6,6-dimethyl-2-(pyrrolidin-1-ylmethyl)-5,6,7,8-tetrahydroquinazolin-4-yl]-7-(2-methyl-1H-benzimidazol-5-yl)-2,3,4,5-tetrahydro-1,4-benzoxazepine |
| 501 | 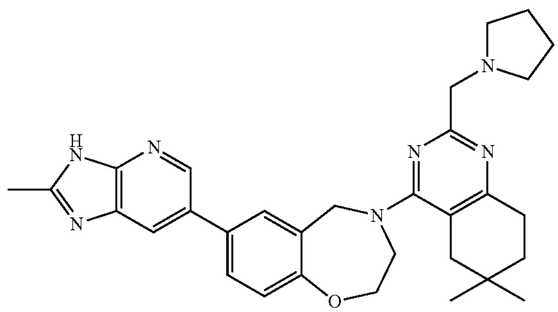 [SMILES: Cc1nc2cc(-c3ccc4c(c3)CN(c3nc(CN5CCCC5)nc5c3CC(C)(C)CC5)CCO4)cnc2[nH]1] | 4-[6,6-dimethyl-2-(pyrrolidin-1-ylmethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine |
| 502 | 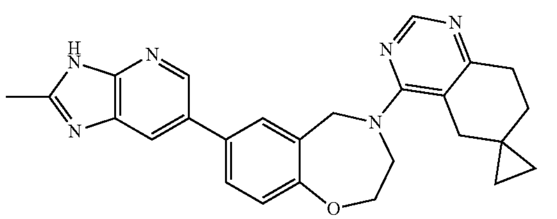 [SMILES: Cc1nc2cc(-c3ccc4c(c3)CN(c3ncnc5c3CC3(CC5)CC3)CCO4)cnc2[nH]1] | 4'-[7-(2-methyl-3H-imidazo[4,5-b]pyridin-6-yl)-2,3-dihydro-1,4-benzoxazepin-4(5H)-7',8'-dihydro-5'H-spiro[cyclopropane-1,6'-quinazoline] |
| 503 | 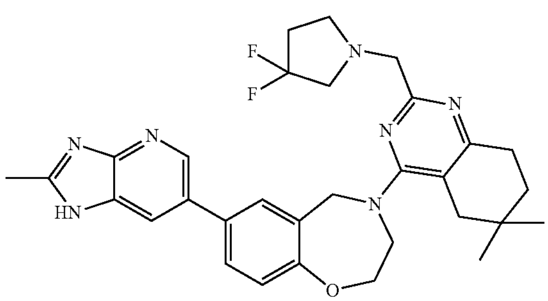 | 4-{2-[(3,3-difluoropyrrolidin-1-yl)methyl]-6,6-dimethyl-5,6,7,8-tetrahydroquinazolin-4-yl}-7-(2-methyl-1H-imidazo[4,5-b]pyridin-6-yl)-2,3,4,5-tetrahydro-1,4-benzoxazepine |
| 504 | 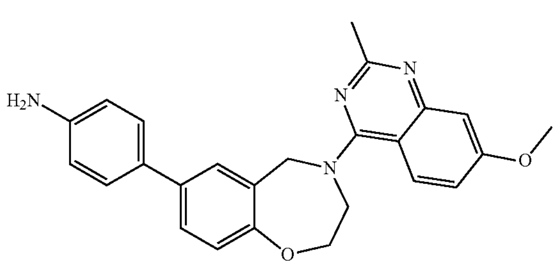 [SMILES: COc1ccc2c(N3CCOc4ccc(-c5ccc(N)cc5)cc4C3)nc(C)nc2c1] | 4-{4-[2-methyl-7-(methyloxy)quinazolin-4-yl]-2,3,4,5-tetrahydro-1,4-benzoxazepin-7-yl}aniline |

-continued

| Cmpd No. | Structure | Name |
|---|---|---|
| 505 | 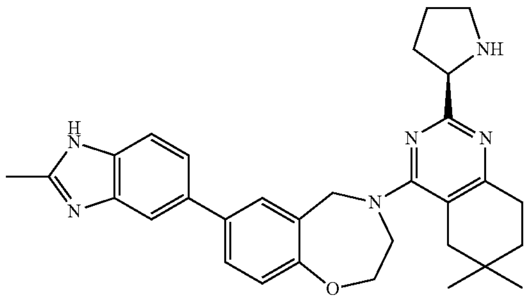 | 4-{6,6-dimethyl-2-[(2R)-pyrrolidin-2-yl]-5,6,7,8-tetrahydroquinazolin-4-yl}-7-(2-methyl-1H-benzimidazol-5-yl)-2,3,4,5-tetrahydro-1,4-benzoxazepine |
| 506 | 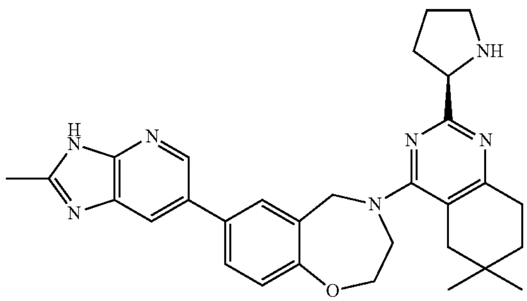 | 4-{6,6-dimethyl-2-[(2R)-pyrrolidin-2-yl]-5,6,7,8-tetrahydroquinazolin-4-yl]-7-(2-methyl-3H-imidazo[4,5-b]pyridin-6-yl)-2,3,4,5-tetrahydro-1,4-benzoxazepine |
| 507 | 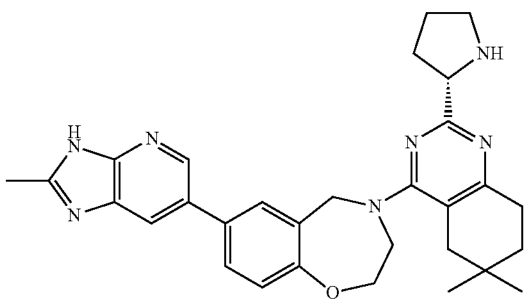 | 4-{6,6-dimethyl-2-[(2S)-pyrrolidin-2-yl]-5,6,7,8-tetrahydroquinazolin-4-yl}-7-(2-methyl-3H-imidazo[4,5-b]pyridin-6-yl)-2,3,4,5-tetrahydro-1,4-benzoxazepine |
| 508 | 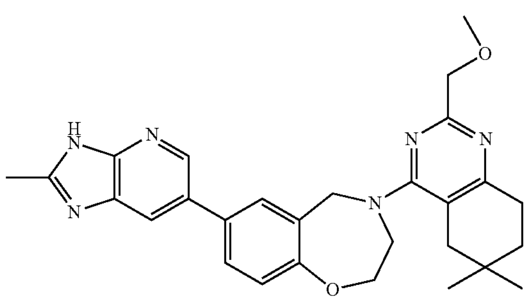 | 4-{6,6-dimethyl-2-[(methyloxy)methyl]-5,6,7,8-tetrahydroquinazolin-4-yl}-7-(2-methyl-3H-imidazo[4,5-b]pyridin-6-yl)-2,3,4,5-tetrahydro-1,4-benzoxazepine |
| 509 | 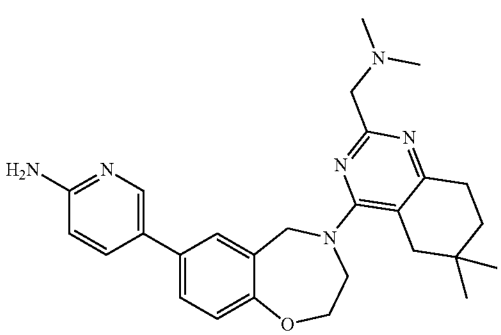 [SMILES: CN(C)Cc1nc2c(c(N3CCOc4ccc(-c5ccc(N)nc5)cc4C3)n1)CC(C)(C)CC2] | 5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)pyridin-2-amine |

-continued

| Cmpd No. | Structure | Name |
|---|---|---|
| 510 | 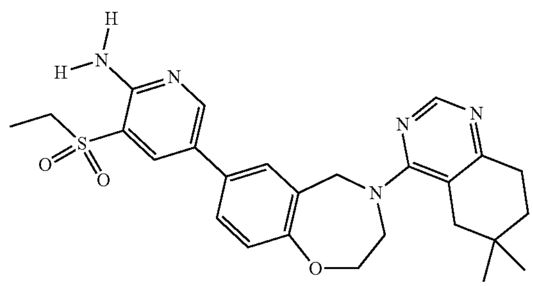 [SMILES: CCS(=O)(=O)c1cc(-c2ccc3c(c2)CN(c2ncnc4c2CC(C)(C)CC4)CCO3)cnc1N] | 5-[4-(6,6-dimethyl-5,6,7,8-tetrahydroquinazolin-4-yl)-2,3,4,5-tetrahydro-1,4-benzoxazepin-7-yl]-3-(ethylsulfonyl)pyridin-2-amine |
| 511 | 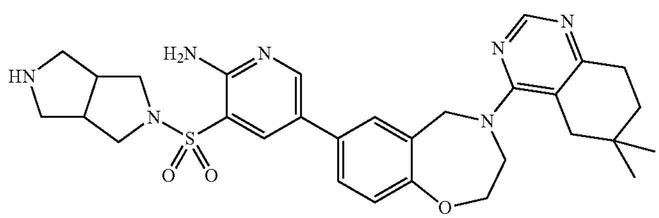 [SMILES: CC1(C)CCc2ncnc(N3CCOc4ccc(-c5cnc(N)c(S(=O)(=O)N6CC7CNCC7C6)c5)cc4C3)c2C1] | 5-[4-(6,6-dimethyl-5,6,7,8-tetrahydroquinazolin-4-yl)-2,3,4,5-tetrahydro-1,4-benzoxazepin-7-yl]-3-(hexahydropyrrolo[3,4-c]pyrrol-2(1H)-ylsulfonyl)pyridin-2-amine |
| 512 | 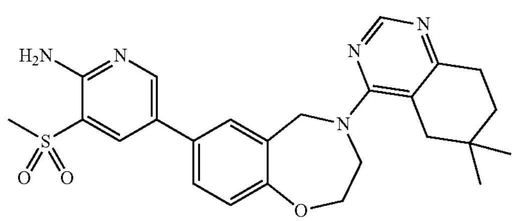 | 5-[4-(6,6-dimethyl-5,6,7,8-tetrahydroquinazolin-4-yl)-2,3,4,5-tetrahydro-1,4-benzoxazepin-7-yl]-3-(methylsulfonyl)pyridin-2-amine |
| 513 | 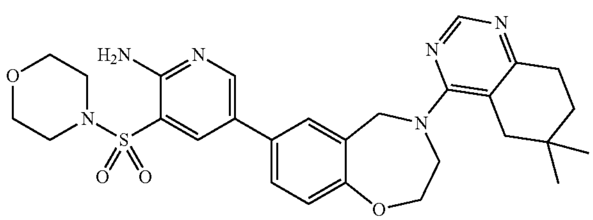 [SMILES: CC1(C)CCc2ncnc(N3CCOc4ccc(-c5cnc(N)c(S(=O)(=O)N6CCOCC6)c5)cc4C3)c2C1] | 5-[4-(6,6-dimethyl-5,6,7,8-tetrahydroquinazolin-4-yl)-2,3,4,5-tetrahydro-1,4-benzoxazepin-7-yl]-3-(morpholin-4-ylsulfonyl)pyridin-2-amine |
| 514 | 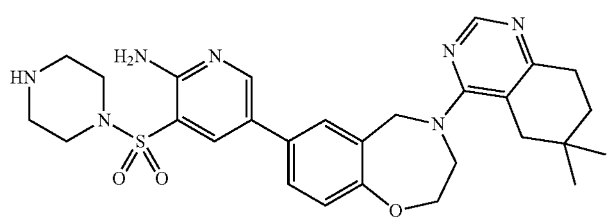 [SMILES: CC1(C)CCc2ncnc(N3CCOc4ccc(-c5cnc(N)c(S(=O)(=O)N6CCNCC6)c5)cc4C3)c2C1] | 5-[4-(6,6-dimethyl-5,6,7,8-tetrahydroquinazolin-4-yl)-2,3,4,5-tetrahydro-1,4-benzoxazepin-7-yl]-3-(piperazin-1-ylsulfonyl)puridin-2-amine |
| 515 | 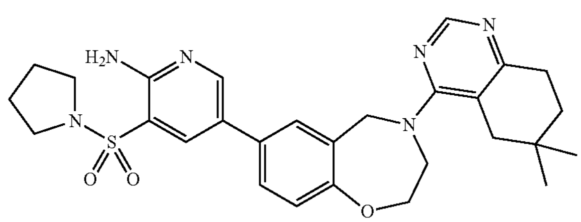 [SMILES: CC1(C)CCc2ncnc(N3CCOc4ccc(-c5cnc(N)c(S(=O)(=O)N6CCCC6)c5)cc4C3)c2C1] | 5-[4-(6,6-dimethyl-5,6,7,8-tetrahydroquinazolin-4-yl)-2,3,4,5-tetrahydro-1,4-benzoxazepin-7-yl]-3-(pyrrolidin-1-ylsulfonyl)pyridin-2-amine |

| Cmpd No. | Structure | Name |
|---|---|---|
| 516 | 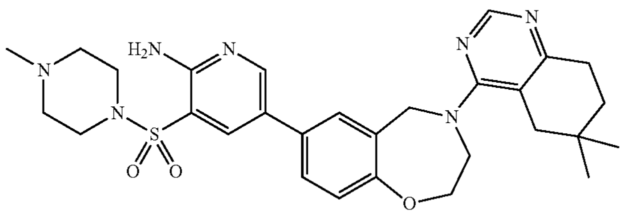 | 5-[4-(6,6-dimethyl-5,6,7,8-tetrahydroquinazolin-4-yl)-2,3,4,5-tetrahydro-1,4-benzoxazepin-7-yl]-3-[(4-methylpiperazin-1-yl)sulfonyl]pyridin-2-amine |
| 517 | 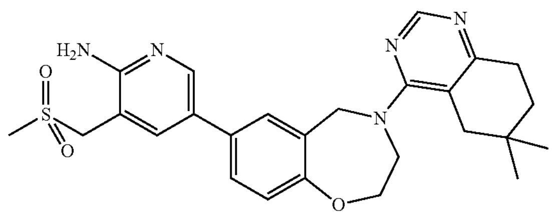 | 5-[4-(6,6-dimethyl-5,6,7,8-tetrahydroquinazolin-4-yl)-2,3,4,5-tetrahydro-1,4-benzoxazepin-7-yl]-3-[(methylsulfonyl)methyl]pyridin-2-amine |
| 518 | 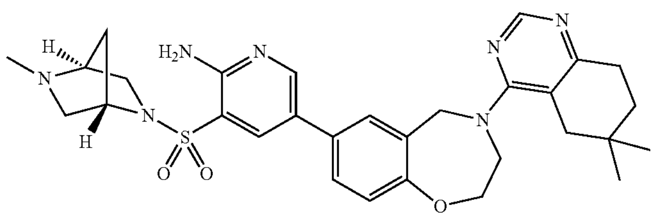 | 5-[4-(6,6-dimethyl-5,6,7,8-tetrahydroquinazolin-4-yl)-2,3,4,5-tetrahydro-1,4-benzoxazepin-7-yl]-3-{[(1S,4S)-5-methyl-2,5-diazabicyclo[2.2.1]hept-2-yl]sulfonyl}pyridin-2-amine |
| 519 | 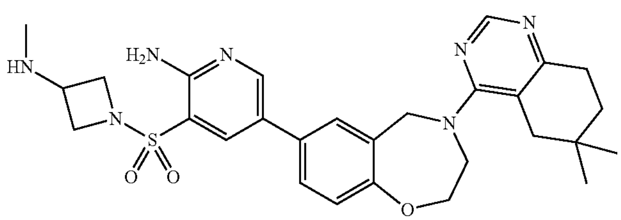 [SMILES: CNC1CN(S(=O)(=O)c2cc(-c3ccc4c(c3)CN(c3ncnc5c3CC(C)(C)CC5)CCO4)cnc2N)C1] | 5-[4-(6,6-dimethyl-5,6,7,8-tetrahydroquinazolin-4-yl)-2,3,4,5-tetrahydro-1,4-benzoxazepin-7-yl]-3-{[3-(methylamino)azetidin-1-yl]sulfonyl}pyridin-2-amine |
| 520 | 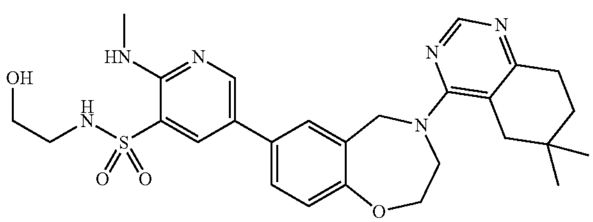 [SMILES: CNc1ncc(-c2ccc3c(c2)CN(c2ncnc4c2CC(C)(C)CC4)CCO3)cc1S(=O)(=O)NCCO] | 5-[4-(6,6-dimethyl-5,6,7,8-tetrahydroquinazolin-4-yl)-2,3,4,5-tetrahydro-1,4-benzoxazepin-7-yl]-N-(2-hydroxyethyl)-2-(methylamino)pyridine-3-sulfonamide |
| 521 | 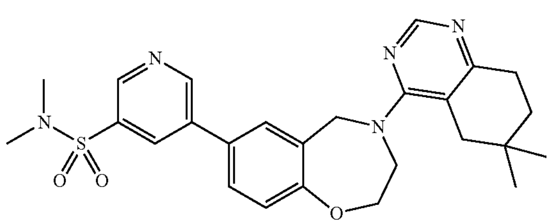 | 5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-sulfonamide |
| 522 | 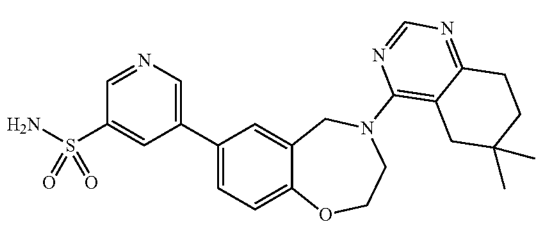 [SMILES: CC1(C)CCc2ncnc(N3CCOc4ccc(-c5cncc(S(N)(=O)=O)c5)cc4C3)c2C1] | 5-[4-(6,6-dimethyl-5,6,7,8-tetrahydroquinazolin-4-yl)-2,3,4,5-tetrahydro-1,4-benzoxazepin-7-yl]pyridin-3-sulfonamide |

-continued

| Cmpd No. | Structure | Name |
|---|---|---|
| 523 | 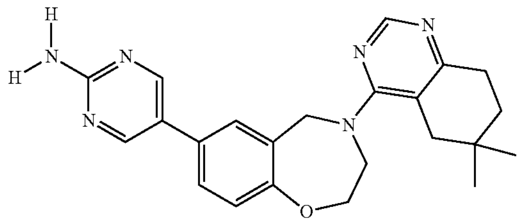 [SMILES: CC1(C)CCc2ncnc(N3CCOc4ccc(-c5cnc(N)nc5)cc4C3)c2C1] | 5-[4-(6,6-dimethyl-5,6,7,8-tetrahydroquinazolin-4-yl)-2,3,4,5-tetrahydro-1,4-benzoxazepin-7-yl]pyrimidin-2-amine |
| 524 | 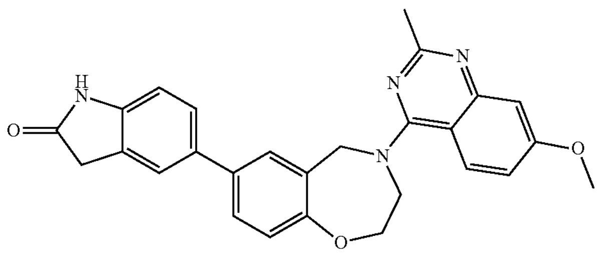 [SMILES: COc1ccc2c(N3CCOc4ccc(-c5ccc6c(c5)CC(=O)N6)cc4C3)nc(C)nc2c1] | 5-{4-[2-methyl-7-(methyloxy)quinazolin-4-yl]-2,3,4,5-tetrahydro-1,4-benzoxazepin-7-yl}-1,3-dihydro-2H-indol-2-one |
| 525 | 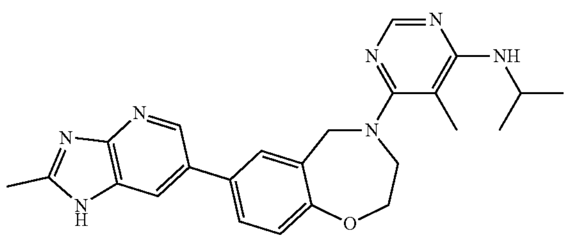 [SMILES: Cc1nc2ncc(-c3ccc4c(c3)CN(c3ncnc(NC(C)C)c3C)CCO4)cc2[nH]1] | 5-methyl-N-(1-methylethyl)-6-[7-(2-methyl-1H-imidazo[4,5-b]pyridin-6-yl)-2,3-dihydro-1,4-benzoxazepin-4(5H)-yl]pyrimidin-4-amine |
| 526 | 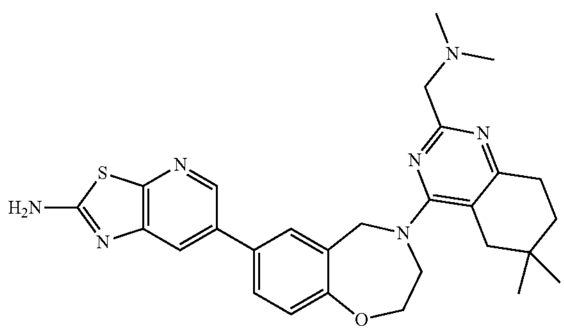 [SMILES: CN(C)Cc1nc2c(c(N3CCOc4ccc(-c5cnc6sc(N)nc6c5)cc4C3)n1)CC(C)(C)CC2] | 6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)[1,3]thiazolo[5,4-b]pyridin-2-amine |
| 527 | 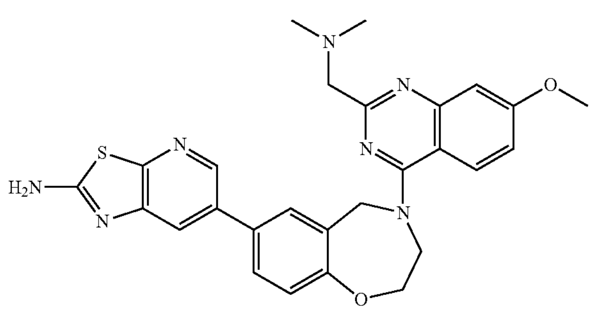 [SMILES: COc1ccc2c(N3CCOc4ccc(-c5cnc6sc(N)nc6c5)cc4C3)nc(CN(C)C)nc2c1] | 6-(4-{2-[(dimethylamino)methyl]-7-(methyloxy)quinazolin-4-yl}-2,3,4,5-tetrahydro-1,4-benzoxazepin-7-yl)[1,3]thiazolo[5,4-b]pyridin-2-amine |

| Cmpd No. | Structure | Name |
|---|---|---|
| 529 | 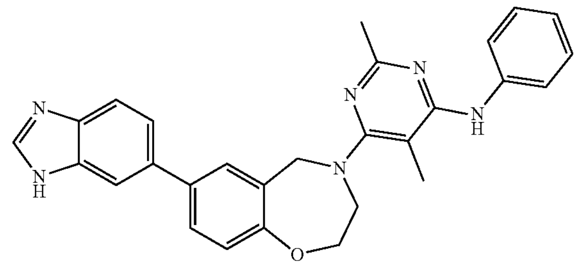 [SMILES: Cc1nc(Nc2ccccc2)c(C)c(N2CCOc3ccc(-c4ccc5nc[nH]c5c4)cc3C2)n1] | 6-[7-(1H-benzimidazol-6-yl)-2,3-dihydro-1,4-benzoxazepin-4(5H)-yl]-2,5-dimethyl-N-phenylpyrimidin-4-amine |
| 530 | 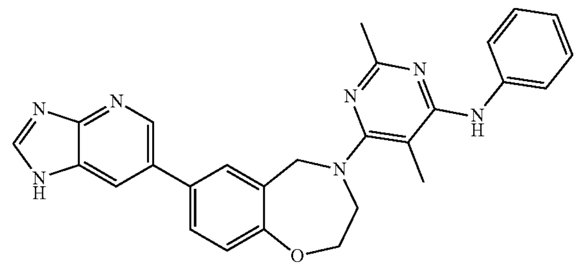 [SMILES: Cc1nc(Nc2ccccc2)c(C)c(N2CCOc3ccc(-c4cnc5nc[nH]c5c4)cc3C2)n1] | 6-[7-(1H-imidazo[4,5-b]pyridin-6-yl)-2,3-dihydro-1,4-benzoxazepin-4(5H)-yl]-2,5-dimethyl-N-phenyl]pyrimidin-4-amine |
| 531 | 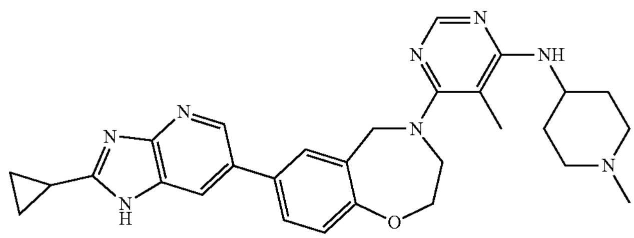 [SMILES: Cc1c(NC2CCN(C)CC2)ncnc1N1CCOc2ccc(-c3cnc4nc(C5CC5)[nH]c4c3)cc2C1] | 6-[7-(2-cyclopropyl-1H-imidazo[4,5-b]pyridin-6-yl)-2,3-dihydro-1,4-benzoxazepin-4(5H)-yl]-5-methyl-N-(1-methylpiperidin-4-yl)pyrimidin-4-amine |
| 532 | 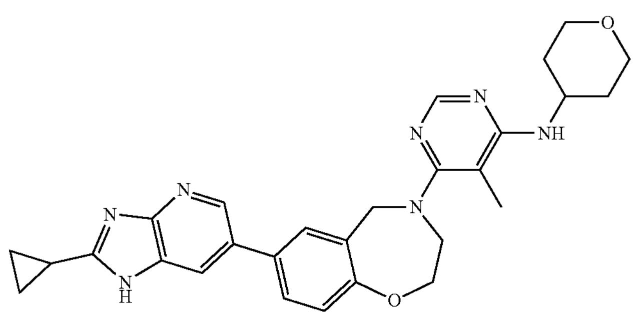 [SMILES: Cc1c(NC2CCOCC2)ncnc1N1CCOc2ccc(-c3cnc4nc(C5CC5)[nH]c4c3)cc2C1] | 6-[7-(2-cyclopropyl-1H-imidazo[4,5-b]pyridin-6-yl)-2,3-dihydro-1,4-benzoxazepin-4(5H)-yl]-5-methyl-N-(tetrahydro-2H-pyran-4-yl)pyrimidin-4-amine |
| 533 | 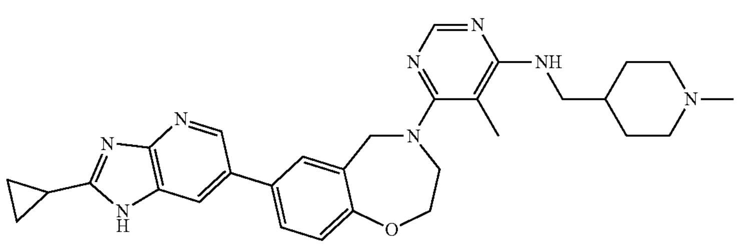 [SMILES: Cc1c(NCC2CCN(C)CC2)ncnc1N1CCOc2ccc(-c3cnc4nc(C5CC5)[nH]c4c3)cc2C1] | 6-[7-(2-cyclopropyl-1H-imidazo[4,5-b]pyridin-6-yl)-2,3-dihydro-1,4-benzoxazepin-4(5H)-yl]-5-methyl-N-[(1-methylpiperidin-4-yl)methyl]pyrimidin-4-amine |
| 534 | 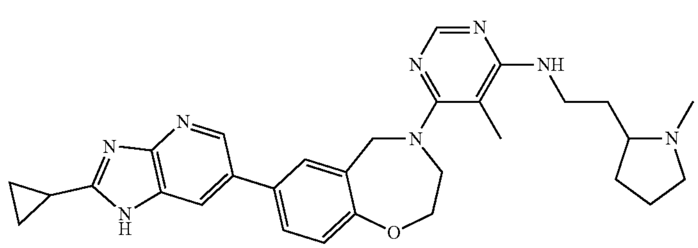 [SMILES: Cc1c(NCCC2CCCN2C)ncnc1N1CCOc2ccc(-c3cnc4nc(C5CC5)[nH]c4c3)cc2C1] | 6-[7-(2-cyclopropyl-1H-imidazo[4,5-b]pyridin-6-yl)-2,3-dihydro-1,4-benzoxazepin-4(5H)-yl]-5-methyl-N-[2-(1-methylpyrrolidin-2-yl)ethyl]pyrimidin-4-amine |

-continued

| Cmpd No. | Structure | Name |
|---|---|---|
| 535 | 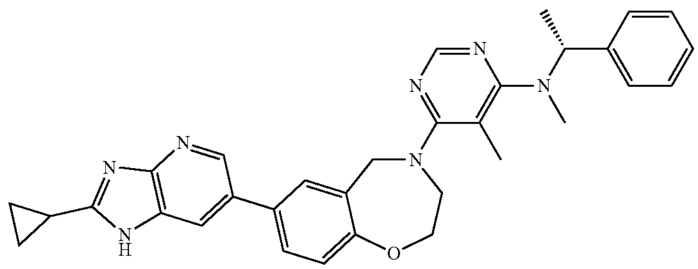 [SMILES: Cc1c(N2CCOc3ccc(-c4cnc5nc(C6CC6)[nH]c5c4)cc3C2)ncnc1N(C)[C@H](C)c1ccccc1] | 6-[7-(2-cyclopropyl-1H-imidazo[4,5-b]pyridin-6-yl)-2,3-dihydro-1,4-benzoxazepin-4(5H)-yl]-N,5-dimethyl-N-[(1R)-1-phenylethyl]pyrimidin-4-amine |
| 536 | 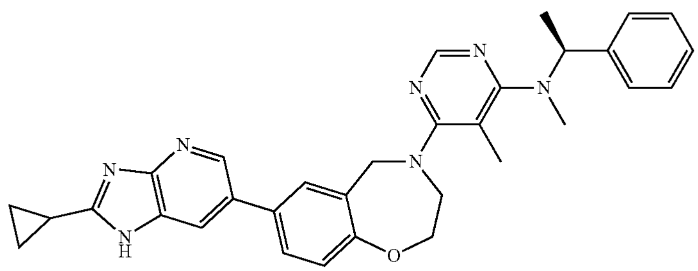 [SMILES: Cc1c(N2CCOc3ccc(-c4cnc5nc(C6CC6)[nH]c5c4)cc3C2)ncnc1N(C)[C@@H](C)c1ccccc1] | 6-[7-(2-cyclopropyl-1H-imidazo[4,5-b]pyridin-6-yl)-2,3-dihydro-1,4-benzoxazepin-4(5H)-yl]-N,5-dimethyl-N-[(1S)-1-phenylethyl]pyrimidin-4-amine |
| 537 | 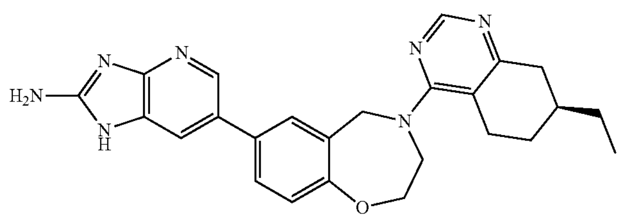 [SMILES: CC[C@H]1CCc2c(ncnc2N2CCOc3ccc(-c4cnc5nc(N)[nH]c5c4)cc3C2)C1] | 6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-amine |
| 538 | 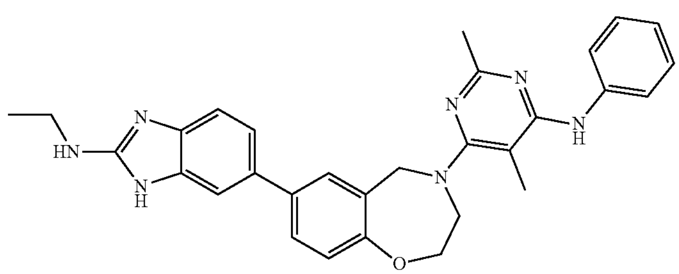 [SMILES: CCNc1nc2ccc(-c3ccc4c(c3)CN(c3nc(C)nc(Nc5ccccc5)c3C)CCO4)cc2[nH]1] | 6-{4-[2,5-dimethyl-6-(phenylamino)pyrimidin-4-yl]-2,3,4,5-tetrahydro-1,4-benzoxazepin-7-yl}-N--ethyl-1H-benzimidazol-2-amine |
| 539 | 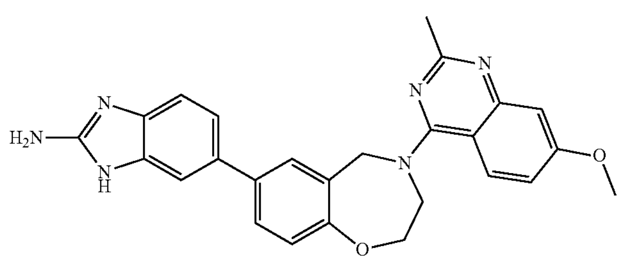 [SMILES: COc1ccc2c(N3CCOc4ccc(-c5ccc6nc(N)[nH]c6c5)cc4C3)nc(C)nc2c1] | 6-{4-[2-methyl-7-(methyloxy)quinazolin-4-yl]-2,3,4,5-tetrahydro-1,4-benzoxazepin-7-yl}-1H-benzimidazol-2-amine |
| 540 | 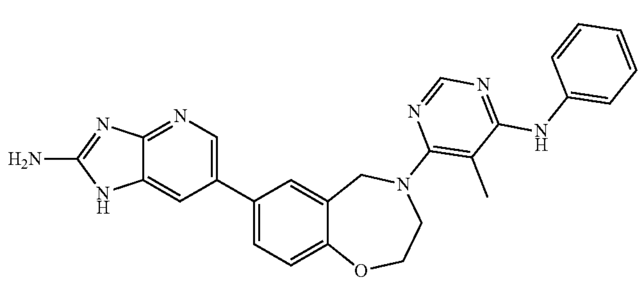 [SMILES: Cc1c(Nc2ccccc2)ncnc1N1CCOc2ccc(-c3cnc4nc(N)[nH]c4c3)cc2C1] | 6-{4-[5-methyl-6-(phenylamino)pyrimidin-4-yl]-2,3,4,5-tetrahydro-1,4-benzoxazepin-7-yl}-1H-imidazo[4,5-b]pyridin-2-amine |

-continued

| Cmpd No. | Structure | Name |
|---|---|---|
| 541 | 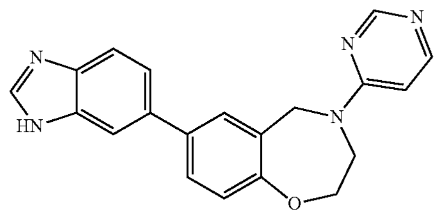 [SMILES: c1cc(N2CCOc3ccc(-c4ccc5nc[nH]c5c4)cc3C2)ncn1] | 7-(1H-benzimidazol-6-yl)-4-pyrimidin-4-yl-2,3,4,5-tetrahydro-1,4-benzoxazepine |
| 542 | 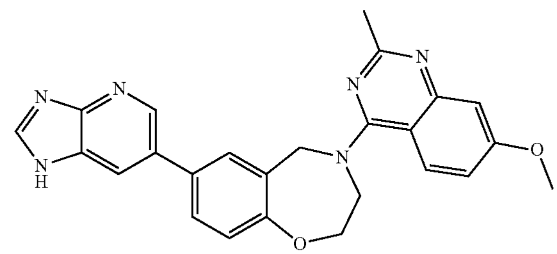 [SMILES: COc1ccc2c(N3CCOc4ccc(-c5cnc6nc[nH]c6c5)cc4C3)nc(C)nc2c1] | 7-(1H-imidazo[4,5-b]pyridin-6-yl)-4-[2-methyl-7-(methyloxy)quinazolin-4-yl]-2,3,4,5-tetrahydro-1,4-benzoxazepine |
| 543 | 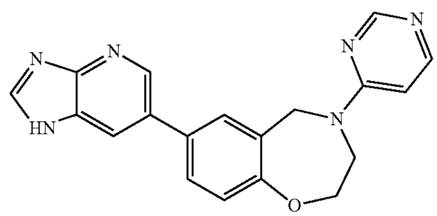 [SMILES: c1cc(N2CCOc3ccc(-c4cnc5nc[nH]c5c4)cc3C2)ncn1] | 7-(1H-imidazo[4,5-b]pyridin-6-yl)-4-pyrimidin-4-yl-2,3,4,5-tetrahydro-1,4-benzoxazepine |
| 544 | 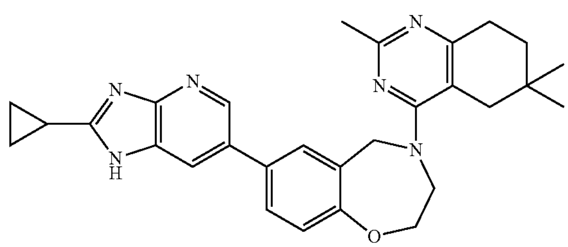 [SMILES: Cc1nc2c(c(N3CCOc4ccc(-c5cnc6nc(C7CC7)[nH]c6c5)cc4C3)n1)CC(C)(C)CC2] | 7-(2-cyclopropyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine |
| 545 | 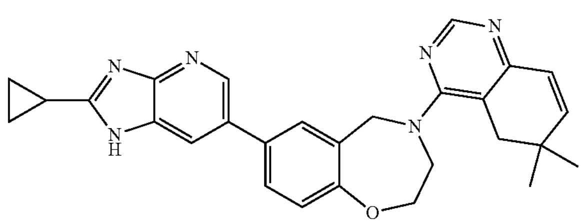 [SMILES: CC1(C)C=Cc2ncnc(N3CCOc4ccc(-c5cnc6nc(C7CC7)[nH]c6c5)cc4C3)c2C1] | 7-(2-cyclopropyl-1H-imidazo[4,5-b]pyridin-6-yl)-4-(6,6-dimethyl-5,6-dihydroquinazolin-4-yl)-2,3,4,5-tetrahydro-1,4-benzoxazepine |
| 546 | 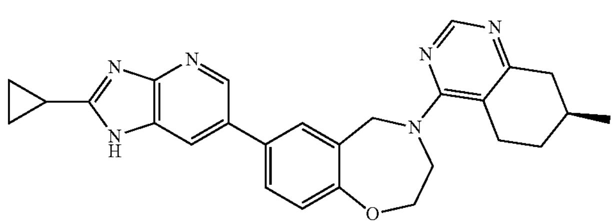 [SMILES: C[C@H]1CCc2c(ncnc2N2CCOc3ccc(-c4cnc5nc(C6CC6)[nH]c5c4)cc3C2)C1] | 7-(2-cyclopropyl-1H-imidazo[4,5-b]pyridin-6-yl)-4-[(7S)-7-methyl-5,6,7,8-tetrahydroquinazolin-4-yl]-2,3,4,5-tetrahydro-1,4-benzoxazepine |

-continued

| Cmpd No. | Structure | Name |
|---|---|---|
| 547 | 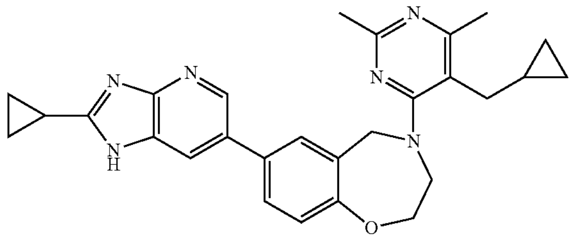 [SMILES: Cc1nc(C)c(CC2CC2)c(N2CCOc3ccc(-c4cnc5nc(C6CC6)[nH]c5c4)cc3C2)n1] | 7-(2-cyclopropyl-1H-imidazo[4,5-b]pyridin-6-yl)-4-[5-(cyclopropylmethyl)-2,6-dimethylpyrimidin-4-yl]-2,3,4,5-tetrahydro-1,4-benzoxazepine |
| 548 | 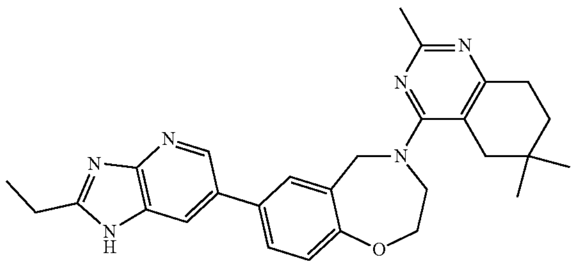 [SMILES: CCc1nc2ncc(-c3ccc4c(c3)CN(c3nc(C)nc5c3CC(C)(C)CC5)CCO4)cc2[nH]1] | 7-(2-ethyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine |
| 550 | 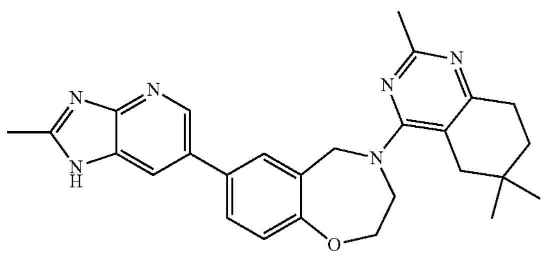 | 7-(2-methyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine |
| 551 | 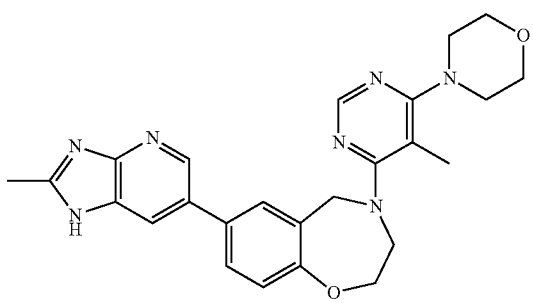 [SMILES: Cc1nc2ncc(-c3ccc4c(c3)CN(c3ncnc(N5CCOCC5)c3C)CCO4)cc2[nH]1] | 7-(2-methyl-1H-imidazo[4,5-b]pyridin-6-yl)-4-(5-methyl-6-morpholin-4-yl]pyrimidin-4-yl)-2,3,4,5-tetrahydro-1,4-benzoxazepine |
| 552 | 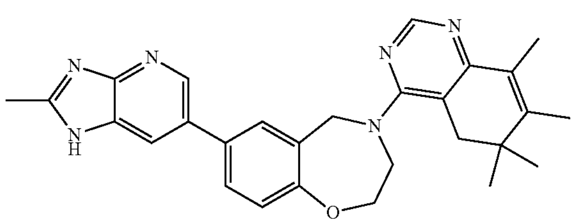 | 7-(2-methyl-1H-imidazo[4,5-b]pyridin-6-yl)-4-(6,6,7,8-tetramethyl-5,6-dihydroquinazolin-4-yl)-2,3,4,5-tetrahydro-1,4-benzoxazepine |
| 553 | 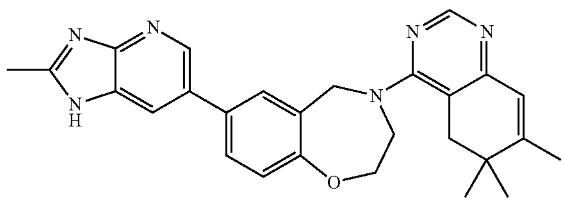 | 7-(2-methyl-1H-imidazo[4,5-b]pyridin-6-yl)-6,6,7-trimethyl-5,6-dihydroquinazolin-4-yl)-2,3,4,5-tetrahydro-1,4-benzoxazepine |

-continued

| Cmpd No. | Structure | Name |
|---|---|---|
| 554 | 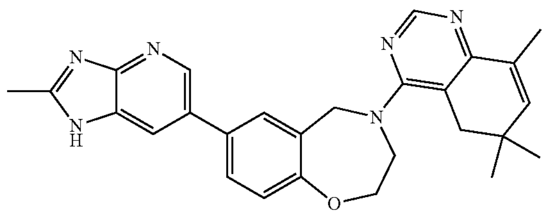 | 7-(2-methyl-1H-imidazo[4,5-b]pyridin-6-yl)-4-(6,6,8-trimethyl-5,6-dihydroquinazolin-4-yl)-2,3,4,5-tetrahydro-1,4-benzoxazepine |
| 555 | 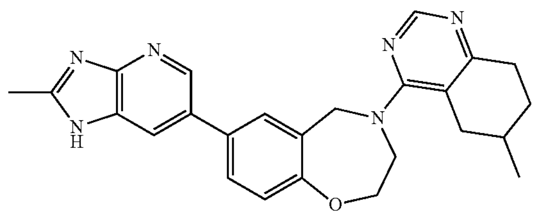 [SMILES: Cc1nc2ncc(-c3ccc4c(c3)CN(c3ncnc5c3CC(C)CC5)CCO4)cc2[nH]1] | 7-(2-methyl-1H-imidazo[4,5-b]pyridin-6-yl)-4-(6-methyl-5,6,7,8-tetrahydroquinazolin-4-yl)-2,3,4,5-tetrahydro-1,4-benzoxazepine |
| 556 | 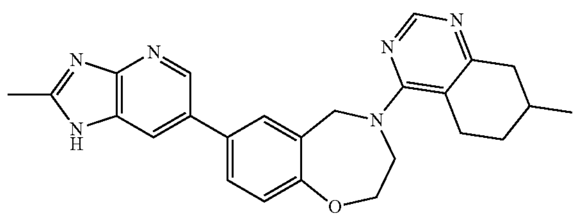 | 7-(2-methyl-1H-imidazo[4,5-b]pyridin-6-yl)-4-(7-methyl-5,6,7,8-tetrahydroquinazolin-4-yl)-2,3,4,5-tetrahydro-1,4-benzoxazepine |
| 557 | 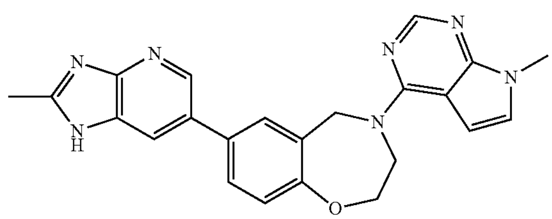 | 7-(2-methyl-1H-imidazo[4,5-b]pyridin-6-yl)-4-(7-methyl-7H-pyrrolo[2,3-d]pyrimidin-4-yl)-2,3,4,5-tetrahydro-1,4-benzoxazepine |
| 558 | 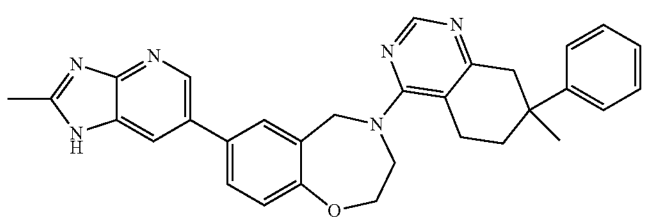 [SMILES: Cc1nc2ncc(-c3ccc4c(c3)CN(c3ncnc5c3CCC(C)(c3ccccc3)C5)CCO4)cc2[nH]1] | 7-(2-methyl-1H-imidazo[4,5-b]pyridin-6-yl)-4-(7-methyl-7-phenyl-5,6,7,8-tetrahydroquinazolin-4-yl)-2,3,4,5-tetrahydro-1,4-benzoxazepine |
| 559 | 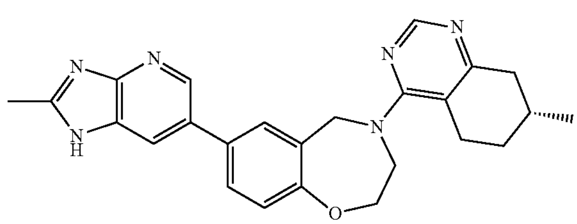 | 7-(2-methyl-1H-imidazo[4,5-b]pyridin-6-yl)-4-[(7R)-7-methyl-5,6,7,8-tetrahydroquinazolin-4-yl]-2,3,4,5-tetrahydro-1,4-benzoxazepine |
| 560 | 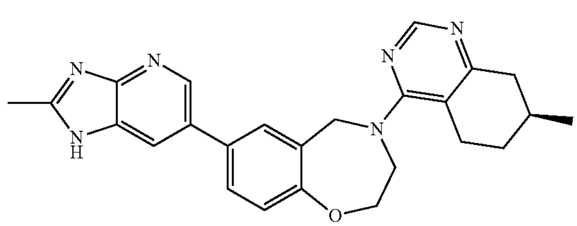 | 7-(2-methyl-1H-imidazo[4,5-b]pyridin-6-yl)-4-[(7S)-7-methyl-5,6,7,8-tetrahydroquinazolin-4-yl]-2,3,4,5-tetrahydro-1,4-benzoxazepine |

| Cmpd No. | Structure | Name |
| --- | --- | --- |
| 561 | 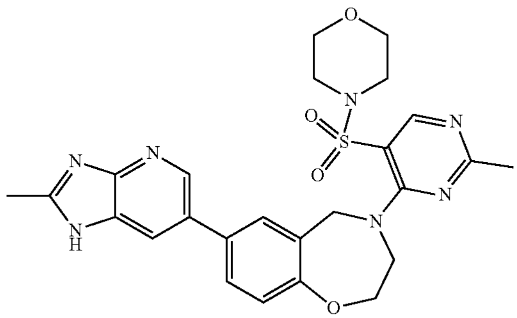 | 7-(2-methyl-1H-imidazo[4,5-b]pyridin-6-yl)-4-[2-methyl-5-(morpholin-4-ylsulfonyl)pyrimidin-4-yl]-2,3,4,5-tetrahydro-1,4-benzoxazepine |
| 562 | 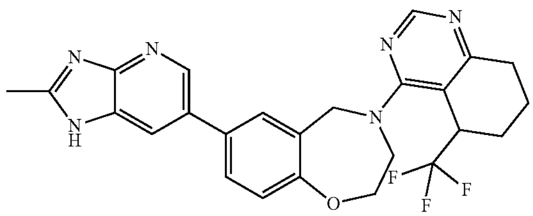 [SMILES: Cc1nc2ncc(-c3ccc4c(c3)CN(c3ncnc5c3C(C(F)(F)F)CCC5)CCO4)cc2[nH]1] | 7-(2-methyl-1H-imidazo[4,5-b]pyridin-6-yl)-4-[5-(trifluoromethyl)-5,6,7,8-tetrahydroquinazolin-4-yl]-2,3,4,5-tetrahydro-1,4-benzoxazepine |
| 563 | 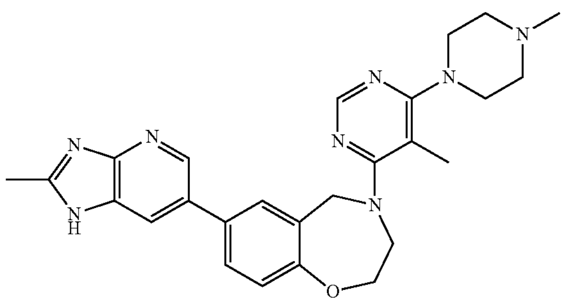 | 7-(2-methyl-1H-imidazo[4,5-b]pyridin-6-yl)-4-[5-methyl-6-(4-methylpiperazin-1-yl)pyrimidin-4-yl]-2,3,4,5-tetrahydro-1,4-benzoxazepine |
| 564 | 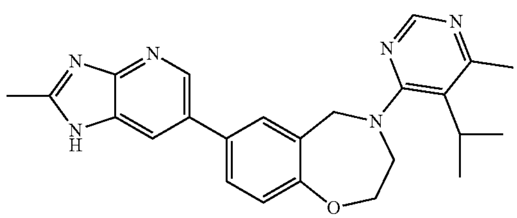 | 7-(2-methyl-1H-imidazo[4,5-b]pyridin-6-yl)-4-[6-methyl-5-(1-methylethyl)pyrimidin-4-yl]-2,3,4,5-tetrahydro-1,4-benzoxazepine |
| 565 | 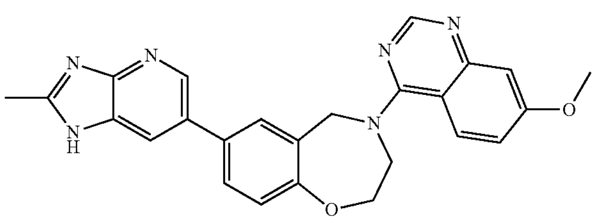 | 7-(2-methyl-1H-imidazo[4,5-b]pyridin-6-yl)-4-[7-(methyloxy)quinazolin-4-yl]-2,3,4,5-tetrahydro-1,4-benzoxazepine |
| 566 | 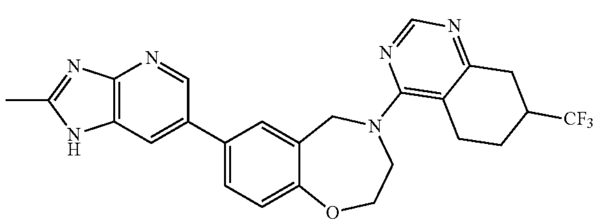 [SMILES: Cc1nc2ncc(-c3ccc4c(c3)CN(c3ncnc5c3CCC(C(F)(F)F)C5)CCO4)cc2[nH]1] | 7-(2-methyl-1H-imidazo[4,5-b]pyridin-6-yl)-4-[7-(trifluoromethyl)-5,6,7,8-tetrahydroquinazolin-4-yl]-2,3,4,5-tetrahydro-1,4-benzoxazepine |

| Cmpd No. | Structure | Name |
|---|---|---|
| 567 | 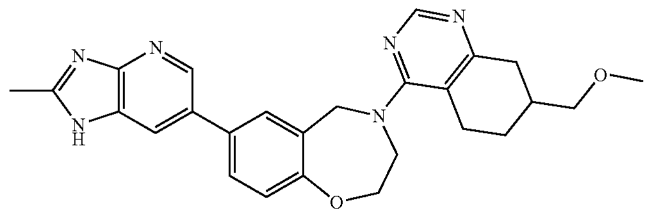 | 7-(2-methyl-1H-imidazo[4,5-b]pyridin-6-yl)-4-{7-[(methyloxy)methyl]-5,6,7,8-tetrahydrquinazolin-4-yl}-2,3,4,5-tetrahydro-1,4-benzoxazepine |
| 568 | 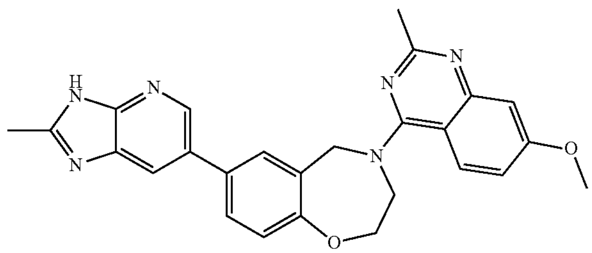 | 7-(2-methyl-1H-imidazo[4,5-b]pyridin-6-yl)-4-[2-methyl-7-(methyloxy)quinazolin-4-yl]-2,3,4,5-tetrahydro-1,4-benzoxazepine |
| 569 | 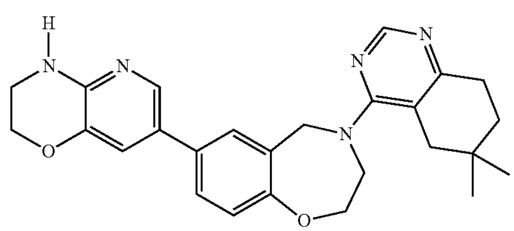 [SMILES: CC1(C)CCc2ncnc(N3CCOc4ccc(-c5cnc6c(c5)OCCN6)cc4C3)c2C1] | 7-(3,4-dihydro-2H-pyrido[2,3-b][1,4]oxazin-7-yl)-4-(6,6-dimethyl-5,6,7,8-tetrahydroquinazolin-4-yl)-2,3,4,5-tetrahydro-1,4-benzoxazepine |
| 570 | 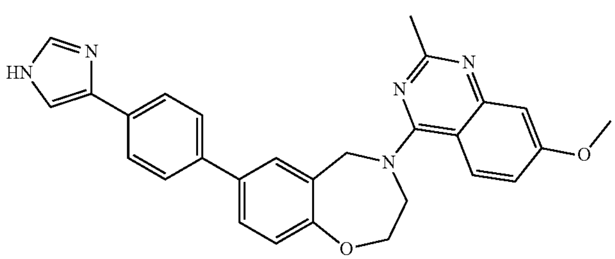 [SMILES: COc1ccc2c(N3CCOc4ccc(-c5ccc(-c6c[nH]cn6)cc5)cc4C3)nc(C)nc2c1] | 7-[4-(1H-imidazol-4-yl)phenyl]-4-[2-methyl-7-(methyloxy)quinazolin-4-yl]-2,3,4,5-tetrahydro-1,4-benzoxazepine |
| 571 | 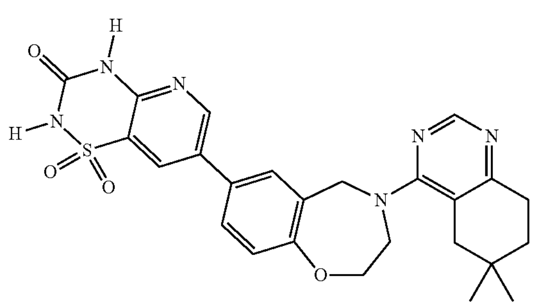 [SMILES: CC1(C)CCc2ncnc(N3CCOc4ccc(-c5cnc6c(c5)S(=O)(=O)NC(=O)N6)cc4C3)c2C1] | 7-[4-(6,6-dimethyl-5,6,7,8-tetrahydroquinazolin-4-yl)-2,3,4,5-tetrahydro-1,4-benzoxazepin-7-yl]-2H-pyrido[2,3-e][1,2,4]thiadiazin-3(4H)-one 1,1-dioxide |
| 572 | 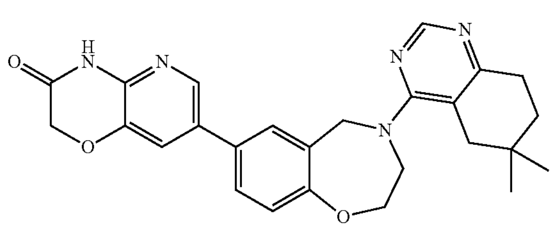 [SMILES: CC1(C)CCc2ncnc(N3CCOc4ccc(-c5cnc6c(c5)OCC(=O)N6)cc4C3)c2C1] | 7-[4-(6,6-dimethyl-5,6,7,8-tetrahydroquinazolin-4-yl)-2,3,4,5-tetrahydro-1,4-benzoxazepin-7-yl]-2H-pyrido[3,2-b][1,4]oxazin-3(4H)-one |

| Cmpd No. | Structure | Name |
|---|---|---|
| 573 | 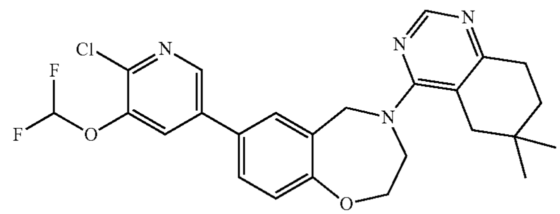 [SMILES: CC1(C)CCc2ncnc(N3CCOc4ccc(-c5cnc(Cl)c(OC(F)F)c5)cc4C3)c2C1] | 7-{6-chloro-5-[(difluoromethyl)oxy]pyridin-3-yl}-4-(6,6-dimethyl-5,6,7,8-tetrahydroquinazolin-4-yl)-2,3,4,5-tetrahydro-1,4-benzoxazepine |
| 574 | 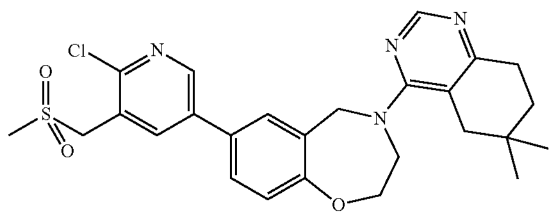 | 7-{6-chloro-5-[(methylsulfonyl)methyl]pyridin-3-yl}-4-(6,6-dimethyl-5,6,7,8-tetrahydroquinazolin-4-yl)-2,3,4,5-tetrahydro-1,4-benzoxazepine |
| 575 | 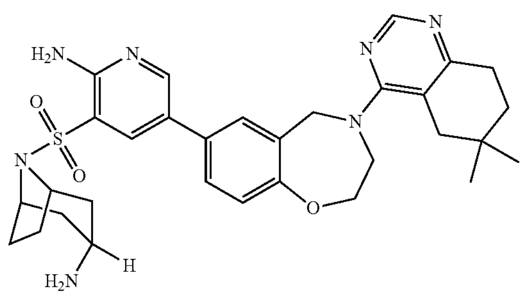 [SMILES: CC1(C)CCc2ncnc(N3CCOc4ccc(-c5cnc(N)c(S(=O)(=O)N6C7CCC6CC(N)C7)c5)cc4C3)c2C1] | 8-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-8-azabicyclo[3.2.1]octan-3-amine |
| 576 | 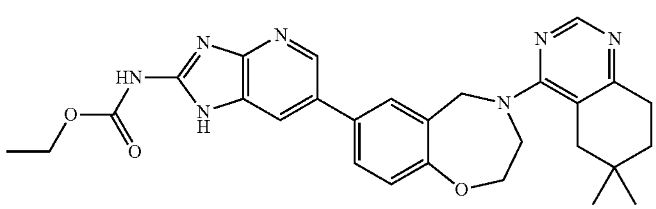 [SMILES: CCOC(=O)Nc1nc2ncc(-c3ccc4c(c3)CN(c3ncnc5c3CC(C)(C)CC5)CCO4)cc2[nH]1] | ethyl {6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}carbamate |
| 577 | 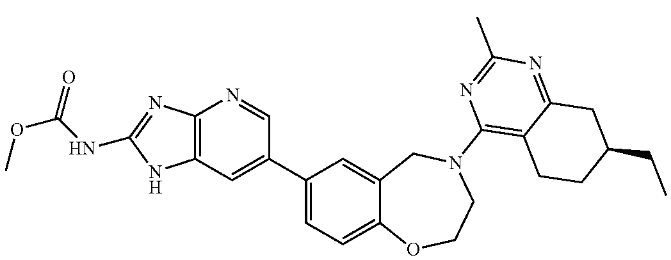 [SMILES: CC[C@H]1CCc2c(nc(C)nc2N2CCOc3ccc(-c4cnc5nc(NC(=O)OC)[nH]c5c4)cc3C2)C1] | methyl (6-{4-[(7S)-7-ethyl-2-methyl-5,6,7,8-tetrahydroquinazolin-4-yl]-2,3,4,5-tetrahydro-1,4-benzoxazepin-7-yl}-1H-imidazo[4,5-b]pyridin-2-yl)carbamate |
| 578 | 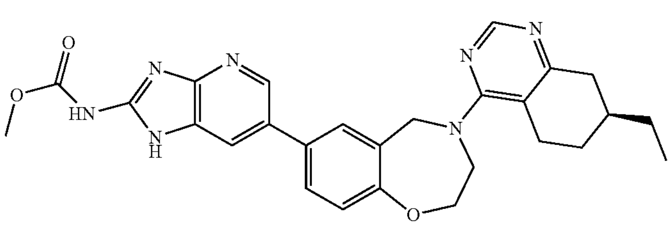 [SMILES: CC[C@H]1CCc2c(ncnc2N2CCOc3ccc(-c4cnc5nc(NC(=O)OC)[nH]c5c4)cc3C2)C1] | methyl (6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)carbamate |

| Cmpd No. | Structure | Name |
|---|---|---|
| 579 | 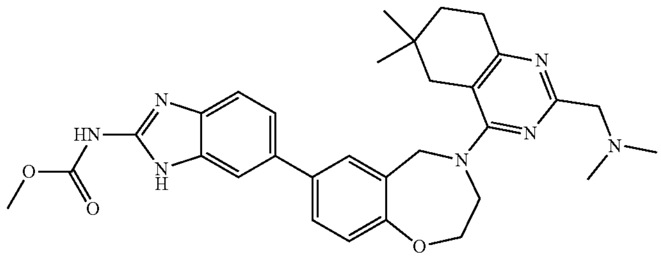 | methyl [6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-1H-benzimidazol-2-yl]carbamate |
| 580 | 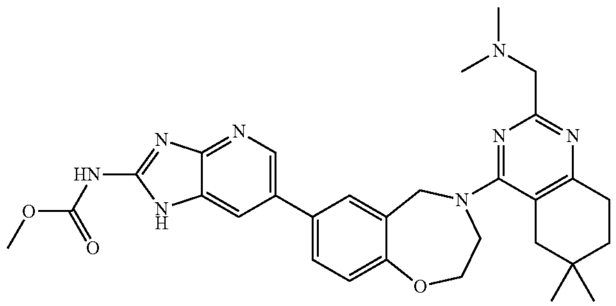 [SMILES: COC(=O)Nc1nc2ncc(-c3ccc4c(c3)CN(c3nc(CN(C)C)nc5c3CC(C)(C)CC5)CCO4)cc2[nH]1] | methyl [6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-1H-imidazo[4,5-b]pyridin-2-yl[carbamate |
| 581 | 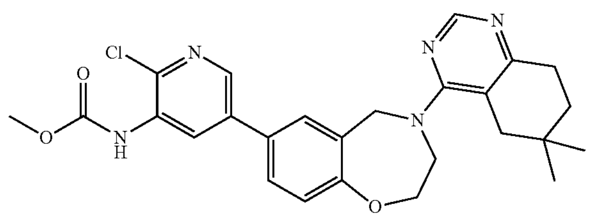 | methyl {2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}carbamate |
| 582 | 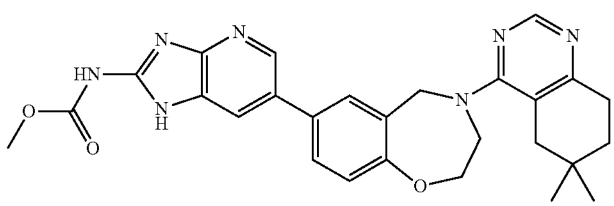 [SMILES: COC(=O)Nc1nc2ncc(-c3ccc4c(c3)CN(c3ncnc5c3CC(C)(C)CC5)CCO4)cc2[nH]1] | methyl {6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}carbamate |
| 583 | 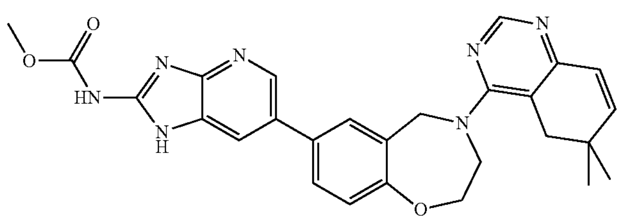 [SMILES: COC(=O)Nc1nc2ncc(-c3ccc4c(c3)CN(c3ncnc5c3CC(C)(C)C=C5)CCO4)cc2[nH]1] | methyl {6-[4-(6,6-dimethyl-5,6-dihydroquinazolin-4-yl)-2,3,4,5-tetrahydro-1,4-benzoxazepin-7-yl]-1H-imidazo[4,5-b]pyridin-2-yl}carbamate |
| 584 | 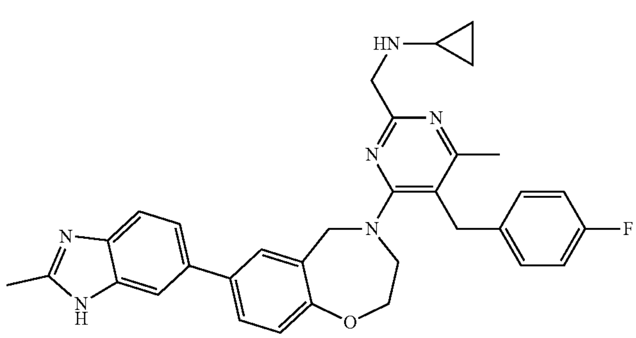 [SMILES: Cc1nc2ccc(-c3ccc4c(c3)CN(c3nc(CNC5CC5)nc(C)c3Cc3ccc(F)cc3)CCO4)cc2[nH]1] | N-({5-[(4-fluorophenyl)methyl]-4-methyl-6-[7-(2-methyl-1H-benzimidazol-6-yl)-2,3-dihydro-1,4-benzoxazepin-4(5H)-yl]pyrimidin-2-yl}methyl)cyclopropanamine |

US 8,648,066 B2

263                                                                      264
-continued

| Cmpd No. | Structure | Name |
|---|---|---|
| 585 | 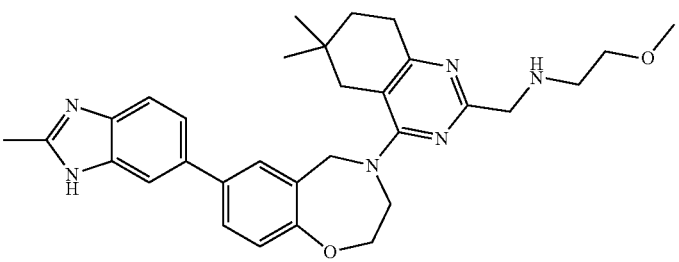 | N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)-2-(methyloxy)ethanamine |
| 586 | 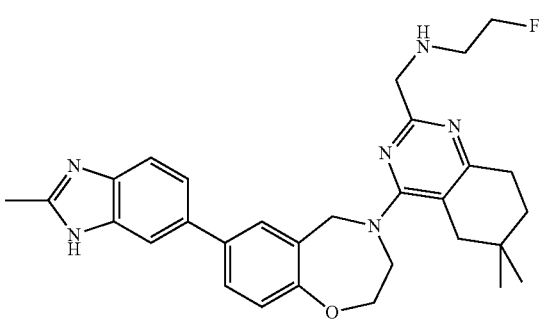 [SMILES: Cc1nc2ccc(-c3ccc4c(c3)CN(c3nc(CNCCF)nc5c3CC(C)(C)CC5)CCO4)cc2[nH]1] | N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)-2-fluoroethanamine |
| 587 | 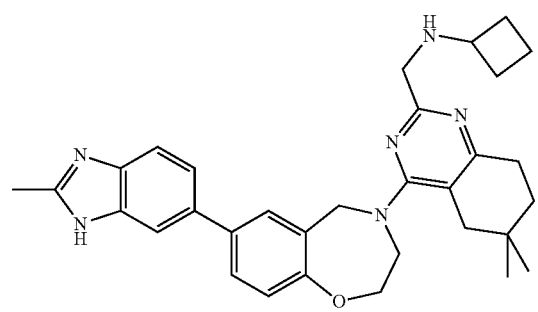 [SMILES: Cc1nc2ccc(-c3ccc4c(c3)CN(c3nc(CNC5CCC5)nc5c3CC(C)(C)CC5)CCO4)cc2[nH]1] | N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)cyclobutanamine |
| 588 | 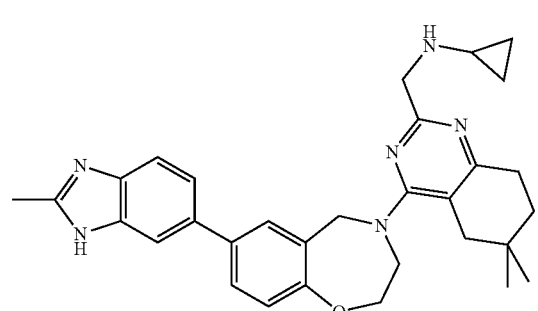 | N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)cyclopropanamine |
| 589 | 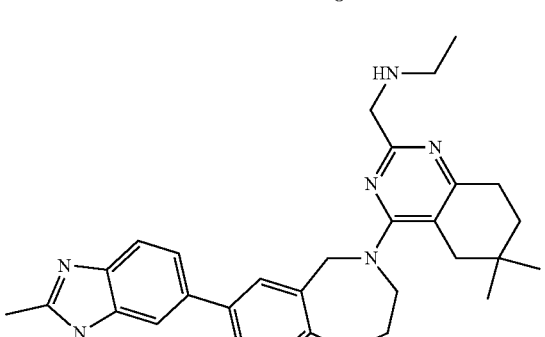 | N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)ethanamine |

-continued

| Cmpd No. | Structure | Name |
|---|---|---|
| 590 | 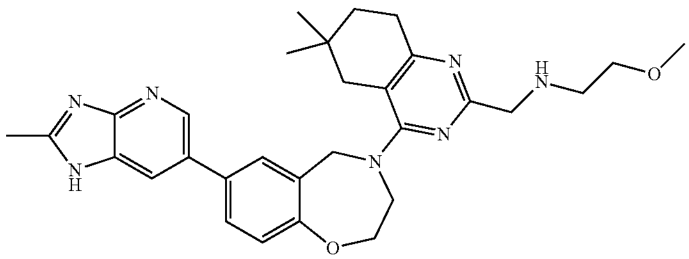 | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-(methyloxy)ethanamine |
| 591 | 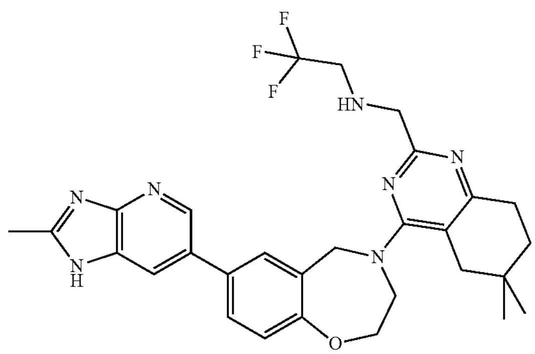 [SMILES: Cc1nc2ncc(-c3ccc4c(c3)CN(c3nc(CNCC(F)(F)F)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2,2,2-trifluoroethanamine |
| 592 | 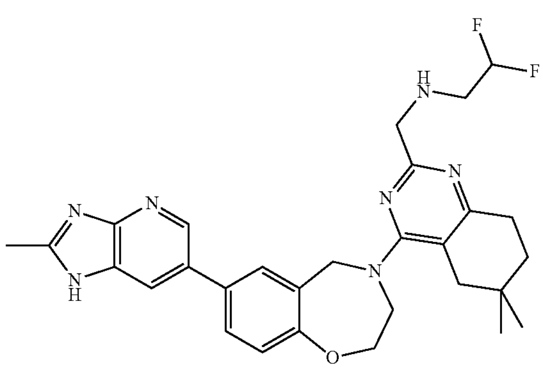 [SMILES: Cc1nc2ncc(-c3ccc4c(c3)CN(c3nc(CNCC(F)F)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2,2-difluoroethanamine |
| 593 | 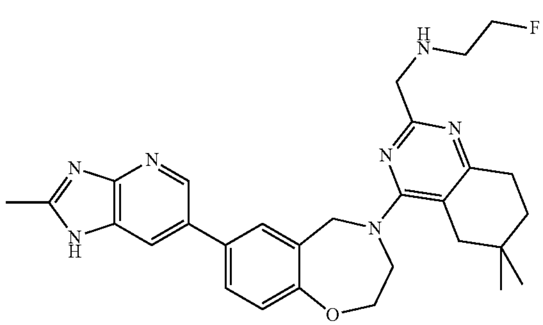 [SMILES: Cc1nc2ncc(-c3ccc4c(c3)CN(c3nc(CNCCF)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-fluoroethanamine |

-continued

| Cmpd No. | Structure | Name |
|---|---|---|
| 594 | 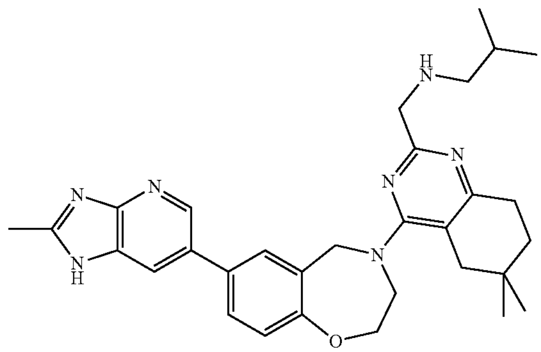 [SMILES: Cc1nc2ncc(-c3ccc4c(c3)CN(c3nc(CNCC(C)C)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-methylpropan-1-amine |
| 595 | 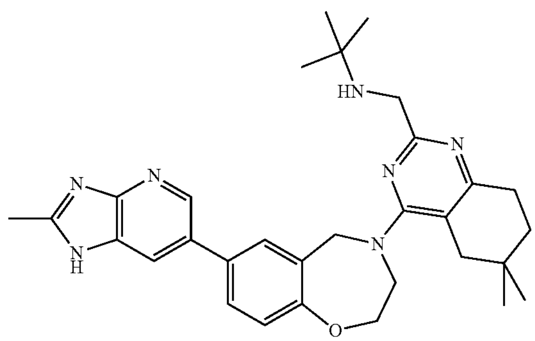 [SMILES: Cc1nc2ncc(-c3ccc4c(c3)CN(c3nc(CNC(C)(C)C)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-methylpropan-2-amine |
| 596 | 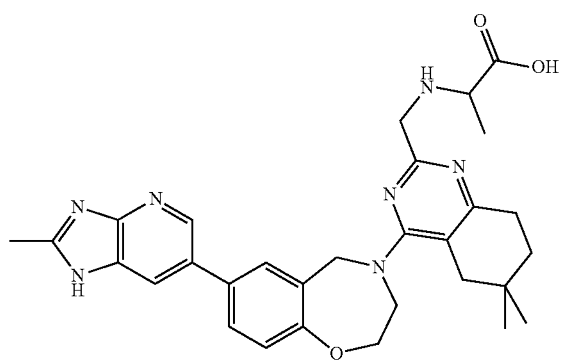 [SMILES: Cc1nc2ncc(-c3ccc4c(c3)CN(c3nc(CNC(C)C(=O)O)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)alanine |
| 597 | 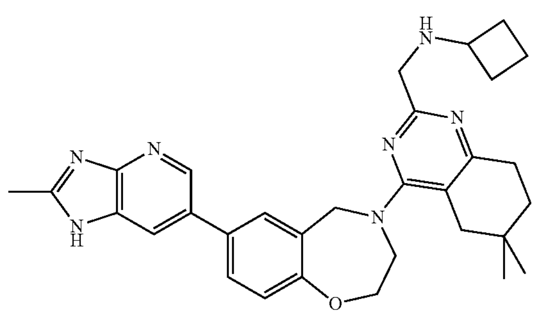 [SMILES: Cc1nc2ncc(-c3ccc4c(c3)CN(c3nc(CNC5CCC5)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclobutanamine |

| Cmpd No. | Structure | Name |
|---|---|---|
| 598 | 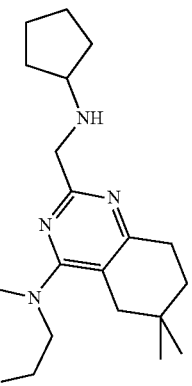 | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclopentanamine |
| 599 | 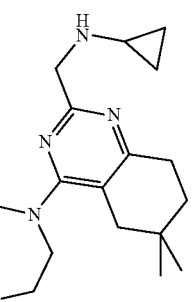 | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclopropanamine |
| 600 | 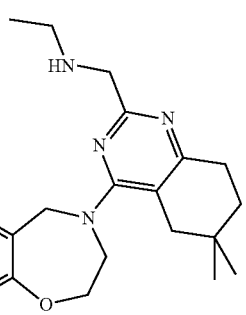 | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)ethanamine |
| 601 | 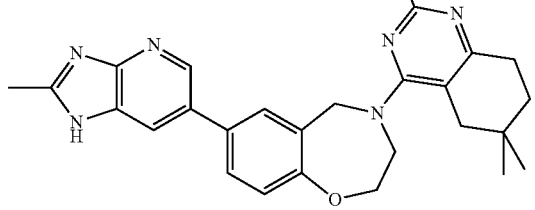 | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl)methyl)methanesulfonamide |

-continued

| Cmpd No. | Structure | Name |
|---|---|---|
| 602 | 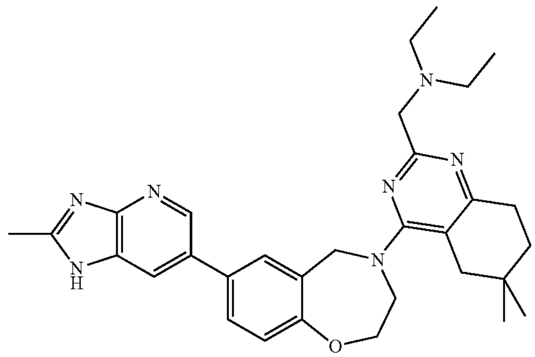 [SMILES: CCN(CC)Cc1nc2c(c(N3CCOc4ccc(-c5cnc6nc(C)[nH]c6c5)cc4C3)n1)CC(C)(C)CC2] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-ethylethanamine |
| 603 | 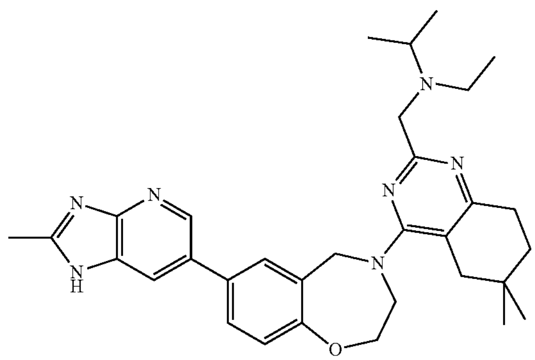 [SMILES: CCN(Cc1nc2c(c(N3CCOc4ccc(-c5cnc6nc(C)[nH]c6c5)cc4C3)n1)CC(C)(C)CC2)C(C)C] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-ethylpropan-2-amine |
| 604 | 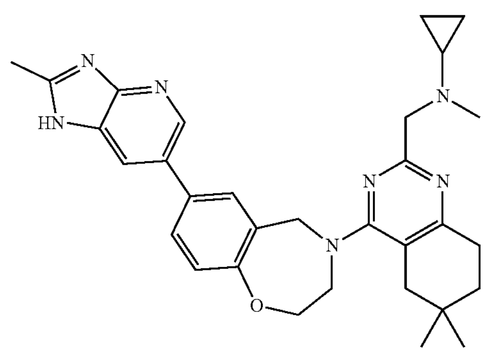 | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylcyclopropanamaine |
| 605 | 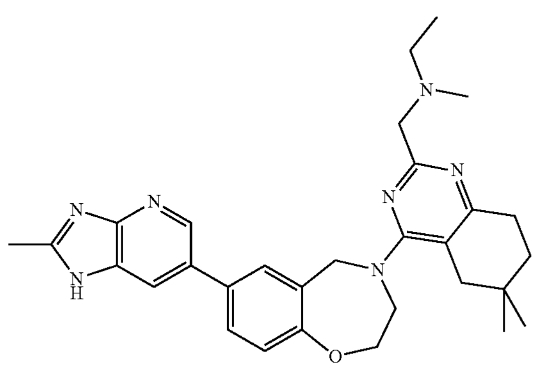 [SMILES: CCN(C)Cc1nc2c(c(N3CCOc4ccc(-c5cnc6nc(C)[nH]c6c5)cc4C3)n1)CC(C)(C)CC2] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylethanamine |

-continued

| Cmpd No. | Structure | Name |
|---|---|---|
| 606 | 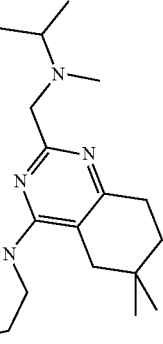 | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylpropan-2-amine |
| 607 | 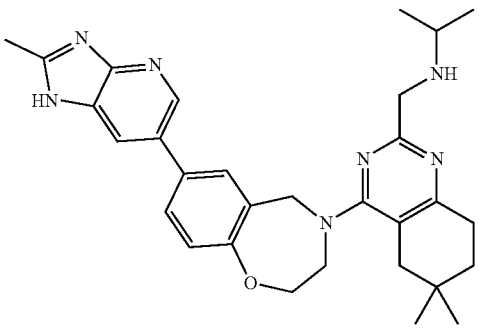 [SMILES: Cc1nc2ncc(-c3ccc4c(c3)CN(c3nc(CNC(C)C)nc5c3CC(C)(C)CC5)CCO4)cc2[nH]1] | N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)propan-2-amine |
| 608 | 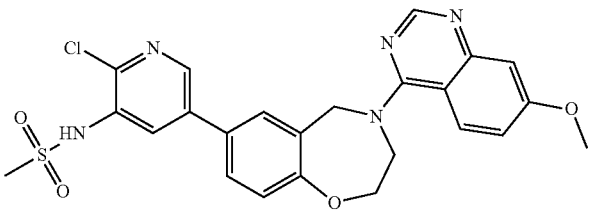 | N-(2-chloro-5-{4-[7-(methyloxy)quinazolin-4-yl]-2,3,4,5-tetrahydro-1,4-benzoxazepin-7-yl}pyridin-3-yl)methanesulfonamide |
| 609 | 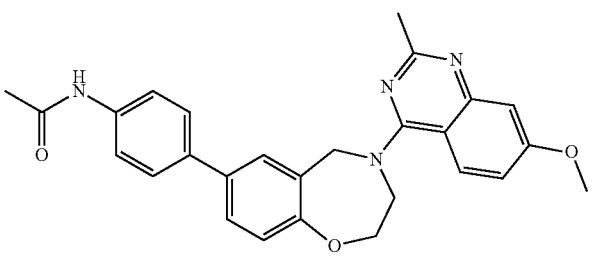 [SMILES: COc1ccc2c(N3CCOc4ccc(-c5ccc(NC(C)=O)cc5)cc4C3)nc(C)nc2c1] | N-(4-{4-[2-methyl-7-(methyloxy)quinazolin-4-yl]-2,3,4,5-tetrahydro-1,4-benzoxazepin-7-yl}phenyl)acetamide |
| 610 | 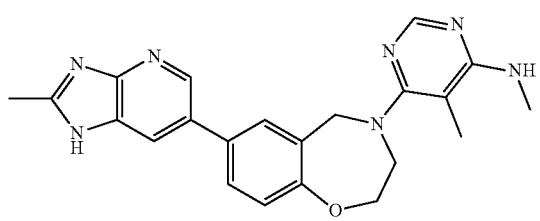 | N,5-dimethyl-6-[7-(2-methyl-1H-imidazo[4,5-b]pyridin-6-yl)-2,3-dihydro-1,4-benzoxazepin-4(5H)-yl]pyrimidin-4-amine |

-continued

| Cmpd No. | Structure | Name |
|---|---|---|
| 611 | 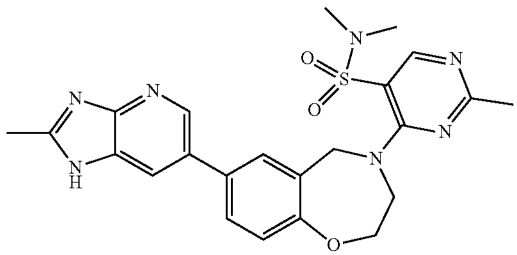 | N,N,2-trimethyl-4-[7-(2-methyl-1H-imidazo[4,5-b]pyridin-6-yl)-2,3-dihydro-1,4-benzoxazepin-4(5H)-yl]pyrimidine-5-sulfonamide |
| 612 | 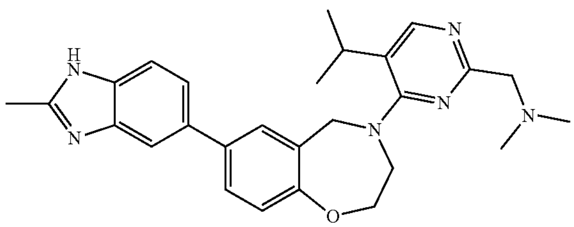 | N,N-dimethyl-1-{4-[7-(2-methyl-1H-benzimidazol-5-yl)-2,3-dihydro-1,4-benzoxazepin-4(5H)-yl]-5-(1-methylethyl)pyrimidin-2-yl}methanamine |
| 613 | 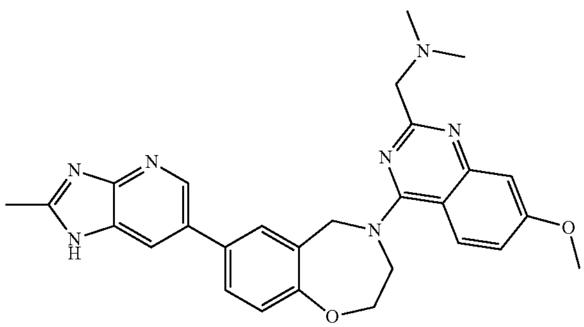 | N,N-dimethyl-1-{4-[7-(2-methyl-1H-imidazo[4,5-b]pyridin-6-yl)-2,3-dihydro-1,4-benzoxazepin-4(5H)-yl]-7-(methyloxy)quinazolin-2-yl}methanamine |
| 614 | 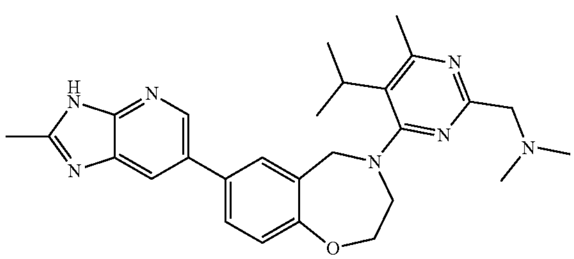 | N,N-dimethyl-1-{4-methyl-5-(1-methylethyl)-6-[7-(2-methyl-3H-imidazo[4,5-b]pyridin-6-yl)-2,3-dihydro-1,4-benzoxazepin-4(5H)-yl]pyrimidin-2-yl}methanamine |
| 615 | 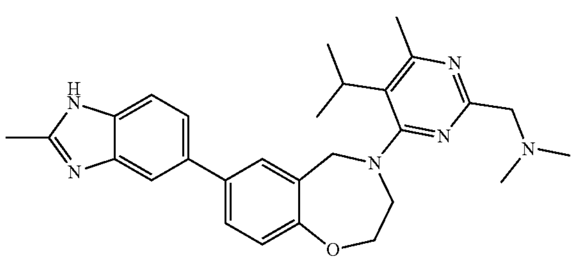 | N,N-dimethyl-1-{4-methyl-6-[7-(2-methyl-1H-benzimidazol-5-yl)-2,3-dihydro-1,4-benzoxazepin-4(5H)-yl]-5-(1-methylethyl)pyrimidin-2-yl}methanamine |

| Cmpd No. | Structure | Name |
|---|---|---|
| 616 | 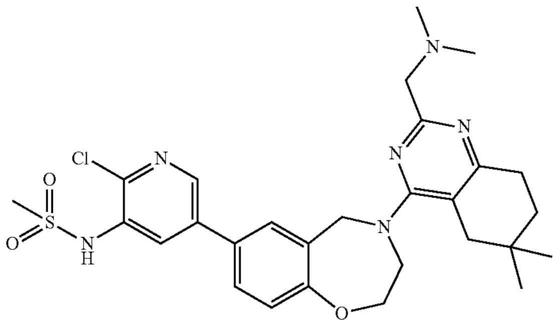 [SMILES: CN(C)Cc1nc2c(c(N3CCOc4ccc(-c5cnc(Cl)c(NS(C)(=O)=O)c5)cc4C3)n1)CC(C)(C)CC2] | N-[2-chloro-5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)puyridin-3-yl]methanesulfonamide |
| 617 | 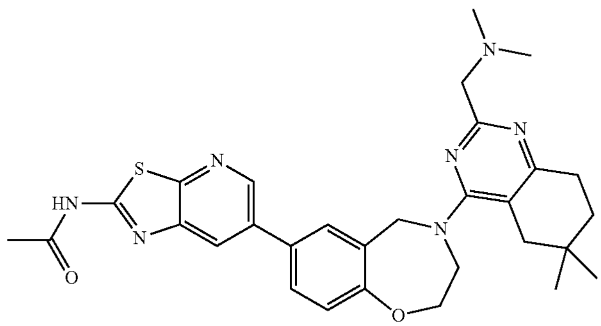 [SMILES: CC(=O)Nc1nc2cc(-c3ccc4c(c3)CN(c3nc(CN(C)C)nc5c3CC(C)(C)CC5)CCO4)cnc2s1] | N-[6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)[1,3]thiazolo[5,4-b]pyridin-2-yl]acetamide |
| 618 | 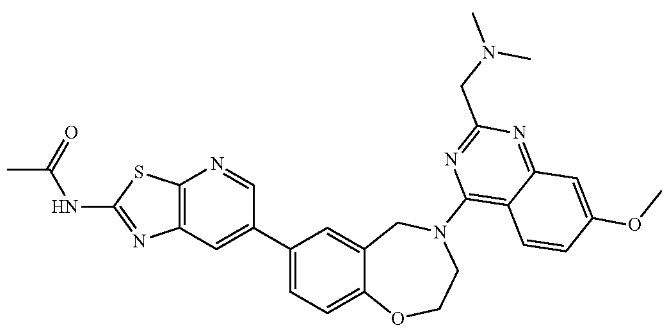 [SMILES: COc1ccc2c(N3CCOc4ccc(-c5cnc6sc(NC(C)=O)nc6c5)cc4C3)nc(CN(C)C)nc2c1] | N-[6-(4-{2-[(dimethylamino)methyl]-7-(methyloxy)quinazolin-4-yl}-2,3,4,5-tetrahydro-1,4-benzoxazepin-7-yl)[1,3]thiazolo[5,4-b]pyridin-2-yl]acetamide |
| 619 | 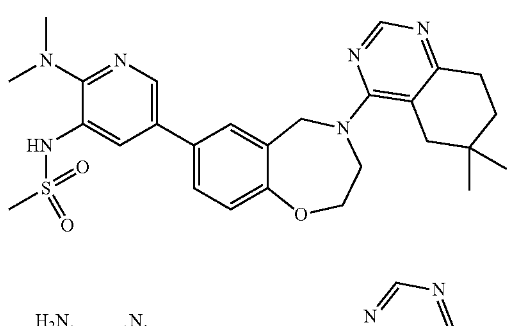 | N-{2-(dimethylamino)-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide |
| 620 | 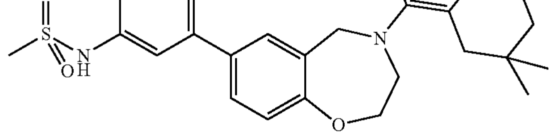 | N-{2-amino-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide |

| Cmpd No. | Structure | Name |
|---|---|---|
| 621 | 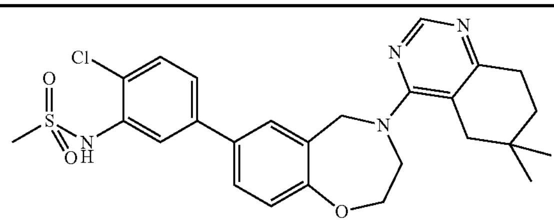 | N-{2-chloro-5-[4-(6,6-dimethyl-5,6,7,8-tetrahydroquinazolin-4-yl)-2,3,4,5-tetrahydro-1,4-benzoxazepin-7-yl[phenyl)methanesulfonamide |
| 622 | 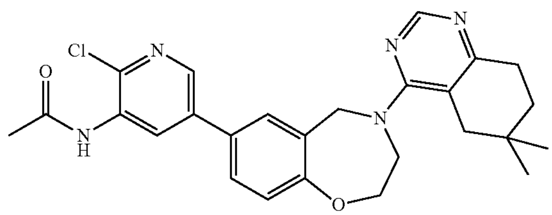 [SMILES: CC(=O)Nc1cc(-c2ccc3c(c2)CN(c2ncnc4c2CC(C)(C)CC4)CCO3)cnc1Cl] | N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}acetamide |
| 623 | 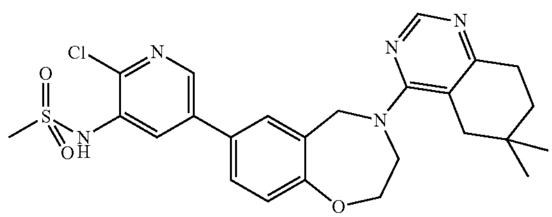 | N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide |
| 624 | 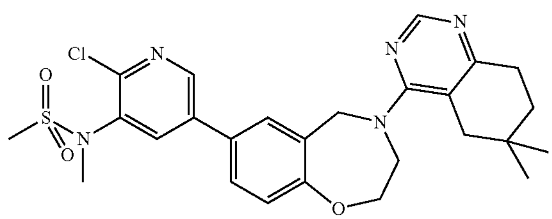 | N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}-N-methylmethanesulfonamide |
| 625 | 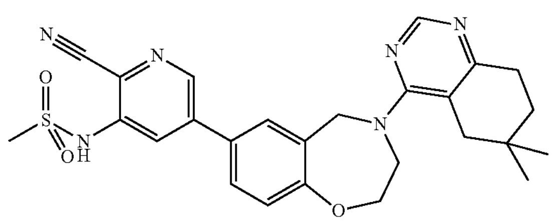 | N-{2-cyano-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide |
| 626 | 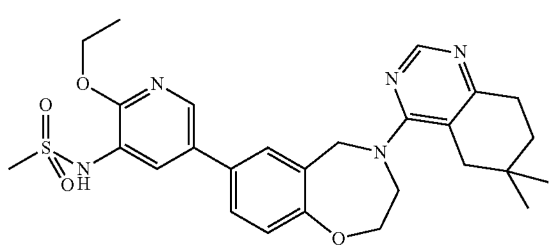 | N-{5-[4-(6,6-dimethyl-5,6,7,8-tetrahydroquinazolin-4-yl)-2,3,4,5-tetrahydro-1,4-benzoxazepin-7-yl]-2-(ethyloxy)pyridin-3-yl}methanesulfonamide |
| 627 | 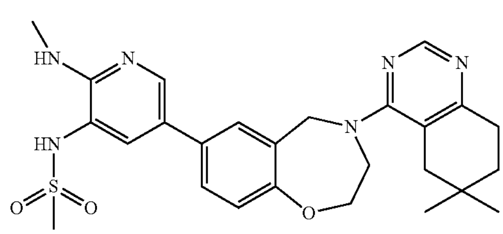 [SMILES: CNc1ncc(-c2ccc3c(c2)CN(c2ncnc4c2CC(C)(C)CC4)CCO3)cc1NS(C)(=O)=O] | N-{5-[4-(6,6-dimethyl-5,6,7,8-tetrahydroquinazolin-4-yl)-2,3,4,5-tetrahydro-1,4-benzoxazepin-7-yl]-2-(methylamino)pyridin-3-yl}methanesulfonamide |

-continued

| Cmpd No. | Structure | Name |
|---|---|---|
| 628 | 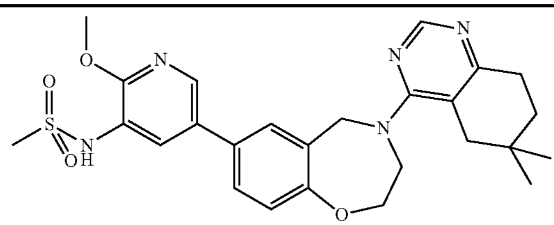 | N-{5-[4-(6,6-dimethyl-5,6,7,8-tetrahydroquinazolin-4-yl)-2,3,4,5-tetrahydro-1,4-benzoxazepin-7-yl]-2-(methyloxy)pyridin-3-yl}methanesulfonamide |
| 629 | 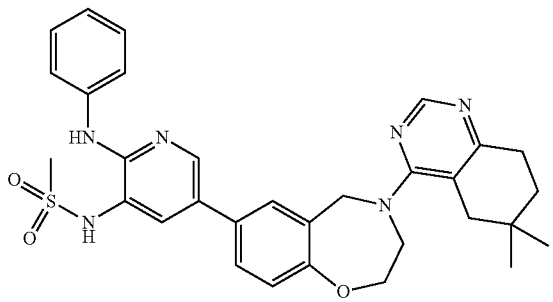 [SMILES: CC1(C)CCc2ncnc(N3CCOc4ccc(-c5cnc(Nc6ccccc6)c(NS(C)(=O)=O)c5)cc4C3)c2C1] | N-{5-[4-(6,6-dimethyl-5,6,7,8-tetrahydroquinazolin-4-yl)-2,3,4,5-tetrahydro-1,4-benzoxazepin-7-yl]-2-(phenylamino)pyridin-3-yl}methanesulfonamide |
| 630 | 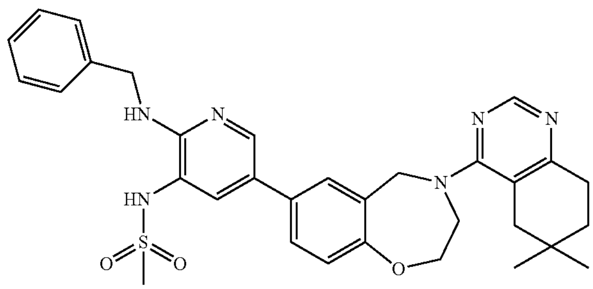 [SMILES: CC1(C)CCc2ncnc(N3CCOc4ccc(-c5cnc(NCc6ccccc6)c(NS(C)(=O)=O)c5)cc4C3)c2C1] | N-{5-[4-(6,6-dimethyl-5,6,7,8-tetrahydroquinazolin-4-yl)-2,3,4,5-tetrahydro-1,4-benzoxazepin-7-yl]-2-[(phenylmethyl)amino]pyrimidin-3-yl}methanesulfonamide |
| 631 | 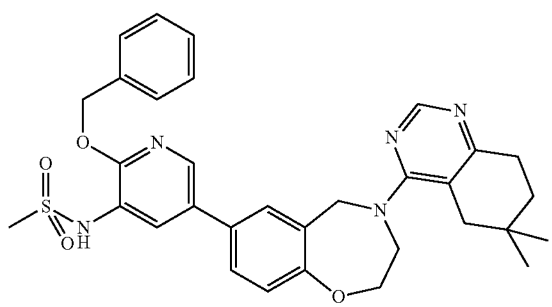 | N-{5-[4-(6,6-dimethyl-5,6,7,8-tetrahydroquinazolin-4-yl)-2,3,4,5-tetrahydro-1,4-benzoxazepin-7-yl]-2-[(phenylmethyl)oxy]pyridin-3-yl}methanesulfonamide |
| 632 | 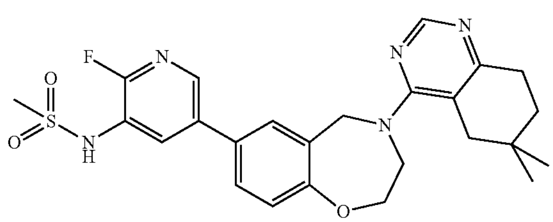 [SMILES: CC1(C)CCc2ncnc(N3CCOc4ccc(-c5cnc(F)c(NS(C)(=O)=O)c5)cc4C3)c2C1] | N-{5-[4-(6,6-dimethyl-5,6,7,8-tetrahydroquinazolin-4-yl)-2,3,4,5-tetrahydro-1,4-benzoxazepin-7-yl]-2-fluoropyridin-3-yl}methanesulfonamide |
| 633 | 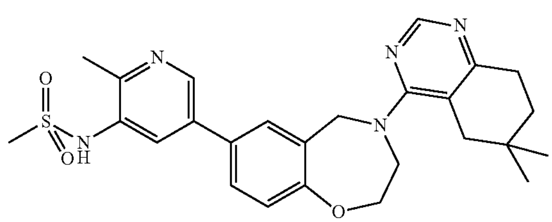 | N-{5-[4-(6,6-dimethyl-5,6,7,8-tetrahydroquinazolin-4-yl)-2,3,4,5-tetrahydro-1,4-benzoxazepin-7-yl]-2-methylpyridin-3-yl}methanesulfonamide |

| Cmpd No. | Structure | Name |
|---|---|---|
| 634 | 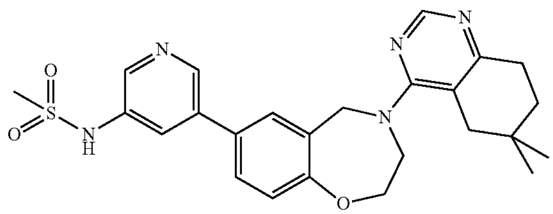 [SMILES: CC1(C)CCc2ncnc(N3CCOc4ccc(-c5cncc(NS(C)(=O)=O)c5)cc4C3)c2C1] | N-{5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide |
| 635 | 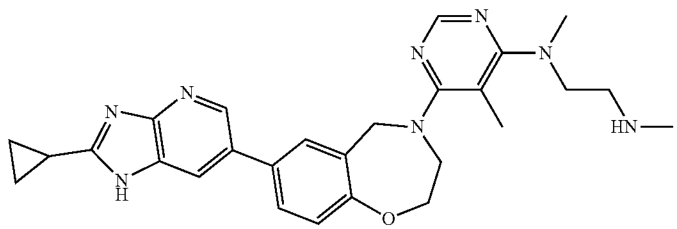 [SMILES: CNCCN(C)c1ncnc(N2CCOc3ccc(-c4cnc5nc(C6CC6)[nH]c5c4)cc3C2)c1C] | N-{6-[7-(2-cyclopropyl-1H-imidazo[4,5-b]pyridin-6-yl)-2,3-dihydro-1,4-benzoxazepin-4(5H)-yl]-5-methylpyrimidin-4-yl}-N,N'-dimethylethane-1,2-diamine |
| 636 | 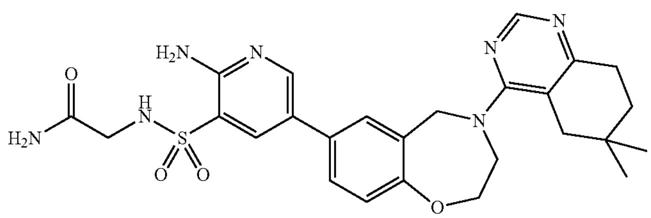 [SMILES: CC1(C)CCc2ncnc(N3CCOc4ccc(-c5cnc(N)c(S(=O)(=O)NCC(N)=O)c5)cc4C3)c2C1] | N~2~-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)glycinamide |
| 637 | 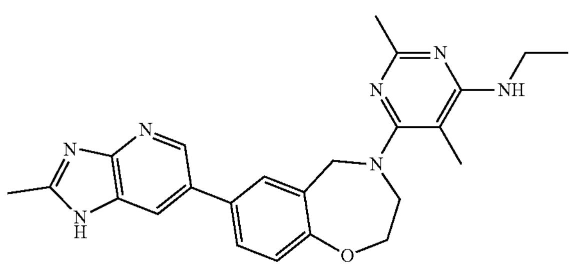 [SMILES: CCNc1nc(C)nc(N2CCOc3ccc(-c4cnc5nc(C)[nH]c5c4)cc3C2)c1C] | N-ethyl-2,5-dimethyl-6-[7-(2-methyl-1H-imidazo[4,5-b]pyridin-6-yl)-2,3-dihydro-1,4-benzoxazepin-4(5H)-yl]pyrimidin-4-amine |
| 638 | 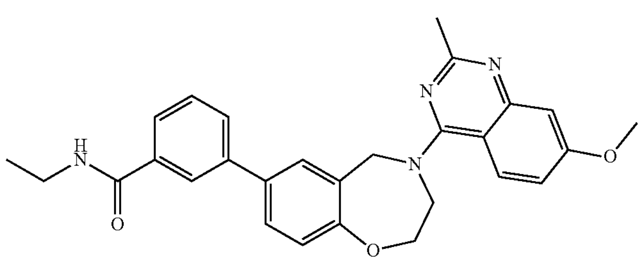 [SMILES: CCNC(=O)c1cccc(-c2ccc3c(c2)CN(c2nc(C)nc4cc(OC)ccc24)CCO3)c1] | N-ethyl-3-{4-[2-methyl-7-(methyloxy)quinazolin-4-yl]-2,3,4,5-tetrahydro-1,4-benzoxazepin-7-yl}benzamide |
| 639 | 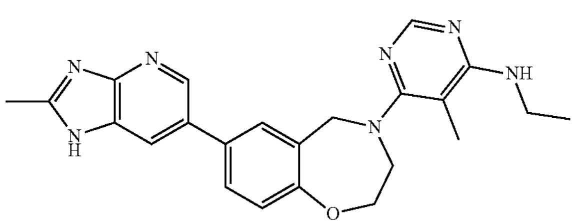 [SMILES: CCNc1ncnc(N2CCOc3ccc(-c4cnc5nc(C)[nH]c5c4)cc3C2)c1C] | N-ethyl-5-methyl-6-[7-(2-methyl-1H-imidazo[4,5-b]pyridin-6-yl)-2,3-dihydro-1,4-benzoxazepin-4(5H)-yl]pyrimidin-4-amine |

| Cmpd No. | Structure | Name |
|---|---|---|
| 640 | 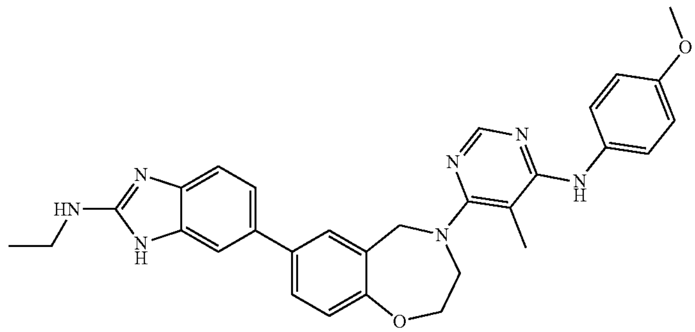 [SMILES: CCNc1nc2ccc(-c3ccc4c(c3)CN(c3ncnc(Nc5ccc(OC)cc5)c3C)CCO4)cc2[nH]1] | N-ethyl-6-[4-(5-methyl-6-{[4-(methyloxy)phenyl]amino}pyrimidin-4-yl)-2,3,4,5-tetrahydro-1,4-benzoxazepin-7-yl]-1H-benzimidazol-2-amine |
| 641 | 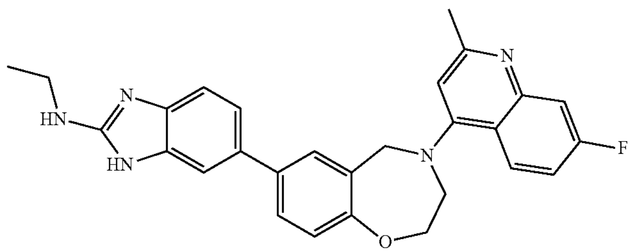 [SMILES: CCNc1nc2ccc(-c3ccc4c(c3)CN(c3cc(C)nc5cc(F)ccc35)CCO4)cc2[nH]1] | N-ethyl-6-[4-(7-fluoro-2-methylquinazolin-4-yl)-2,3,4,5-tetrahydro-1,4-benzoxazepin-7-yl]-1H-benzimidazol-2-amine |
| 642 | 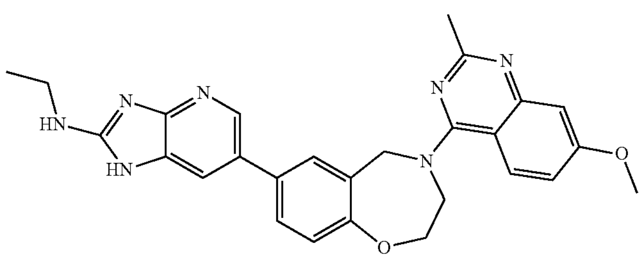 [SMILES: CCNc1nc2ncc(-c3ccc4c(c3)CN(c3nc(C)nc5cc(OC)ccc35)CCO4)cc2[nH]1] | N-ethyl-6-{4-[2-methyl-7-(methyloxy)quinazolin-4-yl]-2,3,4,5-tetrahydro-1,4-benzoxazepin-7-yl}-1H-imidazo[4,5-b]pyridin-2-amine |
| 643 | 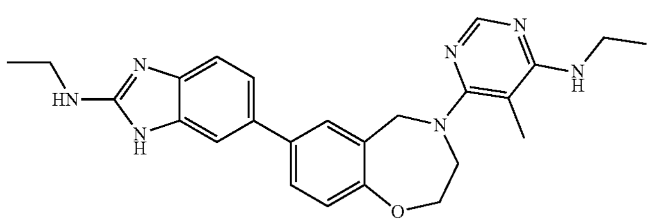 [SMILES: CCNc1nc2ccc(-c3ccc4c(c3)CN(c3ncnc(NCC)c3C)CCO4)cc2[nH]1] | N-ethyl-6-{4-[6-(ethylamino)-5-methylpyrimidin-4-yl]-2,3,4,5-tetrahydro-1,4-benzoxazepin-7-yl}-1H-benzimidazol-2-amine |
| 644 | 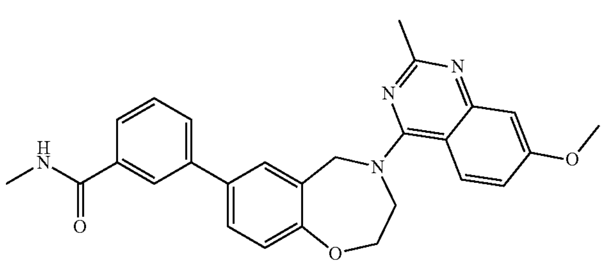 | N-methyl-3-{4-[2-methyl-7-(methyloxy)quinazolin-4-yl]-2,3,4,5-tetrahydro-1,4-benzoxazepin-7-yl}benzamide |

-continued

| Cmpd No. | Structure | Name |
|---|---|---|
| 645 | 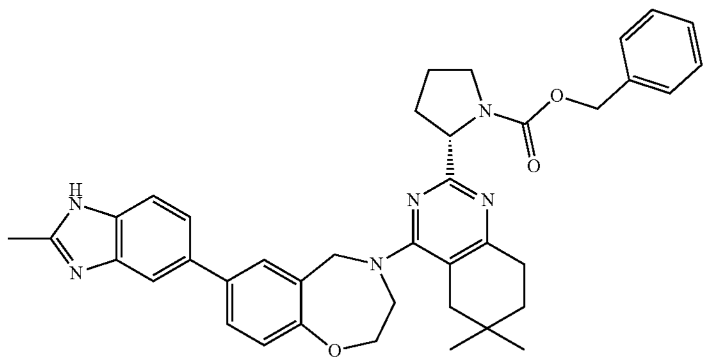 [SMILES: Cc1nc2cc(-c3ccc4c(c3)CN(c3nc([C@@H]5CCCN5C(=O)OCc5ccccc5)nc5c3CC(C)(C)CC5)CCO4)ccc2[nH]1] | phenylmethyl (2S)-2-{6,6-dimethyl-4-[7-(2-methyl-3H-imidazo[4,5-b]pyridin-6-yl)-2,3-dihydro-1,4-benzoxazepin-4(5H)-yl]-5,6,7,8-tetrahydroquinazolin-2-yl}pyrrolidine-1-carboxylate |
| 646 | 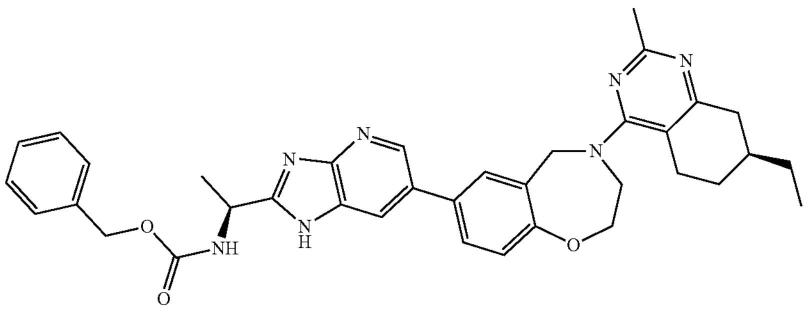 [SMILES: CC[C@H]1CCc2c(nc(C)nc2N2CCOc3ccc(-c4cnc5nc([C@H](C)NC(=O)OCc6ccccc6)[nH]c5c4)cc3C2)C1] | phenylmethyl [(1S)-1-(6-{4-[(7S)-7-ethyl-2-methyl-5,6,7,8-tetrahydroquinazolin-4-yl]-2,3,4,5-tetrahydro-1,4-benzoxazepin-7-yl}-1H-imidazo[4,5-b]pyridin-2-yl)ethyl]carbamate |
| 647 | 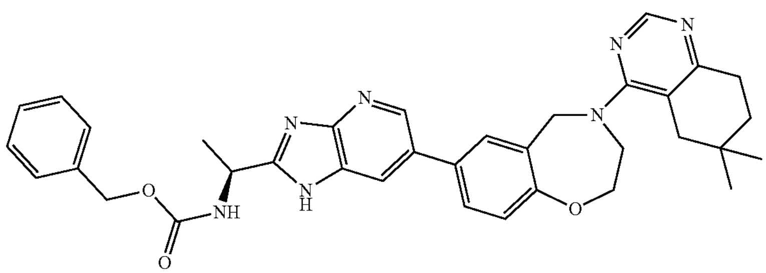 [SMILES: C[C@H](NC(=O)OCc1ccccc1)c1nc2ncc(-c3ccc4c(c3)CN(c3ncnc5c3CC(C)(C)CC5)CCO4)cc2[nH]1] | phenylmethyl [(1S)-1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}ethyl]carbamate |
| 648 | 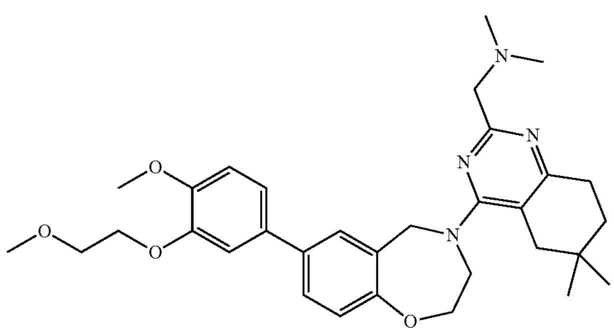 | 1-(6,6-dimethyl-4-{7-[4-(methyloxy)-3-{[2-(methyloxy)ethyl]oxy}phenyl]-2,3-dihydro-1,4-benzoxazepin-4(5H)-yl}-5,6,7,8-tetrahydroquinazolin-2-yl)-N,N-dimethylmethanamine |
| 649 | 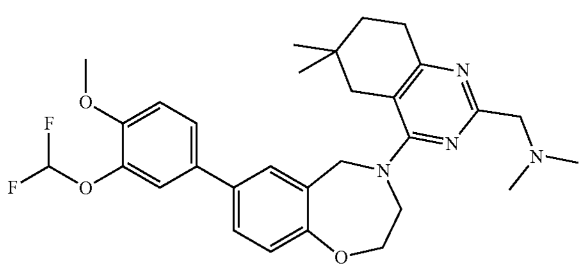 [SMILES: COc1ccc(-c2ccc3c(c2)CN(c2nc(CN(C)C)nc4c2CC(C)(C)CC4)CCO3)cc1OC(F)F] | 1-{4-[7-{3-[(difluoromethyl)oxy]-4-(methyloxy)phenyl}-2,3-dihydro-1,4-benzoxazepin-4(5H)-yl]-6,6-dimethyl-5,6,7,8-tetrahydroquinazolin-2-yl}-N,N-dimethylmethanamine |

-continued

| Cmpd No. | Structure | Name |
|---|---|---|
| 650 | 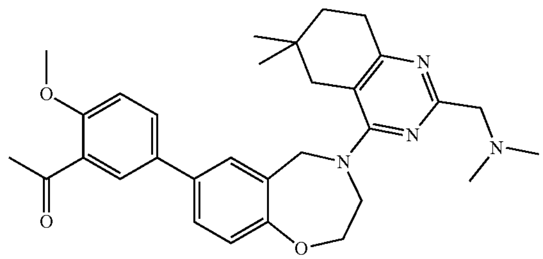 [SMILES: COc1ccc(-c2ccc3c(c2)CN(c2nc(CN(C)C)nc4c2CC(C)(C)CC4)CCO3)cc1C(C)=O] | 1-[5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-2-(methyloxy)phenyl]ethanone |
| 651 | 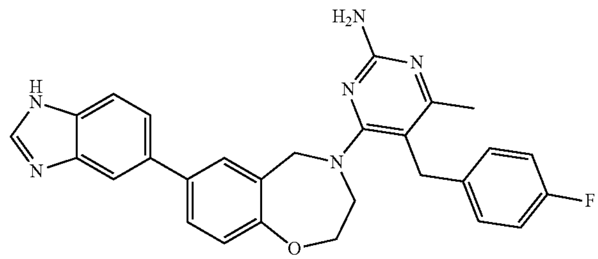 [SMILES: Cc1nc(N)nc(N2CCOc3ccc(-c4ccc5[nH]cnc5c4)cc3C2)c1Cc1ccc(F)cc1] | 4-[7-(1H-benzimidazol-5-yl)-2,3-dihydro-1,4-benzoxazepin-4(5H)-yl]-5-[(4-fluorophenyl)methyl]-6-methylpyrimidin-2-amine |
| 652 | 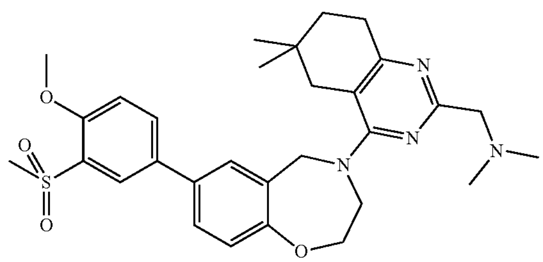 | 1-(6,6-dimethyl-4-{7-[4-(methyloxy)-3-(methylsulfonyl)phenyl]-2,3-dihydro-1,4-benzoxazepin-4(5H)-yl}-5,6,7,8-tetrahydroquinazolin-2-yl)-N,N-dimethylmethanamine |
| 653 | 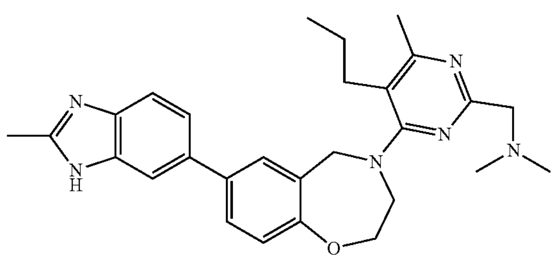 | N,N-dimethyl-1-{4-methyl-6-[7-(2-methyl-1H-benzimidazol-6-yl)-2,3-dihydro-1,4-benzoxazepin-4(5H)-yl]-5-propylpyrimidin-2-yl}methanamine |
| 654 | 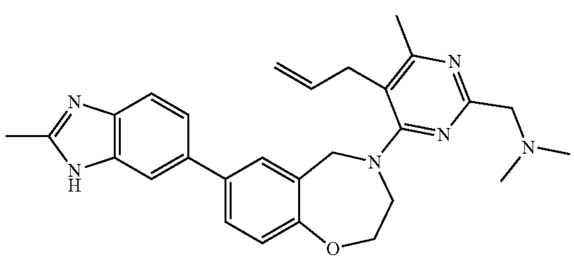 | N,N-dimethyl-1-{4-methyl-6-[7-(2-methyl-1H-benzimidazol-6-yl)-2,3-dihydro-1,4-benzoxazepin-4(5H)-yl]-5-prop-2-en-1-ylpyrimidin-2-yl}methanamine |
| 655 | 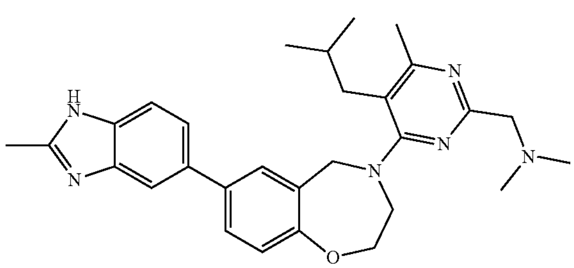 | N,N-dimethyl-1-{4-methyl-6-[7-(2-methyl-1H-benzimidazol-5-yl)-2,3-dihydro-1,4-benzoxazepin-4(5H)-yl]-5-(2-methylpropyl)pyrimidin-2-yl}methanamine |

-continued

| Cmpd No. | Structure | Name |
|---|---|---|
| 656 | 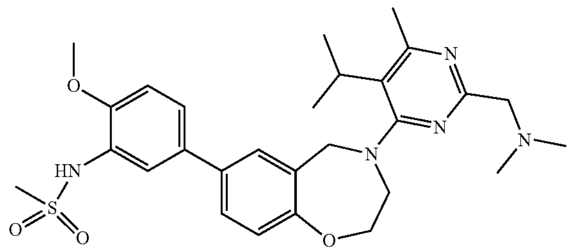 | N-[5-(4-{2-[(dimethylamino)methyl]-6-methyl-5-(1-methylethyl)pyrimidin-4-yl}-2,3,4,5-tetrahydro-1,4-benzoxazepin-7-yl)-2-(methyloxy)phenyl]methane-sulfonamide |
| 657 | 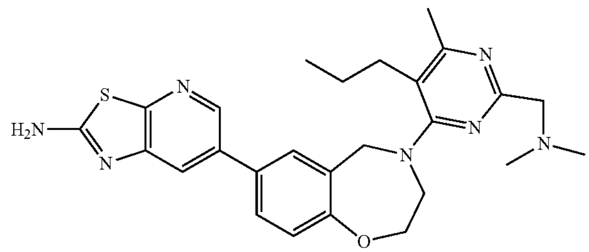 [SMILES: CCCc1c(C)nc(CN(C)C)nc1N1CCOc2ccc(-c3cnc4sc(N)nc4c3)cc2C1] | 6-(4-{2-[(dimethylamino)methyl]-6-methyl-5-propylpyrimidin-4-yl}-2,3,4,5-tetrahydro-1,4-benzoxazepin-7-yl)[1,3]thiazolo[5,4-b]pyridin-2-amine |
| 658 | 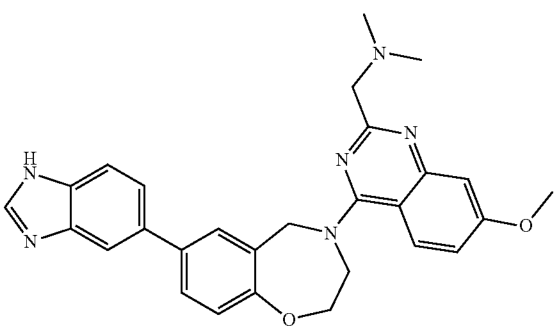 | 1-{4-[7-(1H-benzimidazol-5-yl)-2,3-dihydro-1,4-benzoxazepin-4(5H)-yl]-7-(methyloxy)quinazolin-2-yl}-N,N-dimethylmethanamine |
| 659 | 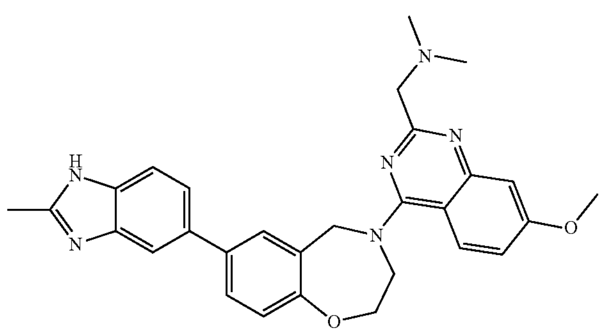 | N,N-dimethyl-1-{4-[7-(2-methyl-1H-benzimidazol-5-yl)-2,3-dihydro-1,4-benzxazepin-4(5H)-yl]-7-(methyloxy)quinazolin-2-yl}methanamine |
| 660 | 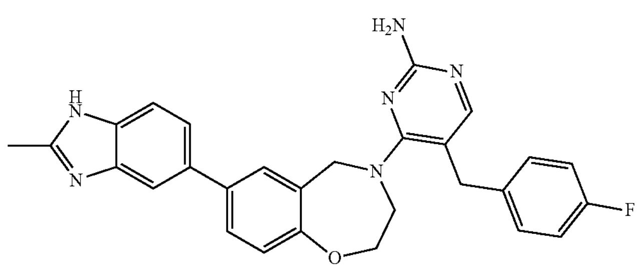 [SMILES: Cc1nc2cc(-c3ccc4c(c3)CN(c3nc(N)ncc3Cc3ccc(F)cc3)CCO4)ccc2[nH]1] | 5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-amine |

| Cmpd No. | Structure | Name |
|---|---|---|
| 661 | 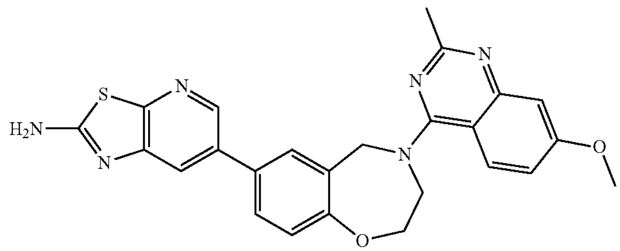 [SMILES: COc1ccc2c(N3CCOc4ccc(-c5cnc6sc(N)nc6c5)cc4C3)nc(C)nc2c1] | 6-{4-[2-methyl-7-(methyloxy)quinazolin-4-yl]-2,3,4,5-tetrahydro-1,4-benzoxazepin-7-yl}[1,3]thiazolo[5,4-b]pyridin-2-amine |
| 662 | 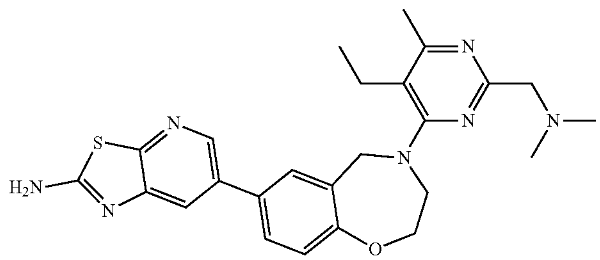 [SMILES: CCc1c(C)nc(CN(C)C)nc1N1CCOc2ccc(-c3cnc4sc(N)nc4c3)cc2C1] | 6-(4-{2-[(dimethylamino)methyl]-5-ethyl-6-methylpyrimidin-4-yl}-2,3,4,5-tetrahydro-1,4-benzoxazepin-7-yl)[1,3]thiazolo[5,4-b]pyridin-2-amine |
| 663 | 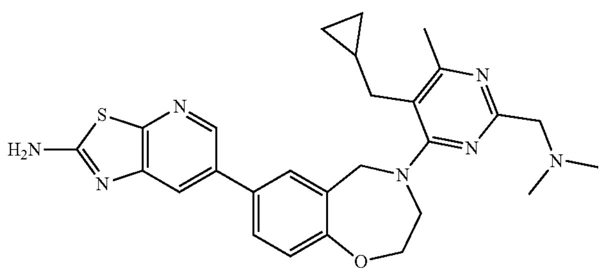 [SMILES: Cc1nc(CN(C)C)nc(N2CCOc3ccc(-c4cnc5sc(N)nc5c4)cc3C2)c1CC1CC1] | 6-(4-{5-(cyclopropylmethyl)-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine |
| 664 | 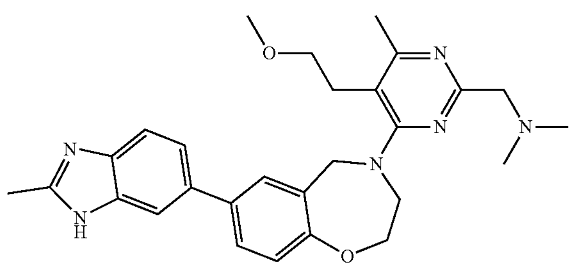 | N,N-dimethyl-1-{4-methyl-6-[7-(2-methyl-1H-benzimidazol-6-yl)-2,3-dihydro-1,4-benzoxazepin-4(5H)-yl]-5-[2-(methyloxy)ethyl]pyrimidin-2-yl}methanamine |
| 665 | 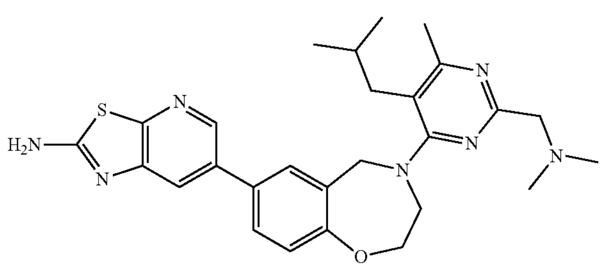 [SMILES: Cc1nc(CN(C)C)nc(N2CCOc3ccc(-c4cnc5sc(N)nc5c4)cc3C2)c1CC(C)C] | 6-(4-{2-[(dimethylamino)methyl]-6-methyl-5-(2-methylpropyl)pyrimidin-4-yl}-2,3,4,5-tetrahydro-1,4-benzoxazepin-7-yl)[1,3]thiazolo[5,4-b]pyridin-2-amine |
| 666 | 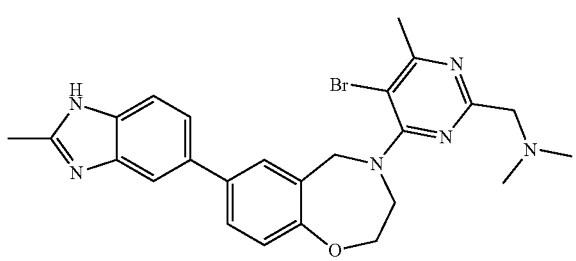 | 1-{5-bromo-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine |

| Cmpd No. | Structure | Name |
|---|---|---|
| 667 | 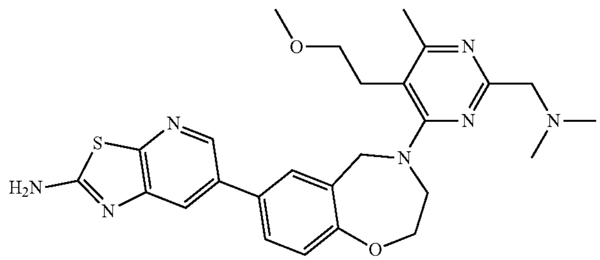 [SMILES: COCCc1c(C)nc(CN(C)C)nc1N1CCOc2ccc(-c3cnc4sc(N)nc4c3)cc2C1] | 6-(4-{2-[(dimethylamino)methyl]-6-methyl-5-[2-(methyloxy)ethyl]pyrimidin-4-yl}-2,3,4,5-tetrahydro-1,4-benzoxazepin-7-yl)[1,3]thiazolo[5,4-b]pyridin-2-amine |
| 668 | 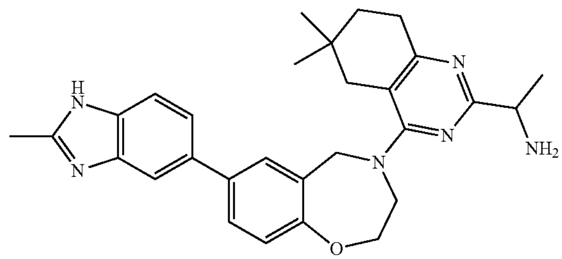 [SMILES: Cc1nc2cc(-c3ccc4c(c3)CN(c3nc(C(C)N)nc5c3CC(C)(C)CC5)CCO4)ccc2[nH]1] | 1-{6,6-dimethyl-4-[7-(2-methyl-1H-benzimidazol-5-yl)-2,3-dihydro-1,4-benzoxazepin-4(5H)-yl]-5,6,7,8-tetrahydroquinazolin-2-yl}ethanamine |
| 669 | 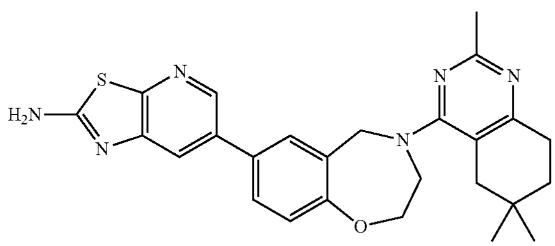 [SMILES: Cc1nc2c(c(N3CCOc4ccc(-c5cnc6sc(N)nc6c5)cc4C3)n1)CC(C)(C)CC2] | 6-[4-(2,6,6-trimethyl-5,6,7,8-tetrahydroquinazolin-4-yl)-2,3,4,5-tetrahydro-1,4-benzoxazepin-7-yl][1,3]thiazolo[5,4-b]pyridin-2-amine |
| 670 | 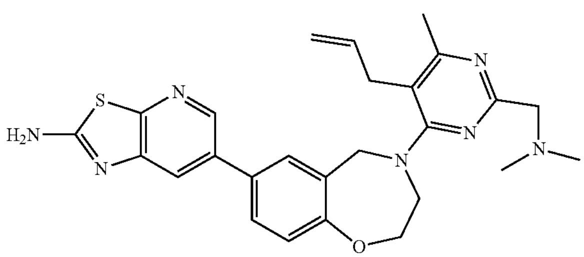 [SMILES: C=CCc1c(C)nc(CN(C)C)nc1N1CCOc2ccc(-c3cnc4sc(N)nc4c3)cc2C1] | 6-(4-{2-[(dimethylamino)methyl]-6-methyl-5-prop-2-en-1-ylpyrimidin-4-yl}-2,3,4,5-tetrahyhdro-1,4-benzoxazepin-7-yl)[1,3]thiazolo[5,4-b]pyridin-2-amine |
| 671 | 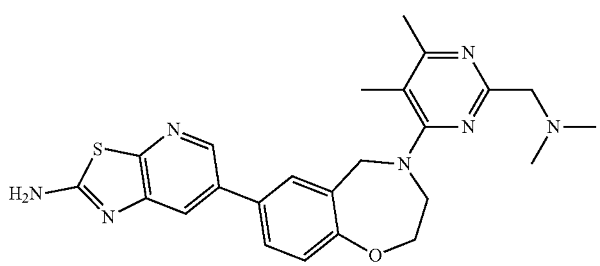 [SMILES: Cc1nc(CN(C)C)nc(N2CCOc3ccc(-c4cnc5sc(N)nc5c4)cc3C2)c1C] | 6-(4-{2-[(dimethylamino)methyl]-5,6-dimethylpyrimidin-4-yl}-2,3,4,5-tetrahydro-1,4-benzoxazepin-7-yl)[1,3]thiazolo[5,4-b]pyridin-2-amine |
| 672 | 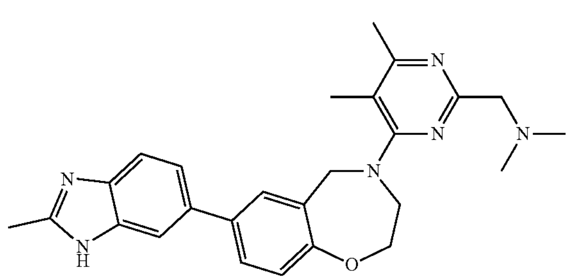 | 1-{4,5-dimethyl-6-[7-(2-methyl-1H-benzimidazol-6-yl)-2,3-dihydro-1,4-benzoxazepin-4(5H)-yl]pyrimidin-2-yl}-N,N-dimethylmethanamine |

-continued

| Cmpd No. | Structure | Name |
|---|---|---|
| 673 | 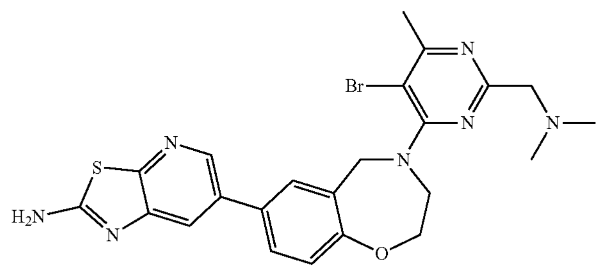 [SMILES: Cc1nc(CN(C)C)nc(N2CCOc3ccc(-c4cnc5sc(N)nc5c4)cc3C2)c1Br] | 6-(4-{5-bromo-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine |
| 674 | 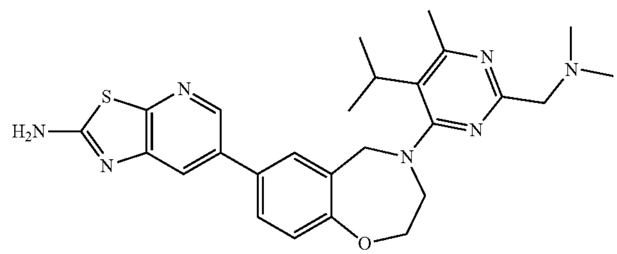 [SMILES: Cc1nc(CN(C)C)nc(N2CCOc3ccc(-c4cnc5sc(N)nc5c4)cc3C2)c1C(C)C] | 6-(4-{2-[(dimethylamino)methyl]-6-methyl-5-(1-methylethyl)pyrimidin-4-yl}-2,3,4,5-tetrahydro-1,4-benzoxazepin-7-yl)[1,3]thiazolo[5,4-b]pyridin-2-amine |
| 675 | 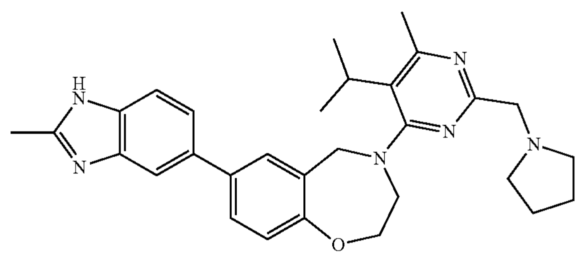 [SMILES: Cc1nc2cc(-c3ccc4c(c3)CN(c3nc(CN5CCCC5)nc(C)c3C(C)C)CCO4)ccc2[nH]1] | 7-(2-methyl-1H-benzimidazol-5-yl)-4-[6-methyl-5-(1-methylethyl)pyrimdin-4-yl]-ylmethyl)pyrimidin-4-yl]-2,3,4,5-tetrahydro-1,4-benzoxazepine |
| 676 | 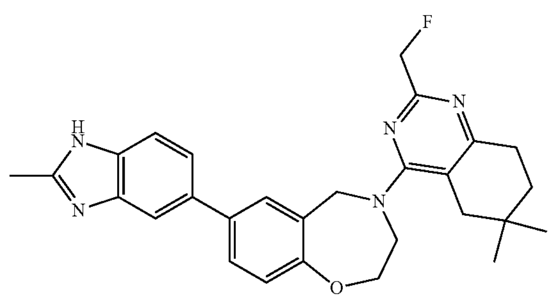 | 4-[2-(fluoromethyl)-6,6-dimethyl-5,6,7,8-tetrahydroquinazolin-4-yl]-7-(2-methyl-1H-benzimidazol-5-yl)-2,3,4,5-tetrahydro-1,4-benzoxazepine |
| 677 | 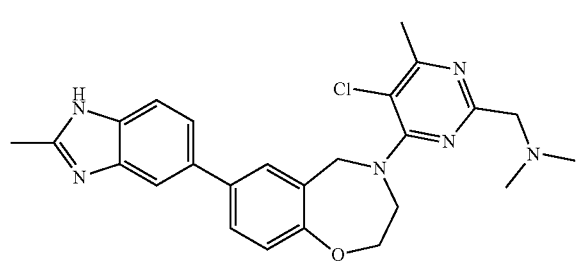 | 1-{5-chloro-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine |

| Cmpd No. | Structure | Name |
|---|---|---|
| 678 | 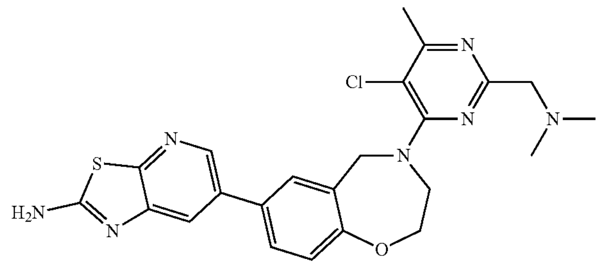 [SMILES: Cc1nc(CN(C)C)nc(N2CCOc3ccc(-c4cnc5sc(N)nc5c4)cc3C2)c1Cl] | 6-(4-{5-chloro-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine |
| 679 | 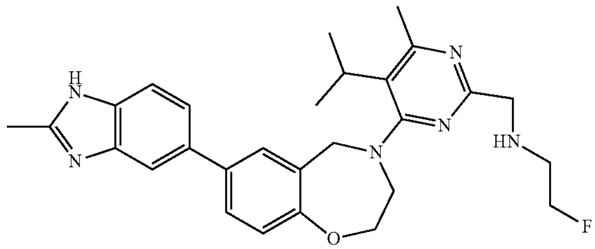 [SMILES: Cc1nc2cc(-c3ccc4c(c3)CN(c3nc(CNCCF)nc(C)c3C(C)C)CCO4)ccc2[nH]1] | 2-fluoro-N-({4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl)ethanamine |
| 680 | 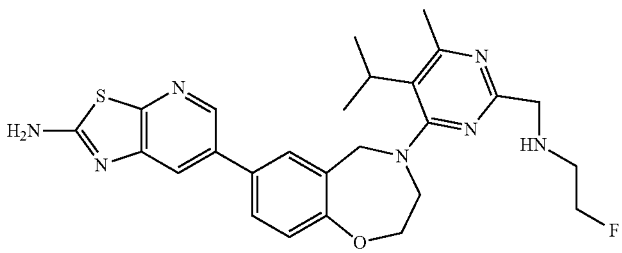 [SMILES: Cc1nc(CNCCF)nc(N2CCOc3ccc(-c4cnc5sc(N)nc5c4)cc3C2)c1C(C)C] | 6-{4-[2-{[(2-fluoroethyl)amino]methyl}-6-methyl-5-(1-methylethyl)pyrimidin-4-yl]-2,3,4,5-tetrahydro-1,4-benzoxazepin-7-yl}[1,3]thiazolo[5,4-b]pyridin-2-amine |
| 681 | 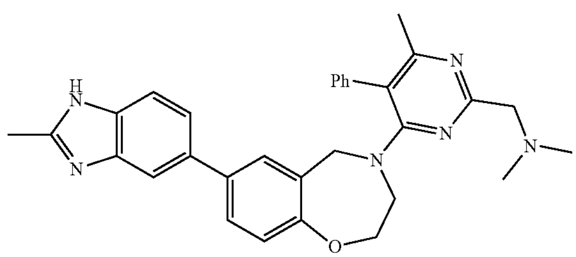 | N,N-dimethyl-1-{4-methyl-6-[7-(2-methyl-1H-benzimidazol-5-yl)-2,3-dihydro-1,4-benzoxazepin-4(5H)-yl]-5-phenylpyrimidin-2-yl}methanamine |
| 682 | 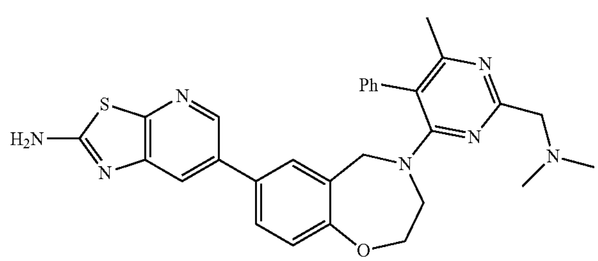 [SMILES: Cc1nc(CN(C)C)nc(N2CCOc3ccc(-c4cnc5sc(N)nc5c4)cc3C2)c1-c1ccccc1] | 6-(4-{2-[(dimethylamino)methyl]-6-methyl-5-phenylpyrimidin-4-yl}-2,3,4,5-tetrahydro-1,4-benzoxazepin-7-yl)[1,3]thiazolo[5,4-b]pyridin-2-amine |
| 683 | 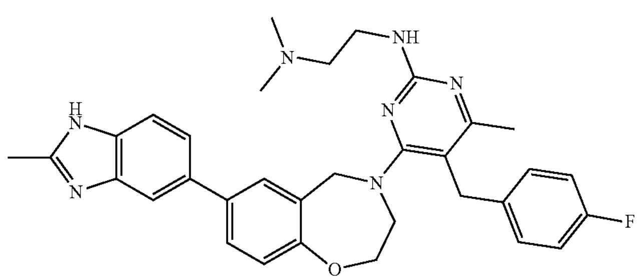 [SMILES: Cc1nc2cc(-c3ccc4c(c3)CN(c3nc(NCCN(C)C)nc(C)c3Cc3ccc(F)cc3)CCO4)ccc2[nH]1] | N'-{5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}-N,N-dimethylethane-1,2-diamine |

| Cmpd No. | Structure | Name |
|---|---|---|
| 684 | 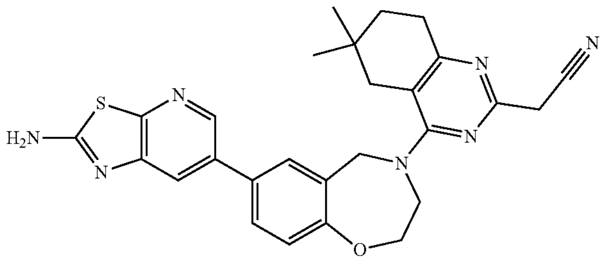 [SMILES: CC1(C)CCc2nc(CC#N)nc(N3CCOc4ccc(-c5cnc6sc(N)nc6c5)cc4C3)c2C1] | {4-[7-(2-amino[1,3]thiazolo[5,4-b]pyridin-6-yl)-2,3-dihydro-1,4-benzoxazepin-4(5H)-yl]-6,6-dimethyl-5,6,7,8-tetrahydroquinazolin-2-yl}acetonitrile |
| 685 | 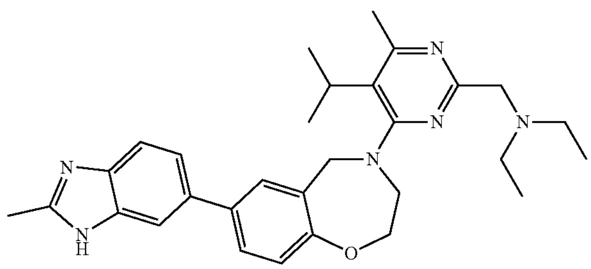 [SMILES: CCN(CC)Cc1nc(C)c(C(C)C)c(N2CCOc3ccc(-c4ccc5nc(C)[nH]c5c4)cc3C2)n1] | N-ethyl-N-({4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl)ethanamine |
| 686 | 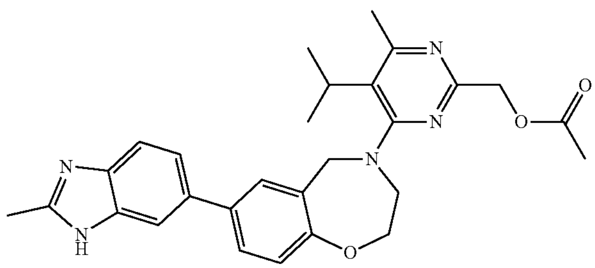 [SMILES: CC(=O)OCc1nc(C)c(C(C)C)c(N2CCOc3ccc(-c4ccc5nc(C)[nH]c5c4)cc3C2)n1] | {4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl acetate |
| 687 | 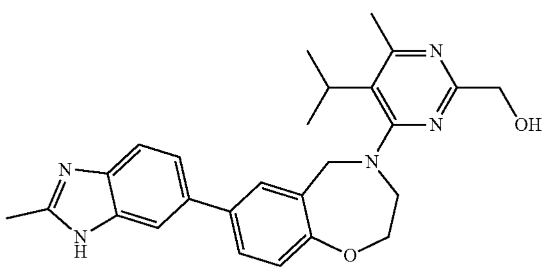 [SMILES: Cc1nc2ccc(-c3ccc4c(c3)CN(c3nc(CO)nc(C)c3C(C)C)CCO4)cc2[nH]1] | {4-methyl-6-[7-(2-methyl-1H-benzimidazol-5-yl)-2,3-dihydro-1,4-benzoxazepin-4(5H)-yl]-5-(1-methylethyl)pyrimidin-2-yl}methanol |
| 688 | 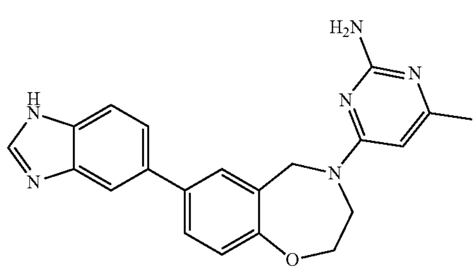 [SMILES: Cc1cc(N2CCOc3ccc(-c4ccc5[nH]cnc5c4)cc3C2)nc(N)n1] | 4-[7-(1H-benzimidazol-5-yl)-2,3-dihydro-1,4-benzoxazepin-4(5H)-yl]-6-methylpyrimidin-2-amine |

| Cmpd No. | Structure | Name |
|---|---|---|
| 689 | 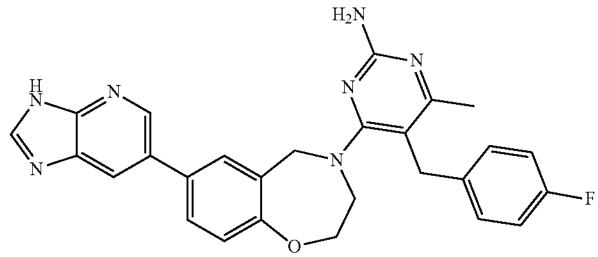 [SMILES: Cc1nc(N)nc(N2CCOc3ccc(-c4cnc5[nH]cnc5c4)cc3C2)c1Cc1ccc(F)cc1] | 5-[(4-fluorophenyl)methyl]-4-[7-(3H-imidazo[4,5-b]pyridin-6-yl)-2,3-dihydro-1,4-benzoxazepin-4(5H)-yl]-6-methylpyrimidin-2-amine |
| 690 | 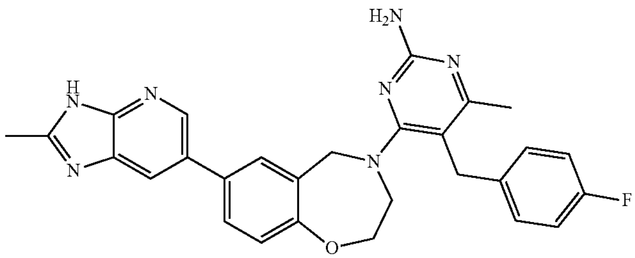 [SMILES: Cc1nc2cc(-c3ccc4c(c3)CN(c3nc(N)nc(C)c3Cc3ccc(F)cc3)CCO4)cnc2[nH]1] | 5-[(4-fluorophenyl)methyl]-4-methyl-6-[7-(2-methyl-3H-imidazo[4,5-b]pyridin-6-yl)-2,3-dihydro-1,4-benzoxazepin-4(5H)-yl]pyrimidin-2-amine |
| 691 | 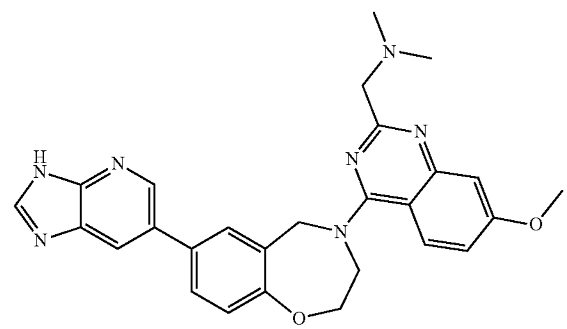 [SMILES: COc1ccc2c(N3CCOc4ccc(-c5cnc6[nH]cnc6c5)cc4C3)nc(CN(C)C)nc2c1] | 1-{4-[7-(3H-imidazo[4,5-b]pyridin-6-yl)-2,3-dihydro-1,4-benzoxazepin-4(5H)-yl]-7-(methyloxy)quinazolin-2-yl}-N,N-dimethylmethanamine |
| 692 | 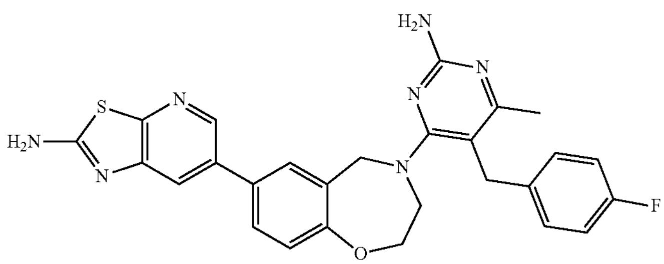 [SMILES: Cc1nc(N)nc(N2CCOc3ccc(-c4cnc5sc(N)nc5c4)cc3C2)c1Cc1ccc(F)cc1] | 6-(4-{2-amino-5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine |

Useful Intermediates: 4-[6,7-bis(methyloxy)quinolin-4-yl]-7-bromo-2,3,4,5-tetrahydro-1,4-benzoxazepine; 4-{4-[6,7-bis(methyloxy)quinolin-4-yl]-2,3,4,5-tetrahydro-1,4-benzoxazepin-7-yl}-2-nitroaniline; 4-{4-[6,7-bis(methyloxy)quinolin-4-yl]-2,3,4,5-tetrahydro-1,4-benzoxazepin-7-yl}benzene-1,2-diamine; N-[5-(4-{5-[(4-fluorophenyl)methyl]-6-methylpyrimidine-4-yl}-2,3,4,5-tetrahydro-1,4-benzoxazepin-7-yl)-1,3-thiazol-2-yl]acetamide; 7-bromo-4-{5-[(4-fluorophenyl)methyl]-6-methylpyrimidin-4-yl}-2,3,4,5-tetrahydro-1,4-benzoxazepine; 4-[6,7-bis(methyloxy)quinazolin-4-yl]-7-bromo-2,3,4,5-tetrahydro-1,4-benzoxazepine; 7-bromo-4-[6-(methyloxy)quinazolin-4-yl]-2,3,4,5-tetrahydro-1,4-benzoxazepine.

General Administration

In one aspect, the invention provides pharmaceutical compositions comprising an inhibitor of PI3K and/or mTOR according to the invention and a pharmaceutically acceptable carrier, excipient, or diluent. In certain other specific embodiments, administration is by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semisolid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a Compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active Compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active Compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a Compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a Compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a Compound of the invention, or a pharmaceutically acceptable salt thereof, for treatment of a disease-state in accordance with the teachings of this invention.

The compounds of the invention, or their pharmaceutically acceptable salts or solvates, are administered in a therapeutically effective amount which will vary depending upon a variety of factors including the activity of the specific Compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the Compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and more specifically at about room (or ambient) temperature, e.g., about 20° C. Unless otherwise stated (as in the case of an hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of the Invention may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Some of the compounds of the invention contain an active ketone —C(O)CF$_3$ and may exist in part or in whole as the —C(OH$_2$)CF$_3$ form. Regardless of whether the Compound is drawn as the —C(O)CF$_3$ or —C(OH$_2$)CF$_3$ form, both are included within the scope of the Invention. Although an individual Compound may be drawn as the —C(O)CF$_3$ form, one of ordinary skill in the art would understand that the Compound may exist in part or in whole as the —C(OH$_2$)CF$_3$ form and that the ratio of the two forms may vary depending on the Compound and the conditions in which it exists.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention. Further, for example, in this application R$^1$ can be 5-oxo-1H-1,2,4-triazol-3-yl, depicted structurally as

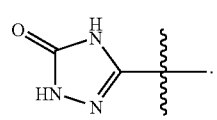

(100)

Both 5-oxo-1H-1,2,4-triazol-3-yl and the structure 100 include, and are equivalent to, 3-hydroxy-4H-1,2,4-triazol-5-yl and its structure

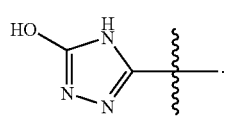

(200)

In another example, in this application $R^1$ can be 2-imino-1(2H)-hydroxy-pyrimidin-5-yl, depicted structurally as

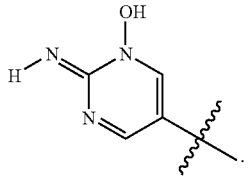 (101)

Both 2-imino-1(2H)-hydroxy-pyrimidin-5-yl and the structure 101 include, and are equivalent to, N-oxide of 2-aminopyrimidin-5-yl and its structure 201:

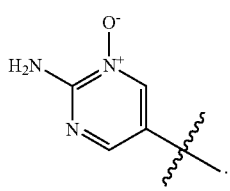 (201)

Regardless of which structure or which terminology is used, each tautomer is included within the scope of the Invention.

The present invention also includes N-oxide derivatives and protected derivatives of compounds of the Invention. For example, when compounds of the Invention contain an oxidizable nitrogen atom, the nitrogen atom can be converted to an N-oxide by methods well known in the art. When compounds of the Invention contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of the Invention can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art. In fact, there may be more than one process to prepare the compounds of the invention. The following examples illustrate but do not limit the invention. All references cited herein are incorporated by reference in their entirety.

An intermediate of formula 4 where PG is a nitrogen-protecting group, $R^{5a}$ and $R^{5c}$ are independently hydrogen or alkyl, $R^{5h}$ is hydrogen or halo, $R^{5b}$ is hydrogen, amino, or halo, and $R^{5d}$, $R^{5e}$, $R^{5f}$, and $R^{5g}$ are hydrogen can be prepared according to Scheme 1.

Scheme 1

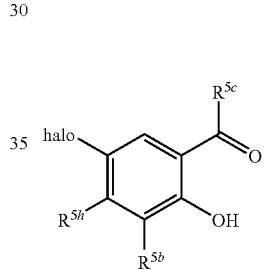

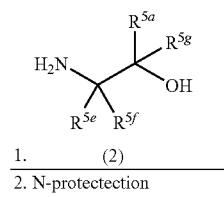

1. (2)
2. N-protectection

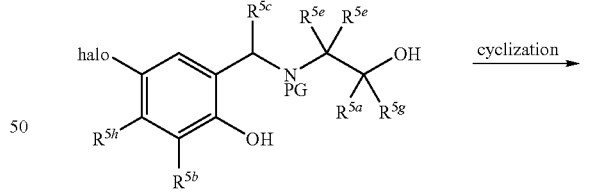

cyclization

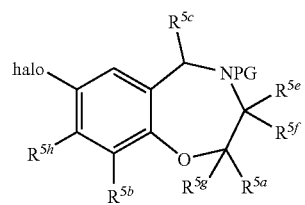

4

In particular, an intermediate of formula 4a can be prepared according to Scheme 1a.

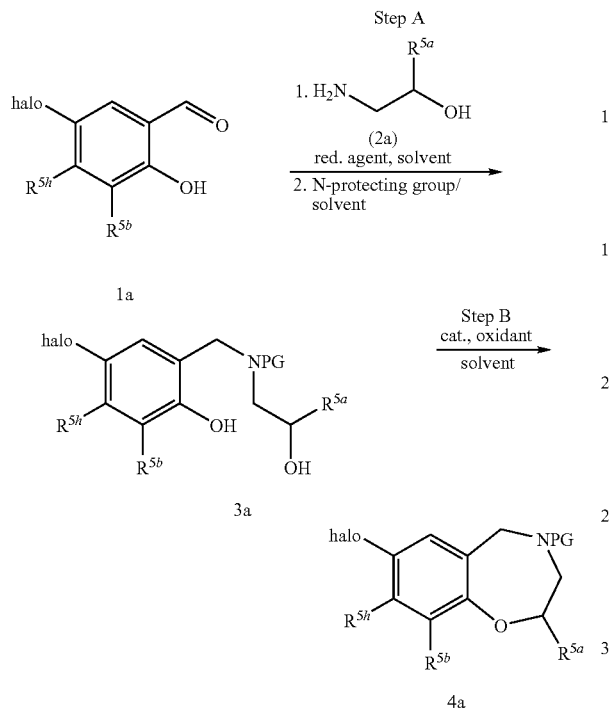

An intermediate of Formula 1a is commercially available or can be prepared using methods known to one of ordinary skill in the art. In particular an intermediate of formula 1a where $R^{5b}$ is hydrogen and $R^{5h}$ is hydrogen, bromo, or chloro is commercially available. An intermediate of formula 1a where $R^{5h}$ is hydrogen and $R^{5b}$ is bromo, chloro, iodo, or fluoro is commercially available. An intermediate of formula 1a where $R^{5h}$ is fluoro and $R^{5b}$ is hydrogen can be prepared using procedures described in J. of Med. Chem., 2004, 47(12), 3163-3179. An intermediate of formula 1a where $R^{5h}$ is hydrogen and $R^{5b}$ is amino can be prepared from the corresponding, commercially-available nitro intermediate using procedures known to one of ordinary skill in the art.

An intermediate of formula 2a where $R^{5a}$ is hydrogen or methyl is commercially available. The intermediate of formula 1a is treated with an intermediate of formula 2a in the presence of a reducing agent such as sodium borohydride, in a solvent(s) such as tetrahydrofuran and/or methanol and allowed to react at a temperature of about 40° C. for approximately 4 hours. The solvent is then removed and the reaction is taken up in a solvent(s) such as ethyl acetate and/or saturated sodium bicarbonate. To this suspension a nitrogen-protecting group precursor, such as di-tert-butyl dicarbonate, is added and the mixture is allowed to stir at room temperature overnight to yield an intermediate of formula 3a where PG is a nitrogen-protecting group.

Intermediate 3a is then treated with a catalyst, such as triphenylphosphine, in the presence of a dehydrating agent such as diisopropyl azodicarboxylate, in a solvent such as DCM. The reaction is allowed to proceed at room temperature for approximately 12 hours and the resulting product is optionally purified by column chromatography to yield an intermediate of formula 4a. Alternatively, the intermediate of formula 4a can be prepared by treating the intermediate of formula 3a with Burgess' reagent.

An intermediate of formula 5 where each R is hydrogen or both R's when taken together form a cyclic boronic ester, PG is a nitrogen-protecting group, $R^{5a}$ and $R^{5c}$ are independently hydrogen or alkyl, $R^{5h}$ is hydrogen or halo, $R^{5b}$ is hydrogen, amino, or halo, $R^{5e}$, $R^{5f}$, and $R^{5g}$ are hydrogen, and $R^1$ is as defined in the Summary of the Invention for a Compound of Formula I can be prepared according to Scheme 2.

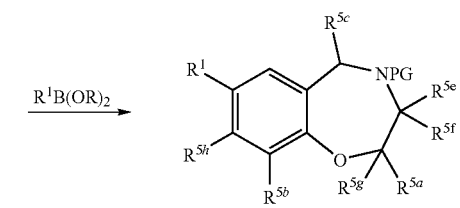

where the intermediate of formula 4 is prepared as described in Scheme 1.

In particular, an intermediate of formula 5a where $R^{5a}$ is hydrogen or alkyl, $R^{5h}$ is hydrogen or halo, $R^{5b}$ is hydrogen, amino, or halo, and $R^1$ is as defined in the Summary of the Invention for a Compound of Formula I, can be prepared according to Scheme 2a.

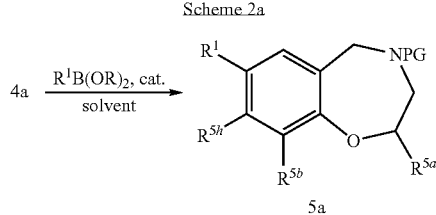

The intermediate of formula 4a, prepared as described in Scheme 1a, is treated with a boronic acid of formula $R^1B(OH)_2$ or

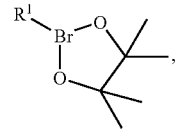

which are commercially available or can be prepared using procedures known to one of ordinary skill in the art. The reaction is carried out in the presence of a catalyst such as Pd(dppf)$_2$Cl$_2$, a base such as potassium carbonate, and in a solvent such as DME at about 80° C. for about 2 hours. The product can then be purified by chromatography to yield an intermediate of formula 5a.

Alternatively, an intermediate of formula 5, as defined above, can be prepared as described in Scheme 4.

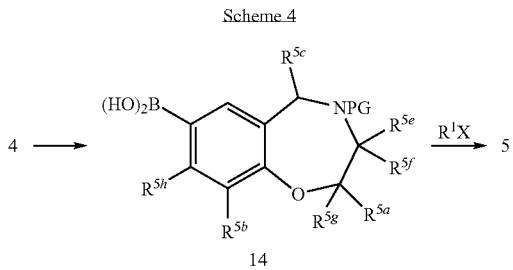

In particular, an intermediate of formula 5b where PG is a nitrogen-protecting group and $R^1$ is as defined in the Summary of the Invention for a Compound of Formula I can be prepared according to Scheme 4a.

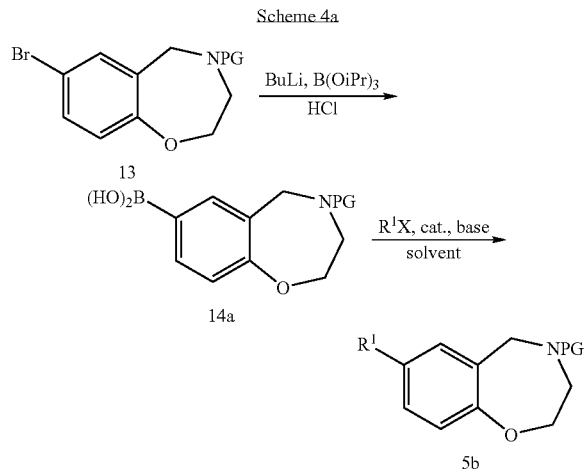

An intermediate of formula 13, where PG is a nitrogen-protecting group, is prepared as described in Scheme 1a. 13 is treated with triisopropylborate in a solvent such as THF at a temperature of about −60° C., followed by dropwise addition of a base such as n-butyllithium in tetrahydrofuran. The reaction was allowed to proceed for about 30 minutes, was treated with an acid such as hydrochloric acid, and allowed to warm to room temperature to yield an intermediate of formula 14a. Intermediate 14a is then treated with an intermediate of formula $R^1X$ (where X is a halide, and which is commercially available or can be prepared using procedures known to one of ordinary skill in the art), in the presence of a base such as potassium carbonate, in the presence of a catalyst such as tetrakis(triphenylphosphine)palladium(0), and in a solvent(s) such as 1,2-dimethoxyethane and/or water. The reaction is allowed to proceed under nitrogen and stirred at reflux for about 3 hours to yield an intermediate of formula 5b.

In particular, a Compound of the Invention where Y is =CH— or =N—, $R^{5a}$, $R^{5b}$, $R^{5c}$, $R^{5d}$, $R^{5e}$, $R^{5f}$, $R^{5g}$, and $R^{5h}$ are hydrogen; $R^1$ is benzimidazol-6-yl substituted at the 2-position with one $R^7$; $R^7$ is alkyl; $R^2$ and all other groups are independently as defined in the Summary of the Invention for a Compound of Formula I, can be prepared according to Scheme 6a.

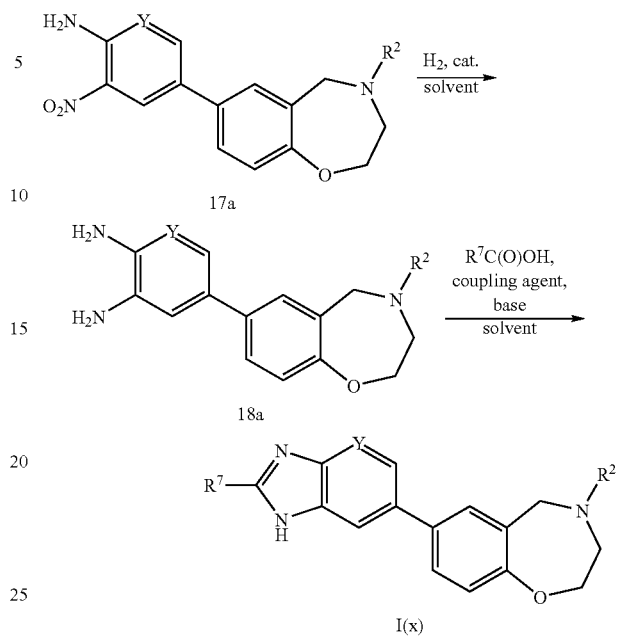

The nitro of the intermediate of formula 17a, prepared as described above in Scheme 4, is reduced in the presence of $H_2$ and palladium on carbon in a solvent(s) such as methanol and/or acetic acid to yield an intermediate of formula 18a. The intermediate of formula 18a is then treated with an intermediate of formula $R^7C(O)OH$, in the presence of a coupling agent such as HATU, in the presence of a base such as DIEA, in a solvent(s) such as DMF and/or acetic acid. The product can be purified by column chromatography to yield a Compound of Formula I(x).

A Compound of the Invention of Formula I where $R^{5a}$ and $R^{5c}$ are independently hydrogen or alkyl, $R^{5h}$ is hydrogen or halo, $R^{5b}$ is hydrogen, amino, or halo, $R^{5e}$, $R^{5f}$, and $R^{5g}$ are hydrogen, and $R^1$ and $R^2$ are independently as defined in the Summary of the Invention for a Compound of Formula I can be prepared as described in Scheme 5,

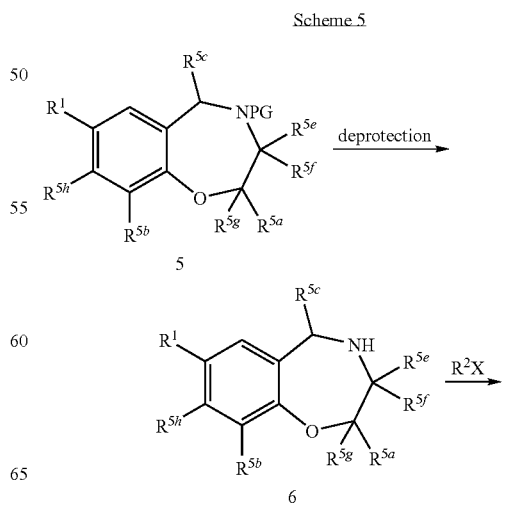

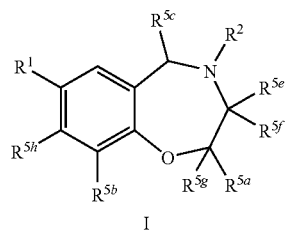

where X is halo or hydroxy.

In particular, a Compound of Formula I(w) where $R^{5a}$ is hydrogen or alkyl, $R^{5h}$ is hydrogen or halo, $R^{5b}$ is hydrogen, amino, or halo, and $R^1$ and $R^2$ are independently as defined in the Summary of the Invention for a Compound of Formula I can be prepared as described in Scheme 5a.

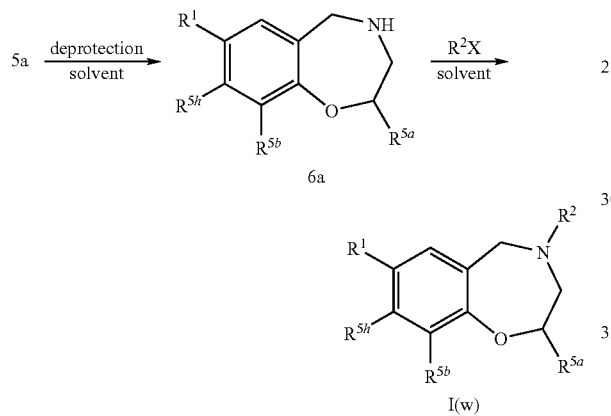

The protecting group on the intermediate of formula 5a is removed. When the protecting group is Boc, it can be removed with HCl to yield an intermediate of formula 6a. The intermediate of formula $R^2X$ (where X is a leaving group such as halo) is commercially available or can be prepared using procedures described herein or procedures known to one of ordinary skill in the art. The intermediate of formula 6a is then treated with $R^2X$, in the presence of a base such as Hünig's base or NMP, in a solvent such as DMF, at a temperature of about 50° C. The product can be purified by column chromatography to yield an intermediate of Formula I(w).

In particular, a Compound of Formula I(a) where $R^1$ and $R^2$ are independently as defined in the Summary of the Invention for a Compound of Formula I can be prepared according to Scheme 5b.

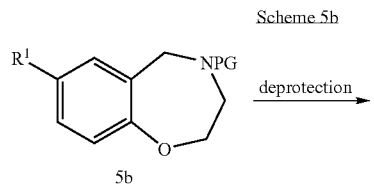

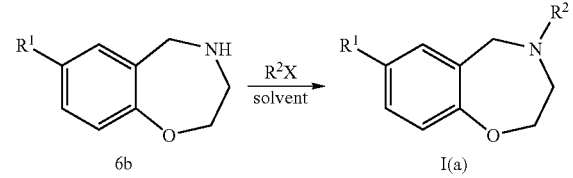

The protecting group on intermediate of formula 5b, prepared as described in Scheme 4a, is removed. When the protecting group is Boc, it can be removed with HCl to yield an intermediate of formula 6b. Intermediate 6b is then treated with an intermediate of formula $R^2X$ where X is a leaving group such as halo using standard alkylating conditions to yield a Compound of Formula I(a).

A Compound of Formula I(aa) where one of $Y_1$ and $Y_2$ is =CH— and the other is =N—, $R^1$ is benzimidazol-6-yl substituted at the 2-position with one $R^7$; $R^7$ and $R^2$ are independently as defined in the Summary of the Invention for a Compound of Formula I can be prepared according to Scheme 6a using conditions known to one of ordinary skill in the art.

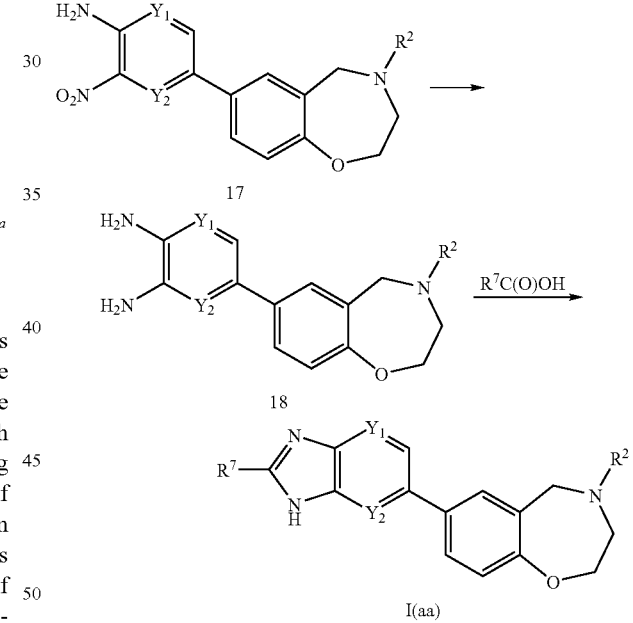

An intermediate of formula 17 is prepared by 1) treating an intermediate of formula 14a, prepared as described in Scheme 4a, with an intermediate of formula

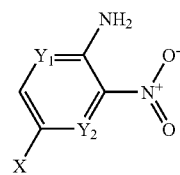

where X is halo using standard Suzuki coupling conditions; followed by 2) treating the with and intermediate of formula $R^2X$ using standard alkylating conditions. 17 is then hydrogenated in the presence of palladium on carbon in a solvent such as acetic acid to yield the intermediate of formula 18. 18 is then treated with an acid of formula $R^7C(O)OH$ to yield the Compound of Formula I(aa).

Alternatively, a Compound of Formula I(aa) can be prepared according to Scheme 6b.

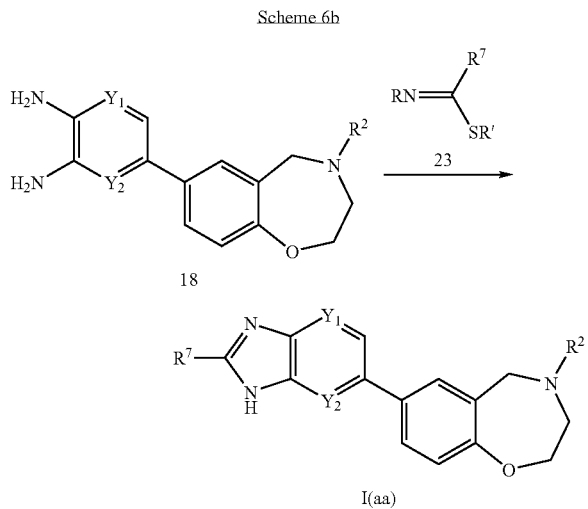

The intermediate of formula 18 is treated with an intermediate of formula 23 in the presence of glacial acetic acid, optionally in the presence of triethyl orthoformate, and heated to yield an a Compound of Formula I(aa).

A Compound of Formula I(v) where $R^2$ is as defined in the Summary of the Invention for a Compound of Formula I can be prepared according to Scheme 7a.

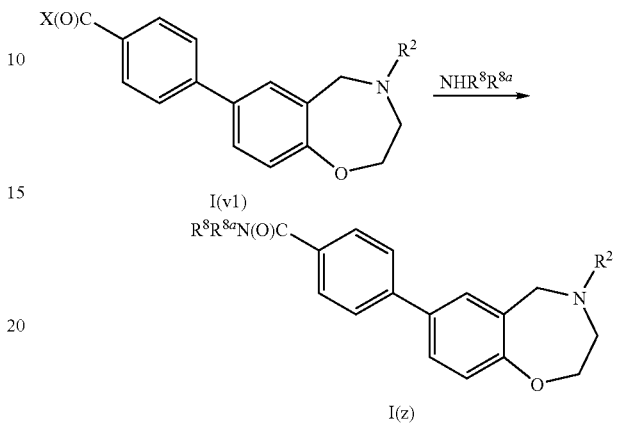

The Compound of Formula I(u) where R is alkyl, prepared using procedures according to Scheme 5b, is treated with a base such as LiOH, in a solvent(s) such as THF and/or water to yield the hydrolyzed Compound of Formula I(y).

A Compound of Formula I(z) where $R^2$, $R^8$, and $R^{8a}$ are independently as defined in the Summary of the Invention for a Compound of Formula I can be prepared according to Scheme 7b.

The Compound of Formula I(v1) where X is halo or hydroxy can be prepared according to Scheme 7a or prepared by making the acid chloride from a Compound of Formula I(v). The Compound of Formula I(v1) is then treated with an amine of formula $NHR^8R^{8a}$ optionally in the presence of a base such as DIEA in a solvent such as THF to yield a Compound of Formula I(z).

A Compound of Formula I where $R^1$, $R^2$, $R^{5a}$, $R^{5b}$, $R^{5c}$, $R^{5d}$, $R^{5e}$, $R^{5f}$, $R^{5g}$, and $R^{5h}$ can be prepared according to the following scheme (where R is $-B(OH)_2$ and Y is halo, or R is halo and Y is $-B(OH)_2$) using Suzuki coupling procedures known to one of ordinary skill in the art.

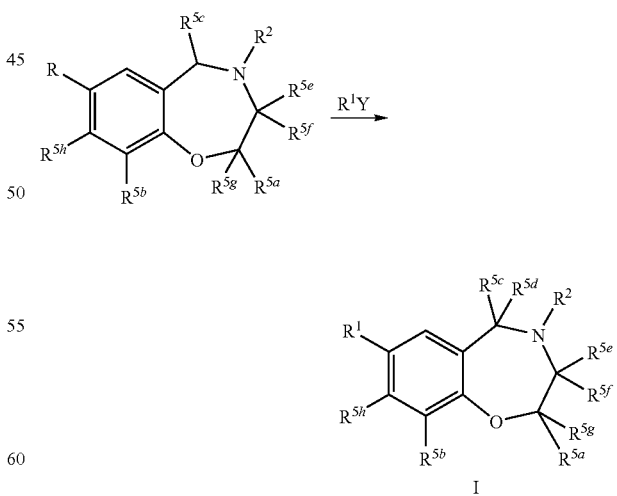

In particular, a Compound of Formula I(a) where $R^1$ and $R^2$ are independently as defined in the Summary of the Invention for a Compound of Formula I can be prepared as described in Scheme 8a.

Scheme 8a

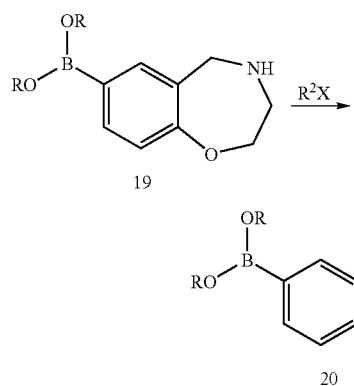

An intermediate of formula 19 (where each R is hydrogen or the two R's together form a boronic ester), which can be prepared by following step 1 of Scheme 4a and subsequent deprotection, is treated with an intermediate of formula R²X in a solvent such as dioxane/H₂O and in the presence of a base such as DIPEA. The resulting mixture is heated to about 90° C. to yield an intermediate of formula 20. 20 is treated with an intermediate of formula R¹X where X is halo and R¹ is as defined in the Summary of the Invention for a Compound of Formula I in a solvent such as DMF/water, in the presence of a base such as DIEA, in the presence of a catalyst such as [1,1'-bis(diphenylphosphino)ferrocene]dichloropalladium (II). The reaction is heated to about 95° C. 20 is then optionally purified to yield a Compound of Formula I(a).

Alternatively, a Compound of Formula I(a) where R¹ and R² are independently as defined in the Summary of the Invention for a Compound of Formula I can be prepared as described in Scheme 8b.

Scheme 8b

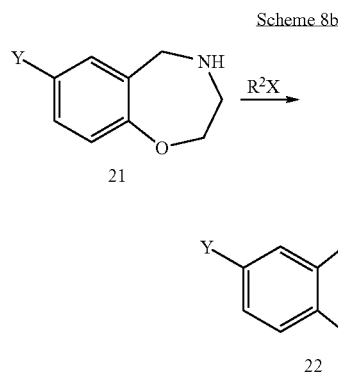

An intermediate of formula 21 where Y is halo, which can be prepared by following Scheme 1a followed by deprotection, is treated with an intermediate of formula R²X where X is halo, a base such as DIEA in a solvent such as 1-butanol and heated to yield an intermediate of formula 22. 22 is then treated with an intermediate of formula R¹B(OR)₂ (where each R is hydrogen or the two R together form a boronic ester), in the presence of a base such as potassium carbonate and in the presence of a catalyst such as dichloro[1,1-bis(diphenylphosphino)ferrocenepalladium (II) dichloromethane adduct in a solvent such as dimethoxyethane/water. The reaction was heated and yielded a Compound of Formula I(a).

SYNTHETIC EXAMPLES

Reagent Preparation 1

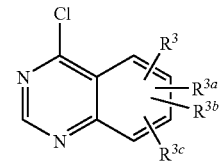

STEP 1: A solution of methyl 2-amino-5-bromo-4-methoxybenzoate (75 mg, 0.29 mmol) and ammonium formate (38 mg, 0.8 mmol) in formamide (1 mL) was heated at 165° C. for 18 h. The mixture was allowed to cool to room temperature then diluted with an excess of water. The solid formed was collected by filtration and washed with water then ethyl acetate and dried to give 6-bromo-7-methoxyquinazolin-4 (3H)-one (53 mg, 72% yield) as a pale yellow solid. MS (EI) for $C_9H_7BrN_2O_2$: 255, 257 (MH⁺).

STEP 2: 6-bromo-7-methoxyquinazolin-4(3H)-one (53 mg, 0.21 mmol) was taken into thionyl chloride (1.5 mL) followed by addition of catalytic DMF. The mixture was heated to 80° C. for 2 h then concentrated. The residue was partitioned with ethyl acetate and saturated aqueous sodium bicarbonate. The organic phase was washed with brine then dried over anhydrous sodium sulfate, filtered and concentrated to give 6-bromo-4-chloro-7-methoxyquinazoline (36 mg, 62% yield) as a brown solid. MS (EI) for $C_9H_6BrClN_2O$: 275 (MH⁺).

Using analogous synthetic techniques and substituting with alternative starting reagents in step 1 the following reagents were prepared.

4-chloro-7-(methylsulfonyl)quinazoline. Synthesized according to the method of reagent preparation 1 using 7-(methylsulfonyl)quinazolin-4(3H)-one in step 2. ¹H NMR (400 MHz, d₆-DMSO): 8.36 (d, 1H), 8.34 (s, 1H), 8.18 (d, 1H), 8.02 (dd, 1H), 3.36 (s, 3H).

4,7-dichloro-6-iodoquinazoline. Synthesized according to the method of reagent preparation 1 using methyl 2-amino-4-chloro-5-iodobenzoate in step 1. MS (EI) for $C_8H_3Cl_2IN_2$: 325 (MH⁺).

4-chloro-6-iodo-8-methylquinazoline. Synthesized according to the method of reagent preparation 1 using 2-amino-5-iodo-3-methylbenzoic acid in step 1. MS (EI) for $C_9H_6ClIN_2$: 305 (MH⁺).

4-chloro-6-(phenylmethoxy)-quinazoline. Prepared according to the method of reagent preparation 1 using 2-amino-5-benzyloxybenzoic acid methyl ester (J. Org. Chem. 2001, 66(8), 2784-2788) in step 1. MS (EI) for $C_{15}H_{11}ClN_2O$: 271 (MH⁺).

4,6-dichloro-7-methoxy-quinazoline. Prepared according to the method of reagent preparation 1 using 5-chloro-4-methoxyanthranilic acid (US 80-126838) in step 1. MS (EI) for $C_9H_6Cl_2N_2O$: 271 (MH⁺).

4-chloro-7,8-dimethoxy-quinazoline. Prepared according to the method of reagent preparation 1 using 2-amino-3,4-dimethoxybenzoic acid methyl ester (U.S. Pat. No. 4,287,341) in step 1. MS (EI) for $C_{10}H_9ClN_2O_2$: 225 MH$^+$).

7-(benzyloxy)-4-chloro-8-methoxyquinazoline. Prepared according to the method of reagent preparation 1 using 2-amino-3-methoxy-4-(phenylmethoxy)benzoic acid (J. Med. Chem. 1992, 35(14), 2703-10) in step 1. MS (EI) for $C_{16}H_{13}ClN_2O_2$: 301 MH$^+$).

4,6-dichloro-7,8-dimethoxyquinazoline. Prepared according to the method of reagent preparation 1 using 2-amino-5-chloro-3,4-dimethoxybenzoic acid (U.S. Pat. No. 4,287,341) in step 1. MS (EI) for $C_{10}H_8Cl_2N_2O_2$: 260 MH$^+$).

6-bromo-4,7-dichloroquinazoline. Synthesized according to the method of reagent preparation 1 by using 2-amino-5-bromo-4-chlorobenzoic acid in step 1. MS (EI) for $C_8H_3BrCl_2N_2$: 277 (MH$^+$).

4-chloro-6-iodo-7-methoxyquinazoline. Synthesized according to the method of reagent preparation 1 by N-iodosuccinimide iodination of methyl 2-amino-4-methoxybenzoate to give methyl 5-iodo-2-amino-4-methoxybenzoate then proceeding with step 1. $^1$H NMR (400 MHz, CDCl$_3$): 8.97, (s, 1H), 8.75, 7.31 (s, 1H), 4.08 (s, 3H). GC-MS for $C_9H_6ClIN_2O$: 319 (M$^+$).

7-bromo-4-chloro-8-methoxyquinazoline and 7-bromo-4-chloro-6-methoxyquinazoline. Synthesized according to the method of reagent preparation 1 by nitration and hydrogenation of methyl 4-bromo-3-methoxybenzoate to give a separable mixture of methyl 4-bromo-3-methoxy-2-aminobenzoate and methyl 4-bromo-5-methoxy-2-aminobenzoate then proceeding with step 1 individually. 7-bromo-4-chloro-8-methoxyquinazoline: $^1$H NMR (400 MHz, CDCl$_3$): 9.09, (s, 1H), 7.92 (d, 1H), 7.87 (d, 1H), 4.21 (s, 3H). GC-MS for $C_9H_6BrClN_2O$: 272 (M$^+$). 7-bromo-4-chloro-6-methoxyquinazoline: $^1$H NMR (400 MHz, CDCl$_3$): 8.95, (s, 1H), 8.40 (d, 1H), 7.45 (d, 1H), 4.18 (s, 3H), GC-MS for $C_9H_6BrClN_2O$: 272 (M$^+$).

8-bromo-4-chloro-6-methyl-quinazoline. Synthesized according to the method of reagent preparation 1 using 2-amino-3-bromo-5-methylbenzoic acid in step 1. GC-MS (EI) for $C_9H_6BrClN_2$: 257 (M$^+$).

4-chloro-6-(methylsulfonyl)quinazoline. Synthesized according to the method of reagent preparation 1 using 6-(methylsulfonyl)quinazolin-4(3H)-one in step 2. 6-(methylsulfonyl)quinazolin-4(3H)-one was obtained by the one step oxidation of 6-(methylthio)quinazolin-4(3H)-one (J. Med. Chem. 1983, 26(3), 420-5). MS (EI) for $C_9H_7ClN_2O_2$: 242 (M$^+$).

Reagent Preparation 2

4-chloro-5-methyl-6-(phenylmethyl)pyrimidine

Prepared from 4,6-dichloro-5-methylpyrimidine and benzyl zinc bromide (0.5 M solution in tetrahydrofuran) according to the procedure described in WO 2007/146824 as a colorless oil. $^1$H NMR (400 MHz, CDCl$_3$): 8.78 (s, 1H), 7.33-7.18 (m, 5H), 4.19 (s, 2H), 2.36 (s, 3H); MS (EI) for $C_{12}H_{11}ClN_2$: 219 (MH$^+$).

Reagent Preparation 3

4-chloro-6,6-dimethyl-5,6,7,8-tetrahydroquinazoline

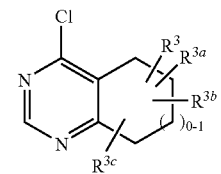

STEP 1: To a cooled (0° C.) solution of 4,4-dimethylcyclohexanone (21 g, 0.17 mol) and dimethyl carbonate (45 g, 0.50 mol) in THF (400 mL) was added NaH (60% wt/wt in mineral oil, 17 g, 0.43 mol) portionwise over 30 minutes. The resulting slurry was allowed to stir at ambient temperature for 30 minutes followed by two hours at reflux. The reaction mixture was cooled (0° C.) and MeOH (30 mL) was added dropwise over 20 minutes. The resulting slurry was partitioned between 10% aqueous citric acid and ethyl acetate. The organic layer was washed with brine, dried over magnesium sulfate and concentrated in vacuo. Purification by vacuum distillation provided methyl 2-hydroxy-5,5-dimethylcyclohex-1-enecarboxylate (22.5 g, 75% yield). $^1$H NMR (400 MHz, CDCl$_3$) δ 12.15 (s, 1H), 3.75 (s, 3H), 2.29 (t, 2H), 2.03 (s, 2H), 1.44 (t, 2H), 0.96 (s, 6H); MS (EI) for $C_{10}H_{16}O_3$: 184 (M$^+$).

STEP 2: A solution of methyl 2-hydroxy-5,5-dimethylcyclohex-1-enecarboxylate (10.0 g, 54 mmol) and ammonium acetate (10 g, 130 mmol) in ethanol (50 mL) was heated to reflux for 2 hours. The reaction was concentrated to one third original volume, and then diluted with ethyl acetate (100 mL). The organic solution was washed with water (100 mL) and brine (50 mL) and then dried over anhydrous sodium sulfate. After filtration and concentration, the residue was purified by silica gel column chromatography (ethyl acetate/hexanes, 1:8) to afford methyl 2-amino-5,5-dimethylcyclohex-1-enecarboxylate (7.42 g, 75% yield) as a yellow solid. MS (EI) for $C_{10}H_{17}NO_2$: 184 (MH$^+$).

STEP 3: 2-amino-5,5-dimethylcyclohex-1-enecarboxylate (7.42 g, 40 mmol) was dissolved in N,N-dimethylformamide dimethylacetal (50 mL) and heated to 110° C. for 18 hours. The resulting solution was cooled to room temperature and concentrated to provide methyl 2-((dimethylamino)methyleneamino)-5,5-dimethylcyclohex-1-enecarboxylate (9.5 g, 98% yield) as an oil. $^1$H NMR (400 MHz, CDCl$_3$): 3.65 (s, 3H), 3.49 (s, 1H), 2.95 (s, 6H), 2.35 (m, 2H), 2.15 (br s, 2H), 1.41 (t, 2H), 0.95 (s, 6H); MS (EI) for $C_{13}H_{22}N_2O_2$: 239 (MH$^+$).

STEP 4: A solution of methyl 2-((dimethylamino)methyleneamino)-5,5-dimethylcyclohex-1-enecarboxylate (9.5 g, 40 mol) in 7.0M ammonia in methanol (35 mL) was stirred at 25° C. for 90 minutes then concentrated to an oil. The residue was purified by silica gel column chromatography (ethyl acetate/hexanes, 1:8) to give 6,6-dimethyl-5,6,7,8-tetrahydroquinazolin-4(3H)-one (6.41 g, 90% yield) as a white solid. $^1$H NMR (400 MHz, d$_6$-DMSO): 7.96 (s, 1H), 2.52 (t, 2H), 2.14 (s, 2H), 1.48 (t, 2H), 0.93 (s, 6H); MS (EI) for $C_{10}H_{14}N_2O$: 179 (MH$^+$).

STEP 5: To 6,6-dimethyl-5,6,7,8-tetrahydroquinazolin-4 (3H)-one (6.41 g, 36 mmol) in chloroform (10 mL) added phosphorus oxychloride (10 mL) and refluxed for 2 hours. The mixture was concentrated to an oil, then diluted with ethyl acetate (80 mL) and washed with saturated sodium carbonate (50 mL) and brine (25 mL). The solution was dried over anhydrous sodium sulfate, filtered and concentrated, then the residue purified by silica gel column chromatography (ethyl acetate/hexanes, 1:8) to give 4-chloro-6,6-dimethyl-5,6,7,8-tetrahydroquinazoline (5.3 g, 75% yield) as a yellow solid. $^1$H NMR (400 MHz, CDCl$_3$): 8.72 (s, 1H), 2.52 (t, 2H), 2.14 (s, 2H), 1.48 (t 2H), 0.93 (s, 6H); MS (EI) for C$_{10}$H$_{13}$ClN$_2$: 197 (MH$^+$).

Using analogous synthetic techniques and substituting with alternative starting reagents in step 1 or 2 the following reagents were prepared. Alternative starting materials were available commercially unless otherwise indicated.

4-chloro-6-methyl-6,7-dihydro-5H-cyclopenta[d]pyrimidine. Prepared according to the method of reagent preparation 3; using 4-methyl-2-oxo-cyclopentanecarboxylic acid methyl ester (J. Chem. Soc. Perkin Trans 1 1987, 7, 1485-8) in step 2. $^1$H NMR (400 MHz, CDCl$_3$): 8.78 (s, 1H), 3.20 (m, 2H), 2.70 (m, 3H), 1.22 (d, 3H). GC/MS (EI) for C$_8$H$_9$ClN$_2$: 168 (M$^+$).

4-chloro-6-cyclopropyl-5,6,7,8-tetrahydropyrido[4,3-d]pyrimidine. Prepared according to the method of reagent preparation 3 using 1-cyclopropyl-4-oxo-3-piperidinecarboxylic acid methyl ester (Heterocycles, 1999, 50(2), 867-874) in step 2. $^1$H NMR (400 MHz, CDCl$_3$): 8.78 (s, 1H), 3.79 (s, 2H), 2.98 (m, 4H), 1.88 (m, 1H), 0.60 (m, 2H), 0.54 (m, 2H). MS (EI) for C$_{10}$H$_{12}$ClN$_3$: 210 (MH$^+$).

4-chloro-6-cyclopropyl-6,7-dihydro-5H-pyrrolo[3,4-d]pyrimidine. Prepared according to the method of reagent preparation 3 using 1-cyclopropyl-4-oxo-3-pyrrolidinecarboxylic acid methyl ester in step 2. MS (EI) for C$_9$H$_{10}$ClN$_3$: 196 (MH$^+$).

4-chloro-6-p-tolyl-6,7-dihydro-5H-pyrrolo[3,4-d]pyrimidine. Prepared according to the method of reagent preparation 3 using 1-(4-methylphenyl)-4-oxo-3-pyrrolidinecarboxilic acid ethyl ester in step 2. $^1$H NMR (400 MHz, CDCl$_3$): 8.92 (s, 1H), 7.14 (d, 2H), 6.62 (d, 2H), 4.70 (m, 4H), 2.30 (s, 3H). MS (EI) for C$_{13}$H$_{12}$ClN$_3$: 246 (MH$^+$).

4-chloro-7-methyl-7-phenyl-5,6,7,8-tetrahydroquinazoline. Prepared according to the method of reagent preparation 3 using 4-methyl-2-oxo-4-phenyl cyclohexanecarboxylic acid methyl ester (J. Org. Chem. 1991, 56(21), 6199-205) in step 1. MS (EI) for C$_{15}$H$_{15}$ClN$_2$: 259 (MH$^+$).

4-chloro-5-phenyl-6,7-dihydro-5H-cyclopenta[d]pyrimidine: Synthesized according to the method of reagent preparation 3 using ethyl 2-oxo-5-phenylcyclopentanecarboxylate in step 2. MS (EI) for C$_{13}$H$_{11}$ClN$_2$: 231 (MH$^+$).

4-chloro-7,7-dimethyl-5,6,7,8-tetrahydroquinazoline: Synthesized according to the method of reagent preparation 3 using ethyl 4,4-dimethyl-2-oxocyclohexanecarboxylate in step 2. $^1$H NMR (400 MHz, CDCl$_3$): 8.91 (s, 1H), 2.90 (s, 2H), 2.88 (tr, 2H), 1.73 (tr, 2H), 1.07 (s, 6H); MS (EI) for C$_{10}$H$_{13}$ClN$_2$: 197 (MH$^+$).

4'-chloro-7',8'-dihydro-5'H-spiro[cyclopropane-1,6'-quinazoline]. Prepared according to the method of reagent preparation 3 using spiro[2.5]octan-6-one in step 1. $^1$H NMR (400 MHz, CDCl$_3$) δ 8.73 (s, 1H), 3.00 (t, 2H), 2.63 (s, 2H), 1.69 (t, 2H), 0.52 (s, 4H); MS (EI) for C$_{10}$H$_{11}$ClN$_2$: 194 (M$^+$).

4-chloro-6,6-difluoro-5,6,7,8-tetrahydroquinazoline. Synthesized according to the method of reagent preparation 3 using 4,4-difluorocyclohexanone in step 1. MS (EI) for C$_8$H$_7$ClF$_2$N$_2$: 204 (M$^+$).

(R)-4-chloro-7-methyl-5,6,7,8-tetrahydroquinazoline. Synthesized according to the method of reagent preparation 3 using (R)-3-methylcyclohexanone in step 1. MS (EI) for C$_9$H$_{11}$ClN$_2$: 182 (M$^+$).

4-chloro-2,6-dimethyl-5,6,7,8-tetrahydroquinazoline. Synthesized according to the method of reagent preparation 3 using 4-methylcyclohexanone in step 1 and 1,1-dimethoxy-N,N-dimethylethanamine in step 3. MS (EI) for C$_{10}$H$_{13}$ClN$_2$: 196 (M$^+$).

4-chloro-6-ethyl-2-methyl-5,6,7,8-tetrahydroquinazoline. Synthesized according to the method of reagent preparation 3 using 4-ethylcyclohexanone in step 1 and 1,1-dimethoxy-N,N-dimethylethanamine in step 3. MS (EI) for C$_{11}$H$_{15}$ClN$_2$: 210 (M$^+$).

4-chloro-7-(trifluoromethyl)-5,6,7,8-tetrahydroquinazoline. Synthesized according to the method of reagent preparation 3 using methyl 2-hydroxy-4-(trifluormethyl)cyclohex-1-enecarboxylate in step 2. MS (EI) for C$_9$H$_8$ClF$_3$N$_2$: 236 (M$^+$).

(trans)-4-chloro-6,7-dimethyl-5,6,7,8-tetrahydroquinazoline. Synthesized according to the method of reagent preparation 3 using (trans) 3,4-dimethylcyclohexanone in step 1. MS (EI) for C$_{10}$H$_{13}$ClN$_2$: 196 (M$^+$).

4-chloro-6-(trifluoromethyl)-5,6,7,8-tetrahydroquinazoline. Synthesized according to the method of reagent preparation 3 using 4-(trifluormethyl)cyclohexanone in step 1. MS (EI) for C$_9$H$_8$ClF$_3$N$_2$: 236 (M$^+$).

(S)-4-chloro-7-methyl-5,6,7,8-tetrahydroquinazoline. Synthesized according to the method of reagent preparation 3 using (S)-3-methylcyclohexanone (US20060293364) in step 1. MS (EI) for C$_9$H$_{11}$ClN$_2$: 182 (M$^+$).

4-chloro-5-(trifluoromethyl)-5,6,7,8-tetrahydroquinazoline. Synthesized according to the method of reagent preparation 3 using methyl 2-hydroxy-6-(trifluormethyl)cyclohex-1-enecarboxylate in step 2. MS (EI) for C$_9$H$_8$ClF$_3$N$_2$: 236 (M$^+$).

4-chloro-7-vinyl-5,6,7,8-tetrahydroquinazoline. Synthesized according to the method of reagent preparation 3 using 3-vinylcyclohexanone (J. Med. Chem. 1987, 30, 1177-1186) in step 1. MS (EI) for C$_{10}$H$_{11}$ClN$_2$: 194 (M$^+$).

4-chloro-8,8-dimethyl-5,6,7,8-tetrahydroquinazoline. Synthesized according to the method of reagent preparation 3 using 2,2-dimethylcyclohexanone in step 1. MS (EI) for C$_{10}$H$_{13}$ClN$_2$: 196 (M$^+$).

4-chloro-6,6,7-trimethyl-5,6-dihydroquinazoline. Synthesized according to the method of reagent preparation 3 using 3,4,4-trimethylcyclohex-2-enone (J. Am. Chem. Soc. 1994, 116, 2902-2913) in step 1. MS (EI) for C$_{11}$H$_{13}$ClN$_2$: 208 (M$^+$).

(S)-4-chloro-8-vinyl-6,7,8,9-tetrahydro-5H-cyclohepta[d]pyrimidine. Synthesized according to the method of reagent preparation 3 using (S)-3-vinylcycloheptanone (prepared using procedure for (S)-3-vinylcyclohexanone in Org. Lett. 2003, 5, 97-99, but starting with (Z)-cyclohept-2-enone) in step 1. MS (EI) for C$_{11}$H$_{13}$ClN$_2$: 208 (M$^+$).

4-chloro-6,6-dimethyl-5,6-dihydroquinazoline. Synthesized according to the method of reagent preparation 3 using 4,4-dimethylcyclohex-2-enone in step 1. MS (ES) for C$_{10}$H$_{11}$ClN$_2$: 195 (MH$^+$).

4-chloro-6,6,8-trimethyl-5,6-dihydroquinazoline. Synthesized according to the method of reagent preparation 3 using 2,4,4-trimethylcyclohex-2-enone in step 1. MS (EI) for C$_{11}$H$_{13}$ClN$_2$: 209 (MH$^+$).

4-chloro-6,6,7,8-tetramethyl-5,6-dihydroquinazoline. Synthesized according to the method of reagent preparation 3 using 2,3,4,4-tetramethylcyclohex-2-enone (J. Org. Chem. 1981, 46, 1515-1521) in step 1. MS (EI) for $C_{12}H_{15}ClN_2$: 223 (MH$^+$).

(S)-4-chloro-7-ethyl-5,6,7,8-tetrahydroquinazoline. Synthesized according to the method of reagent preparation 3 using (S)-3-ethylcyclohexanone (Tetrahedron: Asymmetry, 1997, 8, 1253-1257) in step 1. MS (EI) for $C_{10}H_{13}ClN_2$: 197 (MH$^+$).

Reagent Preparation 4

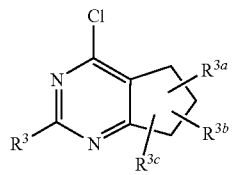

Step 1: A solution of methyl 4-methyl-2-oxocyclopentanecarboxylate (0.42 g, 2.69 mmol), 2-methyl-2-thiopseudourea sulfate (1.10 g, 7.9 mmol) and potassium hydroxide (0.50 g, 8.9 mmol) in water (12 mL) was stirred at 25° C. for 30 minutes, and then heated to reflux for 4 hours. The reaction was cooled to 0° C. by adding ice and a precipitate was formed. The solid product was removed by filtration and the filter cake dried to give 6-methyl-2-(methylthio)-6,7-dihydro-3H-cyclopenta[d]pyrimidin-4(5H)-one (0.19 g, 43% yield) as a white solid. $^1$H NMR (400 MHz, d6-DMSO): 2.87 (m, 2H), 2.53 (s, 3H), 2.37 (m, 2H), 2.28 (s, 3H), 1.49 (m, 1H), 1.02 (d, 3H).

Step 2: A solution of 6-methyl-2-(methylthio)-6,7-dihydro-3H-cyclopenta[d]pyrimidin-4(5H)-one (0.19 g, 0.97 mmol) in phosphorous oxychloride (5.0 mL) was heated to 95° C. for 1 hour. After cooling the reaction was concentrated, and the residue dissolved in ethyl acetate (50 mL) and washed with cold water (25 mL), 0.1 M aqueous sodium hydroxide (25 mL) and brine (20 mL). The organic phase was dried over anhydrous sodium sulfate, filtered and concentrated. The residue was chromatographed on silica gel (diethyl ether/hexanes, 1:10) and the product containing fractions concentrated. The residue thus obtained was purified further by preparative reverse phase HPLC (0.1% aqueous ammonium acetate-acetonitrile to give 4-chloro-6-methyl-2-(methylthio)-6,7-dihydro-5H-cyclopenta[d]pyrimidine (25 mg, 12% yield) as an oil. $^1$H NMR (400 MHz, d6-DMSO): 3.12 (m, 2H), 2.61 (m, 2H), 2.56 (s, 3H), 1.25 (m, 1H), 1.18 (d, 3H); MS (EI) for $C_9H_{11}ClN_2S$: 215 (MH$^+$).

Using analogous synthetic techniques and substituting with alternative starting reagents the following reagents were prepared.

4-chloro-2-(methylthio)-6,7-dihydro-5H-cyclopenta[d]pyrimidine. Synthesized according to the method of reagent preparation 4 by replacement of step 1 with 1,2,3,5,6,7-hexahydro-2-thioxo-4H-cyclopentapyrimidin-4-one S-alkylation with iodomethane and proceeding to step 2. $^1$H NMR (400 MHz, CDCl$_3$): 3.00 (tr, 2H), 2.92 (tr, 2H), 2.56 (s, 3H), 2.14 (m, 2H).

2-(benzylthio)-4-chloro-6,7-dihydro-5H-cyclopenta[d]pyrimidine. Synthesized according to the method of reagent preparation 4 by replacement of step 1 with 1,2,3,5,6,7-hexahydro-2-thioxo-4H-cyclopentapyrimidin-4-one S-alkylation with benzyl bromide and proceeding to step 2. $^1$H NMR (400 MHz, CDCl$_3$): 7.43 (d, 2H), 7.27 (tr, 2H), 7.22-7.18 (m, 1H), 4.38 (s, 2H), 2.95 (tr, 2H), 2.86 (tr, 2H), 2.08 (m, 2H).

4-chloro-2-(ethylthio)-6,7-dihydro-5H-cyclopenta[d]pyrimidine. Synthesized according to the method of reagent preparation 4 by replacement of step 1 with 1,2,3,5,6,7-hexahydro-2-thioxo-4H-cyclopentapyrimidin-4-one S-alkylation with iodoethane and proceeding to step 2. $^1$H NMR (400 MHz, CDCl$_3$): 3.08 (q, 2H), 2.93 (tr, 2H), 2.86 (tr, 2H), 2.08 (m, 2H), 1.32 (tr, 3H).

Reagent Preparation 5

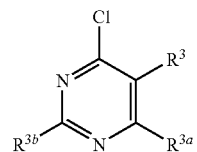

STEP 1: A solution of ethyl 4-methyl-3-oxopentanoate (3.0 g, 19.0 mmol) and potassium carbonate (7.86 g, 56.9 mmol) in THF (40 mL) was stirred at room temperature for 3 h under N$_2$ (g). The mixture was cooled to 0° C. and methyl iodide (3.23 g, 22.8 mmol) was added dropwise over 5 min. The reaction mixture was allowed to warm to room temperature and stirred for 16 h. Subsequent filtration and concentration provided ethyl 2,4-dimethyl-3-oxopentanoate (2.89 g, 89% yield) as a clear yellow oil that was used without further purification. MS (EI) for $C_9H_{16}O_3$: 172 (MH$^+$).

STEP 2: To anhydrous ethanol (110 mL) was added sodium metal (1.16 g, 50.4 mmol) and the mixture was stirred until dissolution was complete. To this solution was added thiourea (1.79 g, 23.5 mmol) and ethyl 2,4-dimethyl-3-oxopentanoate (2.89 g, 16.8 mmol). The reaction mixture was stirred at 85° C. for 20 h then cooled and concentrated. The residue was diluted with water, the pH adjusted to 4 with 1 N hydrochloric acid then extracted with ethyl acetate (3×80 mL). The combined organic layers were washed with brine, dried over anhydrous sodium sulfate, filtered and concentrated to provide 6-isopropyl-5-methyl-2-thioxo-2,3-dihydropyrimidin-4(1H)-one (2.40 g, 78% yield) as a tan solid that was used without further purification. $C_8H_{12}N_2OS$: 185 (MH$^+$).

STEP 3: To a solution of 30% hydrogen peroxide (12 mL) and water (23 mL) was slowly added 6-isopropyl-5-methyl-2-thioxo-2,3-dihydropyrimidin-4(1H)-one (1.0 g, 5.4 mmol). The reaction mixture was stirred at 70° C. for 3 h. After cooling to room temperature, saturated sodium carbonate was slowly added until the pH reached 10. To this mixture was slowly added a 1 M solution of sodium thiosulfate until residual peroxide was quenched, whereupon the aqueous solution was concentrated to dryness. The residue was suspended in chloroform (100 mL), filtered to remove inorganic salts and the filtrate concentrated to provide 6-isopropyl-5-methylpyrimidin-4-ol (0.25 g, 30% yield) as a white solid that was used without further purification. MS (EI) for $C_8H_{12}N_2O$: 153 (MH$^+$).

STEP 4: To 6-isopropyl-5-methylpyrimidin-4-ol (0.25 g, 1.6 mmol) was added neat phosphorous oxychloride (5 mL) and the mixture stirred at 70° C. for 3 h. After cooling to room temperature the solution was concentrated, diluted with water then neutralized by portionwise addition of saturated sodium carbonate solution. The aqueous mixture was extracted with ethyl acetate and the organic solution washed with brine then dried over anhydrous sodium sulfate. Filtration and concentration provided 4-chloro-6-isopropyl-5-methylpyrimidine (30 mg, 11% yield) as a brown oil that was used without further purification. MS (EI) for $C_8H_{11}ClN_2$: 170 (MH$^+$).

Using analogous synthetic techniques and substituting with alternative starting reagents in step 1 the following reagents were prepared.

4-chloro-5-(cyclopropylmethyl)-6-methylpyrimidine. Synthesized according to the method of reagent preparation 5 using methyl 3-oxobutanoate and (bromomethyl)cyclopropane in step 1. MS (EI) for $C_9H_{11}ClN_2$: 182 (MH).

4-chloro-5-(4-chlorobenzyl)-6-methylpyrimidine. Synthesized according to the method of reagent preparation 5 using methyl 3-oxobutanoate and 1-(bromomethyl)-4-chlorobenzene in step 1. MS (EI) for $C_{12}H_{10}Cl_2N_2$: 254 (MH$^+$).

4-chloro-5-(3,5-difluorobenzyl)-6-methylpyrimidine. Synthesized according to the method of reagent preparation 5 using methyl 3-oxobutanoate and 1-(bromomethyl)-3,5-difluorobenzene in step 1. MS (EI) for $C_{12}H_9ClF_2N_2$: 255 (MH$^+$).

4-chloro-6-methyl-5-(3-(trifluoromethyl)benzyl)pyrimidine. Synthesized according to the method of reagent preparation 5 using methyl 3-oxobutanoate and 1-(chloromethyl)-3-(trifluoromethyl)benzene in step 1. MS (EI) for $C_{13}H_{10}ClF_3N_2$: 287 (MH$^+$).

4-chloro-5-(1-(3-fluorophenyl)ethyl)-6-methylpyrimidine. Synthesized according to the method of reagent preparation 5 using methyl 3-oxobutanoate and 1-(3-fluorophenyl)ethyl methanesulfonate in step 1. MS (EI) for $C_{13}H_{12}ClFN_2$: 251 (MH$^+$).

4-chloro-5-(4-chloro-3-fluorobenzyl)-6-methylpyrimidine. Synthesized according to the method of reagent preparation 5 using methyl 3-oxobutanoate and 4-(bromomethyl)-1-chloro-2-fluorobenzene in step 1. MS (EI) for $C_{12}H_9Cl_2FN_2$: 272 (MH$^+$).

4-chloro-5-(4-fluorobenzyl)-6-methylpyrimidine. Synthesized according to the method of reagent preparation 5 using methyl 3-oxobutanoate and 1-(bromomethyl)-4-fluorobenzene in step 1. MS (EI) for $C_{12}H_{10}ClFN_2$: 237 (MH$^+$).

4-chloro-5-(2-fluorobenzyl)-6-methylpyrimidine. Prepared according to the method of reagent preparation 5 by using methyl 3-oxobutanoate and 1-(bromomethyl)-2-fluorobenzene in step 1. $^1$H NMR (400 MHz, CDCl$_3$): 8.79 (1H), 7.28 to 7.12 (m, 1H), 7.14 to 6.97 (m, 2H), 6.82 (dd, 1H), 4.19 (s, 2H), 2.47 (s, 3H), GC-MS for $C_{12}H_{10}ClFN_2$: 236 (M$^+$).

4-chloro-5-ethyl-6-isopropylpyrimidine. Prepared according to reagent preparation 5 by using ethyl isobutyrylacetate and iodoethane in step 1. MS (EI) for $C_9H_{13}ClN_2$: 184 (M$^+$).

5-benzyl-4-chloro-6-methylpyrimidine. Prepared according to reagent preparation 5 by using ethyl 2-benzylacetoacetate in step 2. MS (EI) for $C_{12}H_{11}ClN_2$: 219 (MH$^+$).

4-chloro-6-ethyl-5-methyl-pyrimidine. Prepared according to reagent preparation 5 by using methyl 3-oxopentanoate in step 1. $^1$H NMR (400 MHz, CDCl$_3$): 8.74 (s, 1H), 2.85 (q, 2H), 2.39 (s, 3H), 1.30 (t, 3H); MS (EI) for $C_7H_9ClN_2$: 158 (MH$^+$).

4-chloro-5,6,7,8-tetrahydroquinazoline. Synthesized according to the method of reagent preparation 5 using ethyl 2-oxocyclohexanecarboxylate in step 2. $^1$H NMR (400 MHz, CDCl$_3$): 8.7 (s, 1H), 2.90 (m, 2H), 2.78 (m, 2H), 1.88 (m, 4H). MS (EI) for $C_8H_9ClN_2$: 169 (MH$^+$).

4-chloro-5,6-diethyl-pyrimidine. Prepared according to reagent preparation 5 by using methyl 3-oxopentanoate and iodoethane in step 1.

4-chloro-6-methyl-5-(1-methylethyl)-pyrimidine. Prepared according to reagent preparation 5 by using methyl 3-oxobutanoate and 2-iodopropane in step 1. $^1$H NMR (400 MHz, DMSO-d$_6$): 8.70 (s, 1H), 3.49 (h, 1H), 2.60 (s, 3H), 1.34 (d, 6H); MS (EI) for $C_8H_{11}ClN_2$: 171 (MH$^+$).

4-chloro-5-isobutyl-6-methylpyrimidine. Prepared according to reagent preparation 5 by using methyl 3-oxobutanoate and 1-iodo-2-methylpropane in step 1. MS (EI) for $C_9H_{13}ClN_2$: 184 (M$^+$).

5-benzyl-4-chloro-6-ethylpyrimidine. Prepared according to reagent preparation 5 by using methyl 3-oxopentanoate and benzyl bromide in step 1. $^1$H NMR (400 MHz, CDCl$_3$): 8.83 (s, 1H), 7.27 (m, 3H), 7.08 (m, 2H), 4.22 (s, 2H), 2.79 (q, 2H), 1.20 (t, 3H); MS (EI) for $C_{13}H_{13}ClN_2$: 234 (MH$^+$).

4-chloro-5-(3-fluorobenzyl)-6-methylpyrimidine. Prepared according to reagent preparation 5 by using methyl 3-oxobutanoate and 3-fluorobenzylbromide in step 1. MS (EI) for $C_{12}H_{10}ClFN_2$: 237 (MH$^+$).

4-chloro-5-(3-chlorobenzyl)-6-methylpyrimidine. Prepared according to reagent preparation 5 by using methyl 3-oxobutanoate and 3-chlorobenzylbromide in step 1. MS (EI) for $C_{12}H_{10}Cl_2N_2$: 253 (MH$^+$).

4-chloro-6-methyl-5-phenoxy-pyrimidine. Prepared according to reagent preparation 5 by using ethyl 3-oxo-2-phenoxybutanoate in step 2. MS (EI) for $C_{11}H_9ClN_2O$: 221 (MH$^+$).

4-chloro-6-methyl-5-(1-phenylethyl)pyrimidine. Prepared according to reagent preparation 5 by using methyl 3-oxobutanoate and (1-bromoethyl)benzene in step 1. MS (EI) for $C_{13}H_{13}ClN_2$: 233 (MH$^+$).

4-chloro-5-(2-chlorobenzyl)-6-methylpyrimidine. Prepared according to reagent preparation 5 by using methyl 3-oxobutanoate and 2-chlorobenzyl bromide in step 1.

4-chloro-6-methyl-5-(4-methylbenzyl)pyrimidine. Prepared according to reagent preparation 5 by using methyl 3-oxobutanoate and 4-methylbenzyl bromide in step 1. $^1$H NMR (400 MHz, CDCl$_3$): 8.76 (s, 1H), 7.10 (d, 2H), 6.99 (d, 2H), 4.15 (s, 2H), 2.50 (s, 3H), 2.32 (s, 3H); MS (EI) for $C_{13}H_{13}ClN_2$: 233 (MH$^+$).

4-chloro-5-(4-methoxybenzyl)-6-methylpyrimidine. Prepared according to reagent preparation 5 by using methyl 3-oxobutanoate and 4-methoxybenzyl bromide in step 1. $^1$H NMR (400 MHz, CDCl$_3$): 8.76 (s, 1H), 7.02 (d, 2H), 6.83 (d, 2H), 4.13 (s, 2H), 3.78 (s, 3H), 2.51 (s, 3H); MS (EI) for $C_{13}H_{13}ClN_2O$: 249 (MH$^+$).

4-chloro-5-(3-methoxybenzyl)-6-methylpyrimidine. Prepared according to reagent preparation 5 by using methyl 3-oxobutanoate and 3-methoxybenzyl bromide in step 1. $^1$H NMR (400 MHz, DMSO-d$_6$): 8.81 (s, 1H), 7.22 (m, 1H), 6.81 (m, 1H), 6.70 (s, 1H), 6.63 (d, 1H), 4.17 (s, 2H), 3.71 (s, 3H), 2.47 (s, 3H); MS (EI) for $C_{13}H_{13}ClN_2O$: 249 (MH$^+$).

4-chloro-6-methyl-5-(3-methylbenzyl)pyrimidine. Prepared according to reagent preparation 5 by using methyl 3-oxobutanoate and 3-methylbenzyl bromide in step 1. $^1$H NMR (400 MHz, CDCl$_3$): 8.77 (s, 1H), 7.18 (m, 1H), 7.05 (d, 1H), 6.88 (m, 2H), 4.16 (s, 2H), 2.50 (s, 3H), 2.31 (s, 3H); MS (EI) for $C_{13}H_{13}ClN_2$: 233 (MH$^+$).

5-benzyl-4-chloropyrimidine. Prepared according to reagent preparation 5 by using ethyl 2-benzyl-3-hydroxyacrylate (J. Am. Chem. Soc. 1974, 96, 2121-2129) in step 2. MS (EI) for $C_{11}H_9ClN_2$: 205 (MH$^+$).

4-chloro-5-(3-chloro-5-fluorobenzyl)-6-methylpyrimidine. Prepared according to reagent preparation 5 by using methyl 3-oxobutanoate and 3-chloro-5-fluorobenzyl bromide in step 1. MS (EI) for $C_{12}H_9Cl_2FN_2$: 271 (MH$^+$).

4-chloro-5-(2-methoxybenzyl)-6-methylpyrimidine. Prepared according to reagent preparation 5 by using methyl 3-oxobutanoate and 2-methoxylbenzyl bromide in step 1. $^1$H NMR (400 MHz, methanol-d$_4$): 8.71 (s, 1H), 7.23 (m, 1H), 6.98 (d, 1H), 6.83 (m, 1H), 6.71 (d, 1H), 4.16 (s, 2H), 3.85 (s, 3H), 2.45 (s, 3H).

4-chloro-6-methyl-5-(2-methylbenzyl)pyrimidine. Prepared according to reagent preparation 5 by using methyl 3-oxobutanoate and 2-methylbenzyl bromide in step 1. $^1$H NMR (400 MHz, methanol-$d_4$): 8.77 (s, 1H), 7.23 (d, 1H), 7.12 (m, 1H), 7.03 (m, 1H), 6.45 (d, 1H), 4.16 (s, 2H), 2.43 (s, 3H), 2.42 (s, 3H).

4-chloro-5-(3,4-difluorobenzyl)-6-methylpyrimidine. Prepared according to reagent preparation 5 by using methyl 3-oxobutanoate and 3,4-difluorobenzyl bromide in step 1. MS (EI) for $C_{12}H_9ClF_2N_2$: 255 (MH$^+$).

4-chloro-6-methyl-5-(4-(trifluoromethyl)benzyl)pyrimidine. Prepared according to reagent preparation 5 by using methyl 3-oxobutanoate and 1-(chloromethyl)-4-(trifluoromethyl)-benzene in step 1. MS (EI) for $C_{13}H_{10}ClF_3N_2$: 287 (MH$^+$).

5-benzyl-4-chloro-6-(trifluoromethyl)pyrimidine. Prepared according to reagent preparation 5 by using ethyl 4,4,4-trifluoroacetoacetate and benzyl bromide in step 1. MS (EI) for $C_{12}H_8ClF_3N_2$: 272 (M$^+$).

4-chloro-6,6-dimethyl-6,7-dihydro-5H-cyclopenta[d]pyrimidine. Synthesized according to the method of reagent preparation 5 using ethyl 4,4-dimethyl-2-oxo-cyclopentanecarboxylate in step 2. MS (EI) for $C_9H_{11}ClN_2$: 183 (MH$^+$).

Reagent Preparation 6

6-chloro-5-methyl-N-phenylpyrimidin-4-amine

STEP 1: To a mixture of 4,6-dichloro-5-methylpyrimidine (2.27 g, 13.9 mmol) and aniline (1.0 g, 10.7 mmol) in isopropanol (15 mL) was added concentrated aqueous hydrochloric acid (1.5 mL) and heated to reflux for 2.5 h. The mixture was then concentrated and the residue triturated with ethyl acetate:isopropanol 4:1. The solid was collected by filtration and washed with additional ethyl acetate:isopropanol 4:1 then dried to give 6-chloro-5-methyl-N-phenylpyrimidin-4-amine (2.0 g, 67% yield). $^1$H NMR (400 MHz, $d_6$-DMSO): 8.85 (s, 1H), 8.26 (s, 1H), 7.60 (d, 2H), 7.35 (tr, 2H), 7.11 (tr, 1H), 2.31 (s, 3H). MS (EI) for $C_{11}H_{10}ClN_3$: 220 (MH$^+$).

Reagent Preparation 8

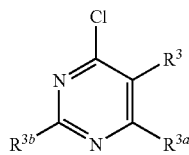

STEP 1: To a suspension of potassium tert-butoxide (10.6 g, 95.0 mmol) in tetrahydrofuran (100 mL) were added methyl acetoacetate (10.0 g, 86.0 mmol) and tert-butanol (0.83 mL, 8.6 mmol) at room temperature. The resulting solution was stirred for 1 h, and then 4-fluorobenzylbromide (11.2 mL, 90 mmol) was added. The reaction mixture was stirred at room temperature for 18 h, and then partitioned between water and ethyl acetate. The aqueous layer was extracted with ethyl acetate (3×), the combined organic extracts were washed with brine, dried over sodium sulfate, filtered and concentrated. Column chromatography of the residue on silica (5-20% ethyl acetate in hexanes) gave methyl 2-(4-fluorobenzyl)-3-oxobutanoate (14.5 g, 75% yield) as a colorless oil which was used in the next step without further purification.

STEP 2: To a suspension of acetamidine hydrochloride (0.54 g, 5.71 mmol) in methanol (8 mL) was added a 30% solution of sodium methoxide in methanol (1.1 mL, 5.7 mmol), and the resulting solution was stirred at room temperature for 45 min. Then, a solution of methyl 2-(4-fluorobenzyl)-3-oxobutanoate (0.80 g, 3.57 mmol) in methanol (3 mL) was added dropwise, and the resulting mixture was stirred at room temperature for 22 h. Water (100 mL) was added, and the mixture was extracted with chloroform (4×50 mL). The combined organic extracts were dried over sodium sulfate, filtered and concentrated to provide 5-(4-fluorobenzyl)-2,6-dimethylpyrimidin-4-ol (0.74 g, 89% yield) as a colorless solid. $^1$H NMR (400 MHz, methanol-$d_4$): 7.21 (m, 2H), 6.96 (m, 2H), 3.84 (s, 2H), 2.35 (s, 3H), 2.25 (s, 3H); MS (EI) for $C_{13}H_{13}FN_2O$: 233 (MH$^+$).

STEP 3: A solution of 5-(4-fluorobenzyl)-2,6-dimethylpyrimidin-4-ol (730 mg, 3.14 mmol) in phosphorus oxychloride (10 mL) was stirred at 60° C. for 90 min. The reaction mixture was concentrated and ethyl acetate (50 mL) was added to the residue. The organic solution was washed with saturated sodium bicarbonate (50 mL), water (50 mL), and brine (50 mL), dried over sodium sulfate, filtered and concentrated. Column chromatography of the residue on silica (5-40% ethyl acetate in hexanes) afforded 4-chloro-5-(4-fluorobenzyl)-2,6-dimethylpyrimidine (527 mg, 67% yield) as a colorless solid. $^1$H NMR (400 MHz, CDCl$_3$): 7.21 (m, 2H), 6.98 (m, 2H), 4.12 (s, 2H), 2.67 (s, 3H), 2.45 (s, 3H); MS (EI) for $C_{13}H_{12}ClFN_2$: 250 (M$^+$).

Using analogous synthetic techniques and substituting with alternative starting reagents in step 1 the following reagents were prepared.

4-Chloro-7-methyl-5,6,7,8-tetrahydroquinazoline. Prepared according to the method of reagent preparation 8 by using ethyl 4-methyl-2-oxocyclohexanecarboxylate and formamidine formate in step 2. GC-MS for $C_9H_{11}ClN_2$: 182 (M$^+$).

4-Chloro-6-ethyl-5,6,7,8-tetrahydroquinazoline. Prepared according to the method of reagent preparation 8 by using methyl 5-ethyl-2-oxocyclohexanecarboxylate and formamidine formate in step 2. GC-MS for $C_{10}H_{13}ClN_2$: 196 (M$^+$).

4-Chloro-5-ethyl-2,6-dimethylpyrimidine. Synthesized according to the method of reagent preparation 8 by using ethyliodide in step 1. MS (EI) for $C_8H_{11}ClN_2$: 171 (MH$^+$).

4-Chloro-5-(cyclopropylmethyl)-2,6-dimethylpyrimidine. Synthesized according to the method of reagent preparation 8 by using cyclopropylmethylbromide in step 1. MS (EI) for $C_{10}H_{13}ClN_2$: 197 (MH$^+$).

4-Chloro-2,6,6-trimethyl-5,6,7,8-tetrahydroquinazoline. Synthesized according to the method of reagent preparation 8 by using methyl 5,5-dimethyl-2-oxocyclohexanecarboxylate in step 2. MS (EI) for $C_{11}H_{15}ClN_2$: 211 (MH$^+$).

4-Chloro-6,6-dimethyl-2-(pyridin-2-yl)-5,6,7,8-tetrahydroquinazoline. Synthesized according to the method of reagent preparation 8 by using 2-hydroxy-5,5-dimethylcyclohex-1-enecarboxylate and picolinimidamide hydrochloride in step 2. MS (ES) for $C_{15}H_{16}ClN_3$: 274 (MH$^+$).

2-(4-chloro-6,6-dimethyl-5,6,7,8-tetrahydroquinazolin-2-yl)propan-2-ol. Synthesized according to the method of reagent preparation 8 using 2-hydroxy-5,5-dimethylcyclohex-1-enecarboxylate and 2-hydroxy-2-methylpropanimidamide hydrochloride in step 2. MS (ES) for $C_{13}H_{19}ClN_2$: 255 (MH$^+$).

4-chloro-2,6-dimethyl-5-(1-methylethyl)pyrimidine. Synthesized according to the method of reagent preparation 8 by using 2-iodopropane in step 1. MS (EI) for $C_9H_{13}ClN_2$: 185 (MH$^+$).

(7S)-4-chloro-7-ethyl-2-methyl-5,6,7,8-tetrahydroquinazoline. Synthesized according to the method of reagent preparation 8 by using methyl (4S)-4-ethyl-2-oxocyclohexanecarboxylate (reagent preparation 3) in step 2. MS (EI) for $C_{11}H_{15}ClN_2$: 211 (MH$^+$).

4-chloro-6,6-dimethyl-2-(2-pyrrolidin-1-ylethyl)-5,6,7,8-tetrahydroquinazoline. Synthesized according to the method of reagent preparation 8 by using 1-pyrrolidinepropanimidamide in step 2. MS (EI) for $C_{16}H_{24}ClN_3$: 294 (MH$^+$).

Reagent Preparation 9

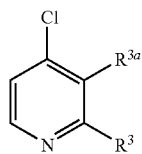

STEP 1: To a solution of phenylmethyl 2-methyl-4-oxo-3,4-dihydropyridine-1(2H)-carboxylate (*J. Bioorg. Med. Chem.* 2007, 1106-1116) (2.4 g, 9.78 mmol) in THF (35 mL) was added dropwise a 1M solution of lithium bis(trimethylsilyl)amide in THF (11 mL) at −78° C. The solution was warmed up to 0° C., stirred at this temperature for 1 h, then cooled again to −78° C. 3-Fluorobenzaldehyde (1.3 mL, 12.7 mmol) was added in one portion. The reaction was stirred for 4 h while allowing it to slowly warm up to 0° C. Then, saturated ammonium chloride (20 mL) was added, and the layers were separated. The aqueous layer was extracted with ethyl acetate (2×20 mL) and the combined organic layers were washed with saturated sodium chloride (50 mL), dried over sodium sulfate, filtered and concentrated. Column chromatography on silica (gradient 20 to 100% ethyl acetate in hexanes) afforded phenylmethyl 3-[(3-fluorophenyl)(hydroxy)methyl]-2-methyl-4-oxo-3,4-dihydropyridine-1(2H)-carboxylate (2.4 g, 66% yield) as mixture of diastereomers. MS (EI) for $C_{21}H_{20}FNO_4$: 370.1 (MH$^+$).

STEP 2: Mesyl chloride (0.31 mL, 3.97 mmol) was added in one portion to a solution of phenylmethyl 3-[(3-fluorophenyl)(hydroxy)methyl]-2-methyl-4-oxo-3,4-dihydropyridine-1(2H)-carboxylate (0.73 g, 1.98 mmol) in anhydrous pyridine (5 mL) at 0° C. The reaction mixture was warmed up to room temperature and stirred for 1 h. Water (5 mL) and ethyl acetate (5 mL) were added, the layers were separated, and the aqueous layer was extracted with ethyl acetate (3×5 mL). The combined organic layers were washed with saturated sodium chloride (15 mL) dried over sodium sulfate, filtered and concentrated to afford phenylmethyl 3-{(3-fluorophenyl)[methylsulfonyl)oxy]methyl}-2-methyl-4-oxo-3,4-dihydropyridine-1(2H)-carboxylate. MS (EI) for $C_{22}H_{22}FNO_6S$: 448.1 (MH$^+$).

STEP 3: Phenylmethyl 3-{(3-fluorophenyl)[methylsulfonyl)oxy]methyl}-2-methyl-4-oxo-3,4-dihydropyridine-1(2H)-carboxylate from step 2 was dissolved in THF (30 mL) and potassium tert-butoxide (1.11 g, 9.9 mmol) was added in one portion. After 15 min the reaction mixture was quenched with saturated ammonium chloride (20 mL). The layers were separated and the aqueous layer was extracted with 5:1 chloroform/isopropanol (3×20 mL). The combined organic layers were dried over sodium sulfate, filtered and concentrated. Column chromatography in silica (10% methanol in dichloromethane) afforded 3-[(3-fluorophenyl)methyl]-2-methylpyridin-4(1H)-one (0.230 g, 53% for two steps) $^1$H NMR (400 MHz, CDCl$_3$): 7.30 (d, 1H), 7.18-7.13 (m, 1H), 6.97 (d, 1H), 6.87-6.79 (m, 2H), 6.35 (d, 1H), 3.91 (s, 2H), 2.22 (s, 3H). MS (EI) for $C_{13}H_{12}FNO$: 218.1 (MH$^+$).

STEP 4: A solution of 3-[(3-fluorophenyl)methyl]-2-methylpyridin-4(1H)-one (0.07 g, 0.32 mmol) in phosphorous oxychloride (3 mL) was heated to 55° C. for 16 h. Then the solution was cooled to room temperature and concentrated. The remaining residue was dissolved in ethyl acetate (10 mL), washed with 5% sodium bicarbonate (2×5 mL), and saturated sodium chloride (5 mL), dried over sodium sulfate, filtered and concentrated to afford 4-chloro-3-[(3-fluorophenyl)methyl]-2-methylpyridine. $^1$H NMR (400 MHz, CDCl$_3$): 8.33 (d, 1H), 7.30-7.23 (m, 2H), 6.92-6.85 (m, 2H), 6.76 (d, 1H), 4.22 (s, 2H), 2.54 (s, 3H). MS (EI) for $C_{13}H_{11}ClF$: 236.0 (MH$^+$).

Using analogous synthetic techniques and substituting with alternative starting reagents in step 1 the following reagents were prepared.

3-benzyl-4-chloro-2-methylpyridine. Synthesized according to the method of reagent preparation 9 using benzaldehyde in step 1. $^1$H NMR (400 MHz, CDCl$_3$): 8.30 (d, 1H), 7.29-7.19 (m, 4H), 7.08 (d, 2H), 4.22 (s, 2H), 2.51 (s, 3H); MS (EI) for $C_{13}H_{12}ClN$: 218 (MH$^+$).

4-chloro-3-(4-fluorobenzyl)-2-methylpyridine. Synthesized according to the method of reagent preparation 9 using 4-fluorobenzaldehyde in step 1. $^1$H NMR (400 MHz, CDCl$_3$): 8.32 (d, 1H), 7.29 (d, 1H), 7.05-6.95 (m, 4H), 4.19 (s, 2H), 2.54 (s, 3H); MS (EI) for $C_{13}H_{11}ClFN$: 236 (MH$^+$).

Reagent Preparation 10

STEP 1: To a solution of ethyl 3-bromobutanoate (6.0 mL, 42 mmol) in N,N-dimethylformamide (20 mL) at 0° C. was added piperidine (8.0 mL, 80 mmol) and the mixture was warmed to room temperature then stirred 16 h. The reaction mixture was diluted with ethyl acetate (200 mL) and washed with a solution of brine and 2.0M aqueous sodium hydroxide (4:1 v/v). The organic phase was then dried over anhydrous sodium sulfate, filtered and concentrated to give ethyl 4-piperidin-1-ylbutanoate (6.8 g, 81% yield) as brown oil. MS (EI) for $C_{11}H_{21}NO_2$: 200 (MH$^+$).

Step 2: To a solution of potassium hydroxide (11 g, 0.20 mol) in water (40 mL) was added a solution of ethyl 4-piperidin-1-ylbutanoate (6.8 g, 34 mmol) in ethanol (30 mL) and the mixture was stirred at 35° C. for 2 hours. The reaction was quenched by dropwise addition of 37% aqueous hydrochloric acid (15 mL) and the mixture was concentrated then dried under vacuum. The residue was suspended in chloroform (100 mL) followed by addition of catalytic N,N-dimethylformamide (0.2 mL) then dropwise addition of oxalyl chloride (15 mL, 170 mmol) and the mixture was stirred at 25° C. for 18 hours. The reaction mixture was concentrated to afford crude 4-piperidin-1-ylbutanoyl chloride hydrochloride. To a suspension of the 4-piperin-1-ylbutanoyl chloride hydrochloride (ca. 40 mmol) and 2-methyl-2-thiopseudourea sulfate (5.6 g, 20 mmol) in acetonitrile (100 mL) was added triethylamine (20 mL, 0.27 mol) in portions while cooling in an ice bath. The reaction was then allowed to warm to 25° C. over 1 h. The reaction mixture was filtered through Celite with an acetonitrile wash (100 mL). The filtrate was concentrated to afford methyl N,N'-bis-(4-piperidin-1-ylbutanoyl)imidothiocarbamate (10.6 g, 79% yield) as a brown oil that was used without further purification. MS (EI) for $C_{20}H_{36}N_4O_2S$: 397 (MH$^+$).

Using analogous synthetic techniques and substituting with alternative starting reagents bis-[2-(methoxy)ethoxy] [(methylthio)methylidene]biscarbamate was prepared according to the method of reagent preparation 10 using 2-methoxyethyl chloroformate in step 2. MS (EI) for $C_{10}H_{18}N_2O_6S$: 295 (MH$^+$).

Reagent Preparation 11

STEP 1: To a solution of 6-bromo-2-methyl-1H-imidazo [4,5-b]pyridine (3.40 g, 16.0 mmol) and diisopropylethylamine (6.5 mL, 65 mmol) in N,N-dimethylformamide (20 mL) cooled in an ice bath was added dropwise isobutyl chloroformate (2.51 mL, 19.2 mmol) and the mixture was warmed to room temperature. After 1 hour the reaction was diluted with ethyl acetate (80 mL) and washed with water (60 mL), 10% aqueous citric acid (40 mL) and brine (20 mL). The organic phase was dried over anhydrous sodium sulfate, filtered and concentrated to a slurry. The residue was triturated diethyl ether (100 mL) and the solid isolated by filtration to give isobutyl 6-bromo-2-methyl-1H-imidazo[4,5-b]pyridine-1-carboxylate (2.3 g, 46% yield). MS (EI) for $C_{12}H_{14}BrN_3O_2$: 313 (MH$^+$).

Using analogous synthetic techniques and substituting with alternative starting reagents in step 1 isobutyl 2-(4-bromophenyl)-1H-imidazole-1-carboxylate was prepared according to the method of reagent preparation 11 using 2-(4-bromophenyl)-1H-imidazole and isobutyl chloroformate in step 1. MS (EI) for $C_{14}H_{15}BrN_2O_2$: 324 (MH$^+$).

Isobutyl 6-bromo-1H-benzo[d]imidazole-1-carboxylate. Prepared according to the method of reagent preparation 11 using 5-bromo-1H-benzo[d]imidazole in step 1. MS (EI) for $C_{12}H_{13}BrN_2O_2$: 297/299 (MH$^+$).

Reagent Preparation 12

5-Bromo-1-ethyl-1H-benzimidazole 5-bromo-1-ethyl-1H-benzimidazole was prepared in 3 steps from 1,4-dibromo-2-nitrobenzene according to the method described in (*Bioorg. and Med. Chem. Lett.* 2003, 13, 2485-2488). MS (EI) for $C_9H_9BrN_2$: 226 (MH$^+$).

Reagent Preparation 13

N-(5-bromothiazolo[5,4-b]pyridin-2-yl)benzamide

STEP 1: To a solution of ammonium thiocyanate (0.4 g, 5.0 mmol) in acetone (5 mL) was slowly added benzoyl chloride (0.6 mL, 5.0 mmol) and the suspension was heated to reflux for ten minutes. A solution of 6-bromo-2-chloro-3-pyridinamine (1.0 g, 4.8 mmol) in acetone (10 mL) was then added and the reaction mixture was refluxed for one hour. After cooling to room temperature the mixture was poured into water and partitioned with ethyl acetate (250 mL). The layers were separated and the aqueous layer was further extracted with ethyl acetate (2×, 100 mL). The combined organic layers were washed with brine (2×, 100 mL), dried over sodium sulfate, filtered and concentrated until a suspension formed. The white solid was collected by filtration to give N-(6-bromo-2-chloropyridin-3-ylcarbamothioyl)benzamide (1.6 g, 89%). $^1$H NMR (400 MHz, d$_6$-DMSO): 12.62 (br s, 1H), 12.00 (br s, 1H), 8.37 (d, 1H), 8.00 (2d, 2H), 7.79 (d, 1H), 7.69 (t, 1H), 7.57 (t, 2H). MS (EI) for $C_{13}H_9BrClN_3OS$: 370 (MH$^+$).

STEP 2: A solution of N-(6-bromo-2-chloropyridin-3-yl-carbamothioyl)benzamide (1.5 g, 4.0 mmol) and sodium ethoxide (0.54 g, 8.0 mmol) in 1-methyl-2-pyrrolidinone (10 mL) was heated to 120° C. for 8 hours. After cooling the reaction mixture to room temperature the mixture was poured into water. The resulting solid was collected by filtration, then washed sequentially with water and diethyl ether. The filter cake was dried to give N-(5-bromothiazolo[5,4-b]pyridin-2-yl)benzamide (1.02 g, 76%). $^1$H NMR (400 MHz, d$_6$-DMSO): 13.2 (br s, 1H), 8.16-8.10 (m, 3H), 7.72 (d, 1H), 7.70 (t, 1H), 7.59 (t, 2H). MS (EI) for $C_{13}H_8BrN_3OS$: 336 (MH$^+$).

Reagent Preparation 14

STEP 1: To a solution of 2-amino-5-bromopyridine (5.0 g, 29 mmol) in dioxane (60 mL) was added ethoxycarbonyl-isothiocyanate (3.4 mL, 29 mmol) in a dropwise manner and the mixture was allowed to stir for 18 h at room temperature. The mixture was then concentrated and the residue triturated with 10% ethyl acetate in hexanes. The solid was collected by filtration and dried to afford ethyl {[(5-bromopyridin-2-yl)amino]carbonothioyl}carbamate (6.2 g, 69%) as a colorless solid. MS (EI) for $C_9H_{10}BrN_3O_2S$: 305 (MH$^+$).

STEP 2: {[(5-Bromopyridin-2-yl)amino]carbonothioyl}carbamate was converted to 6-bromo-[1,2,4]triazolo[1,5-a]pyridin-2-amine according to methods in the literature, see 1) *Monatshefte fuer Chemie*, 1983, 114(6-7), 789-98 and 2) *Synthesis*, 2003, 11, 1649-1652. Thus, a mixture of hydroxylamine hydrochloride (375 mg, 5.4 mmol) and DIPEA (560 uL, 3.2 mmol) in 1:1 methanol:ethanol (8 mL) was stirred for 10 minutes at room temperature followed by addition of {[(5-bromopyridin-2-yl)amino]carbonothioyl}carbamate (500 mg, 1.62 mmol) and the resulting suspension was stirred for 2 h at room temperature then brought to 60° C. for an additional 2 h. The resulting solution was then cooled to room temperature and concentrated. The residue was then partitioned with ethyl acetate and saturated aqueous sodium bicarbonate. The organic solution was washed with brine, dried over anhydrous sodium sulfate then filtered and concentrated to give 6-bromo-[1,2,4]triazolo[1,5-a]pyridin-2-amine (340 mg, 98% yield) as a colorless crystalline solid. MS (EI) for $C_6H_5BrN_4$: 214 (MH$^+$).

STEP 3: A solution of 6-bromo-[1,2,4]triazolo[1,5-a]pyridin-2-amine (340 mg, 1.6 mmol), di-tert-butyl dicarbonate (370 mg, 1.6 mmol) and catalytic DMAP was stirred at 35° C. in THF (5 mL) for 18 h. An additional equivalent of di-tert-butyl dicarbonate was then added and stirring was continued for 48 h. The solution was then partitioned with ethyl acetate and water. The organic phase was washed with brine, dried over anhydrous sodium sulfate then filtered and concentrated. The residue was taken into dichloromethane and insoluble starting material was removed by filtration. The filtrate was concentrated and purified by silica gel chromatography to afford bis-(1,1-dimethylethyl)(6-bromo[1,2,4]triazolo[1,5-c]pyridine-2-yl)imidodicarbonate (284 mg, 43% yield) as an off white solid. $^1$H NMR (400 MHz, d$_6$-DMSO): 9.45 (s, 1H), 7.91 (d, 1H), 7.86 (d, 1H), 1.41 (s, 18H).

Using analogous synthetic techniques and substituting with alternative starting reagents bis(1,1-dimethylethyl)(5-bromo-4-methyl-1,3-thiazol-2-yl)imidodicarbonate was prepared, according to the method of reagent preparation 14 using 5-bromo-4-methylthiazol-2-amine in step 3 and conducting the protection step at reflux temperature. $^1$H NMR (400 MHz, CDCl$_3$): 2.30 (s, 3H), 1.53 (s, 18H).

Reagent Preparation 15

6-bromo-1-trityl-1H-imidazo[4,5-b]pyridine and 6-bromo-3-trityl-3H-imidazo[4,5-b]pyridine STEP 1: A suspension of 2,3-diamino-5-bromopyridine (3.0 g, 16.00 mmol) in formic acid (30 mL) was heated to reflux for 3 hours. After cooling the reaction mixture to room temperature it was concentrated and the residue was taken into 50% ethyl acetate in toluene (100 mL) then concentrated and the process repeated once more to remove excess formic acid. The resulting solid was triturated with ethyl acetate and the solid residue collected by filtration to give 6-bromo-1H-imidazo[4,5-b]pyridine (3.7 g, 95%). GCMS (EI) for $C_6H_4BrN_3$: 198 ($M^+$).

STEP 2: To a solution of 6-bromo-1H-imidazo[4,5-b]pyridine (2.7 g, 11.0 mmol) in dimethylformamide (30 mL) at 0° C. was added 60% sodium hydride in mineral oil (0.53 g, 13.2 mmol) and the reaction mixture was stirred for 30 minutes, followed by the addition of a solution of triphenylmethyl chloride (3.2 g, 11.55 mmol) in dimethylformamide (5 mL). The reaction mixture was stirred at room temperature for 24 hours then quenched by the careful addition of water then partitioned with ethyl acetate (250 mL). The organic phase was washed with 10% aqueous citric acid (2×, 100 mL), brine (100 mL), saturated sodium bicarbonate (100 mL), brine (100 mL) then dried over anhydrous sodium sulfate, filtered and concentrated. Silica gel chromatography (hexane ethyl acetate 9:1 to 4:1) provided 6-bromo-3-trityl-3H-imidazo[4,5-b]pyridine (1.8 g, 37%). $^1$H NMR (400 MHz, $CDCl_3$): 8.18 (d, 1H), 8.14 (d, 1H), 8.02 (s, 1H), 7.36-7.28 (m, 10H), 7.18-7.14 (m, 5H) and 6-bromo-1-trityl-1H-imidazo[4,5-b]pyridine (2.9 g, 60%) $^1$H NMR (400 MHz, $CDCl_3$): 8.50 (d, 1H), 8.14 (s, 1H), 7.38-7.34 (m, 10H), 7.16-7.12 (m, 5H), 6.84 (d, 1H).

Reagent Preparation 16

N-(7-Bromo-[1,2,4]triazolo[1,5-a]pyridin-2-yl)acetamide

STEP 1: To a solution of 7-Bromo-[1,2,4]triazolo[1,5-a]pyridin-2-ylamine (prepared using the procedure in WO2006038116) (0.150 g, 0.704 mmol), diisopropylethylamine (0.363 g, 2.81 mmol), catalytic DMAP (0.09 g, 0.07 mmol) in anhydrous THF (4 mL) was added acetic anhydride (0.216 g, 2.11 mmol). The reaction mixture was stirred at 50° C. for 22 h under $N_2$ (g). After cooling to room temperature the mixture was concentrated, diluted with ethyl acetate (50 mL), washed with saturated sodium bicarbonate (40 mL), brine (40 mL), and dried over anhydrous sodium sulfate. Filtration and concentration followed by column chromatography of the residue on silica (95:5 dichlormethane/methanol) afforded N-(7-bromo-[1,2,4]triazolo[1,5-a]pyridin-2-yl)acetamide (0.170 g, 95% yield) as a brown oil. MS (EI) for $C_8H_7BrN_4O$: 256 ($MH^+$).

Reagent Preparation 17

1-(4-chloro-6,6-dimethyl-5,6,7,8-tetrahydroquinazolin-2-yl)-N,N-dimethylmethanamine

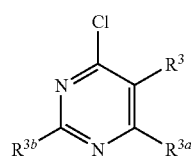

Step 1: To a solution of methyl 5,5-dimethyl-2-oxocyclohexanecarboxylate (6.0 g, 33 mmol) and 2-chloroacetimidamide hydrochloride (4.6 g, 36 mmol) in methanol (30 mL) was added sodium methoxide (4.4 M in MeOH, 9.0 mL, 40 mmol). The reaction mixture was stirred at ambient temperature for three hours and then concentrated. The resulting residue was partitioned between ethyl acetate and aqueous sodium bicarbonate. The organic layer was washed with brine, dried over magnesium sulfate and concentrated. Purification by silica gel chromatography provided 2-(chloromethyl)-6,6-dimethyl-5,6,7,8-tetrahydroquinazolin-4-ol (4.2 g, 57% yield) as a white solid. MS (ES) for $C_{11}H_{15}ClN_2O$: 227 ($MH^+$).

Step 2: To a solution of 2-(chloromethyl)-6,6-dimethyl-5,6,7,8-tetrahydroquinazolin-4-ol (2.5 g, 11 mmol) in THF (10 mL) was added dimethyl amine (2M in THF, 16.5 mL, 33 mmol). The reaction mixture was heated (60° C.) for two hours and then partitioned between ethyl acetate and sodium bicarbonate. The organic layer was washed with brine, dried over magnesium sulfate, filtered and concentrated to provide 2-((dimethylamino)methyl)-6,6-dimethyl-5,6,7,8-tetrahydroquinazolin-4-ol, which was used in step 3 without further purification. MS (ES) for $C_{13}H_{21}N_3O$: 236 ($MH^+$).

Step 3: To a solution of the final residue from step 2 in $CHCl_3$ (10 mL) was added $POCl_3$ (10 mL). The reaction mixture was heated (90° C.) for two hours and concentrated. This residue was partitioned between dichloromethane and aqueous sodium bicarbonate and the resulting organic layer was washed with brine, dried over magnesium sulfate, filtered and concentrated in vacuo. Purification by silica gel chromatography (5-10% concentrated aqueous ammonia in methanol) in chloroform provided 1-(4-chloro-6,6-dimethyl-5,6,7,8-tetrahydroquinazolin-2-yl)-N,N-dimethylmethanamine (1.3 g, 48% yield). $^1$H NMR (400 MHz, $CD_3OD$) δ 4.52 (s, 2H), 3.02 (s, 6H), 2.98 (t, 2H), 2.61 (s, 2H), 1.71 (t, 2H), 1.06 (s, 6H); MS (ES) for $C_{13}H_{20}ClN_3$: 254 ($MH^+$)

Using analogous synthetic techniques and substituting with alternative starting reagents the following compounds of the invention were prepared. Alternative starting materials were obtained commercially unless otherwise indicated.

(S)-4-chloro-2-((3-fluoropyrrolidin-1-yl)methyl)-6,6-dimethyl-5,6,7,8-tetrahydroquinazoline. Synthesized according to the method of reagent preparation 17 using (S)-3-fluoropyrrolidine in step 2. MS (ES) for $C_{15}H_{21}ClFN_3$: 298 ($MH^+$).

(R)-4-chloro-2-((3-fluoropyrrolidin-1-yl)methyl)-6,6-dimethyl-5,6,7,8-tetrahydroquinazoline. Synthesized according to the method of reagent preparation 17 using (R)-3-fluoropyrrolidine in step 2. MS (ES) for $C_{15}H_{21}ClFN_3$: 298 ($MH^+$).

4-chloro-2-((3,3-difluoropyrrolidin-1-yl)methyl)-6,6-dimethyl-5,6,7,8-tetrahydroquinazoline. Synthesized according to the method of reagent preparation 17 using 3,3-difluoropyrrolidine in step 2. MS (ES) for $C_{15}H_{20}ClF_2N_3$: 316 ($MH^+$).

N-((4-chloro-6,6-dimethyl-5,6,7,8-tetrahydroquinazolin-2-yl)methyl)-N-methylethanamine. Synthesized according to the method of reagent preparation 17 using N-methylethanamine in step 2. MS (ES) for $C_{14}H_{22}ClN_3$: 268 ($MH^+$).

4-chloro-6,6-dimethyl-2-(piperidin-1-ylmethyl)-5,6,7,8-tetrahydroquinazoline. Synthesized according to the method of reagent preparation 17 using piperidine in step 2. MS (ES) for $C_{16}H_{24}ClN_3$: 294 ($MH^+$).

N-((4-chloro-6,6-dimethyl-5,6,7,8-tetrahydroquinazolin-2-yl)methyl)-N-methylpropan-2-amine. Synthesized according to the method of reagent preparation 17 using N-methylpropan-2-amine in step 2. MS (ES) for $C_{15}H_{24}ClN_3$: 282 ($MH^+$).

N-((4-chloro-6,6-dimethyl-5,6,7,8-tetrahydroquinazolin-2-yl)methyl)-N-methylcyclopropanamine. Synthesized according to the method of reagent preparation 17 using N-methylcyclopropanamine in step 2. MS (ES) for $C_{15}H_{22}ClN_3$: 280 (MH$^+$).

Benzyl (4-chloro-6,6-dimethyl-5,6,7,8-tetrahydroquinazolin-2-yl)methyl(isopropyl)carbamate. Synthesized according to the method of reagent preparation 17 using propane-2-amine in step 2 followed by Cbz protection. MS (ES) for $C_{22}H_{28}ClN_3O_2$: 402 (MH$^+$).

4-chloro-6,6-dimethyl-2-(pyrrolidin-1-ylmethyl)-5,6,7,8-tetrahydroquinazoline. Synthesized according to the method of reagent preparation 17 using pyrrolidine in step 2. MS (ES) for $C_{15}H_{22}ClN_3$: 280 (MH$^+$).

(S)-1-(4-chloro-7-ethyl-5,6,7,8-tetrahydroquinazolin-2-yl)-N,N-dimethylmethanamine. Synthesized according to the method of reagent preparation 17 using (S)-methyl 4-ethyl-2-hydroxycyclohex-1-enecarboxylate in step 1. MS (ES) for $C_{13}H_{20}ClN_3$: 254 (MH$^+$).

{4-chloro-5-[(4-fluorophenyl)methyl]-6-methylpyrimidin-2-yl}methyl acetate. Synthesized according to the method of reagent preparation 17 using 2-(chloromethyl)-5-[(4-fluorophenyl)methyl]-6-methylpyrimidin-4-ol and sodium acetate in acetic acid in step 2. MS (ES) for $C_{15}H_{14}ClFN_2O_2$: 309 (MH$^+$).

4-chloro-2-(methoxymethyl)-6,6-dimethyl-5,6,7,8-tetrahydroquinazoline. Synthesized according to the method of reagent preparation 17 using sodium methoxide in step 2. MS (ES) for $C_{12}H_{17}ClN_2O$: 241 (MH$^+$).

Benzyl (4-chloro-6,6-dimethyl-5,6,7,8-tetrahydroquinazolin-2-yl)methyl(ethyl)-carbamate. Prepared according to the method of reagent preparation 17 by using ethylamine in step 2 followed by Cbz protection. MS (EI) for $C_{21}H_{26}ClN_3O_2$: 388 (MH$^+$).

Benzyl (4-chloro-6,6-dimethyl-5,6,7,8-tetrahydroquinazolin-2-yl)methyl(2-fluoroethyl)carbamate. Prepared according to the method of reagent preparation 17 by using fluoroethylamine in step 2 followed by Cbz protection. MS (EI) for $C_{21}H_{25}ClFN_3O_2$: 406 (MH$^+$).

N-[(4-chloro-6,6-dimethyl-5,6,7,8-tetrahydroquinazolin-2-yl)methyl]cyclopropanamine. Prepared according to the method of reagent preparation 17 by using cyclopropylamine in step 2. MS (EI) for $C_{14}H_{20}ClN_3$: 266 (MH$^+$).

Benzyl (4-chloro-6,6-dimethyl-5,6,7,8-tetrahydroquinazolin-2-yl)methyl(cyclobutyl)-carbamate. Prepared according to the method of reagent preparation 17 by using cyclobutylamine in step 2 followed by Cbz protection. MS (EI) for $C_{23}H_{28}ClN_3O_2$: 414 (MH$^+$).

1-(4-Chloro-5-(cyclopropylmethyl)-6-methylpyrimidin-2-yl)-N,N-dimethylmethanamine. Prepared according to the method of reagent preparation 17 by using methyl 2-(cyclopropylmethyl)-3-oxobutanoate (reagent preparation 8) in step 1. MS (EI) for $C_{12}H_{18}ClN_3$: 240 (MH$^+$).

N-((4-chloro-6,6-dimethyl-5,6,7,8-tetrahydroquinazolin-2-yl)methyl)-N-ethylethanamine. Prepared according to the method of reagent preparation 17 by using diethylamine in step 2. MS (EI) for $C_{15}H_{24}ClN_3$: 282 (MH$^+$).

4-((Chloro-6,6-dimethyl-5,6,7,8-tetrahydroquinazolin-2-yl)methyl)morpholine. Prepared according to the method of reagent preparation 17 by using morpholine in step 2. MS (EI) for $C_{15}H_{22}ClN_3O$: 296 (MH$^+$).

N-((4-chloro-6,6-dimethyl-5,6,7,8-tetrahydroquinazolin-2-yl)methyl)-N-ethylpropan-2-amine. Prepared according to the method of reagent preparation 17 by using ethylisopropylamine in step 2. MS (EI) for $C_{16}H_{26}ClN_3$: 296 (MH$^+$).

N-((4-chloro-6,6-dimethyl-5,6,7,8-tetrahydroquinazolin-2-yl)methyl)-2-methylpropan-2-amine. Prepared according to the method of reagent preparation 17 by using tert-butylamine in step 2. MS (EI) for $C_{15}H_{24}ClN_3$: 282 (MH$^+$).

N-((4-chloro-6,6-dimethyl-5,6,7,8-tetrahydroquinazolin-2-yl)methyl)-2-methylpropan-1-amine. Prepared according to the method of reagent preparation 17 by using iso-butylamine in step 2. MS (EI) for $C_{15}H_{24}ClN_3$: 282 (MH$^+$).

Benzyl (4-chloro-6,6-dimethyl-5,6,7,8-tetrahydroquinazolin-2-yl)methyl(2,2-difluoroethyl)carbamate. Prepared according to the method of reagent preparation 17 by using 2,2-difluoroethylamine in step 2 followed by Cbz protection. MS (EI) for $C_{21}H_{24}ClF_2N_3O_2$: 424 (MH$^+$).

N-((4-chloro-6,6-dimethyl-5,6,7,8-tetrahydroquinazolin-2-yl)methyl)-2,2,2-trifluoroethanamine. Prepared according to the method of reagent preparation 17 by using 2,2,2-trifluoroethylamine in step 2. MS (EI) for $C_{13}H_{17}ClF_3N_3$: 308 (MH$^+$).

N-((4-chloro-6,6-dimethyl-5,6,7,8-tetrahydroquinazolin-2-yl)methyl)-1-cyclopropylethanamine. Prepared according to the method of reagent preparation 17 by using 1-cyclopropylethanamine in step 2. MS (EI) for $C_{16}H_{24}ClN_3$: 294 (MH$^+$).

(4-Chloro-6,6-dimethyl-5,6,7,8-tetrahydroquinazolin-2-yl)methyl acetate. Prepared according to the method of reagent preparation 17 by using potassium acetate in step 2. MS (EI) for $C_{13}H_{17}ClN_2O_2$: 269 (MH$^+$).

Benzyl (4-chloro-6,6-dimethyl-5,6,7,8-tetrahydroquinazolin-2-yl)methyl(cyclopentyl)carbamate. Prepared according to the method of reagent preparation 17 by using cyclopentylamine in step 2 followed by Cbz protection. MS (EI) for $C_{24}H_{30}ClN_3O_2$: 428 (MH$^+$).

Ethyl 2-((4-chloro-6,6-dimethyl-5,6,7,8-tetrahydroquinazolin-2-yl)methylamino)propanoate. Prepared according to the method of reagent preparation 17 by using alanine ethyl ester in step 2. MS (EI) for $C_{16}H_{24}ClN_3O_2$: 326 (MH$^+$).

1-(4-Chloro-5,6-dimethylpyrimidin-2-yl)-N,N-dimethylmethanamine. Prepared according to the method of reagent preparation 17 by using methyl 2-methyl-3-oxobutanoate in step 1 in step 2. MS (EI) for $C_9H_{14}ClN_3$: 200 (MH$^+$).

1-(4-chloro-5-(4-fluorobenzyl)-6-methylpyrimidin-2-yl)-N,N-dimethylmethanamine. Synthesized according to the method of reagent preparation 17 using methyl 2-(4-fluorobenzyl)-3-oxobutanoate in step 1. $^1$H NMR (400 MHz, CDCl$_3$): 7.08-7.05 (m, 2H), 7.00-6.96 (m, 2H), 4.14 (s, 2H), 3.68 (s, 2H), 2.51 (s, 3H), 2.38 (s, 6H).

1-(4-chloro-5-isopropyl-6-methylpyrimidin-2-yl)-N,N-dimethylmethanamine. Synthesized according to the method of reagent preparation 17 using methyl 2-acetyl-3-methylbutanoate in step 1. MS (EI) for $C_{11}H_{18}N_3Cl$: 228, 230 (MH$^+$, Cl isotope pattern).

(S)-benzyl sec-butyl((4-chloro-6,6-dimethyl-5,6,7,8-tetrahydroquinazolin-2-yl)methyl)carbamate Synthesized according to the method of reagent preparation 17 using (S)-butan-2-amine in step 2 followed Cbz-protection prior to step 3. MS (ES) for $C_{23}H_{30}ClN_3O_2$: 416 (MH$^+$).

(R)-benzyl sec-butyl((4-chloro-6,6-dimethyl-5,6,7,8-tetrahydroquinazolin-2-yl)methyl)carbamate Synthesized according to the method of reagent preparation 17 using (R)-butan-2-amine in step 2 followed Cbz-protection prior to step 3. MS (ES) for $C_{23}H_{30}ClN_3O_2$: 416 (MH$^+$).

1-(4-chloro-6-ethyl-5-methylpyrimidin-2-yl)-N,N-dimethylmethanamine Synthesized according to the method of reagent preparation 17 using methyl 2-methyl-3-oxopentanoate in step 1. MS (ES) for $C_{10}H_{16}ClN_3$: 214 (MH$^+$).

1-(4-chloro-5-isopropylpyrimidin-2-yl)-N,N-dimethylmethanamine Synthesized according to the method of reagent preparation 17 using methyl 2-methyl-3-oxopentanoate (Elaridi et al. *Tetrahedron: Asymmetry* 2005, 16(7), 1309-1319) in step 1.

N-((4-chloro-6,6-dimethyl-5,6,7,8-tetrahydroquinazolin-2-yl)methyl)-N-methyl-2-nitrobenzenesulfonamide Synthesized according to the method of reagent preparation 17 using methylamine in step 2 followed by protection as the 2-nitrobenzenesulfonamide prior to step 3. $^1$H NMR (400 MHz, CDCl$_3$) δ 8.18-8.13 (m, 1H), 7.71-7.62 (m, 2H), 7.61-7.57 (m, 1H), 4.69 (s, 2H), 3.08 (d, 3H), 2.73 (t, 2H), 2.47 (s, 2H), 1.60 (t, 2H), 1.01 (s, 6H); MS (ES) for $C_{18}H_{21}ClN_4O_4S$: 425 (MH$^+$).

N-((4-chloro-6,6-dimethyl-5,6,7,8-tetrahydroquinazolin-2-yl)methyl)methanesulfonamide Synthesized according to the method of reagent preparation 17 using ammonia in step 2 followed by mesylation prior to step 3. $^1$H NMR (400 MHz, CDCl$_3$) δ 4.49 (d, 2H), 3.01 (s, 3H), 2.90 (t, 2H), 2.54 (s, 2H), 1.67 (t, 2H), 1.05 (s, 6H); MS (ES) for $C_{12}H_{18}ClN_3O_2S$: 304 (MH$^+$).

1-(4-chloro-5-ethyl-6-methylpyrimidin-2-yl)-N,N-dimethylmethanamine. Synthesized according to the method of reagent preparation 17 using ethyl 2-ethyl-3-oxobutanoate in step 1. $^1$H NMR (400 MHz, CDCl$_3$) δ 3.64 (s, 2H), 2.78 (q, 2H), 2.58 (s, 3H), 2.36 (s, 6H), 1.19 (t, 3H); MS (ES) for $C_{10}H_{16}ClN_3$: 214 (MH$^+$).

4-chloro-6,6-dimethyl-2-({[2-(methyloxy)ethyl]oxy}methyl)-5,6,7,8-tetrahydroquinazoline. Synthesized according to the method of reagent preparation 17 using sodium hydride and 2-methoxyethanol in N,N-dimethylformamide) in step 2. MS (ES) for $C_{14}H_{21}ClN_2O_2$: 285 (MH$^+$).

N-[(4-chloro-6,6-dimethyl-5,6,7,8-tetrahydroquinazolin-2-yl)methyl]-2-(methyloxy)ethanamine. Synthesized according to the method of reagent preparation 17 using 2-methoxyethanamine in step 2. MS (ES) for $C_{14}H_{22}ClN_3O$: 284 (MH$^+$).

N-((4-chloro-5-(4-fluorobenzyl)-6-methylpyrimidin-2-yl)methyl)cyclopropanamine. Prepared according to the method of reagent preparation 17 by using methyl 2-(4-fluorobenzyl)-3-oxobutanoate in step 1 and cyclopropylamine in step 2. MS (EI) for $C_{16}H_{17}ClFN_3$: 306 (MH$^+$).

1-(4-chloro-7-methoxy-6,6-dimethyl-5,6,7,8-tetrahydroquinazolin-2-yl)-N,N-dimethylmethanamine. Prepared according to the method of reagent preparation 17 using methyl 5,5-dimethyl-2-oxocyclohex-3-enecarboxylate (Can. J. Chem., 1981, 59, 601-608) in step 1. MS (ES) for $C_{14}H_{22}ClN_3O$: 284 (MH$^+$).

Reagent Preparation 18

Phenylmethyl(2R)-2-(4-chloro-6,6-dimethyl-5,6,7,8-tetrahydroquinazolin-2-yl)pyrrolidine-1-carboxylate STEP 1: To sodium methoxide (30 wt % in methanol, 8 mg, 0.05 mmol) was added a solution of (R)-benzyl 2-cyanopyrrolidine-1-carboxylate (189 mg, 0.82 mmol) in methanol (1 mL) at room temperature and the reaction mixture was stirred for one hour. Ammonium chloride (44 mg, 0.82 mmol) was introduced and the stirring was continued for an additional two hours, followed by the addition of methyl 5,5-dimethyl-2-oxocyclohexanecarboxylate (100 mg, 0.54 mmol) and sodium methoxide (30 wt % in methanol, 293 mg, 1.63 mmol). The stirring was continued for two more hours. The reaction mixture was quenched with water (10 mL), neutralized with 1 N hydrochloric acid and extracted with ethyl acetate (3×10 mL). The combined extract was washed with water (20 mL) and brine, dried over sodium sulfate, filtered, concentrated and purified by gradient flash chromatography (25% to 95% ethyl acetate in hexane) to give phenylmethyl (2R)-2-(4-hydroxy-6,6-dimethyl-5,6,7,8-tetrahydroquinazolin-2-yl)pyrrolidine-1-carboxylate (186 mg, 90%). MS (EI) for $C_{22}H_{27}N_3O_3$: 381 (MH$^+$).

STEP 2: A mixture phenylmethyl(2R)-2-(4-hydroxy-6,6-dimethyl-5,6,7,8-tetrahydroquinazolin-2-yl)pyrrolidine-1-carboxylate (150 mg, 0.39 mmol) and phosphorous oxychloride (1 mL) in chloroform (3 mL) was stirred at 80° C. for one hour. After cooling to room temperature the reaction mixture was concentrated and the residue was partitioned between saturated sodium bicarbonate (20 mL) and ethyl acetate (20 mL). The mixture was stirred for 15 minutes and pH was maintained above 7 by the addition of solid sodium bicarbonate. The organic layer was separated and washed with water (10 mL) and brine, dried over sodium sulfate, filtered and concentrated to give phenylmethyl(2R)-2-(4-chloro-6,6-dimethyl-5,6,7,8-tetrahydroquinazolin-2-yl)pyrrolidine-1-carboxylate (117 mg, 74%). MS (EI) for $C_{22}H_{26}ClN_3O_2$: 400 (MH$^+$).

Using analogous synthetic techniques and substituting with alternative starting materials in step 1 the following reagents of the invention were prepared. Alternative starting materials were obtained commercially unless otherwise indicated.

Phenylmethyl(2S)-2-(4-chloro-6,6-dimethyl-5,6,7,8-tetrahydroquinazolin-2-yl)pyrrolidine-1-carboxylate. Prepared according to the method of reagent preparation 18 by using (S)-benzyl 2-cyanopyrrolidine-1-carboxylate in step 1 (118 mg, 75%). MS (EI) for $C_{22}H_{26}ClN_3O_2$: 400 (MH$^+$).

Phenylmethyl 2-(4-chloro-6,6-dimethyl-5,6,7,8-tetrahydroquinazolin-2-yl)pyrrolidine-1-carboxylate. Prepared according to the method of reagent preparation 18 by using (R,S)-benzyl 2-cyanopyrrolidine-1-carboxylate in step 1 (118 mg, 75%). MS (EI) for $C_{22}H_{26}ClN_3O_2$: 400 (MH$^+$).

Reagent Preparation 19

Phenylmethyl{[6-bromo-3-({[2-(trimethylsilyl)ethyl]oxy}methyl)-3H-imidazo[4,5-b]pyridin-2-yl]methyl}methylcarbamate STEP 1: To a mixture of 2-[(benzyloxycarbonyl)(methyl)amino]acetic acid (0.42 g, 1.88 mmol), O-(7-azabenzotriazol-1-yl)-N,N,N',N'-tetramethyluronium hexafluorophosphate (0.75 g, 1.97 mmol) in N,N-dimethylformamide (3.0 mL), N,N-diisopropylethylamine (0.72 mL, 4.12 mmol) was added and the reaction mixture was stirred for 30 minutes at room temperature, followed by the addition of 5-bromo-2,3-diaminopyridine (0.35 g, 1.86 mmol), then stirred for 16 hours. It was diluted with ethyl acetate (50 mL), washed with aqueous lithium chloride (2×20 mL) and brine, dried over sodium sulfate, filtered and concentrated. Gradient flash chromatography (35% to 85% ethyl acetate in hexane) provided phenylmethyl{2-[(2-amino-5-bromopyridin-3-yl)amino]-2-oxoethyl}methylcarbamate (0.70 g, 96%). MS (EI) for $C_{16}H_{17}BrN_4O_3$: 394 (MH$^+$).

STEP 2: A solution of phenylmethyl{2-[(2-amino-5-bromopyridin-3-yl)amino]-2-oxoethyl}methylcarbamate (0.30 g, 0.76 mmol) in acetic acid (7.5 mL) was heated in a microwave apparatus (250 W) for 30 min. at 120° C. After cooling it to room temperature the reaction mixture was concentrated and the pH was adjusted to 8 by the addition of saturated aqueous sodium bicarbonate. The precipitating solid was collected by filtration, washed with water and dried in vacuo to give phenylmethyl[(6-bromo-1H-imidazo[4,5-b]pyridin-2-yl)methyl]methylcarbamate (0.22 g, 76%). MS (EI) for $C_{16}H_{15}BrN_4O_2$: 376 (MH$^+$).

STEP 3: To a solution of phenylmethyl[(6-bromo-1H-imidazo[4,5-b]pyridin-2-yl)methyl]methylcarbamate (0.22 g, 0.59 mmol) in N,N-dimethylformamide (3.0 mL) was added 60% sodium hydride in mineral oil (56 mg, 1.48 mmol) and the reaction mixture was stirred for 30 minutes at room temperature, followed by the addition of 2-(trimethylsilyl) ethoxymethyl chloride (0.11 mL, 0.62 mmol). The reaction mixture was stirred at room temperature for 16 hours then it was quenched by the careful addition of saturated aqueous ammonium chloride and partitioned with ethyl acetate (20 mL) and water (20 mL). The organic layer was separated and washed with 10% aqueous citric acid (2×20 mL) and brine (20 mL), dried over sodium sulfate, filtered and concentrated. Gradient flash chromatography (15% to 35% ethyl acetate in hexane) gave phenylmethyl{[6-bromo-3-({[2-(trimethylsilyl)ethyl]oxy}methyl)-3H-imidazo[4,5-b]pyridin-2-yl]methyl}methylcarbamate (0.28 g, 93%). MS (EI) for $C_{22}H_{29}BrN_4O_3Si$: 506 (MH$^+$).

Using analogous synthetic techniques and substituting with alternative starting materials and reagents in step 1 or step 2 and step 3 the following reagents of the invention were prepared. Alternative starting materials were obtained commercially unless otherwise indicated.

Phenylmethyl{(1R)-1-[6-bromo-3-({[2-(trimethylsilyl)ethyl]oxy}methyl)-3H-imidazo[4,5-b]pyridin-2-yl]ethyl}({[2-(trimethylsilyl)ethyl]oxy}methyl)carbamate. Synthesized according to the method of reagent preparation 19 by using 5-bromo-2,3-diaminopyridine and N-(benzyloxycarbonyl)-D-alanine in step 1 and 2-(trimethylsilyl)ethoxymethyl chloride in step 3. MS (EI) for $C_{28}H_{43}BrN_{34}O_4Si_2$: 636 (MH$^+$).

Phenylmethyl{(1S)-1-[6-bromo-3-({[2-(trimethylsilyl)ethyl]oxy}methyl)-3H-imidazo[4,5-b]pyridin-2-yl]ethyl}({[2-(trimethylsilyl)ethyl]oxy}methyl)carbamate. Synthesized according to the method of reagent preparation 19 by using 5-bromo-2,3-diaminopyridine and N-(benzyloxycarbonyl)-L-alanine in step 1 and 2-(trimethylsilyl)ethoxymethyl chloride in step 3. MS (EI) for $C_{28}H_{43}BrN_{34}O_4Si_2$: 636 (MH$^+$).

7-Bromo-2-methyl-3-({[2-(methyloxy)ethyl]oxy}methyl)-3H-imidazo[4,5-c]pyridine and 7-bromo-2-methyl-1-({[2-(methyloxy)ethyl]oxy}methyl)-1H-imidazo[4,5-c]pyridine. Synthesized according to the method of reagent preparation 19 by using 5-bromopyridine-3,4-diamine and triethyl orthoacetate in step 2 and methoxyethoxymethyl chloride in step 3. $^1$H NMR (400 MHz, CDCl$_3$): 8.83 (s, 2H), 8.44 (s, 2H), 5.88 (s, 2H), 5.66 (s, 2H), 3.36 (s, 3H), 3.37 (s, 3H), 2.98 (s, 4H), 2.91 (s, 4H), 2.73 (s, 3H), 2.75 (s, 3H); MS (EI) for $C_{11}H_{14}BrN_3O_2$: 301 (MH$^+$).

1-(6-Bromo-3H-imidazo[4,5-b]pyridin-2-yl)ethanol. Synthesized according to the method of reagent preparation 19 by using D,L-lactic acid in step 1. MS (EI) for $C_8H_8BrN_3O$: 241 (MH−).

Tert-butyl 6-bromo-2-(difluoromethyl)-1H-benzo[d]imidazole-1-carboxylate. Synthesized according to the method of reagent preparation 19 using 4-bromobenzene-1,2-diamine and difluoroacetic acid in step 1 and BOC protection with di-tert-butyl dicarbonate in step 3. MS (EI) for 6-bromo-2-(difluoromethyl)-1H-benzo[d]imidazole (step 2) $C_8H_5BrF_2N_2$: 247, 249 (MH$^+$, Br isotope pattern).

1,1-Dimethylethyl 6-bromo-2,4-dimethyl-1H-benzimidazole-1-carboxylate. Synthesized according to the method of reagent preparation 19 using 5-bromo-3-methylbenzene-1,2-diamine and acetylation using acetyl chloride in tetrahydrofuran in step 1 the BOC protection with di-tert-butyl dicarbonate in step 3. MS (EI) for $C_{14}H_{17}BrN_2O_2$: 267, 269 (M-Boc, Br isotope pattern).

1,1-Dimethylethyl 5-bromo-6-fluoro-2-methyl-1H-benzimidazole-1-carboxylate. Synthesized according to the method of reagent preparation 19 using 4-bromo-5-fluorobenzene-1,2-diamine and triethyl orthoacetate in step 2 and BOC protection with di-tert-butyl dicarbonate in step 3. MS (EI) for $C_{13}H_{14}BrFN_2O_2$: 271, 273 (M-Boc, Br isotope pattern).

2-Methylpropyl 5-bromo-4-fluoro-2-methyl-1H-benzimidazole-1-carboxylate. Synthesized according to the method of reagent preparation 19 using 5 4-bromo-3-fluorobenzene-1,2-diamine and acetylation with acetic anhydride in tetrahydrofurane in step 1 then treatment with isobutyl chloroformate in step 3. MS (EI) for $C_{13}H_{14}BrN_2O_2$: 328, 330 (MH$^+$, Br isotope pattern).

6-Bromo-2-ethyl-3-({[2-(trimethylsilyl)ethyl]oxy}methyl)-3H-imidazo[4,5-b]pyridine. Synthesized according to the method of reagent preparation 19 by using 5-bromo-2,3-diaminopyridine and trimethyl orthopropionate in step 2 and 2-(trimethylsilyl)ethoxymethyl chloride in step 3. MS (EI) for $C_{14}H_{22}BrN_3OSi$: 357 (MH$^+$).

2-Methylpropyl 6-bromo-2-cyclopropyl-3H-imidazo[4,5-b]pyridine-3-carboxylate. Synthesized according to the method of reagent preparation 19 by using 5-bromo-2,3-diaminopyridine and acylation with cyclopropylcarbonyl chloride in step 1 and treatment with isobutyl chloroformate in step 3. MS (EI) for $C_{14}H_{16}BrN_3O_2$: 339 (MH$^+$).

2-Methylpropyl 5-bromo-2-(fluoromethyl)-1H-benzimidazole-1-carboxylate. Synthesized according to the method of reagent preparation 19 using 4-bromobenzene-1,2-diamine and fluoroacetic acid in step 1 then treatment with isobutyl chloroformate in step 3. MS (EI) for $C_{13}H_{14}BrFN_2O_2$: 330 (MH$^+$).

Reagent Preparation 20

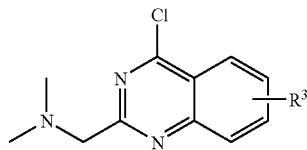

STEP 1: To a solution of 4-methoxyanthranilic acid (5.0 g, 30.0 mmol) in a mixture of 10% methanol in tetrahydrofuran (100 mL) was added dropwise (trimethylsilyl)diazomethane (2.0 M solution in diethyl ether, 18.0 mL, 36.0 mmol) at 0° C. The reaction mixture was stirred for 16 hours at room temperature then quenched by the addition of glacial acetic acid (0.1 mL). The reaction mixture was concentrated and the residue was partitioned between saturated sodium bicarbonate (50 mL) and ethyl acetate (250 mL). The organic layer was separated and washed with water (50 mL), saturated sodium bicarbonate (50 mL) and brine (50 mL), dried over sodium sulfate, filtered and concentrated to give methyl 2-amino-4-methoxybenzoate as an oil (5.4 g, quantitative). MS (EI) for $C_9H_{11}NO_3$: 182 (MH$^+$).

STEP 2: To a mixture of methyl 2-amino-4-methoxybenzoate (5.4 g, 30.0 mmol) and chloroacetonitrile (2.8 mL, 45.0 mmol) was added anhydrous hydrogen chloride (4M solution in 1,4-dioxane, 20.0 mL, 80 mmol) and the reaction mixture was stirred at 50° C. for 30 minutes. After cooling it to room temperature the resulting slurry was diluted with diethyl ether (100 mL) and the stirring was continued for an additional 30 minutes. The off-white precipitate was collected by filtration, washed with diethyl ether and dried in vacuo to provide 2-(chloromethyl)-7-(methyloxy)quinazolin-4-ol hydrochloride (7.5 g, 96%). MS (EI) for $C_{10}H_9ClN_2O_2$: 225 (MH$^+$).

STEP 3: To a solution of dimethylamine (2M solution in tetrahydrofuran, 40.0 mL, 80.0 mmol) was added 2-(chloromethyl)-7-(methyloxy)quinazolin-4-ol hydrochloride (7.5 g, 29 mmol) and the reaction mixture was stirred for 90 minutes at 50° C. After cooling it to room temperature the reaction mixture was concentrated and the residue was partitioned between water (100 mL) and ethyl acetate (250 mL). The organic layer was separated and washed with water (100 mL), saturated sodium bicarbonate (100 mL) and brine (100 mL), dried over sodium sulfate, filtered and concentrated to give 2-[(dimethylamino)methyl]-7-(methyloxy)quinazolin-4-ol (6.6 g, 97%). MS (EI) for $C_{12}H_{15}N_3O_2$: 234 (MH$^+$).

STEP 4: A solution of 2-[(dimethylamino)methyl]-7-(methyloxy)quinazolin-4-ol (6.6 g, 28.0 mmol) in a mixture of chloroform (15.0 mL) and phosphorous oxychloride (15.0 mL) was heated to reflux for 90 minutes. After cooling it to room temperature the reaction mixture was concentrated and the residue was partitioned between saturated sodium bicarbonate (100 mL) and ethyl acetate (400 mL) and the mixture was stirred for 30 minutes. The organic layer was separated and washed with saturated sodium bicarbonate (2×100 mL) and brine (200 mL), dried over sodium sulfate, filtered and concentrated. Purification by silica gel column chromatography using 15% methanol containing 0.5% triethylamine in ethyl acetate provided 1-[4-chloro-7-(methyloxy)quinazolin-2-yl]-N,N-dimethylmethanamine (7.0 g, quantitative). MS (EI) for $C_{12}H_{14}ClN_3O$: 252 (MH$^+$).

Using analogous synthetic techniques and substituting with alternative starting materials in step 2 the following reagents of the invention were prepared. Alternative starting materials were obtained commercially unless otherwise indicated.

1-(4-chloro-6-fluoroquinazolin-2-yl)-N,N-dimethylmethanamine. Prepared according to the method of reagent preparation 20 by using methyl 2-amino-5-fluorobenzoate in step 2. MS (EI) for $C_{11}H_{11}ClFN_3$: 240 (MH$^+$).

Reagent Preparation 21

5-Bromo-1-methyl-1H-pyrrolo[2,3-b]pyridine

STEP 1: To a mixture of 5-bromo-1H-pyrrolo[2,3-b]pyridine (207 mg, 1.05 mmol), sodium hydride (29 mg, 1.21 mmol) in tetrahydrofuran (5 mL) was added iodomethane (164 mg, 1.15 mol) then stirred for 2 h at room temperature. The reaction mixture was carefully quenched with water then extracted with ethyl acetate (3×). The combined organic layers were dried over magnesium sulfate, filtered and concentrated under reduced pressure. The crude product was purified by silica gel chromatography to give 5-bromo-1-methyl-1H-pyrrolo[2,3-b]pyridine. MS (EI) for $C_8H_7BrN_2$: 209, 211 (MH$^+$, Br pattern).

Using analogous synthetic techniques and substituting with alternative starting reagents in step 1 the following reagent was prepared. 5-bromo-1-ethyl-1H-pyrrolo[2,3-b] pyridine. Synthesized according to the method of reagent preparation 21 using iodoethane. MS (EI) for $C_9H_9BrN_2$: 223, 225 (MH$^+$, Br pattern).

Reagent Preparation 22

(4-(4-Bromophenyl)-1H-imidazol-2-yl)methanol

STEP 1: To a solution of ethyl thiooxamate (10.0 g, 75 mmol) in dichloromethane (400 mL) was slowly added trimethyloxonium tetrafluoroborate (13.1 g, 89 mmol) at 0° C. After 10 min the ice bath was removed, and the reaction mixture was stirred overnight. The solvent was removed to afford ethyl 2-imino-2-(methylthio)acetate (12.0 g, 66.6%) as tetrafluoroborate salt which was used without further purification.

STEP 2: A mixture of 2-amino-4-bromoacetophenone hydrochloride (4.0 g, 16.0 mmol), sodium acetate (6.1 g, 90.0 mmol), acetic acid (4.6 mL, 80.0 mmol) and ethyl 2-imino-2-(methylthio)acetate (7.7 g, 32.0 mmol) in dioxane (40 mL) was stirred at 95° C. overnight. The reaction mixture was carefully neutralized with saturated NaHCO3 solution and extracted with ethyl acetate. The organic solution was dried over sodium sulfate and concentrated. Purification by silica gel column chromatography (ethyl acetate:hexanes 1:1) afforded ethyl 4-(4-bromophenyl)-1H-imidazole-2-carboxylate (3.53 g, 75.0%). MS (EI) for $C_{12}H_{11}BrN_2O_2$: 296 (MH$^+$).

STEP 3: To a solution of ethyl 4-(4-bromophenyl)-1H-imidazole-2-carboxylate (1.30 g, 4.40 mmol) in THF (30 mL) was slowly added Red-Al (65 wt % in toluene, 2.0 mL, 6.16 mmol) at −25° C. The reaction mixture was stirred for 4 h at the same temperature then slowly warmed to 0° C. over 1 h and quenched with 20% sodium tartrate solution (30 mL). The reaction was extracted with ethyl acetate (70 mL) and the organic layer was left for 3 h at room temperature. A solid separated and was collected by filtration, washed with ethyl acetate and dried to afford (4-(4-bromophenyl)-1H-imidazol-2-yl)methanol (778 mg, 71.0%). MS (EI) for $C_{10}H_9BrN_2O$: 254.1 (MH$^+$).

Reagent Preparation 23

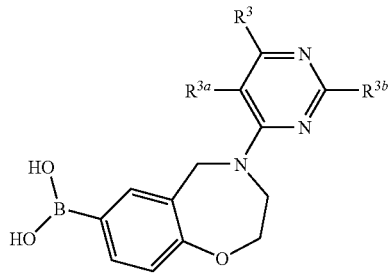

Step 1: To a slurry of 2,3,4,5-tetrahydro-1,4-benzoxazepin-7-ylboronic acid hydrochloride salt (5.7 g, 25 mmol) (example 8, step 1) and 4-chloro-6,6-dimethyl-5,6,7,8-tetrahydroquinazoline (reagent preparation 3) (3.0 g, 15 mmol) in dioxane (75 mL) and $H_2O$ (75 mL) was added DIPEA (17 mL, 100 mmol) and the resulting mixture was heated (90° C.). After 72 hours the solution was concentrated and partitioned between 2M aqueous sodium hydroxide and ethyl ether. The aqueous layer was neutralized and extracted with chloroform. The organic layer was washed with brine, dried over magnesium sulfate, filtered and concentrated in vacuo. Trituration with ethyl ether provided [4-(6,6-dimethyl-5,6,7,8-tetrahydroquinazolin-4-yl)-2,3,4,5-tetrahydro-1,4-benzoxazepin-7-yl]boronic acid (4.2 g, 80% yield) as a white solid. $^1$H NMR (400 MHz, d$_6$-DMSO) δ 8.68 (s, 1H), 7.77 (s, 1H), 7.64 (dd, 1H), 6.86 (dd, 1H), 5.04 (s, 2H), 4.46 (m, 2H), 4.18 (m, 2H), 2.80 (t, 2H), 2.52 (s, 2H), 1.58 (t, 2H), 0.86 (s, 6H); MS (ES) for $C_{19}H_{24}BN_3O_3$: 354 (MH$^+$).

Using analogous synthetic techniques and substituting with alternative starting reagents in step 1 the following compounds of the invention were prepared. Alternative starting materials were obtained commercially unless otherwise indicated.

[4-(6,6,7-trimethyl-5,6-dihydroquinazolin-4-yl)-2,3,4,5-tetrahydro-1,4-benzoxazepin-7-yl]boronic acid. Synthesized according to the method of reagent preparation 23 using 4-chloro-6,6,7-trimethyl-5,6-dihydroquinazoline (reagent preparation 3) in step 1. $^1$H NMR (400 MHz, d$_6$-DMSO) δ 8.34 (s, 1H), 7.94 (s, 2H), 7.66 (s, 1H), 7.62 (dd, 1H), 6.90 (d, 1H), 6.12 (s, 1H), 4.59 (s, 2H), 4.33 (m, 2H), 3.83 (m, 2H), 2.65 (s, 2H), 1.89 (s, 3H), 0.94 (s, 6H); MS (ES) for C$_{20}$H$_{24}$BN$_3$O$_3$: 366 (MH$^+$).

[4-(6,6-dimethyl-5,6-dihydroquinazolin-4-yl)-2,3,4,5-tetrahydro-1,4-benzoxazepin-7-yl]boronic acid. Synthesized according to the method of reagent preparation 23 using 4-chloro-6,6-dimethyl-5,6-dihydroquinazoline (reagent preparation 3) in step 1. $^1$H NMR (400 MHz, d$_6$-DMSO) δ 8.39 (s, 1H), 7.93 (s, 2H), 7.68 (s, 1H), 7.62 (dd, 1H), 6.89 (d, 1H), 6.29 (d, 1H), 6.23 (d, 1H), 4.61 (s, 2H), 4.32 (m, 2H), 3.84 (m, 2H), 2.69 (s, 2H), 0.97 (s, 6H); MS (ES) for C$_{19}$H$_{22}$BN$_3$O$_3$: 352 (MH$^+$).

{4-[7-(methyloxy)quinazolin-4-yl]-2,3,4,5-tetrahydro-1,4-benzoxazepin-7-yl}boronic acid. Synthesized according to the method of reagent preparation 23 using 4-chloro-7-methoxyquinazoline (reagent preparation 1) in step 1. MS (ES) for C$_{18}$H$_{18}$BN$_3$O$_4$: 352 (MH$^+$).

[4-(2,6,6-trimethyl-5,6,7,8-tetrahydroquinazolin-4-yl)-2,3,4,5-tetrahydro-1,4-benzoxazepin-7-yl]boronic acid. Synthesized according to the method of reagent preparation 23 using 4-chloro-2,6,6-trimethyl-5,6,7,8-tetrahydroquinazoline (reagent preparation 8) in step 1. MS (EI) for C$_{20}$H$_{26}$BN$_3$O$_3$: 368 (MH$^+$).

{4-[(7S)-7-ethyl-2-methyl-5,6,7,8-tetrahydroquinazolin-4-yl]-2,3,4,5-tetrahydro-1,4-benzoxazepin-7-yl}boronic acid. Synthesized according to the method of reagent preparation 23 using (S)-4-chloro-7-ethyl-2-methyl-5,6,7,8-tetrahydroquinazoline (reagent preparation 8) in step 1. MS (ES) for C$_{20}$H$_{26}$BN$_3$O$_3$: 368 (MH$^+$).

{4-[(7S)-7-ethyl-5,6,7,8-tetrahydroquinazolin-4-yl]-2,3,4,5-tetrahydro-1,4-benzoxazepin-7-yl}boronic acid. Synthesized according to the method of reagent preparation 23 using (S)-4-chloro-7-ethyl-5,6,7,8-tetrahydroquinazoline (reagent preparation 3) in step 1. $^1$H NMR (400 MHz, d$_6$-DMSO) δ 8.33 (d, 1H), 7.96 (s, 2H), 7.68 (d, 1H), 7.61 (dd, 1H), 6.89 (d, 1H), 4.69 (d, 1H), 4.59 (d, 1H), 4.37 (dt, 1H), 4.25 (dt, 1H), 3.84 (t, 2H), 2.84 (dd, 1H), 2.75 (m, 1H), 2.46 (m, 1H), 2.26 (dd, 1H), 1.89 (m, 1H), 1.70 (m, 1H), 1.37 (m, 2H), 1.10 (m, 1H), 0.95 (t, 3H); MS (ES) for C$_{19}$H$_{24}$BN$_3$O$_3$: 354 (MH$^+$).

[4-(6,6,8-trimethyl-5,6-dihydroquinazolin-4-yl)-2,3,4,5-tetrahydro-1,4-benzoxazepin-7-yl]boronic acid. Synthesized according to the method of reagent preparation 23 using 4-chloro-6,6,8-trimethyl-5,6-dihydroquinazoline (reagent preparation 3) in step 1. $^1$H NMR (400 MHz, d$_6$-DMSO) δ 8.45 (s, 1H), 7.94 (s, 2H), 7.67 (d, 1H), 7.62 (dd, 1H), 6.90 (d, 1H), 5.99 (d, 1H), 4.59 (s, 2H), 4.32 (m, 2H), 3.83 (m, 2H), 2.66 (d, 2H), 1.97 (s, 3H), 0.93 (s, 6H); MS (ES) for C$_{20}$H$_{24}$BN$_3$O$_3$: 366 (MH$^+$).

(4-{2-[(dimethylamino)methyl]-7-methoxy-6,6-dimethyl-5,6,7,8-tetrahydroquinazolin-4-yl}-2,3,4,5-tetrahydro-1,4-benzoxazepin-7-yl)boronic acid. Synthesized according to the method of reagent preparation 23 using 1-(4-chloro-7-methoxy-6,6-dimethyl-5,6,7,8-tetrahydroquinazolin-2-yl)-N,N-dimethylmethanamine (reagent preparation 17) in step 1. MS (ES) for C$_{23}$H$_{33}$BN$_4$O$_4$: 441 (MH$^+$).

(4-{2-[(dimethylamino)methyl]-7-methoxyquinazolin-4-yl}-2,3,4,5-tetrahydro-1,4-benzoxazepin-7-yl)boronic acid. Synthesized according to the method of reagent preparation 23 using 1-(4-chloro-7-methoxyquinazolin-2-yl)-N,N-dimethylmethanamine (reagent preparation 20) in step 1. MS (ES) for C$_{21}$H$_{25}$BN$_4$O$_4$: 409 (MH$^+$).

Reagent Preparation 24

N-(5-bromo-2-chloropyridin-3-yl)methanesulfonamide
STEP 1: A solution of 5-bromo-2-chloropyridin-3-amine (1.0 g, 4.8 mmol) and diisopropylethylamine (1.85 mL, 10.6 mmol) in dichloromethane (25 mL) was cooled to 0° C., and then methanesulfonyl chloride (750 uL, 9.6 mmol) was added slowly. The reaction mixture was stirred at 0° C. for 15 min and was then warmed to rt. After stirring for 2 h, water was added, and then the biphasic mixture was partitioned. The organic phase was dried over magnesium sulfate, filtered, and concentrated in vacuo. The residue was then dissolved in dioxane (10 mL) and water (10 mL). Potassium carbonate (2.76 g, 20 mmol) was added, and the reaction mixture was stirred for 15 h at rt. Water was then added to the mixture which was subsequently acidified with aqueous citric acid (10%). The aqueous mixture was extracted twice with ethyl acetate. The combined organic extracts were dried over magnesium sulfate, filtered, and concentrated in vacuo. The residue was purified by flash chromatography (gradient, 100% hexanes to 50% hexanes:50% ethyl acetate) to provide N-(5-bromo-2-chloropyridin-3-yl)methanesulfonamide (520 mg, 1.82 mmol, 38% yield) as a light pink solid. $^1$H NMR (400 MHz, CDCl$_3$) δ 8.27 (d, 1H), 8.14 (d, 1H), 6.83 (br s, 1H), 3.11 (s, 3H); MS (EI) for C$_6$H$_6$BrClN$_2$O$_2$S: 285, 287, 289 (Br+Cl isotopes, MH$^+$).

Reagent Preparation 25

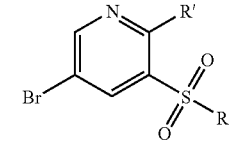

R' = NH$_2$, NHCH$_3$, Cl

STEP 1: To a solution of (R)-pyrrolidin-3-ol (32 mg, 0.37 mmol) and potassium carbonate (102 mg, 0.74 mmol) in dioxane (2 mL) and water (400 uL) was added 2-amino-5-bromopyridine-3-sulfonyl chloride (100 mg, 0.37 mmol, prepared according to the methods in WO2008144463). The reaction mixture was stirred for 2 h at rt. Saturated sodium bicarbonate was then added, and the aqueous solution was extracted twice with ethyl acetate. The combined organic extracts were dried over magnesium sulfate, filtered, and concentrated in vacuo to provide (R)-1-(2-amino-5-bromopyridin-3-ylsulfonyl)pyrrolidin-3-ol (87.3 mg, 0.27 mmol, 73% yield) as a white solid. $^1$H NMR (400 MHz, DMSO-D6-d6) δ 8.31 (d, 1H), 7.92 (d, 1H), 6.85 (br s, 2H), 5.02 (br s, 1H), 4.23 (dt, 1H), 3.38-3.25 (m, 3H), 3.14-3.06 (m, 1H), 1.92-1.81 (m, 1H), 1.77-1.67 (m, 1H); MS (EI) for C$_9$H$_{12}$BrN$_3$O$_3$S: 322, 324 (Br isotopes, MH$^+$).

Using analogous synthetic techniques and substituting with alternative starting reagents in step 1 the following reagents were prepared. Alternative starting materials were obtained commercially unless otherwise indicated.

2-amino-5-bromo-N-(2-methoxyethyl)pyridine-3-sulfonamide. Prepared according to the methods described in reagent preparation 25 using 2-methoxyethanamine in step 1.

2-amino-5-bromo-N-(2,2,2-trifluoroethyl)pyridine-3-sulfonamide. Prepared according to the methods described in reagent preparation 25 using 2,2,2-trifluoroethanamine in step 1.

2-amino-5-bromo-N-(2-hydroxyethyl)-N-methylpyridine-3-sulfonamide. Prepared according to the methods described in reagent preparation 25 using 2-(methylamino) ethanol in step 1.

2-amino-5-bromo-N-(2-hydroxypropyl)pyridine-3-sulfonamide. Prepared according to the methods described in reagent preparation 25 using 1-aminopropan-2-ol in step 1. MS (EI) for $C_8H_{12}BrN_3O_3S$: 310, 312 (Br isotopes, MH+).

2-amino-N-(azetidin-3-yl)-5-bromopyridine-3-sulfonamide. Prepared according to the methods described in reagent preparation 25 using tert-butyl 3-aminoazetidine-1-carboxylate in step 1.

2-amino-5-bromo-N-(2,3-dihydroxypropyl)pyridine-3-sulfonamide. Prepared according to the methods described in reagent preparation 25 using 3-aminopropane-1,2-diol in step 1. MS (EI) for $C_8H_{12}BrN_3O_4S$: 326, 328 (Br isotopes, MH+).

1-(2-amino-5-bromopyridin-3-ylsulfonyl)piperidin-3-ol. Prepared according to the methods described in reagent preparation 25 using piperidin-3-ol in step 1. MS (EI) for $C_{10}H_{14}BrN_3O_3S$: 336, 338 (Br isotopes, MH+).

2-amino-N-(3-amino-2,2-dimethylpropyl)-5-bromopyridine-3-sulfonamide. Prepared according to the methods described in reagent preparation 25 using 2,2-dimethylpropane-1,3-diamine in step 1. MS (EI) for $C_{10}H_{17}BrN_4O_2S$: 337, 339 (Br isotopes, MH+).

2-amino-5-bromo-N-(3-hydroxy-2,2-dimethylpropyl)pyridine-3-sulfonamide. Prepared according to the methods described in reagent preparation 25 using 3-amino-2,2-dimethylpropan-1-ol in step 1. MS (EI) for $C_{10}H_{16}BrN_3O_3S$: 338, 340 (Br isotopes, MH+).

2-amino-5-bromo-N-(1-hydroxy-2-methylpropan-2-yl)pyridine-3-sulfonamide. Prepared according to the methods described in reagent preparation 25 using 2-amino-2-methylpropan-1-ol in step 1. MS (EI) for $C_9H_{14}BrN_3O_3S$: 324, 326 (Br isotopes, MH+).

tert-butyl 4-((2-amino-5-bromopyridine-3-sulfonamido)methyl)piperidine-1-carboxylate. Prepared according to the methods described in reagent preparation 25 using tert-butyl 4-(aminomethyl)piperidine-1-carboxylate in step 1. MS (EI) for $C_{16}H_{25}BrN_4O_4S$: 393, 395 (Br isotopes, MH+-t-butyl).

2-amino-5-bromo-N-((1-methylpiperidin-4-yl)methyl)pyridine-3-sulfonamide. Prepared according to the methods described in reagent preparation 25 using (1-methylpiperidin-4-yl)methanamine in step 1. MS (EI) for $C_{12}H_{19}BrN_4O_2S$: 363, 365 (Br isotopes, MH+).

tert-butyl 1-((2-amino-5-bromopyridine-3-sulfonamido)methyl)cyclopropylcarbamate. Prepared according to the methods described in reagent preparation 25 using tert-butyl 1-(aminomethyl)cyclopropylcarbamate in step 1. MS (EI) for $C_{14}H_{21}BrN_4O_4S$: 365, 367 (Br isotopes, MH+-t-butyl).

tert-butyl trans-4-(2-amino-5-bromopyridine-3-sulfonamido)cyclohexylcarbamate. Prepared according to the methods described in reagent preparation 25 using tert-butyl trans-4-aminocyclohexylcarbamate in step 1.

benzyl 1-(2-amino-5-bromopyridine-3-sulfonamido)propan-2-ylcarbamate. Prepared according to the methods described in reagent preparation 25 using benzyl 1-aminopropan-2-ylcarbamate in step 1.

2-amino-5-bromo-N-ethylpyridine-3-sulfonamide. Prepared according to the methods described in reagent preparation 25 using ethylamine in step 1. $^1$H NMR (400 MHz, CDCl$_3$) δ 8.28 (d, 1H), 8.07 (d, 1H), 5.63 (br s, 2H), 4.61 (t, 1H), 3.06-2.97 (m, 2H), 1.14 (t, 3H); MS (EI) for $C_7H_{10}BrN_3O_2S$: 280, 282 (Br isotopes, MH+).

2-amino-5-bromo-N-isopropylpyridine-3-sulfonamide. Prepared according to the methods described in reagent preparation 25 using isopropylamine in step 1. $^1$H NMR (400 MHz, CDCl$_3$) δ 8.28 (d, 1H), 8.09 (d, 1H), 5.59 (br s, 2H), 4.52 (d, 1H), 3.50-3.39 (m, 1H), 1.11 (d, 6H); MS (EI) for $C_8H_{12}BrN_3O_2S$: 294, 296 (Br isotopes, MH+).

2-amino-5-bromo-N-(2-(dimethylamino)ethyl)pyridine-3-sulfonamide. Prepared according to the methods described in reagent preparation 25 using N,N-dimethylethane-1,2-diamine in step 1. $^1$H NMR (400 MHz, CDCl$_3$) δ 8.27 (d, 1H), 8.08 (d, 1H), 5.66 (br s, 2H), 2.99-2.93 (m, 2H), 2.36-2.30 (m, 2H), 2.12 (s, 6H); MS (EI) for $C_9H_{15}BrN_4O_2S$: 323, 325 (Br isotopes, MH+).

2-amino-5-bromo-N-(2-hydroxyethyl)pyridine-3-sulfonamide. Prepared according to the methods described in reagent preparation 25 using 2-aminoethanol in step 1. $^1$H NMR (400 MHz, CDCl$_3$) δ 8.29 (d, 1H), 8.08 (d, 1H), 5.65 (br s, 3H), 5.23 (br s, 1H), 3.76-3.67 (m, 3H), 3.16-3.07 (m, 3H); MS (EI) for $C_7H_{10}BrN_3O_3S$: 296, 298 (Br isotopes, MH+).

1-(2-amino-5-bromopyridin-3-ylsulfonyl)-3-(hydroxymethyl)azetidin-3-ol. Prepared according to the methods described in reagent preparation 25 using 3-(hydroxymethyl)azetidin-3-ol (prepared according to procedures described in WO2007044515) in step 1. $^1$H NMR (400 MHz, CD$_3$OD) δ 8.28 (d, 1H), 8.00 (d, 1H), 3.90-3.84 (m, 2H), 3.70-3.64 (m, 2H), 3.32-3.29 (m, 2H); MS (EI) for $C_9H_{12}BrN_3O_4S$: 338, 340 (Br isotopes, MH+).

2-(2-amino-5-bromopyridine-3-sulfonamido)acetamide. Prepared according to the methods described in reagent preparation 25 using 2-aminoacetamide hydrochloride in step 1. $^1$H NMR (400 MHz, DMSO-d6) δ 8.26 (d, 1H), 8.18 (br s, 1H), 7.90 (d, 1H), 7.34 (br s, 1H), 7.12 (br s, 1H), 6.84 (br s, 2H), 3.45 (s, 2H); MS (EI) for $C_7H_9BrN_4O_3S$: 309, 311 (Br isotopes, MH+).

tert-butyl 3-(2-amino-5-bromopyridine-3-sulfonamido)-2-hydroxypropylcarbamate. Prepared according to the methods described in reagent preparation 25 using tert-butyl 3-amino-2-hydroxypropylcarbamate in step 1. $^1$H NMR (400 MHz, DMSO-d6) δ 8.26 (d, 1H), 7.88 (d, 1H), 6.82 (br s, 2H), 6.74 (t, 1H), 5.02 (d, 1H), 3.50-3.42 (m, 1H), 2.88 (t, 2H), 2.82 (dd, 1H), 2.57 (dd, 1H), 1.37 (s, 9H); MS (EI) for $C_{13}H_{21}BrN_4O_5S$: 369, 371 (Br isotopes, MH+-t-Bu).

5-bromo-3-(3-(dimethylamino)azetidin-1-ylsulfonyl)pyridin-2-amine. Prepared according to the methods described in reagent preparation 25 using N,N-dimethylazetidin-3-amine hydrochloride in step 1. $^1$H NMR (400 MHz, DMSO-d6) δ 8.39 (d, 1H), 7.92 (d, 1H), 6.90 (br s, 2H), 3.88-3.76 (m, 2H), 3.63-3.54 (m, 2H), 3.07-2.97 (m, 1H), 1.96 (s, 6H); MS (EI) for $C_{10}H_{15}BrN_4O_2S$: 335, 337 (Br isotopes, MH+).

5-bromo-N-(2-hydroxyethyl)-2-(methylamino)pyridine-3-sulfonamide. Prepared according to the methods described in reagent preparation 25 using 5-bromo-2-(methylamino)pyridine-3-sulfonyl chloride (prepared from 5-bromo-N-methylpyridin-2-amine using analogous conditions to those described in WO2008144463) and 2-aminoethanol in step 1. $^1$H NMR (400 MHz, CDCl$_3$) δ 8.28 (d, 1H), 8.00 (d, 1H), 7.10-7.03 (m, 1H), 6.48-6.39 (m, 1H), 3.93 (t, 1H), 3.60 (q, 2H), 3.04-2.96 (m, 5H); MS (EI) for $C_8H_{12}BrN_3O_3S$: 310, 312 (Br isotopes, MH+).

N-(1-(2-amino-5-bromopyridin-3-ylsulfonyl)azetidin-3-yl)-N-methyl-2-nitrobenzenesulfonamide. Prepared according to the methods described in reagent preparation 25 using N-(azetidin-3-yl)-N-methyl-2-nitrobenzenesulfonamide in step 1. $^1$H NMR (400 MHz, CDCl$_3$) δ 8.32 (d, 1H), 8.06-8.03 (m, 1H), 8.00 (d, 1H), 7.77-7.72 (m, 2H), 7.70-7.65 (m, 1H), 5.78 (br s, 2H), 4.90-4.80 (m, 1H), 4.19-4.08 (m, 2H), 4.01 (dd, 2H), 2.91 (s, 3H); MS (EI) for $C_{15}H_{16}BrN_5O_6S$: 506, 508 (Br isotopes, MH+).

tert-butyl 4-(2-amino-5-bromopyridin-3-ylsulfonyl)piperazine-1-carboxylate. Prepared according to the methods described in reagent preparation 25 using tert-butyl piperazine-1-carboxylate in step 1. $^1$H NMR (400 MHz, DMSO-d6) δ 8.34 (d, 1H), 7.86 (d, 1H), 6.90 (br s, 2H), 3.40-3.35 (m, 4H), 3.09-3.02 (m, 4H), 1.37 (s, 9H); MS (EI) for $C_{14}H_{21}BrN_4O_4S$: 367, 365 (Br isotopes, MH$^+$-t-Bu).

3-(3-amino-3-methylazetidin-1-ylsulfonyl)-5-bromopyridin-2-amine. Prepared according to the methods described in reagent preparation 25 using 3-methylazetidin-3-amine hydrochloride (prepared by procedures described in WO2007007057 followed by benzylidene deprotection) in step 1. $^1$H NMR (400 MHz, DMSO-d6) δ 8.37 (d, 1H), 7.88 (d, 1H), 6.86 (br s, 2H), 3.58-3.47 (m, 4H), 2.06 (br s, 2H), 1.22 (s, 3H); MS (EI) for $C_9H_{13}BrN_4O_2S$: 321, 323 (Br isotopes, MH$^+$).

tert-butyl 2-(2-amino-5-bromopyridine-3-sulfonamido)-2-methylpropylcarbamate. Prepared according to the methods described in reagent preparation 25 using tert-butyl 2-amino-2-methylpropylcarbamate in step 1. $^1$H NMR (400 MHz, CDCl$_3$) δ 8.26 (d, 1H), 8.08 (d, 1H), 5.89 (br s, 1H), 5.60 (br s, 2H), 5.04 (t, 1H), 3.12 (d, 2H), 1.46 (s, 9H), 1.19 (s, 6H); MS (EI) for $C_{14}H_{23}BrN_4O_4S$: 367, 369 (Br isotopes, MH$^+$-t-Bu).

tert-butyl 5-((2-amino-5-bromopyridine-3-sulfonamido)methyl)hexahydrocyclopenta[c]pyrrole-2(1H)-carboxylate. Prepared according to the methods described in reagent preparation 25 using tert-butyl 5-(aminomethyl)hexahydrocyclopenta[c]pyrrole-2(1H)-carboxylate (prepared from substrates described in WO2004006846) in step 1. $^1$H NMR (400 MHz, CDCl$_3$) δ 8.28 (d, 1H), 8.06 (d, 1H), 5.65 (br s, 2H), 5.03 (t, 1H), 3.41 (br s, 2H), 3.17 (br s, 2H), 2.93 (t, 2H), 2.63-2.54 (m, 2H), 2.14-1.98 (m, 3H), 1.46 (s, 9H), 1.09-0.98 (m, 2H); MS (EI) for $C_{18}H_{27}BrN_4O_4S$: 419, 421 (Br isotopes, MH$^+$-t-Bu).

tert-butyl 1-(2-amino-5-bromopyridine-3-sulfonamido) butan-2-ylcarbamate. Prepared according to the methods described in reagent preparation 25 using tert-butyl 1-aminobutan-2-ylcarbamate in step 1. $^1$H NMR (400 MHz, DMSO-d6) δ 8.28 (d, 1H), 7.89 (d, 1H), 6.78 (br s, 2H), 6.57 (d, 1H), 3.33-3.26 (m, 1H), 2.77-2.65 (m, 2H), 1.53-1.39 (m, 1H), 1.37 (s, 9H), 1.28-1.15 (m, 1H), 0.76 (t, 3H); MS (EI) for $C_{14}H_{23}BrN_4O_4S$: 367, 369 (Br isotopes, MH$^+$-t-Bu).

tert-butyl 4-(2-amino-5-bromopyridine-3-sulfonamido)-2-methylbutan-2-ylcarbamate. Prepared according to the methods described in reagent preparation 25 using tert-butyl 4-amino-2-methylbutan-2-ylcarbamate in step 1. $^1$H NMR (400 MHz, CDCl$_3$) δ 8.27 (d, 1H), 8.06 (d, 1H), 5.64 (br s, 2H), 5.07 (br s, 1H), 4.41 (br s, 1H), 2.98 (q, 2H), 1.93-1.85 (m, 2H), 1.41 (s, 9H), 1.22 (s, 6H); MS (EI) for $C_{15}H_{25}BrN_4O_4S$: 381, 383 (Br isotopes, MH$^+$-t-Bu).

2-amino-N-(2-amino-2-methylpropyl)-5-bromopyridine-3-sulfonamide. Prepared according to the methods described in reagent preparation 25 using 2-methylpropane-1,2-diamine in step 1. $^1$H NMR (400 MHz, CDCl$_3$) δ 8.27 (d, 1H), 8.07 (d, 1H), 5.69 (br s, 2H), 2.73 (s, 2H), 1.12 (s, 6H); MS (EI) for $C_9H_{15}BrN_4O_2S$: 323, 325 (Br isotopes, MH$^+$).

tert-butyl 1-(2-amino-5-bromopyridin-3-ylsulfonyl)azetidin-3-ylcarbamate. Prepared according to the methods described in reagent preparation 25 using tert-butyl azetidin-3-ylcarbamate in step 1. $^1$H NMR (400 MHz, CDCl$_3$) δ 8.31 (d, 1H), 8.00 (d, 1H), 5.76 (br s, 2H), 4.80 (br s, 1H), 4.50-4.36 (m, 1H), 4.11 (t, 2H), 3.75 (t, 2H), 1.42 (s, 9H); MS (EI) for $C_{13}H_{19}BrN_4O_4S$: 407, 409 (Br isotopes, MH$^+$).

tert-butyl 1-(2-amino-5-bromopyridin-3-ylsulfonyl)piperidin-4-ylcarbamate sulfonamide. Prepared according to the methods described in reagent preparation 25 using tert-butyl piperidin-4-ylcarbamate in step 1.

2-amino-5-bromo-N-(2-hydroxy-2-methylpropyl)pyridine-3-sulfonamide. Prepared according to the methods described in reagent preparation 25 using 1-amino-2-methylpropan-2-ol in step 1.

2-Amino-5-bromo-N,N-dimethylpyridine-3-sulfonamide. Prepared according to the method of reagent preparation 25 by using dimethylamine in step 1. MS (EI) for $C_7H_{10}BrN_3O_2S$: 280 (MH$^+$).

5-Bromo-3-(morpholinosulfonyl)pyridin-2-amine. Prepared according to the method of reagent preparation 25 by using morpholine in step 1. MS (EI) for $C_9H_{12}BrN_3O_3S$: 322 (MH$^+$).

5-Bromo-3-(4-methylpiperazin-1-ylsulfonyl)pyridin-2-amine. Prepared according to the method of reagent preparation 25 by using N-methylpiperazine in step 1. MS (EI) for $C_{10}H_{15}BrN_4O_2S$: 335 (MH$^+$).

3-(Azetidin-1-ylsulfonyl)-5-bromopyridin-2-amine. Prepared according to the method of reagent preparation 25 by using N-methylpiperazine in step 1. MS (EI) for $C_8H_{10}BrN_3O_2S$: 292 (MH$^+$).

2-Amino-5-bromo-N-methylpyridine-3-sulfonamide. Prepared according to the method of reagent preparation 25 by using methylamine in step 1. MS (EI) for $C_6H_8BrN_3O_2S$: 266 (MH$^+$).

1-(2-Amino-5-bromopyridin-3-ylsulfonyl)azetidin-3-ol. Prepared according to the method of reagent preparation 25 by using azetidinol in step 1. MS (EI) for $C_8H_{10}BrN_3O_3S$: 308 (MH$^+$).

5-Bromo-3-(pyrrolidin-1-ylsulfonyl)pyridin-2-amine. Prepared according to the method of reagent preparation 25 by using pyrrolidine in step 1. MS (EI) for $C_9H_{12}BrN_3O_2S$: 306 (MH$^+$).

1-(2-Amino-5-bromopyridin-3-ylsulfonyl)pyrrolidin-3-ol. Prepared according to the method of reagent preparation 25 by using 3-pyrrolidinol in step 1. MS (EI) for $C_9H_{12}BrN_3O_3S$: 322 (MH$^+$).

2-Amino-5-bromo-N-cyclobutylpyridine-3-sulfonamide. Prepared according to the method of reagent preparation 25 by using cyclobutylamine in step 1. MS (EI) for $C_9H_{12}BrN_3O_2S$: 306 (MH$^+$).

2-Amino-5-bromopyridine-3-sulfonamide. Prepared according to the method of reagent preparation 25 by using ammoniumhydroxide in step 1. MS (EI) for $C_5H_6BrN_3O_2S$: 252 (MH$^+$).

2-Amino-5-bromo-N-ethyl-N-methylpyridine-3-sulfonamide. Prepared according to the method of reagent preparation 25 by using N-methylethylamine in step 1. MS (EI) for $C_8H_{12}BrN_3O_2S$: 294 (MH$^+$).

5-Bromo-3-(3,3-difluoroazetidin-1-ylsulfonyl)pyridin-2-amine. Prepared according to the method of reagent preparation 25 by using 3,3-difluoroazetidine in step 1. MS (EI) for $C_8H_8BrF_2N_3O_2S$: 328 (MH$^+$).

2-Amino-5-bromo-N-(1-hydroxypropan-2-yl)pyridine-3-sulfonamide. Prepared according to the method of reagent preparation 25 by using 2-aminopropan-1-ol in step 1. MS (EI) for $C_8H_{12}BrN_3O_3S$: 310 (MH$^+$).

2-Amino-5-bromo-N-(2-fluoroethyl)pyridine-3-sulfonamide. Prepared according to the method of reagent preparation 25 by using 2-fluoroethylamine in step 1. MS (EI) for $C_7H_9BrFN_3O_2S$: 298 (MH$^+$).

tert-Butyl 1-(2-amino-5-bromopyridin-3-ylsulfonyl)pyrrolidin-3-ylcarbamate. Prepared according to the method of reagent preparation 25 by using tert-butyl pyrrolidin-3-ylcarbamate in step 1. MS (EI) for $C_{14}H_{21}BrN_4O_4S$: 365 (MH$^+$-tBu).

1-(2-Amino-5-bromopyridin-3-ylsulfonyl)piperidin-4-ol. Prepared according to the method of reagent preparation 25 by using 4-hydroxypiperidine in step 1. MS (EI) for $C_{10}H_{14}BrN_3O_3S$: 336 (MH$^+$)

tert-Butyl 1-(2-amino-5-bromopyridin-3-ylsulfonyl)piperidin-3-ylcarbamate. Prepared according to the method of reagent preparation 25 by using tert-butyl piperidin-3-ylcarbamate in step 1. MS (EI) for $C_{15}H_{23}BrN_4O_4S$: 379 (MH$^+$-tBu).

tert-Butyl 2-(2-amino-5-bromopyridine-3-sulfonamido)ethylcarbamate. Prepared according to the method of reagent preparation 25 by using tert-butyl 2-aminoethylcarbamate in step 1. MS (EI) for $C_{12}H_{19}BrN_4O_4S$: 339 (MH$^+$-tBu).

2-Amino-5-bromo-N-(3-hydroxypropyl)pyridine-3-sulfonamide. Prepared according to the method of reagent preparation 25 by using 3-hydroxypropylamine in step 1. MS (EI) for $C_8H_{12}BrN_3O_3S$: 310 (MH$^+$).

tert-Butyl 3-(2-amino-5-bromopyridine-3-sulfonamido)propylcarbamate. Prepared according to the method of reagent preparation 25 by using tert-butyl 2-aminopropylcarbamate in step 1. MS (EI) for $C_{13}H_{21}BrN_4O_4S$: 353 (MH$^+$-tBu).

2-Amino-5-bromo-N-(3,3,3-trifluoro-2-hydroxypropyl)pyridine-3-sulfonamide. Prepared according to the method of reagent preparation 25 by using 3-amino-1,1,1-trifluoropropan-2-ol in step 1. MS (EI) for $C_8H_9BrF_3N_3O_3S$: 364 (MH$^+$).

tert-Butyl 5-(2-amino-5-bromopyridin-3-ylsulfonyl)hexahydropyrrolo[3,4-c]pyrrole-2(1H)-carboxylate. Prepared according to the method of reagent preparation 25 by using tert-butyl hexahydropyrrolo[3,4-c]pyrrole-2(1H)-carboxylate in step 1. MS (EI) for $C_{16}H_{23}BrN_4O_4S$: 391 (MH$^+$-tBu)

tert-Butyl 1-(2-amino-5-bromopyridin-3-ylsulfonyl)-3-methylpyrrolidin-3-ylcarbamate. Prepared according to the method of reagent preparation 25 by using tert-butyl 3-methylpyrrolidin-3-ylcarbamate in step 1. MS (EI) for $C_{15}H_{23}BrN_4O_4S$: 379 (MH$^+$-tBu).

(1S,4S)-tert-Butyl 5-(2-amino-5-bromopyridin-3-ylsulfonyl)-2,5-diazabicyclo[2.2.1]-heptane-2-carboxylate. Prepared according to the method of reagent preparation 25 by using (1S,4S)-tert-butyl 2,5-diazabicyclo[2.2.1]heptane-2-carboxylate in step 1. MS (EI) for $C_{15}H_{21}BrN_4O_4S$: 377 (MH$^+$-tBu).

(R)-tert-Butyl 2-((2-amino-5-bromopyridine-3-sulfonamido)methyl)pyrrolidine-1-carboxylate. Prepared according to the method of reagent preparation 25 by using (R)-tert-butyl 2-(aminomethyl)pyrrolidine-1-carboxylate in step 1. MS (EI) for $C_{15}H_{23}BrN_4O_4S$: 335 (MH$^+$-Boc).

(S)-tert-Butyl 2-((2-amino-5-bromopyridine-3-sulfonamido)methyl)pyrrolidine-1-carboxylate. Prepared according to the method of reagent preparation 25 by using (S)-tert-butyl 2-(aminomethyl)pyrrolidine-1-carboxylate in step 1. MS (EI) for $C_{15}H_{23}BrN_4O_4S$: 335 (MH$^+$-Boc).

(1R,4R)-tert-Butyl 5-(2-amino-5-bromopyridin-3-ylsulfonyl)-2,5-diazabicyclo[2.2.1]-heptane-2-carboxylate. Prepared according to the method of reagent preparation 25 by using (1R,4R)-tert-butyl 2,5-diazabicyclo[2.2.1]heptane-2-carboxylate in step 1. MS (EI) for $C_{15}H_{21}BrN_4O_4S$: 377 (MH$^+$-Boc).

tert-Butyl 4-(2-amino-5-bromopyridine-3-sulfonamido)piperidine-1-carboxylate. Prepared according to the method of reagent preparation 25 by using tert-butyl 4-aminopiperidine-1-carboxylate in step 1. MS (EI) for $C_{15}H_{23}BrN_4O_4S$: 379 (MH$^+$-Boc).

5-Bromo-3-((1S,4S)-5-methyl-2,5-diazabicyclo[2.2.1]heptan-2-ylsulfonyl)pyridin-2-amine. Prepared according to the method of reagent preparation 25 by using (1S,4S)-2-methyl-2,5-diazabicyclo[2.2.1]heptane in step 1. MS (EI) for $C_{11}H_{15}BrN_4O_2S$: 347 (MH$^+$).

(S)-tert-Butyl 1-(2-amino-5-bromopyridin-3-ylsulfonyl)pyrrolidin-3-ylcarbamate. Prepared according to the method of reagent preparation 25 by using (S)-tert-butyl pyrrolidin-3-ylcarbamate in step 1. MS (EI) for $C_{14}H_{21}BrN_4O_4S$: 421 (MH$^+$).

(R)-tert-Butyl 1-(2-amino-5-bromopyridin-3-ylsulfonyl)pyrrolidin-3-ylcarbamate. Prepared according to the method of reagent preparation 25 by using (R)-tert-butyl pyrrolidin-3-ylcarbamate in step 1. MS (EI) for $C_{14}H_{21}BrN_4O_4S$: 421 (MH$^+$).

tert-Butyl 8-(2-amino-5-bromopyridin-3-ylsulfonyl)-8-azabicyclo[3.2.1]octan-3-ylcarbamate. Prepared according to the method of reagent preparation 25 by using tert-butyl 8-azabicyclo[3.2.1]octan-3-ylcarbamate (WO 2009055077) in step 1. MS (EI) for $C_{17}H_{25}BrN_4O_4S$: 461 (MH$^+$).

2,2,2-Trichloroethyl 3-(2-amino-5-bromopyridine-3-sulfonamido)-8-azabicyclo[3.2.1]octane-8-carboxylate. Prepared according to the method of reagent preparation 25 by using 2,2,2-trichloroethyl 3-amino-8-azabicyclo[3.2.1]octane-8-carboxylate (WO 2009055077) in step 1. MS (EI) for $C_{15}H_{18}BrCl_3N_4O_4S$: 535 (MH$^+$).

(R)-tert-Butyl 3-((2-amino-5-bromopyridine-3-sulfonamido)methyl)pyrrolidine-1-carboxylate. Prepared according to the method of reagent preparation 25 by using (S)-tert-butyl 3-(aminomethyl)pyrrolidine-1-carboxylate in step 1. MS (EI) for $C_{15}H_{23}BrN_4O_4S$: 435 (MH$^+$).

(S)-tert-Butyl 3-((2-amino-5-bromopyridine-3-sulfonamido)methyl)pyrrolidine-1-carboxylate. Prepared according to the method of reagent preparation 25 by using (R)-tert-butyl 3-(aminomethyl)pyrrolidine-1-carboxylate in step 1. MS (EI) for $C_{15}H_{23}BrN_4O_4S$: 435 (MH$^+$).

(R)-tert-Butyl 3-(2-amino-5-bromopyridine-3-sulfonamido)pyrrolidine-1-carboxylate. Prepared according to the method of reagent preparation 25 by using (R)-tert-butyl 3-aminopyrrolidine-1-carboxylate in step 1. MS (EI) for $C_{14}H_{21}BrN_4O_4S$: 421 (MH$^+$).

(S)-tert-Butyl 3-(2-amino-5-bromopyridine-3-sulfonamido)pyrrolidine-1-carboxylate. Prepared according to the method of reagent preparation 25 by using (S)-tert-butyl 3-aminopyrrolidine-1-carboxylate in step 1. MS (EI) for $C_{14}H_{21}BrN_4O_4S$: 421 (MH$^+$).

tert-Butyl 3-((2-amino-5-bromopyridine-3-sulfonamido)methyl)piperidine-1-carboxylate. Prepared according to the method of reagent preparation 25 by using tert-butyl 3-(aminomethyl)piperidine-1-carboxylate in step 1. MS (EI) for $C_{16}H_{25}BrN_4O_4S$: 449 (MH$^+$).

tert-Butyl 2-((2-amino-5-bromopyridine-3-sulfonamido)methyl)piperidine-1-carboxylate. Prepared according to the method of reagent preparation 25 by using tert-butyl 2-(aminomethyl)piperidine-1-carboxylate in step 1. MS (EI) for $C_{16}H_{25}BrN_4O_4S$: 449 (MH$^+$).

(R)-tert-Butyl 3-((2-amino-5-bromopyridine-3-sulfonamido)methyl)piperidine-1-carboxylate. Prepared according to the method of reagent preparation 25 by using (S)-tert-butyl 3-(aminomethyl)piperidine-1-carboxylate in step 1. MS (EI) for $C_{16}H_{25}BrN_4O_4S$: 449 (MH$^+$).

(S)-tert-Butyl 3-((2-amino-5-bromopyridine-3-sulfonamido)methyl)piperidine-1-carboxylate. Prepared according to the method of reagent preparation 25 by using (R)-tert-butyl 3-(aminomethyl)piperidine-1-carboxylate in step 1. MS (EI) for $C_{16}H_{25}BrN_4O_4S$: 449 (MH$^+$).

(S)-2-amino-5-bromo-N-((1-methylpiperidin-3-yl)methyl)pyridine-3-sulfonamide. Prepared according to the method of reagent preparation 25 by using (R)-(1-methylpiperidin-3-yl)methanamine in step 1. MS (EI) for $C_{12}H_{19}BrN_4O_2S$: 363 (MH$^+$).

2-amino-5-bromo-N-[(3R)-1-methylpyrrolidin-3-yl]pyridine-3-sulfonamide. Synthesized according to the method of reagent preparation 25 by using (R)-1-methylpyrrolidin-3-amine hydrochloride (synthesized according to the method of Journal of Medicinal Chemistry (2002), 45(3), 721-739) in step 1. MS (EI) for $C_{10}H_{15}BrN_4O_2S$: 334, 336 (MH$^+$, Br isotope pattern).

2-amino-5-bromo-N-{[(3S)-1-methylpyrrolidin-3-yl]methyl}pyridine-3-sulfonamide. Synthesized according to the method of reagent preparation 25 by using (R)-(1-methylpyrrolidin-3-yl)methanamine hydrobromide (synthesized according to the methods of WO 2006028904 for the synthesis of benzyl[[(R)-1-(tert-butoxycarbonyl)pyrrolidin-3-yl]methyl]carbamate, WO 2006002047 for the synthesis of (S)-benzyl pyrrolidin-3-ylmethylcarbamate and Journal of Medicinal Chemistry (2002), 45(3), 721-739 for the synthesis of (R)-benzyl (1-methylpyrrolidin-3-yl)methylcarbamate, using (R)-3-(aminomethyl)-1-(tert-butyloxycarbonyl)pyrrolidine as starting material) in step 1. MS (EI) for $C_{11}H_{17}BrN_4O_2S$: 348, 350 (MH$^+$, Br isotope pattern).

tert-Butyl 6-(2-amino-5-bromopyridin-3-ylsulfonyl)-2,6-diazaspiro[3.3]heptane-2-carboxylate. Prepared according to the method of reagent preparation 25 by using tert-butyl 2,6-diazaspiro[3.3]heptane-2-carboxylate in step 1. MS (EI) for $C_{15}H_{21}BrN_4O_4S$: 377 (MH$^+$-tBu).

(S)-tert-Butyl 1-(5-bromo-2-chloropyridin-3-ylsulfonyl)pyrrolidin-3-ylcarbamate. Prepared according to the methods described in reagent preparation 25 using 5-bromo-2-chloropyridine-3-sulfonyl chloride and (S)-tert-butyl pyrrolidin-3-ylcarbamate in step 1. $^1$H NMR (400 MHz, CDCl$_3$) δ 8.61 (d, 1H), 8.52 (d, 1H), 4.67 (s, 1H), 4.25 (s, 1H), 3.57 (m, 4H), 3.34 (m, 1H), 2.22 (m, 1H), 1.92 (m, 1H), 1.45 (s, 9H); MS (ES) for $C_{14}H_{19}BrClN_3O_4S$: 440, 442 (Br isotopes, MH$^+$).

tert-Butyl 3-((2-amino-5-bromopyridine-3-sulfonamido)methyl)azetidine-1-carboxylate. Prepared according to the methods described in reagent preparation 25 using tert-butyl 3-(aminomethyl)azetidine-1-carboxylate in step 1. MS (ES) for $C_{14}H_{21}BrN_4O_4S$: 421, 423 (Br isotopes, MH$^+$).

Reagent Preparation 26

N-(5-bromo-2-methylpyridin-3-yl)methanesulfonamide

STEP 1: A solution of 5-bromo-2-methylpyridin-3-amine (187 mg, 1.0 mmol) and diisopropylethylamine (523 uL, 3.0 mmol) in dichloromethane (5 mL) was cooled to 0° C., and then methanesulfonyl chloride (155 uL, 2.0 mmol) was added slowly. The reaction mixture was stirred at 0° C. for 8 min and was then warmed to rt. After stirring for 1 h, the volatile materials were removed in vacuo. The residue was then dissolved in methanol (2.5 mL) and aqueous sodium hydroxide (2 M, 1.5 mL, 3 mmol) was added. The reaction mixture was stirred for 1 h 40 min at rt. Water was then added to the mixture which was subsequently extracted twice with dichloromethane. The combined organic extracts were extracted with aqueous citric acid (10%). The organic phase was discarded, and the aqueous phase was basified to pH ~7.5 with aqueous sodium hydroxide (1 M). The aqueous mixture was extracted three times with dichloromethane. The combined organic extracts were dried over magnesium sulfate, filtered, and concentrated in vacuo. The residue was purified by flash chromatography (50% hexanes:50% ethyl acetate) to provide N-(5-bromo-2-methylpyridin-3-yl)methanesulfonamide (111 mg, 0.42 mmol, 42% yield) as a white solid. $^1$H NMR (400 MHz, DMSO-d6) δ 9.58 (s, 1H), 8.44 (d, 1H), 7.87 (d, 1H), 3.10 (s, 3H), 2.47 (s, 3H); MS (EI) for $C_7H_9BrN_2O_2S$: 265, 267 (Br isotopes, MH$^+$).

Using analogous synthetic techniques and substituting with alternative starting reagents in step 1 the following reagents were prepared. Alternative starting materials were obtained commercially unless otherwise indicated.

N-(5-Bromo-2-chlorophenyl)methanesulfonamide. Prepared according to the methods described in reagent preparation 26 using 5-bromo-2-chloroaniline in step 1. $^1$H NMR (400 MHz, CDCl$_3$) δ 7.83 (d, 1H), 7.32-7.23 (m, 2H), 6.80 (br s, 1H), 3.06 (s, 3H); MS (EI) for $C_7H_7BrClNO_2S$: 282, 284, 286 (Br+Cl isotopes, MH$^+$).

N-(5-Bromo-2-methoxypyridin-3-yl)methanesulfonamide. Prepared according to the methods described in reagent preparation 26 using 5-bromo-2-methoxypyridin-3-amine in step 1. $^1$H NMR (400 MHz, CDCl$_3$) δ 7.97 (d, 1H), 7.90 (d, 1H), 6.73 (br s, 1H), 4.00 (s, 3H), 3.05 (s, 3H); MS (EI) for $C_7H_9BrN_2O_3S$: 281, 283 (Br isotopes, MH$^+$).

N-(5-Bromo-2-cyanopyridin-3-yl)methanesulfonamide. Prepared according to the methods described in reagent preparation 26 using 3-amino-5-bromopicolinonitrile in step 1. $^1$H NMR (400 MHz, CDCl$_3$) δ 8.55 (d, 1H), 8.29 (d, 1H), 7.00 (br s, 1H), 3.21 (s, 3H); MS (EI) for $C_7H_6BrN_3O_2S$: 276, 278 (Br isotopes, MH$^+$).

N-(5-Bromopyridin-3-yl)methanesulfonamide. Prepared according to the methods described in reagent preparation 26 using 5-bromopyridin-3-amine in step 1. MS (EI) for $C_6H_7BrN_2O_2S$: 251, 253 (Br isotopes, MH$^+$).

N-(5-Bromo-2-chloropyridin-3-yl)-2-chloro-6-methylbenzenesulfonamide. Prepared according to the methods described in reagent preparation 26 using 5-bromo-2-chloropyridin-3-amine and 2-chloro-6-methylbenzene-1-sulfonyl chloride in step 1. MS (EI) for $C_{12}H_9BrCl_2N_2O_2S$: 393, 395, 397 (Br+Cl isotopes, MH$^+$).

N-(5-Bromo-2-fluoropyridin-3-yl)methanesulfonamide. Prepared according to the methods described in reagent preparation 26 using 5-bromo-2-fluoropyridin-3-amine in step 1. MS (EI) for $C_6H_6BrFN_2O_2S$: 269, 271 (Br isotopes, MH$^+$).

N-(5-Bromo-2-chloropyridin-3-yl)acetamide. Prepared according to the methods described in reagent preparation 26 using 5-bromo-2-chloropyridin-3-amine and acetyl chloride in step 1.

Methyl 5-bromo-2-chloropyridin-3-ylcarbamate. Prepared according to the methods described in reagent preparation 26 using 5-bromo-2-chloropyridin-3-amine and methyl chloroformate in step 1.

Reagent Preparation 27

5-bromo-2-chloro-3-(methylsulfonylmethyl)pyridine

STEP 1: A mixture of 5-bromo-2-chloro-3-(chloromethyl)pyridine (124 mg, 0.52 mmol) and sodium methanesulfinate (52 mg, 0.52 mmol) in dioxane (1.4 mL) and water (1.4 mL) was heated to 110° C. in a microwave reactor for 15 min. After cooling to rt, water was added to the reaction mixture which was subsequently extracted twice with ethyl acetate. The combined organic extracts were dried over magnesium sulfate, filtered, and concentrated in vacuo to provide 5-bromo-2-chloro-3-(methylsulfonylmethyl)pyridine (140 mg, 0.49 mmol, 94% yield) as a yellow solid. $^1$H NMR (400 MHz, DMSO-d6) δ 8.63 (d, 1H), 8.21 (d, 1H), 4.70 (s, 2H), 3.10 (s, 3H); MS (EI) for $C_7H_7BrClNO_2S$: 284, 286, 288 (Br+Cl isotopes, MH$^+$).

Using analogous synthetic techniques and substituting with alternative starting reagents in step 1 the following reagent was prepared. Alternative starting materials were obtained commercially unless otherwise indicated.

5-Bromo-3-(methylsulfonylmethyl)pyridin-2-amine. Prepared according to the methods described in reagent preparation 27 using 5-bromo-3-(bromomethyl)pyridin-2-amine hydrochloride in step 1. $^1$H NMR (400 MHz, DMSO-d6) δ 8.03 (d, 1H), 7.59 (d, 1H), 6.35 (br s, 2H), 4.44 (s, 2H), 2.95 (s, 3H); MS (EI) for $C_7H_9BrN_2O_2S$: 265, 267 (Br isotopes, MH$^+$).

Reagent Preparation 28

N-(5-bromo-2-chloropyridin-3-yl)-N-methyl-methanesulfonamide

STEP 1: A solution of N-(5-bromo-2-chloropyridin-3-yl)methanesulfonamide (96 mg, 0.34 mmol, reagent preparation 24) in DMF (1 mL) was treated with potassium carbonate (93 mg, 0.68 mmol) and iodomethane (33 uL, 0.51 mmol) at rt for 18 h. Water was then added, and the resulting aqueous mixture was extracted twice with ethyl acetate. The combined organic extracts were washed with aqueous lithium chloride (10%) followed by water, dried over magnesium sulfate, filtered, and concentrated in vacuo to provide N-(5-bromo-2-chloropyridin-3-yl)-N-methylmethanesulfonamide (91.2 mg, 0.304 mmol, 90% yield) as a light yellow solid. $^1$H NMR (400 MHz, CDCl$_3$) δ 8.46 (d, 1H), 8.00 (d, 1H), 3.32 (s, 3H), 3.07 (s, 3H); MS (EI) for $C_7H_8BrClN_2O_2S$: 299, 301, 303 (Br+Cl isotopes, MH$^+$).

Reagent Preparation 29

5-bromo-2-chloro-3-(difluoromethoxy)pyridine

To a solution of 5-bromo-2-chloropyridin-3-ol (150 mg, 0.72 mmol) in DMF (5 mL) was added potassium carbonate (298 mg, 2.2 mmol). The mixture was heated to 70° C. and bromodifluoromethane was bubbled through for 3 min. After cooling to rt, water was added, and the resulting aqueous mixture was extracted twice with ethyl acetate. The organic extracts were washed with aqueous lithium chloride (10%) followed by water, dried over magnesium sulfate, filtered, and concentrated in vacuo to provide 5-bromo-2-chloro-3-(difluoromethoxy)pyridine (159 mg, 0.61 mmol, 85% yield) as a brown oil. $^1$H NMR (400 MHz, CDCl$_3$) δ 8.36 (d, 1H), 7.76 (d, 1H), 6.61 (t, 1H); MS (EI) for $C_6H_3BrClF_2NO$: 258 (M$^+$).

Reagent Preparation 30

N-(5-bromo-2-ethoxypyridin-3-yl)methanesulfonamide

STEP 1: A solution of 5-bromo-2-chloro-3-nitropyridine (100 mg, 0.42 mmol) and 1,8-diazabicyclo[5.4.0]undec-7-ene (315 uL, 2.11 mmol) in ethanol (1 mL) was heated to 50° C. for 50 min and then cooled to rt. Water was added and the resulting aqueous mixture was extracted twice with ethyl acetate. The combined organic extracts were washed with 1 N HCl, dried over magnesium sulfate, filtered, and concentrated in vacuo. The residue was purified by flash chromatography (gradient, 100% hexanes to 90% hexanes:10% ethyl acetate) to provide 5-bromo-2-ethoxy-3-nitropyridine (52.2 mg, 0.211 mmol, 50% yield) as a yellow oil. $^1$H NMR (400 MHz, CDCl$_3$) δ 8.42 (d, 1H), 8.36 (d, 1H), 4.55 (q, 2H), 1.45 (t, 3H); MS (EI) for $C_7H_7BrN_2O_3$: 246, 248 (M).

STEP 2: To a solution of 5-bromo-2-ethoxy-3-nitropyridine (75.2 mg, 0.304 mmol) in ethyl acetate (3 mL) was added tin(II) chloride (289 mg, 1.52 mmol), and the mixture was heated to reflux for 2 h. After cooling to rt, 50% aqueous sodium hydroxide was added dropwise until a sticky brown solid completely formed. Sodium sulfate was then added, and the mixture was stirred for several minutes. The solids were then removed by filtration. The filtrate was dried over sodium sulfate, filtered, and concentrated in vacuo to provide 5-bromo-2-ethoxypyridin-3-amine (53 mg, 0.25 mmol, 80% yield) as a dark blue film. $^1$H NMR (400 MHz, CDCl$_3$) δ 7.56 (d, 1H), 6.97 (d, 1H), 4.37 (q, 2H), 3.85 (br s, 2H), 1.40 (dd, 3H); MS (EI) for $C_7H_9BrN_2O$: 217, 219 (Br isotopes, MH$^+$).

STEP 3: A solution of 5-bromo-2-ethoxypyridin-3-amine (53 mg, 0.25 mmol) and diisopropylethylamine (96 uL, 0.55 mmol) in dichloromethane (1 mL) was cooled to 0° C. and methanesulfonyl chloride (39 uL, 0.5 mmol) was added. The mixture was allowed to warm to rt over 15 h, and then water was added. The resulting mixture was extracted with dichloromethane. The organic extract was dried over magnesium sulfate, filtered, and concentrated in vacuo. The residue was dissolved in methanol (500 uL) and dioxane (500 uL), and then sodium hydroxide (2 M, 190 uL, 0.38 mmol) was added. The mixture was heated to 60° C. and 3 drops of aqueous sodium hydroxide (50%) were added. After stirring a further 30 min, the mixture was cooled to rt. Dilution with water was followed by acidification with aqueous citric acid (10%) and then two extractions with ethyl acetate. The combined organic extracts were washed with water, dried over magnesium sulfate, filtered, and concentrated in vacuo. The residue was purified by flash chromatography (gradient 100% hexanes to 70% hexanes:30% ethyl acetate) to provide N-(5-bromo-2-ethoxypyridin-3-yl)methanesulfonamide (32.1 mg, 0.11 mmol, 43% yield) as a colorless film. $^1$H NMR (400 MHz, CDCl$_3$) δ 7.95 (d, 1H), 7.89 (d, 1H), 6.75 (br s, 1H), 4.42 (q, 2H), 3.05 (s, 3H), 1.41 (t, 3H); MS (EI) for $C_8H_{11}BrN_2O_3S$: 295, 297 (Br isotopes, MH$^+$).

Using analogous synthetic techniques and substituting with alternative starting reagents in step 1 the following reagent was prepared. Alternative starting materials were obtained commercially unless otherwise indicated.

N-(2-(Benzyloxy)-5-bromopyridin-3-yl)methanesulfonamide. Prepared according to the methods described in reagent preparation 30 using benzyl alcohol in step 1. $^1$H NMR (400 MHz, CDCl$_3$) δ 8.00 (d, 1H), 7.91 (d, 1H), 7.44-7.34 (m, 5H), 6.71 (br s, 1H), 5.40 (s, 2H), 2.99 (s, 3H); MS (EI) for $C_{13}H_{13}BrN_2O_3S$: 357, 359 (Br isotopes, MH$^+$).

Reagent Preparation 31

N-(2-amino-5-bromopyridin-3-yl)methanesulfonamide

STEP 1: To a solution of 5-bromo-3-nitropyridin-2-amine (218 mg, 1 mmol) in THF (5 mL) was added DMAP (183 mg, 1.5 mmol) and di-tert-butyl dicarbonate (655 mg, 3 mmol). After stirring 40 min at rt, the volatile materials were removed in vacuo, and the resulting residue was purified by flash chromatography (gradient, 100% hexanes to 70% hexanes: 30% ethyl acetate). The isolated material indicated the addition of two Boc groups by $^1$H NMR. This material was dissolved in ethyl acetate (8 mL) and was treated with excess N,N-dimethylethylenediamine. After stirring for 17 h at rt, the reaction mixture was diluted with ethyl acetate. The resulting solution was washed with aqueous citric acid (10%) followed by water, dried over magnesium sulfate, filtered, and concentrated in vacuo to provide tert-butyl 5-bromo-3-nitropyridin-2-ylcarbamate (270 mg, 0.85 mmol, 85% yield) as an orange solid. $^1$H NMR (400 MHz, CDCl$_3$) δ 9.48 (br s, 1H), 8.74 (d, 1H), 8.63 (d, 1H), 1.56 (s, 9H); MS (EI) for C$_{10}$H$_{12}$BrN$_3$O$_4$: 316, 318 (Br isotopes, M–H).

STEP 2: Iron powder (293 mg, 5.2 mmol) was added to a solution of tert-butyl 5-bromo-3-nitropyridin-2-ylcarbamate (167 mg, 0.52 mmol) in acetic acid (2.5 mL). The mixture was stirred at 60° C. for 1 h 20 min before cooling to rt. The mixture was then diluted with ethyl acetate, and solids were removed by filtration through celite. The filtrate was washed with water followed by saturated aqueous sodium bicarbonate. The organic phase was dried over magnesium sulfate, filtered, and concentrated in vacuo to provide tert-butyl 3-amino-5-bromopyridin-2-ylcarbamate (96.3 mg, 0.33 mmol, 64% yield) as a gray solid. $^1$H NMR (400 MHz, CDCl$_3$) δ 7.83 (d, 1H), 7.20 (d, 1H), 6.95 (br s, 1H), 4.42 (br s, 2H), 1.51 (s, 9H); MS (EI) for C$_{10}$H$_{14}$BrN$_3$O$_2$: 232, 234 (Br isotopes, MH$^+$-t-butyl).

STEP 3: A solution of tert-butyl 3-amino-5-bromopyridin-2-ylcarbamate (96.3 mg, 0.33 mmol) and diisopropylethylamine (128 uL, 074 mmol) in dichloromethane (2 mL) was cooled to 0° C., and to it was added methanesulfonyl chloride (52 uL, 0.67 mmol). The mixture was allowed to warm to rt over 2 h. The mixture was then diluted with dichloromethane and was then washed with aqueous citric acid (10%) followed by water. The organic phase was then dried over magnesium sulfate, filtered, and concentrated in vacuo. The residue was purified by flash chromatography (gradient, 100% hexanes to 70% hexanes:30% ethyl acetate) to provide tert-butyl 5-bromo-3-(N-(methylsulfonyl)methylsulfonamido)pyridin-2-ylcarbamate (77 mg, 0.17 mmol, 52% yield) as a colorless film. $^1$H NMR (400 MHz, CDCl$_3$) δ 8.64 (d, 1H), 7.79 (d, 1H), 7.10 (s, 1H), 3.44 (s, 6H), 1.52 (s, 9H); MS (EI) for C$_{12}$H$_{18}$BrN$_3$O$_6$S$_2$: 388, 390 (Br isotopes, MH$^+$-t-butyl).

STEP 4: A solution of tert-butyl 5-bromo-3-(N-(methylsulfonyl)methylsulfonamido)pyridin-2-ylcarbamate (68 mg, 0.15 mmol) and N,N-dimethylethylenediamine (169 uL, 1.5 mmol) in dioxane (1 mL) was stirred at rt for 70 min. After diluting with ethyl acetate, the mixture was washed with aqueous citric acid (10%) followed by water. The organic phase was then dried over magnesium sulfate, filtered, and concentrated in vacuo. The residue was then diluted with dichloromethane which was then washed with 1 N HCl. After partitioning, the organic phase was dried over magnesium sulfate, filtered, and concentrated in vacuo to provide tert-butyl 5-bromo-3-(methylsulfonamido)pyridin-2-ylcarbamate (57 mg, 0.15 mmol, quantitative yield) as a white solid. $^1$H NMR (400 MHz, CDCl$_3$) δ 8.24 (d, 1H), 8.07 (d, 1H), 2.98 (s, 3H), 1.54 (s, 9H); MS (EI) for C$_{10}$H$_{16}$BrN$_3$O$_4$S: 310, 312 (Br isotopes, MH$^+$-t-butyl).

STEP 5: A solution of tert-butyl 5-bromo-3-(methylsulfonamido)pyridin-2-ylcarbamate (57 mg, 0.15 mmol) in methanol (1 mL) and HCl (4 M in dioxane, 375 uL, 1.5 mmol) was heated to 60° C. for 90 min. The volatile materials were then removed in vacuo to provide N-(2-amino-5-bromopyridin-3-yl)methanesulfonamide as its hydrochloride salt in quantitative yield. $^1$H NMR (400 MHz, DMSO-d6) δ 9.10 (br s, 1H), 7.95 (d, 1H), 7.54 (d, 1H), 6.42 (br s, 1H), 3.02 (s, 3H); MS (EI) for C$_6$H$_8$BrN$_3$O$_2$S: 266, 268 (Br isotopes, MH$^+$).

Reagent Preparation 32

5-bromo-1-(tetrahydro-2H-pyran-2-yl)-1H-pyrazolo[3,4-b]pyridine

To a solution of 5-bromo-1H-pyrazolo[3,4-b]pyridine (1.4 g, 7.2 mmol) and dihydropyran (3.3 mL, 36.0 mmol) in tetrahydrofuran (20 mL) was added (±)-camphorsulfonic acid (250 mg) and the reaction mixture was stirred at 65° C. for 16 hours. After cooling to room temperature it was diluted with ethyl acetate (250 mL), washed with saturated aqueous sodium bicarbonate (2×100 mL) and brine (100 mL), dried over sodium sulfate, filtered and concentrated. Gradient column chromatography (10% to 30% ethyl acetate in hexane) provided 5-bromo-1-(tetrahydro-2H-pyran-2-yl)-1H-pyrazolo[3,4-b]pyridine (1.8 g, 90%). MS (EI) for C$_{11}$H$_{12}$BrN$_3$O: 283 (MH$^+$).

Reagent Preparation 33

2-Amino-5-bromo-N,N-dimethylnicotinamide

To a suspension of 2-amino-5-bromonicotinic acid (0.35 g, 1.61 mmol) in tetrahydrofuran (5 mL) was added dimethylamine (0.8 mL of a 2M solution in tetrahydrofuran, 1.60 mmol), diethylphosphoryl cyanide (0.29 g, 1.77 mmol), and triethylamine (0.34 g, 3.38 mmol) at 0° C. The mixture was stirred at 0° C. for 30 min and then at room temperature for 4 h. Concentration and purification by column chromatography on silica (5-10% methanol in dichloromethane) gave the title Compound as a white solid. MS (EI) for C$_8$H$_{10}$BrN$_3$O: 244 (MH$^+$).

Reagent Preparation 34

5-Bromo-3-(ethylsulfonyl)pyridin-2-amine

STEP 1: 2-Amino-5-bromopyridine-3-sulfonyl chloride (94 mg, 0.35 mmol) was taken into THF (2 mL) followed by addition of anhydrous hydrazine (40 uL, 1.4 mmol) and the mixture was stirred for 10 minutes at room temperature. The mixture was concentrated and dried to give 2-amino-5-bromopyridine-3-sulfonohydrazide as a white solid, which was then taken into ethanol (2 mL) followed by addition of sodium acetate (320 mg, 3.9 mmol) and ethyl iodide (140 uL, 1.75 mmol). The mixture was refluxed for 12 h then cooled to room temperature and concentrated. The residue was partitioned with ethyl acetate and water and the organic phase washed with brine then dried over sodium sulfate, filtered and concentrated to give 5-bromo-3-(ethylsulfonyl)pyridin-2-amine (67 mg, 72%) as a yellow oil. MS (EI) for C$_7$H$_9$N$_2$SO$_2$Br: 265, 267 (MH$^+$).

Using analogous synthetic techniques and substituting with alternative starting reagents in step 1 the following reagents were prepared.

5-Bromo-3-(methylsulfonyl)pyridin-2-amine. Synthesized according to the method of reagent preparation 34 using iodomethane. GCMS (EI) for C$_6$H$_7$N$_2$SO$_2$Br: 250, 252 (M$^+$).

3-(2-amino-5-bromopyridin-3-ylsulfonyl)propane-1,2-diol. Synthesized according to the method of reagent preparation 34 using 3-bromopropane-1,2-diol followed by silica gel chromatography using ethyl ether then ethyl acetate as eluent. MS (EI) for C$_7$H$_9$N$_2$SO$_2$Br: 311, 313 (MH$^+$).

3-(2-amino-5-bromopyridin-3-ylsulfonyl)propan-1-ol. Synthesized according to the method of reagent preparation 34 using 3-bromopropan-1-ol followed by silica gel chromatography using ethyl ether as eluent. MS (EI) for C$_7$H$_9$N$_2$SO$_2$Br: 295, 297 (MH$^+$).

(S)-3-(2-amino-5-bromopyridin-3-ylsulfonyl)-2-methylpropan-1-ol. Synthesized according to the method of reagent preparation 34 using (S)-3-bromo-2-methylpropan-1-ol followed by silica gel chromatography using 4:1 ethyl ether:hexanes as eluent. MS (EI) for C$_7$H$_9$N$_2$SO$_2$Br: 309, 311 (MH$^+$).

(R)-3-(2-amino-5-bromopyridin-3-ylsulfonyl)-2-methylpropan-1-ol. Synthesized according to the method of reagent preparation 34 using (R)-3-bromo-2-methylpropan-1-ol followed by silica gel chromatography using 4:1 ethyl ether: hexanes as eluent. MS (EI) for $C_7H_9N_2SO_2Br$: 309, 311 (MH$^+$).

Reagent Preparation 35

6-bromo-2-methyl-1-({[2-(trimethylsilyl)ethyl]oxy}methyl)-1H-imidazo[4,5-b]pyridine To a solution of 6-bromo-2-methyl-1H-imidazo[4,5-b]pyridine (3.0 g, 14.1 mmol) in a mixture of N,N-dimethylformamide and tetrahydrofuran (30 mL, 2:1) at 0° C. was added 60% sodium hydride in mineral oil (0.68 g, 17.0 mmol) and the reaction mixture was stirred for 30 minutes, followed by the addition of 2-(trimethylsilyl)ethoxymethyl chloride (2.7 mL, 14.9 mmol). The reaction mixture was stirred for 16 hours at room temperature then it was quenched by the careful addition of water and diluted with ethyl acetate (250 mL), washed with brine (3×150 mL), dried over sodium sulfate, filtered and concentrated. Gradient column chromatography (10% to 30% ethyl acetate in hexane) provided 6-bromo-2-methyl-1-({[2-(trimethylsilyl)ethyl]oxy}methyl)-1H-imidazo[4,5-b]pyridine (4.4 g, 92%). $^1$H NMR (400 MHz, CDCl$_3$): 8.41 (s, 1H), 8.12 (s, 1H), 5.67 (s, 2H), 3.62 (m, 2H), 2.76 (s, 3H), 0.96 (m, 2H), 0.00 (s, 9H). MS (EI) for $C_{13}H_{20}BrN_3OSi$: 342, 344 (MH$^+$, Br iotope pattern).

Reagent Preparation 36

6-bromo-N-ethyl-3-(methoxymethyl)-3H-imidazo[4,5-b]pyridin-2-amine and 6-bromo-N-ethyl-N,3-bis(methoxymethyl)-3H-imidazo[4,5-b]pyridin-2-amine Step 1: To a cooled (0° C.) solution of 5-bromopyridine-2,3-diamine (5.0 g, 27 mmol) in NMP (20 mL) was added isothiocyanatoethane (2.3 mL, 26 mmol). The resulting solution was heated (65° C.) for four hours and then cooled to ambient temperature before 1,3-diisopropylcarbodiimide (4.2 mL, 27 mmol) was added. The reaction mixture was stirred for 18 hours, diluted with water and the resulting suspension was collected by filtration. Trituration with ethyl acetate provided 6-bromo-N-ethyl-3H-imidazo[4,5-b]pyridin-2-amine (4.8 g, 75% yield) as a brown solid. $^1$H NMR (400 MHz, d$_6$-DMSO) δ 11.41 (bs, 1H), 7.91 (s, 1H), 7.53 (s, 1H), 7.17 (s, 1H), 3.33 (q, 2H), 1.17 (t, 3H); MS (ES) for $C_8H_9BrN_4$: 241 (MH$^+$).

Step 2: To a cooled (0° C.) solution of 6-bromo-N-ethyl-3H-imidazo[4,5-b]pyridin-2-amine (0.36 g, 1.5 mmol) in DMF was added NaH (60% dispersion in mineral oil, 0.060 g, 1.5 mmol) portionwise over 15 minutes. The reaction mixture was stirred for 15 minutes and then chloro(methoxy)methane (0.12 mL, 1.5 mmol) was added dropwise over 15 minutes. The resulting slurry was allowed to warm to ambient temperature and was stirred for two hours and was partitioned between ethyl acetate and saturated aqueous sodium bicarbonate. The organic layer was washed with brine, dried over magnesium sulfate, filtered and concentrated in vacuo. Purification by silica gel chromatography provided both 6-bromo-N-ethyl-N,3-bis(methoxymethyl)-3H-imidazo[4,5-b]pyridin-2-amine (0.091 g, 18%) and 6-bromo-N-ethyl-3-(methoxymethyl)-3H-imidazo[4,5-b]pyridin-2-amine (0.15 g, 35% yield). Bisprotected product: MS (ES) for $C_{12}H_{17}BrN_4O_2$: 329 (MH$^+$). Monoprotected product: $^1$H NMR (400 MHz, CDCl$_3$) δ 8.03 (d, 1H), 7.73 (d, 1H), 5.42 (s, 2H), 4.98 (s, 1H), 3.59 (q, 2H), 3.36 (s, 3H), 1.34 (t, 3H); MS (ES) for $C_{10}H_{13}BrN_4O$: 285 (MH$^+$).

Reagent Preparation 37

7-Bromo-2H-pyrido[2,3-e][1,2,4]thiadiazin-3(4H)-one 1,1-dioxide

STEP 1: 2-Amino-5-bromopyridine-3-sulfonyl chloride (reagent preparation 25) (95.5 mg, 0.35 mmol) was treated with 0.5M ammonia in dioxane solution (7 mL) and the mixture was stirred for 1 h at room temperature. Concentrated aqueous ammonia (2 mL) was then added to the mixture then stirred an additional 12 h. The mixture was then concentrated and the residue suspended in water (5 mL). The solid was collected by filtration and dried to give 2-amino-5-bromopyridine-3-sulfonamide (55.7 mg, 89%).

STEP 2: 2-Amino-5-bromopyridine-3-sulfonamide as obtained above (0.22 mmol) was taken into THF (2 mL) followed by addition of diisopropylethylamine (115 uL, 0.66 mmol). Phosgene (20 W % in toluene, 120 uL, 0.22 mmol) was added carefully and the mixture was allowed to stir for 1 h at room temperature. The mixture was partitioned with ethyl acetate and 0.5M aqueous hydrochloric acid. The organic phase was then extracted once with saturated aqueous sodium bicarbonate. The organic layer was discarded and the aqueous phase carefully acidified to pH 1-2 with concentrated aqueous hydrochloric acid. The aqueous mixture was then extracted once with ethyl acetate, dried over sodium sulfate, filtered and concentrated to give 7-bromo-2H-pyrido[2,3-e][1,2,4]thiadiazin-3(4H)-one 1,1-dioxide (17.3 mg, 28%) as a solid. MS (EI) for $C_6H_4N_3O_3SBr$: 277, 279 (M$^-$).

Reagent Preparation 38

2-amino-5-bromopyridine-3-sulfonic acid

STEP 1: 2-Amino-5-bromopyridine-3-sulfonyl chloride (100 mg, 0.37 mmol) was taken into 1:1 aqueous dioxane (3 mL) and the mixture was basified to pH 14 by drop wise addition of 50% aqueous sodium hydroxide solution. The mixture was warmed to 75° C. for 0.5 h then cooled to room temperature and concentrated. The residue was taken into water (2 mL) and carefully acidified to pH 1-2 by concentrated aqueous hydrochloric acid addition and cooled to 0° C. After 1 h at 0° C. the crystalline solid obtained was collected by filtration and dried to give 2-amino-5-bromopyridine-3-sulfonic acid as a solid. $^1$H NMR (DMSO-d$_6$): 8.24 (d, 1H), 8.06 (d, 1H). MS (EI) for $C_5H_5N_2SO_3Br$: 253, 255 (MH$^+$, Br pattern).

Reagent Preparation 39

N-(5-bromo-2-(dimethylamino)pyridin-3-yl)methanesulfonamide

STEP 1: 5-Bromo-2-chloro-3-nitropyridine (J. Heterocyclic Chem. 2003, 40, 261) (128 mg, 0.54 mmol) was taken into THF (0.25 mL) followed by addition of 40 W % aqueous dimethylamine (0.25 mL) and the resulting solution was stirred for 1 h at room temperature. The mixture was then partitioned with ethyl ether and 1 M aqueous hydrochloric acid. The organic solution was then washed with additional 1 M aqueous hydrochloric acid (3×) then dried over magnesium sulfate, filtered and concentrated to give 5-bromo-N,N-dimethyl-3-nitropyridin-2-amine. MS (EI) for $C_7H_8N_3O_2Br$: 246, 248 (MH$^+$, Br pattern).

STEP 2: 5-Bromo-N,N-dimethyl-3-nitropyridin-2-amine as obtained in step 1 (0.54 mmol) was taken into ethyl acetate (10 mL) followed by addition of tin (II) chloride (522 mg, 2.8 mmol) and the mixture was heated to reflux for 15 minutes then cooled to room temperature. 50 W % aqueous sodium hydroxide was added drop wise to the mixture until a precipitate formed then solid sodium sulfate was added. The mixture was filtered and the filter cake washed with ethyl acetate. The organic filtrate was concentrated to give 5-bromo-N2,N2-dimethylpyridine-2,3-diamine (53 mg, 45%) was an amorphous residue. MS (EI) for $C_7H_{10}N_3Br$: 216, 218 (MH$^+$, Br pattern).

STEP 3: 5-Bromo-N2,N2-dimethylpyridine-2,3-diamine (53 mg, 0.25 mmol) was taken into THF (2 mL) followed by addition of diisopropylethylamine (213 uL, 1.25 mmol) and methanesulfonyl chloride (95 ul, 1.25 mmol). The mixture was allowed to stir for 48 h at room temperature then partitioned with ethyl acetate and water. The organic phase was washed with brine then dried over sodium sulfate, filtered and concentrated. The residue was taken into methanol (3 mL) followed by addition of potassium hydroxide (108 mg, 10 eq) in a minimum of water. The mixture was stirred for 15 minutes at room temperature then partitioned with ethyl acetate and 10% aqueous citric acid. The organic solution was dried over magnesium sulfate, filtered and concentrated. The residue was purified by silica gel chromatography to give N-(5-bromo-2-(dimethylamino)pyridin-3-yl)methanesulfonamide (27.9 mg, 39%). MS (EI) for $C_8H_{12}N_3SO_2Br$: 294, 296 (MH$^+$, Br pattern).

Using analogous synthetic techniques and substituting with alternative starting reagents in step 1 the following reagents were prepared.

N-(2-(Benzylamino)-5-bromopyridin-3-yl)methanesulfonamide. Synthesized according to the method of reagent preparation 39 using benzylamine in step 1. MS (EI) for $C_{13}H_{14}N_3SO_2Br$: 356, 358 (MH$^+$, Br pattern).

N-(5-Bromo-2-(phenylamino)pyridin-3-yl)methanesulfonamide. Synthesized according to the method of reagent preparation 39 using neat aniline at 75° C. in step 1. MS (EI) for $C_{12}H_{12}N_3SO_2Br$: 342, 344 (MH$^+$, Br pattern).

N-(5-Bromo-2-(methylamino)pyridin-3-yl)methanesulfonamide. Synthesized according to the method of reagent preparation 39 using methylamine in step 1. MS (EI) for $C_7H_{10}N_3SO_2Br$: 280, 282 (MH$^+$, Br pattern).

Reagent Preparation 40

1,1-dimethylethyl {(3S)-1-[(5-bromo-2-hydroxypyridin-3-yl)sulfonyl]pyrrolidin-3-yl}carbamate and 1,1-dimethylethyl[(3S)-1-({5-bromo-2-[(3S)-3-({[(1,1-dimethylethyl)oxy]carbonyl}amino)pyrrolidin-1-yl]pyridin-3-yl}sulfonyl)pyrrolidin-3-yl]carbamate STEP 1: To a solution of 3-amino-5-bromo-2-chloropyridine (0.23 g, 1.1 mmol) in acetonitrile (3.0 mL) at −15° C. was added a solution of sodium nitrite (0.091 g, 1.3 mmol) in water (1.20 mL), followed by the addition of concentrate hydrochloric acid (1.8 mL, 21.3 mmol) and the reaction mixture was stirred for 5 minutes. A 30 wt % solution of sulfur dioxide in acetic acid 3.0 mL, 1.3 mmol) was prepared and introduced into the reaction mixture, followed by the addition of a solution of copper(II) chloride 0.091 g, 0.68 mmol) in water (1.2 mL). The stirring was continued for an additional 3 hours at −5° C. The pH of the mixture was adjusted to 8 by the addition of a solution of potassium hydrogenphosphate and 2M aqueous sodium hydroxide and partitioned with ethyl acetate (50 mL). The organic layer was separated and washed with water (10 mL) and brine (10 mL), dried over sodium sulfate, filtered and concentrated to give 5-bromo-2-chloropyridine-3-sulfonyl chloride (0.20 g, 63%).

STEP 2: A mixture of 5-bromo-2-chloropyridine-3-sulfonyl chloride (0.19 g, 0.65 mmol), (3S)-(−)-3-(tert-butoxycarbonylamino)pyrrolidine (0.18 g, 0.98 mmol) and N,N-diisopropylethylamine (0.34 mL, 1.95 mmol) in dichloromethane (1.5 mL) was stirred for 16 hours at room temperature. The reaction mixture was partitioned between dichloromethane (50 mL) and brine (10 mL). The organic layer was separated, dried over sodium sulfate, filtered and concentrated. The resulting crude product was dissolved in a mixture of 1,4-dioxane (1.5 mL) and 2M aqueous sodium hydroxide (1.5 mL) and stirred at 100° C. for 2 hours. After cooling to room temperature the reaction mixture was concentrated and the residue was partitioned between brine (20 mL) and ethyl acetate (50 mL). The organic layer was separated and washed with brine (20 mL), dried over sodium sulfate, filtered and concentrated. Gradient flash chromatography (25% to 50% ethyl acetate in hexane) followed by 10% methanol in dichloromethane provided 1,1-dimethylethyl[(3S)-1-({5-bromo-2-[(3S)-3-({[(1,1-dimethylethyl)oxy]carbonyl}amino)pyrrolidin-1-yl]pyridin-3-yl}sulfonyl)pyrrolidin-3-yl]carbamate (80 mg, 21%), MS (EI) for $C_{23}H_{36}BrN_5O_6S$: 591 (MH$^+$); and 1,1-dimethylethyl{(3S)-1-[(5-bromo-2-hydroxypyridin-3-yl)sulfonyl]pyrrolidin-3-yl}carbamate (35 mg, 13%); MS (EI) for $C_{14}H_{20}BrN_3O_5S$: 423 (MH$^+$).

Reagent Preparation 41

4-[(2-amino-5-bromopyridin-3-yl)sulfonyl]-2-methylbutan-2-ol and 4-[(2-amino-5-bromopyridin-3-yl)sulfinyl]-2-methylbutan-2-ol STEP 1: To a solution of 2-amino-5-bromopyridine-3-sulfonyl chloride (reagent preparation 25, step 1) (0.40 g, (1.47 mmol) in a mixture of 1,4-dioxane (8.0 mL) and water (1.0 mL) was added triphenylphosphine (1.64 g, 6.25 mmol) and the reaction mixture was stirred for 50 minutes at room temperature. Potassium carbonate (0.35 g, 2.50 mmol) was introduced, followed by 4-bromo-2-methyl-2-butanol (Tetrahedron Letters 2000, 41(38), 7337-7340) (0.31 g, 1.86 mmol) and the reaction mixture was stirred at 80° C. for 16 hours. After cooling to room temperature the reaction mixture was concentrated and the residue was partitioned between brine (50 mL) and ethyl acetate (100 mL). The organic layer was separated and washed with brine (50 mL), dried over sodium sulfate, filtered and concentrated. Gradient flash chromatography (25% to 50% ethyl acetate in hexane) provided 4-[(2-amino-5-bromopyridin-3-yl)thio]-2-methylbutan-2-ol (0.18 g, 42%); MS (EI) for $C_{10}H_{15}BrN_2OS$: 292 (MH$^+$).

STEP 2A: To a solution of 4-[(2-amino-5-bromopyridin-3-yl)thio]-2-methylbutan-2-ol (90 mg, 0.31 mmol) in a mixture of methanol (750 μL), acetone (750 μL) and water (450 μL) was added potassium peroxymonosulfate (285 mg, 0.46 mmol) and the reaction mixture was stirred for 15 minutes at room temperature. The reaction mixture was partitioned between water (20 mL) and ethyl acetate (50 mL). The organic layer was separated and washed with water (20 mL) and brine (20 mL), dried over sodium sulfate, filtered and concentrated. Purification by flash chromatography (35% to 80% ethyl acetate in hexane) gave 4-[(2-amino-5-bromopyridin-3-yl)sulfonyl]-2-methylbutan-2-ol (48 mg, 48%); MS (EI) for $C_{10}H_{15}BrN_2O_3S$: 323 (MH$^+$).

STEP 2B: To a solution of 4-[(2-amino-5-bromopyridin-3-yl)thio]-2-methylbutan-2-ol (83 mg, 0.28 mmol) in a mixture of methanol (750 μL), acetone (750 μL) and water (450

μL) was added potassium peroxymonosulfate (131 mg, 0.21 mmol) and the reaction mixture was stirred for 90 minutes at 0° C. The reaction mixture was partitioned between water (20 mL) and ethyl acetate (50 mL). The organic layer was separated and washed with water (20 mL) and brine (20 mL), dried over sodium sulfate, filtered and concentrated. Purification by flash chromatography (35% to 80% ethyl acetate in hexane) gave 4-[(2-amino-5-bromopyridin-3-yl)sulfinyl]-2-methylbutan-2-ol (52 mg, 60%); MS (EI) for $C_{10}H_{15}BrN_2O_2S$: 308 (MH$^+$).

Using analogous synthetic techniques and substituting with alternative starting materials in step 1 the following reagents of the invention were prepared. Alternative starting materials were obtained commercially unless otherwise indicated.

(2S)-3-[(2-amino-5-bromopyridin-3-yl)sulfonyl]-2-methylpropan-1-ol. Prepared according to the method of reagent preparation 41 by using (S)-(+)-3-bromo-2-methyl-1-propanol in step 1. MS (EI) for $C_9H_{13}BrN_2O_3S$: 310 (MH$^+$).

(2S)-3-[(2-amino-5-bromopyridin-3-yl)sulfinyl]-2-methylpropan-1-ol. Prepared according to the method of reagent preparation 41 by using (S)-(+)-3-bromo-2-methyl-1-propanol in step 1. MS (EI) for $C_9H_{13}BrN_2O_2S$: 294 (MH$^+$).

Reagent Preparation 42

(4-chloro-5,6,7,8-tetrahydroquinazolin-7-yl)methanol

Ozone was bubbled through a cooled (−78° C.) solution of 4-chloro-7-vinyl-5,6,7,8-tetrahydroquinazoline (reagent preparation 3, 0.35 g, 1.8 mmol) in methanol (5 mL) and dichloromethane (30 mL) until a blue color persisted. The solution was then sparged with $N_2$ for 10 minutes and sodium borohydride (0.14 g, 3.6 mmol) was added portionwise. After 30 minutes the reaction mixture was partitioned between dichloromethane and saturated aqueous sodium bicarbonate. The organic layer was washed with brine, dried over magnesium sulfate, filtered and then concentrated in vacuo to provide (4-chloro-5,6,7,8-tetrahydroquinazolin-7-yl)methanol (0.32 g, 90% yield) as a waxy solid. MS (ES) for $C_9H_{11}ClN_2O$: 199 (MH$^+$).

Reagent Example 43

1-(4-chloro-5,6,7,8-tetrahydroquinazolin-7-yl)ethanol

Step 1: Ozone was bubbled through a cooled (−78° C.) solution of 4-chloro-7-vinyl-5,6,7,8-tetrahydroquinazoline (reagent preparation 3, 0.38 g, 2.0 mmol) in dichloromethane (45 mL) until a blue color persisted. The solution was then sparged with $N_2$ for 10 minutes and triphenylphosphine (0.52 g, 2.0 mmol) was added portionwise. After one hour, the reaction mixture was partitioned between dichloromethane and saturated aqueous sodium bicarbonate. The organic layer was washed with brine, dried over magnesium sulfate, filtered and then concentrated in vacuo. Purification by silica gel chromatography provided 4-chloro-5,6,7,8-tetrahydroquinazoline-7-carbaldehyde (0.33 g, 85% yield) as a viscous oil. MS (ES) for $C_9H_9ClN_2O$: 197 (MH$^+$).

Step 2: To a cooled (0° C.) solution of 4-chloro-5,6,7,8-tetrahydroquinazoline-7-carbaldehyde (0.10 g, 0.51 mmol) in THF (5 mL) was added a solution of MeMgBr (3.0 M in ethyl ether, 0.40 mL, 1.2 mmol). The resulting mixture was stirred at ambient temperature for 30 minutes and then partitioned between ethyl acetate and saturated sodium bicarbonate. The organic layer was washed with brine, dried over magnesium sulfate, filtered and concentrated in vacuo. Purification by silica gel chromatography provided 1-(4-chloro-5,6,7,8-tetrahydroquinazolin-7-yl)ethanol (0.09 g, 83% yield) as a waxy solid. MS (ES) for $C_{10}H_{13}ClN_2O$: 213 (MH$^+$).

Reagent Example 44

4-chloro-7-(methoxymethyl)-5,6,7,8-tetrahydroquinazoline

To a slurry of (4-chloro-5,6,7,8-tetrahydroquinazolin-7-yl)methanol (reagent preparation 42, 0.80 g, 0.40 mmol), potassium carbonate (0.11 g, 0.81 mmol) and THF (15 mL) was added iodomethane (0.09 mL, 0.60 mmol). The reaction mixture was stirred for 18 hours and then partitioned between ethyl acetate and water. The organic layer was washed with brine, dried over magnesium sulfate, filtered and concentrated in vacuo. Purification by silica gel chromatography provided 4-chloro-7-(methoxymethyl)-5,6,7,8-tetrahydroquinazoline (0.03 g, 35% yield) as a waxy solid. MS (ES) for $C_{10}H_{13}ClN_2O$: 213 (MH$^+$).

Reagent Preparation 45

2-(azidomethyl)-4-chloro-6,6-dimethyl-5,6,7,8-tetrahydroquinazoline

STEP 1: To a solution of 2-(chloromethyl)-6,6-dimethyl-5,6,7,8-tetrahydroquinazolin-4(3H)-one (150 mg, 0.66 mmol, reagent preparation 17) in DMF (3 mL) was added sodium azide (215 mg, 3.3 mmol). The resulting mixture was stirred at rt for 35 min. Water was added and the resulting mixture was extracted twice with ethyl acetate. The combined organic extracts were washed with aqueous lithium chloride (10%), dried over magnesium sulfate, filtered, and concentrated in vacuo to provide 2-(azidomethyl)-6,6-dimethyl-5,6,7,8-tetrahydroquinazolin-4(3H)-one (151 mg, 0.65 mmol, 98% yield) as a waxy yellow solid. $^1$H NMR (400 MHz, CDCl$_3$) δ 11.70 (br s, 1H), 4.41 (s, 2H), 2.66 (t, 2H), 2.33 (s, 2H), 1.58 (t, 3H), 1.00 (s, 6H); MS (EI) for $C_{11}H_{15}N_5O$: 234 (MH$^+$).

STEP 2: A solution of 2-(azidomethyl)-6,6-dimethyl-5,6,7,8-tetrahydroquinazolin-4(3H)-one (151 mg, 0.65 mmol) in chloroform (1.2 mL) was treated with phosphorus oxychloride (600 uL) at 60° C. for 1 h 20 min. After cooling to rt, the volatile materials were removed in vacuo, and the resulting residue was dissolved in ethyl acetate. The organic solution was washed with saturated aqueous sodium bicarbonate, and the aqueous phase was back extracted with ethyl acetate. The combined organic extracts were dried over magnesium sulfate, filtered, and concentrated in vacuo to provide 2-(azidomethyl)-4-chloro-6,6-dimethyl-5,6,7,8-tetrahydroquinazoline (136 mg, 0.54 mmol, 83% yield) as an orange oil. $^1$H NMR (400 MHz, CDCl$_3$) δ 4.47 (s, 2H), 2.94 (t, 2H), 2.55 (s, 2H), 1.68 (t, 2H), 1.05 (s, 6H); MS (EI) for $C_{11}H_{14}ClN_5$: 252 (MH$^+$).

Reagent Preparation 46

1-(4-chloro-6,6-dimethyl-5,6,7,8-tetrahydroquinazolin-2-yl)-N,N-dimethylethanamine STEP 1: To a solution of dimethylamine (2M solution in tetrahydrofuran, 4.0 mL, 8.0 mmol) was added 2-(1-chloroethyl)-6,6-dimethyl-5,6,7,8-tetrahydroquinazolin-4-ol (synthesized according to the method of reagent preparation 18 using 2-chloropropionitrile in step 1) (50 mg, 0.21 mmol) and the reaction mixture was stirred in a sealed tube for 16 hours at 80° C. After cooling to room temperature the reaction mixture was concentrated and the residue was partitioned between brine (50 mL) and ethyl acetate (50 mL). The organic layer was separated and washed with brine (20 mL), dried over sodium sulfate, filtered and concentrated to give 2-[1-(dimethylamino)ethyl]-6,6-dimethyl-5,6,7,8-tetrahydroquinazolin-4-ol (50 mg, 96%). MS (EI) for $C_{14}H_{23}N_3O$: 250 (MH$^+$).

STEP 2: A solution of 2-[1-(dimethylamino)ethyl]-6,6-dimethyl-5,6,7,8-tetrahydroquinazolin-4-ol (50 mg, 0.20 mmol) in a mixture of chloroform (1.5 mL) and phosphorous oxychloride (0.5 mL) was heated to reflux for 90 minutes. After cooling to room temperature the reaction mixture was concentrated and the residue was partitioned between saturated aqueous sodium bicarbonate (20 mL) and ethyl acetate (20 mL). The mixture was stirred for 15 minutes and pH was maintained above 7 by the addition of solid sodium bicarbonate. The organic layer was separated and washed with water (10 mL) and brine, dried over sodium sulfate, filtered and concentrated to give 1-(4-chloro-6,6-dimethyl-5,6,7,8-tetrahydroquinazolin-2-yl)-N,N-dimethylethanamine (46 mg, 85%). MS (EI) for $C_{14}H_{22}ClN_3$: 268 (MH$^+$).

Using analogous synthetic techniques and substituting with alternative starting materials in step 1 the following reagent was prepared. Alternative starting materials were obtained commercially unless otherwise indicated.

4-chloro-6,6-dimethyl-2-(1-pyrrolidin-1-ylethyl)-5,6,7,8-tetrahydroquinazoline. Prepared according to the method of reagent preparation 46 by using pyrrolidine in step 1. MS (EI) for $C_{16}H_{24}ClN_3$: 294 (MH$^+$).

Reagent Preparation 47 methyl 6-bromo-1H-imidazo[4,5-c]pyridin-2-ylcarbamate

A solution of 2-bromo-5-nitropyridin-4-amine (1.5 g, 6.9 mmol) in acetic acid (20 mL) was added in portions into a 75° C. suspension of iron powder (1.5 g, 27 mmol) in acetic acid (20 mL). The reaction mixture was stirred at 75° C. for 2 h, cooled to room temperature, and filtered through celite. To the filtrate was added 1,3-bis(methoxycarbonyl)-2-methyl-2-thiopseudourea (1.4 g, 6.9 mmol), and the mixture was stirred at 65° C. for 60 h. The reaction mixture was cooled to room temperature and concentrated. The solid residue was triturated with dichloromethane and dried to give the title Compound (1.8 g, quantitative yield) as an orange solid. MS (EI) for $C_8H_7BrN_4O_2$: 271/273 (MH$^+$).

Reagent Preparation 48 tert-butyl 3-(bis(tert-butoxycarbonyl)amino)-5-bromo-1H-indazole-1-carboxylate

To a cooled (0° C.) solution of 5-bromo-1H-indazol-3-amine (0.30 g, 1.4 mmol), DIPEA (2.5 mL, 14 mmol) and di-tert-butyl dicarbonate (1.5 g, 7.0 mmol) in THF (15 mL) was added DMAP (0.09 g, 0.70 mmol). The reaction mixture was then stirred at ambient temperature for three hours. The resulting solution was diluted with ethyl acetate (75 mL) and washed with saturated aqueous ammonium chloride (2×50 mL). The organic layer was washed with brine, dried over magnesium sulfate, filtered and concentrated in vacuo. Purification by silica gel chromatography provided tert-butyl 3-(bis(tert-butoxycarbonyl)amino)-5-bromo-1H-indazole-1-carboxylate (0.44 g, 61%) as a waxy solid. $^1$H NMR (400 MHz, CDCl$_3$) δ 8.04 (t, 1H), 7.68 (dd, 1H), 7.66-7.58 (m, 1H), 1.53 (s, 18H), 1.43 (s, 9H); MS (EI) for $C_{22}H_{30}BrN_3O_6$: 512 (MH$^+$).

Reagent Preparation 49

6-chloro-N-phenylpyrimidine-4-amine

STEP 1: 6-Chloropyrimidin-4-ol (500 mg, 3.85 mmol), aniline (420 µL, 4.62 mmol) and N,N-diisopropylethylamine (1 mL) in diethylene glycol dimethyl ether (5 mL) was heated to 120° C. and stirred for 8 h. The mixture was cooled to room temperature then diluted with actone:diethyl ether solution (1:1, 15 ml) to give a precipitate. The solid collected by filtration and washed with acetone then dried to afford 6-(phenylamino)pyrimidin-4-ol (255 mg, 35.5%). MS (EI) for $C_{10}H_9N_3O$: 188.2 (MH$^+$).

STEP 2: 6-(Phenylamino)pyrimidin-4-ol (253 mg, 1.35 mmol) was dissolved in neat phosphorous oxychloride (5 mL) and stirred for 3 h at 95° C. then cooled to room temperature and concentrated. The residue was poured into an ice water slurry and extracted with dichloromethane. The extract was washed saturated aqueous sodium bicarbonate solution, dried over sodium sulfate, filtered and the solvent evaporated to afford 6-chloro-N-phenylpyrimidine-4-amine (220 mg) which was used without further purification.

Using analogous synthetic techniques and substituting with alternative starting reagents in step 1 the following reagents were prepared.

6-Chloro-N-(4-methoxyphenyl)pyrimidin-4-amine. Synthesized according to the method of reagent preparation 49 using 4-methoxyaniline in step 1.

6-Chloro-N-(3-methoxyphenyl)pyrimidin-4-amine. Synthesized according to the method of reagent preparation 49 using 3-methoxyaniline in step 1.

6-Chloro-N-(4-methoxyphenyl)-5-methylpyrimidin-4-amine. Synthesized according to the method of reagent preparation 49 using 6-chloro-5-methylpyrimidin-4-ol and 4-methoxyaniline in step 1.

6-Chloro-5-methyl-N-phenylpyrimidin-4-amine. Synthesized according to the method of reagent preparation 49 using 6-chloro-5-methylpyrimidin-4-ol and aniline in step 1.

Reagent Preparation 50

5-(4,4,5,5-tetramethyl-1,3,2-dioxaborolan-2-yl)-1-methyl-1H-indazole

STEP 1: A suspension of 5-bromo-1H-indazole (200 mg, 1.02 mmol), cesium carbonate (661 mg, 2.00 mmol), and iodomethane (156 mg, 1.10 mmol) in dimethylformamide (3 mL) was stirred at room temperature for 15 h. The mixture was partitioned between 5% lithium chloride and ethyl acetate, the aqueous layer was extracted with ethyl acetate (2×), the combined organic extracts were washed with 1 N sodium hydroxide, and brine, dried over anhydrous sodium sulfate, filtered and concentrated. Column chromatography on silica (hexanes/ethyl acetate 4:1) gave 5-bromo-1-methyl-1H-indazole (150 mg, 70% yield) as an orange solid. MS (EI) for $C_8H_7BrN_2$: 212 (MH$^+$).

STEP 2: A suspension of 5-bromo-1-methyl-1H-indazole (150 mg, 0.71 mmol), bis(pinacolato)diboron (200 mg, 0.78 mmol), potassium acetate (206 mg, 2.10 mmol), and dichloro [1,1-bis(diphenylphosphino]ferrocenepalladium (II) dichloromethane adduct (36 mg, 0.04 mmol) in dimethyl sulfoxide (4 mL) was degassed with nitrogen, and then stirred at 80° C. for 18 h. The reaction mixture was cooled to room temperature and partitioned between water and ethyl acetate. The mixture was filtered through celite and then the layers were separated. The aqueous layer was extracted with ethyl acetate (2×), the combined organic extracts were washed with brine, dried over anhydrous sodium sulfate, filtered and concentrated. Column chromatography on silica (hexanes/ethyl acetate 7:3) provided 5-(4,4,5,5-tetramethyl-1,3,2-dioxaborolan-2-yl)-1-methyl-1H-indazole (158 mg, 86% yield) as a yellow oil. MS (EI) for $C_{14}H_{19}BN_2O_2$: 259 (MH$^+$).

Reagent Preparation 51

1,1-dimethylethyl 7-bromo-2,3-dihydro-1,4-benzoxazepine-4(5H)-carboxylate

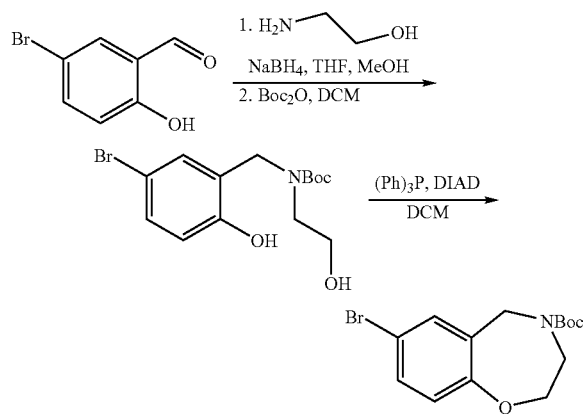

STEP 1: Commercially-available 5-bromo-2-hydroxybenzaldehyde (4.0 g, 10 mmol) and 2-aminoethanol were combined in THF/MeOH (100 mL, 10:1) and sodium borohydride (0.76 g, 2.0 mmol) was added with stirring. The resulting reaction mixture was stirred at 40° C. for 4 h, concentrated on a rotary evaporator then diluted with EtOAc (50 mL) and saturated NaHCO$_3$ (30 mL). To this suspension was added di-tert-butyl dicarbonate (2.83 g, 13 mmol). The mixture was stirred at rt overnight. The organic layer was washed with water, dried over anhydrous magnesium sulfate, filtered, and concentrated on a rotary evaporator. Hexane was subsequently added to the crude reaction product which resulted in the formation of a white solid. This slurry was filtered to obtain tert-butyl-5-bromo-2-hydroxybenzyl(2-hydroxyethyl)carbamate (6.8 g, 98%) as a white solid. MS (EI) for $C_{14}H_{20}BrNO_4$, found 346 (MH$^+$).

STEP 2: tert-Butyl-5-bromo-2-hydroxybenzyl(2-hydroxyethyl)carbamate (3.46 g, 10 mmol) and triphenylphosphine (3.96 g, 15 mmol) were combined in DCM (100 mL) and diisopropyl azodicarboxylate (3.03 g, 15 mmol) was added. The resulting reaction mixture was stirred at rt for 12 h. The reaction mixture was washed with water, dried, filtered, and concentrated on a rotary evaporator. The resulting crude product was purified via silica gel chromatography eluting with 8:2 hexane/ethyl acetate to give the desired product (1.74 g, 53%) as a white solid. MS (EI) for $C_{14}H_{18}BrNO_3$, found 328 (MH$^+$).

Example 1

4-{3-[(3-fluorophenyl)methyl]-2-methylpyridin-4-yl}-7-(2-methyl-1H-benzimidazol-6-yl)-2,3,4,5-tetrahydro-1,4-benzoxazepine STEP 1: To 5-bromo-2-methylbenzimidazole (38 g, 180 mmol) in THF (400 mL) was added di-tert-butyl dicarbonate (39 g, 189 mmol). The reaction mixture was stirred at room temperature for 24 h and then concentrated. Ethyl acetate (400 mL) was added to the residue, and the solution was washed with 10% aqueous citric acid (2×100 mL), water (100 mL), and brine (100 mL), dried over sodium sulfate, and concentrated. Column chromatography on silica (gradient 20-30% ethyl acetate in hexane) provided 1,1-dimethylethyl 6-bromo-2-methyl-1H-benzimidazole-1-carboxylate (27 g, 48% yield) as a beige solid. MS (EI) for $C_{13}H_{15}BrN_2O_2$: 312 (MH$^+$).

STEP 2: A solution of 1,1-dimethylethyl 7-bromo-2,3-dihydro-1,4-benzoxazepine-4(5H)-carboxylate (30.0 g, 91.4 mmol) and triisopropyl borate (22.4 g, 119 mmol) in THF (300 mL) was cooled to −78° C., and a 2.5 M solution of n-butyllithium in hexanes (47.6 mL, 119 mmol) was added dropwise over 40 min at this temperature. The reaction mixture was stirred at −78° C. for an additional 30 min, then quenched by dropwise addition of 2 N hydrochloric acid (80 ml), and allowed to warm up to room temperature. Ethyl acetate (100 mL) and water (100 mL) were added, the organic layer was separated, and the aqueous layer was extracted with ethyl acetate (100 mL). The combined organic layers were washed with water, dried over sodium sulfate, and concentrated. Hexane (200 mL) was added to the residue and the mixture was stirred overnight. The precipitate was filtered, washed several times with hexane, and dried to give (4-{[(1, 1-dimethylethyl)oxy]carbonyl}-2,3,4,5-tetrahydro-1,4-benzoxazepin-7-yl)boronic acid (23.4 g, 87%) as a colorless solid. MS (EI) for $C_{14}H_{20}BNO_5$: 294 (MH$^+$).

STEP 3: A suspension of 1,1-dimethylethyl 6-bromo-2-methyl-1H-benzimidazole-1-carboxylate (11.3 g, 36 mmol), (4-{[(1,1-dimethylethyl)oxy]carbonyl}-2,3,4,5-tetrahydro-1,4-benzoxazepin-7-yl)boronic acid (11.7 g, 40 mmol), dichloro[1,1-bis(diphenyl-phosphino]ferrocenepalladium (II) dichloromethane adduct (3.0 g, 10 mol %) in dioxane (115 mL) and water (28.5 mL) was degassed with nitrogen, and then diisopropylethylamine (18.6 g, 144 mmol) was added. The reaction mixture was stirred at 90° C. for 220 min, cooled to room temperature, and concentrated. Column chromatography on silica of the residue (gradient 25-30% ethyl acetate in hexane) afforded 1,1-dimethylethyl 7-(1-{[(1,1-dimethylethyl)oxy]carbonyl}-2-methyl-1H-benzimidazol-6-yl)-2,3-dihydro-1,4-benzoxazepine-4(5H)-carboxylate (13.2 g, 76% yield) as an amorphous solid. MS (EI) for $C_{27}H_{33}N_3O_5$: 480 (MH$^+$).

STEP 4: A solution of 1,1-dimethylethyl 7-(1-{[(1,1-dimethylethyl)oxy]carbonyl}-2-methyl-1H-benzimidazol-6-yl)-2,3-dihydro-1,4-benzoxazepine-4(5H)-carboxylate (13.1 g, 27 mmol) in a mixture of methanol (20 mL) and 4 N hydrogen chloride in dioxane (30 mL) was refluxed for 15 min. After cooling to room temperature ethyl ether (100 mL) was added, and the reaction mixture was concentrated. Another portion of ethyl ether (100 mL) was added, the precipitate was filtered off, washed several times with ethyl ether, and dried to give 7-(2-methyl-1H-benzimidazol-6-yl)-2,3,4,5-tetrahydro-1,4-benzoxazepine dihydrochloride (8.9 g, 93% yield) as a light beige solid. $^1$HNMR (400 MHz, CD$_3$OD): 7.93 (s, 1H), 7.86-

7.67 (m, 4H), 7.28 (s, 1H), 4.54 (s, 2H), 4.33-4.23 (m, 2H), 3.65-3.54 (m, 2H), 2.91 (s, 3H); MS (EI) for $C_{17}H_{17}N_3O$: 280 (MH$^+$).

STEP 5: A mixture of 4-chloro-3-[(3-fluorophenyl)methyl]-2-methylpyridine (42 mg, 0.178 mmol) synthesized according to reagent preparation 9,7-(2-methyl-1H-benzimidazol-6-yl)-2,3,4,5-tetrahydro-1,4-benzoxazepine hydrochloride (94 mg, 0.267 mmol), and n-tributylamine (0.3 mL, 1.2 mmol) in a minimal amount of n-butanol to form a solution, was stirred in a sealed tube at 180° C. for 6 d. The reaction mixture was then cooled to ambient temperature and diluted with water (5 mL) and the aqueous layer was extracted with ethyl acetate (3×7 mL). The combined organic layers were dried over sodium sulfate, and concentrated. The residue was taken up in methanol and purified by preparative reverse phase HPLC to afford 4-{3-[(3-fluorophenyl)methyl]-2-methylpyridin-4-yl}-7-(2-methyl-1H-benzimidazol-6-yl)-2,3,4,5-tetrahydro-1,4-benzoxazepine (20 mg, 23% yield). $^1$H NMR (400 MHz, CD$_3$OD): 8.22 (d, 1H), 7.50-7.47 (m, 3H), 7.22-7.15 (m, 3H), 7.02 (d, 1H), 6.94-6.89 (m, 1H), 6.83 (d, 1H), 6.77-6.75 (m, 4H), 4.27 (s, 2H), 4.25-4.22 (m, 2H), 4.18 (s, 2H), 3.60-3.57 (m, 2H), 2.59 (s, 3H), 2.29 (s, 3H). MS (EI) for $C_{30}H_{27}FN_4O$: 479.2 (MH$^+$).

Using analogous synthetic techniques and substituting with alternative starting reagents in step 5 the following compounds of the invention were prepared. Protecting group introduction and removal steps were conducted as required according to literature techniques appropriate for a given protecting group (see for example: Greene and Wuts, Protective Groups in Organic Synthetic, Wiley-Interscience). Alternative starting materials were obtained commercially unless otherwise indicated.

7-(2-methyl-1H-benzimidazol-6-yl)-2,3,4,5-tetrahydro-1,4-benzoxazepine: Prepared as the dihydrochloride salt according to the method of example 1 using 4-chloroquinazoline in step 5. $^1$H NMR (400 MHz, d$_6$-DMSO): 8.82 (s, 1H), 8.28 (d, 1H), 8.06-7.70 (m, 7H), 7.61 (dd, 1H), 7.02 (d, 1H), 5.46 (s, 2H), 4.66-4.61 (m, 2H), 4.56-4.49 (m, 2H), 2.81 (s, 3H); MS (EI) for $C_{25}H_{21}N_5O$: 408 (MH$^+$).

7-(2-methyl-1H-benzimidazol-6-yl)-4-pyrimidin-4-yl-2,3,4,5-tetrahydro-1,4-benzoxazepine: Prepared according to the method of example 1 using 4-chloropyrimidine in step 5. $^1$H NMR (400 MHz, d$_6$-DMSO): 12.25 (d, 1H), 8.49 (s, 1H), 8.17 (dd, 1H), 7.85 (br s, 1H), 7.74 (s, 1H), 7.58-7.35 (m, 3H), 7.08-7.00 (m, 2H), 4.87 (br s, 2H), 4.15 (br s, 4H), 3.34 (s, 3H); MS (EI) for $C_{21}H_{19}N_5O$: 358 (MH$^+$).

4-(7-iodoquinazolin-4-yl)-7-(2-methyl-1H-benzimidazol-6-yl)-2,3,4,5-tetrahydro-1,4-benzoxazepine: Prepared according to the method of example 1 using 4-chloro-7-iodoquinazoline in step 5. $^1$H NMR (400 MHz, CDCl$_3$): 8.67 (s, 1H), 8.31 (s, 1H), 7.71-7.65 (m, 3H), 7.62 (d, 1H), 7.53-7.49 (m, 2H), 7.44 (dd, 1H), 7.13 (d, 1H), 4.95 (s, 2H), 4.47-4.42 (m, 2H), 4.26-4.21 (m, 2H), 2.68 (s, 3H); MS (EI) for $C_{25}H_{20}IN_5O$: 534 (MH$^+$).

7-(2-methyl-1H-benzimidazol-6-yl)-4-(2-methylquinazolin-4-yl)-2,3,4,5-tetrahydro-1,4-benzoxazepine: Prepared according to the method of example 1 using 4-chloro-2-methylquinazoline in step 5. $^1$H NMR (400 MHz, d$_6$-DMSO): 12.26 (br s, 1H), 8.02 (d, 1H), 7.78-7.38 (m, 7H), 7.02 (d, 1H), 5.05 (br s, 2H), 4.44 (m, 2H), 4.20 (m, 2H), 3.34 (s, 3H), 2.48 (s, 3H); MS (EI) for $C_{26}H_{23}N_5O$: 422 (MH$^+$).

ethyl 4-[7-(2-methyl-1H-benzimidazol-6-yl)-2,3-dihydro-1,4-benzoxazepin-4(5H)-yl]quinazoline-2-carboxylate: Prepared as the dihydrochloride salt according to the method of example 1 using ethyl-4-chloro-2-quinazoline carboxylate in step 5. $^1$H NMR (400 MHz, d$_6$-DMSO): 8.24 (d, 1H), 8.04-7.94 (m, 3H), 7.89-7.81 (m, 3H), 7.74-7.68 (m, 1H), 7.60 (dd, 1H), 7.04 (d, 1H), 5.30 (s, 2H), 4.58-4.51 (m, 2H), 4.49-4.42 (m, 2H), 4.26 (q, 2H), 2.84 (s, 3H), 1.11 (t, 3H); MS (EI) for $C_{28}H_{25}N_5O_3$: 480 (MH$^+$).

N,N-diethyl-4-[7-(2-methyl-1H-benzimidazol-6-yl)-2,3-dihydro-1,4-benzoxazepin-4(5H)-yl]quinazolin-2-amine: Prepared as the dihydrochloride salt according to the method of example 1 by sequential use of 2,4-dichloroquinazoline and N,N-diethylamine in step 5. $^1$H NMR (400 MHz, d$_6$-DMSO): 12.1 (br s, 1H), 8.11 (br d, 1H), 8.07 (d, 1H), 7.92 (s, 1H), 7.87-7.82 (m, 3H), 7.79 (td, 1H), 7.59 (dd, 1H), 7.43 (br t, 1H), 6.99 (d, 1H), 5.30 (s, 2H), 4.64-4.58 (m, 2H), 4.45 (br s, 2H), 3.58 (br s, 4H), 2.83 (s, 3H), 1.34-0.68 (m, 6H); MS (EI) for $C_{29}H_{30}N_6O$: 479.2 (MH$^+$).

4-(2,6-diphenylpyrimidin-4-yl)-7-(2-methyl-1H-benzimidazol-6-yl)-2,3,4,5-tetrahydro-1,4-benzoxazepine: Prepared as the dihydrochloride salt according to the method of example 1 using 4-chloro-2,6-diphenylpyrimidine in step 5. $^1$H NMR (400 MHz, d$_6$-DMSO): 8.62-8.37 (m, 2H), 8.29-8.22 (m, 2.5H), 8.11-8.00 (m, 0.5H), 7.96 (d, 1H), 7.89-7.66 (m, 2H), 7.61-7.49 (m, 7.5H), 7.42-7.32 (m, 0.5H), 7.10 (d, 1H), 5.27-5.05 (m, 2H), 4.49 (br s, 1H), 4.29 (br s, 3H), 2.83 (s, 3H); MS (EI) for $C_{33}H_{27}N_5O$: 510.3 (MH$^+$).

7-(2-methyl-1H-benzimidazol-6-yl)-4-quinolin-4-yl-2,3,4,5-tetrahydro-1,4-benzoxazepine: Prepared as the dihydrochloride salt according to the method of example 1 using 4-chloroquinoline in step 5. $^1$H NMR (400 MHz, d$_6$-DMSO): 8.57 (d, 1H), 8.32 (d, 1H), 8.10-7.96 (m, 4H), 7.89-7.84 (m, 2H), 7.72-7.64 (m, 2H), 7.03 (d, 1H), 6.98 (d, 1H), 5.32 (s, 2H), 4.65-4.62 (m, 2H), 4.43-4.39 (m, 2H), 2.84 (s, 3H); MS (EI) for $C_{26}H_{22}N_4O$: 407 (MH$^+$).

7-(2-methyl-1H-benzimidazol-6-yl)-4-[2-(trifluoromethyl)quinolin-4-yl]-2,3,4,5-tetrahydro-1,4-benzoxazepine: Prepared according to the method of example 1 using 4-chloro-2-(trifluoromethyl)quinoline in step 5. $^1$H NMR (400 MHz, d$_6$-DMSO): 12.30 (br s, 1H), 8.05-8.15 (m, 2H), 7.75-7.85 (m, 2H), 7.40-7.66 (m, 5H), 7.28 (s, 1H), 7.05-7.10 (d, 1H), 4.85 (s, 2H), 4.40-4.45 (m, 2H), 3.98-4.05 (m, 2H), 3.36 (s, 3H). MS (EI) for $C_{27}H_{21}F_3N_4O$: 475 (M+H), 473 (M–H).

7-(2-methyl-1H-benzimidazol-6-yl)-4-(2-phenylquinolin-4-yl)-2,3,4,5-tetrahydro-1,4-benzoxazepine: Prepared according to the method of example 1 using 4-chloro-2-phenylquinoline in step 5. $^1$H NMR (400 MHz, d$_6$-DMSO): 12.35-12.21 (m, 1H), 8.17-8.10 (m, 2H), 8.07-7.98 (m, 2H), 7.92-7.65 (m, 3H), 7.62-7.41 (m, 8H), 7.07 (d, 1H), 4.80 (s, 2H), 4.40-4.33 (m, 2H), 4.05-3.95 (m, 2H), 2.52 (s, 3H). MS (EI) for $C_{32}H_{26}N_4O$: 483 (MH$^+$).

7-(2-methyl-1H-benzimidazol-6-yl)-4-pyridin-2-yl-2,3,4,5-tetrahydro-1,4-benzoxazepine: Prepared according to the methods of example 1 using 2-chloropyridine in step 5. $^1$H NMR (400 MHz, CD$_3$OD): 8.04-8.08 (m, 1H), 7.67 (d, 1H), 7.54-7.38 (m, 4H), 7.01 (d, 1H), 6.89 (d, 1H), 6.57-6.53 (m, 1H), 4.81 (s, 2H), 4.14 (s, 4H), 2.58 (s, 3H); MS (EI) for $C_{22}H_{20}N_4O$: 357 (MH$^+$).

4-isoquinolin-1-yl-7-(2-methyl-1H-benzimidazol-6-yl)-2,3,4,5-tetrahydro-1,4-benzoxazepine: Prepared according to the method of example 1 using 1-chloroisoquinoline in step 5. $^1$H NMR (400 MHz, CD$_3$OD): 8.15 (d, 1H), 8.03 (d, 1H), 7.84 (d, 1H), 7.71 (d, 1H), 7.69 (td, 1H), 7.61-7.49 (m, 5H), 7.35 (d, 1H), 7.15 (d, 1H), 4.63 (s, 2H), 4.43-4.40 (m, 2H), 3.92-3.88 (m, 2H), 2.66 (s, 3H); MS (EI) for $C_{26}H_{22}N_4O$: 407 (MH$^+$).

7-(2-methyl-1H-benzimidazol-6-yl)-4-pyrimidin-2-yl-2,3,4,5-tetrahydro-1,4-benzoxazepine: Prepared according to the method of example 1 using 2-chloropyrimidine in step 5. $^1$H NMR (400 MHz, CD$_3$OD): 8.22 (d, 2H), 7.56-7.53 (m, 2H), 7.42 (d, 1H), 7.32 (dt, 2H), 6.93 (d, 1H), 6.46 (t, 1H), 4.86 (s, 2H), 4.18-4.14 (m, 2H), 4.06-4.02 (m, 2H), 2.49 (s, 3H); MS (EI) for $C_{21}H_{19}N_5O$: 358 (MH$^+$).

4-[7,8-bis(methyloxy)quinazolin-4-yl]-7-(2-methyl-1H-benzimidazol-6-yl)-2,3,4,5-tetrahydro-1,4-benzoxazepine. Synthesized according to the method of example 1 using 4-chloro-7,8-dimethoxy-quinazoline (reagent preparation 1) in step 5. $^1$H NMR (400 MHz, d$_6$-DMSO): 8.45 (d, 1H), 7.80 (d, 1H), 7.68 (m, 1H), 7.53 (m, 2H), 7.41 (d, 1H) 7.37 (d, 1H), 7.02 (d, 1H), 5.08 (s, 2H), 4.48 (br s, 3H), 4.20 (br s, 2H), 3.93 (s, 3H), 3.86 (s, 3H), 1.78 (s, 3H); MS (EI) for $C_{27}H_{25}N_5O_3$: 468 (MH$^+$).

7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine. Synthesized according to the method of example 1 using 7-(benzyloxy)-4-chloro-8-methoxyquinazoline (reagent preparation 1) in step 5. $^1$H NMR (400 MHz, d$_6$-DMSO): 8.47 (s, 1H), 7.75 (d, 1H), 7.65 (m, 2H), 7.53 (m, 4H), 7.40 (m, 4H), 7.33 (m, 1H), 7.02 (d, 2H), 5.36 (s, 2H), 5.36 (br s, 2H), 5.08 (s, 2H), 4.48 (br s, 2H), 4.18 (br s, 2H), 3.91 (s, 3H); MS (EI) for $C_{33}H_{29}N_5O_3$: 544 (MH$^+$).

4-[6-chloro-7,8-bis(methyloxy)quinazolin-4-yl]-7-(2-methyl-1H-benzimidazol-6-yl)-2,3,4,5-tetrahydro-1,4-benzoxazepine. Synthesized according to the method of example 1 using 4,6-dichloro-7,8-dimethoxyquinazoline (reagent preparation 1) in step 5. $^1$H NMR (400 MHz, d$_6$-DMSO): 8.55 (s, 1H), 7.83 (s, 1H), 7.74 (d, 1H), 7.53 (dd, 2H), 7.46 (m, 1), 7.04 (d, 1H), 5.02 (s, 2H), 4.48 (br s, 3H), 4.14 (br s, 2H), 4.06 (s, 3H), 4.00 (s, 3H); MS (EI) for $C_{27}H_{24}ClN_5O_3$: 502 (MH$^+$).

7-(2-methyl-1H-benzimidazol-6-yl)-4-[6,7,8-tris(methyloxy)quinazolin-4-yl]-2,3,4,5-tetrahydro-1,4-benzoxazepine. Synthesized according to the method of example 1 using 4-chloro-6,7,8-trimethoxyquinazoline in step 5. $^1$H NMR (400 MHz, d$_6$-DMSO): 8.68 (s, 1H), 7.93 (m, 2H), 7.83 (q, 2H), 7.63 (d, 1H), 7.26 (m, 1), 7.04 (d, 1H), 5.42 (s, 2H), 4.66 (br s, 3H) 4.40 (br s, 2H), 3.96 (s, 6H), 2.82 (s, 3H), 2.51 (s, 3H); MS (EI) for $C_{28}H_{27}N_5O_4$: 498 (MH$^+$).

7-(2-methyl-1H-benzimidazol-6-yl)-4-[6-methyl-2-(methylthio)-6,7-dihydro-5H-cyclopenta[d]pyrimidin-4-yl]-2,3,4,5-tetrahydro-1,4-benzoxazepine. Synthesized according to the method of example 1 using 4-chloro-6-methyl-2-(methylthio)-6,7-dihydro-5H-cyclopenta[d]pyrimidine (reagent preparation 4) in step 5. $^1$H NMR (400 MHz, d$_6$-DMSO): 7.93 (br s, 2H), 7.84 (d, 1H), 7.73 (m, 2H), 7.57 (dd, 1) 7.06 (d, 1H), 5.01 (s, 2H), 4.30 (br s, 2H) 4.16 (s, 2H), 3.21 (dd, 1H), 2.81 (s, 3H), 2.71 (dd, 1H), 2.64 (dd, 1H), 2.35 (dd, 1H); MS (EI) for $C_{26}H_{27}N_5OS$: 458 (MH$^+$).

4-(5,7-dihydrothieno[3,4-d]pyrimidin-4-yl)-7-(2-methyl-1H-benzimidazol-6-yl)-2,3,4,5-tetrahydro-1,4-benzoxazepine. Synthesized according to the method of example 1 using 4-chloro-5,7-dihydrothieno[3,4-d]pyrimidine in step 5. $^1$H NMR (400 MHz, d$_6$-DMSO): 8.42 (s, 1H), 7.93 (s, 1H), 7.84 (d, 1H), 7.78 (m, 2H), 7.58 (d, 1H), 7.08 (d, 1H), 5.03 (s, 2H), 4.42 (s, 2H) 4.37 (br s, 2H), 4.18 (br s, 2H), 4.07 (s, 2H), 2.80 (s, 3H); MS (EI) for $C_{23}H_{21}N_5OS$: 416 (MH$^+$).

7-(2-methyl-1H-benzimidazol-6-yl)-4-(6-methyl-6,7-dihydro-5H-cyclopenta[d]pyrimidin-4-yl)-2,3,4,5-tetrahydro-1,4-benzoxazepine. Synthesized according to the method of example 1 using 4-chloro-6-methyl-6,7-dihydro-5H-cyclopenta[d]pyrimidine (reagent preparation 3) in step 5. $^1$H NMR (400 MHz, d$_6$-DMSO): 8.10 (s, 1H), 7.89 (s, 1H), 7.80 (d, 1H), 7.73 (m, 2H), 7.56 (dd, 1H), 7.07 (d, 1H), 5.12 (m, 2H), 4.37 (br s, 2H) 4.26 (br s, 2H), 3.32 (dd, 1H), 3.01 (q, 1H), 2.80 (m, 1H), 2.75 (s, 3H), 1.07 (d, 3H); MS (EI) for $C_{25}H_{25}N_5O$: 412 (MH$^+$).

4-(6-cyclopropyl-6,7-dihydro-5H-pyrrolo[3,4-d]pyrimidin-4-yl)-7-(2-methyl-1H-benzimidazol-6-yl)-2,3,4,5-tetrahydro-1,4-benzoxazepine. Synthesized according to the method of example 1 using 4-chloro-6-cyclopropyl-6,7-dihydro-5H-pyrrolo[3,4-d]pyrimidine (reagent preparation 3) in step 5. $^1$H NMR (400 MHz, d$_6$-DMSO): 8.63 (s, 1H), 7.81 (s, 1H), 7.78 (d, 1H), 7.62 (m, 2H), 7.47 (d, 1H), 7.12 (d, 1H), 5.00 (br s, 2H), 4.90 (s, 2H), 4.51 (s, 2H), 4.33 (br s, 2H), 4.22 (br s, 2H), 3.42 (m, 1H), 2.87 (s, 3H), 0.83 (m, 4H); MS (EI) for $C_{26}H_{26}N_6O$: 439 (MH$^+$).

7-(2-methyl-1H-benzimidazol-6-yl)-4-[6-(4-methylphenyl)-6,7-dihydro-5H-pyrrolo[3,4-d]pyrimidin-4-yl]-2,3,4,5-tetrahydro-1,4-benzoxazepine. Synthesized according to the method of example 1 using 4-chloro-6-p-tolyl-6,7-dihydro-5H-pyrrolo[3,4-c]pyrimidine (reagent preparation 3) in step 5. $^1$H NMR (400 MHz, d$_6$-DMSO): 8.47 (m, 2H), 7.89 (d, 2H), 7.77 (m, 3H), 7.67 (d, 1H), 7.59 (d, 1H), 7.44 (d, 1H), 7.07 (d, 1H), 5.54 (s, 2H), 4.61 (m, 4H), 7.87 (s, 3H), 2.38 (m, 4H); MS (EI) for $C_{30}H_{28}N_6O$: 489 (MH$^+$).

4-[2-chloro-6-(methyloxy)quinazolin-4-yl]-7-(2-methyl-1H-benzimidazol-6-yl)-2,3,4,5-tetrahydro-1,4-benzoxazepine. Synthesized according to the method of example 1 using 2,4-dichloro-6-methoxyquinazoline in step 5. $^1$H NMR (400 MHz, d$_6$-DMSO): 7.97 (s, 1H), 7.93 (d, 1H), 7.86 (d, 1H), 7.83 (dd, 1H), 7.68 (d, 1H), 7.63 (dd, 1H), 7.48 (dd, 1H), 7.20 (d, 1H), 7.09 (d, 1H), 5.14 (s, 2H), 4.53 (m, 2H), 4.22 (m, 1H), 3.60 (s, 3H), 2.82 (s, 3H). MS (EI) for $C_{26}H_{22}ClN_5O_2$: 472 (MH$^+$).

4-[6-chloro-7-(methyloxy)quinazolin-4-yl]-7-(2-methyl-1H-benzimidazol-6-yl)-2,3,4,5-tetrahydro-1,4-benzoxazepine. Synthesized according to the method of example 1 using 4,6-dichloro-7-methoxy-quinazoline (reagent preparation 1) in step 5. $^1$H NMR (400 MHz, d$_6$-DMSO): 8.74 (s, 1H), 8.20 (s, 1H), 8.02 (s, 1H), 7.92 (d, 1H), 7.86 (s, 2H), 7.64 (dd, 1H), 7.38 (s, 1H), 7.06 (d, 1H), 5.34 (s, 2H), 4.62 (m, 2H), 4.38 (m, 2H), 4.06 (s, 3H), 2.81 (s, 3H). MS (EI) for $C_{26}H_{22}ClN_5O_2$: 472 (MH$^+$).

7-(2-methyl-1H-benzimidazol-6-yl)-4-thieno[2,3-c]pyrimidin-4-yl-2,3,4,5-tetrahydro-1,4-benzoxazepine. Synthesized according to the method of example 1 using 4-chlorothieno[2,3-d]pyrimidine in step 5. $^1$H NMR (400 MHz, d$_6$-DMSO): 8.38 (s, 1H), 7.78 (d, 1H), 7.72 (d, 1H), 7.66 (d, 1H), 7.62 (br s, 1H), 7.51 (br s, 0.5H), 7.49 (br s, 0.5H), 7.46 (dd, 1H), 7.36 (dd, 1H), 6.99 (d, 1H), 5.24 (s, 2H), 4.42 (m, 2H), 4.32 (m, 2H), 2.50 (s, 3H). MS (EI) for $C_{23}H_{20}N_5OS$: 414 (MH$^+$).

7-(2-methyl-1H-benzimidazol-6-yl)-4-(5,6,7,8-tetrahydroquinazolin-4-yl)-2,3,4,5-tetrahydro-1,4-benzoxazepine. Synthesized according to the method of example 1 using 4-chloro-5,6,7,8-tetrahydroquinazoline (reagent preparation 5) in step 5. $^1$H NMR (400 MHz, d$_6$-DMSO): 8.68 (s, 1H), 7.95 (d, 1H), 7.86 (s, 0.5H), 7.83 (s, 0.5H), 7.80-7.76 (m, 2H), 7.59 (dd, 1H), 7.05 (d, 1H), 5.12 (s, 2H), 4.48 (m, 2H), 4.21 (m, 2H), 2.82 (s, 3H), 2.76 (m, 2H), 1.78 (m, 2H), 1.62 (m, 2H). MS (EI) for $C_{25}H_{25}N_5O$: 412 (MH$^+$).

7-(2-methyl-1H-benzimidazol-6-yl)-4-(5-methylthieno[2,3-d]pyrimidin-4-yl)-2,3,4,5-tetrahydro-1,4-benzoxazepine. Synthesized according to the method of example 1 using 4-chloro-5-methylthieno[2,3-d]pyrimidine in step 5. $^1$H NMR (400 MHz, d$_6$-DMSO): 8.38 (s, 1H), 7.94 (d, 1H), 7.84 (d, 0.5H), 7.82 (d, 0.5H), 7.79 (d, 0.5H), 7.77 (d, 0.5H), 7.73 (d, 1H), 7.57 (dd, 1H), 7.41 (d, 1H), 7.15 (d, 1H), 4.88 (s, 2H), 4.31 (m, 2H), 3.96 (m, 2H), 2.81 (s, 3H), 2.55 (d, 3H). MS (EI) for $C_{24}H_{21}N_5OS$: 428 (MH$^+$).

4-[7-(2-methyl-1H-benzimidazol-6-yl)-2,3-dihydro-1,4-benzoxazepin-4(5H)-yl]-6,7,8,9-tetrahydropyrimido[4,5-b]indolizine-10-carbonitrile. Synthesized according to the method of example 1 using 4-chloro-6,7,8,9-tetrahydropyrimido[4,5-b]indolizine-10-carbonitrile in step 5. $^1$H NMR (400 MHz, d$_6$-DMSO): 8.44 (s, 1H), 7.66 (d, 1H), 7.62 (m, 1H), 7.51 (dd, 1H), 7.46 (m, 1H), 7.36 (dd, 1H), 7.05 (d, 1H), 4.40 (s, 2H), 4.37 (m, 2H), 4.31 (m, 2H), 3.84 (m, 2H), 3.14 (m, 2H), 2.50 (s, 3H). MS (EI) for C$_{28}$H$_{25}$N$_7$O: 476 (MH$^+$).

7-(2-methyl-1H-benzimidazol-6-yl)-4-(1H-pyrazolo[3,4-d]pyrimidin-4-yl)-2,3,4,5-tetrahydro-1,4-benzoxazepine. Synthesized according to the method of example 1 using 4-chloro-1H-pyrazolo[3,4-d]pyrimidine in step 5. $^1$H NMR (400 MHz, d$_6$-DMSO): 8.30 (br s, 1H), 7.92 (s, 1H), 7.85 (d, 1H), 7.76 (dd, 1H), 7.56 (dd, 1H), 7.06 (d, 1H), 5.31 (s, 2H), 4.42 (br s, 4H), 2.80 (s, 3H). MS (EI) for C$_{22}$H$_{19}$N$_7$O: 398 (MH$^+$).

7-(2-methyl-1H-benzimidazol-6-yl)-4-[7-(phenylmethyl)-5,6,7,8-tetrahydropyrido[3,4-d]pyrimidin-4-yl]-2,3,4,5-tetrahydro-1,4-benzoxazepine. Synthesized according to the method of example 1 using 7-benzyl-4-chloro-5,6,7,8-tetrahydropyrido[3,4-d]pyrimidine in step 5. $^1$H NMR (400 MHz, d$_6$-DMSO): 12.38 (br s, 1H), 8.53 (s, 1H), 7.96 (d, 1H), 7.86 (d, 0.5H), 7.84 (d, 0.5H), 7.81 (s, 1H), 7.78 (s, 0.5H), 77.75-7.70 (m, 2.5H), 7.58 (dd, 1H), 7.48 (m, 3H), 7.06 (d, 1H), 5.00 (d, 2H), 4.54 (br s, 2H), 4.44 (br s, 2H), 4.10 (m, 2H), 3.58 (m, 2H), 3.18 (m, 2H), 2.86 (m, 2H), 2.80 (s, 3H). MS (EI) for C$_{31}$H$_{30}$N$_6$O: 503 (MH$^+$).

4-(7-fluoroquinazolin-4-yl)-7-(2-methyl-1H-benzimidazol-6-yl)-2,3,4,5-tetrahydro-1,4-benzoxazepine. Prepared according to the method of example 1 by using 4-chloro-7-fluoroquinazoline in step 5. $^1$H NMR (400 MHz, methanol-d$_4$): 8.51 (s, 1H), 8.18 (dd, 1H), 7.68 (m, 1H), 7.63 (m, 1H), 7.54 (d, 1H), 7.51 (m, 1H), 7.46 (m, 1H), 7.41 (dd, 1H), 7.33 (m, 1H), 7.05 (d, 1H), 5.13 (s, 2H), 4.49 (m, 2H), 4.30 (m, 2H), 2.59 (s, 3H), 1.97 (s, 3H); MS (EI) for C$_{25}$H$_{20}$FN$_5$O: 426 (MH$^+$).

7-(2-methyl-1H-benzimidazol-6-yl)-4-[8-(methyloxy)quinazolin-4-yl]-2,3,4,5-tetrahydro-1,4-benzoxazepine. Prepared according to the method of example 1 by using 4-chloro-8-methoxyquinazoline in step 5. $^1$H NMR (400 MHz, methanol-d$_4$): 8.53 (s, 1H), 7.67 (m, 1H), 7.63 (m, 1H), 7.59 (m, 1H), 7.54 (d, 1H), 7.51 (m, 1H), 7.45 (m, 2H), 7.29 (d, 1H), 7.06 (d, 1H), 5.08 (s, 2H), 4.47 (m, 2H), 4.26 (m, 2H), 4.00 (s, 3H), 2.59 (s, 3H), 1.97 (s, 3H); MS (EI) for C$_{26}$H$_{23}$N$_5$O$_2$: 438 (MH$^+$).

4-(7-chloroquinazolin-4-yl)-7-(2-methyl-1H-benzimidazol-6-yl)-2,3,4,5-tetrahydro-1,4-benzoxazepine. Prepared according to the method of example 1 by using 4,7-dichloroquinazoline in step 5. $^1$H NMR (400 MHz, methanol-d$_4$): 8.51 (s, 1H), 8.09 (d, 1H), 7.76 (m, 1H), 7.69 (m, 1H), 7.63 (m, 1H), 7.56-7.44 (m, 4H), 7.05 (d, 1H), 5.13 (s, 2H), 4.49 (m, 2H), 4.30 (m, 2H), 2.59 (s, 3H); MS (EI) for C$_{25}$H$_{20}$ClN$_5$O: 442 (MH$^+$).

4-(8-chloroquinazolin-4-yl)-7-(2-methyl-1H-benzimidazol-6-yl)-2,3,4,5-tetrahydro-1,4-benzoxazepine. Prepared according to the method of example 1 by using 4,8-dichloroquinazoline in step 5. $^1$H NMR (400 MHz, methanol-d$_4$): 8.58 (s, 1H), 8.04 (m, 1H), 7.93 (m, 1H), 7.68 (m, 1H), 7.62 (d, 1H), 7.54 (d, 1H), 7.52 (dd, 1H), 7.46 (m, 2H), 7.06 (d, 1H), 5.11 (s, 2H), 4.49 (m, 2H), 4.30 (m, 2H), 2.59 (s, 3H); MS (EI) for C$_{25}$H$_{20}$ClN$_5$O: 442 (MH$^+$).

7-(2-methyl-1H-benzimidazol-6-yl)-4-[5-methyl-6-(phenylmethyl)pyrimidin-4-yl]-2,3,4,5-tetrahydro-1,4-benzoxazepine. Prepared as trifluoroacetate salt according to the method of example 1 by using 4-chloro-5-methyl-6-(phenylmethyl)-pyrimidine (synthesized according to reagent preparation 2) in step 5. $^1$H NMR (400 MHz, methanol-d$_4$): 8.52 (s, 1H), 7.87 (s, 1H), 7.78 (s, 2H), 7.66 (m, 1H), 7.54 (dd, 1H), 7.33-7.16 (m, 5H), 7.06 (d, 1H), 5.12 (m, 2H), 4.46 (m, 2H), 4.24 (m, 2H), 4.19 (s, 2H), 2.87 (s, 3H), 2.33 (s, 3H); MS (EI) for C$_{29}$H$_{27}$N$_5$O: 462 (MH$^+$).

7-(2-methyl-1H-benzimidazol-6-yl)-4-[6-(1-methylethyl)pyrimidin-4-yl]-2,3,4,5-tetrahydro-1,4-benzoxazepine. Prepared according to the method of example 1 by using 4-chloro-6-isopropyl-pyrimidine in step 5. $^1$H NMR (400 MHz, methanol-d$_4$): 8.38 (s, 1H), 7.73 (d, 1H), 7.66 (m, 1H), 7.52 (d, 1H), 7.45 (m, 2H), 7.05 (d, 1H), 6.76 (s, 1H), 4.23 (br. s, 2H), 4.16 (m, 2H), 2.81 (h, 1H), 1.97 (s, 3H), 1.22 (d, 6H); MS (EI) for C$_{24}$H$_{25}$N$_5$O: 400 (MH$^+$).

4-[5-ethyl-6-(1-methylethyl)pyrimidin-4-yl]-7-(2-methyl-1H-benzimidazol-6-yl)-2,3,4,5-tetrahydro-1,4-benzoxazepine. Prepared according to the method of example 1 by using 4-chloro-5-ethyl-6-isopropylpyrimidine (synthesized according to reagent preparation 5) in step 5. $^1$H NMR (400 MHz, methanol-d$_4$): 8.44 (s, 1H), 7.64 (s, 1H), 7.55-7.40 (m, 4H), 7.05 (d, 1H), 4.62 (s, 2H), 4.34 (m, 2H), 3.86 (m, 2H), 2.75 (q, 2H), 2.58 (s, 3H), 1.23 (m, 9H); MS (EI) for C$_{26}$H$_{29}$N$_5$O: 428 (MH$^+$).

7-(2-methyl-1H-benzimidazol-6-yl)-4-{6-methyl-5-[(4-methylphenyl)methyl]pyrimidin-4-yl}-2,3,4,5-tetrahydro-1,4-benzoxazepine. Prepared according to the method of example 1 by using 4-chloro-6-methyl-5-(4-methylbenzyl)pyrimidine (synthesized according to reagent preparation 5) in step 5. $^1$H NMR (400 MHz, methanol-d$_4$): 8.46 (s, 1H), 7.50 (m, 2H), 7.41 (dd, 1H), 7.19 (dd, 1H), 7.03 (d, 2H), 6.98 (d, 1H), 6.93 (d, 2H), 6.64 (m, 1H), 4.50 (s, 2H), 4.29 (m, 2H), 3.95 (s, 2H), 3.89 (m, 2H), 2.60 (s, 3H), 2.24 (s, 3H), 2.21 (s, 3H); MS (EI) for C$_{30}$H$_{29}$N$_5$O: 476 (MH$^+$).

7-(2-methyl-1H-benzimidazol-6-yl)-4-(6-methyl-5-{[4-(trifluoromethyl)phenyl]-methyl}pyrimidin-4-yl)-2,3,4,5-tetrahydro-1,4-benzoxazepine. Prepared according to the method of example 1 by using 4-chloro-6-methyl-5-(4-(trifluoromethyl)benzyl)pyrimidine (synthesized according to reagent preparation 5) in step 5. $^1$H NMR (400 MHz, methanol-d$_4$): 8.49 (s, 1H), 7.49 (m, 4H), 7.43 (dd, 1H), 7.23 (d, 2H), 7.16 (dd, 1H), 7.00 (d, 1H), 6.68 (m, 1H), 4.51 (s, 2H), 4.31 (m, 2H), 4.08 (s, 2H), 3.88 (m, 2H), 2.60 (s, 3H), 2.20 (s, 3H); MS (EI) for C$_{30}$H$_{26}$F$_3$N$_5$O: 530 (MH$^+$).

7-(2-methyl-1H-benzimidazol-6-yl)-4-[2-(methylthio)-6,7-dihydro-5H-cyclopenta[d]pyrimidin-4-yl]-2,3,4,5-tetrahydro-1,4-benzoxazepine. Synthesized according to the method of example 1 using 4-chloro-2-(methylthio)-6,7-dihydro-5H-cyclopenta[d]pyrimidine (reagent preparation 4) in step 5. $^1$H NMR (400 MHz, d$_6$-DMSO): 7.64 (m, 2H), 7.51 (d, 1H), 7.46 (dd, 1H), 7.37 (dd, 1H), 7.01 (d, 1H), 4.94 (s, 2H), 4.24 (m, 2H), 4.20 (m, 2H), 3.00 (t, 2H), 2.64 (t, 2H), 2.42 (s, 3H), 1.92 (s and m, 5H). MS (EI) for C$_{25}$H$_{25}$N$_5$OS: 444 (MH$^+$).

7-(2-methyl-1H-benzimidazol-6-yl)-4-{2-[(phenylmethyl)thio]-6,7-dihydro-5H-cyclopenta[d]pyrimidin-4-yl}-2,3,4,5-tetrahydro-1,4-benzoxazepine. Synthesized according to the method of example 1 using 2-(benzylthio)-4-chloro-6,7-dihydro-5H-cyclopenta[d]pyrimidine (reagent preparation 4) in step 5. $^1$H NMR (400 MHz, d$_6$-DMSO): 7.84 (s, 1H), 7.69 (m, 3H), 7.53 (dd, 1H), 7.18 (m, 5H), 7.06 (d, 1H), 5.00 (s, 2H), 4.31 (s and m, 4H), 4.12 (m, 2H), 3.06 (t, 2H), 2.82 (s, 3H), 2.69 (t, 2H), 1.96 (m, 2H). MS (EI) for C$_{31}$H$_{29}$N$_5$OS: 520 (MH$^+$).

4-[2-(ethylthio)-6,7-dihydro-5H-cyclopenta[d]pyrimidin-4-yl]-7-(2-methyl-1H-benzimidazol-6-yl)-2,3,4,5-tetrahydro-1,4-benzoxazepine. Synthesized according to the method of example 1 using 4-chloro-2-(ethylthio)-6,7-dihydro-5H-cyclopenta[d]pyrimidine (reagent preparation 4) in step 5. $^1$H NMR (400 MHz, d$_6$-DMSO): 7.93 (d, 1H), 7.85 (d, 1H), 7.77 (dd, 1H), 7.72 (d, 1H), 7.56 (dd, 1H), 7.07 (d, 1H), 5.00 (s, 2H), 4.36 (m, 2H), 4.16 (m, 2H), 3.04 (m, 4H), 2.80 (s, 3H), 2.70 (t, 2H), 1.95 (m, 2H), 1.16 (t, 3H). MS (EI) for C$_{26}$H$_{27}$N$_5$OS: 458 (MH$^+$).

4-(7,7-dimethyl-5,6,7,8-tetrahydroquinazolin-4-yl)-7-(2-methyl-1H-benzimidazol-6-yl)-2,3,4,5-tetrahydro-1,4-benzoxazepine. Synthesized according to the method of example 1 using 4-chloro-7,7-dimethyl-5,6,7,8-tetrahydroquinazoline (reagent preparation 3) in step 5. $^1$H NMR (400 MHz, d$_3$-MeOH): 8.32 (s, 1H), 7.61 (d, 1H), 7.51 (s, 1H), 7.49 (d, 1H), 7.45 (dd, 1H), 7.39 (dd, 1H), 7.03 (d, 1H), 4.82 (s, 2H), 4.34 (t, 2H), 4.02 (t, 2H), 2.78 (t, 2H), 2.57 (s, 3H), 2.52 (s, 2H), 1.56 (t, 2H), 1.06 (s, 6H). MS (EI) for C$_{27}$H$_{29}$N$_5$O: 440 (MH$^+$).

4-[6-bromo-7-(methyloxy)quinazolin-4-yl]-7-(2-methyl-1H-benzimidazol-6-yl)-2,3,4,5-tetrahydro-1,4-benzoxazepine. Prepared according to the method of example 1 by using 6-bromo-4-chloro-7-methoxyquinazoline (reagent preparation 1) in step 5. $^1$H NMR (400 MHz, DMSO-d$_6$): 8.54 (s, 1H), 8.21 (s, 1H), 7.77 (m, 2H), 7.53 (m, 3H), 7.32 (s, 1H), 7.05 (d, 1H), 5.04 (s, 2H), 4.50 (m, 2H), 4.14 (m, 2H), 4.00 (s, 3H); MS (EI) for C$_{26}$H$_{22}$BrN$_5$O$_2$: 516 (MH$^+$).

7-(2-methyl-1H-benzimidazol-6-yl)-4-(5-methylpyrimidin-4-yl)-2,3,4,5-tetrahydro-1,4-benzoxazepine. Prepared as trifluoroacetate salt according to the method of example 1 by using 4-chloro-5-methylpyrimidine in step 5. $^1$H NMR (400 MHz, DMSO-d$_6$): 8.78 (br. s, 1H), 8.28 (br. s, 1H), 7.96 (s, 1H), 7.85 (d, 1H), 7.78 (m 2H), 7.60 (m, 1H), 7.07 (d, 1H), 5.17 (s, 2H), 4.47 (m, 2H), 4.28 (m, 2H), 2.82 (s, 3H), 2.41 (s, 3H); MS (EI) for C$_{22}$H$_{21}$N$_5$O: 372 (MH$^+$).

4-(5,6-dimethylpyrimidin-4-yl)-7-(2-methyl-1H-benzimidazol-6-yl)-2,3,4,5-tetrahydro-1,4-benzoxazepine. Prepared according to the method of example 1 by using 4-chloro-5,6-dimethylpyrimidine in step 5. $^1$H NMR (400 MHz, DMSO-d$_6$): 12.00 (br. s, 1H), 8.35 (s, 1H), 7.65 (m, 1H), 7.61 (m, 1H), 7.50 (m, 2H), 7.38 (dd, 1H), 7.03 (d, 1H), 4.62 (s, 2H), 4.32 (m, 2H), 3.81 (m, 2H), 2.33 (s, 3H), 2.20 (s, 3H), 1.91 (s, 3H); MS (EI) for C$_{23}$H$_{23}$N$_5$O: 386 (MH$^+$).

7-(2-methyl-1H-benzimidazol-6-yl)-4-[6-methyl-5-(phenylmethyl)pyrimidin-4-yl]-2,3,4,5-tetrahydro-1,4-benzoxazepine. Prepared according to the method of example 1 by using 5-benzyl-4-chloro-6-methylpyrimidine (reagent preparation 5) in step 5. $^1$H NMR (400 MHz, DMSO-d$_6$): 12.26 (br. s, 1H), 8.51 (s, 1H), 7.50 (br. s, 2H), 7.46 (dd, 1H), 7.36-7.24 (m, 3H), 7.18 (d, 1H), 7.11 (d, 2H), 7.00 (d, 1H), 6.81 (s, 1H), 4.47 (s, 2H), 4.27 (m, 2H), 4.03 (s, 2H), 3.79 (m, 2H), 2.17 (s, 3H), 1.91 (s, 3H); MS (EI) for C$_{29}$H$_{27}$N$_5$O: 462 (MH$^+$).

7-(2-methyl-1H-benzimidazol-6-yl)-4-[6-methyl-5-(1-methylethyl)pyrimidin-4-yl]-2,3,4,5-tetrahydro-1,4-benzoxazepine. Prepared according to the method of example 1 by using 4-chloro-6-methyl-5-(1-methylethyl)-pyrimidine (reagent preparation 5) in step 5. $^1$H NMR (400 MHz, DMSO-d$_6$): 8.43 (s, 1H), 7.63 (s, 1H), 7.52 (m, 3H), 7.37 (dd, 1H), 7.06 (d, 1H), 4.42 (s, 2H), 4.30 (m, 2H), 3.68 (m, 2H), 3.31 (h, 1H), 1.89 (s, 3H), 1.33 (d, 6H); MS (EI) for C$_{25}$H$_{27}$N$_5$O: 414 (MH$^+$).

7-(2-methyl-1H-benzimidazol-6-yl)-4-[6-methyl-5-(2-methylpropyl)pyrimidin-4-yl]-2,3,4,5-tetrahydro-1,4-benzoxazepine. Prepared according to the method of example 1 by using 4-chloro-5-isobutyl-6-methylpyrimidine (reagent preparation 5) in step 5. $^1$H NMR (400 MHz, DMSO-d$_6$): 12.30 (br. s, 1H), 8.37 (s, 1H), 7.62 (m, 2H), 7.49 (m, 2H), 7.37 (d, 1H), 7.01 (d, 1H), 4.59 (s, 2H), 4.33 (m, 2H), 3.75 (m, 2H), 2.61 (d, 2H), 2.37 (s, 3H), 1.68 (m, 1H), 0.53 (d, 6H); MS (EI) for C$_{26}$H$_{29}$N$_5$O: 428 (MH$^+$).

4-{5-[(3-fluorophenyl)methyl]-6-methylpyrimidin-4-yl}-7-(2-methyl-1H-benzimidazol-6-yl)-2,3,4,5-tetrahydro-1,4-benzoxazepine. Prepared according to the method of example 1 by using 4-chloro-5-(3-fluorobenzyl)-6-methylpyrimidine (reagent preparation 5) in step 5. $^1$H NMR (400 MHz, DMSO-d$_6$): 12.35 (br. s, 1H), 8.51 (s, 1H), 7.49 (m, 3H), 7.35 (m, 1H), 7.19 (d, 1H), 7.10 (m, 1H), 7.00 (d, 1H), 6.92 (m, 3H), 4.49 (s, 2H), 4.27 (m, 2H), 4.05 (s, 2H), 3.78 (m, 2H), 2.52 (s, 3H), 2.17 (s, 3H); MS (EI) for C$_{29}$H$_{26}$FN$_5$O: 480 (MH$^+$).

4-{5-[(3-chlorophenyl)methyl]-6-methylpyrimidin-4-yl}-7-(2-methyl-1H-benzimidazol-6-yl)-2,3,4,5-tetrahydro-1,4-benzoxazepine. Prepared according to the method of example 1 by using 4-chloro-5-(3-chlorobenzyl)-6-methylpyrimidine (reagent preparation 5) in step 5. $^1$H NMR (400 MHz, DMSO-d$_6$): 12.31 (br. s, 1H), 8.51 (s, 1H), 7.50 (m, 2H), 7.47 (dd, 1H), 7.33 (m, 2H), 7.19 (dd, 1H), 7.14 (s, 1H), 7.04 (m, 1H), 7.00 (d, 1H), 6.95 (d, 1H), 4.51 (s, 2H), 4.28 (m, 2H), 4.05 (s, 2H), 3.78 (m, 2H), 2.52 (s, 3H), 2.17 (s, 3H); MS (EI) for C$_{29}$H$_{26}$ClN$_5$O: 496 (MH$^+$)

7-(2-methyl-1H-benzimidazol-6-yl)-4-[6-methyl-5-(1-phenylethyl)pyrimidin-4-yl]-2,3,4,5-tetrahydro-1,4-benzoxazepine. Prepared according to the method of example 1 by using 4-chloro-6-methyl-5-(1-phenylethyl)pyrimidine (reagent preparation 5) in step 5. $^1$H NMR (400 MHz, DMSO-d$_6$): 8.60 (s, 1H), 7.76 (d, 1H), 7.72 (s, 1H), 7.54 (dd, 1H), 7.49 (d, 1H), 7.34-7.18 (m, 5H), 7.06 (d, 1H), 7.01 (s, 1H), 4.61-4.44 (m, 3H), 4.37 (m, 1H), 4.28 (m, 1H), 3.87 (m, 1H), 3.77 (m, 1H), 2.77 (s, 3H), 2.11 (s, 3H), 1.66 (d, 3H); MS (EI) for C$_{30}$H$_{29}$N$_5$O: 476 (MH$^+$).

7-(2-methyl-1H-benzimidazol-6-yl)-4-(6-methyl-5-{[3-(methyloxy)phenyl]methyl}-pyrimidin-4-yl)-2,3,4,5-tetrahydro-1,4-benzoxazepine. Prepared according to the method of example 1 by using 4-chloro-5-(3-methoxybenzyl)-6-methylpyrimidine (reagent preparation 5) in step 5. $^1$H NMR (400 MHz, DMSO-d$_6$): 12.27 (br. s, 1H), 8.50 (s, 1H), 7.47 (m, 3H), 7.26 (m, 1H), 7.16 (d, 1H), 7.00 (d, 1H), 6.85 (m, 2H), 6.65 (m, 2H), 4.50 (s, 2H), 4.28 (m, 2H), 3.99 (s, 2H), 3.79 (m, 2H), 3.55 (s, 3H), 2.51 (s, 3H), 2.17 (s, 3H); MS (EI) for C$_{30}$H$_{29}$N$_5$O$_2$: 492 (MH$^+$).

7-(2-methyl-1H-benzimidazol-6-yl)-4-{6-methyl-5-[(3-methylphenyl)methyl]pyrimidin-4-yl}-2,3,4,5-tetrahydro-1,4-benzoxazepine. Prepared according to the method of example 1 by using 4-chloro-6-methyl-5-(3-methylbenzyl)pyrimidine (reagent preparation 5) in step 5. $^1$H NMR (400 MHz, DMSO-d$_6$): 12.21 (d, 1H), 8.48 (s, 1H), 7.50 (m, 1H), 7.43 (dd, 1H), 7.38 (d, 1H), 7.21 (m, 1H), 7.13 (m, 1H), 7.04 (m, 1H), 6.98 (dd, 1H), 6.89 (m, 2H), 6.72 (dd, 1H), 4.45 (s, 2H), 4.26 (m, 2H), 3.93 (m, 2H), 3.77 (m, 2H), 2.49 (s, 3H), 2.14 (s, 3H), 2.04 (d, 3H); MS (EI) for C$_{30}$H$_{29}$N$_5$O: 476 (MH$^+$).

4-{5-[(3-chloro-5-fluorophenyl)methyl]-6-methylpyrimidin-4-yl}-7-(2-methyl-1H-benzimidazol-6-yl)-2,3,4,5-tetrahydro-1,4-benzoxazepine. Prepared according to the method of example 1 by using 4-chloro-5-(3-chloro-5-fluorobenzyl)-6-methylpyrimidine (reagent preparation 5) in step 5. $^1$H NMR (400 MHz, methanol-d$_4$): 8.49 (s, 1H), 7.52 (m, 2H), 7.44 (dd, 1H), 7.27 (d, 1H), 7.06 (m, 1H), 7.00 (d, 1H), 6.88 (m, 2H), 6.76 (d, 1H), 4.54 (s, 2H), 4.30 (m, 2H), 4.04 (s, 2H), 3.88 (m, 2H), 2.59 (s, 3H), 2.22 (s, 3H); MS (EI) for C$_{29}$H$_{25}$ClFN$_5$O: 514 (MH$^+$).

4-{5-[(3,4-difluorophenyl)methyl]-6-methylpyrimidin-4-yl}-7-(2-methyl-1H-benzimidazol-6-yl)-2,3,4,5-tetrahydro-1,4-benzoxazepine. Prepared according to the method of example 1 by using 4-chloro-5-(3,4-difluorobenzyl)-6-methylpyrimidine (reagent preparation 5) in step 5. $^1$H NMR (400 MHz, DMSO-d$_6$): 12.22 (br. s, 1H), 8.50 (s, 1H), 7.62-7.43 (m, 3H), 7.32 (m, 1H), 7.18 (m, 1H), 7.14 (m, 1H), 6.99 (m, 2H), 6.88 (m, 1H), 4.50 (s, 2H), 4.27 (m, 2H), 4.01 (s, 2H), 3.76 (m, 2H), 2.51 (s, 3H), 2.17 (s, 3H); MS (EI) for C$_{29}$H$_{25}$F$_2$N$_5$O: 498 (MH$^+$).

4-{5-[(4-fluorophenyl)methyl]-2,6-dimethylpyrimidin-4-yl}-7-(2-methyl-1H-benzimidazol-6-yl)-2,3,4,5-tetrahydro- 1,4-benzoxazepine. Prepared according to the method of example 1 by using 4-chloro-5-(4-fluorobenzyl)-2,6-dimethylpyrimidine (reagent preparation 8) in step 5. $^1$H NMR (400 MHz, DMSO-d$_6$): 12.25 (br. s, 1H), 7.61-7.43 (m, 3H), 7.18 (dd, 2H), 7.11 (d, 1H), 7.00 (d, 1H), 6.94 (d, 1H), 4.44 (s, 2H), 4.21 (m, 2H), 3.97 (s, 2H), 3.75 (m, 2H), 2.51 (s, 3H), 2.41 (s, 3H), 2.11 (s, 3H); MS (EI) for C$_{30}$H$_{28}$FN$_5$O: 494 (MH$^+$).

4-(7-chloro-6-iodoquinazolin-4-yl)-7-(2-methyl-1H-benzimidazol-6-yl)-2,3,4,5-tetrahydro-1,4-benzoxazepine. Prepared according to the method of example 1 by using 4,7-dichloro-6-iodoquinazoline (reagent preparation 1) in step 5. $^1$H NMR (400 MHz, DMSO-d$_6$): 12.26 (br. s, 1H), 8.59 (s, 1H), 8.49 (s, 1H), 7.99 (s, 1H), 7.77 (m, 2H), 7.58-7.47 (m, 3H), 7.04 (d, 1H), 5.08 (s, 2H), 4.52 (m, 2H), 4.16 (m, 2H); MS (EI) for C$_{25}$H$_{19}$ClIN$_5$O: 568 (MH$^+$).

7-(2-methyl-1H-benzimidazol-6-yl)-4-[7-(methylsulfonyl)quinazolin-4-yl]-2,3,4,5-tetrahydro-1,4-benzoxazepine. Prepared according to the method of example 1 by using 4-chloro-7-(methylsulfonyl)quinazoline (reagent preparation 1) in step 5. $^1$H NMR (400 MHz, methanol-d$_4$): 8.62 (s, 1H), 8.31 (m, 2H), 7.94 (dd, 1H), 7.68 (s, 1H), 7.65 (d, 1H), 7.55 (d, 1H), 7.51 (dd, 1H), 7.46 (dd, 1H), 7.04 (d, 1H), 5.19 (s, 2H), 4.51 (m, 2H), 4.35 (m, 2H), 3.21 (s, 3H), 2.59 (s, 3H); MS (EI) for C$_{26}$H$_{23}$N$_5$O$_3$S: 486 (MH$^+$).

4-(6-ethyl-5-methylpyrimidin-4-yl)-7-(2-methyl-1H-benzimidazol-6-yl)-2,3,4,5-tetrahydro-1,4-benzoxazepine. Prepared according to the method of example 1 by using 4-chloro-6-ethyl-5-methyl-pyrimidine (reagent preparation 5) in step 5. $^1$H NMR (400 MHz, methanol-d$_4$): 8.36 (s, 1H), 7.63 (s, 1H), 7.52 (m, 2H), 7.46 (dd, 1H), 7.42 (dd, 1H), 7.04 (d, 1H), 4.68 (s, 2H), 4.33 (m, 2H), 3.92 (m, 2H), 2.73 (q, 2H), 2.58 (s, 3H), 2.30 (s, 3H), 1.22 (t, 3H); MS (EI) for C$_{24}$H$_{25}$N$_5$O: 400 (MH$^+$).

4-(5,6-diethylpyrimidin-4-yl)-7-(2-methyl-1H-benzimidazol-6-yl)-2,3,4,5-tetrahydro-1,4-benzoxazepine. Prepared according to the method of example 1 by using 4-chloro-5,6-diethyl-pyrimidine (reagent preparation 5) in step 5. $^1$H NMR (400 MHz, methanol-d$_4$): 8.39 (s, 1H), 7.66 (s, 1H), 7.54 (m, 2H), 7.46 (m, 2H), 7.04 (d, 1H), 4.70 (s, 2H), 4.35 (m, 2H), 3.92 (m, 2H), 2.77 (m, 4H), 2.60 (s, 3H), 1.24 (t, 3H), 1.20 (t, 3H); MS (EI) for C$_{25}$H$_{28}$N$_5$O: 414 (MH$^+$).

4-[6-ethyl-5-(phenylmethyl)pyrimidin-4-yl]-7-(2-methyl-1H-benzimidazol-6-yl)-2,3,4,5-tetrahydro-1,4-benzoxazepine. Prepared according to the method of example 1 by using 5-benzyl-4-chloro-6-ethylpyrimidine (reagent preparation 5) in step 5. $^1$H NMR (400 MHz, methanol-d$_4$): 8.52 (s, 1H), 7.50 (d, 1H), 7.466 (s, 1H), 7.42 (dd, 1H), 7.24 (m, 4H), 7.08 (m, 2H), 6.99 (d, 1H), 6.70 (d, 1H), 4.50 (s, 2H), 4.28 (m, 2H), 4.04 (s, 2H), 3.89 (m, 2H), 2.61 (s, 3H), 2.51 (q, 2H), 1.10 (t, 3H); MS (EI) for C$_{30}$H$_{30}$N$_5$O: 476 (MH$^+$).

5-methyl-6-[7-(2-methyl-1H-benzimidazol-6-yl)-2,3-dihydro-1,4-benzoxazepin-4(5H)-yl]-N-phenylpyrimidin-4-amine. Prepared as acetate salt according to the method of example 1 by using 6-chloro-5-methyl-N-phenylpyrimidin-4-amine (reagent preparation 6) in step 5. $^1$H NMR (400 MHz, methanol-d$_4$): 8.07 (s, 1H), 7.64 (s, 1H), 7.53-7.38 (m, 6H), 7.27 (m, 2H), 7.07 (d, 1H), 7.03 (m, 1H), 4.57 (s, 2H), 4.32 (m, 2H), 3.82 (m, 2H), 2.58 (s, 3H), 2.19 (s, 3H), 1.97 (s, 3H); MS (EI) for C$_{28}$H$_{26}$N$_6$O: 463 (MH$^+$).

4-[7-(2-methyl-1H-benzimidazol-6-yl)-2,3-dihydro-1,4-benzoxazepin-4(5H)-yl]pyrimidin-2-amine. Prepared as acetate salt according to the method of example 1 by using 2-amino-4-chloropyrimidine in step 5. $^1$H NMR (400 MHz, methanol-d$_4$): 7.72-7.65 (m, 3H), 7.52 (d, 1H), 7.46 (m, 2H), 7.06 (d, 1H), 6.35 (d, 1H), 4.17 (m, 4H), 2.58 (s, 3H), 1.94 (s, 3H); MS (EI) for C$_{21}$H$_{20}$N$_6$O: 373 (MH$^+$).

7-(2-methyl-1H-benzimidazol-6-yl)-4-(6-methyl-5-{[2-(methyloxy)phenyl]methyl}-pyrimidin-4-yl)-2,3,4,5-tetrahydro-1,4-benzoxazepine. Prepared according to the method of example 1 by using 4-chloro-5-(2-methoxybenzyl)-6-methylpyrimidine (reagent preparation 5) in step 5. $^1$H NMR (400 MHz, methanol-d$_4$): 8.48 (s, 1H), 7.52 (d, 1H), 7.43 (dd, 1H), 7.39 (s, 1H), 7.31 (m, 1H), 7.20 (dd, 1H), 6.98 (d, 2H), 6.95 (m, 1H), 6.86 (d, 1H), 6.60 (d, 1H), 6.50 (d, 1H), 4.42 (s, 2H), 4.29 (m, 2H), 3.90 (m, 2H), 3.77 (s, 2H), 3.22 (s, 3H), 2.61 (s, 3H), 2.15 (s, 3H); MS (EI) for C$_{30}$H$_{29}$N$_5$O$_2$: 492 (MH$^+$).

7-(2-methyl-1H-benzimidazol-6-yl)-4-{6-methyl-5-[(2-methylphenyl)methyl]pyrimidin-4-yl}-2,3,4,5-tetrahydro-1,4-benzoxazepine. Prepared according to the method of example 1 by using 4-chloro-6-methyl-5-(2-methylbenzyl) pyrimidine (reagent preparation 5) in step 5. $^1$H NMR (400 MHz, methanol-d$_4$): 8.50 (s, 1H), 7.51 (d, 1H), 7.45 (dd, 1H), 7.38 (s, 1H), 7.18 (m, 3H), 7.00 (d, 1H), 6.90 (d, 1H), 6.77 (d, 1H), 6.27 (d, 1H), 4.41 (s, 2H), 4.35 (m, 2H), 3.90 (m, 2H), 3.70 (s, 2H), 3.62 (s, 3H), 2.16 (s, 3H), 1.78 (s, 3H); MS (EI) for C$_{30}$H$_{29}$N$_5$O: 476 (MH$^+$).

7-(2-methyl-1H-benzimidazol-6-yl)-4-[2-methyl-3-(phenylmethyl)pyridin-4-yl]-2,3,4,5-tetrahydro-1,4-benzoxazepine. Prepared as acetate salt according to the method of example 1 by using 3-benzyl-4-chloro-2-methylpyridine (reagent preparation 9) in step 5. $^1$H NMR (400 MHz, methanol-d$_4$): 8.20 (d, 1H), 7.49 (d, 1H), 7.44 (m, 2H), 7.20 (m, 4H), 7.15 (d, 1H), 7.02 (m, 3H), 6.66 (d, 1H), 4.30 (s, 2H), 4.25 (m, 2H), 4.16 (s, 2H), 3.62 (m, 2H), 2.60 (s, 3H), 2.29 (s, 3H), 1.96 (s, 3H); MS (EI) for C$_{30}$H$_{28}$N$_4$O: 461 (MH$^+$).

4-{3-[(4-fluorophenyl)methyl]-2-methylpyridin-4-yl}-7-(2-methyl-1H-benzimidazol-6-yl)-2,3,4,5-tetrahydro-1,4-benzoxazepine. Prepared according to the method of example 1 by using 4-chloro-3-(4-fluorobenzyl)-2-methylpyridine (reagent preparation 9) in step 5. $^1$H NMR (400 MHz, methanol-d$_4$): 8.21 (d, 1H), 7.50 (m, 2H), 7.44 (dd, 1H), 7.17 (dd, 1H), 7.13 (d, 1H), 7.03 (d, 1H), 6.99 (m, 2H), 6.88 (m, 2H), 6.68 (s, 1H), 4.22 (m, 4H), 4.13 (s, 2H), 3.56 (m, 2H), 2.60 (s, 3H), 2.28 (s, 3H); MS (EI) for C$_{30}$H$_{27}$FN$_4$O: 479 (MH$^+$).

4-[6,7-bis(methyloxy)quinazolin-4-yl]-7-(2-methyl-1H-benzimidazol-6-yl)-2,3,4,5-tetrahydro-1,4-benzoxazepine. Prepared according to the method of example 1 by using 4-chloro-6,7-dimethoxyquinazoline in step 5. $^1$H NMR (400 MHz, Methanol-D$_4$): 8.50 (1H), 7.74 (br, 1H), 7.70 (br, 1H), 7.62 to 7.53 (m, 3H), 7.17 (s, 1H), 7.14 (s, 1H), 7.09 (d, 1H), 5.14 (s, 2H), 4.60 (m, 2H), 4.27 (m, 2H), 3.96 (s, 3H), 3.54 (s, 3H), 2.66 (s, 3H); MS (EI) for C$_{27}$H$_{25}$N$_5$O$_3$: 468 (MH$^+$).

7-(2-methyl-1H-benzimidazol-6-yl)-4-[7-(methyloxy) quinazolin-4-yl]-2,3,4,5-tetrahydro-1,4-benzoxazepine. Prepared according to the method of example 1 by using 4-chloro-7-methoxyquinazoline in step 5. $^1$H NMR (400 MHz, DMSO-D$_6$): 8.48, (s, 1H), 7.99 (d, 1H), 7.71 to 7.67 (m, 2H), 7.62 to 7.50 (m, 2H), 7.45 (d, 1H), 7.18 (d, 1H), 7.13 (dd, 1H), 7.03 (d, 1H), 5.10 (s, 2H), 4.49 (m, 2H), 4.20 (m, 2H), 3.91 (s, 3H), 2.54 (s, 3H), MS (EI) for C$_{26}$H$_{23}$N$_5$O$_2$: 438 (MH$^+$).

7-(2-methyl-1H-benzimidazol-6-yl)-4-{6-(methyloxy)-7-[(phenylmethyl)oxy]quinazolin-4-yl}-2,3,4,5-tetrahydro-1,4-benzoxazepine. Prepared according to the method of example 1 by using 7-(benzyloxy)-4-chloroquinazoline in step 5. $^1$H NMR (400 MHz, Methanol-D$_4$): 8.43, (s, 1H), 7.99 (d, 2H), 7.54 to 7.49 (m, 2H), 7.45 to 7.41 (m, 3H), 7.38 to 7.29 (m, 3H), 7.18 (d, 1H), 7.08 (dd, 2H), 5.20 (s, 2H), 4.52 (m, 2H), 4.10 (m, 2H), 3.56 (s, 3H), 2.59 (s, 3H); MS (EI) for C$_{33}$H$_{29}$N$_5$O$_3$: 544 (MH$^+$).

7-(2-methyl-1H-benzimidazol-6-yl)-4-[6-(methyloxy) quinazolin-4-yl]-2,3,4,5-tetrahydro-1,4-benzoxazepine. Prepared according to the method of example 1 by using 4-chloro-6-methoxyquinazoline in step 5. $^1$H NMR (400 MHz, Methanol-D$_4$): 8.47, (s, 1H), 7.70 (d, 1H), 7.65 (dd, 2H), 7.54 to 749 (m, 2H), 7.44 (dd, 1H), 7.40 (dd, 1H), 7.15 (d, 1H), 7.07 (d, 1H), 5.00 (s, 2H), 4.52 (m, 2H), 4.19 (m, 2H), 3.49 (s, 3H), 2.60 (s, 3H), MS (EI) for C$_{26}$H$_{23}$N$_5$O$_2$: 438 (MH$^+$).

4-(6-bromoquinazolin-4-yl)-7-(2-methyl-1H-benzimidazol-6-yl)-2,3,4,5-tetrahydro-1,4-benzoxazepine. Prepared according to the method of example 1 by using 6-bromo-4-chloroquinazoline in step 5. $^1$H NMR (400 MHz, DMSO-D$_6$): 8.61, (s, 1H), 8.17 (d, 1H), 7.95 (dd, 1H), 7.77 to 7.73 (m, 3H), 7.44 (dd, 2H), 7.49 (br, 1H), 7.04 (d, 1H), 5.06 (s, 2H), 4.52 (m, 2H), 4.16 (m, 2H), 2.51 (s, 3H), MS (EI) for C$_{25}$H$_{20}$BrN$_5$O: 486 (MH$^+$).

4-(6-chloroquinazolin-4-yl)-7-(2-methyl-1H-benzimidazol-6-yl)-2,3,4,5-tetrahydro-1,4-benzoxazepine. Prepared according to the method of example 1 by using 4,6-dichloroquinazoline in step 5. $^1$H NMR (400 MHz, DMSO-D$_6$): 8.59, (s, 1H), 8.04 (d, 1H), 7.87 to 7.81 (m, 4H), 7.77 (d, 1H), 7.55 (dd, 1H), 7.47 (br, 1H), 7.04 (d, 1H), 5.08 (s, 2H), 4.52 (m, 2H), 4.18 (m, 2H), 2.51 (s, 3H), MS (EI) for C$_{25}$H$_{23}$N$_5$O$_2$: 441 (MH$^+$).

7-(2-methyl-1H-benzimidazol-6-yl)-4-(8-methylquinazolin-4-yl)-2,3,4,5-tetrahydro-1,4-benzoxazepine. Prepared according to the method of example 1 by using 4-chloro-8-methylquinazoline in step 5. $^1$H NMR (400 MHz, Methanol-D$_4$): 8.56, (s, 1H), 7.90 (d, 1H), 7.65 (dd, 2H), 7.57 to 7.37 (m, 6H), 7.05 (d, 1H), 5.04 (s, 2H), 4.45 (m, 2H), 4.24 (m, 2H), 2.63 (s, 3H), 2.58 (s, 3H), MS (EI) for C$_{26}$H$_{23}$N$_5$O: 422 (MH$^+$).

7-(2-methyl-1H-benzimidazol-6-yl)-4-(6-methylquinazolin-4-yl)-2,3,4,5-tetrahydro-1,4-benzoxazepine. Prepared according to the method of example 1 by using 4-chloro-6-methylquinazoline in step 5. $^1$H NMR (400 MHz, Methanol-D$_4$): 8.45, (s, 1H), 7.85 (br, 1H), 7.72 to 7.64 (m, 2H), 7.56 to 7.47 (m, 4H), 7.07 (d, 1H), 5.05 (s, 2H), 4.50 (m, 2H), 4.23 (m, 2H), 2.59 (s, 3H), 2.38 (s, 3H), MS (EI) for C$_{26}$H$_{23}$N$_5$O: 422 (MH$^+$).

4-(6-iodoquinazolin-4-yl)-7-(2-methyl-1H-benzimidazol-6-yl)-2,3,4,5-tetrahydro-1,4-benzoxazepine. Prepared according to the method of example 1 by using 4-chloro-6-iodoquinazoline in step 5. $^1$H NMR (400 MHz, DMSO-D$_6$): 8.61, (s, 1H), 8.33 (d, 1H), 8.08 (d, 1H), 7.83 to 7.74 (m, 2H), 7.59 to 7.47 (m, 4H), 7.05 (d, 1H), 5.05 (s, 2H), 4.51 (m, 2H), 4.15 (m, 2H), 2.53 (s, 3H), MS (EI) for C$_{25}$H$_{20}$IN$_5$O: 534 (MH$^+$).

4-(6-fluoroquinazolin-4-yl)-7-(2-methyl-1H-benzimidazol-6-yl)-2,3,4,5-tetrahydro-1,4-benzoxazepine. Prepared according to the method of example 1 by using 4-chloro-6-fluoroquinazoline in step 5. $^1$H NMR (400 MHz, DMSO-D$_6$): 8.56, (s, 1H), 7.88 (dd, 1H), 7.80 to 7.70 (m, 4H), 7.58 to 7.42 (m, 2H), 7.47 (dd, 1H), 7.05 (d, 1H), 5.10 (s, 2H), 4.53 (m, 2H), 4.20 (m, 2H), 2.54 (s, 3H), MS (EI) for C$_{25}$H$_{20}$FN$_5$O: 426 (MH$^+$).

4-(6,7-difluoroquinazolin-4-yl)-7-(2-methyl-1H-benzimidazol-6-yl)-2,3,4,5-tetrahydro-1,4-benzoxazepine. Prepared according to the method of example 1 by using 4-chloro-6,7-difluoroquinazoline in step 5. $^1$H NMR (400 MHz, DMSO-D$_6$): 8.56, (s, 1H), 8.01 (dd, 1H), 7.87 to 7.70 (m, 3H), 7.55 to 7.51 (m, 2H), 7.45 (d, 1H), 7.02 (d, 1H), 5.11 (s, 2H), 4.53 (m, 2H), 4.20 (m, 2H), 2.53 (s, 3H), MS (EI) for C$_{25}$H$_{19}$F$_2$N$_5$: 444 (MH$^+$).

4-(6-bromo-7-chloroquinazolin-4-yl)-7-(2-methyl-1H-benzimidazol-6-yl)-2,3,4,5-tetrahydro-1,4-benzoxazepine. Prepared according to the method of example 1 by using 6-bromo-4,7-dichloroquinazoline in step 5. $^1$H NMR (400 MHz, DMSO-D$_6$): 8.60, (s, 1H), 8.33 (s, 1H), 8.06 (s, 1H), 7.79 (br, 2H), 7.59 to 7.50 (m, 2H), 7.00 (d, 1H), 5.10 (s, 2H), 4.529 (m, 2H), 4.18 (m, 2H), 2.53 (s, 3H), MS (EI) for C$_{25}$H$_{19}$BrClN$_5$O: 522 (MH$^+$).

4-[7-bromo-8-(methyloxy)quinazolin-4-yl]-7-(2-methyl-1H-benzimidazol-6-yl)-2,3,4,5-tetrahydro-1,4-benzoxazepine. Prepared according to the method of example 1 by using 7-bromo-4-chloro-8-methoxyquinazoline (reagent preparation 1) in step 5. $^1$H NMR (400 MHz, DMSO-D$_6$): 8.56, (s, 1H), 7.72 to 7.63 (m, 3H), 7.54 to 7.45 (m, 2H), 7.41 (dd, 1H), 7.00 (d, 1H), 5.11 (s, 2H), 4.49 (m, 2H), 4.21 (m, 2H), 4.02 (s, 3H), 2.51 (s, 3H), MS (EI) for C$_{26}$H$_{22}$BrN$_5$O$_2$: 516 (MH$^+$).

4-[7-bromo-6-(methyloxy)quinazolin-4-yl]-7-(2-methyl-1H-benzimidazol-6-yl)-2,3,4,5-tetrahydro-1,4-benzoxazepine. Prepared according to the method of example 1 by 7-bromo-4-chloro-6-methoxyquinazoline in step 5. $^1$H NMR (400 MHz, DMSO-D$_6$): 8.52, (s, 1H), 8.09 (s, 1H), 7.83 (br, 1H), 7.55 (dd, 2H), 7.40 (d, 1H), 7.18 (s, 1H), 7.05 (d, 1H), 5.08 (s, 2H), 4.55 (m, 2H), 4.13 (m, 2H), 3.60 (s, 3H), 2.51 (s, 3H), MS (EI) for C$_{26}$H$_{22}$BrN$_5$O$_2$: 516 (MH$^+$).

4-[6-iodo-7-(methyloxy)quinazolin-4-yl]-7-(2-methyl-1H-benzimidazol-6-yl)-2,3,4,5-tetrahydro-1,4-benzoxazepine. Prepared according to the method of example 1 by using 4-chloro-6-iodo-7-methoxyquinazoline in step 5. $^1$H NMR (400 MHz, DMSO-D$_6$): 8.53, (s, 1H), 8.40 (s, 1H), 7.78 (br, 1H), 7.73 (br, 1H), 7.54 (dd, 1H), 7.51 (s, 1H) 7.21 (s, 1H), 7.05 (d, 1H), 5.02 (s, 2H), 4.50 (m, 2H), 4.13 (m, 2H), 3.97 (s, 3H), 2.51 (s, 3H), MS (EI) for C$_{26}$H$_{22}$IN$_5$O$_2$: 564 (MH$^+$).

7-(2-methyl-1H-benzimidazol-6-yl)-4-(7-methyl-5,6,7,8-tetrahydroquinazolin-4-yl)-2,3,4,5-tetrahydro-1,4-benzoxazepine. Prepared according to the method of example 1 by using 4-chloro-7-methyl-5,6,7,8-tetrahydroquinazoline (reagent preparation 8) in step 5. $^1$H NMR (400 MHz, DMSO-D$_6$): 8.34 (s, 1H), 7.65 to 7.59 (m, 2H), 7.51 to 7.46 (m, 2H), 7.36 (dd, 1H), 7.02 (d, 1H), 4.70 (dd, 2H), 4.39 (m, 1H), 4.24 (m, 1H), 3.94 to 3.82 (m, 2H), 2.94 to 2.80 (m, 2H), 2.57 to 2.46 (m, 1H), 2.51 (s, 3H), 2.26 (dd, 1H), 1.92 (m, 1H), 1.82 (dd, 1H), 1.15 (m, 1H), 1.04 (d, 3H), MS (EI) for C$_{26}$H$_{27}$N$_5$O$_2$: 426 (MH$^+$).

4-(6,6-dimethyl-5,6,7,8-tetrahydroquinazolin-4-yl)-7-(2-methyl-1H-benzimidazol-6-yl)-2,3,4,5-tetrahydro-1,4-benzoxazepine. Prepared according to the method of example 1 by using 4-chloro-6,6-dimethyl-5,6,7,8-tetrahydroquinazoline (reagent preparation 3) in step 5. $^1$H NMR (400 MHz, Methano-D$_4$): 8.35 (s, 1H), 7.65 (br, 1H), 7.54 to 7.42 (m, 4H), 7.03 (d, 1H), 4.70 (dd, 2H), 4.35 (m, 2H), 3.95 (m, 2H), 2.78 (t, 2H), 2.58 (s, 3H), 2.50 (s, 2H), 1.68 (t, 2H), 0.90 (s, 6H), MS (EI) for C$_{27}$H$_{29}$N$_5$O: 440 (MH$^+$).

4-(6-ethyl-5,6,7,8-tetrahydroquinazolin-4-yl)-7-(2-methyl-1H-benzimidazol-6-yl)-2,3,4,5-tetrahydro-1,4-benzoxazepine. Prepared according to the method of example 1 by using 4-chloro-6-ethyl-5,6,7,8-tetrahydroquinazoline (reagent preparation 8) in step 5. $^1$H NMR (400 MHz, Methanol-D$_4$): 8.33 (s, 1H), 7.65 (br, 1H), 7.51 (dd, 2H), 7.45 to 7.39 (m, 2H), 7.03 (d, 1H), 4.69 (dd, 2H), 4.45 (m, 1H), 4.24 (m, 1H), 4.07 (m, 1H), 3.83 (m, 1H), 2.85 (dd, 1H), 2.72 (m, 1H), 2.58 (s, 3H), 2.54 (br, 1H), 2.40 (m, 1H), 1.93 (m, 1H), 1.49 to 1.26 (m, 3H), 0.75 (t, 3H), MS (EI) for C$_{27}$H$_{29}$NO: 440 (MH$^+$).

4-{5-[(4-fluorophenyl)methyl]-6-methylpyrimidin-4-yl}-7-(2-methyl-1H-benzimidazol-6-yl)-2,3,4,5-tetrahydro-1,4-benzoxazepine. Prepared according to the method of example 1 by using 4-chloro-5-(4-fluorobenzyl)-6-methylpyrimidine (reagent preparation 5) in step 5. $^1$H NMR (400 MHz, methanol-d$_4$): 8.47 (s, 1H), 7.54-7.50 (m, 2H), 7.43 (d, 1H), 7.24 (d, 1H), 7.11-7.05 (m, 2H), 7.02-6.92 (m, 3H), 6.76 (s, 1H), 4.53

(s, 2H), 4.30 (t, 2H), 4.01 (s, 2H), 3.90 (t, 2H), 2.60 (s, 3H), 2.22 (s, 3H); MS (EI) for $C_{29}H_{26}FN_5O$: 480 (MH$^+$).

4-(7-bromoquinazolin-4-yl)-7-(2-methyl-1H-benzimidazol-6-yl)-2,3,4,5-tetrahydro-1,4-benzoxazepine. Prepared according to the method of example 1 by using 7-bromo-4-chloroquinazoline in step 5. $^1$H NMR (400 MHz, d$_6$-DMSO): 12.26 (br s, 1H), 8.52 (s, 1H), 8.02-7.96 (m, 2H), 7.71-7.61 (m, 3H), 7.54-7.48 (m, 2H), 7.41 (d, 1H), 6.99 (d, 1H), 4.49 (t, 2H), 4.22 (t, 2H), 2.51 (s, 3H); MS (EI) for $C_{25}H_{20}BrN_5O$: 487 (MH$^+$).

4-(8-bromoquinazolin-4-yl)-7-(2-methyl-1H-benzimidazol-6-yl)-2,3,4,5-tetrahydro-1,4-benzoxazepine. Prepared as the acetate salt according to the method of example 1 by using 8-bromo-4-chloroquinazoline in step 5. $^1$H NMR (400 MHz, d$_6$-DMSO): 12.26 (br s, 1H), 8.61 (s, 1H), 8.18 (d, 2H), 8.06 (d, 1H), 7.71-7.66 (m, 2H), 7.52 (d, 2H), 7.45-7.39 (m, 2H), 7.01 (d, 1H), 5.13 (s, 2H), 4.49 (t, 2H), 4.23 (t, 2H), 2.51 (s, 3H); MS (EI) for $C_{25}H_{20}BrN_5O$: 487 (MH$^+$).

7-(2-methyl-1H-benzimidazol-6-yl)-4-(7-methylquinazolin-4-yl)-2,3,4,5-tetrahydro-1,4-benzoxazepine. Prepared as the acetate salt according to the method of example 1 by using 4-chloro-7-methylquinazoline in step 5. $^1$H NMR (400 MHz, d$_6$-DMSO): 12.26 (br s, 1H), 8.50 (s, 1H), 7.95 (d, 1H), 7.67 (s, 2H), 7.58 (s, 1H), 7.54-7.49 (m, 2H), 7.40 (d, 1H), 7.33 (d, 1H), 7.01 (d, 1H), 5.09 (s, 2H), 4.49 (t, 2H), 4.19 (t, 2H), 2.51 (s, 3H), 2.48 (s, 3H); MS (EI) for $C_{26}H_{23}N_5O$: 422 (MH$^+$).

4-(8-fluoroquinazolin-4-yl)-7-(2-methyl-1H-benzimidazol-6-yl)-2,3,4,5-tetrahydro-1,4-benzoxazepine. Prepared according to the method of example 1 by using 4-chloro-8-fluoroquinazoline in step 5. $^1$H NMR (400 MHz, d$_6$-DMSO): 8.60 (s, 1H), 7.98 (s, 1H), 7.93 (d, 1H), 7.89-7.81 (m, 3H), 7.74 (t, 1H), 7.61 (d, 1H), 7.54 (m, 1H), 7.05 (d, 1H), 5.23 (s, 2H), 4.56 (t, 2H), 4.31 (t, 2H), 2.82 (s, 3H); MS (EI) for $C_{25}H_{20}FN_5O$: 426 (MH$^+$).

7-(2-methyl-1H-benzimidazol-6-yl)-4-[8-(trifluoromethyl)quinazolin-4-yl]-2,3,4,5-tetrahydro-1,4-benzoxazepine. Prepared according to the method of example 1 by using 4-chloro-8-(trifluoromethyl)quinazoline in step 5. $^1$H NMR (400 MHz, d$_6$-DMSO): 8.61 (s, 1H), 8.33 (d, 1H), 8.21 (d, 1H), 7.80-7.74 (m, 2H), 7.67-7.54 (m, 2H), 7.22 (s, 1H), 7.10 (s, 1H), 7.03-6.96 (m, 1H), 5.18 (s, 2H), 4.52 (t, 2H), 4.27 (t, 2H), 2.63 (s, 3H); MS (EI) for $C_{26}H_{20}F_3N_5O$: 476 (MH$^+$).

4-(6,8-dichloroquinazolin-4-yl)-7-(2-methyl-1H-benzimidazol-6-yl)-2,3,4,5-tetrahydro-1,4-benzoxazepine. Prepared according to the method of example 1 by using 4,6,8-trichloroquinazoline in step 5. $^1$H NMR (400 MHz, d$_6$-DMSO): 8.64 (s, 1H), 8.19 (s, 1H), 8.00 (s, 1H), 7.80-7.76 (m, 2H), 7.59-7.43 (m, 3H), 7.04 (d, 1H), 5.09 (s, 2H), 4.55 (t, 2H), 4.20 (t, 2H), 2.50 (s, 3H); MS (EI) for $C_{25}H_{19}Cl_2N_5O$: 477 (MH$^+$).

7-(2-methyl-1H-benzimidazol-6-yl)-4-[7-(trifluoromethyl)quinazolin-4-yl]-2,3,4,5-tetrahydro-1,4-benzoxazepine. Prepared according to the method of example 1 by using 4-chloro-7-(trifluoromethyl)quinazoline in step 5. $^1$H NMR (400 MHz, d$_6$-DMSO): 12.00 (br. s, 1H), 8.62 (s, 1H), 8.29 (d, 1H), 8.11 (s, 1H), 7.88 (s, 1H), 7.82-7.71 (m, 3H), 7.67 (d, 1H), 7.57 (d, 1H), 7.03 (d, 1H), 5.21 (s, 2H), 4.53 (t, 2H), 4.29 (t, 2H), 2.70 (s, 3H); MS (EI) for $C_{26}H_{20}F_3N_5O$: 476 (MH$^+$).

7-(2-methyl-1H-benzimidazol-6-yl)-4-[6-(methylsulfonyl)quinazolin-4-yl]-2,3,4,5-tetrahydro-1,4-benzoxazepine. Prepared as the acetate salt according to the method of example 1 by using 4-chloro-6-(methylsulfonyl)quinazoline (reagent preparation 1) in step 5. $^1$H NMR (400 MHz, methanol-d$_4$): 8.68 (d, 1H), 8.63 (d, 1H), 8.24 (d, 1H), 7.95 (d, 1H), 7.77 (s, 1H), 7.72 (s, 1H), 7.54-7.51 (m, 3H), 7.05 (d, 1H), 5.20 (s, 2H), 4.53 (t, 2H), 4.37 (t, 2H), 3.06 (s, 3H), 2.59 (s, 3H); MS (EI) for $C_{26}H_{23}N_5O_3S$: 486 (MH$^+$).

7-(2-methyl-1H-benzimidazol-6-yl)-4-[5-methyl-6-(1-methylethyl)pyrimidin-4-yl]-2,3,4,5-tetrahydro-1,4-benzoxazepine. Prepared according to the method of example 1 by using 4-chloro-6-isopropyl-5-methylpyrimidine (reagent preparation 5) in step 5. $^1$H NMR (400 MHz, methanol-d$_4$): 8.31 (s, 1H), 7.54 (s, 1H), 7.44-7.40 (m, 2H), 7.39-7.31 (m, 2H), 6.95 (d, 1H), 4.55 (s, 2H), 4.24 (t, 2H), 3.80 (t, 2H), 3.21 (m, 1H), 2.49 (s, 3H), 2.20 (s, 3H), 1.12 (d, 6H); MS (EI) for $C_{25}H_{27}N_5O$: 414 (MH$^+$).

4-(5-ethyl-6-methylpyrimidin-4-yl)-7-(2-methyl-1H-benzimidazol-6-yl)-2,3,4,5-tetrahydro-1,4-benzoxazepine. Prepared as the trifluoroacetate salt according to the method of example 1 by using 4-chloro-5-ethyl-6-methylpyrimidine in step 5. $^1$H NMR (400 MHz, methanol-d$_4$): 8.50 (s, 1H), 7.90 (s, 1H), 7.83-7.77 (m, 2H), 7.72 (s, 1H), 7.55 (d, 1H), 7.05 (d, 1H), 5.17 (s, 2H), 4.50 (t, 2H), 4.26 (t, 2H), 2.88 (s, 3H), 2.80 (q, 2H), 2.53 (s, 3H), 1.23 (t, 3H); MS (EI) for $C_{24}H_{25}N_5O$: 400 (MH$^+$).

4-[5-(cyclopropylmethyl)-6-methylpyrimidin-4-yl]-7-(2-methyl-1H-benzimidazol-6-yl)-2,3,4,5-tetrahydro-1,4-benzoxazepine. Prepared as described in example 1 using 4-chloro-5-(cyclopropylmethyl)-6-methylpyrimidine (reagent preparation 5) in step 5. $^1$H NMR (400 MHz, methanol-d$_4$): 8.36 (s, 1H), 7.64 (s, 1H), 7.57-7.41 (m, 4H), 7.04 (d, 1H), 4.65 (s, 2H), 4.35 (t, 1H), 3.89 (t, 2H), 2.71 (d, 2H), 2.58 (s, 3H), 2.49 (s, 3H), 0.86 (m, 1H), 0.36 (m, 2H), 0.04 (m, 2H); MS (EI) for $C_{26}H_{27}N_5O$: 426 (MH$^+$).

4-{5-[(4-chlorophenyl)methyl]-6-methylpyrimidin-4-yl}-7-(2-methyl-1H-benzimidazol-6-yl)-2,3,4,5-tetrahydro-1,4-benzoxazepine. Prepared according to the method of example 1 using 4-chloro-5-(4-chlorobenzyl)-6-methylpyrimidine (reagent preparation 5) in step 5. $^1$H NMR (400 MHz, methanol-d$_4$): 8.47 (s, 1H), 7.55-7.51 (m, 2H), 7.43 (d, 1H), 7.21-7.17 (m, 3H), 7.06-6.98 (m, 3H), 6.71 (s, 1H), 4.51 (s, 1H), 4.31 (t, 2H), 3.99 (s, 2H), 3.88 (t, 2H), 2.60 (s, 3H), 2.21 (s, 3H); MS (EI) for $C_{29}H_{26}ClN_5O$: 497 (MH$^+$).

4-{5-[(3,5-difluorophenyl)methyl]-6-methylpyrimidin-4-yl}-7-(2-methyl-1H-benzimidazol-6-yl)-2,3,4,5-tetrahydro-1,4-benzoxazepine. Prepared according to the method of example 1 using 4-chloro-5-(3,5-difluorobenzyl)-6-methylpyrimidine (reagent preparation 5) in step 5. $^1$H NMR (400 MHz, methanol-d$_4$): 8.49 (s, 1H), 7.52-7.49 (m, 2H), 7.45 (d, 1H), 7.28 (d, 1H), 7.00 (d, 1H), 6.90 (s, 1H), 6.83 (t, 1H), 6.68 (d, 2H), 4.55 (s, 2H), 4.30 (t, 2H), 4.07 (s, 2H), 3.89 (t, 2H); MS (EI) for $C_{29}H_{25}F_2N_5O$: 498 (MH$^+$).

7-(2-methyl-1H-benzimidazol-6-yl)-4-(6-methyl-5-{[3-(trifluoromethyl)phenyl]methyl}pyrimidin-4-yl)-2,3,4,5-tetrahydro-1,4-benzoxazepine. Prepared according to the method of example 1 using 4-chloro-6-methyl-5-(3-(trifluoromethyl)benzyl)pyrimidine (reagent preparation 5) in step 5. $^1$H NMR (400 MHz, methanol-d$_4$): 8.49 (s, 1H), 7.55-7.48 (m, 3H), 7.45-7.37 (m, 2H), 7.35 (s, 1H), 7.30 (d, 1H), 7.24 (d, 1H), 7.00 (d, 1H), 6.88 (s, 1H), 4.57 (s, 2H), 4.28 (t, 2H), 4.15 (s, 2H), 3.88 (t, 2H), 2.60 (s, 3H), 2.21 (s, 3H); MS (EI) for $C_{30}H_{26}F_3N_5O$: 530 (MH$^+$).

2-chloro-N,N-dimethyl-5-({4-methyl-6-[7-(2-methyl-1H-benzimidazol-6-yl)-2,3-dihydro-1,4-benzoxazepin-4(5H)-yl]pyrimidin-5-yl}methyl)aniline. Prepared as the trifluoroacetate salt according to the method of example 1 using 4-chloro-5-(4-chloro-3-fluorobenzyl)-6-methylpyrimidine (reagent preparation 5) in step 5, subsequent side reaction displacement of the 3 fluoro by dimethyl amine yielded the title compound. $^1$H NMR (400 MHz, methanol-d$_4$): 8.64 (s, 1H), 7.80-7.77 (m, 2H), 7.67 (d, 1H), 7.53 (d, 1H), 7.29 (d, 1H), 7.16 (s, 1H), 7.05 (d, 1H), 6.91 (s, 1H), 6.73 (d, 1H), 5.03

(s, 2H), 4.39 (t, 2H), 4.18 (t, 2H), 4.05 (s, 2H), 2.88 (s, 3H), 2.63 (s, 6H), 2.32 (s, 3H); MS (EI) for $C_{31}H_{31}ClN_6O$: 540 (MH$^+$).

4-{5-[1-(3-fluorophenyl)ethyl]-6-methylpyrimidin-4-yl}-7-(2-methyl-1H-benzimidazol-6-yl)-2,3,4,5-tetrahydro-1,4-benzoxazepine. Prepared as the acetate salt according to the method of example 1 using 4-chloro-5-(1-(3-fluorophenyl) ethyl)-6-methylpyrimidine (reagent preparation 5) in step 5. $^1$H NMR (400 MHz, methanol-d$_4$): 8.51 (s, 1H), 7.50-7.43 (m, 3H), 7.32-7.25 (m, 1H), 7.17 (d, 1H), 7.05-6.95 (m, 4H), 6.83 (s, 1H), 4.60 (q, 1H), 4.43-4.35 (m, 2H), 4.26-4.19 (m, 1H), 3.99-3.91 (m, 1H), 3.82-3.74 (m, 1H), 2.60 (s, 3H), 2.14 (s, 3H), 1.63 (d, 3H); MS (EI) for $C_{30}H_{28}FN_5O$: 494 (MH$^+$).

4-(8-bromo-6-methylquinazolin-4-yl)-7-(2-methyl-1H-benzimidazol-6-yl)-2,3,4,5-tetrahydro-1,4-benzoxazepine. Prepared according to the method of example 1 by using 8-bromo-4-chloro-6-methylquinazoline (reagent preparation 1) in step 5. $^1$H NMR (400 MHz, d$_6$-DMSO): 12.25 (br. s, 1H), 8.59 (s, 1H), 8.05 (s, 1H), 7.80-7.76 (m, 2H), 7.65 (s, 1H), 7.55 (d, 1H), 7.47-7.41 (m, 2H), 7.03 (d, 1H), 5.07 (s, 2H), 4.51 (t, 2H), 4.17 (t, 2H), 2.50 (s, 3H), 2.35 (s, 3H); MS (EI) for $C_{26}H_{22}BrN_5O$: 501 (MH$^+$).

1-{4-ethyl-5-methyl-6-[7-(2-methyl-1H-benzimidazol-5-yl)-2,3-dihydro-1,4-benzoxazepin-4(5H)-yl]pyrimidin-2-yl}-N,N-dimethylmethanamine. Prepared according to the method of example 1 by using 1-(4-chloro-6-ethyl-5-methylpyrimidin-2-yl)-N,N-dimethylmethanamine (reagent preparation 17) in step 5. $^1$H NMR (400 MHz, DMSO-d$_6$) δ 7.74-7.30 (m, 5H), 7.00 (d, 1H), 4.60 (s, 2H), 4.32-4.25 (m, 2H), 3.84-3.76 (m, 2H), 3.37 (s, 2H), 2.64 (q, 2H), 2.49 (s, 3H), 2.20 (s, 3H), 2.14 (s, 6H), 1.15 (t, 3H); MS (EI) for $C_{27}H_{32}N_6O$: 457 (MH$^+$).

N,N-dimethyl-1-{4-[7-(2-methyl-1H-benzimidazol-5-yl)-2,3-dihydro-1,4-benzoxazepin-4(5H)-yl]-5-(1-methylethyl)pyrimidin-2-yl}methanamine. Prepared according to the method of example 1 by using 1-(4-chloro-5-isopropylpyrimidin-2-yl)-N,N-dimethylmethanamine (reagent preparation 17) in step 5. $^1$H NMR (400 MHz, DMSO-d6) δ 8.35 (s, 1H), 7.63 (s, 1H), 7.57 (d, 1H), 7.51 (d, 1H), 7.46 (dd, 1H), 7.37 (dd, 1H), 7.00 (d, 1H), 4.63 (s, 2H), 4.35-4.29 (m, 2H), 3.86-3.80 (m, 2H), 3.38 (s, 2H), 3.16-3.05 (m, 2H), 2.50 (s, 3H), 2.11 (s, 6H), 1.88 (s, 3H), 1.25 (d, 6H); MS (EI) for $C_{27}H_{32}N_6O$: 457 (MH$^+$).

1-{5-ethyl-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine. Prepared as an acetate salt by the method of example 1 using 1-(4-chloro-5-ethyl-6-methylpyrimidin-2-yl)-N,N-dimethylmethanamine (reagent preparation 17) in step 5. $^1$H NMR (400 MHz, DMSO-d6) δ 7.69 (br s, 1H), 7.60 (d, 1H), 7.53 (br s, 1H), 7.46 (dd, 1H), 7.40-7.34 (m, 1H), 7.00 (d, 1H), 4.61 (s, 2H), 4.34-4.28 (m, 2H), 3.83-3.76 (m, 2H), 3.42-3.38 (m, 2H), 2.62 (q, 2H), 2.50 (s, 3H), 2.36 (s, 3H), 2.12 (s, 6H), 1.89 (s, 3H), 1.16 (t, 3H); MS (EI) for $C_{27}H_{32}N_6O$: 457 (MH$^+$).

4-[6,6-dimethyl-2-({[2-(methyloxy)ethyl]oxy}methyl)-5,6,7,8-tetrahydroquinazolin-4-yl]-7-(2-methyl-1H-benzimidazol-6-yl)-2,3,4,5-tetrahydro-1,4-benzoxazepine. Prepared according to the method of example 1 by using 4-chloro-6,6-dimethyl-2-({[2-(methyloxy)ethyl]oxy}methyl)-5,6,7,8-tetrahydroquinazoline (reagent preparation 17) in step 5. $^1$H NMR (400 MHz, d$_6$-DMSO): 7.64 (d, 2H), 7.47 (dd, 2H), 7.38 (dd, 1H), 7.01 (d, 1H), 4.63 (s, 2H), 4.29 (m, 2H), 3.86 (m, 2H), 3.56 (m, 2H), 3.38 (m, 2H), 3.32 (brs, 2H), 3.17 (s, 3H), 2.70 (m, 2H), 2.49 (s, 3H), 2.47 (s, 2H), 1.60 (m, 2H), 0.87 (s, 6H); MS (EI) for $C_{31}H_{37}N_5O_3$: 528 (MH$^+$).

N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)-2-(methyloxy)ethanamine. Prepared according to the method of example 1 by using N-[(4-chloro-6,6-dimethyl-5,6,7,8-tetrahydroquinazolin-2-yl)methyl]-2-(methyloxy)ethanamine (reagent preparation 17) in step 5. $^1$H NMR (400 MHz, d$_6$-DMSO): 9.50 (brs, 1H), 7.98 (s, 2H), 7.82 (s, 2H), 7.61 (dd, 1H), 7.05 (d, 1H), 5.08 (brs, 1H), 4.49 (s, 2H), 4.28 (s, 2H), 4.12 (s, 2H), 3.56 (s, 1H), 3.20 (s, 3H), 3.12 (m, 2H), 2.86 (s, 3H), 2.78 (m, 2H), 2.54 (s, 2H), 2.51 (s, 3H), 1.60 (m, 2H), 0.87 (s, 6H); MS (EI) for $C_{31}H_{38}N_6O_2$: 527 (MH$^+$).

4-[6,6-dimethyl-2-(pyrrolidin-1-ylmethyl)-5,6,7,8-tetrahydroquinazolin-4-yl]-7-(2-methyl-1H-benzimidazol-5-yl)-2,3,4,5-tetrahydro-1,4-benzoxazepine. Prepared according to the method of example 1 by using 4-chloro-6,6-dimethyl-2-(pyrrolidin-1-ylmethyl)-5,6,7,8-tetrahydroquinazoline (reagent preparation 17) in step 5. $^1$H NMR (400 MHz, Methanol-d$_4$): 7.70 (br, 1H), 7.63 (br, 1H), 7.56 to 7.44 (m, 3H), 7.02 (d, 1H), 4.83 (s, 2H), 4.39 (m, 2H), 4.18 (s, 2H), 4.01 (m, 2H), 3.17 (m, 4H), 2.88 (t, 2H), 2.59 (s, 3H), 2.51 (s, 2H), 1.88 (m, 4H), 1.69 (t, 2H), 0.92 (s, 6H); MS (EI) for $C_{32}H_{38}N_6O$: 523 (MH$^+$).

4-{6,6-dimethyl-2-[(2R)-pyrrolidin-2-yl]-5,6,7,8-tetrahydroquinazolin-4-yl}-7-(2-methyl-1H-benzimidazol-5-yl)-2,3,4,5-tetrahydro-1,4-benzoxazepine. Prepared according to the method of example 1 by using phenylmethyl(2R)-2-(4-chloro-6,6-dimethyl-5,6,7,8-tetrahydroquinazolin-2-yl)pyrrolidine-1-carboxylate (reagent preparation 18) in step 5 followed by Cbz group deprotection. $^1$H NMR (400 MHz, Methanol-d$_4$): 7.70 (s, 1H), 7.63 (s, 1H), 7.54 (d, 1H), 7.47 (m, 2H), 7.00 (d, 1H), 4.84 (s, 2H), 4.46 (m, 1H), 4.37 (m, 2H), 4.01 (m, 2H), 3.13 (m, 2H), 2.80 (t, 2H), 2.59 (s, 3H), 2.52 (dd, 2H), 2.32 (m, 1H), 1.94 (m, 1H), 1.85 (m, 1H), 1.76 (m, 1H), 1.70 (t, 2H), 0.93 (d, 6H); MS (EI) for $C_{31}H_{36}N_6O$: 509 (MH$^+$).

{5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}methyl acetate. Prepared according to the method of example 1 by using {4-chloro-5-[(4-fluorophenyl)methyl]-6-methylpyrimidin-2-yl}methyl acetate (reagent preparation 17) in step 5. $^1$H NMR (400 MHz, Methanol-d$_4$): 7.57 (s, 1H), 7.50 (s, 1H), 7.43 (d, 1H), 7.25 (d, 1H), 7.09 (m, 2H), 7.03 to 6.93 (m, 3H), 6.83 (d, 1H), 5.07 (s 2H), 4.54 (s, 2H), 4.25 (m, 2H), 4.01 (s, 2H), 3.87 (m, 2H), 2.62 (s, 3H), 2.22 (s, 3H), 2.10 (s, 3H); MS (EI) for $C_{32}H_{30}FN_5O_3$: 552 (MH$^+$).

{5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}methanol. Prepared according to the method of example 1 by using {4-chloro-5-[(4-fluorophenyl)methyl]-6-methylpyrimidin-2-yl}methyl acetate (reagent preparation 17) in step 5, followed by acetate hydrolysis using standard techniques. $^1$H NMR (400 MHz, Methanol-d$_4$): 7.57 to 7.53 (m, 2H), 7.41 (d, 1H), 7.27 (d, 1H), 7.09 (m, 2H), 7.03 to 6.94 (m, 3H), 6.89 (d, 1H), 4.57 (s 2H), 4.55 (s, 2H), 4.26 (m, 2H), 4.00 (s, 2H), 3.91 (m, 2H), 2.59 (s, 3H), 2.21 (s, 3H); MS (EI) for $C_{30}H_{28}FN_5O_2$: 510 (MH$^+$).

N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)-2-fluoroethanamine. Prepared as diacetate salt according to the method of example 1 by using phenylmethyl[(4-chloro-6,6-dimethyl-5,6,7,8-tetrahydroquinazolin-2-yl)methyl](2-fluoroethyl)carbamate (reagent preparation 17) in step 5 followed by Cbz deprotection. $^1$H NMR (400 MHz, methanol-d$_4$): 7.66 (d, 1H), 7.59 (d, 1H), 7.52 (d, 1H), 7.46 (m, 2H), 7.02 (d, 1H), 4.78 (s, 2H), 4.44 (m, 2H), 4.35 (m, 2H), 4.01 (m, 2H), 3.86 (s, 2H), 2.93

(m, 2H), 2.79 (m, 2H), 2.58 (s, 3H), 2.52 (s, 2H), 1.95 (s, 6H), 1.68 (m, 2H), 0.92 (s, 6H); MS (EI) for $C_{30}H_{35}FN_6O$: 515 (MH$^+$).

N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)cyclopropanamine. Prepared as acetate salt according to the method of example 1 by using N-[(4-chloro-6,6-dimethyl-5,6,7,8-tetrahydroquinazolin-2-yl)methyl]cyclopropanamine (reagent preparation 17) in step 5. $^1$H NMR (400 MHz, methanol-d$_4$): 7.68 (d, 1H), 7.64 (d, 1H), 7.52 (d, 1H), 7.47 (m, 2H), 7.00 (d, 1H), 4.81 (s, 2H), 4.33 (m, 2H), 4.02 (m, 2H), 3.83 (s, 2H), 2.78 (m, 2H), 2.58 (s, 3H), 2.52 (s, 2H), 2.17 (m, 1H), 1.95 (s, 3H), 1.67 (m, 2H), 0.93 (s, 6H), 0.33 (m, 4H); MS (EI) for $C_{31}H_{36}N_6O$: 509 (MH$^+$).

N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)ethanamine. Prepared as acetate salt according to the method of example 1 by using benzyl (4-chloro-6,6-dimethyl-5,6,7,8-tetrahydroquinazolin-2-yl)methyl(ethyl)carbamate (reagent preparation 17) in step 5 followed by Cbz deprotection. $^1$H NMR (400 MHz, methanol-d$_4$): 7.66 (s, 1H), 7.60 (d, 1H), 7.53-7.43 (m, 3H), 7.03 (d, 1H), 4.81 (s, 2H), 4.36 (m, 2H), 4.02 (m, 2H), 3.98 (s, 2H), 2.88 (q, 2H), 2.80 (t, 2H), 2.58 (s, 3H), 2.52 (s, 2H), 1.90 (s, 3H), 1.69 (t, 2H), 1.10 (t, 3H), 0.92 (s, 6H); MS (EI) for $C_{30}H_{36}N_6O$: 497 (MH$^+$).

1-{5-(cyclopropylmethyl)-4-methyl-6-[7-(2-methyl-1H-benzimidazol-6-yl)-2,3-dihydro-1,4-benzoxazepin-4(5H)-yl]pyrimidin-2-yl}-N,N-dimethylmethanamine. Prepared as dihydrochloride salt according to the method of example 1 by using 1-(4-chloro-5-(cyclopropylmethyl)-6-methylpyrimidin-2-yl)-N,N-dimethylmethanamine (reagent preparation 17) in step 5. $^1$H NMR (400 MHz, methanol-d$_4$): 8.00 (s, 1H), 7.88 (m, 2H), 7.81 (d, 1H), 7.60 (dd, 1H), 7.08 (d, 1H), 5.20 (s, 2H), 4.58 (m, 2H), 4.54 (s, 2H), 4.24 (m, 2H), 2.92 (s, 6H), 2.81 (s, 3H), 2.74 (d, 2H), 2.59 (s, 3H), 0.86 (m, 1H), 0.44 (m, 2H), 0.02 (m, 2H); MS (EI) for $C_{20}H_{34}N_6O$: 483 (MH$^+$).

N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)cyclobutanamine. Prepared as acetate salt according to the method of example 1 by using benzyl (4-chloro-6,6-dimethyl-5,6,7,8-tetrahydroquinazolin-2-yl)methyl(cyclobutyl)carbamate (reagent preparation 17) in step 5 followed by Cbz deprotection. $^1$H NMR (400 MHz, methanol-d$_4$): 7.67 (s, 1H), 7.62 (s, 1H), 7.54-7.44 (m, 3H), 7.03 (d, 1H), 4.81 (s, 2H), 4.35 (m, 2H), 4.03 (m, 2H), 3.83 (s, 2H), 3.50 (m, 1H), 2.79 (t, 2H), 2.58 (s, 3H), 2.52 (s, 2H), 2.04 (m, 2H), 1.92 (s, 3H), 1.83 (m, 2H), 1.66 (m, 2H), 0.93 (s, 6H); MS (EI) for $C_{32}H_{38}N_6O$: 523 (MH$^+$).

4-[7-(2-methyl-1H-benzimidazol-6-yl)-2,3-dihydro-1,4-benzoxazepin-4(5H)-yl]-N-phenylpyrimidin-2-amine. Prepared by the method of example 1 using 2-anilino-4-chloropyrimidine in step 5. $^1$H NMR (400 MHz, DMSO-d6) δ 12.03 (br s, 1H), 9.01 (s, 1H), 7.98 (d, 1H), 7.50 (m, 9H), 7.01 (d, 1H), 6.89 (t, 1H), 4.87 (br s, 2H), 4.24 (s, 4H), 2.48 (s, 3H); MS (EI) for $C_{27}H_{24}N_6O$: 449.1 (MH$^+$).

1-{6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}-N,N-dimethylmethanamine. The trihydrochloride salt was prepared as in example 1 using 1-(4-chloro-6,6-dimethyl-5,6,7,8-tetrahydroquinazolin-2-yl)-N,N-dimethylmethanamine (reagent preparation 17) in step 5. $^1$H NMR (400 MHz, CD$_3$OD) δ 8.03 (s, 1H), 7.97 (s, 1H), 7.91 (dd, 1H), 7.81 (d, 1H), 7.62 (dd, 1H), 7.07 (d, 1H), 5.32 (s, 2H), 4.62-4.55 (m, 4H), 4.39-4.31 (m, 2H), 2.88 (s, 6H), 2.97-2.80 (m, 2H), 2.62 (s, 2H), 1.71 (t, 2H), 0.92 (s, 6H); MS (ES) for $C_{30}H_{36}N_6O$: 497.2 (MH$^+$).

4-(2-{[(3S)-3-fluoropyrrolidin-1-yl]methyl}-6,6-dimethyl-5,6,7,8-tetrahydroquinazolin-4-yl)-7-(2-methyl-1H-benzimidazol-6-yl)-2,3,4,5-tetrahydro-1,4-benzoxazepine. The trihydrochloride salt was prepared as in example 1 using (S)-4-chloro-2-((3-fluoropyrrolidin-1-yl)methyl)-6,6-dimethyl-5,6,7,8-tetrahydroquinazoline (reagent example 17) in step 5. $^1$H NMR (400 MHz, CD$_3$OD) δ 7.99 (s, 1H), 7.92-7.86 (m, 1H), 7.84 (bs, 1H), 7.79 (d, 1H), 7.61 (dd, 1H), 7.09 (d, 1H), 5.41-5.20 (m, 1H), 5.19-5.02 (m, 2H), 4.64-4.55 (m, 2H), 4.55-4.48 (m, 2H), 4.24-4.13 (m, 2H), 3.88-3.50 (m, 4H), 2.88 (s, 3H), 2.90-2.79 (m, 2H), 2.64-2.51 (m, 2H), 2.25 (s, 2H), 1.70 (t, 2H), 0.91 (d, 6H); MS (ES) for $C_{32}H_{37}FN_6O$: 541.4 (MH$^+$).

4-(2-{[(3R)-3-fluoropyrrolidin-1-yl]methyl}-6,6-dimethyl-5,6,7,8-tetrahydroquinazolin-4-yl)-7-(2-methyl-1H-benzimidazol-6-yl)-2,3,4,5-tetrahydro-1,4-benzoxazepine. The trihydrochloride salt was prepared as in example 1 using (R)-4-chloro-2-((3-fluoropyrrolidin-1-yl)methyl)-6,6-dimethyl-5,6,7,8-tetrahydroquinazoline (reagent preparation 17) in step 5. $^1$H NMR (400 MHz, CD$_3$OD) δ 7.95 (s, 1H), 7.89-7.84 (m, 1H), 7.80 (s, 1H), 7.78 (s, 1H), 7.59 (dd, 1H), 7.09 (d, 1H), 5.44-5.23 (m, 1H), 5.00 (s, 2H), 4.52 (s, 2H), 4.50-4.45 (m, 2H), 4.16-4.07 (m, 2H), 3.59 (s, 4H), 2.88 (s, 3H), 2.91-2.78 (m, 2H), 2.55 (s, 2H), 2.36-2.19 (m, 2H), 1.70 (t, 2H), 0.90 (d, 6H); MS (ES) for $C_{32}H_{37}FN_6O$: 541.4 (MH$^+$).

4-(6,6-dimethyl-2-pyridin-2-yl-5,6,7,8-tetrahydroquinazolin-4-yl)-7-(2-methyl-1H-benzimidazol-6-yl)-2,3,4,5-tetrahydro-1,4-benzoxazepine. The trihydrochloride salt was prepared as in example 1 using 4-chloro-6,6-dimethyl-2-(pyridin-2-yl)-5,6,7,8-tetrahydroquinazoline (reagent preparation 17) in step 5. $^1$H NMR (400 MHz, d$_6$-DMSO) δ 8.80 (d, 1H), 8.48 (d, 1H), 8.10 (s, 1H), 8.01 (d, 1H), 7.98 (s, 1H), 7.85 (d, 1H), 7.79 (d, 1H), 7.69 (t, 1H), 7.57 (d, 1H), 6.99 (d, 1H), 5.26 (s, 2H), 4.55 (bs, 2H), 4.30 (bs, 2H), 2.94 (t, 2H), 2.85 (s, 3H), 2.64 (s, 2H), 1.62 (t, 2H), 0.92 (s, 6H); MS (ES) for $C_{32}H_{32}N_6O$: 517.3 (MH$^+$).

2-{6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}propan-2-ol. The dihydrochloride salt was prepared as in example 1 using 2-(4-chloro-6,6-dimethyl-5,6,7,8-tetrahydroquinazolin-2-yl)propan-2-ol (reagent preparation 17) in step 5. $^1$H NMR (400 MHz, CD$_3$OD) δ 7.88 (s, 1H), 7.78 (s, 2H), 7.74 (d, 1H), 7.53 (dd, 1H), 7.01 (d, 1H), 5.16 (s, 2H), 4.54-4.46 (m, 2H), 4.31-4.24 (m, 2H), 2.89 (t, 2H), 2.85 (s, 3H), 2.61 (s, 2H), 1.70 (t, 2H), 1.39 (d, 6H), 0.96 (s, 6H); MS (ES) for $C_{30}H_{35}N_5O_2$: 498.2 (MH$^+$).

N,N-dimethyl-1-{4-methyl-6-[7-(2-methyl-1H-benzimidazol-5-yl)-2,3-dihydro-1,4-benzoxazepin-4(5H)-yl]-5-(1-methylethyl)pyrimidin-2-yl}methanamine. Synthesized according to the method of example 1 using 1-(4-chloro-5-(4-fluorobenzyl)-6-methylpyrimidin-2-yl)-N,N-dimethylmethanamine (reagent preparation 17) in step 5. $^1$H NMR (400 MHZ, CDCl$_3$): 9.84 (br, 1H), 7.69 (br, 1H), 7.41 (dd, 2H), 7.23 (br, 1H), 7.03-6.97 (m, 3H), 6.92-6.88 (m, 2H), 6.69 (br, 1H), 4.35 (s, 2H), 4.21 (tr, 2H), 3.91 (s, 2H), 3.83 (tr, 2H), 3.60 (s, 2H), 2.67 (s, 3H), 2.39 (s, 6H), 2.23 (s, 3H). MS (EI) for $C_{32}H_{33}N_6OF$: 537 (MH$^+$).

N,N-dimethyl-1-{4-methyl-6-[7-(2-methyl-1H-benzimidazol-5-yl)-2,3-dihydro-1,4-benzoxazepin-4(5H)-yl]-5-(1-methylethyl)pyrimidin-2-yl}methanamine. Synthesized according to the method of example 1 using 1-(4-chloro-5-isopropyl-6-methylpyrimidin-2-yl)-N,N-dimethylmethanamine (reagent preparation 17) in step 5. $^1$H NMR (400 MHZ, DMSO-d$_6$): 10.85 (br, 1H), 8.02 (s, 1H), 7.99 (s, 1H), 7.83 (m, 2H), 7.55 (d, 1H), 6.98 (d, 1H), 5.04 (br s, 2H), 4.47 (br s, 2H), 4.43 (s, 2H), 3.95 (br s, 2H), 3.14 (m, 1H), 2.81 (s, 3H), 2.67 (s, 6H), 2.56 (s, 3H), 1.32 (d, 6H). MS (EI) for $C_{28}H_{34}N_6O$: 471 (MH$^+$).

N-({5-[(4-fluorophenyl)methyl]-4-methyl-6-[7-(2-methyl-1H-benzimidazol-6-yl)-2,3-dihydro-1,4-benzoxazepin-4(5H)-yl]pyrimidin-2-yl}methyl)cyclopropanamine. Prepared as acetate salt according to the method of example 1 by using N-((4-chloro-5-(4-fluorobenzyl)-6-methylpyrimidin-2-yl)methyl)cyclopropanamine (reagent preparation 17) in step 5 $^1$H NMR (400 MHz, methanol-d$_4$): 7.59 (s, 1H), 7.53 (d, 1H), 7.44 (dd, 1H), 7.34 (d, 1H), 7.10 (m, 3H), 6.99 (m, 3H), 4.67 (s, 2H), 4.25 (m, 2H), 4.05 (s, 2H), 3.90 (m, 2H), 3.85 (s, 2H), 2.66 (s, 3H), 2.22 (s, 3H), 2.17 (m, 1H), 1.94 (s, 3H), 0.37 (m, 2H), 0.32 (m, 2H); MS (EI) for $C_{33}H_{33}FN_6O$: 549 (MH$^+$).

4-[7-(2-methyl-1H-benzimidazol-6-yl)-2,3-dihydro-1,4-benzoxazepin-4(5H)-yl]pyridin-2-amine. Prepared according to the method of example 1 using 4-chloro-2-nitropyridine in step 5 followed by nitro group reduction using palladium on carbon hydrogenation in methanol at 35 psi. $^1$H NMR (400 MHz, CD$_3$OD) δ 7.76-7.62 (m, 2H), 7.60-7.37 (m, 4H), 7.07 (d, 1H), 6.57 (dd, 1H), 6.06 (d, 1H), 4.82 (s, 2H), 4.29-4.18 (m, 2H), 4.06-3.97 (m, 2H), 2.59 (s, 3H).

Example 2

Methyl (6-{4-[6,7-bis(methyloxy)quinolin-4-yl]-2,3,4,5-tetrahydro-1,4-benzoxazepin-7-yl}-1H-benzimidazol-2-yl)carbamate STEP 1: 1,1-dimethylethyl 7-bromo-2,3-dihydro-1,4-benzoxazepine-4(5H)-carboxylate (10 g, 30.5 mmol) was taken into hot ethanol (10 mL) followed by addition of 4 M hydrogen chloride in dioxane solution (2.1 eq, 16 mL) and the resulting solution was allowed to slowly cool to ambient temperature over one hour. An excess of ethyl ether was then added and the resulting slurry was filtered. The filter cake was washed with ethyl ether and dried to give 7-bromo-2,3,4,5-tetrahydro-1,4-benzoxazepine hydrochloride (7.9 g, 98% yield) as a colorless crystalline solid. MS (EI) for $C_9H_{10}NOBr$: 229 (MH$^+$).

STEP 2: A mixture of 7-bromo-2,3,4,5-tetrahydro-1,4-benzoxazepine hydrochloride (300 mg, 1.13 mmol), 4-chloro-6,7-dimethoxyquinoline (253 mg, 1.13 mmol), and potassium carbonate (470 mg, 3.40 mmol) in N-methylpyrrolidine (2 mL) was stirred at 160° C. for 17 h. Ethyl acetate (75 mL) was added and the mixture was washed with water (3×25 mL) and brine (25 mL), dried over sodium sulfate, and concentrated. Column chromatography on silica (dichloromethane:methanol 95:5) afforded 4-[6,7-bis(methyloxy)quinolin-4-yl]-7-bromo-2,3,4,5-tetrahydro-1,4-benzoxazepine (80 mg). MS (EI) for $C_{20}H_{19}BrN_2O_3$: 416 (MH$^+$).

STEP 3: A mixture 4-[6,7-bis(methyloxy)quinolin-4-yl]-7-bromo-2,3,4,5-tetrahydro-1,4-benzoxazepine (78 mg, 0.19 mmol), 4-amino-3-nitrophenylboronic acid pinacol ester (59 mg, 0.23 mmol), potassium carbonate (105 mg, 0.76 mmol), and dichloro[1,1'-bis(diphenylphosphino)ferrocene]palladium (II) dichloromethane adduct (20 mg, 0.02 mmol) in dimethoxyethane (3 mL) was stirred at 80° C. for 3 h. Ethyl acetate (50 mL) was added and the mixture was washed with water (20 mL), and brine (20 mL), dried over sodium sulfate, and concentrated. Column chromatography on silica (dichloromethane:methanol 95:5) gave 4-{4-[6,7-bis(methyloxy)quinolin-4-yl]-2,3,4,5-tetrahydro-1,4-benzoxazepin-7-yl}-2-nitroaniline (56 mg, 63% yield). MS (EI) for $C_{26}H_{24}N_4O_5$: 473 (MH$^+$).

STEP 4: A solution of 4-{4-[6,7-bis(methyloxy)quinolin-4-yl]-2,3,4,5-tetrahydro-1,4-benzoxazepin-7-yl}-2-nitroaniline (56 mg, 0.12 mmol) in methanol (20 mL) was hydrogenated at 30 psi over 10% Pd—C (25 mg) for 4 h. The catalyst was filtered off, and the filtrate was concentrated to give 4-{4-[6,7-bis(methyloxy)quinolin-4-yl]-2,3,4,5-tetrahydro-1,4-benzoxazepin-7-yl}benzene-1,2-diamine (40 mg, 77% yield) as a brown oil. MS (EI) for $C_{26}H_{26}N_4O_3$: 443 (MH STEP 5: To a solution of 4-{4-[6,7-bis(methyloxy)quinolin-4-yl]-2,3,4,5-tetrahydro-1,4-benzoxazepin-7-yl}benzene-1,2-diamine (40 mg, 0.09 mmol) in acetic acid (2 mL) was added 1,3-bis(methoxycarbonyl)-2-methyl-2-thiopseudourea (19 mg, 0.09 mmol) and the reaction mixture was stirred at 80° C. for 30 min. After cooling to room temperature the mixture was concentrated, and purified by preparative reverse phase HPLC to provide methyl (6-{4-[6,7-bis(methyloxy)quinolin-4-yl]-2,3,4,5-tetrahydro-1,4-benzoxazepin-7-yl}-1H-benzimidazol-2-yl)carbamate (17 mg, 25% yield) as a brown solid. $^1$H NMR (400 MHz, CD$_3$OD): 8.30 (d, 1H), 7.78 (m, 2H), 7.68 (m, 2H), 7.60 (m, 1H), 7.27 (d, 2H), 7.11 (d, 1H), 7.04 (d, 1H), 5.17 (s, 2H), 4.64 (m, 2H), 4.25 (m, 2H), 4.01 (s, 3H), 3.96 (s 3H), 3.63 (s, 3H); MS (EI) for $C_{29}H_{27}N_5O_5$: 526 (MH$^+$).

Using analogous synthetic techniques and substituting with alternative starting reagents in steps 2, 3 or 5 the following compounds of the invention were prepared. Alternative starting materials were obtained commercially unless otherwise indicated.

Methyl[6-(4-quinolin-4-yl-2,3,4,5-tetrahydro-1,4-benzoxazepin-7-yl)-1H-benzimidazol-2-yl]carbamate. Synthesized according to the method of example 2 using 4-chloroquinoline in step 2. $^1$H NMR (400 MHz, d$_6$-DMSO): 8.72 (d, 1H), 8.03 (d, 1H), 7.96 (d, 1H), 7.69 (m, 3H), 7.53 (m, 2H), 7.46 (d, 1H), 7.39 (d, 1H), 7.11 (d, 1H) 7.02 (d, 1H) 4.63 (s, 2H), 4.38 (br s, 2H), 3.81 (br s, 2H), 3.77 (s, 3H); MS (EI) for $C_{27}H_{23}N_5O_3$: 466 (MH$^+$).

Methyl [1-methyl-5-(4-quinolin-4-yl-2,3,4,5-tetrahydro-1,4-benzoxazepin-7-yl)-1H-benzimidazol-2-yl]carbamate. Synthesized according to the method of example 2 using 4-chloroquinoline in step 2 and 4-methylamino-3-nitrophenylboronic acid pinacol ester (Bioorg. Med. Chem. Lett. 2007, 17(19), 5406-5409) in step 3. $^1$H NMR (400 MHz, d$_6$-DMSO): 8.62 (d, 1H), 8.01 (d, 1H), 7.94 (d, 1H), 7.70 (m, 3H), 7.64 (m, 2H), 7.51 (m, 4H), 7.13 (d, 1H) 7.01 (d, 1H) 4.64 (s, 2H), 4.39 (br s, 2H), 3.82 (br s, 2H), 3.64 (s, 3H), 3.54 (s, 3H); MS (EI) for $C_{28}H_{25}N_5O_3$: 480 (MH$^+$).

1-Methyl-5-(4-quinolin-4-yl-2,3,4,5-tetrahydro-1,4-benzoxazepin-7-yl)-1H-benzimidazol-2-amine. Synthesized according to the method of example 2 using 4-chloroquinoline in step 2 and 4-methylamino-3-nitrophenylboronic acid pinacol ester (Bioorg. Med. Chem. Lett. 2007, 17(19), 5406-5409) in step 3. Material obtained as a co-product in the formation of methyl [1-methyl-5-(4-quinolin-4-yl-2,3,4,5-tetrahydro-1,4-benzoxazepin-7-yl)-1H-benzimidazol-2-yl]carbamate. $^1$H NMR (400 MHz, d$_6$-DMSO): 8.62 (d, 1H), 8.04 (d, 1H), 7.96 (d, 1H), 7.68 (m, 2H), 7.52 (m, 2H), 7.42 (s, 1H), 7.13 (dt, 2H) 7.08 (d, 1H), 7.04 (d, 1H), 6.48 (br s, 2H), 4.68 (s, 2H), 4.38 (br s, 2H), 3.81 (br s, 2H), 3.52 (s, 3H); MS (EI) for $C_{26}H_{23}N_5O$: 422 (MH$^+$).

Methyl [1-methyl-6-(4-quinolin-4-yl-2,3,4,5-tetrahydro-1,4-benzoxazepin-7-yl)-1H-benzimidazol-2-yl]carbamate. Synthesized according to the method of example 2 using 4-chloroquinoline in step 2 and 4-nitro-3-methylaminophenylboronic acid pinacol ester (Bioorg. Med. Chem. Lett. 2007, 17(19), 5406-5409) in step 3. $^1$H NMR (400 MHz, d$_6$-DMSO): 8.63 (d, 1H), 8.02 (d, 1H), 7.94 (d, 1H), 7.71 (m, 2H), 7.62 (s, 1H), 7.50 (m, 4H), 7.13 (d, 1H) 7.03 (d, 1H) 4.64

(s, 2H), 4.40 (br s, 2H), 3.81 (br s, 2H), 3.63 (s, 3H), 3.55 (s, 3H); MS (EI) for $C_{28}H_{25}N_5O_3$: 480 (MH$^+$).

2-(Methyloxy)ethyl [6-(4-quinolin-4-yl-2,3,4,5-tetrahydro-1,4-benzoxazepin-7-yl)-1H-benzimidazol-2-yl]carbamate. Synthesized according to the method of example 2 using 4-chloroquinoline in step 2 and 1,3-bis-[2-(methoxy)ethoxycarbonyl]-2-methyl-2-thiopseudourea (reagent preparation 10) in step 5. $^1$H NMR (400 MHz, d$_6$-DMSO): 8.62 (d, 1H), 8.03 (d, 1H), 7.94 (d, 1H), 7.71 (m, 3H), 7.53 (m, 2H), 7.47 (d, 1H), 7.38 (m, 1H), 7.11 (d, 1H) 7.01 (d, 1H) 4.64 (s, 2H), 4.31 (br s, 2H), 3.83 (br s, 2H), 3.61 (m, 2H), 3.34 (br s, 2H), 3.30 (s, 3H); MS (EI) for $C_{29}H_{27}N_5O_4$: 510 (MH$^+$).

4-Piperidin-1-yl-N-[6-(4-quinolin-4-yl-2,3,4,5-tetrahydro-1,4-benzoxazepin-7-yl)-1H-benzimidazol-2-yl]butanamide. Synthesized according to the method of example 2 using 4-chloroquinoline in step 2 and 1,3-bis-[3-(piperidin-1-yl)propylcarbonyl]-2-methyl-2-thiopseudourea (reagent preparation 10) in step 5. $^1$H NMR (400 MHz, d$_6$-DMSO): 9.22 (br s, 1H), 8.67 (d, 1H), 8.33 (d, 1H), 7.95 (m, 3H), 7.78 (s, 1H), 7.73 (t, 1H), 7.57 (m, 3H), 6.98 (d, 2H), 5.31 (s, 2H), 4.61 (br s, 2H), 4.41 (br s, 2H), 3.43 (d, 2H), 3.11 (m, 2H), 2.91 (m, 2H), 2.59 (m, 2H), 2.02 (m, 2H), 1.81 (m, 2H); MS (EI) for $C_{34}H_{36}N_6O_2$: 561 (MH$^+$).

Methyl [6-(4-{5-[(4-fluorophenyl)methyl]-6-methylpyrimidin-4-yl}-2,3,4,5-tetrahydro-1,4-benzoxazepin-7-yl)-1H-benzimidazol-2-yl]carbamate. Synthesized according to the method of example 2 using 4-chloro-5-(4-fluorobenzyl)-6-methylpyrimidine in step 2. $^1$H NMR (400 MHz, DMSO-D$_6$): 11.70 (bs, 1H), 8.50 (s, 1H), 7.49 (s, 1H), 7.38-7.46 (m, 2H), 7.09-7.16 (m, 5H), 6.99 (d, 1H), 6.88 (s, 1H), 4.48 (s, 2H), 4.23-4.30 (m, 2H), 4.00 (s, 2H), 3.74-3.81 (m, 5H), 2.16 (s; 3H); MS (EI) for $C_{30}H_{27}FN_6O_3$: 539 (MH$^+$).

Methyl [6-(4-pyrimidin-4-yl-2,3,4,5-tetrahydro-1,4-benzoxazepin-7-yl)-1H-benzimidazol-2-yl]carbamate. Prepared according to the method of example 2 by using 4-chloropyrimidine in step 2. $^1$H NMR (400 MHz, DMSO-d$_6$): 8.49 (s, 1H), 8.17 (d, 1H), 7.80 (s, 1H), 7.60 (s, 1H), 7.44 (m, 2H), 7.34 (m, 1H), 7.03 (m, 2H), 4.87 (s, 2H), 4.15 (s, 4H), 3.76 (s, 3H); MS (EI) for $C_{22}H_{20}N_6O_3$: 417 (MH$^+$).

Methyl {6-[4-(7H-pyrrolo[2,3-d]pyrimidin-4-yl)-2,3,4,5-tetrahydro-1,4-benzoxazepin-7-yl]-1H-benzimidazol-2-yl}carbamate. Prepared according to the method of example 2 by using 4-chloropyrrolo[2,3-d]pyrimidine in step 2. $^1$H NMR (400 MHz, DMSO-d$_6$): 12.25 (br. s, 1H), 8.30 (s, 1H), 7.78 (d, 1H), 7.67 (s, 1H), 7.57 (d, 1H), 7.47 (m, 2H), 7.35 (m, 1H), 7.04 (d, 1H), 6.92 (s, 1H), 5.25 (s, 2H), 4.39 (m, 4H), 3.84 (s, 3H); MS (EI) for $C_{24}H_{21}N_7O_3$: 456 (MH$^+$).

Methyl {6-[4-(3-methylpyridin-2-yl)-2,3,4,5-tetrahydro-1,4-benzoxazepin-7-yl]-1H-benzimidazol-2-yl}carbamate. Prepared according to the method of example 2 by using 2-chloro-3-methylpyridine in step 2. $^1$H NMR (400 MHz, DMSO-d$_6$): 11.69 (br. s, 1H), 8.07 (m, 1H), 7.59 (d, 1H), 7.54 (d, 1H), 7.51 (d, 1H), 7.44 (m, 2H), 7.32 (dd, 1H), 7.06 (d, 1H), 6.89 (m, 1H), 4.42 (s, 2H), 4.28 (m, 2H), 3.76 (s, 3H), 3.65 (m, 2H), 2.30 (s, 3H); MS (EI) for $C_{24}H_{23}N_5O_3$: 430 (MH$^+$).

Methyl {6-[4-(2-methylquinazolin-4-yl)-2,3,4,5-tetrahydro-1,4-benzoxazepin-7-yl]-1H-benzimidazol-2-yl}carbamate. Prepared according to the method of example 2 by using 4-chloro-2-methylquinazoline in step 2. $^1$H NMR (400 MHz, DMSO-d$_6$): 7.99 (d, 1H), 7.74 (m, 1H), 7.68 (d, 1H), 7.61 (m, 2H), 7.44 (m, 3H), 7.34 (d, 1H), 7.00 (d, 1H), 5.01 (s, 2H), 4.42 (s, 2H), 4.17 (m, 2H), 3.74 (s, 3H), 2.45 (s, 3H); MS (EI) for $C_{27}H_{24}N_6O_3$: 481 (MH$^+$).

Methyl [6-(4-quinazolin-4-yl-2,3,4,5-tetrahydro-1,4-benzoxazepin-7-yl)-1H-benzimidazol-2-yl]carbamate. Prepared as trifluoroacetate salt according to the method of example 2 by using 4-chloroquinazoline in step 2. $^1$H NMR (400 MHz, DMSO-d$_6$): 8.84 (s, 1H), 8.31 (s, 1H), 7.83 (d, 1H), 7.78-7.69 (m, 3H), 7.56-7.46 (m, 3H), 7.01 (d, 1H), 5.45 (s, 2H), 4.63 (m, 2H), 4.54 (m, 2H), 3.81 (s, 3H); MS (EI) for $C_{26}H_{22}N_6O_3$: 4678 (MH$^+$).

Methyl [6-(4-isoquinolin-1-yl-2,3,4,5-tetrahydro-1,4-benzoxazepin-7-yl)-1H-benzimidazol-2-yl]carbamate. Prepared as trifluoroacetate salt according to the method of example 2 by using 1-chloroisoquinoline in step 2. $^1$H NMR (400 MHz, methanol-d$_4$): 8.26 (d, 1H), 8.04 (d, 1H), 7.96 (m, 1H), 7.83 (m, 2H), 7.68 (m, 5H), 7.56 (d, 1H), 7.21 (d, 1H), 5.14 (s, 2H), 4.67 (m, 2H), 4.14 (m, 2H), 3.96 (s, 3H); MS (EI) for $C_{27}H_{23}N_5O_3$: 466 (MH$^+$).

Methyl (6-{4-[6,7-bis(methyloxy)quinazolin-4-yl]-2,3,4,5-tetrahydro-1,4-benzoxazepin-7-yl}-1H-benzimidazol-2-yl)carbamate. Prepared according to the method of example 2 by using 4-chloro-6,7-dimethoxyquinazoline in step 2. $^1$H NMR (400 DMSO-D$_6$): 8.49 (1H), 7.73 (br, 1H), 7.62 (br, 1H), 7.49 (dd, 1H), 7.44 (d, 1H), 7.35 (dd, 1H), 7.20 (s, 1H), 7.09 (d, 2H), 5.02 (s, 2H), 4.53 (m, 2H), 4.06 (m, 2H), 3.90 (s, 3H), 3.75 (s, 3H), 3.54 (s, 3H), MS (EI) for $C_{28}H_{26}N_6O_5$: 527 (MH$^+$).

Methyl (6-{4-[6-(methyloxy)quinazolin-4-yl]-2,3,4,5-tetrahydro-1,4-benzoxazepin-7-yl}-1H-benzimidazol-2-yl) carbamate. Prepared according to the method of example 2 by using 4-chloro-6-methoxyquinazoline in step 2. $^1$H NMR (400 DMSO-D$_6$): 8.53 (1H), 7.75 (d, 2H), 7.62 (br, 1H), 7.52 to 7.42 (m, 3H), 7.35 (dd, 1H), 7.17 (s, 1H), 7.05 (d, 1H), 5.04 (s, 2H), 4.53 (m, 2H), 4.11 (m, 2H), 3.78 (s, 3H), 3.58 (s, 3H), MS (EI) for $C_{27}H_{24}N_6O_4$: 497 (MH$^+$).

Example 3

5-(4-{5-[(4-Fluorophenyl)methyl]-6-methylpyrimidin-4-yl}-2,3,4,5-tetrahydro-1,4-benzoxazepin-7-yl)-1,3-thiazol-2-amine STEP 1: A mixture of N-(5-bromo-1,3-thiazol-2-yl)acetamide (1.00 g, 4.5 mmol), (4-{[(1,1-dimethylethyl)oxy]carbonyl}-2,3,4,5-tetrahydro-1,4-benzoxazepin-7-yl)boronic acid (example 1, step 2) (1.59 g, 5.4 mmol), potassium carbonate (2.50 g, 18 mmol), [1,1'-bis(diphenylphosphino)ferrocene] dichloropalladium(II) (0.33 g, 0.45 mmol), 1,4-dioxane (20 mL), and water (2 mL) was degassed with nitrogen for 2 min, and then stirred at 95° C. for 16 h. The reaction mixture was cooled, diluted with ethyl acetate (100 mL), and filtered through celite. The filtrate was washed with brine (2×30 mL), dried over sodium sulfate, and concentrated. Column chromatography on silica (gradient 20-85% ethyl acetate in hexane) gave 1,1-dimethylethyl 7-[2-(acetylamino)-1,3-thiazol-5-yl]-2,3-dihydro-1,4-benzoxazepine-4(5H)-carboxylate (0.99 g, 56% yield). MS (EI) for $C_{19}H_{23}N_3O_4$: 390 (MH$^+$).

STEP 2: A solution of 1,1-dimethylethyl 7-[2-(acetylamino)-1,3-thiazole-5-yl]-2,3-dihydro-1,4-benzoxazepine-4(5H)-carboxylate (300 mg, 0.77 mmol) in a mixture of methanol (2 mL) and 4 N hydrogen chloride in dioxane (2 mL) was refluxed for 1 min. After cooling to room temperature the reaction mixture was concentrated, and azeotroped with methanol (3×) to give N-[5-(2,3,4,5-tetrahydro-1,4-benzoxazepin-7-yl)-1,3-thiazol-2-yl]acetamide hydrochloride (221 mg, 88% yield) as a colorless solid. MS (EI) for $C_{14}H_{15}N_3O_2S$: 290 (MH$^+$).

STEP 3: A mixture of N-[5-(2,3,4,5-tetrahydro-1,4-benzoxazepin-7-yl)-1,3-thiazol-2-yl]acetamide hydrochloride (220 mg, 0.68 mmol), 4-chloro-5-[(4-fluorophenyl)methyl]-6-methylpyrimidine (reagent preparation 5) (152 mg, 0.64 mmol) and diisopropylethylamine (500 mg, 3.87 mmol) in N-methylpyrrolidine (4 mL) was heated in a microwave reactor at 120° C. for 3 h. The reaction mixture was concentrated, diluted with water (10 mL), the precipitate was filtered off, washed with water (2×5 mL) and methanol (5 mL), and dried to provide N-[5-(4-{5-[(4-fluorophenyl)methyl]-6-methylpyrimidine-4-yl}-2,3,4,5-tetrahydro-1,4-benzoxazepin-7-yl)-1,3-thiazol-2-yl]acetamide (147 mg, 47% yield) as a off-white solid. MS (EI) $C_{26}H_{24}FN_5O_2S$: 490 (MH$^+$).

STEP 4: A solution of N-[5-(4-{5-[(4-fluorophenyl)methyl]-6-methylpyrimidine-4-yl}-2,3,4,5-tetrahydro-1,4-benzoxazepin-7-yl)-1,3-thiazol-2-yl]acetamide (75 mg, 0.15 mmol) in 6 N hydrochloric acid (4 mL) was stirred at 95° C. for 15 h. After cooling to room temperature the mixture was neutralized with 50% aqueous sodium hydroxide, concentrated to dryness, and the solid residue extracted with ethanol (3×10 mL). Evaporation of the solvent and purification of the residue by preparative HPLC afforded 5-(4-{5-[(4-fluorophenyl)methyl]-6-methylpyrimidin-4-yl}-2,3,4,5-tetrahydro-1,4-benzoxazepin-7-yl)-1,3-thiazol-2-amine (43 mg, 62% yield) as a colorless solid. $^1$H NMR (400 MHz, CD$_3$OD): 8.46 (s, 1H), 7.21 (m, 1H), 7.11 (m, 4H), 6.98 (s, 1H), 6.90 (d, 1H), 6.61 (m, 1H), 4.46 (s, 2H), 4.26 (ms, 2H), 3.97 (s, 2H), 3.87 (m, 2H), 2.21 (s, 3H); MS (EI) $C_{24}H_{22}FN_5OS$: 448 (MH$^+$).

Using analogous synthetic techniques and substituting with alternative starting reagents in steps 1 or 3 and conducting protecting group removal step 4 as required according to literature techniques appropriate for a given protecting group (see for example: Greene and Wuts, Protective Groups in Organic Synthetic, Wiley-Interscience) the following compounds of the invention were prepared. Alternative starting materials were obtained commercially unless otherwise indicated.

4-{5-[(4-Fluorophenyl)methyl]-6-methylpyrimidin-4-yl}-7-(2-methyl-3H-imidazo[4,5-b]pyridin-6-yl)-2,3,4,5-tetrahydro-1,4-benzoxazepine. Synthesized according to the method of example 3 using isobutyl 6-bromo-2-methyl-3H-imidazo[4,5-b]pyridine-3-carboxylate (reagent preparation 11) in step 1. $^1$H NMR (400 MHz, CDCl$_3$): 8.62 (s, 1H), 7.42 (d, 2H), 7.11 (d, 1H), 7.03 (m, 2H), 6.95 (t, 2H), 6.79 (s, 1H), 4.47 (s, 2H), 4.26 (br s, 2H), 3.97 (s, 2H), 3.88 (br s, 2H), 2.77 (s, 3H), 2.27 (s, 3H); MS (EI) for $C_{28}H_{25}FN_6O$: 481 (MH$^+$).

7-(1H-Benzimidazol-6-yl)-4-quinazolin-4-yl-2,3,4,5-tetrahydro-1,4-benzoxazepine. Prepared according to the method of example 3 by using 6-bromo-1H-benzo[d]imidazole in step 1 and 4-chloroquinazoline in step 3. $^1$H NMR (400 MHz, methanol-d$_4$): 8.53 (s, 1H), 8.21 (s, 1H), 8.12 (d, 1H), 7.80 (m, 3H), 7.68 (d, 1H), 7.63 (m, 1H), 7.53 (m, 3H), 7.07 (d, 1H), 5.13 (s, 2H), 4.49 (m, 2H), 4.30 (m, 2H), 1.96 (s, 3H); MS (EI) for $C_{24}H_{19}N_5O$: 394 (MH$^+$).

4-{5-[(4-Fluorophenyl)methyl]-6-methylpyrimidin-4-yl}-7-[4-(1H-imidazol-2-yl)phenyl]-2,3,4,5-tetrahydro-1,4-benzoxazepine. Prepared according to the method of example 3 by using isobutyl 2-(4-bromophenyl)-1H-imidazole-1-carboxylate in step 1 and 4-chloro-5-(4-fluorobenzyl)-6-methylpyrimidine (reagent preparation 5) in step 3. $^1$H NMR (400 DMSO-D$_6$): 8.51 (1H), 8.01 (d, 2H), 7.54 (d, 3H), 7.20 (br 1H), 7.12 (d, 5H), 7.02 (d, 1H), 6.91 (br, 1H), 4.49 (s, 2H), 4.29 (m, 2H), 3.97 (s, 2H), 3.78 (s, 2H), 2.16 (s, 3H), MS (EI) for $C_{30}H_{26}N_5FO$: 492 (MH$^+$).

7-(1-Ethyl-1H-benzimidazol-5-yl)-4-quinolin-4-yl-2,3,4,5-tetrahydro-1,4-benzoxazepine. Prepared as the trifluoroacetate salt according to the method of example 3 by using 5-bromo-1-ethyl-1H-benzimidazole (reagent preparation 12) in step 1 and 4-chloroquinoline in step 3. $^1$H NMR (400 MHz, d$_6$-DMSO): 8.57 (d, 1H), 8.31 (d, 1H), 8.07-7.91 (m, 6H), 7.82 (s, 1H), 7.72-7.62 (m, 2H), 7.03-6.98 (m, 2H), 5.31 (s, 2H), 4.63 (t, 1H), 4.47-4.38 (m, 4H), 1.51 (t, 3H); MS (EI) for $C_{27}H_{24}N_4O$: 421 (MH$^+$).

7-(2-Methyl-1,3-benzothiazol-5-yl)-4-quinolin-4-yl-2,3,4,5-tetrahydro-1,4-benzoxazepine. Prepared as the trifluoroacetate salt according to the method of example 3 by using 5-bromo-2-methylbenzothiazole in step 1 and 4-chloroquinoline in step 3. $^1$H NMR (400 MHz, d$_6$-DMSO): 8.57 (d, 1H), 8.33 (d, 1H), 8.27 (s, 1H), 8.14 (d, 1H), 8.06 (s, 1H), 8.01-7.92 (m, 2H), 7.77 (d, 1H), 7.71-7.65 (m, 2H), 7.03-6.98 (m, 2H), 5.31 (s, 2H), 4.62 (t, 2H), 4.42 (t, 2H), 2.84 (s, 3H); MS (EI) for $C_{26}H_{21}N_3OS$: 424 (MH$^+$).

7-(1,3-Benzothiazol-5-yl)-4-quinolin-4-yl-2,3,4,5-tetrahydro-1,4-benzoxazepine. Prepared as the trifluoroacetate salt according to the method of example 3 by using 5-bromobenzothiazole in step 1 and 4-chloroquinoline in step 3. $^1$H NMR (400 MHz, d$_6$-DMSO): 9.47 (s, 1H), 8.57 (d, 1H), 8.46 (s, 1H), 8.33 (d, 1H), 8.29 (d, 1H), 8.11 (s, 1H), 8.01-7.92 (m, 2H), 7.88 (d, 1H), 7.73-7.66 (m, 2H), 7.03-6.99 (m, 2H), 5.31 (s, 2H), 4.63 (t, 2H), 4.42 (t, 2H); MS (EI) for $C_{25}H_{19}N_3OS$: 410 (MH$^+$).

7-(1-Methyl-1H-benzimidazol-5-yl)-4-quinolin-4-yl-2,3,4,5-tetrahydro-1,4-benzoxazepine. Prepared as the acetate salt according to the method of example 3 by using 5-bromo-1-methylbenzimidazole in step 1 and 4-chloroquinoline in step 3. $^1$H NMR (400 MHz, d$_6$-DMSO): 8.61 (d, 1H), 8.23 (s, 1H), 8.09 (d, 1H), 7.97-7.93 (m, 2H), 7.81 (s, 1H), 7.75 (t, 1H), 7.68-7.59 (m, 3H), 7.56-7.50 (m, 1H), 7.07 (d, 1H), 7.02 (d, 1H), 4.81 (s, 2H), 4.43 (t, 2H), 3.95 (t, 2H), 3.88 (s, 3H); MS (EI) for $C_{26}H_{22}N_4O$: 407 (MH$^+$).

7-(1H-Benzimidazol-6-yl)-4-quinolin-4-yl-2,3,4,5-tetrahydro-1,4-benzoxazepine. Prepared as the trifluoroacetate salt according to the method of example 3 by using 5-bromobenzimidazole in step 1 and 4-chloroquinoline in step 3. $^1$H NMR (400 MHz, d$_6$-DMSO): 9.02 (br. s, 1H), 8.57 (d, 1H), 8.33 (d, 1H), 8.03-7.92 (m, 4H), 7.87-7.76 (m, 2H), 7.71-7.61 (m, 2H), 7.04-6.97 (m, 2H), 5.31 (s, 2H), 4.63 (t, 2H), 4.41 (t, 2H); MS (EI) for $C_{25}H_{20}N_4O$: 393 (MH$^+$).

4-Quinolin-4-yl-7-(3-thienyl)-2,3,4,5-tetrahydro-1,4-benzoxazepine. Prepared as the trifluoroacetate salt according to the method of example 3 by using thiophen-3-ylboronic acid in step 1 and 4-chloroquinoline in step 3. $^1$H NMR (400 MHz, d$_6$-DMSO): 8.56 (d, 1H), 8.32 (d, 1H), 8.01-7.91 (m, 3H), 7.85 (s, 1H), 7.71-7.65 (m, 2H), 7.63-7.58 (m, 2H), 6.97-6.91 (m, 2H), 5.25 (s, 2H), 4.60 (t, 2H), 4.40 (t, 2H); MS (EI) for $C_{22}H_{18}N_2OS$: 359 (MH$^+$).

7-Quinolin-3-yl-4-quinolin-4-yl-2,3,4,5-tetrahydro-1,4-benzoxazepine. Prepared as the trifluoroacetate salt according to the method of example 3 by using quinolin-3-ylboronic acid in step 1 and 4-chloroquinoline in step 3. $^1$H NMR (400 MHz, d$_6$-DMSO): 9.39 (s, 1H), 8.77 (s, 1H), 8.56 (d, 1H), 8.34 (d, 1H), 8.21 (s, 1H), 8.11 (d, 2H), 8.02-7.94 (m, 2H), 7.85-7.80 (m, 2H), 7.74-7.68 (m, 2H), 7.09 (d, 1H), 7.02 (d, 1H), 5.34 (s, 2H), 4.67 (t, 2H), 4.44 (t, 2H); MS (EI) for $C_{27}H_{21}N_3O$: 404 (MH$^+$).

7-(1-Benzothien-2-yl)-4-quinolin-4-yl-2,3,4,5-tetrahydro-1,4-benzoxazepine. Prepared as the trifluoroacetate salt according to the method of example 3 by using benzothiophen-2-ylboronic acid in step 1 and 4-chloroquinoline in step 3. $^1$H NMR (400 MHz, d$_6$-DMSO): 8.58 (d, 1H), 8.31 (d, 1H), 8.06 (s, 1H), 8.01-7.92 (m, 3H), 7.88-7.84 (m, 2H), 7.72-7.65 (m, 2H), 7.44-7.34 (m, 2H), 7.00 (d, 1H), 6.96 (d, 1H), 5.29 (s, 2H), 4.63 (t, 2H), 4.39 (t, 2H); MS (EI) for $C_{26}H_{20}N_2OS$: 409 (MH$^+$).

N-[2-chloro-5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)pyridin-3-yl]methanesulfonamide. Prepared according to the method of example 3 by using N-(5-bromo-2-chloropyridin-3-yl)methanesulfonamide (reagent preparation 24) in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, DMSO-d6) δ 8.12 (s, 1H), 7.88 (d, 1H), 7.64 (d, 1H), 7.45 (dd, 1H), 7.03 (d, 1H), 4.70 (s, 2H), 4.37-4.30 (m, 2H), 3.93-3.86 (m, 2H), 3.69 (s, 2H), 2.89 (s, 3H), 2.70 (t, 2H), 2.43 (s, 2H), 2.37 (s, 6H), 1.59 (t, 2H), 0.91-0.82 (m, 6H); MS (EI) for $C_{28}H_{35}ClN_6O_3S$: 571, 573 (Cl isotopes, MH$^+$).

7-(1-methyl-1H-pyrrolo[2,3-b]pyridin-5-yl)-4-quinolin-4-yl-2,3,4,5-tetrahydro-1,4-benzoxazepine. Synthesized according to the method of example 3 using 5-bromo-1-methyl-1H-indole (reagent preparation 21) in step 1 and 4-chloroquinoline in step 3. $^1$H NMR (400 MHz, DMSO-d$_6$): 8.62 (d, 1H), 8.58 (d, 1H), 8.23 (d, 1H), 8.01 (d, 1H), 7.94 (d, 1H), 7.74 (d, 1H), 7.68 (t, 1H), 7.62 (dd, 1H), 7.58 (dd, 1H), 7.53 (t, 1H), 7.12 (d, 1H), 7.03 (d, 1H), 6.52 (d, 1H), 4.66 (s, 2H), 4.38 (m, 2H), 3.85 (s, 3H), 3.82 (m, 2H); MS (EI) for $C_{26}H_{22}N_4O_2$: 407.1 (MH$^+$).

7-(1-ethyl-1H-pyrrolo[2,3-b]pyridin-5-yl)-4-quinolin-4-yl-2,3,4,5-tetrahydro-1,4-benzoxazepine. Synthesized according to the method of example 3 using 5-bromo-1-ethyl-1H-indole (reagent preparation 21) in step 1 and 4-chloroquinoline in step 3. $^1$H NMR (400 MHz, DMSO-d$_6$): 8.62 (d, 1H), 8.57 (d, 1H), 8.22 (d, 1H), 8.01 (d, 1H), 7.94 (d, 1H), 7.74 (d, 1H), 7.69 (t, 1H), 7.64 (dd, 1H), 7.61 (dd, 1H), 7.50 (t, 1H), 7.12 (d, 1H), 7.03 (d, 1H), 6.52 (d, 1H), 4.66 (s, 2H), 4.42 (m, 2H), 4.31 (qr. 2H), 3.85 (s, 3H), 3.82 (m, 2H), 1.39 (t, 3H); MS (EI) for $C_{27}H_{24}N_4O_2$: 421.2 (MH$^+$).

5-(4-quinolin-4-yl-2,3,4,5-tetrahydro-1,4-benzoxazepin-7-yl)pyridin-2-amine. Synthesized according to the method of example 3 using 5-bromopyridin-2-amine in step 1 and 4-chloroquinoline in step 3. $^1$H NMR (400 MHz, DMSO-d$_6$): 8.61 (d, 1H), 8.24 (d, 1H), 7.99 (d, 1H), 7.93 (d, 1H), 7.71-7.69 (m, 2H), 7.59 (m, 1H), 7.50 (m, 1H), 7.44 (dd, 1H), 7.04 (d, 1H), 7.00 (dd, 1H), 6.52 (d, 1H), 6.04 (s, 2H), 4.61 (s, 2H), 4.34 (m, 2H), 3.80 (m, 2H), 1.88 (s, 3H, AcOH); MS (EI) for $C_{23}H_{20}N_4O_2$: 369.13 (MH$^+$).

4-[6,7-bis(methyloxy)quinolin-4-yl]-7-[4-(1H-imidazol-2-yl)phenyl]-2,3,4,5-tetrahydro-1,4-benzoxazepine. Synthesized according to the method of example 3 using 2-(4-bromophenyl)-1H-imidazole in step 1 and 4-chloro-6,7-dimethoxyquinoline in step 3. $^1$H NMR (400 MHz, DMSO-d$_6$): 8.47 (d, 1H), 8.01 (d, 2H), 7.87 (d, 1H), 7.77 (d, 2H), 7.65 (dd, 1H), 7.31 (s, 1H), 7.16 (bs, 2H), 7.12 (d, 1H), 7.10 (s, 1H), 6.94 (d, 1H), 4.65 (s, 2H), 4.44 (m, 2H), 3.89 (s, 3H), 3.77 (m, 2H), 3.54 (s, 3H); MS (EI) for $C_{29}H_{26}N_4O_3$: 478.9 (MH$^+$).

7-[4-(1H-imidazol-2-yl)phenyl]-4-(2-methylquinazolin-4-yl)-2,3,4,5-tetrahydro-1,4-benzoxazepine. Synthesized according to the method of example 3 using 2-(4-bromophenyl)-1H-imidazole in step 1 and 4-chloro-2-methylquinazoline in step 3. $^1$H NMR (400 MHz, DMSO-d$_6$): 12.5 (s, 1H), 8.02 (d, 2H), 7.99 (d, 1H), 7.78-7.74 (m, 4H), 7.70 (m, 1H), 7.59 (m, 1H), 7.43 (m, 1H), 7.26 (bs, 1H), 7.03 (d, 2H), 5.06 (s, 2H), 4.74 (s, 2H), 4.19 (s, 2H), 2.46 (s, 3H); MS (EI) for $C_{27}H_{23}N_5O$: 434.0 (MH$^+$).

5-[4-(2-methylquinazolin-4-yl)-2,3,4,5-tetrahydro-1,4-benzoxazepin-7-yl]pyridin-2-amine. Synthesized according to the method of example 3 using 5-bromo-2-aminopyridine in step 1 and 4-chloro-2-methylquinazoline in step 3. $^1$H NMR (400 MHz, DMSO-d$_6$): 8.21 (m, 1H), 7.97 (dd, 1H), 7.75 (m, 1H), 7.69 (m, 1H), 7.66 (m, 1H), 7.57 (m, 1H), 7.40 (m, 2H), 6.97 (d, 1H), 6.52 (d, 1H), 6.03 (s, 2H), 5.00 (s, 2H), 4.42 (s, 2H), 4.17 (s, 2H), 2.46 (s, 3H); MS (EI) for $C_{23}H_{21}N_5O$: 384.2 (MH$^+$).

4-[2-methyl-7-(methyloxy)quinazolin-4-yl]-7-(1H-pyrrolo[2,3-b]pyridin-5-yl)-2,3,4,5-tetrahydro-1,4-benzoxazepine. Synthesized according to the method of example 3 using 5-bromo-1H-pyrrolo[2,3-b]pyridine in step 1 and 4-chloro-7-methoxy-2-methylquinazoline in step 3. $^1$H NMR (400 MHz, DMSO-d$_6$): 11.7 (s, 1H), 8.49 (s, 1H), 8.16 (s, 1H), 7.90 (d, 1H), 7.71 (s, 1H), 7.53 (m, 2H), 7.11 (s, 1H), 7.03 (d, 2H), 6.50 (m, 1H), 5.02 (s, 2H), 4.44 (s, 2H), 4.15 (d, 2H), 3.87 (s, 3H), 2.43 (s, 3H); MS (EI) for $C_{26}H_{23}N_5O_2$: 438.2 (MH$^+$).

(5-{4-[2-methyl-7-(methyloxy)quinazolin-4-yl]-2,3,4,5-tetrahydro-1,4-benzoxazepin-7-yl}pyridin-2-amine. Synthesized according to the method of example 3 using 5-bromo-2-aminopyridine in step 1 and 4-chloro-7-methoxy-2-methylquinazoline in step 3. $^1$H NMR (400 MHz, DMSO-d$_6$): 11.9 (s, 1H, AcOH), 8.21 (d, 1H), 7.87 (d, 1H), 7.67 (dd, 1H), 7.55 (m, 1H), 7.38 (dd, 1H), 7.10 (d, 1H), 7.02 (dd, 1H), 6.96 (d, 1H), 6.52 (d, 1H), 6.03 (s, 2H), 4.96 (s, 2H), 4.38 (m, 2H), 4.13 (m, 2H), 3.87 (s, 3H), 2.42 (s, 3H), 1.90 (s, 3H, AcOH); MS (EI) for $C_{24}H_{23}N_5O_2$: 413.9 (MH$^+$).

7-(1H-indazol-5-yl)-4-[2-methyl-7-(methyloxy)quinazolin-4-yl]-2,3,4,5-tetrahydro-1,4-benzoxazepine. Synthesized according to the method of example 3 using 5-bromo-1H-pyrazolo[3,4-b]pyridine in step 1 and 4-chloro-7-methoxy-2-methylquinazoline in step 3. $^1$H NMR (400 MHz, DMSO-d$_6$): 13.1 (s, 1H), 11.9 (s, 1H, AcOH), 8.12 (s, 1H), 7.99 (m, 1H), 7.92 (d, 1H), 7.69 (m, 1H), 7.64 (m, 2H), 7.53 (d, 1H), 7.10 (d, 1H), 7.05 (dd, 1H), 7.02 (dd, 1H), 5.04 (s, 2H), 4.45 (m, 2H), 4.17 (bs, 2H), 3.88 (s, 3H), 2.43 (s, 3H), 1.90 (s, 3H, AcOH); MS (EI) for $C_{26}H_{23}N_5O_2$: 437.9 (MH$^+$).

5-{4-[2-methyl-7-(methyloxy)quinazolin-4-yl]-2,3,4,5-tetrahydro-1,4-benzoxazepin-7-yl}pyrimidin-2-amine. Synthesized according to the method of example 3 using 5-bromo-2-aminopyrimidine in step 1 and 4-chloro-7-methoxy-2-methylquinazoline in step 3. $^1$H NMR (400 MHz, DMSO-d$_6$): 8.55 (s, 2H), 7.86 (d, 1H), 7.62 (d, 1H), 7.45 (dd, 2H), 7.10 (d, 1H), 7.03 (dd, 1H), 6.99 (d, 1H), 6.75 (s, 2H), 4.97 (s, 2H), 4.42 (bs, 2H), 4.12 (bs, 2H), 3.87 (s, 3H), 2.42 (s, 3H); MS (EI) for $C_{23}H_{22}N_6O_2$: 415.0 (MH$^+$).

5-{4-[2-methyl-7-(methyloxy)quinazolin-4-yl]-2,3,4,5-tetrahydro-1,4-benzoxazepin-7-yl}-1,3-thiazol-2-amine. Synthesized according to the method of example 3 using 4-chloro-7-methoxy-2-methylquinazoline in step 3. $^1$H NMR (400 MHz, DMSO-d$_6$): 7.86 (d, 1H), 7.39 (d, 1H), 7.30 (s, 1H), 7.26 (dd, 1H), 7.10 (m, 3H), 7.01 (dd, 1H), 6.90 (d, 1H), 4.90 (s, 2H), 4.36 (m, 2H), 4.12 (m, 2H), 3.87 (s, 3H), 2.42 (s, 3H); MS (EI) for $C_{22}H_{21}N_5O_2S$: 419.9 (MH$^+$).

N-(5-{4-[2-methyl-7-(methyloxy)quinazolin-4-yl]-2,3,4,5-tetrahydro-1,4-benzoxazepin-7-yl}-1,3-thiazol-2-yl)acetamide. Synthesized according to the method of example 3 using 4-chloro-7-methoxy-2-methylquinazoline in step 3. $^1$H NMR (400 MHz, DMSO-d$_6$): 7.86 (d, 1H), 7.78 (s, 1H), 7.63 (d, 1H), 7.46 (dd, 1H), 7.10 (d, 1H), 6.98 (dd, 1H), 6.57 (d, 1H), 4.96 (s, 2H), 4.41 (m, 2H), 4.14 (m, 2H), 3.87 (s, 3H), 2.41 (s, 3H), 2.16 (s, 3H); MS (EI) for $C_{24}H_{23}N_5O_3S$: 462.1 (MH$^+$).

7-(1,3-benzothiazol-6-yl)-4-[2-methyl-7-(methyloxy)quinazolin-4-yl]-2,3,4,5-tetrahydro-1,4-benzoxazepine. Synthesized according to the method of example 3 using 6-bromobenzo[d]thiazole in step 1 and 4-chloro-7-methoxy-2-methylquinazoline in step 3. $^1$H NMR (400 MHz, DMSO-d$_6$): 9.40 (s, 1H), 8.46 (d, 1H), 8.16 (dd, 1H), 7.88 (d, 1H), 7.80 (dd, 1H), 7.78 (d, 1H), 7.61 (dd, 1H), 7.10 (d, 1H), 7.05

(m, 2H), 5.03 (s, 2H), 4.47 (m, 2H), 4.15 (m, 2H), 3.87 (s, 3H), 2.42 (s, 3H), 1.90 (s, 3H, AcOH); MS (EI) for $C_{26}H_{22}N_4O_2S$: 455.1 (MH$^+$).

5-{4-[2-methyl-7-(methyloxy)quinazolin-4-yl]-2,3,4,5-tetrahydro-1,4-benzoxazepin-7-yl}-1,3-dihydro-2H-benzimidazol-2-one. Synthesized according to the method of example 3 using 5-bromo-1H-benzo[d]imidazol-2(3H)-one in step 1 and 4-chloro-7-methoxy-2-methylquinazoline in step 3. $^1$H NMR (400 MHz, DMSO-d$_6$): 10.7 (d, 2H), 7.90 (d, 1H), 7.58 (s, 1H), 7.24 (d, 1H), 7.14 (d, 1H), 7.04 (d, 2H), 7.01 (m, 3H), 4.98 (s, 2H), 4.42 (s, 2H), 4.14 (s, 2H), 2.43 (s, 3H); MS (EI) for $C_{26}H_{23}N_5O_3$: 453.9 (MH$^+$).

5-{4-[2-methyl-7-(methyloxy)quinazolin-4-yl]-2,3,4,5-tetrahydro-1,4-benzoxazepin-7-yl}-1,3-dihydro-2H-indol-2-one. Synthesized according to the method of example 3 using 5-bromoindolin-2-one in step 1 and 4-chloro-7-methoxy-2-methylquinazoline in step 3. $^1$H NMR (400 MHz, DMSO-d$_6$): 10.4 (s, 1H), 7.87 (d, 1H), 7.58 (s, 1H), 7.48 (s, 1H), 7.43 (t, 2H), 7.10 (s, 1H), 6.99 (dd, 1H), 6.97 (d, 1H), 6.89 (d, 1H), 4.98 (s, 2H), 4.42 (s, 2H), 4.13 (s, 2H), 3.89 (s, 3H), 3.53 (s, 2H), 2.42 (s, 2H); MS (EI) for $C_{27}H_{24}N_4O_3$: 452.9 (MH$^+$).

N-[6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)[1,3]thiazolo[5,4-b]pyridin-2-yl]acetamide. Prepared according to the method of example 3 by using N-(6-bromo[1,3]thiazolo[5,4-b]pyridin-2-yl)acetamide (Journal of Heterocyclic Chemistry (200), 40(2), 621-628) in step 1 and 1-(4-chloro-6,6-dimethyl-5,6,7,8-tetrahydroquinazolin-2-yl)-N,N-dimethylmethanamine (reagent preparation 17) in step 3. MS (EI) for $C_{30}H_{35}N_7O_2S$ 558 (MH$^+$).

6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)[1,3]thiazolo[5,4-b]pyridin-2-amine. Prepared according to the method of example 3 by using N-(6-bromo[1,3]thiazolo[5,4-b]pyridin-2-yl)acetamide (Journal of Heterocyclic Chemistry (200), 40(2), 621-628) in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, d$_6$-DMSO): 8.40 (d, 1H), 7.90 (s, 2H), 7.84 (d, 1H), 7.74 (d, 1H), 7.54 (dd, 1H), 7.01 (d, 1H), 4.67 (s, 2H), 4.32 (s, 2H), 3.89 (s, 2H), 3.43 (s, 2H), 2.68 (m, 2H), 2.46 (m, 2H), 2.20 (s, 6H), 1.60 (m, 2H), 0.84 (s, 6H); MS (EI) for $C_{28}H_{33}N_7OS$: 516 (MH$^+$).

1-(4-{7-[2-(fluoromethyl)-1H-benzimidazol-5-yl]-2,3-dihydro-1,4-benzoxazepin-4(5H)-yl}-6,6-dimethyl-5,6,7,8-tetrahydroquinazolin-2-yl)-N,N-dimethylmethanamine. Prepared according to the method of example 3 by using 1,1-dimethylethyl 5-bromo-2-(fluoromethyl)-1H-benzimidazole-1-carboxylate (reagent preparation 19) in step 1, and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, Methanol-D$_4$): 7.79 (br, 1H), 7.67 to 7.60 (m, 2H), 7.56 (d, 1H), 7.50 (d, 1H), 7.04 (d, 1H), 5.62 (d, 2H), 4.79 (s, 2H), 4.37 (m, 2H), 4.01 (m, 2H), 3.91 (s, 2H), 2.79 (t, 2H), 2.59 (s, 6H), 2.52 (s, 2H), 1.70 (t, 2H), 0.92 (s, 6H); MS (EI) for $C_{30}H_{35}FN_6O$: 515 (MH$^+$).

1-(4-{7-[2-(fluoromethyl)-1H-benzimidazol-5-yl]-2,3-dihydro-1,4-benzoxazepin-4(5H)-yl}-5-[(4-fluorophenyl)methyl]-6-methylpyrimidin-2-yl)-N,N-dimethylmethanamine. Prepared according to the method of example 3 by using 1,1-dimethylethyl 5-bromo-2-(fluoromethyl)-1H-benzimidazole-1-carboxylate (reagent preparation 19) in step 1, and 1-{4-chloro-5-[(4-fluorophenyl)methyl]-6-methylpyrimidin-2-yl}-N,N-dimethylmethanamine (reagent preparation 17) in step 3. $^1$H NMR (400 MHz, Methanol-D$_4$): 7.66 (br, 2H), 7.46 (d, 1H), 7.38 (d, 1H), 7.09 (m, 2H), 7.01 to 6.93 (m, 4H), 5.63 (d, 2H), 4.77 (s, 2H), 4.36 (m, 2H), 4.02 (m, 2H), 3.91 (br, 4H), 2.59 (s, 2H), 2.26 (s, 3H); MS (EI) for $C_{32}H_{32}FN_6O$: 555 (MH$^+$).

1-[4-{7-[2-(fluoromethyl)-1H-benzimidazol-5-yl]-2,3-dihydro-1,4-benzoxazepin-4(5H)-yl}-6-methyl-5-(1-methylethyl)pyrimidin-2-yl]-N,N-dimethylmethanamine. Prepared according to the method of example 3 using 1,1-dimethylethyl 5-bromo-2-(fluoromethyl)-1H-benzimidazole-1-carboxylate (reagent preparation 19) in step 1, and 1-[4-chloro-6-methyl-5-(1-methylethyl)pyrimidin-2-yl]-N,N-dimethylmethanamine (reagent preparation 17) in step 3. $^1$H NMR (400 MHz, Methanol-D$_4$): 7.78 (br, 1H), 7.65 (br, 1H), 7.58 to 7.50 (m, 3H), 7.04 (d, 1H), 5.62 (d, 2H), 4.62 (s, 2H), 4.37 (m, 2H), 3.86 (m, 2H), 3.37 (m, 1H), 2.56 (s, 3H), 2.54 (s, 3H), 1.41 (d, 6H); MS (EI) for $C_{28}H_{33}FN_6O$: 489 (MH$^+$).

1-{4-[7-(4-fluoro-2-methyl-1H-benzimidazol-5-yl)-2,3-dihydro-1,4-benzoxazepin-4(5H)-yl]-6,6-dimethyl-5,6,7,8-tetrahydroquinazolin-2-yl}-N,N-dimethylmethanamine. Prepared according to the method of example 3 by using 1,1-dimethylethyl 5-bromo-4-fluoro-2-methyl-1H-benzimidazole-1-carboxylate (reagent preparation 19) in step 1, and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, Methanol-D$_4$): 7.49 (br, 1H), 7.59 (d, 1H), 7.36 (d, 1H), 7.28 (d, 1H), 7.01 (d, 1H), 4.75 (s, 2H), 4.36 (m, 2H), 4.00 (m, 2H), 3.80 (s, 2H), 2.79 (t, 2H), 2.56 (s, 3H), 2.49 (br, 6H), 1.65 (t, 2H), 0.91 (s, 6H); MS (EI) for $C_{30}H_{35}FN_6O$: 515 (MH$^+$).

4-(6,6-dimethyl-5,6-dihydroquinazolin-4-yl)-7-[4-(1H-imidazol-2-yl)phenyl]-2,3,4,5-tetrahydro-1,4-benzoxazepine. Prepared according to the method of example 3 by using isobutyl 2-(4-bromophenyl)-1H-imidazole-1-carboxylate (reagent preparation 11) in step 1 and 4-chloro-6,6-dimethyl-5,6-dihydroquinazoline (reagent preparation 3) in step 3. $^1$H NMR (400 MHz, methanol-d$_4$): 8.38 (s, 1H), 7.92 (m, 2H), 7.70 (m, 2H), 7.59 (m, 1H), 7.53 (m, 1H), 7.15 (brs, 2H), 7.07 (d, 1H), 6.33 (d, 1H), 6.26 (d, 1H), 4.71 (s, 2H), 4.36 (m, 2H), 3.97 (m, 2H), 2.78 (s, 2H), 1.01 (s, 6H); MS (EI) for $C_{28}H_{27}N_5O$: 450 (MH$^+$).

1-(4-{7-[4-(1H-imidazol-2-yl)phenyl]-2,3-dihydro-1,4-benzoxazepin-4(5H)-yl}-6,6-dimethyl-5,6,7,8-tetrahydroquinazolin-2-yl)-N,N-dimethylmethanamine. Prepared as dihydrochloride salt according to the method of example 3 by using isobutyl 2-(4-bromophenyl)-1H-imidazole-1-carboxylate (reagent preparation 11) in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, methanol-d$_4$): 8.00 (m, 4H), 7.85 (s, 1H), 7.68 (s, 2H), 7.64 (dd, 1H), 7.09 (d, 1H), 5.04 (s, 2H), 4.52 (m, 2H), 4.42 (s, 2H), 4.18 (m, 2H), 2.93 (s, 6H), 2.85 (t, 2H), 2.55 (s, 2H), 1.70 (t, 2H), 0.89 (s, 6H); MS (EI) for $C_{31}H_{36}N_6O$: 509 (MH$^+$).

7-[4-(1H-imidazol-2-yl)phenyl]-4-[2-methyl-7-(methyloxy)quinazolin-4-yl]-2,3,4,5-tetrahydro-1,4-benzoxazepine. Prepared according to the method of example 3 by using 2-(4-bromophenyl)-1H-imidazole in step 1 and 4-chloro-7-methoxy-2-methylquinazoline in step 3. $^1$H NMR (400 MHz, DMSO-d6); δ 11.99 (s, 1H), 8.10-7.94 (m, 3H), 7.86-7.75 (m, 3H), 7.65-7.57 (m, 3H), 7.27 (s, 1H), 7.15-7.09 (m, 2H), 7.06-6.99 (d, 1H), 5.15 (s, 2H), 4.55-4.47 (m, 2H), 4.30-4.22 (m, 2H), 3.90 (3H), 2.46 (s, 3H); MS (EI) for $C_{28}H_{25}N_5O_2$: 464 (MH$^+$).

7-[4-(1H-imidazol-4-yl)phenyl]-4-[2-methyl-7-(methyloxy)quinazolin-4-yl]-2,3,4,5-tetrahydro-1,4-benzoxazepine. Prepared according to the method of example 3 by using 4-(4-bromophenyl)-1H-imidazole in step 1 and 4-chloro-7-methoxy-2-methylquinazoline in step 3. $^1$H NMR (400 MHz, DMSO-d6); δ 12.2 (s, 1H), 7.93-7.84 (m, 3H), 7.78-7.61 (m, 5H), 7.57-7.50 (m, 1H), 7.11 (d, 1H), 7.05-7.00 (m, 2H), 5.01 (s, 2H), 4.48-4.40 (m, 2H), 4.18-4.11 (m, 2H), 3.88 (s, 3H), 2.43 (s, 3H); MS (EI) for $C_{28}H_{25}N_5O_2$: 464 (MH$^+$).

7-[4-(1H-benzimidazol-2-yl)phenyl]-4-[2-methyl-7-(methyloxy)quinazolin-4-yl]-2,3,4,5-tetrahydro-1,4-benzoxazepine. Prepared according to the method of example 3 by using 2-(4-bromophenyl)-1H-benzo[d]imidazole in step 1 and 4-chloro-7-methoxy-2-methylquinazoline in step 3. $^1$H NMR (400 MHz, DMSO-d6); δ 8.36-7.85 (m, 7H), 7.73-7.59 (m, 3H), 7.33-7.20 (m, 3H), 7.15-7.11 (m, 1H), 7.07-6.99 (m, 1H), 5.39 (s, 2H), 4.69-4.58 (m, 2H), 4.53-4.40 (m, 2H), 3.95 (s, 3H), 2.54 (s, 3H); MS (EI) for $C_{32}H_{27}N_5O_2$: 514 (MH$^+$).

4-{4-[2-methyl-7-(methyloxy)quinazolin-4-yl]-2,3,4,5-tetrahydro-1,4-benzoxazepin-7-yl}aniline. Prepared according to the method of example 3 by using 4-bromoaniline in step 1 and 4-chloro-7-methoxy-2-methylquinazoline in step 3. $^1$H NMR (400 MHz, DMSO-d6); δ 7.89 (d, 1H), 7.51-7.47 (m, 1H), 7.37-7.28 (m, 3H), 7.11-7.08 (m, 1H), 7.04-6.99 (m, 1H), 6.96-6.92 (m, 1H), 6.65-6.60 (m, 2H), 5.19 (s, 2H), 4.95 (s, 2H), 4.41-4.35 (m, 2H), 4.15-4.09 (m, 2H), 3.88 (s, 3H), 2.43 (s, 3H); MS (EI) for $C_{25}H_{24}N_4O_2$: 413 (MH$^+$).

{5-[4-(4-pyrido[3,2-d]pyrimidin-4-yl-2,3,4,5-tetrahydro-1,4-benzoxazepin-7-yl)phenyl]-1H-imidazol-2-yl}methanol. Prepared according to the method of example 3 by using (4-(4-bromophenyl)-1H-imidazol-2-yl)methanol (reagent preparation 22) in step 1 and 4-chloropyrido[3,2-d]pyrimidine in step 3. $^1$H NMR (400 MHz, DMSO-d6) δ 12.03 (br s, 1H), 9.01 (d, 1H), 8.57 (s, 1H), 8.50 (d, 1H), 7.80 (m, 8H), 7.02 (d, 1H), 5.50 (br s, 1H), 5.20 (s, 2H), 4.52 (s, 4H), 4.34 (s, 2H); MS (EI) for $C_{26}H_{22}N_6O_2$: 451.1 (MH$^+$)

7-(2,4-dimethyl-1H-benzimidazol-6-yl)-4-pyrido[3,2-d]pyrimidin-4-yl-2,3,4,5-tetrahydro-1,4-benzoxazepine. Prepared according to the method of example 3 by using tert-butyl 6-bromo-2,4-dimethyl-1H-benzo[d]imidazole-1-carboxylate (reagent preparation 19) in step 1 and 4-chloropyrido[3,2-d]pyrimidine in step 3. $^1$H NMR (400 MHz, DMSO-d6) δ 12.03 (br s, 1H), 9.01 (d, 1H), 8.57 (s, 1H), 8.50 (d, 1H), 7.70 (s, 1H), 7.50 (m, 3H), 7.25 (s, 1H), 6.98 (d, 1H), 5.20 (s, 2H), 4.51 (s, 2H), 4.25 (s, 2H), 3.31 (s, 3H), 2.51 (s, 3H); MS (EI) for $C_{25}H_{22}N_6O$: 423.1 (MH$^+$).

1-(4-{7-[3,4-bis(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine. Prepared according to the method of example 3 by using 4-bromo-1,2-dimethoxybenzene in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, DMSO-d$_6$): 7.62 (d, 1H), 7.47-7.42 (m, 1H), 7.19-7.13 (m, 2H), 7.04-6.96 (m, 2H), 4.61 (s, 2H), 4.28 (t, 2H), 3.87-3.81 (m, 5H), 3.78 (s, 3H), 3.37 (s, 2H), 2.69 (t, 2H), 2.45 (s, 2H), 2.15 (s, 6H), 1.59 (t, 2H), 0.86 (s, 6H); MS (EI) for $C_{30}H_{38}N_4O_3$: 503 (MH$^+$).

1-(6,6-dimethyl-4-{7-[6-(methyloxy)pyridin-3-yl]-2,3-dihydro-1,4-benzoxazepin-4(5H)-yl}-5,6,7,8-tetrahydroquinazolin-2-yl)-N,N-dimethylmethanamine. Prepared according to the method of example 3 by using 5-bromo-2-methoxypyridine in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, DMSO-d$_6$): 8.45 (d, 1H), 8.00-7.95 (m, 1H), 7.65 (d, 1H), 7.46 (m, 1H), 7.00 (d, 1H), 6.91 (d, 1H), 4.62 (s, 2H), 4.30 (m, 2H), 3.91-3.83 (m, 5H), 3.36 (m, 2H), 2.69 (m, 2H), 2.43 (s, 2H), 2.13 (s, 6H), 1.59 (t, 2H), 0.85 (s, 6H); MS (EI) for $C_{28}H_{35}N_5O_2$: 474 (MH$^+$).

1-(6,6-dimethyl-4-{7-[3-(methyloxy)phenyl]-2,3-dihydro-1,4-benzoxazepin-4(5H)-yl}-5,6,7,8-tetrahydroquinazolin-2-yl)-N,N-dimethylmethanamine. Prepared according to the method of example 3 by using 1-bromo-3-methoxybenzene in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, DMSO-d$_6$): 7.66 (d, 1H), 7.50-7.45 (m, 1H), 7.36 (t, 1H), 7.22-7.18 (m, 1H), 7.15 (m, 1H), 7.00 (d, 1H), 6.93-6.88 (m, 1H), 4.62 (s, 2H), 4.29 (t, 2H), 3.85 (t, 2H), 3.81 (s, 3H), 2.68 (t, 2H), 2.44 (s, 2H), 2.12 (s, 6H), 1.59 (t, 2H), 0.85 (s, 6H); MS (EI) for $C_{29}H_{36}N_4O_2$: 473 (MH$^+$).

1-[4-{7-[3,4-bis(methyloxy)phenyl]-2,3-dihydro-1,4-benzoxazepin-4(5H)-yl}-7-(methyloxy)quinazolin-2-yl]-N,N-dimethylmethanamine. Prepared according to the method of example 3 using 4-bromo-1,2-dimethoxybenzene in step 1 and 1-(4-chloro-7-methoxyquinazolin-2-yl)-N,N-dimethylmethanamine (reagent preparation 17) in step 3. $^1$H NMR (400 MHz, DMSO-d$_6$): 7.95 (d, 1H), 7.64 (d, 1H), 7.47-7.43 (m, 1H), 7.20-7.14 (m, 3H), 7.09-7.01 (m, 2H), 6.95 (d, 1H), 5.04 (s, 2H), 4.44 (m, 2H), 4.19 (m, 2H), 3.89 (s, 3H), 3.85 (s, 3H), 3.79 (s, 3H), 3.48 (s, 2H), 2.17 (s, 6H); MS (EI) for $C_{29}H_{32}N_4O_4$: 501 (MH$^+$).

1-{4-[7-(1,3-benzothiazol-5-yl)-2,3-dihydro-1,4-benzoxazepin-4(5H)-yl]-5-[(4-fluorophenyl)methyl]-6-methylpyrimidin-2-yl}-N,N-dimethylmethanamine. Synthesized according to the method of example 3 using 5-bromobenzo[d]thiazole in step 1. $^1$H NMR (400 MHz, d$_6$-DMSO): 9.47 (s, 1H), 8.25 (d, 1H), 8.23 (d, 1H), 7.64 (m, 2H), 7.14 (d, 4H), 7.10 (m, 1H), 7.03 (d, 1H), 4.64 (s, 2H), 4.38-4.34 (m, 4H), 4.01 (s, 2H), 3.87 (m, 2H); MS (EI) for $C_{31}H_{30}FN_5OS$: 540 (MH$^+$).

1-{4-[7-(1,3-benzothiazol-5-yl)-2,3-dihydro-1,4-benzoxazepin-4(5H)-yl]-6,6-dimethyl-5,6,7,8-tetrahydroquinazolin-2-yl}-N,N-dimethylmethanamine. Synthesized according to the method of example 3 using 5-bromobenzo[d]thiazole in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, d$_6$-DMSO): 9.44 (s, 1H), 8.37 (d, 1H), 8.25 (d, 1H), 7.86 (d, 1H), 7.80 (dd, 1H), 7.64 (dd, 1H), 7.05 (d, 1H), 4.81 (s, 2H), 4.42 (m, 2H), 4.31 (s, 2H), 3.97 (br t, 2H), 2.80 (s, 6H), 2.75 (t, 2H), 1.62 (t, 2H), 0.86 (s, 6H); MS (EI) for $C_{29}H_{33}N_5OS$: 500 (MH$^+$).

1-{4-[7-(6-fluoro-2-methyl-1H-benzimidazol-5-yl)-2,3-dihydro-1,4-benzoxazepin-4(5H)-yl]-6,6-dimethyl-5,6,7,8-tetrahydroquinazolin-2-yl}-N,N-dimethylmethanamine. Synthesized according to the method of example 3 using 5-bromo-6-fluoro-2-methyl-1H-benzo[d]imidazole (reagent preparation 19) in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, d$_6$-DMSO) δ 7.88-7.78 (m, 2H), 7.69 (s, 1H), 7.42 (d, 1H), 7.06 (d, 1H), 4.90 (s, 2H), 4.48-4.39 (m, 2H), 4.33 (s, 2H), 4.06-3.99 (m, 2H), 2.80 (s, 3H), 2.79 (s, 6H), 2.75 (t, 2H), 2.48 (s, 2H), 1.59 (t, 2H), 0.85 (s, 6H); MS (EI) for $C_{30}H_{35}FN_6O$: 515 (MH$^+$).

1-(4-{7-[2-(difluoromethyl)-1H-benzimidazol-5-yl]-2,3-dihydro-1,4-benzoxazepin-4(5H)-yl}-5-[(4-fluorophenyl)methyl]-6-methylpyrimidin-2-yl)-N,N-dimethylmethanamine. Synthesized according to the method of example 3 using tert-butyl 6-bromo-2-(difluoromethyl)-1H-benzo[d]imidazole-1-carboxylate (reagent preparation 19) in step 1 and 1-(4-chloro-5-(4-fluorobenzyl)-6-methylpyrimidin-2-yl)-N,N-dimethylmethanamine (reagent preparation 17) in step 3. $^1$H NMR (400 MHZ, CDCl$_3$): 7.50-7.26 (br, 2H), 7.33 (dd, 1H), 7.25 (dd, 1H), 6.99 (d, 1H), 6.95 (tr, CHF$_2$, 1H), 6.92-6.81 (m, 5H), 6.54 (br s, 1H), 4.10 (br s, 4H), 3.81 (s, 2H), 3.70 (s, 2H), 3.61 (tr, 2H), 2.47 (s, 6H), 2.17 (s, 3H). MS (EI) for $C_{32}H_{31}N_6OF_3$: 573 (MH$^+$).

1-[4-{7-[2-(difluoromethyl)-1H-benzimidazol-5-yl]-2,3-dihydro-1,4-benzoxazepin-4(5H)-yl}-6-methyl-5-(1-methylethyl)pyrimidin-2-yl]-N,N-dimethylmethanamine. Synthesized according to the method of example 3 using tert-butyl 6-bromo-2-(difluoromethyl)-1H-benzo[d]imidazole-1-carboxylate (reagent preparation 19) in step 1 and 1-(4-chloro-5-isopropyl-6-methylpyrimidin-2-yl)-N,N-dimethylmethanamine (reagent preparation 17) in step 3. $^1$H NMR (400 MHZ, CDCl$_3$): 7.50-7.26 (br, 2H), 7.38-7.32 (br m, 2H), 7.15 (br, 1H), 7.03 (d, 1H), 6.94 (tr, CHF$_2$, 1H), 4.13 (br s, 2H), 3.66 (s, 2H), 3.43 (br, 2H), 3.24 (m, 1H), 2.50 (s, 6H), 2.47 (s, 3H), 1.21 (d, 6H). MS (EI) for $C_{28}H_{32}N_6OF_2$: 507 (MH$^+$).

1-(4-{7-[2-(difluoromethyl)-1H-benzimidazol-5-yl]-2,3-dihydro-1,4-benzoxazepin-4(5H)-yl}-6,6-dimethyl-5,6,7,8-tetrahydroquinazolin-2-yl)-N,N-dimethylmethanamine. Synthesized according to the method of example 3 using tert-butyl 6-bromo-2-(difluoromethyl)-1H-benzo[d]imidazole-1-carboxylate (reagent preparation 19) in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHZ, CDCl$_3$): 7.50-7.26 (br, 2H), 7.36 (br d, 1H), 7.31 (br dd, 1H), 7.20 (br, 1H), 7.02 (d, 1H), 6.97 (tr, CHF$_2$, 1H), 4.16 (tr, 2H), 4.07 (br, 2H), 3.65 (s, 2H), 3.60 (br s, 2H), 2.73 (tr, 2H), 2.47 (s, 6H), 2.22 (br s, 2H), 1.50 (tr, 2H), 0.86 (s, 6H). MS (EI) for $C_{30}H_{34}N_6OF_2$: 533 (MH$^+$).

1-(6,6-dimethyl-4-{7-[3-(methyloxy)-4-{[2-(methyloxy)ethyl]oxy}phenyl]-2,3-dihydro-1,4-benzoxazepin-4(5H)-yl}-5,6,7,8-tetrahydroquinazolin-2-yl)-N,N-dimethylmethanamine. Prepared according to the method of example 3 by using 4-bromo-2-methoxy-1-(2-methoxyethoxy)benzene in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, (DMSO-d$_6$): 7.62 (d, 1H), 7.47-7.43 (m, 1H), 7.18 (d, 1H), 7.15-7.11 (m, 1H), 7.04-6.95 (m, 2H), 4.60 (s, 2H), 4.28 (m, 2H), 4.10 (m, 2H), 3.87-3.82 (m, 5H), 3.67 (m, 2H), 3.36 (m, 2H), 3.32 (s, 3H), 2.69 (t, 2H), 2.45 (s, 2H), 2.14 (s, 6H), 1.59 (t, 2H), 0.86 (s, 6H); MS (EI) for $C_{32}H_{42}N_4O_4$: 547 (MH$^+$).

1-(6,6-dimethyl-4-{7-[4-(methyloxy)phenyl]-2,3-dihydro-1,4-benzoxazepin-4(5H)-yl}-5,6,7,8-tetrahydroquinazolin-2-yl)-N,N-dimethylmethanamine. Prepared according to the method of example 3 by using 1-bromo-4-methoxybenzene in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, (DMSO-d$_6$): 7.61-7.54 (m, 3H), 7.43-7.38 (m, 1H), 7.04-6.95 (m, 3H), 4.60 (s, 2H), 4.27 (m, 2H), 3.85 (m, 2H), 3.79 (s, 3H), 3.36 (m, 2H), 2.68 (t, 2H), 2.44 (s, 2H), 2.13 (s, 6H), 1.59 (t, 2H), 0.85 (s, 6H); MS (EI) for $C_{29}H_{36}N_4O_2$: 473 (MH$^+$).

1-(4-{7-[3-chloro-4-(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine. Prepared according to the method of example 3 by using 4-bromo-2-chloro-1-methoxybenzene in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, (DMSO-d$_6$): 7.70 (d, 1H), 7.65 (d, 1H), 7.62-7.57 (m, 1H), 7.48-7.43 (m, 1H), 7.22 (d, 1H), 6.98 (d, 1H), 4.60 (s, 2H), 4.28 (m, 2H), 3.89 (s, 3H), 3.85 (m, 2H), 3.36 (m, 2H), 2.69 (t, 2H), 2.44 (s, 2H), 2.13 (s, 6H), 1.59 (t, 2H), 0.86 (s, 6H); MS (EI) for $C_{29}H_{35}ClN_4O_2$: 507 (MH$^+$).

Example 4

4-(6,6-dimethyl-5,6,7,8-tetrahydroquinazolin-4-yl)-7-(2-propyl-3H-imidazo[4,5-b]pyridin-6-yl)-2,3,4,5-tetrahydro-1,4-benzoxazepine STEP 1: A mixture of 2-amino-5-bromo-3-nitropyridine (0.31 g, 1.4 mmol [4-(6,6-dimethyl-5,6,7,8-tetrahydroquinazolin-4-yl)-2,3,4,5-tetrahydro-1,4-benzoxazepin-7-yl] boronic acid (0.50 g, 1.4 mmol), [1,1'-Bis(diphenylphosphino)ferrocene]dichloropalladium(II) (103 mg, 0.1 mmol), diisopropylethylamine (0.94 g, 7.1 mmol), 1,4-dioxane (20 mL), and water (2 mL) was stirred at 90° C. for 4 hours. The reaction mixture was cooled, diluted with ethyl acetate (100 mL) then filtered through celite. The filtrate was washed with 50 mL portion each of 5% aqueous citric acid, water, then brine solution, dried over sodium sulfate, filtered and concentrated to give a brown solid residue. It was washed with 35% ethyl acetate-hexane to give 5-[4-(6,6-dimethyl-5,6,7,8-tetrahydroquinazolin-4-yl)-2,3,4,5-tetrahydro-1,4-benzoxazepin-7-yl]-3-nitropyridin-2-amine (0.63 g, 97% yield). MS (EI) for $C_{24}H_{26}N_6O_3$: 447 (MH$^+$).

STEP 2: A mixture of 5-[4-(6,6-dimethyl-5,6,7,8-tetrahydroquinazolin-4-yl)-2,3,4,5-tetrahydro-1,4-benzoxazepin-7-yl]-3-nitropyridin-2-amine (0.63 g, 1.4 mmol), 10% palladium on charcoal (0.50 g) in 30 mL of methanol was shaken in a Parr hydrogenation at 38 psi for 18 hours. The reaction mixture was filtered through a pad of celite and concentrated to give to give 5-[4-(6,6-dimethyl-5,6,7,8-tetrahydroquinazolin-4-yl)-2,3,4,5-tetrahydro-1,4-benzoxazepin-7-yl]pyridine-2,3-diamine (0.58 g, 99% yield). MS (EI) for $C_{24}H_{28}N_6O$: 417 (MH$^+$).

STEP 3: To a solution of 5-[4-(6,6-dimethyl-5,6,7,8-tetrahydroquinazolin-4-yl)-2,3,4,5-tetrahydro-1,4-benzoxazepin-7-yl]pyridine-2,3-diamine (32 mg, 0.077 mmol) and triethylamine (11 uL, 0.077 mmol) in tetrahydrofuran (1 mL) was add butyryl chloride (7.0 uL, 0.077 mmol), and the resulting mixture was stirred at room temperature for one hour. The reaction mixture was concentrated to give N-{2-amino-5-[4-(6,6-dimethyl-5,6,7,8-tetrahydroquinazolin-4-yl)-2,3,4,5-tetrahydro-1,4-benzoxazepin-7-yl]pyridin-3-yl}butanamide crude product (50 mg). MS (EI) for $C_{28}H_{34}N_6O_2$: 487 (MH$^+$).

STEP 4: N-{2-amino-5-[4-(6,6-dimethyl-5,6,7,8-tetrahydroquinazolin-4-yl)-2,3,4,5-tetrahydro-1,4-benzoxazepin-7-yl]pyridin-3-yl}butanamide (50 mg) was dissolved in acetic acid (0.2 mL) and heated in a microwave oven at 150 watts, 120° C. for 30 minutes. The reaction mixture was concentrated, dissolved in methanol (2 mL) and purified by preparative reverse phase HPLC (0.1% aqueous ammonium acetate-acetonitrile) to give 4-(6,6-dimethyl-5,6,7,8-tetrahydroquinazolin-4-yl)-7-(2-propyl-3H-imidazo[4,5-b]pyridin-6-yl)-2,3,4,5-tetrahydro-1,4-benzoxazepine (12 mg, 32% yield), $^1$H NMR (400 MHz, Methanol-d$_4$): 8.51 (br, 1H), 8.37 (s, 1H), 8.06 (s, 1H), 7.61 (s, 1H), 7.51 (d, 1H), 7.10 (d, 1H), 4.74 (s, 2H), 4.36 (m, 2H), 3.96 (m, 2H), 2.94 (t, 2H), 2.77 (t, 2H), 2.48 (s, 2H), 1.89 (m, 2H), 1.66 (t, 2H), 1.01 (t, 3H), 0.81 (s, 6H); MS (EI) for $C_{28}H_{32}N_6O$: 469 (MH$^+$).

Using analogous synthetic techniques and substituting with alternative starting reagents in steps 3 or step 4 the following compounds of the invention were prepared. Alternative starting materials were obtained commercially unless otherwise indicated.

4-(6,6-dimethyl-5,6,7,8-tetrahydroquinazolin-4-yl)-7-(2-ethyl-3H-imidazo[4,5-b]pyridin-6-yl)-2,3,4,5-tetrahydro-1,4-benzoxazepine. Prepared according to the method of example 4 by omitting step 3, and using trimethyl orthopropionate and 5-[4-(6,6-dimethyl-5,6,7,8-tetrahydroquinazolin-4-yl)-2,3,4,5-tetrahydro-1,4-benzoxazepin-7-yl]pyridine-2,3-diamine in step 4. $^1$H NMR (400 MHz, Methanol-d$_4$): 8.77 (br, 1H), 8.34 (s, 1H), 8.06 (s, 1H), 7.59 (s, 1H), 7.50 (d, 1H), 7.09 (d, 1H), 4.74 (s, 2H), 4.38 (m, 2H), 3.94 (m, 2H), 2.97 (q, 2H), 2.77 (t, 2H), 2.47 (s, 2H), 1.67 (t, 2H), 1.26 (t, 3H), 0.90 (s, 6H); MS (EI) for C$_{27}$H$_{30}$N$_6$O: 455 (MH$^+$).

7-(2-cyclopropyl-3H-imidazo[4,5-b]pyridin-6-yl)-4-(6,6-dimethyl-5,6,7,8-tetrahydroquinazolin-4-yl)-2,3,4,5-tetrahydro-1,4-benzoxazepine. Prepared according to the method of example 4 by using cyclopropylcarbonyl chloride in step 3. $^1$H NMR (400 MHz, Methanol-d$_4$): 8.41 (br, 1H), 8.25 (s, 1H), 7.88 (s, 1H), 7.47 (s, 1H), 7.41 (d, 1H), 7.01 (d, 1H), 4.64 (s, 2H), 4.27 (m, 2H), 3.86 (m, 2H), 2.70 (t, 2H), 2.39 (s, 2H), 2.08 (m, 1H), 1.56 (t, 2H), 1.11 (m, 4H), 0.79 (s, 6H); MS (EI) for C$_{28}$H$_{30}$N$_6$O: 467 (MH$^+$).

7-[2-(difluoromethyl)-3H-imidazo[4,5-b]pyridin-6-yl]-4-(6,6-dimethyl-5,6,7,8-tetrahydroquinazolin-4-yl)-2,3,4,5-tetrahydro-1,4-benzoxazepine. Prepared according to the method of example 4 by omitting step 3, and using difluoroacetic acid and 5-[4-(6,6-dimethyl-5,6,7,8-tetrahydroquinazolin-4-yl)-2,3,4,5-tetrahydro-1,4-benzoxazepin-7-yl]pyridine-2,3-diamine in step 4. $^1$H NMR (400 MHz, Methanol-d$_4$): 8.70 (br, 1H), 8.34 (s, 1H), 8.23 (s, 1H), 7.64 (s, 1H), 7.55 (d, 1H), 7.12 (d, 1H), 7.05 (t, 1H), 4.63 (s, 2H), 4.37 (m, 2H), 3.95 (m, 2H), 2.79 (t, 2H), 2.49 (s, 2H), 1.66 (t, 2H), 0.88 (s, 6H); MS (EI) for C$_{26}$H$_{26}$F$_2$N$_6$O: 477 (MH$^+$).

4-(6,6-dimethyl-5,6,7,8-tetrahydroquinazolin-4-yl)-7-[2-(fluoromethyl)-3H-imidazo[4,5-b]pyridin-6-yl]-2,3,4,5-tetrahydro-1,4-benzoxazepine hydrochloride. Prepared according to the method of example 4 by omitting step 3, and using fluoroacetic acid and 5-[4-(6,6-dimethyl-5,6,7,8-tetrahydroquinazolin-4-yl)-2,3,4,5-tetrahydro-1,4-benzoxazepin-7-yl]pyridine-2,3-diamine in step 4. $^1$H NMR (400 MHz, Methanol-4$_4$): 8.66 (br, 1H), 8.52 (s, 1H), 8.21 (s, 1H), 7.74 (s, 1H), 7.56 (d, 1H), 7.09 (d, 1H), 5.69 (d, 1H), 5.13 (s, 2H), 4.47 (m, 2H), 4.32 (m, 2H), 2.84 (t, 2H), 2.61 (s, 2H), 1.69 (t, 2H), 0.94 (s, 6H); MS (EI) for C$_{26}$H$_{27}$FN$_6$O: 459 (MH$^+$).

7-[2-(difluoromethyl)-1H-benzimidazol-5-yl]-4-(6,6-dimethyl-5,6,7,8-tetrahydroquinazolin-4-yl)-2,3,4,5-tetrahydro-1,4-benzoxazepine. Prepared according to the method of example 4 by omitting step 3, and using difluoroacetic acid and 5-[4-(6,6-dimethyl-5,6,7,8-tetrahydroquinazolin-4-yl)-2,3,4,5-tetrahydro-1,4-benzoxazepin-7-yl]pyridine-2,3-diamine in step 4. $^1$H NMR (400 MHz, DMSO-d$_6$): 8.38 (s, 1H), 7.83 (br, 1H), 7.74 to 7.67 (m, 2H), 7.61 (d, 1H), 7.54 (d, 1H), 7.31 (t, 1H), 7.05 (d, 1H), 4.64 (s, 2H), 4.33 (m, 2H), 3.80 (m, 2H), 2.70 (t, 2H), 2.47 (s, 2H), 1.60 (t, 2H), 0.83 (s, 6H); MS (EI) for C$_{27}$H$_{27}$F$_2$N$_5$O: 476 (MH$^+$).

Example 5

4-(6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine STEP 1: A solution of 6-bromo-2-methyl-1-({[2-(trimethylsilyl)ethyl]oxy}methyl)-1H-imidazo[4,5-b]pyridine (reagent preparation 35) (0.43 g, 1.30 mmol), [4-(6,6-dimethyl-5,6,7,8-tetrahydroquinazolin-4-yl)-2,3,4,5-tetrahydro-1,4-benzoxazepin-7-yl]boronic acid (reagent preparation 23) (0.45 g, 1.30 mmol) and N,N-diisopropylethylamine (1.10 mL, 6.50 mmol) in N,N-dimethylformamide (4 mL), and water (1 mL) was degassed by bubbling nitrogen gas for five minutes followed by the addition of [1,1'-bis(diphenylphosphino)ferrocene]dichloropalladium(II) (52 mg, 0.065 mmol), then stirred at 95° C. for 16 hours. The reaction mixture was cooled to room temperature, diluted with ethyl acetate (100 mL), and filtered through a pad of Celite. The filtrate was washed with 1M aqueous lithium chloride (50 mL) and brine, dried over sodium sulfate, filtered and concentrated. Column chromatography on silica (gradient 1-2% 7N ammonia in methanol in chloroform) gave 4-(6,6-dimethyl-5,6,7,8-tetrahydroquinazolin-4-yl)-7-[2-methyl-1-({[2-(trimethylsilyl)ethyl]oxy}methyl)-1H-imidazo[4,5-b]pyridin-6-yl]-2,3,4,5-tetrahydro-1,4-benzoxazepine (0.54 g, 73% yield). MS (EI) for C$_{32}$H$_{42}$N$_6$O$_2$Si: 571 (MH$^+$).

STEP 2: A solution of 4-(6,6-dimethyl-5,6,7,8-tetrahydroquinazolin-4-yl)-7-[2-methyl-1-({[2-(trimethylsilyl)ethyl]oxy}methyl)-1H-imidazo[4,5-b]pyridin-6-yl]-2,3,4,5-tetrahydro-1,4-benzoxazepine (0.54 g, 0.95 mmol) in a mixture of methanol (30 mL) and concentrated hydrochloric acid (1 mL) was stirred at reflux for 16 hours. On cooling to room temperature the solution was concentrated and the pH was adjusted to ~9 by the addition of 50% aqueous sodium hydroxide and diluted with ethyl acetate (100 mL). The organic layer was washed with 2M aqueous sodium hydroxide (20 mL) and brine, dried over anhydrous sodium sulfate, filtered and concentrated. The precipitating white solid was collected by filtration and washed with hexane to provide 4-(6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine (0.28 g, 67%). $^1$H NMR (400 MHz, d$_6$-DMSO): 8.53 (d, 1H), 8.38 (s, 1H), 8.03 (d, 1H), 7.70 (d, 1H), 7.54 (dd, 1H), 7.05 (d, 1H), 4.63 (s, 2H), 4.33 (m, 2H), 3.85 (m, 2H), 2.72 (m, 2H), 2.58 (s, 3H), 2.47 (s, 2H), 1.60 (m, 2H), 0.86 (s, 6H); MS (EI) for C$_{26}$H$_{28}$N$_6$O: 441 (MH$^+$).

Using analogous synthetic techniques and substituting with alternative starting reagents in steps 1 and conducting protecting group removal in step 2 as required according to literature techniques appropriate for a given protecting group (see for example: Greene and Wuts, Protective Groups in Organic Synthetic, Wiley-Interscience) the following compounds of the invention were prepared. Alternative starting materials were obtained commercially unless otherwise indicated.

6-[4-(6,6-dimethyl-5,6,7,8-tetrahydroquinazolin-4-yl)-2,3,4,5-tetrahydro-1,4-benzoxazepin-7-yl][1,3]thiazolo[5,4-b]pyridin-2-amine. Prepared according to the method of example 5 by using N-(6-bromo[1,3]thiazolo[5,4-b]pyridin-2-yl)acetamide (Journal of Heterocyclic Chemistry (2003), 40, 261-268) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, d$_6$-DMSO): 8.38 (m, 2H), 7.88 (brs, 2H), 7.83 (d, 1H), 7.72 (d, 1H), 7.76 (dd, 1H), 7.05 (d, 1H), 4.63 (s, 2H), 4.33 (m, 2H), 3.83 (m, 2H), 2.72 (m, 2H), 2.46 (s, 2H), 1.61 (m, 2H), 0.83 (s, 6H); MS (EI) for C$_{25}$H$_{26}$N$_6$OS: 459 (MH$^+$).

4-(6,6-dimethyl-5,6,7,8-tetrahydroquinazolin-4-yl)-7-(1H-pyrazolo[3,4-b]pyridin-5-yl)-2,3,4,5-tetrahydro-1,4-benzoxazepine. Prepared according to the method of example 5 by using 5-bromo-1-(tetrahydro-2H-pyran-2-yl)-1H-pyrazolo[3,4-b]pyridine (reagent preparation 32) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, d$_6$-DMSO): 13.71 (s, 1H), 8.82 (d, 1H), 8.43 (d, 1H), 8.38 (s, 1H), 8.18 (d, 1H), 7.74 (d, 1H), 7.58 (dd, 1H), 7.07 (d, 1H), 4.66 (s, 2H), 4.34 (m, 2H), 3.85 (m, 2H), 2.71 (m, 2H), 2.45 (s, 2H), 1.59 (m, 2H), 0.84 (s, 6H); MS (EI) for C$_{25}$H$_{26}$N$_6$O: 427 (MH$^+$).

4-(6,6-dimethyl-5,6,7,8-tetrahydroquinazolin-4-yl)-7-(1H-imidazo[4,5-b]pyridin-6-yl)-2,3,4,5-tetrahydro-1,4-benzoxazepine. Prepared according to the method of example 5 by using 6-bromo-1-(triphenylmethyl)-1H-imidazo[4,5-b]pyridine (reagent preparation 15) and [4-(6,6-dimethyl-5,6, 7,8-tetrahydroquinazolin-4-yl)-2,3,4,5-tetrahydro-1,4-benzoxazepin-7-yl]boronic acid (reagent preparation 23) in step 1. $^1$H NMR (400 MHz, d$_6$-DMSO): 8.64 (s, 1H), 8.48 (s, 1H), 8.39 (s, 1H), 8.22 (brs, 1H), 7.75 (d, 1H), 7.58 (dd, 1H), 7.06 (d, 1H), 4.67 (s, 2H), 4.35 (m, 2H), 3.85 (m, 2H), 2.72 (m, 2H), 2.46 (s, 2H), 1.61 (m, 2H), 0.85 (s, 6H); MS (EI) for C$_{25}$H$_{26}$N$_6$O: 427 (MH$^+$).

3-{[(3R)-3-aminopyrrolidin-1-yl]sulfonyl}-5-[4-(6,6-dimethyl-5,6-dihydroquinazolin-4-yl)-2,3,4,5-tetrahydro-1,4-benzoxazepin-7-yl]pyridin-2-amine. Prepared according to the method of example 5 by using [4-(6,6-dimethyl-5,6-dihydroquinazolin-4-yl)-2,3,4,5-tetrahydro-1,4-benzoxazepin-7-yl]boronic acid (reagent preparation 23) and 1,1-dimethylethyl {(3R)-1-[(2-amino-5-bromopyridin-3-yl)sulfonyl]pyrrolidin-3-yl}carbamate (reagent preparation 25) in step 1. $^1$H NMR (400 MHz, d$_6$-DMSO): 8.57 (d, 1H), 8.41 (s, 1H), 8.02 (d, 1H), 7.58 (d, 1H), 7.47 (dd, 1H), 7.02 (d, 1H), 6.75 (brs, 2H), 6.26 (dd, 2H), 4.63 (s, 2H), 4.33 (m, 2H), 3.84 (m, 2H), 3.37 (m, 2H), 3.27 (m, 2H), 2.89 (m, 1H), 2.71 (s, 2H), 1.86 (m, 3H), 1.53 (m, 1H), 0.95 (s, 6H); MS (EI) for C$_{28}$H$_{33}$N$_7$O$_3$S: 548 (MH$^+$).

3-{[(3R)-3-aminopyrrolidin-1-yl]sulfonyl}-5-{4-[(7S)-7-ethyl-5,6,7,8-tetrahydroquinazolin-4-yl]-2,3,4,5-tetrahydro-1,4-benzoxazepin-7-yl}pyridin-2-amine. Prepared according to the method of example 5 by using {4-[(7S)-7-ethyl-5,6,7,8-tetrahydroquinazolin-4-yl]-2,3,4,5-tetrahydro-1,4-benzoxazepin-7-yl}boronic acid (reagent preparation 23) and 1,1-dimethylethyl {(3R)-1-[(2-amino-5-bromopyridin-3-yl)sulfonyl]pyrrolidin-3-yl}carbamate (reagent preparation 25) in step 1. $^1$H NMR (400 MHz, d$_6$-DMSO): 8.53 (d, 1H), 8.33 (s, 1H), 7.99 (d, 1H), 7.57 (d, 1H), 7.44 (dd, 1H), 7.01 (d, 1H), 6.75 (brs, 2H), 4.70 (dd, 2H), 4.36 (m, 1H), 4.24 (m, 1H), 3.86 (m, 2H), 3.36 (m, 2H), 3.26 (m, 2H), 2.87, 2.83 (m, dd, 3H), 2.27 (dd, 1H), 1.89 (m, 3H), 1.68 (m, 1H), 1.52 (m, 1H), 1.37 (m, 2H), 1.11 (m, 1H), 0.94 (t, 3H); MS (EI) for C$_{28}$H$_{35}$N$_7$O$_3$S: 550 (MH$^+$).

2-amino-N-(2-amino-2-methylpropyl)-5-{4-[(7S)-7-ethyl-5,6,7,8-tetrahydroquinazolin-4-yl]-2,3,4,5-tetrahydro-1,4-benzoxazepin-7-yl}pyridine-3-sulfonamide. Prepared according to the method of example 5 by using {4-[(7S)-7-ethyl-5,6,7,8-tetrahydroquinazolin-4-yl]-2,3,4,5-tetrahydro-1,4-benzoxazepin-7-yl}boronic acid (reagent preparation 23) and 2-amino-N-(2-amino-2-methylpropyl)-5-bromopyridine-3-sulfonamide (reagent preparation 25) in step 1. $^1$H NMR (400 MHz, d$_6$-DMSO): 8.48 (d, 1H), 8.33 (s, 1H), 8.01 (d, 1H), 7.54 (d, 1H), 7.42 (dd, 1H), 7.01 (d, 1H), 7.72 (brs, 2H), 4.69 (dd, 2H), 4.37 (m, 1H), 4.23 (m, 1H), 3.85 (m, 2H), 2.93 (m, 2H), 2.60 (s, 2H), 2.27 (dd, 1H), 1.87 (m, 1H), 1.70 (m, 1H), 1.35 (m, 2H), 1.10 (m, 1H), 0.93 (t, 3H), 0.92 (s, 6H); MS (EI) for C$_{28}$H$_{37}$N$_7$O$_3$S: 552 (MH$^+$).

7-(2-methyl-1H-imidazo[4,5-b]pyridin-6-yl)-4-[7-(methyloxy)quinazolin-4-yl]-2,3,4,5-tetrahydro-1,4-benzoxazepine. Prepared as hydrochloride, according to the method of example 5 by using {4-[7-(methyloxy)quinazolin-4-yl]-2,3,4,5-tetrahydro-1,4-benzoxazepin-7-yl}boronic acid (reagent preparation 23) and 6-bromo-2-methyl-1-({[2-(trimethylsilyl)ethyl]oxy}methyl)-1H-imidazo[4,5-b]pyridine (reagent preparation 35) in step 1. $^1$H NMR (400 MHz, d$_6$-DMSO): 8.84 (d, 1H), 8.78 (s, 1H), 8.39 (d, 1H), 8.24 (brd, 1H), 7.95 (d, 1H), 7.68 (dd, 1H), 7.35 (d, 1H), 7.31 (s, 1H), 7.04 (d, 1H), 5.46 (s, 2H), 4.68 (m, 2H), 4.50 (m, 2H), 3.96 (s, 3H), 2.78 (s, 3H); MS (EI) for C$_{25}$H$_{22}$N$_6$O$_2$: 439 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[2-(methyloxy)ethyl]pyridine-3-sulfonamide. Prepared according to the method of example 5 by using 2-amino-5-bromo-N-(2-methoxyethyl)pyridine-3-sulfonamide (reagent preparation 25) in step 1. $^1$H NMR (400 MHz, DMSO-d6) δ 8.51 (d, 1H), 8.37 (s, 1H), 8.06 (d, 1H), 7.96 (br s, 1H), 7.59 (d, 1H), 7.45 (dd, 1H), 7.02 (d, 1H), 6.69 (br s, 2H), 4.62 (s, 2H), 4.35-4.28 (m, 2H), 3.86-3.80 (m, 2H), 3.29 (t, 2H), 3.15 (s, 3H), 2.94 (t, 2H), 2.71 (t, 2H), 2.44 (s, 2H), 1.60 (t, 2H), 0.84 (s, 6H); MS (EI) for C$_{27}$H$_{34}$N$_6$O$_4$S: 539 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2,2,2-trifluoroethyl)pyridine-3-sulfonamide. Prepared according to the method of example 5 by using 2-amino-5-bromo-N-(2,2,2-trifluoroethyl)pyridine-3-sulfonamide (reagent preparation 25) in step 1. $^1$H NMR (400 MHz, DMSO-d6) δ 8.43 (d, 1H), 8.36 (s, 1H), 8.04 (d, 1H), 7.56 (s, 1H), 7.46-7.39 (m, 2H), 7.02 (d, 1H), 6.56 (br s, 2H), 5.16-5.07 (m, 2H), 4.62 (s, 2H), 4.35-4.26 (m, 2H), 3.86-3.80 (m, 2H), 2.71 (t, 2H), 2.45 (s, 2H), 1.60 (t, 2H), 0.85 (s, 6H); MS (EI) for C$_{26}$H$_{29}$F$_3$N$_6$O$_3$S: 563 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2-hydroxyethyl)-N-methylpyridine-3-sulfonamide. Prepared according to the method of example 5 by using 2-amino-5-bromo-N-(2-hydroxyethyl)-N-methylpyridine-3-sulfonamide (reagent preparation 25) in step 1. $^1$H NMR (400 MHz, DMSO-d6) δ 8.54 (d, 1H), 8.37 (s, 1H), 8.00 (d, 1H), 7.60 (d, 1H), 7.47 (dd, 1H), 7.02 (d, 1H), 6.79 (br s, 2H), 4.87 (t, 1H), 4.62 (s, 2H), 4.35-4.28 (m, 2H), 3.89-3.77 (m, 2H), 3.54 (q, 2H), 3.19 (t, 2H), 2.79 (s, 3H), 2.71 (s, 2H), 2.45 (s, 2H), 1.61 (d, 2H), 0.85 (s, 6H); MS (EI) for C$_{27}$H$_{34}$N$_6$O$_4$S: 539 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2-hydroxypropyl)pyridine-3-sulfonamide. Prepared according to the method of example 5 by using 2-amino-5-bromo-N-(2-hydroxypropyl)pyridine-3-sulfonamide (reagent preparation 25) in step 1. $^1$H NMR (400 MHz, DMSO-d6) δ 8.50 (d, 1H), 8.37 (s, 1H), 8.05 (d, 1H), 7.58 (d, 1H), 7.45 (dd, 1H), 7.02 (d, 1H), 6.71 (br s, 2H), 4.62 (s, 2H), 4.35-4.27 (m, 2H), 3.87-3.80 (m, 2H), 3.63-3.55 (m, 1H), 2.75-2.64 (m, 4H), 2.44 (s, 2H), 1.60 (t, 2H), 0.98 (d, 3H), 0.84 (d, 6H); MS (EI) for C$_{27}$H$_{34}$N$_6$O$_4$S: 539 (MH$^+$).

2-amino-N-azetidin-3-yl-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as a diacetate salt according to the method of example 5 by using tert-butyl 3-(2-amino-5-bromopyridine-3-sulfonamido)azetidine-1-carboxylate (reagent preparation 25) in step 1 followed by Boc deprotection. $^1$H NMR (400 MHz, DMSO-d6) δ 8.51 (d, 1H), 8.37 (s, 1H), 8.03 (d, 1H), 7.59 (d, 1H), 7.45 (dd, 1H), 7.03 (d, 1H), 6.70 (br s, 2H), 4.62 (s, 2H), 4.35-4.27 (m, 2H), 4.00-3.90 (m, 1H), 3.86-3.79 (m, 2H), 3.25 (d, 4H), 2.71 (t, 2H), 2.44 (s, 2H), 1.88 (s, 6H), 1.60 (t, 2H), 0.84 (s, 6H); MS (EI) for C$_{27}$H$_{33}$N$_7$O$_3$S: 536 (MH$^+$).

2-amino-N-(2,3-dihydroxypropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared according to the method of example 5 by using 2-amino-5-bromo-N-(2,3-dihydroxypropyl)pyridine-3-sulfonamide (reagent preparation 25) in step 1. $^1$H NMR (400 MHz, DMSO-d6) δ 8.50 (d, 1H), 8.37 (s, 1H), 8.05 (d, 1H), 7.58 (d, 1H), 7.44 (dd, 1H), 7.02 (d, 1H), 6.72 (br s, 2H), 4.85 (br s, 1H), 4.66-4.51 (m, 3H), 4.36-4.26 (m, 2H), 3.87-3.78 (m, 2H), 3.50-3.43 (m, 1H), 3.29-3.19 (m, 2H), 2.90 (dd, 1H), 2.71 (t, 2H), 2.62 (dd, 1H), 2.44 (s, 2H), 1.60 (t, 2H), 0.85 (s, 6H); MS (EI) for C$_{27}$H$_{34}$N$_6$O$_5$S: 555 (MH$^+$).

1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)piperidin-3-ol. Prepared according to the method of example 5 by using 1-(2-amino-5-bromopyridin-3-ylsulfonyl)piperidin-3-ol (reagent preparation 25) in step 1. $^1$H NMR (400 MHz, DMSO-d6) δ 8.56 (d, 1H), 8.37 (s, 1H), 7.94 (d, 1H), 7.59 (d, 1H), 7.47 (dd, 1H), 7.03 (d, 1H), 6.78 (br s, 2H), 5.00 (d, 1H), 4.62 (s, 2H), 4.36-4.27 (m, 2H), 3.88-3.78 (m, 2H), 3.60-3.43 (m, 2H), 3.42-3.29 (m, 1H), 2.71 (t, 2H), 2.60 (t, 1H), 2.47-2.42 (m, 3H), 1.79-1.67 (m, 2H), 1.60 (t, 2H), 1.50-1.36 (m, 1H), 1.26-1.12 (m, 1H), 0.84 (s, 6H); MS (EI) for $C_{29}H_{36}N_6O_4S$: 565 (MH$^+$).

2-amino-N-(3-amino-2,2-dimethylpropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as an acetate salt according to the method of example 5 by using 2-amino-N-(3-amino-2,2-dimethylpropyl)-5-bromopyridine-3-sulfonamide (reagent preparation 25) in step 1. $^1$H NMR (400 MHz, DMSO-d6) δ 8.50 (d, 1H), 8.37 (s, 1H), 8.05 (d, 1H), 7.58 (d, 1H), 7.45 (dd, 1H), 7.02 (d, 1H), 6.71 (br s, 2H), 4.62 (s, 2H), 4.35-4.26 (m, 2H), 3.87-3.78 (m, 2H), 2.71 (t, 2H), 2.58 (s, 2H), 2.44 (s, 2H), 2.34 (s, 2H), 1.88 (s, 3H), 1.59 (t, 2H), 0.84 (s, 6H), 0.75 (s, 6H); MS (EI) for $C_{29}H_{39}N_7O_3S$: 566 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(3-hydroxy-2,2-dimethylpropyl)pyridine-3-sulfonamide. Prepared according to the method of example 5 by using 2-amino-5-bromo-N-(3-hydroxy-2,2-dimethylpropyl)pyridine-3-sulfonamide (reagent preparation 25) in step 1. $^1$H NMR (400 MHz, DMSO-d6) δ 8.50 (d, 1H), 8.37 (s, 1H), 8.04 (d, 1H), 7.62-7.55 (m, 2H), 7.45 (dd, 1H), 7.02 (d, 1H), 6.72 (br s, 2H), 4.62 (s, 2H), 4.50 (t, 1H), 4.34-4.28 (m, 2H), 3.86-3.79 (m, 2H), 3.08 (d, 2H), 2.71 (t, 2H), 2.58 (d, 2H), 2.44 (s, 2H), 1.60 (t, 2H), 0.84 (s, 6H), 0.75 (s, 6H); MS (EI) for $C_{29}H_{38}N_6O_4S$: 567 (MH$^+$).

N-{5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide. Prepared according to the method of example 5 by using N-(5-bromopyridin-3-yl)methanesulfonamide (reagent preparation 26) in step 1. $^1$H NMR (400 MHz, DMSO-d6) δ 10.11 (s, 1H), 8.61 (d, 1H), 8.42-8.33 (m, 2H), 7.79 (t, 1H), 7.67 (d, 1H), 7.51 (dd, 1H), 7.08 (d, 1H), 4.67 (s, 2H), 4.39-4.32 (m, 2H), 3.88-3.81 (m, 2H), 3.11 (s, 3H), 2.71 (t, 2H), 2.43 (s, 2H), 1.59 (t, 2H), 0.84 (s, 6H); MS (EI) for $C_{25}H_{29}N_5O_3S$: 480 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-1,1-dimethylethyl)pyridine-3-sulfonamide. Prepared as an acetate salt according to the method of example 5 by using 2-amino-5-bromo-N-(1-hydroxy-2-methylpropan-2-yl)pyridine-3-sulfonamide (reagent preparation 25) in step 1. $^1$H NMR (400 MHz, DMSO-d6) δ 8.48 (d, 1H), 8.37 (s, 1H), 8.09 (d, 1H), 7.56 (d, 1H), 7.43 (dd, 1H), 7.02 (d, 1H), 6.69 (br s, 2H), 4.61 (s, 2H), 4.35-4.28 (m, 2H), 3.88-3.79 (m, 2H), 3.21 (s, 2H), 2.71 (t, 2H), 2.44 (s, 2H), 1.82 (s, 3H), 1.60 (t, 2H), 1.03 (s, 6H), 0.84 (s, 6H); MS (EI) for $C_{28}H_{36}N_6O_4S$: 553 (MH$^+$).

2-chloro-N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}-6-methylbenzenesulfonamide. Prepared according to the method of example 5 by using N-(5-bromo-2-chloropyridin-3-yl)-2-chloro-6-methylbenzenesulfonamide (reagent preparation 26) in step 1. $^1$H NMR (400 MHz, DMSO-d6) δ 8.48 (br s, 1H), 8.39 (s, 1H), 7.94 (d, 1H), 7.62 (d, 1H), 7.51-7.41 (m, 3H), 7.34 (dd, 1H), 7.06 (d, 1H), 4.68 (s, 2H), 4.41-4.34 (m, 2H), 3.90-3.83 (m, 2H), 2.71 (t, 2H), 2.52 (s, 3H), 2.40 (s, 2H), 1.59 (t, 2H), 0.82 (s, 6H); MS (EI) for $C_{31}H_{31}Cl_2N_5O_3S$: 624, 626 (Cl isotopes, MH$^+$).

N-{5-[4-(6,6-dimethyl-5,6,7,8-tetrahydroquinazolin-4-yl)-2,3,4,5-tetrahydro-1,4-benzoxazepin-7-yl]-2-fluoropyridin-3-yl}methanesulfonamide. Prepared according to the method of example 5 by using N-(5-bromo-2-fluoropyridin-3-yl)methanesulfonamide (reagent preparation 26) in step 1. $^1$H NMR (400 MHz, DMSO-d6) δ 8.37 (s, 1H), 8.27 (s, 1H), 8.07 (d, 1H), 7.68 (s, 1H), 7.53 (d, 1H), 7.08 (d, 1H), 4.67 (s, 2H), 4.40-4.32 (m, 2H), 3.89-3.82 (m, 2H), 3.15 (s, 3H), 2.71 (t, 2H), 2.43 (s, 2H), 1.60 (t, 2H), 0.85 (s, 6H); MS (EI) for $C_{25}H_{28}FN_5O_3S$: 498 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(piperidin-4-ylmethyl)pyridine-3-sulfonamide. Prepared as an acetate salt according to the method of example 5 by using tert-butyl 4-((2-amino-5-bromopyridine-3-sulfonamido)methyl)piperidine-1-carboxylate (reagent preparation 25) in step 1 followed by Boc deprotection. $^1$H NMR (400 MHz, DMSO-d6) δ 8.51 (d, 1H), 8.37 (s, 1H), 8.05 (d, 1H), 7.59 (d, 1H), 7.45 (dd, 1H), 7.02 (d, 1H), 6.68 (br s, 2H), 4.62 (s, 2H), 4.35-4.28 (m, 2H), 3.87-3.79 (m, 2H), 2.97-2.87 (m, 2H), 2.71 (t, 2H), 2.63 (d, 2H), 2.39 (dd, 4H), 1.84 (s, 3H), 1.64-1.51 (m, 4H), 1.51-1.35 (m, 1H), 1.04-0.90 (m, 2H), 0.84 (s, 6H); MS (EI) for $C_{30}H_{39}N_7O_3S$: 578 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(1-methylpiperidin-4-yl)methyl]pyridine-3-sulfonamide. Prepared as a diacetate salt according to the method of example 5 by using 2-amino-5-bromo-N-((1-methylpiperidin-4-yl)methyl)pyridine-3-sulfonamide (reagent preparation 25) in step 1. $^1$H NMR (400 MHz, DMSO-d6) δ 8.51 (d, 1H), 8.37 (s, 1H), 8.04 (d, 1H), 7.58 (d, 1H), 7.45 (dd, 1H), 7.02 (d, 1H), 6.67 (br s, 2H), 4.62 (s, 2H), 4.36-4.28 (m, 2H), 3.87-3.79 (m, 2H), 2.76-2.60 (m, 6H), 2.44 (s, 2H), 2.08 (s, 3H), 1.89 (s, 6H), 1.75-1.66 (m, 2H), 1.63-1.52 (m, 4H), 1.32-1.20 (m, 1H), 1.10-0.95 (m, 2H), 0.84 (s, 6H); MS (EI) for $C_{31}H_{41}N_7O_3S$: 592 (MH$^+$).

2-amino-N-[(1-aminocyclopropyl)methyl]-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as a diacetate salt according to the method of example 5 by using tert-butyl 1-((2-amino-5-bromopyridine-3-sulfonamido)methyl)cyclopropylcarbamate (reagent preparation 25) in step 1 followed by Boc deprotection. $^1$H NMR (400 MHz, DMSO-d6) δ 8.50 (d, 1H), 8.37 (s, 1H), 8.05 (d, 1H), 7.58 (d, 1H), 7.45 (dd, 1H), 7.02 (d, 1H), 6.70 (br s, 2H), 4.62 (s, 2H), 4.34-4.27 (m, 2H), 3.86-3.79 (m, 2H), 2.77 (s, 2H), 2.70 (t, 2H), 2.44 (s, 2H), 1.89 (s, 6H), 1.59 (t, 2H), 0.84 (s, 6H), 0.32 (d, 1H); MS (EI) for $C_{28}H_{35}N_7O_3S$: 550 (MH$^+$).

2-amino-N-(trans-4-aminocyclohexyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared according to the method of example 5 by using tert-butyl trans-4-(2-amino-5-bromopyridine-3-sulfonamido)cyclohexylcarbamate (reagent preparation 25) in step 1 followed by Boc deprotection. $^1$H NMR (400 MHz, DMSO-d6) δ 8.51 (d, 1H), 8.37 (s, 1H), 8.07 (d, 1H), 7.59 (d, 1H), 7.46 (dd, 1H), 7.03 (d, 1H), 6.66 (br s, 2H), 4.62 (s, 2H), 4.35-4.28 (m, 2H), 3.87-3.80 (m, 2H), 2.89-2.78 (m, 1H), 2.71 (t, 2H), 2.44 (s, 2H), 2.42-2.36 (m, 1H), 1.68-1.55 (m, 6H), 1.27-1.07 (m, 2H), 0.98-0.81 (m, 8H); MS (EI) for $C_{30}H_{39}N_7O_3S$: 578 (MH$^+$).

2-amino-N-[(1-methylpiperidin-4-yl)methyl]-5-[4-(2,6,6-trimethyl-5,6,7,8-tetrahydroquinazolin-4-yl)-2,3,4,5-tetrahydro-1,4-benzoxazepin-7-yl]pyridine-3-sulfonamide. Prepared as a diacetate salt according to the method of example 5 by using [4-(2,6,6-trimethyl-5,6,7,8-tetrahydroquinazolin-4-yl)-2,3,4,5-tetrahydro-1,4-benzoxazepin-7-yl]boronic acid (reagent preparation 23) and 2-amino-5-bromo- N-((1-methylpiperidin-4-yl)methyl)pyridine-3-sulfonamide (reagent preparation 25) in step 1. $^1$H NMR (400 MHz, DMSO-d6) δ 8.51 (d, 1H), 8.05 (d, 1H), 7.60 (d, 1H), 7.45 (dd, 1H), 7.03 (d, 1H), 6.67 (br s, 2H), 4.57 (s, 2H), 4.30-4.24 (m, 2H), 3.86-3.79 (m, 2H), 2.70-2.61 (m, 6H), 2.40 (s, 2H), 2.33 (s, 3H), 2.08 (s, 3H), 1.87 (s, 6H), 1.69 (t, 2H), 1.62-1.50 (m, 4H), 1.32-1.19 (m, 1H), 1.08-0.95 (m, 2H), 0.84 (s, 6H); MS (EI) for $C_{32}H_{43}N_7O_3S$: 606 (MH$^+$).

2-amino-N-[(1-methylpiperidin-4-yl)methyl]-5-[4-(6,6,7-trimethyl-5,6-dihydroquinazolin-4-yl)-2,3,4,5-tetrahydro-1,4-benzoxazepin-7-yl]pyridine-3-sulfonamide. Prepared according to the method of example 5 by using [4-(6,6,7-trimethyl-5,6-dihydroquinazolin-4-yl)-2,3,4,5-tetrahydro-1,4-benzoxazepin-7-yl]boronic acid (reagent preparation 23) and 2-amino-5-bromo-N-((1-methylpiperidin-4-yl)methyl)pyridine-3-sulfonamide (reagent preparation 25) in step 1. $^1$H NMR (400 MHz, DMSO-d6) δ 8.50 (d, 1H), 8.37 (s, 1H), 8.03 (d, 1H), 7.84 (t, 1H), 7.55 (d, 1H), 7.45 (dd, 1H), 7.02 (d, 1H), 6.67 (br s, 2H), 6.13 (d, 1H), 4.62 (s, 2H), 4.37-4.29 (m, 2H), 3.88-3.78 (m, 2H), 2.72-2.60 (m, 6H), 2.07 (s, 3H), 1.88 (s, 3H), 1.74-1.62 (m, 2H), 1.61-1.50 (m, 2H), 1.34-1.16 (m, 1H), 1.09-0.95 (m, 2H), 0.91 (s, 6H); MS (EI) for $C_{32}H_{41}N_7O_3S$: 604 (MH$^+$).

2-amino-N-(2-aminopropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared according to the method of example 5 by using benzyl 1-(2-amino-5-bromopyridine-3-sulfonamido)propan-2-ylcarbamate (reagent preparation 25) in step 1 followed by Cbz deprotection. $^1$H NMR (400 MHz, DMSO-d6) δ 8.49 (d, 1H), 8.37 (s, 1H), 8.04 (d, 1H), 7.58 (s, 1H), 7.45 (dd, 1H), 7.02 (d, 1H), 6.69 (br s, 2H), 4.62 (s, 2H), 4.35-4.27 (m, 2H), 3.87-3.79 (m, 2H), 3.01 (t, 2H), 2.71 (s, 2H), 2.60 (t, 1H), 2.45 (s, 2H), 1.78-1.70 (m, 3H), 1.60 (s, 2H), 0.85 (s, 6H); MS (EI) for $C_{27}H_{35}N_7O_3S$: 538 (MH$^+$).

N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}acetamide. Prepared according to the method of example 5 by using N-(5-bromo-2-chloropyridin-3-yl)acetamide (reagent preparation 26) in step 1. $^1$H NMR (400 MHz, DMSO-d6) δ 9.84 (s, 1H), 8.68 (s, 1H), 8.52 (d, 1H), 8.43 (d, 1H), 7.77 (d, 1H), 7.57 (dd, 1H), 7.04 (d, 1H), 5.08 (s, 2H), 4.54-4.45 (m, 2H), 4.23-4.13 (m, 2H), 2.77 (t, 2H), 2.54 (s, 2H), 2.17 (d, 3H), 1.58 (t, 2H), 0.86 (s, 6H); MS (EI) for $C_{26}H_{28}ClN_5O_2$: 478 (MH$^+$).

methyl {2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}carbamate. Prepared according to the method of example 5 by using methyl 5-bromo-2-chloropyridin-3-ylcarbamate (reagent preparation 26) in step 1. $^1$H NMR (400 MHz, CD$_3$OD) δ 8.56 (d, 1H), 8.36-8.31 (m, 2H), 7.60 (d, 1H), 7.51 (dd, 1H), 7.09 (d, 1H), 4.73 (s, 2H), 4.40-4.32 (m, 2H), 4.00-3.92 (m, 2H), 3.82 (s, 3H), 2.80 (t, 2H), 2.48 (s, 2H), 1.69 (t, 2H), 0.90 (s, 6H); MS (EI) for $C_{26}H_{28}ClN_5O_3$: 494 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-ethylpyridine-3-sulfonamide. Prepared by the method of example 5 using 2-amino-5-bromo-N-ethylpyridine-3-sulfonamide (reagent preparation 25) in step 1. $^1$H NMR (400 MHz, DMSO-d6) δ 8.50 (d, 1H), 8.37 (s, 1H), 8.04 (d, 1H), 7.79 (br s, 1H), 7.61-7.48 (m, 2H), 7.45 (dd, 1H), 7.02 (d, 1H), 6.67 (br s, 2H), 4.62 (s, 2H), 4.36-4.27 (m, 2H), 3.88-3.77 (m, 2H), 2.80 (q, 2H), 2.70 (t, 2H), 2.44 (s, 2H), 1.60 (t, 2H), 0.97 (t, 3H), 0.84 (s, 6H); MS (EI) for $C_{26}H_{32}N_6O_3S$: 509 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(1-methylethyl)pyridine-3-sulfonamide. Prepared by the method of example 5 using 2-amino-5-bromo-N-isopropylpyridine-3-sulfonamide (reagent preparation 25) in step 1. $^1$H NMR (400 MHz, DMSO-d6) δ 8.49-8.43 (m, 1H), 8.37 (s, 1H), 8.05 (d, 1H), 7.76 (br s, 1H), 7.57 (d, 1H), 7.44 (dd, 1H), 7.02 (d, 1H), 6.66 (br s, 2H), 4.61 (s, 2H), 4.35-4.27 (m, 2H), 3.86-3.79 (m, 2H), 3.24-3.13 (m, 1H), 2.69 (t, 2H), 2.44 (s, 2H), 1.59 (t, 2H), 0.96 (d, 6H), 0.84 (s, 6H); MS (EI) for $C_{27}H_{34}N_6O_3S$: 523 (MH$^+$).

2-amino-N-[2-(dimethylamino)ethyl]-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared by the method of example 5 using 2-amino-5-bromo-N-(2-(dimethylamino)ethyl)pyridine-3-sulfonamide (reagent preparation 25) in step 1. $^1$H NMR (400 MHz, DMSO-d6) δ 8.42 (d, 1H), 8.36 (s, 1H), 8.02 (d, 1H), 7.72 (br s, 1H), 7.56 (d, 1H), 7.42 (dd, 1H), 7.01 (d, 1H), 6.69 (br s, 2H), 4.61 (s, 2H), 4.34-4.27 (m, 2H), 3.87-3.79 (m, 2H), 2.80 (t, 2H), 2.71 (t, 2H), 2.44 (s, 2H), 2.20 (t, 2H), 2.03 (s, 6H), 1.59 (t, 2H), 0.84 (s, 6H); MS (EI) for $C_{28}H_{37}N_7O_3S$: 552 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2-hydroxyethyl)pyridine-3-sulfonamide. Prepared by the method of example 5 using 2-amino-5-bromo-N-(2-hydroxyethyl)pyridine-3-sulfonamide (reagent preparation 25) in step 1. $^1$H NMR (400 MHz, DMSO-d6) δ 8.48 (d, 1H), 8.37 (s, 1H), 8.04 (d, 1H), 7.87 (br s, 1H), 7.58 (d, 1H), 7.44 (dd, 1H), 7.02 (d, 1H), 6.69 (br s, 2H), 4.70 (br s, 1H), 4.62 (s, 2H), 4.36-4.27 (m, 2H), 3.87-3.80 (m, 2H), 3.36 (t, 2H), 2.80 (t, 2H), 2.71 (t, 2H), 2.44 (s, 2H), 1.60 (t, 2H), 0.84 (s, 6H); MS (EI) for $C_{26}H_{32}N_6O_4S$: 525 (MH$^+$).

1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-3-(hydroxymethyl)azetidin-3-ol. Prepared by the method of example 5 using 1-(2-amino-5-bromopyridin-3-ylsulfonyl)-3-(hydroxymethyl)azetidin-3-ol (reagent preparation 25) in step 1. $^1$H NMR (400 MHz, DMSO-d6) δ 8.61 (d, 1H), 8.37 (s, 1H), 7.99 (d, 1H), 7.61 (d, 1H), 7.50 (dd, 1H), 7.03 (d, 1H), 6.79 (br s, 2H), 5.74 (br s, 1H), 4.94 (br s, 1H), 4.62 (s, 2H), 4.35-4.27 (m, 2H), 3.88-3.73 (m, 4H), 3.54 (d, 2H), 3.32 (s, 2H), 2.71 (t, 2H), 2.46 (s, 2H), 1.60 (t, 2H), 0.85 (s, 6H); MS (EI) for $C_{28}H_{34}N_6O_5S$: 567 (MH$^+$).

N$^2$-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)glycinamide. Prepared by the method of example 5 using 2-(2-amino-5-bromopyridine-3-sulfonamido)acetamide (reagent preparation 25) in step 1. $^1$H NMR (400 MHz, DMSO-d6) δ 8.50 (d, 1H), 8.37 (s, 1H), 8.08 (br s, 1H), 8.05 (d, 1H), 7.58 (d, 1H), 7.45 (dd, 1H), 7.31 (br s, 1H), 7.12 (br s, 1H), 7.02 (d, 1H), 6.75 (br s, 2H), 4.62 (s, 2H), 4.35-4.27 (m, 2H), 3.88-3.79 (m, 2H), 3.43 (s, 2H), 2.71 (t, 2H), 2.45 (s, 2H), 1.60 (t, 2H), 0.85 (s, 6H); MS (EI) for $C_{26}H_{31}N_7O_4S$: 538 (MH$^+$).

(3R)-1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-ol. Prepared by the method of example 5 using (R)-1-(2-amino-5-bromopyridin-3-ylsulfonyl)pyrrolidin-3-ol (reagent preparation 25) in step 1. $^1$H NMR (400 MHz, DMSO-d6) δ 8.54 (d, 1H), 8.37 (s, 1H), 8.00 (d, 1H), 7.59 (d, 1H), 7.47 (dd, 1H), 7.02 (d, 1H), 6.76 (s, 2H), 5.03 (d, 1H), 4.62 (s, 2H), 4.35-4.28 (m, 2H), 4.27-4.20 (m, 1H), 3.86-3.80 (m, 2H), 3.45-3.27 (m, 4H (buried)), 3.16-3.10 (m, 1H), 2.71 (t, 2H), 2.45 (s, 2H), 1.93-1.81 (m, 1H), 1.73 (s, 1H), 1.60 (t, 2H), 0.85 (s, 6H), 0.85 (s, 6H); MS (EI) for $C_{28}H_{34}N_6O_4S$: 551 (MH$^+$).

(3R)-1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-ol. Prepared by the method of example 5 using tert-butyl 3-(2-amino-5-bromopyridine-3-sulfonamido)-2-hydroxypropylcarbamate (reagent preparation 25) in step 1 followed by Boc deprotection. $^1$H NMR (400 MHz, DMSO-d6) δ 8.50 (d, 1H), 8.37 (s, 1H), 8.05 (d, 1H), 7.58 (d, 1H), 7.45 (dd, 1H), 7.02 (d, 1H), 6.71 (br s, 2H), 4.62 (s, 2H), 4.35-4.26 (m, 2H), 3.87-3.77 (m, 2H), 3.43-3.23 (m, 2H (buried)), 2.82 (dd, 1H), 2.75-2.61 (m, 3H), 2.47-2.37 (m, 3H), 1.60 (t, 2H), 0.84 (s, 6H); MS (EI) for $C_{27}H_{35}N_7O_4S$: 554 (MH$^+$).

3-{[3-(dimethylamino)azetidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine. Prepared by the method of example 5 using 5-bromo-3-(3-(dimethylamino)azetidin-1-ylsulfonyl)pyridin-2-amine (reagent preparation 25) in step 1. $^1$H NMR (400 MHz, DMSO-d6) δ 8.62 (d, 1H), 8.37 (s, 1H), 8.00 (d, 1H), 7.63 (d, 1H), 7.50 (dd, 1H), 7.03 (d, 1H), 6.82 (br s, 2H), 4.62 (s, 2H), 4.36-4.29 (m, 2H), 3.87-3.78 (m, 4H), 3.63-3.56 (m, 2H), 3.02 (p, 1H), 2.71 (t, 2H), 2.45 (s, 2H), 1.94 (s, 6H), 1.59 (t, 2H), 0.84 (s, 6H); MS (EI) for $C_{29}H_{37}N_7O_3S$: 564 (MH$^+$).

5-[4-(6,6-dimethyl-5,6,7,8-tetrahydroquinazolin-4-yl)-2,3,4,5-tetrahydro-1,4-benzoxazepin-7-yl]-N-(2-hydroxyethyl)-2-(methylamino)pyridine-3-sulfonamide. Prepared by the method of example 5 using 5-bromo-N-(2-hydroxyethyl)-2-(methylamino)pyridine-3-sulfonamide (reagent preparation 25) in step 1. $^1$H NMR (400 MHz, DMSO-d6) δ 8.60 (d, 1H), 8.37 (s, 1H), 8.06 (d, 1H), 7.85 (t, 1H), 7.58 (d, 1H), 7.45 (dd, 1H), 7.02 (d, 1H), 6.57 (q, 1H), 4.76 (t, 1H), 4.62 (s, 2H), 4.35-4.28 (m, 2H), 3.87-3.80 (m, 2H), 3.37 (q, 2H), 2.97 (d, 3H), 2.81 (q, 2H), 2.71 (t, 2H), 2.44 (s, 2H), 1.60 (t, 2H), 0.84 (s, 6H); MS (EI) for $C_{27}H_{34}N_6O_4S$: 539 (MH$^+$).

5-[4-(6,6-dimethyl-5,6,7,8-tetrahydroquinazolin-4-yl)-2,3,4,5-tetrahydro-1,4-benzoxazepin-7-yl]-3-{[3-(methylamino)azetidin-1-yl]sulfonyl}pyridin-2-amine. Prepared by the method of example 5 using N-(1-(2-amino-5-bromopyridin-3-ylsulfonyl)azetidin-3-yl)-N-methyl-2-nitrobenzenesulfonamide (reagent preparation 25) in step 1 followed by 2-benzenesulfonyl-group deprotection. $^1$H NMR (400 MHz, DMSO-d6) δ 8.61 (d, 1H), 8.37 (s, 1H), 7.98 (d, 1H), 7.62 (d, 1H), 7.49 (dd, 1H), 7.03 (d, 1H), 6.79 (br s, 2H), 4.62 (s, 2H), 4.35-4.29 (m, 2H), 3.90-3.80 (m, 4H), 3.54-3.45 (m, 2H), 3.43-3.35 (m, 1H), 2.71 (t, 2H), 2.45 (s, 2H), 2.07 (s, 3H), 1.60 (t, 2H), 0.85 (s, 6H); MS (EI) for $C_{28}H_{35}N_7O_3S$: 550 (MH$^+$).

5-[4-(6,6-dimethyl-5,6,7,8-tetrahydroquinazolin-4-yl)-2,3,4,5-tetrahydro-1,4-benzoxazepin-7-yl]-3-(piperazin-1-ylsulfonyl)pyridin-2-amine. Prepared by the method of example 5 using tert-butyl 4-(2-amino-5-bromopyridin-3-ylsulfonyl)piperazine-1-carboxylate (reagent preparation 25) in step 1 followed by Boc deprotection. $^1$H NMR (400 MHz, DMSO-d6) δ 8.57 (d, 1H), 8.37 (s, 1H), 7.92 (d, 1H), 7.60 (d, 1H), 7.47 (dd, 1H), 7.03 (d, 1H), 6.80 (br s, 2H), 4.62 (s, 2H), 4.36-4.29 (m, 2H), 3.87-3.78 (m, 2H), 2.99-2.90 (m, 4H), 2.75-2.65 (m, 6H), 2.44 (s, 2H), 1.59 (t, 2H), 0.84 (s, 6H); MS (EI) for MS (EI) for $C_{28}H_{35}N_7O_3S$: 550 (MH$^+$).

N-{2-chloro-5-[4-(6,6-dimethyl-5,6,7,8-tetrahydroquinazolin-4-yl)-2,3,4,5-tetrahydro-1,4-benzoxazepin-7-yl]phenyl}methanesulfonamide. Prepared by the method of example 5 using N-(5-bromo-2-chlorophenyl)methanesulfonamide (reagent preparation 26) in step 1. $^1$H NMR (400 MHz, DMSO-d6) δ 9.58 (s, 1H), 8.35 (s, 1H), 7.68-7.57 (m, 3H), 7.56-7.45 (m, 2H), 7.05 (d, 1H), 4.65 (s, 2H), 4.37-4.29 (m, 2H), 3.88-3.80 (m, 2H), 3.07 (s, 3H), 2.70 (t, 2H), 2.43 (s, 2H), 1.59 (t, 2H), 0.84 (s, 6H); MS (EI) for $C_{26}H_{29}ClN_4O_3S$: 513 (MH$^+$).

3-[(3-amino-3-methylazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared by the method of example 5 using 3-(3-amino-3-methylazetidin-1-ylsulfonyl)-5-bromopyridin-2-amine (reagent preparation 25) in step 1. $^1$H NMR (400 MHz, DMSO-d6) δ 8.61 (d, 1H), 8.37 (s, 1H), 7.98 (d, 1H), 7.61 (d, 1H), 7.49 (dd, 1H), 7.03 (d, 1H), 6.78 (br s, 2H), 4.62 (s, 2H), 4.36-4.28 (m, 2H), 3.87-3.79 (m, 2H), 3.60-3.48 (m, 4H), 2.71 (t, 2H), 2.45 (s, 2H), 2.02 (s, 2H), 1.60 (t, 2H), 1.19 (s, 3H), 0.85 (s, 6H); MS (EI) for MS (EI) for $C_{28}H_{35}N_7O_3S$: 550 (MH$^+$).

5-[4-(6,6-dimethyl-5,6,7,8-tetrahydroquinazolin-4-yl)-2,3,4,5-tetrahydro-1,4-benzoxazepin-7-yl]-3-[(methylsulfonyl)methyl]pyridin-2-amine. Prepared by the method of example 5 using 5-bromo-3-(methylsulfonylmethyl)pyridin-2-amine (reagent preparation 27) in step 1. $^1$H NMR (400 MHz, DMSO-d6) δ 8.37 (s, 1H), 8.28 (d, 1H), 7.73 (d, 1H), 7.53 (d, 1H), 7.37 (dd, 1H), 7.01 (d, 1H), 6.22 (s, 2H), 4.60 (s, 2H), 4.47 (s, 2H), 4.34-4.25 (m, 2H), 3.87-3.80 (m, 2H), 2.95 (s, 3H), 2.71 (t, 2H), 2.45 (s, 2H), 1.60 (t, 2H), 0.86 (s, 6H); MS (EI) for $C_{26}H_{31}N_5O_3S$: 494 (MH$^+$).

7-{6-chloro-5-[(methylsulfonyl)methyl]pyridin-3-yl}-4-(6,6-dimethyl-5,6,7,8-tetrahydroquinazolin-4-yl)-2,3,4,5-tetrahydro-1,4-benzoxazepine. Prepared by the method of example 5 using 5-bromo-2-chloro-3-(methylsulfonylmethyl)pyridine (reagent preparation 27) in step 1. $^1$H NMR (400 MHz, DMSO-d6) δ 8.74 (d, 1H), 8.36 (s, 1H), 8.23 (d, 1H), 7.73 (d, 1H), 7.57 (dd, 1H), 7.10 (d, 1H), 4.72 (s, 2H), 4.68 (s, 2H), 4.40-4.33 (m, 2H), 3.88-3.81 (m, 2H), 3.11 (s, 3H), 2.71 (t, 2H), 2.42 (s, 2H), 1.59 (t, 2H), 0.84 (s, 6H); MS (EI) for $C_{26}H_{29}ClN_4O_3S$: 513 (MH$^+$).

2-amino-N-(2-amino-1,1-dimethylethyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as an acetate salt by the method of example 5 using tert-butyl 2-(2-amino-5-bromopyridine-3-sulfonamido)-2-methylpropylcarbamate (reagent preparation 25) in step 1 followed by Boc deprotection. $^1$H NMR (400 MHz, DMSO-d6) δ 8.49 (d, 1H), 8.37 (s, 1H), 8.08 (d, 1H), 7.56 (d, 1H), 7.44 (dd, 1H), 7.02 (d, 1H), 6.68 (br s, 2H), 4.61 (s, 2H), 4.35-4.27 (m, 2H), 3.87-3.79 (m, 2H), 2.71 (t, 2H), 2.44 (s, 2H), 2.42 (s, 2H), 1.89 (s, 4H), 1.60 (t, 2H), 1.02 (s, 6H), 0.84 (s, 6H); MS (EI) for $C_{28}H_{37}N_7O_3S$: 552 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3aR,5r,6aS)-octahydrocyclopenta[c]pyrrol-5-ylmethyl]pyridine-3-sulfonamide. Prepared by the method of example 5 using tert-butyl 5-((2-amino-5-bromopyridine-3-sulfonamido)methyl)hexahydrocyclopenta[c]pyrrole-2(1H)-carboxylate (reagent preparation 25) in step 1 followed by Boc deprotection. $^1$H NMR (400 MHz, DMSO-d6) δ 8.51 (d, 1H), 8.37 (s, 1H), 8.03 (d, 1H), 7.77 (br s, 1H), 7.58 (d, 1H), 7.44 (dd, 1H), 7.02 (d, 1H), 6.68 (br s, 2H), 4.62 (s, 2H), 4.36-4.26 (m, 2H), 3.88-3.77 (m, 2H), 2.79-2.63 (m, 3H), 2.54-2.34 (m, 9H), 1.95-1.82 (m, 3H), 1.82-1.70 (m, 1H), 1.59 (t, 2H), 0.82 (s, 6H), 0.80-0.67 (m, 2H); MS (EI) for $C_{32}H_{41}N_7O_3S$: 604 (MH$^+$).

2-amino-N-(2-aminobutyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared by the method of example 5 using tert-butyl 1-(2-amino-5-bromopyridine-3-sulfonamido)butan-2-ylcarbamate (reagent preparation 25) in step 1 followed by Boc deprotection. $^1$H NMR (400 MHz, DMSO-d6) δ 8.50 (d, 1H), 8.37 (s, 1H), 8.04 (d, 1H), 7.58 (d, 1H), 7.45 (dd, 1H), 7.02 (d, 1H), 6.70 (br s, 2H), 4.62 (s, 2H), 4.35-4.27 (m, 2H), 3.86-3.79 (m, 2H), 2.75-2.65 (m, 4H), 2.62-2.54 (m, 1H), 2.48-2.41 (m, 3H), 1.64-1.55 (m, 4H), 1.39-1.25 (m, 1H), 1.16-1.03 (m, 1H), 0.84 (s, 6H), 0.76 (t, 3H); MS (EI) for MS (EI) for $C_{28}H_{37}N_7O_3S$: 552 (MH$^+$).

N-{5-[4-(6,6-dimethyl-5,6,7,8-tetrahydroquinazolin-4-yl)-2,3,4,5-tetrahydro-1,4-benzoxazepin-7-yl]-2-methylpyridin-3-yl}methanesulfonamide. Prepared by the method of example 5 using N-(5-bromo-2-methylpyridin-3-yl)methanesulfonamide (reagent preparation 26) in step 1. $^1$H NMR (400 MHz, DMSO-d6) δ 8.59 (d, 1H), 8.36 (s, 1H), 7.82 (d, 1H), 7.66 (d, 1H), 7.52 (dd, 1H), 7.07 (d, 1H), 4.65 (s, 2H), 4.39-4.29 (m, 2H), 3.90-3.79 (m, 2H), 3.07 (s, 3H), 2.71 (t, 2H), 2.53 (s, 3H), 2.44 (s, 2H), 1.60 (t, 2H), 0.85 (s, 6H); MS (EI) for $C_{26}H_{31}N_5O_3S$: 494 (MH$^+$).

2-amino-N-(3-amino-3-methylbutyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared by the method of example 5 using tert-butyl 4-(2-amino-5-bromopyridine-3-sulfonamido)-2-methylbutan-2-ylcarbamate (reagent preparation 25) in step 1 followed by Boc deprotection. $^1$H NMR (400 MHz, DMSO-d6) δ 8.51 (d, 1H), 8.37 (s, 1H), 8.04 (d, 1H), 7.58 (d, 1H), 7.44 (dd, 1H), 7.02 (d, 1H), 6.66 (br s, 2H), 4.62 (s, 2H), 4.36-4.27 (m, 2H), 3.87-3.79 (m, 2H), 2.89-2.80 (m, 2H), 2.71 (t, 2H), 2.45 (s, 2H), 1.59 (t, 2H), 1.43-1.34 (m, 2H), 0.90 (s, 6H), 0.84 (s, 6H); MS (EI) for $C_{29}H_{39}N_7O_3S$: 566 (MH$^+$).

N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}-N-methylmethanesulfonamide. Prepared by the method of example 5 using N-(5-bromo-2-chloropyridin-3-yl)-N-methylmethanesulfonamide (reagent preparation 28) in step 1. $^1$H NMR (400 MHz, DMSO-d6) δ 8.70 (s, 1H), 8.34 (s, 1H), 8.28 (s, 1H), 7.79 (s, 1H), 7.64 (d, 1H), 7.05 (d, 1H), 4.65 (s, 2H), 4.40-4.24 (m, 2H), 3.87-3.76 (m, 2H), 3.23 (s, 3H), 3.21 (s, 3H), 2.75-2.61 (m, 2H), 2.41 (s, 2H), 1.64-1.48 (m, 2H), 0.81 (s, 6H); MS (EI) for $C_{26}H_{30}ClN_5O_3S$: 528 (MH$^+$).

7-{6-chloro-5-[(difluoromethyl)oxy]pyridin-3-yl}-4-(6,6-dimethyl-5,6,7,8-tetrahydroquinazolin-4-yl)-2,3,4,5-tetrahydro-1,4-benzoxazepine. Prepared by the method of example 5 using 5-bromo-2-chloro-3-(difluoromethoxy)pyridine (reagent preparation 29) in step 1. $^1$H NMR (400 MHz, DMSO-d6) δ 8.64 (d, 1H), 8.36 (s, 1H), 8.08 (d, 1H), 7.81 (d, 1H), 7.66 (dd, 1H), 7.47 (t, 1H), 7.09 (d, 1H), 4.67 (s, 2H), 4.40-4.33 (m, 2H), 3.88-3.80 (m, 2H), 2.71 (t, 2H), 2.42 (s, 2H), 1.59 (t, 2H), 0.83 (s, 6H); MS (EI) for $C_{25}H_{25}F_2ClN_4O_2$: 487 (MH$^+$).

N-{5-[4-(6,6-dimethyl-5,6,7,8-tetrahydroquinazolin-4-yl)-2,3,4,5-tetrahydro-1,4-benzoxazepin-7-yl]-2-(methyloxy)pyridin-3-yl}methanesulfonamide. Prepared by the method of example 5 using N-(5-bromo-2-methoxypyridin-3-yl)methanesulfonamide (reagent preparation 26) in step 1. $^1$H NMR (400 MHz, DMSO-d6) δ 9.33 (s, 1H), 8.36 (s, 1H), 8.27 (d, 1H), 7.83 (d, 1H), 7.59 (d, 1H), 7.46 (dd, 1H), 7.04 (d, 1H), 4.64 (s, 2H), 4.36-4.28 (m, 2H), 3.95 (s, 3H), 3.88-3.79 (m, 2H), 3.07 (s, 3H), 2.71 (t, 2H), 2.44 (s, 2H), 1.60 (t, 2H), 0.85 (s, 6H); MS (EI) for $C_{26}H_{31}N_5O_4S$: 510 (MH$^+$).

N-{5-[4-(6,6-dimethyl-5,6,7,8-tetrahydroquinazolin-4-yl)-2,3,4,5-tetrahydro-1,4-benzoxazepin-7-yl]-2-(ethyloxy)pyridin-3-yl}methanesulfonamide. Prepared by the method of example 5 using N-(5-bromo-2-ethoxypyridin-3-yl)methanesulfonamide (reagent preparation 30) in step 1. $^1$H NMR (400 MHz, DMSO-d6) δ 9.27 (br s, 1H), 8.36 (s, 1H), 8.24 (d, 1H), 7.81 (d, 1H), 7.59 (d, 1H), 7.45 (dd, 1H), 7.04 (d, 1H), 4.63 (s, 2H), 4.40 (q, 2H), 4.36-4.29 (m, 2H), 3.88-3.80 (m, 2H), 3.06 (s, 3H), 2.71 (t, 2H), 2.44 (s, 2H), 1.60 (t, 2H), 1.37 (t, 3H), 0.85 (s, 6H); MS (EI) for $C_{27}H_{33}N_5O_4S$: 524 (MH$^+$).

3-amino-5-[4-(6,6-dimethyl-5,6,7,8-tetrahydroquinazolin-4-yl)-2,3,4,5-tetrahydro-1,4-benzoxazepin-7-yl]pyridine-2-carboxamide. Prepared by the method of example 5 using 3-amino-5-bromopicolinonitrile in step 1. The nitrile substituent hydrolyzes to the carboxamide under the aqueous reaction conditions for the coupling. $^1$H NMR (400 MHz, DMSO-d6) δ 8.36 (s, 1H), 8.06 (d, 1H), 7.93 (d, 1H), 7.65 (d, 1H), 7.48 (dd, 1H), 7.37-7.31 (m, 2H), 7.06 (d, 1H), 6.90 (br s, 2H), 4.66 (s, 2H), 4.38-4.32 (m, 2H), 3.87-3.81 (m, 2H), 2.71 (t, 2H), 2.41 (s, 2H), 1.59 (t, 2H), 0.83 (s, 6H); MS (EI) for $C_{25}H_{28}N_6O_2$: 445 (MH$^+$).

N-{2-amino-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide. Prepared as an acetate salt by the method of example 5 using N-(2-amino-5-bromopyridin-3-yl)methanesulfonamide (reagent preparation 31) in step 1. $^1$H NMR (400 MHz, DMSO-d6) δ 8.36 (s, 1H), 8.13 (d, 1H), 7.60 (d, 1H), 7.51 (d, 1H), 7.37 (dd, 1H), 7.00 (d, 1H), 6.07 (br s, 2H), 4.60 (s, 2H), 4.32-4.26 (m, 2H), 3.87-3.79 (m, 2H), 2.97 (s, 3H), 2.71 (t, 2H), 2.45 (s, 2H), 1.91 (s, 3H), 1.60 (t, 2H), 0.86 (s, 6H); MS (EI) for $C_{25}H_{30}N_6O_3S$: 495 (MH$^+$).

N-{2-cyano-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide. Prepared as an acetate salt by the method of example 5 using N-(5-bromo-2-cyanopyridin-3-yl)methanesulfonamide (reagent preparation 26) in step 1. This coupling was completed using water free conditions to prevent nitrile hydrolysis. $^1$H NMR (400 MHz, DMSO-d6) δ 8.68 (br s, 1H), 8.37 (s, 1H), 8.03 (s, 1H), 7.77 (s, 1H), 7.61 (d, 1H), 7.09 (d, 1H), 4.71 (s, 2H), 4.42-4.35 (m, 2H), 3.91-3.83 (m, 2H), 3.09 (br s, 3H), 2.71 (t, 2H), 2.42 (s, 2H), 1.91 (s, 1H), 1.59 (t, 2H), 0.82 (d, 6H); MS (EI) for $C_{26}H_{28}N_6O_3S$: 505 (MH$^+$).

N-{5-[4-(6,6-dimethyl-5,6,7,8-tetrahydroquinazolin-4-yl)-2,3,4,5-tetrahydro-1,4-benzoxazepin-7-yl]-2-[(phenylmethyl)oxy]pyridin-3-yl}methanesulfonamide. Prepared by the method of example 5 using N-(2-(benzyloxy)-5-bromopyridin-3-yl)methanesulfonamide (reagent preparation 30) in step 1. $^1$H NMR (400 MHz, DMSO-d6) δ 9.41 (br s, 1H), 8.36 (s, 1H), 8.27 (d, 1H), 7.85 (d, 1H), 7.60 (d, 1H), 7.57-7.52 (m, 2H), 7.47 (dd, 1H), 7.43-7.36 (m, 2H), 7.36-7.30 (m, 1H), 7.04 (d, 1H), 5.45 (s, 2H), 4.64 (s, 2H), 4.35-4.29 (m, 2H), 3.88-3.80 (m, 2H), 3.01 (s, 3H), 2.71 (t, 2H), 2.44 (s, 2H), 1.60 (t, 2H), 0.85 (s, 6H); MS (EI) for $C_{32}H_{35}N_5O_4S$: 586 (MH$^+$).

2-amino-N-(2-amino-2-methylpropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared by the method of example 5 using 2-amino-N-(2-amino-2-methylpropyl)-5-bromopyridine-3-sulfonamide (reagent preparation 25) in step 1. $^1$H NMR (400 MHz, DMSO-d6) δ 8.45 (br s, 1H), 8.37 (s, 1H), 8.02 (d, 1H), 7.57 (s, 1H), 7.43 (dd, 1H), 7.02 (d, 1H), 6.71 (br s, 2H), 4.62 (s, 2H), 4.35-4.28 (m, 2H), 3.86-3.80 (m, 2H), 2.71 (t, 2H), 2.54 (s, 2H), 2.44 (s, 2H), 1.59 (t, 2H), 0.92 (s, 6H), 0.84 (s, 6H); MS (EI) for $C_{28}H_{37}N_7O_3S$: 552 (MH$^+$).

3-[(3-aminoazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared by the method of example 5 using tert-butyl 1-(2-amino-5-bromopyridin-3-ylsulfonyl)azetidin-3-ylcarbamate (reagent preparation 25) in step 1 followed by Boc deprotection. $^1$H NMR (400 MHz, DMSO-d6) δ 8.61 (d, 1H), 8.37 (s, 1H), 7.98 (d, 1H), 7.61 (d, 1H), 7.49 (dd, 1H), 7.03 (d, 1H), 6.77 (br s, 2H), 4.62 (s, 2H), 4.36-4.29 (m, 2H), 3.91-3.80 (m, 4H), 3.57 (p, 1H), 3.39 (t, 2H), 2.71 (t, 2H), 2.45 (s, 2H), 1.60 (t, 2H), 0.85 (s, 6H); MS (EI) for $C_{27}H_{33}N_7O_3S$: 536 (MH$^+$).

N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide. Prepared by the method of example 5 using N-(5-bromo-2-chloropyridin-3-yl)methanesulfonamide (reagent preparation 24) in step 1. $^1$H NMR (400 MHz, DMSO-d6) δ 9.86 (br s, 1H), 8.56 (d, 1H), 8.36 (s, 1H), 8.04 (d, 1H), 7.72 (d, 1H), 7.57 (dd, 1H), 7.08 (d, 1H), 4.67 (s, 2H), 4.39-4.32 (m, 2H), 3.89-3.81 (m, 2H), 3.16 (s, 3H), 2.71 (t, 2H), 2.43 (s, 2H), 1.59 (t, 2H), 0.84 (s, 6H); MS (EI) for $C_{25}H_{28}ClN_5O_3S$: 514 (MH$^+$).

1-{6-[4-(6,6-dimethyl-5,6,7,8-tetrahydroquinazolin-4-yl)-2,3,4,5-tetrahydro-1,4-benzoxazepin-7-yl]-3H-imidazo[4,5-b]pyridin-2-yl}ethanol. Prepared according to the method of example 5 by using 1-(6-bromo-3H-imidazo[4,5-b]pyridin-2-yl)ethanol (reagent preparation 19) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.56 (br, 1H), 8.34 (s, 1H), 8.11 (br, 1H), 7.61 (s, 1H), 7.54 (d, 1H), 7.10 (d, 1H), 5.11 (m, 1H), 4.73 (s, 2H), 4.37 (m, 2H), 3.95 (m, 2H), 2.79 (t, 2H), 2.48 (s, 2H), 1.68 (t, 2H), 1.64 (d, 3H), 0.88 (s, 6H); MS (EI) for $C_{27}H_{30}N_6O_2$: 471 (MH$^+$).

4-(6,6-dimethyl-5,6,7,8-tetrahydroquinazolin-4-yl)-7-[5-(methyloxy)pyridin-3-yl]-2,3,4,5-tetrahydro-1,4-benzoxazepine. Prepared according to the method of example 5 by using 3-bromo-5-methoxypyridine and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, DMSO-d$_6$): 8.49 (s, 1H), 8.40 (s, 1H), 8.26 (s, 1H), 7.75 (s, 1H), 7.59 (m, 2H), 7.07 (d, 1H), 4.65 (s, 2H), 4.35 (m, 2H), 3.90 (s, 3H), 3.84 (m, 2H), 2.67 (t, 2H), 2.44 (s, 2H), 1.57 (t, 2H), 0.82 (s, 6H); MS (EI) for $C_{25}H_{28}N_4O_2$: 417 (MH$^+$).

7-[4-(6,6-dimethyl-5,6,7,8-tetrahydroquinazolin-4-yl)-2,3,4,5-tetrahydro-1,4-benzoxazepin-7-yl]-2H-pyrido[3,2-b][1,4]oxazin-3(4H)-one. Prepared according to the method of example 5 by using 7-bromo-2H-pyrido[3,2-b][1,4]oxazin-3(4H)-one and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, DMSO-d$_6$): 8.38 (s, 1H), 8.21 (s, 1H), 7.70 (s, 1H), 7.62 (s, 1H), 7.53 (d, 1H), 7.07 (d, 1H), 4.68 (s, 2H), 4.62 (s, 2H), 4.33 (m, 2H), 3.82 (m, 2H), 2.71 (t, 2H), 2.45 (s, 2H), 1.56 (t, 2H), 0.84 (s, 6H); MS (EI) for $C_{26}H_{27}N_5O_3$: 458 (MH$^+$).

4-(6,6-dimethyl-5,6,7,8-tetrahydroquinazolin-4-yl)-7-pyrido[2,3-b]pyrazin-7-yl-2,3,4,5-tetrahydro-1,4-benzoxazepine. Prepared according to the method of example 5 by using 7-bromopyrido[2,3-b]pyrazine and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, DMSO-d$_6$): 9.56 (s, 1H), 9.13 (s, 1H), 9.10 (s, 1H), 8.78 (s, 1H), 8.39 (s, 1H), 8.05 (s, 1H), 7.88 (d, 1H), 7.14 (d, 1H), 4.71 (s, 2H), 4.41 (m, 2H), 3.85 (m, 2H), 2.71 (t, 2H), 2.49 (s, 2H), 1.62 (t, 2H), 0.84 (s, 6H); MS (EI) for $C_{26}H_{26}N_6O$: 439 (MH$^+$).

1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}-N-methylmethanamine. Prepared according to the method of example 5 by using phenylmethyl{[6-bromo-3-({[2-(trimethylsilyl)ethyl]oxy}methyl)-3H-imidazo[4,5-b]pyridin-2-yl]methyl}methylcarbamate (reagent preparation 19) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.62 (br, 1H), 8.35 (s, 1H), 8.10 (s, 1H), 7.62 (br, 1H), 7.53 (d, 1H), 7.09 (d, 1H), 4.74 (s, 2H), 4.38 (m, 2H), 4.22 (s, 2H), 3.97 (m, 2H), 2.77 (t, 2H), 2.59 (s, 3H), 2.48 (s, 2H), 1.68 (t, 2H), 0.88 (s, 6H); MS (EI) for $C_{27}H_{31}N_7O$: 470 (MH$^+$).

1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}-N,N-dimethylmethanamine. Prepared according to the method of example 5 by using phenylmethyl ({6-[4-(6,6-dimethyl-5,6,7,8-tetrahydroquinazolin-4-yl)-2,3,4,5-tetrahydro-1,4-benzoxazepin-7-yl]-3-({[2-(trimethylsilyl)ethyl]oxy}methyl)-3H-imidazo[4,5-b]pyridin-2-yl}methyl)methylcarbamate in step 2. $^1$H NMR (400 MHz, Methanol-d$_4$): 8.58 (s, 1H), 8.34 (s, 1H), 8.11 (s, 1H), 7.62 (br, 1H), 7.52 (d, 1H), 7.10 (d, 1H), 4.74 (s, 2H), 4.35 (m, 2H), 3.96 (m, 2H), 3.81 (s, 2H), 2.77 (t, 2H), 2.48 (s, 2H), 2.39 (s, 6H), 1.77 (t, 2H), 0.90 (s, 6H); MS (EI) for $C_{28}H_{33}N_7O$: 484 (MH$^+$).

Phenylmethyl[(1S)-1-(6-{4-[(7S)-7-ethyl-2-methyl-5,6,7,8-tetrahydroquinazolin-4-yl]-2,3,4,5-tetrahydro-1,4-benzoxazepin-7-yl}-1H-imidazo[4,5-b]pyridin-2-yl)ethyl]carbamate. Prepared according to the method of example 5 by using phenylmethyl{(1S)-1-[6-bromo-3-({[2-(trimethylsilyl)ethyl]oxy}methyl)-3H-imidazo[4,5-b]pyridin-2-yl]ethyl}({[2-(trimethylsilyl)ethyl]oxy}methyl)carbamate (reagent preparation 19) and {4-[(7S)-7-ethyl-2-methyl-5,6,7,8-tetrahydroquinazolin-4-yl]-2,3,4,5-tetrahydro-1,4-benzoxazepin-7-yl}boronic acid (reagent preparation 23) in step 1. $^1$H NMR (400 MHz, Methanol-d$_4$): 8.54 (br, 1H), 8.05 (br, 1H), 7.61 (s, 1H), 7.48 (d, 1H), 7.41 to 7.29 (m, 5H), 7.09 (d, 1H), 4.77 (d, 2H), 4.61 (d, 2H), 4.43 (m, 1H), 4.20 (m, 1H), 4.04 (m, 1H), 3.95 (m, 1H), 3.88 (s, 3H), 3.29 (m, 1H), 2.87 (m, 1H), 2.78 (m, 1H), 2.60 (m, 1H), 2.35 (s, 3H), 2.29 (m, 1H), 1.96 (m, 1H), 1.69 (m, 1H), 1.63 (d, 3H), 1.41 (m, 2H), 1.16 (m, 1H), 0.99 (t, 3H); MS (EI) for $C_{36}H_{39}N_7O_3$: 618 (MH$^+$).

Phenylmethyl[(1S)-1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}ethyl]carbamate. Prepared according to the method of example 5 by using phenylmethyl{(1S)-1-[6-bromo-3-({[2-(trimethylsilyl)ethyl]oxy}methyl)-3H-imidazo[4,5-b]pyridin-2-yl]ethyl}({[2-(trimethylsilyl)ethyl]oxy}methyl)carbamate (reagent preparation 19) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.56 (br, 1H), 8.36 (br, 1H), 8.09 (br, 1H), 7.60 (s, 1H), 7.51 (d, 1H), 7.42 to 7.25 (m, 5H), 7.10 (d, 1H), 5.17 to 5.03 (dd, 2H), 4.73 (s, 2H), 4.61 (m, 1H), 4.37 (m, 1H), 3.95 (m, 1H), 2.79 (t, 2H), 2.48 (s, 2H), 1.72 to 1.56 (m, 5H), 0.90 (s, 6H); MS (EI) for $C_{35}H_{37}N_7O_3$: 604 (MH$^+$).

(1S)-1-(6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)ethanamine. Prepared according to the method of example 5 by using phenylmethyl{(1S)-1-[6-bromo-3-({[2-(trimethylsilyl)ethyl]oxy}methyl)-3H-imidazo[4,5-b]pyridin-2-yl]ethyl}({[2-(trimethylsilyl)ethyl]oxy}methyl)carbamate (reagent preparation 19) and {4-[(7S)-7-ethyl-5,6,7,8-tetrahydroquinazolin-4-yl]-2,3,4,5-tetrahydro-1,4-benzoxazepin-7-yl}boronic acid (reagent preparation 23) in step 1. $^1$H NMR (400 MHz, Methanol-d$_4$): 8.56 (s, 1H), 8.31 (s, 1H), 8.15 (s, 1H), 7.59 (s, 1H), 7.50 (d, 1H), 7.07 (d, 1H), 4.80 (m, 2H), 4.60 (q, 1H), 4.44 (m, 1H), 4.26 (m, 1H), 4.07 to 3.91 (m, 2H), 2.96 to 2.81 (m, 2H), 2.60 (m, 1H), 2.33 (m, 1H), 1.98 (m, 1H), 1.73 (m, 1H), 1.68 (d, 3H), 1.41 (m, 2H), 1.16 (m, 1H), 0.99 (t, 3H); MS (EI) for $C_{27}H_{31}N_7O$: 470 (MH$^+$).

(1R)-1-(6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)ethanamine. Prepared according to the method of example 5 by using phenylmethyl{(1R)-1-[6-bromo-3-({[2-(trimethylsilyl)ethyl]oxy}methyl)-3H-imidazo[4,5-b]pyridin-2-yl]ethyl}({[2-(trimethylsilyl)ethyl]oxy}methyl)carbamate (reagent preparation 19) and {-4-[(7S)-7-ethyl-5,6,7,8-tetrahydroquinazolin-4-yl]-2,3,4,5-tetrahydro-1,4-benzoxazepin-7-yl}boronic acid (reagent preparation 23) in step 1. $^1$H NMR (400 MHz, Methanol-d$_4$): 8.59 (s, 1H), 8.31 (s, 1H), 8.12 (s, 1H), 7.61 (s, 1H), 7.50 (d, 1H), 7.09 (d, 1H), 4.80 (m, 2H), 4.53 (m, 1H), 4.43 (m, 1H), 4.27 (m, 1H), 4.06 to 3.93 (m, 2H), 2.96 to 2.78 (m, 2H), 2.62 (m, 1H), 2.32 (m, 1H), 1.95 (m, 1H), 1.75 (m, 1H), 1.67 (d, 3H), 1.41 (m, 2H), 1.16 (m, 1H), 0.99 (t, 3H); MS (EI) for C$_{27}$H$_{31}$N$_7$O: 470 (MH$^+$).

3-[(3-amino-3-methylpyrrolidin-1-yl)sulfonyl]-5-{4-[(7S)-7-ethyl-2-methyl-5,6,7,8-tetrahydroquinazolin-4-yl]-2,3,4,5-tetrahydro-1,4-benzoxazepin-7-yl}pyridin-2-amine. Prepared according to the method of example 5 by using 1,1-dimethylethyl {1-[(2-amino-5-bromopyridin-3-yl)sulfonyl]-3-methylpyrrolidin-3-yl}carbamate (reagent preparation 25) and {4-[(7S)-7-ethyl-2-methyl-5,6,7,8-tetrahydroquinazolin-4-yl]-2,3,4,5-tetrahydro-1,4-benzoxazepin-7-yl}boronic acid (reagent preparation 23) in step 1. $^1$H NMR (400 MHz, Methanol-d$_4$): 8.37 (s, 1H), 7.97 (s, 1H), 7.41 (s, 1H), 7.29 (d, 1H), 6.94 (d, 1H), 4.64 (m, 2H), 4.27 (m, 1H), 4.05 (m, 1H), 3.94 (m, 2H), 3.47 (m, 1H), 3.31 (m, 1H), 3.12 (m, 2H), 2.81 to 2.66 (m, 2H), 2.49 (m, 1H), 2.28 (s, 3H), 2.21 (m, 1H), 1.90 (m, 1H), 1.84 (m, 1H), 1.62 (m, 1H), 1.36 (m, 2H), 1.14 (s, 3H), 1.09 (m, 1H), 0.99 (t, 3H); MS (EI) for C$_{30}$H$_{39}$N$_7$O$_3$S: 578 (MH$^+$).

3-{[(3S)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-ol. Prepared according to the method of example 5 by using 1,1-dimethylethyl {(3S)-1-[(5-bromo-2-hydroxypyridin-3-yl)sulfonyl]pyrrolidin-3-yl}carbamate (reagent preparation 40) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.53 (d, 2H), 8.00 (s, 1H), 7.57 (s, 1H), 7.41 (d, 1H), 7.03 (d, 1H), 5.12 (s, 2H), 4.45 (m, 1H), 4.29 (m, 1H), 3.93 (m, 1H), 3.72 to 3.55 (m, 6H), 2.85 (t, 2H), 2.56 (s, 2H), 2.35 (m, 1H), 2.06 (m, 1H), 1.69 (t, 2H), 0.93 (s, 6H); MS (EI) for C$_{28}$H$_{34}$N$_6$O$_4$S: 551 (MH$^+$).

(3S)-1-({2-[(3S)-3-aminopyrrolidin-1-yl]-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-amine. Prepared according to the method of example 5 by using 1,1-dimethylethyl[(3S)-1-({5-bromo-2-[(3S)-3-({[(1,1-dimethylethyl)oxy]carbonyl}amino)pyrrolidin-1-yl]pyridin-3-yl}sulfonyl)pyrrolidin-3-yl]carbamate (reagent preparation 40) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.56 (s, 1H), 8.55 (s, 1H), 8.53 (s, 1H), 7.74 (s, 1H), 7.52 (d, 1H), 7.01 (d, 1H), 5.12 (s, 2H), 4.47 (m, 2H), 4.32 (m, 3H), 4.22 (m, 1H), 4.05 (m, 2H), 3.85 (m, 1H), 3.74 to 3.56 (m, 5H), 2.85 (t, 2H), 2.59 (s, 2H), 2.35 (m, 2H), 2.22 (m, 2H), 1.70 (t, 2H), 0.93 (s, 6H); MS (EI) for C$_{32}$H$_{42}$N$_8$O$_3$S: 619 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3R)-1-methylpyrrolidin-3-yl]pyridine-3-sulfonamide. Prepared according to the method of example 5 by using 2-amino-5-bromo-N-[(3R)-1-methylpyrrolidin-3-yl]pyridine-3-sulfonamide (reagent preparation 25) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.45 (s, 1H), 8.34 (s, 1H), 8.17 (s, 1H), 7.50 (s, 1H), 7.42 (d, 1H), 7.04 (d, 1H), 4.71 (s, 2H), 4.33 (m, 2H), 3.96 (m, 2H), 3.84 (m, 1H), 2.94 (m, 1H), 2.83 to 2.69 (m, 4H), 2.61 (m, 1H), 2.47 (s, 2H), 2.45 (s, 3H), 1.74 to 1.65 (m, 3H), 0.91 (s, 6H); MS (EI) for C$_{29}$H$_{37}$N$_7$O$_3$S: 564 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-{[(3S)-1-methylpyrrolidin-3-yl]methyl}pyridine-3-sulfonamide. Prepared according to the method of example 5 by using 2-amino-5-bromo-N-{[(3S)-1-methylpyrrolidin-3-yl]methyl}pyridine-3-sulfonamide (reagent preparation 25) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.44 (br, 1H), 8.34 (s, 1H), 8.17 (s, 1H), 7.50 (s, 1H), 7.40 (d, 1H), 7.05 (d, 1H), 4.70 (s, 2H), 4.31 (m, 2H), 3.97 (m, 2H), 3.16 (m, 1H), 3.04 (t, 2H), 2.94 (d, 2H), 2.67 (t, 2H), 2.67 (s, 3H), 2.47 (s, 2H), 2.52 (m, 1H), 2.10 (m, 1H), 1.90 (m, 1H), 1.65 (m, 3H), 0.92 (s, 6H); MS (EI) for C$_{29}$H$_{37}$N$_7$O$_3$S: 564 (MH$^+$).

2-amino-N-{[(3S)-1-methylpyrrolidin-3-yl]methyl}-5-[4-(6,6,7-trimethyl-5,6-dihydroquinazolin-4-yl)-2,3,4,5-tetrahydro-1,4-benzoxazepin-7-yl]pyridine-3-sulfonamide. Prepared according to the method of 5 by using 2-amino-5-bromo-N-{[(3S)-1-methylpyrrolidin-3-yl]methyl}pyridine-3-sulfonamide (reagent preparation 25) and [4-(6,6,7-trimethyl-5,6-dihydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.35 (s, 1H), 8.25 (s, 1H), 8.07 (s, 1H), 7.37 (s, 1H), 7.32 (d, 1H), 6.97 (d, 1H), 6.07 (s, 1H), 4.58 (s, 2H), 4.23 (m, 2H), 3.84 (m, 2H), 2.86 to 2.78 (m, 3H), 2.72 (m, 2H), 2.63 (s, 2H), 2.46 (m, 1H), 2.40 (s, 3H), 2.34 (m, 1H), 1.93 (m, 1H), 1.83 (s, 3H), 1.46 (m, 1H), 0.99 (s, 6H); MS (EI) for C$_{31}$H$_{39}$N$_7$O$_3$S: 590 (MH$^+$).

4-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylbutan-2-ol. Prepared according to the method of example 5 by using 4-[(2-amino-5-bromopyridin-3-yl)sulfonyl]-2-methylbutan-2-ol (reagent preparation 41) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.52 (s, 1H), 8.35 (s, 1H), 8.14 (s, 1H), 7.50 (s, 1H), 7.43 (d, 1H), 7.06 (d, 1H), 4.70 (s, 2H), 4.30 (m, 2H), 3.95 (m, 2H), 3.35 (m, 2H), 2.79 (t, 2H), 2.48 (s, 2H), 1.82 (m, 2H), 1.68 (t, 2H), 1.15 (s, 6H), 0.90 (s, 6H); MS (EI) for C$_{29}$H$_{37}$N$_5$O$_4$S: 552 (MH$^+$).

4-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfinyl)-2-methylbutan-2-ol. Prepared according to the method of example 5 by using 4-[(2-amino-5-bromopyridin-3-yl)sulfinyl]-2-methylbutan-2-ol (reagent preparation 41) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-d$_4$): 8.40 (s, 1H), 8.34 (s, 1H), 8.03 (s, 1H), 7.51 (s, 1H), 7.42 (d, 1H), 7.05 (d, 1H), 4.68 (s, 2H), 4.33 (m, 2H), 3.94 (m, 2H), 3.20 (m, 2H), 2.79 (t, 2H), 2.47 (s, 2H), 1.80 (m, 2H), 1.67 (t, 2H), 1.21 (s, 6H), 0.88 (s, 6H); MS (EI) for C$_{29}$H$_{37}$N$_5$O$_3$S: 536 (MH$^+$).

N-{5-[4-(6,6-dimethyl-5,6,7,8-tetrahydroquinazolin-4-yl)-2,3,4,5-tetrahydro-1,4-benzoxazepin-7-yl]-2-[(phenylmethyl)amino]pyridin-3-yl}methanesulfonamide. Prepared according to the method of example 5 by using N-{5-bromo-2-[(phenylmethyl)amino]pyridin-3-yl}methanesulfonamide (reagent preparation 39) and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, Methanol-D$_4$): 8.26 (s, 1H), 8.06 (s, 1H), 7.64 (s, 1H), 7.37 to 7.08 (m, 7H), 6.94 (d, 1H), 4.59 (s, 2H), 4.57 (s, 2H), 4.20 (m, 2H), 3.85 (m, 2H), 2.91 (s, 3H), 2.67 (t, 2H), 2.36 (s, 1.59 (t, 2H), 1.21 (s, 6H), 0.82 (s, 6H); MS (EI) for C$_{32}$H$_{36}$N$_6$O$_3$S: 585 (MH$^+$).

N-{5-[4-(6,6-dimethyl-5,6,7,8-tetrahydroquinazolin-4-yl)-2,3,4,5-tetrahydro-1,4-benzoxazepin-7-yl]-2-(methylamino)pyridin-3-yl}methanesulfonamide. Prepared according to the method of example 5 by using N-[5-bromo-2-(methylamino)pyridin-3-yl]methanesulfonamide (reagent preparation 39) and [4-(6,6-dimethyl-5,6,7,8-tetrahydroquinazolin-4-yl)-2,3,4,5-tetrahydro-1,4-benzoxazepin-7-yl] boronic acid (reagent preparation 23) in step 1. $^1$H NMR (400 MHz, Methanol-d$_4$): 8.35 (s, 1H), 8.13 (s, 1H), 7.71 (s, 1H), 7.44 (s, 1H), 7.39 (d, 1H), 7.03 (d, 1H), 4.68 (s, 2H), 4.32 (m, 2H), 3.94 (m, 2H), 3.00 (s, 3H), 2.98 (s, 3H), 2.79 (t, 2H), 2.46 (s, 2H), 1.67 (t, 2H), 0.90 (s, 6H); MS (EI) for C$_{26}$H$_{32}$N$_6$O$_3$S: 509 (MH$^+$).

(2S)-3-[(2-amino-5-{4-[7-(methyloxy)quinazolin-4-yl]-2,3,4,5-tetrahydro-1,4-benzoxazepin-7-yl}pyridin-3-yl)sulfinyl]-2-methylpropan-1-ol. Prepared according to the method of example 5 by using (2S)-3-[(2-amino-5-bromopyridin-3-yl)sulfinyl]-2-methylpropan-1-ol (reagent preparation 41) and {4-[7-(methyloxy)quinazolin-4-yl]-2,3,4,5-tetrahydro-1,4-benzoxazepin-7-yl}boronic acid (reagent preparation 23) in step 1. $^1$H NMR (400 MHz, Methanol-d$_4$): 8.42 (s, 1H), 8.36 (br, 1H), 8.02 (br, 1H), 7.93 (d, 1H), 7.52 (br, 1H), 7.40 (d, 1H), 7.08 (m, 2H), 7.01 (d, 1H), 5.03 (s, 2H), 4.43 (m, 2H), 4.22 (m, 2H), 3.90 (s, 3H), 3.64 (dd, 0.5H), 3.57 to 3.46 (m, 1.5H), 3.40 (dd, 0.5H), 3.14 (dd, 0.5H), 3.01 (dd, 0.5H), 2.82 (dd, 0.5H), 2.15 (m, 1H), 1.12 (dd, 3H); MS (EI) for C$_{27}$H$_{29}$N$_5$O$_4$S: 520 (MH$^+$).

(2S)-3-[(2-amino-5-{4-[7-(methyloxy)quinazolin-4-yl]-2,3,4,5-tetrahydro-1,4-benzoxazepin-7-yl}pyridin-3-yl)sulfonyl]-2-methylpropan-1-ol. Prepared according to the method of example 5 by using (2S)-3-[(2-amino-5-bromopyridin-3-yl)sulfonyl]-2-methylpropan-1-ol (reagent preparation 41) and {4-[7-(methyloxy)quinazolin-4-yl]-2,3,4,5-tetrahydro-1,4-benzoxazepin-7-yl}boronic acid (reagent preparation 23) in step 1. $^1$H NMR (400 MHz, Methanol-d$_4$): 8.42 (s, 1H), 8.34 (br, 1H), 8.07 (br, 1H), 7.89 (d, 1H), 7.44 (s, 1H), 7.35 (d, 1H), 7.08 (m, 2H), 6.94 (d, 1H), 4.96 (s, 2H), 4.34 (m, 2H), 4.14 (m, 2H), 3.84 (s, 3H), 3.41 (m, 2H), 3.31 (dd, 1H), 2.98 (dd, 1H), 2.12 (m, 1H), 0.99 (d, 3H); MS (EI) for C$_{27}$H$_{29}$N$_5$O$_5$S: 536 (MH$^+$).

4-(6,6-dimethyl-5,6,7,8-tetrahydroquinazolin-4-yl)-7-[4-(1H-imidazol-2-yl)phenyl]-2,3,4,5-tetrahydro-1,4-benzoxazepine. Prepared according to the method of example 5 by using 2-methylpropyl 2-(4-bromophenyl)-1H-imidazole-1-carboxylate (reagent preparation 11) in step 1 followed by isobutylcarbamate deprotection. $^1$H NMR (400 MHz, DMSO-d$_6$): 12.54 (s, 1H), 8.38 (s, 1H), 8.00 (d, 2H), 7.74 (d, 2H), 7.72 (m, 1H), 7.57 (m, 1H), 7.27 (m, 1H), 7.04 (m, 2H), 4.65 (s, 2H), 4.34 (m, 2H), 3.84 (m, 2H), 2.71 (t, 2H), 2.47 (s, 2H), 1.61 (t, 2H), 0.85 (s, 6H); MS (EI) for C$_{28}$H$_{29}$N$_5$O: 452 (MH$^+$).

N-ethyl-6-[4-(2,6,6-trimethyl-5,6,7,8-tetrahydroquinazolin-4-yl)-2,3,4,5-tetrahydro-1,4-benzoxazepin-7-yl]-1H-imidazo[4,5-b]pyridin-2-amine. Prepared according to the method of example 5 by using 6-bromo-N-ethyl-1-[(methyloxy)methyl]-1H-imidazo[4,5-b]pyridin-2-amine (reagent preparation 36) and [4-(2,6,6-trimethyl-5,6,7,8-tetrahydroquinazolin-4-yl)-2,3,4,5-tetrahydro-1,4-benzoxazepin-7-yl] boronic acid (reagent preparation 23) in step 1 followed by MOM deprotection. $^1$H NMR (400 MHz, methanol-d$_4$): 8.15 (d, 1H), 7.64 (d, 1H), 7.55 (d, 1H), 7.43 (dd, 1H), 7.06 (d, 1H), 4.71 (s, 2H), 4.31 (m, 2H), 3.99 (m, 2H), 3.46 (q, 2H), 2.75 (t, 2H), 2.47 (s, 2H), 2.41 (s, 3H), 1.66 (t, 2H), 1.30 (t, 3H), 0.91 (s, 6H); MS (EI) for C$_{27}$H$_{30}$N$_6$O: 455 (MH$^+$).

7-(2-methyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine. Prepared as acetate salt according to the method of example 5 by using 6-bromo-2-methyl-1-({[2-(trimethylsilyl)ethyl]oxy}methyl)-1H-imidazo[4,5-b]pyridine (reagent preparation 35) and [4-(2,6,6-trimethyl-5,6,7,8-tetrahydroquinazolin-4-yl)-2,3,4,5-tetrahydro-1,4-benzoxazepin-7-yl]boronic acid (reagent preparation 23) in step 1 followed by SEM deprotection. $^1$H NMR (400 MHz, methanol-d$_4$): 8.52 (d, 1H), 8.05 (d, 1H), 7.63 (d, 1H), 7.50 (dd, 1H), 7.09 (d, 1H), 4.73 (s, 2H), 4.33 (m, 2H), 4.00 (m, 2H), 2.75 (t, 2H), 2.64 (s, 3H), 2.47 (s, 2H), 2.41 (s, 3H), 1.96 (s, 3H), 1.66 (t, 2H), 0.91 (s, 6H); MS (EI) for C$_{27}$H$_{30}$N$_6$O: 455 (MH$^+$).

7-(1H-benzimidazol-6-yl)-4-(6,6-dimethyl-5,6,7,8-tetrahydroquinazolin-4-yl)-2,3,4,5-tetrahydro-1,4-benzoxazepine. Prepared according to the method of example 5 by using isobutyl 6-bromo-1H-benzo[d]imidazole-1-carboxylate (reagent preparation 11) in step 1. $^1$H NMR (400 MHz, methanol-d$_4$): 8.34 (s, 1H), 8.18 (s, 1H), 7.78 (s, 1H), 7.64 (d, 1H), 7.56-7.46 (m, 3H), 7.04 (d, 1H), 4.67 (s, 2H), 4.33 (m, 2H), 3.94 (m, 2H), 2.78 (t, 2H), 2.48 (s, 2H), 1.66 (t, 2H), 0.89 (s, 6H); MS (EI) for C$_{26}$H$_{27}$N$_5$O: 426 (MH$^+$).

3-{[(3S)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as acetate salt according to the method of example 5 by using (S)-tert-butyl 1-(2-amino-5-bromopyridin-3-ylsulfonyl)pyrrolidin-3-ylcarbamate (reagent preparation 25) in step 1 followed by Boc deprotection. $^1$H NMR (400 MHz, methanol-d$_4$): 8.48 (d, 1H), 8.33 (s, 1H), 8.10 (d, 1H), 7.48 (d, 1H), 7.41 (dd, 1H), 7.05 (d, 1H), 4.70 (s, 2H), 4.34 (m, 2H), 3.96 (m, 2H), 3.73 (m, 1H), 3.55 (m, 2H), 3.35 (m, 1H), 2.79 (t, 2H), 2.49 (s, 2H), 2.25 (m, 1H), 1.93 (s, 3H), 1.88 (m, 2H), 1.69 (t, 2H), 0.91 (s, 6H); MS (EI) for C$_{28}$H$_{35}$N$_7$O$_3$S: 550 (MH$^+$).

3-{[(3R)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as acetate salt according to the method of example 5 by using (R)-tert-butyl 1-(2-amino-5-bromopyridin-3-ylsulfonyl)pyrrolidin-3-ylcarbamate (reagent preparation 25) in step 1 followed by Boc deprotection. $^1$H NMR (400 MHz, methanol-d$_4$): 8.48 (d, 1H), 8.33 (s, 1H), 8.10 (d, 1H), 7.48 (d, 1H), 7.41 (dd, 1H), 7.05 (d, 1H), 4.70 (s, 2H), 4.34 (m, 2H), 3.96 (m, 2H), 3.66 (m, 1H), 3.55 (m, 2H), 3.35 (m, 1H), 2.79 (t, 2H), 2.49 (s, 2H), 2.25 (m, 1H), 1.93 (s, 3H), 1.88 (m, 2H), 1.69 (t, 2H), 0.91 (s, 6H); MS (EI) for C$_{28}$H$_{35}$N$_7$O$_3$S: 550 (MH$^+$).

8-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-8-azabicyclo[3.2.1]octan-3-amine. Prepared according to the method of example 5 by using tert-butyl 8-(2-amino-5-bromopyridin-3-ylsulfonyl)-8-azabicyclo[3.2.1]octan-3-ylcarbamate (reagent preparation 25) in step 1 followed by Boc deprotection. MS (EI) for C$_{31}$H$_{39}$N$_7$O$_3$S: 590 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3R)-pyrrolidin-3-ylmethyl]pyridine-3-sulfonamide. Prepared as acetate salt according to the method of example 5 by using (R)-tert-butyl 3-((2-amino-5-bromopyridine-3-sulfonamido)methyl)pyrrolidine-1-carboxylate (reagent preparation 25) in step 1 followed by Boc deprotection. $^1$H NMR (400 MHz, methanol-d$_4$): 8.45 (d, 1H), 8.33 (s, 1H), 8.16 (d, 1H), 7.50 (d, 1H), 7.41 (dd, 1H), 7.06 (d, 1H), 4.71 (s, 2H), 4.34 (m, 2H), 3.96 (m, 2H), 3.15 (m, 1H), 2.98-2.89 (m, 3H), 2.79 (t, 2H), 2.48 (s, 2H), 2.09 (m, 1H), 1.90 (s, 3H), 1.69 (t, 2H), 0.92 (s, 6H); MS (EI) for $C_{29}H_{37}N_7O_3S$: 564 (MH$^+$).

2-amino-N-8-azabicyclo[3.2.1]oct-3-yl-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as acetate salt according to the method of example 5 by using 2,2,2-trichloroethyl 3-(2-amino-5-bromopyridine-3-sulfonamido)-8-azabicyclo[3.2.1]octane-8-carboxylate (reagent preparation 25) in step 1 followed by Troc deprotection. $^1$H NMR (400 MHz, methanol-d$_4$): 8.53 (s, 1H), 8.49 (d, 1H), 8.45 (s, 1H), 7.67 (d, 1H), 7.48 (dd, 1H), 7.06 (d, 1H), 5.15 (s, 2H), 4.47 (m, 2H), 4.31 (m, 2H), 4.01 (m, 2H), 3.44 (m, 1H), 2.86 (t, 2H), 2.60 (s, 2H), 2.46 (m, 2H), 2.26-2.08 (m, 6H), 1.71 (t, 2H), 0.96 (s, 6H); MS (EI) for $C_{31}H_{39}N_7O_3S$: 590 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3S)-pyrrolidin-3-ylmethyl]pyridine-3-sulfonamide. Prepared according to the method of example 5 by using (S)-tert-butyl 3-((2-amino-5-bromopyridine-3-sulfonamido)methyl)pyrrolidine-1-carboxylate (reagent preparation 25) in step 1 followed by Boc deprotection. $^1$H NMR (400 MHz, methanol-d$_4$): 8.45 (d, 1H), 8.33 (s, 1H), 8.16 (d, 1H), 7.49 (d, 1H), 7.41 (dd, 1H), 7.05 (d, 1H), 4.71 (s, 2H), 4.34 (m, 2H), 3.96 (m, 2H), 3.26-3.06 (m, 3H), 2.94 (d, 2H), 2.85 (m, 1H), 2.80 (t, 2H), 2.48 (s, 2H), 2.43 (m, 1H), 2.04 (m, 1H), 1.69 (t, 2H), 1.62 (m, 1H), 0.92 (s, 6H); MS (EI) for $C_{29}H_{37}N_7O_3S$: 564 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3R)-pyrrolidin-3-yl]pyridine-3-sulfonamide. Prepared as acetate salt according to the method of example 5 by using (R)-tert-butyl 3-(2-amino-5-bromopyridine-3-sulfonamido)pyrrolidine-1-carboxylate (reagent preparation 25) in step 1 followed by Boc deprotection. $^1$H NMR (400 MHz, methanol-d$_4$): 8.48 (d, 1H), 8.33 (s, 1H), 8.18 (d, 1H), 7.50 (d, 1H), 7.41 (dd, 1H), 7.05 (d, 1H), 4.70 (s, 2H), 4.34 (m, 2H), 3.96 (m, 2H), 3.90 (m, 1H), 3.20 (m, 3H), 2.80 (t, 2H), 2.49 (s, 2H), 2.11 (m, 1H), 1.92 (s, 3H), 1.88 (m, 2H), 1.68 (t, 2H), 0.91 (s, 6H); MS (EI) for $C_{28}H_{35}N_7O_3S$: 550 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3S)-pyrrolidin-3-yl]pyridine-3-sulfonamide. Prepared as acetate salt according to the method of example 5 by using (S)-tert-butyl 3-(2-amino-5-bromopyridine-3-sulfonamido)pyrrolidine-1-carboxylate (reagent preparation 25) in step 1 followed by Boc deprotection. $^1$H NMR (400 MHz, methanol-d$_4$): 8.48 (d, 1H), 8.33 (s, 1H), 8.18 (d, 1H), 7.50 (d, 1H), 7.41 (dd, 1H), 7.05 (d, 1H), 4.70 (s, 2H), 4.34 (m, 2H), 3.96 (m, 2H), 3.90 (m, 1H), 3.20 (m, 3H), 2.80 (t, 2H), 2.49 (s, 2H), 2.11 (m, 1H), 1.92 (s, 3H), 1.88 (m, 2H), 1.68 (t, 2H), 0.91 (s, 6H); MS (EI) for $C_{28}H_{35}N_7O_3S$: 550 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(piperidin-3-ylmethyl)pyridine-3-sulfonamide. Prepared as acetate salt according to the method of example 5 by using tert-butyl 3-((2-amino-5-bromopyridine-3-sulfonamido)methyl)piperidine-1-carboxylate (reagent preparation 25) in step 1 followed by Boc deprotection. $^1$H NMR (400 MHz, methanol-d$_4$): 8.45 (d, 1H), 8.33 (s, 1H), 8.15 (d, 1H), 7.50 (d, 1H), 7.41 (dd, 1H), 7.06 (d, 1H), 4.71 (s, 2H), 4.33 (m, 2H), 3.96 (m, 2H), 2.81 (m, 5H), 2.48 (s, 2H), 1.90 (s, 3H), 1.86 (m, 2H), 1.69 (t, 2H), 0.91 (s, 6H); MS (EI) for $C_{30}H_{39}N_7O_3S$: 578 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(piperidin-2-ylmethyl)pyridine-3-sulfonamide. Prepared as dihydrochloride salt according to the method of example 5 by using tert-butyl 2-((2-amino-5-bromopyridine-3-sulfonamido)methyl)piperidine-1-carboxylate (reagent preparation 25) in step 1 followed by Boc deprotection. MS (EI) for $C_{30}H_{39}N_7O_3S$: 578 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3R)-piperidin-3-ylmethyl]pyridine-3-sulfonamide. Prepared as acetate salt according to the method of example 5 by using (R)-tert-butyl 3-((2-amino-5-bromopyridine-3-sulfonamido)methyl)piperidine-1-carboxylate (reagent preparation 25) in step 1 followed by Boc deprotection. $^1$H NMR (400 MHz, methanol-d$_4$): 8.45 (d, 1H), 8.33 (s, 1H), 8.15 (d, 1H), 7.49 (d, 1H), 7.41 (dd, 1H), 7.05 (d, 1H), 4.71 (s, 2H), 4.33 (m, 2H), 3.96 (m, 2H), 2.87-2.76 (m, 6H), 2.64 (m, 1H), 2.49 (s, 2H), 1.91 (s, 3H), 1.87 (m, 2H), 1.71-1.57 (m, 3H), 1.22 (m, 1H), 0.91 (s, 6H); MS (EI) for $C_{30}H_{39}N_7O_3S$: 578 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(3S)-piperidin-3-ylmethyl]pyridine-3-sulfonamide. Prepared as acetate salt according to the method of example 5 by using (S)-tert-butyl 3-((2-amino-5-bromopyridine-3-sulfonamido)methyl)piperidine-1-carboxylate (reagent preparation 25) in step 1 followed by Boc deprotection. $^1$H NMR (400 MHz, methanol-d$_4$): 8.45 (d, 1H), 8.33 (s, 1H), 8.15 (d, 1H), 7.49 (d, 1H), 7.41 (dd, 1H), 7.05 (d, 1H), 4.71 (s, 2H), 4.33 (m, 2H), 3.96 (m, 2H), 2.87-2.76 (m, 6H), 2.64 (m, 1H), 2.49 (s, 2H), 1.91 (s, 3H), 1.87 (m, 2H), 1.71-1.57 (m, 3H), 1.22 (m, 1H), 0.91 (s, 6H); MS (EI) for $C_{30}H_{39}N_7O_3S$: 578 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-{[(3S)-1-methylpiperidin-3-yl]methyl}pyridine-3-sulfonamide. Prepared as acetate salt according to the method of example 5 by using (S)-2-amino-5-bromo-N-((1-methylpiperidin-3-yl)methyl)pyridine-3-sulfonamide (reagent preparation 25) in step 1. $^1$H NMR (400 MHz, methanol-d$_4$): 8.44 (d, 1H), 8.34 (s, 1H), 8.15 (d, 1H), 7.49 (d, 1H), 7.41 (dd, 1H), 7.06 (d, 1H), 4.71 (s, 2H), 4.34 (m, 2H), 3.96 (m, 2H), 3.08 (m, 1H), 2.80 (m, 4H), 2.48 (s, 5H), 2.31 (m, 1H), 2.06 (m, 1H), 1.91 (s, 3H), 1.77 (m, 3H), 1.69 (t, 2H), 1.60 (m, 1H), 1.01 (m, 1H), 0.91 (s, 6H); MS (EI) for $C_{31}H_{41}N_7O_3S$: 592 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-sulfonamide. Prepared according to the method of example 5 by using 2-amino-5-bromo-N,N-dimethylpyridine-3-sulfonamide (reagent preparation 25) in step 1. $^1$H NMR (400 MHz, methanol-d$_4$): 8.47 (s, 1H), 8.35 (s, 1H), 8.05 (s, 1H), 7.49 (s, 1H), 7.42 (d, 1H), 7.07 (d, 1H), 4.71 (s, 2H), 4.35 (m, 2H), 3.97 (m, 2H), 2.81 (m, 8H), 2.49 (s, 2H), 1.70 (m, 2H), 0.91 (s, 6H); MS (EI) for $C_{26}H_{32}N_6O_3S$: 509 (MH$^+$).

5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as acetate salt according to the method of example 5 by using 5-bromopyridine-3-sulfonamide in step 1. $^1$H NMR (400 MHz, methanol-d$_4$): 9.00 (s, 1H), 8.96 (s, 1H), 8.46 (s, 1H), 8.34 (s, 1H), 7.69 (s, 1H), 7.58 (d, 1H), 7.13 (d, 1H), 4.77 (s, 2H), 4.38 (m, 2H), 3.98 (m, 2H), 2.79 (m, 2H), 2.48 (s, 2H), 1.98 (s, 3H), 1.68 (m, 2H), 0.89 (s, 6H); MS (EI) for $C_{24}H_{27}N_5O_3S$: 466 (MH$^+$).

2-amino-N,N-dimethyl-5-[4-(2,6,6-trimethyl-5,6,7,8-tetrahydroquinazolin-4-yl)-2,3,4,5-tetrahydro-1,4-benzoxazepin-7-yl]pyridine-3-sulfonamide. Prepared according to the method of example 5 by using 4-(2,6,6-trimethyl-5,6,7,8-tetrahydroquinazolin-4-yl)-2,3,4,5-tetrahydrobenzo[f][1,4]oxazepin-7-ylboronic acid (reagent preparation 23) and 2-amino-5-bromo-N,N-dimethylpyridine-3-sulfonamide (reagent preparation 25) in step 1. $^1$H NMR (400 MHz, methanol-d$_4$): 8.47 (s, 1H), 8.04 (s, 1H), 7.52 (s, 1H), 7.41 (d, 1H), 7.06 (d, 1H), 4.71 (s, 2H), 4.31 (m, 2H), 4.00 (m, 2H), 2.80 (s, 6H), 2.75 (m, 2H), 2.45 (s, 2H), 2.40 (s, 3H), 1.67 (m, 2H), 0.91 (s, 6H); MS (EI) for $C_{27}H_{34}N_6O_3S$: 523 (MH$^+$).

5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-sulfonamide. Prepared according to the method of example 5 by using 5-bromo-N,N-dimethylpyridine-3-sulfonamide in step 1. $^1$H NMR (400 MHz, methanol-d$_4$): 9.08 (s, 1H), 8.88 (s, 1H), 8.33 (m, 2H), 7.60 (d, 1H), 7.14 (d, 1H), 4.77 (s, 2H), 4.40 (m, 2H), 3.99 (m, 2H), 2.79 (m, 8H), 2.49 (s, 2H), 1.69 (m, 2H), 0.90 (s, 6H); MS (EI) for $C_{26}H_{31}N_5O_3S$: 494 (MH$^+$).

5-[4-(6,6-dimethyl-5,6,7,8-tetrahydroquinazolin-4-yl)-2,3,4,5-tetrahydro-1,4-benzoxazepin-7-yl]-3-(morpholin-4-ylsulfonyl)pyridin-2-amine. Prepared as acetate salt according to the method of example 5 by using 5-bromo-3-(morpholinosulfonyl)pyridin-2-amine (reagent preparation 25) in step 1. $^1$H NMR (400 MHz, methanol-d$_4$): 8.48 (d, 1H), 8.35 (s, 1H), 8.03 (d, 1H), 7.49 (d, 1H), 7.42 (dd, 1H), 7.06 (d, 1H), 4.71 (s, 2H), 4.35 (m, 2H), 3.97 (m, 2H), 3.70 (m, 4H), 3.13 (m, 4H), 2.80 (t, 2H), 2.48 (s, 2H), 1.98 (s, 3H), 1.61 (t, 2H), 0.90 (s, 6H); MS (EI) for $C_{28}H_{34}N_6O_4S$: 551 (MH$^+$).

5-[4-(6,6-dimethyl-5,6,7,8-tetrahydroquinazolin-4-yl)-2,3,4,5-tetrahydro-1,4-benzoxazepin-7-yl]-3-[(4-methylpiperazin-1-yl)sulfonyl]pyridin-2-amine. Prepared as diacetate salt according to the method of example 5 by using 5-bromo-3-(4-methylpiperazin-1-ylsulfonyl)pyridin-2-amine (reagent preparation 25) in step 1. $^1$H NMR (400 MHz, methanol-d$_4$): 8.58 (d, 1H), 8.34 (s, 1H), 8.04 (d, 1H), 7.49 (d, 1H), 7.41 (dd, 1H), 7.06 (d, 1H), 4.71 (s, 2H), 4.35 (m, 2H), 3.96 (m, 2H), 3.22 (m, 4H), 2.80 (t, 2H), 2.55 (m, 4H), 2.49 (s, 2H), 2.31 (s, 3H), 1.97 (s, 3H), 1.69 (t, 2H), 0.90 (s, 6H); MS (EI) for $C_{29}H_{37}N_7O_3S$: 564 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-carboxamide. Prepared as trifluoroacetate salt according to the method of example 5 by using 2-amino-5-bromo-N,N-dimethylnicotinamide (reagent preparation 33) in step 1. $^1$H NMR (400 MHz, methanol-d$_4$): 8.51 (d, 1H), 8.23 (s, 2H), 7.66 (d, 1H), 7.50 (dd, 1H), 7.05 (d, 1H), 5.14 (s, 2H), 4.48 (m, 2H), 4.32 (m, 2H), 3.14 (s, 3H), 3.07 (s, 3H), 2.85 (t, 2H), 2.59 (s, 2H), 1.70 (t, 2H), 0.95 (s, 6H); MS (EI) for $C_{27}H_{32}N_6O_2$: 473 (MH$^+$).

3-(azetidin-1-ylsulfonyl)-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as acetate salt according to the method of example 5 by using 3-(azetidin-1-ylsulfonyl)-5-bromopyridin-2-amine (reagent preparation 25) in step 1. $^1$H NMR (400 MHz, methanol-d$_4$): 8.51 (d, 1H), 8.34 (s, 1H), 8.09 (d, 1H), 7.50 (d, 1H), 7.43 (dd, 1H), 7.07 (d, 1H), 4.71 (s, 2H), 4.35 (m, 2H), 3.96 (m, 2H), 3.88 (t, 4H), 2.79 (t, 2H), 2.49 (s, 2H), 2.15 (m, 2H), 1.96 (s, 3H), 1.69 (t, 2H), 0.90 (s, 6H); MS (EI) for $C_{27}H_{32}N_6O_3S$: 521 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-methylpyridine-3-sulfonamide. Prepared according to the method of example 5 by using 2-amino-5-bromo-N-methylpyridine-3-sulfonamide (reagent preparation 25) in step 1. $^1$H NMR (400 MHz, methanol-d$_4$): 8.44 (d, 1H), 8.34 (s, 1H), 8.15 (d, 1H), 7.49 (d, 1H), 7.42 (dd, 1H), 7.06 (d, 1H), 4.70 (s, 2H), 4.35 (m, 2H), 3.96 (m, 2H), 2.79 (t, 2H), 2.55 (s, 3H), 2.48 (s, 2H), 1.69 (t, 2H), 0.90 (s, 6H); MS (EI) for $C_{25}H_{30}N_6O_3S$: 495 (MH$^+$).

1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)azetidin-3-ol. Prepared according to the method of example 5 by using 1-(2-amino-5-bromopyridin-3-ylsulfonyl)azetidin-3-ol (reagent preparation 25) in step 1. $^1$H NMR (400 MHz, methanol-d$_4$): 8.51 (d, 1H), 8.34 (s, 1H), 8.09 (d, 1H), 7.50 (d, 1H), 7.43 (dd, 1H), 7.07 (d, 1H), 4.70 (s, 2H), 4.45 (m, 2H), 4.35 (m, 2H), 4.02 (m, 2H), 3.96 (m, 2H), 3.65 (m, 2H), 2.80 (t, 2H), 2.49 (s, 2H), 1.69 (t, 2H), 0.91 (s, 6H); MS (EI) for $C_{27}H_{32}N_6O_4S$: 537 (MH$^+$).

5-[4-(6,6-dimethyl-5,6,7,8-tetrahydroquinazolin-4-yl)-2,3,4,5-tetrahydro-1,4-benzoxazepin-7-yl]-3-(pyrrolidin-1-ylsulfonyl)pyridin-2-amine. Prepared as acetate salt according to the method of example 5 by using 5-bromo-3-(pyrrolidin-1-ylsulfonyl)pyridin-2-amine (reagent preparation 25) in step 1. $^1$H NMR (400 MHz, methanol-d$_4$): 8.45 (d, 1H), 8.34 (s, 1H), 8.10 (d, 1H), 7.48 (d, 1H), 7.41 (dd, 1H), 7.06 (d, 1H), 4.70 (s, 2H), 4.35 (m, 2H), 3.96 (m, 2H), 3.32 (m, 4H), 2.80 (t, 2H), 2.49 (s, 2H), 1.96 (s, 3H), 1.84 (m, 4H), 1.69 (t, 2H), 0.91 (s, 6H); MS (EI) for $C_{28}H_{34}N_6O_3S$: 535 (MH$^+$).

1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-ol. Prepared according to the method of example 5 by using 1-(2-amino-5-bromopyridin-3-ylsulfonyl)pyrrolidin-3-ol (reagent preparation 25) in step 1. $^1$H NMR (400 MHz, methanol-d$_4$): 8.44 (d, 1H), 8.34 (s, 1H), 8.11 (d, 1H), 7.48 (d, 1H), 7.41 (dd, 1H), 7.06 (d, 1H), 4.70 (s, 2H), 4.35 (m, 2H), 3.95 (m, 2H), 3.47 (m, 3H), 2.79 (t, 2H), 2.49 (s, 2H), 2.03-1.80 (m, 4H), 1.69 (t, 2H), 0.91 (s, 6H); MS (EI) for $C_{28}H_{34}N_6O_4S$: 551 (MH$^+$).

2-amino-N-cyclobutyl-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared according to the method of example 5 by using 2-amino-5-bromo-N-cyclobutylpyridine-3-sulfonamide (reagent preparation 25) in step 1. $^1$H NMR (400 MHz, methanol-d$_4$): 8.42 (d, 1H), 8.34 (s, 1H), 8.15 (d, 1H), 7.48 (d, 1H), 7.41 (dd, 1H), 7.06 (d, 1H), 4.70 (s, 2H), 4.35 (m, 2H), 3.95 (m, 2H), 3.72 (m, 1H), 2.80 (t, 2H), 2.48 (s, 2H), 2.02 (m, 2H), 1.82 (m, 2H), 1.68 (t, 2H), 1.57 (m, 2H), 0.90 (s, 6H); MS (EI) for $C_{28}H_{34}N_6O_3S$: 535 (MH$^+$).

5-[4-(6,6-dimethyl-5,6,7,8-tetrahydroquinazolin-4-yl)-2,3,4,5-tetrahydro-1,4-benzoxazepin-7-yl]-3-(methylsulfonyl)pyridin-2-amine. Prepared as acetate salt according to the method of example 5 by using 5-bromo-3-(methylsulfonyl)pyridin-2-amine (reagent preparation 34) in step 1. $^1$H NMR (400 MHz, methanol-d$_4$): 8.52 (d, 1H), 8.34 (s, 1H), 8.19 (d, 1H), 7.52 (d, 1H), 7.43 (dd, 1H), 7.06 (d, 1H), 4.71 (s, 2H), 4.34 (m, 2H), 3.96 (m, 2H), 3.15 (s, 3H), 2.79 (t, 2H), 2.49 (s, 2H), 1.97 (s, 3H), 1.69 (t, 2H), 0.91 (s, 6H); MS (EI) for $C_{25}H_{29}N_5O_3S$: 480 (MH$^+$).

2-amino-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared according to the method of example 5 by using 2-amino-5-bromopyridine-3-sulfonamide (reagent preparation 25) in step 1. MS (EI) for $C_{24}H_{28}N_6O_3S$: 481 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-ethyl-N-methylpyridine-3-sulfonamide. Prepared according to the method of example 5 by using 2-amino-5-bromo-N-ethyl-N-methylpyridine-3-sulfonamide (reagent preparation 25) in step 1. $^1$H NMR (400 MHz, methanol-d$_4$): 8.44 (d, 1H), 8.34 (s, 1H), 8.07 (d, 1H), 7.48 (d, 1H), 7.41 (dd, 1H), 7.06 (d, 1H), 4.70 (s, 2H), 4.35 (m, 2H), 3.96 (m, 2H), 3.24 (q, 2H), 2.83 (s, 3H), 2.80 (t, 2H), 2.48 (s, 2H), 1.69 (t, 2H), 1.14 (t, 3H), 0.90 (s, 6H); MS (EI) for C$_{27}$H$_{34}$N$_6$O$_3$S: 523 (MH$^+$).

3-[(3,3-difluoroazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared according to the method of example 5 by using 5-bromo-3-(3,3-difluoroazetidin-1-ylsulfonyl)pyridin-2-amine (reagent preparation 25) in step 1. $^1$H NMR (400 MHz, methanol-d$_4$): 8.55 (d, 1H), 8.34 (s, 1H), 8.14 (d, 1H), 7.52 (d, 1H), 7.44 (dd, 1H), 7.07 (d, 1H), 4.70 (s, 2H), 4.32 (m, 6H), 3.96 (m, 2H), 2.79 (t, 2H), 2.49 (s, 2H), 1.69 (t, 2H), 0.90 (s, 6H); MS (EI) for C$_{27}$H$_{30}$F$_2$N$_6$O$_3$S: 523 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-1-methylethyl)pyridine-3-sulfonamide. Prepared according to the method of example 5 by using 2-amino-5-bromo-N-(1-hydroxypropan-2-yl)pyridine-3-sulfonamide (reagent preparation 25) in step 1. $^1$H NMR (400 MHz, methanol-d$_4$): 8.43 (d, 1H), 8.34 (s, 1H), 8.20 (d, 1H), 7.50 (d, 1H), 7.42 (dd, 1H), 7.06 (d, 1H), 4.70 (s, 2H), 4.35 (m, 2H), 3.95 (m, 2H), 3.44 (m, 1H), 3.30 (m, 2H), 2.80 (t, 2H), 2.48 (s, 2H), 1.69 (t, 2H), 1.03 (d, 3H), 0.90 (s, 6H); MS (EI) for C$_{27}$H$_{34}$N$_6$O$_4$S: 539 (MH$^+$).

2-amino-5-[4-(6,6-dimethyl-5,6-dihydroquinazolin-4-yl)-2,3,4,5-tetrahydro-1,4-benzoxazepin-7-yl]-N-methylpyridine-3-sulfonamide. Prepared according to the method of example 5 by using 4-chloro-6,6-dimethyl-5,6-dihydroquinazoline (reagent preparation 23) and 2-amino-5-bromo-N-methylpyridine-3-sulfonamide (reagent preparation 25) in step 1. $^1$H NMR (400 MHz, methanol-d$_4$): 8.43 (d, 1H), 8.38 (s, 1H), 8.15 (d, 1H), 7.48 (d, 1H), 7.42 (dd, 1H), 7.06 (d, 1H), 6.33 (d, 1H), 6.27 (d, 1H), 4.69 (s, 2H), 4.35 (m, 2H), 3.95 (m, 2H), 2.76 (s, 2H), 2.55 (s, 3H), 1.01 (s, 6H); MS (EI) for C$_{25}$H$_{28}$N$_6$O$_3$S: 493 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2-fluoroethyl)pyridine-3-sulfonamide. Prepared according to the method of example 5 by using 2-amino-5-bromo-N-(2-fluoroethyl)pyridine-3-sulfonamide (reagent preparation 25) in step 1. $^1$H NMR (400 MHz, methanol-d$_4$): 8.43 (d, 1H), 8.34 (s, 1H), 8.17 (d, 1H), 7.49 (d, 1H), 7.41 (dd, 1H), 7.05 (d, 1H), 4.70 (s, 2H), 4.40 (m, 2H), 4.34 (m, 2H), 3.95 (m, 2H), 3.20 (m, 2H), 2.79 (t, 2H), 2.48 (s, 2H), 1.69 (t, 2H), 0.90 (s, 6H); MS (EI) for C$_{26}$H$_{31}$FN$_6$O$_3$S: 527 (MH$^+$).

3-[(3-aminopyrrolidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as dihydrochloride salt according to the method of example 5 by using tert-butyl 1-(2-amino-5-bromopyridin-3-ylsulfonyl)pyrrolidin-3-ylcarbamate (reagent preparation 25) in step 1 followed by Boc deprotection. $^1$H NMR (400 MHz, methanol-d$_4$): 8.51 (m, 2H), 7.70 (s, 1H), 7.51 (d, 1H), 7.07 (d, 1H), 5.17 (s, 2H), 4.48 (m, 2H), 4.31 (m, 2H), 3.95 (m, 1H), 3.69 (m, 2H), 3.57 (m, 1H), 3.45 (m, 1H), 2.86 (t, 2H), 2.61 (s, 2H), 2.41 (m, 1H), 2.06 (m, 1H), 1.71 (t, 2H), 0.96 (s, 6H); MS (EI) for C$_{28}$H$_{35}$N$_7$O$_3$S: 550 (MH$^+$).

1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)piperidin-4-ol. Prepared according to the method of example 5 by using 1-(2-amino-5-bromopyridin-3-ylsulfonyl)piperidin-4-ol (reagent preparation 25) in step 1. MS (EI) for C$_{29}$H$_{36}$N$_6$O$_4$S: 565 (MH$^+$).

3-[(3-aminopiperidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as acetate salt according to the method of example 5 by using tert-butyl 1-(2-amino-5-bromopyridin-3-ylsulfonyl)piperidin-3-ylcarbamate (reagent preparation 25) in step 1 followed by Boc deprotection. $^1$H NMR (400 MHz, methanol-d$_4$): 8.49 (d, 1H), 8.33 (s, 1H), 8.04 (d, 1H), 7.48 (d, 1H), 7.40 (dd, 1H), 7.06 (d, 1H), 4.71 (s, 2H), 4.34 (m, 2H), 3.96 (m, 2H), 3.58 (m, 1H), 3.38 (m, 1H), 3.19 (m, 1H), 2.97 (m, 1H), 2.88 (m, 1H), 2.80 (t, 2H), 2.49 (s, 2H), 1.93 (s, 3H), 1.87 (m, 2H), 1.67 (m, 3H), 1.42 (m, 1H), 0.91 (s, 6H); MS (EI) for C$_{29}$H$_{37}$N$_7$O$_3$S: 564 (MH$^+$).

2-amino-N-(2-aminoethyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as acetate salt according to the method of example 5 by using tert-butyl 2-(2-amino-5-bromopyridine-3-sulfonamido)ethylcarbamate (reagent preparation 25) in step 1 followed by Boc deprotection. $^1$H NMR (400 MHz, methanol-d$_4$): 8.47 (d, 1H), 8.33 (s, 1H), 8.17 (d, 1H), 7.50 (d, 1H), 7.41 (dd, 1H), 7.06 (d, 1H), 4.72 (s, 2H), 4.34 (m, 2H), 3.96 (m, 2H), 3.08 (t, 2H), 2.97 (t, 2H), 2.78 (t, 2H), 2.48 (s, 2H), 1.92 (s, 3H), 1.68 (m, 3H), 0.91 (s, 6H); MS (EI) for C$_{26}$H$_{33}$N$_7$O$_3$S: 524 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(3-hydroxypropyl)pyridine-3-sulfonamide. Prepared according to the method of example 5 by using 2-amino-5-bromo-N-(3-hydroxypropyl)pyridine-3-sulfonamide (reagent preparation 25) in step 1. $^1$H NMR (400 MHz, methanol-d$_4$): 8.43 (d, 1H), 8.34 (s, 1H), 8.16 (d, 1H), 7.49 (d, 1H), 7.42 (dd, 1H), 7.05 (d, 1H), 4.70 (s, 2H), 4.35 (m, 2H), 3.95 (m, 2H), 3.55 (t, 2H), 2.98 (t, 2H), 2.80 (t, 2H), 2.48 (s, 2H), 1.67 (m, 4H), 0.90 (s, 6H); MS (EI) for C$_{27}$H$_{34}$N$_6$O$_4$S: 539 (MH$^+$).

2-amino-N-(3-aminopropyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. Prepared as dihydrochloride salt according to the method of example 5 by using tert-butyl 3-(2-amino-5-bromopyridine-3-sulfonamido)propylcarbamate (reagent preparation 25) in step 1 followed by Boc deprotection. $^1$H NMR (400 MHz, methanol-d$_4$): 8.57 (s, 1H), 8.53 (s, 1H), 8.46 (s, 1H), 7.73 (s, 1H), 7.52 (d, 1H), 7.07 (d, 1H), 5.16 (s, 2H), 4.48 (m, 2H), 4.32 (m, 2H), 3.31 (t, 2H), 3.04 (t, 2H), 2.86 (t, 2H), 2.61 (s, 2H), 1.90 (m, 2H), 1.71 (t, 2H), 0.96 (s, 6H); MS (EI) for C$_{27}$H$_{35}$N$_7$O$_3$S: 538 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(3,3,3-trifluoro-2-hydroxypropyl)pyridine-3-sulfonamide. Prepared according to the method of example 5 by using 2-amino-5-bromo-N-(3,3,3-trifluoro-2-hydroxypropyl)pyridine-3-sulfonamide (reagent preparation 25) in step 1. $^1$H NMR (400 MHz, methanol-d$_4$): 8.44 (d, 1H), 8.34 (s, 1H), 8.18 (d, 1H), 7.48 (d, 1H), 7.42 (dd, 1H), 7.06 (d, 1H), 4.69 (s, 2H), 4.35 (m, 2H), 4.00 (m, 1H), 3.96 (m, 2H), 3.21 (m, 2H), 3.01 (m, 2H), 2.80 (t, 2H), 2.48 (s, 2H), 1.69 (t, 2H), 0.90 (s, 6H); MS (EI) for C$_{27}$H$_{31}$F$_3$N$_6$O$_4$S: 593 (MH$^+$).

5-[4-(6,6-dimethyl-5,6,7,8-tetrahydroquinazolin-4-yl)-2,3,4,5-tetrahydro-1,4-benzoxazepin-7-yl]-3-(hexahydropyrrolo[3,4-c]pyrrol-2(1H)-ylsulfonyl)pyridin-2-amine. Prepared as dihydrochloride salt according to the method of example 5 by using tert-butyl 5-(2-amino-5-bromopyridin-3-ylsulfonyl)hexahydropyrrolo[3,4-c]pyrrole-2(1H)-carboxylate (reagent preparation 25) in step 1 followed by Boc deprotection. $^1$H NMR (400 MHz, methanol-d$_4$): 8.52 (m, 2H), 8.41 (m, 1H), 7.67 (s, 1H), 7.50 (s, 1H), 7.07 (d, 1H), 5.16 (s, 2H), 4.47 (m, 2H), 4.32 (m, 2H), 3.57 (m, 2H), 3.48 (m, 2H), 3.30 (m, 2H), 3.14 (m, 4H), 2.86 (t, 2H), 2.60 (s, 2H), 1.71 (t, 2H), 0.96 (s, 6H); MS (EI) for $C_{30}H_{37}N_7O_3S$: 576 (MH$^+$).

3-[(3-amino-3-methylpyrrolidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as dihydrochloride salt according to the method of example 5 by using tert-butyl 1-(2-amino-5-bromopyridin-3-ylsulfonyl)-3-methylpyrrolidin-3-ylcarbamate (reagent preparation 25) in step 1 followed by Boc deprotection. $^1$H NMR (400 MHz, methanol-d$_4$): 8.52 (m, 2H), 8.32 (m, 1H), 7.66 (m, 1H), 7.48 (m, 1H), 7.06 (m, 1H), 5.16 (s, 2H), 4.47 (m, 2H), 4.32 (m, 2H), 3.72-3.44 (m, 2H), 2.86 (t, 2H), 2.60 (s, 2H), 2.16 (m, 2H), 1.71 (t, 2H), 1.45 (m, 3H), 0.96 (s, 6H); MS (EI) for $C_{29}H_{37}N_7O_3S$: 564 (MH$^+$)

3-[(1S,4S)-2,5-diazabicyclo[2.2.1]hept-2-ylsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as diacetate salt according to the method of example 5 by using (1S,4S)-tert-butyl 5-(2-amino-5-bromopyridin-3-ylsulfonyl)-2,5-diazabicyclo[2.2.1]heptane-2-carboxylate (reagent preparation 25) in step 1 followed by Boc deprotection. $^1$H NMR (400 MHz, methanol-d$_4$): 8.49 (d, 1H), 8.34 (s, 1H), 8.15 (d, 1H), 7.50 (d, 1H), 7.42 (dd, 1H), 7.06 (d, 1H), 4.71 (s, 2H), 4.63 (s, 1H), 4.35 (m, 2H), 4.02 (s, 1H), 3.95 (m, 2H), 3.50-3.05 (m, 4H), 2.79 (t, 2H), 2.49 (s, 2H), 1.95 (s, 6H), 1.79-1.63 (m, 4H), 0.90 (s, 6H); MS (EI) for $C_{29}H_{35}N_7O_3S$: 562 (MH$^+$).

3-[(3-amino-3-methylpyrrolidin-1-yl)sulfonyl]-5-{4-[(7S)-7-ethyl-5,6,7,8-tetrahydroquinazolin-4-yl]-2,3,4,5-tetrahydro-1,4-benzoxazepin-7-yl}pyridin-2-amine. Prepared as dihydrochloride salt according to the method of example 5 by using {4-[(7S)-7-ethyl-5,6,7,8-tetrahydroquinazolin-4-yl]-2,3,4,5-tetrahydro-1,4-benzoxazepin-7-yl}boronic acid (reagent preparation 23) and tert-butyl 1-(2-amino-5-bromopyridin-3-ylsulfonyl)-3-methylpyrrolidin-3-ylcarbamate (reagent preparation 25) in step 1 followed by Boc deprotection. $^1$H NMR (400 MHz, methanol-d$_4$): 8.50 (m, 3H), 7.70 (s, 1H), 7.50 (d, 1H), 7.07 (d, 1H), 5.23 (d, 1H), 5.13 (d, 1H), 4.57 (m, 1H), 4.46 (m, 1H), 4.35 (m, 1H), 4.21 (m, 1H), 3.70 (m, 3H), 3.55 (m, 1H), 3.45 (m, 1H), 2.98 (m, 2H), 2.73 (m, 1H), 2.41 (m, 1H), 2.19 (m, 2H), 2.05 (m, 1H), 1.82 (m, 1H), 1.48 (m, 4H), 1.24 (m, 1H), 1.02 (t, 3H); MS (EI) for $C_{29}H_{37}N_7O_3S$: 564 (MH$^+$).

3-[(1S,4S)-2,5-diazabicyclo[2.2.1]hept-2-ylsulfonyl]-5-{4-[(7S)-7-ethyl-5,6,7,8-tetrahydroquinazolin-4-yl]-2,3,4,5-tetrahydro-1,4-benzoxazepin-7-yl}pyridin-2-amine. Prepared as dihydrochloride salt according to the method of example 5 by using {4-[(7S)-7-ethyl-5,6,7,8-tetrahydroquinazolin-4-yl]-2,3,4,5-tetrahydro-1,4-benzoxazepin-7-yl}boronic acid (reagent preparation 23) and (1S,4S)-tert-butyl 5-(2-amino-5-bromopyridin-3-ylsulfonyl)-2,5-diazabicyclo[2.2.1]heptane-2-carboxylate (reagent preparation 25) in step 1 followed by Boc deprotection. $^1$H NMR (400 MHz, methanol-d$_4$): 8.65 (s, 1H), 8.52 (s, 2H), 7.74 (s, 1H), 7.53 (d, 1H), 7.08 (d, 1H), 5.24 (d, 1H), 5.14 (d, 1H), 4.56 (m, 2H), 4.46 (m, 1H), 4.36 (m, 1H), 4.21 (m, 1H), 3.69 (m, 3H), 3.53 (m, 1H), 3.38 (m, 1H), 2.99 (m, 2H), 2.74 (m, 1H), 2.42 (m, 1H), 2.05 (m, 3H), 1.83 (m, 1H), 1.47 (m, 2H), 1.24 (m, 1H), 1.01 (t, 3H); MS (EI) for $C_{29}H_{35}N_7O_3S$: 562 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(2S)-pyrrolidin-2-ylmethyl]pyridine-3-sulfonamide. Prepared as dihydrochloride salt according to the method of example 5 by using (R)-tert-butyl 2-((2-amino-5-bromopyridine-3-sulfonamido)methyl)pyrrolidine-1-carboxylate (reagent preparation 25) in step 1 followed by Boc deprotection. $^1$H NMR (400 MHz, methanol-d$_4$): 8.66-8.48 (m, 3H), 7.75 (m, 1H), 7.52 (m, 1H), 7.06 (d, 1H), 5.16 (s, 2H), 4.48 (m, 2H), 4.31 (m, 2H), 3.73 (m, 1H), 2.86 (t, 2H), 2.61 (s, 2H), 2.17 (m, 1H), 2.07 (m, 2H), 1.72 (m, 3H), 0.95 (s, 6H); MS (EI) for $C_{29}H_{37}N_7O_3S$: 564 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-[(2R)-pyrrolidin-2-ylmethyl]pyridine-3-sulfonamide. Prepared as dihydrochloride salt according to the method of example 5 by using (S)-tert-butyl 2-((2-amino-5-bromopyridine-3-sulfonamido)methyl)pyrrolidine-1-carboxylate (reagent preparation 25) in step 1 followed by Boc deprotection. $^1$H NMR (400 MHz, methanol-d$_4$): 8.78 (s, 1H), 8.54 (s, 1H), 8.49 (s, 1H), 7.84 (s, 1H), 7.56 (m, 1H), 7.07 (d, 1H), 5.18 (s, 2H), 4.49 (m, 2H), 4.31 (m, 2H), 3.75 (m, 1H), 3.38 (m, 2H), 2.86 (m, 2H), 2.62 (s, 2H), 2.20 (m, 1H), 2.08 (m, 2H), 1.74 (m, 3H), 0.95 (s, 6H); MS (EI) for $C_{29}H_{37}N_7O_3S$: 564 (MH$^+$).

3-(2,6-diazaspiro[3.3]hept-2-ylsulfonyl)-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as diacetate salt according to the method of example 5 by using tert-butyl 6-(2-amino-5-bromopyridin-3-ylsulfonyl)-2,6-diazaspiro[3.3]heptane-2-carboxylate (reagent preparation 25) in step 1 followed by Boc deprotection. $^1$H NMR (400 MHz, methanol-d$_4$): 8.52 (d, 1H), 8.33 (s, 1H), 8.09 (d, 1H), 7.50 (d, 1H), 7.43 (dd, 1H), 7.06 (d, 1H), 4.71 (s, 2H), 4.34 (m, 2H), 4.06 (s, 8H), 3.96 (m, 2H), 2.80 (t, 2H), 2.49 (s, 2H), 1.93 (s, 2H), 1.93 (s, 6H), 1.69 (t, 2H), 0.92 (s, 6H); MS (EI) for $C_{29}H_{35}N_7O_3S$: 562 (MH$^+$).

3-[(1R,4R)-2,5-diazabicyclo[2.2.1]hept-2-ylsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as dihydrochloride salt according to the method of example 5 by using (1R,4R)-tert-butyl 5-(2-amino-5-bromopyridin-3-ylsulfonyl)-2,5-diazabicyclo[2.2.1]heptane-2-carboxylate (reagent preparation 25) in step 1 followed by Boc deprotection. $^1$H NMR (400 MHz, methanol-d$_4$): 8.53 (m, 2H), 8.29 (m, 1H), 7.64 (s, 1H), 7.48 (d, 1H), 7.05 (d, 1H), 5.15 (s, 2H), 4.47 (m, 2H), 4.31 (m, 2H), 3.57 (m, 2H), 3.50 (m, 1H), 2.85 (t, 2H), 2.61 (s, 2H), 1.95 (m, 2H), 1.71 (t, 2H), 0.90 (s, 6H); MS (EI) for MS (EI) for $C_{29}H_{35}N_7O_3S$: 562 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-piperidin-4-ylpyridine-3-sulfonamide. Prepared as dihydrochloride salt according to the method of example 5 by using tert-butyl 4-(2-amino-5-bromopyridine-3-sulfonamido)piperidine-1-carboxylate (reagent preparation 25) in step 1 followed by Boc deprotection. MS (EI) for $C_{29}H_{37}N_7O_3S$: 564 (MH$^+$).

5-[4-(6,6-dimethyl-5,6,7,8-tetrahydroquinazolin-4-yl)-2,3,4,5-tetrahydro-1,4-benzoxazepin-7-yl]-3-{[(1S,4S)-5-methyl-2,5-diazabicyclo[2.2.1]hept-2-yl]sulfonyl}pyridin-2-amine. Prepared as dihydrochloride salt according to the method of example 5 by using 5-bromo-3-((1S,4S)-5-methyl-2,5-diazabicyclo[2.2.1]heptan-2-ylsulfonyl)pyridin-2-amine (reagent preparation 25) in step 1. $^1$H NMR (400 MHz, methanol-d$_4$): 8.48 (d, 1H), 8.34 (s, 1H), 8.14 (d, 1H), 7.49 (d, 1H), 7.42 (dd, 1H), 7.06 (d, 1H), 4.70 (s, 2H), 4.51 (s, 1H), 4.34 (m, 2H), 3.95 (m, 2H), 3.69 (s, 1H), 3.53 (d, 1H), 3.28 (m, 1H), 3.00 (d, 1H), 2.92 (m, 1H), 2.79 (t, 2H), 2.50 (s, 3H), 2.48 (s, 2H), 1.96 (s, 6H), 1.95 (m, 1H), 1.68 (t, 2H), 1.58 (d, 1H), 0.91 (s, 3H), 0.90 (s, 3H); MS (EI) for MS (EI) for $C_{30}H_{37}N_7O_3S$: 576 (MH$^+$).

3-{[(3R)-3-aminopyrrolidin-1-yl]sulfonyl}-5-[4-(6,6,8-trimethyl-5,6-dihydroquinazolin-4-yl)-2,3,4,5-tetrahydro-1,4-benzoxazepin-7-yl]pyridin-2-amine. Synthesized according to the method of example 5 using (R)-tert-butyl 1-(2-amino-5-bromopyridin-3-ylsulfonyl)pyrrolidin-3-ylcarbamate (reagent preparation 25) and [4-(6,6,8-trimethyl-5,6-dihydroquinazolin-4-yl)-2,3,4,5-tetrahydro-1,4-benzoxazepin-7-yl]boronic acid (reagent preparation 23) in step 1 and BOC group deprotection. $^1$H NMR (400 MHz, d$_6$-DMSO): 8.54 (s, 1H), 8.48 (br s, 1H), 8.01 (d, 1H), 8.58 (d, 1H), 7.47 (dd, 1H), 7.02 (d, 1H), 6.76 (br s, 2H), 5.99 (d, 1H), 4.60 (s, 2H), 4.32 (m, 2H), 383 (m, 2H), 3.40-3.32 (m, 4H), 3.30-3.26 (m, 2H), 2.90 (m, 1H), 2.70 (s, 2H), 1.97 (s, 3H), 1.89 (s, 6H), 1.63 (m, 1H), 0.93 (s, 6H); MS (EI) for C$_{29}$H$_{35}$N$_7$O$_3$S: 562 (MH$^+$).

4-(6,6-dimethyl-5,6,7,8-tetrahydroquinazolin-4-yl)-7-(2-methyl-3H-imidazo[4,5-c]pyridin-7-yl)-2,3,4,5-tetrahydro-1,4-benzoxazepine. Synthesized according to the method of example 5 using 7-bromo-3-((2-methoxyethoxy)methyl)-2-methyl-3H-imidazo[4,5-c]pyridine (reagent preparation 19) in step 1. $^1$H NMR (400 MHz, d$_6$-DMSO): 8.72 (s, 1H), 8.48 (br s, 1H) 8.36 (s, 1H), 8.11 (br s, 1H), 7.62 (br m, 1H), 7.22 (br d, 1H), 4.67 (s, 2H), 4.36 (m, 2H), 3.88 (m, 2H), 2.70 (t, 2H), 2.57 (s, 3H), 2.47 (s, 2H), 1.59 (t, 2H), 0.85 (s, 6H); MS (EI) for C$_{26}$H$_{28}$N$_6$O: 441 (MH$^+$).

2-amino-N-[(3R)-1-methylpyrrolidin-3-yl]-5-[4-(2,6,6-trimethyl-5,6,7,8-tetrahydroquinazolin-4-yl)-2,3,4,5-tetrahydro-1,4-benzoxazepin-7-yl]pyridine-3-sulfonamide. Synthesized according to the method of example 5 using (S)-2-amino-5-bromo-N-(1-methylpyrrolidin-3-yl)pyridine-3-sulfonamide (reagent preparation 25) and [4-(2,6,6-trimethyl-5,6,7,8-tetrahydroquinazolin-4-yl)-2,3,4,5-tetrahydro-1,4-benzoxazepin-7-yl]boronic acid (reagent preparation 23) in step 1. $^1$H NMR (400 MHz, d$_6$-DMSO): 8.52 (d, 1H), 8.07 (d, 1H), 7.61 (d, 1H), 7.45 (dd, 1H), 7.02 (d, 1H), 6.68 (br s, 2H), 4.57 (s, 2H), 4.25 (br t, 2H), 3.82 (br m, 2H), 3.63 (br m, 1H), 2.65 (t, 2H), 2.43 (m, 4H), 2.33 (s, 3H), 2.22 (br m, 2H), 2.13 (s, 3H), 1.84 (s, 5H), 1.57 (t, 2H), 1.45 (m, 1H), 0.83 (s, 6H); MS (EI) for C$_{30}$H$_{39}$N$_7$O$_3$S: 578 (MH$^+$).

2-amino-N-[(3R)-1-methylpyrrolidin-3-yl]-5-[4-(6,6,8-trimethyl-5,6-dihydroquinazolin-4-yl)-2,3,4,5-tetrahydro-1,4-benzoxazepin-7-yl]pyridine-3-sulfonamide. Synthesized according to the method of example 5 using (S)-2-amino-5-bromo-N-(1-methylpyrrolidin-3-yl)pyridine-3-sulfonamide (reagent preparation 25) and [4-(6,6,8-trimethyl-5,6-dihydroquinazolin-4-yl)-2,3,4,5-tetrahydro-1,4-benzoxazepin-7-yl]boronic acid (reagent preparation 23) in step 1. $^1$H NMR (400 MHz, d$_6$-DMSO): 8.52 (d, 1H), 8.37 (s, 1H), 8.12 (s, H), 8.06 (d, 1H), 7.56 (d, 1H), 7.45 (dd, 1H), 7.02 (d, 1H), 6.69 (br s, 2H), 6.12 (s, 1H), 4.62 (s, 2H), 4.32 (br t, 2H), 3.84 (br m, 2H), 3.63 (br s, 1H), 2.68 (s, 2H), 2.44 (m, 2H), 2.26-2.16 (m, 2H), 2.14 (s, 3H), 1.88 (s, 3H), 1.86 (s, 2H), 1.48-1.42 (m, 1H), 0.91 (s, 6H); MS (EI) for C$_{30}$H$_{37}$N$_7$O$_3$S: 576 (MH$^+$).

3-{[(3S)-3-aminopyrrolidin-1-yl]sulfonyl}-5-{4-[7-(methyloxy)quinazolin-4-yl]-2,3,4,5-tetrahydro-1,4-benzoxazepin-7-yl}pyridin-2-amine. Synthesized according to the method of example 5 using (S)-tert-butyl 1-(2-amino-5-bromopyridin-3-ylsulfonyl)pyrrolidin-3-ylcarbamate (reagent preparation 25) and {4-[7-(methyloxy)quinazolin-4-yl]-2,3,4,5-tetrahydro-1,4-benzoxazepin-7-yl}boronic acid (reagent preparation 23) in step 1 and BOC group deprotection. $^1$H NMR (400 MHz, d$_6$-DMSO): 8.80 (s, 1H), 8.65 (d, 1H), 8.41 (m, 2H), 8.22 (m, 1H), 8.04 (d, 1H), 7.78 (s, 1H), 7.53 (d, 1H), 7.35 (m, 2H), 6.98 (br m, 2H), 5.43 (S, 2H), 4.62 (s, 2H), 4.49 (s, 2H), 3.92 (s, 3H), 3.79 (m, 1H), 3.69 (m, 1H), 3.55-3.45 (m, 3H), 3.32 (m, 2H), 2.20 (m, 1H), 1.91 (M, 1H); MS (EI) for C$_{27}$H$_{29}$N$_7$O$_4$S: 548 (MH$^+$).

N-(2-chloro-5-{4-[7-(methyloxy)quinazolin-4-yl]-2,3,4,5-tetrahydro-1,4-benzoxazepin-7-yl}pyridin-3-yl)methanesulfonamide. Synthesized according to the method of example 5 using N-(5-bromo-2-chloropyridin-3-yl)methanesulfonamide (reagent preparation 25) and {4-[7-(methyloxy)quinazolin-4-yl]-2,3,4,5-tetrahydro-1,4-benzoxazepin-7-yl}boronic acid (reagent preparation 23) in step 1. $^1$H NMR (400 MHz, d$_6$-DMSO): 8.92 (br s, 1H), 8.75 (s, 1H), 8.62 (d, 1H), 8.19 (d, 1H), 8.10 (d, 1H), 7.89 (s, 1H), 7.62 (dd, 1H), 7.33 (dd, 1H), 7.25 (d, 1H), 7.04 (d, 1H), 5.41 (s, 2H), 4.65 (s, 2H), 4.47 (s, 2H), 3.96 (s, 3H), 3.19 (s, 3H); MS (EI) for C$_{24}$H$_{22}$ClN$_5$O$_4$S: 514 (MH$^+$).

N-[6-(4-{2-[(dimethylamino)methyl]-7-(methyloxy)quinazolin-4-yl}-2,3,4,5-tetrahydro-1,4-benzoxazepin-7-yl)[1,3]thiazolo[5,4-b]pyridin-2-yl]acetamide. Synthesized according to the method of example 5 using N-(6-bromothiazolo[5,4-b]pyridin-2-yl)acetamide (J. Heterocyclic Chemistry 2003, 40, 261) and {4-[7-(methyloxy)quinazolin-4-yl]-2,3,4,5-tetrahydro-1,4-benzoxazepin-7-yl}boronic acid (reagent preparation 23) in step 1. $^1$H NMR (400 MHz, d$_6$-DMSO) δ 12.60 (s, 1H), 8.86 (d, 1H), 8.45 (d, 1H), 8.23-8.07 (m, 2H), 7.70 (dd, 1H), 7.27-7.17 (m, 2H), 7.02 (d, 1H), 5.43 (s, 2H), 4.65-4.57 (m, 2H), 4.46 (s, 2H), 4.43-4.37 (m, 2H), 3.94 (s, 3H), 2.73 (s, 6H), 2.25 (s, 3H); MS (EI) for C$_{29}$H$_{29}$N$_7$O$_3$S: 556 (MH$^+$).

(3S)-1-({2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-amine. Prepared as in example 5 using (R)-tert-butyl 1-(2-amino-5-bromopyridin-3-ylsulfonyl)pyrrolidin-3-ylcarbamate (reagent preparation 25) in step 1 and BOC group deprotection. $^1$H NMR (400 MHz, CD$_3$OD) δ 8.83 (d, 1H), 8.59 (d, 1H), 8.33 (s, 1H), 7.68 (d, 1H), 7.58 (dd, 1H), 7.12 (d, 1H), 4.75 (s, 2H), 4.44-4.33 (m, 2H), 4.01-3.92 (m, 2H), 3.75-3.42 (m, 4H), 3.23 (dd, 1H), 2.79 (t, 2H), 2.47 (s, 2H), 2.28-2.09 (m, 1H), 1.88-1.77 (m, 1H), 1.69 (t, 2H), 0.90 (s, 6H); MS (ES) for C$_{28}$H$_{33}$ClN$_6$O$_3$S: 569.2 (MH$^+$).

3-{[(3R)-3-aminopyrrolidin-1-yl]sulfonyl}-5-[4-(6,6,7-trimethyl-5,6-dihydroquinazolin-4-yl)-2,3,4,5-tetrahydro-1,4-benzoxazepin-7-yl]pyridin-2-amine. Prepared as in example 5 using (R)-tert-butyl 1-(2-amino-5-bromopyridin-3-ylsulfonyl)pyrrolidin-3-ylcarbamate (reagent preparation 25) and [4-(6,6,7-trimethyl-5,6-dihydroquinazolin-4-yl)-2,3,4,5-tetrahydro-1,4-benzoxazepin-7-yl]boronic acid (reagent preparation 23) in step 1 and BOC group deprotection. $^1$H NMR (400 MHz, d$_6$-DMSO) δ 8.54 (s, 1H), 8.37 (s, 1H), 8.01 (d, 1H), 7.57 (d, 1H), 7.48 (dd, 1H), 7.02 (d, 1H), 6.76 (s, 2H), 6.13 (d, 1H), 4.62 (s, 2H), 4.33 (s, 2H), 3.84 (s, 2H), 3.44-3.20 (m, 3H), 2.89 (d, 1H), 2.69 (s, 2H), 1.88 (d, 5H), 1.53 (s, 1H), 0.92 (s, 6H); MS (ES) for C$_{29}$H$_{35}$N$_7$O$_3$S: 562.2 (MH$^+$).

2-amino-N-(azetidin-3-ylmethyl)-5-[4-(6,6-dimethyl-5,6,7,8-tetrahydroquinazolin-4-yl)-2,3,4,5-tetrahydro-1,4-benzoxazepin-7-yl]pyridine-3-sulfonamide. The diacetate salt was prepared as in example 5 using tert-butyl 3-((2-amino-5-bromopyridine-3-sulfonamido)methyl)azetidine-1-carboxylate (reagent preparation 25) in step 1 and BOC group deprotection. $^1$H NMR (400 MHz, d$_6$-DMSO) δ 8.52 (d, 1H), 8.37 (s, 1H), 8.06 (d, 1H), 7.60 (d, 1H), 7.46 (dd, 1H), 7.03 (d, 1H), 6.68 (bs, 2H), 4.62 (s, 2H), 4.37-4.24 (m, 2H), 3.87-3.77 (m, 2H), 3.48 (t, 2H), 3.26-3.14 (m, 2H), 2.96 (d, 2H), 2.76-2.56 (m, 3H), 2.45 (s, 2H), 1.60 (t, 2H), 0.84 (s, 6H); MS (ES) for C$_{28}$H$_{35}$N$_7$O$_3$S: 550.2 (MH$^+$).

2-amino-N-(2-amino-2-methylpropyl)-5-[4-(6,6,7-trimethyl-5,6-dihydroquinazolin-4-yl)-2,3,4,5-tetrahydro-1,4-benzoxazepin-7-yl]pyridine-3-sulfonamide. The diacetate salt was prepared as in example 5 using 2-amino-N-(2-amino-2-methylpropyl)-5-bromopyridine-3-sulfonamide (reagent preparation 25) and [4-(6,6,7-trimethyl-5,6-dihydroquinazolin-4-yl)-2,3,4,5-tetrahydro-1,4-benzoxazepin-7-yl]boronic acid (reagent preparation 23) in step 1. $^1$H NMR (400 MHz, d₆-DMSO) δ 8.50 (d, 1H), 8.37 (s, 1H), 8.05 (d, 1H), 7.55 (s, 1H), 7.45 (d, 1H), 7.02 (d, 1H), 6.73 (s, 2H), 6.12 (s, 1H), 4.62 (s, 2H), 4.38-4.26 (m, 2H), 3.88-3.79 (m, 2H), 2.69 (s, 2H), 2.60 (s, 2H), 2.50 (s, 3H), 1.02-0.83 (m, 12H); MS (ES) for $C_{29}H_{37}N_7O_3S$: 564.3 (MH⁺).

7-(3,4-dihydro-2H-pyrido[3,2-b][1,4]oxazin-7-yl)-4-(6,6-dimethyl-5,6,7,8-tetrahydroquinazolin-4-yl)-2,3,4,5-tetrahydro-1,4-benzoxazepine. Synthesized according to the method of example 5 using 7-bromo-3,4-dihydro-2H-pyrido[3,2-b][1,4]oxazine in step 1. ¹H NMR (400 MHZ, DMSO-d₆): 8.37 (s, 1H), 7.89 (d, 1H), 7.54 (d, 1H), 7.39 (dd, 1H), 7.22 (d, 1H), 6.97 (d, 1H), 6.83 (s, 1H), 4.57 (s, 2H), 4.29 (br s, 2H), 4.14 (tr, 2H), 3.82 (br s, 2H), 3.42 (br s, 2H), 2.71 (tr, 2H), 2.45 (tr, 2H), 1.60 (tr, 2H), 0.85 (s, 6H); MS (EI) for $C_{26}H_{29}N_5O_2$: 444 (MH⁺).

5-[4-(6,6-dimethyl-5,6,7,8-tetrahydroquinazolin-4-yl)-2,3,4,5-tetrahydro-1,4-benzoxazepin-7-yl]pyrimidin-2-amine. Synthesized according to the method of example 5 using 5-bromo-2-aminopyrimidine in step 1. ¹H NMR (400 MHZ, DMSO-d₆): 8.54 (s, 2H), 8.37 (s, 1H), 7.59 (d, 1H), 7.44 (dd, 1H), 7.00 (d, 1H), 6.75 (s, 2H), 4.59 (s, 2H), 4.30 (br s, 2H), 3.83 (br s, 2H), 2.71 (tr, 2H), 2.45 (s, 2H), 1.60 (tr, 2H), 0.84 (s, 6H); MS (EI) for $C_{23}H_{26}N_6O$: 403 (MH⁺).

(2E)-5-[4-(6,6-dimethyl-5,6,7,8-tetrahydroquinazolin-4-yl)-2,3,4,5-tetrahydro-1,4-benzoxazepin-7-yl]-2-iminopyrimidin-1(2H)-ol. Synthesized according to the method of example 5 using 5-bromo-2-iminopyrimidin-1(2H)-ol in step 1. ¹H NMR (400 MHZ, CD₃OD): 8.59 (d, 1H), 8.38 (d, 1H), 8.34 (s, 1H), 7.55 (d, 1H), 7.44 (dd, 1H), 7.08 (d, 1H), 4.72 (s, 2H), 4.35 (tr, 2H), 3.95 (tr, 2H), 2.79 (tr, 2H), 2.46 (s, 2H), 1.68 (tr, 2H), 0.90 (s, 6H); MS (EI) for $C_{23}H_{26}N_6O_2$: 419 (MH⁺).

5-[4-(6,6-dimethyl-5,6,7,8-tetrahydroquinazolin-4-yl)-2,3,4,5-tetrahydro-1,4-benzoxazepin-7-yl]-3-(ethylsulfonyl)pyridin-2-amine. Synthesized according to the method of example 5 using 5-bromo-3-(ethylsulfonyl)pyridin-2-amine (reagent preparation 34) in step 1. ¹H NMR (400 MHZ, CD₃CN): 8.56 (d, 1H), 8.37 (s, 1H), 8.10 (d, 1H), 7.50 (d, 1H), 7.45 (dd, 1H), 7.06 (d, 1H), 6.13 (s, 2H), 4.64 (s, 2H), 4.34 (tr, 2H), 3.90 (tr, 2H), 3.24 (q, 2H), 2.78 (tr, 2H), 2.46 (s, 2H), 1.66 (tr, 2H), 1.23 (tr, 3H), 0.90 (s, 6H). MS (EI) for $C_{26}H_{31}N_5SO_3$: 494 (MH⁺).

3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)propane-1,2-diol. Synthesized according to the method of example 5 using 3-(2-amino-5-bromopyridin-3-ylsulfonyl)propane-1,2-diol in step 1. ¹H NMR (400 MHZ, CD₃OD): 8.49 (d, 1H), 8.33 (s, 1H), 8.18 (d, 1H), 7.50 (d, 1H), 7.42 (dd, 1H), 7.04 (d, 1H), 4.69 (s, 2H), 4.34 (tr, 2H), 4.15-4.06 (m, 1H), 3.95 (tr, 2H), 3.54-3.37 (m, 4H), 2.79 (tr, 2H), 2.48 (s, 2H), 1.68 (tr, 2H), 0.90 (s, 6H). MS (EI) for $C_{27}H_{33}N_5SO_5$: 540 (MH⁺).

3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)propan-1-ol. Synthesized according to the method of example 5 using 3-(2-amino-5-bromopyridin-3-ylsulfonyl)propan-1-ol (reagent preparation 34) in step 1. ¹H NMR (400 MHZ, CD₃OD): 8.52 (d, 1H), 8.34 (s, 1H), 8.14 (d, 1H), 7.50 (d, 1H), 7.42 (dd, 1H), 7.06 (d, 1H), 4.69 (d, 2H), 4.34 (tr, 2H), 3.95 (tr, 2H), 3.61 (tr, 2H), 3.37-3.33 (m, 2H), 2.80 (tr, 2H), 2.48 (s, 2H), 1.94-1.86 (m, 2H), 1.69 (tr, 2H), 0.90 (s, 6H). MS (EI) for $C_{27}H_{33}N_5SO_4$: 524 (MH⁺).

(2S)-3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylpropan-1-ol. Synthesized according to the method of example 5 using (S)-3-(2-amino-5-bromopyridin-3-ylsulfonyl)-2-methylpropan-1-ol (reagent preparation 34) in step 1. ¹H NMR (400 MHZ, CD₃OD): 8.51 (d, 1H), 8.33 (s, 1H), 8.15 (d, 1H), 7.50 (d, 1H), 7.42 (dd, 1H), 7.05 (d, 1H), 4.69 (s, 2H), 4.34 (tr, 2H), 3.95 (tr, 2H), 3.52-3.37 (m, 3H), 3.06 (dd, 1H), 2.79 (tr, 2H), 2.48 (s, 2H), 2.23-2.16 (m, 1H), 1.68 (tr, 2H), 1.08 (d, 3H), 0.90 (s, 6H). MS (EI) for $C_{28}H_{35}N_5SO_4$: 538 (MH⁺).

(2R)-3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylpropan-1-ol. Synthesized according to the method of example 5 using (R)-3-(2-amino-5-bromopyridin-3-ylsulfonyl)-2-methylpropan-1-ol (reagent preparation 34) in step 1. ¹H NMR (400 MHZ, CD₃OD): 8.51 (d, 1H), 8.33 (s, 1H), 8.15 (d, 1H), 7.50 (d, 1H), 7.42 (dd, 1H), 7.05 (d, 1H), 4.69 (s, 2H), 4.34 (tr, 2H), 3.95 (tr, 2H), 3.52-3.37 (m, 3H), 3.06 (dd, 1H), 2.79 (tr, 2H), 2.48 (s, 2H), 2.23-2.16 (m, 1H), 1.68 (tr, 2H), 1.08 (d, 3H), 0.90 (s, 6H). MS (EI) for $C_{28}H_{35}N_5SO_4$: 538 (MH⁺).

7-[4-(6,6-dimethyl-5,6,7,8-tetrahydroquinazolin-4-yl)-2,3,4,5-tetrahydro-1,4-benzoxazepin-7-yl]-2H-pyrido[2,3-e][1,2,4]thiadiazin-3(4H)-one 1,1-dioxide. Synthesized according to the method of example 5 using 7-bromo-2H-pyrido-[2,3-e][1,2,4]-thiadiazin-3(4H)-one 1,1-dioxide (reagent preparation 37) in step 1. ¹H NMR (400 MHZ, CD₃OD): 8.66 (d, 1H), 8.39 (s, 1H), 8.24 (d, 1H), 7.61 (d, 1H), 7.50 (dd, 1H), 7.07 (d, 1H), 4.81 (s, 2H), 4.38 (tr, 2H), 4.04 (tr, 2H), 2.80 (tr, 2H), 2.51 (tr, 2H), 1.68 (tr, 2H), 0.91 (s, 6H). MS (EI) for $C_{25}H_{26}N_6SO_4$: 507 (MH⁺).

2-amino-5-[4-(6,6-dimethyl-5,6,7,8-tetrahydroquinazolin-4-yl)-2,3,4,5-tetrahydro-1,4-benzoxazepin-7-yl]pyridine-3-sulfonic acid. Synthesized according to the method of example 5 using 2-amino-5-bromopyridine-3-sulfonic acid (reagent preparation 38) in step 1. ¹H NMR (400 MHZ, CD₃OD): 8.37 (s, 1H), 8.24 (d, 1H), 8.20 (d, 1H), 7.49 (d, 1H), 7.40 (dd, 1H), 7.03 (d, 1H), 4.74 (s, 2H), 4.35 (tr, 2H), 3.99 (tr, 2H), 2.80 (tr, 2H), 2.49 (s, 2H), 1.68 (tr, 2H), 0.90 (s, 6H). MS (EI) for $C_{24}H_{27}N_5SO_4$: 482 (MH⁺).

N-{5-[4-(6,6-dimethyl-5,6,7,8-tetrahydroquinazolin-4-yl)-2,3,4,5-tetrahydro-1,4-benzoxazepin-7-yl]-2-(phenylamino)pyridin-3-yl}methanesulfonamide. Synthesized according to the method of example 5 using N-(5-bromo-2-(phenylamino)pyridin-3-yl)methanesulfonamide (reagent preparation 39) in step 1. ¹H NMR (400 MHZ, DMSO-d₆): 9.27 (br s, 1H), 8.35 (s, 2H), 8.30 (s, 1H), 7.78 (s, 1H), 7.67 (d, 2H), 7.57 (s, 1H), 7.44 (d, 1H), 7.27 (s, 2H), 7.01 (d, 1H), 6.94 (s, 1H), 4.62 (br s, 2H), 4.30 (br s, 2H), 3.82 (br s, 2H), 3.05 (s, 3H), 2.69 (br s, 2H), 2.42 (s, 2H), 1.58 (br s, 2H), 0.83 (s, 6H). MS (EI) for $C_{31}H_{34}N_6SO_3$: 572 (MH⁺).

N-{2-(dimethylamino)-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide. Synthesized according to the method of example 5 using N-(5-bromo-2-(dimethylamino)pyridin-3-yl)methanesulfonamide (reagent preparation 39) in step 1. ¹H NMR (400 MHZ, DMSO-d₆): 9.09 (br s, 1H), 8.36 (s, 1H), 8.35 (d, 1H), 7.71 (d, 1H), 7.56 (d, 1H), 7.44 (dd, 1H), 7.03 (d, 1H), 4.64 (s, 2H), 4.32 (br, 2H), 3.84 (br, 1H), 3.11 (s, 3H), 2.94 (s, 6H), 2.71 (tr, 2H), 2.44 (s, 2H), 1.60 (tr, 2H), 0.85 (s, 6H). MS (EI) for $C_{27}H_{34}N_6SO_3$: 523 (MH⁺).

3-[(4-aminopiperidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine. Prepared as a dihydrochloride salt according to the method of example 5 by using tert-butyl 1-(2-amino-5-bromopyridin-3-ylsulfonyl)piperidin-4-ylcarbamate (reagent preparation 25) in step 1 followed by Boc deprotection. ¹H NMR (400 MHz, DMSO-d6) δ 8.72 (s, 1H), 8.66 (d, 1H), 8.39 (br s, 3H), 8.10 (d, 1H), 7.73 (s, 1H), 7.54 (d, 1H), 7.00 (d, 1H), 5.11 (s, 2H), 4.53-4.45 (m, 2H), 4.37-4.22 (m, 4H, buried), 3.78 (d, 2H), 3.14 (br s, 1H), 2.86-2.78 (m, 2H), 2.73 (t, 2H), 2.53 (s, 2H), 2.00 (d, 2H), 1.68-1.52 (m, 4H), 0.85 (s, 6H); MS (EI) for $C_{29}H_{37}N_7O_3S$: 564 (MH$^+$).

2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-2-methylpropyl)pyridine-3-sulfonamide. Prepared according to the method of example 5 by using 2-amino-5-bromo-N-(2-hydroxy-2-methylpropyl)pyridine-3-sulfonamide (reagent preparation 25) in step 1. $^1$H NMR (400 MHz, DMSO-d6) δ 8.50 (d, 1H), 8.37 (s, 1H), 8.05 (d, 1H), 7.71 (t, 1H), 7.58 (d, 1H), 7.45 (dd, 1H), 7.02 (d, 1H), 6.74 (br s, 2H), 4.62 (s, 2H), 4.31 (s, 2H), 3.83 (s, 2H), 2.71 (t, 2H), 2.64 (d, 2H), 2.44 (s, 2H), 1.59 (t, 2H), 1.04 (s, 6H), 0.84 (s, 6H); MS (EI) for $C_{28}H_{36}N_6O_4S$: 553 (MH$^+$).

6-[4-(6,6-dimethyl-5,6,7,8-tetrahydroquinazolin-4-yl)-2,3,4,5-tetrahydro-1,4-benzoxazepin-7-yl]-N-ethyl-1H-imidazo[4,5-b]pyridin-2-amine. Prepared as in example 5 using 6-bromo-N-ethyl-3-(methoxymethyl)-3H-imidazo[4,5-b]pyridin-2-amine (reagent preparation 36) in step 1 and MOM group deprotection. $^1$H NMR (400 MHz, CD$_3$OD) δ 8.53 (s, 1H), 8.29 (d, 1H), 7.99 (d, 1H), 7.72 (d, 1H), 7.53 (dd, 1H), 7.07 (d, 1H), 5.17 (s, 2H), 4.48 (m, 2H), 4.32 (m, 2H), 3.56 (q, 2H), 2.86 (t, 2H), 2.61 (s, 2H), 1.70 (t, 2H), 1.36 (t, 3H); MS (ES) for $C_{27}H_{31}N_7O$: 470 (MH$^+$).

1-{4-[7-(1,3-benzothiazol-5-yl)-2,3-dihydro-1,4-benzoxazepin-4(5H)-yl]-6,6-dimethyl-7-(methyloxy)-5,6,7,8-tetrahydroquinazolin-2-yl}-N,N-dimethylmethanamine. The trifluoroacetate salt was synthesized according to the method of example 5 using 5-bromobenzo[d]thiazole and (4-{2-[(dimethylamino)methyl]-7-methoxy-6,6-dimethyl-5,6,7,8-tetrahydroquinazolin-4-yl}-2,3,4,5-tetrahydro-1,4-benzoxazepin-7-yl)boronic acid (reagent preparation 23) in step 1. $^1$H NMR (400 MHz, d$_6$-DMSO) δ 9.45 (s, 1H), 8.36 (d, 1H), 8.26 (d, 1H), 7.81 (m, 2H), 7.64 (dd, 1H), 7.05 (d, 1H), 4.84 (s, 2H), 4.41 (m, 2H), 4.30 (s, 2H), 3.97 (m, 2H), 3.35 (s, 3H), 3.28 (t, 1H), 3.00 (dd, 1H), 2.80 (s, 6H), 2.72 (dd, 1H), 2.62 (d, 1H), 2.44 (d, 1H), 0.85 (d, 6H). MS (ES) for $C_{30}H_{35}N_5O_2S$: 530 (MH$^+$).

1-{6,6-dimethyl-4-[7-(2-methyl-1H-imidazo[4,5-b]pyridin-6-yl)-2,3-dihydro-1,4-benzoxazepin-4(5H)-yl]-7-(methyloxy)-5,6,7,8-tetrahydroquinazolin-2-yl}-N,N-dimethylmethanamine. The bistrifluoroacetate salt was synthesized according to the method of example 5 using isobutyl 6-bromo-2-methyl-1H-imidazo[4,5-b]pyridine-1-carboxylate (reagent preparation 19) and (4-{2-[(dimethylamino)methyl]-7-methoxy-6,6-dimethyl-5,6,7,8-tetrahydroquinazolin-4-yl}-2,3,4,5-tetrahydro-1,4-benzoxazepin-7-yl)boronic acid (reagent preparation 23) in step 1. $^1$H NMR (400 MHz, d$_6$-DMSO) δ 9.55 (s, 1H), 8.75 (d, 1H), 8.31 (s, 1H), 7.80 (d, 1H), 7.63 (dd, 1H), 7.09 (d, 1H), 4.82 (s, 2H), 4.42 (m, 2H), 4.30 (s, 2H), 3.97 (m, 2H), 3.35 (s, 3H), 3.27 (t, 1H), 3.00 (dd, 1H), 2.81 (s, 6H), 2.72 (m, 1H), 2.71 (s, 3H), 2.61 (d, 1H), 2.43 (d, 1H), 0.83 (d, 6H); MS (ES) for $C_{30}H_{37}N_7O_2$: 528 (MH$^+$).

6-(4-{2-[(dimethylamino)methyl]-7-(methyloxy)quinazolin-4-yl}-2,3,4,5-tetrahydro-1,4-benzoxazepin-7-yl)[1,3]thiazolo[5,4-b]pyridin-2-amine. The dihydrochloride salt was synthesized according to the method of example 5 using N-(6-bromothiazolo[5,4-b]pyridin-2-yl)acetamide (J. Heterocyclic Chem 2003, 40, 261) and (4-{2-[(dimethylamino)methyl]-7-methoxyquinazolin-4-yl}-2,3,4,5-tetrahydro-1,4-benzoxazepin-7-yl)boronic acid (reagent preparation 23) in step 1 and acetyl group hydrolysis. $^1$H NMR (400 MHz, d$_6$-DMSO) δ 8.48 (d, 1H), 8.16-7.96 (m, 4H), 7.94 (d, 1H), 7.60 (dd, 1H), 7.26-7.17 (m, 2H), 7.00 (d, 1H), 5.37 (s, 2H), 4.63-4.53 (m, 2H), 4.43 (s, 2H), 4.41-4.31 (m, 2H), 3.93 (s, 3H), 2.76 (s, 6H); MS (ES) for $C_{27}H_{27}N_7O_2S$: 514 (MH$^+$).

Example 6

1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N,N-dimethylmethanamine STEP 1: A mixture of isobutyl 6-bromo-2-methyl-1H-imidazo[4,5-b]pyridine-1-carboxylate (2.2 g, 7.1 mmol) (reagent preparation 19), (4-{[(1,1-dimethylethyl)oxy]carbonyl}-2,3,4,5-tetrahydro-1,4-benzoxazepin-7-yl)boronic acid (2.7 g, 9.2 mmol, example 1, step 2), potassium acetate (2.8 g, 28.3 mmol), and dichloro[1,1-bis(diphenylphosphino]-ferrocenepalladium (II) dichloromethane adduct (0.78 g, 1.1 mmol) in dioxane (50 ml) was stirred at 95° C. under nitrogen for 29 h. The mixture was cooled to room temperature, filtered through celite, and the filter cake was washed with ethyl acetate (100 ml). The filtrate was concentrated and purified by column chromatography on silica (0-100% ethyl acetate in hexanes) to give 1,1-dimethylethyl 7-(2-methyl-1-{[(2-methylpropyl)oxy]carbonyl}-1H-imidazo[4,5-b]pyridine-6-yl)-2,3-dihydro-1,4-benzoxazepine-4(5H)carboxylate (1.1 g, 33% yield) as a yellow solid. $^1$H NMR (400 MHz, CDCl$_3$): 8.74 (d, 1H), 8.39 (s, 1H), 7.47 (d, 1H), 7.43 (s, 1H), 7.14 (d, 1H), 4.50 (s, 2H), 4.34 (d, 2H), 4.12 (m, 2H), 3.88 (m, 2H), 2.96 (s, 3H), 2.22 (m, 1H), 1.42 (s, 9H), 1.21 (d, 6H); MS (EI) for $C_{26}H_{32}N_4O_5$: 481 (MH$^+$).

STEP 2: A mixture of 1,1-dimethylethyl 7-(2-methyl-1-{[(2-methylpropyl)-oxy]carbonyl}-1H-imidazo[4,5-b]pyridine-6-yl)-2,3-dihydro-1,4-benzoxazepine-4(5H)carboxylate (1.1 g, 2.3 mmol) in methanol (6 ml) and 4 N hydrochloric acid in dioxane (12 ml) was stirred at room temperature for 1 h and then concentrated. The resulting solid was triturated with ethyl acetate to afford the hydrochloride salt of 2-methylpropyl 2-methyl-6-(2,3,4,5-tetrahydro-1,4-benzoxazepin-7-yl)-1H-imidazo[4,5-b]pyridine-1-carboxylate (0.92 g, 91% yield) as a yellow solid. $^1$H NMR (400 MHz, DMSO-d$_6$): 9.78 (s, 1H), 8.79 (d, 1H), 8.42 (d, 1H), 7.88 (d, 1H), 7.70 (dd, 1H), 7.24 (d, 1H), 4.42 (brs, 2H), 4.32 (d, 2H), 4.27 (brs, 2H), 3.50 (brs, 2H), 2.82 (s, 3H), 2.19 (m, 1H), 1.06 (d, 6H); MS (EI) for $C_{21}H_{24}N_4O_3$: 381 (MH$^+$).

STEP 3: A solution of 2-methylpropyl 2-methyl-6-(2,3,4,5-tetrahydro-1,4-benzoxazepin-7-yl)-1H-imidazo[4,5-b]pyridine-1-carboxylate hydrochloride (73 mg, 0.16 mmol), 1-(4-chloro-6,6-dimethyl-5,6,7,8-tetrahydroquinazolin-2-yl)-N,N-dimethylmethanamine (41 mg, 0.16 mmol, reagent preparation 17), and diisopropylethyl amine (0.13 ml, 0.8 mmol) in N-methylpyrrolidinone (1.5 mL) was stirred at 135° C. for 3 h. Purification by preparatory HPLC (0.1% aqueous ammonium acetate-acetonitrile) provided the triacetate salt of the title Compound (10 mg, 9% yield). $^1$H NMR (400 MHz, methanol-d$_4$) δ 8.53 (d, 1H), 8.07 (d, 1H), 7.64 (d, 1H), 7.51 (dd, 1H), 7.08 (d, 1H), 4.79 (s, 2H), 4.38 (s, 2H), 4.01 (s, 2H), 3.84 (s, 2H), 2.81 (t, 2H), 2.64 (s, 3H), 2.55 (s, 6H), 1.92 (s, 9H), 1.68 (t, 2H), 0.91 (s, 6H); MS (EI) for $C_{29}H_{35}N_7O$: 498 (MH$^+$)

Using analogous synthetic techniques and substituting with alternative starting reagents the following compounds of the invention were prepared. Alternative starting materials were obtained commercially unless otherwise indicated.

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-ethylethanamine. Prepared as triacetate salt according to the method of example 6 by using N-((4-chloro-6,6-dimethyl-5,6,7,8-tetrahydroquinazolin-2-yl)methyl)-N-ethylethanamine (reagent preparation 17) in step 3. $^1$H NMR (400 MHz, methanol-$d_4$) δ 8.52 (s, 1H), 8.06 (s, 1H), 7.63 (s, 1H), 7.52 (d, 1H), 7.08 (d, 1H), 4.80 (s, 2H), 4.39 (m, 2H), 4.05 (s, 2H), 4.02 (m, 2H), 3.05 (q, 4H), 2.82 (t, 2H), 2.64 (s, 3H), 2.52 (s, 2H), 1.92 (s, 9H), 1.69 (t, 2H), 1.17 (t, 6H), 0.91 (s, 6H); MS (EI) for $C_{31}H_{39}N_7O$: 526 (MH$^+$).

4-[6,6-dimethyl-2-(morpholin-4-ylmethyl)-5,6,7,8-tetrahydroquinazolin-4-yl]-7-(2-methyl-1H-imidazo[4,5-b]pyridin-6-yl)-2,3,4,5-tetrahydro-1,4-benzoxazepine. Prepared as acetate salt according to the method of example 6 by using 4-((4-chloro-6,6-dimethyl-5,6,7,8-tetrahydroquinazolin-2-yl)methyl)morpholine (reagent preparation 17) in step 3. $^1$H NMR (400 MHz, methanol-$d_4$) δ $^1$H NMR (400 MHz, methanol-$d_4$) δ 8.53 (s, 1H), 8.06 (s, 1H), 7.64 (s, 1H), 7.49 (d, 1H), 7.06 (d, 1H), 4.78 (s, 2H), 4.36 (s, 2H), 4.36 (s, 2H), 4.00 (s, 2H), 3.58 (s, 4H), 3.49 (s, 2H), 2.79 (t, 2H), 2.64 (s, 3H), 2.50 (s, 3H), 2.46 (m, 4H), 1.95 (s, 3H), 1.68 (t, 2H), 0.92 (s, 6H); MS (EI) for $C_{31}H_{37}N_7O_2$: 540 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-ethylpropan-2-amine. Prepared according to the method of example 6 by using N-((4-chloro-6,6-dimethyl-5,6,7,8-tetrahydroquinazolin-2-yl)methyl)-N-ethylpropan-2-amine (reagent preparation 17) in step 3. $^1$H NMR (400 MHz, methanol-$d_4$) δ $^1$H NMR (400 MHz, methanol-$d_4$) δ 8.52 (s, 1H), 8.06 (s, 1H), 7.63 (s, 1H), 7.51 (d, 1H), 7.08 (d, 1H), 4.79 (s, 2H), 4.37 (s, 2H), 4.01 (m, 2H), 2.81 (t, 2H), 2.64 (s, 3H), 2.51 (s, 2H), 1.68 (t, 2H), 1.07 (m, 9H), 0.91 (s, 6H); MS (EI) for $C_{32}H_{41}N_7O$: 540 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-methylpropan-1-amine. Prepared according to the method of example 6 by using N-((4-chloro-6,6-dimethyl-5,6,7,8-tetrahydroquinazolin-2-yl)methyl)-2-methylpropan-1-amine (reagent preparation 17) in step 3. $^1$H NMR (400 MHz, methanol-$d_4$) δ $^1$H NMR (400 MHz, methanol-$d_4$) δ 8.53 (s, 1H), 8.06 (s, 1H), 7.63 (d, 1H), 7.51 (dd, 1H), 7.07 (d, 1H), 4.81 (s, 2H), 4.37 (s, 2H), 4.02 (m, 2H), 3.78 (s, 2H), 2.79 (t, 2H), 2.64 (s, 3H), 2.51 (s, 2H), 2.43 (s, 2H), 1.68 (m, 3H), 0.93 (s, 6H), 0.82 (d, 6H); MS (EI) for $C_{31}H_{39}N_7O$: 526 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclopropanamine. Prepared according to the method of example 6 by using N-((4-chloro-6,6-dimethyl-5,6,7,8-tetrahydroquinazolin-2-yl)methyl)cyclopropanamine (reagent preparation 17) in step 3. $^1$H NMR (400 MHz, methanol-$d_4$) δ $^1$H NMR (400 MHz, methanol-$d_4$) δ 8.57 (s, 1H), 8.10 (s, 1H), 7.70 (d, 1H), 7.51 (dd, 1H), 7.04 (d, 1H), 4.83 (s, 2H), 4.35 (s, 2H), 4.01 (m, 2H), 3.70 (s, 2H), 2.77 (t, 2H), 2.64 (s, 3H), 2.50 (s, 2H), 2.00 (m, 1H), 1.67 (t, 2H), 0.94 (s, 6H), 0.24 (m, 2H), 0.13 (m, 2H); MS (EI) for $C_{30}H_{35}N_7O$: 510 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2,2-difluoroethanamine. Prepared according to the method of example 6 by using benzyl (4-chloro-6,6-dimethyl-5,6,7,8-tetrahydroquinazolin-2-yl)methyl(2,2-difluoroethyl)carbamate (reagent preparation 17) in step 3 followed by Cbz deprotection. $^1$H NMR (400 MHz, methanol-$d_4$) δ $^1$H NMR (400 MHz, methanol-$d_4$) δ 8.53 (s, 1H), 8.06 (s, 1H), 7.64 (s, 1H), 7.50 (dd, 1H), 7.07 (d, 1H), 5.75 (m, 1H), 4.79 (s, 2H), 4.37 (s, 2H), 4.01 (m, 2H), 3.72 (s, 2H), 2.78 (m, 4H), 2.64 (s, 3H), 2.50 (s, 2H), 1.68 (t, 2H), 0.92 (s, 6H); MS (EI) for $C_{29}H_{33}F_2N_7O$: 534 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclobutanamine. Prepared as acetate salt according to the method of example 6 by using benzyl (4-chloro-6,6-dimethyl-5,6,7,8-tetrahydroquinazolin-2-yl)methyl(cyclobutyl)carbamate (reagent preparation 17) in step 3 followed by Cbz deprotection. $^1$H NMR (400 MHz, methanol-$d_4$) δ $^1$H NMR (400 MHz, methanol-$d_4$) δ 8.54 (s, 1H), 8.07 (s, 1H), 7.65 (s, 1H), 7.52 (d, 1H), 7.08 (d, 1H), 4.82 (s, 2H), 4.38 (m, 2H), 4.03 (m, 2H), 3.82 (m, 2H), 3.51 (m, 1H), 2.80 (t, 2H), 2.64 (s, 3H), 2.51 (s, 2H), 2.07 (m, 2H), 1.92 (s, 3H), 1.83 (m, 2H), 1.68 (m, 4H), 0.92 (s, 6H); MS (EI) for $C_{31}H_{37}N_7O$: 524 (MH$^+$).

{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl acetate. Prepared according to the method of example 6 by using (4-chloro-6,6-dimethyl-5,6,7,8-tetrahydroquinazolin-2-yl)methyl acetate (reagent preparation 17) in step 3. $^1$H NMR (400 MHz, methanol-$d_4$) δ $^1$H NMR (400 MHz, methanol-$d_4$) δ 8.53 (s, 1H), 8.07 (s, 1H), 7.61 (d, 1H), 7.50 (dd, 1H), 7.09 (d, 1H), 4.99 (s, 2H), 4.74 (s, 2H), 4.34 (m, 2H), 3.99 (m, 2H), 2.78 (t, 2H), 2.64 (s, 3H), 2.50 (s, 2H), 2.08 (s, 3H), 1.67 (t, 2H), 0.92 (s, 6H); MS (EI) for $C_{29}H_{32}N_6O_3$: 513 (MH$^+$).

6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methanol. Prepared from {6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl acetate by ester saponification using standard techniques. $^1$H NMR (400 MHz, methanol-$d_4$) δ $^1$H NMR (400 MHz, methanol-$d_4$) δ 8.54 (s, 1H), 8.08 (s, 1H), 7.65 (d, 1H), 7.50 (dd, 1H), 7.08 (d, 1H), 4.78 (s, 2H), 4.48 (s, 2H), 4.35 (m, 2H), 4.03 (m, 2H), 2.79 (t, 2H), 2.64 (s, 3H), 2.50 (s, 2H), 1.68 (t, 2H), 0.92 (s, 6H); MS (EI) for $C_{27}H_{30}N_6O_2$: 471 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)alanine. Prepared as acetate salt according to the method of example 6 by using ethyl 2-((4-chloro-6,6-dimethyl-5,6,7,8-tetrahydroquinazolin-2-yl)methylamino)propanoate (reagent preparation 17) in step 3 followed by saponification using standard techniques. $^1$H NMR (400 MHz, methanol-$d_4$) δ $^1$H NMR (400 MHz, methanol-$d_4$) δ 8.51 (s, 1H), 8.07 (d, 1H), 7.64 (s, 1H), 7.52 (dd, 1H), 7.09 (d, 1H), 4.82 (s, 2H), 4.40 (m, 2H), 4.15 (s, 2H), 4.05 (m, 2H), 3.66 (q, 1H), 2.81 (t, 2H), 2.64 (s, 3H), 2.52 (s, 2H), 1.94 (s, 3H), 1.68 (t, 2H), 1.45 (d, 3H), 0.91 (d, 6H); MS (EI) for $C_{30}H_{35}N_7O_3$: 542 (MH$^+$).

4-[5-(cyclopropylmethyl)-6-methylpyrimidin-4-yl]-7-(2-methyl-1H-imidazo[4,5-b]pyridin-6-yl)-2,3,4,5-tetrahydro-1,4-benzoxazepine. Prepared according to the method of example 6 by using 4-chloro-5-(cyclopropylmethyl)-6-methylpyrimidine (reagent preparation 5) in step 3. $^1$H NMR (400 MHz, methanol-$d_4$) δ 8.51 (s, 1H), 8.35 (s, 1H), 8.05 (s, 1H), 7.61 (d, 1H), 7.51 (dd, 1H), 7.09 (d, 1H), 4.69 (s, 2H), 4.41-4.33 (m, 2H), 3.95-3.86 (m, 2H), 2.70 (d, 2H), 2.63 (s, 3H), 2.48 (s, 3H), 0.96-0.81 (m, 1H), 0.46-0.31 (m, 4H); MS (EI) for $C_{25}H_{26}N_6O$: 427 (MH$^+$).

4-(5-ethyl-6-methylpyrimidin-4-yl)-7-(2-methyl-1H-imidazo[4,5-b]pyridin-6-yl)-2,3,4,5-tetrahydro-1,4-benzoxazepine. Prepared according to the method of example 6 by using 4-chloro-5-ethyl-6-methylpyrimidine in step 3. $^1$H NMR (400 MHz, methanol-$d_4$) δ 8.51 (s, 1H), 8.33 (s, 1H), 8.04 (s, 1H), 7.59 (d, 1H), 7.51 (dd, 1H), 7.09 (d, 1H), 4.71 (s, 2H), 4.37 (m, 2H), 3.90 (m, 2H), 2.74 (q, 2H), 2.64 (s, 3H), 2.44 (s, 3H), 1.20 (t, 3H); MS (EI) for $C_{23}H_{24}N_6O$: 401 (MH$^+$).

4-(5-ethyl-2,6-dimethylpyrimidin-4-yl)-7-(2-methyl-1H-imidazo[4,5-b]pyridin-6-yl)-2,3,4,5-tetrahydro-1,4-benzoxazepine. Prepared according to the method of example 6 by using 4-chloro-5-ethyl-2,6-dimethylpyrimidine (reagent preparation 8) in step 3. $^1$H NMR (400 MHz, methanol-d$_4$) δ 8.86 (d, 1H), 8.44 (d, 1H), 7.83 (d, 1H), 7.61 (dd, 1H), 7.09 (d, 1H), 5.16 (s, 2H), 4.50 (m, 2H), 4.27 (m, 2H), 2.92 (s, 3H), 2.78 (q, 2H), 2.51 (s, 3H), 2.49 (s, 3H), 1.22 (t, 3H); MS (EI) for $C_{24}H_{26}N_6O$: 415 (MH$^+$).

4-[5-(cyclopropylmethyl)-2,6-dimethylpyrimidin-4-yl]-7-(2-methyl-1H-imidazo[4,5-b]pyridin-6-yl)-2,3,4,5-tetrahydro-1,4-benzoxazepine. Prepared according to the method of example 6 by using 4-chloro-5-(cyclopropylmethyl)-2,6-dimethylpyrimidine (reagent preparation 8) in step 3. $^1$H NMR (400 MHz, methanol-d$_4$) δ 8.52 (s, 1H), 8.05 (s, 1H), 7.63 (d, 1H), 7.51 (dd, 1H), 7.09 (d, 1H), 4.66 (s, 2H), 4.33 (m, 2H), 3.91 (m, 2H), 2.67 (d, 2H), 2.64 (s, 3H), 2.44 (s, 3H), 2.42 (s, 3H), 0.87 (m, 1H), 0.38 (m, 4H); MS (EI) for $C_{26}H_{28}N_6O$: 441 (MH$^+$).

7-(2-cyclopropyl-1H-imidazo[4,5-b]pyridin-6-yl)-4-[5-(cyclopropylmethyl)-2,6-dimethylpyrimidin-4-yl]-2,3,4,5-tetrahydro-1,4-benzoxazepine. Prepared according to the method of example 6 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (reagent preparation 19) and 4-chloro-5-(cyclopropylmethyl)-2,6-dimethylpyrimidine (reagent preparation 8) in step 3. $^1$H NMR (400 MHz, methanol-d$_4$) δ 8.71 (s, 1H), 8.25 (s, 1H), 7.78 (d, 1H), 7.58 (dd, 1H), 7.09 (d, 1H), 5.14 (s, 2H), 4.50 (m, 2H), 4.29 (m, 2H), 2.72 (d, 2H), 2.52 (s, 3H), 2.51 (s, 3H), 2.39 (m, 1H), 1.43 (m, 4H), 0.88 (m, 1H), 0.50 (m, 2H), 0.10 (m, 2H); MS (EI) for $C_{28}H_{30}N_6O$: 467 (MH$^+$).

7-(2-cyclopropyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine. Prepared according to the method of example 6 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (reagent preparation 19) and 4-chloro-2,6,6-trimethyl-5,6,7,8-tetrahydroquinazoline (reagent preparation 8) in step 3. $^1$H NMR (400 MHz, methanol-d$_4$) δ 8.50 (s, 1H), 7.98 (s, 1H), 7.61 (d, 1H), 7.49 (dd, 1H), 7.09 (d, 1H), 4.71 (s, 2H), 4.32 (m, 2H), 3.97 (m, 2H), 2.75 (t, 2H), 2.46 (s, 2H), 2.40 (s, 3H), 2.21 (m, 1H), 1.66 (t, 2H), 1.22 (m, 4H), 0.91 (s, 6H); MS (EI) for $C_{29}H_{32}N_6O$: 481 (MH$^+$).

1-cyclopropyl-N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)ethanamine. Prepared according to the method of example 6 by using N-((4-chloro-6,6-dimethyl-5,6,7,8-tetrahydroquinazolin-2-yl)methyl)-1-cyclopropylethanamine (reagent preparation 17) in step 3. $^1$H NMR (400 MHz, methanol-d$_4$) δ 8.52 (s, 1H), 8.05 (s, 1H), 7.63 (d, 1H), 7.50 (dd, 1H), 7.08 (d, 1H), 5.49 (s, 2H), 4.80 (s, 2H), 4.37 (m, 2H), 4.02 (m, 2H), 3.81 (m, 1H), 2.79 (m, 2H), 2.64 (s, 3H), 2.50 (s, 3H), 1.68 (m, 2H), 1.07 (d, 3H), 0.92 (s, 6H), 0.60 (m, 1H), 0.40 (m, 2H), 0.14 (m, 1H); MS (EI) for $C_{32}H_{39}N_7O$: 538 (MH$^+$).

1-{5-(cyclopropylmethyl)-4-methyl-6-[7-(2-methyl-1H-imidazo[4,5-b]pyridin-6-yl)-2,3-dihydro-1,4-benzoxazepin-4(5H)-yl]pyrimidin-2-yl}-N,N-dimethylmethanamine. Prepared according to the method of example 6 by using 1-(4-chloro-5-(cyclopropylmethyl)-6-methylpyrimidin-2-yl)-N,N-dimethylmethanamine (reagent preparation 17) in step 3. $^1$H NMR (400 MHz, methanol-d$_4$) δ 8.52 (s, 1H), 8.05 (s, 1H), 7.64 (d, 1H), 7.49 (dd, 1H), 7.07 (d, 1H), 4.73 (s, 2H), 4.37 (m, 2H), 3.95 (m, 2H), 3.50 (s, 2H), 2.70 (d, 2H), 2.65 (s, 3H), 2.48 (s, 3H), 2.27 (s, 6H), 0.88 (m, 1H), 0.39 (m, 2H), 0.02 (m, 2H); MS (EI) for $C_{28}H_{33}N_7O$: 538 (MH$^+$).

4-(5,6-dimethylpyrimidin-4-yl)-7-(2-methyl-1H-imidazo[4,5-b]pyridin-6-yl)-2,3,4,5-tetrahydro-1,4-benzoxazepine. Prepared according to the method of example 6 by using 4-chloro-5,6-dimethylpyrimidine in step 3. $^1$H NMR (400 MHz, methanol-d$_4$): 8.50 (s, 1H), 8.31 (s, 1H), 8.04 (s, 1H), 7.57 (s, 1H), 7.50 (d, 1H), 7.09 (d, 1H), 4.71 (s, 2H), 4.35 (m, 2H), 3.93 (s, 2H), 2.64 (s, 3H), 2.39 (s, 3H), 2.27 (s, 3H); MS (EI) for $C_{22}H_{22}N_6O$: 387 (MH$^+$).

4-(6-ethyl-5-methylpyrimidin-4-yl)-7-(2-methyl-1H-imidazo[4,5-b]pyridin-6-yl)-2,3,4,5-tetrahydro-1,4-benzoxazepine. Prepared according to the method of example 6 by using 4-chloro-6-ethyl-5-methylpyrimidine (reagent preparation 5) in step 3. $^1$H NMR (400 MHz, methanol-d$_4$): 8.72 (d, 1H), 8.51 (s, 1H), 8.26 (d, 1H), 7.74 (d, 1H), 7.57 (dd, 1H), 7.08 (d, 1H), 5.17 (s, 2H), 4.48 (m, 2H), 4.27 (m, 2H), 2.82 (q, 2H), 2.80 (s, 3H), 2.38 (s, 3H), 1.29 (t, 3H); MS (EI) for $C_{23}H_{24}N_6O$: 401 (MH$^+$).

4-(5-bromo-6-methylpyrimidin-4-yl)-7-(2-methyl-1H-imidazo[4,5-b]pyridin-6-yl)-2,3,4,5-tetrahydro-1,4-benzoxazepine. Prepared according to the method of example 6 by using 5-bromo-4-chloro-6-methylpyrimidine in step 3. $^1$H NMR (400 MHz, methanol-d$_4$): 8.49 (br. s, 1H), 8.33 (s, 1H), 8.02 (br. s, 1H), 7.60 (d, 1H), 7.48 (dd, 1H), 7.08 (d, 1H), 5.05 (s, 2H), 4.36 (m, 2H), 4.16 (m, 2H), 2.64 (s, 3H), 2.55 (s, 3H); MS (EI) for $C_{21}H_{19}BrN_6O$: 451/453 (MH$^+$).

7-(2-ethyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine. Prepared as trifluoroacetate salt according to the method of example 6 by using 2-methylpropyl 2-ethyl-6-(2,3,4,5-tetrahydro-1,4-benzoxazepin-7-yl)-1H-imidazo[4,5-b]pyridine-1-carboxylate hydrochloride (reagent preparation 19) and 4-chloro-6,6-dimethyl-5,6,7,8-tetrahydroquinazolin (reagent preparation 8) in step 3. $^1$H NMR (400 MHz, methanol-d$_4$): 8.67 (d, 1H), 8.19 (d, 1H), 7.76 (s, 1H), 7.57 (d, 1H), 7.09 (d, 1H), 5.13 (s, 2H), 4.45 (m, 2H), 4.31 (m, 2H), 3.09 (m, 2H), 2.81 (m, 2H), 2.57 (s, 2H), 2.50 (s, 3H), 1.68 (m, 2H), 1.48 (m, 3H), 0.94 (s, 6H); MS (EI) for $C_{28}H_{32}N_6O$: 469 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-methylpropan-2-amine. Prepared as acetate salt according to the method of example 6 by using N-[(4-chloro-6,6-dimethyl-5,6,7,8-tetrahydroquinazolin-2-yl)methyl]-2-methylpropanamine (reagent preparation 17) in step 3. $^1$H NMR (400 MHz, methanol-d$_4$): 8.52 (d, 1H), 8.06 (d, 1H), 7.63 (d, 1H), 7.52 (dd, 1H), 7.09 (d, 1H), 4.83 (s, 2H), 4.39 (m, 2H), 4.04 (m, 4H), 2.82 (m, 2H), 2.64 (s, 3H), 2.52 (s, 2H), 1.92 (s, 3H), 1.69 (m, 2H), 1.29 (s, 9H), 0.92 (s, 6H); MS (EI) for $C_{31}H_{39}N_7O$: 526 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2,2,2-trifluoroethanamine. Prepared according to the method of example 6 by using N-[(4-chloro-6,6-dimethyl-5,6,7,8-tetrahydroquinazolin-2-yl)methyl]-2,2,2-trifluoroethanamine (reagent preparation 17) in step 3. $^1$H NMR (400 MHz, methanol-d$_4$): 8.53 (s, 1H), 8.06 (s, 1H), 7.65 (d, 1H), 7.50 (dd, 1H), 7.07 (d, 1H), 4.80 (s, 2H), 4.37 (m, 2H), 4.01 (m, 2H), 3.75 (s, 2H), 3.03 (q, 2H), 2.77 (m, 2H), 2.64 (s, 3H), 2.50 (s, 2H), 1.68 (m, 2H), 0.92 (s, 6H); MS (EI) for $C_{29}H_{32}F_3N_7O$: 552 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclopentanamine. Prepared as acetate salt according to the method of example 6 by using phenylmethyl[(4-chloro-6,6-dimethyl-5,6,7,8-tetrahydroquinazolin-2-yl)methyl]cyclopentylcarbamate (reagent preparation 17) in step 3 followed by Cbz deprotection. $^1$H NMR (400 MHz, methanol-$d_4$): 8.53 (s, 1H), 8.07 (s, 1H), 7.65 (d, 1H), 7.51 (dd, 1H), 7.07 (d, 1H), 4.84 (s, 2H), 4.36 (m, 2H), 4.03 (m, 2H), 3.81 (s, 2H), 3.13 (m, 1H), 2.78 (m, 2H), 2.64 (s, 3H), 2.51 (s, 2H), 1.89 (s, 3H), 1.76 (m, 2H), 1.68 (m, 2H), 1.54 (m, 2H), 1.43 (m, 2H), 1.25 (m, 2H), 0.92 (s, 6H); MS (EI) for $C_{32}H_{39}N_7O$: 538 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)ethanamine. Prepared as acetate salt according to the method of example 6 by using phenylmethyl[(4-chloro-6,6-dimethyl-5,6,7,8-tetrahydroquinazolin-2-yl)methyl](2-fluoroethyl)carbamate (reagent preparation 17) in step 3 followed by Cbz deprotection. $^1$H NMR (400 MHz, methanol-$d_4$): 8.52 (d, 1H), 8.06 (d, 1H), 7.63 (d, 1H), 7.52 (dd, 1H), 7.09 (d, 1H), 4.82 (s, 2H), 4.40 (m, 2H), 4.05 (s, 2H), 4.03 (m, 2H), 2.99 (q, 2H), 2.80 (m, 2H), 2.64 (s, 3H), 2.52 (s, 2H), 1.91 (s, 3H), 1.69 (m, 2H), 1.17 (t, 3H), 0.91 (s, 6H); MS (EI) for $C_{29}H_{35}N_7O$: 498 (MH$^+$).

1-{4,5-dimethyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine. Prepared as triacetate salt according to the method of example 6 by using 1-(4-chloro-5,6-dimethylpyrimidin-2-yl)-N,N-dimethylmethanamine (reagent preparation 17) in step 3. $^1$H NMR (400 MHz, methanol-$d_4$): 8.51 (d, 1H), 8.05 (d, 1H), 7.62 (d, 1H), 7.49 (dd, 1H), 7.06 (d, 1H), 4.78 (s, 2H), 4.36 (m, 2H), 3.97 (m, 2H), 3.79 (s, 2H), 2.64 (s, 3H), 2.49 (s, 6H), 2.41 (s, 3H), 2.27 (s, 3H), 1.91 (s, 9H); MS (EI) for $C_{25}H_{29}N_7O$: 444 (MH$^+$).

(2R)—N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)butan-2-amine. Prepared as a trifluoroacetate salt according to the method of example 6 by using 2-methylpropyl 2-methyl-6-(2,3,4,5-tetrahydro-1,4-benzoxazepin-7-yl)-1H-imidazo[4,5-b]pyridine-1-carboxylate and (R)-benzyl sec-butyl((4-chloro-6,6-dimethyl-5,6,7,8-tetrahydroquinazolin-2-yl)methyl)carbamate (reagent preparation 17) in step 3 followed by Cbz deprotection. $^1$H NMR (400 MHz, DMSO-d6) δ 8.69 (br s, 3H), 8.24 (br s, 1H), 7.80 (s, 1H), 7.62 (d, 1H), 7.09 (d, 1H), 4.79 (s, 2H), 4.43-4.36 (m, 2H), 4.17-4.11 (m, 2H), 4.00-3.94 (m, 2H), 3.15 (br s, 1H), 2.75 (t, 2H), 2.67 (s, 2H), 2.50 (s, 2H, buried), 1.79-1.66 (m, 1H), 1.62 (t, 2H), 1.46-1.33 (m, 1H), 1.17 (d, 3H), 0.89-0.78 (m, 9H); MS (EI) for $C_{31}H_{39}N_7O$: 526 (MH$^+$).

(2S)—N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)butan-2-amine. Prepared according to the method of example 6 by using 2-methylpropyl 2-methyl-6-(2,3,4,5-tetrahydro-1,4-benzoxazepin-7-yl)-1H-imidazo[4,5-b]pyridine-1-carboxylate and (S)-benzyl sec-butyl((4-chloro-6,6-dimethyl-5,6,7,8-tetrahydroquinazolin-2-yl)methyl)carbamate (reagent preparation 17) in step 3 followed by Cbz deprotection. $^1$H NMR (400 MHz, DMSO-d6) δ 8.61-8.44 (m, 1H), 8.12-7.93 (m, 1H), 7.71 (d, 1H), 7.54 (dd, 1H), 7.03 (d, 1H), 4.67 (s, 2H), 4.35-4.27 (m, 2H), 3.92-3.84 (m, 2H), 3.56 (q, 2H), 2.69 (t, 3H), 2.54 (s, 2H), 2.45 (s, 3H), 2.42-2.30 (m, 1H), 1.59 (t, 2H), 1.27 (dd, 2H), 1.18-1.04 (m, 1H), 0.87 (s, 6H), 0.83 (d, 3H), 0.70 (t, 3H); MS (EI) for $C_{31}H_{39}N_7O$: 526 (MH$^+$).

1-{4-ethyl-5-methyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine. Prepared according to the method of example 6 by using 2-methylpropyl 2-methyl-6-(2,3,4,5-tetrahydro-1,4-benzoxazepin-7-yl)-1H-imidazo[4,5-b]pyridine-1-carboxylate and 1-(4-chloro-6-ethyl-5-methylpyrimidin-2-yl)-N,N-dimethylmethanamine (reagent preparation 17) in step 3. $^1$H NMR (400 MHz, DMSO-d6) δ 8.51 (br s, 1H), 8.03 (br s, 1H), 7.70 (d, 1H), 7.52 (dd, 1H), 7.03 (d, 1H), 4.61 (s, 2H), 4.33-4.28 (m, 2H), 3.84-3.79 (m, 2H), 3.36 (s, 2H), 2.63 (q, 2H), 2.53 (d, 3H), 2.20 (s, 3H), 2.13 (s, 6H), 1.89 (s, 3H), 1.14 (t, 3H); MS (EI) for $C_{26}H_{31}N_7O$: 458 (MH$^+$).

1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methanamine. Prepared as an acetate salt by the method of example 6 using 2-methylpropyl 2-methyl-6-(2,3,4,5-tetrahydro-1,4-benzoxazepin-7-yl)-1H-imidazo[4,5-b]pyridine-1-carboxylate and 2-(azidomethyl)-4-chloro-6,6-dimethyl-5,6,7,8-tetrahydroquinazoline (reagent preparation 45) in step 3 followed by reduction of the azide to the amine (LaRock, R. C. *Comprehensive Organic Transformations: A Guide to Functional Group Preparations* 1989, VCH Publishers, Inc., New York). $^1$H NMR (400 MHz, DMSO-d6) δ 8.52 (d, 1H), 8.04 (d, 1H), 7.74 (d, 1H), 7.54 (dd, 1H), 7.04 (d, 1H), 4.68 (s, 2H), 4.34-4.28 (m, 2H), 3.92-3.87 (m, 2H), 3.63-3.59 (m, 2H), 2.69 (t, 2H), 2.54 (s, 3H), 2.46 (s, 2H), 1.86 (s, 5H), 1.59 (t, 2H), 0.86 (s, 6H); MS (EI) for $C_{27}H_{31}N_7O$: 470 (MH$^+$).

1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N-methylmethanamine. Prepared by the method of example 6 using 2-methylpropyl 2-methyl-6-(2,3,4,5-tetrahydro-1,4-benzoxazepin-7-yl)-1H-imidazo[4,5-b]pyridine-1-carboxylate and N-((4-chloro-6,6-dimethyl-5,6,7,8-tetrahydroquinazolin-2-yl)methyl)-N-methyl-2-nitrobenzenesulfonamide (reagent preparation 17) in step 3 followed by 2-nitrobenzenesulfonyl-group deprotection. $^1$H NMR (400 MHz, DMSO-d6) δ 8.53 (br s, 1H), 8.06 (br s, 1H), 7.75 (d, 1H), 7.53 (dd, 1H), 7.01 (d, 1H), 4.68 (s, 2H), 4.33-4.27 (m, 2H), 3.91-3.85 (m, 2H), 3.48 (s, 2H), 2.68 (t, 2H), 2.54 (s, 3H), 2.45 (s, 2H), 2.12 (s, 3H), 1.59 (t, 2H), 0.87 (s, 6H); MS (EI) for $C_{28}H_{33}N_7O$: 484 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-fluoroethanamine. Prepared by the method of example 6 using 2-methylpropyl 2-methyl-6-(2,3,4,5-tetrahydro-1,4-benzoxazepin-7-yl)-1H-imidazo[4,5-b]pyridine-1-carboxylate and benzyl (4-chloro-6,6-dimethyl-5,6,7,8-tetrahydroquinazolin-2-yl)methyl(2-fluoroethyl)carbamate (reagent preparation 17) in step 3 followed by Cbz deprotection. $^1$H NMR (400 MHz, DMSO-d6) δ 12.83 (s, 0.5H), 12.55 (s, 0.5H), 8.57 (d, 0.5H), 8.49 (d, 0.5H), 8.09 (d, 0.5H), 7.97 (d, 0.5H), 7.73 (d, 1H), 7.54 (dd, 1H), 7.03 (dd, 1H), 4.68 (s, 2H), 4.45 (t, 1H), 4.38-4.25 (m, 3H), 3.93-3.82 (m, 2H), 3.66 (s, 2H), 2.85-2.65 (m, 4H), 2.57-2.52 (m, 3H), 2.46 (s, 2H), 1.59 (t, 2H), 0.86 (s, 6H); MS (EI) for $C_{29}H_{34}FN_7O$: 516 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)methanesulfonamide. Prepared by the method of example 6 using 2-methylpropyl 2-methyl-6-(2,3,4,5-tetrahydro-1,4-benzoxazepin-7-yl)-1H-imidazo[4,5-b]pyridine-1-carboxylate and N-((4-chloro-6,6-dimethyl-5,6,7,8-tetrahydroquinazolin-2-yl)methyl)methanesulfonamide (reagent preparation 17) in step 3. $^1$H NMR (400 MHz, DMSO-d6) δ 8.52 (br s, 1H), 8.05 (br s, 1H), 7.74

(d, 1H), 7.56 (dd, 1H), 7.27 (t, 1H), 7.06 (d, 1H), 4.68 (s, 2H), 4.37-4.31 (m, 2H), 4.12 (d, 2H), 3.93-3.87 (m, 2H), 2.85 (s, 3H), 2.71 (t, 2H), 2.54 (s, 3H), 2.47 (s, 2H), 1.60 (t, 2H), 0.85 (s, 6H); MS (EI) for $C_{28}H_{33}N_7O_3S$: 548 (MH$^+$).

1-{5-ethyl-4-methyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine. Prepared as a diacetate salt by the method of example 6 using 2-methylpropyl 2-methyl-6-(2,3,4,5-tetrahydro-1,4-benzoxazepin-7-yl)-1H-imidazo[4,5-b]pyridine-1-carboxylate and 1-(4-chloro-5-ethyl-6-methylpyrimidin-2-yl)-N,N-dimethylmethanamine (reagent preparation 17) in step 3. $^1$H NMR (400 MHz, DMSO-d6) δ 8.51 (br s, 1H), 8.03 (br s, 1H), 7.67 (d, 1H), 7.52 (dd, 1H), 7.02 (d, 1H), 4.63 (s, 2H), 4.35-4.30 (m, 2H), 3.83-3.78 (m, 2H), 3.32 (s, 2H), 2.65-2.57 (m, 1H), 2.54 (s, 3H), 2.52-2.45 (m, 1H (buried)), 2.36 (s, 3H), 2.10 (s, 6H), 1.86 (s, 8H), 1.15 (t, 3H); MS (EI) for $C_{28}H_{31}N_7O$: 458 (MH$^+$).

1-{4-[7-(2-cyclopropyl-1H-imidazo[4,5-b]pyridin-6-yl)-2,3-dihydro-1,4-benzoxazepin-4(5H)-yl]-6,6-dimethyl-5,6,7,8-tetrahydroquinazolin-2-yl}-N,N-dimethylmethanamine. Prepared as acetate according to the method of example 6 by using 2-methylpropyl 2-cyclopropyl-6-(2,3,4,5-tetrahydro-1,4-benzoxazepin-7-yl)-1H-imidazo[4,5-b]pyridine-1-carboxylate (reagent preparation 19) in step 1 and 1-(4-chloro-6,6-dimethyl-5,6,7,8-tetrahydroquinazolin-2-yl)-N,N-dimethylmethanamine (reagent preparation 17) in step 3. $^1$H NMR (400 MHz, d$_6$-DMSO): 8.49 (s, 1H), 7.98 (s, 1H), 7.68 (d, 1H), 7.51 (dd, 1H), 7.01 (d, 1H), 4.63 (s, 2H), 4.30 (m, 2H), 3.85 (m, 2H), 2.68 (m, 2H), 2.44 (s, 2H), 2.14 (m, 1H), 2.10 (s, 6H), 1.88 (s, 2H), 1.59 (m, 2H), 1.10 (m, 4H), 0.85 (s, 6H). MS (EI) for $C_{31}H_{37}N_7O$: 524 (MH$^+$).

4-[6,6-dimethyl-2-({[2-(methyloxy)ethyl]oxy}methyl)-5,6,7,8-tetrahydroquinazolin-4-yl]-7-(2-methyl-1H-imidazo[4,5-b]pyridin-6-yl)-2,3,4,5-tetrahydro-1,4-benzoxazepine. Prepared according to the method of example 6 by using 4-chloro-6,6-dimethyl-2-({[2-(methyloxy)ethyl]oxy}methyl)-5,6,7,8-tetrahydroquinazoline (reagent preparation 17) in step 3. MS (EI) for $C_{30}H_{36}N_6O_3$: 529 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-(methyloxy)ethanamine. Prepared according to the method of example 6 by using N-[(4-chloro-6,6-dimethyl-5,6,7,8-tetrahydroquinazolin-2-yl)methyl]-2-(methyloxy)ethanamine (reagent preparation 17) in step 3. $^1$H NMR (400 MHz, d$_6$-DMSO): 9.50 (brs, 1H), 8.89 (s, 1H), 8.46 (s, 1H), 8.06 (brs, 1H), 7.69 (dd, 1H), 7.08 (d, 1H), 5.08 (brs, 1H), 4.48 (s, 2H), 4.26 (s, 2H), 4.12 (m, 2H), 3.54 (m, 1H), 3.20 (s, 3H), 3.12 (m, 2H), 2.84 (s, 3H), 2.76 (m, 2H), 2.54 (s, 2H), 2.51 (s, 3H), 1.62 (m, 2H), 0.84 (s, 6H). MS (EI) for $C_{30}H_{37}N_7O_2$: 527 (MH$^+$).

4-[(7S)-7-ethyl-5,6,7,8-tetrahydroquinazolin-4-yl]-7-(2-methyl-1H-imidazo[4,5-b]pyridin-6-yl)-2,3,4,5-tetrahydro-1,4-benzoxazepine. Prepared according to the method of example 6 by using (7S)-4-chloro-7-ethyl-5,6,7,8-tetrahydroquinazoline (reagent preparation 17) in step 3. $^1$H NMR (400 MHz, Methanol-d$_4$): 8.49 (br, 1H), 8.32 (s, 1H), 8.04 (br, 1H), 7.57 (s, 1H), 7.46 (d, 1H), 7.08 (d, 1H), 4.74 (b, 2H), 4.42 (m, 1H), 4.27 (m, 1H), 4.08 to 3.89 (m, 2H), 2.94 to 2.80 (m, 2H), 2.65 (s, 2H), 2.60 (m, 1H), 2.29 (m, 1H), 1.97 (m, 1H), 1.72 (m, 1H), 1.40 (m, 2H), 1.11 (m, 1H), 0.97 (t, 3H); MS (EI) for $C_{26}H_{28}N_6O$: 441 (MH$^+$).

4-[(7S)-7-ethyl-2-methyl-5,6,7,8-tetrahydroquinazolin-4-yl]-7-(2-methyl-1H-imidazo[4,5-b]pyridin-6-yl)-2,3,4,5-tetrahydro-1,4-benzoxazepine. Prepared according to the method of example 6 by using (7S)-4-chloro-7-ethyl-2-methyl-5,6,7,8-tetrahydroquinazoline (reagent preparation 8) in step 3. $^1$H NMR (400 MHz, Methanol-d$_4$): 8.39 (s, 1H), 7.95 (s, 1H), 7.52 (s, 1H), 7.31 (d, 1H), 6.98 (d, 1H), 4.75 (b, 2H), 4.43 (m, 1H), 4.12 (m, 1H), 4.00 (m, 1H), 3.88 (m, 1H), 2.82 to 2.67 (m, 2H), 2.54 (s, 3H), 2.49 (m, 1H), 2.28 (s, 3H), 2.19 (m, 1H), 1.86 (m, 1H), 1.63 (m, 1H), 1.31 (m, 2H), 1.05 (m, 1H), 0.91 (t, 3H); MS (EI) for $C_{27}H_{30}N_6O$: 455 (MH$^+$).

4-[6,6-dimethyl-2-(pyrrolidin-1-ylmethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine. Prepared as the trifluoroacetic acid salt according to the method of example 6 by using 4-chloro-6,6-dimethyl-2-(pyrrolidin-1-ylmethyl)-5,6,7,8-tetrahydroquinazoline (reagent preparation 17) in step 3. $^1$H NMR (400 MHz, Methanol-d$_4$): 8.95 (br, 1H), 8.44 (br, 1H), 7.85 (s, 1H), 7.59 (s, 1H), 7.48 (d, 1H), 7.12 (d, 1H), 5.09 (s, 2H), 4.56 (s, 2H), 4.54 (m, 2H), 4.22 (m, 2H), 3.38 (m, 4H), 2.85 (t, 2H), 2.85 (s, 3H), 2.56 (s, 2H), 1.93 (m, 4H), 1.68 (t, 2H), 0.90 (s, 6H); MS (EI) for $C_{31}H_{37}N_7O$: 524 (MH$^+$).

1-{6,6-dimethyl-4-[7-(2-methyl-3H-imidazo[4,5-b]pyridin-6-yl)-2,3-dihydro-1,4-benzoxazepin-4(5H)-yl]-5,6,7,8-tetrahydroquinazolin-2-yl}-N,N-dimethylethanamine. Prepared according to the method of example 6 by using 1-(4-chloro-6,6-dimethyl-5,6,7,8-tetrahydroquinazolin-2-yl)-N,N-dimethylethanamine (reagent preparation 46) in step 3. $^1$H NMR (400 MHz, Methanol-d$_4$): 8.52 (s, 1H), 8.04 (s, 1H), 7.63 (s, 1H), 7.54 (d, 1H), 7.03 (d, 1H), 5.03 (s, 2H), 4.78 (m, 2H), 3.99 (m, 2H), 3.52 (s, 1H), 2.77 (t, 2H), 2.63 (s, 3H), 2.49 (s, 2H), 2.13 (s, 6H), 1.66 (t, 2H), 1.28 (d, 3H), 0.91 (s, 6H); MS (EI) for $C_{30}H_{37}N_7O$: 512 (MH$^+$).

4-[6,6-dimethyl-2-(1-pyrrolidin-1-ylethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine. Prepared according to the method of example 6 by using 4-chloro-6,6-dimethyl-2-(1-pyrrolidin-1-ylethyl)-5,6,7,8-tetrahydroquinazoline (reagent preparation 46) in step 3. $^1$H NMR (400 MHz, Methanol-d$_4$): 8.54 (s, 1H), 8.05 (s, 1H), 7.65 (s, 1H), 7.48 (d, 1H), 7.05 (d, 1H), 4.77 (s, 2H), 4.37 (m, 2H), 4.02 (m, 2H), 3.57 (s, 1H), 2.77 (t, 2H), 2.67 (m, 2H), 2.63 (s, 3H), 2.50 (s, 2H), 2.47 (m, 2H), 1.69 to 1.64 (m, 6H), 1.37 (d, 3H), 0.90 (s, 6H); MS (EI) for $C_{32}H_{39}N_7O$: 538 (MH$^+$).

Phenylmethyl(2S)-2-{6,6-dimethyl-4-[7-(2-methyl-3H-imidazo[4,5-b]pyridin-6-yl)-2,3-dihydro-1,4-benzoxazepin-4(5H)-yl]-5,6,7,8-tetrahydroquinazolin-2-yl}pyrrolidine-1-carboxylate. Prepared according to the method of example 6 by using phenylmethyl((2S))-2-(4-chloro-6,6-dimethyl-5,6,7,8-tetrahydroquinazolin-2-yl)pyrrolidine-1-carboxylate (reagent preparation 18) in step 3. $^1$H NMR (400 MHz, Methanol-d$_4$): 8.47 (s, 0.35H), 8.43 (s, 0.65H), 7.99 (s, 0.35H), 7.95 (0.65H), 7.48 (br, 1H), 7.45 to 7.38 (m, 2H), 7.32 (br, 1H), 7.08 to 7.01 (m, 3H), 6.72 (dd, 1H), 5.03 (dd, 2H), 4.77 (s, 0.35H), 4.73 (s, 0.65H), 4.69 to 4.64 (m, 3H), 4.44 to 4.21 (m, 2H), 4.01 to 3.77 (m, 2H), 3.53 to 3.58 (m, 2H), 2.78 to 1.68 (m, 2H), 2.63 (s, 3H), 2.51 (d, 2H), 2.25 (m, 1H), 1.76 (m, 1H), 1.64 (m, 2H), 0.98 to 0.83 (m, 6H); MS (EI) for $C_{38}H_{41}N_7O_3$: 644 (MH$^+$).

4-{6,6-dimethyl-2-[(2S)-pyrrolidin-2-yl]-5,6,7,8-tetrahydroquinazolin-4-yl}-7-(2-methyl-3H-imidazo[4,5-b]pyridin-6-yl)-2,3,4,5-tetrahydro-1,4-benzoxazepine. Prepared according to the method of example 6 by using phenylmethyl ((2S))-2-(4-chloro-6,6-dimethyl-5,6,7,8-tetrahydroquinazolin-2-yl)pyrrolidine-1-carboxylate (reagent preparation 18) in step 3 followed by Cbz group deprotection. $^1$H NMR (400 MHz, Methanol-d$_4$): 8.53 (s, 1H), 8.07 (s, 1H), 7.67 (s, 1H), 7.52 (d, 1H), 7.08 (d, 1H), 4.84 (s, 2H), 4.50 (m, 1H), 4.38 (m, 2H), 4.02 (m, 2H), 3.27 to 3.10 (m, 3H), 2.82 (t, 2H), 2.66 (s, 3H), 2.51 (s, 2H), 2.33 (m, 1H), 1.99 (m, 1H), 1.81 (m, 1H), 1.68 (t, 2H), 0.90 (d, 6H); MS (EI) for $C_{30}H_{35}N_7O$: 510 (MH$^+$).

4-{6,6-dimethyl-2-[(2R)-pyrrolidin-2-yl]-5,6,7,8-tetrahydroquinazolin-4-yl}-7-(2-methyl-3H-imidazo[4,5-b]pyridin-6-yl)-2,3,4,5-tetrahydro-1,4-benzoxazepine. Prepared according to the method of example 6 by using phenylmethyl (2R)-2-(4-chloro-6,6-dimethyl-5,6,7,8-tetrahydroquinazolin-2-yl)pyrrolidine-1-carboxylat (reagent preparation 18) in step 3 followed by Cbz group deprotection. $^1$H NMR (400 MHz, Methanol-d$_4$): 8.55 (s, 1H), 8.09 (s, 1H), 7.67 (s, 1H), 7.52 (d, 1H), 7.07 (d, 1H), 4.85 (s, 2H), 4.49 (m, 1H), 4.38 (m, 2H), 4.01 (m, 2H), 3.28 to 3.10 (m, 3H), 2.79 (t, 2H), 2.63 (s, 3H), 2.52 (s, 2H), 2.32 (m, 1H), 1.99 (m, 1H), 1.79 (m, 1H), 1.67 (t, 2H), 0.91 (d, 6H); MS (EI) for $C_{30}H_{35}N_7O$: 510 (MH$^+$).

4-(6,6-dimethyl-2-pyrrolidin-2-yl-5,6,7,8-tetrahydroquinazolin-4-yl)-7-(2-methyl-3H-imidazo[4,5-b]pyridin-6-yl)-2,3,4,5-tetrahydro-1,4-benzoxazepine. Prepared according to the method of example 6 by using phenylmethyl 2-(4-chloro-6,6-dimethyl-5,6,7,8-tetrahydroquinazolin-2-yl)pyrrolidine-1-carboxylate (reagent preparation 18) in step 3 followed by Cbz group deprotection. $^1$H NMR (400 MHz, Methanol-d$_4$): 8.53 (s, 1H), 8.08 (s, 1H), 7.67 (s, 1H), 7.51 (d, 1H), 7.04 (d, 1H), 4.83 (s, 2H), 4.37 (m, 3H), 4.02 (m, 2H), 3.27 (m, 1H), 3.17 to 3.01 (m, 2H), 2.80 (t, 2H), 2.64 (s, 3H), 2.51 (s, 2H), 2.28 (m, 1H), 1.90 (m, 1H), 1.76 (m, 1H), 1.69 (t, 2H), 0.91 (d, 6H); MS (EI) for $C_{30}H_{35}N_7O$: 510 (MH$^+$).

4-{6,6-dimethyl-2-[(methyloxy)methyl]-5,6,7,8-tetrahydroquinazolin-4-yl}-7-(2-methyl-3H-imidazo[4,5-b]pyridin-6-yl)-2,3,4,5-tetrahydro-1,4-benzoxazepine. Prepared according to the method of example 6 by using 4-chloro-6,6-dimethyl-2-[(methyloxy)methyl]-5,6,7,8-tetrahydroquinazoline (reagent preparation 17) in step 3. $^1$H NMR (400 MHz, Methanol-d$_4$): 8.55 (br, 1H), 8.07 (br, 1H), 7.66 (s, 1H), 7.50 (d, 1H), 7.08 (d, 1H), 4.76 (s, 2H), 4.37 (s, 2H), 4.32 (m, 2H), 4.01 (m, 2H), 3.33 (s, 3H), 2.77 (t, 2H), 2.63 (s, 3H), 2.49 (s, 2H), 1.67 (t, 2H), 0.91 (s, 6H); MS (EI) for $C_{28}H_{32}N_6O_2$: 485 (MH$^+$).

4-(2-ethenyl-6,6-dimethyl-5,6,7,8-tetrahydroquinazolin-4-yl)-7-(2-methyl-3H-imidazo[4,5-b]pyridin-6-yl)-2,3,4,5-tetrahydro-1,4-benzoxazepine. Prepared according to the method of example 6 by using 4-[6,6-dimethyl-2-(2-pyrrolidin-1-ylethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine in step 3. $^1$H NMR (400 MHz, Methanol-d$_4$): 8.51 (s, 1H), 8.07 (s, 1H), 7.63 (s, 1H), 7.49 (d, 1H), 7.06 (d, 1H), 6.59 (dd, 1H), 6.40 (d, 1H), 5.51 (d, 1H), 4.77 (2H), 4.37 (m, 2H), 4.00 (m, 2H), 2.77 (t, 2H), 2.63 (s, 3H), 2.51 (s, 2H), 1.67 (t, 2H), 0.92 (s, 6H); MS (EI) for $C_{28}H_{30}N_6O$: 485 (MH$^+$).

4-[6,6-dimethyl-2-(2-pyrrolidin-1-ylethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine. Prepared according to the method of example 6 by using 4-chloro-6,6-dimethyl-2-(2-pyrrolidin-1-ylethyl)-5,6,7,8-tetrahydroquinazoline (reagent preparation 8) in step 3. $^1$H NMR (400 MHz, Methanol-d$_4$): 8.56 (s, 1H), 8.11 (s, 1H), 7.68 (s, 1H), 7.52 (d, 1H), 7.06 (d, 1H), 4.81 (2H), 4.37 (m, 2H), 4.00 (m, 2H), 3.34 (m, 2H), 2.99 (m, 6H), 2.75 (t, 2H), 2.64 (s, 3H), 2.49 (s, 2H), 1.95 (m, 4H), 1.67 (t, 2H), 0.92 (s, 6H); MS (EI) for $C_{32}H_{39}N_7O$: 538 (MH$^+$).

7-(2-methyl-1H-imidazo[4,5-b]pyridin-6-yl)-4-(5-methylpyrimidin-4-yl)-2,3,4,5-tetrahydro-1,4-benzoxazepine. Synthesized according to the method of example 6 using 4-chloro-5-methylpyrimidine in step 3. $^1$H NMR (400 MHz, d$_6$-DMSO): 8.89 (d, 1H), 8.80 (s, 1H), 8.45 (d, 1H), 8.28 (s, 1), 7.91 (d, 1H), 7.69 (dd, 1H), 7.10 (d, 1H), 5.27 (s, 2H), 4.50 (m, 2H), 4.33 (m, 2H), 2.84 (s, 3H), 2.43 (s, 3H), 1.76 (s, 3H); MS (EI) for $C_{21}H_{20}N_6O$: 373 (MH$^+$).

4-[2,6-dimethyl-5-(1-methylethyl)pyrimidin-4-yl]-7-(2-methyl-1H-imidazo[4,5-b]pyridin-6-yl)-2,3,4,5-tetrahydro-1,4-benzoxazepine. Synthesized according to the method of example 6 using 4-chloro-5-isopropyl-2,6-dimethylpyrimidine (reagent preparation 8) in step 3. $^1$H NMR (400 MHz, d$_6$-DMSO): 8.74 (s, 1H), 8.29 (s, 1H), 7.82 (s, 1H), 7.63 (dd, 1H), 7.30 (s, 1H), 7.17 (s, 1H), 7.04 (s, 1H), 5.06 (s, 2H), 4.50 (m, 2H), 4.03 (m, 2H), 3.08 (m, 1H) 2.71 (s, 3H), 2.54 (s, 3H), 2.41 (s, 3H), 1.32 (d, 6H); MS (EI) for $C_{25}H_{28}N_6O$: 429 (MH$^+$).

7-(2-methyl-1H-imidazo[4,5-b]pyridin-6-yl)-4-[6-methyl-5-(1-methylethyl)pyrimidin-4-yl]-2,3,4,5-tetrahydro-1,4-benzoxazepine. Synthesized according to the method of example 6 using 4-chloro-5-isopropyl-6-methylpyrimidine (reagent preparation 5) in step 3. $^1$H NMR (400 MHz, d$_6$-DMSO): 8.81 (s, 1H), 8.64 (s, 1H), 8.36 (s, 1H), 7.65 (d, 1H), 7.03 (d, 1H), 5.04 (s, 2H), 4.53 (s, 2H), 4.02 (s, 2H), 3.11 (m, 1H), 2.76 (s, 3H), 2.56 (s, 3H), 1.34 (d, 6H); MS (EI) for $C_{24}H_{26}N_6O$: 415 (MH$^+$).

7-(2-methyl-1H-imidazo[4,5-b]pyridin-6-yl)-4-(7-methyl-7-phenyl-5,6,7,8-tetrahydroquinazolin-4-yl)-2,3,4,5-tetrahydro-1,4-benzoxazepine. Synthesized according to the method of example 6 using 4-chloro-7-methyl-7-phenyl-5,6,7,8-tetrahydroquinazoline (reagent preparation 3) in step 3. $^1$H NMR (400 MHz, d$_6$-DMSO): 8.49 (s, 1H), 8.37 (s, 1H), 7.92 (d, 1H), 7.48 (d, 1H), 7.31 (s, 1H), 7.29 (s, 1H), 7.22 (d, 1H), 7.13 (m, 2H), 7.02 (m, 1H), 6.94-6.80 (m, 1H), 4.42-4.56 (m, 2H), 4.32 (m, 2H), 3.94 (d, 1H), 3.76 (m, 1H), 3.14 (d, 1H), 2.81 (d, 1H), 2.68 (d, 1H), 2.55 (d, 3H), 2.55 (d, 3H), 2.29 (m, 1H), 2.09 (m, 1H), 1.84 (m, 1H), 1.32 (s, 3H); MS (EI) for $C_{31}H_{30}N_6O$: 503 (MH$^+$).

N,N,2-trimethyl-4-[7-(2-methyl-1H-imidazo[4,5-b]pyridin-6-yl)-2,3-dihydro-1,4-benzoxazepin-4(5H)-yl]pyrimidine-5-sulfonamide. Synthesized according to the method of example 6 using 4-chloro-N,N,2-trimethylpyrimidine-5-sulfonamide in step 3. $^1$H NMR (400 MHz, d$_6$-DMSO): 8.51 (s, 1H), 8.03 (s, 1H), 7.94 (s, 1H), 7.52 (dd, 1H) 7.04 (d, 1H), 6.71 (d, 1H), 5.05 (s, 2H), 4.31 (d, 2H), 4.24 (d, 2H), 2.84 (s, 6H), 2.54 (s, 3H), 2.40 (s, 3H); MS (EI) for $C_{23}H_{25}N_7O_3S$: 480 (MH$^+$).

7-(2-methyl-1H-imidazo[4,5-b]pyridin-6-yl)-4-[2-methyl-5-(morpholin-4-ylsulfonyl)pyrimidin-4-yl]-2,3,4,5-tetrahydro-1,4-benzoxazepine. Synthesized according to the method of example 6 using 4-(4-chloro-2-methylpyrimidin-5-ylsulfonyl)morpholine in step 3. $^1$H NMR (400 MHz, d$_6$-DMSO): 8.58 (s, 1H), 8.50 (d, 1H), 8.03 (d, 1H), 7.81 (s, 1H), 7.53 (d, 1H), 7.03 (d, 1H), 5.04 (s, 2H), 4.29 (s, 2H), 3.61 (s, 2H), 3.12 (s, 2H), 2.42 (s, 3H); MS (EI) for $C_{25}H_{27}N_7O_4S$: 522 (MH$^+$).

7-(2-cyclopropyl-1H-imidazo[4,5-b]pyridin-6-yl)-4-(6,6-dimethyl-5,6-dihydroquinazolin-4-yl)-2,3,4,5-tetrahydro-1,4-benzoxazepine. Synthesized according to the method of example 6 using isobutyl 6-bromo-2-cyclopropyl-1H-imidazo[4,5-b]pyridine-1-carboxylate (reagent preparation 19) in step 1 and 4-chloro-6,6-dimethyl-5,6-dihydroquinazoline (reagent preparation 3) in step 3. $^1$H NMR (400 MHz, d$_6$-DMSO): 8.64 (s, 1H), 8.61 (s, 1H), 8.14 (m, 1H), 7.77 (d 1H), 7.59 (dd, 1H), 7.04 (d, 1H), 6.47 (d, 1H), 6.34 (d, 1H), 5.00 (s, 2H), 4.46 (m, 2H), 4.11 (s, 2H), 2.83 (s, 2H), 2.24 (m, 1H), 1.24-1.18 (m, 5H), 0.99 (s, 6H); MS (EI) for $C_{28}H_{28}N_6O$: 465 (MH$^+$).

4-(6,6-dimethyl-5,6-dihydroquinazolin-4-yl)-7-(2-methyl-1H-imidazo[4,5-b]pyridin-6-yl)-2,3,4,5-tetrahydro-1,4-benzoxazepine. Synthesized according to the method of example 6 using 4-chloro-6,6-dimethyl-5,6-dihydroquinazoline (reagent preparation 3) in step 3. $^1$H NMR (400 MHz, d$_6$-DMSO): 8.64 (s, 1H), 8.59 (s, 1H), 8.18 (s, 1H), 7.77 (d, 1H), 7.60 (dd, 1H), 7.05 (d, 1H), 6.43 (d, 1H), 6.32 (d, 1H), 4.94 (s, 2H), 4.43 (m, 2H), 4.06 (br s, 2H), 2.82 (s, 2H), 2.62 (s, 3H), 0.99 (s, 6H); MS (EI) for C$_{26}$H$_{26}$N$_6$O: 439 (MH$^+$).

7-(2-methyl-1H-imidazo[4,5-b]pyridin-6-yl)-4-(6,6,8-trimethyl-5,6-dihydroquinazolin-4-yl)-2,3,4,5-tetrahydro-1,4-benzoxazepine. Synthesized according to the method of example 6 using 4-chloro-6,6,8-trimethyl-5,6-dihydroquinazoline (reagent preparation 3) in step 3. $^1$H NMR (400 MHz, d$_6$-DMSO): 8.74 (d, 1H), 8.54 (s, 1H), 8.30 (d, 1H), 7.77 (d, 1H), 7.61 (dd, 1H), 7.05 (d, 1H), 6.09 (s, 1H), 4.82 (s, 2H), 4.42 (m, 2H), 3.96 (br s, 2H), 2.73 (s, 2H), 2.69 (s, 3H), 1.96 (d, 3H), 0.92 (s, 6H); MS (EI) for C$_{27}$H$_{26}$N$_6$O: 453 (MH$^+$).

7-(2-methyl-1H-imidazo[4,5-b]pyridin-6-yl)-4-(6,6,7,8-tetramethyl-5,6-dihydroquinazolin-4-yl)-2,3,4,5-tetrahydro-1,4-benzoxazepine. Synthesized according to the method of example 6 using 4-chloro-6,6,7,8-tetramethyl-5,6-dihydroquinazoline (reagent preparation 3) in step 3. $^1$H NMR (400 MHz, d$_6$-DMSO): 8.69 (s, 1H), 8.53 (s, 1H), 8.24 (s, 1H), 7.77 (d, 1H), 7.61 (dd, 1H), 7.06 (d, 1H), 4.86 (s, 2H), 4.42 (m, 2H), 4.00 (br s, 2H), 2.71 (s, 2H), 2.66 (s, 3H), 1.97 (s, 3H), 1.87 (s, 3H), 0.88 (s, 6H); MS (EI) for C$_{28}$H$_{30}$N$_6$O: 467 (MH$^+$).

N,N-dimethyl-1-{4-[7-(2-methyl-1H-imidazo[4,5-b]pyridin-6-yl)-2,3-dihydro-1,4-benzoxazepin-4(5H)-yl]-7-(methyloxy)quinazolin-2-yl}methanamine. Synthesized according to the method of example 6 using 1-(4-chloro-7-methoxyquinazolin-2-yl)-N,N-dimethylmethanamine (reagent preparation 20) in step 3. $^1$H NMR (400 MHz, d$_6$-DMSO): 8.59-8.50 (br d, 1H), 8.11-7.98 (br d, 1H), 7.94 (d, 1H), 7.76 (d, 1H), 7.53 (dd, 1H), 7.16 (d, 1H), 7.08 (dd, 1H), 6.99 (d, 1H), 5.06 (s, 2H), 4.46 (s, 2H), 4.21 (m, 2H), 3.89 (s, 3H), 3.45 (s, 2H), 2.52 (s, 3H), 2.13 (s, 6H), 1.91 (s, 2H); MS (EI) for C$_{28}$H$_{29}$N$_7$O$_2$: 496 (MH$^+$).

1-{6-fluoro-4-[7-(2-methyl-1H-imidazo[4,5-b]pyridin-6-yl)-2,3-dihydro-1,4-benzoxazepin-4(5H)-yl]quinazolin-2-yl}-N,N-dimethylmethanamine. Synthesized according to the method of example 6 using 1-(4-chloro-6-fluoroquinazolin-2-yl)-N,N-dimethylmethanamine (reagent preparation 20) in step 3. $^1$H NMR (400 MHz, d$_6$-DMSO): 8.63-8.54 (br d, 1H), 8.15-8.03 (br d, 1H), 7.90-7.75 (m, 4H), 7.58 (dd, 1H), 7.02 (d, 1H), 5.16 (s, 1H), 4.54 (br m, 2H), 4.27 (br m, 2H), 4.00 (br s, 2H), 3.34 (s, 6H), 2.54 (s, 3H); MS (EI) for C$_{27}$H$_{26}$FN$_7$O: 484 (MH$^+$).

4-{2-[(3,3-difluoropyrrolidin-1-yl)methyl]-6,6-dimethyl-5,6,7,8-tetrahydroquinazolin-4-yl}-7-(2-methyl-1H-imidazo[4,5-b]pyridin-6-yl)-2,3,4,5-tetrahydro-1,4-benzoxazepine. Synthesized according to the method of example 6 using 2-((3,3-difluoropyrrolidin-1-yl)methyl)-4,6,6-trimethyl-5,6,7,8-tetrahydroquinazoline (reagent preparation 17) in step 3. $^1$H NMR (400 MHz, d$_6$-DMSO): 8.88 (d, 1H), 8.44 (d, 1H), 7.99 (s, 1H), 7.67 (dd, 1H), 7.05 (d, 1H), 5.08 (s, 1H), 4.49 (br m, 2H), 4.15 (br m, 2H), 4.10 (br s, 2H), 3.24 (br t, 2H), 3.10 (br m, 2), 2.81 (m, 4H), 2.54 (s, 2H), 2.31-2.23 (m, 2H), 1.59 (t, 2H), 0.87 (s, 6H); MS (EI) for C$_{31}$H$_{35}$F$_2$N$_7$O: 560 (MH$^+$).

4'-[7-(2-methyl-3H-imidazo[4,5-b]pyridin-6-yl)-2,3-dihydro-1,4-benzoxazepin-4(5H)-yl]-7',8'-dihydro-5'H-spiro[cyclopropane-1,6'-quinazoline]. The dihydrochloride salt was prepared as in example 6 using 4'-chloro-7',8'-dihydro-5'H-spiro[cyclopropane-1,6'-quinazoline] (reagent example 3) in step 3. $^1$H NMR (400 MHz, CD$_3$OD) δ 8.87 (d, 1H), 8.53 (s, 1H), 8.41 (d, 1H), 7.80 (d, 1H), 7.61 (dd, 1H), 7.11 (d, 1H), 5.19 (s, 2H), 4.48 (t, 2H), 4.31 (t, 2H), 2.93 (t, 2H), 2.91 (s, 3H), 2.72 (bs, 2H), 1.75 (t, 3H), 0.52-0.34 (m, 4H); MS (ES) for C$_{26}$H$_{26}$N$_6$O: 439.2 (MH$^+$).

4-(7,7-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine. The dihydrochloride was prepared as in example 6 using 4-chloro-7,7-dimethyl-5,6,7,8-tetrahydroquinazoline (reagent preparation 3) in step 3. $^1$H NMR (400 MHz, CD$_3$OD) δ 8.85 (t, 1H), 8.54 (s, 1H), 8.41 (t, 1H), 7.82 (d, 1H), 7.66-7.55 (m, 1H), 7.12 (d, 1H), 5.25 (s, 2H), 4.54-4.46 (m, 2H), 4.45-4.37 (m, 2H), 2.91 (s, 3H), 2.88 (t, 2H), 2.60 (s, 2H), 1.60 (t, 2H), 1.10 (s, 6H); MS (ES) for C$_{26}$H$_{28}$N$_6$O: 441.2 (MH$^+$).

7-(2-methyl-1H-imidazo[4,5-b]pyridin-6-yl)-4-(6-methyl-5,6,7,8-tetrahydroquinazolin-4-yl)-2,3,4,5-tetrahydro-1,4-benzoxazepine. The dihydrochloride salt was prepared as in example 6 using 4-chloro-6-methyl-5,6,7,8-tetrahydroquinazoline (reagent preparation 3) in step 3. $^1$H NMR (400 MHz, CD$_3$OD) δ 8.87 (d, 1H), 8.53 (s, 1H), 8.43 (d, 1H), 7.81 (d, 1H), 7.61 (dd, 1H), 7.10 (d, 1H), 5.20 (dd, 2H), 4.70-4.47 (m, 2H), 4.42-4.10 (m, 2H), 2.91 (s, 3H), 2.94-2.86 (m, 2H), 2.71-2.58 (m, 2H), 2.02-1.91 (m, 1H), 1.74-1.48 (m, 2H), 1.08 (d, 3H) MS (ES) for C$_{25}$H$_{26}$N$_6$O: 427.2 (MH$^+$).

4-(6-ethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine. The dihydrochloride was prepared as in example 6 using 4-chloro-6-ethyl-5,6,7,8-tetrahydroquinazoline (reagent preparation 3) in step 3. $^1$H NMR (400 MHz, CD$_3$OD) δ 8.86 (d, 1H), 8.54 (s, 1H), 8.41 (d, 1H), 7.81 (d, 1H), 7.62 (dd, 1H), 7.12 (d, 1H), 5.19 (q, 2H), 4.70-4.48 (m, 2H), 4.27 (dd, 2H), 2.91 (s, 3H), 2.97-2.76 (m, 2H), 2.72-2.53 (m, 2H), 2.01 (dd, 1H), 1.62-1.46 (m, 1H), 1.46-1.32 (m, 3H), 0.83 (t, 3H); MS (ES) for C$_{26}$H$_{28}$N$_6$O: 441.2 (MH$^+$).

7-(2-methyl-1H-imidazo[4,5-b]pyridin-6-yl)-4-(7-methyl-5,6,7,8-tetrahydroquinazolin-4-yl)-2,3,4,5-tetrahydro-1,4-benzoxazepine. Prepared as in example 6 using 4-chloro-7-methyl-5,6,7,8-tetrahydroquinazoline (reagent preparation 3) in step 3. $^1$H NMR (400 MHz, CD$_3$OD) δ 8.48 (d, 1H), 8.31 (s, 1H), 8.02 (d, 1H), 7.57 (d, 1H), 7.48 (dd, 1H), 7.07 (d, 1H), 4.86-4.72 (m, 2H), 4.48-4.22 (m, 2H), 4.10-3.91 (m, 2H), 2.95-2.81 (m, 2H), 2.64 (s, 3H), 2.68-2.55 (m, 1H), 2.30 (dd, 1H), 2.05-1.86 (m, 2H), 1.29-1.13 (m, 1H), 1.09 (d, 3H); MS (ES) for C$_{25}$H$_{26}$N$_6$O: 427.2 (MH$^+$).

4-(6,6-difluoro-5,6,7,8-tetrahydroquinazolin-4-yl)-7-(2-methyl-1H-imidazo[4,5-b]pyridin-6-yl)-2,3,4,5-tetrahydro-1,4-benzoxazepine. The dihydrochloride salt was prepared as in example 6 using 4-chloro-6,6-difluoro-5,6,7,8-tetrahydroquinazoline (reagent preparation 3) in step 3. $^1$H NMR (400 MHz, CD$_3$OD) δ 8.86 (d, 1H), 8.60 (s, 1H), 8.40 (d, 1H), 7.81 (d, 1H), 7.62 (dd, 1H), 7.11 (d, 1H), 5.20 (s, 2H), 4.54 (t, 2H), 4.34 (t, 2H), 3.46 (t, 2H), 3.10 (t, 2H), 2.90 (s, 3H), 2.50-2.34 (m, 2H). MS (ES) for C$_{24}$H$_{22}$F$_2$N$_6$O: 449.3 (MH$^+$).

7-(2-methyl-1H-imidazo[4,5-b]pyridin-6-yl)-4-[(7R)-7-methyl-5,6,7,8-tetrahydroquinazolin-4-yl]-2,3,4,5-tetrahydro-1,4-benzoxazepine. The dihydrochloride salt was prepared as in example 6 using (R)-4-chloro-7-methyl-5,6,7,8-tetrahydroquinazoline (reagent preparation 3) in step 3. $^1$H NMR (400 MHz, CD$_3$OD) δ 8.85 (d, 1H), 8.52 (s, 1H), 8.40 (d, 1H), 7.80 (d, 1H), 7.61 (dd, 1H), 7.11 (d, 1H), 5.26 (d, 1H), 5.17 (d, 1H), 4.64-4.42 (m, 2H), 4.42-4.17 (m, 2H), 3.10-2.83 (m, 2H), 2.90 (s, 3H), 2.74 (d, 1H), 2.40 (dd, 1H), 2.14-1.87 (m, 2H), 1.35-1.21 (m, 1H), 1.12 (d, 3H); MS (ES) for C$_{25}$H$_{26}$N$_6$O: 427.2 (MH$^+$).

4-(2,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine. The dihydrochloride salt was prepare as in example 6 using 4-chloro-2,6-dimethyl-5,6,7,8-tetrahydroquinazoline (reagent preparation 3) in step 3. $^1$H NMR (400 MHz, CD$_3$OD) δ 8.84 (s, 1H), 8.37 (s, 1H), 7.82 (s, 1H), 7.61 (d, 1H), 7.11 (d, 1H), 5.21 (d, 1H), 5.10 (d, 1H), 4.66-4.42 (m, 2H), 4.40-3.99 (m, 2H), 2.88 (s, 3H), 2.95-2.72 (m, 2H), 2.72-2.37 (m, 2H), 2.50 (s, 3H), 1.98-1.88 (m, 1H), 1.74-1.60 (m, 1H), 1.58-1.43 (m, 1H), 1.07 (d, 3H); MS (ES) for C$_{26}$H$_{28}$N$_6$O: 441.2 (MH$^+$).

4-(6-ethyl-2-methyl-5,6,7,8-tetrahydroquinazolin-4-yl)-7-(2-methyl-1H-imidazo[4,5-b]pyridin-6-yl)-2,3,4,5-tetrahydro-1,4-benzoxazepine. The dihydrochloride salt was prepared as in example 6 using 4-chloro-6-ethyl-2-methyl-5,6,7,8-tetrahydroquinazoline (reagent preparation 3) in step 3. $^1$H NMR (400 MHz, CD$_3$OD) δ 8.82 (d, 1H), 8.35 (d, 1H), 7.80 (d, 1H), 7.61 (dd, 1H), 7.12 (d, 1H), 5.19 (d, 1H), 5.11 (d, 1H), 4.68-4.46 (m, 2H), 4.44-4.01 (m, 2H), 2.87 (s, 3H), 2.96-2.71 (m, 2H), 2.69-2.42 (m, 2H), 2.51 (s, 3H), 2.01 (d, 1H), 1.59-1.30 (m, 4H), 0.82 (s, 3H); MS (ES) for C$_{27}$H$_{30}$N$_6$O: 455.3 (MH$^+$).

7-(2-methyl-1H-imidazo[4,5-b]pyridin-6-yl)-4-[7-(trifluoromethyl)-5,6,7,8-tetrahydroquinazolin-4-yl]-2,3,4,5-tetrahydro-1,4-benzoxazepine. The dihydrochloride was prepared as in example 6 using 4-chloro-7-(trifluoromethyl)-5,6,7,8-tetrahydroquinazoline (reagent preparation 3) in step 3. $^1$H NMR (400 MHz, CD$_3$OD) δ 8.86 (d, 1H), 8.57 (s, 1H), 8.42 (d, 1H), 7.82 (d, 1H), 7.61 (dd, 1H), 7.11 (d, 1H), 5.28 (d, 1H), 5.19 (d, 1H), 4.68-4.44 (m, 2H), 4.44-4.15 (m, 2H), 3.22-3.01 (m, 2H), 2.89 (s, 3H), 2.98-2.73 (m, 3H), 2.25 (d, 1H), 1.66-1.47 (m, 1H); MS (ES) for C$_{25}$H$_{23}$F$_3$N$_6$O: 481.2 (MH$^+$).

4-[trans-6,7-dimethyl-5,6,7,8-tetrahydroquinazolin-4-yl]-7-(2-methyl-1H-imidazo[4,5-b]pyridin-6-yl)-2,3,4,5-tetrahydro-1,4-benzoxazepine. The dihydrochloride salt was prepared as in example 6 using trans-4-chloro-6,7-dimethyl-5,6,7,8-tetrahydroquinazoline (reagent preparation 3) in step 3. $^1$H NMR (400 MHz, CD$_3$OD) δ 8.86 (s, 1H), 8.53 (s, 1H), 8.43 (s, 1H), 7.82 (s, 1H), 7.62 (d, 1H), 7.11 (d, 1H), 5.24 (s, 2H), 4.49 (s, 2H), 4.45-4.24 (m, 2H), 3.03-2.78 (m, 2H), 2.91 (s, 3H), 2.70-2.44 (m, 2H), 2.20-1.90 (m, 2H), 1.02 (d, 3H), 0.89 (d, 3H); MS (ES) for C$_{26}$H$_{28}$N$_6$O: 441.2 (MH$^+$).

7-(2-methyl-1H-imidazo[4,5-b]pyridin-6-yl)-4-[(7S)-7-methyl-5,6,7,8-tetrahydroquinazolin-4-yl]-2,3,4,5-tetrahydro-1,4-benzoxazepine. The dihydrochloride salt was prepared as in example 6 using (S)-4-chloro-7-methyl-5,6,7,8-tetrahydroquinazoline, (reagent preparation 3) in step 3. $^1$H NMR (400 MHz, CD$_3$OD) δ 8.84 (s, 1H), 8.52 (d, 1H), 8.39 (s, 1H), 7.79 (s, 1H), 7.60 (d, 1H), 7.11 (d, 1H), 5.27 (d, 1H), 5.18 (d, 1H), 4.65-4.43 (m, 2H), 4.32 (dd, 2H), 3.11-2.83 (m, 2H), 2.90 (s, 3H), 2.75 (d, 1H), 2.41 (dd, 1H), 2.10-1.89 (m, 2H), 1.36-1.22 (m, 1H), 1.12 (d, 3H); MS (ES) for C$_{25}$H$_{26}$N$_6$O: 427.2 (MH$^+$).

7-(2-methyl-1H-imidazo[4,5-b]pyridin-6-yl)-4-[5-(trifluoromethyl)-5,6,7,8-tetrahydroquinazolin-4-yl]-2,3,4,5-tetrahydro-1,4-benzoxazepine. The dihydrochloride salt was prepared as in example 6 using 4-chloro-5-(trifluoromethyl)-5,6,7,8-tetrahydroquinazoline (reagent preparation 3) in step 3. $^1$H NMR (400 MHz, CD$_3$OD) δ 8.86 (d, 1H), 8.51 (s, 1H), 8.40 (d, 1H), 7.81 (d, 1H), 7.60 (dd, 1H), 7.05 (d, 1H), 5.39 (d, 1H), 5.28 (d, 1H), 4.86-4.74 (m, 1H), 4.55-4.39 (m, 1H), 4.38-4.03 (m, 3H), 3.06-2.64 (m, 2H), 2.89 (s, 3H), 2.41-2.13 (m, 2H), 2.13-1.81 (m, 2H); MS (ES) for C$_{25}$H$_{23}$F$_3$N$_6$O: 481.2 (MH$^+$).

7-(2-cyclopropyl-1H-imidazo[4,5-b]pyridin-6-yl)-4-[(7S)-7-methyl-5,6,7,8-tetrahydroquinazolin-4-yl]-2,3,4,5-tetrahydro-1,4-benzoxazepine. The dihydrochloride salt was prepared as in example 6 using isobutyl 6-bromo-2-cyclopropyl-1H-imidazo[4,5-b]pyridine-1-carboxylate (reagent preparation 19) in step 1 and (S)-4-chloro-7-methyl-5,6,7,8-tetrahydroquinazoline (reagent preparation 3) in step 3. $^1$H NMR (400 MHz, CD$_3$OD) δ 8.78 (d, 1H), 8.52 (s, 1H), 8.39 (d, 1H), 7.80 (d, 1H), 7.60 (dd, 1H), 7.11 (d, 1H), 5.25 (d, 1H), 5.17 (d, 1H), 4.64-4.43 (m, 2H), 4.42-4.18 (m, 2H), 3.15-2.85 (m, 2H), 2.74 (d, 1H), 2.54-2.33 (m, 2H), 2.10-1.90 (m, 2H), 1.61-1.40 (m, 4H), 1.37-1.20 (m, 1H), 1.12 (d, 3H); MS (ES) for C$_{27}$H$_{28}$N$_6$O: 453.4 (MH$^+$).

7-(2-methyl-1H-imidazo[4,5-b]pyridin-6-yl)-4-(7-methyl-7H-pyrrolo[2,3-d]pyrimidin-4-yl)-2,3,4,5-tetrahydro-1,4-benzoxazepine. The dihydrochloride salt was prepared as in example 6 using 4-chloro-7-methyl-7H-pyrrolo[2,3-d]pyrimidine in step 3. $^1$H NMR (400 MHz, CD$_3$OD) δ 8.84 (s, 1H), 8.47 (s, 1H), 8.40 (s, 1H), 8.04-7.77 (m, 1H), 7.65-7.23 (m, 2H), 7.20-6.97 (m, 2H), 5.43 (s, 2H), 4.66-4.37 (m, 4H), 4.00 (s, 3H), 2.91 (s, 3H); MS (ES) for C$_{23}$H$_{21}$N$_7$O: 412.3 (MH$^+$).

{4-[7-(2-methyl-1H-imidazo[4,5-b]pyridin-6-yl)-2,3-dihydro-1,4-benzoxazepin-4(5H)-yl]-5,6,7,8-tetrahydroquinazolin-7-yl}methanol. Prepared as in example 6 using 4-chloro-7-methyl-7H-pyrrolo[2,3-d]pyrimidine (reagent preparation 42) in step 3. $^1$H NMR (400 MHz, d$_6$-DMSO) δ 8.50 (bs, 1H), 8.35 (s, 1H), 8.04 (bs, 1H), 7.69 (d, 1H), 7.54 (dd, 1H), 7.05 (d, 1H), 4.80-4.57 (m, 3H), 4.47-4.19 (m, 2H), 3.96-3.78 (m, 2H), 2.94-2.63 (m, 3H), 2.54 (s, 3H), 2.40-2.25 (m, 2H), 1.92 (bs, 2H), 1.20-1.00 (m, 1H); MS (ES) for C$_{25}$H$_{26}$N$_6$O$_2$: 443.4 (MH$^+$).

1-{4-[7-(2-methyl-1H-imidazo[4,5-b]pyridin-6-yl)-2,3-dihydro-1,4-benzoxazepin-4(5H)-yl]-5,6,7,8-tetrahydroquinazolin-7-yl}ethanol. The dihydrochloride salt was prepared as in example 6 using 1-(4-chloro-5,6,7,8-tetrahydroquinazolin-7-yl)ethanol (reagent preparation 43) in step 3. $^1$H NMR (400 MHz, CD$_3$OD) δ 8.62 (s, 1H), 8.42 (s, 1H), 8.17 (s, 1H), 7.68 (s, 1H), 7.48 (dd, 1H), 7.00 (d, 1H), 5.15 (d, 1H), 5.06 (d, 1H), 4.57-4.32 (m, 2H), 4.30-4.05 (m, 2H), 3.67-3.53 (m, 1H), 2.99-2.42 (m, 4H), 2.70 (s, 3H), 2.18-1.62 (m, 2H), 1.38-1.03 (m, 4H); MS (ES) for C$_{26}$H$_{28}$N$_6$O$_2$: 457.4 (MH$^+$).

7-(2-methyl-1H-imidazo[4,5-b]pyridin-6-yl)-4-{7-[(methyloxy)methyl]-5,6,7,8-tetrahydroquinazolin-4-yl}-2,3,4,5-tetrahydro-1,4-benzoxazepine. The dihydrochloride salt was prepared as in example 6 using 4-chloro-7-(methoxymethyl)-5,6,7,8-tetrahydroquinazoline (reagent preparation 44) in step 3. $^1$H NMR (400 MHz, CD$_3$OD) δ 8.74 (s, 1H), 8.53 (s, 1H), 8.31 (s, 1H), 7.77 (s, 1H), 7.58 (d, 1H), 7.10 (d, 1H), 5.24 (d, 1H), 5.16 (d, 1H), 4.64-4.41 (m, 2H), 4.41-4.17 (m, 2H), 3.46-3.33 (m, 2H), 3.35 (s, 3H), 2.82 (s, 3H), 3.09-2.49 (m, 4H), 2.29-2.11 (m, 1H), 2.07-1.96 (m, 1H), 1.42-1.28 (m, 1H); MS (ES) for C$_{26}$H$_{28}$N$_6$O$_2$: 457.4 (MH$^+$).

4-(8,8-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine. The dihydrochloride salt was prepared as in example 6 using 4-chloro-8,8-dimethyl-5,6,7,8-tetrahydroquinazoline (reagent preparation 3) in step 3. $^1$H NMR (400 MHz, CD$_3$OD) δ 8.74 (d, 1H), 8.52 (s, 1H), 8.30 (d, 1H), 7.77 (d, 1H), 7.58 (dd, 1H), 7.09 (d, 1H), 5.20 (s, 2H), 4.53-4.41 (m, 2H), 4.38-4.24 (m, 2H), 2.83 (s, 3H), 2.87-2.74 (m, 2H), 1.88-1.63 (m, 4H), 1.38 (s, 6H); MS (ES) for C$_{26}$H$_{28}$N$_6$O: 441.2 (MH$^+$).

7-(2-methyl-1H-imidazo[4,5-b]pyridin-6-yl)-4-(6,6,7-trimethyl-5,6-dihydroquinazolin-4-yl)-2,3,4,5-tetrahydro-1,4-benzoxazepine. The dihydrochloride salt was prepared as in example 6 using 4-chloro-6,6,7-trimethyl-5,6-dihydroquinazoline (reagent preparation 3) in step 3. $^1$H NMR (400 MHz, d$_6$-DMSO) δ 8.80 (s, 1H), 8.66 (s, 1H), 8.36 (s, 1H), 7.86 (s, 1H), 7.66 (d, 1H), 7.06 (d, 1H), 6.24 (s, 1H), 5.10 (s, 2H), 4.50 (bs, 2H), 4.17 (bs, 2H), 2.84 (s, 2H), 2.75 (s, 3H), 1.97 (s, 3H), 0.96 (s, 6H); MS (ES) for $C_{27}H_{28}N_6O$: 453.2 (MH$^+$).

4-[(8S)-8-ethenyl-6,7,8,9-tetrahydro-5H-cyclohepta[d] pyrimidin-4-yl]-7-(2-methyl-1H-imidazo[4,5-b]pyridin-6-yl)-2,3,4,5-tetrahydro-1,4-benzoxazepine. The dihydrochloride salt was prepared as in example 6 using (S)-4-chloro-8-vinyl-6,7,8,9-tetrahydro-5H-cyclohepta[d]pyrimidine (reagent preparation 3) in step 3. $^1$H NMR (400 MHz, CD$_3$OD) δ 8.75 (d, 1H), 8.47 (s, 1H), 8.29 (d, 1H), 7.73 (d, 1H), 7.58 (dd, 1H), 7.08 (d, 1H), 5.87 (ddd, 1H), 5.23-5.00 (m, 4H), 4.51 (t, 2H), 4.28-3.97 (m, 2H), 3.13-2.71 (m, 4H), 2.82 (s, 3H), 2.53-2.38 (m, 1H), 2.16-1.93 (m, 2H), 1.84-1.48 (m, 2H); MS (ES) for $C_{27}H_{28}N_6O$: 453.2 (MH$^+$).

4-[(8S)-8-ethyl-6,7,8,9-tetrahydro-5H-cyclohepta[d]pyrimidin-4-yl]-7-(2-methyl-1H-imidazo[4,5-b]pyridin-6-yl)-2,3,4,5-tetrahydro-1,4-benzoxazepine. The dihydrochloride salt was prepared as in example 6 using (S)-4-chloro-8-vinyl-6,7,8,9-tetrahydro-5H-cyclohepta[d]pyrimidine (reagent preparation 3) in step 3, followed by hydrogenation. $^1$H NMR (400 MHz, CD$_3$OD) δ 8.77 (d, 1H), 8.47 (s, 1H), 8.32 (d, 1H), 7.74 (d, 1H), 7.59 (dd, 1H), 7.08 (d, 1H), 5.18-5.04 (m, 2H), 4.51 (t, 2H), 4.25-4.05 (m, 2H), 2.97-2.67 (m, 2H), 2.84 (s, 3H), 2.12-1.86 (m, 2H), 1.69-1.52 (m, 3H), 1.47-1.33 (m, 2H), 0.98 (t, 3H); MS (ES) for $C_{27}H_{30}N_6O$: 455.2 (MH$^+$).

1-{(7S)-7-ethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N,N-dimethylmethanamine. Prepared as in example 6 using (S)-1-(4-chloro-7-ethyl-5,6,7,8-tetrahydroquinazolin-2-yl)-N,N-dimethylmethanamine, (reagent preparation 17) in step 3. $^1$H NMR (400 MHz, d$_6$-DMSO) δ 12.33 (m, 1H), 8.48 (d, 1H), 7.96 (d, 1H), 7.63 (d, 1H), 7.47 (dd, 1H), 7.01 (d, 1H), 4.71 (s, 2H), 4.34 (dd, 2H), 4.04-3.78 (m, 2H), 3.34 (s, 2H), 2.81 (dd, 2H), 2.64-2.50 (m, 4H), 2.27 (dd, 1H), 2.17 (d, 6H), 1.88 (d, 1H), 1.70 (s, 1H), 1.45-1.06 (m, 3H), 0.94 (t, 3H); MS (ES) for $C_{29}H_{35}N_7O$: 498.2 (MH$^+$).

4-(2-{[(3R)-3-fluoropyrrolidin-1-yl]methyl}-6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine. The trihydrochloride salt was prepared as in example 6 using (R)-4-chloro-2-((3-fluoropyrrolidin-1-yl)methyl)-6,6-dimethyl-5,6,7,8-tetrahydroquinazoline (reagent preparation 17) in step 3. $^1$H NMR (400 MHz, CD$_3$OD) δ 8.94 (s, 1H), 8.52 (s, 1H), 8.00 (s, 1H), 7.69 (d, 1H), 7.13 (d, 1H), 5.40-5.21 (m, 3H), 4.77-4.64 (m, 2H), 4.64-4.55 (m, 2H), 4.42-4.27 (m, 2H), 3.63 (s, 4H), 2.90 (s, 3H), 2.94-2.81 (m, 2H), 2.61 (s, 2H), 2.23 (s, 2H), 1.72 (t, 2H), 0.93 (d, 6H); MS (ES) for $C_{31}H_{36}FN_7O$: 542.4 (MH$^+$).

4-(2-{[(3R)-3-fluoropyrrolidin-1-yl]methyl}-6,6-dimethyl-5,6,7,8-tetrahydroquinazolin-4-yl)-7-(2-methyl-1H-benzimidazol-6-yl)-2,3,4,5-tetrahydro-1,4-benzoxazepine. The trihydrochloride salt was prepared as in example 6 using (S)-4-chloro-2-((3-fluoropyrrolidin-1-yl)methyl)-6,6-dimethyl-5,6,7,8-tetrahydroquinazoline (reagent preparation 17) in step 3. $^1$H NMR (400 MHz, d$_6$-DMSO) δ 8.95 (d, 1H), 8.53 (d, 1H), 8.17 (s, 1H), 7.71 (dd, 1H), 7.07 (d, 1H), 5.37-5.03 (m, 3H), 4.63-4.52 (m, 2H), 4.52-4.46 (m, 2H), 4.16 (bs, 2H), 3.73-3.22 (m, 4H), 2.82 (s, 3H), 2.79 (t, 2H), 2.55 (s, 2H), 2.25-2.01 (m, 2H), 1.60 (t, 2H), 0.87 (d, 6H); MS (ES) for $C_{31}H_{36}FN_7O$: 542.4 (MH$^+$).

4-(6,6-dimethyl-2-pyridin-2-yl-5,6,7,8-tetrahydroquinazolin-4-yl)-7-(2-methyl-1H-imidazo[4,5-b]pyridin-6-yl)-2,3,4,5-tetrahydro-1,4-benzoxazepine. The trihydrochloride salt was prepared as in example 6 using 4-chloro-6,6-dimethyl-2-(pyridin-2-yl)-5,6,7,8-tetrahydroquinazoline (reagent preparation 17) in step 3. $^1$H NMR (400 MHz, d$_6$-DMSO) δ 8.90 (s, 1H), 8.81 (d, 1H), 8.54 (d, 1H), 8.48 (s, 1H), 8.25 (s, 1H), 8.07 (t, 1H), 7.71 (dd, 1H), 7.66 (dd, 1H), 7.01 (d, 1H), 5.31 (s, 2H), 4.59 (bs, 2H), 4.33 (bs, 2H), 2.95 (t, 2H), 2.87 (s, 3H), 2.66 (s, 2H), 1.62 (t, 2H), 0.93 (s, 6H); MS (ES) for $C_{31}H_{31}N_7O$: 518.3 (MH$^+$).

7-(2-methyl-1H-imidazo[4,5-b]pyridin-6-yl)-4-(5-methylpyrimidin-4-yl)-2,3,4,5-tetrahydro-1,4-benzoxazepine. Synthesized according to the method of example 6 using 4-chloro-5-methylpyrimidine in step 3. $^1$H NMR (400 MHz, d$_6$-DMSO): 8.89 (d, 1H), 8.80 (s, 1H), 8.45 (d, 1H), 8.28 (s, 1), 7.91 (d, 1H), 7.69 (dd, 1H), 7.10 (d, 1H), 5.27 (s, 2H), 4.50 (m, 2H), 4.33 (m, 2H), 2.84 (s, 3H), 2.43 (s, 3H), 1.76 (s, 3H); MS (EI) for $C_{21}H_{20}N_6O$: 373 (MH$^+$).

4-[2,6-dimethyl-5-(1-methylethyl)pyrimidin-4-yl]-7-(2-methyl-1H-imidazo[4,5-b]pyridin-6-yl)-2,3,4,5-tetrahydro-1,4-benzoxazepine. Synthesized according to the method of example 6 using 4-chloro-5-isopropyl-2,6-dimethylpyrimidine (reagent preparation 8) in step 3. $^1$H NMR (400 MHz, d$_6$-DMSO): 8.74 (s, 1H), 8.29 (s, 1H), 7.82 (s, 1H), 7.63 (dd, 1H), 7.30 (s, 1H), 7.17 (s, 1H), 7.04 (s, 1H), 5.06 (s, 2H), 4.50 (m, 2H), 4.03 (m, 2H), 3.08 (m, 1H) 2.71 (s, 3H), 2.54 (s, 3H), 2.41 (s, 3H), 1.32 (d, 6H); MS (EI) for $C_{25}H_{28}N_6O$: 429 (MH$^+$).

7-(2-methyl-1H-imidazo[4,5-b]pyridin-6-yl)-4-[6-methyl-5-(1-methylethyl)pyrimidin-4-yl]-2,3,4,5-tetrahydro-1,4-benzoxazepine. Synthesized according to the method of example 6 using 4-chloro-5-isopropyl-6-methylpyrimidine (reagent preparation 5) in step 3. $^1$H NMR (400 MHz, d$_6$-DMSO): 8.81 (s, 1H), 8.64 (s, 1H), 8.36 (s, 1H), 7.65 (d, 1H), 7.03 (d, 1H), 5.04 (s, 2H), 4.53 (s, 2H), 4.02 (s, 2H), 3.11 (m, 1H), 2.76 (s, 3H), 2.56 (s, 3H), 1.34 (d, 6H); MS (EI) for $C_{24}H_{26}N_6O$: 415 (MH$^+$).

7-(2-methyl-1H-imidazo[4,5-b]pyridin-6-yl)-4-(7-methyl-7-phenyl-5,6,7,8-tetrahydroquinazolin-4-yl)-2,3,4,5-tetrahydro-1,4-benzoxazepine. Synthesized according to the method of example 6 using 4-chloro-7-methyl-7-phenyl-5,6,7,8-tetrahydroquinazoline (reagent preparation 3) in step 3. $^1$H NMR (400 MHz, d$_6$-DMSO): 8.49 (s, 1H), 8.37 (s, 1H), 7.92 (d, 1H), 7.48 (d, 1H), 7.31 (s, 1H), 7.29 (s, 1H), 7.22 (d, 1H), 7.13 (m, 2H), 7.02 (m, 1H), 6.94-6.80 (m, 1H), 4.42-4.56 (m, 2H), 4.32 (m, 2H), 3.94 (d, 1H), 3.76 (m, 1H), 3.14 (d, 1H), 2.81 (d, 1H), 2.68 (d, 1H), 2.55 (d, 3H), 2.55 (d, 1H), 2.29 (m, 1H), 2.09 (m, 1H), 1.84 (m, 1H), 1.32 (s, 3H); MS (EI) for $C_{31}H_{30}N_6O$: 503 (MH$^+$).

N,N,2-trimethyl-4-[7-(2-methyl-1H-imidazo[4,5-b]pyridin-6-yl)-2,3-dihydro-1,4-benzoxazepin-4(5H)-yl]pyrimidine-5-sulfonamide. Synthesized according to the method of example 6 using 4-chloro-N,N,2-trimethylpyrimidine-5-sulfonamide in step 3. $^1$H NMR (400 MHz, d$_6$-DMSO): 8.51 (s, 1H), 8.03 (s, 1H), 7.94 (s, 1H), 7.52 (dd, 1H) 7.04 (d, 1H), 6.71 (d, 1H), 5.05 (s, 2H), 4.31 (d, 2H), 4.24 (d, 2H), 2.84 (s, 6H), 2.54 (s, 3H), 2.40 (s, 3H); MS (EI) for $C_{23}H_{25}N_7O_3S$: 480 (MH$^+$).

7-(2-methyl-1H-imidazo[4,5-b]pyridin-6-yl)-4-[2-methyl-5-(morpholin-4-ylsulfonyl)pyrimidin-4-yl]-2,3,4,5-tetrahydro-1,4-benzoxazepine. Synthesized according to the method of example 6 using 4-(4-chloro-2-methylpyrimidin-5-ylsulfonyl)morpholine in step 3. $^1$H NMR (400 MHz, d$_6$-DMSO): 8.58 (s, 1H), 8.50 (d, 1H), 8.03 (d, 1H), 7.81 (s, 1H), 7.53 (d, 1H), 7.03 (d, 1H), 5.04 (s, 2H), 4.29 (s, 2H), 3.61 (s, 2H), 3.12 (s, 2H), 2.42 (s, 3H); MS (EI) for $C_{25}H_{27}N_7O_4S$: 522 (MH$^+$).

7-(2-cyclopropyl-1H-imidazo[4,5-b]pyridin-6-yl)-4-(6,6-dimethyl-5,6-dihydroquinazolin-4-yl)-2,3,4,5-tetrahydro-1,4-benzoxazepine. Synthesized according to the method of example 6 using isobutyl 6-bromo-2-cyclopropyl-1H-imidazo[4,5-b]pyridine-1-carboxylate (reagent preparation 19)

in step 1 and 4-chloro-6,6-dimethyl-5,6-dihydroquinazoline (reagent preparation 3) in step 3. $^1$H NMR (400 MHz, d$_6$-DMSO): 8.64 (s, 1H), 8.61 (s, 1H), 8.14 (m, 1H), 7.77 (d 1H), 7.59 (dd, 1H), 7.04 (d, 1H), 6.47 (d, 1H), 6.34 (d, 1H), 5.00 (s, 2H), 4.46 (m, 2H), 4.11 (s, 2H), 2.83 (s, 2H), 2.24 (m, 1H), 1.24-1.18 (m, 5H), 0.99 (s, 6H); MS (EI) for C$_{28}$H$_{28}$N$_6$O: 465 (MH$^+$).

4-(6,6-dimethyl-5,6-dihydroquinazolin-4-yl)-7-(2-methyl-1H-imidazo[4,5-b]pyridin-6-yl)-2,3,4,5-tetrahydro-1,4-benzoxazepine. Synthesized according to the method of example 6 using 4-chloro-6,6-dimethyl-5,6-dihydroquinazoline (reagent preparation 3) in step 3. $^1$H NMR (400 MHz, d$_6$-DMSO): 8.64 (s, 1H), 8.59 (s, 1H), 8.18 (s, 1H), 7.77 (d, 1H), 7.60 (dd, 1H), 7.05 (d, 1H), 6.43 (d, 1H), 6.32 (d, 1H), 4.94 (s, 2H), 4.43 (m, 2H), 4.06 (br s, 2H), 2.82 (s, 2H), 2.62 (s, 3H), 0.99 (s, 6H); MS (EI) for C$_{26}$H$_{26}$N$_6$O: 439 (MH$^+$).

7-(2-methyl-1H-imidazo[4,5-b]pyridin-6-yl)-4-(6,6,8-trimethyl-5,6-dihydroquinazolin-4-yl)-2,3,4,5-tetrahydro-1,4-benzoxazepine. Synthesized according to the method of example 6 using 4-chloro-6,6,8-trimethyl-5,6-dihydroquinazoline (reagent preparation 3) in step 3. $^1$H NMR (400 MHz, d$_6$-DMSO): 8.74 (d, 1H), 8.54 (s, 1H), 8.30 (d, 1H), 7.77 (d, 1H), 7.61 (dd, 1H), 7.05 (d, 1H), 6.09 (s, 1H), 4.82 (s, 2H), 4.42 (m, 2H), 3.96 (br s, 2H), 2.73 (s, 2H), 2.69 (s, 3H), 1.96 (d, 3H), 0.92 (s, 6H); MS (EI) for C$_{27}$H$_{28}$N$_6$O: 453 (MH$^+$).

7-(2-methyl-1H-imidazo[4,5-b]pyridin-6-yl)-4-(6,6,7,8-tetramethyl-5,6-dihydroquinazolin-4-yl)-2,3,4,5-tetrahydro-1,4-benzoxazepine. Synthesized according to the method of example 6 using 4-chloro-6,6,7,8-tetramethyl-5,6-dihydroquinazoline (reagent preparation 3) in step 3. $^1$H NMR (400 MHz, d$_6$-DMSO): 8.69 (s, 1H), 8.53 (s, 1H), 8.24 (s, 1H), 7.77 (d, 1H), 7.61 (dd, 1H), 7.06 (d, 1H), 4.86 (s, 2H), 4.42 (m, 2H), 4.00 (br s, 2H), 2.71 (s, 2H), 2.66 (s, 3H), 1.97 (s, 3H), 1.87 (s, 3H), 0.88 (s, 6H); MS (EI) for C$_{28}$H$_{30}$N$_6$O: 467 (MH$^+$).

N,N-dimethyl-1-{4-[7-(2-methyl-1H-imidazo[4,5-b]pyridin-6-yl)-2,3-dihydro-1,4-benzoxazepin-4(5H)-yl]-7-(methyloxy)quinazolin-2-yl}methanamine. Synthesized according to the method of example 6 using 1-(4-chloro-7-methoxyquinazolin-2-yl)-N,N-dimethylmethanamine (reagent preparation 20) in step 3. $^1$H NMR (400 MHz, d$_6$-DMSO): 8.59-8.50 (br d, 1H), 8.11-7.98 (br d, 1H), 7.94 (d, 1H), 7.76 (d, 1H), 7.53 (dd, 1H), 7.16 (d, 1H), 7.08 (dd, 1H), 6.99 (d, 1H), 5.06 (s, 2H), 4.46 (s, 2H), 4.21 (m, 2H), 3.89 (s, 3H), 3.45 (s, 2H), 2.52 (s, 3H), 2.13 (s, 6H), 1.91 (s, 2H); MS (EI) for C$_{28}$H$_{29}$N$_7$O$_2$: 496 (MH$^+$).

1-{6-fluoro-4-[7-(2-methyl-1H-imidazo[4,5-b]pyridin-6-yl)-2,3-dihydro-1,4-benzoxazepin-4(5H)-yl]quinazolin-2-yl}-N,N-dimethylmethanamine. Synthesized according to the method of example 6 using 1-(4-chloro-6-fluoroquinazolin-2-yl)-N,N-dimethylmethanamine (reagent preparation 20) in step 3. $^1$H NMR (400 MHz, d$_6$-DMSO): 8.63-8.54 (br d, 1H), 8.15-8.03 (br d, 1H), 7.90-7.75 (m, 4H), 7.58 (dd, 1H), 7.02 (d, 1H), 5.16 (s, 1H), 4.54 (br m, 2H), 4.27 (br m, 2H), 4.00 (br s, 2H), 3.34 (s, 2H), 2.54 (s, 3H); MS (EI) for C$_{27}$H$_{26}$FN$_7$O: 484 (MH$^+$).

4-{2-[(3,3-difluoropyrrolidin-1-yl)methyl]-6,6-dimethyl-5,6,7,8-tetrahydroquinazolin-4-yl}-7-(2-methyl-1H-imidazo[4,5-b]pyridin-6-yl)-2,3,4,5-tetrahydro-1,4-benzoxazepine. Synthesized according to the method of example 6 using 2-(3,3-difluoropyrrolidin-1-yl)methyl)-4,6,6-trimethyl-5,6,7,8-tetrahydroquinazoline (reagent preparation 17) in step 3. $^1$H NMR (400 MHz, d$_6$-DMSO): 8.88 (d, 1H), 8.44 (d, 1H), 7.99 (s, 1H), 7.67 (dd, 1H), 7.05 (d, 1H), 5.08 (s, 1H), 4.49 (br m, 2H), 4.15 (br m, 2H), 4.10 (br s, 2H), 3.24 (br t, 2H), 3.10 (br m, 2), 2.81 (m, 4H), 2.54 (s, 2H), 2.31-2.23 (m, 2H), 1.59 (t, 2H), 0.87 (s, 6H); MS (EI) for C$_{31}$H$_{35}$F$_2$N$_7$O: 560 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylethanamine. Prepared according to the method of example 6 by using N-((4-chloro-6,6-dimethyl-5,6,7,8-tetrahydroquinazolin-2-yl)methyl)-N-methylethanamine (reagent preparation 17) in step 3. $^1$H NMR (400 MHz, DMSO-d$_6$): 12.70 (d, 1H), 8.53 (d, 1H), 8.02 (d, 1H), 7.71 (d, 1H), 7.55-7.50 (m, 1H), 7.03 (d, 1H), 4.64 (s, 2H), 4.31 (m, 2H), 3.86 (m, 2H), 3.44 (s, 2H), 2.68 (t, 2H), 2.54 (s, 3H), 2.45 (s, 2H), 2.38 (q, 2H), 2.13 (s, 3H), 1.59 (t, 2H), 0.91 (t, 3H), 0.85 (s, 6H); MS (EI) for C$_{30}$H$_{37}$N$_7$O: 512 (MH$^+$).

4-[6,6-dimethyl-2-(piperidin-1-ylmethyl)-5,6,7,8-tetrahydroquinazolin-4-yl]-7-(2-methyl-1H-imidazo[4,5-b]pyridin-6-yl)-2,3,4,5-tetrahydro-1,4-benzoxazepine. Prepared according to the method of example 6 by using 4-chloro-6,6-dimethyl-2-(piperidin-1-ylmethyl)-5,6,7,8-tetrahydroquinazoline (reagent preparation 17) in step 3. $^1$H NMR (400 MHz, (DMSO-d$_6$): 12.70 (d, 1H), 8.52 (m, 1H), 8.00 (m, 1H), 7.70 (d, 1H), 7.54-7.50 (m, 1H), 7.02 (m, 1H), 4.66 (s, 2H), 4.33 (m, 2H), 3.87 (m, 2H), 2.68 (t, 2H), 2.56 (s, 2H), 2.46 (s, 2H), 2.33 (m, 4H), 1.59 (t, 2H), 1.38 (m, 4H), 1.26 (m, 2H). 0.86 (s, 6H); MS (EI) for C$_{32}$H$_{39}$N$_7$O: 538 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylpropan-2-amine. Prepared according to the method of example 6 by using N-((4-chloro-6,6-dimethyl-5,6,7,8-tetrahydroquinazolin-2-yl)methyl)-N-methylpropan-2-amine (reagent preparation 17) in step 3. $^1$H NMR (400 MHz, DMSO-d$_6$): 12.68 (d, 1H), 8.52 (m, 1H), 8.01 (m, 1H), 7.71 (d, 1H), 7.55-7.50 (m, 1H), 7.03 (m, 1H), 4.65 (s, 2H), 4.31 (m, 2H), 3.86 (m, 2H), 2.69 (t, 2H), 2.56 (s, 2H), 2.45 (s, 2H), 2.11 (m, 3H), 1.59 (t, 2H), 1.23 (m, 2H), 0.91-0.84 (m, 12H); MS (EI) for C$_{31}$H$_{39}$N$_7$O: 526 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylcyclopropanamine. Prepared according to the method of example 6 by using N-((4-chloro-6,6-dimethyl-5,6,7,8-tetrahydroquinazolin-2-yl)methyl)-N-methylcyclopropanamine (reagent preparation 17) in step 3. $^1$H NMR (400 MHz, Methanol-d$_4$): 8.48 (s, 1H), 8.01 (s, 1H), 7.58 (d, 1H), 7.46-7.41 (m, 1H), 7.02 (d, 1H), 4.73 (s, 2H), 4.31 (t, 2H), 3.96 (t, 2H), 3.62 (s, 2H), 2.75 (t, 2H), 2.61 (s, 3H), 2.46 (s, 2H), 2.30 (s, 3H), 1.83-1.76 (m, 1H), 1.64 (t, 2H), 0.89 (s, 6H), 0.32-0.23 (m, 4H); MS (EI) for C$_{31}$H$_{37}$N$_7$O: 524 (MH$^+$).

N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)propan-2-amine. Prepared according to the method of example 6 by using benzyl (4-chloro-6,6-dimethyl-5,6,7,8-tetrahydroquinazolin-2-yl)methyl(isopropyl)carbamate (reagent preparation 17) in step 3 and Cbz group removal. $^1$H NMR (400 MHz, DMSO-d$_6$): 12.7 (d, 1H), 8.60-8.46 (m, 1H), 8.11-7.94 (m, 1H), 7.72 (s, 1H), 7.54 (d, 1H), 7.03 (d, 1H), 4.68 (s, 2H), 4.32 (m, 2H), 3.89 (m, 2H), 3.65 (s, 2H), 2.69 (t, 2H), 2.53 (m, 1H), 2.46 (s, 2H), 1.59 (t, 2H), 1.23 (s, 1H), 0.92 (d, 6H), 0.86 (s, 6H); MS (EI) for C$_{30}$H$_{37}$N$_7$O: 512 (MH$^+$).

1-{5-[(4-fluorophenyl)methyl]-4-methyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine. Synthesized according to the method of example 6 using 1-(4-chloro-5-(4-fluorobenzyl)-6-methylpyrimidin-2- yl)-N,N-dimethylmethanamine (reagent preparation 17) in step 3. $^1$H NMR (400 MHZ, CD$_3$OD): 8.38 (d, 1H), 7.92 (d, 1H), 7.44 (dd, 1H), 7.09 (dd, 2H), 7.03-6.95 (m, 3H), 6.92 (d, 1H), 4.60 (s, 2H), 4.28 (tr, 2H), 4.01 (s, 2H), 3.92 (tr, 2H), 3.54 (s, 2H), 2.66 (s, 3H), 2.30 (s, 6H), 2.21 (s, 3H). MS (EI) for C$_{31}$H$_{32}$N$_7$OF: 538 (MH$^+$).

N,N-dimethyl-1-{4-methyl-5-(1-methylethyl)-6-[7-(2-methyl-3H-imidazo[4,5-b]pyridin-6-yl)-2,3-dihydro-1,4-benzoxazepin-4(5H)-yl]pyrimidin-2-yl}methanamine. Synthesized according to the method of example 6 using 1-(4-chloro-5-isopropyl-6-methylpyrimidin-2-yl)-N,N-dimethylmethanamine (reagent preparation 17) in step 3. $^1$H NMR (400 MHZ, CDCl$_3$): 12.78 (br, 1H), 8.51 (s, 1H), 8.08 (br, 1H), 7.46 (d, 1H), 7.43 (s, 1H), 7.14 (d, 1H), 4.37 (s, 2H), 4.30 (tr, 2H), 3.76 (tr, 2H), 3.55 (s, 2H), 3.40 (m, 1H), 2.75 (s, 3H), 2.55 (s, 3H), 2.34 (s, 6H), 1.35 (d, 6H). MS (EI) for C$_{28}$H$_{34}$N$_7$O: 472 (MH$^+$). 7-(2-methyl-3H-imidazo[4,5-b]pyridin-6-yl)-4-[2-methyl-7-(methyloxy)quinazolin-4-yl]-2,3,4,5-tetrahydro-1,4-benzoxazepine. Synthesized according to the method of example 6 using 4-chloro-7-methoxy-2-methylquinazoline in step 3. $^1$H NMR (400 MHz, DMSO-d$_6$) δ 8.53 (s, 1H), 8.06 (s, 1H), 7.90 (d, 1H), 7.74 (d, 1H), 7.56 (dd, 1H), 7.11 (d, 1H), 7.03 (m, 3H), 5.02 (s, 3H), 4.41 (t, 3H), 4.11 (d, J=36.2 Hz, 3H), 3.88 (s, 5H), 2.55 (s, 5H), 2.43 (s, 5H), 1.90 (s, 1H); MS (EI) for C$_{26}$H$_{24}$N$_6$O$_2$: 453.3 (MH$^+$).

{4-[7-(2-amino[1,3]thiazolo[5,4-b]pyridin-6-yl)-2,3-dihydro-1,4-benzoxazepin-4(5H)-yl]-6,6-dimethyl-5,6,7,8-tetrahydroquinazolin-2-yl}methanol. The dihydrochloride salt was prepared as in example 6 using (4-chloro-6,6-dimethyl-5,6,7,8-tetrahydroquinazolin-2-yl)methyl acetate (reagent preparation 17) in step 3 and acetate ester hydrolysis. $^1$H NMR (400 MHz, CD$_3$OD) δ 8.66 (d, 1H), 8.02 (d, 1H), 7.79 (d, 1H), 7.57 (dd, 1H), 7.09 (d, 1H), 5.14 (s, 2H), 4.62 (s, 2H), 4.52-4.39 (m, 2H), 4.37-4.25 (m, 2H), 2.88 (t, 2H), 2.58 (s, 2H), 1.69 (t, 2H), 0.94 (s, 6H); MS (ES) for C$_{26}$H$_{28}$N$_6$O$_2$S: 498.2 (MH$^+$).

7-(2-methyl-1H-imidazo[4,5-b]pyridin-6-yl)-4-[6-methyl-5-(1-methylpropyl)pyrimidin-4-yl]-2,3,4,5-tetrahydro-1,4-benzoxazepine. Prepared according to the method of example 6 by using 4-chloro-6-methylpyrimidine in step 3. $^1$H NMR (400 MHz, methanol-d$_4$): 8.52 (s, 1H), 8.06 (s, 1H), 8.01 (d, 1H), 7.76 (d, 1H), 7.49 (dd, 1H), 7.10 (d, 1H), 6.74 (d, H), 4.24 (br. s, 2H), 4.19 (m, 2H), 2.64 (s, 3H), 2.42 (s, 3H); MS (EI) for C$_{21}$H$_{20}$N$_6$O: 373 (MH$^+$).

Example 7

7-(1-Methyl-1H-indazol-5-yl)-4-quinolin-4-yl-2,3,4,5-tetrahydro-1,4-benzoxazepine STEP 1: A solution of 7-bromo-2,3,4,5-tetrahydro-1,4-benzoxazepine hydrochloride (1.50 g, 5.67 mmol) (example 2, step 1), 4-chloroquinoline (0.973 g, 5.95 mmol), diisopropylethylamine (2.93 g, 22.7 mmol) in 1-butanol (15 mL) was stirred at 170° C. for 1 hour in a microwave synthesizer. The reaction mixture was diluted with ethyl acetate (100 mL), washed with saturated sodium bicarbonate (50 mL) and brine (50 mL), dried over sodium sulfate. Filtration and concentration afforded a crude brown oil that was purified by silica gel chromatography (9:1 dichloromethane/methanol) to provide 7-bromo-4-quinolin-4-yl-2,3,4,5-tetrahydro-1,4-benzoxazepine (1.70 g, 84.6% yield) as a yellow oil. MS (EI) for C$_{18}$H$_{15}$BrN$_2$O: 356 (MH$^+$).

STEP 2: A mixture of 7-bromo-4-quinolin-4-yl-2,3,4,5-tetrahydro-1,4-benzoxazepine (206 mg, 0.58 mmol), 5-(4,4,5,5-tetramethyl-1,3,2-dioxaborolan-2-yl)-1-methyl-1H-indazole (158 mg (0.58 mmol) (reagent preparation 50), potassium carbonate (320 mg, 2.32 mmol), and dichloro[1,1-bis(diphenylphosphino)ferrocenepalladium (II) dichloromethane adduct (50 mg, 0.06 mmol) in dimethoxyethane (4.0 mL) and water (1.0 mL) was degassed with nitrogen, and then stirred at 100° C. for 1 h. The reaction mixture was cooled to room temperature and partitioned between water and ethyl acetate. The mixture was filtered through celite and then the layers were separated. The organic layer was washed with brine, dried over anhydrous sodium sulfate, filtered and concentrated. Column chromatography on silica ((2S)-100% ethyl acetate in hexanes) afforded the title Compound (23 mg, 10% yield) as a yellow solid. $^1$H NMR (400 MHz, DMSO-d$_6$): 8.63 d, 1H), 8.11 (s, 1H), 8.03 (m, 2H), 7.95 (d, 1H), 7.75 (m, 3H), 7.70 (m, 1H), 7.61 (dd, 1H), 7.51 (m, 1H), 7.11 (d, 1H), 7.02 (d, 1H), 4.61 (s, 2H), 4.39 (m, 2H), 4.09 (s, 3H), 3.84 (m, 2H); MS (EI) for C$_{26}$H$_{22}$N$_4$O: 407 (MH$^+$).

Using analogous synthetic techniques and substituting with alternative starting reagents in steps 1 or 2 the following compounds of the invention were prepared. Alternative starting materials were obtained commercially unless otherwise indicated.

7-(1H-indazol-5-yl)-4-quinolin-4-yl-2,3,4,5-tetrahydro-1,4-benzoxazepine. Prepared according to the method of example 7 by using 5-(4,4,5,5-tetramethyl-1,3,2-dioxaborolan-2-yl)-1H-imidazole in step 2. $^1$H NMR (400 MHz, methanol-d$_4$): 8.41 (s, 1H), 8.38 (d, 1H), 8.34 (d, 1H), 8.14 (s, 1H), 7.97 (m, 1H), 7.90 (m, 2H), 7.83 (d, 1H), 7.73 (d, 1H), 7.69 (m, 1H), 7.62 (dd, 1H), 7.07 (m, 2H), 5.28 (s, 2H), 4.63 (m, 2H), 4.44 (m, 2H); MS (EI) for C$_{25}$H$_{20}$N$_4$O: 393 (MH$^+$).

7-(1H-indazol-6-yl)-4-quinolin-4-yl-2,3,4,5-tetrahydro-1,4-benzoxazepine. Prepared as the trifluoroacetate salt according to the method of example 7 by using tert-butyl 6-(4,4,5,5-tetramethyl-1,3,2-dioxaborolan-2-yl)-1H-indazole-1-carboxylate in step 2. $^1$H NMR (400 MHz, d$_6$-DMSO): 13.18 (br. s, 1H), 8.56 (d, 1H), 8.33 (d, 1H), 8.12 (s, 1H), 8.03-7.92 (m, 3H), 7.87 (d, 1H), 7.79 (s, 1H), 7.72-7.62 (m, 2H), 7.50 (d, 1H), 7.02-6.96 (m, 2H), 5.31 (s, 2H), 4.63 (t, 2H), 4.42 (t, 2H); MS (EI) for C$_{25}$H$_{20}$N$_4$O: 393 (MH$^+$).

7-(1H-pyrazol-4-yl)-4-quinolin-4-yl-2,3,4,5-tetrahydro-1,4-benzoxazepine. Prepared as the trifluoroacetate salt according to the method of example 7 by using 4-(4,4,5,5-tetramethyl-1,3,2-dioxaborolan-2-yl)-1H-pyrazole in step 2. $^1$H NMR (400 MHz, d$_6$-DMSO): 8.57 (d, 1H), 8.31 (d, 1H), 8.08-7.92 (m, 4H), 7.83 (s, 1H), 7.68 (t, 1H), 7.47 (d, 1H), 6.94 (d, 1H), 6.89 (d, 1H), 5.20 (s, 2H), 4.56 (t, 2H), 4.38 (t, 2H); MS (EI) for C$_{21}$H$_{18}$N$_4$O: 343 (MH$^+$).

7-(2,3-dihydro-1-benzofuran-5-yl)-4-quinolin-4-yl-2,3,4,5-tetrahydro-1,4-benzoxazepine. Prepared as trifluoroacetate salt according to the method of example 7 by using 2,3-dihydro-1-benzofuran-1-ylboronic acid in step 2. $^1$H NMR (400 MHz, methanol-d$_4$): 8.37 (d, 1H), 8.32 (d, 1H), 7.97 (m, 1H), 7.89 (d, 1H), 7.67 (m, 2H), 7.51 (s, 1H), 7.46 (dd, 1H), 7.37 (d, 1H), 7.05 (d, 1H), 6.98 (d, 1H), 6.80 (d, 1H), 5.22 (s, 2H), 4.59 (m, 4H), 4.41 (m, 2H), 3.26 (m, 2H); MS (EI) for C$_{26}$H$_{22}$N$_2$O$_2$: 395 (MH$^+$).

7-(1-methyl-1H-indol-5-yl)-4-quinolin-4-yl-2,3,4,5-tetrahydro-1,4-benzoxazepine. Prepared according to the method of example 7 by using 1-methyl-1H-indol-5-ylboronic acid in step 2. $^1$H NMR (400 MHz, DMSO-d$_6$): 8.57 (d, 1H), 8.34 (d, 1H), 7.96 (m, 4H), 7.88 (s, 1H), 7.69 (m, 1H), 7.55 (m, 3H), 7.38 (m, 1H), 6.98 (m, 2H), 6.50 (m, 1H), 5.29 (s, 2H), 4.60 (m, 2H), 4.42 (m, 2H), 3.84 (s, 3H); MS (EI) for C$_{27}$H$_{23}$N$_3$O: 406 (MH$^+$).

N,N-dimethyl-3-(4-quinolin-4-yl-2,3,4,5-tetrahydro-1,4-benzoxazepin-7-yl)benzamide. Prepared as the trifluoroacetate salt according to the method of example 7 by 3-(dimethylcarbamoyl)phenylboronic acid in step 2. $^1$H NMR (400

MHz, DMSO-d$_6$): 8.56 (d, 1H), 8.34 (d, 1H), 8.01 (m, 1H), 7.98 (d, 1H), 7.94 (m, 1H), 7.80 (d, 1H), 7.76 (m, 1H), 7.68 (m, 1H), 7.62 (dd, 1H), 7.55 (m, 1H), 7.39 (d, 1H), 6.97 (m, 2H), 5.30 (s, 2H), 4.63 (m, 2H), 4.43 (m, 2H), 3.03 (s, 3H), 2.98 (s, 3H); MS (EI) for C$_{27}$H$_{25}$N$_3$O$_2$: 424 (MH$^+$).

4-quinolin-4-yl-7-quinoxalin-6-yl-2,3,4,5-tetrahydro-1,4-benzoxazepine. Prepared as the trifluoroacetate salt according to the method of example 7 by using quinoxalin-6-ylboronic acid in step 2. $^1$H NMR (400 MHz, d$_6$-DMSO): 8.99 (d, 2H), 8.57 (d, 1H), 8.46 (s, 1H), 8.37-8.29 (m, 2H), 8.27-8.20 (m, 2H), 8.01-7.92 (m, 2H), 7.84 (d, 1H), 7.69 (t, 1H), 7.06 (d, 1H), 7.01 (d, 1H), 5.35 (s, 2H), 4.67 (t, 2H), 4.45 (t, 2H); MS (EI) for C$_{26}$H$_{20}$N$_4$O: 405 (MH$^+$).

N-(4-{4-[2-methyl-7-(methyloxy)quinazolin-4-yl]-2,3,4,5-tetrahydro-1,4-benzoxazepin-7-yl}phenyl)acetamide. Synthesized according to the method of example 7 using 4-chloro-7-methoxy-2-methylquinazoline in step 1 and 4-acetamidophenylboronic acid in step 2. $^1$H NMR (400 MHz, DMSO-d$_6$): 10.0 (s, 1H), 7.99 (s, 2H), 7.89 (d, 1H), 7.60 (s, 1H), 7.50 (dd, 1H), 7.40 (t, 1H), 7.31 (m, 1H), 7.11 (m, 2H), 7.03 (d, 1H), 4.97 (s, 2H), 4.44 (s, 2H), 4.15 (s, 2H), 3.88 (s, 3H), 2.42 (s, 3H); MS (EI) for C$_{27}$H$_{26}$N$_4$O$_3$: 455.2 (MH$^+$).

1-methyl-3-(4-{4-[2-methyl-7-(methyloxy)quinazolin-4-yl]-2,3,4,5-tetrahydro-1,4-benzoxazepin-7-yl}phenyl)urea. Prepared according to the method of example 7 by using 4-chloro-7-methoxy-2-methylquinazoline in step 1 and 1-methyl-3-(4-(4,4,5,5-tetramethyl-1,3,2-dioxaborolan-2-yl)phenyl)urea in step 2. $^1$H NMR (400 MHz, DMSO-D6); δ 8.62 (s, 1H), 7.89 (d, 1H), 7.64-7.36 (m, 6H), 7.24-6.95 (m, 3H), 6.11-6.03 (m, 1H), 4.99 (s, 2H), 4.47-4.37 (m, 2H), 4.18-4.09 (m, 2H), 3.88 (s, 3H), 2.70-2.60 (m, 3H), 2.43 (s, 3H); MS (EI) for C$_{27}$H$_{27}$N$_5$O$_3$: 470 (MH$^+$).

5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)pyridin-2-amine. Prepared according to the method of example 7 by using 1-(4-chloro-6,6-dimethyl-5,6,7,8-tetrahydroquinazolin-2-yl)-N,N-dimethylmethanamine (reagent preparation 17) in step 1 and 5-(4,4,5,5-tetramethyl-1,3,2-dioxaborolan-2-yl)pyridin-2-amine in step 2. $^1$H NMR (400 MHz, DMSO-d$_6$): 8.22 (d, 1H), 7.68-7.63 (m, 1H), 7.55 (d, 1H), 7.39-7.32 (m, 1H), 6.96 (d, 1H), 6.50 (d, 1H), 6.02 (s, 2H), 4.58 (s, 2H), 4.26 (m, 2H), 3.85 (m, 2H), 3.39 (m, 2H), 2.69 (m, 2H), 2.44 (s, 2H), 2.17 (s, 6H), 1.59 (t, 2H), 0.85 (s, 6H); MS (EI) for C$_{27}$H$_{34}$N$_6$O: 459 (MH$^+$).

2-chloro-5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)benzamide. Prepared according to the method of example 7 by using 1-(4-chloro-6,6-dimethyl-5,6,7,8-tetrahydroquinazolin-2-yl)-N,N-dimethylmethanamine (reagent preparation 17) in step 1 and 2-chloro-5-(4,4,5,5-tetramethyl-1,3,2-dioxaborolan-2-yl)benzamide in step 2. $^1$H NMR (400 MHz, DMSO-d$_6$): 7.95 (s, 1H), 7.73-7.64 (m, 4H), 7.57-7.49 (m, 2H), 7.01 (d, 1H), 4.64 (s, 2H), 4.31 (m, 2H), 3.86 (m, 2H), 3.38 (m, 2H), 2.69 (t, 2H), 2.43 (s, 2H), 2.14 (s, 6H), 1.59 (t, 2H), 0.85 (s, 6H); MS (EI) for C$_{29}$H$_{34}$ClN$_5$O$_2$: 520 (MH$^+$).

3-(4-{2-[(dimethylamino)methyl]-6,6-dimethyl-5,6,7,8-tetrahydroquinazolin-4-yl}-2,3,4,5-tetrahydro-1,4-benzoxazepin-7-yl)benzamide. Prepared according to the method of example 7 by using 1-(4-chloro-6,6-dimethyl-5,6,7,8-tetrahydroquinazolin-2-yl)-N,N-dimethylmethanamine (reagent preparation 17) in step 1 and 3-(4,4,5,5-tetramethyl-1,3,2-dioxaborolan-2-yl)benzamide in step 2. $^1$H NMR (400 MHz, DMSO-d$_6$): 8.14 (m, 1H), 8.08 (m, 1H), 7.84-7.71 (m, 3H), 7.58-7.49 (m, 2H), 7.44 (m, 1H), 7.03 (d, 1H), 4.65 (s, 2H), 4.32 (m, 2H), 3.87 (m, 2H), 2.69 (t, 2H), 2.44 (s, 2H), 2.15 (s, 6H), 1.59 (t, 2H), 0.85 (s, 6H); MS (EI) for C$_{29}$H$_{35}$N$_5$O$_2$: 486 (MH$^+$).

1-(4-{7-[4-chloro-3-(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine. Prepared according to the method of example 7 by using 1-(4-chloro-6,6-dimethyl-5,6,7,8-tetrahydroquinazolin-2-yl)-N,N-dimethylmethanamine (reagent preparation 17) in step 1 and 2-(4-chloro-3-methoxyphenyl)-4,4,5,5-tetramethyl-1,3,2-dioxaborolane in step 2. $^1$H NMR (400 MHz, Methanol-d$_4$): 7.60 (s, 1H), 7.49-7.43 (m, 1H), 7.39 (d, 1H), 7.23 (d, 1H), 7.17-7.12 (m, 1H), 7.02 (d, 1H), 4.75 (s, 2H), 4.34 (t, 2H), 4.00 (m, 2H), 3.95 (s, 3H), 3.55 (s, 2H), 2.79 (t, 2H), 2.49 (s, 2H), 2.31 (s, 6H), 1.67 (t, 2H), 0.90 (s, 6H); MS (EI) for C$_{29}$H$_{35}$ClN$_4$O$_2$: 507 (MH$^+$).

Example 8

5-(4-{5-[(4-Fluorophenyl)methyl]-6-methylpyrimidin-4-yl}-2,3,4,5-tetrahydro-1,4-benzoxazepin-7-yl)[1,3]thiazolo[5,4-b]pyridin-2-amine STEP 1: (4-{[(1,1-dimethylethyl)oxycarbonyl]-2,3,4,5-tetrahydro-1,4-benzoxazepin-7-yl)boronic acid (Example 1, step 2) (1.07 g, 3.64 mmol) was dissolved into 4M hydrogen chloride in dioxane and the resulting solution was allowed to stir at room temperature for 1.3 h. The heterogeneous mixture was then diluted with ethyl ether (100 mL) and the solid collected by filtration to give 2,3,4,5-tetrahydro-1,4-benzoxazepin-7-ylboronic acid hydrochloride salt (791 mg, 95%). $^1$H NMR (400 MHz, D$_2$O): 7.79 (dd, 1H), 7.74 (d, 1H), 7.21 (d, 1H), 4.47 (s, 2H), 4.36 (m, 2H), 3.69 (m, 2H).

STEP 2: A mixture of 2,3,4,5-tetrahydro-1,4-benzoxazepin-7-ylboronic acid hydrochloride salt (1.20 g, 5.2 mmol), 4-chloro-5-(4-fluorobenzyl)-6-methylpyrimidine (reagent preparation 5) (1.24 g, 5.2 mmol), diisopropylethylamine (0.40 mL, 2.10 mmol) 50% aqueous 1,4-dioxane (50 mL) was deoxygenated for five minutes by bubbling nitrogen gas then stirred at 95° C. for 18 hours. The reaction mixture was concentrated, diluted with water (50 mL), adjusted to pH 14, and then washed with isopropyl acetate (3×30 mL). The aqueous mixture was adjusted to pH 8 and the white solid precipitated was collected by filtration, washed with water and dried to give (4-{5-[(4-fluorophenyl)methyl]-6-methylpyrimidin-4-yl}-2,3,4,5-tetrahydro-1,4-benzoxazepin-7-yl)boronic acid (0.72 g, 35% yield). MS (EI) for C$_2$H$_{21}$BFN$_3$O$_3$: 394 (MH$^+$).

STEP 3: A solution of N-(5-bromothiazolo[5,4-b]pyridin-2-yl)benzamide (reagent preparation 13) (0.14 g, 0.42 mmol), (4-{5-[(4-fluorophenyl)methyl]-6-methylpyrimidin-4-yl}-2,3,4,5-tetrahydro-1,4-benzoxazepin-7-yl)boronic acid (0.14 g, 0.35 mmol) and diisopropyethylamine (0.40 mL, 2.10 mmol) in 10% aqueous dimethylformamide (3 mL) was deoxygenated for five minutes by bubbling nitrogen gas, followed by the addition of 1,1'-bis(diphenylphosphino)ferrocenedichloropalladium(II) complex with dichloromethane (20 mg, 0.021 mmol). The reaction mixture was heated to 105° C. for 4 hours. On cooling to room temperature the mixture was diluted with ethyl acetate (50 mL) then it was filtered through a pad of Celite. The organic filtrate was washed with 10% aqueous citric acid (20 mL), brine, aqueous saturated sodium bicarbonate (20 mL) and brine then dried over anhydrous sodium sulfate, filtered and concentrated. Silica gel chromatography (chloroform/methanol 95:5 to 9:1) provided N-[5-(4-{5-[(4-fluorophenyl)methyl]-6-methylpyrimidin-4-yl}-2,3,4,5-tetrahydro-1,4-benzoxazepin-7-yl)[1, 3]thiazolo[5,4-b]pyridin-2-yl]benzamide (86 mg. 41%). MS (EI) for $C_{34}H_{27}FN_6O_2S$: 603 (MH$^+$).

STEP 4: A solution of N-[5-(4-{5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-yl]benzamide (84 mg, 0.14 mmol) in 70% aqueous sulfuric acid (2 mL) was heated to reflux for thirty minutes. On cooling to room temperature the pH of the mixture was adjusted to ~5 by the addition of 50% aqueous sodium hydroxide. Concentration and purification by preparative reverse phase HPLC (0.1% aqueous ammonium acetate-acetonitrile) provided 5-(4-{5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine (26 mg, 37%). $^1$H NMR (400 MHz, d$_6$-DMSO): 8.44 (d, 1H), 8.36 (s, 1H), 8.08 (d, 1H), 8.01 (br s, 2H), 7.52 (dd, 1H), 7.16-7.10 (m, 4H), 7.00 (d, 1H), 6.90 (d, 1H), 4.48 (s, 2H), 4.28 (m, 2H), 3.96 (s, 2H), 3.76 (m, 2H), 2.14 (s, 3H). MS (EI) for $C_{27}H_{23}FN_6OS$: 499 (MH$^+$).

Using analogous synthetic techniques and substituting with alternative starting reagents in step 3 and conducting protecting group removal step 4 as required according to literature techniques appropriate for a given protecting group (see for example: Greene and Wuts, Protective Groups in Organic Synthetic, Wiley-Interscience) the following compounds of the invention were prepared. Alternative starting materials were obtained commercially unless otherwise indicated.

4-{5-[(4-fluorophenyl)methyl]-6-methylpyrimidin-4-yl}-7-(1H-imidazo[4,5-b]pyridin-6-yl)-2,3,4,5-tetrahydro-1,4-benzoxazepine. Synthesized according to the method of example 8 using 6-bromo-1-trityl-1H-imidazo[4,5-b]pyridine (reagent preparation 15) in step 3. 1H NMR (400 MHz, d$_6$-DMSO); 8.49 (m, 3H), 7.54 (d, 1H), 7.08 (m, 5H), 6.99 (m, 1H), 4.52 (s, 2H), 4.24 (br s, 2H), 3.96 (s, 2H), 3.77 (br s, 2H), 2.16 (s, 3H); MS (EI) for $C_{27}H_{23}FN_6O$: 467 (MH$^+$).

5-(4-{5-[(4-fluorophenyl)methyl]-6-methylpyrimidin-4-yl}-2,3,4,5-tetrahydro-1,4-benzoxazepin-7-yl)[1,3]thiazolo[4,5-b]pyridin-2-amine. Synthesized according to the method of example 8 using N-(6-bromothiazolo[4,5-b]pyridin-2-yl)benzamide (*J. of Heterocyclic Chemistry* 2003, 40(2), 261-268) in step 3. $^1$H NMR (400 MHz, d$_6$-DMSO): 8.51 (s, 1H), 8.37 (d, 1H), 8.10 (d, 1H), 8.02 (br s, 2H), 7.49 (dd, 1H), 7.13-7.08 (m, 4H), 7.02 (d, 1H), 6.88 (d, 1H), 4.50 (s, 2H), 4.29 (m, 2H), 3.98 (s, 2H), 3.78 (m, 2H), 2.16 (s, 3H). MS (EI) for $C_{27}H_{23}N_6O_2$: 499 (MH$^+$).

6-(4-{5-[(4-fluorophenyl)methyl]-6-methylpyrimidin-4-yl}-2,3,4,5-tetrahydro-1,4-benzoxazepin-7-yl)quinazolin-2-amine. Synthesized according to the method of example 8 using 6-bromoquinazolin-2-amine in step 3. MS (EI) for $C_{29}H_{25}FN_6O$: 493 (MH$^+$).

6-(4-{5-[(4-fluorophenyl)methyl]-6-methylpyrimidin-4-yl}-2,3,4,5-tetrahydro-1,4-benzoxazepin-7-yl)[1,2,4]triazolo[1,5-c]pyridin-2-amine. Prepared according to the method of example 8 by using bis(1,1-dimethylethyl)(6-bromo[1,2,4]triazolo[1,5-a]pyridine-2-yl)imidodicarbonate (reagent preparation 14) in step 3. $^1$H NMR (400 MHz, DMSO-d$_6$): 8.69 (m, 1H), 8.48 (s, 1H), 7.51 (m, 2H), 7.40 (d, 1H), 7.10 (d, 4H), 6.99 (d, 1H), 6.91 (m, 1H), 6.06 (s, 2H), 4.47 (s, 2H), 4.26 (m, 2H), 3.95 (s, 2H), 3.74 (m, 2H), 2.14 (s, 3H); MS (EI) for $C_{27}H_{24}FN_7O$: 482 (MH$^+$).

6-(4-{5-[(4-fluorophenyl)methyl]-6-methylpyrimidin-4-yl}-2,3,4,5-tetrahydro-1,4-benzoxazepin-7-yl)imidazo[1,2-c]pyridin-2-amine. Prepared according to the method of example 8 by using N-(6-bromoimidazo[1,2-a]pyridin-2-yl)-2,2,2-trifluoroacetamide (Tetrahedron Letters 2002, 43(50), 9051-9054) in step 3. $^1$H NMR (400 MHz, methanol-d$_4$): 8.47 (s, 1H), 8.25 (s, 1H), 7.41 (dd, 1H), 7.32 (d, 1H), 7.24 (dd, 1H), 7.10 (m, 2H), 7.00 (m, 3H), 6.71 (m, 1H), 4.53 (s, 2H), 4.29 (m, 2H), 3.98 (s, 2H), 3.88 (m, 2H), 2.21 (s, 3H); MS (EI) for $C_{28}H_{25}FN_6O$: 481 (MH$^+$).

5-(4-{5-[(4-fluorophenyl)methyl]-6-methylpyrimidin-4-yl}-2,3,4,5-tetrahydro-1,4-benzoxazepin-7-yl)-1,3-benzothiazol-2-amine. Prepared according to the method of example 8 by using N-(5-bromobenzo[d]thiazol-2-yl)acetamide (Journal of the Indian Chemical Society (1958), 35 807-10) in step 3. $^1$H NMR (400 MHz, methanol-d$_4$): 8.47 (s, 1H), 7.62 (d, 1H), 7.46 (d, 1H), 7.43 (dd, 1H), 7.08 (m, 3H), 6.99 (m, 3H), 6.81 (d, 1H), 4.53 (s, 2H), 4.29 (m, 2H), 4.00 (s, 2H), 3.89 (m, 2H), 2.22 (s, 3H); MS (EI) for $C_{28}H_{24}FN_5OS$: 498 (MH$^+$).

6-(4-{5-[(4-fluorophenyl)methyl]-6-methylpyrimidin-4-yl}-2,3,4,5-tetrahydro-1,4-benzoxazepin-7-yl)imidazo[1,2-a]pyrimidin-2-amine. Synthesized according to the method of example 8 using N-(6-bromoimidazo[1,2-a]pyrimidin-2-yl)-2,2,2-trifluoroacetamide (Synthesis 1999, 12, 2124-2130) in step 3. $^1$H NMR (400 DMSO-D$_6$): 8.91 (s, 1H), 8.61 (br, 1H), 8.46 (s, 1H), 8.33 (br, 1H), 7.44 (dd, 1H), 7.13 to 6.98 (m, 5H), 6.78 (br, 1H), 4.56 (s, 2H), 4.29 (m, 2H), 4.00 (s, 2H), 3.88 (m, 2H), 2.22 (s, 3H), MS (EI) for $C_{27}H_{24}FN_7O$: 482 (MH$^+$).

7-(4-{5-[(4-fluorophenyl)methyl]-6-methylpyrimidin-4-yl}-2,3,4,5-tetrahydro-1,4-benzoxazepin-7-yl)[1,2,4]triazolo[1,5-a]pyridin-2-amine. Prepared according to the method of example 8 by using N-(7-bromo-[1,2,4]triazolo[1,5-a]pyridin-2-yl)acetamide (reagent preparation 16) in step 3. $^1$H NMR (400 MHz, methanol-d$_4$): 8.47-8.42 (m, 2H), 7.55 (d, 1H), 7.40 (s, 1H), 7.12-6.99 (m, 6H), 6.91 (s, 1H), 4.58 (s, 2H), 4.32 (t, 2H), 4.00 (s, 2H), 3.89 (t, 2H), 2.22 (s, 3H); MS (EI) for $C_{27}H_{24}FN_7O$: 482 (MH$^+$).

6-(4-{5-[(4-fluorophenyl)methyl]-6-methylpyrimidin-4-yl}-2,3,4,5-tetrahydro-1,4-benzoxazepin-7-yl)-1H-imidazo[4,5-c]pyridin-2-amine. Prepared according to the method of example 8 by using methyl (6-bromo-1H-imidazo[4,5-c]pyridine-2-yl)carbamate (reagent preparation 45) in step 3. $^1$H NMR (400 MHz, methanol-d$_4$): 8.45 (s, 1H), 8.35 (s, 1H), 7.62 (m, 1H), 7.72 (m, 1H), 7.41 (s, 1H), 7.04 (m, 4H), 6.93 (m, 2H), 4.57 (s, 2H), 4.32 (m, 2H), 3.97 (s, 2H), 3.88 (m, 2H), 2.21 (s, 3H), 1.96 (s, 3H); MS (EI) for $C_{27}H_{24}FN_7O$: 482 (MH$^+$).

2-amino-5-(4-{5-[(4-fluorophenyl)methyl]-6-methylpyrimidin-4-yl}-2,3,4,5-tetrahydro-1,4-benzoxazepin-7-yl)-N-methylpyridine-3-sulfonamide. Prepared according to the method of example 8 by using 2-amino-5-bromo-N-methylpyridine-3-sulfonamide (WO 2008144463) in step 3. $^1$H NMR (400 MHz, DMSO-d$_6$): 8.48 (s, 1H), 8.36 (m, 1H), 7.93 (m, 1H), 7.71 (br. s, 1H), 7.41 (m, 1H), 7.09 (m, 4H), 7.00 (d, 1H), 6.92 (m, 1H), 6.70 (br. s, 1H), 4.50 (s, 2H), 4.26 (m, 2H), 3.96 (s, 2H), 3.75 (m, 2H), 2.45 (s, 3H), 2.15 (s, 3H); MS (EI) for $C_{27}H_{27}FN_6O_3S$: 535 (MH$^+$).

6-(4-{5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine. Synthesized according to the method of example 8 using N-(6-bromothiazolo[5,4-b]pyridin-2-yl)acetamide (J. Heterocyclic Chemistry 2003, 40, 261) in step 3. $^1$H NMR (400 MHz, d$_6$-DMSO): 8.47 (s, 1H), 8.20 (d, 1H), 7.88 (s, 2H), 7.69 (d, 1H), 7.54 (dd, 1H), 7.09 (d, 4H), 6.99 (d, 1H), 6.94 (d, 1H), 4.45 (s, 2H), 4.24 (m, 2H), 3.97 (s, 2H), 3.77 (m, 2H), 2.14 (s, 3H); MS (EI) for $C_{27}H_{23}FN_6OS$: 499 (MH$^+$).

N-ethyl-6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine. Prepared as in example 8 using 6-bromo-N-ethyl-N,3-bis(methoxymethyl)-3H-imidazo[4,5-b]pyridin-2-amine (reagent preparation 36) in step 3. ¹H NMR (400 MHz, d₆-DMSO) δ 11.04 (s, 1H), 8.49 (s, 1H), 8.04 (s, 1H), 7.89 (s, 1H), 7.52-7.35 (m, 2H), 7.10 (d, 4H), 7.00 (d, 1H), 6.91 (d, 1H), 4.48 (s, 2H), 4.26 (t, 2H), 4.00 (s, 2H), 3.77 (t, 2H), 3.33 (q, 2H), 2.16 (s, 3H), 1.20 (q, 3H); MS (ES) for $C_{29}H_{28}FN_7O$: 510.2 (MH⁺).

5-(4-{5-[(4-fluorophenyl)methyl]-6-methylpyrimidin-4-yl}-2,3,4,5-tetrahydro-1,4-benzoxazepin-7-yl)-1H-indazol-3-amine. Prepared according to example 8 using tert-butyl 3-(bis(tert-butoxycarbonyl)amino)-5-bromo-1H-indazole-1-carboxylate (reagent preparation 48) in step 1 and BOC group deprotection. ¹H NMR (400 MHz, d₆-DMSO) δ 11.44 (s, 1H), 8.50 (s, 1H), 7.86 (s, 1H), 7.42 (dd, 1H), 7.28 (s, 2H), 7.19-7.07 (m, 4H), 7.01 (d, 1H), 6.87 (s, 1H), 5.42 (s, 2H), 4.49 (s, 2H), 4.26 (t, 2H), 4.00 (s, 2H), 3.77 (t, 2H), 2.17 (s, 3H). MS (EI) for $C_{28}H_{25}FN_6O$: 481 (MH⁺).

Example 9

5-(4-{5-[(4-fluorophenyl)methyl]-6-methylpyrimidin-4-yl}-2,3,4,5-tetrahydro-1,4-benzoxazepin-7-yl)pyrazin-2-amine STEP 1: 1,1-Dimethylethyl 7-bromo-2,3-dihydro-1,4-benzoxazepine-4(5H)-carboxylate (5.0 g, 20.1 mmol), bis(pinacolato)diboron (5.6 g, 22.1 mmol), potassium acetate (5.9 g, 60.2 mmol) and [1,1'-bis(diphenylphosphino)ferrocene]dichloropalladium(II) (440 mg, 0.62 mmol) were heated in DMSO (5 mL) solution at 80 C for 1.5 h. The mixture was then cooled to room temperature and diluted with an excess of ethyl acetate and filtered through a bed of celite. The filtrate was partitioned with 1M aqueous hydrochloric acid and the organic phase washed with brine and dried over anhydrous sodium sulfate. The mixture was filtered and concentrated and the residue purified by silica chromatography using 4:1 hexanes:ethyl acetate as eluent to give 1,1-dimethylethyl 7-(4,4,5,5-tetramethyl-1,3,2-dioxaborolan-2-yl)-2,3-dihydro-1,4-benzoxazepine-4(5H)-carboxylate (7.6 g, 100%). ¹H NMR (400 MHz, CDCl₃): 7.77 (s, 0.4H), 7.67 (s, 1H), 7.65 (s, 0.6H), 7.04-6.98 (m, 1H), 4.54 (s, 0.7H), 4.43 (s, 1.3H), 4.09-4.01 (m, 2H), 3.79 (dd, 2H), 1.40 (br s, 9H), 1.26 (s, 12H). MS (EI) for $C_{20}H_{30}BNO_5$: 376 (MH⁺).

STEP 2: A solution of 1,1-dimethylethyl 7-(4,4,5,5-tetramethyl-1,3,2-dioxaborolan-2-yl)-2,3-dihydro-1,4-benzoxazepine-4(5H)-carboxylate (3.0 g, 8.00 mmol) in dichloromethane (90 mL) and trifluoroacetic acid (10 mL) was heated to reflux for 1 h, and then cooled to room temperature. The reaction mixture was concentrated and the residue was azeotroped with toluene (100 mL) to give 7-(4,4,5,5-tetramethyl-1,3,2-dioxaborolan-2-yl)-2,3-dihydro-1,4-benzoxazepine trifluoroacetate salt (2.9 g, quantitative yield). MS (EI) for $C_{15}H_{22}BNO_3$: 276 (MH⁺).

STEP 3: A mixture of 7-(4,4,5,5-tetramethyl-1,3,2-dioxaborolan-2-yl)-2,3-dihydro-1,4-benzoxazepine trifluoroacetate salt (2.9 g, 8.00 mmol, 4-chloro-5-[(4-fluorophenyl)methyl]-6-methylpyrimidine (reagent preparation 5) (1.9 g, 8.00 mmol) and N,N-diisopropylethylamine (7.0 mL, 40.0 mmol) in N-methyl-2-pyrrolidone (10 mL) was reacted in a microwave apparatus (250 W) for 2 h at 150° C. After cooling to room temperature the reaction mixture was partitioned between ethyl acetate (500 mL) and brine (100 mL). The organic layer was separated, washed with brine (100 mL), dried over sodium sulfate then filtered and concentrated. Column chromatography of the residue on silica (gradient 20 to 40% ethyl acetate in hexane) gave 4-{5-[(4-fluorophenyl)methyl]-6-methylpyrimidin-4-yl}-7-(4,4,5,5-tetramethyl-1,3,2-dioxaborolan-2-yl)-2,3,4,5-tetrahydro-1,4-benzoxazepine (1.6 g, 42% yield). ¹H NMR (400 MHz, DMSO-D₆): 8.58 (s, 1H), 7.62 (dd, 1H), 7.08 (m, 4H), 7.02 (d, 1H), 6.96 (d, 1H), 4.36 (s, 2H), 4.30 (m, 2H), 3.92 (s, 2H), 3.84 (m, 2H), 2.26 (s, 3H), 1.36 (s, 12H); MS (EI) for $C_{27}H_{31}BFN_3O_3$: 476 (MH⁺).

STEP 4: A solution of 4-{5-[(4-fluorophenyl)methyl]-6-methylpyrimidin-4-yl}-7-(4,4,5,5-tetramethyl-1,3,2-dioxaborolan-2-yl)-2,3,4,5-tetrahydro-1,4-benzoxazepine (0.10 g, 0.21 mmol), 2-amino-5-bromopyrazine (40 mg, 0.21 mmol) and potassium carbonate (0.12 g, 0.84 mmol) in N,N-dimethylformamide (5 mL), and water (0.5 mL) was degassed by bubbling nitrogen gas for five minutes followed by the addition of [1,1'-bis(diphenylphosphino)ferrocene]dichloropalladium(II) (15 mg, 0.021 mmol), then stirred at 95° C. for 16 hours. After cooling to room temperature the reaction mixture was partitioned between ethyl acetate (50 mL) and brine (30 mL). The organic layer was separated, washed with brine, dried over sodium sulfate then filtered and concentrated. Purification by preparative reverse phase HPLC (0.1% aqueous ammonium acetate-acetonitrile) provided 5-(4-{5-[(4-fluorophenyl)methyl]-6-methylpyrimidin-4-yl}-2,3,4,5-tetrahydro-1,4-benzoxazepin-7-yl)pyrazin-2-amine (18 mg, 20%). ¹H NMR (400 MHz, d₆-DMSO): 8.80 (s, 1H), 8.38 (s, 1H), 7.96 (s, 1H), 7.72 (d, 1H), 7.50 (br s, 1H), 7.25-7.14 (m, 4H), 6.93 (d, 1H), 4.90 (s, 2H), 4.32 (m, 2H), 4.00 (m, 4H), 2.22 (s, 3H). MS (EI) for $C_{25}H_{23}FN_6O$: 443 (MH⁺).

Using analogous synthetic techniques and substituting with alternative starting reagents in steps 3 or 4 the following compounds of the invention were prepared. Alternative starting materials were obtained commercially unless otherwise indicated.

6-(4-{5-[(4-fluorophenyl)methyl]-6-methylpyrimidin-4-yl}-2,3,4,5-tetrahydro-1,4-benzoxazepin-7-yl)pyridazin-3-amine. Synthesized according to the method of example 9 using 6-bromopyridazin-3-amine in step 4. ¹H NMR (400 MHz, d₆-DMSO): 8.46 (s, 1H), 7.74 (dd, 1H), 7.54 (d, 1H), 7.28 (d, 1H), 7.18-7.06 (m, 4H), 6.98 (d, 1H), 6.82 (d, 1H), 6.47 (s, 2H), 4.51 (s, 2H), 4.29) m, 2H), 3.95 (s, 2H), 3.75 (m, 2H), 2.16 (s, 3H). MS (EI) for $C_{25}H_{23}FN_6O$: 463 (MH⁺).

5-(4-{5-[(4-fluorophenyl)methyl]-6-methylpyrimidin-4-yl}-2,3,4,5-tetrahydro-1,4-benzoxazepin-7-yl)pyrimidin-2-amine. Synthesized according to the method of example 9 using 5-bromopyrimidin-2-amine in step 4. ¹H NMR (400 MHz, DMSO-D₆): 8.49 (s, 1H), 8.37 (s, 2H), 7.42 (d, 1H), 7.09 (d, 4h), 6.98 (d, 1H), 6.76-6.83 (m, 3H), 4.46 (s, 2H), 4.25-4.27 (m, 2H), 3.96 (s, 2H), 3.74-3.76 (m, 2H), 2.15 (s; 3H); MS (EI) for $C_{25}H_{23}FN_6O$: 443 (MH⁺).

6-(4-{5-[(4-fluorophenyl)methyl]-6-methylpyrimidin-4-yl}-2,3,4,5-tetrahydro-1,4-benzoxazepin-7-yl)-N-methylpyridine-3-carboxamide. Synthesized according to the method of example 9 using 6-bromo-N-methylnicotinamide in step 4. ¹H NMR (400 MHz, DMSO-D₆): 9.05 (s, 1H), 8.65-8.72 (m, 2H), 8.47 (s, 1H), 8.23 (dd, 1h), 7.95 (dd, 1H), 7.83 (d, 1H), 7.45 (s, 1H), 7.02-7.18 (m, 5H), 4.54 (s, 2H), 4.31-4.38 (m, 2H), 3.94 (s, 2H), 3.75-3.81 (m, 2H), 2.84 (s, 3H), 2.15 (s; 3H); MS (EI) for $C_{28}H_{26}FN_5O_2$: 484 (MH⁺).

4-{5-[(4-fluorophenyl)methyl]-6-methylpyrimidin-4-yl}-7-(1,3-thiazol-5-yl)-2,3,4,5-tetrahydro-1,4-benzoxazepine. Synthesized according to the method of example 9 using 5-bromothiazole in step 4. ¹H NMR (400 MHz, d₆-DMSO): 9.05 (s, 1H), 8.48 (s, 1H), 8.08 (s, 1H), 7.51 (dd, 1H), 7.18-7.06 (m, 4H), 6.99 (d, 1H), 6.90 (d, 1H), 4.49 (s, 2H), 4.29 (m, 2H), 3.92 (s, 2H), 3.72 (m 2H), 2.14 (s, 3H). MS (EI) for $C_{24}H_{21}FN_4OS$: 433 (MH⁺).

4-(7,7-dimethyl-5,6,7,8-tetrahydroquinazolin-4-yl)-7-(2-methyl-1,3-thiazol-5-yl)-2,3,4,5-tetrahydro-1,4-benzoxazepine. Synthesized according to the method of example 9 using 4-chloro-7,7-dimethyl-5,6,7,8-tetrahydroquinazoline (reagent preparation 3) in step 3 and 5-bromo-2-methylthiazole in step 4. $^1$H NMR (400 MHz, d$_6$-DMSO): 8.32 (s, 1H), 7.91 (s, 1H), 7.53 (d, 1H), 7.40 (dd, 1H), 7.08 (d, 1H), 4.72 (s, 2H), 4.34 (m, 2H), 3.90 (m, 2H), 2.68 (m ands, 5H), 2.46 (s, 2H), 1.46 (t, 2H), 1.00 (6H). MS (EI) for C$_{23}$H$_{26}$N$_4$OS: 407 (MH$^+$).

5-(4-{5-[(4-fluorophenyl)methyl]-6-methylpyrimidin-4-yl}-2,3,4,5-tetrahydro-1,4-benzoxazepin-7-yl)-4-methyl-1,3-thiazol-2-amine. Synthesized according to the method of example 9 using bis(1,1-dimethylethyl)(5-bromo-4-methyl-1,3-thiazol-2-yl)imidodicarbonate (reagent preparation 14) in step 4. $^1$H NMR (400 MHz, d$_6$-DMSO): 8.46 (s, 1H), 7.13-7.02 (m, 5H), 6.94 (br s, 2H), 6.91 (s, 1H), 6.68 (d, 1H), 4.42 (s, 2H), 4.22 (m, 2H), 4.14 (s, 2H), 3.73 (m, 2H), 2.14 (s, 3H), 2.06 (s, 3H). MS (EI) for C$_{25}$H$_{24}$FN$_5$OS: 462 (MH$^+$).

5-[4-(7,7-dimethyl-5,6,7,8-tetrahydroquinazolin-4-yl)-2,3,4,5-tetrahydro-1,4-benzoxazepin-7-yl]-4-methyl-1,3-thiazol-2-amine. Synthesized according to the method of example 9 using 4-chloro-7,7-dimethyl-5,6,7,8-tetrahydroquinazoline (reagent preparation 3) in step 3 and bis(1,1-dimethylethyl)(5-bromo-4-methyl-1,3-thiazol-2-yl)imidodicarbonate (reagent preparation 14) in step 4. $^1$H NMR (400 MHz, d$_6$-DMSO): 8.34 (s, 1H), 7.24 (d, 1H), 7.11 (dd, 1H), 6.96 (d, 1H), 6.92 (s, 2H), 4.68 (s, 2H), 4.30 (m, 2H), 3.89 (m, 2H), 2.62 (t, 2H), 2.44 (s, 2H), 2.12 (s, 3H), 1.42 (t, 2H), 1.00 (s, 6H). MS (EI) for C$_{23}$H$_{27}$N$_5$OS: 422 (MH$^+$).

Example 10

N,N-dimethyl-3-({4-[7-(2-methyl-1H-benzimidazol-6-yl)-2,3-dihydro-1,4-benzoxazepin-4(5H)-yl]quinazolin-6-yl}oxy)propan-1-amine and 4-[7-(2-methyl-1H-benzimidazol-6-yl)-2,3-dihydro-1,4-benzoxazepin-4(5H)-yl]quinazolin-6-ol STEP 1; A solution of 7-(2-methyl-1H-benzimidazol-6-yl)-4-{6-[(phenylmethyl)oxy]quinazolin-4-yl}-2,3,4,5-tetrahydro-1,4-benzoxazepine (example 1) (26 mg, 0.05 mmol) in trifluoroacetic acid (3.0 mL) was heated to 68° C. for 3.5 hours then concentrated and dried. This material was then carried forward into step 2 without further purification. A sample of material obtained in this manner was purified by preparative reverse phase HPLC to give 4-[7-(2-methyl-1H-benzimidazol-6-yl)-2,3-dihydro-1,4-benzoxazepin-4(5H)-yl]quinazolin-6-ol. $^1$H NMR (400 MHz, d$_6$-DMSO): 10.1 (s, 1H), 8.44 (s, 1H), 7.73 (d, 1H), 7.70 (d, 1H), 7.65 (d, 1H), 7.55-7.51 (m, 2H), 7.48 (d, 0.5H), 7.46 (d, 0.5H), 7.40 (dd, 1H), 7.33 (d, 1H), 7.04 (d, 1H), 5.00 (s, 2H), 4.46 (t, 2H), 4.24 (t, 2H), 2.54 (s, 3H). MS (EI) for C$_{25}$H$_{22}$N$_5$O$_2$: 424 (MH$^+$).

STEP 2: 4-[7-(2-Methyl-1H-benzimidazol-6-yl)-2,3-dihydro-1,4-benzoxazepin-4(5H)-yl]quinazolin-6-ol as obtained in step 1 without purification was taken into N,N-dimethylacetamide (5.0 mL), and then combined with 3-chloro-N,N-dimethylpropan-1-amine hydrochloride (9.61 mg, 0.06 mmol) and potassium carbonate (41 mg, 0.30 mmol) and heated to 50° C. for 18 hours. The reaction mixture was concentrated and the residue purified by preparative reverse phase HPLC to give N,N-dimethyl-3-({4-[7-(2-methyl-1H-benzimidazol-6-yl)-2,3-dihydro-1,4-benzoxazepin-4(5H)-yl]quinazolin-6-yl}oxy)propan-1-amine as the trifluoroacetic acid salt (6.5 mg, 21% yield). $^1$H NMR (400 MHz, d6-DMSO): 8.69 (s, 1H), 7.97 (s, 2H), 8.23 (m, 3H), 7.61 (dd, 2H), 7.30 (br s, 1H), 7.07 (d, 1H), 5.30 (br s, 2H), 4.63 (br s, 2H), 4.37 (br s, 2H), 3.98 (br, s, 2H), 2.98 (br s, 2H), 2.80 (s, 2H), 2.68 (s, 3H), 2.50 (s, 6H); MS (EI) for C$_{30}$H$_{32}$N$_6$O$_2$: 509 (MH$^+$).

Using analogous synthetic techniques and substituting with alternative starting reagents in steps 1 or 2 the following compounds of the invention were prepared. Alternative starting materials were obtained commercially unless otherwise indicated.

4-[6-(ethyloxy)quinazolin-4-yl]-7-(2-methyl-1H-benzimidazol-6-yl)-2,3,4,5-tetrahydro-1,4-benzoxazepine. Synthesized according to the method of example 10 using iodoethane in step 2. $^1$H NMR (400 MHz, d$_6$-DMSO): 12.22 (s, 1H), 8.53 (s, 1H), 7.84 (d, 1H), 7.79 (m, 0.5H), 7.73 (d, 1H), 7.65 (m, 0.5H), 7.58 (dd, 1H), 7.54 (m, 0.5H), 7.46 (br s, 1H), 7.44 (m, 0.5H), 7.40 (dd, 1H), 7.09 (br s, 1H), 7.05 (d, 1H), 5.06 (s, 2H), 4.54 (t, 2H), 4.08 (t, 2H), 3.72 (dd, 2H), 2.50 (s, 3H), 0.78 (t, 3H). MS (EI) for C$_{27}$H$_{26}$N$_5$O$_2$: 452 (MH$^+$).

({4-[7-(2-methyl-1H-benzimidazol-6-yl)-2,3-dihydro-1,4-benzoxazepin-4(5H)-yl]quinazolin-6-yl}oxy)acetonitrile. Synthesized according to the method of example 10 using bromoacetonitrile in step 2. $^1$H NMR (400 MHz, d$_6$-DMSO): 12.22 (s, 1H), 8.53 (s, 1H), 7.83 (s, 0.5H), 7.81 (s, 0.5H), 7.72 (d, 1H), 7.67 (m, 0.5H), 7.62 (d, 0.5H), 7.59 (d, 0.5H), 7.53 (d, 1H), 7.52 (d, 1H), 7.50 (m, 0.5H), 7.44 (d, 1H), 7.40 (dd, 1H), 7.04 (d, 1H), 5.22 (s, 2H), 5.10 (s, 2H), 4.50 (t, 2H), 4.18 (t, 2H), 2.50 (s, 3H). MS (EI) for C$_{27}$H$_{23}$N$_6$O$_2$: 463 (MH$^+$).

7-(2-methyl-1H-benzimidazol-6-yl)-4-[6-(propyloxy)quinazolin-4-yl]-2,3,4,5-tetrahydro-1,4-benzoxazepine. Synthesized according to the method of example 10 using 1-bromopropane in step 2. $^1$H NMR (400 MHz, d$_6$-DMSO): 8.75 (s, 1H), 7.97 (s, 2H), 7.81 (s, 2H), 7.75 (d, 1H), 7.70 (d, 1H), 7.58 (d, 1H), 7.22 (br s, 1H), 7.11 (d, 1H), 5.27 (s, 2H), 4.62 (br s, 2H) 4.32 (br s, 2H), 3.73 (br s, 2H), 1.33 (br s, 2H), 0.70 (br s, 3H); MS (EI) for C$_{28}$H$_{27}$N$_5$O$_2$: 466 (MH$^+$).

7-(2-methyl-1H-benzimidazol-6-yl)-4-(6-{[2-(methyloxy)ethyl]oxy}quinazolin-4-yl)-2,3,4,5-tetrahydro-1,4-benzoxazepine. Synthesized according to the method of example 10 using 2-(methoxy)-1-bromoethane in step 2. $^1$H NMR (400 MHz, d$_6$-DMSO): 8.52 (s, 1H), 7.88 (d, 1H), 7.58 (dd, 1H), 7.43 (m, 3H), 7.40 (m, 3H), 7.06 (m, 2H), 5.07 (s, 2H), 4.57 (br s, 2H) 4.08 (br s, 2H), 3.75 (br s, 2H), 2.85 (br s, 2H), 2.79 (s, 3H), 1.82 (s, 3H); MS (EI) for C$_{28}$H$_{27}$N$_5$O$_3$: 482 (MH$^+$).

N,N-dimethyl-2-({4-[7-(2-methyl-1H-benzimidazol-6-yl)-2,3-dihydro-1,4-benzoxazepin-4(5H)-yl]-8-(methyloxy)quinazolin-7-yl}oxy)ethanamine. Synthesized according to the method of example 10 using 7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine (example 1) in step 1 and 2-(N,N-dimethylamino)-1-chloroethane in step 2. $^1$H NMR (400 MHz, d$_6$-DMSO): 8.57 (s, 1H), 7.93 (s, 1H), 7.82 (m, 3H), 7.59 (d, 1H), 7.51 (d, 1H), 7.01 (d, 1H), 7.01 (d, 1H), 5.38 (br s, 2H), 4.61 (m, 4H), 4.45 (br s, 2H), 3.95 (br s, 2H), 3.72 (t, 2H), 2.90 (s, 6H), 2.77 (s, 3H); MS (EI) for C$_{30}$H$_{32}$N$_6$O$_3$: 525 (MH$^+$).

7-(2-methyl-1H-benzimidazol-6-yl)-4-{8-(methyloxy)-7-[(2-methylpropyl)oxy]quinazolin-4-yl}-2,3,4,5-tetrahydro-1,4-benzoxazepine. Synthesized according to the method of example 10 using 7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine (example 1) in step 1 and isobutyl bromide in step 2. $^1$H NMR (400 MHz, d$_6$-DMSO): 8.48 (s, 1H), 7.96 (s, 1H), 7.83 (m, 3H), 7.63 (d, 1H), 7.52 (d, 1H), 7.04 (d, 1H), 5.46 (s, 2H), 4.65 (br s, 3H) 4.53 (br s, 2H), 4.07 (d, 3H), 3.92 (s, 3H), 2.79 (s, 3H), 2.13 (m, 1H), 1.04 (d, 6H); MS (EI) for C$_{30}$H$_{31}$N$_5$O$_3$: 510 (MH$^+$).

4-{7-[(cyclopropylmethyl)oxy]-8-(methyloxy)quinazolin-4-yl}-7-(2-methyl-1H-benzimidazol-6-yl)-2,3,4,5-tetrahydro-1,4-benzoxazepine. Synthesized according to the method of example 10 using 7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine (example 1) in step 1 and cyclopropylmethyl bromide in step 2. $^1$H NMR (400 MHz, d$_6$-DMSO): 8.66 (s, 1H), 8.08 (s, 1H), 7.92 (s, 1H), 7.81 (m, 3H), 7.63 (d, 1H), 7.50 (d, 1H), 7.04 (d, 1H), 5.44 (s, 2H), 4.63 (br s, 3H) 4.53 (br s, 2H), 4.17 (d, 2H), 3.92 (s, 3H), 0.83 (m, 1H), 0.61 (m, 2H), 0.41 (m, 2H); MS (EI) for $C_{30}H_{29}N_5O_3$: 508 (MH$^+$).

7-(2-methyl-1H-benzimidazol-6-yl)-4-{8-(methyloxy)-7-[(quinolin-2-ylmethyl)oxy]quinazolin-4-yl}-2,3,4,5-tetrahydro-1,4-benzoxazepine. Synthesized according to the method of example 10 using 7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine (example 1) in step 1 and 2-bromomethylquinoline in step 2. $^1$H NMR (400 MHz, d$_6$-DMSO): 8.64 (s, 1H), 8.47 (d, 1H), 8.03 (m, 4H), 7.83 (m, 4H), 7.73 (d, 1H), 7.63 (m, 3H), 7.02 (d, 1H), 5.64 (s, 2H), 5.43 (br s, 3H) 4.62 (br s, 2H), 4.51 (br s, 2H), 4.01 (s, 1H), 2.80 (s, 3H); MS (EI) for $C_{36}H_{30}N_6O_3$: 595 (MH$^+$).

4-[7-(2-methyl-1H-benzimidazol-6-yl)-2,3-dihydro-1,4-benzoxazepin-4(5H)-yl]-8-(methyloxy)quinazolin-7-ol. Synthesized according to the method of example 10 using 7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine (example 1) in step 1. $^1$H NMR (400 MHz, d$_6$-DMSO): 12.86 (br s, 1H), 10.29 (br s, 1H), 8.48 (s, 1H), 7.76-7.67 (m, 3H), 7.56 (d, 1H), 7.51 (dd, 1H), 7.46 (dd, 1H), 7.11 (d, 1H), 7.00 (d, 1H), 5.12 (s, 2H), 4.50 (m, 2H), 4.22 (m, 2H), 3.88 (s, 3H), 2.54 (s, 3H). MS (EI) for $C_{26}H_{23}N_5O_3$: 454 (MH$^+$)

4-[7-(2-methyl-1H-benzimidazol-6-yl)-2,3-dihydro-1,4-benzoxazepin-4(5H)-yl]-6-(methyloxy)quinazolin-7-ol. Prepared according to the method of example 10 by using 7-(2-methyl-1H-benzimidazol-6-yl)-4-{6-(methyloxy)-7-[(phenylmethyl)oxy]quinazolin-4-yl}-2,3,4,5-tetrahydro-1,4-benzoxazepine (example 1) in step 1. $^1$H NMR (400 MHz, Methanol-D$_4$): 8.41, (s, 1H), 7.67 (br, 2H), 7. (dd, 2H), 7.45 (dd, 1H), 7.10 (d, 2H), 7.03 (dd, 1H), 5.03 (s, 2H), 4.54 (m, 2H), 4.15 (m, 2H), 3.48 (s, 3H), 2.60 (s, 3H), MS (EI) for $C_{26}H_{23}N_5O_3$: 454 (MH$^+$).

N-ethyl-6-{4-[7-(ethyloxy)-2-methylquinazolin-4-yl]-2,3,4,5-tetrahydro-1,4-benzoxazepin-7-yl}-1H-benzimidazol-2-amine. Prepared according to the method of example 10 using 4-{7-[2-(ethylamino)-1H-benzimidazol-6-yl]-2,3-dihydro-1,4-benzoxazepin-4(5H)-yl}-2-methylquinazolin-7-ol (example 11) and ethyl iodide in step 2. $^1$H NMR (400 MHz, DMSO-d6) δ 10.36 (s, 1H), 7.91-7.82 (m, 1H), 7.63 (dd, 1H), 7.52-7.36 (m, 2H), 7.26-7.13 (m, 2H), 6.99 (dd, 1H), 6.94-6.86 (m, 2H), 6.70 (q, 1H), 4.96 (s, 2H), 4.45-4.35 (m, 2H), 4.16-3.98 (m, 4H), 3.46-3.36 (m, 2H), 2.44-2.37 (m, 3H), 1.28-1.17 (m, 6H); MS (EI) for $C_{29}H_{30}N_6O_2$: 495 (MH$^+$).

Example 11

N-ethyl-6-{4-[2-methyl-7-(methyloxy)quinazolin-4-yl]-2,3,4,5-tetrahydro-1,4-benzoxazepin-7-yl}-1H-benzimidazol-2-amine STEP 1: To a solution of 1,1-dimethylethyl 7-(4-amino-3-nitrophenyl)-2,3-dihydro-1,4-benzoxazepine-4(5H)-carboxylate (Example 26, 1.35 g, 3.1 mmol) in ethyl acetate (30 mL) was added 5% palladium on carbon (wet). The resulting suspension was subjected to an atmosphere of hydrogen (40 psi) for 15 h. The catalyst was then removed by filtration through celite. The filtrate was concentrated to provide 1,1-dimethylethyl 7-(3,4-diaminophenyl)-2,3-dihydro-1,4-benzoxazepine-4(5H)-carboxylate (748 mg, 210 mmol, 68% yield) as an orange viscous syrup. MS (EI) for $C_{20}H_{25}N_3O_3$: 356 (MH$^+$).

STEP 2: A solution of 1,1-dimethylethyl 7-(3,4-diaminophenyl)-2,3-dihydro-1,4-benzoxazepine-4(5H)-carboxylate (750 mg, 2.10 mmol) in ethyl acetate (20 mL) was treated with ethyl isothiocyanate (184 uL, 2.10 mmol). The mixture was heated to 60° C. for 4.25 h. After cooling to rt, water was added and the layers were partitioned. The organic phase was washed once with saturated sodium bicarbonate, dried over magnesium sulfate, filtered, and concentrated. The residue was then dissolved in ethyl acetate (20 mL), and N-(3-dimethylaminopropyl)-N'-ethylcarbodiimide hydrochloride (403 mg, 2.10 mmol) was added. The mixture was heated to 60° C. for 50 minutes before cooling to rt. Water was added, and the biphasic mixture was partitioned. The aqueous phase was extracted with ethyl acetate. The combined organic extracts were dried over magnesium sulfate, filtered, and concentrated. The residue was purified by silica gel chromatography (gradient: 98:2 dichloromethane:methanol to 90:10 dichloromethane:methanol) to provide 1,1-dimethylethyl 7-[2-(ethylamino)-1H-benzimidazol-6-yl]-2,3-dihydro-1,4-benzoxazepine-4(5H)-carboxylate (337 mg, 0.83 mmol, 39% yield) as an orange film. $^1$H NMR (400 MHz, DMSO-d6) δ 10.83 (br s, 1H), 7.47-7.38 (m, 2H), 7.32 (s, 1H), 7.20-7.08 (m, 2H), 7.05-6.96 (m, 1H), 6.68-6.58 (m, 1H), 4.55-4.40 (m, 2H), 4.09-3.98 (m, 2H), 3.77-3.65 (m, 2H), 3.33-3.26 (m, 2H), 1.41-1.28 (m, 9H), 1.18 (t, 3H); MS (EI) for $C_{23}H_{28}N_4O_3$: 409 (MH$^+$).

STEP 3: A solution of hydrogen chloride in dioxane (4 M, 2.09 mL, 8.3 mmol) was added to 1,1-dimethylethyl 7-[2-(ethylamino)-1H-benzimidazol-6-yl]-2,3-dihydro-1,4-benzoxazepine-4(5H)-carboxylate (337 mg, 0.83 mmol) in methanol (4 mL). The mixture was heated to 60° C. and stirred for 1 h before cooling to rt. The volatile materials were removed to provide N-ethyl-5-(2,3,4,5-tetrahydro-1,4-benzoxazepin-7-yl)-1H-benzimidazol-2-amine dihydrochloride in quantitative yield. $^1$H NMR (400 MHz, DMSO-d6) δ 12.85 (d, 1H), 9.48 (br s, 2H), 9.11-9.03 (m, 1H), 7.77 (d, 1H), 7.63 (dd, 1H), 7.55 (d, 1H), 7.52-7.42 (m, 2H), 7.19 (d, 1H), 4.42 (br s, 2H), 4.28-4.20 (m, 2H), 3.55-3.41 (m, 4H), 1.26 (t, 3H); MS (EI) for $C_{18}H_{20}N_4O$: 309 (MH$^+$).

STEP 4: To a mixture of N-ethyl-5-(2,3,4,5-tetrahydro-1,4-benzoxazepin-7-yl)-1H-benzimidazol-2-amine dihydrochloride (50 mg, 0.13 mmol) and 4-chloro-7-methoxy-2-methylquinazoline (27 mg, 0.13 mmol) in NMP (1 mL) was added diisopropylethylamine (91 uL, 0.52 mmol). The mixture was heated to 90° C. and stirred for 1 h. After cooling to rt, water was added, and the resulting aqueous mixture was extracted twice with 10% methanol in ethyl acetate. The organic extracts were combined, dried over magnesium sulfate, filtered, and then concentrated. The residue was purified by reverse-phase preparative HPLC to provide N-ethyl-6-{4-[2-methyl-7-(methyloxy)quinazolin-4-yl]-2,3,4,5-tetrahydro-1,4-benzoxazepin-7-yl}-1H-benzimidazol-2-amine as an acetate salt (34.2 mg, 0.063 mmol, 49% yield). $^1$H NMR (400 MHz, DMSO-d6) δ 11.91 (br s, 1H), 10.83 (br s, 1H), 7.92 (d, 1H), 7.58 (d, 1H), 7.43 (dd, 1H), 7.35 (s, 1H), 7.20-7.10 (m, 3H), 7.05-6.97 (m, 2H), 6.61 (br s, 1H), 4.99 (s, 2H), 4.44-4.38 (m, 2H), 4.18-4.11 (m, 2H), 3.33-3.25 (m, 2H), 2.44 (s, 3H), 1.91 (s, 4H), 1.19 (t, 3H); MS (EI) for $C_{28}H_{28}N_6O_2$: 481 (MH$^+$).

Using analogous synthetic techniques and substituting with alternative starting reagents in step 4 the following compounds of the invention were prepared. Protecting group introduction and removal steps were conducted as required according to literature techniques appropriate for a given protecting group (see for example: Greene and Wuts, Protective Groups in Organic Synthetic, Wiley-Interscience). Alternative starting materials were obtained commercially unless otherwise indicated.

N-ethyl-6-{4-[2-methyl-6,7-bis(methyloxy)quinazolin-4-yl]-2,3,4,5-tetrahydro-1,4-benzoxazepin-7-yl}-1H-benzimidazol-2-amine. Prepared as an acetate salt according to the method of example 11 by using 4-chloro-6,7-dimethoxy-2-methylquinazoline in step 4. $^1$H NMR (400 MHz, DMSO-d6) δ 10.80 (s, 1H), 7.68 (s, 1H), 7.46 (d, 1H), 7.35 (br s, 1H), 7.21-7.06 (m, 3H), 7.06-6.97 (m, 2H), 6.60 (t, 1H), 4.94 (s, 2H), 4.49-4.41 (m, 2H), 4.09-3.97 (m, 2H), 3.87 (s, 3H), 3.51 (s, 3H), 3.32-3.26 (m, 2H), 2.47 (s, 3H), 1.90 (s, 3H), 1.18 (t, 3H); MS (EI) for $C_{29}H_{30}N_6O_3$: 511 (MH$^+$).

N-ethyl-6-[4-(7-fluoroquinazolin-4-yl)-2,3,4,5-tetrahydro-1,4-benzoxazepin-7-yl]-1H-benzimidazol-2-amine. Prepared as an acetate salt according to the method of example 11 by using 4-chloro-7-fluoroquinazoline in step 4. $^1$H NMR (400 MHz, DMSO-d6) δ 10.79 (s, 1H), 8.52 (s, 1H), 8.15 (dd, 1H), 7.65-7.58 (m, 1H), 7.56-7.49 (m, 1H), 7.48-7.32 (m, 3H), 7.23-7.08 (m, 2H), 6.97 (d, 1H), 6.60 (t, 1H), 5.11 (s, 2H), 4.54-4.44 (m, 2H), 4.27-4.16 (m, 2H), 3.31-3.24 (m, 2H), 1.90 (s, 2H), 1.18 (t, 3H); MS (EI) for $C_{26}H_{23}FN_6O$: 455 (MH$^+$).

4-{7-[2-(ethylamino)-1H-benzimidazol-6-yl]-2,3-dihydro-1,4-benzoxazepin-4(5H)-yl}-2-methylquinazolin-7-ol. Prepared as an acetate salt according to the method of example 11 by using 7-(benzyloxy)-4-chloro-2-methylquinazoline in step 4 followed by benzyl deprotection. $^1$H NMR (400 MHz, DMSO-d6) δ 7.87 (d, 1H), 7.57 (d, 1H), 7.43 (dd, 1H), 7.33 (s, 1H), 7.19-7.11 (m, 2H), 7.02-6.93 (m, 2H), 6.91 (d, 1H), 6.83-6.73 (m, 1H), 4.94 (s, 2H), 4.43-4.35 (m, 2H), 4.15-4.08 (m, 2H), 3.36-3.28 (m, 2H), 2.41 (s, 3H), 1.87 (s, 10H), 1.18 (t, 3H); MS (EI) for $C_{27}H_{26}N_6O_2$: 467 (MH$^+$).

N-ethyl-6-[4-(2-methylquinolin-4-yl)-2,3,4,5-tetrahydro-1,4-benzoxazepin-7-yl]-1H-benzimidazol-2-amine. Prepared as an acetate salt according to the method of example 11 by using 4-chloro-2-methylquinoline in step 4. $^1$H NMR (400 MHz, DMSO-d6) δ 10.84 (br s, 1H), 7.95 (d, 1H), 7.85 (d, 1H), 7.64 (t, 1H), 7.61-7.56 (m, 1H), 7.50 (dd, 1H), 7.43 (t, 1H), 7.38 (s, 1H), 7.17 (br s, 2H), 7.08 (d, 1H), 6.98 (s, 1H), 6.63 (t, 1H), 4.55 (s, 2H), 4.39-4.30 (m, 2H), 3.79-3.70 (m, 2H), 3.35-3.27 (m, 2H), 2.55 (s, 3H), 1.18 (t, 3H); MS (EI) for $C_{28}H_{27}N_5O$: 450 (MH$^+$).

N-ethyl-6-{4-[2-methyl-7-(methyloxy)quinolin-4-yl]-2,3,4,5-tetrahydro-1,4-benzoxazepin-7-yl}-1H-benzimidazol-2-amine. Prepared as an acetate salt according to the method of example 11 by using 4-chloro-7-methoxy-2-methylquinoline in step 4. $^1$H NMR (400 MHz, DMSO-d6) δ 10.81 (br s, 1H), 7.84 (d, 1H), 7.57 (br s, 1H), 7.49 (dd, 1H), 7.37 (br s, 1H), 7.26 (d, 1H), 7.17 (br s, 2H), 7.09-7.03 (m, 2H), 6.84 (s, 1H), 6.61 (t, 1H), 4.53 (s, 2H), 4.37-4.30 (m, 2H), 3.88 (s, 3H), 3.75-3.67 (m, 2H), 3.34-3.27 (m, 2H), 2.51 (s, 3H), 1.93-1.89 (m, 3H), 1.18 (t, 3H); MS (EI) for $C_{29}H_{29}N_5O_2$: 480 (MH$^+$).

6-{4-[6,7-bis(methyloxy)quinazolin-4-yl]-2,3,4,5-tetrahydro-1,4-benzoxazepin-7-yl}-N-ethyl-1H-benzimidazol-2-amine. Prepared as an acetate salt according to the method of example 11 by using 4-chloro-6,7-dimethoxyquinazoline in step 4. $^1$H NMR (400 MHz, DMSO-D6-d6) δ 8.48 (s, 1H), 7.68 (s, 1H), 7.46-7.41 (m, 1H), 7.36-7.32 (m, 1H), 7.20 (s, 1H), 7.17-7.13 (m, 2H), 7.07 (s, 1H), 7.01 (d, 1H), 6.60 (d, 1H), 4.99 (s, 2H), 4.53-4.48 (m, 2H), 4.07-4.02 (m, 2H), 3.90 (s, 3H), 3.53 (s, 3H), 3.33-3.28 (m, 2H), 1.92-1.89 (m, 4H), 1.18 (t, 3H); MS (EI) for $C_{28}H_{28}N_6O_3$: 497 (MH$^+$).

N-ethyl-6-[4-(2-ethylquinazolin-4-yl)-2,3,4,5-tetrahydro-1,4-benzoxazepin-7-yl]-1H-benzimidazol-2-amine. Prepared as an acetate salt according to the method of example 11 by using 4-chloro-2-ethylquinazoline in step 4. $^1$H NMR (400 MHz, DMSO-D6-d6) δ 8.03 (d, 1H), 7.78-7.69 (m, 2H), 7.60 (d, 1H), 7.47-7.39 (m, 2H), 7.35 (s, 1H), 7.19-7.11 (m, 2H), 6.96 (d, 1H), 6.69 (s, 1H), 5.05 (s, 2H), 4.47-4.40 (m, 2H), 4.24-4.18 (m, 2H), 3.37-3.28 (m, 2H), 2.71 (q, 2H), 1.90 (s, 4H), 1.22-1.15 (m, 6H); MS (EI) for $C_{28}H_{28}N_6O$: 465 (MH$^+$).

6-{4-[6,7-bis(methyloxy)quinolin-4-yl]-2,3,4,5-tetrahydro-1,4-benzoxazepin-7-yl}-N-ethyl-1H-benzimidazol-2-amine. Prepared as an acetate salt according to the method of example 11 by using 4-chloro-6,7-dimethoxyquinoline in step 4. $^1$H NMR (400 MHz, DMSO-d6) δ 10.79 (br s, 1H), 8.47 (d, 1H), 7.67 (br s, 1H), 7.52-7.46 (m, 1H), 7.42-7.32 (m, 1H), 7.31 (s, 1H), 7.21-7.13 (m, 2H), 7.11 (s, 1H), 7.06 (d, 1H), 6.95 (d, 1H), 6.60 (t, 1H), 4.55 (s, 2H), 4.42-4.35 (m, 2H), 3.89 (s, 3H), 3.75-3.67 (m, 2H), 3.53 (s, 3H), 3.32-3.26 (m, 2H), 1.91 (s, 3H), 1.18 (t, 3H); MS (EI) for $C_{29}H_{29}N_5O_3$: 496 (MH$^+$).

N-ethyl-6-{4-[6-(methyloxy)quinolin-4-yl]-2,3,4,5-tetrahydro-1,4-benzoxazepin-7-yl}-1H-benzimidazol-2-amine. Prepared as an acetate salt according to the method of example 11 by using 4-chloro-6-methoxyquinoline in step 4. $^1$H NMR (400 MHz, DMSO-d6) δ 10.81 (br s, 1H), 8.53 (d, 1H), 7.86 (d, 1H), 7.67 (br s, 1H), 7.49 (d, 1H), 7.45-7.29 (m, 2H), 7.24-7.11 (m, 3H), 7.10-7.02 (m, 2H), 6.61 (t, 1H), 4.57 (s, 2H), 4.43-4.35 (m, 2H), 3.78-3.69 (m, 2H), 3.58 (s, 3H), 3.33-3.27 (m, 2H), 1.90 (s, 3H), 1.18 (t, 3H); MS (EI) for $C_{28}H_{27}N_5O_2$: 466 (MH$^+$).

N-ethyl-6-{4-[2-ethyl-7-(methyloxy)quinazolin-4-yl]-2,3,4,5-tetrahydro-1,4-benzoxazepin-7-yl}-1H-benzimidazol-2-amine. Prepared as its acetate salt according to the method of example 11 by using 4-chloro-2-ethyl-7-methoxyquinazoline (prepared according to the methods described by Abe et al. *J. Med. Chem.* 1998, 41, 4062-4079 using 2-amino-4-methoxybenzoic acid and propionyl chloride) in step 4. $^1$H NMR (400 MHz, DMSO-D6-d6) δ 7.93 (d, 1H), 7.58 (d, 1H), 7.44-7.38 (m, 1H), 7.34 (s, 1H), 7.19-7.10 (m, 3H), 7.04-6.99 (m, 1H), 6.94 (d, 1H), 6.64 (s, 1H), 5.02 (s, 2H), 4.43 (s, 2H), 4.17 (s, 2H), 3.88 (s, 3H), 3.33-3.28 (m, 2H), 2.68 (q, 2H), 1.89 (s, 6H), 1.21-1.16 (m, 6H); MS (EI) for $C_{29}H_{30}N_6O_2 \cdot 2C_2H_4O_2$: 495 (MH$^+$).

N-ethyl-6-{4-[7-(methyloxy)quinolin-4-yl]-2,3,4,5-tetrahydro-1,4-benzoxazepin-7-yl}-1H-benzimidazol-2-amine. Prepared as an acetate salt according to the method of example 11 by using 4-chloro-7-methoxyquinoline in step 4. $^1$H NMR (400 MHz, DMSO-d6) δ 10.81 (br s, 1H), 8.53 (d, 1H), 7.91 (d, 1H), 7.60 (s, 1H), 7.49 (dd, 1H), 7.38 (br s, 1H), 7.31 (d, 1H), 7.24-7.09 (m, 3H), 7.05 (d, 1H), 6.88 (d, 1H), 6.67-6.57 (m, 1H), 4.60 (s, 2H), 4.39-4.30 (m, 2H), 3.82-3.74 (m, 2H), 3.33-3.27 (m, 2H), 1.90 (s, 3H), 1.18 (t, 3H); MS (EI) for $C_{28}H_{27}N_5O_2$: 466 (MH$^+$).

N-ethyl-6-[4-(7-fluoro-2-methylquinazolin-4-yl)-2,3,4,5-tetrahydro-1,4-benzoxazepin-7-yl]-1H-benzimidazol-2-amine. Prepared as an acetate salt according to the method of example 11 by using 4-chloro-7-fluoro-2-methylquinazoline (prepared according to the methods described by Abe et al. *J. Med. Chem.* 1998, 41, 4062-4079 using 2-amino-4-fluorobenzoic acid and acetyl chloride) in step 4. $^1$H NMR (400 MHz, DMSO-d6) δ 8.13-8.06 (m, 1H), 7.61 (d, 1H), 7.45-7.41 (m, 2H), 7.37-7.30 (m, 1H), 7.19-7.12 (m, 2H), 6.98 (d, 1H), 6.68-6.62 (m, 1H), 5.05 (s, 2H), 4.43 (d, 2H), 4.20 (d, 2H), 3.35-3.28 (m, 2H), 2.46 (s, 3H), 1.89 (s, 4H), 1.18 (t, 3H); MS (EI) for $C_{27}H_{25}FN_6O$: 469 (MH$^+$).

N-ethyl-6-[4-(7-fluoro-2-methylquinolin-4-yl)-2,3,4,5-tetrahydro-1,4-benzoxazepin-7-yl]-1H-benzimidazol-2-amine. Prepared as an acetate salt according to the method of example 11 by using 4-chloro-7-fluoro-2-methylquinoline in step 4. $^1$H NMR (400 MHz, DMSO-d6) δ 10.86 (br s, 1H), 8.00 (dd, 1H), 7.64-7.53 (m, 2H), 7.49 (dd, 1H), 7.43-7.30 (m, 2H), 7.17 (br s, 2H), 7.07 (d, 1H), 6.96 (s, 1H), 6.63 (t, 1H), 4.57 (s, 2H), 4.39-4.30 (m, 2H), 3.80-3.69 (m, 2H), 3.36-3.26 (m, 2H), 2.54 (s, 3H), 1.89 (s, 3H), 1.18 (t, 3H); MS (EI) for $C_{28}H_{26}FN_5O$: 468 (MH$^+$).

N-ethyl-6-(4-pyrimidin-4-yl-2,3,4,5-tetrahydro-1,4-benzoxazepin-7-yl)-1H-imidazo[4,5-b]pyridin-2-amine. Prepared as an acetate salt according to the method of example 11 by using tert-butyl 7-(6-amino-5-nitropyridin-3-yl)-2,3-dihydro-1,4-benzoxazepine-4(5H)-carboxylate (Example 26) in step 1 and 4-chloropyrimidine in step 4. $^1$H NMR (400 MHz, DMSO-D6-d6) δ 8.13-8.06 (m, 1H), 7.61 (d, 1H), 7.45-7.41 (m, 2H), 7.37-7.30 (m, 2H), 7.19-7.12 (m, 2H), 6.98 (d, 1H), 6.68-6.62 (m, 1H), 5.05 (s, 2H), 4.43 (d, 2H), 4.20 (d, 2H), 3.35-3.28 (m, 2H), 2.46 (s, 3H), 1.89 (s, 4H), 1.18 (t, 3H); MS (EI) for $C_{21}H_{21}N_7O$: 388 (MH$^+$).

N-ethyl-6-{4-[2-methyl-7-(methyloxy)quinazolin-4-yl]-2,3,4,5-tetrahydro-1,4-benzoxazepin-7-yl}-1H-imidazo[4,5-b]pyridin-2-amine. Prepared according to the method of example 11 by using tert-butyl 7-(6-amino-5-nitropyridin-3-yl)-2,3-dihydro-1,4-benzoxazepine-4(5H)-carboxylate (Example 26) in step 1 and 4-chloro-7-methoxy-2-methylquinazoline in step 4. $^1$H NMR (400 MHz, DMSO-d6) δ 8.22 (s, 0.5H), 8.07 (s, 0.5H), 7.90 (d, 1H), 7.68-7.42 (m, 3H), 7.17-6.84 (m, 4H), 5.00 (s, 2H), 4.47-4.39 (m, 2H), 4.18-4.10 (m, 2H), 3.88 (s, 3H), 3.40-3.30 (m, 2H), 2.43 (s, 3H), 1.26-1.13 (m, 3H); MS (EI) for $C_{27}H_{27}N_7O_2$: 482 (MH$^+$).

6-{4-[2,5-dimethyl-6-(phenylamino)pyrimidin-4-yl]-2,3,4,5-tetrahydro-1,4-benzoxazepin-7-yl}-N-ethyl-1H-benzimidazol-2-amine. Prepared as a trifluoroacetate salt according to the method of example 11 by using 6-chloro-2,5-dimethyl-N-phenylpyrimidin-4-amine (prepared according to the methods described by Chen et al. *J. Med. Chem.* 1996, 39, 4358-4360 using 4,6-dichloro-2,5-dimethylpyrimidine and aniline) in step 4. $^1$H NMR (400 MHz, DMSO-d6) δ 8.99 (t, 1H), 7.60 (d, 1H), 7.56-7.39 (m, 5H), 7.29 (s, 2H), 7.11-6.97 (m, 2H), 4.65 (s, 2H), 4.35-4.29 (m, 2H), 3.87-3.80 (m, 2H), 3.47-3.37 (m, 2H), 2.30 (s, 3H), 2.09 (s, 3H), 1.26 (t, 3H); MS (EI) for $C_{30}H_{31}N_7O$: 506 (MH$^+$).

N-ethyl-6-{4-[6-(phenylamino)pyrimidin-4-yl]-2,3,4,5-tetrahydro-1,4-benzoxazepin-7-yl}-1H-benzimidazol-2-amine. Prepared according to the method of example 11 by using 6-chloro-N-phenylpyrimidin-4-amine (reagent preparation 49) in step 4. $^1$H NMR (400 MHz, DMSO-d6) δ 12.03 (br s, 1H), 9.01 (s, 1H), 8.13 (s, 1H), 7.50 (m, 6H), 7.01 (m, 6H), 6.02 (s, 1H), 4.87 (br s, 2H), 4.24 (br s, 4H), 3.48 (q, 2H), 1.23 (t, 3H); MS (EI) for $C_{28}H_{27}N_7O$: 478.3 (MH$^+$).

N-ethyl-6-[4-(6-{[4-(methyloxy)phenyl]amino}pyrimidin-4-yl)-2,3,4,5-tetrahydro-1,4-benzoxazepin-7-yl]-1H-benzimidazol-2-amine. Prepared according to the method of example 11 by using 6-chloro-N-(4-methoxyphenyl)pyrimidin-4-amine (reagent preparation 49) in step 4. $^1$H NMR (400 MHz, DMSO-d6) δ 12.03 (br s, 1H), 9.23 (br s, 1H), 9.02 (t, 1H), 8.13 (s, 1H), 7.50 (m, 5H), 7.30 (d, 2H), 7.01 (d, 1H), 6.75 (br s, 2H), 6.02 (s, 1H), 4.87 (br s, 2H), 4.24 (br s, 4H), 3.77 (s, 3H), 3.48 (q, 2H), 1.23 (t, 3H); MS (EI) for $C_{29}H_{29}N_7O_2$: 508.2 (MH$^+$).

N-ethyl-6-(4-pyrimidin-4-yl-2,3,4,5-tetrahydro-1,4-benzoxazepin-7-yl)-1H-benzimidazol-2-amine. Prepared according to the method of example 11 by using 4-chloropyrimidine in step 4. $^1$H NMR (400 MHz, DMSO-d6) δ 12.03 (br s, 1H), 9.23 (br s, 1H), 8.75 (s, 1H), 8.47 (d, 1H), 8.03 (br s, 1H), 7.50 (m, 5H), 7.01 (d, 1H), 5.02 (br s, 2H), 4.34 (br s, 4H), 3.48 (q, 2H), 1.23 (t, 3H); MS (EI) for $C_{22}H_{22}N_6O$: 387.3 (MH$^+$).

N-ethyl-6-[4-(6-{[3-(methyloxy)phenyl]amino}pyrimidin-4-yl)-2,3,4,5-tetrahydro-1,4-benzoxazepin-7-yl]-1H-benzimidazol-2-amine. Prepared according to the method of example 11 by using 6-chloro-N-(3-methoxyphenyl)pyrimidin-4-amine (reagent preparation 49) in step 4. $^1$H NMR (400 MHz, DMSO-d6) δ 12.03 (br s, 1H), 8.20 (s, 1H), 7.60 (s, 1H), 7.40 (m, 2H), 7.15 (m, 7H), 6.70 (br s, 1H), 6.50 (m, 1H), 6.15 (s, 1H), 4.72 (br s, 2H), 4.18 (s, 4H), 3.77 (s, 3H), 3.48 (q, 2H), 1.23 (t, 3H); MS (EI) for $C_{29}H_{29}N_7O_2$: 508.2 (MH$^+$).

N-ethyl-6-[4-(5-methyl-6-{[4-(methyloxy)phenyl]amino}pyrimidin-4-yl)-2,3,4,5-tetrahydro-1,4-benzoxazepin-7-yl]-1H-benzimidazol-2-amine. Prepared according to the method of example 11 by using 6-chloro-N-(4-methoxyphenyl)-5-methylpyrimidin-4-amine (reagent preparation 49) in step 4. $^1$H NMR (400 MHz, DMSO-d6) δ 12.03 (br s, 1H), 8.20 (s, 1H), 8.01 (s, 1H), 7.51 (m, 5H), 7.18 (m, 2H), 7.01 (d, 1H), 6.81 (d, 2H), 6.75 (br s, 1H), 4.50 (s, 2H), 4.23 (br s, 2H), 3.78 (br s, 2H), 3.33 (q, 2H), 2.18 (s, 3H), 1.81 (s, 3H), 1.23 (t, 3H); MS (EI) for $C_{30}H_{31}N_7O_2$: 522.0 (MH$^+$).

N-ethyl-6-{4-[5-methyl-6-(phenylamino)pyrimidin-4-yl]-2,3,4,5-tetrahydro-1,4-benzoxazepin-7-yl}-1H-benzimidazol-2-amine. Prepared according to the method of example 11 by using 6-chloro-5-methyl-N-phenylpyrimidin-4-amine (reagent preparation 49) in step 4. $^1$H NMR (400 MHz, MeOH-d4) δ 8.01 (s, 1H), 7.51 (m, 10H), 7.02 (d, 1H), 6.75 (br s, 2H), 4.50 (br s, 4H), 4.14 (br s, 4H), 3.48 (q, 2H), 2.21 (s, 3H), 1.38 (t, 3H); MS (EI) for $C_{29}H_{29}N_7O$: 492.2 (MH$^+$).

Example 12

4-(4-{5-[(4-fluorophenyl)methyl]-6-methylpyrimidin-4-yl}-2,3,4,5-tetrahydro-1,4-benzoxazepin-7-yl)-N-methylbenzamide STEP 1: A suspension of {4-[(methyloxy)carbonyl]phenyl}boronic acid (0.36 g, 2.0 mmol), 1,1-dimethylethyl 7-bromo-2,3-dihydro-1,4-benzoxazepine-4(5H)-carboxylate (0.66 g, 2.0 mmol), [1,1'-bis(diphenylphosphino)ferrocene]dichloropalladium(II) (70.0 mg, 0.10 mmol), and tripotassium phosphate (1.30 g, 12.0 mmol) in dioxane (20 mL) was refluxed for 3 h, and then cooled to room temperature. The reaction mixture was partitioned between ethyl acetate (50 mL) and water (80 mL), the organic layer was washed with brine (40 mL), dried over sodium sulfate then filtered and concentrated. Column chromatography on silica (ethyl acetate:hexanes 1:4) gave 1,1-dimethylethyl 7-{4-[(methyloxy)carbonyl]phenyl}-2,3-dihydro-1,4-benzoxazepine-4(5H)-carboxylate (0.47 g, 60% yield). $^1$H NMR (400 MHZ, DMSO-D$_6$): 8.11 (m, 2H), 7.63-7.52 (m, 2H), 7.43 (m, 2H), 7.10 (t, 1H), 4.57-4.43 (br, 2H), 4.08 (m, 2H), 3.82 (m, 2H), 1.40 (s, 9H); MS (EI) for $C_{22}H_{25}NO_5$: 469 (MH$^+$).

STEP 2: To a solution of 1,1-dimethylethyl 7-{4-[(methyloxy)carbonyl]phenyl}-2,3-dihydro-1,4-benzoxazepine-4(5H)-carboxylate (1.90 g, 4.96 mmol) in dry methanol (10 mL) was added drop wise 4 N hydrogen chloride in dioxane (10 mL) at room temperature. The reaction mixture was warmed to 55° C. for 60 min, at which time it was cooled to room temperature. The precipitated product was isolated by filtration, washed with diethyl ether, and dried to yield methyl 4-(2,3,4,5-tetrahydro-1,4-benzoxazepin-7-yl)benzoate hydrochloride (1.53 g, 97% yield) as a white solid.

STEP 3: A suspension of -(2,3,4,5-tetrahydro-1,4-benzoxazepin-7-yl)benzoate hydrochloride (1.30 g, 4.14 mmol), 4-chloro-5-[(4-fluorophenyl)methyl]-6-methylpyrimidine (reagent preparation 5) (0.98 g, 4.14 mmol), and potassium carbonate (1.71 g, 12.4 mmol) in DMF (20 mL) was heated to 130° C. for 18 h. The reaction mixture was cooled to room temperature, diluted with ethyl acetate (40 mL), and then washed with water (50 mL) and brine (20 mL). The organic layer was dried over sodium sulfate then filtered and concentrated. Column chromatography on silica (gradient 10 to 20% ethyl acetate in hexane) followed by recrystallization from 1:1 ethyl acetate and ether (40 mL) provided methyl 4-(4-{5-[(4-fluorophenyl)methyl]-6-methylpyrimidin-4-yl}-2,3,4,5-tetrahydro-1,4-benzoxazepin-7-yl)benzoate (1.05 g, 50% yield) as a white solid. $^1$H NMR (400 MHZ, DMSO-D$_6$): 8.48 (s, 1H), 8.01 (d, 2H), 7.62 (d, 2H), 7.56 (dd, 1H), 7.11 (d, 4H), 7.02 (d, 1H), 6.91 (d, 1H), 4.52 (s, 2H), 4.32 (m, 2H), 3.95 (s, 2H), 3.90 (s, 3H), 3.76 (m, 2H), 2.13 (s, 3H); MS (EI) for $C_{29}H_{26}FN_3O_3$: 484 (MH$^+$).

STEP 4: To a solution of methyl 4-(4-{5-[(4-fluorophenyl)methyl]-6-methylpyrimidin-4-yl}-2,3,4,5-tetrahydro-1,4-benzoxazepin-7-yl)benzoate (1.0 g, 2.0 mmol) in 1:1 methanol and THF (10 mL) was added drop wise 2N aqueous potassium hydroxide (8 mL). The reaction mixture was stirred at room temperature for 18 h and then refluxed for 90 min. The mixture was cooled by adding ice, and the pH adjusted to 6 with 2N aqueous hydrochloric acid. The precipitate was filtered, washed with water, azeotroped with toluene (20 mL), and dried to afford 4-(4-{5-[(4-fluorophenyl)methyl]-6-methylpyrimidin-4-yl}-2,3,4,5-tetrahydro-1,4-benzoxazepin-7-yl)benzoic acid (0.97 g, 100% yield).

STEP 5: To a solution of 4-(4-{5-[(4-fluorophenyl)methyl]-6-methylpyrimidin-4-yl}-2,3,4,5-tetrahydro-1,4-benzoxazepin-7-yl)benzoic acid (0.50 g, 1.07 mmol) and DMF (20 μL) in chloroform (15 mL) was added drop wise oxalyl chloride (0.35 mL, 4.0 mmol). The reaction mixture was refluxed for 15 min, and then concentrated to give 4-(4-{5-[(4-fluorophenyl)-methyl]-6-methylpyrimidin-4-yl}-2,3,4,5-tetrahydro-1,4-benzoxazepin-7-yl)benzoyl chloride as an oil.

STEP 6: To a solution of 4-(4-{5-[(4-fluorophenyl)methyl]-6-methylpyrimidin-4-yl}-2,3,4,5-tetrahydro-1,4-benzoxazepin-7-yl)benzoyl chloride (30.0 mg, 62 μmol) in THF (5 mL) was added drop wise 40% aqueous methylamine (0.25 mL, 2.0 mmol) at 0° C. The reaction mixture was stirred at room temperature for 1 h, at which time it was concentrated. The resulting solid was dissolved in chloroform (30 mL), washed with water (20 mL), and dried over sodium sulfate then filtered. To the solution was then added drop wise 4N hydrogen chloride in dioxane (0.25 mL) and the mixture concentrated. The residue was taken up in 4:1 water and acetonitrile (2 mL) and lyophilized to give 4-(4-{5-[(4-fluorophenyl)methyl]-6-methylpyrimidin-4-yl}-2,3,4,5-tetrahydro-1,4-benzoxazepin-7-yl)-N-methylbenzamide hydrochloride salt (16.5 mg, 53% yield) as a white powder. $^1$H NMR (400 MHZ, DMSO-d$_6$): 8.79 (s, 1H), 8.53 (dd, 1H), 7.97 (d, 2H), 7.65 (d, 2H), 7.57 (d, 1H), 7.30-7.13 (m, 5H), 6.97 (d, 1H), 4.92 (s, 1H), 4.35 (br 2H), 4.04-3.97 (m, 4H), 3.83 (d, 3H), 2.24 (s, 3H); MS (EI) for $C_{29}H_{27}FN_4O_2$: 483 (MH$^+$).

Using analogous synthetic techniques and substituting with alternative starting reagents in step 6 the following compounds of the invention were prepared. Alternative starting materials were obtained commercially unless otherwise indicated.

N-cyclopropyl-4-(4-{5-[(4-fluorophenyl)methyl]-6-methylpyrimidin-4-yl}-2,3,4,5-tetrahydro-1,4-benzoxazepin-7-yl)benzamide. Synthesized according to the method of example 12 using cyclopropylamine in step 6. $^1$H NMR (400 MHz, d$_6$-DMSO): 8.79 (s, 1H), 8.53 (d, 1H), 7.92 (d, 2H), 7.61 (d, 2H), 7.58 (d, 1H), 7.12 (m, 5H), 7.02 (d, 1H), 4.92 (s, 2H), 4.38 (br s, 2H), 4.05 (s, 2H), 4.00 (br s, 2H), 2.88 (m, 1H), 2.25 (s, 3H), 0.73 (m, 2H), 0.61 (m, 2H); MS (EI) for $C_{31}H_{26}FN_4O_2$: 509 (MH$^+$).

4-(4-{5-[(4-fluorophenyl)methyl]-6-methylpyrimidin-4-yl}-2,3,4,5-tetrahydro-1,4-benzoxazepin-7-yl)-N-[(3S)-pyrrolidin-3-yl]benzamide. Synthesized according to the method of example 12 using ((3S))—N$^1$—BOC-pyrrolidin-3-ylamine in step 6. $^1$H NMR (400 MHz, d$_6$-DMSO): 9.38 (br s, 1H), 9.14 (br s, 1H), 8.03 (d, 2H), 7.67 (d, 2H), 7.59 (d, 1H), 7.21 (m, 4H), 7.05 (d, 1H), 4.92 (s, 2H), 4.60 (m, 1H), 4.36 (br s, 2H), 4.08 (br s, 2H), 3.98 (br s, 2H), 3.68 (m, 3H), 3.49 (m, 3H), 3.24 (m, 1H), 2.24 (s, 3H); MS (EI) for $C_{32}H_{32}FN_5O_2$: 538 (MH$^+$).

N-(2,2-difluoroethyl)-4-(4-{5-[(4-fluorophenyl)methyl]-6-methylpyrimidin-4-yl}-2,3,4,5-tetrahydro-1,4-benzoxazepin-7-yl)benzamide. Synthesized according to the method of example 12 using 2,2-difluoroethylamine in step 6. $^1$H NMR (400 MHz, d$_6$-DMSO); 8.95 (t, 1H), 8.80 (s, 1H), 7.98 (d, 2H), 7.68 (d, 2H), 7.59 (d, 1H), 7.21 (m, 4H), 7.04 (d, 1H), 6.17 (tt, 1H), 4.93 (s, 2H), 4.37 (br s, 2H), 4.08 (s, 2H), 3.99 (br s, 2H), 3.61 (br m, 2H), 2.25 (s, 3H); MS (EI) for $C_{30}H_{27}F_3N_4O_2$: 533 (MH$^+$).

4-(4-{5-[(4-fluorophenyl)methyl]-6-methylpyrimidin-4-yl}-2,3,4,5-tetrahydro-1,4-benzoxazepin-7-yl)benzamide. Synthesized according to the method of example 12 using ammonia in step 6. $^1$H NMR (400 MHz, d$_6$-DMSO): 8.63 (br s, 1H), 8.05 (br s, 1H), 7.96 (d, 2H), 7.59 (d, 2H), 7.55 (dd, 1H), 7.41 (br s, 1H), 7.16 (m, 4H), 7.10 (br s, 1H), 7.01 (d, 1H), 4.70 (br s, 2H), 4.32 (m, 2H), 4.00 (s, 2H), 3.86 (m, 2H), 2.20 (s, 3H). MS (EI) for $C_{28}H_{25}FN_4O_2$: 469 (MH$^+$).

4-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-N-methylbenzamide. Prepared according to the method of example 12 by using 1-(4-chloro-6,6-dimethyl-5,6,7,8-tetrahydroquinazolin-2-yl)-N,N-dimethylmethanamine (reagent preparation 17) in step 3. $^1$H NMR (400 MHz, methanol-d$_4$): 7.88 (d, 2H), 7.72 (d, 2H), 7.66 (d, 1H), 7.52 (dd, 1H), 7.04 (d, 1H), 4.78 (s, 2H), 4.37 (m, 2H), 4.01 (m, 2H), 3.76 (s, 2H), 2.94 (s, 3H), 2.80 (t, 2H), 2.50 (s, 2H), 2.47 (s, 6H), 1.92 (s, 3H), 1.68 (t, 2H), 0.90 (s, 6H); MS (EI) for $C_{30}H_{37}N_5O_2$: 500 (MH$^+$).

N-methyl-4-(4-quinolin-4-yl-2,3,4,5-tetrahydro-1,4-benzoxazepin-7-yl)benzamide. Prepared according to the method of example 12 using 4-chloroquinoline in step 3 and methylamine in step 6. $^1$H NMR (400 MHz, DMSO-d6); δ 8.60 (d, 1H), 8.53-8.46 (m, 1H), 8.06 (d, 1H), 7.98-7.70 (m, 6H), 7.68-7.62 (m, 1H), 7.56-7.50 (m, 1H), 7.09 (d, 1H), 6.99 (d, 1H), 4.82 (s, 2H), 4.50-4.41 (m, 2H), 4.02-3.89 (m, 2H), 2.81 (d, 3H); MS (EI) for $C_{26}H_{23}N_3O_2$: 410 (MH$^+$).

N-ethyl-4-(4-quinolin-4-yl-2,3,4,5-tetrahydro-1,4-benzoxazepin-7-yl)benzamide. Prepared according to the method of example 12 using 4-chloroquinoline in step 3 and ethylamine in step 6. $^1$H NMR (400 MHz, DMSO-d$_6$); δ 8.61 (d, 1H), 8.55-8.50 (m, 1H), 8.02-7.90 (m, 4H), 7.81-7.76 (m, 3H), 7.72-7.62 (m, 2H), 7.50-7.45 (m, 1H), 7.12 (d, 1H), 7.00 (d, 1H), 4.68 (s, 2H), 4.43-4.37 (m, 2H), 3.86-3.80 (m, 2H), 1.14 (t, 3H); MS (EI) for $C_{27}H_{25}N_3O_2$: 424 (MH$^+$).

N-propyl-4-(4-quinolin-4-yl-2,3,4,5-tetrahydro-1,4-benzoxazepin-7-yl)benzamide. Prepared according to the method of example 12 using 4-chloroquinoline in step 3 and propylamine in step 6. $^1$H NMR (400 MHz, DMSO-d$_6$); δ 8.61 (d, 1H), 8.54-8.48 (m, 1H), 8.03 (d, 1H), 7.98-7.91 (m, 3H), 7.84-7.77 (m, 3H), 7.75-7.68 (m, 1H), 7.68-7.62 (m, 1H), 7.55-7.48 (m, 1H), 7.10 (d, 1H), 7.00 (d, 1H), 4.75 (s, 2H), 4.46-4.39 (m, 2H), 3.93-3.85 (m, 2H), 3.28-3.20 (m, 2H), 1.61-1.49 (m, 2H), 0.91 (t, 3H); MS (EI) for $C_{28}H_{27}N_3O_2$: 438 (MH$^+$).

3-{4-[2-methyl-7-(methyloxy)quinazolin-4-yl]-2,3,4,5-tetrahydro-1,4-benzoxazepin-7-yl}benzoic acid. Prepared according to the method of example 12 using 3-(methoxycarbonyl)phenylboronic acid in step 1 and 4-chloro-7-methoxy-2-methylquinazoline in step 3 and omission of steps 5 and 6. $^1$H NMR (400 MHz, DMSO-d6); δ 8.21 (m, 1H), 7.96-7.86 (m, 1H), 7.78-7.72 (m, 3H), 7.64-7.50 (m, 2H), 7.15-7.00 (m, 3H), 5.03 (s, 2H), 4.49-4.42 (m, 2H), 4.20-4.12 (m, 2H), 3.88 (s, 3H), 2.42 (s, 3H); MS (EI) for $C_{26}H_{23}N_3O_4$: 440 (M$^-$).

N-methyl-3-{4-[2-methyl-7-(methyloxy)quinazolin-4-yl]-2,3,4,5-tetrahydro-1,4-benzoxazepin-7-yl}benzamide. Prepared according to the method of example 12 using 3-(methoxycarbonyl)phenylboronic acid in step 1,4-chloro-7-methoxy-2-methylquinazoline in step 3, and methylamine in step 6. $^1$H NMR (400 MHz, DMSO-d6); δ 8.61-8.52 (m, 1H), 8.12-8.09 (m, 1H), 7.89 (d, 1H), 7.84-7.73 (m, 3H), 7.61-7.51 (m, 2H), 7.12-7.09 (m, 1H), 7.08-7.00 (m, 2H), 5.03 (s, 2H), 4.51-4.41 (m, 2H), 4.22-4.12 (m, 2H), 3.88 (s, 3H), 2.85-2.79 (d, 3H), 2.42 (s, 3H); MS (EI) for $C_{27}H_{26}N_4O_3$: 455 (MH$^+$).

N-ethyl-3-{4-[2-methyl-7-(methyloxy)quinazolin-4-yl]-2,3,4,5-tetrahydro-1,4-benzoxazepin-7-yl}benzamide. Prepared according to the method of example 12 using 3-(methoxycarbonyl)phenylboronic acid in step 1,4-chloro-7-methoxy-2-methylquinazoline in step 3, and ethylamine in step 6. $^1$H NMR (400 MHz, DMSO-d6); δ 8.64-8.57 (m, 1H), 8.14-8.08 (m, 1H), 7.97-7.89 (d, 1H), 7.84-7.75 (m, 3H), 7.61-7.51 (m, 2H), 7.12 (d, 1H), 7.08-7.02 (m, 2H), 5.06 (s, 2H), 4.53-4.43 (m, 2H), 4.23-4.14 (m, 2H), 3.88 (s, 3H), 2.44 (s, 3H), 1.15 (t, 3H); MS (EI) for $C_{28}H_{28}N_4O_3$: 469 (MH$^+$).

Example 13

Methyl [6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-yl]carbamate and 6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine STEP 1: To a slurry of 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) (3.3 g, 8.8 mmol) in methanol (25 mL) was added anhydrous hydrogen chloride (6.0 mL, 4 N in dioxane, 24 mmol). The reaction mixture was heated (60° C.) for 1.5 h and was concentrated. The resulting solid was suspended in ethyl ether (50 mL), collected by filtration and washed with ethyl ether (2×30 mL) to afford 7-(4,4,5,5-tetramethyl-1,3,2-dioxaborolan-2-yl)-2,3,4,5-tetrahydro-1,4-benzoxazepine hydrochloride (1.4 g, 50% yield) as a white solid. MS (EI) for $C_{15}H_{22}BNO_3$: 276 (MH$^+$).

STEP 2: To a solution of 7-(4,4,5,5-tetramethyl-1,3,2-dioxaborolan-2-yl)-2,3,4,5-tetrahydro-1,4-benzoxazepine hydrochloride (1.4 g, 4.5 mmol) and DIPEA (6.4 mL, 37 mmol) in NMP (24 mL) was added and 4-chloro-5-(4-fluorobenzyl)-6-methylpyrimidine (reagent preparation 5) (1.7 g, 7.3 mmol). The resulting mixture was heated (120° C.) for 12 h and then partitioned between ethyl acetate (100 mL) and 1N aqueous hydrochloric acid (50 mL). The organic layer was washed with additional 1N aqueous hydrochloric acid (50 mL), brine (50 mL), dried over anhydrous magnesium sulfate, filtered and concentrated. Column chromatography on silica (0-30% ethyl acetate/hexanes) provided 4-{5-[(4-fluorophenyl)methyl]-6-methylpyrimidin-4-yl}-7-(4,4,5,5-tetramethyl-1,3,2-dioxaborolan-2-yl)-2,3,4,5-tetrahydro-1,4-benzoxazepine (1.7 g, 47% yield) as a white foam. MS (EI) for $C_{27}H_{31}BFN_3O_3$: 476 (MH$^+$).

STEP 3: To a solution of 4-{5-[(4-fluorophenyl)methyl]-6-methylpyrimidin-4-yl}-7-(4,4,5,5-tetramethyl-1,3,2-dioxaborolan-2-yl)-2,3,4,5-tetrahydro-1,4-benzoxazepine (1.3 g, 2.7 mmol), potassium hydrogen carbonate (1.4 g, 14 mmol), 2-amino-5-bromo-3-nitropyridine (0.98 g, 4.5 mmol) and DIPEA (1.4 mL, 8.2 mmol) in dioxane (8 mL) and water (1 mL) was added dichloro[1,1-bis(diphenylphosphino]ferrocenepalladium (II) dichloromethane adduct (0.20 g, 0.27 mmol). The biphasic mixture was then heated (90° C.) for 2 h and the organic layer was separated and purified by column chromatography on silica (0-10% methanol/dichloromethane) to provide 5-(4-{5-[(4-fluorophenyl)methyl]-6-methylpyrimidin-4-yl}-2,3,4,5-tetrahydro-1,4-benzoxazepin-7-yl)-3-nitropyridin-2-amine (0.49 g, 37% yield) as a orange-red solid. MS (EI) for $C_{26}H_{23}FN_6O_3$: 487 (MH$^+$).

STEP 4: To a solution of 5-(4-{5-[(4-fluorophenyl)methyl]-6-methylpyrimidin-4-yl}-2,3,4,5-tetrahydro-1,4-benzoxazepin-7-yl)-3-nitropyridin-2-amine (0.36 g, 0.75 mmol) in acetic acid (10 mL) was added tin (II) chloride (0.75 g, 3.8 mmol). The reaction mixture was heated (50° C.) for 2 h and then partitioned between ethyl acetate (10 mL) and 1 N aqueous sodium hydroxide (20 mL). The resulting mixture was filtered through Celite and the organic layer was washed with brine (10 mL), dried over anhydrous magnesium sulfate then filtered and concentrated. Column chromatography on silica (5% methanol/dichloromethane) provided 5-(4-{5-[(4-fluorophenyl)methyl]-6-methylpyrimidin-4-yl}-2,3,4,5-tetrahydro-1,4-benzoxazepin-7-yl)pyridine-2,3-diamine (0.21 g, 60% yield) as a pale yellow solid. MS (EI) for $C_{26}H_{25}FN_6O$: 457 (MH$^+$).

STEP 5: To a solution of 5-(4-{5-[(4-fluorophenyl)methyl]-6-methylpyrimidin-4-yl}-2,3,4,5-tetrahydro-1,4-benzoxazepin-7-yl)pyridine-2,3-diamine (0.21 g, 0.45 mmol) in acetic acid (5 mL) was added 1,3-bis(methoxycarbonyl)-2-methyl-2-thiopseudourea (0.09 g, 0.45 mmol). The reaction mixture was heated (60° C.) for 12 h and then concentrated. The resulting residue was dissolved in acetonitrile and purified by preparative reverse phase HPLC to provide methyl [6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-yl]carbamate (0.01 g, 4% yield) as a white solid. $^1$H NMR (400 MHz, DMSO-D$_6$): δ 11.97 (bs, 1H), 8.51 (d, 1H), 8.28 (s, 1H), 7.79 (s, 1h), 7.42-7.50 (m, 1H), 6.95-7.13 (m, 6H), 4.53 (s, 2H), 4.25-4.32 (m, 2H), 4.00 (s, 2H), 3.74-3.84 (m, 5H), 2.16 (s; 3H); MS (EI) for $C_{29}H_{26}FN_7O_3$: 540 (MH$^+$).

STEP 6: A mixture of methyl [6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-yl]carbamate (15 mg, 0.028 mmol) in methanol and 2 M aqueous potassium hydroxide (1:1, 2 mL) was stirred at 65° C. for 18 hours. The reaction mixture was cooled, adjusted to pH 10 with 2 N hydrochloric acid, concentrated, diluted with ethyl acetate (10 mL), washed with brine solution (5 mL), dried over sodium sulfate, filtered and concentrated. The residue was purified by preparative reverse phase HPLC to give 6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine (8.9 mg, 67% yield). $^1$H NMR (400 MHz, DMSO-D$_6$): 8.46 (1H), 8.02 (br, 1H), 7.47 (d, 1H), 7.39 (dd, 1H), 7.10 to 6.96 (m, 5H), 7.75 (br, 1H), 4.53 (s, 2H), 4.30 (m, 2H), 4.00 (s, 2H), 3.89 (m, 2H), 2.22 (s, 3H), MS (EI) for $C_{27}H_{24}FN_7O$: 428 (MH$^+$).

Using analogous synthetic techniques and substituting with alternative starting reagents in step 2 the following compounds of the invention were prepared. Alternative starting materials were obtained commercially unless otherwise indicated.

6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-amine. Synthesized as the dihydrochloride salt according to the method of example 13 using (4-{[(1,1-dimethylethyl)oxy]carbonyl}-2,3,4,5-tetrahydro-1,4-benzoxazepin-7-yl)boronic acid (example 1, step 2) in step 1 and with 4-chloro-6,6-dimethyl-5,6,7,8-tetrahydroquinazoline (reagent preparation 3) in step 2. $^1$H NMR (400 MHz, DMSO-D$_6$): 8.68 (s, 1H), 8.62 (bs, 2H), 8.41 (s, 1H), 7.96 (s, 1h), 7.78 (s, 1H), 7.57 (d, 1H), 7.06 (d, 1H), 5.07 (s, 2H), 4.43-4.51 (m, 2H), 4.13-4.22 (m, 1H), 2.74-2.84 (m, 2H), 2.53 (s, 2H), 1.53-1.62 (m, 2H), 0.86 (s, 6H); MS (EI) for $C_{25}H_{27}N_7O$: 442.4 (MH$^+$).

6-[4-(6-bromoquinazolin-4-yl)-2,3,4,5-tetrahydro-1,4-benzoxazepin-7-yl]-1H-imidazo[4,5-b]pyridin-2-amine. Synthesized as the dihydrochloride salt according to the method of example 13 using (4-{[(1,1-dimethylethyl)oxy]carbonyl}-2,3,4,5-tetrahydro-1,4-benzoxazepin-7-yl)boronic acid (example 1, step 2) in step 1 and 6-bromo-4-chloroquinazoline in step 2. $^1$H NMR (400 MHz, DMSO-D$_6$): δ 8.69 (s, 1H), 8.47 (s, 1H), 8.36 (s, 1H), 8.15 (dd, 1h), 8.11 (s, 1H), 7.82 (s, 1H), 7.79 (d, 1H), 7.64 (d, 1H), 7.16 (s, 1H), 5.14 (s, 2H), 4.66-4.74 (m, 2H), 4.54-4.61 (m, 2H); MS (EI) for $C_{23}H_{18}BrN$ 6-[4-(6-fluoroquinazolin-4-yl)-2,3,4,5-tetrahydro-1,4-benzoxazepin-7-yl]-1H-imidazo[4,5-b]pyridin-2-amine. Synthesized according to the method of example 13 using 4-chloro-6-fluoroquinazoline in step 2. $^1$H NMR (400 MHz, CDCl$_3$): 8.68 (s, 1H), 8.39 (d, 1H), 8.10-7.84 (m, 4H), 7.79 (d, 1H), 7.59-7.54 (dd, 1H), 7.09 (d, 1H), 5.47 (s, 2H), 4.69-4.59 (m, 4H). MS (EI) for $C_{25}H_{22}FN_7O_4$: 428.1 (MH$^+$).

6-[4-(6-chloroquinazolin-4-yl)-2,3,4,5-tetrahydro-1,4-benzoxazepin-7-yl]-1H-imidazo[4,5-b]pyridin-2-amine. Synthesized according to the method of example 13 using 4,6-dichloroquinazoline in step 2. $^1$H NMR (400 MHz, MeOH): 8.55 (s, 1H), 8.31 (m, 1H), 8.09 (m, 1H), 7.83-7.79 (m, 3H), 7.68 (m, 1H), 7.55-7.52 (m, 1H), 7.13-7.09 (m, 1H), 5.08 (s, 2H), 4.55-4.50 (m, 2H), 4.30-4.25 (m, 2H); MS (EI) for $C_{23}H_{18}ClN_7O$: 444.1 (MH$^+$).

6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 4-chloro-5-(4-fluorobenzyl)-6-methylpyrimidine (reagent preparation 5) followed by step 6. $^1$H NMR (400 MHz, DMSO-D$_6$): 8.46 (s, 1H), 8.02 (br, 1H), 7.47 (d, 1H), 7.39 (dd, 1H), 7.10 to 6.96 (m, 5H), 7.75 (br, 1H), 4.53 (s, 2H), 4.30 (m, 2H), 4.00 (s, 2H), 3.89 (m, 2H), 2.22 (s, 3H), MS (EI) for $C_{27}H_{24}FN_7O$: 428 (MH$^+$).

6-[4-(6-ethyl-5,6,7,8-tetrahydroquinazolin-4-yl)-2,3,4,5-tetrahydro-1,4-benzoxazepin-7-yl]-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 4-chloro-6-ethyl-5,6,7,8-tetrahydroquinazoline (reagent preparation 8) followed by step 6. $^1$H NMR (400 MHz, Methanol-D$_4$): 8.39 (s, 1H), 8.18 (s, 1H), 7.61 (s, 1H), 7.54 (br, 1H), 7.40 (d, 1H), 7.02 (d, 1H), 4.72 (dd, 2H), 4.50 (m, 1H), 4.33 (m, 1H), 4.09 (m, 1H), 3.84 (dd, 1H), 2.88 (m, 1H), 2.76 (m, 1H), 2.57 (dd, 1H), 2.41 (dd, 1H), 1.95 (m, 1H), 1.46 (m, 1H), 1.36 (m, 2H), 0.88 (t, 3H). MS (EI) for $C_{25}H_{27}N_7O$: 442 (MH$^+$).

6-[4-(7-methyl-5,6,7,8-tetrahydroquinazolin-4-yl)-2,3,4,5-tetrahydro-1,4-benzoxazepin-7-yl]-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 4-chloro-7-methyl-5,6,7,8-tetrahydroquinazoline (reagent preparation 8) followed by step 6. $^1$H NMR (400 MHz, DMSO-D$_6$): 8.31 (1H), 8.13 (br, 1H), 7.64 (d, 1H), 7.49 (br, 1H), 7.41 (dd, 1H), 7.02 (d, 2H), 4.76 (dd, 2H), 4.41 (m, 1H), 4.23 (m, 1H), 4.06 to 3.91 (m, 2H), 2.88 (m, 2H0, 2.59 (dt, 1H), 2.30 (dd, 1H), 1.92 (m, 2H), 1.19 (m, 1H), 1.08 (d, 3H), MS (EI) for $C_{24}H_{25}N_7O$: 428 (MH$^+$).

6-{4-[6,7-bis(methyloxy)quinazolin-4-yl]-2,3,4,5-tetrahydro-1,4-benzoxazepin-7-yl}-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 4-chloro-6,7-dimethoxyquinazoline followed by step 6. $^1$H NMR (400 MHz, Methanol-D$_4$): 8.46 (s, 1H), 8.19 (br, 1H), 7.69 (br, 1H), 7.64 (d, 1H), 7.50 (dd, 1H), 7.14 (s, 1H), 7.12 (s, 1H), 7.10 (d, 1H), 5.04 (s, 2H), 4.54 (m, 2H), 4.16 (m, 2H), 3.95 (s, 3H), 3.56 (s, 3H), MS (EI) for $C_{25}H_{23}FN_7O_3$: 470 (MH$^+$).

6-{4-[6-(methyloxy)quinazolin-4-yl]-2,3,4,5-tetrahydro-1,4-benzoxazepin-7-yl}-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 4-chloro-6-methoxyquinazoline followed by step 6. $^1$H NMR (400 MHz, Methanol-D$_4$): 8.45 (s, 1H), 8.19 (br, 1H), 7.71 (br, 1H), 7.67 (br, 1H), 7.61 (br, 1H), 7.48 (dd, 1H), 7.42 (dd, 1H), 7.18 (d, 1H), 7.10 (d, 1H), 5.02 (s, 2H), 4.53 (m, 2H), 4.17 (m, 2H), 3.58 (s, 3H), MS (EI) for $C_{24}H_{21}N_7O_2$: 440 (MH$^+$).

6-[4-(6-iodoquinazolin-4-yl)-2,3,4,5-tetrahydro-1,4-benzoxazepin-7-yl]-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 4-chloro-6-iodoquinazoline followed by step 6. $^1$H NMR (400 MHz, Methanol-D$_4$): 8.56 (s, 1H), 8.38 (br, 1H), 8.34 (br, 1H), 8.03 (dd, 1H), 7.81 (br, 1H), 7.65 (br, 1H), 7.54 (s, 1H), 7.52 (s, 1H), 7.11 (d, 1H), 5.01 (s, 2H), 4.51 (m, 2H), 4.21 (m, 2H), MS (EI) for $C_{23}H_{18}N_7O$: 536 (MH$^+$).

6-{4-[7-bromo-6-(methyloxy)quinazolin-4-yl]-2,3,4,5-tetrahydro-1,4-benzoxazepin-7-yl}-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 7-bromo-4-chloro-6-methoxyquinazoline (reagent preparation 1) followed by step 6. $^1$H NMR (400 MHz, Methanol-D$_4$): 8.48 (s, 1H), 8.19 (br, 1H), 8.00 (br, 1H), 7.67 (br, 1H), 7.66 (br, 1H), 7.58 (dd, 1H), 7.17 (s, 1H), 7.10 (d, 1H), 5.07 (s, 2H), 4.55 (m, 2H), 4.19 (m, 2H), 3.59 (s, 3H), MS (EI) for $C_{24}H_{20}BrN_7O_2$: 518 (MH$^+$).

6-[4-(6-bromo-7-chloroquinazolin-4-yl)-2,3,4,5-tetrahydro-1,4-benzoxazepin-7-yl]-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 6-bromo-4,7-dichloroquinazoline (reagent preparation 1) followed by step 6. $^1$H NMR (400 MHz, Methanol-D$_4$): 8.55 (s, 1H), 8.36 (s, 1H), 8.31 (br, 1H), 7.91 (br, 1H), 7.78 (br, 1H), 7.68 (br, 1H), 7.53 (dd, 1H), 7.10 (d, 1H), 5.05 (s, 2H), 4.52 (m, 2H), 4.25 (m, 2H), MS (EI) for $C_{23}H_{17}BrClN_7O$: 522 (MH$^+$).

6-{4-[6,7-bis(methyloxy)quinolin-4-yl]-2,3,4,5-tetrahydro-1,4-benzoxazepin-7-yl}-1H-imidazo[4,5-b]pyridin-2-amine. Prepared by a modification of the example 13 sequence starting with step 3 using 1,1-dimethylethyl 7-(4,4,5,5-tetramethyl-1,3,2-dioxaborolan-2-yl)-2,3-dihydro-1,4-benzoxazepine-4(5H)-carboxylate (example 9, step 1) and 2-amino-5-bromo-3-nitropyridine, followed by conducting steps 4 and 5, then 1. Subsequently step 2 was carried out using 4-chloro-6,7-dimethoxyquinoline followed by step 6. $^1$H NMR (400 Methanol-D$_4$): 8.51 (d, 1H), 8.19 (d, 1H), 7.68 (br, 1H), 7.61 (br, 1H), 7.51 (dd, 1H), 7.24 (s, 1H), 7.20 (s, 1H), 7.12 (d, 1H), 7.00 (d, 1H), 4.75 (s, 2H), 4.49 (m, 2H), 4.00 (s, 3H), 3.92 (m, 2H), 3.59 (s, 3H), MS (EI) for $C_{26}H_{24}N_6O_3$: 469 (MH$^+$).

Methyl (6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)carbamate. Prepared according to the method of example 13 by using (4-{[(1,1-dimethylethyl)oxy]carbonyl}-2,3,4,5-tetrahydro-1,4-benzoxazepin-7-yl)boronic acid (example 8, step 1) in step 1 and (7S)-4-chloro-7-ethyl-5,6,7,8-tetrahydroquinazoline (reagent preparation 3) in step 2. $^1$H NMR (400 MHz, Methanol-d$_4$): 8.44 (s, 1H), 8.34 (s, 1H), 7.88 (s, 1H), 7.60 (s, 1H), 7.47 (d, 1H), 7.05 (d, 1H), 4.72 (dd, 2H), 4.38 (m, 1H), 4.29 (m, 1H), 3.95 to 3.81 (m, 2H), 2.85 (m, 2H), 2.48 (m, 1H), 2.26 (m, 1H), 1.88 (m, 1H), 1.69 (m, 1H), 1.35 (m, 2H), 1.11 (m, 1H), 0.92 (t, 3H); MS (EI) for $C_{27}H_{29}N_7O_2$: 500 (MH$^+$).

Methyl (6-{4-[(7S)-7-ethyl-2-methyl-5,6,7,8-tetrahydroquinazolin-4-yl]-2,3,4,5-tetrahydro-1,4-benzoxazepin-7-yl}-1H-imidazo[4,5-b]pyridin-2-yl)carbamate. Prepared according to the method of example 13 by using (4-{[(1,1-dimethylethyl)oxy]carbonyl}-2,3,4,5-tetrahydro-1,4-benzoxazepin-7-yl)boronic acid (example 8, step 1) in step 1 and (7S)-4-chloro-7-ethyl-2-methyl-5,6,7,8-tetrahydroquinazoline (reagent preparation 3) in step 2. $^1$H NMR (400 MHz, Methanol-d$_4$): 8.42 (s, 1H), 7.95 (s, 1H), 7.58 (s, 1H), 7.45 (d, 1H), 7.06 (d, 1H), 4.62 (br, 2H), 4.44 (m, 1H), 4.19 (m, 1H), 4.06 (m, 1H), 3.95 (m, 1H), 3.88 (s, 3H), 2.88 (m, 2H), 2.78 (m, 1H), 2.61 (m, 1H), 2.39 (s, 3H), 2.28 (m, 1H), 1.97 (m, 1H), 1.74 (m, 1H), 1.41 (m, 2H), 1.16 (m, 1H), 0.98 (t, 3H); MS (EI) for $C_{28}H_{31}N_7O_3$: 514 (MH$^+$).

Methyl [6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-1H-imidazo[4,5-b]pyridin-2-yl]carbamate. The dihydrochloride salt was prepared as in example 13 using 1-(4-chloro-6,6-dimethyl-5,6,7,8-tetrahydroquinazolin-2-yl)-N,N-dimethylmethanamine (reagent preparation 17) in step 2 and omission of step 6. $^1$H NMR (400 MHz, CD$_3$OD) δ 8.70-8.54 (m, 2H), 8.02 (d, 1H), 7.61 (dt, 1H), 7.10 (d, 1H), 5.18 (s, 2H), 4.57-4.50 (m, 2H), 4.47 (s, 2H), 4.27-4.15 (m, 2H), 3.93 (s, 3H), 2.93-2.81 (m, 8H), 2.57 (s, 2H), 1.71 (t, 2H), 0.92 (s, 6H); MS (ES) for $C_{30}H_{36}N_8O_3$: 557.2 (MH$^+$).

Methyl [6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-1H-benzimidazol-2-yl]carbamate. Prepared as in example 13 using 1-(4-chloro-6,6-dimethyl-5,6,7,8-tetrahydroquinazolin-2-yl)-N,N-dimethylmethanamine (reagent preparation 17) in step 2,4-bromo-2-nitroaniline in step 3 then omission of step 6. $^1$H NMR (400 MHz, CD$_3$OD) δ 7.62 (d, 1H), 7.58 (d, 1H), 7.45 (td, 2H), 7.40 (dd, 1H), 7.01 (d, 1H), 4.76 (s, 2H), 4.37-4.31 (m, 2H), 4.03-3.96 (m, 2H), 3.85 (s, 3H), 3.65 (s, 2H), 2.79 (t, 2H), 2.50 (s, 2H), 2.37 (s, 6H), 1.68 (t, 2H), 0.91 (s, 6H); MS (ES) for $C_{31}H_{37}N_7O_3$: 556.2 (MH$^+$).

Example 14

6-(4-{5-[(4-Fluorophenyl)methyl]-6-methylpyrimidin-4-yl}-2,3,4,5-tetrahydro-1,4-benzoxazepin-7-yl)-1H-benzimidazol-2-amine STEP 1: A mixture of methyl [6-(4-{5-[(4-fluorophenyl)methyl]-6-methylpyrimidin-4-yl}-2,3,4,5-tetrahydro-1,4-benzoxazepin-7-yl)-1H-benzimidazol-2-yl]carbamate (example 2) (60 mg, 0.11 mmol) in methanol and 2M potassium hydroxide (1:1, 2 mL) was stirred at 65° C. for 18 hours. The reaction mixture was cooled, adjusted to pH 10 with 2M hydrochloric acid, concentrated, diluted with ethyl acetate (10 mL), washed with brine solution (5 mL), dried over sodium sulfate, filtered, concentrated. The residue was purified by preparative reverse phase HPLC to give 6-(4-{5-[(4-fluorophenyl)methyl]-6-methylpyrimidin-4-yl}-2,3,4,5-tetrahydro-1,4-benzoxazepin-7-yl)-1H-benzimidazol-2-amine (29 mg, 54% yield). $^1$H NMR (400 MHz, Methanol-d$_4$): 8.44 (1H), 7.37 (dd, 1H), 7.31 (s, 1H), 7.29 (s, 1H), 7.14 (dd, 1H), 7.07-7.01 (m, 2H), 6.99 to 6.91 (m, 3H), 6.70 (br, 1H), 4.49 (s, 2H), 4.26 (m, 2H), 3.95 (s, 2H), 3.86 (m, 2H), 2.19 (s, 3H), MS (EI) for $C_{28}H_{25}FN_6O$: 481 (MH$^+$).

Using analogous synthetic techniques and substituting with alternative starting reagents in step 1 the following compounds of the invention were prepared. Alternative starting materials were obtained commercially unless otherwise indicated.

6-{4-[6,7-bis(methyloxy)quinolin-4-yl]-2,3,4,5-tetrahydro-1,4-benzoxazepin-7-yl}-1H-benzimidazol-2-amine. Prepared according to the method of example 14 by using methyl (6-{4-[6,7-bis(methyloxy)quinolin-4-yl]-2,3,4,5-tetrahydro-1,4-benzoxazepin-7-yl}-1H-benzimidazol-2-yl)carbamate (example 2). $^1$H NMR (400 MHz, Methanol-D$_4$): 8.51 (d, 1H), 8.19 (d, 1H), 7.68 (br, 1H), 7.61 (br, 1H), 7.51 (dd, 1H), 7.24 (s, 1H), 7.20 (s, 1H), 7.12 (d, 1H), 7.00 (d, 1H), 4.75 (s, 2H), 4.49 (m, 2H), 4.00 (s, 3H), 3.92 (m, 2H), 3.59 (s, 3H), MS (EI) for $C_{27}H_{25}N_5O_3$: 468 (MH$^+$).

6-[4-(6,6-dimethyl-5,6,7,8-tetrahydroquinazolin-4-yl)-2,3,4,5-tetrahydro-1,4-benzoxazepin-7-yl]-1H-benzimidazol- 2-amine. Prepared according to the method of example 14 by using methyl {6-[4-(6,6-dimethyl-5,6,7,8-tetrahydroquinazolin-4-yl)-2,3,4,5-tetrahydro-1,4-benzoxazepin-7-yl]-1H-benzimidazol-2-yl}carbamate (example 27). $^1$H NMR (400 MHz, d$_6$-DMSO): 8.70 (s, 1H), 8.56 (s, 2H), 7.68 (m, 1H), 7.58 (s, 1H), 7.51-7.47 (m, 2H), 7.01 (d, 1H), 5.08 (br s, 2H), 4.47 (m, 2H), 4.19 (m, 2H), 2.79 (t, 2H), 2.54 (s, 2H), 1.73 (s, 3H), 1.58 (t, 2H), 0.84 (s, 6H); MS (EI) for C$_{26}$H$_{28}$N$_6$O: 441 (MH$^+$).

Example 15

N-(2-Fluoroethyl)-5-(4-{5-[(4-fluorophenyl)methyl]-6-methylpyrimidin-4-yl}-2,3,4,5-tetrahydro-1,4-benzoxazepin-7-yl)-1H-benzimidazol-2-amine STEP 1: 2-Fluoroethylamine hydrochloride salt (282.4 mg, 2.83 mmol) was suspended in 1:1 THF:DCM (6 mL) followed by addition of DIPEA (2.5 mL, 14.35 mmol). The mixture was cooled to 0° C. followed by slow addition of thiophosgene (217 uL, 2.8 mmol) by syringe over five minutes then allowed to slowly warm to room temperature over 30 minutes. 4-Bromobenzene-1,2-diamine (530 mg, 2.8 mmol) was then added and the reaction mixture was allowed to stir at room temperature over an additional 12 h. The mixture was concentrated and the residue partitioned with ethyl acetate and 10% aqueous citric acid. The organic phase was washed twice with additional 10% aqueous citric acid then brine, dried over anhydrous sodium sulfate, filtered and concentrated. The crude mixture of thiourea thus obtained was taken into THF (15 mL) followed by addition of mercury (II) oxide (640 mg, 2.95 mmol). The mixture was brought to reflux for 6 h then stirred an additional 60 h at room temperature. The crude mixture was filtered through a bed of celite with ethyl acetate washing and the filtrate concentrated then taken back into ethyl acetate. The organic solution was washed once with 1 M aqueous hydrochloric acid and the organic phase discarded. The aqueous phase was filtered to remove trace insoluble residue and the filtrate basified to pH 9-10 by dropwise addition of 50% aqueous sodium hydroxide. The aqueous phase was then extracted once with ethyl acetate and the organic solution was washed with brine then dried over anhydrous sodium sulfate, filtered and concentrated to afford crude 5-bromo-N-(2-fluoroethyl)-1H-benzo[d]imidazol-2-amine (390 mg, 53% yield) which was carried forward without further purification. MS (EI) for C$_9$H$_9$BrFN$_3$: 258, 260 (MH$^+$).

STEP 2: 5-bromo-N-(2-fluoroethyl)-1H-benzo[d]imidazol-2-amine (390 mg, 1.51 mmol) thus obtained in step 1 was taken into THF (15 mL) followed by addition of DIPEA (600 uL, 3.4 mmol) and isobutyl chloroformate (400 uL, 3.06 mmol) and the mixture was stirred at room temperature for 1 h. The mixture was concentrated and the residue partitioned with ethyl acetate and 10% aqueous citric acid. The organic phase was washed with brine, dried over anhydrous sodium sulfate, filtered and concentrated. The residue was purified by silica gel chromatography to afford isobutyl 5-bromo-2-(2-fluoroethylamino)-1H-benzo[d]imidazole-1-carboxylate (290 mg, 54% yield) as a colorless crystalline solid. MS (EI) for C$_{14}$H$_{17}$BrFN$_3$O$_2$: 358, 360 (MH$^+$).

STEP 3: Isobutyl 5-bromo-2-(2-fluoroethylamino)-1H-benzo[d]imidazole-1-carboxylate (76 mg, 0.21 mmol) and (4-{5-[(4-fluorophenyl)methyl]-6-methylpyrimidin-4-yl}-2,3,4,5-tetrahydro-1,4-benzoxazepin-7-yl)boronic acid (example 8 step 2) (100 mg, 0.25 mmol), and [1,1'-Bis(diphenylphosphino)ferrocene]dichloropalladium(II) (8.5 mg, 0.01 mmol) were taken into dioxane (1 mL) and water (200 uL) followed by addition of DIPEA (180 uL, 1.03 mmol) and the mixture was heated to 95° C. over 12 h. On cooling to room temperature the crude mixture was diluted with ethyl acetate and dried over anhydrous sodium sulfate then filtered through a bed of silica gel. The filtrate was concentrated and the residue taken into methanol (5 mL) and basified by addition of 5 drops of 50% aqueous sodium hydroxide. The methanol solution was stirred for 0.5 h at room temperature then concentrated. The residue was partitioned with isopropyl acetate and 1M aqueous sodium hydroxide. The organic phase was washed twice with additional 1M aqueous sodium hydroxide then dried over anhydrous sodium sulfate, filtered and concentrated. The residue was purified by silica gel chromatography using 20:1 ethyl acetate:ethanol then 10% methanol in dichloromethane as eluent. Fractions containing pure material were concentrated and the residue triturated with ethyl ether. The suspension collected by filtration to give N-(2-fluoroethyl)-5-(4-{5-[(4-fluorophenyl)methyl]-6-methylpyrimidin-4-yl}-2,3,4,5-tetrahydro-1,4-benzoxazepin-7-yl)-1H-benzimidazol-2-amine (27.4 mg, 25% yield). $^1$H NMR (400 MHZ, DMSO-d$_6$): 10.84 (br s, 1H), 8.50 (s, 1H), 7.34 (d, 1H), 7.26 (br s, 1H), 7.18 (d, 1H), 7.12 (d, 4H), 6.98-6.91 (m, 3H), 6.85 (s, 1H), 4.68 (m, 1H), 4.55 (m, 1H), 4.46 (s, 2H), 4.25 (br s, 2H), 4.01 (s, 2H), 3.77 (br s, 2H), 2.16 (s, 3H). MS (EI) for C$_{30}$H$_{28}$F$_2$N$_6$O: 528 (MH$^+$).

Using analogous synthetic techniques and substituting with alternative starting reagents in step 1 and conducting protecting group introduction/removal in steps 2 and 3 as required according to literature techniques appropriate for a given protecting group (see for example: Greene and Wuts, Protective Groups in Organic Synthetic, Wiley-Interscience) the following compounds of the invention were prepared. Alternative starting materials were obtained commercially unless otherwise indicated.

N-Ethyl-6-(4-{5-[(4-fluorophenyl)methyl]-6-methylpyrimidin-4-yl}-2,3,4,5-tetrahydro-1,4-benzoxazepin-7-yl)-1H-benzimidazol-2-amine. Synthesized according to the method of example 15 using ethyl isothiocyanate in step 1. $^1$H NMR (400 MHz, d$_6$-DMSO): 10.78 (s, 1H), 8.50 (s, 1H), 7.38 (br s, 1H), 7.24 (br d, 1H), 7.14 (d, 6H), 6.98 (d, 1H), 6.86 (br s, 1H), 6.60 (br s, 1H), 4.46 (s, 2H), 4.25 (m, 2H), 4.02 (s, 2H), 3.77 (m, 2H), 3.32 (dd, 2H), 2.16 (s, 3H), 1.19 (t, 3H). MS (EI) for C$_{30}$H$_{29}$FN$_6$O: 509 (MH$^+$).

6-[4-(6,6-dimethyl-5,6,7,8-tetrahydroquinazolin-4-yl)-2,3,4,5-tetrahydro-1,4-benzoxazepin-7-yl]-N-(2-fluoroethyl)-1H-benzimidazol-2-amine. Synthesized according to the method of example 15 using [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 3. $^1$H NMR (400 MHZ, DMSO-d$_6$): 9.41 (tr, 1H), 8.71 (s, 1H), 7.69 (s, 1H), 7.60 (s, 1H), 7.53-7.45 (m, 3H), 7.01 (d, 1H), 5.09 (s, 2H), 4.73 (tr, 1H), 4.62 (tr, 1H), 4.47 (s, 2H), 4.20 (s, 2H), 3.86 (q, 1H), 3.79 (q, 1H), 2.54 (s, 2H), 1.57 (tr, 2H), 0.86 (s, 6H); MS (EI) for C$_{28}$H$_{31}$FN$_6$O: 487 (MH$^+$).

6-[4-(6,6-dimethyl-5,6,7,8-tetrahydroquinazolin-4-yl)-2,3,4,5-tetrahydro-1,4-benzoxazepin-7-yl]-N-ethyl-1H-benzimidazol-2-amine. Prepared according to the method of example 15 by using ethyl isothiocyanate in step 1 and [4-(6,6-dimethyl-5,6,7,8-tetrahydroquinazolin-4-yl)-2,3,4,5-tetrahydro-1,4-benzoxazepin-7-yl]boronic acid (reagent preparation 23) in step 3. $^1$H NMR (400 MHz, d$_6$-DMSO): 8.37 (s, 1H), 7.56 (d, 1), 7.43 (dd, 1H), 7.38 (s, 1H), 7.20 (s, 2H), 7.00 (d, 1H), 4.62 (s, 2H), 4.29 (m, 2H), 3.83 (m, 2H), 3.35 (q, 2H), 2.70 (t, 2H), 2.47 (s, 2H), 1.60 (t, 2H), 1.19 (t, 3H), 0.86 (s, 6H); MS (EI) for C$_{28}$H$_{32}$N$_6$O: 469 (MH$^+$).

Example 16

5-(4-{5-[(4-fluorophenyl)methyl]-6-methylpyrimidin-4-yl}-2,3,4,5-tetrahydro-1,4-benzoxazepin-7-yl)-3H-imidazo[4,5-b]pyridin-2-amine STEP 1: To a solution of (4-{5-[(4-fluorophenyl)methyl]pyrimidin-4-yl}-2,3,4,5-tetrahydro-1,4-benzoxazepin-7-yl)boronic acid (example 8, step 2) (0.200 g, 0.509 mmol) and 2-amino-6-chloro-3-nitropyridine (0.106 g, 0.610 mmol) in dioxane (3 mL) and water (0.4 ml) was added potassium carbonate (0.211 g, 1.53 mmol). The solution was sparged with $N_2$ (g) for five minutes before the addition of dichloro[1,1-bis(diphenylphosphino)ferrocenepalladium (II) dichloromethane adduct (0.042 g, 10 mol %). The resulting suspension was heated at 90° C. for 20 h in a sealed tube vessel. On cooling to room temperature the mixture was diluted with acetonitrile (25 mL) then filtered and concentrated to afford 6-(4-{5-[(4-fluorophenyl)methyl]pyrimidin-4-yl}-2,3,4,5-tetrahydro-1,4-benzoxazepin-7-yl)-3-nitropyridin-2-amine (0.247 g, 100% yield) as an oil that was used without further purification. MS (EI) for $C_{26}H_{23}FN_6O_3$: 487 (MH$^+$).

STEP 2: To a solution 6-(4-{5-[(4-fluorophenyl)methyl]pyrimidin-4-yl}-2,3,4,5-tetrahydro-1,4-benzoxazepin-7-yl)-3-nitropyridin-2-amine as obtained in step 1 (0.247 g, 0.508) in ethanol (20 mL) was added 10% palladium on carbon (0.200 g) and glacial acetic acid (1 mL). The solution was sparged with $N_2$ (g) for five minutes then hydrogenated using a Parr apparatus for 1 hour under $H_2$ (g) at 40 psi. Filtration and concentration afforded a brown residue that was purified by silica gel chromatography (9:1 dichloromethane/methanol) to provide 6-(4-{5-[(4-fluorophenyl)methyl]pyrimidin-4-yl}-2,3,4,5-tetrahydro-1,4-benzoxazepin-7-yl)pyridine-2,3-diamine (0.200 g, 86%) as a light brown oil. MS (EI) for $C_{26}H_{25}FN_6O$: 457 (MH$^+$).

STEP 3: To a solution of 6-(4-{5-[(4-fluorophenyl)methyl]pyrimidin-4-yl}-2,3,4,5-tetrahydro-1,4-benzoxazepin-7-yl)pyridine-2,3-diamine (0.200 g, 0.438 mmol) in glacial acetic acid (3 mL) was added 1,3-bis(methoxycarbonyl)-2-methyl-2-thiopseudourea (0.117 g, 0.570 mmol). The reaction mixture was stirred at 80° C. for 2 h and then concentrated. Ethyl acetate (100 mL) was added to the residue, and the solution was washed with saturated sodium bicarbonate (50 mL) then dried over anhydrous sodium sulfate. Filtration and concentration afforded a brown residue that was taken up in diethyl ether (10 mL) and the resulting precipitate was collected by filtration to give methyl [5-(4-{5-[(4-fluorophenyl)methyl]pyrimidin-4-yl}-2,3,4,5-tetrahydro-1,4-benzoxazepin-7-yl)-3H-imidazo[4,5-b]pyridine-2-yl]carbamate (0.70 g, 30% yield) as a brown solid. MS (EI) for $C_{26}H_{25}FN_6O$: 457 (MH$^+$).

STEP 4: To a solution of methyl [5-(4-{5-[(4-fluorophenyl)methyl]pyrimidin-4-yl}-2,3,4,5-tetrahydro-1,4-benzoxazepin-7-yl)-3H-imidazo[4,5-b]pyridine-2-yl]carbamate (0.70 g, 0.129 mmol) in methanol (3 mL) was added 2 M aqueous potassium hydroxide (3 mL) and the mixture was heated at 100° C. for 1 hour. After cooling to room temperature the reaction mixture was concentrated and then diluted with water (5 mL) and the pH adjusted to 9 with 1 M hydrochloric acid. The resulting precipitate was collected by filtration, dissolved in a minimum of methanol and purified by preparative reverse phase HPLC to afford 5-(4-{5-[(4-fluorophenyl)methyl]-6-methylpyrimidin-4-yl}-2,3,4,5-tetrahydro-1,4-benzoxazepin-7-yl)-3H-imidazo[4,5-b]pyridin-2-amine (0.0283 g, 46% yield. $^1$H NMR (400 MHz, methanol-d$_4$): 8.45 (s, 1H), 7.75 (d, 1H), 7.51 (d, 1H), 7.17 (d, 1H), 7.11-7.06 (m, 3H), 7.01-6.96 (m, 3H), 4.55 (s, 2H), 4.30 (t, 2H), 4.00 (s, 2H), 3.89 (t, 2H), 2.22 (s, 3H); MS (EI) for $C_{27}H_{24}FN_7O$: 482 (MH$^+$)

Example 17

N,N-dimethyl-6-(4-quinolin-4-yl-2,3,4,5-tetrahydro-1,4-benzoxazepin-7-yl)-1H-benzimidazol-2-amine STEP 1: A solution of 4-(4-quinolin-4-yl-2,3,4,5-tetrahydrobenzoxazepin-7-yl)benzene-1,2-diamine (example 2) (50 mg, 0.13 mmol), N-(chloro(dimethylamino)methylene)-N-methylmethanaminium hexafluorophosphate (44 mg, 0.16 mmol) and N-methylmorpholine (0.20 g, 1.9 mmol) in N,N-dimethylformamide (10 mL) was heated to 140° C. for 1 hour. After cooling the reaction was diluted with ethyl acetate (80 mL), and washed twice with water (2×20 mL) and brine (20 mL). The solution was dried over anhydrous sodium sulfate, filtered and concentrated to a solid residue. The residue was then taken into N,N-dimethylformamide (3 mL), then diluted with chloroform (15 mL). The resulting solid was collected by filtration and the filter cake was precipitated once more using the same technique to give N,N-dimethyl-6-(4-quinolin-4-yl-2,3,4,5-tetrahydro-1,4-benzoxazepin-7-yl)-1H-benzimidazol-2-amine (27 mg, 48% yield) as a gray powder. $^1$H NMR (400 MHz, d6-DMSO): 8.56 (d, 1H), 8.30 (d, 1H), 8.06-7.97 (m, 2H), 7.90 (br s, 1H), 7.72 (t, 1H), 7.62 (br s, 1H), 7.56 (m, 2H), 7.48 (d, 1H), 6.99 (dd, 2H), 5.28 (s, 2H), 4.61 (s, 2H), 4.38 (s, 2H), 3.28 (s, 6H); MS (EI) for $C_{27}H_{25}N_5O$: 436 (MH$^+$).

Example 18

7-(2-cyclopropyl-1H-benzimidazol-6-yl)-4-quinolin-4-yl-2,3,4,5-tetrahydro-1,4-benzoxazepine STEP 1: To cyclopropanecarboxylic acid (33 mg, 0.39 mmol) in N,N-dimethylformamide (10 mL) added O-benzotriazole-N,N,N',N'-tetramethyluronium hexafluorophosphate (0.15 g, 0.40 mmol) and the mixture stirred at 25° C. for 30 minutes. 4-(4-quinolin-4-yl-2,3,4,5-tetrahydrobenzoxazepin-7-yl)benzene-1,2-diamine (example 2) (100 mg, 0.26 mmol) was added followed by and N-methylmorpholine (66 uL, 0.60 mmol) and stirred 18 hours at 25° C. The reaction was diluted with ethyl acetate (80 mL), and washed with 2M aqueous sodium hydroxide (40 mL), water (40 mL) and brine (20 mL). The organic phase was dried over anhydrous sodium sulfate, filtered and concentrated. The residue was purified by silica gel column chromatography (methanol/ethyl acetate, 1:8). This afforded N-(2-amino-5-(4-quinolin-4-yl-2,3,4,5-tetrahydrobenzoxazepin-7-yl)phenyl)cyclopropanecarboxamide (55 mg, 47% yield). MS (EI) for $C_{28}H_{26}N_4O_2$: 451 (MH$^+$).

STEP 2: As solution of N-(2-amino-5-(4-quinolin-4-yl-2,3,4,5-tetrahydrobenzoxazepin-7-yl)phenyl)cyclopropanecarboxamide (55 mg, 0.12 mmol) in acetic acid (10 mL) was heated to 110° C. for 4 hours. The reaction mixture was then cooled and concentrated. The residue was chromatographed on silica gel using (methanol/ethyl acetate, 1:10) as eluent. Product containing fractions were concentrated and the residue purified by preparative reverse phase HPLC (0.1% trifluoroacetic acid buffered aqueous acetonitrile mobile phase) to give 7-(2-cyclopropyl-1H-benzimidazol-6-yl)-4-quinolin-4-yl-2,3,4,5-tetrahydro-1,4-benzoxazepine (16.6 mg, 32% yield) as the trifluoroacetic acid salt. $^1$H NMR (400 MHz, d$_6$-DMSO): 8.57 (d, 1H), 8.31 (d, 1H), 7.98 (m, 3H), 7.88 (s, 1H), 7.70 (m, 3H), 7.61 (dd, 1H), 6.99 (dd, 2H), 5.30 (br s, 2H), 4.62 (br s, 2H), 4.41 (br s, 2H), 2.46 (m, 1H), 1.36 (m, 4H); MS (EI) for $C_{28}H_{24}N_4O$: 433 (MH$^+$).

Using analogous synthetic techniques and substituting with alternative starting reagents in step 1 the following compounds of the invention were prepared. Alternative starting materials were obtained commercially unless otherwise indicated.

7-{2-[(methyloxy)methyl]-1H-benzimidazol-6-yl}-4-quinolin-4-yl-2,3,4,5-tetrahydro-1,4-benzoxazepine. Synthesized according to the method of example 18 using methoxyacetic acid in step 1. $^1$H NMR (400 MHz, d$_6$-DMSO): 8.57 (d, 1H), 8.33 (d, 1H), 7.96 (m, 3H), 7.89 (s, 1H), 7.68 (m, 3H), 7.61 (d, 1H), 6.98 (dd, 2H), 5.33 (s, 2H), 4.81 (s, 2H) 4.58 (br s, 2H), 4.39 (br s, 2H), 3.47 (s, 3H); MS (EI) for $C_{27}H_{24}N_4O_2$: 437 (MH$^+$).

7-(2-propyl-1H-benzimidazol-6-yl)-4-quinolin-4-yl-2,3,4,5-tetrahydro-1,4-benzoxazepine. Synthesized according to the method of example 18 using butyric acid in step 1. $^1$H NMR (400 MHz, d$_6$-DMSO): 8.62 (d, 1H), 8.03 (d, 1H), 7.94 (d, 1H), 7.68 (m, 3H), 7.58 (d, 1H), 7.50 (t, 1H), 7.42 (m, 1H), 7.11 (d 1H), 7.02 (d, 1H), 4.61 (s, 2H) 4.38 (br s, 2H), 4.82 (br s, 2H), 2.81 (t, 2H), 1.82 (q, 2H), 0.95 (t, 3H)); MS (EI) for $C_{28}H_{26}N_4O$: 435 (MH$^+$).

7-(2-cyclopentyl-1H-benzimidazol-6-yl)-4-quinolin-4-yl-2,3,4,5-tetrahydro-1,4-benzoxazepine. Synthesized according to the method of example 18 using cyclopentanecarboxylic acid in step 1. $^1$H NMR (400 MHz, d$_6$-DMSO): 8.61 (d, 1H), 8.04 (d, 1H), 7.95 (d, 1H), 7.70 (m, 2H), 7.59-7.41 (m, 4H), 7.11 (d, 1H), 7.04 (d, 1H), 4.63 (s, 2H) 4.38 (br s, 2H), 3.82 (br s, 2H), 2.11 (m, 2H), 1.90 (m, 2H), 1.79 (m, 2H), 1.67 (m, 2H); MS (EI) for $C_{30}H_{28}N_4O$: 462 (MH$^+$).

7-(2-cyclohexyl-1H-benzimidazol-6-yl)-4-quinolin-4-yl-2,3,4,5-tetrahydro-1,4-benzoxazepine. Synthesized according to the method of example 18 using cyclohexanecarboxylic acid in step 1. $^1$H NMR (400 MHz, d$_6$-DMSO): 8.62 (d, 1H), 8.03 (d, 1H), 7.95 (m, 3H), 7.68 (m, 3H), 7.63 (m, 3H), 7.42 (d, 1H), 7.10 (d, 1H), 7.03 (d, 1H), 4.63 (s, 2H), 4.39 (br s, 2H), 3.81 (br s, 2H), 2.84 (m, 1H), 2.03 (d, 2H), 1.89-1.74 (m, 8H), 1.63-1.25 (m, 2H); MS (EI) for $C_{31}H_{30}N_4O$: 475 (MH$^+$).

7-(2-azetidin-3-yl-1H-benzimidazol-6-yl)-4-quinolin-4-yl-2,3,4,5-tetrahydro-1,4-benzoxazepine. Synthesized according to the method of example 18 using N—BOC azetidine-3-carboxylic acid in step 1. $^1$H NMR (400 MHz, d$_6$-DMSO): 8.96 (br d, 2H), 8.61 (d, 1H), 7.55 (d, 1H), 7.95 (m, 3H), 7.88 (s, 1H), 7.70 (m, 2H), 7.60 (m, 1H), 7.02 (d, 2H), 5.30 (s, 2H), 4.62 (br s, 2H), 4.22 (br s, 2H), 4.38 (br s, 5H); MS (EI) for $C_{28}H_{25}N_5O$: 448 (MH$^+$).

7-(2-piperidin-2-yl-1H-benzimidazol-6-yl)-4-quinolin-4-yl-2,3,4,5-tetrahydro-1,4-benzoxazepine. Synthesized according to the method of example 18 using racemic N—BOC pipecolinic acid in step 1. $^1$H NMR (400 MHz, d$_6$-DMSO): 9.96 (br d, 1H), 9.37 (m, 1H), 8.58 (d, 1H), 8.35 (d, 1H), 7.98 (m, 3H), 7.90 (s, 1H), 7.77-7.58 (m, 4H), 7.00 (m, 2H), 5.30 (s, 2H), 4.62 (m, 3H) 4.42 (br s, 2H), 3.41 (d, 1H), 3.13 (m, 1H), 2.42 (m, 2H), 0.80 (m, 5H); MS (EI) for $C_{31}H_{33}N_5O$: 492 (MH$^+$).

7-[2-(1-methylethyl)-1H-benzimidazol-6-yl]-4-quinolin-4-yl-2,3,4,5-tetrahydro-1,4-benzoxazepine. Synthesized according to the method of example 18 using isobutyric acid in step 1. $^1$H NMR (400 MHz, d$_6$-DMSO): 8.59 (d, 1H), 8.35 (d, 1H), 7.97 (m, 3H), 7.91 (br s, 1H), 7.75 (br s, 2H), 7.68 (m, 1H), 7.61 (m, 1H), 7.00 (dd, 2H), 5.29 (s, 2H), 4.62 (br s, 3H) 4.40 (br s, 2H), 3.43 (m, 1H), 1.44 (d, 6H); MS (EI) for $C_{29}H_{30}N_4O$: 451 (MH$^+$).

4-(6,6-dimethyl-5,6,7,8-tetrahydroquinazolin-4-yl)-7-(2-ethyl-1H-benzimidazol-6-yl)-2,3,4,5-tetrahydro-1,4-benzoxazepine. Prepared according to the method of example 18 omitting step 1 and by using 4-[4-(6,6-dimethyl-5,6,7,8-tetrahydroquinazolin-4-yl)-2,3,4,5-tetrahydro-1,4-benzoxazepin-7-yl]benzene-1,2-diamine and trimethyl orthopropionate in step 2. $^1$H NMR (400 MHz, d$_6$-DMSO): 8.69 (s, 1H), 7.94 (s, 1H), 7.84-7.78 (m, 3H), 7.60 (m, 1H), 7.35 (s, 1H), 7.23 (s, 1H), 7.04 (d, 1H), 5.09 (s, 2H), 4.48 (m, 2H), 4.19 (m, 2H), 3.18 (dd, 2H), 2.70 (t, 2H), 2.54 (s, 2H), 1.58 (t, 2H), 1.45 (t, 3H), 0.85 (s, 6H); MS (EI) for $C_{28}H_{31}N_5O$: 454 (MH$^+$).

Example 19

7-[2-(methylthio)-1H-benzimidazol-6-yl]-4-quinolin-4-yl-2,3,4,5-tetrahydro-1,4-benzoxazepine STEP 1: To a solution of 4-(4-quinolin-4-yl-2,3,4,5-tetrahydro-1,4-benzoxazepin-7-yl)-benzene-1,2-diamine (630 mg, 1.65 mmol, synthesized according to the method of example 2 step) in tetrahydrofuran (30 mL) was added 1,1'-thiocarbonyldiimidazole (587 mg, 3.29 mmol), and the reaction mixture was stirred at room temperature for 20 h. The mixture was concentrated and the residue crystallized from methanol to give 5-(4-quinolin-4-yl-2,3,4,5-tetrahydro-1,4-benzoxazepin-7-yl)-1,3-dihydro-2H-benzimidazole-2-thione (357 mg, 51% yield) as a brown solid. $^1$H NMR (400 MHz, DMSO-d$_6$): 12.74 (s, 1H), 12.66 (s, 1H), 8.57 (d, 1H), 8.28 (d, 1H), 8.00 (d, 1H), 7.95 (m, 1H), 7.88 (d, 1H), 7.67 (m, 1H), 7.53 (dd, 1H), 7.49 (dd, 1H), 7.40 (s, 1H), 7.24 (d, 1H), 6.97 (m, 2H), 5.21 (s, 2H), 4.58 (m, 2H), 4.33 (m, 2H); MS (EI) for $C_{25}H_{20}N_4OS$: 425 (MH$^+$).

STEP 2: A suspension of 5-(4-quinolin-4-yl-2,3,4,5-tetrahydro-1,4-benzoxazepin-7-yl)-1,3-dihydro-2H-benzimidazole-2-thione (355 mg, 0.84 mmol), potassium carbonate (578 mg, 4.18 mmol), and methyl iodide (119 mg, 0.84 mmol) in dimethylformamide (5 mL) was stirred at room temperature for 1 h. Ethyl acetate (100 mL) was added, and the organic layer was washed with water (2×20 mL), 5% aqueous lithium chloride (2×20 mL), and brine (20 mL), dried over sodium sulfate, filtered and concentrated. Column chromatography on silica (dichloromethane/methanol 95:5) provided the title Compound (220 mg, 60% yield) as a brown solid. $^1$H NMR (400 MHz, CDCl$_3$): 8.71 (d, 1H), 8.09 (m, 2H), 7.66 (m, 1H), 7.57-7.42 (m, 5H), 7.17 (d, 1H), 6.98 (d, 1H), 4.54 (s, 2H), 4.36 (m, 2H), 3.84 (m, 2H), 2.82 (s, 3H); MS (EI) for $C_{26}H_{22}N_4OS$: 439 (MH$^+$).

Example 20

N-ethyl-6-(4-quinolin-4-yl-2,3,4,5-tetrahydro-1,4-benzoxazepin-7-yl)-1H-benzimidazol-2-amine A solution of 7-[2-(methylthio)-1H-benzimidazol-6-yl]-4-quinolin-4-yl-2,3,4,5-tetra-hydro-1,4-benzoxazepine (52 mg, 0.12 mmol, prepared according to the method of example 19) and ethylamine (1.5 mL) in ethanol (3 mL) heated with microwave irradiation at 150° C. for 8 h. Purification of the crude material by preparative reverse phase HPLC (0.1% aqueous ammonium acetate-acetonitrile) provided the title Compound as acetate salt (4 mg, 7% yield) as a colorless solid. $^1$H NMR (400 MHz, methanol-d$_4$): 8.55 (d, 1H), 8.15 (d, 1H), 7.95 (d, 1H), 7.73 (m, 1H), 7.60-7.50 (m, 3H), 7.42 (m, 1H), 7.33 (dd, 1H), 7.29 (d, 1H), 7.09 (m, 2H), 4.69 (s, 2H), 4.41 (m, 2H), 3.92 (m, 2H), 3.44 (q, 2H), 1.94 (s, 3H), 1.31 (t, 3H); MS (EI) for $C_{27}H_{25}N_5O$: 436 (MH$^+$).

Using analogous synthetic techniques and substituting with alternative starting reagents the following compounds of the invention were prepared. Alternative starting materials were obtained commercially unless otherwise indicated.

N-(1-methylethyl)-6-(4-quinolin-4-yl-2,3,4,5-tetrahydro-1,4-benzoxazepin-7-yl)-1H-benzimidazol-2-amine. Prepared as trifluoroacetate salt according to the method of example 20 by using isopropylamine. $^1$H NMR (400 MHz, methanol-d$_4$): 8.38 (d, 1H), 8.33 (d, 1H), 7.98 (m, 1H), 7.91 (d, 1H), 7.76 (m, 1H), 7.68 (m, 1H), 7.60 (m, 2H), 7.56 (dd, 1H), 7.46 (d, 1H), 7.06 (m, 2H), 5.26 (s, 2H), 4.63 (m, 2H), 4.43 (m, 2H), 3.92 (h, 1H), 1.40 (d, 6H); MS (EI) for C$_{28}$H$_{27}$N$_5$O: 450 (MH$^+$).

Example 21

Methyl (6-{4-[6,7-bis(methyloxy)quinolin-4-yl]-2,3,4,5-tetrahydro-1,4-benzoxazepin-7-yl}-1H-imidazo[4,5-b]pyridin-2-yl)carbamate STEP 1: A mixture of commercially available 4-chloro-6,7-dimethoxyquinoline (120 mg, 0.53 mmol), 7-bromo-2,3-dihydro-1,4-benzoxazepine hydrochloride (example 2, step 1) (200 mg, 0.53 mmol), diisopropylethylamine (0.14 g, 1.1 mmol), in NMP (2 mL) was stirred in a microwave reactor at 120° C. for 45 min. After cooling to room temperature, the reaction mixture was purified directly by silica gel flash chromatography (0-10% methanol-dichloromethane gradient) to give 4-[6,7-bis(methyloxy)quinolin-4-yl]-7-bromo-2,3,4,5-tetrahydro-1,4-benzoxazepine (155 mg, 70% yield), MS (EI) for C$_{20}$H$_{19}$N$_2$O$_3$: 415 (MH$^+$).

STEP 2: A mixture of commercially available 3-nitro-5-(4,4,5,5-tetramethyl-1,3,2-dioxaborolan-2-yl)pyridin-2-amine (125 mg, 0.47 mmol), 4-[6,7-bis(methyloxy)quinolin-4-yl]-7-bromo-2,3,4,5-tetrahydro-1,4-benzoxazepine (155 mg, 0.47 mmol), [1,1'-bis(diphenylphosphino)ferrocene]dichloropalladium(II), complex with dichloromethane (34 mg, 0.05 mmol), cesium carbonate (300 mg, 2.4 mmol) in 1,4-dioxane (20 mL) and water (2 mL) was degassed with nitrogen for 5 minutes and then stirred at 93° C. for 18 hours. The reaction mixture was cooled to room temperature, diluted with ethyl acetate (80 mL) then filtered through a celite bed. The filtrate was washed with brine (2×50 mL), dried over sodium sulfate, filtered and concentrated. The residue was purified by silica gel flash chromatography (0 to 10% methanol-dichloromethane) to give 5-{4-[6,7-bis(methyloxy)quinolin-4-yl]-2,3,4,5-tetrahydro-1,4-benzoxazepin-7-yl}-3-nitropyridin-2-amine (135 mg, 76% yield); MS (EI) for C$_{25}$H$_{23}$N$_5$O$_5$: 474 (MH$^+$).

STEP 3: A mixture of 5-{4-[6,7-bis(methyloxy)quinolin-4-yl]-2,3,4,5-tetrahydro-1,4-benzoxazepin-7-yl}-3-nitropyridin-2-amine (135 mg, 0.28 mmol), palladium (10% on charcoal, 135 mg) and methanol (15 mL) was hydrogenated in a Parr apparatus at 45 psi for 18 hours. The mixture was filtered then concentrated to give 5-{4-[6,7-bis(methyloxy)quinolin-4-yl]-2,3,4,5-tetrahydro-1,4-benzoxazepin-7-yl}pyridine-2,3-diamine (115 mg, 91% yield), MS (EI) for C$_{25}$H$_{25}$N$_5$O$_3$: 444 (MH$^+$).

STEP 4: To a solution of 5-{4-[6,7-bis(methyloxy)quinolin-4-yl]-2,3,4,5-tetrahydro-1,4-benzoxazepin-7-yl}pyridine-2,3-diamine (85 mg, 0.19 mmol) in acetic acid (3 mL) was added 1,3-bis(methoxycarbonyl)-2-methyl-2-thiopseudourea (40 mg, 0.19 mmol). The reaction mixture was heated (65° C.) for 18 h and then concentrated. The resulting residue was dissolved in acetonitrile and purified by preparative reverse phase HPLC to provide methyl (6-{4-[6,7-bis(methyloxy)quinolin-4-yl]-2,3,4,5-tetrahydro-1,4-benzoxazepin-7-yl}-1H-imidazo[4,5-b]pyridin-2-yl)carbamate (55 mg, 54% yield) as a white solid. $^1$H NMR (400 MHz, DMSO-D$_6$): δ 7.93 (br, 2H), 7.93 (br, 1H), 7.78 (br, 1H), 7.59 (dd, 1h), 7.31 (s, 1H), 7.14 (dd, 1H), 7.09 (s, 1H), 6.95 (d, 1H), 4.60 (s, 2H), 4.43 (m, 2H), 3.89 (s, 3H), 3.78 (s, 3H), 3.73 (m, 2H), 3.53 (s, 3H), MS (EI) for C$_{28}$H$_{26}$N$_6$O$_5$: 527 (MH$^+$).

Example 22

4-(7-ethyl-5,6,7,8-tetrahydropyrido[3,4-d]pyrimidin-4-yl)-7-(2-methyl-1H-benzimidazol-6-yl)-2,3,4,5-tetrahydro-1,4-benzoxazepine STEP 1: A solution of 7-(2-methyl-1H-benzimidazol-6-yl)-4-[7-(phenylmethyl)-5,6,7,8-tetrahydropyrido[3,4-d]pyrimidin-4-yl]-2,3,4,5-tetrahydro-1,4-benzoxazepine (Example 1) (0.13 g, 0.26 mmol) in a mixture of 50% acetic acid in methanol (5 mL) was hydrogenated in the presence of 10% Pd/C at 30 psi using a Parr shaker apparatus. The catalyst was filtered off and the solvent was concentrated to give 7-(2-methyl-1H-benzimidazol-6-yl)-4-(5,6,7,8-tetrahydropyrido[4,3-d]pyrimidin-4-yl)-2,3,4,5-tetrahydro-1,4-benzoxazepine (0.1 g, quantitative). MS (EI) for C$_{24}$H$_{24}$N$_6$O: 413 (MH$^+$).

STEP 2: To a solution of 7-(2-methyl-1H-benzimidazol-6-yl)-4-(5,6,7,8-tetrahydropyrido[4,3-d]pyrimidin-4-yl)-2,3,4,5-tetrahydro-1,4-benzoxazepine (0.1 g, 0.26 mmol) and acetaldehyde (18 µL, 0.31 mmol) in a mixture of 10% aqueous tetrahydrofuran (5 mL) at 0° C. was added sodium triacetoxyborohydride (66 mg, 0.31 mmol) and the reaction mixture was stirred overnight at room temperature. The reaction mixture was diluted with ethyl acetate (50 mL), washed with brine (25 mL), dried over sodium sulfate, filtered and the solvent was concentrated. Purification by preparative reverse phase HPLC (0.1% aqueous ammonium acetate-acetonitrile) provided 4-(7-ethyl-5,6,7,8-tetrahydropyrido[3,4-d]pyrimidin-4-yl)-7-(2-methyl-1H-benzimidazol-6-yl)-2,3,4,5-tetrahydro-1,4-benzoxazepine (48 mg, 42%). $^1$H NMR (400 MHz, d$_6$-DMSO): 8.44 (s, 1H), 7.94 (d, 1H), 7.83 (d, 1H), 7.76 (dd, 1H), 7.70 (d, 1H), 7.56 (dd, 1H), 7.06 (d, 1H), 4.84 (br d, 2H), 4.40 (br s, 4H), 4.18 (br s, 1H), 3.98 (br s, 1H), 3.62 (br s, 1H), 3.28 (dd, 2H), 3.18 (br s, 2H), 2.84 (br s, 1H), 1.22 (t, 3H). MS (EI) for C$_{26}$H$_{28}$N$_6$O: 441 (MH$^+$).

Example 23

6-(4-quinolin-4-yl-2,3,4,5-tetrahydro-1,4-benzoxazepin-7-yl)-1H-benzimidazol-2-amine To a solution of 4-(4-quinolin-4-yl-2,3,4,5-tetrahydro-1,4-benzoxazepin-7-yl)-benzene-1,2-diamine (90 mg, 0.14 mmol, synthesized according to the method of example 2) in methanol (1 mL) was added a 3M solution of cyanogen bromide in dichloromethane (0.10 mL), and the reaction mixture was stirred at room temperature for 8 d. During this time additional cyanogen bromide was added after 1 d (0.10 mL), 2 d (0.20 mL), 3 d (0.20 mL), and 4 d (0.20 mL) reaction time. Ethyl acetate (50 mL) was added, and the solution was washed with 0.5N aqueous sodium hydroxide (2×50 mL), water (50 mL), and brine (50 mL), dried over sodium sulfate, filtered and concentrated. Purification by preparative reverse phase HPLC (0.1% aqueous ammonium acetate-acetonitrile) provided the title Compound as the acetate salt (8 mg, 7% yield) as an off-white solid. $^1$H NMR (400 MHz, methanol-d$_4$): 8.54 (d, 1H), 8.14 (d, 1H), 7.94 (d, 1H), 7.73 (m, 1H), 7.60-7.47 (m, 4H), 7.38 (m, 1H), 7.31 (d, 1H), 7.10 (d, 1H), 7.07 (d, 1H), 4.70 (s, 2H), 4.41 (m, 2H), 3.93 (m, 2H), 1.94 (s, 3H); MS (EI) for C$_{25}$H$_{21}$N$_5$O: 408 (MH$^+$).

Example 24

N-ethyl-6-[4-(2-methylquinazolin-4-yl)-2,3,4,5-tetrahydro-1,4-benzoxazepin-7-yl]-1H-benzimidazol-2-amine STEP 1: To a solution of 1,1-dimethylethyl 7-(4-amino-3-nitrophenyl)-2,3-dihydro-1,4-benzoxazepine-4(5H)-carboxylate (10 g, 26 mmol) in dioxane (50 mL) was added hydrogen chloride in dioxane (4 M, 50 mL, 200 mmol), and the mixture was stirred at rt for 16 h. The volatile materials were then removed to provide 2-nitro-4-(2,3,4,5-tetrahydro-1,4-benzoxazepin-7-yl)aniline dihydrochloride in quantitative yield. MS (EI) for $C_{15}H_{15}N_3O_3$: 286 (MH$^+$).

STEP 2: A solution of 2-nitro-4-(2,3,4,5-tetrahydro-1,4-benzoxazepin-7-yl)aniline dihydrochloride (323 mg, 1.0 mmol), 4-chloro-2-methylquinazoline (179 mg, 1.0 mmol), and diisopropylethylamine (700 uL, 4.0 mmol) in NMP (11 mL) was heated to 90° C. and stirred for 40 min. After cooling to rt, water was added to the reaction mixture. The orange precipitate formed was collected by filtration and then dried to provide 4-[4-(2-methylquinazolin-4-yl)-2,3,4,5-tetrahydro-1,4-benzoxazepin-7-yl]-2-nitroaniline (380 mg, 0.89 mmol, 89% yield) as a bright orange powder. MS (EI) for $C_{24}H_{21}N_5O_3$: 428 (MH$^+$).

STEP 3: To a solution of 4-[4-(2-methylquinazolin-4-yl)-2,3,4,5-tetrahydro-1,4-benzoxazepin-7-yl]-2-nitroaniline (380 mg, 0.89 mmol) in THF (12 mL) was added palladium on carbon (wet, 100 mg). The resulting suspension was subjected to an atmosphere of hydrogen at 40 psi for 5 h. The catalyst was removed by filtration through celite, and the filtrate was concentrated to provide 4-[4-(2-methylquinazolin-4-yl)-2,3,4,5-tetrahydro-1,4-benzoxazepin-7-yl]benzene-1,2-diamine (333 mg, 0.84 mmol, 94% yield) as a yellow-orange solid. MS (EI) for $C_{24}H_{23}N_5O$: 398 (MH$^+$).

STEP 4: To a solution of 4-[4-(2-methylquinazolin-4-yl)-2,3,4,5-tetrahydro-1,4-benzoxazepin-7-yl]benzene-1,2-diamine (333 mg, 0.84 mmol) in THF (5 mL) at 0° C. was added ethyl isothiocyanate (74 uL, 0.84 mmol). After stirring for 2 h at 0° C., the reaction mixture was warmed to rt for 1 h and was then heated to 45° C. for 4 h. The mixture was then cooled back to rt and allowed to stir for 3 d. Addition of water was followed by extraction into ethyl acetate. The organic phase was then dried over magnesium sulfate, filtered, and concentrated. The residue obtained was then dissolved in acetonitrile (5 mL) and ethyl acetate (2 mL). To this solution was added N-(3-dimethylaminopropyl)-N'-ethylcarbodiimide hydrochloride (161 mg, 0.84 mmol). The mixture was heated to reflux for 1.5 h and was then cooled to rt. Water and ethyl acetate were then added. The biphasic mixture was filtered to remove solid materials, and the filtrate was then partitioned. The aqueous phase was extracted with ethyl acetate. The combined organic extracts were dried over magnesium sulfate, filtered, and then concentrated. The residue was purified by reverse-phase preparative HPLC to provide N-ethyl-6-[4-(2-methylquinazolin-4-yl)-2,3,4,5-tetrahydro-1,4-benzoxazepin-7-yl]-1H-benzimidazol-2-amine as a diacetate salt (137 mg, 0.24 mmol, 29% yield). $^1$H NMR (400 MHz, dmso) δ 8.01 (d, 1H), 7.79-7.72 (m, 1H), 7.72-7.67 (m, 1H), 7.60 (d, 1H), 7.47-7.39 (m, 2H), 7.35 (s, 1H), 7.20-7.11 (m, 2H), 6.99 (d, 1H), 6.72 (br s, 1H), 5.02 (s, 2H), 4.47-4.38 (m, 2H), 4.22-4.13 (m, 2H), 3.37-3.27 (m, 2H), 2.48 (s, 3H), 1.89 (s, 7H), 1.18 (t, 3H); MS (EI) for $C_{27}H_{26}N_6O$: 451 (MH$^+$).

Using analogous synthetic techniques and substituting with alternative starting reagents in step 4 the following compounds of the invention were prepared. Alternative starting materials were obtained commercially unless otherwise indicated.

N-ethyl-6-[4-(7-fluoroquinolin-4-yl)-2,3,4,5-tetrahydro-1,4-benzoxazepin-7-yl]-1H-benzimidazol-2-amine. Prepared according to the method of example 24 by using 4-chloro-7-fluoroquinoline in step 2. $^1$H NMR (400 MHz, CD$_3$OD): 8.50 (d, 1H), 8.09 (t, 1H), 7.56-7.44 (m, 4H), 7.38-7.26 (m, 3H), 7.06 (d, 1H), 6.97 (d, H), 4.67 (s, br, 2H), 4.36 (s, br, 2H), 3.85 (s, br, 2H), 3.46 (q, 2H), 1.37 (t, 3H); MS (EI) for $C_{27}H_{24}FN_5O$: 454 (MH$^+$).

N-ethyl-6-[4-(8-fluoroquinolin-4-yl)-2,3,4,5-tetrahydro-1,4-benzoxazepin-7-yl]-1H-benzimidazol-2-amine. Prepared according to the method of example 24 by using 4-chloro-8-fluoroquinoline in step 2. $^1$H NMR (400 MHz, CD$_3$OD): 8.53 (d, 1H), 7.85 (d, 1H), 7.52-7.36 (m, 5H), 7.22 (m, 2H), 7.07-7.02 (m, 2H), 4.56 (s, 2H), 4.36-4.30 (m, 2H), 3.84-3.78 (m, 2H), 3.42 (q, 2H), 1.28 (t, 3H); MS (EI) for $C_{27}H_{25}FN_5O_2$: 452 (MH$^+$).

N-ethyl-6-[4-(6-fluoroquinolin-4-yl)-2,3,4,5-tetrahydro-1,4-benzoxazepin-7-yl]-1H-benzimidazol-2-amine. Prepared according to the method of example 24 by using reagent 4-chloro-6-fluoroquinoline in step 2. $^1$H NMR (400 MHz, CD$_3$OD): 8.55 (d, 1H), 8.02-7.96 (dd, 1H), 7.79-7.73 (dd, 1H), 7.60-7.42 (m, 4H), 7.30-7.21 (m, 2H), 7.12-7.07 (m, 2H), 4.56 (s, 2H), 4.39-4.34 (m, 2H), 3.84-3.79 (m, 2H), 3.42 (q, 2H), 1.29 (t, 3H); MS (EI) for $C_{27}H_{24}FN_5O$: 454 (MH$^+$).

Example 25

N-ethyl-5-methyl-6-[7-(2-methyl-1H-imidazo[4,5-b]pyridin-6-yl)-2,3-dihydro-1,4-benzoxazepin-4(5H)-yl]pyrimidin-4-amine and 4-(6-chloro-5-methylpyrimidin-4-yl)-7-(2-methyl-1H-imidazo[4,5-b]pyridin-6-yl)-2,3,4,5-tetrahydro-1,4-benzoxazepine STEP 1: A solution of 1-methylpropyl 2-methyl-6-(2,3,4,5-tetrahydro-1,4-benzoxazepin-7-yl)-1H-imidazo[4,5-b]pyridine-1-carboxylate hydrochloride (0.213 g, 0.512 mmol, example 6, step 2), 4,6-dichloro-5-methylpyrimidine (0.100 g, 0.613 mmol), and diisopropylethylamine (0.330 g, 2.56 mmol) in N-methylpyrrolidinone (2 mL) was stirred at room temperature for 17 h. The reaction mixture was diluted with ethyl acetate (100 mL), washed with saturated sodium bicarbonate (50 mL) and brine (25 mL), and dried over sodium sulfate. Filtration, concentration and purification by column chromatography on silica (97:3 dichloromethane/methanol) provided 4-(6-chloro-5-methylpyrimidin-4-yl)-7-(2-methyl-1H-imidazo[4,5-b]pyridin-6-yl)-2,3,4,5-tetrahydro-1,4-benzoxazepine (0.06 g, 31% yield) as a white solid. $^1$H NMR (400 MHz, CD$_3$OD) δ 8.50 (s, 1H), 8.22 (s, 1H), 8.04 (s, 1H), 7.60 (s, 1H), 7.50 (d, 1H), 7.08 (d, 1H), 4.81 (s, 2H), 4.39-4.32 (m, 2H), 4.03-3.97 (m, 2H), 2.64 (s, 3H), 2.37 (s, 3H); MS (EI) for $C_{21}H_{19}ClN_6O$: 407 (MH$^+$).

STEP 2: A suspension of 4-(6-chloro-5-methylpyrimidin-4-yl)-7-(2-methyl-1H-imidazo[4,5-b]pyridin-6-yl)-2,3,4,5-tetrahydro-1,4-benzoxazepine (44 mg, 0.11 mmol), and ethylamine (29 mg, 0.65 mmol), in N-methylpyrrolidinone (2 mL) was stirred at 100° C. for 6 h. The reaction mixture was diluted with ethyl acetate (75 mL), washed with saturated sodium bicarbonate (75 mL) and brine (50 mL), and dried over sodium sulfate. Concentration and purification by preparatory HPLC (0.1% aqueous ammonium acetate-acetonitrile) gave N-ethyl-5-methyl-6-[7-(2-methyl-1H-imidazo[4,5-b]pyridin-6-yl)-2,3-dihydro-1,4-benzoxazepin-4(5H)-yl]pyrimidin-4-amine (13 mg, 30% yield) as a white solid. $^1$H NMR (400 MHz, CD$_3$OD) δ 8.50 (s, 1H), 8.07 (s, 1H), 8.04

(d, 1H), 7.56-7.48 (m, 2H), 7.11 (d, 1H), 4.57 (s, 2H), 4.33 (d, 2H), 3.79 (d, 2H), 3.53-3.39 (q, 2H), 2.64 (s, 3H), 2.04 (s, 3H), 1.21 (t, 3H); MS (EI) for $C_{23}H_{25}N_7O$: 416 (MH$^+$).

Using analogous synthetic techniques and substituting with alternative starting reagents the following compounds of the invention were prepared. Alternative starting materials were obtained commercially unless otherwise indicated.

N,5-dimethyl-6-[7-(2-methyl-1H-imidazo[4,5-b]pyridin-6-yl)-2,3-dihydro-1,4-benzoxazepin-4(5H)-yl]pyrimidin-4-amine. Prepared as diacetate salt according to the method of example 25 by using methylamine in step 2. $^1$H NMR (400 MHz, methanol-d$_4$): 8.49 (s, 1H), 8.07 (s, 1H), 8.03 (m, 1H), 7.50 (m, 2H), 7.11 (d, 1H), 4.49 (s, 2H), 4.30 (m, 2H), 3.74 (m, 2H), 2.93 (s, 3H), 2.64 (s, 3H), 2.02 (s, 3H), 1.93 (s, 6H); MS (EI) for $C_{22}H_{23}N_7O$: 402 (MH$^+$).

5-methyl-N-(1-methylethyl)-6-[7-(2-methyl-1H-imidazo[4,5-b]pyridin-6-yl)-2,3-dihydro-1,4-benzoxazepin-4(5H)-yl]pyrimidin-4-amine. Prepared according to the method of example 25 by using isopropylamine in step 2. $^1$H NMR (400 MHz, methanol-d$_4$): 8.50 (s, 1H), 8.05 (s, 2H), 7.51 (m, 2H), 7.12 (d, 1H), 4.49 (s, 2H), 4.31 (m, 2H), 4.26 (m, 1H), 3.74 (m, 2H), 2.64 (s, 3H), 2.02 (s, 3H), 1.22 (d, 6H); MS (EI) for $C_{24}H_{27}N_7O$: 430 (MH$^+$).

7-(2-methyl-1H-imidazo[4,5-b]pyridin-6-yl)-4-(5-methyl-6-morpholin-4-ylpyrimidin-4-yl)-2,3,4,5-tetrahydro-1,4-benzoxazepine. Prepared according to the method of example 25 by using morpholine in step 2. $^1$H NMR (400 MHz, methanol-d$_4$): 8.49 (s, 1H), 8.11 (s, 1H), 8.03 (s, 1H), 7.57 (d, 1H), 7.48 (dd, 1H), 7.09 (d, 1H), 4.71 (s, 2H), 4.35 (m, 2H), 3.92 (m, 2H), 3.75 (t, 4H), 3.33 (t, 4H), 2.64 (s, 3H), 2.19 (s, 3H); MS (EI) for $C_{25}H_{27}N_7O_2$: 458 (MH$^+$).

7-(2-methyl-1H-imidazo[4,5-b]pyridin-6-yl)-4-[5-methyl-6-(4-methylpiperazin-1-yl)pyrimidin-4-yl]-2,3,4,5-tetrahydro-1,4-benzoxazepine. Prepared as triacetate salt according to the method of example 25 by using N-methylpiperazine in step 2. $^1$H NMR (400 MHz, methanol-d$_4$): 8.50 (s, 1H), 8.10 (s, 1H), 8.04 (s, 1H), 7.56 (d, 1H), 7.49 (dd, 1H), 7.09 (d, 1H), 4.71 (s, 2H), 4.34 (m, 2H), 3.92 (m, 2H), 3.40 (m, 4H), 2.64 (s, 3H), 2.59 (m, 4H), 2.34 (s, 3H), 2.19 (s, 3H), 1.93 (s, 9H); MS (EI) for $C_{26}H_{30}N_8O$: 471 (MH$^+$).

4-(6-azetidin-1-yl-5-methylpyrimidin-4-yl)-7-(2-methyl-1H-imidazo[4,5-b]pyridin-6-yl)-2,3,4,5-tetrahydro-1,4-benzoxazepine. Prepared according to the method of example 25 by using azetidine in step 2. $^1$H NMR (400 MHz, methanol-d$_4$): 8.50 (s, 1H), 8.04 (s, 1H), 7.99 (s, 1H), 7.55 (d, 1H), 7.49 (dd, 1H), 7.09 (d, 1H), 4.62 (s, 2H), 4.32 (m, 2H), 4.18 (t, 4H), 3.84 (m, 2H), 2.63 (s, 3H), 2.33 (m, 2H), 2.07 (s, 3H); MS (EI) for $C_{24}H_{25}N_7O$: 428 (MH$^+$).

N-{6-[7-(2-cyclopropyl-1H-imidazo[4,5-b]pyridin-6-yl)-2,3-dihydro-1,4-benzoxazepin-4(5H)-yl]-5-methylpyrimidin-4-yl}-N,N'-dimethylethane-1,2-diamine. Prepared as acetate salt according to the method of example 25 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (example 6) in step 1 and N,N'-dimethylethylenediamine in step 2. $^1$H NMR (400 MHz, methanol-d$_4$): 8.44 (d, 1H), 8.06 (s, 1H), 7.96 (d, 1H), 7.55 (d, 1H), 7.46 (dd, 1H), 7.06 (d, 1H), 4.75 (s, 2H), 4.34 (m, 2H), 3.94 (m, 2H), 3.69 (t, 2H), 3.21 (t, 2H), 3.07 (s, 3H), 2.67 (s, 3H), 2.21 (m, 4H), 1.91 (s, 3H), 1.22 (m, 4H); MS (EI) for $C_{27}H_{32}N_8O$: 485 (MH$^+$).

6-[7-(2-cyclopropyl-1H-imidazo[4,5-b]pyridin-6-yl)-2,3-dihydro-1,4-benzoxazepin-4(5H)-yl]-5-methyl-N-(1-methylpiperidin-4-yl)pyrimidin-4-amine. Prepared according to the method of example 25 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (example 6) in step 1 and 4-amino-1-methylpiperidine in step 2. $^1$H NMR (400 MHz, methanol-d$_4$): 8.46 (s, 1H), 8.06 (s, 1H), 7.98 (s, 1H), 7.50 (m, 2H), 7.12 (d, 1H), 4.52 (s, 2H), 4.32 (m, 2H), 4.04 (m, 1H), 3.77 (m, 2H), 3.13 (m, 2H), 2.56 (m, 2H), 2.53 (s, 3H), 2.21 (m, 1H), 2.08 (m, 2H), 2.05 (s, 3H), 1.71 (m, 2H), 1.23 (m, 4H); MS (EI) for $C_{29}H_{34}N_8O$: 511 (MH$^+$).

6-[7-(2-cyclopropyl-1H-imidazo[4,5-b]pyridin-6-yl)-2,3-dihydro-1,4-benzoxazepin-4(5H)-yl]-N,5-dimethyl-N-[(1R)-1-phenylethyl]pyrimidin-4-amine. Prepared according to the method of example 25 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (example 6) in step 1 and (R)-(+)-N-methyl-1-phenylethylamine in step 2. $^1$H NMR (400 MHz, methanol-d$_4$): 8.43 (s, 1H), 8.02 (s, 1H), 7.92 (s, 1H), 7.54 (d, 1H), 7.48 (dd, 1H), 7.17-7.08 (m, 6H), 5.28 (m, 1H), 4.72 (m, 2H), 4.36 (m, 2H), 3.94 (m, 2H), 2.63 (s, 3H), 2.25 (s, 3H), 2.19 (m, 1H), 1.59 (d, 3H), 1.21 (m, 4H); MS (EI) for $C_{32}H_{33}N_7O$: 532 (MH$^+$).

6-[7-(2-cyclopropyl-1H-imidazo[4,5-b]pyridin-6-yl)-2,3-dihydro-1,4-benzoxazepin-4(5H)-yl]-N,5-dimethyl-N-[(1S)-1-phenylethyl]pyrimidin-4-amine. Prepared according to the method of example 25 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (example 6) in step 1 and (S)-(−)-N-methyl-1-phenylethylamine in step 2. $^1$H NMR (400 MHz, methanol-d$_4$): 8.43 (s, 1H), 8.02 (s, 1H), 7.92 (s, 1H), 7.54 (d, 1H), 7.48 (dd, 1H), 7.17-7.08 (m, 6H), 5.28 (m, 1H), 4.72 (m, 2H), 4.36 (m, 2H), 3.94 (m, 2H), 2.63 (s, 3H), 2.25 (s, 3H), 2.19 (m, 1H), 1.59 (d, 3H), 1.21 (m, 4H); MS (EI) for $C_{32}H_{33}N_7O$: 532 (MH$^+$).

6-[7-(2-cyclopropyl-1H-imidazo[4,5-b]pyridin-6-yl)-2,3-dihydro-1,4-benzoxazepin-4(5H)-yl]-5-methyl-N-[(1-methylpiperidin-4-yl)methyl]pyrimidin-4-amine. Prepared according to the method of example 25 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (example 6) in step 1 and 4-aminomethyl-1-methylpiperidine in step 2. $^1$H NMR (400 MHz, methanol-d$_4$): 8.44 (d, 1H), 8.03 (s, 1H), 7.97 (d, 1H), 7.48 (m, 2H), 7.10 (d, 1H), 4.50 (m, 2H), 4.31 (m, 2H), 3.75 (m, 2H), 3.35 (m, 2H), 3.24 (m, 2H), 2.62 (s, 3H), 2.58 (m, 2H), 2.21 (m, 1H), 2.04 (s, 3H), 1.88 (m, 2H), 1.41 (m, 2H), 1.22 (m, 4H); MS (EI) for $C_{30}H_{36}N_8O$: 525 (MH$^+$).

6-[7-(2-cyclopropyl-1H-imidazo[4,5-b]pyridin-6-yl)-2,3-dihydro-1,4-benzoxazepin-4(5H)-yl]-5-methyl-N-[2-(1-methylpyrrolidin-2-yl)ethyl]pyrimidin-4-amine. Prepared as acetate salt according to the method of example 25 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (example 6) in step 1 and 2-aminoethyl-1-methylpyrrolidine in step 2. $^1$H NMR (400 MHz, methanol-d$_4$): 8.44 (d, 1H), 8.07 (s, 1H), 7.97 (d, 1H), 7.48 (m, 2H), 7.10 (d, 1H), 4.52 (m, 2H), 4.31 (m, 2H), 3.76 (m, 2H), 3.52 (m, 2H), 3.46 (m, 1H), 3.08 (m, 1H), 2.91 (m, 1H), 2.74 (s, 3H), 2.31 (m, 1H), 2.19 (m, 2H), 2.04 (s, 3H), 1.98 (m, 1H), 1.92 (s, 3H), 1.75 (m, 2H), 1.22 (m, 4H); MS (EI) for $C_{30}H_{36}N_8O$: 525 (MH$^+$).

6-[7-(2-cyclopropyl-1H-imidazo[4,5-b]pyridin-6-yl)-2,3-dihydro-1,4-benzoxazepin-4(5H)-yl]-5-methyl-N-(tetrahydro-2H-pyran-4-yl)pyrimidin-4-amine. Prepared according to the method of example 25 by using 1-methylpropyl 2-cyclopropyl-6-(2,3,4,5-tetrahydro-1,4-benzoxazepin-7-yl)-1H-imidazo[4,5-b]pyridine-1-carboxylate hydrochloride (example 6) in step 1 and 4-aminotetrahydropyran in step 2. $^1$H NMR (400 MHz, methanol-d$_4$): 8.47 (s, 1H), 8.11 (s, 1H), 7.99 (s, 1H), 7.52 (m, 2H), 7.11 (d, 1H), 4.66 (s, 2H), 4.35 (m, 2H), 4.11 (m, 1H), 3.98 (m, 2H), 3.84 (m, 2H), 3.50 (m, 2H), 2.22 (m, 1H), 2.07 (s, 3H), 1.89 (m, 2H), 1.67 (m, 2H), 1.23 (m, 4H); MS (EI) for $C_{28}H_{31}N_7O_2$: 498 (MH+).

N-ethyl-2,5-dimethyl-6-[7-(2-methyl-1H-imidazo[4,5-b]pyridin-6-yl)-2,3-dihydro-1,4-benzoxazepin-4(5H)-yl]pyrimidin-4-amine. Prepared according to the method of example 25 by using 4,6-dichloro-2,5-dimethylpyrimidine in step 1. $^1$H NMR (400 MHz, methanol-d$_4$): 8.49 (d, 1H), 8.03 (d, 1H), 7.49 (m, 2H), 7.11 (d, 1H), 4.46 (s, 2H), 4.27 (m, 2H), 3.72 (m, 2H), 3.45 (q, 2H), 2.63 (s, 3H), 2.34 (s, 3H), 1.98 (s, 3H), 1.19 (t, 3H); MS (EI) for $C_{24}H_{27}N_7O$: 430 (MH+).

4-{7-[2-(ethylamino)-1H-benzimidazol-6-yl]-2,3-dihydro-1,4-benzoxazepin-4(5H)-yl}-N-methylquinazolin-2-amine. Prepared according to the method of example 25 by using N-ethyl-5-(2,3,4,5-tetrahydro-1,4-benzoxazepin-7-yl)-1H-benzimidazol-2-amine dihydrochloride (example 11, step 3) and 2,4-dichloroquinazoline in step 1 and methylamine in step 2. $^1$H NMR (400 MHz, DMSO-d6) δ 7.80 (d, 1H), 7.51 (d, 2H), 7.43 (d, 1H), 7.33 (s, 1H), 7.15 (t, 2H), 7.06-6.96 (m, 2H), 6.74-6.61 (m, 2H), 4.94 (s, 2H), 4.43 (s, 2H), 4.07 (s, 2H), 3.31 (q, 2H), 2.77 (s, 3H), 1.87 (s, 6H), 1.18 (t, 3H); MS (EI) for $C_{27}H_{27}N_7O$: 466.

N-ethyl-4-{7-[2-(ethylamino)-1H-benzimidazol-6-yl]-2,3-dihydro-1,4-benzoxazepin-4(5H)-yl}quinazolin-2-amine. Prepared according to the method of example 25 by using N-ethyl-5-(2,3,4,5-tetrahydro-1,4-benzoxazepin-7-yl)-1H-benzimidazol-2-amine dihydrochloride (example 11, step 3) and 2,4-dichloroquinazoline in step 1 and ethylamine in step 2. $^1$H NMR (400 MHz, DMSO-d6) δ 7.80 (d, 1H), 7.57-7.48 (m, 2H), 7.43 (s, 1H), 7.36-7.28 (m, 2H), 7.19-7.11 (m, 2H), 7.07-6.95 (m, 2H), 6.72-6.58 (m, 1H), 4.95 (s, 2H), 4.43 (s, 2H), 4.11 (s, 2H), 3.32-3.25 (m, 4H), 1.91 (d, 4H), 1.18 (t, 6H); MS (EI) for $C_{28}H_{29}N_7O$: 480 (MH+).

N-ethyl-6-{4-[6-(ethylamino)-5-methylpyrimidin-4-yl]-2,3,4,5-tetrahydro-1,4-benzoxazepin-7-yl}-1H-benzimidazol-2-amine. Prepared as an acetate salt according to the method of example 25 by using N-ethyl-5-(2,3,4,5-tetrahydro-1,4-benzoxazepin-7-yl)-1H-benzimidazol-2-amine dihydrochloride (example 11, step 3) in step 1 and ethylamine in step 2. $^1$H NMR (400 MHz, DMSO-d6) δ 8.01 (s, 1H), 7.45 (br s, 1H), 7.38 (d, 1H), 7.30 (br s, 1H), 7.16-7.04 (m, 2H), 6.98 (d, 1H), 6.60 (t, 1H), 6.42 (t, 1H), 4.40 (s, 2H), 4.24-4.18 (m, 2H), 3.68-3.61 (m, 2H), 3.30-3.25 (m, 4H), 1.96 (s, 3H), 1.89-1.86 (m, 3H), 1.16 (t, 3H), 1.08 (t, 3H); MS (EI) for $C_{25}H_{29}N_7O$: 444 (MH+).

Example 26

6-[4-(6-methylquinazolin-4-yl)-2,3,4,5-tetrahydro-1,4-benzoxazepin-7-yl]-1H-imidazo[4,5-b]pyridin-2-amine STEP 1: A suspension of 5-bromo-3-nitropyridin-2-amine (4.84 g, 22.2 mmol), (4-{[(1,1-dimethylethyl)oxy]carbonyl}-2,3,4,5-tetrahydro-1,4-benzoxazepin-7-yl)boronic acid (6.51 g, 22.2 mmol) (example 1, step 2), dichloro[1,1-bis(diphenyl)phosphino]ferrocenepalladium (II) dichloromethane adduct (1.60 g, 10 mol %) in dioxane (75 mL) and water (15 mL) was degassed with nitrogen, and then cesium carbonate (14.46 g, 44.4 mmol) was added. The reaction mixture was stirred at 90° C. overnight. The mixture was cooled to room temperature, water (150 ml) was added and stirred for 30 min to give a precipitate. The product 1,1-dimethylethyl-7-(6-amino-5-nitropyridin-3-yl)-2,3-dihydro-1,4-benzoxazepine-4(5H)-carboxylate (8.1 g, 94% yield) was collected by filtration, dried under vacuum. MS (EI) for $C_{19}H_{22}N_4O_5$: 387.1 (MH+).

STEP 2: A suspension of 1,1-dimethylethyl-7-(6-amino-5-nitropyridin-3-yl)-2,3-dihydro-1,4-benzoxazepine-4(5H)-carboxylate (6.12 g, 15.84 mmol), palladium on carbon (0.6 g) in acetic acid (100 mL) was degassed with nitrogen for 10 minutes. The reaction mixture was hydrogenated (45 psi) on a parr shaker for 60 minutes. Upon completion of hydrogenation, the reaction mixture was filtered through a pad of celite. The filtrate was concentrated and the residue was diluted with ethyl acetate (200 ml), washed with water, saturated sodium bicarbonate solution and brine then dried over sodium sulfate and filtered. Evaporation of ethyl acetate afforded 1,1-dimethylethyl-7-(5,6-diaminopyridin-3-yl)-2,3-dihydro-1,4-benzoxazepine-4(5H)-carboxylate (5.6 g, 99% yield). $^1$H NMR (400 MHz, CD$_3$OD): 7.56-7.27 (m, 4H), 7.08-7.02 (m, 1H), 4.51 (s, 2H), 4.07-4.03 (m, 2H), 3.86-3.74 (m, 2H), 1.3 (s, 9H).

STEP 3: A solution of 1,1-dimethylethyl-7-(5,6-diaminopyridin-3-yl)-2,3-dihydro-1,4-benzoxazepine-4(5H)-carboxylate (5.64 g, 15.84 mmol) and 1,3-bis(benzyloxycarbonyl)-2-methyl-2-thiopseudourea (11.8 g, 32.92 mmol) in acetic acid (30 mL) was heated to 86° C. for 3 hours. After cooling to room temperature, ethyl acetate (100 mL) was added and the precipitate was collected by filtration, washed several times with ethyl acetate, and dried to give 1,1-dimethylethyl-7-[2-({[(phenylmethyl)oxy]carbonyl}amino)-1H-imidazo[4,5-b]pyridine-6-yl]-2,3-dihydro-1,4-benzoxazepine-4(5H)-carboxylate (4.50 g, 55% yield). $^1$HNMR (400 MHz, DMSO-d$_6$): 11.9 (s, br, 2H), 8.42 (s, 1H), 7.90 (s, 1H), 7.52-7.36 (m, 7H), 5.28 (s, 2H), 4.60-4.34 (m, 2H), 4.18-4.02 (m, 2H), 3.79-3.67 (m, 2H), 1.38 (s, 9H).

STEP 4: To the solution of 1,1-dimethylethyl-7-[2-({[(phenylmethyl)oxy]carbonyl}amino)-1H-imidazo[4,5-b]pyridine-6-yl]-2,3-dihydro-1,4-benzoxazepine-4(5H)-carboxylate (4.5 g, 8.73 mmol) in methanol (20 ml) was added 4 N HCl in dioxane at room temperature. Then the reaction mixture was heated to 55° C. for 3 hours. After cooling to room temperature, the precipitate collected by filtration, washed with a minimum of methanol and dried to give phenylmethyl[6-(2,3,4,5-tetrahydro-1,4-benzoxazepin-7-yl)-1H-imidazo[4,5-b]pyridin-2-yl]carbamate hydrochloride (3.0 g, 76% yield). $^1$HNMR (400 MHz, CD$_3$OD): 8.59 (m, 1H), 8.51 (s, 1H), 7.85 (m, 1H), 7.79-7.75 (m, 1H), 5.37 (s, 2H), 4.53 (s, 2H), 4.37-4.32 (m, 2H), 3.67-3.64 (m, 2H).

STEP 5: Diisopropylethylamine (0.23 g, 1.76 mmol) was added to a solution of phenylmethyl[6-(2,3,4,5-tetrahydro-1,4-benzoxazepin-7-yl)-1H-imidazo[4,5-b]pyridin-2-yl]carbamate hydrochloride (0.2 g, 0.44 mmol) and 4-chloro-6-methylquinazoline (0.08 g, 0.44 mmol), in NMP (5 ml) at room temperature. The reaction mixture was heated to 90° C. for 30 minutes, and then cooled to room temperature. Water was added and the resulting suspension was stirred overnight. The precipitate was collected by filtration and dried under vacuum to give phenylmethyl{6-[4-(6-methylquinazolin-4-yl)-2,3,4,5-tetrahydro-1,4-benzoxazepin-7-yl]-3H-imidazo[4,5-b]pyridin-2-yl}carbamate (0.215 g, 87% yield). MS (EI) for $C_{32}H_{27}N_7O_3$: 558.1 (MH+).

STEP 6: Phenylmethyl{6-[4-(6-methylquinazolin-4-yl)-2,3,4,5-tetrahydro-1,4-benzoxazepin-7-yl]-3H-imidazo[4,5-b]pyridin-2-yl}carbamate (0.1 g, 0.18 mmol) in acetic acid (8 ml) was placed under nitrogen. Palladium on carbon (0.25 g, 10 W %) was added and the reaction mixture saturated with hydrogen then stirred at room temperature for 12 h. The reaction mixture was filtered through a pad of celite then concentrated. The residue was taken into a minimum of methanol and purified by preparative reverse phase HPLC to give 6-[4-(6-methylquinazolin-4-yl)-2,3,4,5-tetrahydro-1,4-benzoxazepin-7-yl]-3H-imidazo[4,5-b]pyridin-2-amine (0.0033 g). $^1$H NMR (400 MHz, d$_6$-DMSO); δ 8.52 (s, 1H), 8.32-8.12 (s, 1H), 7.84-7.47 (m, 6H), 7.07-7.00 (d, 1H), 6.80-

6.50 (s, 1H), 5.04 (s, 2H), 4.56-4.44 (m, 2H), 4.20-4.09 (m, 2H), 2.83 (s, 3H); MS (EI) for $C_{24}H_{21}N_7O$: 424.1 (MH$^+$).

Using analogous synthetic techniques and substituting with alternative starting reagents in steps 1, 3 or 5 the following compounds of the invention were prepared. Alternative starting materials were obtained commercially unless otherwise indicated.

6-[7-(1H-benzimidazol-6-yl)-2,3-dihydro-1,4-benzoxazepin-4(5H)-yl]-2,5-dimethyl-N-phenylpyrimidin-4-amine. Synthesized according to the method of example 26 using 4-bromo-2-nitroaniline in step 1, triethyl orthoformate in refluxing ethanol step 3, and 6-chloro-2,5-dimethyl-N-phenylpyrimidin-4-amine (Prepared according to the general method in Journal of Medicinal Chemistry (1996), 39(22), 4358-4360) in step 5. $^1$H NMR (400 MHz, dmso-d6) δ 12.03 (brs, 1H), 8.21 (s, 1H), 8.18 (s, 1H), 7.80 (brs, 1H), 7.60 (m, 6H), 7.21 (t, 2H), 7.18 (d, 1H), 6.92 (t, 1H), 4.60 (s, 2H), 4.23 (brs, 2H), 3.78 (brs, 2H), 2.23 (s, 3H), 2.18 (s, 3H); MS (EI) for $C_{28}H_{26}N_6O$: 463.2 (MH$^+$).

6-[7-(1H-imidazo[4,5-b]pyridin-6-yl)-2,3-dihydro-1,4-benzoxazepin-4(5H)-yl]-2,5-dimethyl-N-phenylpyrimidin-4-amine. Synthesized according to the method of example 26 using triethyl orthoformate in refluxing ethanol step 3 and 6-chloro-2,5-dimethyl-N-phenylpyrimidin-4-amine (Prepared according to the general method in Journal of Medicinal Chemistry (1996), 39(22), 4358-4360) in step 5. $^1$H NMR (400 MHz, MeOH-d4): δ 8.61 (s, 1H), 8.41 (s, 1H), 8.21 (s, 1H), 7.60 (m, 4H), 7.21 (t, 2H), 7.18 (d, 1H), 6.92 (t, 1H), 4.60 (s, 2H), 4.23 (brs, 2H), 3.78 (brs, 2H), 2.23 (s, 3H), 2.18 (s, 3H); MS (EI) for $C_{27}H_{25}N_7O$: 464.2 (MH$^+$).

7-(1H-benzimidazol-6-yl)-4-pyrimidin-4-yl-2,3,4,5-tetrahydro-1,4-benzoxazepine. Synthesized according to the method of example 26 by using 4-bromo-2-nitroaniline in step 1, triethylorthoformate in refluxing ethanol step 3, and using 4-chloropyrimidine in step 5. $^1$H NMR (400 MHz, DMSO-d6) δ 8.49 (s, 1H), 8.25 (s, 1H), 8.17 (d, 1H), 7.93-7.86 (m, 2H), 7.71 (s, 1H), 7.55-7.43 (m, 2H), 7.04 (d, 2H), 4.87 (s, 2H), 4.16 (s, 4H); MS (EI) for $C_{20}H_{17}N_5O$: 344 (MH$^+$).

7-(1H-imidazo[4,5-b]pyridin-6-yl)-4-pyrimidin-4-yl-2,3,4,5-tetrahydro-1,4-benzoxazepine. Synthesized according to the method of example 26 using triethylorthoformate in refluxing ethanol in step 3 and 4-chloropyrimidine in step 5. $^1$H NMR (400 MHz, DMSO-d6): δ 8.65 (d, 1H), 8.51-8.46 (m, 2H), 8.23 (d, 1H), 8.17 (d, 1H), 7.96 (s, 1H), 7.59-7.55 (m, 1H), 7.07 (d, 2H), 4.88 (s, 2H), 4.18 (s, 4H), 1.85 (s, 8H); MS (EI) for $C_{19}H_{16}N_6O$: 343 (MH$^+$).

6-(4-pyrido[3,2-d]pyrimidin-4-yl)-2,3,4,5-tetrahydro-1,4-benzoxazepin-7-yl)-1H-imidazo[4,5-b]pyridin-2-amine. Synthesized according to the method of example 26 using 4-chloropyrido[3,2-d]pyrimidine in step 5. $^1$H NMR (400 MHz, MeOH-d4): δ 9.01 (d, 1H), 8.75 (br, 2H), 8.43 (s, 1H), 8.01 (s, 1H), 7.75 (m, 2H), 7.52 (brs, 1H), 7.01 (brs, 1H), 5.70 (s, 2H), 4.71 (s, 4H); MS (EI) for $C_{22}H_{18}N_8O$: 410.9 (MH$^+$).

6-{4-[5-Methyl-6-(phenylamino)pyrimidin-4-yl]-2,3,4,5-tetrahydro-1,4-benzoxazepin-7-yl}-1H-imidazo[4,5-b]pyridine-2-amine. Synthesized according to the method of example 26 using 6-chloro-5-methyl-N-phenylpyrimidin-4-amine (reagent preparation 49) in step 5. $^1$HNMR (400 MHz, dmso-d6) δ 12.03 (brs, 1H), 8.25 (s, 1H), 8.18 (s, 1H), 7.60 (m, 5H), 7.42 (d, 1H), 7.21 (t, 2H), 7.05 (d, 1H), 6.89 (t, 1H), 6.60 (br, 2H), 4.58 (s, 2H), 4.32 (s, 2H), 3.78 (s, 2H), 2.15 (s, 3H); MS (EI) for $C_{26}H_{24}N_8O$: 464.2 (MH$^+$).

7-(1H-benzimidazol-6-yl)-4-(2-phenylquinazolin-4-yl)-2,3,4,5-tetrahydro-1,4-benzoxazepine. Synthesized according to the method of example 26 using 4-bromo-2-nitroaniline in step 1, triethylorthoformate in refluxing ethanol in step 3 and 4-chloro-2-phenylquinazoline in step 5. $^1$H NMR (400 MHz, DMSO-d$_6$): 12.60-12.46 (m, 1H), 8.55-8.22 (m, 3H), 8.21-7.72 (m, 6H), 7.70-7.22 (m, 7H), 5.24 (s, br, 2H), 4.53 (s, br, 2H), 4.38 (s, br, 2H); MS (EI) for $C_{30}H_{23}N_5O$: 470.2 (MH$^+$).

6-[4-(2-phenylquinazolin-4-yl)-2,3,4,5-tetrahydro-1,4-benzoxazepin-7-yl]-1H-benzimidazol-2-amine. Synthesized according to the method of example 26 using 4-bromo-2-nitroaniline in step 1, and 4-chloro-2-phenylquinazoline in step 5. $^1$H NMR (400 MHz, DMSO-d$_6$): 8.36 (m, 2H), 8.25 (s, 1H), 8.21-8.11 (m, 2H), 7.92-7.73 (m, 3H), 7.65 (d, 1H), 7.612-7.36 (m, 4H), 7.30 (t, 2H), 6.91 (d, 2H), 6.70 (s, br, 2H), 5.22 (s, 2H), 4.52 (m, 2H), 4.37 (m, 2H); MS (EI) for $C_{30}H_{24}N_6O$: 486.1 (MH$^+$).

4-(7-fluoroquinolin-4-yl)-7-(2-methyl-1H-benzimidazol-6-yl)-2,3,4,5-tetrahydro-1,4-benzoxazepine. Synthesized according to the method of example 26 using 4-bromo-2-nitroaniline in step 1, triethylorthoacetate in refluxing ethanol in step 3 and 4-chloro-7-fluoroquinoline in step 5. $^1$H NMR (400 MHz, CD$_3$OD): 8.52 (d, 1H), 8.19-8.11 (m, 1H), 7.69 (s, 1H), 7.65-7.44 (m, 5H), 7.38-7.29 (m, 1H), 7.14-6.98 (m, 2H), 4.67 (s, 2H), 4.39 (m, 2H), 3.89 (m, 2H), 2.59 (s, 3H); MS (EI) for $C_{26}H_{21}FN_4O$ 425.0 (MH$^+$).

4-[7-(2-methyl-1H-benzimidazol-6-yl)-2,3-dihydro-1,4-benzoxazepin-4(5H)-yl]quinoline-7-carbonitrile. Synthesized according to the method of example 26 using 4-bromo-2-nitroaniline in step 1, triethylorthoacetate in refluxing ethanol in step 3 and 4-chloro-7-cyanoquinoline in step 5. $^1$H NMR (400 MHz, CD$_3$OD): 8.64 (d, 1H), 8.22 (d, 1H), 8.07 (d, 1H), 7.82 (t, 1H), 7.71-7.34 (m, 6H), 7.09 (d, 1H), 4.85-4.52 (dd, 2H), 4.48-4.38 (m, 1H), 4.24-3.66 (m, 3H), 2.57 (s, 3H); MS (EI) for $C_{27}H_{21}N_5O$: 432.0 (MH$^+$).

7-(2-methyl-1H-benzimidazol-6-yl)-4-[2-methyl-7-(methyloxy)quinazolin-4-yl]-2,3,4,5-tetrahydro-1,4-benzoxazepine. Synthesized according to the method of example 26 using 4-bromo-2-nitroaniline in step 1, triethylorthoacetate in refluxing ethanol in step 3 and 4-chloro-7-methoxy-2-methylquinazoline in step 5. $^1$H NMR (400 MHz, CD$_3$OD): 8.20 (d, 2H), 7.92 (s, 1H), 7.87-7.78 (m, 3H), 7.58 (d, 1H), 7.26 (dd, 1H), 7.11-7.02 (m, 2H), 5.44 (s, 2H), 4.65-4.54 (m, 4H), 3.99 (s, 3H), 2.88 (s, 3H), 2.58 (s, 3H); MS (EI) for $C_{30}H_{24}N_6O$: 486.1 (MH$^+$).

7-(1H-benzimidazol-6-yl)-4-[2-methyl-7-(methyloxy)quinazolin-4-yl]-2,3,4,5-tetrahydro-1,4-benzoxazepine. Synthesized according to the method of example 26 using 4-bromo-2-nitroaniline in step 1, triethylorthoformate in refluxing ethanol in step 3 and 4-chloro-7-methoxy-2-methylquinazoline in step 5. $^1$H NMR (400 MHz, DMSO); δ 8.25 (s, 1H), 8.00-7.42 (m, 6H), 7.17-6.98 (m, 3H), 5.02 (s, 2H), 4.50-4.38 (m, 2H), 4.21-4.10 (m, 2H), 3.88 (s, 3H), 2.44 (s, 2H); MS (EI) for C26H23N5O2: 438.2 (MH$^+$).

6-{4-[2-methyl-7-(methyloxy)quinazolin-4-yl]-2,3,4,5-tetrahydro-1,4-benzoxazepin-7-yl}-1H-imidazo[4,5-b]pyridin-2-amine. Synthesized according to the method of example 26 using 4-chloro-7-methoxy-2-methylquinazoline in step 5. $^1$H NMR (400 MHz, DMSO); δ 8.15 (s, 1H), 7.90 (d, 1H), 7.71-7.42 (m, 3H), 7.17-6.95 (m, 3H), 6.70 (s, 2H), 5.00 (s, 2H), 4.48-4.38 (m, 2H), 4.20-4.09 (m, 2H), 3.87 (s, 3H), 2.44 (s, 3H); MS (EI) for $C_{25}H_{23}N_7O_2$: 454.2 (MH$^+$).

6-{4-[2-methyl-7-(methyloxy)quinazolin-4-yl]-2,3,4,5-tetrahydro-1,4-benzoxazepin-7-yl}-1H-benzimidazol-2-amine. Synthesized according to the method of example 26 using 4-bromo-2-nitroaniline in step 1 and 4-chloro-7-methoxy-2-methylquinazoline in step 5. $^1$H NMR (400 MHz, DMSO); δ 7.92 (d, 1H), 7.61-7.57 (m, 1H), 7.46-7.40 (m, 1H), 7.33 (s, 1H), 7.18-7.09 (m, 3H), 7.06-6.96 (m, 2H), 6.23

(s, 2H), 4.99 (s, 2H), 4.45-4.32 (m, 2H), 4.18-4.10 (m, 2H), 3.88 (s, 3H), 2.44 (s, 3H); MS (EI) for $C_{26}H_{24}N_6O_2$: 453.0 (MH+).

7-(1H-imidazo[4,5-b]pyridin-6-yl)-4-[2-methyl-7-(methyloxy)quinazolin-4-yl]-2,3,4,5-tetrahydro-1,4-benzoxazepine. Synthesized according to the method of example 26 using triethylorthoformate in refluxing ethanol in step 3 and 4-chloro-7-methoxy-2-methylquinazoline in step 5. $^1$H NMR (400 MHz, DMSO); δ 8.68-8.64 (m, 1H), 8.48 (s, 1H), 8.21 (s, 1H), 7.93-7.87 (d, 1H), 7.80-7.75 (m, 1H), 7.62-7.56 (m, 1H), 7.11 (d, 1H), 7.08-7.00 (m, 2H), 5.03 (s, 2H), 4.50-4.25 (m, 2H), 4.20-4.12 (m, 2H), 3.88 (s, 2H), 2.43 (s, 3H); MS (EI) for $C_{25}H_{22}N_6O_2$: 438.9 (MH+).

Example 27 methyl {6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}carbamate STEP 1: A mixture of 1,1-dimethylethyl 7-(6-amino-5-nitropyridin-3-yl)-2,3-dihydro-1,4-benzoxazepine-4(5H)-carboxylate (3.5 g, 9.1 mmol, example 26, step 1) in methanol (75 mL) and 4N hydrogen chloride in dioxane (11 mL) was stirred at 50° C. for 1.5 h and then concentrated. The resulting residue was triturated with a 10% methanol in diethyl ether solution (50 mL) to provide 3-nitro-5-(2,3,4,5-tetrahydro-1,4-benzoxazepin-7-yl)pyridin-2-amine dihydrochloride (3.1 g, 95%) as a red solid. $^1$H NMR (400 MHz, d$_6$-DMSO) δ 9.76 (bs, 2H), 8.80 (d, 1H), 8.60 (s, 1H), 7.90 (s, 1H), 7.73 (dd, 1H), 7.16 (d, 1H), 4.39 (bs, 2H), 4.25 (bs, 2H), 3.48 (bs, 2H); MS (EI) for $C_{14}H_{14}N_4O_3$: 287 (MH+).

STEP 2: A solution of 3-nitro-5-(2,3,4,5-tetrahydro-1,4-benzoxazepin-7-yl)pyridin-2-amine dihydrochloride (540 mg, 1.50 mmol), 4-chloro-6,6-dimethyl-5,6,7,8-tetrahydroquinazoline (270 mg, 1.37 mmol, reagent preparation 3), and diisopropylethylamine (970 mg, 7.49 mmol) in N-methylpyrrolidinone (3 mL) was stirred at 120° C. for 18 h. After cooling to room temperature ethyl acetate (100 mL) was added, the formed precipitate was filtered off, the organic filtrate was washed with saturated sodium bicarbonate (50 mL), water (2×50 mL), and brine (50 mL), dried over sodium sulfate, filtered and concentrated to afford crude 5-[4-(6,6-dimethyl-5,6,7,8-tetrahydroquinazolin-4-yl)-2,3,4,5-tetrahydro-1,4-benzoxazepin-7-yl]-3-nitropyridine-2-amine (0.5 g) as a brown solid which was used in the next step without further purification. MS (EI) for $C_{24}H_{26}N_6O_3$: 447 (MH+).

STEP 3: A mixture of 5-[4-(6,6-dimethyl-5,6,7,8-tetrahydroquinazolin-4-yl)-2,3,4,5-tetrahydro-1,4-benzoxazepin-7-yl]-3-nitropyridine-2-amine (0.5 g, 1.37 mmol) and palladium on carbon (0.5 g, 50% water) in methanol (50 mL) was hydrogenated in a Parr apparatus at 40 psi for 90 min. The mixture was filtered through celite and concentrated. Column chromatography of the residue on silica (dichloromethane/methanol 9:1) provided 5-[4-(6,6-dimethyl-5,6,7,8-tetrahydroquinazolin-4-yl)-2,3,4,5-tetrahydro-1,4-benzoxazepin-7-yl]pyridine-2,3-diamine (174 mg, 30% yield over 2 steps) as a brown solid. MS (EI) for $C_{24}H_{28}N_6O$: 417 (MH+).

STEP 4: A mixture of 5-[4-(6,6-dimethyl-5,6,7,8-tetrahydroquinazolin-4-yl)-2,3,4,5-tetrahydro-1,4-benzoxazepin-7-yl]pyridine-2,3-diamine (174 mg, 0.42 mmol) and 1,3-bis(methoxycarbonyl)-2-methyl-2-thiopseudourea (86 mg, 0.42 mmol) in acetic acid (5 mL) was stirred at 80° C. for 10 h. After cooling to room temperature the mixture was concentrated, methanol (10 mL) was added, the precipitate was filtered off, and lyophilized from a mixture of acetonitrile (2 mL), water (6 mL), and 1N hydrochloric acid (0.25 mL) to give the hydrochloride salt of the title Compound (107 mg, 48% yield) as a yellow solid. $^1$H NMR (400 MHz, methanol-d$_4$): 8.53 (m, 2H), 8.35 (s, 1H), 7.78 (s, 1H), 7.58 (d, 1H), 7.10 (d, 1H), 5.18 (s, 2H), 4.49 (m, 2H), 4.34 (m, 2H), 3.93 (s, 3H), 2.86 (m, 2H), 2.61 (s, 2H), 1.71 (m, 2H), 0.95 (s, 6H); MS (EI) for $C_{27}H_{29}N_7O_3$: 500 (MH+).

Methyl {6-[4-(6,6-dimethyl-5,6,7,8-tetrahydroquinazolin-4-yl)-2,3,4,5-tetrahydro-1,4-benzoxazepin-7-yl]-1H-benzimidazol-2-yl}carbamate. Prepared according to the method of example 27 by 4-[4-(6,6-dimethyl-5,6,7,8-tetrahydroquinazolin-4-yl)-2,3,4,5-tetrahydro-1,4-benzoxazepin-7-yl]-2-nitroaniline in step 3. $^1$H NMR (400 MHz, d$_6$-DMSO): 8.71 (s, 1H), 7.61 (s, 1H), 7.58-7.44 (m, 3H), 6.99 (d, 1H), 5.10 (s, 2H), 4.43 (m, 2H), 4.18 (m, 2H), 3.81 (s, 3H), 2.78 (t, 2H), 2.56 (s, 2H), 1.57 (t, 2H), 0.86 (s, 6H); MS (EI) for $C_{28}H_{30}N_6O_3$: 499 (MH+).

Example 28 ethyl {6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}carbamate STEP 1: A solution of 5-[4-(6,6-dimethyl-5,6,7,8-tetrahydroquinazolin-4-yl)-2,3,4,5-tetrahydro-1,4-benzoxazepin-7-yl]pyridine-2,3-diamine (188 mg, 0.45 mmol, example 27, step 3) and ethyl isothiocyanatoformate (59 mg, 0.45 mmol) in dioxane (2 mL) was stirred at room temperature for 30 h. After 24 h and 48 h reaction time, additional ethyl isothiocyanatoformate (50 mg, 0.38 mmol) was added each time. The mixture was concentrated and the residue purified directly by column chromatography on silica (ethyl acetate) to give crude ethyl [1-({3-amino-5-[4-(6,6-dimethyl-5,6,7,8-tetrahydroquinazolin-4-yl)-2,3,4,5-tetrahydro-1,4-benzoxazepin-7-yl]pyridine-2-yl}amino)ethenyl]carbamate (82 mg) which was used in the next step without further purification. MS (EI) for $C_{28}H_{33}N_7O_3S$: 548 (MH+).

STEP 2: A mixture of ethyl [1-({3-amino-5-[4-(6,6-dimethyl-5,6,7,8-tetrahydroquinazolin-4-yl)-2,3,4,5-tetrahydro-1,4-benzoxazepin-7-yl]pyridine-2-yl}amino)ethenyl]carbamate (82 mg, 0.15 mmol) and mercury(II) oxide (33 mg, 0.15 mmol) in tetrahydrofuran (8 mL) was stirred at 70° C. for 24 h. On cooling to room temperature, the mixture filtered then concentrated and the residue purified by preparative reverse phase HPLC to afford the title Compound (6 mg, 3% yield over 2 steps) as a colorless solid. $^1$H NMR (400 MHz, methanol-d$_4$): 8.51 (s, 1H), 8.49 (d, 1H), 8.22 (d, 1H), 7.72 (d, 1H), 7.66 (dd, 1H), 7.09 (d, 1H), 5.17 (s, 2H), 4.48 (m, 2H), 4.36 (q, 2H), 4.33 (m, 2H), 2.85 (m, 2H), 2.60 (s, 2H), 1.69 (m, 2H), 1.38 (t, 3H), 0.95 (s, 6H); MS (EI) for $C_{28}H_{31}N_7O_3$: 514 (MH+).

Example 29 methyl {6-[4-(6,6-dimethyl-5,6-dihydroquinazolin-4-yl)-2,3,4,5-tetrahydro-1,4-benzoxazepin-7-yl]-1H-imidazo[4,5-b]pyridin-2-yl}carbamate STEP 1: To a solution of 3-nitro-5-(2,3,4,5-tetrahydro-1,4-benzoxazepin-7-yl)pyridin-2-amine dihydrochloride (1.0 g, 2.8 mmol) in acetic acid (20 mL) and ethanol (20 mL) was added Pd/C (10% wt/wt, 0.5 g) and the reaction mixture was stirred under H$_2$ (45 PSI) for 1 hour. The resulting pale yellow solution was filtered through Celite and the filtrate was concentrated to give 5-(2,3,4,5-tetrahydro-1,4-benzoxazepin-7- yl)pyridine-2,3-diamine dihydrochloride (0.92 g, 100%) as a yellow powder. MS (EI) for $C_{14}H_{16}N_4O$: 257.3 (MH+).

STEP 2: To a slurry of 5-(2,3,4,5-tetrahydro-1,4-benzoxazepin-7-yl)pyridine-2,3-diamine dihydrochloride (0.92 g, 2.8 mmol) and 4-chloro-6,6-dimethyl-5,6-dihydroquinazoline (0.55 g, 2.8 mmol) in NMP was added diisopropylethylamine (2.4 mL, 14 mmol) and the reaction mixture was heated (90° C.) for 12 hours. The resulting dark red solution was loaded directly on to a column of dry silica and elution with MeOH (w/8% NH$_4$OH v/v) in CH$_2$Cl$_2$ (0-5%) provided 5-[4-(6,6-dimethyl-5,6-dihydroquinazolin-4-yl)-2,3,4,5-tetrahydro-1,4-benzoxazepin-7-yl]pyridine-2,3-diamine (0.86, 74% yield) as a brown solid. MS (EI) for $C_{24}H_{26}N_6O$: 415.1 (MH+).

Step 3: To a solution of 5-[4-(6,6-dimethyl-5,6-dihydroquinazolin-4-yl)-2,3,4,5-tetrahydro-1,4-benzoxazepin-7-yl]pyridine-2,3-diamine (0.24 g, 0.58 mmol) in acetic acid (3 mL) was added 1,3-bis(methoxycarbonyl)-2-methyl-2-thiopseudourea (0.19 g, 0.93 mmol). The reaction mixture was heated (60° C.) for 12 h and then concentrated. Purification by preparative reverse phase HPLC followed by the formation of the dihydrochloride salt provided methyl {6-[4-(6,6-dimethyl-5,6-dihydroquinazolin-4-yl)-2,3,4,5-tetrahydro-1,4-benzoxazepin-7-yl]-1H-imidazo[4,5-b]pyridin-2-yl}carbamate dihydrochloride (0.12 g, 38% yield) as a white solid. $^1$H NMR (400 MHz, CD$_3$OD) δ 8.57-8.44 (m, 2H), 8.25 (bs, 1H), 7.73 (bs, 1H), 7.56 (dd, 1H), 7.09 (d, 1H), 6.59 (d, 1H), 6.35 (d, 1H), 5.15 (s, 2H), 4.53-4.42 (m, 2H), 4.33-4.21 (m, 2H), 3.91 (s, 3H), 2.92 (s, 2H), 1.09 (s, 6H); MS (ES) for $C_{27}H_{27}N_7O_3$: 498.6 (MH+).

Example 30

6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-amine STEP 1: A mixture of 2-amino-5-bromo-3-nitropyridine (0.70 g, 3.2 mmol), (4-{[(1,1-dimethylethyl)oxy]carbonyl}-2,3,4,5-tetrahydro-1,4-benzoxazepin-7-yl)boronic acid (example 1, step 2) (1.0 g, 3.1 mmol), [1,1'-bis(diphenylphosphino)ferrocene]dichloropalladium(II) complex with dichloromethane (0.15 mg, 0.2 mmol), diisopropylethylamine (1.8 g, 14 mmol) in 50% aqueous 1,4-dioxane (40 mL) was degassed with nitrogen for 5 minutes and then stirred at 90° C. for one hour. The reaction mixture was cooled to room temperature, diluted with ethyl acetate (80 mL) then filtered over celite. The filtrate was washed twice with brine (50 mL), filtered and the filtrate dried over sodium sulfate, filtered again and concentrated. The residue was purified by silica gel chromatography (25% to 95% ethyl acetate in hexanes gradient) to give 1,1-dimethylethyl 7-(6-amino-5-nitropyridin-3-yl)-2,3-dihydro-1,4-benzoxazepine-4(5H)-carboxylate (0.58 g, 48% yield); MS (EI) for $C_{19}H_{22}N_4O_5$: 389 (MH+).

STEP 2: A mixture of 1,1-dimethylethyl 7-(6-amino-5-nitropyridin-3-yl)-2,3-dihydro-1,4-benzoxazepine-4(5H)-carboxylate (0.58 g, 1.5 mmol), palladium (10% on charcoal, 0.50 g) and methanol (30 mL) was hydrogenated in a Parr apparatus at 45 psi for 18 hours. The mixture was filtered then concentrated and dried to give 1,1-dimethylethyl 7-(5,6-diaminopyridin-3-yl)-2,3-dihydro-1,4-benzoxazepine-4(5H)-carboxylate (0.51 g, 96% yield), MS (EI) for $C_{19}H_{24}N_4O_3$: 357 (MH+).

STEP 3: To a solution of 1,1-dimethylethyl 7-(5,6-diaminopyridin-3-yl)-2,3-dihydro-1,4-benzoxazepine-4(5H)-carboxylate (0.51 g, 1.4 mmol) in acetic acid (5 mL) was added 1,3-bis(methoxycarbonyl)-2-methyl-2-thiopseudourea (0.3 g, 1.4 mmol). The reaction mixture was heated 65° C. for 18 h and then concentrated. The resulting residue was suspended in water and basified with portion wise addition of solid sodium bicarbonate. After complete neutralization of the aqueous mixture the insoluble solid was collected by filtration and washed with water then 50% ethyl acetate in hexanes and the filter cake dried to give 1,1-dimethylethyl 7-(2-{[(methyloxy)carbonyl]amino}-1H-imidazo[4,5-b]pyridin-6-yl)-2,3-dihydro-1,4-benzoxazepine-4(5H)-carboxylate (0.52 g, 83% yield), MS (EI) for $C_{22}H_{25}N_5O_5$: 440 (MH+).

STEP 4: To a mixture of 1,1-dimethylethyl 7-(2-{[(methyloxy)carbonyl]amino}-3H-imidazo[4,5-b]pyridin-6-yl)-2,3-dihydro-1,4-benzoxazepine-4(5H)-carboxylate (0.52 g, 1.2 mmol) was taken into acetonitrile (5 mL) followed by addition of 4M hydrogen chloride in 1,4-dioxane (5 mL) and the mixture was stirred at room temperature for 10 minutes. The reaction mixture was concentrated to give a white solid. It was washed with ether then dried to give methyl [6-(2,3,4,5-tetrahydro-1,4-benzoxazepin-7-yl)-1H-imidazo[4,5-b]pyridin-2-yl]carbamate hydrochloride salt (0.40 g, 100% yield), MS (EI) for $C_{17}H_{17}N_5O_3$: 340 (MH+).

STEP 5: A mixture of methyl [6-(2,3,4,5-tetrahydro-1,4-benzoxazepin-7-yl)-1H-imidazo[4,5-b]pyridin-2-yl]carbamate hydrochloride (84 mg, 0.23 mmol, (7S)-4-chloro-7-ethyl-5,6,7,8-tetrahydroquinazoline (reagent preparation 3) (35 mg, 0.18 mmol) and N,N-diisopropylethylamine (0.15 mL, 0.90 mmol) in N-methyl-2-pyrrolidone (2.0 mL) was reacted in a microwave apparatus (250 W) for 5 min. at 110° C. After cooling to room temperature the reaction mixture was diluted with methanol (2 mL) and purified by preparative reverse phase HPLC (0.1% aqueous ammonium acetate-acetonitrile) to give 6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-amine. $^1$H NMR (400 MHz, Methanol-d$_4$): 8.33 (s, 1H), 8.13 (brs, 1H), 7.63 (s, 1H), 7.50 (brs, 1H), 7.31 (d, 1H), 7.04 (d, 1H), 4.75 (b, 2H), 4.44 (m, 1H), 4.24 (m, 1H), 3.99 to 3.86 (m, 2H), 2.94 to 2.86 (m, 2H), 2.60 (m, 1H), 2.28 (m, 1H), 1.97 (m, 1H), 1.75 (m, 1H), 1.36 (m, 2H), 1.14 (m, 1H), 0.97 (t, 3H); MS (EI) for $C_{25}H_{27}N_7O$: 442 (MH+).

The following compounds were prepared using the procedures described herein.

| Compound Name | NMR | MS |
| --- | --- | --- |
| 1-(6,6-dimethyl-4-{7-[4-(methyloxy)-3-{[2-(methyloxy)ethyl]oxy}phenyl]-2,3-dihydro-1,4-benzoxazepin-4(5H)-yl}-5,6,7,8-tetrahydroquinazolin-2-yl)-N,N-dimethylmethanamine | $^1$H NMR (400 MHz, DMSO-d6) δ 7.61 (d, 1H), 7.44 (dd, 1H), 7.20-7.14 (m, 2H), 7.02 (d, 1H), 6.97 (d, 1H), 4.60 (s, 2H), 4.31-4.24 (m, 2H), 4.18-4.13 (m, 2H), 3.87-3.82 (m, 2H), 3.79 (s, 3H), 3.70-3.66 (m, 2H), 3.33 (s, 3H), 2.69 (t, 2H), 2.45 (s, 2H), 2.14 (s, 6H), 1.59 (t, 2H), 0.86 (s, 6H) | MS (EI) for $C_{32}H_{42}N_4O_4$: 547 (MH+) |

-continued

| Compound Name | NMR | MS |
|---|---|---|
| 1-{4-[7-{3-[(difluoromethyl)oxy]-4-(methyloxy)phenyl}-2,3-dihydro-1,4-benzoxazepin-4(5H)-yl]-6,6-dimethyl-5,6,7,8-tetrahydroquinazolin-2-yl}-N,N-dimethylmethanamine. | $^1$H NMR (400 MHz, DMSO-d6) δ 7.66 (d, 1H), 7.54 (dd, 1H), 7.51-7.44 (m, 2H), 7.24 (d, 1H), 7.13 (t, 3H), 7.00 (d, 1H), 4.74 (br s, 2H), 4.41-4.32 (m, 2H), 4.31-4.18 (m, 2H), 3.97-3.89 (m, 2H), 3.87 (s, 3H), 2.84-2.69 (m, 8H), 2.48 (s, 2H), 1.62 (t, 2H), 0.85 (s, 6H) | MS (EI) for $C_{30}H_{36}F_2N_4O_3$: 539 (MH$^+$) |
| 1-[5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-2-(methyloxy)phenyl]ethanone. | $^1$H NMR (400 MHz, DMSO-d6) δ 7.84-7.78 (m, 2H), 7.62 (d, 1H), 7.44 (dd, 1H), 7.26 (d, 1H), 6.99 (d, 1H), 4.62 (s, 2H), 4.33-4.25 (m, 2H), 3.93 (s, 3H), 3.88-3.82 (m, 2H), 3.39 (br s, 2H), 2.69 (t, 2H), 2.57 (s, 3H), 2.44 (s, 2H), 2.15 (s, 6H), 1.59 (t, 2H), 0.86 (s, 6H) | MS (EI) for $C_{31}H_{38}N_4O_3$: 515 (MH$^+$) |
| 1-(6,6-dimethyl-4-{7-[4-(methyloxy)-3-(methylsulfonyl)phenyl]-2,3-dihydro-1,4-benzoxazepin-4(5H)-yl}-5,6,7,8-tetrahydroquinazolin-2-yl)-N,N-dimethylmethanamine. | $^1$H NMR (400 MHz, DMSO-d6) δ 8.00 (d, 1H), 7.96 (dd, 1H), 7.63 (d, 1H), 7.45 (dd, 1H), 7.40 (d, 1H), 7.01 (d, 1H), 4.66 (s, 2H), 4.34-4.28 (m, 2H), 4.00 (s, 3H), 3.90-3.83 (m, 2H), 3.41 (br s, 2H), 3.28 (s, 3H), 2.68 (t, 2H), 2.43 (s, 2H), 2.16 (br s, 7H), 1.59 (t, 2H), 0.85 (s, 6H) | MS (EI) for $C_{30}H_{38}N_4O_4S$: 551 (MH$^+$) |
| N-[5-(4-{2-[(dimethylamino)methyl]-6-methyl-5-(1-methylethyl)pyrimidin-4-yl}-2,3,4,5-tetrahydro-1,4-benzoxazepin-7-yl)-2-(methyloxy)phenyl]methanesulfonamide. | $^1$H NMR (400 MHz, DMSO-d6) δ 9.03 (s, 1H), 7.51 (d, 1H), 7.49-7.39 (m, 3H), 7.17 (d, 1H), 7.02 (d, 1H), 4.45 (s, 2H), 4.33-4.26 (m, 2H), 3.87 (s, 3H), 3.74-3.66 (m, 2H), 3.32 (s, 2H), 3.30-3.21 (m, 1H), 2.98 (s, 3H), 2.48 (s, 3H), 2.30 (br s, 6H), 1.32 (d, 6H) | MS (EI) for $C_{28}H_{37}N_5O_4S$: 540 (MH$^+$) |
| N'-{5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}-N,N-dimethylethane-1,2-diamine | $^1$H NMR (400 MHz, CD$_3$OD) δ 7.58-7.47 (m, 2H), 7.42 (dd, 1H), 7.25 (dd, 1H), 7.15-7.08 (m, 2H), 7.01-6.92 (m, 3H), 6.86 (s, 1H), 4.49 (s, 2H), 4.28-4.22 (m, 2H), 3.90 (s, 2H), 3.84-3.78 (m, 2H), 3.45 (t, 2H), 2.63-2.53 (m, 5H), 2.34 (s, 6H), 2.06 (s, 3H) | MS (EI) for $C_{33}H_{36}FN_7O$: 566 (MH$^+$) |
| 2-fluoro-N-({4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl)ethanamine | $^1$H NMR (400 MHz, DMSO-d6) δ 7.63 (s, 1H), 7.55 (d, 1H), 7.50 (d, 2H), 7.37 (d, 1H), 7.02 (d, 1H), 4.45 (dd, 3H), 4.36-4.22 (m, 3H), 3.71 (s, 2H), 3.63 (s, 2H), 3.40-3.21 (m, 2H), 2.76 (t, 1H), 2.69 (t, 1H), 2.47 (s, 3H), 1.87 (s, 3H), 1.33 (d, 6H) | MS (EI) for $C_{28}H_{33}FN_6O$: 489 (MH$^+$) |
| 6-{4-[2-{[(2-fluoroethyl)amino]methyl}-6-methyl-5-(1-methylethyl)pyrimidin-4-yl]-2,3,4,5-tetrahydro-1,4-benzoxazepin-7-yl}[1,3]thiazolo[5,4-b]pyridin-2-amine. | $^1$H NMR (400 MHz, DMSO-d6) δ 8.37 (d, 1H), 7.88 (s, 2H), 7.81 (d, 1H), 7.63 (s, 1H), 7.57 (d, 1H), 7.04 (d, 1H), 4.51 (s, 2H), 4.43 (t, 1H), 4.31 (s, 3H), 3.71 (s, 2H), 3.61 (s, 2H), 3.24 (s, 1H), 2.74 (t, 1H), 2.67 (s, 1H), 2.46 (s, 3H), 1.31 (d, 6H) | MS (EI) for $C_{26}H_{30}FN_7O$: 508 (MH$^+$) |
| N,N-dimethyl-1-{4-methyl-6-[7-(2-methyl-1H-benzimidazol-6-yl)-2,3-dihydro-1,4-benzoxazepin-4(5H)-yl]-5-propylpyrimidin-2-yl}methanamine | $^1$H NMR (400 MHz, DMSO-d6) δ 7.61 (d, 2H), 7.46 (dd, 2H), 7.37 (d, 1H), 6.99 (d, 1H), 4.61 (s, 2H), 4.32 (s, 2H), 3.78 (s, 2H), 3.34 (br s, 2H), 2.50 (m, 5H), 2.35 (s, 3H), 2.12 (s, 6H), 1.45 (d, 2H), 0.75 (t, 3H) | MS (EI) for $C_{28}H_{34}N_6O$: 471 (MH$^+$) |
| N,N-dimethyl-1-{4-methyl-6-[7-(2-methyl-1H-benzimidazol-6-yl)-2,3-dihydro-1,4-benzoxazepin-4(5H)-yl]-5-prop-2-en-1-ylpyrimidin-2-yl}methanamine | $^1$H NMR (400 MHz, DMSO-d6) δ 7.61 (d, 1H), 7.55-7.41 (m, 3H), 7.35 (dt, 1H), 6.97 (dd, 1H), 6.23-6.01 (m, 1H), 5.25 (t, 1H), 4.93 (t, 1H), 4.61 (s, 2H), 4.27 (d, 2H), 3.82 (s, 2H), 3.37 (s, 2H), 3.32 (s, 2H), 2.50 (m, 3H), 2.27 (s, 3H), 2.15 (s, 6H) | MS (EI) for $C_{28}H_{32}N_6O$: 469 (MH$^+$) |
| 6-(4-{2-[(dimethylamino)methyl]-6-methyl-5-propylpyrimidin-4-yl}-2,3,4,5-tetrahydro-1,4-benzoxazepin-7- | $^1$H NMR (400 MHz, DMSO-d6) δ 8.38 (d, 1H), 7.88 (s, 2H), 7.82 (d, 1H), 7.70 (s, 1H), 7.53 (d, 1H), 7.01 (d, 1H), 4.63 (s, 2H), 4.34 (s, 2H), 3.78 (s, 2H), 3.33 (d, 2H), | MS (EI) for $C_{26}H_{31}N_7OS$: 490 (MH$^+$) |

| Compound Name | NMR | MS |
|---|---|---|
| yl)[1,3]thiazolo[5,4-b]pyridin-2-amine | 2.51 (m, 2H), 2.34 (s, 3H), 2.11 (s, 6H), 1.46 (s, 2H), 0.75 (t, 3H) | |
| 6-(4-{2-[(dimethylamino)methyl]-6-methyl-5-prop-2-en-1-ylpyrimidin-4-yl}-2,3,4,5-tetrahydro-1,4-benzoxazepin-7-yl)[1,3]thiazolo[5,4-b]pyridin-2-amine | $^1$H NMR (400 MHz, DMSO-d6) δ 8.36 (d, 1H), 7.88 (s, 2H), 7.80 (d, 1H), 7.60 (d, 1H), 7.53 (dd, 1H), 7.02 (d, 1H), 6.10 (dd, 1H), 5.23 (d, 1H), 4.94 (d, 1H), 4.63 (s, 2H), 4.28 (s, 2H), 3.83 (s, 2H), 3.34 (s, 2H), 3.30 (s, 2H), 2.26 (s, 3H), 2.13 (s, 6H) | MS (EI) for $C_{26}H_{29}N_7OS$: 488 (MH$^+$) |
| N,N-dimethyl-1-{4-methyl-6-[7-(2-methyl-1H-benzimidazol-5-yl)-2,3-dihydro-1,4-benzoxazepin-4(5H)-yl]-5-phenylpyrimidin-2-yl}methanamine | $^1$H NMR (400 MHz, DMSO-d6) δ 7.73-7.42 (m, 4H), 7.41-7.27 (m, 5H), 7.23 (d, 1H), 6.92 (dd, 1H), 4.51 (d, 2H), 4.07-3.91 (m, 2H), 3.53 (d, 2H), 3.38 (d2H), 2.49 (s, 3H), 2.16 (d, 6H), 2.02 (d, 3H) | MS (EI) for $C_{31}H_{32}N_6O$: 505.0 (MH$^+$) |
| 6-(4-{2-[(dimethylamino)methyl]-6-methyl-5-phenylpyrimidin-4-yl}-2,3,4,5-tetrahydro-1,4-benzoxazepin-7-yl)[1,3]thiazolo[5,4-b]pyridin-2-amine | $^1$H NMR (400 MHz, DMSO-d6) δ 8.34 (d, 1H), 7.89 (s, 2H), 7.78 (d, 1H), 7.52-7.39 (m, 3H), 7.32 (t, 4H), 6.95 (d, 1H), 4.57 (s, 2H), 4.04 (s, 2H), 3.48 (s, 2H), 3.36 (d, 2H), 2.15 (s, 6H), 2.01 (s, 3H) | MS (EI) for $C_{29}H_{29}N_7OS$: 523.9 (MH$^+$) |
| N,N-dimethyl-1-{4-methyl-6-[7-(2-methyl-1H-benzimidazol-5-yl)-2,3-dihydro-1,4-benzoxazepin-4(5H)-yl]-5-(2-methylpropyl)pyrimidin-2-yl}methanamine | $^1$H NMR (400 MHz, DMSO-d6) δ12.22 (s, 1H), 7.67 (s, 1H), 7.59 (d, 1H), 7.56-7.39 (m, 2H), 7.34 (d, 1H), 6.96 (d, 1H), 4.56 (s, 2H), 4.29 (s, 2H), 3.73 (s, 2H), 2.60 (t, 2H), 2.32 (s, 3H), 2.10 (s, 6H), 1.88 (s, 2H, OAc), 1.76-1.53 (m, 1H), 0.52 (d 6H) | MS (EI) for $C_{29}H_{36}N_6O$: 485.0 (MH$^+$) |
| 6-(4-{5-(cyclopropylmethyl)-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine | $^1$H NMR (400 MHz, DMSO-d6) δ 8.42 (d, 1H), 7.93 (s, 2H), 7.87 (d, 1H), 7.76 (d, 1H), 7.58 (dd, 1H), 7.07 (d, 1H), 4.70 (s, 2H), 4.37 (s, 2H), 3.85 (s, 2H), 3.50-3.42 (m, 2H), 2.74-2.58 (m, 2H), 2.42 (d, 3H), 2.28-2.03 (m, 6H), 0.90 (s, 1H), 0.48-0.31 (m, 2H), 0.14--0.28 (m, 2H) | MS (EI) for $C_{27}H_{31}N_7OS$: 502.0 (MH$^+$) |
| 6-(4-{2-[(dimethylamino)methyl]-6-methyl-5-(2-methylpropyl)pyrimidin-4-yl}-2,3,4,5-tetrahydro-1,4-benzoxazepin-7-yl)[1,3]thiazolo[5,4-b]pyridin-2-amine | $^1$H NMR (400 MHz, DMSO-d6) δ 8.37 (d, 1H), 7.88 (s, 2H), 7.81 (d, 1H), 7.72 (s, 1H), 7.53 (d, 1H), 7.01 (d, 1H), 4.61 (s, 2H), 4.33 (s, 2H), 3.76 (s, 2H), 3.37 (s, 2H), 2.59 (d, 2H), 2.35 (s, 3H), 2.14 (s, 6H), 1.79-1.53 (m, 1H), 0.55 (d, 6H) | MS (EI) for $C_{27}H_{33}N_7OS$: 504.0 (MH$^+$) |
| 7-(2-methyl-1H-benzimidazol-5-yl)-4-[6-methyl-5-(1-methylethyl)-2-(pyrrolidin-1-ylmethyl)pyrimidin-4-yl]-2,3,4,5-tetrahydro-1,4-benzoxazepine | $^1$H NMR (400 MHz, DMSO-d6) δ 7.60 (s, 1H), 7.52-7.43 (m, 3H), 7.33 (dt, 1H), 6.99 (t, 1H), 4.40 (s, 2H), 4.27 (d, 2H), 3.65 (br s, 2H), 3.47 (s, 2H), 3.28 (dt, 1H), 2.47 (s, 3H), 2.44 (s, 3H), 2.41 (m, 4H), 1.85 (s, 6H, OAc), 1.64-1.49 (m, 4H), 1.30 (d, 6H) | MS (EI) for $C_{30}H_{36}N_6O$: 497.2 (MH$^+$) |
| 1-{6,6-dimethyl-4-[7-(2-methyl-1H-benzimidazol-5-yl)-2,3-dihydro-1,4-benzoxazepin-4(5H)-yl]-5,6,7,8-tetrahydroquinazolin-2-yl}ethanamine | $^1$H NMR (400 MHz, dmso) δ 8.60 (s, 2H), 8.02-7.89 (m, 2H), 7.85 (d, 1H), 7.82 (d, 1H), 7.59 (d, 1H), 7.05 (d, 1H), 5.02 (s, 2H), 4.53-4.29 (m, 3H), 4.24-3.99 (m, 2H), 2.83 (s, 3H), 2.79 (t, 2H), 2.52 (s, 2H), 1.60 (t, 2H), 1.44 (d, 3H), 0.86 (s, 6H) | MS (ES) for $C_{29}H_{34}N_6O$: 483 (MH$^+$) |
| 6-[4-(2,6,6-trimethyl-5,6,7,8-tetrahydroquinazolin-4-yl)-2,3,4,5-tetrahydro-1,4-benzoxazepin-7-yl][1,3]thiazolo[5,4-b]pyridin-2-amine | $^1$H NMR (400 MHz, dmso) δ 8.38 (d, 1H), 7.89 (s, 2H), 7.83 (d, 1H), 7.73 (d, 1H), 7.56 (dd, 1H), 7.05 (d, 1H), 4.59 (s, 2H), 4.29 (m, 2H), 3.84 (m, 2H), 2.66 (t, 2H), 2.42 (s, 2H), 2.34 (s, 3H), 1.58 (t, 2H), 0.84 (s, 6H) | MS (ES) for $C_{26}H_{28}N_6OS$: 473 (MH$^+$) |
| 4-[2-(fluoromethyl)-6,6-dimethyl-5,6,7,8-tetrahydroquinazolin-4-yl]-7-(2-methyl-1H-benzimidazol-5-yl)- | $^1$H NMR (400 MHz, dmso) δ 7.69 (s, 1H), 7.67 (d, 1H), 7.54 (d, 1H), 7.50 (dd, 1H), 7.44 (dd, 1H), 7.03 (d, 1H), 5.23 (d, 2H), 4.66 (s, 2H), | MS (ES) for $C_{28}H_{30}FN_5O$: 472 (MH$^+$) |

| Compound Name | NMR | MS |
|---|---|---|
| 2,3,4,5-tetrahydro-1,4-benzoxazepine | 4.30 (m, 2H), 3.89 (s, 1H), 2.73 (t, 2H), 2.54 (s, 3H), 1.91 (s, 2H), 1.61 (t, 2H), 0.86 (s, 6H) | |
| 6-{4-[2-methyl-7-(methyloxy)quinazolin-4-yl]-2,3,4,5-tetrahydro-1,4-benzoxazepin-7-yl}[1,3]thiazolo[5,4-b]pyridin-2-amine. Prepared as a dihydrochloride salt. | $^1$H NMR (400 MHz, dmso) δ 8.45 (d, 1H), 8.25-8.1 (br, 3H), 7.89 (d, 2H), 7.59 (s, 1H), 7.34-7.19 (m, 2H), 7.01 (d, 1H), 4.72-4.32 (m, 6H), 3.95 (s, 3H), 2.56 (s, 3H) | MS (EI) Calculated for $C_{25}H_{22}N_6O_2S$: 470.6 Found: 471.2 (MH$^+$) |
| 6-(4-{5-chloro-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine. Prepared as an acetate salt. | $^1$H NMR (400 MHz, methanol-$d_4$): 8.34 (d, 1H), 7.81 (d, 1H), 7.65 (d, 1H), 7.48 (dd, 1H), 7.06 (d, 1H), 5.07 (s, 2H), 4.36 (m, 2H), 4.23 (m, 2H), 3.76 (s, 2H), 2.50 (s, 3H), 2.47 (s, 6H), 1.94 (s, 3H) | MS (EI) for $C_{23}H_{24}ClN_7OS$: 482 (MH$^+$) |
| 6-(4-{5-bromo-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine. Prepared as a diacetate salt. | $^1$H NMR (400 MHz, methanol-$d_4$): 8.35 (d, 1H), 7.81 (d, 1H), 7.65 (d, 1H), 7.48 (dd, 1H), 7.05 (d, 1H), 5.06 (s, 2H), 4.38 (m, 2H), 4.19 (m, 2H), 3.78 (s, 2H), 2.56 (s, 3H), 2.48 (s, 6H), 1.94 (s, 3H) | MS (EI) for $C_{23}H_{24}BrN_7OS$: 526 (MH$^+$) |
| 1-{5-chloro-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine. Prepared as a diacetate salt. | $^1$H NMR (400 MHz, methanol-$d_4$): 7.63 (s, 1H), 7.61 (d, 1H), 7.52 (d, 1H), 7.43 (m, 2H), 7.02 (d, 1H), 5.08 (s, 2H), 4.34 (m, 2H), 4.23 (m, 2H), 3.84 (s, 2H), 2.58 (s, 3H), 2.52 (s, 6H), 2.50 (s, 3H), 1.94 (s, 6H) | MS (EI) for $C_{25}H_{27}ClN_6O$: 463 (MH$^+$) |
| 1-{5-bromo-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine. Prepared as a diacetate salt. | $^1$H NMR (400 MHz, methanol-$d_4$): 7.64 (d, 1H), 7.61 (d, 1H), 7.52 (d, 1H), 7.43 (m, 2H), 7.00 (d, 1H), 5.06 (s, 2H), 4.36 (m, 2H), 4.19 (m, 2H), 3.79 (s, 2H), 2.58 (s, 3H), 2.56 (s, 3H), 2.47 (s, 6H), 1.93 (s, 6H) | MS (EI) for $C_{25}H_{27}BrN_6O$: 507 (MH$^+$) |
| 4-[7-(1H-benzimidazol-5-yl)-2,3-dihydro-1,4-benzoxazepin-4(5H)-yl]-6-methylpyrimidin-2-amine | $^1$H NMR (400 MHz, DMSO) δ 8.22 (s, 1H), 7.81 (s, 1H), 7.62 (s, 1H), 7.45 (dd, 2H), 7.00 (d, 1H), 6.09 (s, 1H), 5.94 (s, 2H), 4.73 (s, 2H), 4.03 (dd, 4H), 2.03 (d, 3H) | MS (EI) for $C_{21}H_{20}N_6O$: 373.2 (MH$^+$) |
| 5-(4-fluorobenzyl)-4-[7-(3H-imidazo[4,5-b]pyridin-6-yl)-2,3-dihydro-1,4-benzoxazepin-4(5H)-yl]-6-methylpyrimidin-2-amine | $^1$H NMR (400 MHz, DMSO) δ 8.47 (dd, 2H), 8.12-7.95 (d, 1H), 7.53 (s, 1H), 7.12 (t, 2H), 7.05 (t, 3H), 6.88 (d, 1H), 6.13 (s, 2H), 4.34 (s, 2H), 4.22 (s, 2H), 3.83 (s, 2H), 3.65 (s, 2H), 1.97 (s, 3H) | MS (EI) for $C_{27}H_{24}FN_7O$: 482.2 (MH$^+$) |
| 5-(4-fluorobenzyl)-4-methyl-6-[7-(2-methyl-3H-imidazo[4,5-b]pyridin-6-yl)-2,3-dihydro-1,4-benzoxazepin-4(5H)-yl]pyrimidin-2-amine | $^1$H NMR (400 MHz, DMSO) δ 8.29 (s, 1H), 7.94 (s, 1H), 7.50 (d, 1H), 7.11 (t, 2H), 7.05 (t, 3H), 6.86 (s, 1H), 6.12 (s, 2H), 4.33 (s, 2H), 4.22 (s, 2H), 3.83 (s, 2H), 3.65 (s, 2H), 2.54 (s, 3H), 1.89 (s, 3H) | MS (EI) for $C_{28}H_{26}FN_7O$: 496.2 (MH$^+$) |
| 1-{4-[7-(3H-imidazo[4,5-b]pyridin-6-yl)-2,3-dihydro-1,4-benzoxazepin-4(5H)-yl]-7-methoxyquinazolin-2-yl}-N,N-dimethylmethanamine | $^1$H NMR (400 MHz, DMSO) δ 8.62 (t, 1H), 8.45 (d, 1H), 8.17 (d, 1H), 7.90 (t, 1H), 7.74 (t, 1H), 7.52 (dt, 1H), 7.12 (t, 1H), 7.05 (dd, 1H), 6.98 (d, 1H), 5.04 (s, 2H), 4.44 (d, 2H), 4.18 (s, 2H), 3.86 (s, 3H), 3.41 (s, 2H), 2.08 (d, 6H) | MS (EI) for $C_{27}H_{27}N_7O_2$: 482.3 (MH$^+$) |
| 6-{4-[2-amino-5-(4-fluorobenzyl)-6-methylpyrimidin-4-yl]-2,3,4,5-tetrahydro-1,4-benzoxazepin-7-yl}[1,3]thiazolo[5,4-b]pyridin-2-amine | $^1$H NMR (400 MHz, DMSO) δ 8.13 (d, 1H), 7.82 (s, 2H), 7.62 (d, 1H), 7.44 (dt, 1H), 7.09-6.92 (m, 5H), 6.83 (d, 1H), 6.05 (s, 2H), 4.27 (s, 2H), 4.14 (s, 2H), 3.72 (d, 2H), 3.55 (d, 2H), 1.91 (d, 3H) | MS (EI) for C27H24FN7OS: 514.2 (MH$^+$) |
| 4-[7-(1H-benzimidazol-5-yl)-2,3-dihydro-1,4-benzoxazepin-4(5H)-yl]-5-[(4-fluorophenyl)methyl]-6-methylpyrimidin-2-amine | $^1$H NMR (400 MHz, DMSO-$d_6$) δ 8.24 (d, 1H), 7.92-7.50 (m, 1H), 7.47 (d, 1H), 7.20 (d, 1H), 7.12 (dq, 5H), 7.02 (d, 1H), 6.75 (d, 1H), 6.11 (d, 2H), 4.31 (s, 2H), 4.20 (d, 2H), 3.82 (d, 2H), 3.65 (s, 2H), 1.98 (s, 3H) | MS (EI) for $C_{28}H_{25}FN_6O$: 481.0 (MH$^+$) |

-continued

| Compound Name | NMR | MS |
|---|---|---|
| 1-{4-[7-(1H-benzimidazol-5-yl)-2,3-dihydro-1,4-benzoxazepin-4(5H)-yl]-7-(methyloxy)quinazolin-2-yl}-N,N-dimethylmethanamine | $^1$H NMR (400 MHz, DMSO-$d_6$) δ 8.25 (s, 1H), 7.95 (d, 1H), 7.81 (s, 1H), 7.74-7.62 (m, 2H), 7.49 (s, 2H), 7.16 (s, 1H), 7.10-7.03 (m, 1H), 6.98 (d, 1H), 5.05 (s, 2H), 4.45 (s, 2H), 4.20 (s, 2H), 3.87 (d, 3H), 3.47 (s, 2H), 2.13 (d, 6H) | MS (EI) for $C_{28}H_{28}N_6O_2$: 481.3 (MH$^+$) |
| N,N-dimethyl-1-{4-[7-(2-methyl-1H-benzimidazol-5-yl)-2,3-dihydro-1,4-benzoxazepin-4(5H)-yl]-7-(methyloxy)quinazolin-2-yl}methanamine | $^1$H NMR (400 MHz, DMSO-$d_6$) δ 7.97-7.91 (m, 1H), 7.67 (d, 2H), 7.52 (d, 1H), 7.47 (dd, 1H), 7.40 (dd, 1H), 7.16 (d, 1H), 7.06 (dd, 1H), 6.96 (dd, 1H), 5.04 (s, 2H), 4.45 (s, 2H), 4.19 (s, 2H), 3.90 (d, 3H), 3.44 (s, 2H), 2.58 (s, 3H), 2.24 (m, 6H) | MS (EI) for $C_{29}H_{30}N_6O_2$: 495.2 (MH$^+$) |
| 5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-amine | $^1$H NMR (400 MHz, DMSO-$d_6$) δ 7.62 (s, 1H), 7.48 (m, 3H), 7.26-7.06 (m, 6H), 7.00 (d, 1H), 6.84 (s, 1H), 6.45 (s, 2H), 4.40 (s, 2H), 4.22 (s, 2H), 3.85 (s, 2H), 3.71 (s, 2H), 2.52 (s, 3H), 2.01 (s, 3H) | MS (EI) for C29H27FN6O: 495.3 (MH$^+$) |
| 6-(4-{2-[(methylamino)methyl]-6-methyl-5-(1-methylethyl)pyrimidin-4-yl}-2,3,4,5-tetrahydro-1,4-benzoxazepin-7-yl)[1,3]thiazolo[5,4-b]pyridin-2-amine | $^1$H NMR (400 MHz, $d_6$-DMSO): 8.38 (d, 1H), 7.88 (brs, 2H), 7.81 (d, 1H), 7.61 (d, 1H), 7.54 (dd, 1H), 7.03 (d, 1H), 4.46 (s, 2H), 4.30 (brt, 2H), 3.68 (brt, 2H), 3.35 (s, 2H), 3.25 (m, 1H), 2.47 (s, 3H), 2.10 (s, 6H), 1.30 (d, 6H) | MS (EI) for $C_{26}H_{31}N_7OS$: 490 (MH$^+$) |
| N-ethyl-N-({4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl)ethanamine | $^1$H NMR (400 MHz, DMSO-d6) δ 7.62 (s, 1H), 7.55 (br s, 1H), 7.47 (m, 3H), 7.35 (d, 1H), 6.99 (d, 1H), 4.43 (s, 2H), 4.27 (br t, 2H), 3.68 (br s, 2H), 3.59 (s, 2H), 2.47 (s, 3H), 1.91 (s, 3H), 1.32 (d, 6H), 0.89 (t, 6H) | MS (EI) for $C_{30}H_{38}N_6O$: 499.3 (MH$^+$) |
| {4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl acetate | $^1$H NMR (400 MHz, DMSO-d6 plus D$_2$O) δ 7.70 (s, 1H), 7.56 (m, 3H), 7.38 (m, 1H), 7.06 (d, 1H), 4.96 (s, 2H), 4.43 (s, 2H), 4.30 (br s, 2H), 3.68 (br s, 2H), 3.31-3.20 (m, 1H), 2.46 (s, 3H), 2.08 (s, 3H), 1.32 (d, 6H) | MS (EI) for $C_{28}H_{31}N_5O_3$: 486.3 (MH$^+$) |
| {4-methyl-6-[7-(2-methyl-1H-benzimidazol-5-yl)-2,3-dihydro-1,4-benzoxazepin-4(5H)-yl]-5-(1-methylethyl)pyrimidin-2-yl}methanol | $^1$H NMR (400 MHz, DMSO-d6 plus D$_2$O) δ 7.59 (m, 1H), 7.54-7.45 (m, 3H), 7.36 (d, 1H), 7.01 (d, 1H), 4.80 (br t, 0.2H), 4.43 (s, 2H), 4.32 (s, 2H), 4.26 (br s, 2H), 3.66 (br s, 2H), 3.25 (m, 1H), 2.47 (s, 3H), 2.45 (s, 3H), 1.87 (s, 1H-OAc peak), 1.29 (d, 6H) | MS (EI) for $C_{26}H_{29}N_5O_2$: 444.3 (MH$^+$) |
| 6-(4-{2-[(dimethylamino)methyl]-5-ethyl-6-methylpyrimidin-4-yl}-2,3,4,5-tetrahydro-1,4-benzoxazepin-7-yl)[1,3]thiazolo[5,4-b]pyridin-2-amine | $^1$H NMR (400 MHz, DMSO-d6) δ 8.37 (d, 1H), 7.87 (s, 2H), 7.81 (d, 1H), 7.68 (d, 1H), 7.53 (dd, 1H), 7.01 (d, 1H), 4.63 (s, 2H), 4.33 (br t, 2H), 3.81 (br t, 2H), 2.62 (q, 2H), 2.35 (s, 3H), 2.10 (s, 6H), 1.88 (s, 2H-OAc peak), 1.13 (t, 3H) | MS (EI) for $C_{25}H_{29}N_7OS$: 476.2 (MH$^+$) |
| N,N-dimethyl-1-{4-methyl-6-[7-(2-methyl-1H-benzimidazol-6-yl)-2,3-dihydro-1,4-benzoxazepin-4(5H)-yl]-5-[2-(methyloxy)ethyl]pyrimidin-2-yl}methanamine | $^1$H NMR (400 MHz, DMSO-d6) δ 12.25 (s, 1H), 7.67 (m, 2H), 7.47 (dd, 2H), 7.39 (br d, 1H), 7.01 (d, 1H), 4.60 (s, 2H), 4.29 (br t, 2H), 3.79 (br t, 2H), 3.53 (t, 2H), 3.18 (s, 3H), 3.17 (s, 1H), 2.92 (t, 2H), 2.39 (s, 3H), 2.13 (s, 6H) | MS (EI) for $C_{28}H_{34}N_6O_2$: 487.3 (MH$^+$) |
| 6-(4-{2-[(dimethylamino)methyl]-6-methyl-5-[2-(methyloxy)ethyl]pyrimidin-4-yl}-2,3,4,5-tetrahydro-1,4-benzoxazepin-7-yl)[1,3]thiazolo[5,4-b]pyridin-2-amine | $^1$H NMR (400 MHz, DMSO-d6) δ 8.36 (d, 1H), 7.89 (br s, 2H), 7.82 (d, 1H), 7.68 (d, 1H), 7.52 (dd, 1H), 7.00 (d, 1H), 4.59 (s, 2H), 4.29 (br t, 2H), 3.78 (br t, 2H), 3.49 (t, 2H), 3.18 (s, 3H), 2.85 (t, 2H), 2.35 (s, 3H), 2.09 (s, 6H), 1.87 (s, 2H-OAc peak) | MS (EI) for $C_{26}H_{31}N_7O_2S$: 506.3 (MH$^+$) |
| 6-(4-{2-[(dimethylamino)methyl]-5,6-dimethylpyrimidin-4-yl}-2,3,4,5-tetrahydro-1,4- | $^1$H NMR (400 MHz, DMSO-d6) δ 8.37 (d, 1H), 7.87 (s, 2H), 7.82 (d, 1H), 7.70 (d, 1H), 7.52 (dd, 1H), 7.02 (d, 1H), 4.63 (s, 2H), 4.30 (br | MS (EI) for $C_{24}H_{27}N_7OS$: 462.2 (MH$^+$) |

| Compound Name | NMR | MS |
|---|---|---|
| benzoxazepin-7-yl)[1,3]thiazolo[5,4-b]pyridin-2-amine | t, 2H), 3.82 (br t, 2H), 3.33 (s, 2H), 2.30 (s, 3H), 2.16 (s, 3H), 2.10 (s, 6H), 1.90 (s, 3H-OAc peak) | |
| 1-{4,5-dimethyl-6-[7-(2-methyl-1H-benzimidazol-6-yl)-2,3-dihydro-1,4-benzoxazepin-4(5H)-yl]pyrimidin-2-yl}-N,N-dimethylmethanamine | $^1$H NMR (400 MHz, DMSO-d6) δ 7.61 (m, 2H), 7.53-7.43 (m, 2H), 7.36 (d, 1H), 7.00 (d, 1H), 4.61 (s, 2H), 4.29 (br t, 2H), 3.82 (br t, 2H), 3.39 (s, 2H), 2.31 (s, 3H), 2.17 (s, 3H), 2.16 (s, 6H), 1.91 (s, 3H-OAc Peak) | MS (EI) for $C_{26}H_{30}N_6O$: 443.3 (MH$^+$) |
| {4-[7-(2-amino[1,3]thiazolo[5,4-b]pyridin-6-yl)-2,3-dihydro-1,4-benzoxazepin-4(5H)-yl]-6,6-dimethyl-5,6,7,8-tetrahydroquinazolin-2-yl}acetonitrile | $^1$H NMR (400 MHz, d6-DMSO) δ 8.39 (d, 1H), 7.88 (d, 1H), 7.85 (s, 2H), 7.75 (s, 1H), 7.56 (d, 1H), 7.05 (d, 1H), 4.70 (s, 2H), 4.34 (m, 2H), 4.06 (s, 2H), 3.91 (m, 2H), 2.70 (t, 2H), 2.46 (s, 2H), 1.59 (t, 2H), 0.85 (s, 6H) | MS (ES) for $C_{27}H_{27}N_7OS$: 498.2 (MH$^+$) |

Biological Examples

Compounds of the Invention have activity for PI3K-alpha, mTOR, or for both. Compounds of this invention have been tested using the assays described in Biological Examples 1 and 3 and have been determined to be inhibitors of PI3K-alpha, mTOR, or for both.

Suitable in vitro assays for measuring PI3K, mTORc1, and mTORc2 activity and the inhibition thereof by compounds are known in the art. Biological Examples, Example 1, 2, and 3 describe in vitro assay for measuring PI3K and mTOR activity. Cell-based assays for measurement of in vitro efficacy in treatment of cancer are known in the art. Biological Examples, Example 5 and 6 describe assays to measure in vitro cell activity. Suitable in vivo models for cancer are known to those of ordinary skill in the art. Biological Examples 7, 8, 9, 10, 11, 12, and 13 describe in vivo models for prostate adenocarcinoma, glioblastoma, lung carcinoma, and melanoma. Following the examples disclosed herein, as well as that disclosed in the art, a person of ordinary skill in the art can determine the PI3K-inhibitory and/or mTOR-inhibitory activity of a Compound of this invention.

Thus, compounds of Formula I are useful for treating diseases, particularly cancer in which activity against PI3K-alpha, mTOR, or both contributes to the pathology and/or symptomatology of the disease. For example, cancer in which activity against PI3K-alpha, mTOR, or both contributes to its pathology and/or symptomatology include breast cancer, mantle cell lymphoma, renal cell carcinoma, acute myelogenous leukemia, chronic myelogenous leukemia, NPM/ALK-transformed anaplastic large cell lymphoma, diffuse large B cell lymphoma, rhabdomyosarcoma, ovarian cancer, endometrial cancer, cervical cancer, non small cell lung carcinoma, small cell lung carcinoma, adenocarcinoma, colon cancer, rectal cancer, gastric cancer, hepatocellular carcinoma, melanoma, pancreatic cancer, prostate carcinoma, thyroid carcinoma, anaplastic large cell lymphoma, hemangioma, glioblastoma, or head and neck cancer.

Biological Example 1 mTOR/GbL/Raptor (mTORC1) ELISA Assay

The measurement of mTORC1 enzyme activity was performed in an ELISA assay format following the phosphorylation of 4E-BP1 protein. All experiments were performed in the 384-well format. Generally, 0.5 μL DMSO containing varying concentrations of the test Compound was mixed with 15 μL enzyme solution. Kinase reactions were initiated with the addition of 15 μL of substrates-containing solution. The assay conditions were as follows; 0.2 nM mTORC1, 10 μM ATP and 50 nM NHis-tagged 4E-BP1 in 20 mM Hepes, pH 7.2, 1 mM DTT, 50 mM NaCl, 10 mM $MnCl_2$, 0.02 mg/mL BSA, 0.01% CHAPS, 50 mM β-glycerophosphate. Following an incubation of 120 minutes at ambient temperature, 20 μL of the reaction volume was transferred to a Ni-Chelate-coated 384-well plate. The binding step of the 4E-BP1 protein proceeded for 60 minutes, followed by washing 4 times each with 50 μL of Tris-buffered saline solution (TBS). Anti-phospho-4E-BP1 rabbit-IgG (20 μL, 1:5000) in 5% BSA-TBST (0.2% Tween-20 in TBS) was added and further incubated for 60 minutes. Incubation with a secondary HRP-tagged anti-IgG was similarly performed after washing off the primary antibody (4 washes of 50 μL). Following the final wash step with TBST, 20 μL of SuperSignal ELISA Femto (Pierce Biotechnology) was added and the luminescence measured using an EnVision plate reader.

As numbered in Table 1, Compounds 12, 13, 55, 65, 66, 70, 72-74, 78-80, 83, 89, 93, 94, 97, 102, 103, 124, 131, 142, 147, 148, 153, 170, 171, 174-178, 181, 183, 189, 192, 193, 213, 215, 217-221, 224-225, 229, 234, 236, 238, 248, 250, 252, 254, 255, 264-265, 290, 304, 308, 310-313, 321, 325, 339, 347-348, 352-354, 369, 371, 373, 375, 387, 397, 399, 401-402, 405-406, 409, 436, 439-440, 443, 447-450, 452, 474, 478-479, 483-484, 486, 488-491, 495, 500-502, 506-508, 514, 520, 537, 544-545, 548, 550, 552-555, 558, 564, 582-584, 586, 589, 590, 592-593, 596-601, 605, 607, 651, 660, 668-669, 676, 680, 684, 687, 689-690, and 692 have an $IC_{50}$ in this assay of less than or equal to 10 nM. As numbered in Table 1, Compounds 9, 11, 15, 16, 17, 21, 30, 37, 38, 68, 81, 82, 84, 86, 90-91, 95, 101, 113, 140-141, 143-146, 156, 158, 179-180, 182, 185-187, 194, 216, 226, 251, 256, 289, 291, 299-301, 305, 314-316, 318, -320, 322, 334, 351, 358, 360, 363-368, 370, 372, 376, 380, 382, 388-391, 396, 403, 407, 408, 411, 412, 414, 415, 418, 425, 426, 430-432, 434, 435, 437, 441, 442, 444-446, 451, 460, 462, 464, 465, 473, 482, 485, 487, 487, 492-494, 497, 503, 505, 510, 512, 517, 519, 526, 530, 540, 547, 556, 559, 566, 575-578, 585, 587-588, 591, 594-595, 602, 604, 606, 608, 614, 617, 619, 623, 626, 628, 636, 642, 665, 670, 674, 679, 682-683, and 686 have an $IC_{50}$ in this assay of greater than 10 nM but less than or equal to 50 nM. As numbered in Table 1, Compounds 1, 3, 8, 14, 19, 20, 22, 24-26, 28, 29, 32, 34-36, 39, 40, 43, 49, 58-61, 63, 64, 69, 76, 85, 98, 99, 105, 123, 149-151, 154, 159, 172, 188, 207, 208, 227, 228, 230, 233, 235, 239, 243, 244-246, 249, 253, 259, 260, 263, 268, 272, 275, 278, 281, 282, 283, 285, 287, 292, 295, 297, 298, 309, 317, 331-332, 336, 340, 346, 350, 355, 356, 362, 374, 377-379, 383-385, 392-395, 398, 400, 410, 413, 416-417, 422-424, 427, 438, 453, 455, 457-459, 461, 463, 466, 468, 469-472, 481, 498-499, 509, 511, 513, 515-516, 518, 523, 536, 538-539, 542, 546, 560, 565, 567-571, 580, 603, 612, 616-617, 620, 625, 627, 633, 641, 650, 654, 657, 662-663, 667, 675, 681, and 685 have an $IC_{50}$ in this assay of greater than 50 nM but less than or equal to 250 nM. As numbered in Table 1, Compounds 4, 5, 10, 18, 23, 27, 31, 33, 41, 42, 45, 46, 50, 51, 53-54, 56, 62, 67, 75, 87, 92, 96, 100, 108-109, 112, 114, 126-127, 129, 130, 152, 155, 157, 160, 162, 164, 166, 168-169, 173, 184, 190-191, 199, 202, 210, 212, 214, 222, 237, 241, 247, 257, 258, 261, 266-267, 269-271, 273, 276, 279, 280, 284, 302-303, 306-307, 323-324, 326-327, 330, 337, 341-342, 344-345, 349, 357, 359, 381, 386, 419-421, 429, 454, 476-477, 480, 496, 504, 521-522, 525, 527, 529, 531-532, 535, 551, 557, 561-563, 573, 579, 610-611, 613, 618, 621-622, 624, 629, 632, 634-635, 637, 639-640, 643, 647-649, 652-653, 655-656, 659, 661, 664, 671, 673, 678, and 688 have an $IC_{50}$ in this assay of greater than 250 nM but less than or equal to 1000 nM. As numbered in Table 1, Compounds 6, 7, 44, 48, 52, 71, 77, 88, 106, 111, 116, 133, 135-137, 161, 195, 197, 200-201, 203, 205-206, 211, 231, 277, 335, 343, 524, 534, 543, 574, 581, and 691 have an $IC_{50}$ in this assay of greater than 1000 nM but less than 2000 nM. As numbered in Table 1, Compounds 2, 47, 57, 104, 107, 110, 115, 117-122, 128, 132, 134, 138, 163, 165, 167, 196, 198, 204, 209, 223, 232, 240, 242, 262, 274, 286, 288, 293-294, 296, 328-329, 333, 338, 361, 428, 433, 456, 475, 533, 541, 572, 609, 630, 631, 638, 644-646, 658, 666, 672, and 677 have an $IC_{50}$ in this assay of greater than or equal to 2,000 nM or are not active under the conditions the assay was run.

Biological Example 2

Immune-Complex mTORC2 Kinase (mTORC2 IP-Kinase) Assay

HeLa (ATCC) cells are grown in suspension culture and lysed in ice-cold lysis buffer containing 40 mM HEPES pH 7.5, 120 mM NaCl, 1 mM EDTA, 10 mM sodium pyrophosphate, 10 mM β-glycerophosphate, 10 mM NaF, 10 mM NaN$_3$, one tablet of protease inhibitors (Complete-Mini, EDTA-free, Roche), 0.3% cholamidopropyldimethylammoniopropanesulfonate (CHAPS), 1 mM AEBSF, 0.5 mM benzamidine HCl, 20 μg/mL heparin, and 1.5 mM Na$_3$VO$_4$. The mTORC2 complex is immunoprecipitated with anti-RICTOR antibody for 2 h. The immune complexes are immobilized on Protein A sepharose (GE Healthcare, 17-5280-01), washed sequentially 3 times with wash buffer (40 mM HEPES pH 7.5, 120 mM NaCl, 10 mM β-glycerophosphate, 0.3% CHAPS, 1 mM AEBSF, 20 μg/mL heparin, 1.5 mM Na$_3$VO$_4$, and Complete-Mini, EDTA-free) and resuspended in kinase buffer (40 mM HEPES, pH 7.5, 120 mM NaCl, 0.3% CHAPS, 20 μg/mL heparin, 4 mM MgCl$_2$, 4 mM MnCl$_2$, 10% Glycerol, and 10 mM DTT). The immune complexes (equivalent to 1×10$^7$ cells) are pre-incubated at 37° C. with a test Compound or 0.6% DMSO for 5 min, and then subjected to a kinase reaction for 8 min in a final volume of 33 μL (including 5 μL bed volume) containing kinase buffer, 50 μM ATP, and 0.75 μg full length dephosphorylated AKT1. Kinase reactions are terminated by addition of 11 μL 4×SDS sample buffer containing 20% β-mercaptoethanol and resolved in a 10% Tris Glycine gels. The gels are transferred onto PVDF membrane at 50 V for 20 h at 4° C. The membranes are blocked in 5% non-fat milk in TBST for 1 h and incubated overnight at 4° C. with 1/1000 dilution of rabbit anti-pAKT (S473) (Cell Signaling Technology, 4060) in 3% BSA/TBST. The membranes are washed 3 times in TBST and incubated for 1 h with a 1/10000 dilution of secondary goat anti-rabbit HRP antibody (Cell Signaling Technology, 2125) in 5% non-fat milk/TBST. The signal is detected using Amersham ECL-plus. The scanned data are analyzed using ImageQuant software. $IC_{50}$ for the test Compound is determined relative to DMSO treated sample using XLfit4 software.

Biological Example 3

PI3K Biochemical Assays

PI3Kα activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP, substrate (PIP2), and kinase in a 20 μL volume in a buffer solution. The standard PI3Kalpha assay buffer is composed 50 mM Tris, pH 7.5, 1 mM EGTA, 10 mM MgCl$_2$, 1 mM DTT and 0.03% CHAPS. The standard assay concentrations for enzyme, ATP, and substrate are 1.5 nM, 1 μM, and 10 μM, respectively. The reaction mixture was incubated at ambient temperature for approximately 2 h. Following the kinase reaction, a 10 μL aliquot of luciferase-luciferin mix (Promega Kinase-Glo) was added and the chemiluminescence signal measured using a Victor2 plate reader (Perkin Elmer). Total ATP consumption was limited to 40-60% and IC50 values of control compounds correlate well with literature references. Substituting PI3Kα with PI3Kβ, PI3Kγ, or PI3Kδ, the inhibitory activity of the compounds for the other isoforms of I3K were measured.

As numbered in Table 1, Compounds 9, 94, 103, 113, 119, 124, 131, 175-183, 185-188, 192, 208, 217-218, 237, 241, 246-247, 250, 256, 264, 268, 279-282, 285, 289-292, 295, 301, 303, 308, 310, 315, 319, 321-322, 325, 332, 334, 339, 346-348, 350-355, 364, 366, 368, 370-371, 375, 397, 399, 412, 414, 441, 454, 462, 487-488, 499-501, 506, 526, 527, 537, 539-540, 542, 565, 568, 577-580, 582-583, 586, 589, 596, 600-601, 605-608, 613-616, 623, 628, 641-643, 651, 654, 657-664, 670, 671, 674, 680, and 689-692 have an $IC_{50}$ for PI3Kα in this assay of less than or equal to 10 nM. As numbered in Table 1, Compounds 1, 3, 4, 13-15, 18, 19, 21, 26, 30, 37-39, 55, 63, 65, 68, 70, 72-74, 79-81, 83, 89-91, 93, 97-98, 101-102, 108-109, 111-112, 123, 125-126, 142, 145-147, 157, 160, 164, 168, 170-171, 184, 189, 190-191, 193, 194, 199, 207, 210, 213, 215, 220-221, 224, 227-228, 234-235, 238, 248, 251, 255, 258-261, 263, 265, 271, 278, 283, 287, 293, 299-300, 302, 304-305, 309, 311-314, 316, 318, 320, 323, 331, 333, 335, 340-341, 343, 344-345, 349, 356, 359-360, 369, 372-373, 377-378, 380-381, 387-388, 390-392, 396, 401-402, 405, 407-409, 413, 415-416, 424, 426-427, 430-432, 434, 436-437, 439-440, 442-443, 445-446, 447, 449-452, 459-461, 463-464, 474, 478-479, 482-483, 489-492, 495, 497-498, 502, 505, 507-508, 510, 512, 519-520, 525, 530-531, 545, 546-548, 550, 552-556, 558, 560, 564, 567, 575, 584-585, 587-588, 590, 592-595, 597-598, 599, 602-603, 610, 612, 617-619, 633, 636-637, 639-640, 649, 652-653, 656, 667-669, 672-673, 675-676, 678-679, 682-685, and 687 have an $IC_{50}$ for PI3Kα in this assay of greater than 10 nM but less than or equal to 50 nM. As numbered in Table 1, Compounds 5, 8, 11, 12, 16, 17, 20, 22, 23, 25, 27, 29, 36, 40, 42, 43, 46, 48, 51, 56-58, 62, 64, 66, 69, 76-78, 82, 84, 86, 92, 95, 99-100, 105, 120-122, 132, 140-141, 144, 148, 153, 156, 158-159, 166, 174, 197, 214, 216, 219, 225-226, 229-230, 233, 236, 239, 242, 245, 249, 252, 254, 257, 267, 269, 270, 272-273, 275, 286, 297-298, 317, 327, 330, 342, 358, 361-363, 365, 367, 374, 376, 382-386, 389, 393-395, 398, 400, 403, 406, 410-411, 417-423, 425, 429, 435, 438, 444, 448, 453, 455, 458, 465-466, 468-470, 473, 480-481, 485-486, 493-494, 496, 503, 509, 511, 513-518, 521-522, 529, 532, 534, 538, 544, 551, 559, 563, 566, 570-571, 576, 591, 604, 620, 625, 626-627, 632, 634, 648, 665-666, 677, 681, and 686 have an $IC_{50}$ for PI3Kα in this assay of greater than 50 nM but less than or equal to 250 nM. As numbered in Table 1, Compounds 2, 10, 24, 28, 31-33, 44, 45, 47, 49, 50, 54, 59-61, 96, 107, 110, 116-117, 129, 137-138, 143, 149-152, 154-155, 161, 162-163, 165, 167, 169, 172, 195-196, 209, 211, 222, 240, 243-244, 253, 266, 274, 276-277, 284, 296, 306-307, 324, 336-338, 357, 379, 428, 456-457, 471-472, 476-477, 504, 523-524, 533, 536, 541, 543, 569, 573-574, 609, 621, 624, 635, 650, and 655 have an $IC_{50}$ for PI3Kα in this assay of greater than 250 nM but less than or equal to 1000 nM. As numbered in Table 1, Compounds 41, 67, 71, 75, 85, 106, 115, 118, 130, 139, 204-205, 232, 288, 294, 326, 328-329, 433, 535, 561-562, 572, 611, 622, 645, 646, and 688 have an $IC_{50}$ for PI3Kα in this assay of greater than 1000 nM but less than 2000 nM. As numbered in Table 1, Compounds 6, 7, 52-53, 87-88, 104, 127-128, 133-135, 173, 198, 200-203, 206, 212, 223, 231, 262, 475, 557, 581, 629-631, 638, 644, and 647 have an $IC_{50}$ for PI3Kα in this assay of greater than or equal to 2,000 nM or are not active under the conditions the assay was run.

Biological Example 5 pS6 (S240/244) ELISA Assay

MCF-7 cells (ATCC) cells were seeded at 24000 cells per well in 96-well plates (Corning, 3904) in DMEM (Cellgro) containing 10% FBS (Cellgro), 1% NEAA (Cellgro) and 1% penicillin-streptomycin (Cellgro). Cells were incubated at 37° C., 5% CO2 for 48 h, and the growth medium was replaced with serum-free DMEM or in medium containing 0.4% BSA. Serial dilutions of the test Compound in 0.3% DMSO (vehicle) were added to the cells and incubated for 3 h. To fix the cells, medium was removed and 100 μL/well of 4% formaldehyde (Sigma Aldrich, F8775) in TBS (20 mM Tris, 500 mM NaCl) was added to each well at RT for 30 min. Cells were washed 4 times with 200 μL TBS containing 0.1% Triton X-100 (Sigma, catalog #T9284). Plates were blocked with 100 μL Odyssey blocking buffer (Li-Cor Biosciences, 927-40000) for 1 h at RT. Anti-pS6 (S240/244) antibody (Cell Signaling Technology, 2215) and anti-total-S6 antibody (R&D systems, MAB5436) were diluted 1:400 in Odyssey blocking buffer, and 50 μL of the antibody solution containing both antibodies was added to one plate to detect pS6 and total S6. After incubation overnight at 4° C., plates were washed 4 times with 200 μL TBS containing 0.1% Tween20 (Bio-Rad, catalog #170-6351) (TBST). Goat anti-rabbit and Goat anti-mouse secondary antibody (Li-Cor Biosciences, catalog #926-32221 and 926-32210) conjugated to IRDye were diluted 1:400 in Odyssey blocking buffer containing 0.1% Tween20. 50 μL of antibody solution containing both antibodies was added to each well and incubated for 1 h at RT. Plates were washed 3 times with 200 μL TBST and 2 times with 200 μL TBS. Fluorescence was read on an Odyssey plate reader. $IC_{50}$ values were determined based on the ratio of pS6 to total S6 signal for Compound treated wells, normalized to the DMSO-treated control wells.

In one embodiment, the Compounds of the Invention tested in this assay in MCF-7 cells had an inhibitory activity of 1.5 μM or less. In another embodiment, the Compounds of the Invention tested in this assay in MCF-7 cells had an inhibitory activity of 1.0 μM or less. In another embodiment, the Compounds of the Invention tested in this assay in MCF-7 cells had an inhibitory activity of 0.5 μM or less. In one embodiment, the Compounds of the Invention tested in this assay in MCF-7 cells had an inhibitory activity of 0.3 μM or less. In one embodiment, the Compounds of the Invention tested in this assay in MCF-7 cells had an inhibitory activity of 0.1 μM or less. In one embodiment, the Compounds of the Invention tested in this assay in MCF-7 cells had an inhibitory activity of 0.03 μM or less.

In one embodiment, the Compound of the Invention tested in this assay in PC-3 cells had an inhibitory activity of about 1.7 μM or less. In another embodiment, the Compound of the Invention tested in this assay in PC-3 cells had an inhibitory activity of about 0.55 μM or less. In another embodiment, the Compound of the Invention tested in this assay in PC-3 cells had an inhibitory activity of about 0.55 μM or less. In another embodiment, the Compound of the Invention tested in this assay in PC-3 cells had an inhibitory activity of about 0.3 μM or less. In another embodiment, the Compound of the Invention tested in this assay in PC-3 cells had an inhibitory activity of about 0.1 μM or less. In another embodiment, the Compound of the Invention tested in this assay in PC-3 cells had an inhibitory activity of about 0.05 μM or less.

Biological Example 6 pAKT (T308) ELISA Assay

MCF-7 cells (ATCC) cells were seeded at 24000 cells per well in 96-well plates (Corning, 3904) in DMEM (Cellgro) containing 10% FBS (Cellgro), 1% NEAA (Cellgro) and 1% penicillin-streptomycin (Cellgro). Cells were incubated at 37° C., 5% CO2 for 48 h, and the growth medium was replaced with serum-free DMEM or in medium containing 0.4% BSA. Serial dilutions of the test Compound in 0.3% DMSO (vehicle) were added to the cells and incubated for 3 h. At the end of the incubation period, cells were stimulated for 10 minutes by the addition of L-IGF (Sigma, I-1271) at a final concentration of 100 ng/ml. Afterwards, media was discarded from cell plates and 110 W/well of cold lysis buffer (see table below) were added. Cell plates were incubated on ice and then put on shaker in 4° C. cold room for 1 h. Two capture plates (Thermo Scientific, Reacti-bind plate, 15042) were prepared for each cell plate by pre-coating with capture Akt antibody from the two sandwich ELISA antibody pairs used (Cell Signaling Technology 7142 and 7144). The Akt capture antibodies were diluted 1:100 in PBS and 100 μl of diluted capture antibody was added per well. Capture plates were incubated at 4 C overnight. Prior to use, capture plates were washed 3 times in TBS containing 0.1% Tween20 (Bio-Rad, 170-6351) (TBST) and blocked in blocking buffer (Thermo Scientific, Starting Block T20, 37543) for 1-2 h at room temperature. After 1 h of cell lysis, 85 μl of cell lysate/ well was transferred to the capture plate for detection of pAkt(T308). 15 μl of cell lysate was transferred from same well to the second capture plate for detection of total Akt1. After incubation overnight at 4° C., plates were washed 3 times with 200 μL TBST. Primary antibodies, diluted 1:100 in blocking buffer, were added to the corresponding capture plates for pAkt(T308) (Cell Signaling Technology, 7144) and total Akt1 (Cell Signaling Technology, 7142) detection and incubated at room temperature for 1 h. Plates were washed 3 times with 200 µL of TBST. Goat anti-mouse secondary antibody (Cell Signaling Technology, 7076) conjugated to HRP was diluted 1:1000 in blocking buffer and 100 µl were added to each well and incubated for 30 minutes at room temperature. Plates were then washed 3 times with 200 µL of TBST. 100 µL of SuperSignal ELISA Femto stable peroxidase solution (Thermo Scientific, 37075) was added to each well. After 1 minute incubation, chemiluminescence was read on a Wallac Victor2 1420 multilabel counter. IC50 values were determined based on the ratio of pAkt(T308) to total Akt1 signal for Compound treated wells, normalized to the DMSO-treated control wells.

|  | Stock | Final | /10 mL |
|---|---|---|---|
| Water |  |  | 6 mL |
| Complete Protease Inhibitors (Roche 1 836 170) |  |  | 1 mini-tablet |
| 5x RIPA | 5x | 1x | 2 mL |
| NaF | 200 mM | 1 mM | 50 µL |
| B-glycerophosphate | 100 mM | 20 mM | 1.8 mL |
| Phosphatase Inhibitor I (Sigma P2850) | 100x | 1x | 100 µL |
| Na orthovanadate | 200 mM | 1 mM | 50 µL |
| EDTA, pH 8 | 500 mM | 1 mM | 20 µL |

In one embodiment, the Compounds of the Invention tested in this assay in PC-3 cells had an inhibitory activity of about 2.0 µM or less. In another embodiment, the Compounds of the Invention tested in this assay in PC-3 cells had an inhibitory activity of about 1.0 µM or less. In another embodiment, the Compounds of the Invention tested in this assay in PC-3 cells had an inhibitory activity of about 0.3 µM or less. In another embodiment, the Compounds of the Invention tested in this assay in PC-3 cells had an inhibitory activity of about 0.2 µM or less.

In one embodiment, the Compounds of the Invention tested in this assay in MCF-7 cells had an inhibitory activity of about 3.0 µM or less. In another embodiment, the Compounds of the Invention tested in this assay in MCF-7 cells had an inhibitory activity of about 3.0 µM or less. In another embodiment, the Compounds of the Invention tested in this assay in MCF-7 cells had an inhibitory activity of about 1.5 µM or less. In another embodiment, the Compounds of the Invention tested in this assay in MCF-7 cells had an inhibitory activity of about 0.75 µM or less. In another embodiment, the Compounds of the Invention tested in this assay in MCF-7 cells had an inhibitory activity of about 0.5 µM or less. In another embodiment, the Compounds of the Invention tested in this assay in MCF-7 cells had an inhibitory activity of about 0.25 µM or less. In another embodiment, the Compounds of the Invention tested in this assay in MCF-7 cells had an inhibitory activity of about 0.1 µM or less.

Biological Example 7-13

Pharmacodynamic Xenograft Tumor Models

Female and male athymic nude mice (NCr) 5-8 weeks of age and weighing approximately 20-25 g are used in the following models. Prior to initiation of a study, the animals are allowed to acclimate for a minimum of 48 h. During these studies, animals are provided food and water ad libitum and housed in a room conditioned at 70-75° F. and 60% relative humidity. A 12 h light and 12 h dark cycle is maintained with automatic timers. All animals are examined daily for compound-induced or tumor-related deaths.

MCF-7 Breast Adenocarcinoma Model

MCF7 human mammary adenocarcinoma cells are cultured in vitro in DMEM (Cellgro) supplemented with 10% Fetal Bovine Serum (Cellgro), Penicillin-Streptomycin and non-essential amino acids at 37° C. in a humidified 5% $CO_2$ atmosphere. On day 0, cells are harvested by trypsinization, and $5\times10^6$ cells in 100 µL of a solution made of 50% cold Hanks balanced salt solution with 50% growth factor reduced matrigel (Becton Dickinson) implanted subcutaneously into the hindflank of female nude mice. A transponder is implanted into each mouse for identification and data tracking, and animals are monitored daily for clinical symptoms and survival.

Tumors are established in female athymic nude mice and staged when the average tumor weight reached 100-200 mg. A Compound of the Invention is orally administered as a solution/fine suspension in water (with 1:1 molar ratio of 1 NHCL) once-daily (qd) or twice-daily (bid) at 10, 25, 50 and 100 mg/kg for 14 days. During the dosing period of 14-19 days, tumor weights are determined twice-weekly and body weights are recorded daily.

Colo-205 Colon Model

Colo-205 human colorectal carcinoma cells are cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells are harvested by trypsinization, and $3\times10^6$ cells (passage 10-15, >95% viability) in 0.1 mL ice-cold Hank's balanced salt solution are implanted intradermally in the hind-flank of 5-8 week old female athymic nude mice. A transponder is implanted in each mouse for identification, and animals are monitored daily for clinical symptoms and survival.

Tumors are established in female athymic nude mice and staged when the average tumor weight reached 100-200 mg. A Compound of the Invention is orally administered as a solution/fine suspension in water (with 1:1 molar ratio of 1 NHCL) once-daily (qd) or twice-daily (bid) at 10, 25, 50 and 100 mg/kg for 14 days. During the dosing period of 14 days, tumor weights are determined twice-weekly and body weights are recorded daily.

PC-3 Prostate Adenocarcinoma Model

PC-3 human prostate adenocarcinoma cells are cultured in vitro in DMEM (Mediatech) supplemented with 20% Fetal Bovine Serum (Hyclone), Penicillin-Streptomycin and non-essential amino acids at 37° C. in a humidified 5% $CO_2$ atmosphere. On day 0, cells are harvested by trypsinization and $3\times10^6$ cells (passage 10-14, >95% viability) in 0.1 mL of ice-cold Hank's balanced salt solution are implanted subcutaneously into the hindflank of 5-8 week old male nude mice. A transponder is implanted in each mouse for identification, and animals are monitored daily for clinical symptoms and survival.

Tumors are established in male athymic nude mice and staged when the average tumor weight reached 100-200 mg. A Compound of the Invention is orally administered as a solution/fine suspension in water (with 1:1 molar ratio of 1 N HCl) once-daily (qd) or twice-daily (bid) at 10, 25, 50, or 100-mg/kg for 19 days. During the dosing period of 14-19 days, tumor weights are determined twice-weekly and body weights are recorded daily.

U-87 MG Human Glioblastoma Model

U-87 MG human glioblastoma cells are cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells are harvested by trypsinization and $2 \times 10^6$ cells (passage 5, 96% viability) in 0.1 mL of ice-cold Hank's balanced salt solution are implanted intradermally into the hindflank of 5-8 week old female nude mice. A transponder is implanted in each mouse for identification, and animals are monitored daily for clinical symptoms and survival. Body weights are recorded daily.

A549 Human Lung Carcinoma Model

A549 human lung carcinoma cells are cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells are harvested by trypsinization and $10 \times 10^6$ cells (passage 12, 99% viability) in 0.1 mL of ice-cold Hank's balanced salt solution are implanted intradermally into the hindflank of 5-8 week old female nude mice. A transponder is implanted in each mouse for identification, and animals are monitored daily for clinical symptoms and survival. Body weights are recorded daily.

A2058 Human Melanoma Model

A2058 human melanoma cells are cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells are harvested by trypsinization and $3 \times 10^6$ cells (passage 3, 95% viability) in 0.1 mL ice-cold Hank's balanced salt solution are implanted intradermally in the hindflank of 5-8 week old female athymic nude mice. A transponder is implanted in each mouse for identification, and animals are monitored daily for clinical symptoms and survival. Body weights are recorded daily.

WM-266-4 Human Melanoma Model

WM-266-4 human melanoma cells are cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells are harvested by trypsinization and $3 \times 10^6$ cells (passage 5, 99% viability) in 0.1 mL ice-cold Hank's balanced salt solution are implanted intradermally in the hindflank of 5-8 week old female athymic nude mice. A transponder is implanted in each mouse for identification, and animals are monitored daily for clinical symptoms and survival. Body weights are recorded daily.

Tumor weight (TW) in the above models is determined by measuring perpendicular diameters with a caliper, using the following formula:

tumor weight (mg)=[tumor volume=length (mm)× width$^2$ (mm$^2$)]/2

These data were recorded and plotted on a tumor weight vs. days post-implantation line graph and presented graphically as an indication of tumor growth rates. Percent inhibition of tumor growth (TGI) is determined with the following formula:

$$\left[1 - \left(\frac{(X_f - X_0)}{(Y_f - X_0)}\right)\right] * 100$$

where $X_0$=average TW of all tumors on group day
$X_f$=TW of treated group on Day f
$Y_f$=TW of vehicle control group on Day f
If tumors regress below their starting sizes, then the percent tumor regression is determined with the following formula:

$$\left(\frac{X_0 - X_f}{X_0}\right) * 100$$

Tumor size is calculated individually for each tumor to obtain a mean±SEM value for each experimental group. Statistical significance is determined using the 2-tailed Student's t-test (significance defined as P<0.05).

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:
1. The compound according to formula I(a)

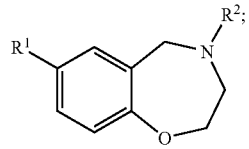

I(a)

or a single stereoisomer or mixture of stereoisomers thereof and additionally optionally as a pharmaceutically acceptable salt thereof, where
$R^1$ is phenyl optionally substituted with one, two, or three $R^6$ groups; or
$R^1$ is heteroaryl optionally substituted with one, two, or three $R^7$;
$R^2$ is heteroaryl substituted with $R^3$, $R^{3a}$, $R^{3b}$, $R^{3c}$, and $R^{3d}$;
$R^3$, $R^{3a}$, $R^{3b}$, $R^{3c}$, and $R^{3d}$ are independently hydrogen; cyano; alkyl; alkenyl; halo; haloalkyl; hydroxyalkyl; alkoxyalkyl; cyanoalkyl; —$SR^{12}$; —$S(O)_2R^{20}$; alkoxycarbonyl; halocarbonyl; —$NR^{11}R^{11a}$; —$OR^{11a}$; phenyl optionally substituted with one or two groups which are independently alkyl or halo; phenylalkyl optionally substituted with one or two $R^{19}$; cycloalkylalkyl; heterocycloalkyl optionally substituted with one or two groups which are independently alkyl or alkoxycarbonyl; heterocycloalkylalkyl optionally substituted with one or two groups which are independently alkyl or alkoxycarbonyl; heteroaryl; heteroarylalkyl; or alkyl substituted with one or two $R^{16}$; or two of $R^3$, $R^{3a}$, $R^{3b}$, $R^{3c}$, and $R^{3d}$, when attached to the same carbon, form a cycloalkyl or a heterocycoalkyl; and the other of $R^3$, $R^{3a}$, $R^{3b}$, $R^{3c}$, and $R^{3d}$ are hydrogen;

each $R^6$, when $R^6$ is present, is independently nitro; cyano; halo; alkyl;
haloalkyl; —$OR^{8a}$; —$NR^8R^{8a}$; —$C(O)NR^8R^{8a}$; —$S(O)_2R^8$; —$NR^8C(O)R^9$; —$NR^8S(O)_2R^{8a}$; —$NHC(O)NHR^9$; carboxy, —$C(O)OR^9$; or heteroaryl optionally substituted with 1, 2, or 3 $R^{14}$;

each $R^7$, when $R^7$ is present, is independently oxo; nitro; cyano; alkyl; alkenyl; halo; haloalkyl; hydroxyalkyl; alkoxyalkyl; —$OR^{8a}$; —$SR^{13}$; —$S(O)R^{13}$; —$S(O)_2R^{13a}$; —$NR^8R^{8a}$; —$C(O)NR^8R^{8a}$; —$NR^8C(O)OR^9$; —$NR^8C(O)R^9$; —$NR^8S(O)_2R^{8a}$; —$NR^8C(O)NR^{8a}R^9$; —$C(O)OR^9$;
halocarbonyl; —$S(O)_2NR^8R^9$; alkylsulfonylalkyl; alkyl substituted with one or two —$NR^8R^{8a}$; alkyl substituted with one or two —$NR^8C(O)R^{8a}$; alkyl substituted with one or two —$NR^8C(O)OR^9$; alkyl substituted with one or two —$S(O)_2R^{13a}$; cycloalkyl; cycloalkylalkyl; heterocycloalkyl optionally substituted with one or two groups which are independently alkyl or amino; phenyl; phenylalkyl; heterocycloalkylalkyl; heteroaryl; or heteroarylalkyl;

$R^8$, $R^{11}$, $R^{15}$, $R^{17}$, and $R^{18}$ are independently hydrogen, alkyl, alkenyl, alkynyl, hydroxyalkyl, alkoxyalkyl, or haloalkyl;

$R^{8a}$; $R^{11a}$; and $R^{15a}$ are independently hydrogen; alkyl; alkenyl; alkynyl; haloalkyl; hydroxyalkyl; cyanoalkyl; aminoalkyl; alkylaminoalkyl; dialkylaminoalkyl; alkoxyalkyl; carboxyalkyl; cycloalkyl; cycloalkylalkyl; heterocycloalkyl optionally substituted with one or two groups which are independently alkyl or alkoxycarbonyl; heterocycloalkylalkyl optionally substituted with one or two groups which are independently alkyl or alkoxycarbonyl; phenyl optionally substituted with one or two groups which are independently halo, alkyl, or alkoxy; phenylalkyl; heteroaryl; or heteroarylalkyl;

$R^9$ is hydrogen; alkyl; alkenyl; alkynyl; hydroxyalkyl; alkoxyalkyl; aminoalkyl; alkylaminoalkyl; dialkylaminoalkyl; haloalkyl; hydroxyalkyl substituted with one, two, or three groups which are independently halo, amino, alkylamino, or dialkylamino; alkyl substituted with one or two aminocarbonyl; phenyl; phenylalkyl; cycloalkyl; cycloalkylalkyl optionally substituted with one or two groups which are independently amino or alkyl; heterocycloalkyl optionally substituted with one or two groups which are independently alkyl or alkoxycarbonyl; or heterocycloalkylalkyl optionally substituted with one or two groups which are independently alkyl or alkoxycarbonyl;

$R^{12}$ is alkyl or phenylalkyl;

$R^{13}$ is alkyl, hydroxyalkyl, or haloalkyl; and $R^{13a}$ is hydroxy, alkyl, haloalkyl, hydroxyalkyl, or heterocycloalkyl optionally substituted with one or two groups which are independently halo, amino, alkylamino, dialkylamino, hydroxy, alkyl, or hydroxyalkyl;

each $R^{14}$, when $R^{14}$ is present, is independently amino, alkylamino, dialkylamino, acylamino, halo, hydroxy, alkyl, haloalkyl, hydroxyalkyl, aminoalkyl, alkylaminoalkyl, dialkylaminoalkyl, alkoxycarbonyl, aminocarbonyl, alkylaminocarbonyl, dialkylaminocarbonyl, or phenyl;

each $R^{16}$ is independenity —$NR^{11}R^{11a}$, —$NR^{15}S(O)R^{15a}$, —$OC(O)R^{17}$, or —$OR^{18}$;

each $R^{19}$ is independently halo, alkyl, haloalkyl, amino, alkylamino, dialkylamino, or alkoxy; and $R^{20}$ is amino, alkylamino, dialkylamino, or heterocycloalkyl.

2. The compound of claim 1 where $R^1$ is phenyl optionally substituted with one, two, or three $R^6$ groups; or a single stereoisomer or mixture of stereoisomers thereof and additionally optionally as a pharmaceutically acceptable salt thereof.

3. The compound of claim 2 where $R^1$ is phenyl substituted with one or two $R^6$ groups independently nitro, halo, alkoxy, —$OR^{8a}$, —$S(O)_2R^8$; —$NR^8R^{8a}$, —$NR^8S(O)_2R^{8a}$, —$NR^8C(O)R^9$, —$C(O)NR^8R^{8a}$, —$NHC(O)NHR^9$, carboxy, alkoxycarbonyl, or heteroaryl optionally substituted with one or two $R^{14}$; or a single stereoisomer or mixture of stereoisomers thereof and additionally optionally as a pharmaceutically acceptable salt thereof.

4. The compound of claim 3 where $R^1$ is phenyl substituted with one $R^6$ where $R^6$ is —$S(O)_2R^8$, —$C(O)NR^8R^{8a}$ or heteroaryl optionally substituted with one or two $R^{14}$; or a single stereoisomer or mixture of stereoisomers thereof and additionally optionally as a pharmaceutically acceptable salt thereof.

5. The compound of claim 1 where $R^1$ is heteroaryl optionally substituted with one, two, or three $R^7$; or a single stereoisomer or mixture of stereoisomers thereof and additionally optionally as a pharmaceutically acceptable salt thereof.

6. The compound of claim 5 where $R^1$ is a 9-membered heteroaryl optionally substituted with one, two, or three $R^7$; or a single stereoisomer or mixture of stereoisomers thereof and additionally optionally as a pharmaceutically acceptable salt thereof.

7. The compound of claim 6 where $R^1$ is a 9-membered heteroaryl and the 9-membered heteroaryl is benzimidazolyl, 1H-imidazo[4,5-b]pyridinyl, 3H-imidazo[4,5-b]pyridinyl, 1H-imidazo[4,5-c]pyridinyl, 3H-imidazo[4,5-c]pyridinyl, thiazolo[4,5-b]pyridinyl, thiazolo[4,5-c]pyridinyl, thiazolo[5,4-c]pyridinyl, or thiazolo[5,4-b]pyridinyl where $R^1$ is optionally substituted with one, two, or three $R^7$; or a single stereoisomer or mixture of stereoisomers thereof and additionally optionally as a pharmaceutically acceptable salt thereof.

8. The compound of claim 5 where $R^1$ is a 5-membered heteroaryl that is thiazolyl or pyrazolyl and where the 5-membered heteroaryl is optionally substituted with one, two, or three $R^7$; or a single stereoisomer or mixture of stereoisomers thereof and additionally optionally as a pharmaceutically acceptable salt thereof.

9. The compound of claim 5 where $R^1$ is a 6-membered heteroaryl that is pyrimidinyl, pyridinyl, pyrazinyl, or pyridazinyl and where the 6-membered heteroaryl is optionally substituted with one, two, or three $R^7$; or a single stereoisomer or mixture of stereoisomers thereof and additionally optionally as a pharmaceutically acceptable salt thereof.

10. The compound of claim 9 where $R^1$ is pyridinyl optionally substituted with one, two, or three $R^7$; or a single stereoisomer or mixture of stereoisomers thereof and additionally optionally as a pharmaceutically acceptable salt thereof.

11. The compound of claim 5 where $R^1$ is optionally substituted with one or two $R^7$ where each $R^7$, when $R^7$ is present, is independently halo, alkyl, cycloalkyl, haloalkyl, hydroxyalkyl, alkoxyalkyl, —NR⁸R⁸ᵃ, or —NR⁸C(O)OR⁹; or a single stereoisomer or mixture of stereoisomers thereof and additionally optionally as a pharmaceutically acceptable salt thereof.

12. The compound of claim 5 where R² is quinazolin-4-yl substituted with R³, R³ᵃ, R³ᵇ, R³ᶜ, and R³ᵈ; where R³ᶜ and R³ᵈ are hydrogen; or a single stereoisomer or mixture of stereoisomers thereof and additionally optionally as a pharmaceutically acceptable salt thereof.

13. The compound of claim 5 where R² is quinolin-4-yl substituted with R³, R³ᵃ, R³ᵇ, R³ᶜ and R³ᵈ; where R³ᶜ and R³ᵈ are hydrogen; or a single stereoisomer or mixture of stereoisomers thereof and additionally optionally as a pharmaceutically acceptable salt thereof.

14. The compound of claim 5 where R² is isoquinolin-4-yl substituted with R³, R³ᵃ, R³ᵇ, R³ᶜ and R³ᵈ; where R³ᶜ and R³ᵈ are hydrogen; or a single stereoisomer or mixture of stereoisomers thereof and additionally optionally as a pharmaceutically acceptable salt thereof.

15. The compound of claim 5 where R² is according to formula (a)

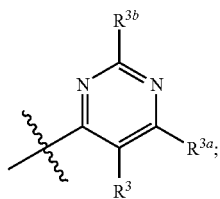

(a)

or a single stereoisomer or mixture of stereoisomers thereof and additionally optionally as a pharmaceutically acceptable salt thereof.

16. The compound of claim 15 where R³ is hydrogen, halo, alkyl, cycloalkylalkyl, or phenylalkyl optionally substituted with one or two R¹⁹; R³ᵃ is hydrogen, alkyl, halo, optionally substituted heterocycloalkyl, or —NR¹¹R¹¹ᵃ; and R³ᵇ is hydrogen, alkyl, hydroxyalkyl, or alkyl substituted with one or two R¹⁶; or a single stereoisomer or mixture of stereoisomers thereof and additionally optionally as a pharmaceutically acceptable salt thereof.

17. The compound according to claim 5 where R² is according to formula (g)

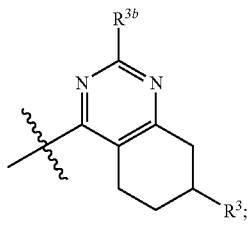

(g)

or a single stereoisomer or mixture of stereoisomers thereof and additionally optionally as a pharmaceutically acceptable salt thereof.

18. The compound according to claim 5 where R² is according to formula (d)

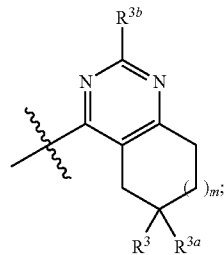

(d)

where m is 1; or a single stereoisomer or mixture of stereoisomers thereof and additionally optionally as a pharmaceutically acceptable salt thereof.

19. The compound of claim 18 where R³ and R³ᵃ together with the carbon to which they are attached form an optionally substituted cycloalkyl; or a single stereoisomer or mixture of stereoisomers thereof and additionally optionally as a pharmaceutically acceptable salt thereof.

20. The compound of claim 18 where R³ and R³ᵃ are halo or R³ and R³ᵃ are alkyl; or a single stereoisomer or mixture of stereoisomers thereof and additionally optionally as a pharmaceutically acceptable salt thereof.

21. The compound according to claim 17 where R³ᵇ is hydrogen, alkyl, alkenyl, hydroxyalkyl, cyanoalkyl, optionally substituted heteorcycloalkyl, optionally substituted heteorcycloalkylalkyl, or alkyl substituted with one R¹⁶; or a single stereoisomer or mixture of stereoisomers thereof and additionally optionally as a pharmaceutically acceptable salt thereof.

22. The compound according to claim 5 where R² is according to formula (e)

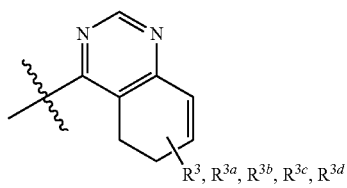

(e)

where R³, R³ᵃ, R³ᵇ, R³ᶜ, and R³ᵈ are positioned on any substitutable carbon on the ring of formula (e); or a single stereoisomer or mixture of stereoisomers thereof and additionally optionally as a pharmaceutically acceptable salt thereof.

23. A compound selected from:
7-(2-methyl-1H-benzimidazol-6-yl)-4-quinazolin-4-yl-2,3,4,5-tetrahydro-1,4-benzoxazepine
7-(2-methyl-1H-benzimidazol-6-yl)-4-pyrimidin-4-yl-2,3,4,5-tetrahydro-1,4-benzoxazepine
4-(7-iodoquinazolin-4-yl)-7-(2-methyl-1H-benzimidazol-6-yl)-2,3,4,5-tetrahydro-1,4-benzoxazepine
7-(2-methyl-1H-benzimidazol-6-yl)-4-(2-methylquinazolin-4-yl)-2,3,4,5-tetrahydro-1,4-benzoxazepine
ethyl 4-[7-(2-methyl-1H-benzimidazol-6-yl)-2,3-dihydro-1,4-benzoxazepin-4(5H)-yl]quinazoline-2-carboxylate
N,N-diethyl-4-[7-(2-methyl-1H-benzimidazol-6-yl)-2,3-dihydro-1,4-benzoxazepin-4(5H)-yl]quinazolin-2-amine
4-(2,6-diphenylpyrimidin-4-yl)-7-(2-methyl-1H-benzimidazol-6-yl)-2,3,4,5-tetrahydro-1,4-benzoxazepine 4-[6,7-bis(methyloxy)quinazolin-4-yl]-7-(2-methyl-1H-benzimidazol-6-yl)-2,3,4,5-tetrahydro-1,4-benzoxazepine 7-(2-methyl-1H-benzimidazol-6-yl)-4-[7-(methyloxy)quinazolin-4-yl]-2,3,4,5-tetrahydro-1,4-benzoxazepine 7-(2-methyl-1H-benzimidazol-6-yl)-4-{6-(methyloxy)-7-[(phenylmethyl)oxy]quinazolin-4-yl}-2,3,4,5-tetrahydro-1,4-benzoxazepine 7-(2-methyl-1H-benzimidazol-6-yl)-4-[6-(methyloxy)quinazolin-4-yl]-2,3,4,5-tetrahydro-1,4-benzoxazepine 4-(6-bromoquinazolin-4-yl)-7-(2-methyl-1H-benzimidazol-6-yl)-2,3,4,5-tetrahydro-1,4-benzoxazepine 4-(6-chloroquinazolin-4-yl)-7-(2-methyl-1H-benzimidazol-6-yl)-2,3,4,5-tetrahydro-1,4-benzoxazepine 7-(2-methyl-1H-benzimidazol-6-yl)-4-(8-methylquinazolin-4-yl)-2,3,4,5-tetrahydro-1,4-benzoxazepine 7-(2-methyl-1H-benzimidazol-6-yl)-4-(6-methylquinazolin-4-yl)-2,3,4,5-tetrahydro-1,4-benzoxazepine 4-(6-iodoquinazolin-4-yl)-7-(2-methyl-1H-benzimidazol-6-yl)-2,3,4,5-tetrahydro-1,4-benzoxazepine 4-(6-fluoroquinazolin-4-yl)-7-(2-methyl-1H-benzimidazol-6-yl)-2,3,4,5-tetrahydro-1,4-benzoxazepine 4-(7-fluoroquinazolin-4-yl)-7-(2-methyl-1H-benzimidazol-6-yl)-2,3,4,5-tetrahydro-1,4-benzoxazepine 7-(2-methyl-1H-benzimidazol-6-yl)-4-[8-(methyloxy)quinazolin-4-yl]-2,3,4,5-tetrahydro-1,4-benzoxazepine 4-(7-chloroquinazolin-4-yl)-7-(2-methyl-1H-benzimidazol-6-yl)-2,3,4,5-tetrahydro-1,4-benzoxazepine 4-(8-chloroquinazolin-4-yl)-7-(2-methyl-1H-benzimidazol-6-yl)-2,3,4,5-tetrahydro-1,4-benzoxazepine 4-(7-bromoquinazolin-4-yl)-7-(2-methyl-1H-benzimidazol-6-yl)-2,3,4,5-tetrahydro-1,4-benzoxazepine 4-(6,7-difluoroquinazolin-4-yl)-7-(2-methyl-1H-benzimidazol-6-yl)-2,3,4,5-tetrahydro-1,4-benzoxazepine 4-(6-bromo-7-chloroquinazolin-4-yl)-7-(2-methyl-1H-benzimidazol-6-yl)-2,3,4,5-tetrahydro-1,4-benzoxazepine 4-(8-bromoquinazolin-4-yl)-7-(2-methyl-1H-benzimidazol-6-yl)-2,3,4,5-tetrahydro-1,4-benzoxazepine 7-(2-methyl-1H-benzimidazol-6-yl)-4-(7-methylquinazolin-4-yl)-2,3,4,5-tetrahydro-1,4-benzoxazepine 4-(8-fluoroquinazolin-4-yl)-7-(2-methyl-1H-benzimidazol-6-yl)-2,3,4,5-tetrahydro-1,4-benzoxazepine 7-(2-methyl-1H-benzimidazol-6-yl)-4-[8-(trifluoromethyl)quinazolin-4-yl]-2,3,4,5-tetrahydro-1,4-benzoxazepine 4-(8-bromo-6-methylquinazolin-4-yl)-7-(2-methyl-1H-benzimidazol-6-yl)-2,3,4,5-tetrahydro-1,4-benzoxazepine 4-[7-bromo-8-(methyloxy)quinazolin-4-yl]-7-(2-methyl-1H-benzimidazol-6-yl)-2,3,4,5-tetrahydro-1,4-benzoxazepine 4-[7-bromo-6-(methyloxy)quinazolin-4-yl]-7-(2-methyl-1H-benzimidazol-6-yl)-2,3,4,5-tetrahydro-1,4-benzoxazepine 4-(6,8-dichloroquinazolin-4-yl)-7-(2-methyl-1H-benzimidazol-6-yl)-2,3,4,5-tetrahydro-1,4-benzoxazepine 4-[2-chloro-6-(methyloxy)quinazolin-4-yl]-7-(2-methyl-1H-benzimidazol-6-yl)-2,3,4,5-tetrahydro-1,4-benzoxazepine 4-[7,8-bis(methyloxy)quinazolin-4-yl]-7-(2-methyl-1H-benzimidazol-6-yl)-2,3,4,5-tetrahydro-1,4-benzoxazepine 4-(7-chloro-6-iodoquinazolin-4-yl)-7-(2-methyl-1H-benzimidazol-6-yl)-2,3,4,5-tetrahydro-1,4-benzoxazepine 7-(2-methyl-1H-benzimidazol-6-yl)-4-[7-(trifluoromethyl)quinazolin-4-yl]-2,3,4,5-tetrahydro-1,4-benzoxazepine 4-[6-iodo-7-(methyloxy)quinazolin-4-yl]-7-(2-methyl-1H-benzimidazol-6-yl)-2,3,4,5-tetrahydro-1,4-benzoxazepine 4-[6-chloro-7-(methyloxy)quinazolin-4-yl]-7-(2-methyl-1H-benzimidazol-6-yl)-2,3,4,5-tetrahydro-1,4-benzoxazepine 7-(2-methyl-1H-benzimidazol-6-yl)-4-{8-(methyloxy)-7-[(phenylmethyl)oxy]quinazolin-4-yl}-2,3,4,5-tetrahydro-1,4-benzoxazepine 7-(2-methyl-1H-benzimidazol-6-yl)-4-[7-(methylsulfonyl)quinazolin-4-yl]-2,3,4,5-tetrahydro-1,4-benzoxazepine 7-(2-methyl-1H-benzimidazol-6-yl)-4-[5-methyl-6-(phenylmethyl)pyrimidin-4-yl]-2,3,4,5-tetrahydro-1,4-benzoxazepine 4-[6-chloro-7,8-bis(methyloxy)quinazolin-4-yl]-7-(2-methyl-1H-benzimidazol-6-yl)-2,3,4,5-tetrahydro-1,4-benzoxazepine 4-[6-bromo-7-(methyloxy)quinazolin-4-yl]-7-(2-methyl-1H-benzimidazol-6-yl)-2,3,4,5-tetrahydro-1,4-benzoxazepine 7-(2-methyl-1H-benzimidazol-6-yl)-4-(5-methylpyrimidin-4-yl)-2,3,4,5-tetrahydro-1,4-benzoxazepine 7-(2-methyl-1H-benzimidazol-6-yl)-4-thieno[2,3-d]pyrimidin-4-yl-2,3,4,5-tetrahydro-1,4-benzoxazepine 7-(2-methyl-1H-benzimidazol-6-yl)-4-(5,6,7,8-tetrahydroquinazolin-4-yl)-2,3,4,5-tetrahydro-1,4-benzoxazepine 7-(2-methyl-1H-benzimidazol-6-yl)-4-(5-methylthieno[2,3-d]pyrimidin-4-yl)-2,3,4,5-tetrahydro-1,4-benzoxazepine 4-(5,6-dimethylpyrimidin-4-yl)-7-(2-methyl-1H-benzimidazol-6-yl)-2,3,4,5-tetrahydro-1,4-benzoxazepine 7-(2-methyl-1H-benzimidazol-6-yl)-4-[2-(methylthio)-6,7-dihydro-5H-cyclopenta[d]pyrimidin-4-yl]-2,3,4,5-tetrahydro-1,4-benzoxazepine 7-(2-methyl-1H-benzimidazol-6-yl)-4-[6-(methylsulfonyl)quinazolin-4-yl]-2,3,4,5-tetrahydro-1,4-benzoxazepine 4-[7-(2-methyl-1H-benzimidazol-6-yl)-2,3-dihydro-1,4-benzoxazepin-4(5H)-yl]-6,7,8,9-tetrahydropyrimido[4,5-b]indolizine-10-carbonitrile 7-(2-methyl-1H-benzimidazol-6-yl)-4-(1H-pyrazolo[3,4-d]pyrimidin-4-yl)-2,3,4,5-tetrahydro-1,4-benzoxazepine 7(2-methyl-1H-benzimidazol-6-yl)-4-{2-[(phenylmethyl)thio]-6,7-dihydro-5H-cyclopenta[d]pyrimidin-4-yl}-2,3,4,5-tetrahydro-1,4-benzoxazepine 4-[2-(ethylthio)-6,7-dihydro-5H-cyclopenta[d]pyrimidin-4-yl]-7-(2-methyl-1H-benzimidazol-6-yl)-2,3,4,5-tetrahydro-1,4-benzoxazepine 7-(2-methyl-1H-benzimidazol-6-yl)-4-[6-methyl-5-(phenylmethyl)pyrimidin-4-yl]-2,3,4,5-tetrahydro-1,4-benzoxazepine 4(6-ethyl-5-methylpyrimidin-4-yl)-7(2-methyl-1H-benzimidazol-6-yl)-2,3,4,5-tetrahydro-1,4-benzoxazepine 7-(2-methyl-1H-benzimidazol-6-yl)-4-[6,7,8-tris(methyloxy)quinazolin-4-yl]-2,3,4,5-tetrahydro-1,4-benzoxazepine 4-(5,6-diethylpyrimidin-4-yl)-7-(2-methyl-1H-benzimidazol-6-yl)-2,3,4,5-tetrahydro-1,4-benzoxazepine 7-(2-methyl-1H-benzimidazol-6-yl)-4-[6-(1-methylethyl)pyrimidin-4-yl]-2,3,4,5-tetrahydro-1,4-benzoxazepine 7-(2-methyl-1H-benzimidazol-6-yl)-4-[7-(phenylmethyl)-5,6,7,8-tetrahydropyrido[3,4-d]pyrimidin-4-yl]-2,3,4,5-tetrahydro-1,4-benzoxazepine 4-[5-ethyl-6-(1-methylethyl)pyrimidin-4-yl]-7-(2-methyl-1H-benzimidazol-6-yl)-2,3,4,5-tetrahydro-1,4-benzoxazepine 7-(2-methyl-1H-benzimidazol-6-yl)-4-[5-methyl-6-(1-methylethyl)pyrimidin-4-yl]-2,3,4,5-tetrahydro-1,4-benzoxazepine 7(2-methyl-1H-benzimidazol-6-yl)-4-[7-methyl-5,6,7,8-tetrahydroquinazolin-4-yl]-2,3,4,5-tetrahydro-1,4-benzoxazepine 4(5-ethyl-6-methylpyrimidin-4-yl)-7(2-methyl-1H-benzimidazol-6-yl)-2,3,4,5-tetrahydro-1,4-benzoxazepine 4(6,6-dimethyl-5,6,7,8-tetrahydroquinazolin-4-yl)-7-(2-methyl-1H-benzimidazol-6-yl)-2,3,4,5-tetrahydro-1,4-benzoxazepine 7-(2-methyl-1H-benzimidazol-6-yl)-4-[6-methyl-5-(1-methylethyl)pyrimidin-4-yl]-2,3,4,5-tetrahydro-1,4-benzoxazepine 7-(2-methyl-1H-benzimidazol-6-yl)-4-[6-methyl-5-(2-methylpropyl)pyrimidin-4-yl]-2,3,4,5-tetrahydro-1,4-benzoxazepine 4-(6-ethyl-5,6,7,8-tetrahydroquinazolin-4-yl)-7-(2-methyl-1H-benzimidazol-6-yl)-2,3,4,5-tetrahydro-1,4-benzoxazepine 4-[5-(cyclopropylmethyl)-6-methylpyrimidin-4-yl]-7-(2-methyl-1H-benzimidazol-6-yl)-2,3,4,5-tetrahydro-1,4-benzoxazepine 4-[6-ethyl-5-(phenylmethyl)pyrimidin-4-yl]-7-(2-methyl-1H-benzimidazol-6-yl)-2,3,4,5-tetrahydro-1,4-benzoxazepine 7-(2-methyl-1H-benzimidazol-6-yl)-4-[6-methyl-2-(methylthio)-6,7-dihydro-5H-cyclopenta[d]pyrimidin-4-yl]-2,3,4,5-tetrahydro-1,4-benzoxazepine 4-{5-[(3-fluorophenyl)methyl]-6-methylpyrimidin-4-yl}-7-(2-methyl-1H-benzimidazol-6-yl)-2,3,4,5-tetrahydro-1,4-benzoxazepine 4-{5-[(3-chlorophenyl)methyl]-6-methylpyrimidin-4-yl}-7-(2-methyl-1H-benzimidazol-6-yl)-2,3,4,5-tetrahydro-1,4-benzoxazepine 7-(2-methyl-1H-benzimidazol-6-yl)-4-[6-methyl-5-(1-phenylethyl)pyrimidin-4-yl]-2,3,4,5-tetrahydro-1,4-benzoxazepine 4-(5,7-dihydrothieno[3,4-d]pyrimidin-4-yl)-7-(2-methyl-1H-benzimidazol-6-yl)-2,3,4,5-tetrahydro-1,4-benzoxazepine 7-(2-methyl-1H-benzimidazol-6-yl)-4-(6-methyl-6,7-dihydro-5H-cyclopenta[d]pyrimidin-4-yl)-2,3,4,5-tetrahydro-1,4-benzoxazepine 5-methyl-6-[7-(2-methyl-1H-benzimidazol-6-yl)-2,3-dihydro-1,4-benzoxazepin-4(5H)-yl]-N-phenylpyrimidin-4-amine 7-(2-methyl-1H-benzimidazol-6-yl)-4-{6-methyl-5-[(4-methylphenyl)methyl]pyrimidin-4-yl}-2,3,4,5-tetrahydro-1,4-benzoxazepine 4-{5-[(4-fluorophenyl)methyl]-6-methylpyrimidin-4-yl}-7-(2-methyl-1H-benzimidazol-6-yl)-2,3,4,5-tetrahydro-1,4-benzoxazepine 4-{5-[(4-chlorophenyl)methyl]-6-methylpyrimidin-4-yl}-7-(2-methyl-1H-benzimidazol-6-yl)-2,3,4,5-tetrahydro-1,4-benzoxazepine 7-(2-methyl-1H-benzimidazol-6-yl)-4-(6-methyl-5-{[3-(methyloxy)phenyl]methyl}pyrimidin-4-yl)-2,3,4,5-tetrahydro-1,4-benzoxazepine 7-(2-methyl-1H-benzimidazol-6-yl)-4-{6-methyl-5-[(3-methylphenyl)methyl]pyrimidin-4-yl}-2,3,4,5-tetrahydro-1,4-benzoxazepine 4-{5-[(3-chloro-5-fluorophenyl)methyl]-6-methylpyrimidin-4-yl}-7-(2-methyl-1H-benzimidazol-6-yl)-2,3,4,5-tetrahydro-1,4-benzoxazepine 7-(2-methyl-1H-benzimidazol-6-yl)-4-(6-methyl-5-{[2-(methyloxy)phenyl]methyl}pyrimidin-4-yl)-2,3,4,5-tetrahydro-1,4-benzoxazepine 7-(2-methyl-1H-imidazo[4,5-b]pyridin-6-yl)-4-(2-methylpyrimidin-4-yl)-2,3,4,5-tetrahydro-1,4-benzoxazepine 7-(2-methyl-1H-benzimidazol-6-yl)-4-{6-methyl-5-[(2-methylphenyl)methyl]pyrimidin-4-yl}-2,3,4,5-tetrahydro-1,4-benzoxazepine 4-(6-cyclopropyl-6,7-dihydro-5H-pyrrolo[3,4-d]pyrimidin-4-yl)-7-(2-methyl-1H-benzimidazol-6-yl)-2,3,4,5-tetrahydro-1,4-benzoxazepine 7-(2-methyl-1H-benzimidazol-6-yl)-4-[6-(4-methylphenyl)-6,7-dihydro-5H-pyrrolo[3,4-d]pyrimidin-4-yl]-2,3,4,5-tetrahydro-1,4-benzoxazepine 4-{5-[(3,4-difluorophenyl)methyl]-6-methylpyrimidin-4-yl}-7-(2-methyl-1H-benzimidazol-6-yl)-2,3,4,5-tetrahydro-1,4-benzoxazepine 7-(2-methyl-1H-benzimidazol-6-yl)-4-(6-methyl-5-{[4-(trifluoromethyl)phenyl]methyl}pyrimidin-4-yl)-2,3,4,5-tetrahydro-1,4-benzoxazepine 4-{5-[(3,5-difluorophenyl)methyl]-6-methylpyrimidin-4-yl}-7-(2-methyl-1H-benzimidazol-6-yl)-2,3,4,5-tetrahydro-1,4-benzoxazepine 7-(2-methyl-1H-benzimidazol-6-yl)-4-(6-methyl-5-{[3-(trifluoromethyl)phenyl]methyl}pyrimidin-4-yl)-2,3,4,5-tetrahydro-1,4-benzoxazepine 2-chloro-N,N-dimethyl-5-({4-methyl-6-[7-(2-methyl-1H-benzimidazol-6-yl)-2,3-dihydro-1,4-benzoxazepin-4(5H)-yl]pyrimidin-5-yl}methyl)aniline 4-{5-[1-(3-fluorophenyl)ethyl]-6-methylpyrimidin-4-yl)-7-(2-methyl-1H-benzimidazol-6-yl}-2,3,4,5-tetrahydro-1,4-benzoxazepine 4-(7,7-dimethyl-5,6,7,8-tetrahydroquinazolin-4-yl)-7-(2-methyl-1H-benzimidazol-6-yl)-2,3,4,5-tetrahydro-1,4-benzoxazepine 4-[7-(2-methyl-1H-benzimidazol-6-yl)-2,3-dihydro-1,4-benzoxazepin-4(5H)-yl]pyrimidin-2-amine 4-{5-[(4-fluorophenyl)methyl]-2,6-dimethylpyrimidin-4-yl}-7-(2-methyl-1H-benzimidazol-6-yl}-2,3,4,5-tetrahydro-1,4-benzoxazepine 7-(2-methyl-1H-benzimidazol-6-yl)-4-quinolin-4-yl-2,3,4,5-tetrahydro-1,4-benzoxazepine 7-(2-methyl-1H-benzimidazol-6-yl)-4-[2-(trifluoromethyl)quinolin-4-yl]-2,3,4,5-tetrahydro-1,4-benzoxazepine 7-(2-methyl-1H-benzimidazol-6-yl)-4-[2-phenylquinolin-4-yl]-2,3,4,5-tetrahydro-1,4-benzoxazepine 7-(2-methyl-1H-benzimidazol-6-yl)-4-[2-methyl-3-(phenylmethyl)pyridin-4-yl]-2,3,4,5-tetrahydro-1,4-benzoxazepine 4-{3-[(4-fluorophenyl)methyl]-2-methylpyridin-4-yl}-7-(2-methyl-1H-benzimidazol-6-yl)-2,3,4,5-tetrahydro-1,4-benzoxazepine 4-{3-[(3-fluorophenyl)methyl]-2-methylpyridin-4-yl}-7-(2-methyl-1H-benzimidazol-6-yl)-2,3,4,5-tetrahydro-1,4-benzoxazepine 7-(2-methyl-1H-benzimidazol-6-yl)-4-pyridin-2-yl-2,3,4,5-tetrahydro-1,4-benzoxazepine 4-isoquinolin-1-yl-7-(2-methyl-1H-benzimidazol-6-yl)-2,3,4,5-tetrahydro-1,4-benzoxazepine 7-(2-methyl-1H-benzimidazol-6-yl)-4-pyrimidin-2-yl-2, 3,4,5-tetrahydro-1,4-benzoxazepine methyl [6-(4-pyrimidin-4-yl-2,3,4,5-tetrahydro-1,4-benzoxazepin-7-yl)-1H-benzimidazol-2-yl]carbamate methyl {6-[4-(2-methylquinazolin-4-yl)-2,3,4,5-tetrahydro-1,4-benzoxazepin-7-yl]-1H-benzimidazol-2-yl}carbamate methyl [6-[4-quinazolin-4-yl-2,3,4,5-tetrahydro-1,4-benzoxazepin-7-yl)-1H-benzimidazol-2-yl]carbamate methyl {6-[4-(7H-pyrrolo[2,3-d]pyrimidin-4-yl)-2,3,4,5-tetrahydro-1,4-benzoxazepin-7-yl]-1H-benzimidazol-2-yl}carbamate methyl (6-{4-[6,7-bis(methyloxy)quinazolin-4-yl]-2,3,4,5-tetrahydro-1,4-benzoxazepin-7-yl}-1H-benzimidazol-2-yl)carbamate methyl (6-{4-[6-(methyloxy)quinazolin-4-yl]-2,3,4,5-tetrahydro-1,4-benzoxazepin-7-yl}-1H-benzimidazol-2-yl)carbamate methyl [6-(4-{5-[(4-fluorophenyl)methyl]-6-methylpyrimidin-4-yl}-2,3,4,5-tetrahydro-1,4-benzoxazepin-7-yl)-1H-benzimidazol-2-yl]carbamate methyl [6-(4-quinolin-4-yl-2,3,4,5-tetrahydro-1,4-benzoxazepin-7-yl)-1H-benzimidazol-2-yl]carbamate methyl [1-methyl-5-(4-quinolin-4-yl-2,3,4,5-tetrahydro-1,4-benzoxazepin-7-yl)-1H-benzimidazol-2-yl]carbamate 1-methyl-5-(4-quinolin-4-yl-2,3,4,5-tetrahydro-1,4-benzoxazepin-7-yl)-1H-benzimidazol-2-amine methyl [1-methyl-6-(4-quinolin-4-yl-2,3,4,5-tetrahydro-1,4-benzoxazepin-7-yl)-1H-benzimidazol-2-yl]carbamate 2-(methyloxy)ethyl [6-(4-quinolin-4-yl-2,3,4,5-tetrahydro-1,4-benzoxazepin-7-yl)-1H-benzimidazol-2-yl]carbamate methyl (6-{4-[6,7-bis(methyloxy)quinolin-4-yl]-2,3,4,5-tetrahydro-1,4-benzoxazepin-7-yl}-1H-benzimidazol-2-yl)carbamate 4-piperidin-1-yl-N-[6-(4-quinolin-4-yl-2,3,4,5-tetrahydro-1,4-benzoxazepin-7-yl)-1H-benzimidazol-2-yl]butanamide methyl [6-(4-isoquinolin-1-yl-2,3,4,5-tetrahydro-1,4-benzoxazepin-7-yl)-1H-benzimidazol-2-yl]carbamate methyl {6-[4-(3-methylpyridin-2-yl)-2,3,4,5-tetrahydro-1,4-benzoxazepin-7-yl]-1H-benzimidazol-2-yl}carbamate 7-(1H-benzimidazol-6-yl)-4-quinazolin-4-yl-2,3,4,5-tetrahydro-1,4-benzoxazepine 5-(4-{5-[(4-fluorophenyl)methyl]-6-methylpyrimidin-4-yl}-2,3,4,5-tetrahydro-1,4-benzoxazepin-7-yl)-1,3-thiazol-2-amine 4-{5-[(4-fluorophenyl)methyl]-6-methylpyrimidin-4-yl}-7-(2-methyl-3H-imidazo[4,5-b]pyridin-6-yl)-2,3,4,5-tetrahydro-1,4-benzoxazepine 7-(1H-benzimidazol-6-yl)-4-quinolin-4-yl-2,3,4,5-tetrahydro-1,4-benzoxazepine 7-(1-ethyl-1H-benzimidazol-5-yl)-4-quinolin-4-yl-2,3,4,5-tetrahydro-1,4-benzoxazepine 7-(2-methyl-1,3-benzothiazol-5-yl)-4-quinolin-4-yl-2,3,4,5-tetrahydro-1,4-benzoxazepine 7-(1,3-benzothiazol-5-yl)-4-quinolin-4-yl-2,3,4,5-tetrahydro-1,4-benzoxazepine 7-(1-methyl-1H-benzimidazol-5-yl)-4-quinolin-4-yl-2,3,4,5-tetrahydro-1,4-benzoxazepine 4-{5-[(4-fluorophenyl)methyl]-6-methylpyrimidin-4-yl}-7-[4-(1H-imidazol-2-yl)phenyl]-2,3,4,5-tetrahydro-1,4-benzoxazepine 4-quinolin-4-yl-7-quinoxalin-6-yl-2,3,4,5-tetrahydro-1,4-benzoxazepine 7-(1-methyl-1H-indol-5-yl)-4-quinolin-4-yl-2,3,4,5-tetrahydro-1,4-benzoxazepine N,N-dimethyl-3-(4-quinolin-4-yl-2,3,4,5-tetrahydro-1,4-benzoxazepin-7-yl)benzamide 7-(2,3-dihydro-1-benzofuran-5-yl)-4-quinolin-4-yl-2,3,4,5-tetrahydro-1,4-benzoxazepine 7-(1H-indazol-6-yl)-4-quinolin-4-yl-2,3,4,5-tetrahydro-1,4-benzoxazepine 7-(1H-pyrazol-4-yl)-4-quinolin-4-yl-2,3,4,5-tetrahydro-1,4-benzoxazepine 7-(1H-indazol-5-yl)-4-quinolin-4-yl-2,3,4,5-tetrahydro-1,4-benzoxazepine 7-(1-methyl-1H-indazol-5-yl)-4-quinolin-4-yl-2,3,4,5-tetrahydro-1,4-benzoxazepine 5-(4-{5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine 6-(4-{5-[(4-fluorophenyl)methyl]-6-methylpyrimidin-4-yl}-2,3,4,5-tetrahydro-1,4-benioiazepin-7-yl)[1,2,4]triazolo[1,5-a]pyridin-2-amine 4-{5-[(4-fluorophenyl)methyl]-6-methylpyrimidin-4-yl}-7-(1H-imidazo[4,5-b]pyridin-6-yl)-2,3,4,5-tetrahydro-1,4-benzoxazepine 6-(4-{5-[(4-fluorophenypmethyl]-6-methylpyrimidin-4-yl}-2,3,4,5-tetrahydro-1,4-benzoxazepin-7-yl)quinazolin-2-amine 6-(4-{5-[(4-fluorophenypmethyl]-6-methylpyrimidin-4-yl}-2,3,4,5-tetrahydro-1,4-benzoxazepin-7-ypimidazo[1,2-a]pyrimidin-2-amine 6-(4-{5-[(4-fluorophenyl)methyl]-6-methylpyrimidin-4-yl}-2,3,4,5-tetrahydro-1,4-benzoxazepin-7-yl)imidazo[ 1,2-a]pyridin-2-amine 7-(4-{5-[(4-fluorophenyl)methyl]-6-methylpyrimidin-4-yl}-2,3,4,5-tetrahydro-1,4-benzoxazepin-7-yl)[ 1,2,4]triazolo [ 1,5-a]pyridin-2-amine 5-(4-{5-[(4-fluorophenyl)methyl]-6-methylpyrimidin-4-yl}-2,3,4,5-tetrahydro-1,4-benzoxazepin-7-yl)[1,3]thiazolo[4,5-b]pyridin-2-amine 5-(4-{5-[(4-fluorophenyl)methyl]-6-methylpyrimidin-4-yl}-2,3,4,5-tetrahydro-1,4-benzoxazepin-7-yl)-1,3-benzothiazol-2-amine 6-(4-{5-[(4-fluorophenyl)methyl]-6-methylpyrimidin-4-yl}-2,3,4,5-tetrahydro-1,4-benzoxazepin-7-yl)pyridazin-3-amine 4-{5-[(4-fluorophenyl)methyl]-6-methylpyrimidin-4-yl}-7-(1,3-thiazol-5-yl)-2,3,4,5-tetrahydro-1,4-benzoxazepine 5-(4-{5-[(4-fluorophenyl)methyl]-6-methylpyrimidin-4-yl}-2,3,4,5-tetrahydro-1,4-benzoxazepin-7-yl)pyrazin-2-amine 4-(7,7-dimethyl-5,6,7,8-tetrahydroquinazolin-4-yl)-7-(2-methyl-1,3-thiazol-5-yl)-2,3,4,5-tetrahydro-1,4-benzoxazepine 5-(4-{5-[(4-fluorophenyl)methyl]-6-methylpyrimidin-4-yl}-2,3,4,5-tetrahydro-1,4-benzoxazepin-7-yl)pyrimidin-2-amine 5-(4-{5-[(4-fluorophenyl)methyl]-6-methylpyrimidin-4-yl}-2,3,4,5-tetrahydro-1,4-benzoxazepin-7-yl)-4-methyl-1,3-thiazol-2-amine 6-(4-{5-[(4-fluorophenyl)methyl]-6-methylpyrimidin-4-yl}-2,3,4,5-tetrahydro-1,4-benzoxazepin-7-yl)-N-methylpyridine-3-carboxamide 5-[4-(7,7-dimethyl-5,6,7,8-tetrahydroquinazolin-4-yl)-2,3,4,5-tetrahydro-1,4-benzoxazepin-7-yl]-4-methyl-1,3-thiazol-2-amine 4-[7-(2-methyl-1H-benzimidazol-6-yl)-2,3-dihydro-1,4-benzoxazepin-4(5H)-yl]-6-(methyloxy)quinazolin-7-ol
4-[7-(2-methyl-1H-benzimidazol-6-yl)-2,3-dihydro-1,4-benzoxazepin-4(5H)-yl]quinazolin-6-ol
4-[6-(ethyloxy)quinazolin-4-yl]-7-(2-methyl-1H-benzimidazol-6-yl)-2,3,4,5-tetrahydro-1,4-benzoxazepine
({4-[7-(2-methyl-1H-benzimidazol-6-yl)-2,3-dihydro-1,4-benzoxazepin-4(5H)-yl]quinazolin-6-yl}oxy)acetonitrile
N,N-dimethyl-3-({4-[7-(2-methyl-1H-benzimidazol-6-yl)-2,3-dihydro-1,4-benzoxazepin-4(5H)-yl]quinazolin-6-yl}oxy)propan-1-amine
7-(2-methyl-1H-benzimidazol-6-yl)-4-[6-(propyloxy)quinazolin-4-yl]-2,3,4,5-tetrahydro-1,4-benzoxazepine
7-(2-methyl-1H-benzimidazol-6-yl)-4-(6-{[2-(methyloxy)ethyl]oxy}quinazolin-4-yl)-2,3,4,5-tetrahydro-1,4-benzoxazepine
4-[7-(2-methyl-1H-benzimidazol-6-yl)-2,3-dihydro-1,4-benzoxazepin-4(5H)-yl]-8-(methyloxy)quinazolin-7-ol
N,N-dimethyl-2-({4-[7-(2-methyl-1H-benzimidazol-6-yl)-2,3-dihydro-1,4-benzoxazepin-4(5H)-yl]-8-(methyloxy)quinazolin-7-yl}oxy)ethanamine
7-(2-methyl-1H-benzimidazol-6-yl)-4-{ 8-(methyloxy)-7-[(2-methylpropyl)oxy]quinazolin-4-yl}-2,3,4,5-tetrahydro-1,4-benzoxazepine
7-(2-methyl-1H-benzimidazol-6-yl)-4-{8-(methyloxy)-7-[(quinolin-2-ylmethyl)oxy]quinazolin-4-yl}-2,3,4,5-tetrahydro-1,4-benzoxazepine
4-{7-[(cyclopropylmethyl)oxy]-8-(methyloxy)quinazolin-4-yl}-7-(2-methyl-1H-benzimidazol-6-yl)-2,3,4,5-tetrahydro-1,4-benzoxazepine
7-(2-methyl-1H-imidazo[4,5-b]pyridin-6-yl)-4-(5-methylppimidin-4-yl)-3,4,5-tetrahydro-1,4-benzoxazepine
4-(4-{5-[(4-fluorophenypmethyl]-6-methylpyrimidin-4-yl}-2,3,4,5-tetrahydro-1,4-benzoxazepin-7-yl)benzamide
4-(4-{5-[(4-fluorophenyl)methyl]-6-methylpyrimidin-4-yl}-2,3,4,5-tetrahydro-1,4-benzoxazepin-7-yl)-N-methylbenzamide
N-cyclopropyl-4-(4-{5-[(4-fluorophenyl)methyl]-6-methylpyrimidin-4-yl}-2,3,4,5-tetrahydro-1,4-benzoxazepin-7-yl)benzamide
4-(4-{5-[(4-fluorophenyl)methyl]-6-methylpyrimidin-4-yl}-2,3,4,5-tetrahydro-1,4-benzoxazepin-7-yl)-N-[(3S)-pyrrolidin-3-yl]benzamide
N-(2,2-difluoroethyl)-4-(4-{5-[(4-fluorophenyl)methyl]-6-methylpyrimidin-4-yl}-2,3,4,5-tetrahydro-1,4-benzoxazepin-7-yl)benzamide
methyl [6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-yl]carbamate
6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine
6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-amine
6-[4-(6-ethyl-5,6,7,8-tetrahydroquinazolin-4-yl)-2,3,4,5-tetrahydro-1,4-benzoxazepin-7-yl]-1H-imidazo[4,5-b]pyridin-2-amine
6-[4-(7-methyl-5,6,7,8-tetrahydroquinazolin-4-yl)-2,3,4,5-tetrahydro-1,4-benzoxazepin-7-yl]-1H-imidazo[4,5-b]pyridin-2-amine
6-{4-[6,7-bis(methyloxy)quinazolin-4-yl]-2,3,4,5-tetrahydro-1,4-benzoxazepin-7-yl}-1H-imidazo[4,5-b]pyridin-2-amine
6-[4-(6-bromoquinazolin-4-yl)-2,3,4,5-tetrahydro-1,4-benzoxazepin-7-yl]-1H-imidazo[4,5-b]pyridin-2-amine
6-{4-[6-(methyloxy)quinazolin-4-yl]-2,3,4,5-tetrahydro-1,4-benzoxazepin-7-yl}-1H-imidazo[4,5-b]pyridin-2-amine
6-[4-(6-iodbquinazolin-4-yl)-2,3,4,5-tetrahydro-1,4-benzoxazepin-7-yl]-1H-imidazo[4,5-b]pyridin-2-amine
6-{4-[7-bromo-6-(methyloxy)quinazolin-4-yl]-2,3,4,5-tetrahydro-1,4-benzoxazepin-7-yl}-1H-imidazo[4,5-b]pyridin-2-amine
6-[4-(6-bromo-7-chloroquinazolin-4-yl)-2,3,4,5-tetrahydro-1,4-benzoxazepin-7-yl]-1H-imidazo[4,5-b]pyridin-2-amine
6-[4-(6-chloroquinazolin-4-yl)-2,3,4,5-tetrahydro-1,4-benzoxazepin-7-yl]-1H-imidazo[4,5-b]pyridin-2-amine
6-[4-(6-fluoroquinazolin-4-yl)-2,3,4,5-tetrahydro-1,4-benzoxazepin-7-yl]-1H-imidazo[4,5-b]pyridin-2-amine
6-{4-[6,7-bis(methyloxy)quinolin-4-yl]-2,3,4,5-tetrahydro-1,4-benzoxazepin-7-yl}-1H-imidazo[4,5-b]pyridin-2-amine
6-(4-{5-[(4-fluorophenyl)methyl]-6-methylpyrimidin-4-yl}-2,3,4,5-tetrahydro-1,4-benzoxazepin-7-yl)-1H-benzimidazol-2-amine
6-(4-quinolin-4-yl-2,3,4,5-tetrahydro-1,4-benzoxazepin-7-yl)-1H-benzimidazol-2-amine
6-{4-[6,7-bis(methyloxy)quinolin-4-yl]-2,3,4,5-tetrahydro-1,4-benzoxazepin-7-yl}-1H-benzimidazol-2-amine
N-ethyl-6-(4-{5-[(4-fluorophenyl)methyl]-6-methylpyrimidin-4-yl}-2,3,4,5-tetrahydro-1,4-benzoxazepin-7-yl)-1H-benzimidazol-2-amine
N-(2-fluoroethyl)-5-(4-{5-[(4-fluorophenyl)methyl]-6-methylpyrimidin-4-yl}-2,3,4,5-tetrahydro-1,4-benzoxazepin-7-yl)-1H-benzimidazol-2-amine
5-(4-{5-[(4-fluorophenyl)methyl]-6-methylpyrimidin-4-yl}-2,3,4,5-tetrahydro-1,4-benzoxazepin-7-yl)-3H-imidazo[4,5-b]pyridin-2-amine
N,N-dimethyl-6-(4-quinolin-4-yl-2,3,4,5-tetrahydro-1,4-benzoxazepin-7-yl)-1H-benzimidazol-2-amine
7-{2-[(methyloxy)methyl]-1H-benzimidazol-6-yl}-4-quinolin-4-yl-2,3,4,5-tetrahydro-1,4-benzoxazepine
7-(2-propyl-1H-benzimidazol-6-yl)-4-quinolin-4-yl-2,3,4,5-tetrahydro-1,4-benzoxazepine
7-(2-cyclopentyl-1H-benzimidazol-6-yl)-4-quinolin-4-yl-2,3,4,5-tetrahydro-1,4-benzoxazepine
7-(2-cyclopropyl-1H-b enzimidazol-6-yl)-4-quinolin-4-yl-2,3,4,5-tetrahydro-1,4-benzoxazepine
7-(2-cyclohexyl-1H-benzimidazol-6-yl)-4-quinolin-4-yl-2,3,4,5-tetrahydro-1,4-benzoxazepine
7-(2-azetidin-3-yl-1H-benzimidazol-6-yl)-4-quinolin-4-yl-2,3,4,5-tetrahydro-1,4-benzoxazepine
7-(2-piperidin-2-yl-1H-benzimidazol-6-yl)-4-quinolin-4-yl-2,3,4,5-tetrahydro-1,4-benzoxazepine
7-[2-(1-methyl ethyl)-1H-benzimidazol-6-yl]-4-quinolin-4-yl-2,3,4,5-tetrahydro-1,4-benzoxazepine
4-quinolin-4-yl-7-(3-thienyl)-2,3,4,5-tetrahydro-1,4-benzoxazepine
7-quinolin-3-yl-4-quinolin-4-yl-2,3,4,5-tetrahydro-1,4-benzoxazepine
7-(1-benzothien-2-yl)-4-quinolin-4-yl-2,3,4,5-tetrahydro-1,4-benzoxazepine
7-[2-(methylthio)-1H-benzimidazol-6-yl]-4-quinolin-4-yl-2,3,4,5-tetrahydro-1,4-benzoxazepine N-ethyl-6-(4-quinolin-4-yl-2,3,4,5-tetrahydro-1,4-benzoxazepin-7-yl)-1H-benzimidazol-2-amine
N-(1-methylethyl)-6-(4-quinolin-4-yl-2,3,4,5-tetrahydro-1,4-benzoxazepin-7-yl)-1H-benzimidazol-2-amine
methyl (6-{4-[6,7-bis(methyloxy)quinolin-4-yl]-2,3,4,5-tetrahydro-1,4-benzoxazepin-7-yl}-1H-imidazo[4,5-b]pyridin-2-yl)carbamate
4-(7-ethyl-5,6,7,8-tetrahydropyrido[3,4-d]pyrimidin-4-yl)-7-(2-methyl-1H-benzimidazol-6-yl)-2,3,4,5-tetrahydro-1,4-benzoxazepine
{5-[4-(4-pyrido[3,2-d]pyrimidin-4-yl-2,3,4,5-tetrahydro-1,4-benzoxazepin-7-yl)phenyl]-1H-imidazol-2-yl}methanol
4-(6,6-dimethyl-5,6,7,8-tetrahydroquinazolin-4-yl)-7-[4-(1H-imidazol-2-yl)phenyl]-2,3,4,5-tetrahydro-1,4-benzoxazepine
7-(2,4-dimethyl-1H-benzimidazol-6-yl)-4-pyrido[3,2-d]pyrimidin-4-yl-2,3,4,5-tetrahydro-1,4-benzoxazepine
6-[4-(6,6-dimethyl-5,6,7,8-tetrahydroquinazolin-4-yl)-2,3,4,5-tetrahydro-1,4-benzoxazepin-7-yl]-N-(2-fluoroethyl)-1H-benzimidazol-2-amine
6-(4-{5-[(4-fluorophenyl)methyl]-6-methylpyrimidin-4-yl}-2,3,4,5-tetrahydro-1,4-benzoxazepin-7-yl)-1H-imidazo[4,5-c]pyridin-2-amine
6-(4-{5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine
6-[4-(6-methylquinazolin-4-yl)-2,3,4,5-tetrahydro-1,4-benzoxazepin-7-yl]-1H-imidazo[4,5-b]pyridin-2-amine
7-(1H-benzimidazol-6-yl)-4-(6,6-dimethyl-5,6,7,8-tetrahydroquinazolin-4-yl)-2,3,4,5-tetrahydro-1,4-benzoxazepine
4-(6,6-dimethyl-5,6,7,8-tetrahydroquinazolin-4-yl)-7-(2-ethyl-3H-imidazo[4,5-b]pyridin-6-yl)-2,3,4,5-tetrahydro-1,4-benzoxazepine
4-(6,6-dimethyl-5,6,7,8-tetrahydroquinazolin-4-yl)-7-(1H-imidazo[4,5-b]pyridin-6-yl)-2,3,4,5-tetrahydro-1,4-benzoxazepine
7-(1-methyl-1H-pyrrolo[2,3-b]pyridin-5-yl)-4-quinolin-4-yl-2,3,4,5-tetrahydro-1,4-benzoxazepine
7-(1-ethyl-1H-pyrrolo[2,3-b]pyridin-5-yl)-4-quinolin-4-yl-2,3,4,5-tetrahydro-1,4-benzoxazepine
7-(2-cyclopropyl-3H-imidazo[4,5-b]pyridin-6-yl)-4-(6,6-dimethyl-5,6,7,8-tetrahydroquinazolin-4-yl)-2,3,4,5-tetrahydro-1,4-benzoxazepine
4-(6,6-dimethyl-5,6,7,8-tetrahydroquinazolin-4-yl)-7-(2-propyl-3H-imidazo[4,5-b]pyridin-6-yl)-2,3,4,5-tetrahydro-1,4-benzoxazepine
5-(4-quinolin-4-yl-2,3,4,5-tetrahydro-1,4-benzoxazepin-7-yl)pyridin-2-amine
6-(4-pyrido[3,2-d]pyrimidin-4-yl-2,3,4,5-tetrahydro-1,4-benzoxazepin-7-yl)-1H-imidazo[4,5-b]pyridin-2-amine
N-ethyl-6-[4-(2-methylquinazolin-4-yl)-2,3,4,5-tetrahydro-1,4-benzoxazepin-7-yl]-1H-benzimidazol-2-amine
7-[2-(difluoromethyl)-3H-imidazo[4,5-b]pyridin-6-yl]-4-(6,6-dimethyl-5,6,7,8-tetrahydroquinazolin-4-yl)-2,3,4,5-tetrahydro-1,4-benzoxazepine
N-ethyl-6-(4-pyrimidin-4-yl-2,3,4,5-tetrahydro-1,4-benzoxazepin-7-yl)-1H-imidazo[4,5-b]pyridin-2-amine
(2E)-5-[4-(6,6-dimethyl-5,6,7,8-tetrahydroquinazolin-4-yl)-2,3,4,5-tetrahydro-1,4-benzoxazepin-7-yl]-2-iminopyrimidin-1(2H)-ol
7-(1H-benzimidazol-6-yl)-4-(2-phenylquinazolin-4-yl)-2,3,4,5-tetrahydro-1,4-benzoxazepine
6-[4-(2-phenylquinazolin-4-yl)-2,3,4,5-tetrahydro-1,4-benzoxazepin-7-yl]-1H-benzimidazol-2-amine
4-(6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine
methyl {6-[4-(6,6-dimethyl-5,6,7,8-tetrahydroquinazolin-4-yl)-2,3,4,5-tetrahydro-1,4-benzoxazepin-7-yl]-1H-benzimidazol-2-yl}carbamate
6-[4-(6,6-dimethyl-5,6,7,8-tetrahydroquinazolin-4-yl)-2,3,4,5-tetrahydro-1,4-benzoxazepin-7-yl]-1H-benzimidazol-2-amine
N-ethyl-6-{4-[2-methyl-7-(methyloxy)quinazolin-4-yl]-2,3,4,5-tetrahydro-1,4-benzoxazepin-7-yl}-1H-benzimidazol-2-amine
4-(6,6-dimethyl-5,6,7,8-tetrahydroquinazolin-4-yl)-7-[2-(fluoromethyl)-3H-imidazo[4,5-b]pyridin-6-yl]-2,3,4,5-tetrahydro-1,4-benzoxazepine
N-methyl-4-(4-quinolin-4-yl-2,3,4,5-tetrahydro-1,4-benzoxazepin-7-yl)benzamide
7-[4-(1H-benzimidazol-2-yl)phenyl]-4-[2-methyl-7-(methyloxy)quinazolin-4-yl]-2,3,4,5-tetrahydro-1,4-benzoxazepine
4-(7-fluoroquinolin-4-yl)-7-(2-methyl-1H-benzimidazol-6-yl)-2,3,4,5-tetrahydro-1,4-benzoxazepine
4-[7-(2-methyl-1H-benzimidazol-6-yl)-2,3-dihydro-1,4-benzoxazepin-4(5H)-yl]quinoline-7-carbonitrile
N-ethyl-4-(4-quinolin-4-yl-2,3,4,5-tetrahydro-1,4-benzoxazepin-7-yl)benzamide
N-propyl-4-(4-quinolin-4-yl-2,3,4,5-tetrahydro-1,4-benzoxazepin-7-yl)benzamide
4-(6-ethyl-5-methylpyrimidin-4-yl)-7-(2-methyl-1H-imidazo[4,5-b]pyridin-6-yl)-2,3,4,5-tetrahydro-1,4-benzoxazepine
N-ethyl-6-[4-(2-methylquinolin-4-yl)-2,3,4,5-tetrahydro-1,4-benzoxazepin-7-yl]-1H-benzimidazol-2-amine
N-ethyl-6-{4-[2-methyl-7-(methyloxy)quinolin-4-yl]-2,3,4,5-tetrahydro-1,4-benzoxazepin-7-yl}-1H-benzimidazol-2-amine
6-[4-(6,6-dimethyl-5,6,7,8-tetrahydroquinazolin-4-yl)-2,3,4,5-tetrahydro-1,4-benzoxazepin-7-yl][1,3]thiazolo[5,4-b]pyridin-2-amine
5-(4-{5-[(4-fluorophenyl)methyl]-6-methylpyrimidin-4-yl}-2,3,4,5-tetrahydro-1,4-benzoxazepin-7-yl)-1H-indazol-3-amine
N-ethyl-6-(4-{5-[(4-fluorophenyl)methyl]-6-methylpyrimidin-4-yl}-2,3,4,5-tetrahydro-1,4-benzoxazepin-7-yl)-1H-imidazo[4,5-b]pyridin-2-amine
7-[4-(1H-imidazol-2-yl)phenyl]-4-(2-methylquinazolin-4-yl)-2,3,4,5-tetrahydro-1,4-benzoxazepine
1-{6-[4-(6,6-dimethyl-5,6,7,8-tetrahydroquinazolin-4-yl)-2,3,4,5-tetrahydro-1,4-benzoxazepin-7-yl]-3H-imidazo[4,5-b]pyridin-2-yl}ethanol
4-[7-(2-methyl-1H-benzimidazol-6-yl)-2,3-dihydro-1,4-benzoxazepin-4(5H)-yl]-N-phenylpyrimidin-2-amine
4-(6,6-dimethyl-5,6,7,8-tetrahydroquinazolin-4-yl)-7-(2-ethyl-1H-benzimidazol-6-yl)-2,3,4,5-tetrahydro-1,4-benzoxazepine
6-[4-(6,6-dimethyl-5,6,7,8-tetrahydroquinazolin-4-yl)-2,3,4,5-tetrahydro-1,4-benzoxazepin-7-yl]-N-ethyl-1H-benzimidazol-2-amine
7-[4-(1H-imidazol-2-yl)phenyl]-4-[2-methyl-7-(methyloxy)quinazolin-4-yl]-2,3,4,5-tetrahydro-1,4-benzoxazepine
4-(5,6-dimethylpyrimidin-4-yl)-7-(2-methyl-1H-imidazo[4,5-b]pyridin-6-yl)-2,3,4,5-tetrahydro-1,4-benzoxazepine 7-(2-methyl-1H-benzimidazol-6-yl)-4-[2-methyl-7-(methyloxy)quinazolin-4-yl]-2,3,4,5-tetrahydro-1,4-benzoxazepine 6-{4-[6,7-bis(methyloxy)quinazolin-4-yl]-2,3,4,5-tetrahydro-1,4-benzoxazepin-7-yl}-N-ethyl-1H-benzimidazol-2-amine N-ethyl-6-[4-(2-ethylquinazolin-4-yl)-2,3,4,5-tetrahydro-1,4-benzoxazepin-7-yl]-1H-benzimidazol-2-amine 6-{4-[6,7-bis(methyloxy)quinolin-4-yl]-2,3,4,5-tetrahydro-1,4-benzoxazepin-7-yl}-N-ethyl-1H-benzimidazol-2-amine 4-[7-(2-methyl-1H-benzimidazol-6-yl)-2,3-dihydro-1,4-benzoxazepin-4(5H)-yl]pyridin-2-amine 4-(6,6-dimethyl-5,6,7,8-tetrahydroquinazolin-4-yl)-7-[1H-pyrazolo[3,4-b]pyridin-5-yl]-2,3,4,5-tetrahydro-1,4-benzoxazepine 6-[4-(6,6-dimethyl-5,6,7,8-tetrahydroquinazolin-4-yl)-2,3,4,5-tetrahydro-1,4-benzoxazepin-7-yl]-N-ethyl-1H-imidazo[4,5-b]pyridin-2-amine 7-[2-(difluoromethyl)-1H-benzimidazol-5-yl]-4-(6,6-dimethyl-5,6,7,8-tetrahydroquinazolin-4-yl)-2,3,4,5-tetrahydro-1,4-benzoxazepine 5-[4-(2-methylquinazolin-4-yl)-2,3,4,5-tetrahydro-1,4-benzoxazepin-7-yl]pyridin-2-amine 4-[2-methyl-7-(methyloxy)quinazolin-4-yl]-7-(1H-pyrrolo[2,3-b]pyridin-5-yl)-2,3,4,5-tetrahydro-1,4-benzoxazepine N-ethyl-6-[4-(7-fluoroquinolin-4-yl)-2,3,4,5-tetrahydro-1,4-benzoxazepin-7-yl]-1H-benzimidazol-2-amine 4-{7-[2-(ethylamino)-1H-benzimidazol-6-yl]-2,3-dihydro-1,4-benzoxazepin-4(5H)-yl}-N-methylquinazolin-2-amine N-ethyl-4-{7-[2-(ethylamino)-1H-benzimidazol-6-yl]-2,3-dihydro-1,4-benzoxazepin-4(5H)-yl}quinazolin-2-amine N-ethyl-6-{4-[2-methyl-6,7-bis(methyloxy)quinazolin-4-yl]-2,3,4,5-tetrahydro-1,4-benzoxazepin-7-yl}-1H-benzimidazol-2-amine 4-[6,7-bis(methyloxy)quinolin-4-yl]-7-[4-(1H-imidazol-2-yl)phenyl]-2,3,4,5-tetrahydro-1,4-benzoxazepine 5-{4-[2-methyl-7-(methyloxy)quinazolin-4-yl]-2,3,4,5-tetrahydro-1,4-benzoxazepin-7-yl}pyridin-2-amine 7-(1H-indazol-5-yl)-4-[2-methyl-7-(methyloxy)quinazolin-4-yl]-2,3,4,5-tetrahydro-1,4-benzoxazepine N-ethyl-6-{4-[6-(phenylamino)pyrimidin-4-yl]-2,3,4,5-tetrahydro-1,4-benzoxazepin-7-yl}-1H-benzimidazol-2-amine N-ethyl-6-[4-(6-{[4-(methyloxy)phenyl]amino}pyrimidin-4-yl)-2,3,4,5-tetrahydro-1,4-benzoxazepin-7-yl]-1H-benzimidazol-2-amine N-ethyl-6-(4-pyrimidin-4-yl-2,3,4,5-tetrahydro-1,4-benzoxazepin-7-yl)-1H-benzimidazol-2-amine N-ethyl-6-{4-[6-(methyloxy)quinolin-4-yl]-2,3,4,5-tetrahydro-1,4-benzoxazepin-7-yl}-1H-benzimidazol-2-amine N-ethyl-6-{4-[2-ethyl-7-(methyloxy)quinazolin-4-yl]-2,3,4,5-tetrahydro-1,4-benzoxazepin-7-yl}-1H-benzimidazol-2-amine 7-(1H-benzimidazol-6-yl)-4-[2-methyl-7-(methyloxy)quinazolin-4-yl]-2,3,4,5-tetrahydro-1,4-benzoxazepine N-ethyl-6-[4-(7-fluoroquinazolin-4-yl)-2,3,4,5-tetrahydro-1,4-benzoxazepin-7-yl]-1H-benzimidazol-2-amine N-ethyl-6-[4-(8-fluoroquinolin-4-yl)-2,3,4,5-tetrahydro-1,4-benzoxazepin-7-yl]-1H-benzimidazol-2-amine N-ethyl-6-[4-(6-fluoroquinolin-4-yl)-2,3,4,5-tetrahydro-1,4-benzoxazepin-7-yl]-1H-benzimidazol-2-amine N-ethyl-6-[4-(6-{[3-(methyloxy)phenyl]amino}pyrimidin-4-yl)-2,3,4,5-tetrahydro-1,4-benzoxazepin-7-yl]-1H-benzimidazol-2-amine 4-{7-[2-(ethylamino)-1H-benzimidazol-6-yl]-2,3-dihydro-1,4-benzoxazepin-4(5H)-yl}-2-methylquinazolin-7-ol 5-{4-[2-methyl-7-(methyloxy)quinazolin-4-yl]-2,3,4,5-tetrahydro-1,4-benzoxazepin-7-yl}pyrimidin-2-amine N-ethyl-6-{4-[5-methyl-6-(phenylamino)pyrimidin-4-yl]-2,3,4,5-tetrahydro-1,4-benzoxazepin-7-yl}-1H-benzimidazol-2-amine N-ethyl-6-{4-[7-(ethyloxy)-2-methylquinazolin-4-yl]-2,3,4,5-tetrahydro-1,4-benzoxazepin,7-yl}-1H-benzimidazol-2-amine 6-{4-[2-methyl-7-(methyloxy)quinazolin-4-yl]-2,3,4,5-tetrahydro-1,4-benzoxazepin-7-yl}-1H-imidazo[4,5-b]pyridin-2-amine N-ethyl-6-[4-(2,6,6-trimethyl-5,6,7,8-tetrahydroquinazolin-4-yl)-2,3,4,5-tetrahydro-1,4-benzoxazepin-7-yl]-1H-imidazo[4,5-b]pyridin-2-amine N-ethyl-6-{4-[7-(methyloxy)quinolin-4-yl]-2,3,4,5-tetrahydro-1,4-benzoxazepin-7-yl}-1H-benzimidazol-2-amine 5-{4-[2-methyl-7-(methyloxy)quinazolin-4-yl]-2,3,4,5-tetrahydro-1,4-benzoxazepin-7-yl}-1,3-thiazol-2-amine N-(5-{4-[2-methyl-7-(methyloxy)quinazolin-4-yl]-2,3,4,5-tetrahydro-1,4-benzoxazepin-7-yl}-1,3-thiazol-2-yl)acetamide 7-(1,3-benzothiazol-6-yl)-4-[2-methyl-7-(methyloxy)quinazolin-4-yl]-2,3,4,5-tetrahydro-1,4-benzoxazepine N-ethyl-6-[4-(7-fluoro-2-methylquinazolin-4-yl)-2,3,4,5-tetrahydro-1,4-benzoxazepin-7-yl]-1H-benzimidazol-2-amine 5-{4-[2-methyl-7-(methyloxy)quinazolin-4-yl]-2,3,4,5-tetrahydro-1,4-benzoxazepin-7-yl}-1,3-dihydro-2H-benzimidazol-2-one (1R)-1-(6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)ethanamine (1S)-1-(6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)ethanamine (2R)-3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylpropan-1-ol (2R)—N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)butan-2-amine (2S)-3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylpropan-1-ol (2S)-3-[(2-amino-5-{4-[7-(methyloxy)quinazolin-4-yl]-2,3,4,5-tetrahydro-1,4-benzoxazepin-7-yl}pyridin-3-yl)sulfinyl]-2-methylpropan-1-ol (2S)-3-[(2-amino-5-{4-[7-(methyloxy)quinazolin-4-yl]-2,3,4,5-tetrahydro-1,4-benzoxazepin-7-yl}pyridin-3-yl)sulfonyl]-2-methylpropan-1-ol (2S)—N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)butan-2-amine (3R)-1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-ol (3S)-1-({2-[(3S)-3-aminopyrrolidin-1-yl]-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-amine (3S)-1-({2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-amine {4-[7-(2-amino[1,3]thiazolo[5,4-b]pyridin-6-yl)-2,3-dihydro-1,4-benzoxazepin-4(5H)-yl]-6,6-dimethyl-5,6,7,8-tetrahydroquinazolin-2-yl}methanol {4-[7-(2-methyl-1H-imidazo[4,5-b]pyridin-6-yl)-2,3-dihydro-1,4-benzoxazepin-4(5H)-yl]-5,6,7,8-tetrahydroquinazolin-7-yl}methanol {5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}methanol {5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}methyl acetate {6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methanol {6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl acetate 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-3-(hydroxymethyl)azetidin-3-ol 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)azetidin-3-ol 1-({2-amino-5-[4-(6;6-dimethyl-5,6,7,8-tetrahydroquinazolin-4-yl)-2,3,4,5-tetrahydro-1,4-benzoxazepin-7-yl]pyridin-3-yl}sulfonyl)piperidin-3-ol 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)piperidin-4-ol 1-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)pyrrolidin-3-ol 1-(4-{7-[2-(difluoromethyl)-1H-benzimidazol-5-yl]-2,3-dihydro-1,4-benzoxazepin-4(5H)-yl}-5-[(4-fluorophenyl)methyl]-6-methylpyrimidin-2-yl)-N,N-dimethylmethanamine 1-(4-{7-[2-(difluoromethyl)-1H-benzimidazol-5-yl]-2,3-dihydro-1,4-benzoxazepin-4(5H)-yl}-6,6-dimethyl-5,6,7,8-tetrahydroquinazolin-2-yl)-N,N-dimethylmethanamine 1-{4-(7-[2-(fluoromethyl)-1H-benzimidazol-5-yl]-2,3-dihydro-1,4-benzoxazepin-4(5H)-yl}-5-[(4-fluorophenypmethyl]-6-methylpyrimidin-2-yl)-N,N-dimethylmethanamine 1-(4-{7-[2-(fluoromethyl)-1H-benzimidazol-5-yl]-2,3-dihydro-1,4-benzoxazepin-4(5H)-yl}-6,6-dimethyl-5,6,7,8-tetrahydroquinazolin-2-yl)-N,N-dimethylmethanamine 1-(4-{7-[3,4-bis(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine 1-(4-{7-[3-chloro-4-(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine 1-(4-{7-[4-(1H-imidazol-2-yl)phenyl]-2,3-dihydro-1,4-benzoxazepin-4(5H)-yl}-6,6-dimethyl-5,6,7,8-tetrahydroquinazolin-2-yl)-N,N-dimethylmethanamine 1-(4-{7-[4-chloro-3-(methyloxy)phenyl]-2,3-dihydro-1,4-benzoxazepin-4(5H)-yl}-6,6-dimethyl-5,6,7,8-tetrahydroquinazolin-2-yl)-N,N-dimethylmethanamine 1-(6,6-dimethyl-4-{7-[3-(methyloxy)-4-{[2-(methyloxy)ethyl]oxy}phenyl]-2,3-dihydro-1,4-benzoxazepin-4(5H)-yl}-5,6,7,8-tetrahydroquinazolin-2-yl)-N,N-dimethylmethanamine 1-(6,6-dimethyl-4-{7-[3-(methyloxy)phenyl]-2,3-dihydro-1,4-benzoxazepin-4(5H)-yl}-5,6,7,8-tetrahydroquinazolin-2-yl)-N,N-dimethylmethanamine 1-(6,6-dimethyl-4-{7-[4-(methyloxy)phenyl]-2,3-dihydro-1,4-benzoxazepin-4(5H)-yl}-5,6,7,8-tetrahydroquinazolin-2-yl)-N,N-dimethylmethanamine 1-(6,6-dimethyl-4-{7-[6-(methyloxy)pyridin-3-yl]-2,3-dihydro-1,4-benzoxazepin-4(5H)-yl}-5,6,7,8-tetrahydroquinazolin-2-yl)-N,N-dimethylmethanamine 1-[4-{7-[2-(difluoromethyl)-1H-benzimidazol-5-yl]-2,3-dihydro-1,4-benzoxazepin-4(5H)-yl}-6-methyl-5-(1-methylethyl)pyrimidin-2-yl]-N,N-dimethylmethanamine 1-[4-{7-[2-(fluoromethyl)-1H-benzimidazol-5-yl]-2,3-dihydro-1,4-benzoxazepin-4(5H)-yl}-6-methyl-5-(1-methylethyl)pyrimidin-2-yl]-N,N-dimethylmethanamine 1-[4-{7-[3,4-bis(methyloxy)phenyl]-2,3-dihydro-1,4-benzoxazepin-4(5H)-yl}-7-(methyloxy)quinazolin-2-yl]-N,N-dimethylmethanamine 1-{(7S)-7-ethyl-4-[7-(2-methyl-1H-imidazo[4,5-b]pyridin-6-yl]-2,3-dihydro-1,4-benzoxazepin-4(5H)-yl]-5,6,7,8-tetrahydroquinazolin-2-yl)-N,N-dimethylmethanamine 1-{4,5-dimethyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine 1-{4-[7-(1,3-benzothiazol-5-yl)-2,3-dihydro-1,4-benzoxazepin-4(5H)-yl]-5-(4-fluorophenyl)methyl]-6-methylpyrimidin-2-yl}-N,N-dimethylmethanamine 1-{4-[7-(1,3-benzothiazol-5-yl)-2,3-dihydro-1,4-benzoxazepin-4(5H)-yl]-6,6-dimethyl-5,6,7,8-tetrahydroquinazolin-2-yl}-N,N-dimethylmethanamine 1-{4-(7-(1,3-benzothiazol-5-yl)-2,3-dihydro-1,4-benzoxazepin-4(5H)-yl]-6,6-dimethyl-7-(methyloxy)-5,6,7,8-tetrahydroquinazolin-2-yl}-N,N-dimethylmethanamine 1-{4-[7-(2-cyclopropyl-1H-imidazo[4,5-b]pyridin-6-yl)-2,3-dihydro-1,4-benzoxazepin-4(5H)-yl]-6,6-dimethyl-5,6,7,8-tetrahydroquinazolin-2-yl}-N,N-dimethylmethanamine 1-{4-[7-(2-methyl-1H-imidazo[4,5-b]pyridin-6-yl)-2,3-dihydro-1,4-benzoxazepin-4(5H)-yl]-5,6,7,8-tetrahydroquinazolin-7-yl}ethanol 1-{4-[7-(4-fluoro-2-methyl-1H-benzimidazol-5-yl)-2,3-dihydro-1,4-benzoxazepin-4(5H)-yl]-6,6-dimethyl-5,6,7,8-tetrahydroquinazolin-2-yl)-N,N-dimethylmethanamine 1-{4-[7-(6-fluoro-2-methyl-1H-benzimidazol-5-yl)-2,3-dihydro-1,4-benzoxazepin-4(5H)-yl]-6,6-dimethyl-5,6,7,8-tetrahydroquinazolin-2-yl}-N,N-dimethylmethanamine 1-{4-ethyl-5-methyl-6-[7-(2-methyl-1H-benzimidazol-5-yl)-2,3-dihydro-1,4-benzoxazepin-4(5H)-yl]pyrimidin-2-yl}-N,N-dimethylmethanamine 1-{4-ethyl-5-methyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine 1-{5-(cyclopropylmethyl)-4-methyl-6-[7(2-methyl-1H-benzimidazol-6-yl)-2,3-dihydro-1,4-benzoxazepin-4(5H)-yl]pyrimidin-2-yl}-N,N-dimethylmethanamine 1-[5-(cyclopropylmethyl)-4-methyl-6-[7(2-methyl-1H-imidazo[4,5-b]pyridin-6-yl)-2,3-dihydro-1,4-benzoxazepin-4(5H)-yl]pyrimidin-2-yl]-N,N-dimethylmethanamine 1-[5-(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl)-N,N-dimethylmethanamine 1-{5-[(4-fluorophenyl)methyl]-4-methyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine 1-{5-ethyl-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine 1-{5-ethyl-4-methyl-6-[7-(2-methyl-3H-imidazo[4,5-b]pyridin-6-yl)-2,3-dihydro-1,4-benzoxazepin-4(5H)-yl]pyrimidin-2-yl}-N,N-dimethylmethanamine 1-{6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}-N,N-dimethylmethanamine 1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methanamine 1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N,N-dimethylmethanamine 1-{6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}-N-methylmethanamine 1-{6,6-dimethyl-4-[7-(2-methyl-1H-imidazo[4,5-b]pyridin-6-yl)-2,3-dihydro-1,4-benzoxazepin-4(5H)-yl]-7-(methyloxy)-5,6,7,8-tetrahydroquinazolin-2-yl}-N,N-dimethylmethanamine 1-{6,6-dimethyl-4-[7-(2-methyl-3H-imidazo[4,5-b]pyridin-6-yl)-2,3-dihydro-1,4-benzoxazepin-4(5H)-yl]-5,6,7,8-tetrahydroquinazolin-2-yl}-N,N-dimethylethanamine 1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}-N,N-dimethylmethanamine 1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}-N-methylmethanamine 1-{6-fluoro-4-[7-(2-methyl-1H-imidazo[4,5-b]pyridin-6-yl)-2,3-dihydro-1,4-benzoxazepin-4(5H)-yl]quinazolin-2-yl}-N,N-dimethylmethanamine 1-cyclopropyl-N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)ethanamine 1-methyl-3-(4-{4-[2-methyl-7-(methyloxy)quinazolin-4-yl]-2,3,4,5-tetrahydro-1,4-benzoxazepin-7-yl}phenyl)urea 2-{6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}propan-2-ol 2-amino-5-(4-{5-[(4-fluorophenyl)methyl]-6-methylpyrimidin-4-yl}-2,3,4,5-tetrahydro-1,4-benzoxazepin-7-yl)-N-methylpyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(1-methylethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2,2,2-trifluoroethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2-fluoroethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-1,1-dimethylethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-1-methylethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxy-2-methylpropyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxyethyl)-N-methylpyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxyethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(2-hydroxypropyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(3,3,3-trifluoro-2-hydroxypropyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(3-hydroxy-2,2-dimethylpropyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(3-hydroxypropyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(piperidin-2-ylmethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(piperidin-3-ylmethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-(piperidin-4-ylmethyl)pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-carboxamide 2-amino-5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-[(1-methylpiperidin-4-yl)methyl]pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-[(2R)-pyrrolidin-2-ylmethyl]pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-[(2S)-pyrrolidin-2-ylmethyl]pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-[(3aR,5r,6aS)-octahydrocyclopenta[c]pyrrol-5-ylmethyl]pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-[(3R)-1-methylpyrrolidin-3-yl]pyridine-3-sulfonamide 2-amino-5-[4-(6,6-dimethyl-5,6,7,8-tetrahydroquinazolin-4-yl)-2,3,4,5-tetrahydro-1,4-benzoxazepin-7-yl]-N-[(3R)-piperidin-3-ylmethyl]pyridine-3-sulfonamide 2-amino-5-[4-(6,6-dimethyl-5,6,7,8-tetrahydroquinazo-
lin-4-yl)-2,3,4,5-tetrahydro-1,4-benzoxazepin-7-yl]-N-
[(3R)-pyrrolidin-3-yl]pyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
[(3R)-pyrrolidin-3-ylmethyl]pyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
[(3S)-piperidin-3-ylmethyl]pyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
[(3S)-pyrrolidin-3-yl]pyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
[(3S)-pyrrolidin-3-ylmethyl]pyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
[2-(methyloxy)ethyl]pyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
{[(3,5)-1-methylpiperidin-3-yl]methyl}pyridine-3-sul-
fonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
{[(3S)-1-methylpyrrolidin-3-yl]methyl}pyridine-3-sul-
fonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
ethyl-N-methylpyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
ethylpyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
methylpyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]-N-
piperidin-4-ylpyridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]py-
ridine-3-sulfonamide
2-amino-5-[4-(6,6-dimethyl-5,6,7,8-tetrahydroquinazo-
lin-4-yl)-2,3,4,5-tetrahydro-1,4-benzoxazepin-7-yl]py-
ridine-3-sulfonic acid
2-amino-5-[4-(6,6-dimethyl-5,6-dihydroquinazolin-4-yl)-
2,3,4,5-tetrahydro-1,4-benzoxazepin-7-yl]-N-meth-
ylpyridine-3-sulfonamide
2-amino-N-(2,3-dihydroxypropyl-5-[4-(6,6-dimethyl-5,6,
7,8-tetrahydroquinazolin-4-yl)-2,3,4,5-tetrahydro-1,4-
benzoxazepin-7-yl]pyridine-3-sulfonamide
2-amino-N-(2-amino-1,1-dimethylethyl)-5-[4-(6,6-dim-
ethyl-5,6,7,8-tetrahydroquinazolin-4-yl)-2,3,4,5-tet-
rahydro-1,4-benzoxazepin-7-yl]pyridine-3-sulfona-
mide
2-amino-N-(2-amino-2-methylpropyl)-5-[4-(6,6,7-trim-
ethyl-5,6-dihydroquinazolin-4-yl)-2,3,4,5-tetrahydro-
1,4-benzoxazepin-7-yl]pyridine-3-sulfonamide
2-amino-N-(2-amino-2-methylpropyl)-5-[4-(6,6-dim-
ethyl-5,6,7,8-tetrahydroquinazolin-4-yl)-2,3,4,5-tet-
rahydro-1,4-benzoxazepin-7-yl]pyridine-3-sulfona-
mide
2-amino-N-(2-amino-2-methylpropyl)-5-{4-[(7S)-7-
ethyl-5,6,7,8-tetrahydroquinazolin-4-yl]-2,3,4,5-tet-
rahydro-1,4-benzoxazepin-7-yl}pyridine-3-sulfona-
mide 2-amino-N-(2-aminobutyl)-5-[4-(6,6-dimethyl-5,6,7,8-
tetrahydroquinazolin-4-yl)-2,3,4,5-tetrahydro-1,4-ben-
zoxazepin-7-yl]pyridine-3-sulfonamide
2-amino-N-(2-aminoethyl)-5-[4-(6,6-dimethyl-5,6,7,8-
tetrahydroquinazolin-4-yl)-2,3,4,5-tetrahydro-1,4-ben-
zoxazepin-7-yl]pyridine-3-sulfonamide
2-amino-N-(2-aminopropyl)-5-[4-(6,6-dimethyl-5,6,7,8-
tetrahydroquinazolin-4-yl)-2,3,4,5-tetrahydro-1,4-ben-
zoxazepin-7-yl]pyridine-3-sulfonamide
2-amino-N-(3-amino-2,2-dimethylpropyl)-5-[4-(6,6-dim-
ethyl-5,6,7,8-tetrahydroquinazolin-4-yl)-2,3,4,5-tet-
rahydro-1,4-benzoxazepin-7-yl]pyridine-3-sulfona-
mide
2-amino-N-(3-amino-2-hydroxypropyl)-5-[4-(6,6-dim-
ethyl-5,6,7,8-tetrahydroquinazolin-4-yl)-2,3,4,5-tet-
rahydro-1,4-benzoxazepin-7-yl]pyridine-3-sulfona-
mide
2-amino-N-(3-amino-3-methylbutyl)-5-[4-(6,6-dimethyl-
5,6,7,8-tetrahydroquinazolin-4-yl)-2,3,4,5-tetrahydro-
1,4-benzoxazepin-7-yl]pyridine-3-sulfonamide
2-amino-N-(3-aminopropyl)-5-[4-(6,6=dimethyl-5,6,7,8-
tetrahydroquinazolin-4-yl)-2,3,4,5-tetrahydro-1,4-ben-
zoxazepin-7-yl]pyridine-3-sulfonamide
2-amino-N-(azetidin-3-ylmethyl)-5-[4-(6,6-dimethyl-5,6,
7,8-tetrahydroquinazolin-4-yl)-2,3,4,5-tetrahydro-1,4-
benzoxazepin-7-yl]pyridine-3-sulfonamide
2-amino-N-(trans-4-aminocyclohexyl)-5-[4-(6,6-dim-
ethyl-5,6,7,8-tetrahydroquinazolin-4-yl)-2,3,4,5-tet-
rahydro-1,4-benzoxazepin-7-yl]pyridine-3-sulfona-
mide
2-amino-N,N-dimethyl-5-[4-(2,6,6-trimethyl-5,6,7,8-tet-
rahydroquinazolin-4-yl)-2,3,4,5-tetrahydro-1,4-ben-
zoxazepin-7-yl]pyridine-3-sulfonamide
2-amino-N-[(1-aminocyclopropyl)methyl]-5-[4-(6,6-
dimethyl-5,6,7,8-tetrahydroquinazolin-4-yl)-2,3,4,5-
tetrahydro-1,4-benzoxazepin-7-yl]pyridine-3-sulfona-
mide
2-amino-N-[(1-methylpiperidin-4-yl)methyl]-5-[4-(2,6,6-
trimethyl-5,6,7,8-tetrahydroquinazolin-4-yl)-2,3,4,5-
tetrahydro-1,4-benzoxazepin-7-yl]pyridine-3-sulfona-
mide
2-amino-N-[(1-methylpiperidin-4-ypmethyl]-5-[4-(6,6,7-
trimethyl-5,6-dihydroquinazolin-4-yl)-2,3,4,5-tetrahy-
dro-1,4-benzoxazepin-7-yl]pyridine-3-sulfonamide
2-amino-N-[(3R)-1-methylpyrrolidin-3-yl]-5-[4-(2,6,6-
trimethyl-5,6,7,8-tetrahydroquinazolin-4-yl)-2,3,4,5-
tetrahydro-1,4-benzoxazepin-7-yl]pyridine-3-sulfona-
mide
2-amino-N-[(3R)-1-methylpyrrolidin-3-yl]-5-[4-(6,6,8-
trimethyl-5,6-dihydroquinazolin-4-yl)-2,3,4,5-tetrahy-
dro-1,4-benzoxazepin-7-yl]pyridine-3-sulfonamide
2-amino-N-[2-(dimethylamino)ethyl]-5-[4-(6,6-dim-
ethyl-5,6,7,8-tetrahydroquinazolin-4-yl)-2,3,4,5-tet-
rahydro-1,4-benzoxazepin-7-yl]pyridine-3-sulfona-
mide
2-amino-N-{[(3S)-1-methylpyrrolidin-3-yl]methyl}-5-
[4-(6,6,7-trimethyl-5,6-dihydroquinazolin-4-yl)-2,3,4,
5-tetrahydro-1,4-benzoxazepin-7-yl]pyridine-3-sul-
fonamide
2-amino-N-8-azabicyclo[3.2.1]oct-3-yl-5-[4-(6,6-dim-
ethyl-5,6,7,8-tetrahydroquinazolin-4-yl)-2,3,4,5-tet-
rahydro-1,4-benzoxazepin-7-yl]pyridine-3-sulfona-
mide
2-amino-N-azetidin-3-yl-5-[4-(6,6-dimethyl-5,6,7,8-tet-
rahydroquinazolin-4-yl)-2,3,4,5-tetrahydro-1,4-ben-
zoxazepin-7-yl]pyridine-3-sulfonamide 2-amino-N-cyclobutyl-5-[4-(6,6-dimethyl-5,6,7,8-tetrahydroquinazolin-4-yl)-2,3,4,5-tetrahydro-1,4-benzoxazepin-7-yl]pyridine-3-sulfonamide 2-chloro-5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)benzamide 2-chloro-N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}-6-methylbenzenesulfonamide 3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)propan-1-ol 3-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)propane-1,2-diol 3-(2,6-diazaspiro [3.3]hept-2-ylsulfonyl)-5-[4-(6,6-dimethyl-5,6,7,8-tetrahydroquinazolin-4-yl)-2,3,4,5-tetrahydro-1,4-benzoxazepin-7-yl]pyridin-2-amine 3-(4-{2-[(dimethylamino)methyl]-6,6-dimethyl-5,6,7,8-tetrahydroquinazolin-4-yl}-2,3,4,5-tetrahydro-1,4-benzoxazepin-7-yl)benzamide 3-(azetidin-1-ylsulfonyl)-5-[4-(6,6-dimethyl-5,6,7,8-tetrahydroquinazolin-4-yl)-2,3,4,5-tetrahydro-1,4-benzoxazepin-7-yl]pyridin-2-amine 3-[(1R,4R)-2,5-diazabicyclo [2.2.1]hept-2-ylsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(1S,4S)-2,5-diazabicyclo[2.2.1]hept-2-ylsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(1S,4S)-2,5-diazabicyclo [2.2.1]hept-2-ylsulfonyl]-5-{4-[(7S)-7-ethyl-5,6,7,8-tetrahydroquinazolin-4-yl]-2,3,4,5-tetrahydro-1,4-benzoxazepin-7-yl}pyridin-2-amine 3-[(3,3-difluoroazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(3-amino-3-methylazetidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(3-amino-3-methylpyrrolidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(3-amino-3-methylpyrrolidin-1-yl)sulfonyl]-5-{4-[(7S)-7-ethyl-2-methyl-5,6,7,8-tetrahydroquinazolin-4-yl]-2,3,4,5-tetrahydro-1,4-benzoxazepin-7-yl}pyridin-2-amine 3-[(3-amino-3-methylpyrrolidin-1-yl)sulfonyl]-5-{4-[(7S)-7-ethyl-5,6,7,8-tetrahydroquinazolin-4-yl]-2,3,4,5-tetrahydro-1,4-benzoxazepin-7-yl}pyridin-2-amine 3-[(3-aminoazetidin-1-ypsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(3-aminopiperidin-1-yl)sulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(3-aminopyrrolidin-1-ypsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-[(4-aminopiperidin-1-ypsulfonyl]-5-[4-(6,6-dimethyl-5,6,7,8-tetrahydroquinazolin-4-yl)-2,3,4,5-tetrahydro-1,4-benzoxazepin-7-yl]pyridin-2-amine 3-{[(3R)-3-aminopyrrolidin-1-yl]sulfonyl}-5-[4-(6,6,7-trimethyl-5,6-dihydroquinazolin-4-yl)-2,3,4,5-tetrahydro-1,4-benzoxazepin-7-yl]pyridin-2-amine 3-{[(3R)-3-aminopyrrolidin-1-yl]sulfonyl}-5-[4-(6,6,8-trimethyl-5,6-dihydroquinazolin-4-yl)-2,3,4,5-tetrahydro-1,4-benzoxazepin-7-yl]pyridin-2-amine 3-{[(3R)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine 3-{[(3R)-3-aminopyrrolidin-1-yl]sulfonyl}-5-[4-(6,6-dimethyl-5,6-dihydroquinazolin-4-yl)-2,3,4,5-tetrahydro-1,4-benzoxazepin-7-yl]pyridin-2-amine 3-{[(3R)-3-aminopyrrolidin-1-yl]sulfonyl}-5-{4-[(7S)-7-ethyl-5,6,7,8-tetrahydroquinazolin-4-yl]-2,3,4,5-tetrahydro-1,4-benzoxazepin-7-yl}pyridin-2-amine 3-{[(3S)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine 3-{[(3S)-3-aminopyrrolidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-ol 3-{[(3S)-3-aminopyrrolidin-1-yl]sulfonyl}-5-{4-[7-(methyloxy)quinazolin-4-yl]-2,3,4,5-tetrahydro-1,4-benzoxazepin-7-yl}pyridin-2-amine 3-{[3-(dimethylamino)azetidin-1-yl]sulfonyl}-5-[4-(6,6-dimethyl-5,6,7,8-tetrahydroquinazolin-4-yl)-2,3,4,5-tetrahydro-1,4-benzoxazepin-7-yl]pyridin-2-amine 3-{4-[2-methyl-7-(methyloxy)quinazolin-4-yl]-2,3,4,5-tetrahydro-1,4-benzoxazepin-7-yl}benzoic acid 3-amino-5-[4-(6,6-dimethyl-5,6,7,8-tetrahydroquinazolin-4-yl)-2,3,4,5-tetrahydro-1,4-benzoxazepin-7-yl]pyridine-2-carboxamide 4-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfinyl)-2-methylbutan-2-ol 4-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-2-methylbutan-2-ol 4-(2,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(2-{[(3R)-3-fluoropyrrolidin-1-yl]methyl}-6,6-dimethyl-5,6,7,8-tetrahydroquinazolin-4-yl)-7-(2-methyl-1H-benzimidazol-6-yl)-2,3,4,5-tetrahydro-1,4-benzoxazepine 4-(2-{[(3R)-3-fluoropyrrolidin-1-yl]methyl}-6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(2-{[(3S)-3-fluoropyrrolidin-1-yl]methyl}-6,6-dimethyl-5,6,7,8-tetrahydroquinazolin-4-yl)-7-(2-methyl-1H-benzimidazol-6-yl)-2,3,4,5-tetrahydro-1,4-benzoxazepine 4-(2-{[(3S)-3-fluoropyrrolidin-1-yl]methyl}-6,6-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(2-ethenyl-6,6-dimethyl-5,6,7,8-tetrahydroquinazolin-4-yl)-7-(2-methyl-3H-imidazo[4,5-b]pyridin-6-yl)-2,3,4,5-tetrahydro-1,4-benzoxazepine 4-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-N-methylbenzamide 4-(5-bromo-6-methylpyrimidin-4-yl)-7-(2-methyl-1H-imidazo[4,5-b]pyridin-6-yl)-2,3,4,5-tetrahydro-1,4-benzoxazepine 4-(5-ethyl-2,6-dimethylpyrimidin-4-yl)-7-(2-methyl-1H-imidazo[4,5-b]pyridin-6-yl)-2,3,4,5-tetrahydro-1,4-benzoxazepine 4-(5-ethyl-6-methylpyrimidin-4-yl)-7-(2-methyl-1H-imidazo[4,5-b]pyridin-6-yl)-2,3,4,5-tetrahydro-1,4-benzoxazepine 4-(6,6-difluoro-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(6,6-dimethyl-2-pyridin-2-yl-5,6,7,8-tetrahydroquinazolin-4-yl)-7-(2-methyl-1H-benzimidazol-6-yl)-2,3,4,5-tetrahydro-1,4-benzoxazepine 4-(6,6-dimethyl-2-pyridin-2-yl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(6,6-dimethyl-2-pyrrolidin-2-yl-5,6,7,8-tetrahydroquinazolin-4-yl)-7-(2-methyl-3H-imidazo[4,5-b]pyridin-6-yl)-2,3,4,5-tetrahydro-1,4-benzoxazepine 4-(6,6-dimethyl-5,6,7,8-tetrahydroquinazolin-4-yl)-7-(2-methyl-3H-imidazo[4,5-c]pyridin-7-yl)-2,3,4,5-tetrahydro-1,4-benzoxazepine 4-(6,6-dimethyl-5,6,7,8-tetrahydroquinazolin-4-yl)-7-[5-(methyloxy)pyridin-3-yl]-2,3,4,5-tetrahydro-1,4-benzoxazepine 4-(6,6-dimethyl-5,6,7,8-tetrahydroquinazolin-4-yl)-7-pyrido[2,3-b]pyrazin-7-yl-2,3,4,5-tetrahydro-1,4-benzoxazepine 4-(6,6-dimethyl-5,6-dihydroquinazolin-4-yl)-7-(2-methyl-1H-imidazo[4,5-b]pyridin-6-yl)-2,3,4,5-tetrahydro-1,4-benzoxazepine 4-(6,6-dimethyl-5,6-dihydroquinazolin-4-yl)-7-[4-(1H-imidazol-2-yl)phenyl]-2,3,4,5-tetrahydro-1,4-benzoxazepine 4-(6-azetidin-1-yl-5-methylpyrimidin-4-yl)-7-(2-methyl-1H-imidazo[4,5-b]pyridin-6-yl)-2,3,4,5-tetrahydro-1,4-benzoxazepine 4-(6-chloro-5-methylpyrimidin-4-yl)-7-(2-methyl-1H-imidazo[4,5-b]pyridin-6-yl)-2,3,4,5-tetrahydro-1,4-benzoxazepine 4-(6-ethyl-2-methyl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(6-ethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(7,7-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-(8,8-dimethyl-5,6,7,8-tetrahydroquinazolin-4-yl)-7-(2-methyl-1H-imidazo[4,5-b]pyridin-6-yl)-2,3,4,5-tetrahydro-1,4-benzoxazepine 4-[(6S,7S)-6,7-dimethyl-5,6,7,8-tetrahydroquinazolin-4-yl]-7-(2-methyl-1H-imidazo[4,5-b]pyridin-6-yl)-2,3,4,5-tetrahydro-1,4-benzoxazepine 4-[(7S)-7-ethyl-2-methyl-5,6,7,8-tetrahydroquinazolin-4-yl]-7-(2-methyl-1H-imidazo[4,5-b]pyridin-6-yl)-2,3,4,5-tetrahydro-1,4-benzoxazepine 4-[(7S)-7-ethyl-5,6,7,8-tetrahydroquinazolin-4-yl]-7-(2-methyl-1H-imidazo[4,5-b]pyridin-6-yl)-2,3,4,5-tetrahydro-1,4-benzoxazepine 4-[(8S)-8-ethenyl-6,7,8,9-tetrahydro-5H-cyclohepta[d]pyrimidin-4-yl]-7-(2-methyl-1H-imidazo[4,5-b]pyridin-6-yl)-2,3,4,5-tetrahydro-1,4-benzoxazepine 4-[(8S)-8-ethyl-6,7,8,9-tetrahydro-5H-cyclohepta[d]pyrimidin-4-yl]-7-(2-methyl-1H-imidazo[4,5-b]pyridin-6-yl)-2,3,4,5-tetrahydro-1,4-benzoxazepine 4-[2,6-dimethyl-5-(1-methylethyl)pyrimidin-4-yl]-7-(2-methyl-1H-imidazo[4,5-b]pyridin-6-yl)-2,3,4,5-tetrahydro-1,4-benzoxazepine 4-[5-(cyclopropylmethyl)-2,6-dimethylpyrimidin-4-yl]-7-(2-methyl-1H-imidazo[4,5-b]pyridin-6-yl)-2,3,4,5-tetrahydro-1,4-benzoxazepine 4-[5-(cyclopropylmethyl)-6-methylpyrimidin-4-yl]-7-(2-methyl-1H-imidazo[4,5-b]pyridin-6-yl)-2,3,4,5-tetrahydro-1,4-benzoxazepine 4-[6,6-dimethyl-2-({[2-(methyloxy)ethyl]oxy}methyl)-5,6,7,8-tetrahydroquinazolin-4-yl]-7-(2-methyl-1H-benzimidazol-6-yl)-2,3,4,5-tetrahydro-1,4-benzoxazepine 4-[6,6-dimethyl-2-({[2-(methyloxy)ethyl]oxy}methyl)-5,6,7,8-tetrahydroquinazolin-4-yl]-7-(2-methyl-1H-imidazo[4,5-b]pyridin-6-yl)-2,3,4,5-tetrahydro-1,4-benzoxazepine 4-[6,6-dimethyl-2-(1-pyrrolidin-1-ylethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine 4-[6,6-dimethyl-2-(2-pyrrolidin-1-ylethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine 4-[6,6-dimethyl-2-(morpholin-4-ylmethyl)-5,6,7,8-tetrahydroquinazolin-4-yl]-7-(2-methyl-1H-imidazo[4,5-b]pyridin-6-yl)-2,3,4,5-tetrahy dro-1,4-benzoxazepine 4-[6,6-dimethyl-2-(piperidin-1-ylmethyl)=5,6;7;8-tetrahydroquinazolin-4-yl]-7-(2-methyl-1H-imidazo[4,5-b]pyridin-6-yl)-2,3,4,5-tetrahydro-1,4-benzoxazepine 4-[6,6-dimethyl-2-(pyrrolidin-1-ylmethyl)-5,6,7,8-tetrahydroquinazolin-4-yl]-7-(2-methyl-1H-benzimidazol-5-yl)-2,3,4,5-tetrahydro-1,4-benzoxazepine 4-[6,6-dimethyl-2-(pyrrolidin-1-ylmethyl)-5,6,7,8-tetrahydroquinazolin-4-yl]-7-(2-methyl-3H-imidazo[4,5-b]pyridin-6-yl)-2,3,4,5-tetrahydro-1,4-benzoxazepine 4'-[7-(2-methyl-3H-imidazo[4,5-b]pyridin-6-yl)-2,3-dihydro-1,4-benzoxazepin-4(5H)-yl]-7',8'-dihydro-5'H-spiro[cyclopropane-1,6'-quinazoline]

4-{2-[(3,3-difluoropyrrolidin-1-yl)methyl]-6,6-dimethyl-5,6,7,8-tetrahydroquinazolin-4-yl}-7-(2-methyl-1H-imidazo[4,5-b]pyridin-6-yl)-2,3,4,5-tetrahydro-1,4-benzoxazepine 4-{4-[2-methyl-7-(methyloxy)quinazolin-4-yl]-2,3,4,5-tetrahydro-1,4-benzoxazepin-7-yl}aniline 4-{6,6-dimethyl-2-[(2R)-pyrrolidin-2-yl]-5,6,7,8-tetrahydroquinazolin-4-yl}-7-(2-methyl-1H-benzimidazol-5-yl)-2,3,4,5-tetrahydro-1,4-benzoxazepine 4-{6,6-dimethyl-2-[(2R)-pyrrolidin-2-yl]-5,6,7,8-tetrahydroquinazolin-4-yl}-7-(2-methyl-3H-imidazo[4,5-b]pyridin-6-yl)-2,3,4,5-tetrahydro-1,4-benzoxazepine 4-{6,6-dimethyl-2-[(2S)-pyrrolidin-2-yl]-5,6,7,8-tetrahydroquinazolin-4-yl}-7-(2-methyl-3H-imidazo[4,5-b]pyridin-6-yl)-2,3,4,5-tetrahydro-1,4-benzoxazepine 4-{6,6-dimethyl-2-[(methyloxy)methyl]-5,6,7,8-tetrahydroquinazolin-4-yl}-7-(2-methyl-3H-imidazo[4,5-b]pyridin-6-yl)-2,3,4,5-tetrahydro-1,4-benzoxazepine 5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)pyridin-2-amine 5-[4-(6,6-dimethyl-5,6,7,8-tetrahydroquinazolin-4-yl)-2,3,4,5-tetrahydro-1,4-benzoxazepin-7-yl]-3-(ethylsulfonyl)pyridin-2-amine 5-[4-(6,6-dimethyl-5,6,7,8-tetrahydroquinazolin-4-yl)-2,3,4,5-tetrahydro-1,4-benzoxazepin-7-yl]-3-(hexahydropyrrolo[3,4-c]pyrrol-2(1H)-ylsulfonyl)pyridin-2-amine 5-[4-(6,6-dimethyl-5,6,7,8-tetrahydroquinazolin-4-yl)-2,3,4,5-tetrahydro-1,4-benzoxazepin-7-yl]-3-(methylsulfonyl)pyridin-2-amine
5-[4-(6,6-dimethyl-5,6,7,8-tetrahydroquinazolin-4-yl)-2,3,4,5-tetrahydro-1,4-benzoxazepin-7-yl]-3-(morpholin-4-ylsulfonyl)pyridin-2-amine
5-[4-(6,6-dimethyl-5,6,7,8-tetrahydroquinazolin-4-yl)-2,3,4,5-tetrahydro-1,4-benzoxazepin-7-yl]-3-(piperazin-1-ylsulfonyl)pyridin-2-amine
5-[4-(6,6-dimethyl-5,6,7,8-tetrahydroquinazolin-4-yl)-2,3,4,5-tetrahydro-1,4-benzoxazepin-7-yl]-3-(pyrrolidin-1-ylsulfonyl)pyridin-2-amine
5-[4-(6,6-dimethyl-5,6,7,8-tetrahydroquinazolin-4-yl)-2,3,4,5-tetrahydro-1,4-benzoxazepin-7-yl]-3-[(4-methylpiperazin-1-yl)sulfonyl]pyridin-2-amine
5-[4-(6,6-dimethyl-5,6,7,8-tetrahydroquinazolin-4-yl)-2,3,4,5-tetrahydro-1,4-benzoxazepin-7-yl]-3-[(methylsulfonyl)methyl]pyridin-2-amine
5-[4-(6,6-dimethyl-5,6,7,8-tetrahydroquinazolin-4-yl)-2,3,4,5-tetrahydro-1,4-benzoxazepin-7-yl]-3-{[(1S,4S)-5-methyl-2,5-diazabicyclo[2.2.1]hept-2-yl]sulfonyl}pyridin-2-amine
5-[4-(6,6-dimethyl-5,6,7,8-tetrahydroquinazolin-4-yl)-2,3,4,5-tetrahydro-1,4-benzoxazepin-7-yl]-3-{[3-(methylamino)azetidin-1-yl]sulfonyl}pyridin-2-amine
5-[4-(6,6-dimethyl-5,6,7,8-tetrahydroquinazolin-4-yl)-2,3,4,5-tetrahydro-1,4-benzoxazepin-7-yl]-N-(2-hydroxyethyl)-2-(methylamino)pyridine-3-sulfonamide
5-[4-(6,6-dimethyl-5,6,7,8-tetrahydroquinazolin-4-yl)-2,3,4,5-tetrahydro-1,4-benzoxazepin-7-yl]-N,N-dimethylpyridine-3-sulfonamide
5-[4-(6,6-dimethyl-5,6,7,8-tetrahydroquinazolin-4-yl)-2,3,4,5-tetrahydro-1,4-benzoxazepin-7-yl]pyridine-3-sulfonamide
5-[4-(6,6-dimethyl-5,6,7,8-tetrahydroquinazolin-4-yl)-2,3,4,5-tetrahydro-1,4-benzoxazepin-7-yl]pyrimidin-2-amine
5-{4-[2-methyl-7-(methyloxy)quinazolin-4-yl]-2,3,4,5-tetrahydro-1,4-benzoxazepin-7-yl}-1,3-dihydro-2H-indol-2-one
5-methyl-N-(1-methylethyl)-6-[7-(2-methyl-1H-imidazo[4,5-b]pyridin-6-yl)-2,3-dihydro-1,4-benzoxazepin-4(5H)-yl]pyrimidin-4-amine
6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)[1,3]thiazolo[5,4-b]pyridin-2-amine
6-(4-{2-[(dimethylamino)methyl]-7-(methyloxy)quinazolin-4-yl}-2,3,4,5-tetrahydro-1,4-benzoxazepin-7-yl)[1,3]thiazolo[5,4-b]pyridin-2-amine
6-[7-(1H-benzimidazol-6-yl)-2,3-dihydro-1,4-benzoxazepin-4(5H)-yl]-2,5-dimethyl-N-phenylpyrimidin-4-amine
6-[7-(1H-imidazo[4,5-b]pyridin-6-yl)-2,3-dihydro-1,4-benzoxazepin-4(5H)-yl]-2,5-dimethyl-N-phenylpyrimidin-4-amine
6-[7-(2-cyclopropyl-1H-imidazo[4,5-b]pyridin-6-yl)-2,3-dihydro-1,4-benzoxazepin-4(5H)-yl]-5-methyl-N-(1-methylpiperidin-4-yl)pyrimidin-4-amine
6-[7-(2-cyclopropyl-1H-imidazo[4,5-b]pyridin-6-yl)-2,3-dihydro-1,4-benzoxazepin-4(5H)-yl]-5-methyl-N-(tetrahydro-2H-pyran-4-yl)pyrimidin-4-amine
6-[7-(2-cyclopropyl-1H-imidazo[4,5-b]pyridin-6-yl)-2,3-dihydro-1,4-benzoxazepin-4(5H)-yl]-5-methyl-N4(1-methylpiperidin-4-yl)methyl]pyrimidin-4-amine
6-[7-(2-cyclopropyl-1H-imidazo[4,5-b]pyridin-6-yl)-2,3-dihydro-1,4-benzoxazepin-4(5H)-yl]-5-methyl-N-[2-(1-methylpyrrolidin-2-yl)ethyl]pyrimidin-4-amine
6-[7-(2-cyclopropyl-1H-imidazo[4,5-b]pyridin-6-yl)-2,3-dihydro-1,4-benzoxazepin-4(5H)-yl]-N,5-dimethyl-N-[(1R)-1-phenylethyl]pyrimidin-4-amine
6-[7-(2-cyclopropyl-1H-imidazo[4,5-b]pyridin-6-yl)-2,3-dihydro-1,4-benzoxazepin-4(5H)-yl]-N,5-dimethyl-N-[(1 S')-1-phenylethyl]pyrimidin-4-amine
6-{4-[(73)-7-ethyl-5,6,7,8-tetrahydroquinazolin-4-yl]-2,3,4,5-tetrahydro-1,4-benzoxazepin-7-yl}-1H-imidazo[4,5-b]pyridin-2-amine
6-{4-[2,5-dimethyl-6-(phenylamino)pyrimidin-4-yl]-2,3,4,5-tetrahydro-1,4-benzoxazepin-7-yl}-N-ethyl-1H-benzimidazol-2-amine
6-{4-[2-methyl-7-(methyloxy)quinazolin-4-yl]-2,3,4,5-tetrahydro-1,4-benzoxazepin-7-yl}-1H-benzimidazol-2-amine
6-{4-[5-methyl-6-(phenylamino)pyrimidin-4-yl]-2,3,4,5-tetrahydro-1,4-benzoxazepin-7-yl}-1H-imidazo[4,5-b]pyridin-2-amine
7-(1H-benzimidazol-6-yl)-4-pyrimidin-4-yl-2,3,4,5-tetrahydro-1,4-benzoxazepine 7-(1H-imidazo[4,5-b]pyridin-6-yl)-4-[2-methyl-7-(methyloxy)quinazolin-4-yl]-2,3,4,5-tetrahydro-1,4-benzoxazepine
7-(1H-imidazo[4,5-b]pyridin-6-yl)-4-pyrimidin-4-yl-2,3,4,5-tetrahydro-1,4-benzoxazepine
7-(2-cyclopropyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine
7-(2-cyclopropyl-1H-imidazo[4,5-b]pyridin-6-yl)-4-(6,6-dimethyl-5,6-dihydroquinazolin-4-yl)-2,3,4,5-tetrahydro-1,4-benzoxazepine
7-(2-cyclopropyl-1H-imidazo[4,5-b]pyridin-6-yl)-4-[(7S)-7-methyl-5,6,7,8-tetrahydroquinazolin-4-yl]-2,3,4,5-tetrahydro-1,4-benzoxazepine
7-(2-cyclopropyl-1H-imidazo[4,5-b]pyridin-6-yl)-4-[5-(cyclopropylmethyl)-2,6-dimethylpyrimidin-4-yl]-2,3,4,5-tetrahydro-1,4-benzoxazepine
7-(2-ethyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine
7-(2-methyl-1H-imidazo[4,5-b]pyridin-6-yl)-4-(2,6,6-trimethyl-5,6,7,8-tetrahydroquinazolin-4-yl)-2,3,4,5-tetrahydro-1,4-benzoxazepine
7-(2-methyl-1H-imidazo[4,5-b]pyridin-6-yl)-4-(5-methyl-6-morpholin-4-ylpyrimidin-4-yl)-2,3,4,5-tetrahydro-1,4-benzoxazepine
7-(2-methyl-1H-imidazo[4,5-b]pyridin-6-yl)-4-(6,6,7,8-tetramethyl-5,6-dihydroquinazolin-4-yl)-2,3,4,5-tetrahydro-1,4-benzoxazepine
7-(2-methyl-1H-imidazo[4,5-b]pyridin-6-yl)-4-(6,6,7-trimethyl-5,6-dihydroquinazolin-4-yl)-2,3,4,5-tetrahydro-1,4-benzoxazepine
7-(2-methyl-1H-imidazo[4,5-b]pyridin-6-yl)-4-(6,6,8-trimethyl-5,6-dihydroquinazolin-4-yl)-2,3,4,5-tetrahydro-1,4-benzoxazepine
7-(2-methyl-1H-imidazo[4,5-b]pyridin-6-yl)-4-(6-methyl-5,6,7,8-tetrahydroquinazolin-4-yl)-2,3,4,5-tetrahydro-1,4-benzoxazepine
7-(2-methyl-1H-imidazo[4,5-b]pyridin-6-yl)-4-(7-methyl-5,6,7,8-tetrahydroquinazolin-4-yl)-2,3,4,5-tetrahydro-1,4-benzoxazepine
7-(2-methyl-1H-imidazo[4,5-b]pyridin-6-yl)-4-(7-methyl-7H-pyrrolo[2,3-d]pyrimidin-4-yl)-2,3,4,5-tetrahydro-1,4-benzoxazepine
7-(2-methyl-1H-imidazo[4,5-b]pyridin-6-yl)-4-(7=methyl-7-phenyl-5,6,7,8-tetrahydroquinazolin-4-yl)-2,3,4,5-tetrahydro-1,4-benzoxazepine 7-(2-methyl-1H-imidazo[4,5-b]pyridin-6-yl)-4-[(7R)-7-methyl-5,6,7,8-tetrahydroquinazolin-4-yl]-2,3,4,5-tetrahydro-1,4-benzoxazepine 7-(2-methyl-1H-imidazo[4,5-b]pyridin-6-yl)-4-[(7S)-7-methyl-5,6,7,8-tetrahydroquinazolin-4-yl]-2,3,4,5-tetrahydro-1,4-benzoxazepine 7-(2-methyl-1H-imidazo[4,5-b]pyridin-6-yl)-4-[2-methyl-5-(morpholin-4-ylsulfonyl)pyrimidin-4-yl]-2,3,4,5-tetrahydro-1,4-benzoxazepine 7-(2-methyl-1H-imidazo[4,5-b]pyridin-6-yl)-4-[5-(trifluoromethyl)-5,6,7,8-tetrahydroquinazolin-4-yl]-2,3,4,5-tetrahydro-1,4-benzoxazepine 7-(2-methyl-1H-imidazo[4,5-b]pyridin-6-yl)-4-[5-methyl-6-(4-methylpiperazin-1-yl)pyrimidin-4-yl]-2,3,4,5-tetrahydro-1,4-benzoxazepine 7-(2-methyl-1H-imidazo[4,5-b]pyridin-6-yl)-4-[6-methyl-5-(1-methylethyl)pyrimidin-4-yl]-2,3,4,5-tetrahydro-1,4-benzoxazepine 7-(2-methyl-1H-imidazo[4,5-b]pyridin-6-yl)-4-[7-(methyloxy)quinazolin-4-yl]-2,3,4,5-tetrahydro-1,4-benzoxazepine 7-(2-methyl-1H-imidazo[4,5-b]pyridin-6-yl)-4-[7-(trifluoromethyl)-5,6,7,8-tetrahydroquinazolin-4-yl]-2,3,4,5-tetrahydro-1,4-benzoxazepine 7-(2-methyl-1H-imidazo[4,5-b]pyridin-6-yl)-4-{7-[(methyloxy)methyl]-5,6,7,8-tetrahydroquinazolin-4-yl}-2,3,4,5-tetrahydro-1,4-benzoxazepine 7-(2-methyl-3H-imidazo[4,5-b]pyridin-6-yl)-4-[2-methyl-7-(methyloxy)quinazolin-4-yl]-2,3,4,5-tetrahydro-1,4-benzoxazepine 7-(3,4-dihydro-2H-pyrido[3,2-b][1,4]oxazin-7-yl)-4-(6,6-dimethyl-5,6,7,8-tetrahydroquinazolin-4-yl)-2,3,4,5-tetrahydro-1,4-benzoxazepine 7-[4-(1H-imidazol-4-yl)phenyl]-4-[2-methyl-7-(methyloxy)quinazolin-4-yl]-2,3,4,5-tetrahydro-1,4-benzoxazepine 7-[4-(6,6-dimethyl-5,6,7,8-tetrahydroquinazolin-4-yl)-2,3,4,5-tetrahydro-1,4-benzoxazepin-7-yl]-2H-pyrido[2,3-e][1,2,4]thiadiazin-3(4H)-one 1,1-dioxide 7-[4-(6,6-dimethyl-5,6,7,8-tetrahydroquinazolin-4-yl]=2,3,4,5-tetrahydro-1,4-benzoxazepin-7-yl]-2H-pyrido[3,2-b][1,4]oxazin-3(4H)-one 7-{6-chloro-5-[(difluoromethyl)oxy]pyridin-3-yl}-4-(6,6-dimethyl-5,6,7,8-tetrahydroquinazolin-4-yl)-2,3,4,5-tetrahydro-1,4-benzoxazepine 7-{6-chloro-5-[(methylsulfonyl)methyl]pyridin-3-yl}-4-(6,6-dimethyl-5,6,7,8-tetrahydroquinazolin-4-yl)-2,3,4,5-tetrahydro-1,4-benzoxazepine 8-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)-8-azabicyclo[3.2.1]octan-3-amine ethyl {6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}carbamate methyl (6-{4-[(7S)-7-ethyl-2-methyl-5,6,7,8-tetrahydroquinazolin-4-yl]-2,3,4,5-tetrahydro-1,4-benzoxazepin-7-yl}-1H-imidazo[4,5-b]pyridin-2-yl)carbamate methyl (6-{4-[(7S)-7-ethyl-5,6,7,8-tetrahydroquinazolin-4-yl]-2,3,4,5-tetrahydro-1,4-benzoxazepin-7-yl}-1H-imidazo[4,5-b]pyridin-2-yl)carbamate methyl [6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-1H-benzimidazol-2-yl]carbamate methyl [6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-1H-imidazo[4,5-b]pyridin-2-yl]carbamate methyl {2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}carbamate methyl {6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}carbamate methyl {6-[4-(6,6-dimethyl-5,6-dihydroquinazolin-4-yl)-2,3,4,5-tetrahydro-1,4-benzoxazepin-7-yl]-1H-imidazo[4,5-b]pyridin-2-yl}carbamate N-({5-[(4-fluorophenyl)methyl]-4-methyl-6-[7-(2-methyl-1H-benzimidazol-6-yl)-2,3-dihydro-1,4-benzoxazepin-4(5H)-yl]pyrimidin-2-yl}methyl)cyclopropanamine N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)-2-(methyloxy)ethanamine N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)-2-fluoroethanamine N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)cyclobutanamine N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)cyclopropanamine N-({6,6-dimethyl-4-[7-(2-methyl-1H-benzimidazol-6-yl)-2,3-dihydro-1,4-benzoxazepin-4(5H)-yl]-5,6,7,8-tetrahydroquinazolin-2-yl}methyl)ethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-(methyloxy)ethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2,2,2-trifluoroethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2,2-difluoroethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-fluoroethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-methylpropan-1-amine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-2-methylpropan-2-amine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)alanine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclobutanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclopentanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)cyclopropanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)ethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)methanesulfonamide N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-ethylethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-ethylpropan-2-amine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylcyclopropanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylethanamine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)-N-methylpropan-2-amine N-({6,6-dimethyl-4-[7-(2-methyl-1H-imidazo[4,5-b]pyridin-6-yl)-2,3-dihydro-1,4-benzoxazepin-4(5H)-yl]-5,6,7,8-tetrahydroquinazolin-2-yl}methyl)propan-2-amine N-(2-chloro-5-{4-[7-(methyloxy)quinazolin-4-yl]-2,3,4,5-tetrahydro-1,4-benzoxazepin-7-yl}pyridin-3-yl)methanesulfonamide N-(4-{4-[2-methyl-7-(methyloxy)quinazolin-4-yl]-2,3,4,5-tetrahydro-1,4-benzoxazepin-7-yl}phenyl)acetamide N,5-dimethyl-6-[7-(2-methyl-1H-imidazo[4,5-b]pyridin-6-yl)-2,3-dihydro-1,4-benzoxazepin-4(5H)-yl]pyrimidin-4-amine N,N,2-trimethyl-4-[7-(2-methyl-1H-imidazo[4,5-b]pyridin-6-yl)-2,3-dihydro-1,4-benzoxazepin-4(5H)-yl]pyrimidine-5-sulfonamide N,N-dimethyl-1-{4-[7-(2-methyl-1H-benzimidazol-5-yl)-2,3-dihydro-1,4-benzoxazepin-4(5H)-yl]-5-(1-methylethyl)pyrimidin-2-yl}methanamine N,N-dimethyl-1-{4-[7-(2-methyl-1H-imidazo[4,5-b]pyridin-6-yl)-2,3-dihydro-1,4-benzoxazepin-4(5H)-yl]-7-(methyloxy)quinazolin-2-yl}methanamine N,N-dimethyl-1-{4-methyl-5-(methylethyl)-6-[7-(2-methyl-3H-imidazo[4,5-b]pyridin-6-yl)-2,3-dihydro-1,4-benzoxazepin-4(5H)-yl]pyrimidin-2-yl}methanamine N,N-dimethyl-1-{4-methyl-6-[7-(2-methyl-1H-benzimidazol-5-yl)-2,3-dihydro-1,4-benzoxazepin-4(5H)-yl]-5-(1-methylethyl)pyrimidin-2-yl}methanamine N-[2-chloro-5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)pyridin-3-yl]methanesulfonamide N-[6-(4-{2-[(dimethylamino)methyl]-6,6-dimethyl-5,6,7,8-tetrahydroquinazolin-4-yl}-2,3,4,5-tetrahydro-1,4-benzoxazepin-7-yl)[1,3]thiazolo[5,4-b]pyridin-2-yl]acetamide N-[6-(4-{2-[(dimethylamino)methyl]-7-(methyloxy)quinazolin-4-yl}-2,3,4,5-tetrahydro-1,4-benzoxazepin-7-yl)[1,3]thiazolo[5,4-b]pyridin-2-yl]acetamide N-{2-(dimethylamino)-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide N-{2-amino-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide N-{2-chloro-5-[4-(6,6-dimethyl-5,6,7,8-tetrahydroquinazolin-4-yl)-2,3,4,5-tetrahydro-1,4-benzoxazepin-7-yl]phenyl}methanesulfonamide N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}acetamide N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide N-{2-chloro-5-[4-(6,6-dimethyl-5,6,7,8-tetrahydroquinazolin-4-yl)-2,3,4,5-tetrahydro-1,4-benzoxazepin-7-yl]pyridin-3-yl}-N-methylmethanesulfonamide N-{2-cyano-5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-(ethyloxy)pyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-(methylamino)pyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-(methyloxy)pyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-(phenylamino)pyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-[(phenylmethyl)amino]pyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-[(phenylmethyl)oxy]pyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-fluoropyridin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]-2-methylppidin-3-yl}methanesulfonamide N-{5-[4-(6,6-dimethyl-5,6,7,8-tetrahydroquinazolin-4-yl)-2,3,4,5-tetrahydro-1,4-benzoxazepin-7-yl]pyridin-3-yl}methanesulfonamide N-{6-[7-(2-cyclopropyl-1H-imidazo[4,5-b]pyridin-6-yl)-2,3-dihydro-1,4-benzoxazepin-4(5H)-yl]-5-methylpyrimidin-4-yl}-N,N'-dimethyl ethane-1,2-diamine N~2~-({2-amino-5-[4-(6,6-dimethyl-5,6,7,8-tetrahydroquinazolin-4-yl)-2,3,4,5-tetrahydro-1,4-benzoxazepin-7-yl]pyridin-3-yl}sulfonyl)glycinamide N-ethyl-2,5-dimethyl-6-[7-(2-methyl-1H-imidazo[4,5-b]pyridin-6-yl)-2,3-dihydro-1,4-benzoxazepin-4(5H)-yl]pyrimidin-4-amine N-ethyl-3-{4-[2-methyl-7-(methyloxy)quinazolin-4-yl]-2,3,4,5-tetrahydro-1,4-benzoxazepin-7-yl}benzamide N-ethyl-5-methyl-6-[7-(2-methyl-1H-imidazo[4,5-b]py-ridin-6-yl)-2,3-dihydro-1,4-benzoxazepin-4(5H)-yl]pyrimidin-4-amine N-ethyl-6-[4-(5-methyl-6-{[4-(methyloxy)phenyl]amino}pyrimidin-4-yl)-2,3,4,5-tetrahydro-1,4-benzoxazepin-7-yl]-1H-benzimidazol-2-amine N-ethyl-6-[4-(7-fluoro-2-methylquinolin-4-yl)-2,3,4,5-tetrahydro-1,4-benzoxazepin-7-yl]-1H-benzimidazol-2-amine N-ethyl-6-{4-[2-methyl-7-(methyloxy)quinazolin-4-yl]-2,3,4,5-tetrahydro-1,4-benzoxazepin-7-yl}-1H-imidazo[4,5-b]pyridin-2-amine N-ethyl-6-{4-[6-(ethylamino)-5-methylpyrimidin-4-yl]-2,3,4,5-tetrahydro-1,4-benzoxazepin-7-yl}-1H-benzimidazol-2-amine N-methyl-3-{4-[2-methyl-7-(methyloxy)quinazolin-4-yl]-2,3,4,5-tetrahydro-1,4-benzoxazepin-7-yl}benzamide phenylmethyl (2S)-2-{6,6-dimethyl-4-[7-(2-methyl-3H-imidazo[4,5-b]pyridin-6-yl)-2,3-dihydro-1,4-benzoxazepin-4(5H)-yl]-5,6,7,8-tetrahydroquinazolin-2-yl}pyrrolidine-1-carboxylate phenylmethyl [(1S)-1-(6-{4-[(7S)-7-ethyl-2-methyl-5,6,7,8-tetrahydroquinazolin-4-yl]-2,3,4,5-tetrahydro-1,4-benzoxazepin-7-yl}-1H-imidazo[4,5-b]pyridin-2-yl)ethyl]carbamate phenylmethyl [(1S)-1-{6-[4-(6,6-dimethyl-5,6,7,8-tetrahydroquinazolin-4-yl)-2,3,4,5-tetrahydro-1,4-benzoxazepin-7-yl]-1H-imidazo[4,5-b]pyridin-2-yl}ethyl]carbamate 1-(6,6-dimethyl-4-{7-[4-(methyloxy)-3-{[2-(methyloxy)ethyl]oxy}phenyl]-2,3-dihydro-1,4-benzoxazepin-4(5H)-yl}-5,6,7,8-tetrahydroquinazolin-2-yl)-N,N-dimethylmethanamine 1-{4-[7-{3-[(difluoromethyl)oxy]-4-(methyloxy)phenyl}-2,3-dihydro-1,4-benzoxazepin-4(5H)-yl]-6,6-dimethyl-5,6,7,8-tetrahydroquinazolin-2-yl}-N,N-dimethylmethanamine 1-[5-(4-{2-[(dimethylamino)methyl]-6,6-dimethyl-5,6,7,8-tetrahydroquinazolin-4-yl}-2,3,4,5-tetrahydro-1,4-benzoxazepin-7-yl)-2-(methyloxy)phenyl]ethanone 4-[7-(1H-benzimidazol-5-yl)-2,3-dihydro-1,4-benzoxazepin-4(5H)-yl]-5-[(4-fluorophenyl)methyl]-6-methylpyrimidin-2-amine 1-(6,6-dimethyl-4-{7-[4-(methyloxy)-3-(methylsulfonyl)phenyl]-2,3-dihydro-1,4-benzoxazepin-4(5H)-yl}-5,6,7,8-tetrahydroquinazolin-2-yl)-N,N-dimethylmethanamine N,N-dimethyl-1-{4-methyl-6-[7-(2-methyl-1H-benzimidazol-6-yl)-2,3-dihydro-1,4-benzoxazepin-4(5H)-yl]-5-propylpyrimidin-2-yl}methanamine N,N-dimethyl-1-{4-methyl-6-[7-(2-methyl-1H-benzimidazol-6-yl)-2,3-dihydro-1,4-benzoxazepin-4(5H)-yl]-5-prop-2-en-1-ylpyrimidin-2-yl}methanamine N,N-dimethyl-1-{4-methyl-6-[7-(2-methyl-1H-benzimidazol-5-yl)-2,3-dihydro-1,4-benzoxazepin-4(5H)-yl]-5-(2-methylpropyl)pyrimidin-2-yl}methanamine N-[5-(4-{2-[(dimethylamino)methyl]-6-methyl-5-(1-methylethyl)pyrimidin-4-yl}-2,3,4,5-tetrahydro-1,4-benzoxazepin-7-yl)-2-(methyloxy)phenyl]methanesulfonamide 6-(4-{2-[(dimethylamino)methyl]-6-methyl-5-propylpyrimidin-4-yl}-2,3,4,5-tetrahydro-1,4-benzoxazepin-7-yl)[1,3]thiazolo[5,4-b]pyridin-2-amine 1-{4-[7-(1H-benzimidazol-5-yl)-2,3-dihydro-1,4-benzoxazepin-4(5H)-yl]-7-(methyloxy)quinazolin-2-yl}-N,N-dimethylmethanamine N,N-dimethyl-1-{4-[7-(2-methyl-1H-benzimidazol-5-yl)-2,3-dihydro-1,4-benzoxazepin-4(5H)-yl]-7-(methyloxy)quinazolin-2-yl}methanamine 5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-amine 6-{4-[2-methyl-7-(methyloxy)quinazolin-4-yl]-2,3,4,5-tetrahydro-1,4-benzoxazepin-7-yl}[1,3]thiazolo[5,4-b]pyridin-2-amine 6-(4-{2-[(dimethylamino)methyl]-5-ethyl-6-methylpyrimidin-4-yl}-2,3,4,5-tetrahydro-1,4-benzoxazepin-7-yl)[1,3]thiazolo[5,4-b]pyridin-2-amine 6-(4-{5-(cyclopropylmethyl)-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine N,N-dimethyl-1-{4-methyl-6-[7-(2-methyl-1H-benzimidazol-6-yl)-2,3-dihydro-1,4-benzoxazepin-4(5H)-yl]-5-[2-(methyloxy)ethyl]pyrimidin-2-yl}methanamine 6-(4-{2-[(dimethylamino)methyl]-6-methyl-5-(2-methylpropyl)pyrimidin-4-yl}-2,3,4,5-tetrahydro-1,4-benzoxazepin-7-yl)[1,3]thiazolo[5,4-b]pyridin-2-amine 1-{5-bromo-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine 6-(4-{2-[(dimethylamino)methyl]-6-methyl-5-[2-(methyloxy)ethyl]pyrimidin-4-yl}-2,3,4,5-tetrahydro-1,4-benzoxazepin-7-yl)[1,3]thiazolo[5,4-b]pyridin-2-amine 1-{6,6-dimethyl-4-[7-(2-methyl-1H-benzimidazol-5-yl)-2,3-dihydro-1,4-benzoxazepin-4(5H)-yl]-5,6,7,8-tetrahydroquinazolin-2-yl}ethanamine 6-[4-(2,6,6-trimethyl-5,6,7,8-tetrahydroquinazolin-4-yl)-2,3,4,5-tetrahydro-1,4-benzoxazepin-7-yl][1,3]thiazolo[5,4-b]pyridin-2-amine 6-(4-{2-[(dimethylamino)methyl]-6-methyl-5-prop-2-en-1-ylpyrimidin-4-yl}-2,3,4,5-tetrahydro-1,4-benzoxazepin-7-yl)[1,3]thiazolo[5,4-b]pyridin-2-amine 6-(4-{2-[(dimethylamino)methyl]-5,6-dimethylpyrimidin-4-yl}-2,3,4,5-tetrahydro-1,4-benzoxazepin-7-yl)[1,3]thiazolo[5,4-b]pyridin-2-amine 1-{4,5-dimethyl-6-[7-(2-methyl-1H-benzimidazol-6-yl)-2,3-dihydro-1,4-benzoxazepin-4(5H)-yl]pyrimidin-2-yl}-N,N-dimethylmethanamine 6-(4-{5-bromo-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine 6-(4-{2-[(dimethylamino)methyl]-6-methyl-5-(1-methylethyl)pyrimidin-4-yl}-2,3,4,5-tetrahydro-1,4-benzoxazepin-7-yl)[1,3]thiazolo[5,4-b]pyridin-2-amine 7-(2-methyl-1H-benzimidazol-5-yl)-4-[6-methyl-5-(1-methylethyl)-2-(pyrrolidin-1-ylmethyl)pyrimidin-4-yl]-2,3,4,5-tetrahydro-1,4-benzoxazepine 4-[2-(fluoromethyl)-6,6-dimethyl-5,6,7,8-tetrahydroquinazolin-4-yl]-7-(2-methyl-1H-benzimidazol-5-yl)-2,3,4,5-tetrahydro-1,4-benzoxazepine 1-{5-chloro-4-methyl-6-[7-(2-methyl-1H-benzimidazol-5-yl)-2,3-dihydro-1,4-benzoxazepin-4(5H)-yl]pyrimidin-2-yl}-N,N-dimethylmethanamine 6-(4-{5-chloro-2-[(dimethylamino)methyl]-6-methylpyrimidin-4-yl}-2,3,4,5-tetrahydro-1,4-benzoxazepin-7-yl)[1,3]thiazolo[5,4-b]pyridin-2-amine 2-fluoro-N-({4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl)ethanamine 6-{4-[2-{[(2-fluoroethyl)amino]methyl}-6-methyl-5-(1-methylethyl)pyrimidin-4-yl]-2,3,4,5-tetrahydro-1,4-benzoxazepin-7-yl}[1,3]thiazolo[5,4-b]pyridin-2-amine N,N-dimethyl-1-{4-methyl-6-[7-(2-methyl-1H-benzimidazol-5-yl)-2,3-dihydro-1,4-benzoxazepin-4(5H)-yl]-5-phenylpyrimidin-2-yl}methanamine 6-(4-{2-[(dimethylamino)methyl]-6-methyl-5-phenylpyrimidin-4-yl}-2,3,4,5-tetrahydro-1,4-benzoxazepin-7-yl)[1,3]thiazolo[5,4-b]pyridin-2-amine N'-{5-[(4-fluorophenyl)methyl]-4-methyl-6-[7-(2-methyl-1H-benzimidazol-5-yl)-2,3-dihydro-1,4-benzoxazepin-4(5H)-yl]pyrimidin-2-yl}-N,N-dimethylethane-1,2-diamine {4-[7-(2-amino[1,3]thiazolo[5,4-b]pyridin-6-yl)-2,3-dihydro-1,4-benzoxazepin-4(5H)-yl]-6,6-dimethyl-5,6,7,8-tetrahydroquinazolin-2-yl}acetonitrile N-ethyl-N-({4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl)ethanamine {4-methyl-6-[7-(2-methyl-1H-benzimidazol-5-yl)-2,3-dihydro-1,4-benzoxazepin-4(5H)-yl]-5-(1-methylethyl)pyrimidin-2-yl}methyl acetate {4-methyl-6-[7-(2-methyl-1H-benzimidazol-5-yl)-2,3-dihydro-1,4-benzoxazepin-4(5H)-yl]-5-(1-methylethyl)pyrimidin-2-yl}methanol 4-[7-(1H-benzimidazol-5-yl)-2,3-dihydro-1,4-benzoxazepin-4(5H)-yl]-6-methylpyrimidin-2-amine 5-[(4-fluorophenyl)methyl]-4-[7-(3H-imidazo[4,5-b]pyridin-6-yl)-2,3-dihydro-1,4-benzoxazepin-4(5H)-yl]-6-methylpyrimidin-2-amine 5-[(4-fluorophenyl)methyl]-4-methyl-6-[7-(2-methyl-3H-imidazo[4,5-b]pyridin-6-yl)-2,3-dihydro-1,4-benzoxazepin-4(5H)-yl]pyrimidin-2-amine 1-{4-[7-(3H-imidazo[4,5-b]pyridin-6-yl)-2,3-dihydro-1,4-benzoxazepin-4(5H)-yl]-7-(methyloxy)quinazolin-2-yl}-N,N-dimethylmethanamine; and 6-(4-{2-amino-5-[(4-fluorophenyl)methyl]-6-methylpyrimidin-4-yl}-2,3,4,5-tetrahydro-1,4-benzoxazepin-7-yl)[1,3]thiazolo[5,4-b]pyridin-2-amine or a single stereoisomer or mixture of stereoisomers thereof and additionally optionally as a pharmaceutically acceptable salt thereof.

24. A pharmaceutical composition which comprises a compound, optionally as pharmaceutically acceptable salt thereof, of claim 1 and a pharmaceutically acceptable carrier, excipient, or diluent.

25. A method of making a compound of formula Ia, according to claim 1 which method comprises (a) reacting the following, or a salt thereof:

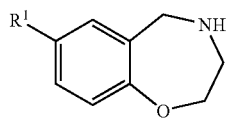

where $R^1$ is as defined in claim 1; with an intermediate of formula $R^2X$ where X is halo, and $R^2$ is as defined in claim 1 to yield a compound of formula Ia; and optionally separating individual isomers; and optionally modifying any of the $R^1$ and $R^2$ groups; and optionally forming a pharmaceutically acceptable salt thereof; or (b) reacting the following intermediate, or a salt thereof:

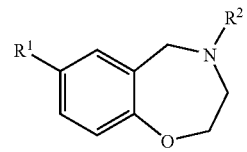

where R is halo or —B(OR')$_2$ (where both R' are hydrogen or the two R' together form a boronic ester), and $R^2$ is as defined in claim 1; with an intermediate of formula $R^1Y$ where Y is halo when R is —B(OR')$_2$ and Y is —B(OR')$_2$ when R is halo, and $R^2$ is as defined in claim 1 to yield a compound of the invention of formula Ia; and optionally separating individual isomers; and optionally modifying any of the $R^1$ and $R^2$ groups; and optionally forming a pharmaceutically acceptable salt thereof.

26. The compound of claim 2 where $R^2$ is quinazolin-4-yl substituted with $R^3$, $R^{3a}$, $R^{3b}$, $R^{3c}$, and $R^{3d}$; where $R^{3c}$ and $R^{3d}$ are hydrogen; or a single stereoisomer or mixture of stereoisomers thereof and additionally optionally as a pharmaceutically acceptable salt thereof.

27. The compound of claim 2 where $R^2$ is quinolin-4-yl substituted with $R^3$, $R^{3a}$, $R^{3b}$, $R^{3c}$, and $R^{3d}$; where $R^{3c}$ and $R^{3d}$ are hydrogen; or a single stereoisomer or mixture of stereoisomers thereof and additionally optionally as a pharmaceutically acceptable salt thereof.

28. The compound of claim 2 where $R^2$ is isoquinolin-4-yl substituted with $R^3$, $R^{3a}$, $R^{3b}$, $R^{3c}$, and $R^{3d}$; where $R^{3c}$ and $R^{3d}$ are hydrogen; or a single stereoisomer or mixture of stereoisomers thereof and additionally optionally as a pharmaceutically acceptable salt thereof.

29. The compound of claim 2 where $R^2$ is according to formula (a)

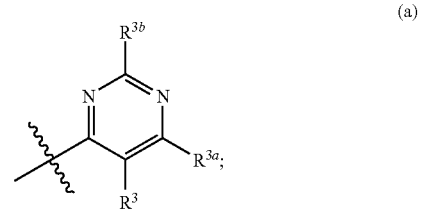

or a single stereoisomer or mixture of stereoisomers thereof and additionally optionally as a pharmaceutically acceptable salt thereof.

30. The compound according to claim 2 where $R^2$ is according to formula (g)

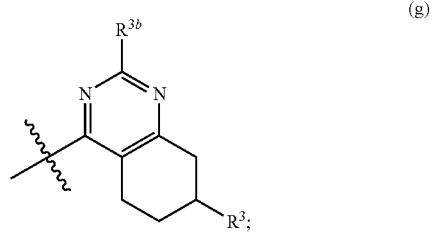

or a single stereoisomer or mixture of stereoisomers thereof and additionally optionally as a pharmaceutically acceptable salt thereof.

31. The compound according to claim 2 where $R^2$ is according to formula (d)

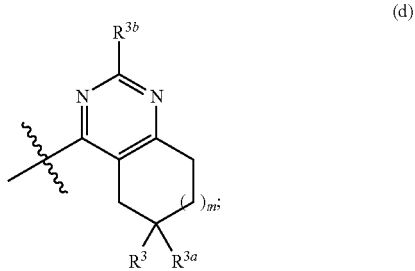

(d)

where m is 1; or a single stereoisomer or mixture of stereoisomers thereof and additionally optionally as a pharmaceutically acceptable salt thereof.

32. The compound according to claim 2 where $R^2$ is according to formula (e)

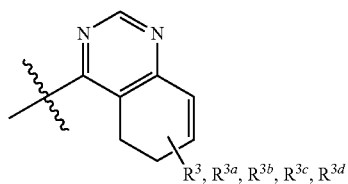

(e)

where $R^3$, $R^{3a}$, $R^{3b}$, $R^{3c}$, $R^{3d}$ are positioned on any substitutable carbon on the ring of formula (e); or a single stereoisomer or mixture of stereoisomers thereof and additionally optionally as a pharmaceutically acceptable salt thereof.

33. The compound according to claim 18 where $R^{3b}$ is hydrogen, alkyl, alkenyl, hydroxyalkyl, cyanoalkyl, optionally substituted heteorcycloalkyl, optionally substituted heteorcycloalkylalkyl, or alkyl substituted with one $R^{16}$; or a single stereoisomer or mixture of stereoisomers thereof and additionally optionally as a pharmaceutically acceptable salt thereof.

34. A method of treating cancer, where the cancer is mammary adenocarcinoma, colorectal carcinoma, prostate adenocarcinoma, glioblastoma, lung carcinoma, or melanoma, the method comprising administering to a patient a therapeutically effective amount of a compound of claim 1, optionally as a pharmaceutically acceptable salt thereof, or a pharmaceutical composition comprising a compound of claim 1 and a pharmaceutically acceptable carrier, excipient, or diluent.

* * * * *